(12) United States Patent
Dolle et al.

(10) Patent No.: US 7,598,261 B2
(45) Date of Patent: Oct. 6, 2009

(54) SPIROCYCLIC HETEROCYCLIC DERIVATIVES AND METHODS OF THEIR USE

(75) Inventors: Roland E. Dolle, King of Prussia, PA (US); Bertrand Le Bourdonnec, East Fallowfield, PA (US); Guo-Hua Chu, Wilmington, DE (US)

(73) Assignee: Adolor Corporation, Exton, PA (US)

( * ) Notice: Subject to any disclaimer, the term of this patent is extended or adjusted under 35 U.S.C. 154(b) by 224 days.

(21) Appl. No.: 11/393,133

(22) Filed: Mar. 30, 2006

(65) Prior Publication Data

US 2006/0270695 A1 Nov. 30, 2006

Related U.S. Application Data

(60) Provisional application No. 60/667,177, filed on Mar. 31, 2005.

(51) Int. Cl.
*A61K 31/438* (2006.01)
*C07D 491/107* (2006.01)

(52) U.S. Cl. .................. 514/278; 546/17; 544/124; 514/232.8

(58) Field of Classification Search .......... 514/278, 514/232.8; 546/17; 544/124
See application file for complete search history.

(56) References Cited

U.S. PATENT DOCUMENTS

| | | | |
|---|---|---|---|
| 5,106,998 A | 4/1992 | Tanaka et al. ............. 549/331 |
| 5,132,307 A | 7/1992 | Baumgarth et al. ......... 514/247 |
| 5,349,065 A | 9/1994 | Tanaka et al. ............. 546/15 |
| 5,354,863 A | 10/1994 | Dappen et al. ............. 546/35 |
| 5,356,915 A | 10/1994 | Almansa et al. ............ 514/357 |
| 5,387,587 A | 2/1995 | Häusler et al. ............ 514/254 |
| 5,403,846 A | 4/1995 | Baldwin et al. ............ 514/278 |
| 5,628,935 A | 5/1997 | Hughes et al. ............. 252/589 |
| 5,656,420 A | 8/1997 | Chien ................... 435/1.2 |
| 5,705,102 A | 1/1998 | Hughes et al. ............. 252/375 |
| 5,786,378 A | 7/1998 | Hamilton et al. ........... 514/423 |
| 5,990,131 A | 11/1999 | Hamilton et al. ........... 514/330 |
| 6,031,115 A | 2/2000 | Bell et al. ................ 549/362 |
| 6,040,308 A | 3/2000 | Häusler et al. ............ 514/253 |
| 6,153,627 A | 11/2000 | Häusler et al. ............ 514/253 |
| 6,200,978 B1 | 3/2001 | Maw et al. ............. 514/254.05 |
| 6,218,424 B1 | 4/2001 | Hamilton et al. ........... 514/423 |
| 6,319,939 B1 | 11/2001 | Mabire et al. ............. 514/381 |
| 6,417,209 B2 | 7/2002 | Hamilton et al. ........... 514/365 |
| 6,436,959 B1 | 8/2002 | Carson et al. ............. 514/326 |
| 6,596,758 B1 | 7/2003 | Brunet et al. ............. 514/450 |
| 6,645,973 B1 | 11/2003 | Gibson et al. ............. 514/278 |
| 7,338,962 B2 * | 3/2008 | Dolle et al. .............. 514/278 |
| 2001/0056103 A1 | 12/2001 | Hamilton et al. ........... 514/327 |
| 2002/0115653 A1 | 8/2002 | Mabire et al. ............. 514/212 |
| 2002/0193420 A1 | 12/2002 | Hamilton et al. ........... 514/438 |
| 2003/0069241 A1 | 4/2003 | Mchardy et al. ............ 514/241 |
| 2004/0082612 A1 | 4/2004 | Baxter et al. ............. 514/317 |
| 2004/0106652 A1 | 6/2004 | Hamilton et al. ........... 514/355 |
| 2005/0159438 A1 | 7/2005 | Dolle et al. .............. 514/278 |

FOREIGN PATENT DOCUMENTS

| | | |
|---|---|---|
| EP | 0 420 266 A3 | 4/1991 |
| EP | 0 362 119 B1 | 7/1993 |
| EP | 0 600 147 A1 | 6/1994 |
| EP | 0 401 958 B1 | 1/1995 |
| EP | 0 376 524 B1 | 3/1995 |
| EP | 0 708 164 A2 | 4/1996 |
| EP | 0 582 338 B1 | 10/1999 |
| EP | 1 179 551 A1 | 2/2002 |
| EP | 0 864 559 B1 | 6/2002 |
| JP | 4-275288 A | 9/1992 |
| JP | 9-301973 | 11/1997 |
| WO | 93/17026 A1 | 9/1993 |
| WO | 93/19755 A1 | 10/1993 |
| WO | 94/17045 A1 | 8/1994 |
| WO | WO 95/04734 A1 | 2/1995 |
| WO | WO 95/31464 A1 | 11/1995 |
| WO | WO 96/22276 A1 | 7/1996 |
| WO | WO 97/10216 A1 | 3/1997 |
| WO | 99/04795 A1 | 2/1999 |
| WO | 99/29674 A1 | 6/1999 |
| WO | 00/39113 A1 | 7/2000 |
| WO | 01/36423 A1 | 5/2001 |
| WO | WO 01/46192 A1 | 6/2001 |

(Continued)

OTHER PUBLICATIONS

Bhargava, H.N., et al., "Effect of nitric oxide synthase inhibition on tolerance to the analgesic action of D-Pen$^2$, D-Pen$^5$ enkephalin and morphine in the mouse," *Neuropeptides*, 1996, 30(3), 219-223.

Bilsky, E.J., et al., "SNC 80, a selective, nonpeptidic and systemically active opioid *delta* agonist," *J. of Pharmacology and Experimental Therapeutics*, 1995, 273(1), 359-366.

Bilsky, E.J., et al., "Effects of naloxone and D-Phe-Cys-Tyr-D-Trp-Arg-Thr-Pen-Thr-NH$_2$ and the protein kinase inhibitors H7 and H8 on acute morphine dependence and antinociceptive tolerance in mice," *J. of Pharmacol Exp. Ther.*, 1996, 277(1), 484-490.

Borlongan, C.V., et al., "Delta opioid peptide (D-ALA 2, D-LEU 5) enkephalin: linking hibernation and neuroprotection," *Frontiers in Bioscience*, 2004, 9(Suppl.), 3392-3398.

DeHaven R.N., et al., "Characterization of opioid receptors," *Current Protocols in Pharmacology*, 2000, John Wiley & Sons, 1.4.1-1.4.12.

Dondio, et al., "Central & peripheral nervous systems: non-peptide δ opioid agonists and antagonists," *Exp. Opin. Ther. Patents*, 1997, 7(10), 1075-1098.

(Continued)

*Primary Examiner*—Charanjit S Aulakh
(74) *Attorney, Agent, or Firm*—Feldman Gale, P.A.; David A. Cherry

(57) ABSTRACT

Spirocyclic heterocyclic derivatives, pharmaceutical compositions containing these compounds, and methods for their pharmaceutical use are disclosed. In certain embodiments, the spirocyclic heterocyclic derivatives are ligands of the δ opioid receptor and may be useful, inter alia, for treating and/or preventing pain, anxiety, gastrointestinal disorders, and other δ opioid receptor-mediated conditions.

93 Claims, No Drawings

FOREIGN PATENT DOCUMENTS

| | | |
|---|---|---|
| WO | 01/83476 A1 | 11/2001 |
| WO | WO 02/48122 A3 | 6/2002 |
| WO | 02/094782 A1 | 11/2002 |
| WO | WO 02/094783 A1 | 11/2002 |
| WO | WO 02/094784 A1 | 11/2002 |
| WO | WO 02/094785 A1 | 11/2002 |
| WO | WO 02/094786 A1 | 11/2002 |
| WO | WO 02/094794 A1 | 11/2002 |
| WO | WO 02/094810 A1 | 11/2002 |
| WO | WO 02/094811 A1 | 11/2002 |
| WO | WO 02/094812 A1 | 11/2002 |
| WO | WO 03/029215 A1 | 4/2003 |
| WO | WO 03/033486 A1 | 4/2003 |
| WO | WO 03/037342 A1 | 5/2003 |
| WO | WO 03/057223 A1 | 7/2003 |
| WO | WO 93/15062 A1 | 8/2003 |
| WO | WO2004/026819 A3 | 4/2004 |
| WO | WO2004/035541 A1 | 4/2004 |
| WO | WO2004/035574 A3 | 4/2004 |
| WO | WO2004/041784 A1 | 5/2004 |
| WO | WO2004/041800 A1 | 5/2004 |
| WO | WO2004/041801 A1 | 5/2004 |
| WO | WO2004/041802 A1 | 5/2004 |
| WO | WO2004/060321 A3 | 7/2004 |
| WO | WO2004/062562 A3 | 7/2004 |
| WO | WO2004/063157 A1 | 7/2004 |
| WO | WO2004/063193 A1 | 7/2004 |
| WO | 2004/082612 A1 | 9/2004 |
| WO | 2005/033073 A3 | 4/2005 |

OTHER PUBLICATIONS

Dourish, C.T., et al., "Enhancement of morphine analgesia and prevention of morphine tolerance in the rat by the cholecystokinin antagonist L-364, 718," *Eur. J. Pharmacol.*, 1988, 147, 469-472.

Fraser, M.O., "Urinary incontinence: neuropharmacological approaches," *Annual Reports in Medicinal Chemistry*, 2003, Chapter 6, 51-60.

Galligan, J.J., et al., "Cerebral *delta* opioid receptors mediate analgesia but not the intestinal motility effects of intracerebroventicularly administered opioids," *J. Pharm. Exp. Ther.*, 1984, 229(3), 641-648.

Jain, K.K., "A guide to drug evaluation for chronic pain," *Emerging Drugs*, 2000, 5(2), 241-257.

Lord, J.A.H., et al., "Endogenous opioid peptides: multiple agonists and receptors," *Nature*, 1977, 267, 495-499.

Mao, M.J., et al., "Oral administration of dextromethorphan prevents the development of morphine tolerance and dependence in rats," *Pain*, 1996, 67, 361-368.

Moreland, R.B., et al., "Emerging pharmacologic approaches for the treatment of lower urinary tract disorders," *Perspectives in Pharmacology*, 2004, 308(3), 797-804.

Moulin, D.E., et al., The analgesic efficacy of intrathecal D-Ala$^2$ -D-Leu$^5$. *Pain*, 1985, 23, 213-221.

Nichols, M.L., et al., "Enhancement of the antiallodynic and antinociceptive efficacy of spinal morphine by antisera to dynorphin A (1-13) or MK-801 in a nerve-ligation model of peripheral neuropathy," *Pain*, 1997, 69, 317-322.

Raynor, K., et al., "Pharmacological characterization of the cloned κ-, δ-, and μ-opioid receptors," *Molecular Pharmacology*, 1994, 45, 330-334.

Su, T.-P., "Delta opioid peptide [$D$-Ala$^2$,$D$-Leu$^5$]enkephalin promotes cell survival," *J. of Biomedical Science*, 2000, 7, 195-199.

U.S. Appl. No. 60/507,864, filed Oct. 1, 2003, Roland Dolle.

U.S. Appl. No. 10/957,554, filed Oct. 1, 2004, Roland Dolle.

Dorland's Illustrated Medical Dictionary, 27$^{th}$ Ed., *W.B. Saunders co.*, Phila., 1988, p. 375.

Livingston, E.H., et al., "Postoperative Ileus," *Digestive Diseases and Sciences*, 1990, 35(1), 121-132.

Resnick, J., "Delayed gastric emptying and postoperative Ileus after nongastric abdominal surgery: Part I," *Am. J. of Gastroenterology*, 1997, 92(5), 751-762.

Resnick, J., "Delayed gastric emptying and postoperative Ileus after nongastric abdominal surgery: Part II," *Am. J. of Gastroenterology*, 1997, 92(6), 934-940.

Schultz, J.J. et al, "Ischemic Preconditioning and Morphine-Induced Cardioprotection Involve the delta-Opioid Receptor in the Intact Rat Heart", *J. Mol. Cell. Cardiol.*, 1997, 29, 2187-2195.

Schultz, J.J. et al., "Ischemic Preconditioning is Mediated by a Peripheral Opioid Receptor Mechanism in the Intact Rat Heart", *J. Mol. Cell. Cardiol.*, 1997, 29, 1355-1362.

Tsung-Ping Su, "Delta Opioid Peptide [$D$-Ala$^2$,$D$-Leu$^5$]Enkephalin Promotes Cell Survival," *J. of Biomedical Science*, 2000, 7, 195-199.

Watson, M.J. et al., "ARD-353 [4-((2R,5S)-4-(R)-(4-Diethylcarbamoylphenyl)(3-hydroxyphenyl)methyl)-2,5-dimethylpiperazin-1-ylmethyl)benzoic Acid], A Novel Nonpeptide δ Receptor Agonist, Reduces Myocardial Infarct Size without Central Effects," *J. Pharm. Exp. Ther.*, 2006, 316(1), 423-430.

Xenopoulos, N.P. et al., "Morphine Mimics Ischemic Preconditioning in Human Myocardium during PTCA", *J. Am. Coll. Cardiol.*, 1998, 31 (Suppl. A), 65A-66A, Abstract No. 810-3.

* cited by examiner

SPIROCYCLIC HETEROCYCLIC DERIVATIVES AND METHODS OF THEIR USE

CROSS REFERENCE TO RELATED APPLICATIONS

This application claims priority to U.S. Provisional Application Ser. No. 60/667,177, filed Mar. 31, 2005 the disclosure of which is incorporated herein by reference in its entirety.

FIELD OF THE INVENTION

The invention relates to spirocyclic heterocyclic derivatives (including derivatives of spiro(2H-1-benzopyran-2,4'-piperidines), pharmaceutical compositions containing these compounds, and methods for their pharmaceutical use. In certain embodiments, the spirocyclic heterocyclic derivatives are ligands of the δ opioid receptor and are useful, inter alia, for treating and/or preventing pain, anxiety, gastrointestinal disorders, and other δ opioid receptor-mediated conditions.

BACKGROUND OF THE INVENTION

There are at least three different opioid receptors (μ, δ and κ) that are present in both central and peripheral nervous systems of many species, including humans. Lord, J. A. H., et al., *Nature*, 1977, 267, 495. Activation of the δ opioid receptors induces analgesia in various animal models. Moulin, et al., *Pain*, 1985, 23, 213. Some work suggests that the analgesics working at δ opioid receptors do not have the attendant side effects associated with μ and κ opioid receptor activation. Galligan, et al., *J. Pharm. Exp. Ther.*, 1985, 229, 641. The δ opioid receptor has also been identified as having a role in circulatory systems. Ligands for the δ receptor have also been shown to possess immunomodulatory activities. Dondio, et al., *Exp. Opin. Ther. Patents*, 1997, 10, 1075. Further, selective δ opioid receptor agonists have been shown to promote organ and cell survival. Su, T-P, *Journal of Biomedical Science*, 2000, 9(3), 195-199. Ligands for the δ opioid receptor may therefore find potential use as analgesics, as antihypertensive agents, as immunomodulatory agents, and/or agents for the treatment of cardiac disorders.

Numerous selective δ opioid ligands are peptidic in nature and thus are unsuitable for administration by systemic routes. Several non-peptidic δ opioid receptor ligands have been developed. See, for example, E. J. Bilsky, et al., *Journal of Pharmacology and Experimental Therapeutics*, 1995, 273 (1), 359-366; WO 93/15062, WO 95/04734, WO 95/31464, WO 96/22276, WO 97/10216, WO 01/46192, WO 02/094794, WO 02/094810, WO 02/094811, WO 02/094812, WO 02/48122, WO 03/029215, WO 03/033486, JP-4275288, EP-A-0,864,559, U.S. Pat. Nos. 5,354,863, 6,200,978, 6,436,959 and US 2003/0069241.

While there are a large number of non-peptidic δ opioid receptor modulators, there is still an unfulfilled need for compounds with selective δ opioid receptor activity that may be used in methods to provide beneficial pharmaceutical characteristics while minimizing undesirable side effects. The present invention is directed to these, as well as other important ends.

SUMMARY OF THE INVENTION

In one embodiment, the invention is directed to compounds of formula XIV:

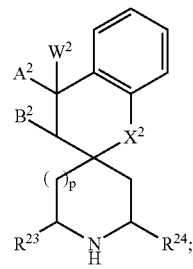

XIV wherein:
  $W^2$ is aryl or heteroaryl, wherein the aryl or heteroaryl is substituted with 0-3 groups selected independently from hydroxy, aminocarbonyl (—C(=O)—NH$_2$), N-alkylaminocarbonyl (—C(=O)—NH(alkyl)), and N,N-dialkylaminocarbonyl (—C(=O)—N(alkyl)(alkyl));
  $R^{23}$ and $R^{24}$ are each independently H or alkyl, provided that at least one of $R^{23}$ and $R^{24}$ is alkyl;
  p is 1 or 2;
  $A^2$ and $B^2$ are each H, or together form a double bond; and
  $X^2$ is —CH$_2$— or —O—;
  or a stereoisomer, prodrug, pharmaceutically acceptable salt, hydrate, solvate, acid salt hydrate, or N-oxide thereof.

In another embodiment, the invention is directed to compounds of formula XVII:

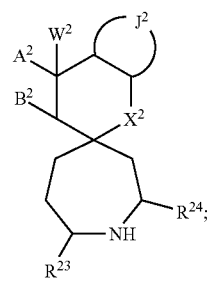

XVII wherein:
  $W^2$ is aryl or heteroaryl, wherein the aryl or heteroaryl is substituted with 0-3 groups selected independently from hydroxy, aminocarbonyl (—C(=O)—NH$_2$), N-alkylaminocarbonyl (—C(=O)—NH(alkyl)), and N,N-dialkylaminocarbonyl (—C(=O)—N(alkyl)(alkyl));
  $R^{23}$ and $R^{24}$ are each independently H or alkyl;
  $A^2$ and $B^2$ are each H, or together form a double bond;
  $X^2$ is —CH$_2$— or —O—; and
  $J^2$ when taken together with the carbon atoms to which it is attached forms a 6-membered aryl ring substituted with 0-3 groups selected independently from halo, hydroxy, and —S(=O)$_2$-alkyl;

or a stereoisomer, prodrug, pharmaceutically acceptable salt, hydrate, solvate, acid salt hydrate, or N-oxide thereof;

provided that:
when $W^2$ is para-diethylaminocarbonylphenyl, $X^2$ is O, and $A^2$ and $B^2$ together form a double bond, then the aryl ring of $J^2$ is substituted with at least one group selected independently from halo and —S(=O)$_2$-alkyl in which the alkyl group is $C_2$-$C_6$ alkyl;
when $W^2$ is para-diethylaminocarbonylphenyl, $X^2$ is O, and $A^2$ and $B^2$ are each H, then the aryl ring of $J^2$ is substituted with 1-3 groups selected independently from halo, hydroxy, and —S(=O)$_2$-alkyl; and
the compound of formula XVII is other than:

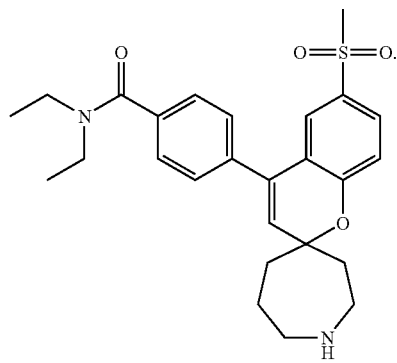

In yet another embodiment, the invention is directed to compounds of formula XX:

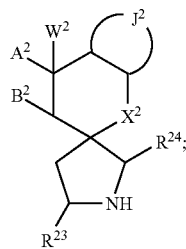

XX wherein:
$W^2$ is aryl or heteroaryl, wherein the aryl or heteroaryl is substituted with 0-3 groups selected independently from hydroxy, aminocarbonyl (—C(=O)—NH$_2$), N-alkylaminocarbonyl (—C(=O)—NH(alkyl)), and N,N-dialkylaminocarbonyl (—C(=O)—N(alkyl)(alkyl));
$R^{23}$ and $R^{24}$ are each independently H or alkyl;
$A^2$ and $B^2$ are each H, or together form a double bond;
$X^2$ is —CH$_2$— or —O—; and
$J^2$ when taken together with the carbon atoms to which it is attached forms a 6-membered aryl ring substituted independently with 0-3 hydroxy or halo groups;
or a stereoisomer, prodrug, pharmaceutically acceptable salt, hydrate, solvate, acid salt hydrate, or N-oxide thereof;
provided that the compound of formula XX is other than 4-[(4-N,N-diethylaminocarbonyl)phenyl]-spiro[2H,1-benzopyran-2,3'-pyrrolidine].

In still another embodiment, the invention is directed to compounds of formula XXII:

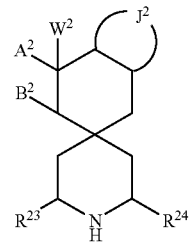

XXII wherein:
$W^2$ is aryl or heteroaryl, wherein the aryl or heteroaryl is substituted with 0-3 groups selected independently from heteroaryl, hydroxy, carboxy (—COOH), —C(=O)-alkyl, —C(=O)-aryl, —C(=O)—O-alkyl, —S(=O)$_2$—N(alkyl)(alkyl); aminocarbonyl (—C(=O)—NH$_2$), N-alkylaminocarbonyl (—C(=O)—NH(alkyl)), and N,N-dialkylaminocarbonyl (—C(=O)—N(alkyl)(alkyl));
$R^{23}$ and $R^{24}$ are each independently H or alkyl;
$A^2$ and $B^2$ are each H, or together form a double bond; and
$J^2$ when taken together with the carbon atoms to which it is attached forms a 6-membered aryl ring substituted with 0-3 groups selected independently from halo, heterocycloalkyl, hydroxy, alkoxy, —S(=O)$_2$-alkyl, —S(=O)$_2$—NH$_2$, —S(=O)$_2$—NH(alkyl), —S(=O)$_2$—N(alkyl)(alkyl), carboxy (—COOH), —C(=O)—O-alkyl, and N,N-dialkylaminocarbonyl (—C(=O)—N(alkyl)(alkyl));
or a stereoisomer, prodrug, pharmaceutically acceptable salt, hydrate, solvate, acid salt hydrate, or N-oxide thereof;

provided that:
when $W^2$ is para-diethylaminocarbonylphenyl, para-prop-2-ylaminocarbonylphenyl, or para-pent-3-ylaminocarbonylphenyl, $R^{23}$ and $R^{24}$ are each H, and A and B are each H or together form a double bond, then $J^2$ is other than unsubstituted phenyl or anisyl; and
when $W^2$ is:

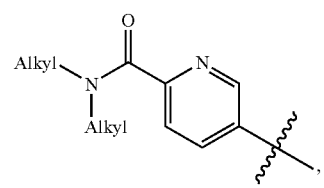

$R^{23}$ and $R^{24}$ are each H, and A and B together form a double bond; then $J^2$ is other than unsubstituted phenyl.

In another embodiment, the invention is directed to compounds of formula XXV:

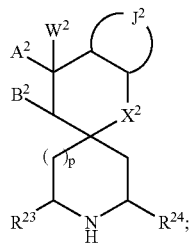

XXV wherein:
$W^2$ is aryl optionally substituted with —C(═O)-alkyl or —C(═O)-aryl;
$R^{23}$ and $R^{24}$ are each independently H or alkyl;
p is 1 or 2;
$A^2$ and $B^2$ are each H, or together form a double bond;
$X^2$ is —CH$_2$— or —O—; and
$J^2$ when taken together with the carbon atoms to which it is attached forms a 6-membered aryl ring substituted with 0-3 groups selected independently from hydroxy, alkoxy, —S(═O)$_2$-alkyl, —S(═O)$_2$—NH$_2$, —S(═O)$_2$—NH(alkyl), —S(═O)$_2$—N(alkyl)(alkyl), —C(═O)—N(alkyl)(alkyl), carboxy (—COOH), and —C(═O)—O-alkyl;
or a stereoisomer, prodrug, pharmaceutically acceptable salt, hydrate, solvate, acid salt hydrate, or N-oxide thereof;
provided that the compound of formula XXV is other than 4-phenyl-spiro[2H,1-benzopyran-2,4'-piperidine].

In yet another embodiment, the invention is directed to compounds of formula XXVII:

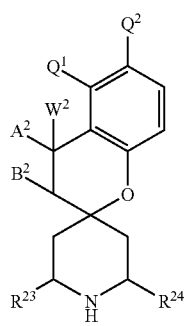

XXVII wherein:
$W^2$ is para-dialkylaminocarbonyiphenyl, the phenyl group of which is further optionally substituted with 1-2 groups independently selected from tetrazolyl, N-alkyltetrazolyl, hydroxy, carboxy (—COOH), and aminocarbonyl (—C(═O)—NH$_2$);
$R^{23}$ and $R^{24}$ are each independently H or alkyl;
$A^2$ and $B^2$ are each H, or together form a double bond;
$Q^1$ and $Q^2$ are each independently H, hydroxy, alkoxy, haloalkoxy, halo, or heterocycloalkyl;
or a stereoisomer, prodrug, pharmaceutically acceptable salt, hydrate, solvate, acid salt hydrate, or N-oxide thereof;

provided that:
when one of $Q^1$ and $Q^2$ is hydroxy and the other is H, or both $Q^1$ and $Q^2$ are hydroxy, then the phenyl group of $W^2$ is further substituted with 1-2 groups selected from tetrazolyl, N-alkyltetrazolyl, hydroxy, carboxy (—COOH), and aminocarbonyl (—C(═O)—NH$_2$);
when $Q^1$, $Q^2$, $R^{23}$, and $R^{24}$ are each H and the phenyl group of $W^2$ is further substituted with one hydroxy, then $A^2$ and $B^2$ are each H;
when $W^2$ is para-dialkylaminocarbonyiphenyl, then at least one of $Q^1$, $Q^2$, $R^{23}$, and $R^{24}$ is other than H;
when $W^2$ is para-dialkylaminocarbonyiphenyl, $R^{23}$ and $R^{24}$ are each H, and $Q^2$ is halo, then $Q^1$ is other than H or hydroxy;
when $W^2$ is para-dialkylaminocarbonylphenyl, $R^{23}$ and $R^{24}$ are each H, $Q^1$ is methoxy or cyclopropylmethoxy, and $Q^2$ is H, then $A^2$ and $B^2$ are each H; and
when $W^2$ is para-dialkylaminocarbonylphenyl, $R^{23}$ and $R^{24}$ are each H, and $Q^1$ is H or OH, then $Q^2$ is other than methoxy or cyclopropylmethoxy.

In still another embodiment, the invention is directed to compounds of formula XXVIII:

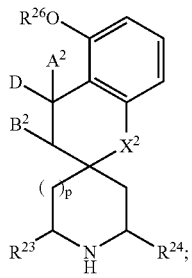

XXVIII wherein:
D is:

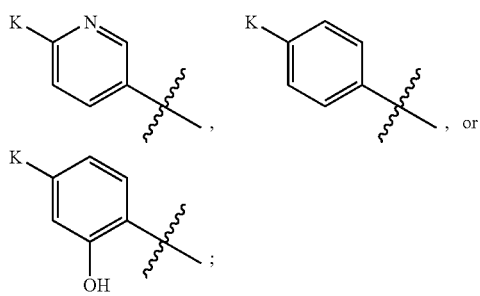

K is carboxy (—COOH), —C(═O)—O-alkyl, —S(═O)$_2$—N(alkyl)(alkyl), heteroaryl, alkylheteroaryl, aminocarbonyl (—C(═O)—NH$_2$), or N-alkylaminocarbonyl (—C(═O)—NH(alkyl));
$R^{23}$, $R^{24}$, and $R^{26}$ are each independently H or alkyl;
p is 1 or 2;
$A^2$ and $B^2$ are each H, or together form a double bond; and
$X^2$ is —CH$_2$— or —O—;
or a stereoisomer, prodrug, pharmaceutically acceptable salt, hydrate, solvate, acid salt hydrate, or N-oxide thereof.

In another embodiment, the invention is directed to compounds of formula XXIX:

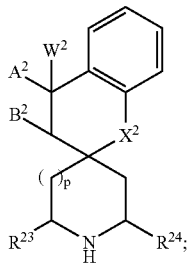

XXIX wherein:
W² is para-N(alkyl),N(alkyl-Z)aminocarbonylaryl or para-N(alkyl),N(alkyl-Z)aminocarbonylheteroaryl, wherein the aryl or heteroaryl ring of W² is substituted with 0-2 groups selected independently from hydroxy and alkoxy;
Z is alkoxy, alkylamino, or dialkylamino;
R²³ and R²⁴ are each independently H or alkyl;
p is 1 or 2;
A² and B² are each H, or together form a double bond; and
X² is —CH₂— or —O—;
or a stereoisomer, prodrug, pharmaceutically acceptable salt, hydrate, solvate, acid salt hydrate, or N-oxide thereof.

In yet another embodiment, the invention is directed to compounds of formula XXX:

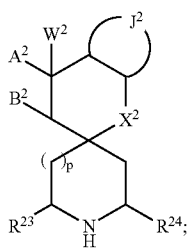

XXX wherein:
W² is:

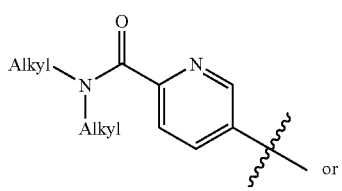 or

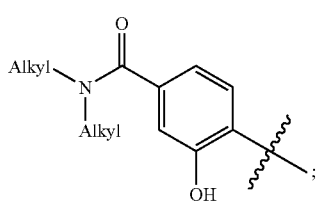;

R²³ and R²⁴ are each independently H or alkyl;
p is 1 or 2;
A² and B² are each H, or together form a double bond;
X² is —CH₂— or —O—; and
J² when taken together with the carbon atoms to which it is attached forms a 6-membered aryl ring substituted with 1-3 groups selected independently from halo or haloalkoxy;
or a stereoisomer, prodrug, pharmaceutically acceptable salt, hydrate, solvate, acid salt hydrate, or N-oxide thereof;
provided that when W² is:

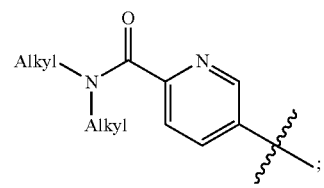;

then the aryl ring of J² is substituted with at least one haloalkoxy.

In another embodiment, the invention is directed to compounds of formula XXXII:

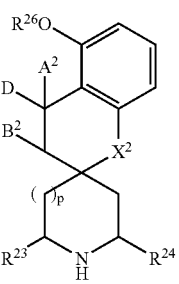

XXXII wherein:
D is N(alkyl),N(alkyl)aminocarbonylheteroaryl;
R²³, R²⁴, and R²⁶ are each independently H or alkyl;
p is 1 or 2;
A² and B² are each H, or together form a double bond; and
X² is —CH₂— or —O—;
or a stereoisomer, prodrug, pharmaceutically acceptable salt, hydrate, solvate, acid salt hydrate, or N-oxide thereof;
provided that when D is:

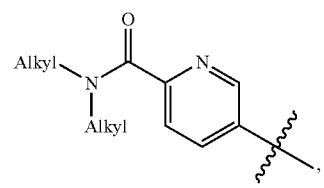, and X² is —O—, then A² and B² are each H.

In one embodiment, the invention is directed to compounds of formula XXXIII:

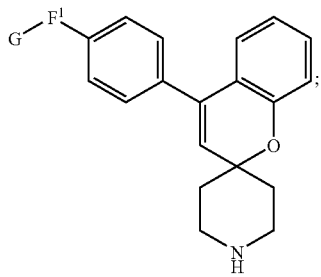

XXXIII wherein:
F¹ is heteroaryl; and
G is $C_{1-6}$alkylene substituted with $NH_2$, NHC(=O)alkyl, NH(C(O)N(H)alkyl, or NHS(=O)$_2$alkyl;
or a stereoisomer, prodrug, pharmaceutically acceptable salt, hydrate, solvate, acid salt hydrate, or N-oxide thereof.

In another embodiment, the invention is directed to compounds of formula XXXIV:

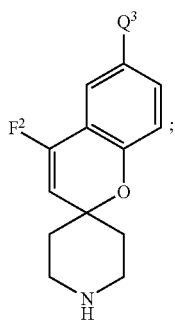

XXXIV wherein:
F² is aryl or heteroaryl; and
Q³ is hydroxy or alkoxy;
or a stereoisomer, prodrug, pharmaceutically acceptable salt, hydrate, solvate, acid salt hydrate, or N-oxide thereof.

In still another embodiment, the invention is directed to pharmaceutical compositions, comprising:
a pharmaceutically acceptable carrier; and a compound as described herein including, for example, a compound of formula XIV, XVII, XX, XXII, XXV, XXVII, XXVIIA, XXVIII, XXIX, XXX, XXXII, XXXIII, and/or XXXIV.

In still another embodiment, the invention is directed to methods of binding opioid receptors in a patient in need thereof, comprising the step of:
administering to said patient an effective amount of a compound as described herein including, for example, a compound of formula XIV, XVII, XX, XXII, XXV, XXVII, XXVIIA, XXVIII, XXIX, XXX, XXXII, XXXIII, and/or XXXIV.

These and other embodiments of the invention will become more apparent from the following detailed description.

DETAILED DESCRIPTION OF ILLUSTRATIVE EMBODIMENTS

The invention relates to spirocyclic heterocyclic derivatives, pharmaceutical compositions containing these compounds, and methods for their pharmaceutical use. This invention is related by subject matter to co-pending U.S. application Ser. No. 10/957,554, filed Oct. 1, 2004 and Provisional application Ser. No. 60/507,864, filed Oct. 1, 2003, the disclosures of which are hereby incorporated herein by reference, in their entireties.

In certain embodiments, the spirocyclic heterocyclic derivatives are ligands of the δ opioid receptor and may be useful, inter alia, in methods for treating and/or preventing diseases and conditions that may be mediated or modulated by the δ opioid receptor including, for example, pain, gastrointestinal disorders, urogenital tract disorders including incontinence and overactive bladder, immunomodulatory disorders, inflammatory disorders, respiratory function disorders, anxiety, mood disorders, stress-related disorders, attention deficit hyperactivity disorders, sympathetic nervous system disorders, depression, tussis, motor disorders, traumatic injuries, especially to the central nervous system, stroke, cardiac arrhythmias, glaucoma, sexual dysfunctions, shock, brain edema, cerebral ischemia, cerebral deficits subsequent to cardiac bypass surgery and grafting, systemic lupus erythematosus, Hodgkin's disease, Sjogren's disease, epilepsy, rejections in organ transplants and skin grafts, and substance addiction. In certain other embodiments, the spirocyclic heterocyclic derivatives are ligands of the δ opioid receptor and may be useful in, inter alia, methods for improving organ and cell survival, methods for providing cardioprotection following myocardial infarction, methods for reducing the need for anesthesia, methods for producing and/or maintaining an anaesthetic state, and methods of detecting, imaging or monitoring degeneration or dysfunction of opioid receptors in a patient.

As employed above and throughout the disclosure, the following terms, unless otherwise indicated, shall be understood to have the following meanings.

"Alkyl" refers to an optionally substituted, saturated straight, or branched, hydrocarbon having from about 1 to about 20 carbon atoms (and all combinations and subcombinations of ranges and specific numbers of carbon atoms therein), preferably from about 1 to about 8 carbon atoms, herein referred to as "lower alkyl," more preferably from about 1 to about 6, still more preferably from about 1 to about 4, with from about 2 to about 3 being most preferred. In certain alternative preferred embodiments, the alkyl group, more preferably, has one carbon atom. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, 3-methylpentyl, 2,2-dimethylbutyl, and 2,3-dimethylbutyl.

As used herein, "alkylene" refers to an optionally substituted bivalent alkyl radical having the general formula —$(CH_2)_n$—, where n is 1 to 10, preferably 1 to 6, with 1 to 4 being most preferred. In alternative embodiments, n is preferably 4 to 6. Non-limiting examples include methylene, dimethylene, trimethylene, tetramethylene, pentamethylene, and hexamethylene.

"Cycloalkyl" refers to an optionally substituted alkyl group having one or more rings in their structures and having from about 3 to about 20 carbon atoms (and all combinations and subcombinations of ranges and specific numbers of carbon atoms therein), with from about 3 to about 10 carbon atoms being preferred. Multi-ring structures may be bridged or fused ring structures. Cycloalkyl groups include, but are not limited to, cyclopropyl, cyclobutyl, cyclopentyl, cyclohexyl, cyclooctyl, 2-[4-isopropyl-1-methyl-7-oxa-bicyclo[2.2.1]heptanyl], 2-[1,2,3,4-tetrahydro-naphthalenyl], and adamantyl.

"Alkylcycloalkyl" refers to an optionally substituted ring system comprising a cycloalkyl group having one or more alkyl substituents, wherein cycloalkyl and alkyl are each as previously defined. Exemplary alkylcycloalkyl groups include, for example, 2-methylcyclohexyl, 3,3-dimethylcyclopentyl, trans-2,3-dimethylcyclooctyl, and 4-methyldecahydronaphthalenyl.

"Heterocycloalkyl" refers to an optionally substituted ring system composed of a cycloalkyl radical wherein in at least one of the rings, one or more of the carbon atom ring members is independently replaced by a heteroatom group selected from the group consisting of O, S, N, and NH, wherein cycloalkyl is as previously defined. Heterocycloalkyl ring systems having a total of from about 5 to about 14 carbon atom ring members and heteroatom ring members (and all combinations and subcombinations of ranges and specific numbers of carbon and heteroatom ring members) are preferred. In other preferred embodiments, the heterocyclic groups may be fused to one or more aromatic rings. Exemplary heterocycloalkyl groups include, but are not limited to, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydro-cyclopenta[c]pyranyl, 1,2,3,4,-tetrahydroquinolyl, octahydro-[2]pyrindinyl, decahydro-cycloocta[c]furanyl, tetrahydroquinolyl, and imidazolidinyl.

"Alkylheterocycloalkyl" refers to an optionally substituted ring system comprising a heterocycloalkyl group having one or more alkyl substituents, wherein heterocycloalkyl and alkyl are each as previously defined. Exemplary alkylheterocycloalkyl groups include, for example, 2-methylpiperidinyl, 3,3-dimethylpyrrolidinyl, trans-2,3-dimethylmorpholinyl, and 4-methyldecahydroquinolinyl.

"Alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined.

"Alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined.

"Aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Aralkyl" refers to an optionally substituted moiety composed of an alkyl radical bearing an aryl substituent and having from about 6 to about 50 carbon atoms (and all combinations and subcombinations of ranges and specific numbers of carbon atoms therein), with from about 6 to about 10 carbon atoms being preferred. Non-limiting examples include, for example, benzyl, diphenylmethyl, triphenylmethyl, phenylethyl, and diphenylethyl.

"Halo" refers to a fluoro, chloro, bromo, or iodo moiety, preferably fluoro.

"Heteroaryl" refers to an optionally substituted aryl ring system wherein in at least one of the rings, one or more of the carbon atom ring members is independently replaced by a heteroatom group selected from the group consisting of S, O, N, and NH, wherein aryl is as previously defined. Heteroaryl groups having a total of from about 5 to about 14 carbon atom ring members and heteroatom ring members (and all combinations and subcombinations of ranges and specific numbers of carbon and heteroatom ring members) are preferred. Exemplary heteroaryl groups include, but are not limited to, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached via a carbon or a heteroatom to the rest of the molecule.

"Heteroarylalkyl" and "heteroaralkyl" each refers to an optionally substituted, heteroaryl substituted alkyl radical where heteroaryl and alkyl are as previously defined Non-limiting examples include, for example, 2-(1H-pyrrol-3-yl)ethyl, 3-pyridylmethyl, 5-(2H-tetrazolyl)methyl, and 3-(pyrimidin-2-yl)-2-methylcyclopentanyl.

"Perhaloalkyl" refers to an alkyl group, wherein two or more hydrogen atoms are replaced by halo (F, Cl, Br, I) atoms, and alkyl is as previously defined. Exemplary perhaloalkyl groups include, for example, perhalomethyl, such as perfluoromethyl and difluoromethyl.

"Alkoxy" and "alkoxyl" refer to an optionally substituted alkyl-O— group wherein alkyl is as previously defined. Exemplary alkoxy and alkoxyl groups include, for example, methoxy, ethoxy, n-propoxy, i-propoxy, n-butoxy, and heptoxy.

"Alkenyloxy" refers to an optionally substituted alkenyl-O— group wherein alkenyl is as previously defined. Exemplary alkenyloxy and alkenyloxyl groups include, for example, allyloxy, butenyloxy, heptenyloxy, 2-methyl-3-buten-1-yloxy, and 2,2-dimethylallyloxy.

"Alkynyloxy" refers to an optionally substituted alkynyl-O— group wherein alkynyl is as previously defined. Exemplary alkynyloxy and alkynyloxyl groups include, for example, propargyloxy, butenyloxy, heptynyloxy, 2-methyl-3-buten-1-yloxy, and 2,2-dimethylpropargyloxy.

"Aryloxy" and "aryloxyl" refer to an optionally substituted aryl-O— group wherein aryl is as previously defined. Exemplary aryloxy and aryloxyl groups include, for example, phenoxy and naphthoxy.

"Aralkoxy" and "aralkoxyl" refer to an optionally substituted aralkyl-O— group wherein aralkyl is as previously defined. Exemplary aralkoxy and aralkoxyl groups include, for example, benzyloxy, 1-phenylethoxy, 2-phenylethoxy, and 3-naphthylheptoxy.

"Cycloalkoxy" refers to an optionally substituted cycloalkyl-O— group wherein cycloalkyl is as previously defined. Exemplary cycloalkoxy groups include, for example, cyclopropanoxy, cyclobutanoxy, cyclopentanoxy, cyclohexanoxy, and cycloheptanoxy.

"Heteroaryloxy" refers to an optionally substituted heteroaryl-O— group wherein heteroaryl is as previously defined. Exemplary heteroaryloxy groups include, but are not limited to, pyrryloxy, furyloxyl, pyridyloxy, 1,2,4-thiadiazolyloxy, pyrimidyloxy, thienyloxy, isothiazolyloxy, imidazolyloxy, tetrazolyloxy, pyrazinyloxy, pyrimidyloxy, quinolyloxy, isoquinolyloxy, thiophenyloxy, benzothienyloxy, isobenzofuryloxy, pyrazolyloxy, indolyloxy, purinyloxy, carbazolyloxy, benzimidazolyloxy, and isoxazolyloxy.

"Heteroaralkoxy" refers to an optionally substituted heteroarylalkyl-O— group wherein heteroarylalkyl is as previously defined. Exemplary heteroaralkoxy groups include, but are not limited to, pyrrylethyloxy, furylethyloxy, pyridylmethyloxy, 1,2,4-thiadiazolylpropyloxy, pyrimidylmethyloxy, thienylethyloxy, isothiazolylbutyloxy, and imidazolyl-2-methylpropyloxy.

"Heterocycloalkylaryl" refers to an optionally substituted ring system composed of an aryl radical bearing a heterocycloalkyl substituent wherein heterocycloalkyl and aryl are as previously defined. Exemplary heterocycloalkylaryl groups include, but are not limited to, morpholinylphenyl, piperidinylnaphthyl, piperidinylphenyl, tetrahydrofuranylphenyl, and pyrrolidinylphenyl.

"Alkylheteroaryl" refers to an optionally substituted ring system composed of a heteroaryl radical bearing an alkyl substituent wherein heteroaryl and alkyl are as previously defined. Exemplary alkylheteroaryl groups include, but are not limited to, methylpyrryl, ethylfuryl, 2,3-dimethylpyridyl, N-methyl-1,2,4-thiadiazolyl, propylpyrimidyl, 2-butylthienyl, methylisothiazolyl, 2-ethylimidazolyl, butyltetrazolyl, 5-ethylbenzothienyl, and N-methylindolyl. Alkyheteroaryl groups may be attached via a carbon or a heteroatom to the rest of the molecule.

"Heteroarylaryl" refers to an optionally substituted ring system composed of an aryl radical bearing a heteroaryl substituent wherein heteroaryl and aryl are as previously defined. Exemplary heteroarylaryl groups include, but are not limited to, pyrrylphenyl, furylnaphthyl, pyridylphenyl, 1,2,4-thiadiazolylnaphthyl, pyrimidylphenyl, thienylphenyl, isothiazolylnaphthyl, imidazolylphenyl, tetrazolylphenyl, pyrazinylnaphthyl, pyrimidylphenyl, quinolylphenyl, isoquinolylnaphthyl, thiophenylphenyl, benzothienylphenyl, isobenzofurylnaphthyl, pyrazolylphenyl, indolylnaphthyl, purinylphenyl, carbazolylnaphthyl, benzimidazolylphenyl, and isoxazolylphenyl. Heteroarylaryl may be attached via a carbon or a heteroatom to the rest of the molecule.

"Alkylheteroarylaryl" refers to an optionally substituted ring system composed of an aryl radical bearing an alkylheteroaryl substituent and have from about 12 to about 50 carbon atoms (and all combinations and subcombinations of ranges and specific numbers of carbon atoms therein), with from about 12 to about 30 carbon atoms being preferred wherein aryl and alkylheteroaryl are as previously defined. Exemplary heteroarylaryl groups include, but are not limited to, methylpyrrylphenyl, ethylfurylnaphthyl, methylethylpyridylphenyl, dimethylethylpyrimidylphenyl, and dimethylthienylphenyl.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), oxo (=O), alkoxyl, aryloxyl, aralkoxyl, nitro (—NO$_2$), cyano (—CN), amino (—NH$_2$), —N-substituted amino (—NHR"), -N,N-disubstituted amino (—N(R") R"), carboxyl (—COOH), —C(=O)R", —OR", —C(=O) OR", —C(=O)NHSO$_2$R", —NHC(=O)R", aminocarbonyl (—C(=O)NH$_2$), —N-substituted aminocarbonyl (—C(=O)NHR"), -N,N-disubstituted aminocarbonyl (—C(=O) N(R")R"), thiol, thiolato (SR"), sulfonic acid and its esters (SO$_3$R"), phosphonic acid and its mono-esters (P(=O) OR"OH) and di-esters (P(=O)OR"OR"), S(=O)$_2$R", S(=O)$_2$NH$_2$, S(=O)$_2$NHR", S(=O)$_2$NR"R", SO$_2$NHC(=O)R", NHS(=O)$_2$R", NR"S(=O)$_2$R", CF$_3$, CF$_2$CF$_3$, NHC(=O)NHR", NHC(=O)NR"R", NR"C(=O)NHR", NR"C(=O)NR"R", NR"C(=O)R", NR"C(=N—CN) NR"R", and the like. Aryl substituents may also include (CH$_2$)$_p$SO$_2$NR"(CH$_2$)$_q$ and (CH$_2$)$_p$CO$_2$NR"(CH$_2$)$_q$, where p and q are independently integers from 0 to 3, where the methylene units are attached in a 1,2 arrangement yielding substituted aryls of the type:

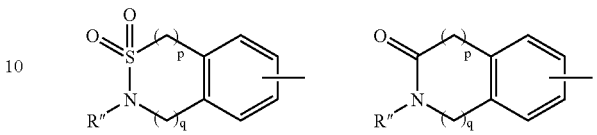

In relation to the aforementioned substituents, each moiety R" can be, independently, any of H, alkyl, cycloalkyl, alkenyl, aryl, aralkyl, heteroaryl, or heterocycloalkyl, or when (R" (R")) is attached to a nitrogen atom, R" and R" can be taken together to form a 4- to 8-membered nitrogen heterocycloalkyl ring, wherein said heterocycloalkyl ring is optionally interrupted by one or more additional —O—, —S—, —SO, —SO$_2$—, —NH—, —N(alkyl)-, or —N(aryl)- groups, for example.

As used herein, an "*" denotes the presence of a non-racemic stereoisomeric center in a molecule, wherein one stereoisomeric form (R or S) predominates, but for which the absolute configuration at this center has not been conclusively established. This is equivalently expressed by saying that the molecule's configuration at the asterisked carbon atom is either greater than 50% R or greater than 50% S. More preferably the compound, or its stereoisomeric center, is "substantially enriched", and even more preferably is substantially enantiomerically pure.

As used herein, the term "substantially enriched", when referring to a stereoisomer or stereoisomeric center, denotes that at least about 60%, preferably about 70% more preferably about 80%, still more preferably about 90% of one stereoisomer or one stereoisomeric center predominating in the mixture, with at least about 95% of one stereoisomer or one stereoisomeric center being even more preferred. In some preferred embodiments, the compound is "substantially enantiomerically pure", that is, at least about 97.5%, more preferably about 99%, even more preferably about 99.5% of one stereoisomeric forms predominates. For example, a compound having one stereoisomeric center may be represented by one of two stereoisomeric forms (R or S), differing only in the spatial arrangement of atoms about a single carbon atom. The "*" denotes non-equal amounts of the two isomers. When a compound has two or more stereoisomeric centers, each center denoted by an asterisk is evaluated individually. A predominance of one stereoisomeric form (R or S) occurring at least one center is considered non-racemic within the definition herein provided. The range of possible non-racemic compounds extends from the point at which a stereoisomeric form predominates at a single chiral center and includes all combinations and subcombinations up to and including the compound wherein all stereoisomeric centers in the compound are each individually R or S.

Use of the "*" can be expressed, for example in a compound's identification number such as 4*, and indicates that the stereochemical configuration of at least one chiral center of the identified compound has not been established. The specific center is identified within a structure by placing the "*" adjacent the chiral center in question, such as, for example, in the structure below.

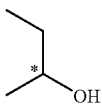

In some compounds, several chiral centers may be present. The presence of two asterisks "*" in a single structure indicates that two racemic pairs may be present, but that each pair is diastereomeric relative to the other pair. As such, the first pair of enantiomers having two chiral centers may have the configurations, for example, (R, R) and (S, S). The second pair then have configurations, for example, (R, S) and (S, R). Alternatively, where only two stereoisomers bearing an enantiomeric relationship to each other are initially provided, such as the (R, R) and (S,S) pair, the asterisks may indicate that the enantiomers have been enriched (partially resolved) or preferably fully resolved, into the individual enantiomers.

"Ligand" or "modulator" refers to a compound that binds to a receptor to form a complex, and includes, agonists, partial agonists, antagonists and inverse agonists.

"Agonist" refers to a compound that may bind to a receptor to form a complex that may elicit a full pharmacological response, which is typically peculiar to the nature of the receptor involved and which may alter the equilibrium between inactive and active receptor.

"Partial agonist" refers to a compound that may bind to a receptor to form a complex that may elicit only a proportion of the full pharmacological response, typically peculiar to the nature of the receptor involved, even if a high proportion of the receptors are occupied by the compound.

"Antagonist" refers to a compound that may bind to a receptor to form a complex that may not elicit any response, typically in the same manner as an unoccupied receptor, and which preferably does not alter the equilibrium between inactive and active receptor.

"Inverse agonist" refers to a compound that may bind to a receptor to form a complex that may preferentially stabilize the inactive conformation of the receptor.

"Prodrug" refers to compounds specifically designed to maximize the amount of active species that reaches the desired site of reaction that are themselves typically inactive or minimally active for the activity desired, but through biotransformation are converted into biologically active metabolites.

"Stereoisomers" refers to compounds that have identical chemical constitution, but differ as regards the arrangement of the atoms or groups in space.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

"Hydrate" refers to a compound as described herein which is associated with water in the molecular form, i.e., in which the H—OH bond is not split, and may be represented, for example, by the formula R.H2O, where R is a compound as described herein. A given compound may form more than one hydrate including, for example, monohydrates (R.H2O), dihydrates (R.2H2O), trihydrates (R.3H2O), and the like.

As used herein, "haloalkoxy" refers to an alkoxy group, wherein one, preferably two or more, hydrogen(s) of the alkyl moiety of said alkoxy are replaced by halo atoms, and alkoxy, alkyl, and halo are each as previously defined.

"Solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n(solvent)) wherein n is an integer>1) including, for example, disolvates (R.2(solvent)), trisolvates (R.3(solvent)), and the like, or hemisolvates, such as, for example, R.n/2(solvent), R.n/3(solvent), R.n/4(solvent) and the like wherein n is an integer. Solvents herein include mixed solvents, for example, methanol/water, and as such, the solvates may incorporate one or more solvents within the solvate.

"Acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds as described herein may exist as zwitterions. All forms of the compounds, including free acid, free base and zwitterions, are contemplated to be within the scope of the present invention. It is well known in the art that compounds containing both basic nitrogen atom and acidic groups often exist in equilibrium with their zwitterionic forms. Thus, any of the compounds described herein throughout that contain, for example, both basic nitrogen and acidic groups, also include reference to their corresponding zwitterions.

"Effective amount" refers to an amount of a compound as described herein that may be therapeutically effective to inhibit, prevent or treat the symptoms of particular disease, disorder, condition, or side effect. Such diseases, disorders, conditions, and side effects include, but are not limited to, those pathological conditions associated with the binding of δ opioid receptor (for example, in connection with the treatment and/or prevention of pain), wherein the treatment or prevention comprises, for example, agonizing the activity thereof by contacting cells, tissues or receptors with compounds as described herein. Thus, for example, the term "effective amount", when used in connection with compounds as described herein, opioids, or opioid replacements, for example, for the treatment of pain, refers to the treatment and/or prevention of the painful condition. The term "effective amount," when used in connection with compounds active against gastrointestinal dysfunction, refers to the treatment and/or prevention of symptoms, diseases, disorders, and conditions typically associated with gastrointestinal dysfunction. The term "effective amount," when used in connection with compounds useful in the treatment and/or prevention of urogenital tract disorders, refers to the treatment and/or prevention of symptoms, diseases, disorders, and conditions typically associated with urogenital tract disorders and other related conditions. The term "effective amount," when used in connection with compounds useful in the treatment and/or prevention of immunomodulatory disorders, refers to the treatment and/or prevention of symptoms, diseases, disorders, and conditions typically associated with immunomodulatory disorders and other related conditions. The term "effective amount," when used in connection with compounds useful in the treatment and/or prevention of inflammatory disorders, refers to the treatment and/or prevention of symptoms, diseases, disorders, and conditions typically associated with inflammatory disorders and other related conditions. The term "effective amount," when used in connection with compounds useful in the treatment and/or prevention of respiratory function disorders, refers to the treatment and/or prevention of symptoms, diseases, disorders, and conditions typically associated with respiratory function disorders and other related conditions. The term "effective amount," when used in connection with compounds useful in the treatment and/or prevention of anxiety, mood disorders, stress-related disorders, and attention deficit hyperactivity disorder, refers to the treatment and/or prevention of symptoms, diseases, disorders, and conditions typically associated with anxiety, mood disorders, stress-related disorders, attention deficit hyperactivity disorder and other related conditions. The term "effective amount," when used in connection with compounds useful in the treatment and/or prevention of sympathetic nervous system disorders, refers to the treatment and/or prevention of symptoms, diseases, disorders, and conditions typically associated with sympathetic nervous system disorders and other related conditions. The term "effective amount," when used in connection with compounds useful in the treatment and/or prevention of tussis, refers to the treatment and/or prevention of symptoms, diseases, disorders, and conditions typically associated with tussis and other related conditions. The term "effective amount," when used in connection with compounds useful in the treatment and/or prevention of motor disorders, refers to the treatment and/or prevention of symptoms, diseases, disorders, and conditions typically associated with motor disorders and other related conditions. The term "effective amount," when used in connection with compounds useful in the treatment of traumatic injuries of the central nervous system, refers to the treatment and/or prevention of symptoms, diseases, disorders, and conditions typically associated with the central nervous system and other related conditions. The term "effective amount," when used in connection with compounds useful in the treatment and/or prevention of stroke, cardiac arrhythmia or glaucoma, refers to the treatment and/or prevention of symptoms, diseases, disorders, and conditions typically associated with stroke, cardiac arrhythmia, glaucoma and other related conditions. The term "effective amount," when used in connection with compounds useful in the treatment and/or prevention of sexual dysfunction, refers to the treatment and/or prevention of symptoms, diseases, disorders, and conditions typically associated with sexual dysfunction and other related conditions. The term "effective amount," when used in connection with compounds useful in improving organ and cell survival, refers to refers to the maintenance and/or improvement of a minimally-acceptable level of organ or cell survival, including organ preservation. The term "effective amount," when used in connection with compounds useful in the treatment and/or prevention of myocardial infarction, refers to the minimum level of compound necessary to provide cardioprotection after myocardial infarction. The term "effective amount," when used in connection with compounds useful in the treatment and/or prevention of shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts, refers to the treatment and/or prevention of symptoms, diseases, disorders, and conditions typically associated with shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts and other related conditions. The term "effective amount," when used in connection with compounds useful in the treatment of substance addiction, refers to the treatment of symptoms, diseases, disorders, and conditions typically associated with substance addiction and other related conditions. The term "effective amount," when used in connection with compounds useful in reducing the need for anesthesia or producing and/or maintaining an anesthetic state, refers to the production and/or maintenance of a minimally-acceptable anesthetic state.

"Pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. The term specifically encompasses veterinary uses.

"In combination with," "combination therapy," and "combination products" refer, in certain embodiments, to the concurrent administration to a patient of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII, and/or XXXIV, and one or more additional agents including, for example, an opioid, an anaesthetic agent (such as for example, an inhaled anesthetic, hypnotic, anxiolytic, neuromuscular blocker and opioid), an anti-Parkinson's agent (for example, in the case of treating or preventing a motor disorder, particularly Parkinson's disease), an antidepressant (for example, in the case of treating or preventing a mood disorder, particularly depression), an agent for the treatment of incontinence (for example, in the case of treating or preventing a urogenital tract disorder), an agent for the treatment of pain, including neuralgias or neuropathic pain, and/or other optional ingredients (including, for example, antibiotics, antivirals, antifungals, anti-inflammatories, anesthetics and mixtures thereof). When administered in combination, each component may be administered at the same time or sequentially in any order at different points in time. Thus, each component may be administered separately but sufficiently closely in time so as to provide the desired therapeutic effect.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

"Pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds.; *Analgesics*, Wiley-VCH, Verlag GMbH & Co. KgaA, Weinheim; 2002; Jain, K. K. "A Guide to Drug Evaluation for Chronic Pain"; *Emerging Drugs*, 5(2), 241-257(2000)). Non-limiting examples of pain include, for example, nociceptive pain, inflammatory pain, visceral pain, somatic pain, neuralgias, neuropathic pain, AIDS pain, cancer pain, phantom pain, and psychogenic pain, and pain resulting from hyperalgesia, pain caused by rheumatoid arthritis, migraine, allodynia and the like.

"Gastrointestinal dysfunction" refers collectively to maladies of the stomach, small and large intestine. Non-limiting examples of gastrointestinal dysfunction include, for example, diarrhea, nausea, emesis, post-operative emesis, opioid-induced emesis, irritable bowel syndrome, opioid-bowel dysfunction, inflammatory bowel disease, colitis, increased gastric motility, increased gastric emptying, stimulation of small intestinal propulsion, stimulation of large intestinal propulsion, decreased amplitude of non-propulsive segmental contractions, disorders associated with sphincter of Oddi, disorders associated with anal sphincter tone, impaired reflex relaxation with rectal distention, disorders associated with gastric, biliary, pancreatic or intestinal secretions, changes to the absorption of water from bowel contents, gastro-esophageal reflux, gastroparesis, cramping, bloating, distension, abdominal or epigastric pain and discomfort, non-ulcerogenic dyspepsia, gastritis, or changes to the absorption of orally administered medications or nutritive substances.

"Urogenital tract disorders" refers collectively to maladies of the urinary and genital apparati. Non-limiting examples of urogenital tract disorders include incontinence (i.e., involuntary loss of urine) such as stress urinary incontinence, urge urinary incontinence and benign prostatic hyperplasia, overactive bladder disorder, urinary retention, renal colic, glomerulonephritis, and interstitial cystitis.

"Overactive bladder disorder" refers to a condition with symptoms of urgency with or without incontinence, and is typically associated with increased urinary frequency and nocturia. Overactive bladder disorders are typically associated with urodynamic finding of involuntary bladder contractions, generally referred to as bladder instability.

"Immunomodulatory disorders" refers collectively to maladies characterized by a compromised or over-stimulated immune system. Non-limiting examples of immunomodulatory disorders include autoimmune diseases (such as arthritis, autoimmune disorders associated with skin grafts, autoimmune disorders associated with organ transplants, and autoimmune disorders associated with surgery), collagen diseases, allergies, side effects associated with the administration of an anti-tumor agent, side effects associated with the administration of an antiviral agent, multiple sclerosis and Guillain-Barre syndrome.

"Inflammatory disorders" refers collectively to maladies characterized by cellular events in injured tissues. Non-limiting examples of inflammatory diseases include arthritis, psoriasis, asthma, and inflammatory bowel disease.

"Respiratory function disorders" refers to conditions in which breathing and/or airflow into the lung is compromised. Non-limiting examples of respiratory function disorders include asthma, apnea, tussis, chronic obstruction pulmonary disease, and lung edema.

"Lung edema" refers to the presence of abnormally large amounts of fluid in the intercellular tissue spaces of the lungs.

"Anxiety" refers to the unpleasant emotional state consisting of psychophysiological responses to anticipation of real, unreal or imagined danger, ostensibly resulting from unrecognized intrapsychic conflict.

"Mood disorders" refers to disorders that have a disturbance in mood as their predominant feature, including depression, bipolar manic-depression, borderline personality disorder, and seasonal affective disorder.

"Depression" refers to a mental state of depressed mood characterized by feelings of sadness, despair and discouragement, including the blues, dysthymia, and major depression.

"Stress-related disorders" refer collectively to maladies characterized by a state of hyper- or hypo-arousal with hyper- and hypo-vigilance. Non-limiting examples of stress-related disorders include post-traumatic stress disorder, panic disorder, generalized anxiety disorder, social phobia, and obsessive-compulsive disorder.

"Attention deficit hyperactivity disorder" refers to a condition characterized by an inability to control behavior due to difficulty in processing neural stimuli.

"Sympathetic nervous system disorders" refer collectively to maladies characterized by disturbances of the autonomic nervous system. Non-limiting examples of sympathetic nervous system disorders include hypertension, and the like.

"Tussis" refers to a coughing condition, and "antitussive" agents refer to those materials that modulate the coughing response.

"Motor disorders" refers to involuntary manifestations of hyper or hypo muscle activity and coordination Non-limiting examples of motor disorders include tremors, Parkinson's disease, tourette syndrome, parasomnias (sleep disorders) including restless leg syndrome, postoperative shivering and dyskinesia.

"Traumatic injury of the central nervous system" refers to a physical wound or injury to the spinal cord or brain.

"Stroke" refers to a condition due to the lack of oxygen to the brain.

"Cardiac arrhythmia" refers to a condition characterized by a disturbance in the electrical activity of the heart that manifests as an abnormality in heart rate or heart rhythm. Patients with a cardiac arrhythmia may experience a wide variety of symptoms ranging from palpitations to fainting.

"Glaucoma" refers collectively to eye diseases characterized by an increase in intraocular pressure that causes pathological changes in the optic disk and typical defects in the field of vision.

"Sexual dysfunction" refers collectively to disturbances, impairments or abnormalities of the functioning of the male or female sexual organs, including, but not limited to premature ejaculation and erectile dysfunction.

"Cardioprotection" refers to conditions or agents that protect or restore the heart from dysfunction, heart failure and reperfusion injury.

"Myocardial infarction" refers to irreversible injury to heart muscle caused by a local lack of oxygen.

"Addiction" refers to a pattern of compulsive substance abuse (alcohol, nicotine, or drug) characterized by a continued craving for the substance and, in some cases, the need to use the substance for effects other than its prescribed or legal use.

"Anaesthetic state" refers to the state of the loss of feeling or sensation, including not only the loss of tactile sensibility or of any of the other senses, but also to the loss of sensation of pain, as it is induced to permit performance of surgery or other painful procedures, and specifically including amnesia, analgesia, muscle relaxation and sedation.

"Improving organ and cell survival" refers to the maintenance and/or improvement of a minimally-acceptable level of organ or cell survival.

"Patient" refers to animals, including mammals, preferably humans.

"Side effect" refers to a consequence other than the one(s) for which an agent or measure is used, as the adverse effects produced by a drug, especially on a tissue or organ system other then the one sought to be benefited by its administration. In the case, for example, of opioids, the term "side effect" may refer to such conditions as, for example, constipation, nausea, vomiting, dyspnea and pruritus.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

In certain preferred embodiments, the compounds, pharmaceutical compositions and methods of the present invention may involve a peripheral δ opioid modulator compound. The term "peripheral" designates that the compound acts primarily on physiological systems and components external to the central nervous system. In preferred form, the peripheral δ opioid modulator compounds employed in the methods of the present invention exhibit high levels of activity with respect to peripheral tissue, such as, gastrointestinal tissue, while exhibiting reduced, and preferably substantially no, CNS activity. The phrase "substantially no CNS activity," as used herein, means that less than about 50% of the pharmacological activity of the compounds employed in the present methods is exhibited in the CNS, preferably less than about 25%, more preferably less than about 10%, even more preferably less than about 5% and most preferably 0% of the pharmacological activity of the compounds employed in the present methods is exhibited in the CNS.

Furthermore, it is preferred in certain embodiments of the invention that the δ opioid modulator compound does not substantially cross the blood-brain barrier. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration, for example, by determining plasma and brain levels following i.v. administration.

Accordingly, in one embodiment, the invention is directed to compounds of formula XIV:

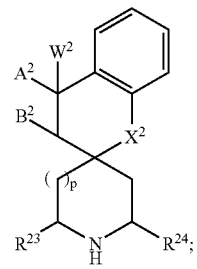

XIV wherein:
$W^2$ is aryl or heteroaryl, wherein the aryl or heteroaryl is substituted with 0-3 groups selected independently from hydroxy, aminocarbonyl (—C(=O)—NH$_2$), N-alkylaminocarbonyl (—C(=O)—NH(alkyl)), and N,N-dialkylaminocarbonyl (—C(=O)—N(alkyl)(alkyl));

$R^{23}$ and $R^{24}$ are each independently H or alkyl, provided that at least one of $R^{23}$ and $R^{24}$ is alkyl;

p is 1 or 2;

$A^2$ and $B^2$ are each H, or together form a double bond; and $X^2$ is —CH$_2$— or —O—;

or a stereoisomer, prodrug, pharmaceutically acceptable salt, hydrate, solvate, acid salt hydrate, or N-oxide thereof.

In preferred embodiments of formula XIV compounds, $W^2$ is aryl or heteroaryl. When $W^2$ is aryl, the aryl ring is preferably phenyl. When $W^2$ is heteroaryl, the heteroaryl ring is preferably pyridyl.

As set forth above, $W^2$ is substituted with 0-3 groups selected independently from hydroxy, aminocarbonyl (—C(=O)—NH$_2$), N-alkylaminocarbonyl (—C(=O)—NH(alkyl)), and N,N-dialkylaminocarbonyl (—C(=O)—N(alkyl)(alkyl)). In preferred embodiments, $W^2$ is substituted with 1-2 groups, selected independently from hydroxy, aminocarbonyl (—C(=O)—NH$_2$), N-alkylaminocarbonyl (—C(=O)—NH(alkyl)), and N,N-dialkylaminocarbonyl (—C(=O)—N(alkyl)(alkyl)). More preferably, $W^2$ is substituted with N,N-dialkylaminocarbonyl and/or hydroxyl.

In preferred embodiments of formula XIV compounds, $W^2$ is:

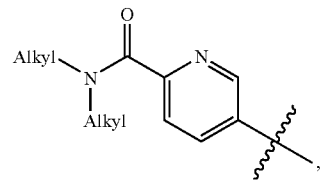

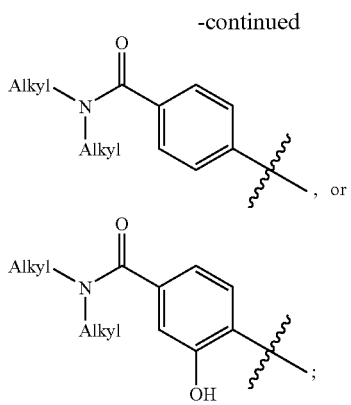

, or

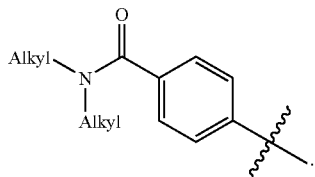

;

more preferably:

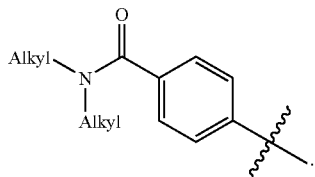

.

In embodiments in which $W^2$ is substituted with N-alkylaminocarbonyl (—C(=O)—NH(alkyl)) or N,N-dialkylaminocarbonyl (—C(=O)—N(alkyl)(alkyl)), the alkyl group is preferably lower alkyl, with alkyl groups of 1 to 3 carbons being more preferred, and with alkyl groups of 2 carbons being still more preferred. In particularly preferred embodiments, the alkyl group is ethyl.

In preferred embodiments of formula XIV compounds, p is 1.

In preferred embodiments of formula XIV compounds, $A^2$ and $B^2$ together form a double bond.

In preferred embodiments of formula XIV compounds, $X^2$ is —O—.

In preferred embodiments of formula XIV compounds, $R^{23}$ and $R^{24}$ are each independently H or alkyl, preferably H or $C_1$-$C_3$ alkyl, more preferably H or methyl. In certain preferred embodiments, one of $R^{23}$ and $R^{24}$ is H and the other is alkyl.

In preferred embodiments, the compounds of formula XIV have the following formula XV:

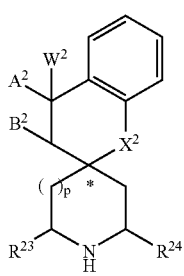

with compounds of formula XVI being even more preferred:

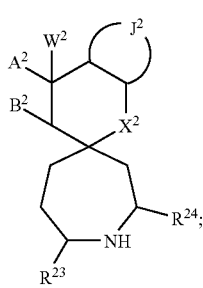

In preferred embodiments, the compound of formula XIV is:

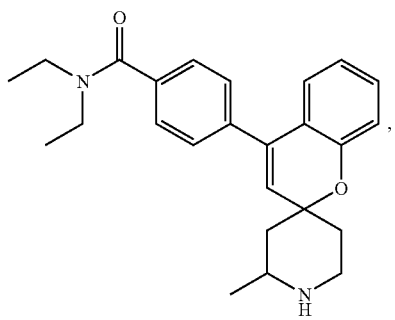

, more preferably:

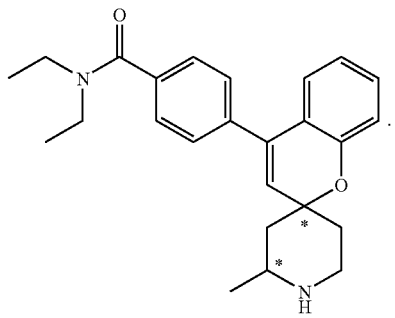

.

In an alternative embodiment, the invention is directed to compounds of formula XVII:

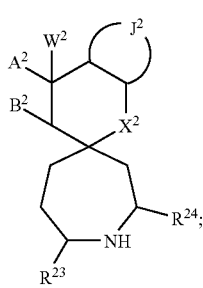

;

wherein:
- $W^2$ is aryl or heteroaryl, wherein the aryl or heteroaryl is substituted with 0-3 groups selected independently from hydroxy, aminocarbonyl (—C(=O)—NH$_2$), N-alkylaminocarbonyl (—C(=O)—NH(alkyl)), and N,N-dialkylaminocarbonyl (—C(=O)—N(alkyl)(alkyl));
- $R^{23}$ and $R^{24}$ are each independently H or alkyl;
- $A^2$ and $B^2$ are each H, or together form a double bond;
- $X^2$ is —CH$_2$— or —O—; and
- $J^2$ when taken together with the carbon atoms to which it is attached forms a 6-membered aryl ring substituted with 0-3 groups selected independently from halo, hydroxy, and —S(=O)$_2$-alkyl;
- or a stereoisomer, prodrug, pharmaceutically acceptable salt, hydrate, solvate, acid salt hydrate, or N-oxide thereof;

provided that:
- when $W^2$ is para-diethylaminocarbonylphenyl, $X^2$ is O, and $A^2$ and $B^2$ together form a double bond, then the aryl ring of $J^2$ is substituted with at least one group selected independently from halo, and —S(=O)$_2$-alkyl in which the alkyl group is $C_2$-$C_6$ alkyl;
- when $W^2$ is para-diethylaminocarbonylphenyl, $X^2$ is O, and $A^2$ and $B^2$ are each H, then the aryl ring of $J^2$ is substituted with 1-3 groups selected independently from halo, hydroxy, and —S(=O)$_2$-alkyl; and
- the compound of formula XVII is other than:

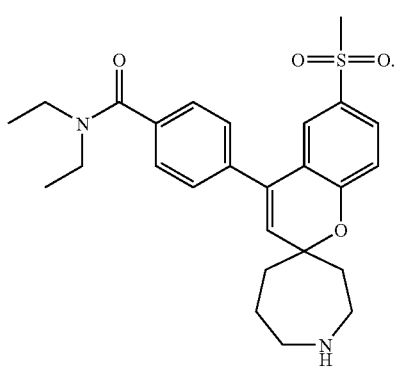

In preferred embodiments of formula XVII compounds, $W^2$ is aryl or heteroaryl. When $W^2$ is aryl, the aryl ring is preferably phenyl. When $W^2$ is heteroaryl, the heteroaryl ring is preferably pyridyl.

As set forth above, $W^2$ is substituted with 0-3 groups selected independently from hydroxy, aminocarbonyl (—C(=O)—NH$_2$), N-alkylaminocarbonyl (—C(=O)—NH(alkyl)), and N,N-dialkylaminocarbonyl (—C(=O)—N(alkyl)(alkyl)). In preferred embodiments, $W^2$ is substituted with 1-2 groups, selected independently from hydroxy, aminocarbonyl (—C(=O)—NH$_2$), N-alkylaminocarbonyl (—C(=O)—NH(alkyl)), and N,N-dialkylaminocarbonyl (—C(=O)—N(alkyl)(alkyl)). More preferably, $W^2$ is substituted with N,N-dialkylaminocarbonyl and/or hydroxyl.

In preferred embodiments of formula XVII compounds, $W^2$ is:

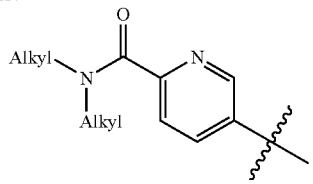

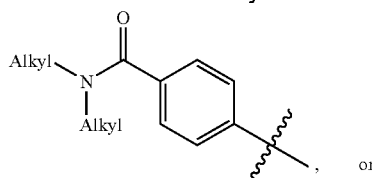

, or

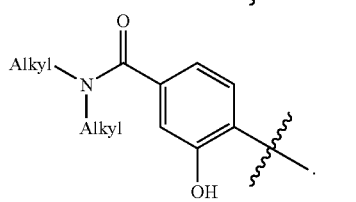

.

In embodiments in which $W^2$ is substituted with N-alkylaminocarbonyl (—C(=O)—NH(alkyl)) or N,N-dialkylaminocarbonyl (—C(=O)—N(alkyl)(alkyl)), the alkyl group is preferably lower alkyl, with alkyl groups of 1 to 3 carbons being more preferred, and with alkyl groups of 2 carbons being still more preferred. In particularly preferred embodiments, the alkyl group is ethyl.

In preferred embodiments of formula XVII compounds, $X^2$ is —O—.

In preferred embodiments of formula XVII compounds, $A^2$ and $B^2$ together form a double bond.

In preferred embodiments of formula XVII compounds, $R^{23}$ and $R^{24}$ are each independently H or alkyl, preferably H or $C_1$-$C_3$ alkyl, more preferably H or methyl, yet more preferably H.

In preferred embodiments of formula XVII compounds, $J^2$ when taken together with the carbon atoms to which it is attached forms a 6-membered aryl ring, preferably phenyl.

As set forth above, $J^2$ is substituted with 0-3 groups, preferably 0-2, more preferably 0-1 groups, selected independently from halo, hydroxy, and —S(=O)$_2$-alkyl. In embodiments wherein $J^2$ is substituted with halo, the halo group is preferably fluoro. In embodiments wherein $J^2$ is substituted with —S(=O)$_2$-alkyl, the alkyl group is preferably lower alkyl, with alkyl groups of 1 to 3 carbons being more preferred, still more preferably alkyl groups of 1 to 2 carbons, yet more preferably methyl or ethyl.

In preferred embodiments, the compounds of formula XVII have the following formula XVIII:

XVIII

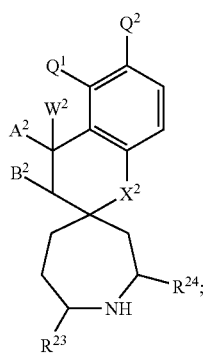

wherein:

Q¹ and Q² are each independently H, halo, hydroxy, or —S(=O)₂-alkyl. In embodiments wherein Q¹ or Q² is halo, the halo group is preferably fluoro. In embodiments wherein Q¹ or Q² is —S(=O)₂-alkyl, the alkyl group is preferably lower alkyl, with alkyl groups of 1 to 3 carbons being more preferred, still more preferably alkyl groups of 1 to 2 carbons, yet more preferably methyl or ethyl. Still more preferably, the compounds of formula XVIII have the following formula XIX:

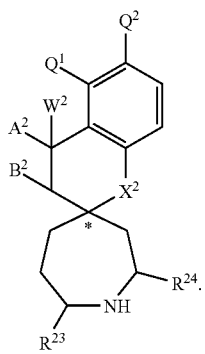

XIX

In preferred embodiments, the compounds of formula XVII have the following structures:

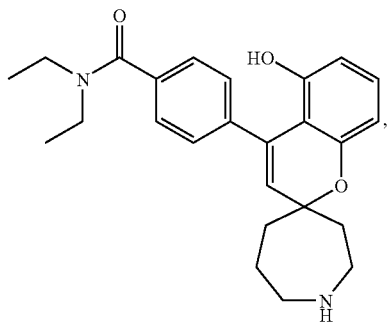

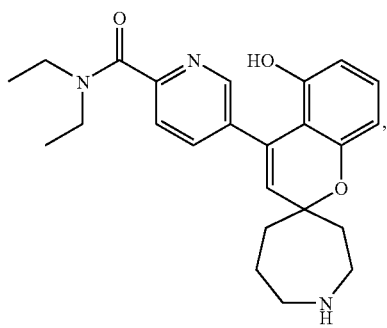

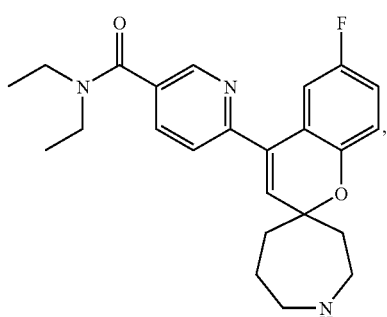

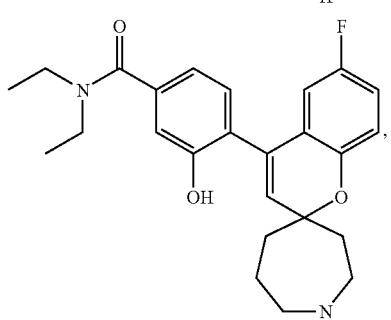

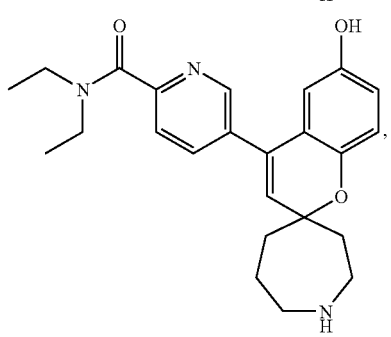

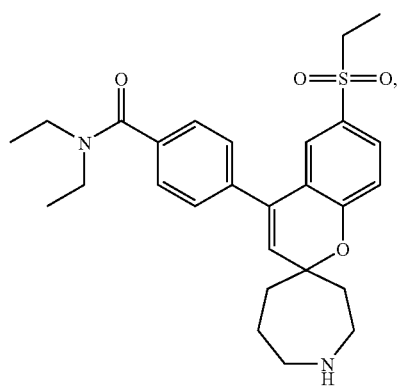
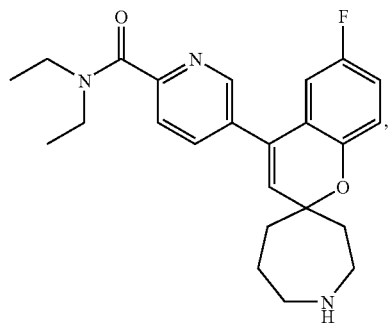
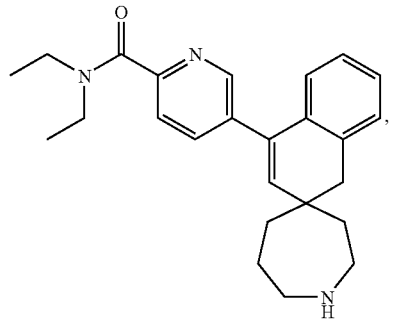
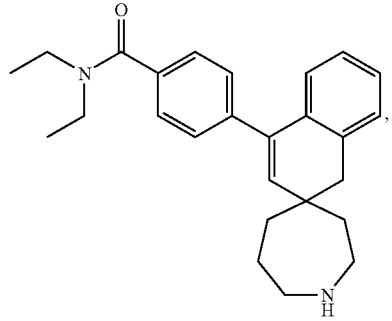
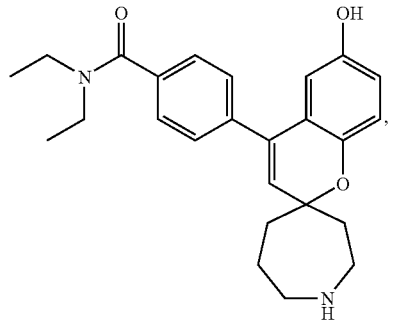
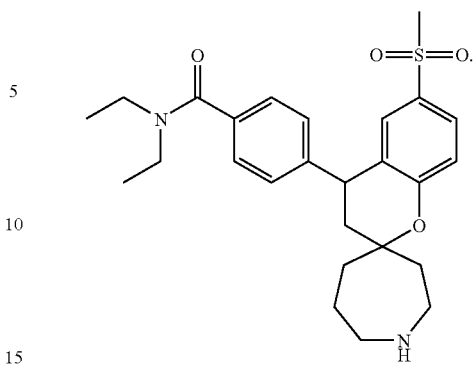
In certain embodiments, the above compounds may be resolved into any of their R and S, or (R,R), (S,S), (R,S), and (S,R) enantiomers, or partially resolved into any of their non-racemic mixtures.
More preferably, the compounds of formula XVII have the following structures:
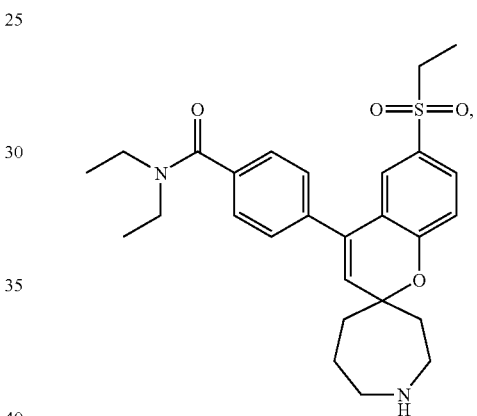
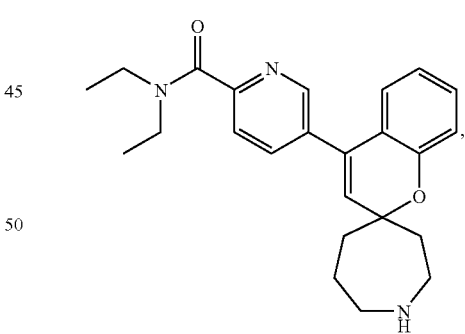
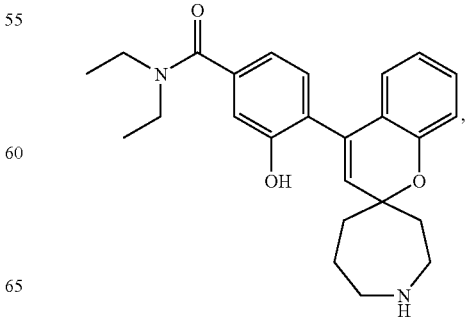

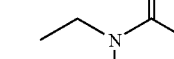

-continued
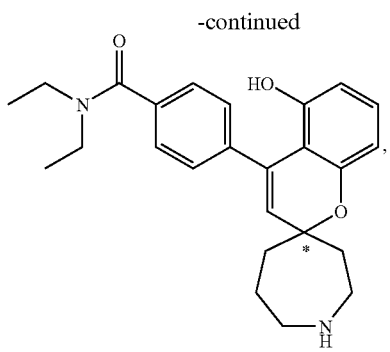
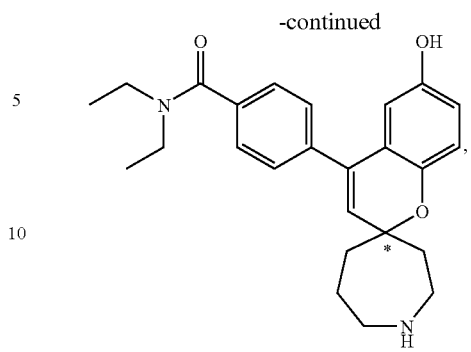
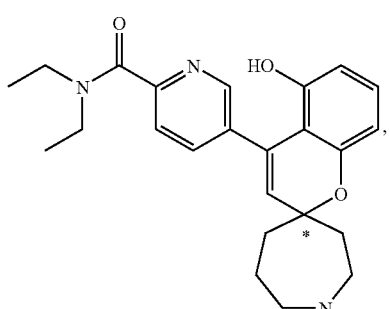
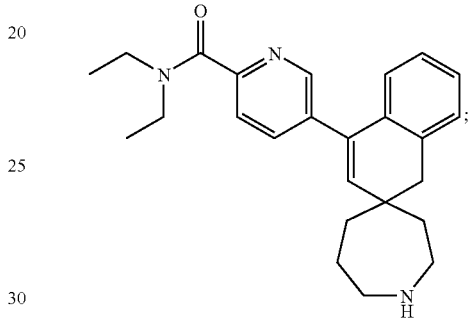
still more preferably:
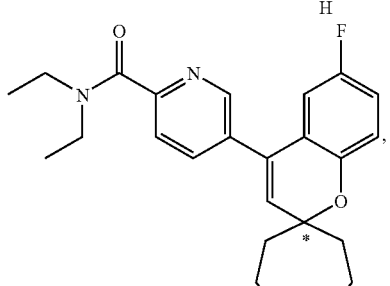
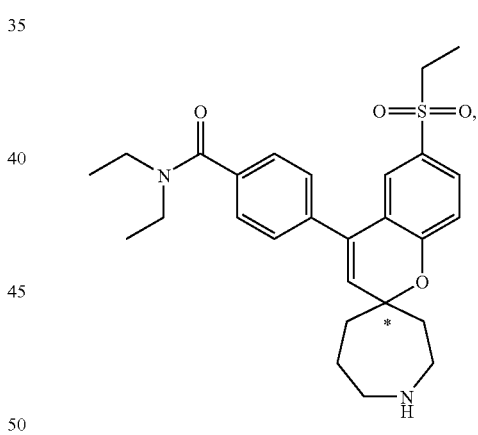
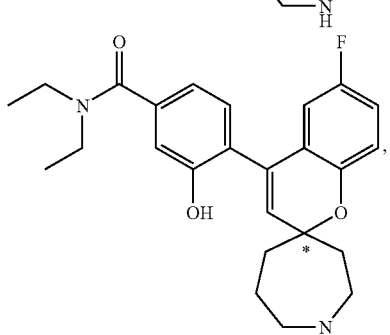
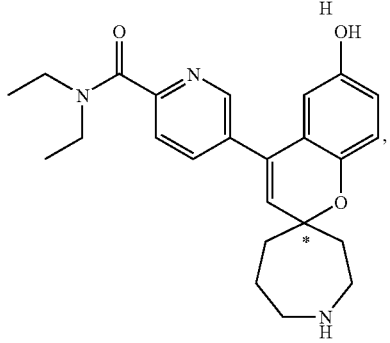
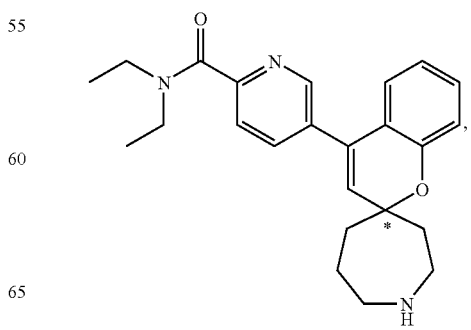

-continued

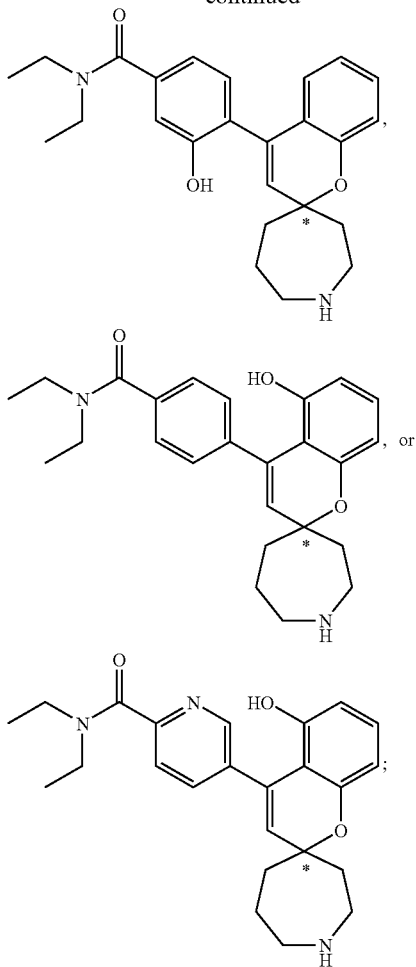

even more preferably:

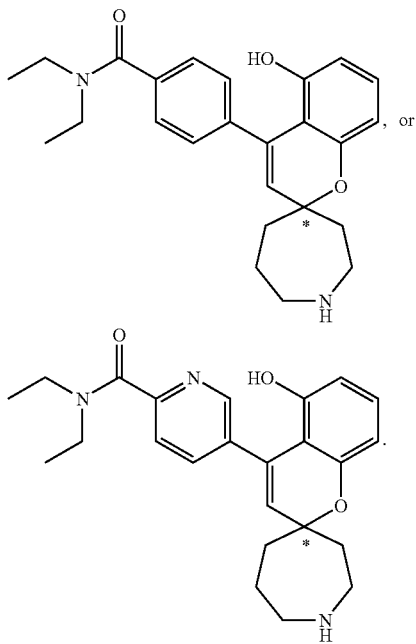

In certain embodiments, the invention is directed to compounds of formula XX:

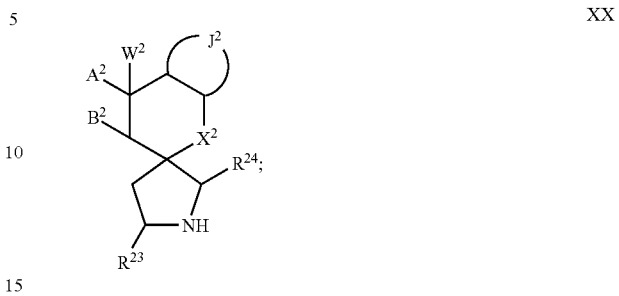

XX wherein:
W² is aryl or heteroaryl, wherein the aryl or heteroaryl is substituted with 0-3 groups selected independently from hydroxy, aminocarbonyl (—C(=O)—NH₂), N-alkylaminocarbonyl (—C(=O)—NH(alkyl)), and N,N-dialkylaminocarbonyl (—C(=O)—N(alkyl)(alkyl));
R²³ and R²⁴ are each independently H or alkyl;
A² and B² are each H, or together form a double bond;
X² is —CH₂— or —O—; and
J² when taken together with the carbon atoms to which it is attached forms a 6-membered aryl ring substituted independently with 0-3 hydroxy or halo groups;
or a stereoisomer, prodrug, pharmaceutically acceptable salt, hydrate, solvate, acid salt hydrate, or N-oxide thereof;
provided that the compound of formula XX is other than 4-[(4-N,N-diethylaminocarbonyl)phenyl]-spiro[2H,1-benzopyran-2,3'-pyrrolidine].

In preferred embodiments of formula XX compounds, W² is aryl or heteroaryl. When W² is aryl, the aryl ring is preferably phenyl. When W² is heteroaryl, the heteroaryl ring is preferably pyridyl.

As set forth above, W² is substituted with 0-3 groups selected independently from hydroxy, aminocarbonyl (—C(=O)—NH₂), N-alkylaminocarbonyl (—C(=O)—NH(alkyl)), and N,N-dialkylaminocarbonyl (—C(=O)—N(alkyl)(alkyl)). In preferred embodiments, W² is substituted with 1-2 groups, selected independently from hydroxy, aminocarbonyl (—C(=O)—NH₂), N-alkylaminocarbonyl (—C(=O)—NH(alkyl)), and N,N-dialkylaminocarbonyl (—C(=O)—N(alkyl)(alkyl)). More preferably, W² is substituted with N,N-dialkylaminocarbonyl and/or hydroxyl.

In preferred embodiments of formula XX compounds, W² is:

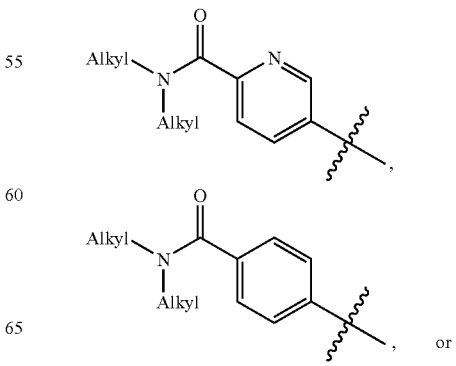

-continued

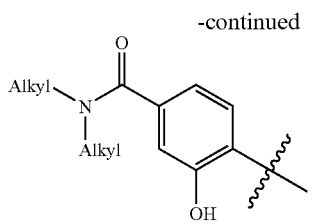

In embodiments in which $W^2$ is substituted with N-alkylaminocarbonyl (—C(=O)—NH(alkyl)) or N,N-dialkylaminocarbonyl (—C(=O)—N(alkyl)(alkyl)), the alkyl group is preferably lower alkyl, with alkyl groups of 1 to 3 carbons being more preferred, and with alkyl groups of 2 carbons being still more preferred. In particularly preferred embodiments, the alkyl group is ethyl.

In preferred embodiments of formula XX compounds, $A^2$ and $B^2$ together form a double bond.

In preferred embodiments of formula XX compounds, $X^2$ is —O—.

In preferred embodiments of formula XX compounds, $R^{23}$ and $R^{24}$ are each independently H or alkyl, preferably H or $C_1$-$C_3$ alkyl, more preferably H or methyl, yet more preferably H.

In preferred embodiments of formula XX compounds, $J^2$ when taken together with the carbon atoms to which it is attached forms a 6-membered aryl ring, preferably phenyl.

As set forth above, $J^2$ is substituted independently with 0-3, preferably 0-2, more preferably 0-1, hydroxy or halo groups, more preferably still, 0-1 hydroxy groups.

In preferred embodiments, the compounds of formula XX have the following formula XXI:

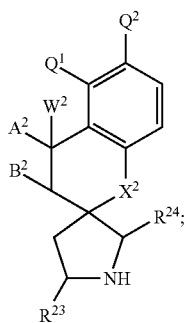

XXI wherein:
$Q^1$ and $Q^2$ are each independently H, hydroxy, or halo. In embodiments wherein at least one of $Q^1$ and $Q^2$ is halo, the halo is preferably fluoro.

In preferred embodiments, the compounds of formula XX have the following structures:

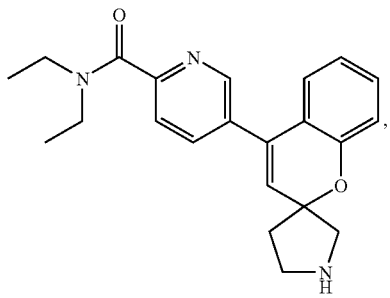

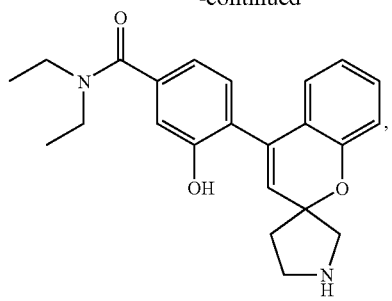

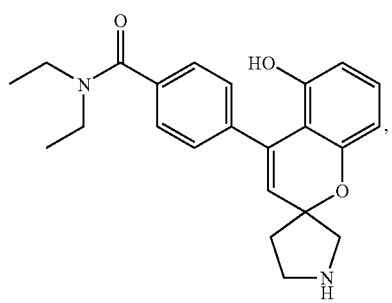

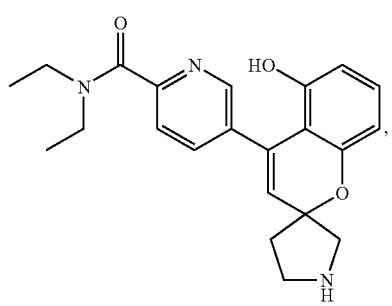

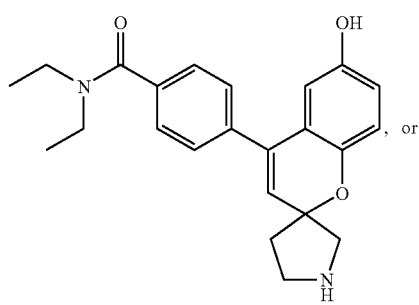

, or

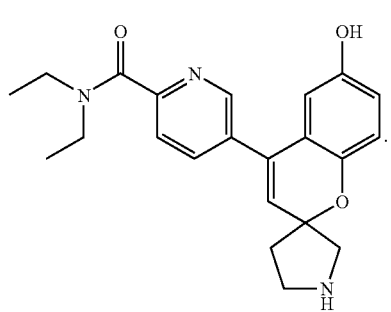

.

In an alternative embodiment, the invention is directed to compounds of formula XXII:

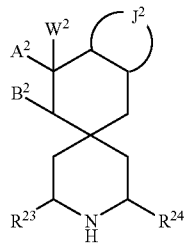

XXII wherein:
W² is aryl or heteroaryl, wherein the aryl or heteroaryl is substituted with 0-3 groups selected independently from heteroaryl, hydroxy, carboxy (—COOH), —C(=O)-alkyl, —C(=O)-aryl, —C(=O)—O-alkyl, —S(=O)₂—N(alkyl)(alkyl); aminocarbonyl (—C(=O)—NH₂), N-alkylaminocarbonyl (—C(=O)—NH(alkyl)), and N,N-dialkylaminocarbonyl (—C(=O)—N(alkyl)(alkyl));
R²³ and R²⁴ are each independently H or alkyl;
A² and B² are each H, or together form a double bond; and
J² when taken together with the carbon atoms to which it is attached forms a 6-membered aryl ring substituted with 0-3 groups selected independently from halo, heterocycloalkyl, hydroxy, alkoxy, —S(=O)₂-alkyl, —S(=O)₂—NH₂, —S(=O)₂—NH(alkyl), —S(=O)₂—N(alkyl)(alkyl), carboxy (—COOH), —C(=O)—O-alkyl, and N,N-dialkylaminocarbonyl (—C(=O)—N(alkyl)(alkyl));
or a stereoisomer, prodrug, pharmaceutically acceptable salt, hydrate, solvate, acid salt hydrate, or N-oxide thereof;
provided that:
when W² is para-diethylaminocarbonylphenyl, para-prop-2-ylaminocarbonylphenyl, or para-pent-3-ylaminocarbonylphenyl, R²³ and R²⁴ are each H, and A and B are each H or together form a double bond, then J² is other than unsubstituted phenyl or anisyl; and
when W² is:

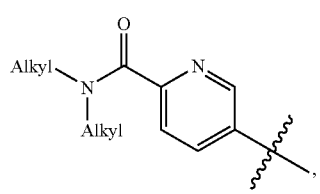

R²³ and R²⁴ are each H, and A and B together form a double bond; then J² is other than unsubstituted phenyl.

In preferred embodiments of formula XXII compounds, W² is aryl or heteroaryl. When W² is aryl, the aryl ring is preferably phenyl. When W² is heteroaryl, the heteroaryl ring is preferably pyridyl.

As set forth above, W² is substituted with 0-3 groups selected independently from hydroxy, aminocarbonyl (—C(=O)—NH₂), N-alkylaminocarbonyl (—C(=O)—NH(alkyl)), and N,N-dialkylaminocarbonyl (—C(=O)—N(alkyl)(alkyl)). In preferred embodiments, W² is substituted with 1-2 groups, selected independently from hydroxy, aminocarbonyl (—C(=O)—NH₂), N-alkylaminocarbonyl (—C(=O)—NH(alkyl)), and N,N-dialkylaminocarbonyl (—C(=O)—N(alkyl)(alkyl)). More preferably, W² is substituted with N,N-dialkylaminocarbonyl and/or hydroxyl.

In preferred embodiments of formula XXII compounds, W² is:

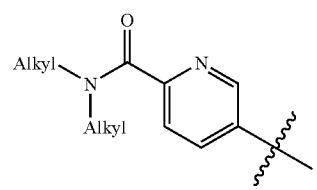

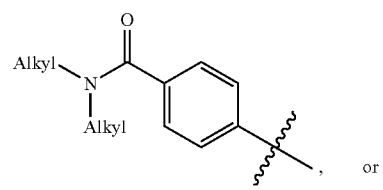

, or

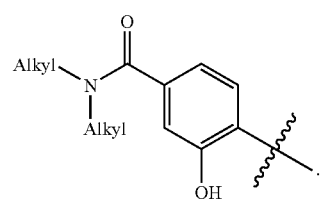

.

In embodiments in which W² is substituted with N-alkylaminocarbonyl (—C(=O)—NH(alkyl)) or N,N-dialkylaminocarbonyl (—C(=O)—N(alkyl)(alkyl)), the alkyl group is preferably lower alkyl, with alkyl groups of 1 to 3 carbons being more preferred, and with alkyl groups of 2 carbons being still more preferred. In particularly preferred embodiments, the alkyl group is ethyl.

In preferred embodiments of formula XXII compounds, R²³ and R²⁴ are each independently H or alkyl, preferably H or C₁-C₃ alkyl, more preferably H or methyl, yet more preferably H.

In preferred embodiments of formula XXII compounds, J² when taken together with the carbon atoms to which it is attached forms a 6-membered aryl ring, preferably phenyl.

As set forth above, J² is substituted with 0-3 groups, preferably 0-2 groups, selected independently from halo, heterocycloalkyl, hydroxy, alkoxy, —S(=O)₂-alkyl, —S(=O)₂—NH₂, —S(=O)₂—NH(alkyl), —S(=O)₂—N(alkyl)(alkyl), carboxy (—COOH), —C(=O)—O-alkyl, and N,N-dialkylaminocarbonyl (—C(=O)—N(alkyl)(alkyl)). In embodiments wherein J² is substituted with alkoxy, —S(=O)₂-alkyl, —S(=O)₂—NH(alkyl), —S(=O)₂—N(alkyl)(alkyl), —C(=O)—O-alkyl, or N,N-dialkylaminocarbonyl (—C(=O)—N(alkyl)(alkyl)), the alkyl group is preferably lower alkyl, with alkyl groups of 1 to 3 carbons being more preferred, and with alkyl groups of 1 to 2 carbons being still more preferred. In particularly preferred embodiments, the alkyl group is methyl or ethyl. In embodiments wherein J² is substituted with halo, the halo group is preferably fluoro.

In preferred embodiments of formula XXII compounds, the compounds have the following formula XXIII:

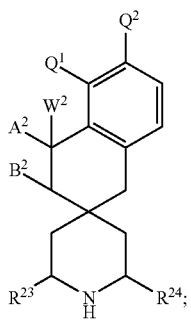

XXIII wherein:
$Q^1$ and $Q^2$ are each independently H, halo, heterocycloalkyl, hydroxy, alkoxy, —S(=O)$_2$-alkyl, —S(=O)$_2$—NH$_2$, —S(=O)$_2$—NH(alkyl), —S(=O)$_2$—N(alkyl)(alkyl), carboxy (—COOH), —C(=O)—O-alkyl, or N,N-dialkylaminocarbonyl (—C(=O)—N(alkyl)(alkyl)). In certain preferred embodiments, at least one of $Q^1$ or $Q^2$ is H, more preferably, one of $Q^1$ or $Q^2$ is H. In embodiments wherein $Q^1$ or $Q^2$ is alkoxy, —S(=O)$_2$-alkyl, —S(=O)$_2$—NH(alkyl), —S(=O)$_2$—N(alkyl)(alkyl), —C(=O)—O-alkyl, or N,N-dialkylaminocarbonyl (—C(=O)—N(alkyl)(alkyl)), the alkyl group is preferably lower alkyl, with alkyl groups of 1 to 3 carbons being more preferred, and with alkyl groups of 1 to 2 carbons being still more preferred. In particularly preferred embodiments, the alkyl group is methyl or ethyl. In embodiments wherein $Q^1$ or $Q^2$ is halo, the halo group is preferably fluoro. In certain preferred embodiments, one of $Q^1$ or $Q^2$ is H.

In preferred embodiments, the compounds of formula XXII have the following formula XXIV:

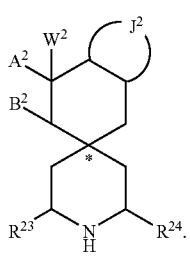

XXIV

In preferred embodiments, the compounds of formula XXII have the following structure:

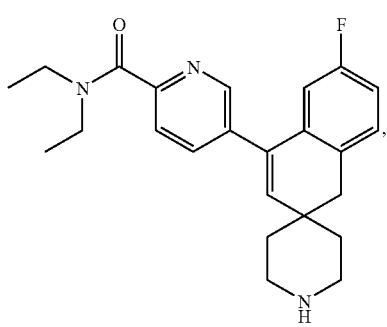

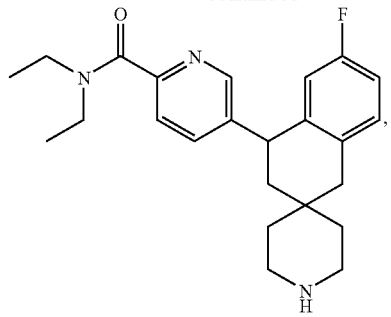

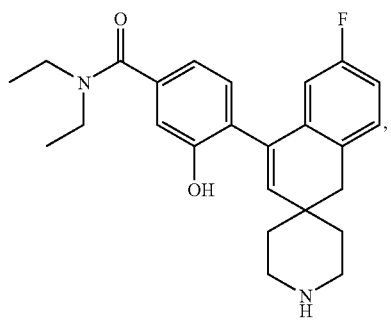

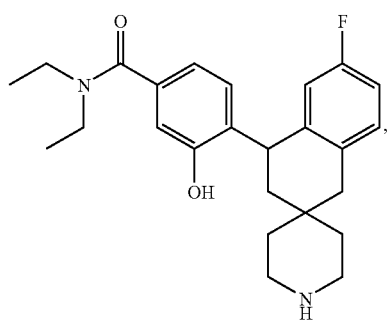

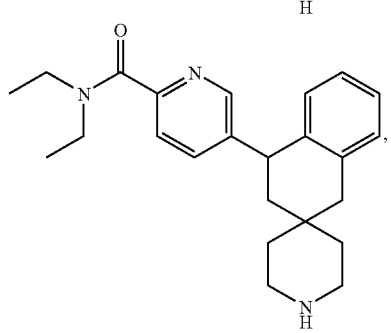

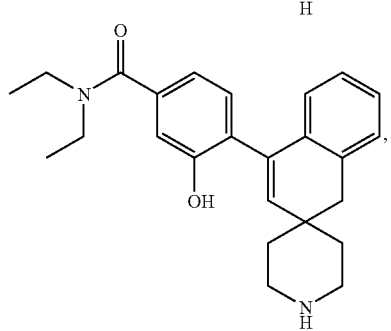

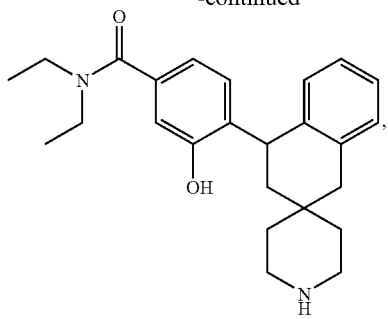
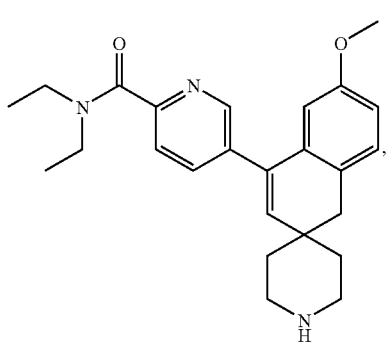
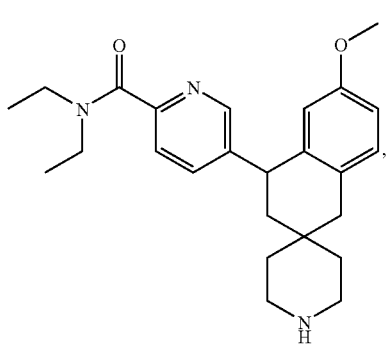
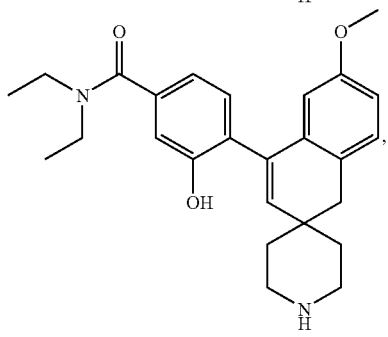
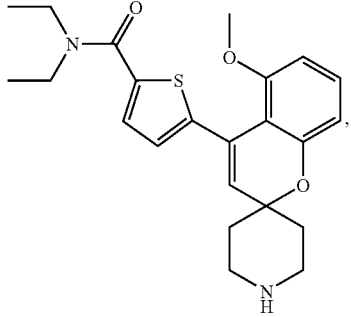
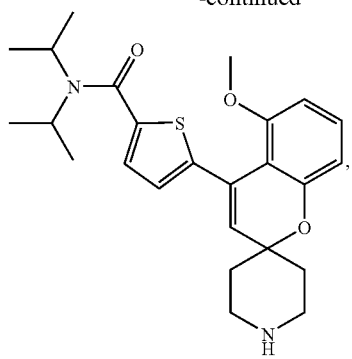
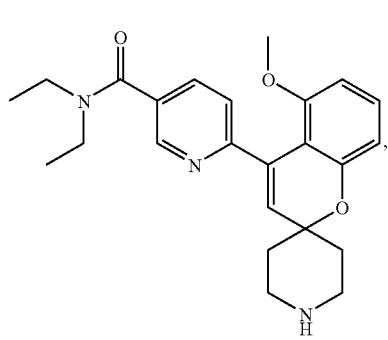
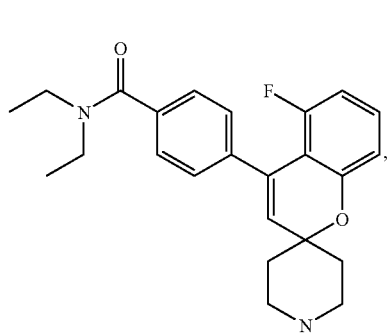
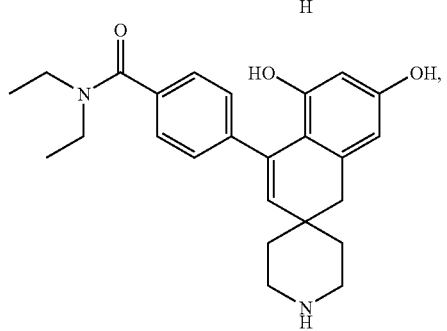
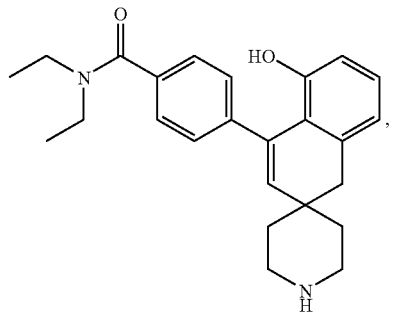

-continued

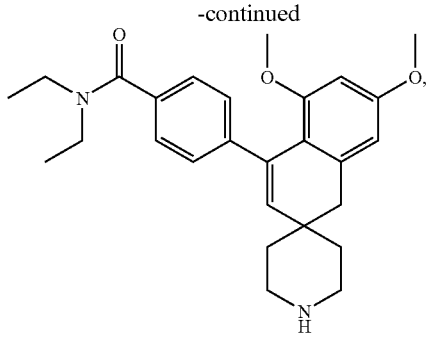

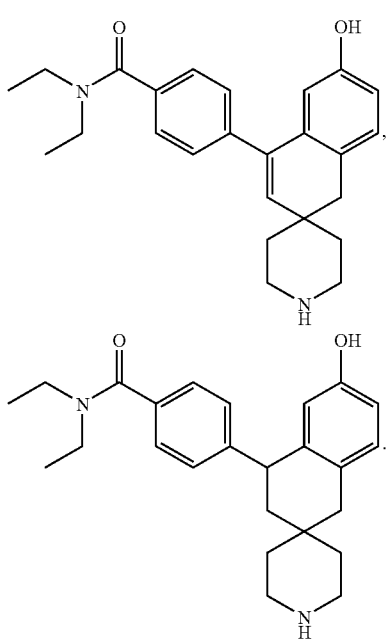

In preferred embodiments, the compounds of formula XXII have the following structure:

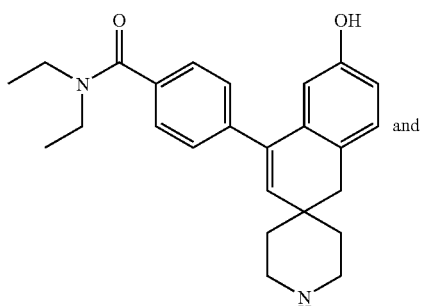
and

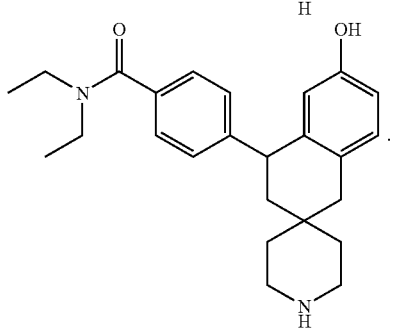

In certain embodiments, the above compounds may be resolved into any of their R and S, or (R,R), (S,S), (R,S), and (S,R) enantiomers, or partially resolved into any of their non-racemic mixtures.

More preferably, compounds of formula XXII have the following structures:

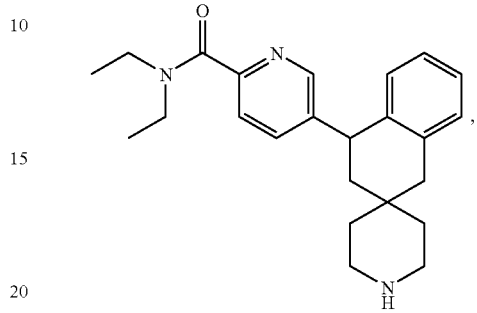

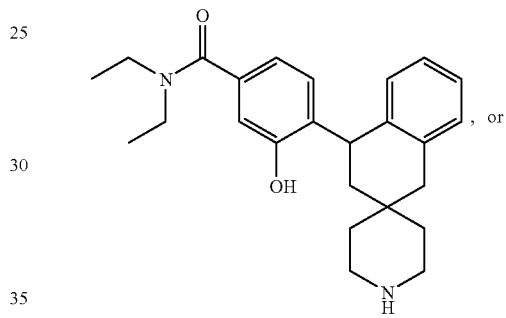

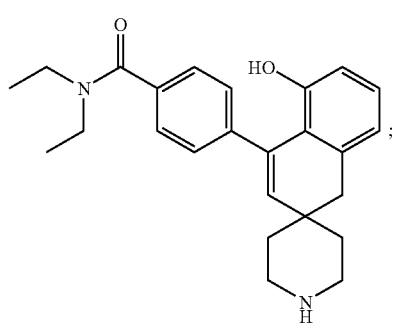

still more preferably

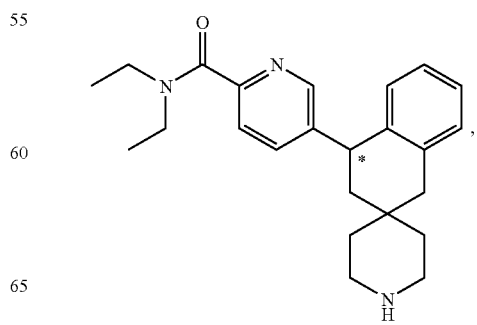

-continued

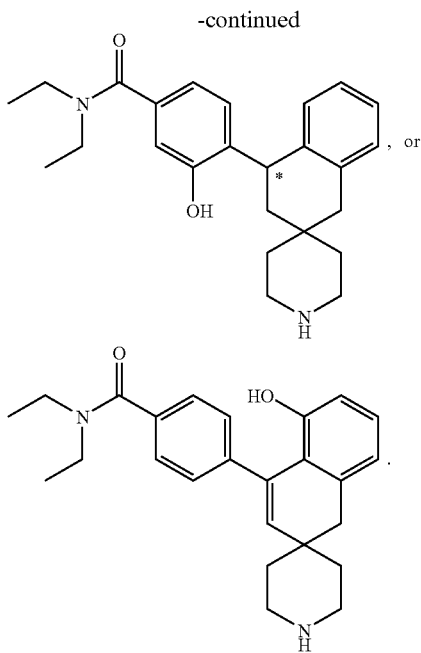

In an alternative embodiment, the invention is directed to compounds of formula XXV:

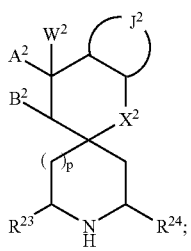

XXV wherein:
$W^2$ is aryl optionally substituted with —C(=O)-alkyl or —C(=O)-aryl;
$R^{23}$ and $R^{24}$ are each independently H or alkyl;
p is 1 or 2;
$A^2$ and $B^2$ are each H, or together form a double bond;
$X^2$ is —CH$_2$— or —O—; and
$J^2$ when taken together with the carbon atoms to which it is attached forms a 6-membered aryl ring substituted with 0-3 groups selected independently from hydroxy, alkoxy, —S(=O)$_2$-alkyl, —S(=O)$_2$—NH$_2$, —S(=O)$_2$—NH(alkyl), —S(=O)$_2$—N(alkyl)(alkyl), —C(=O)—N(alkyl)(alkyl), carboxy (—COOH), and —C(=O)—O-alkyl;
or a stereoisomer, prodrug, pharmaceutically acceptable salt, hydrate, solvate, acid salt hydrate, or N-oxide thereof;
provided that the compound of formula XXV is other than 4-phenyl-spiro[2H, 1-benzopyran-2,4'-piperidine].

In preferred embodiments of compounds of formula XXV, $W^2$ is aryl more preferably phenyl.
In embodiments wherein $W^2$ is substituted with —C(=O)-alkyl, the alkyl group is preferably lower alkyl, with alkyl groups of 1 to 3 carbons being more preferred, and with alkyl groups of 1 carbon being still more preferred. In particularly preferred embodiments, the alkyl group is methyl.

In embodiments wherein $W^2$ is substituted with or —C(=O)-aryl, preferably the aryl group is a 6-membered aryl ring, more preferably phenyl.

In preferred embodiments of formula XXV compounds, $A^2$ and $B^2$ together form a double bond.

In preferred embodiments of formula XXV compounds, $X^2$ is —O—.

In preferred embodiments of formula XXV compounds, p is 1.

In preferred embodiments of formula XXV compounds, $R^{23}$ and $R^{24}$ are each independently H or alkyl, preferably H or $C_1$-$C_3$ alkyl, more preferably H or methyl, yet more preferably H.

In preferred embodiments of formula XXV compounds, $J^2$ when taken together with the carbon atoms to which it is attached forms a 6-membered aryl ring, preferably phenyl.

As set forth above, $J^2$ is substituted with 0-3 groups, preferably 0-2, yet more preferably 0-1 groups, selected independently from halo, heterocycloalkyl, hydroxy, alkoxy, —S(=O)$_2$-alkyl, —S(=O)$_2$—NH$_2$, —S(=O)$_2$—NH(alkyl), —S(=O)$_2$—N(alkyl)(alkyl), carboxy (—COOH), —C(=O)—O-alkyl, and N,N-dialkylaminocarbonyl (—C(=O)—N(alkyl)(alkyl)). In embodiments wherein $J^2$ is substituted with alkoxy, —S(=O)$_2$-alkyl, —S(=O)$_2$—NH(alkyl), —S(=O)$_2$—N(alkyl)(alkyl), —C(=O)—O-alkyl, or N,N-dialkylaminocarbonyl (—C(=O)—N(alkyl)(alkyl)), the alkyl group is preferably lower alkyl, with alkyl groups of 1 to 3 carbons being more preferred, and with alkyl groups of 1 to 2 carbons being still more preferred. In particularly preferred embodiments, the alkyl group is methyl or ethyl. In embodiments wherein $J^2$ is substituted with halo, the halo group is preferably fluoro.

In preferred embodiments, the compounds of formula XXV have the following formula XXVI:

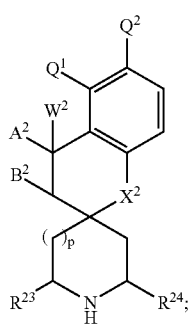

XXVI wherein:
$Q^1$ and $Q^2$ are each independently H, hydroxy, alkoxy, —S(=O)$_2$-alkyl, —S(=O)$_2$—NH$_2$, —S(=O)$_2$—NH(alkyl), —S(=O)$_2$—N(alkyl)(alkyl), —C(=O)—N(alkyl)(alkyl), carboxy (—COOH), or —C(=O)—O-alkyl. In embodiments wherein $Q^1$ or $Q^2$ is alkoxy, —S(=O)$_2$-alkyl, —S(=O)$_2$—NH(alkyl), —S(=O)$_2$—N(alkyl)(alkyl), —C(=O)—O-alkyl, or N,N-dialkylaminocarbonyl (—C(=O)—N(alkyl)(alkyl)), the alkyl group is preferably lower alkyl, with alkyl groups of 1 to 3 carbons being more preferred, and with alkyl groups of 1 to 2 carbons being still more preferred.

In particularly preferred embodiments, the alkyl group is methyl or ethyl. In embodiments wherein $Q^1$ or $Q^2$ is halo, the halo group is preferably fluoro.

In preferred embodiments, the compounds of formula XXV have the following structure:

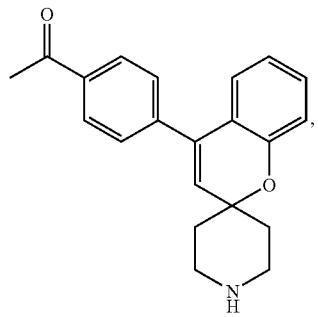

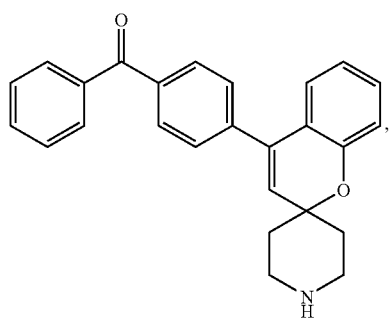

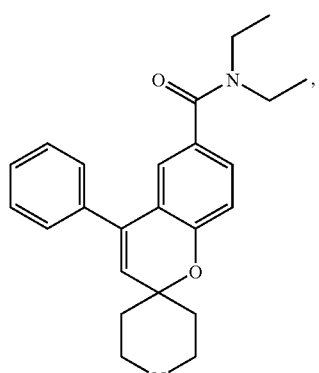

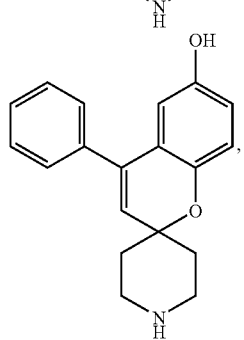

-continued

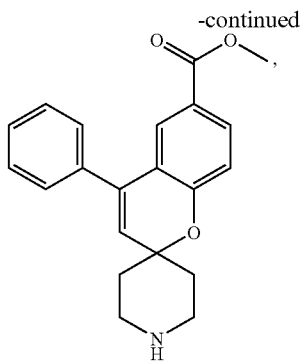

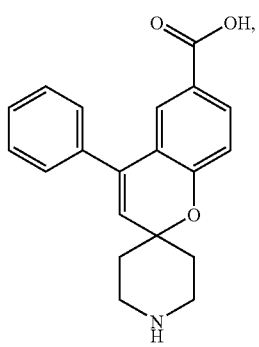

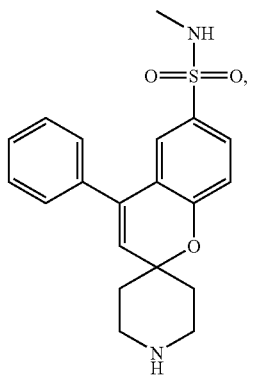

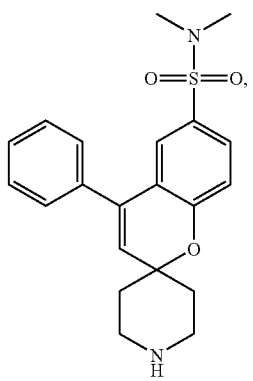

-continued

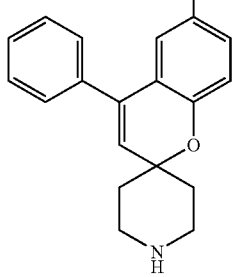

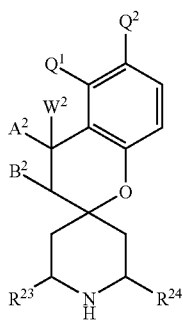

In an alternative embodiment, the invention is directed to compounds of formula XXVII:

XXVII

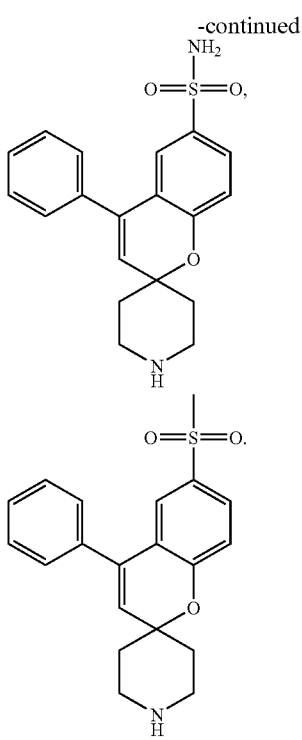

wherein:
$W^2$ is para-dialkylaminocarbonylphenyl, the phenyl group of which is further optionally substituted with 1-2 groups independently selected from tetrazolyl, N-alkyltetrazolyl, hydroxy, carboxy (—COOH), and aminocarbonyl (—C(=O)—NH$_2$);
$R^{23}$ and $R^{24}$ are each independently H or alkyl;
$A^2$ and $B^2$ are each H, or together form a double bond;
$Q^1$ and $Q^2$ are each independently H, hydroxy, alkoxy, haloalkoxy, halo, or heterocycloalkyl;
or a stereoisomer, prodrug, pharmaceutically acceptable salt, hydrate, solvate, acid salt hydrate, or N-oxide thereof;

provided that:
when one of $Q^1$ and $Q^2$ is hydroxy and the other is H, or both $Q^1$ and $Q^2$ are hydroxy, then the phenyl group of $W^2$ is further substituted with 1-2 groups selected from tetrazolyl, N-alkyltetrazolyl, hydroxy, carboxy (—COOH), and aminocarbonyl (—C(=O)—NH$_2$);

when $Q^1$, $Q^2$, $R^{23}$, and $R^{24}$ are each H and the phenyl group of $W^2$ is further substituted with one hydroxy, then $A^2$ and $B^2$ are each H;

when $W^2$ is para-dialkylaminocarbonylphenyl, then at least one of $Q^1$, $Q^2$, $R^{23}$, and $R^{24}$ is other than H;

when $W^2$ is para-dialkylaminocarbonylphenyl, $R^{23}$ and $R^{24}$ are each H, and $Q^2$ is halo, then $Q^1$ is other than H or hydroxy;

when $W^2$ is para-dialkylaminocarbonylphenyl, $R^{23}$ and $R^{24}$ are each H, $Q^1$ is methoxy or cyclopropylmethoxy, and $Q^2$ is H, then $A^2$ and $B^2$ are each H; and when $W^2$ is para-dialkylaminocarbonylphenyl, $R^{23}$ and $R^{24}$ are each H, and $Q^1$ is H or OH, then $Q^2$ is other than methoxy or cyclopropylmethoxy.

In preferred embodiments of formula XXVII compounds, $W^2$ is para-dialkylaminocarbonylphenyl. As set forth above, $W^2$ is further optionally substituted with 1-2 groups independently selected from tetrazolyl, N-alkyltetrazolyl, hydroxy, carboxy (—COOH), and aminocarbonyl (—C(=O)—NH$_2$). In preferred embodiments wherein $W^2$ is substituted with 1-2 groups, $W^2$ is preferably substituted with hydroxy.

In preferred embodiments of formula XXVII compounds, $W^2$ is:

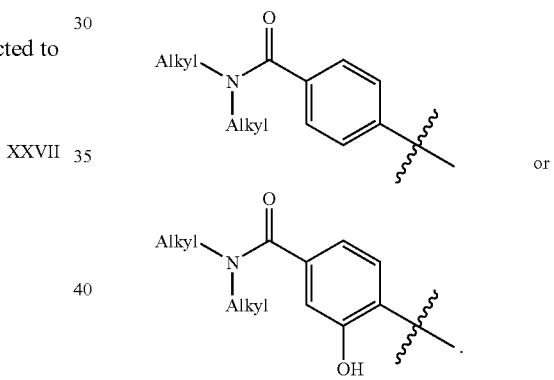

In embodiments in which $W^2$ is substituted with N,N-dialkylaminocarbonyl (—C(=O)—N(alkyl)(alkyl)), the alkyl group is preferably lower alkyl, with alkyl groups of 1 to 3 carbons being more preferred, and with alkyl groups of 2 carbons being still more preferred. In particularly preferred embodiments, the alkyl group is ethyl.

In preferred embodiments of formula XXVII compounds, $R^{23}$ and $R^{24}$ are each independently H or alkyl, preferably H or $C_1$-$C_3$ alkyl, more preferably H or methyl, yet more preferably H.

In preferred embodiments of formula XXVII compounds, $Q^1$ and $Q^2$ are each independently H, hydroxy, alkoxy, haloalkoxy, halo, or heterocycloalkyl. In embodiments where $Q^1$ or $Q^2$ is alkoxy, the alkoxy is preferably $C_1$-$C_3$ alkoxy, more preferably $C_1$ alkoxy, yet more preferably, methoxy. In embodiments where $Q^1$ or $Q^2$ is halo, the halo is preferably fluoro. In embodiments where $Q^1$ or $Q^2$ is heterocycloalkyl, the heterocycloalkyl is preferably a 5- or 6-membered ring heterocycloalkyl, more preferably pyrrolidinyl or morpholinyl. In embodiments where $Q^1$ or $Q^2$ is haloalkoxy, the alkoxy is substituted with one or more, preferably two or more, fluoro atoms.

In preferred embodiments, the compounds of formula XXVII, the compounds have the structures:
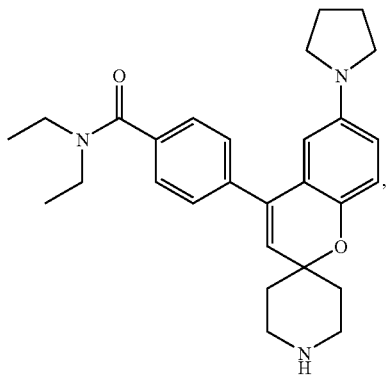
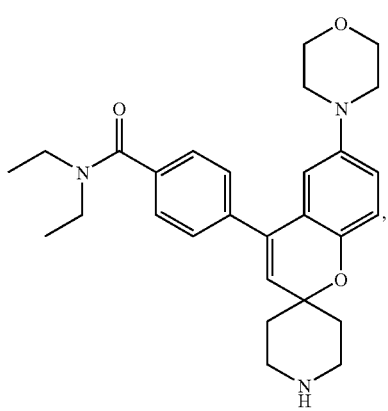
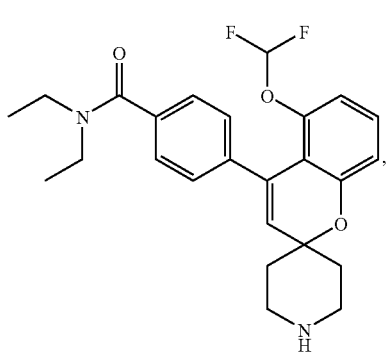
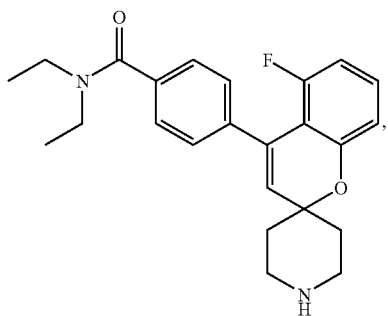
-continued
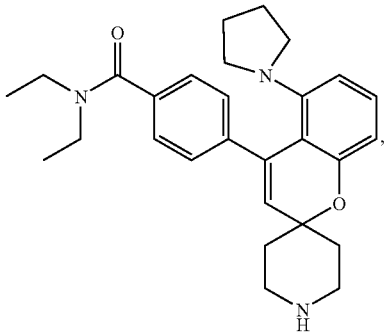
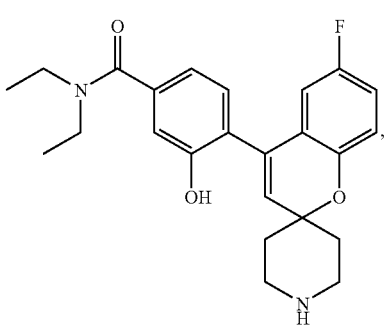
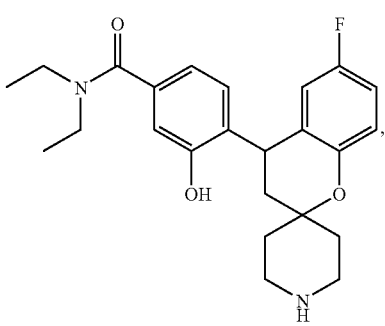
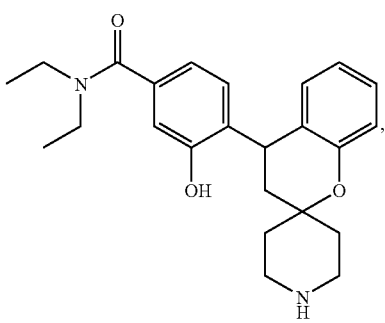

-continued

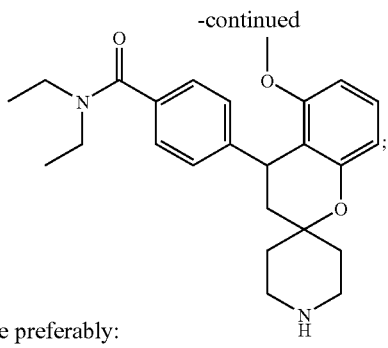

more preferably:

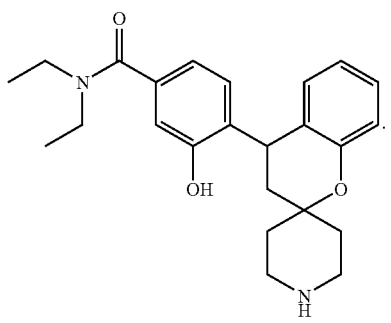

In some preferred embodiments, the compound of formula XXVII has the structure:

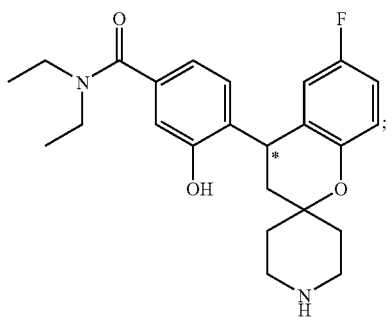

wherein denotes "*" a chiral center, as described herein above. In certain preferred embodiments, the compound is substantially enantiomerically pure.

In an alternative embodiment, the invention is directed to compounds of formula XXVIII:

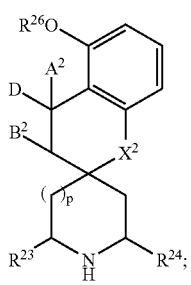

XXVIII wherein:
D is:

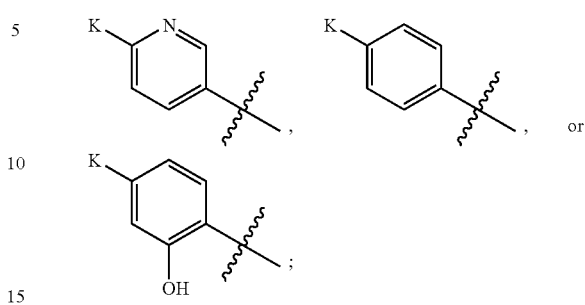

K is carboxy (—COOH), —C(=O)—O-alkyl, —S(=O)$_2$—N(alkyl)(alkyl), heteroaryl, alkylheteroaryl, aminocarbonyl (—C(=O)—NH$_2$), or N-alkylaminocarbonyl (—C(=O)—NH(alkyl));
$R^{23}$, $R^{24}$, and $R^{26}$ are each independently H or alkyl;
p is 1 or 2;
$A^2$ and $B^2$ are each H, or together form a double bond; and
$X^2$ is —CH$_2$— or —O—;
or a stereoisomer, prodrug, pharmaceutically acceptable salt, hydrate, solvate, acid salt hydrate, or N-oxide thereof.

In preferred embodiments of formula XXVIII compounds, D is:

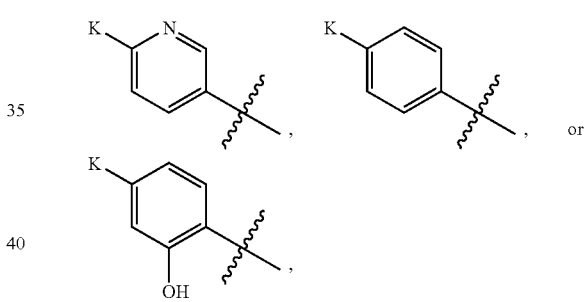

more preferably:

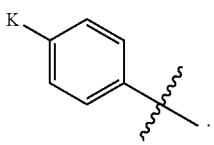

In preferred embodiments of formula XXVIII compounds wherein K is —S(=O)$_2$—N(alkyl)(alkyl), or N-alkylaminocarbonyl (—C(=O)—NH(alkyl)), the alkyl group independently is preferably lower alkyl, with alkyl groups of 1 to 3 carbons being more preferred, and with alkyl groups of 2 carbons being still more preferred. In particularly preferred embodiments, the alkyl group is ethyl.

In preferred embodiments of formula XXVIII compounds wherein K is —C(=O)—O-alkyl or alkyltetrazolyl, the alkyl group independently is preferably lower alkyl, with alkyl groups of 1 to 3 carbons being more preferred, and with alkyl groups of 1-2 carbon being still more preferred. In particularly preferred embodiments, the alkyl group is methyl or ethyl.

In preferred embodiments of formula XXVIII compounds wherein K is heteroaryl or alkylheteroaryl, the heteroaryl group is preferably a 5-membered ring heteroaryl, more preferably a tetrazolyl ring.

In preferred embodiments of formula XXVIII compounds, $A^2$ and $B^2$ together form a double bond.

In preferred embodiments of formula XXVIII compounds, p is 1.

In preferred embodiments of formula XXVIII compounds, $X^2$ is —O—.

In preferred embodiments of formula XXVIII compounds, $R^{23}$, $R^{24}$, and $R^{26}$ are each independently H or alkyl, preferably H or $C_1$-$C_3$ alkyl, more preferably H or methyl, yet more preferably H. In certain preferred embodiments, one of $R^{23}$ and $R^{24}$ is H and the other is alkyl.

In preferred embodiments, the compounds of formula XXVIII, have the structures:

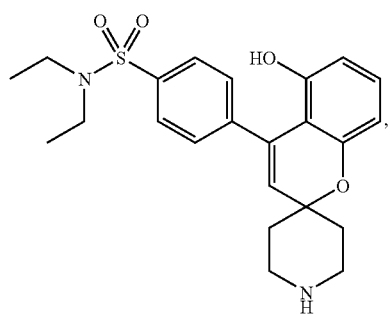

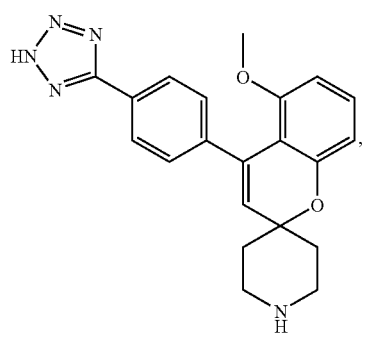

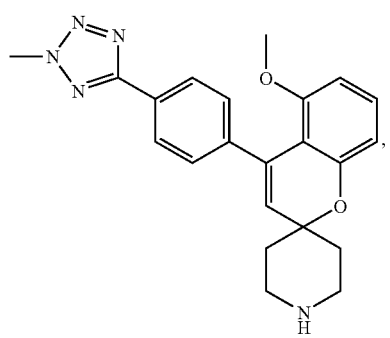

-continued

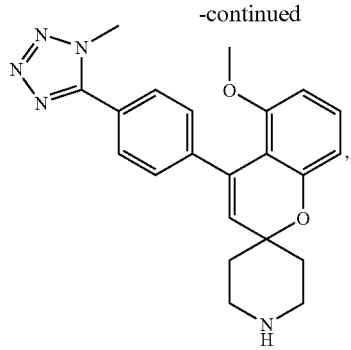

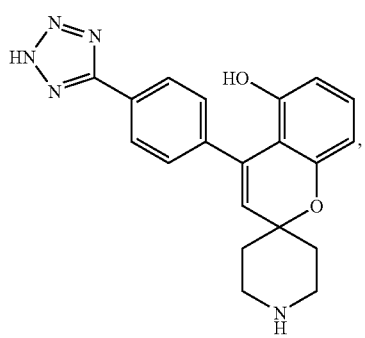

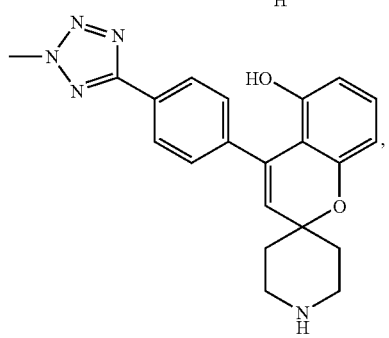

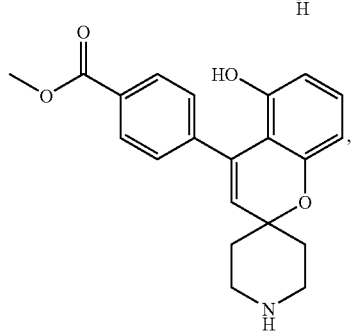

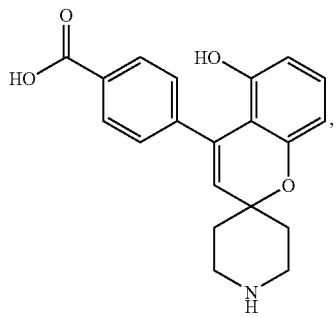

-continued

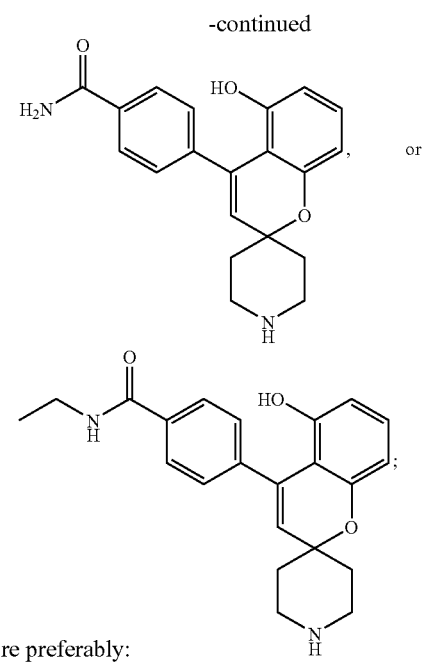

more preferably:

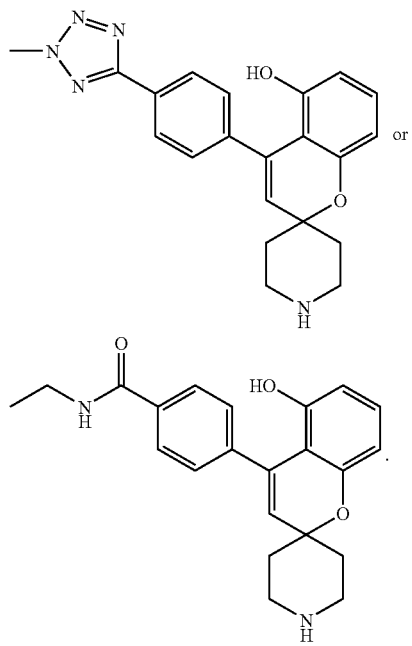

In an alternative embodiment, the invention is directed to compounds of formula XXIX:

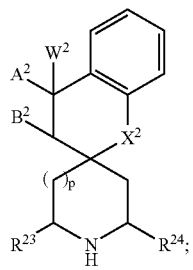

XXIX wherein:
$W^2$ is para-N(alkyl),N(alkyl-Z)aminocarbonylaryl or para-N(alkyl),N(alkyl-Z)aminocarbonylheteroaryl, wherein the aryl or heteroaryl ring of $W^2$ is substituted with 0-2 groups selected independently from hydroxy and alkoxy;
Z is alkoxy, alkylamino, or dialkylamino;
$R^{23}$ and $R^{24}$ are each independently H or alkyl;
p is 1 or 2;
$A^2$ and $B^2$ are each H, or together form a double bond; and
$X^2$ is —CH$_2$— or —O—;
or a stereoisomer, prodrug, pharmaceutically acceptable salt, hydrate, solvate, acid salt hydrate, or N-oxide thereof.

In preferred embodiments of formula XXIX compounds, $W^2$ is para-N(alkyl),N(alkyl-Z)-aminocarbonylaryl or para-N(alkyl),N(alkyl-Z)-aminocarbonylheteroaryl. When $W^2$ is para-N(alkyl),N(alkyl-Z)aminocarbonylaryl, the aryl ring is preferably phenyl. When para-N(alkyl),N(alkyl-Z)aminocarbonylheteroaryl, the heteroaryl ring is preferably pyridyl.

As set forth above, $W^2$ is substituted with 0-2 groups selected independently from selected independently from hydroxy and alkoxy. In preferred embodiments, $W^2$ is substituted with 0-1 groups, selected independently from hydroxy and alkoxy, more preferably hydroxy.

In preferred embodiments of formula XXIX compounds, $W^2$ is:

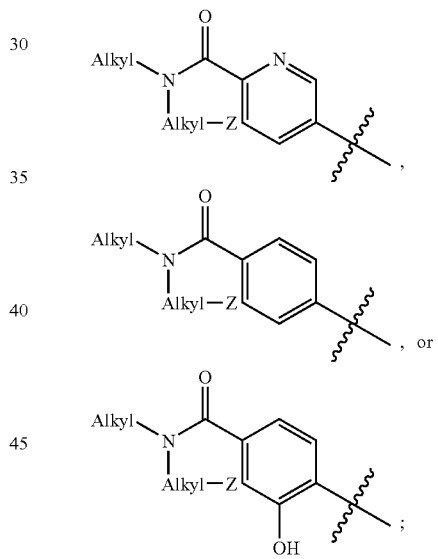

more preferably:

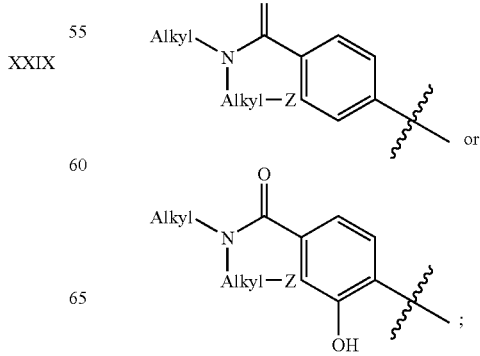

more preferably still:

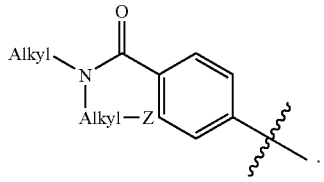

In embodiments in which $W^2$ is para-N(alkyl),N(alkyl-Z)aminocarbonylaryl or para-N(alkyl),N(alkyl-Z)aminocarbonylheteroaryl, the alkyl group is preferably lower alkyl, with alkyl groups of 1 to 3 carbons being more preferred, and with alkyl groups of 2 carbons being still more preferred. In particularly preferred embodiments, the alkyl group is ethyl.

In preferred embodiments of formula XXIX compounds, p is 1.

In preferred embodiments of formula XXIX compounds, $A^2$ and $B^2$ together form a double bond.

In preferred embodiments of formula XXIX compounds, $X^2$ is —O—.

In preferred embodiments of formula XXIX compounds, $R^{23}$ and $R^{24}$ are each independently H or alkyl, preferably H or $C_1$-$C_3$ alkyl, more preferably H or methyl. In certain preferred embodiments, one of $R^{23}$ and $R^{24}$ is H and the other is alkyl.

In preferred embodiments of formula XXIX compounds, Z is alkoxy, alkylamino, or dialkylamino, preferably alkoxy. In embodiments wherein Z is alkoxy, alkylamino, or dialkylamino the alkyl group is preferably lower alkyl, with alkyl groups of 1 to 3 carbons being more preferred, and with alkyl groups of 1 carbon being still more preferred. In particularly preferred embodiments, the alkyl group is methyl.

In certain embodiments, the compounds of formula XXIX have the structures:

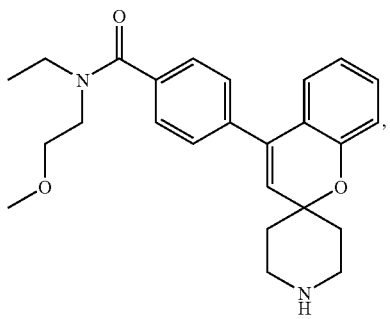

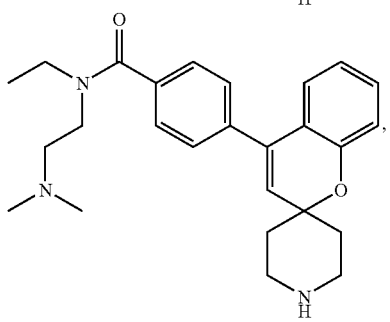

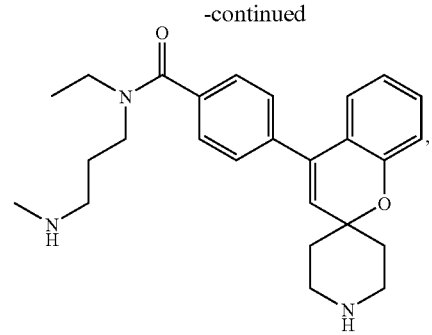

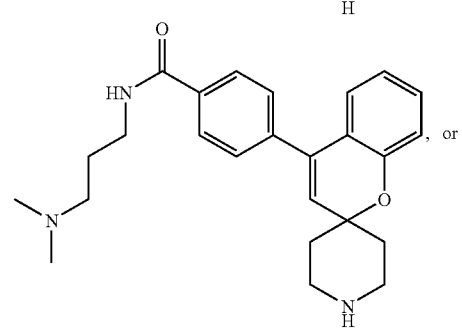

, or

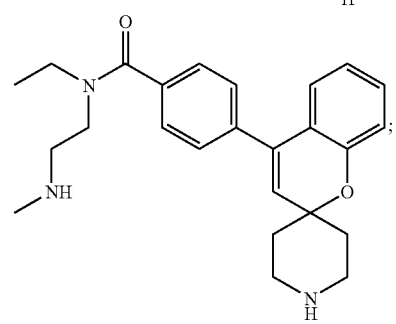

;

more preferably:

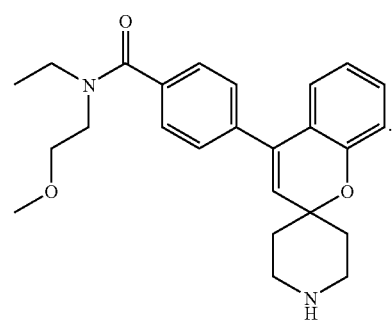

.

In an alternative embodiment, the invention is directed to compounds of formula XXX:

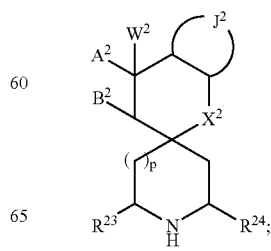

XXX wherein:

W² is:

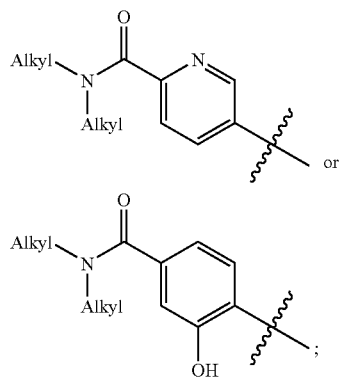

R²³ and R²⁴ are each independently H or alkyl;
p is 1 or 2;
A² and B² are each H, or together form a double bond;
X² is —CH₂— or —O—; and
J² when taken together with the carbon atoms to which it is attached forms a 6-membered aryl ring substituted with 1-3 groups selected independently from halo and haloalkoxy;
or a stereoisomer, prodrug, pharmaceutically acceptable salt, hydrate, solvate, acid salt hydrate, or N-oxide thereof;
provided that when W² is:

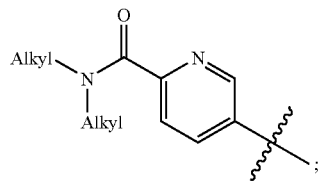

then the aryl ring of J² is substituted with at least one haloalkoxy.

In preferred embodiments of compounds of formula XXX, W² is:

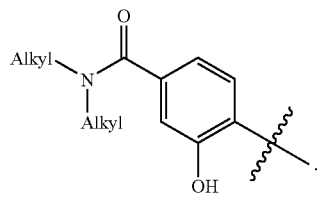

In preferred embodiments of formula XXX compounds, p is 1.

In preferred embodiments of formula XXX compounds, R²³ and R²⁴ are each independently H or alkyl, preferably H or C₁-C₃ alkyl, more preferably H or methyl, yet more preferably H. In certain preferred embodiments, one of R²³ and R²⁴ is H and the other is alkyl.

In preferred embodiments of formula XXX compounds, J² when taken together with the carbon atoms to which it is attached forms a 6-membered aryl ring, preferably a phenyl ring. In embodiments wherein J² is substituted with 1-3 groups selected independently from halo and haloalkoxy, the halo group of halo or haloalkoxy is preferably fluoro.

In preferred embodiments, the compounds of formula XXX have the following formula XXXI:

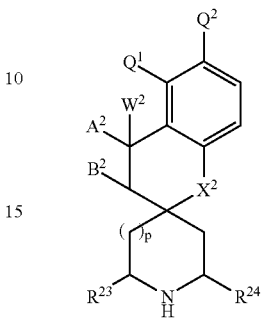

wherein:

Q¹ and Q² are each independently H, halo, or haloalkoxy, provided that at least one of Q¹ and Q² is other than H. In embodiments wherein Q¹ or Q² is halo or haloalkoxy, the halo group of halo or haloalkoxy is preferably fluoro.

In preferred embodiments, the compounds of formula XXX have the structures:

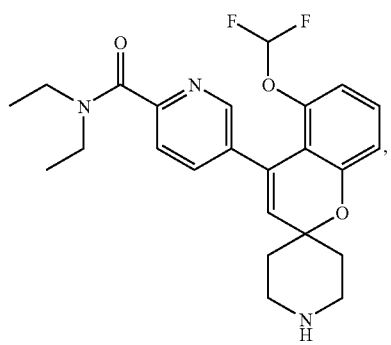

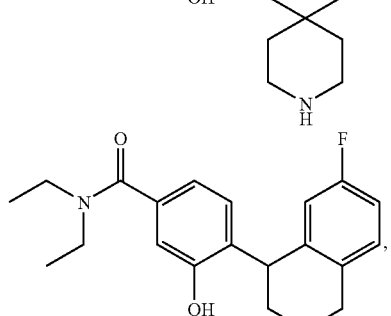

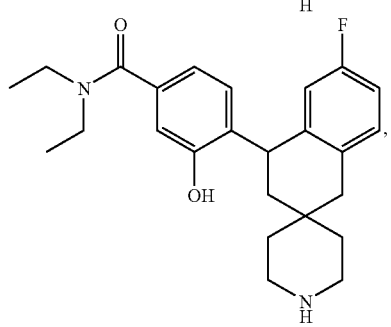

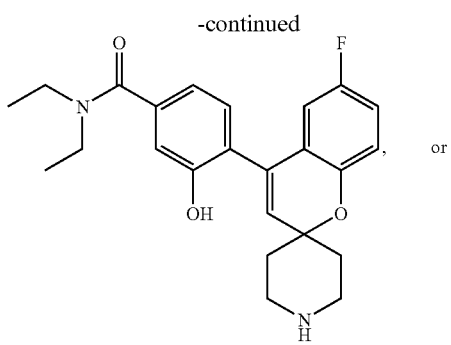, or

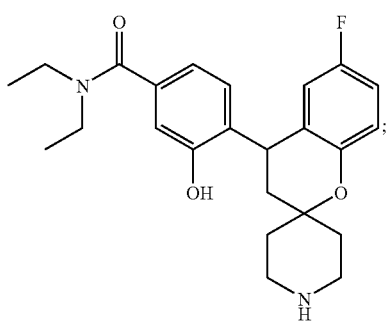;

more preferably:

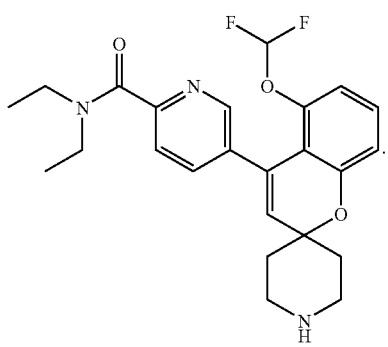.

In an alternative embodiment, the invention is directed to compounds of formula XXXII:

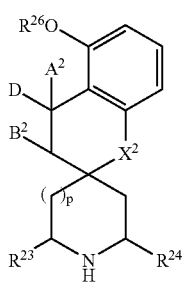

XXXII wherein:

D is N(alkyl),N(alkyl)aminocarbonylheteroaryl;

$R^{23}$, $R^{24}$, and $R^{26}$ are each independently H or alkyl;

p is 1 or 2;

$A^2$ and $B^2$ are each H, or together form a double bond; and $X^2$ is —$CH_2$— or —O—;

or a stereoisomer, prodrug, pharmaceutically acceptable salt, hydrate, solvate, acid salt hydrate, or N-oxide thereof;

provided that when D is:

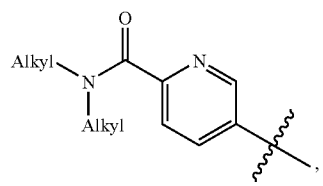

and $X^2$ is —O—, then $A^2$ and $B^2$ are each H.

In embodiments of formula XXXII compounds wherein D is N(alkyl),N(alkyl)aminocarbonylheteroaryl, the heteroaryl group is preferably pyridyl or thienyl.

In embodiments of formula XXXII compounds wherein D is N(alkyl),N(alkyl)aminocarbonylheteroaryl, the alkyl group is preferably lower alkyl, with alkyl groups of 1 to 3 carbons being more preferred, and with alkyl groups of 2-3 carbons being still more preferred. In particularly preferred embodiments, the alkyl group is ethyl or isopropyl.

In preferred embodiments of formula XXXII compounds, $A^2$ and $B^2$ are each H.

In preferred embodiments of formula XXXII compounds, $X^2$ is —O—.

In preferred embodiments of formula XXXII compounds, $R^{23}$, $R^{24}$, and $R^{26}$ are each independently H or alkyl, preferably H or $C_1$-$C_3$ alkyl, more preferably H or methyl, yet more preferably H. In certain preferred embodiments, one of $R^{23}$ and $R^{24}$ is H and the other is alkyl.

In certain embodiments, the compounds of formula XXXII, have the structures:

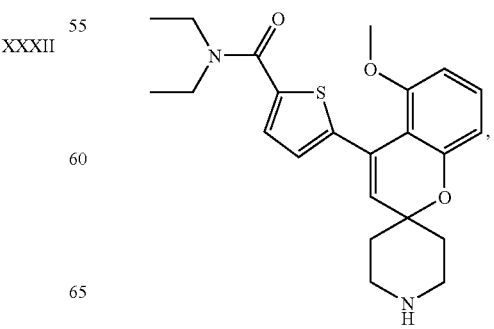,

-continued

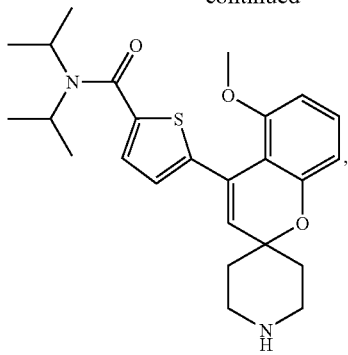

,

, or

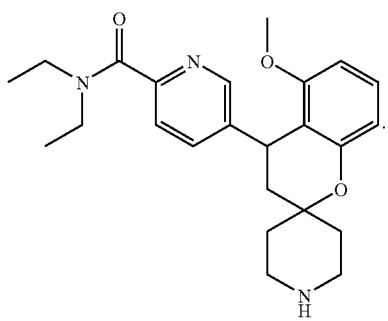

;

preferably:

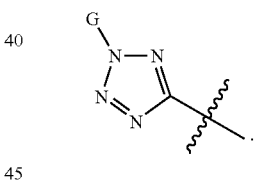

.

In another embodiment, the present invention is directed, in part, to compounds of formula XXXIII:

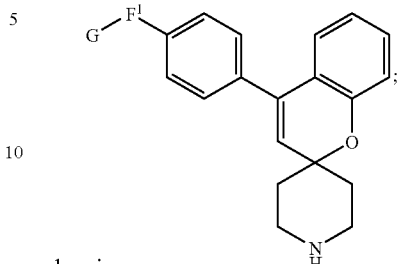

XXXIII wherein:

F$^1$ is heteroaryl; and

G is C$_{1-6}$alkylene substituted with NH$_2$, NHC(=O)alkyl, NH(C(O)N(H)alkyl, or NHS(=O)$_2$alkyl;

or a stereoisomer, prodrug, pharmaceutically acceptable salt, hydrate, solvate, acid salt hydrate, or N-oxide thereof.

In formula XXXIII above, F$^1$ is heteroaryl, preferably a 5- or 6-membered heteroaryl having 1 to 4 heteroatoms, with 2 to 4 heteroaroms being more preferred. In certain more preferred embodiments, F$^1$ is a 5-membered heteroaryl, still more preferably a tetrazole.

Also in formula XXXIII above, G is C$_{1-6}$alkylene substituted with NH$_2$, NHC(=O)alkyl, NH(C(O)N(H)alkyl, or NHS(=O)$_2$alkyl. In preferred embodiments, G is C$_{1-6}$alkylene substituted with NH$_2$. In other preferred embodiments, G is C$_{1-6}$alkylene substituted with NHC(=O)alkyl. In still other preferred embodiments, G is C$_{1-6}$alkylene substituted with NHS(=O)$_2$alkyl. More preferably, G is C$_{1-6}$alkylene substituted with NH$_2$.

In some preferred embodiments of compounds of formula XXXIII, F$^1$-G is:

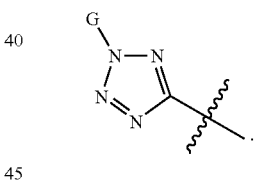

.

In certain preferred embodiments, the compounds of formula XXXIII are selected from the group consisting of:

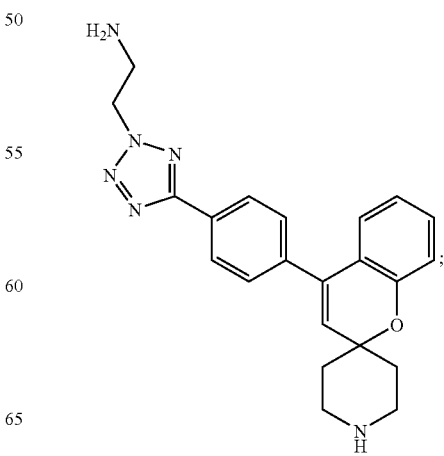

;

69
-continued
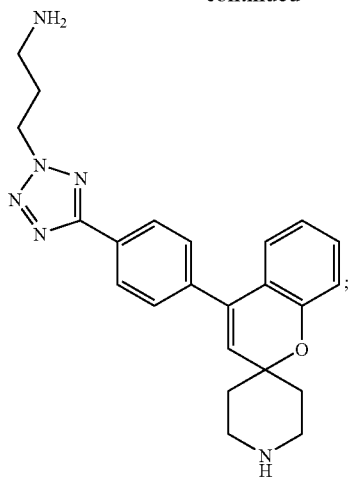
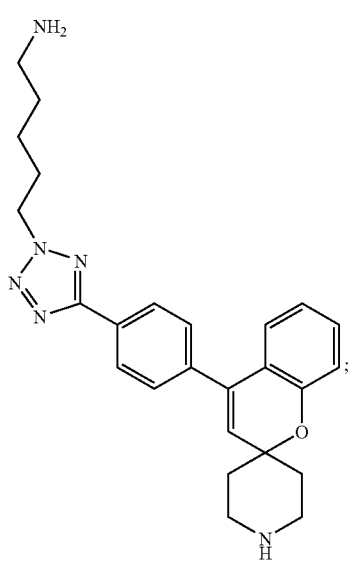
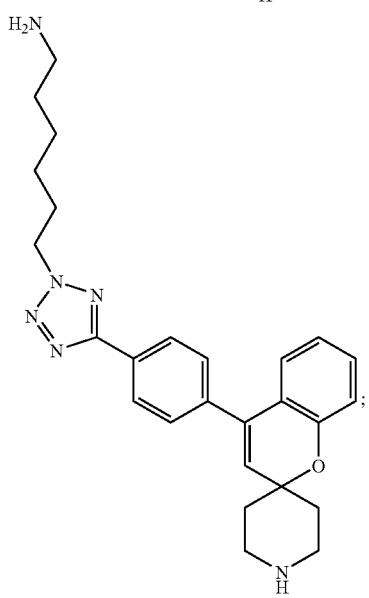
70
-continued
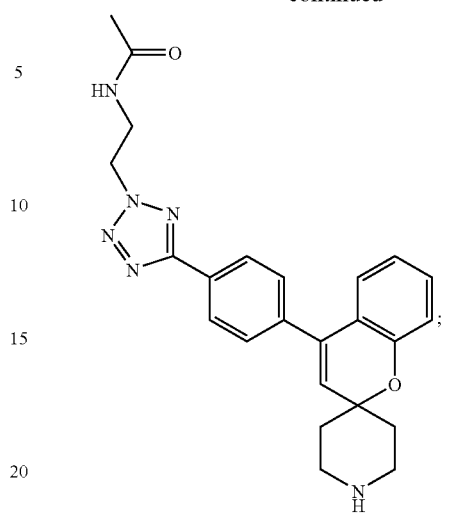

71
-continued
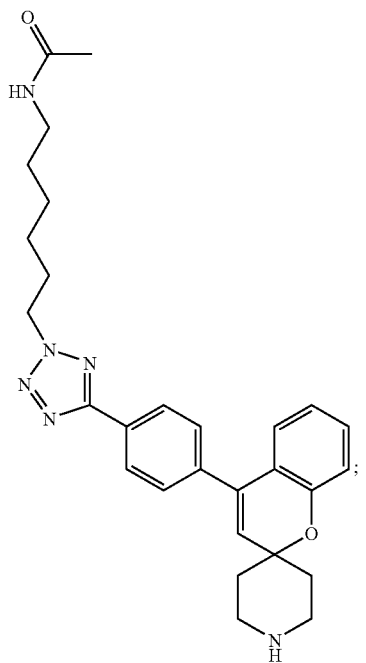
72
-continued
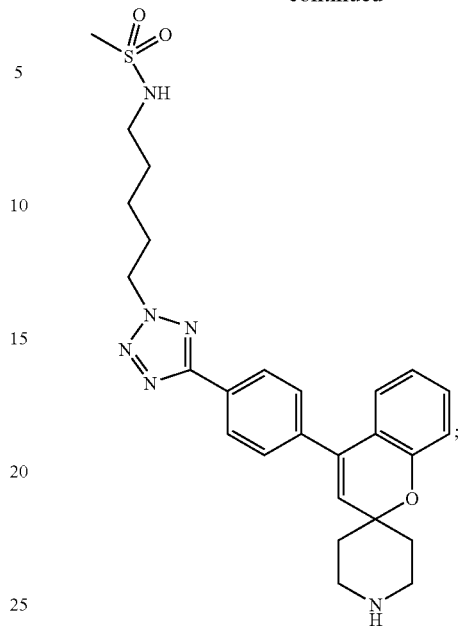
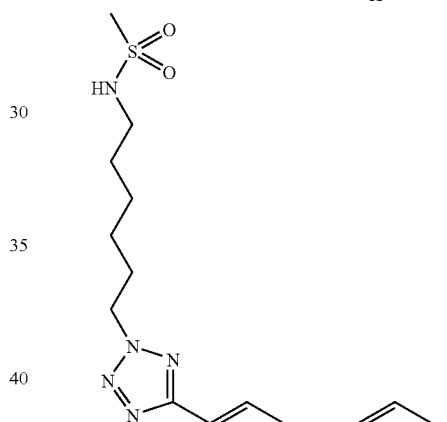
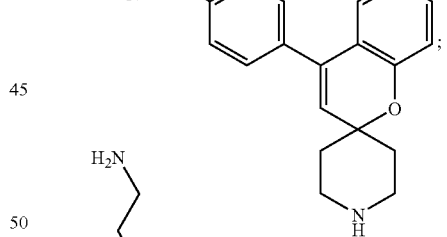
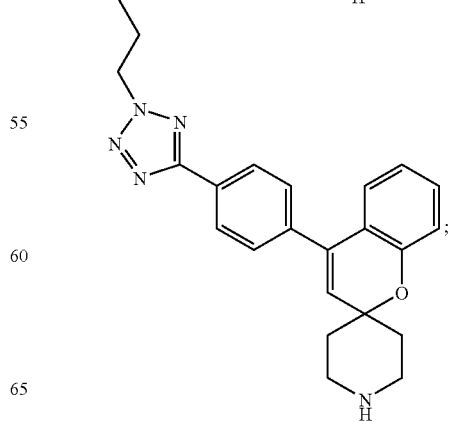

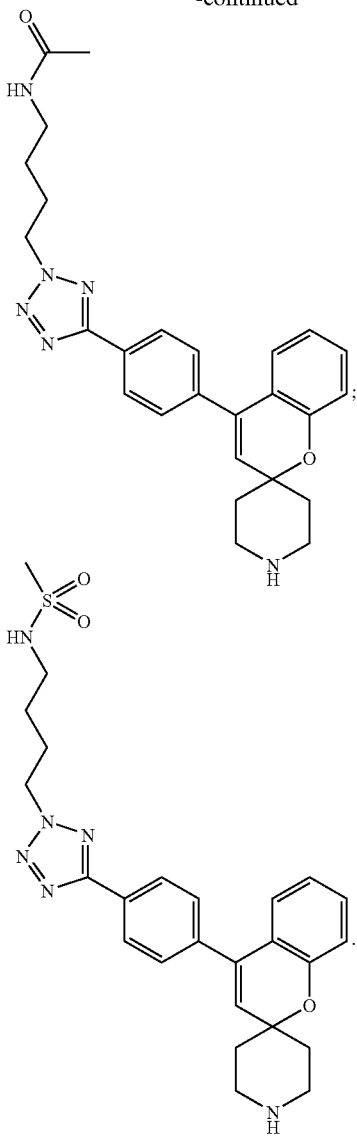

In one embodiment, the present invention is directed, in part, to compounds of formula XXXIV:

XXXIV

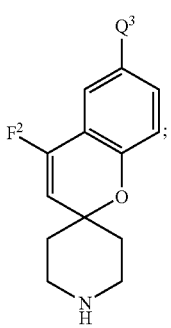

wherein:
F² is aryl or heteroaryl; and
Q³ is hydroxy or alkoxy;

or a stereoisomer, prodrug, pharmaceutically acceptable salt, hydrate, solvate, acid salt hydrate, or N-oxide thereof.

In formula XXXIV above, F² is aryl or heteroaryl. When F² is aryl, preferably it is $C_{6\text{-}10}$aryl, more preferably $C_6$aryl, with phenyl being even more preferred. When F² is heteroaryl, preferably it is $C_{6\text{-}10}$heteroaryl, with pyridyl or benzothiophenyl being more preferred.

Also in formula XXXIV above, Q³ is hydroxy or alkoxy, preferably hydroxy.

In another embodiment, the compound of the invention is selected from the group consisting of:

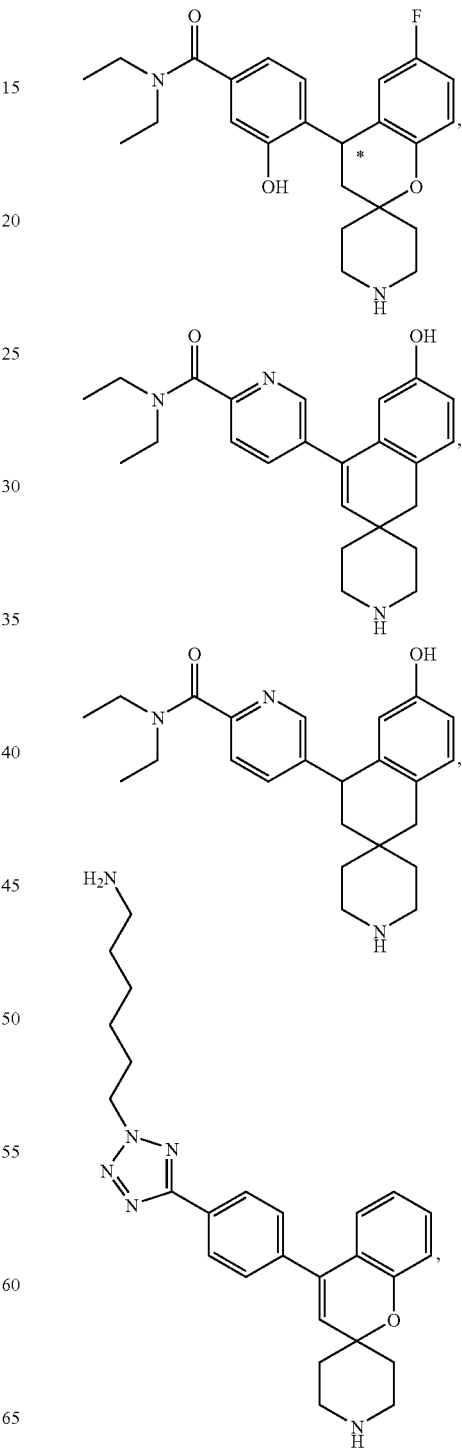

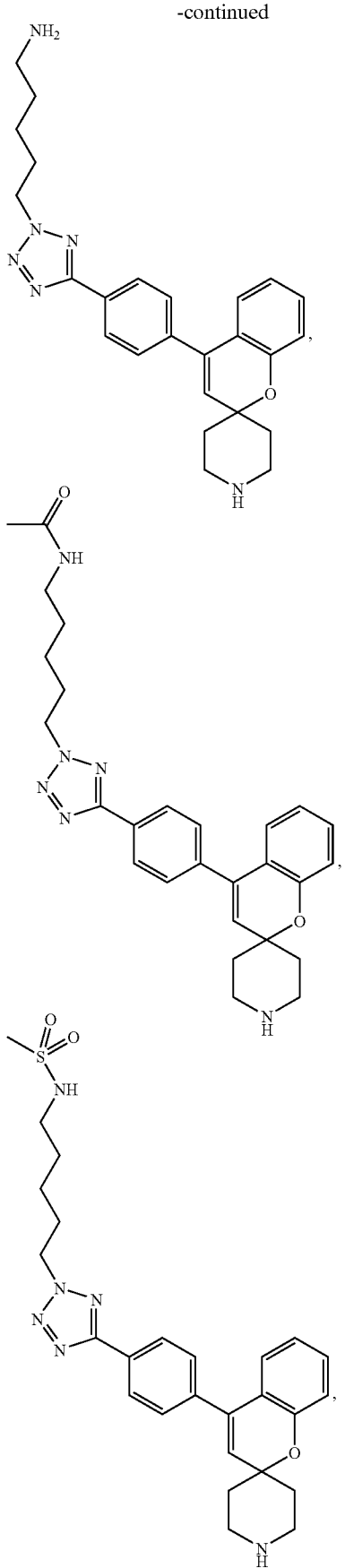
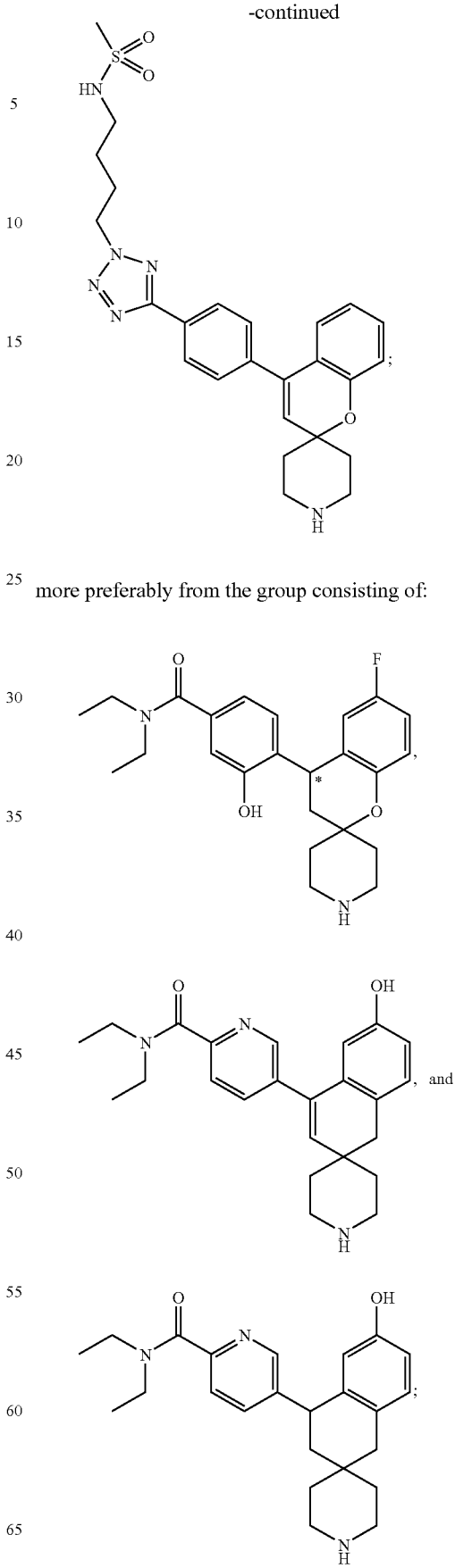
more preferably from the group consisting of:

or a stereoisomer, prodrug, pharmaceutically acceptable salt, hydrate, solvate, acid salt hydrate, or N-oxide thereof.

The present invention is further directed to pharmaceutical compositions, comprising:

a pharmaceutically acceptable carrier; and an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV. In certain embodiments, the pharmaceutical composition further comprises an effective amount of at least one opioid.

In a preferred embodiment, the invention is directed to pharmaceutical compositions, comprising:

a pharmaceutically acceptable cater; and an effective amount of a compound of formula XXVIIA:

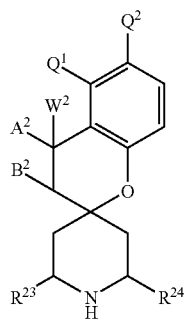

XXVIIA wherein:
$W^2$ is para-dialkylaminocarbonylphenyl, the phenyl group of which is further optionally substituted with 1-2 groups independently selected from tetrazolyl, N-alkyltetrazolyl, hydroxy, carboxy (—COOH), and aminocarbonyl (—C(═O)—NH$_2$);
$R^{23}$ and $R^{24}$ are each independently H or alkyl;
$A^2$ and $B^2$ are each H, or together form a double bond;
$Q^1$ and $Q^2$ are each independently H, hydroxy, alkoxy, haloalkoxy, halo, or heterocycloalkyl;
or a stereoisomer, prodrug, pharmaceutically acceptable salt, hydrate, solvate, acid salt hydrate, or N-oxide thereof;
provided that:
when one of $Q^1$ and $Q^2$ is hydroxy and the other is H, then the phenyl group of $W^2$ is further substituted with 1-2 groups selected from tetrazolyl, N-alkyltetrazolyl, hydroxy, carboxy (—COOH), and aminocarbonyl (—C(═O)—NH$_2$);
when $Q^1$, $Q^2$, $R^{23}$, and $R^{24}$ are each H and the phenyl group of $W^2$ is further substituted with one hydroxy, then $A^2$ and $B^2$ are each H;
when $W^2$ is para-dialkylaminocarbonylphenyl, then at least one of $Q^1$, $Q^2$, $R^{23}$, and $R^{24}$ is other than H;
when $W^2$ is para-dialkylaminocarbonylphenyl, $R^{23}$ and $R^{24}$ are each H, and $Q^2$ is halo, then $Q^1$ is other than H;
when $W^2$ is para-dialkylaminocarbonylphenyl, $R^{23}$ and $R^{24}$ are each H, $Q^1$ is methoxy or cyclopropylmethoxy, and $Q^2$ is H, then $A^2$ and $B^2$ are each H; and
when $W^2$ is para-dialkylaminocarbonylphenyl, $R^{23}$ and $R^{24}$ are each H, and $Q^1$ is H or OH, then $Q^2$ is other than methoxy or cyclopropylmethoxy.

Compounds as described herein may be useful as analgesic agents for use during general anesthesia and monitored anesthesia care. Combinations of agents with different properties are often used to achieve a balance of effects needed to maintain the anaesthetic state (e.g., amnesia, analgesia, muscle relaxation and sedation). Included in this combination are inhaled anesthetics, hypnotics, anxiolytics, neuromuscular blockers and opioids.

In any of the above teachings, a compound as described herein may be either a compound of one of the formulae herein described, or a stereoisomer, prodrug, pharmaceutically acceptable salt, hydrate, solvate, acid salt hydrate, N-oxide or isomorphic crystalline form thereof.

The compounds employed in the methods and compositions of the present invention may exist in prodrug form. As used herein, "prodrug" is intended to include any covalently bonded carriers which release the active parent drug, for example, as according to formula XIV, XV, XVI, XVII, XVIII, XIX, XX, XXI, XXII, XXIII, XXIV, XXV, XXVI, XXVII, XXVIII, XXIX, XXX, XXXI, XXXII, XXXIII and/or XXXIV, or other formulas or compounds as described herein, such as for example, compounds of formula XXVIIA, in vivo when such prodrug is administered to a mammalian subject. Since prodrugs are known to enhance numerous desirable qualities of pharmaceuticals (e.g., solubility, bioavailability, manufacturing, etc.), the compounds described herein may, if desired, be delivered in prodrug form. Thus, the present invention contemplates compositions and methods involving prodrugs. Prodrugs of the compounds employed in the present invention, for example formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

Compounds described herein may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

The compounds as herein described may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991, the disclosures of which are hereby incorporated herein by reference, in their entirety.

The δ agonist compounds as described herein may be administered by any means that results in the contact of the active agent with the agent's site of action in the body of a patient. The compounds may be administered by any conventional means available for use in conjunction with pharmaceuticals, either as individual therapeutic agents or in a combination of therapeutic agents. For example, they may be administered as the sole active agent in a pharmaceutical composition, or they can be used in combination with other therapeutically active ingredients including, for example, opioid analgesic agents. In such combinations, selected compounds as described herein may provide equivalent or even enhanced therapeutic activity such as, for example, pain amelioration, while providing reduced adverse side effects associated with opioids, such as addiction or pruritus, by lowering the amount of opioid required to achieve a therapeutic effect.

The compounds are preferably combined with a pharmaceutical carrier selected on the basis of the chosen route of administration and standard pharmaceutical practice as described, for example, in *Remington's Pharmaceutical Sciences* (Mack Publishing Co., Easton, Pa., 1980), the disclosures of which are hereby incorporated herein by reference, in their entirety.

In addition to the pharmaceutical carrier, the compounds of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV, may be co-administered with at least one opioid, preferably a μ opioid receptor modulator compound. In certain embodiments, the combination of the compounds of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV, with at least one opioid, preferably a μ opioid receptor modulator compound, provides a synergistic analgesic effect. The utility of the instant combination product may be determined by those skilled in the art using established animal models. Suitable opioids include, without limitation, alfentanil, allylprodine, alphaprodine, anileridine, benzyl-morphine, bezitramide, buprenorphine, butorphanol, clonitazene, codeine, cyclazocine, desomorphine, dextromoramide, dezocine, diampromide, diamorphone, dihydrocodeine, dihydromorphine, dimenoxadol, dimepheptanol, dimethylthiambutene, dioaphetylbutyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, loperamide, meperidine (pethidine), meptazinol, metazocine, methadone, metopon, morphine, myrophine, nalbuphine, narceine, nicomorphine, norlevorphanol, normethadone, nalorphine, normorphine, norpinanone, opium, oxycodone, oxymorphone, papaveretum, pentazocine, phenadoxone, phenomorphan, phanazocine, phenoperidine, piminodine, piritramide, propheptazine, promedol, properidine, propiram, propoxyphene, sulfentanil, tilidine, tramadol, diastereoisomers thereof, pharmaceutically acceptable salts thereof, complexes thereof; and mixtures thereof.

The pain ameliorating and/or opioid combination products of the present compositions may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference,* 1999, the disclosure of which is hereby incorporated herein by reference, in its entirety.

In addition, the opioid component may further include one or more compounds that may be designed to enhance the analgesic potency of the opioid and/or to reduce analgesic tolerance development. Such compounds include, for example, dextromethorphan or other NMDA antagonists (Mao, M. J. et al., *Pain* 1996, 67, 361), L-364,718 and other CCK antagonists (Dourish, C. T. et al., *Eur J Pharmacol* 1988, 147, 469), NOS inhibitors (Bhargava, H. N. et al., *Neuropeptides* 1996, 30, 219), PKC inhibitors (Bilsky, E. J. et al., *J Pharmacol Exp Ther* 1996, 277, 484), and dynorphin antagonists or antisera (Nichols, M. L. et al., *Pain* 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

Compounds as described herein can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least 0.1% of active compound. The percentage of the compositions and preparations may, of course, be varied and may conveniently be, for example, from about 2 to about 6% of the weight of the unit. The amount of active compound in such therapeutically useful compositions is preferably such that a suitable dosage will be obtained.

Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze-drying technique that yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds as described herein that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage, based on physiological studies using rats, may generally range from about 0.01 mg to about 100 mg/kg of body weight per day, and all combinations and subcombinations of ranges and specific dosages therein. Alternatively, the therapeutic human dosage may be from about 0.4 mg to about 10 g or higher, and may be administered in several different dosage units from once to several times a day. Generally speaking, oral administration may require higher dosages.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

The compounds as described herein may also be formulated with other optional active ingredients, in addition to or instead of the optional opioids, and in addition to the optional pharmaceutical-acceptable carriers. Other active ingredients include, but are not limited to, antibiotics, antivirals, antifungals, anti-inflammatories, including steroidal and non-steroidal anti-inflammatories, anesthetics and mixtures thereof. Such additional ingredients include any of the following:

a. Antibacterial Agents

Aminoglycosides, such as Amikacin, Apramycin, Arbekacin, Bambermycins, Butirosin, Dibekacin, Dihydrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols, such as Azidamfenicol, Chloramphenicol, Chloramphenicol Palmirate, Chloramphenicol Pantothenate, Florfenicol, Thiamphenicol;

Ansamycins, such as Rifamide, Rifampin, Rifamycin and Rifaximin;

β-Lactams;

Carbapenems, such as Imipenem;

Cephalosporins, such as 1-Carba (dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefotetan and Cefoxitin;

Monobactams such as Aztreonam, Carumonam and Tigemonan;

Oxacephems such as Flomoxef and Moxolactam;

Penicillins such as Amidinocillin, Amdinocillin, Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydragamine, Penicillin G Potassium, Penicillin G. Procaine, Penicillin N, Penicillin O, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin and Ticarcillin;

Lincosumides such as Clindamycin and Lincomycin;

Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Spicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and others such as Cycloserine, Mupirocin, Tuberin.

b. Synthetic Antibacterials 2,4-Diaminopyrimidines such as Brodimoprim, Tetroxoprim and Trimethoprim;

Nitrofurans such as Furaltadone, Furazolium, Nifuradene, Nifuratel, Nifurfoline, Nifurpirinol, Nifurprazine, Nifurtoinol and Nitrofurantoin;

Quinolones and analogs thereof, such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Perfloxacin, Pipemnidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-β, Chloramine-T, Dichloramine-T, Formosulfathiazole, N.sup.2-Formyl-sulfisomidine, N.sup.4 -β-D-Glucosylsulfanilamide, Mafenide, 4'-(Methylsulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, sulfamidochrysoidine, Sulfamoxole, Sulfanilamide, Sulfanilamidomethanesulfonic Acid Triethanolamine Salt, 4-Sulfanilamidosalicyclic Acid, $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-sulfonyldianiline-N,N'-digalactoside, Sulfoxone and Thiazolsulfone;

Others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine and Xibomol.

c. Antifungal (Antibiotics)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin; and others, such as Azaserine, Griseofulvin, Oligomycins, Pyrrolnitrin, Siccanin, Tubercidin and Viridin.

d. Antifungal (Synthetic)

Allylamines such as Naftifine and terbinafine;

Imidazoles such as Bifonazole, Butoconazole, Chlordantoin, Chlormidazole, Cloconazole, Clotrimazole, Econazole, Enilconazole, Finticonazole, Isoconazole, Ketoconazole, Miconazole, Omoconazole, Oxiconazole Nitrate, Sulconazole and Tioconazole;

Triazoles such as Fluconazole, Itraconazole, Terconazole;

Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sulbentine, Tenonitrozole, Tolciclate, Tolindate, Tolnaftate, Tricetin, Ujothion, and Undecylenic Acid.

e. Antiglaucoma Agents

Antiglaucoma agents, such as Dapiprazoke, Dichlorphenamide, Dipivefrin and Pilocarpine.

f. Anti-Inflammatory Agents

Corticosteroids, aminoarylcarboxylic Acid Derivatives such as Etofenamate, Meclofenamic Acid, Mefanamic Acid, Niflumic Acid;

Arylacetic Acid Derivatives such as Acemetacin, Amfenac Cinmetacin, Clopirac, Diclofenac, Fenclofenac, Fenclorac, Fenclozic Acid, Fentiazac, Glucametacin, Isozepac, Lonazolac, Metiazinic Acid, Oxametacine, Proglumetacin, Sulindac, Tiaramide and Tolmetin;

Arylbutyric Acid Derivatives such as Butibufen and Fenbufen;

Arylcarboxylic Acids such as Clidanac, Ketorolac and Tinoridine;

Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid and Tiaprofenic Add;

Pyrazoles such as Mepirizole;

Pyrazolones such as Clofezone, Feprazone, Mofebutazone, Oxyphenbutazone, Phenylbutazone, Phenyl Pyrazolidininones, Suxibuzone and Thiazolinobutazone;

Salicylic Acid Derivatives such as Bromosaligenin, Fendosal, Glycol Salicylate, Mesalamine, 1-Naphthyl Salicylate, Olsalazine and Sulfasalazine;

Thiazinecarboxamides such as Droxicam, Isoxicam and Piroxicam;

Others such as e-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocyclic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4,6-di-tertiary-butyl-s-hydroxy-1,3-pyrimidines, Proquazone and Tenidap.

g. Antiseptics

Guanidines such as Alexidine, Ambazone, Chlorhexidine and Picloxydine;

Halogens/Halogen Compounds such as Bomyl Chloride, Calcium Iodate, Iodine, Iodine Monochloride, Iodine Trichloride, Iodoform, Povidone-Iodine, Sodium Hypochlorite, Sodium Iodate, Symclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chloroxylenol, Hexachlorophene, 1-Naphthyl Salicylate, 2,4,6-Tribromo-m-cresol and 3',4',5-Trichlorosalicylanilide;

Quinolines such as Aminoquinuride, Chloroxine, Chlorquinaldol, Cloxyquin, Ethylhydrocupreine, Halquinol, Hydrastine, 8-Hydroxyquinoline and Sulfate; and others, such as Boric Acid, Chloroazodin, m-Cresyl Acetate, Cupric sulfate and Ichthammol.

h. Antivirals

Purines/Pyrimidinones, such as 2-Acetyl-Pyridine 5-((2-pyridylamino)thiocarbonyl) Thiocarbonohydrazone, Acyclovir, Dideoxyadenosine, Dideoxycytidine, Dideoxyinosine, Edoxudine, Floxuridine, Ganciclovir, Idoxuridine, MADU, Pyridinone, Trifluridine, Vidrarbine and Zidovudline;

others such as Acetylleucine Monoethanolamine, Acridinamine, Alkylisooxazoles, Amantadine, Amidinomycin, Cuminaldehyde Thiosemicarbzone, Foscamet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

i. Agents for Neuralgia/Neuropathic Pain

Mild OTC (over the counter) analgesics, such as aspirin, acetaminophen, and ibuprophen.

Narcotic analgesics, such as codeine.

Anti seizure medications, such as carbamazepine, gabapentin, lamotrigine and phenyloin.

Anti-depressants, such as amitryptiline.

j. Agents for the Treatment of Depression

Selective serotonin re-uptake inhibitors (SSRIs), such as Fluoxetine, Paroxetine, Fluvoxamine, Citaprolam, and Sertraline.

Tricyclics, such as Imipramine, Amitriptyline, Desipramine, Nortriptyline Protriptyline, Trimipramine, Doxepin, Amoxapine, and Clomipramine.

Monoamine Oxidase Inhibitors (MAOIs), such as Tranylcypromine, Phenelzine, and Isocarboxazid.

Heterocyclics, such as Amoxipine, Maprotiline and Trazodone.

others such as Venlafaxine, Nefazodone and Mirtazapine.

k. Agents for the Treatment of Incontinence

Anticholinergic agents such as propantheline.

Antispasmodic medications such as oxybutenin, tolterodine, and flavoxate.

Tricyclic antidepressants such as imipramine, and doxepin.

Calcium channel blockers such as tolterodine.

Beta agonists such as terbutaline.

l. Anti-Parkinson's Agents

Deprenyl, Amantadine, Levodopa, and Carbidopa.

In yet another embodiment, the invention is directed to methods of binding opioid receptors, preferably δ opioid receptors, in a patient in need thereof, comprising the step of administering to said patient an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV. The δ opioid receptors may be located in the central nervous system or located peripherally to the central nervous system. In certain preferred embodiments, the binding of the present compounds modulates the activity, preferably as an agonist, of said opioid receptors. In certain preferred embodiments, the compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV does not substantially cross the blood-brain barrier. Preferably, the compounds as described herein are peripherally selective.

The spirocyclic heterocyclic derivatives of the present invention and pharmaceutical compositions containing these compounds may be utilized in a number of ways. In certain embodiments, the spirocyclic heterocyclic derivatives are ligands of the δ opioid receptor and are useful, inter alia, in methods for treating and/or preventing pain, gastrointestinal disorders, urogenital tract disorders including incontinence, for example, stress urinary incontinence, urge urinary incontinence and benigh prostatic hyperplasia, and overactive bladder disorder (see, e.g., R. B. Moreland et al., *Perspectives in Pharmacology, Vol.* 308(3), pp. 797-804 (2004) and M. O. Fraser, *Annual Reports in Medicinal Chemistry*, Chapter 6, pp. 51-60 (2003), the disclosures of which are hereby incorporated herein by reference, in their entireties), immunomodulatory disorders, inflammatory disorders, respiratory function disorders, depression, anxiety, mood disorders, stress-related disorders, sympathetic nervous system disorder, tussis, motor disorder, traumatic injury, stroke, cardiac arrhythmia, glaucoma, sexual dysfunction, shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts, and substance addiction. In certain other embodiments, the spirocyclic heterocyclic derivatives are ligands of the δ opioid receptor and are useful, inter alia, in methods for providing cardioprotection following myocardial infarction, in methods for providing and maintaining an anaesthetic state, and in methods of detecting, imaging or monitoring degeneration or dysfunction of opioid receptors in a patient.

Thus, in accordance with preferred embodiments of the invention, there are provided methods of preventing or treating pain, comprising the step of administering to said patient an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In certain preferred embodiments, the present methods of preventing or treating pain may further comprise the administration to a patient of an effective amount of an agent for the treatment of neuralgia and/or neuropathic pain.

In another embodiment, the invention is directed to methods for preventing or treating gastrointestinal dysfunction, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for preventing or treating a urogenital tract disorder, such as incontinence (including, for example, stress urinary incontinence and urge urinary incontinence, and overactive bladder), comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In certain preferred embodiments, the present methods of preventing or treating a urogenital tract disorder may further comprise the administration to a patient of an effective amount of an agent for the treatment of incontinence.

In another embodiment, the invention is directed to methods of preventing or treating an immunomodulatory disorder, comprising the step of administering to a patient in need thereof an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV. Immunomodulatory disorders include, but are not limited to, autoimmune diseases, collagen diseases, allergies, side effects associated with the administration of an anti-tumor agent, and side effects associated with the administration of an antiviral agent. Autoimmune diseases include, but are not limited to, arthritis, autoimmune disorders associated with skin grafts, autoimmune disorders associated with organ transplants, and autoimmune disorders associated with surgery.

In another embodiment, the invention is directed to methods of preventing or treating an inflammatory disorder, comprising the step of administering to a patient in need thereof an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV. Inflammatory disorders include, but are not limited to, arthritis, psoriasis, asthma, or inflammatory bowel disease.

In another embodiment, the invention is directed to methods of preventing or treating a respiratory function disorder, comprising the step of administering to a patient in need thereof an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV. Respiratory function disorders include but are not limited to asthma or lung edema.

In another embodiment, the invention is directed to methods for preventing or treating anxiety, comprising the step of administering to a patient in need of such treatment an effective amount of a compound as described hereiin including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for preventing or treating a mood disorder, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In certain preferred embodiments, the present methods of preventing or treating a mood disorder may further comprise the administration to a patient of an effective amount of an agent for the treatment of depression.

In another embodiment, the invention is directed to methods for preventing or treating a stress-related disorder, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV. Stress-related disorders include, but are not limited to, post-traumatic stress disorder, panic disorder, generalized anxiety disorder, social phobia, and obsessive compulsive disorder.

In another embodiment, the invention is directed to methods for preventing or treating attention deficit hyperactivity disorder, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for preventing or treating sympathetic nervous system disorders, including hypertension, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for preventing or treating tussis, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for preventing or treating a motor disorder, including tremors, Parkinson's disease, Tourette's syndrome and dyskenesia, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In certain preferred embodiments, the present methods of preventing or treating a motor disorder may further comprise the administration to a patient of an effective amount of an agent for the treatment of Parkinson's disease.

In another embodiment, the invention is directed to methods for treating a traumatic injury to the central nervous system, including the spinal cord or brain, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for preventing or treating stroke, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for preventing or treating cardiac arrhythmia, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for preventing or treating glaucoma, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for preventing or treating sexual dysfunction, including premature ejaculation, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for treating a condition selected from the group consisting of shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts, comprising the step of administering to a patient in need of such treatment an effective amount of a compound of the invention including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for treating substance addiction, including addictions to alcohol, nicotine or drugs such as opioids, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for improving organ and cell survival, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

Techniques for evaluating and/or employing the present compounds in methods for improving organ and cell survival and organ preservation are described, for example, in C. V. Borlongan et al., *Frontiers in Bioscience* (2004), 9(Suppl.), 3392-3398, Su, *Journal of Biomedical Science* (Basel) (2000), 7(3), 195-199, and U.S. Pat. No. 5,656,420, the disclosures of each of which are hereby incorporated herein by reference in their entireties.

In another embodiment, the invention is directed to methods for providing cardioprotection following myocardial infarction, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods for reducing the need for anesthesia, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV.

In another embodiment, the invention is directed to methods of producing or maintaining an anesthetic state, comprising the step of administering to a patient in need of such treatment an effective amount of a compound as described herein including, for example, a compound of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV. The method may further comprise the step of administering to said patient an anesthetic agent, which may be co-administered with compound(s) of the invention. Suitable anesthetic agents include, for example, an inhaled anaesthetic, a hypnotic, an anxiolytic, a neuromuscular blocker and an opioid. Thus, in the present embodiment, compounds of the invention may be useful as analgesic agents for use during general anesthesia and monitored anesthesia care. Combinations of agents with different properties may be used to achieve a balance of effects needed to maintain the anaesthetic state.

Additional diseases and/or disorders which may be treated and/or prevented with the compounds and pharmaceutical compositions of the present invention include those described, for example, in WO2004/062562 A2, WO 2004/063157 A1, WO 2004/063193 A1,
WO 2004/041801 A1, WO 2004/041784 A1, WO 2004/041800 A1, WO 2004/060321 A2,
WO 2004/035541 A1, WO 2004/035574 A2, WO 2004041802 A1, US 2004082612 A1,
WO 2004026819 A2, WO 2003057223 A1, WO 2003037342 A1, WO 2002094812 A1,
WO 2002094810 A1, WO 2002094794 A1, WO 2002094786 A1, WO 2002094785 A1,
WO 2002094784 A1, WO 2002094782 A1, WO 2002094783 A1, WO 2002094811 A1, the disclosures of each of which are hereby incorporated herein by reference in their entireties.

In certain embodiments, the present invention is directed to radiolabeled derivatives and isotopically labeled derivatives of compounds as described herein including, for example, compounds of formula XIV, XV, XVI, XVII, XVIII, XIX, XX, XXI, XXII, XXIII, XXIV, XXV, XXVI, XXVII, XXVIIA, XXVIII, XXIX, XXX, XXXI, XXXII, XXXIII and/or XXXIV. Suitable labels include, for example, $^2$H $^3$H, $^{11}$C, $^{13}$C, $^{13}$N, $^{15}$N, $^{15}$O, $^{18}$O, $^{18}$F and $^{34}$S. Such labeled derivatives may be useful for biological studies, for example, using positron emission tomography, for metabolite identification studies and the like. Such diagnostic imaging methods may comprise, for example, administering to a patient a radiolabeled derivative or isotopically labeled derivative of a compound of the invention, and imaging the patient, for example, by application of suitable energy, such as in positron emission tomography. Isotopically- and radio-labeled derivatives may be prepared utilizing techniques well known to the ordinarily skilled artisan.

The present invention will now be illustrated by reference to the following specific, non-limiting examples. Those skilled in the art of organic synthesis may be aware of still other synthetic routes to the invention compounds. The reagents and intermediates used herein are commercially available or may be prepared according to standard literature procedures.

Methods of Preparation

The examples listed in Tables 1, 2, and 3 may be prepared according to Schemes 1-57. The synthesis of compounds 1A-1U is outlined in Scheme 1. The 2'-hydroxyacetophenone derivatives 1.1a-1.1m were condensed with 1-Boc-4-piperidone 1.2 in neat pyrrolidine (method 1A) at room temperature or in refluxing methanol in the presence of pyrrolidine (method 1B) to provide N-Boc-spiro[2H-1-benzopyran-2,4'-piperidine]-4(3H)-one derivatives 1.3. Conversion of the ketones 1.3 to the enol triflate derivatives 1.5 was achieved using N-phenylbis(trifluoromethanesulphonimide) 1.4 as triflating reagent. Suzuki type coupling of the enol triflate derivatives 1.5 with either 4-(N,N-diethylaminocarbonyl) phenyl boronic acid 1.6 (commercially available from Combi-Blocks Inc.) or 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0) (method 1C) or palladium, 10 wt. % (dry basis) on activated carbon (method 1D), lithium chloride, and an aqueous solution of sodium carbonate afforded compounds 1.8 which were converted to the final products (compounds 1A-1T) under acidic conditions (method 1E: anhydrous HCl, diethyl ether, room temperature or method 1F: neat trifluoroacetic acid, room temperature). Demethylation of compound 1G using boron tribromide provided the corresponding phenolic derivative (compound 1U). The boronate derivative 1.7 was prepared in 4 steps from 2,5-dibromopyridine 1.9. Treatment of 2,5-dibromopyridine with n-butyllithium provided the corresponding lithiated derivative, which reacted with carbon dioxide to provide 5-bromopyridine-2-carboxylic acid 1.10. Treatment of the carboxylic acid derivative 1.10 with oxalyl chloride furnished the acyl chloride 1.11, which reacted with diethylamine 1.12 to provide 5-bromo-2-(N,N-diethylaminocarbonyl)-pyridine 1.13. Conversion of the aryl bromide 1.13 to the corresponding boron derivative 1.7 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene]palladium(II) dichloromethane adduct, abbreviated as [Pd(dppf) Cl$_2$.CH$_2$Cl$_2$].

The synthesis of compounds 2A-2F is outlined in Scheme 2. The 2'-5'-dihydroxyacetophenone derivative 2.1 was condensed with 1-Boc-4-piperidone 1.2 in refluxing methanol in the presence of pyrrolidine to provide N-Boc-spiro[2H-1-benzopyran-2,4'-piperidine]-4(3H)-one derivative 2.2 which was converted to the silyl ether derivative 2.4 using tert-butyldimethylsilyl chloride 2.3. Conversion of the ketone 2.4 to the enol triflate derivative 2.5 was achieved using N-phenylbis(trifluoromethanesulphonimide) 1.4 as triflating reagent. Suzuki type coupling of the enol triflate derivative 2.5 with either 4-(N,N-diethylaminocarbonyl)-phenyl boronic acid 1.6 or 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0) (method 1C) or palladium, 10 wt. % (dry basis) on activated carbon (method 1D), lithium chloride, and an aqueous solution of sodium carbonate afforded compounds 2.6. Removal of the silyl protecting group of 2.6 using a solution of tetrabutylammonium fluoride (TBAF) in tetrahydrofuran gave the phenolic derivatives 2.7 which were converted to the final products compounds 2A and 2B under acidic conditions. Preparation of each of the ether derivatives 2.9 from the phenols 2.7 was achieved by alkylation reaction using the appropriate alkyl bromide (2.8a, 2.8b) (method 2A) or alkyl iodide (2.8c) reagent (method 2C). In some instances, the ether derivatives 2.9 were also obtained from the phenols 2.7 using the Mitsunobu conditions, i.e., condensation of the phenols 2.7 with the appropriate alcohol (2.8d, 2.8e) in the presence of triphenylphosphine and diisopropyl azodicarboxylate (DIAD) (method 2B). Treatment of the Boc derivatives 2.9 with hydrochloric acid provided the final compounds 2C-F.

The synthesis of compounds 3A-AC is outlined in Scheme 3. Conversion of the phenols 2.7 to the triflate derivatives 3.1 was achieved using the triflating reagent N-phenylbis(trifluoromethanesulphonimide) 1.4. Palladium catalyzed carbonylation of 3.1, conducted in methanol or in a mixture dimethylsulfoxide/methanol using palladium (II) acetate, 1,1'-bis(diphenylphosphino)ferrocene (dppf) and carbon monoxide, provided the methyl esters 3.2 which were hydrolyzed under basic conditions to give the carboxylic acid derivatives 3.3. Coupling of the carboxylic acids 3.3 with various amines (3.4a-3.4q) using O-benzotriazol-1-yl-N,N,N',N'-tetramethyluronium tetrafluoroborate (TBTU) as coupling agent afforded the primary, secondary, and tertiary amides 3.5. Treatment of the Boc derivatives 3.2, 3.3 and 3.5 with hydrochloric acid provided the final compounds 3A-3Y. Suzuki type coupling of the triflate derivative 3.1a (X=CH) with various organoboron reagents (3.6a-3.6d) in ethylene glycol dimethyl ether in the presence of tetrakis triphenylphosphine palladium (0), and/or dichloro[1,1'-bis(diphenylphosphino) ferrocene]palladium(II)dichloromethane, [Pd(dppf) Cl$_2$CH$_2$Cl$_2$], lithium chloride, and an aqueous solution of sodium carbonate afforded compounds 3.7 which were converted to the final products (compounds 3Z-3AC) under acidic conditions.

The synthesis of compounds 4A-4I is outlined in Scheme 4. Treatment of compound 1A with trifluoroacetic anhydride in tetrahydrofuran in the presence of triethylamine provided the trifluoroacetamide derivative 4.2 which was converted to the sulfonyl chloride 4.4 using sulfur trioxide N,N-dimethylformamide complex (4.3) as sulfating agent. Condensation of 4.4 with various primary and secondary amines (3.4, 4.5) afforded the sulfonamide derivatives 4.6 which were converted to the compounds 4A-4G under basic conditions. Treatment of the sulfonyl chloride 4.4 with ammonium hydroxide in acetonitrile provided the sulfonamide compound 4H, which was further protected as its tert-butyloxycarbonyl (Boc) derivative 4.8 buy treatment with tert-butyloxycarbonyl anhydride (4.7). Acetylation of 4.8 using acetic anhydride (4.9) gave the acetylsulfonamide derivative 4.10 which was converted to compound 4I by treatment with iodotrimethylsilane.

The synthesis of compound 5A is described in Scheme 5. Condensation of hydrazine hydrate (5.1) with the sulfonyl chloride derivative 4.4 provided the sulfonyl hydrazide 5.2, which was converted to the sulfone 5.3 by treatment with methyl iodide (2.8c) in the presence of sodium acetate. Deprotection of the trifluoroacetamide protecting group of 5.3 under basic conditions (potassium carbonate, methanol/tetrahydrofuran/water) provided the final compound 5A.

The synthesis of compounds 6A-6E is described in Scheme 6. Nitration of the trifluoroacetamide 4.2 using nitronium tetrafluoroborate complex (6.1) as nitrating reagent provided predominantly the mono-nitro isomer 6.2. Reduction of the nitro functionality of 6.2 using tin(II) chloride dihydrate (6.3) gave the aniline derivative 6.4, which reacted with the sulfonyl chloride derivatives 6.5 or with acetyl chloride (6.7) to provide the sulfonamides 6.6 or the acetamide 6.8, respectively. Deprotection of the trifluoroacetamide protecting group of 6.2, 6.4, 6.6 and 6.8 under basic conditions (potassium carbonate, methanol/tetrahydrofuran/water) provided the final compounds (compounds 6A-6E).

The synthesis of compounds 7A-7E is described in Scheme 7. Buchwald type coupling of the triflate derivative 3.1a with diphenylmethanimine (7.1) in toluene in the presence of tris (dibenzylideneacetone)dipalladium (0) [Pd$_2$(dba)$_3$], 1,1'-bis (diphenylphosphino)ferrocene (dppf) and sodium tert-butoxide afforded the benzophenone imine derivative 7.2, which was converted to the aniline 7.3 by treatment with hydroxylamine hydrochloride in the presence of sodium acetate. Treatment of 7.3 with methanesulfonyl chloride (7.4) in dichloromethane in the presence of triethylamine provided the bis-methanesulfonamide 7.5, which was hydrolyzed to the mono methanesulfonamide derivative 7.6 under basic conditions. Deprotection of the tert-butyloxycarbonyl protecting group of 7.6 under acidic conditions provided the final compound 7A. Compound 7B was obtained in two steps from 7.6. Alkylation of 7.6 with methyl iodide (2.8c) in tetrahydrofuran in the presence of sodium hydride provided the N-methylsulfonamide 7.7, which was converted to compound 7B under acidic conditions. Treatment of the aniline derivative 6.4 with methanesulfonyl chloride (7.4) in dichloromethane in the presence of triethylamine provided the bis-methanesulfonamide 7.8, which was hydrolyzed to the mono-methanesulfonamide derivative compound 7A under basic conditions. During the course of this reaction, the N-methyl piperidine derivative compound 7C was identified as a side product. The separation of the mixture containing compounds 7A and 7C was achieved by first treating the mixture of compounds 7A/7C with tert-butyloxycarbonyl anhydride (4.7) which provided the Boc derivative 7.6 and unreacted compound 7C, followed by purification of compound 7C using flash colum chromatography. Buchwald type coupling of the triflate derivative 3.1a with pyrrolidine (3.4k) or morpholine (3.4p) in ethylene glycol dimethyl ether in the presence of tris(dibenzylideneacetone)dipalladium (0) [Pd$_2$ (dba)$_3$], the phosphine ligand 2-(di-t-butylphosphino)biphenyl 7.9 and potassium phosphate afforded the derivatives 7.10, which were converted to compounds 7D,E under acidic conditions.

The synthesis of compounds 8A-8F is outlined in Scheme 8. The 2'-3'-dihydroxyacetophenone derivative 8.1 was condensed with 1-Boc-4-piperidone 1.2 in refluxing methanol in the presence of pyrrolidine to provide the N-Boc-spiro[2H-1-benzopyran-2,4'-piperidine]-4(3H)-one derivative 8.2 which was converted to the silyl ether derivative 8.3 using tert-butyldimethylsilyl chloride 2.3. The ketone 8.3 was converted to the enol triflate derivative 8.4 using the triflating reagent N-phenylbis(trifluoromethanesulphonimide) 1.4. Suzuki type coupling of the enol triflate derivative 8.4 with either 4-(N,N-diethylaminocarbonyl)phenyl boronic acid 1.6 or 2-(N,N-diethylaminocarbonyl)-5-(4,4,5,5-tetramethyl-1,3,2-dioxoborolan-2-yl)pyridine 1.7 in ethylene glycol dimethyl ether in the presence of palladium, 10 wt. % (dry basis) on activated carbon, lithium chloride, and an aqueous solution of sodium carbonate afforded compounds 8.5. Removal of the silyl protecting group of 8.5 using a solution of tetrabutylammonium fluoride (TBAF) in tetrahydrofuran gave the phenolic derivatives 8.6 which were converted to the final products (compounds 8A and 8B) under acidic conditions. Preparation of the ether derivatives 8.7 from the phenols 8.6 was achieved by alkylation using the appropriate alkyl bromide (2.8a) or methyl iodide (2.8c) reagent. Treatment of the Boc derivatives 8.7 with hydrochloric acid provided the final compounds 8C-8F.

The synthesis of compounds 9A-9B is outlined in Scheme 9. The 2'-4'-dihydroxyacetophenone derivative 9.1 was condensed with 1-Boc-4-piperidone 1.2 in refluxing methanol in the presence of pyrrolidine to provide the N-Boc-spiro[2H-1-benzopyran-2,4'-piperidine]-4(3H)-one derivative 9.2 which was converted to the silyl ether derivative 9.3 using tert-butyldimethylsilyl chloride 2.3. Conversion of the ketone 9.3 to the enol triflate derivative 9.4 was achieved using N-phenylbis(trifluoromethanesulphonimide) 1.4 as triflating reagent. Suzuki type coupling of the enol triflate derivative 9.4 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the phenolic derivative 9.5 (simultaneous removal of the silyl protecting group occurred under the Suzuki coupling conditions). Alkylation of the phenol 9.5 with (bromomethyl) cyclopropane (2.8a) in acetone in the presence of potassium carbonate provided the ether derivative 9.6 which was converted to compound 9A under acidic conditions. Treatment of the phenol 9.5 with methyl chlorodifluoroacetate (9.7) in N,N-dimethylformamide in the presence of cesium carbonate provided the ether derivative 9.8 which was converted to compound 9B under acidic conditions.

The synthesis of compounds 10A-10J is outlined in Scheme 10. Conversion of the phenol 9.5 to the triflate derivative 10.1 was achieved using N-phenylbis(trifluoromethanesulphonimide) 1.4 as triflating reagent. Palladium catalyzed carbonylation of 10.1, conducted in a mixture N,N-dimethylformamide/methanol using palladium (II) acetate, 1,1'-bis (diphenylphosphino)ferrocene (dppf), and carbon monoxide, provided the methyl ester 10.2 which was hydrolyzed under basic conditions to give the carboxylic acid derivative 10.3. Coupling of the carboxylic acid 10.3 with various amines (3.4a,c,j,k,p; 1.12) using either O-(7-azabenzotriazol-1-yl)-N,N,N',N'-tetramethyluronium hexafluorophosphate (HATU) (method 10B) or O-benzotriazol-1-yl-N,N,N',N'-tetramethyluronium tetrafluoroborate (TBTU) (method 10A) as coupling agents afforded the primary, secondary, and tertiary amides 10.4. The dimethylamide derivative 10.4b ($R_1$=H, $R_2$=CH$_3$) was obtained by heating a mixture of the ester 10.2 with methylamine (3.4b) in methanol in a sealed tube. Treatment of the Boc derivatives 10.2, 10.3 and 10.4 with hydrochloric acid provided the final compounds 10A-10I. Treatment of the ester 10.2 with lithium borohydride in tetrahydrofuran provided the primary alcohol 10.5 which was converted to the compound 10J under acidic conditions.

The synthesis of compounds 11A-11I is outlined in Scheme 11. The 2'-6'-dihydroxyacetophenone derivative 11.1 was condensed with 1-Boc-4-piperidone 1.2 in refluxing methanol in the presence of pyrrolidine to provide the N-Boc-spiro[2H-1-benzopyran-2,4'-piperidine]-4(3H)-one derivative 11.2 which was converted to the methoxymethyl (MOM) ether derivative 11.4 using chloro(methoxy)methane (11.3). Conversion of the ketone 11.4 to the enol triflate derivative 11.5 was achieved using N-phenylbis(trifluoromethanesulphonimide) 1.4 as triflating reagent. Suzuki type coupling of the enol triflate derivative 11.5 with either 4-(N,N-diethylaminocarbonyl)phenyl boronic acid 1.6 or 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded compounds 11.6. Removal of the MOM and the Boc protecting groups of 11.6 in methanol at room temperature in the presence of hydrochloric acid (anhydrous solution in dioxane) afforded the phenolic compounds 11A and 11B which were converted to the corresponding Boc derivatives 11.7 by treatment with tert-butyloxycarbonyl anhydride (4.7). Preparation of the ether derivatives 11.9a [X=CH; R=CH$_2$c(C$_3$H$_5$)], 11.9b [X=N; R=CH$_2$c(C$_3$H$_5$)] and 11.9d [X=N; R=c(C$_5$H$_9$)] from the corresponding phenols 11.7a [X=CH] or 11.7b [X=N] was achieved using the Mitsunobu conditions, i.e., condensation of the phenols 11.7a or 11.7b with cyclopropylmethanol (2.8e) or cyclopentanol (11.10) in dichloromethane in the presence of triphenylphosphine and diethyl azodicarboxylate (DEAD). The cyclobutyl ether 11.9c [X=CH; R=c(C$_4$H$_7$)] was obtained by alkylation of the corresponding phenol 11.7a [X=CH] with bromocyclobutane in acetone in the presence of potassium carbonate. Treatment of the Boc derivatives 11.9 with hydrochloric acid provided the final compounds 11C-11F. Treatment of the phenol 11.2 with methyl chlorodifluoroacetate (9.7) in N,N-dimethylformamide in the presence of cesium carbonate provided the ether derivative 11.11. Conversion of the ketone 11.11 to the enol triflate derivative-11.12 was achieved using N-phenylbis(trifluoromethanesulphonimide) 1.4 as triflating reagent. Suzuki type coupling of the enol triflate derivative 11.12 with either 4-(N,N-diethylaminocarbonyl)phenyl boronic acid 1.6 or 2-(N,N-diethylaminocarbonyl)-5-(4,4,5,5-tetramethyl-1,3,2-dioxoborolan-2-yl)pyridine 1.7 in dioxane in the presence of dichloro[1,1'-bis(diphenylphosphino)ferrocene]palladium(II) dichloromethane adduct, potassium phosphate, and potassium bromide, afforded compounds 11.13. Removal of the Boc protecting group of 11.13 in dichloromethane at room temperature in the presence of hydrochloric acid (anhydrous solution in diethyl ether) afforded the compounds 11G and 11H. Conversion of the aryl bromide 32.2b to the corresponding boron derivative 11.14 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene]palladium(II) dichloromethane adduct. Suzuki type coupling of the enol triflate derivative 11.5 with the boron derivative 11.14 in ethylene glycol dimethyl ether in the presence of tetrakis triphenylphosphine palladium (0), potassium bromide and potassium phosphate afforded compound 11.15. Removal of the Boc and the MOM protecting groups of 11.15 in methanol at room temperature in the presence of hydrochloric acid (anhydrous solution in diethyl ether) afforded the compound 11I.

The synthesis of compounds 12A-12L is outlined in Scheme 12. Conversion of the phenol 11.2 to the triflate derivative 12.1 was achieved using N-phenylbis(trifluoromethanesulphonimide) 1.4 as triflating reagent. Palladium catalyzed Negishi-type coupling of 12.1 with methylzinc chloride (12.2a), propylzinc bromide (12.2b), or butylzinc bromide (12.2c), conducted in tetrahydrofuran using tetrakis triphenylphosphine palladium (0) as catalyst, provided the ketones 12.3. Conversion of the ketones 12.3 to the enol triflate derivatives 12.4 was achieved using N-phenylbis(trifluoromethanesulphonimide) 1.4 as triflating reagent. Suzuki type coupling of the enol triflate derivative 12.4 with 4-(N,N-diethylaminocarbonyl)phenyl boronic acid 1.6 or 2-(N,N-diethylaminocarbonyl)-5-(4,4,5,5-tetramethyl-1,3,2-dioxoborolan-2-yl)pyridine 1.7 using either method 1C (tetrakis triphenylphosphine palladium (0), lithium chloride, aqueous solution of sodium carbonate, ethylene glycol dimethyl ether) or method 12A (tetrakis triphenylphosphine palladium (0), potassium bromide, potassium phosphate, dioxane) afforded compounds 12.5. Removal of the Boc protecting group of 12.5 in dichloromethane at room temperature in the presence of hydrochloric acid (anhydrous solution in diethyl ether) afforded compounds 12A and 12H-12L. Palladium catalyzed carbonylation of 12.1, conducted in a mixture N,N-dimethylformamide/methanol using palladium (II) acetate, 1,3-bis(diphenylphosphino)propane (dppp) and carbon monoxide, provided the methyl ester 12.6 which was hydrolyzed under basic conditions (lithium hydroxide, methanol/tetrahydrofuran) to give the carboxylic acid derivative 12.7. Coupling of the carboxylic acid 12.7 with dimethylamine (3.4j) using O-benzotriazol-1-yl-N,N,N',N'-tetramethyluronium tetrafluoroborate (TBTU) as coupling agent afforded the dimethylaminocarbonyl derivative 12.8. Conversion of 12.8 to the enol triflate derivative 12.9 was achieved using N-phenylbis(trifluoromethanesulphonimide) 1.4 as triflating reagent. Suzuki type coupling of the enol triflate derivative 12.9 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded compound 12.10. Removal of the Boc protecting group of 12.10 in dichloromethane at room temperature in the presence of hydrochloric acid (anhydrous solution in diethyl ether) afforded compound 12G ($R_1$=$R_2$=$CH_3$). Conversion of 12.6 to the enol triflate derivative 12.11 was achieved using N-phenylbis(trifluoromethanesulphonimide) 1.4 as triflating reagent. Suzuki type coupling of the enol triflate derivative 12.11 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the ester 12.12 which was hydrolyzed under basic conditions (potassium tert-butoxide, diethyl ether, water) to give the carboxylic acid 12.13. Coupling of the carboxylic acid 12.13 with various amines (12.15 or 3.4b-3.4d) using O-benzotriazol-1-yl-N,N,N',N'-tetramethyluronium tetrafluoroborate (TBTU) as coupling agent afforded the primary and secondary aminocarbonyl derivatives 12.14. Treatment of the Boc derivatives 12.13 and 12.14 with hydrochloric acid provided the final compounds 12B-12F.

The synthesis of compounds 13A-13S is outlined in Scheme 13. The 2'-hydroxyacetophenone derivative 1.1a was condensed with 1-Boc-4-piperidone 1.2 in refluxing methanol in the presence of pyrrolidine to provide N-Boc-spiro[2H-1-benzopyran-2,4'-piperidine]-4(3H)-one 1.3a. Conversion of 1.3a to the enol triflate derivative 1.5a was achieved using N-phenylbis(trifluoromethanesulphonimide) 1.4 as triflating reagent. Suzuki type coupling of the enol triflate derivative 1.5a with 4-(methoxycarbonyl)phenylboronic acid (13.1) in ethylene glycol dimethyl ether in the presence of tetrakis triphenylphosphine palladium (0), lithium chloride, and an aqueous solution of sodium carbonate afforded the ester 13.2 which was hydrolyzed under basic conditions (lithium hydroxide, methanol/tetrahydrofuran/water) to give the carboxylic acid 13.3. Coupling of the carboxylic acid 13.3 with various amines (3.4a-3.4c, 3.4e, 3.4j-3.4k, 3.4o-3.4q; 13.4a-13.4h) using O-benzotriazol-1-yl-N,N,N',N'-tetramethyluronium tetrafluoroborate (TBTU) as coupling agent afforded the primary, secondary, and tertiary aminocarbonyl derivatives 13.5. Treatment of the Boc derivatives 13.3 and 13.5 with hydrochloric acid provided the final compounds 13A-13R. Hydrolysis of compound 13O under basic conditions (sodium hydroxide, ethanol/tetrahydrofuran) provided the carboxylic acid compound 13S.

The synthesis of compounds 14A-14C is outlined in Scheme 14. Suzuki type coupling of the enol triflate derivative 1.5a with 4-cyanophenylboronic acid (14.1) in ethylene glycol dimethyl ether in the presence of tetrakis triphenylphosphine palladium (0), lithium chloride, and an aqueous solution of sodium carbonate afforded the cyanide 14.2 which was converted to the tetrazole 14.4 using sodium azide (14.3) and zinc bromide in a solution isopropanol/water. Alkylation of 14.4 with methyl iodide (2.8c) in N,N-dimethylformamide in the presence of triethylamine afforded the two regioisomers 14.5 (major isomer) and 14.6 (minor isomer) separated by silica gel column chromatography. The Boc protecting group of 14.4, 14.5, and 14.6 was removed using hydrochloric acid to generate the compounds 14A-14C. Alternatively, the Boc protecting group of 14.4 was also removed using trifluoroacetic acid to give 14A.

The synthesis of compounds 15A-15N is outlined in Scheme 15. Alkylation of 14.4 with the alkyl bromide derivatives 15.1a-15.1e in N,N-dimethylformamide in the presence of triethylamine afforded the regioisomers 15.2 (major isomers) and 15.3 (minor isomers) separated by silica gel column chromatography. The Boc protecting group of 15.2 and 15.3 was removed using hydrochloric acid to generate the compounds 15A-15J. Hydrolysis of compounds 15A or 15C-15E under basic conditions (sodium hydroxide, methanol (or ethanol)/tetrahydrofuran/water) provided the corresponding carboxylic acids compounds 15K-15N, respectively. In some instances, compounds 15K-15N were also obtained in two steps from 15.2, i.e. by basic hydrolysis of the ester functionality of 15.2 followed by deprotection of the Boc derivatives 15.4 under acidic conditions.

The synthesis of compounds 16A-16C is outlined in Scheme 16. Suzuki type coupling of the enol triflate derivative 1.5a with 3-cyanophenylboronic acid (16.1) in ethylene glycol dimethyl ether in the presence of tetrakis triphenylphosphine palladium (0), lithium chloride, and an aqueous solution of sodium carbonate afforded the cyanide 16.2 which was converted to the tetrazole 16.3 using sodium azide (14.3) and zinc bromide in a solution isopropanol/water. Alkylation of 16.3 with methyl iodide (2.8c) in N,N-dimethylformamide in the presence of triethylamine afforded the two regioisomers 16.4 (major isomer) and 16.5 (minor isomer) separated by silica gel column chromatography. The Boc protecting group of 16.3, 16.4, and 16.5 was removed using hydrochloric acid to generate the compounds 16A-16C.

The synthesis of compounds 17A-17F is outlined in Scheme 17. Alkylation of 16.3 with the alkyl bromide derivatives 15.1a or 15.1c in N,N-dimethylformamide in the presence of triethylamine afforded the regioisomers 17.1 (major isomers) and 17.2 (minor isomers) separated by silica gel column chromatography. Alkylation of 16.3 with 4-(2-bromoethyl)morpholine (17.3) in N,N-dimethylformamide in the presence of triethylamine afforded the isomer 17.4. The Boc protecting group of 17.1, 17.2, and 17.4 was removed using hydrochloric acid to generate the compounds 17A-17D. Hydrolysis of compounds 17A and 17B under basic conditions (sodium hydroxide, methanol/tetrahydrofuran/water) provided the corresponding carboxylic acids compound 17E and compound 17F, respectively. In some instances compounds 17E and 17F could also be obtained in two steps from 17.1, i.e. by basic hydrolysis of the ester functionality of 17.1 followed by deprotection of the Boc derivatives 17.5 under acidic conditions.

The synthesis of compounds 18A-18C is outlined in Scheme 18. Coupling of the carboxylic acid 13.3 with ammonium chloride (3.4a) in acetonitrile in the presence of diisopropylethylamine using O-benzotriazol-1-yl-N,N,N',N'-tetramethyluronium tetrafluoroborate (TBTU) as coupling agent afforded the primary aminocarbonyl derivative 13.5a which was converted to the thioamide 18.2 using the Lawesson's reagent (18.1) [2,4-bis(4-methoxyphenyl)-1,3-dithia-2,4-diphosphetane-2,4-disulfide]. Condensation of the thioamide 18.2 with 1-bromo-3,3-dimethylbutan-2-one (18.3a) or 2-bromo-1-phenylethanone (18.3b) afforded the thiazole derivatives 18.4 which were converted to the final compounds (compounds 18A and 18B) under acidic conditions. Condensation of the nitrile derivative 14.2 with hydroxylamine hydrochloride (18.5) in ethanol in the presence of triethylamine afforded the N-hydroxybenzamidine derivative 18.6 which reacted with acetyl chloride (6.7) in refluxing pyridine to give the 1,2,4-oxadiazole derivative 18.7. Deprotection of the Boc functionality of 18.7 under acidic conditions afforded compound 18C.

The synthesis of compound 19A-19D is outlined in Scheme 19. The 2'-hydroxyacetophenone 1.1a was condensed with benzyl 4-oxopiperidine-1-carboxylate (19.1) in refluxing methanol in the presence of pyrrolidine to provide N-Cbz-spiro[2H-1-benzopyran-2,4'-piperidine]-4(3H)-one (19.2). Conversion of the ketone 19.2 to the enol triflate derivative 19.3 was achieved using N-phenylbis(trifluoromethanesulphonimide) 1.4 as triflating reagent. Conversion of the enol triflate 19.3 to the corresponding boron derivative 19.4 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene]palladium(II) dichloromethane adduct, abbreviated as [Pd(dppf)Cl$_2$.CH$_2$Cl$_2$]. Suzuki type coupling of the boronate derivative 19.4 with tert-butyl 4-bromophenylcarbamate 19.5 in ethylene glycol dimethyl ether in the presence of tetrakis triphenylphosphine palladium (0), lithium chloride, and an aqueous solution of sodium carbonate afforded the tert-butyloxycarbonyl (Boc) protected aniline derivative 19.6. Acidic hydrolysis of 19.6 provided the aniline derivative 19.7 which reacted with acyl chlorides 19.8a, 19.8b, isopropylsulfonyl chloride (6.5b) or ethyl isocyanate (19.11) to give the corresponding amide derivatives 19.9, sulfonamide derivative 19.10 or urea derivative 19.12, respectively. The derivatives 19.9, 19.10 and 19.12 were converted to compounds 19A-19D by treatment with iodotrimethylsilane.

The synthesis of compounds 20A-20R is outlined in Scheme 20. The tertiary amine derivatives compounds 20A-20R were obtained from the secondary amines of general formula 20I, by reductive amination methods (methods 20A or 20B) using the aldehydes 20.1a-20.1d and sodium cyanoborohydride as reducing agent or by alkylation method (method 20C) using the bromides 2.8a, 20.2a-e as the alkylating reagent.

The synthesis of compounds 21A-21F is outlined in Scheme 21. Condensation of 1-Boc-4-piperidone 1.2 with ethyl diazoacetate (21.1) in the presence of boron trifluoride diethyl etherate provided 1-tert-butyl 4-ethyl 3-oxoazepane-1,4-dicarboxylate in equilibrium with its enol form (21.2). Ester hydrolysis followed by decarboxylation of 21.2 under acidic conditions provided the azepan-3-one (21.3), which was protected as its Boc derivative 21.4 by treatment with tert-butyloxycarbonyl anhydride (4.7). The 2'-hydroxyacetophenone 1.1a was condensed with 21.4 in refluxing methanol in the presence of pyrrolidine to provide the racemic ketone 21.5. Conversion of 21.5 to the enol triflate derivative 21.6 was achieved using the triflating reagent N-phenylbis(trifluoromethanesulphonimide) 1.4. Suzuki type coupling of the enol triflate derivative 21.6 with 4-(N,N-diethylaminocarbonyl)phenyl boronic acid (1.6) in ethylene glycol dimethyl ether in the presence of tetrakis triphenylphosphine palladium (0), lithium chloride, and an aqueous solution of sodium carbonate afforded the racemic derivative 21.7, which was hydrolyzed under acidic conditions to give the compound 21A (racemic mixture). The two enantiomers derived from 21.7, i.e. compounds 21.7a and 21.7b, were separated by chiral HPLC. The pure enantiomers 21.7a and 21.7b were converted to compounds 21B and 21C, respectively under acidic conditions. Palladium catalyzed hydrogenation of compounds 21B and 21C afforded compounds 21D (diastereoisomeric mixture) and 21E (diastereoisomeric mixture), respectively. Treatment of compound 21A with benzyl chloroformate (21.8) in dichloromethane in the presence of triethylamine provided the Cbz-protected derivative 21.9, which was converted to the sulfonyl chloride 21.10 using sulfur trioxide N,N-dimethylformamide complex (4.3) as sulfating agent. Condensation of 21.10 with ethylamine (3.4c) in dichloromethane in the presence of triethylamine, afforded the ethyl sulfonamide derivative 21.11 which was converted to compound 21F by treatment with iodotrimethylsilane.

The synthesis of compounds 22A-22F is outlined in Scheme 22. Treatment of compound 21B (most active enantiomer) with trifluoroacetic anhydride (4.1) in tetrahydrofuran in the presence of triethylamine provided the trifluoroacetamide derivative 22.1 which was converted to the sulfonyl chloride 22.2 using sulfur trioxide N,N-dimethylformamide complex (4.3) as sulfating agent. Condensation of 22.2 with various primary amines (3.4b, 3.4c, 3.4d, 3.4g) afforded the sulfonamide derivatives 22.3 which were converted to compounds 22A-22D under basic conditions. Condensation of hydrazine hydrate (5.1) with the sulfonyl chloride derivative 22.2 provided the sulfonyl hydrazide 22.4, which was converted to the sulfones 22.5 and 22.7 by treatment with methyl iodide (2.8c) and ethyl iodide (22.6), respectively, in the presence of sodium acetate. Deprotection of the trifluoroacetamide protecting group of 22.5 and 22.7 under basic conditions (potassium carbonate, methanol, water) provided the corresponding methyl sulfone (compound 22E) and ethyl sulfone (compound 22F) derivatives.

The synthesis of compounds 23A-23C is outlined in Scheme 23. The 2'-hydroxyacetophenone 1.1a was condensed with tert-butyl 3-oxopyrrolidine-1-carboxylate (23.1a) or tert-butyl 3-oxopiperidine-1-carboxylate (23.1b) in refluxing methanol in the presence of pyrrolidine to provide the racemic ketones 23.2a (n=0) and 23.2b (n=1), respectively. Conversion of the ketones 23.2 to the enol triflate derivatives 23.3 was achieved using N-phenylbis(trifluoromethanesulphonimide) 1.4 as triflating reagent. Suzuki type coupling of the enol triflate derivatives 23.3 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the Boc derivatives 23.4 which were converted to the final products compounds 23A and 23B (racemic mixtures) under acidic conditions. The 2'-hydroxyacetophenone 1.1a was also condensed with 1-Boc-4-nortropinone (23.5) in refluxing methanol in the presence of pyrrolidine to provide the ketone 23.6. Conversion of the ketone 23.6 to the enol triflate derivative 23.7 was achieved using N-phenylbis(trifluoromethanesulphonimide) 1.4 as triflating reagent. Suzuki type coupling of the enol triflate derivative 23.7 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the Boc derivative 23.8 which was converted to the final product compound 23C under acidic conditions.

The synthesis of compounds 24A-24G is outlined in Scheme 24. The 2'-hydroxyacetophenone 1.1a was condensed with 1,4-cyclohexanedione mono-ethylene ketal (24.1) in refluxing methanol in the presence of pyrrolidine to provide the ketone 24.2. Conversion of the ketone 24.2 to the enol triflate derivative 24.3 was achieved using N-phenylbis(trifluoromethanesulphonimide) 1.4 as triflating reagent. Suzuki type coupling of the enol triflate derivative 24.3 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the derivative 24.4 which was converted to the ketone compound 24A under acidic conditions. The reduction of the ketone compound 24A, conducted in tetrahydrofuran in the presence of sodium borohydride, provided the corresponding alcohol derivatives compounds 24B and 24C. Treatment of the ketone compound 24A with propylamine (3.4d) or dimethylamine (3.4j) under reductive amination conditions using sodium cyanoborohydride as reducing agent, provided the amines compounds 24D-24G.

The synthesis of compound 25A is outlined in Scheme 25. The 2'-hydroxyacetophenone 1.1a was also condensed with tetrahydropyran-4-one (25.1) in refluxing methanol in the presence of pyrrolidine to provide the ketone 25.2. Conversion of the ketone 25.2 to the enol triflate derivative 25.3 was achieved using N-phenylbis(trifluoromethanesulphonimide) 1.4 as triflating reagent. Suzuki type coupling of the enol triflate derivative 25.3 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded compound 25A.

The synthesis of compounds 26A-26B is outlined in Scheme 26. Palladium catalyzed Negishi-type coupling of 1.5a with 4-cyanobenzylzinc bromide (26.1) conducted in tetrahydrofuran using tetrakis triphenylphosphine palladium (0) as catalyst, provided the nitrile 26.2. Acidic hydroysis of the nitrile 26.2 provided the carboxylic acid derivatives 26.3a and 26.3b (compounds 26.3a and 26.3b were separated by column chromatography; however, the following step was conducted using the mixture 26.3a/26.3b). Treatment of the mixture 26.3a/26.3b with methanol in the presence of hydrochloric acid afforded the piperidine esters 26.4a/26.4b which were converted to the corresponding Boc derivatives 26.5a/26.5b by treatment with tert-butyloxycarbonyl anhydride (4.7). Hydrolysis of the esters 26.5a/26.5b in basic conditions gave the carboxylic acid derivatives 26.6a/26.6b. Coupling of the carboxylic acid derivatives 26.6a/26.6b with diethylamine (1.12) using O-benzotriazol-1-yl-N,N,N',N'-tetramethyluronium tetrafluoroborate (TBTU) as coupling agent afforded the dimethylaminocarbonyl derivatives 26.7a/26.7b.

Removal of the Boc protecting group of 26.7a/26.7b in dichloromethane at room temperature in the presence of hydrochloric acid (anhydrous solution in dioxane) afforded compounds 26A and 26.8 which were separated by column chromatography. Palladium catalyzed hydrogenation of compound 26.8 afforded compound 26B.

The synthesis of compounds 27A-27W is outlined in Scheme 27. The saturated derivatives (compounds 27A, 27D, 27G, 27H, 27K, 27N, and 27W, as their racemic mixtures) were obtained by hydrogenation of the unsaturated analogs (compounds 1A, 1D, 2C, 1N, 1O, 1S, and 1E), respectively, in methanol in the presence of palladium, 10 wt. % (dry basis) on activated carbon (method 27A) or palladium hydroxide, 20 wt. % Pd (dry basis) on carbon (Pearlman's catalyst (method 27B)). Hydrogenation of 11.6a in methanol in the presence of palladium hydroxide, 20 wt. % Pd (dry basis) on carbon (Pearlman's catalyst) provided the saturated derivative 27.1. Acidic hydrolysis of 27.1 provided compound 27T. Hydrolysis of 2.7a in methanol in the presence of palladium, 10 wt. % (dry basis) on activated carbon, provided the saturated derivative 27.6. Acidic hydrolysis of 27.6 provided the compound 27Q. Chiral separation of the enantiomers derived from 27.1 provided compounds 27.4 and 27.5. The enantiomers 27.4 and 27.5 were converted to compounds 27U and 27V, respectively under acidic conditions. Chiral separation of the enantiomers derived from each of the racemic compounds (compounds 27A, 27 D, 27G, 27H, 27K, 27N, 27Q and 27W) provided compounds 27B, 27E, 27I, 27L, 27O, 27R (pure enantiomer) and compounds 27C, 27F, 27J, 27M, 27P, 27S (pure enantiomer). Condensation of compound 27B with (1S)-(+)-10-camphorsulfonyl chloride (27.2) (used as chiral resolving agent) in dichloromethane in the presence of triethylamine provided the chiral sulfonamide derivative 27.3. The absolute configuration of 27.3 was determined by X-ray crystallography, therefore establishing the absolute configuration of compound 27B, and therefore by inference, its enantiomer, compound 29C.

The synthesis of compounds 28A-28E is outlined in Scheme 28. Condensation of benzyl 4-oxopiperidine-1-carboxylate (19.1) with ethyl cyanoacetate (28.1) in the presence of acetic acid and ammonium acetate gave the unsaturated ester 28.2. Compound 28.2 was subjected to conjugate addition by reaction with organo cuprate reagents derived from benzyl or methoxybenzyl magnesium chloride (28.3a and 28.3b, respectively) and copper (I) cyanide to yield the cyano esters 28.4. Treatment of the conjugate addition product 28.4a ($R^v$=H) with concentrated sulfuric acid at 90° C. provided the amino ketone 28.5. Treatment of 28.5 with benzyl chloroformate (21.8) in dichloromethane in the presence of triethylamine provided the corresponding Cbz-protected derivative 28.6a ($R^v$=H). Decarboxylation of 28.4b ($R^v$=OCH$_3$) by treatment with sodium chloride in dimethylsulfoxide containing small amount of water at 160° C. afforded the nitrile 28.9. Hydrolysis of the nitrile functionality of 28.9 to the methyl ester group by treatment with methanol in the presence of sulfuric acid provided the corresponding piperidine derivative (Cleavage of the Cbz protecting group of 28.9 occured during the course of the hydrolysis). Treatment of the piperidine derivative with benzyl chloroformate afforded the compound 28.10. The ester 28.10 was hydrolyzed with lithium hydroxide to furnish the carboxylic acid 28.11. Treatment of the acid 28.11 with oxalyl chloride followed by reaction of the resulting acyl chloride with aluminum chloride yielded the corresponding spiro piperidine derivative which was further protected as its CBz derivative 28.6b ($R^v$=OCH$_3$) by treatment with benzylchloroformate.

Conversion of the ketones 28.6 to the enol triflate derivatives 28.7 was achieved using N-phenylbis(trifluoromethanesulphonimide) 1.4 as triflating reagent. Suzuki type coupling of the enol triflate derivatives 28.7 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the derivatives 28.8 which were converted to the compounds 28A and 28B by treatment with iodotrimethylsilane. The compounds 28C and 28D (racemic mixtures) were obtained by hydrogenation of unsaturated derivatives 28.8 in methanol in the presence of palladium, 10 wt. % (dry basis) on activated carbon. Suzuki type coupling of the enol triflate derivative 28.7a ($R^v$=H) with 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded the derivative 28.12 which was converted to the compound 28E by treatment with iodotrimethylsilane.

The synthesis of compounds 29A-29D is outlined in Scheme 29. The Negishi coupling of the enol triflate 28.7a with 4-(ethoxycarbonyl)phenylzinc iodide (29.1) in tetrahydrofuran in the presence of tetrakis triphenylphosphine palladium (0) gave the ester 29.2, which was hydrolyzed with lithium hydroxide to afford the carboxylic acid 29.3. Coupling of the carboxylic acid 29.3 with isopropylamine (3.4h) or 1-ethylpropylamine (29.4) using 2-chloro-1-methylpyridinium iodide (Mukaiyama acylating reagent) as coupling agent afforded the secondary aminocarbonyl derivatives 29.5, which were converted to the compounds 29A and 29B by treatment with iodotrimethylsilane. Curtius rearrangement of the carboxylic acid 29.3 by reaction with diphenylphosphoryl azide (29.6) in the presence of tert-butyl alcohol provided the tert-butyloxycarbonyl (Boc) protected aniline derivative 29.7. Acidic hydrolysis of 29.7 provided the aniline derivative 29.8 which reacted with propionyl chloride 29.9 or methanesulfonyl chloride (7.4) to give the corresponding amide derivative 29.10 or sulfonamide derivative 29.11, respectively. The derivatives 29.10 and 29.11 were converted to compounds 29C and 29D, respectively, by treatment with iodotrimethylsilane.

The synthesis of compound 30A is outlined in Scheme 30. Wittig type condensation of 1-benzoyl-4-piperidone (30.1) with methyl(triphenylphosphoranylidene)acetate (30.2) in toluene gave the unsaturated ester 30.3. Compound 30.3 was subjected to conjugate addition by reaction with benzenethiol (30.4) to yield the thioether 30.5. Treatment of the conjugate addition product 30.5 with concentrated sulfuric acid provided the cyclized product 30.6, which was converted to the sulfone 30.7 by oxidation using a solution of hydrogen peroxide in glacial acetic acid. Acidic hydrolysis of 30.7 provided the amine 30.8, which was treated with tert-butyloxycarbonyl anhydride (4.7) to give the Boc protected derivative 30.9. Conversion of the ketone 30.9 to the enol triflate derivative 30.10 was achieved using N-phenylbis(trifluoromethanesulphonimide) 1.4 as triflating reagent. Suzuki type coupling of the enol triflate derivative 30.10 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the derivative 30.11 which was converted to compound 30A under acidic conditions.

The synthesis of compounds 31A-31AA is outlined in Scheme 31. Suzuki type coupling of the enol triflate derivative 1.5a with the commercially available boronic acid derivatives 13.1, 14.1, 16.1 or 31.1a-31.1u in ethylene glycol dimethyl ether in the presence of tetrakis triphenylphosphine palladium (0), lithium chloride, and an aqueous solution of sodium carbonate afforded compounds 13.2, 14.2, 16.2 and 31.2, respectively. Compounds 13.2, 14.2, 16.2 and 31.2 were converted to the final products compounds 31A-31X under acidic conditions (method 1E: anhydrous HCl, diethyl ether, room temperature or method 1F: neat trifluoroacetic acid (with optional dichloromethane), room temperature or method 31A: anhydrous HCl, methanol, dioxane, reflux). Treatment of the nitrile 16.2 with lithium aluminum hydride in tetrahydrofuran provided the diamine compound 31Y, which reacted with acetyl chloride (6.7) or methanesulfonyl chloride (7.4) to give the corresponding amide derivative compounds 31Z or the sulfonamide derivative compound 31AA, respectively.

The synthesis of compounds 32A-32Z is outlined in Scheme 32. Conversion of the enol triflate 1.5a to the corresponding boron derivative 32.1 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene]palladium(II) dichloromethane adduct, abbreviated as [Pd(dppf)Cl$_2$.CH$_2$Cl$_2$]. Suzuki type coupling of the boronate derivative 32.1 with various aryl bromide derivatives 32.2 under different conditions [method 1C: ethylene glycol dimethyl ether, tetrakis triphenylphosphine palladium (0), lithium chloride, aqueous solution of sodium carbonate; method 1D: ethylene glycol dimethyl ether, palladium, 10 wt. % (dry basis) on activated carbon, lithium chloride, aqueous solution of sodium carbonate; method 12A: tetrakis triphenylphosphine palladium (0), potassium bromide, potassium phosphate, dioxane] afforded the derivatives 32.3, which were converted to compounds 32A-32I or 32K-32Z under acidic conditions. The tert-butyl sulfonamide derivative compound 32.3b was converted to the sulfonamide compound 32J by treatment with trifluoroacetic acid. The derivatives 32.2 used in the Suzuki coupling step were prepared as follows. Coupling of the carboxylic acid 32.4 with diethylamine (1.12) using 2-chloro-1-methylpyridinium iodide (Mukalyama acylating reagent) as coupling agent afforded 2-(4-bromophenyl)-N,N-diethylacetamide (32.2a). The sulfone derivatives 32.2j-32.2p were obtained in two steps from 4-bromobenzenethiol (32.7). Alkylation of 32.7 with the alkyl bromide derivatives 20.2, 2.8 or 32.8 in acetonitrile in the presence of triethylamine (method 32A) or in N,N-dimethylformamide in the presence of sodium hydride (method 32B) provided the thioether derivatives 32.9, which were oxidized to the sulfone derivatives 32.2j-32.2p in glacial acetic acid in the presence of an aqueous solution of hydrogen peroxide. Coupling of 4-bromobenzene-1-sulfonyl chloride (32.5) with various amines (3.4, 1.12, 13.4 or 32.6) in tetrahydrofuran in the presence of triethylamine provided the sulfonamides 32.2b-32.2i. Acylation of N-methyl-4-bromoaniline (32.10) with various acyl chloride derivatives (19.8, 32.11 or 6.7) in dichloromethane in the presence of triethylamine provided the amides 32.2q-32.2u, 32.2x, 32.2y. The aryl bromides 32.2v and 32.2w are commercially available.

The synthesis of compounds 33A-33N is outlined in Scheme 33. Suzuki type coupling of the boronate derivative 32.1 with various aryl bromide derivatives 33.1 under different conditions [method 1C: ethylene glycol dimethyl ether, tetrakis triphenylphosphine palladium (0), lithium chloride, aqueous solution of sodium carbonate; method 1D: ethylene glycol dimethyl ether, palladium, 10 wt. % (dry basis) on activated carbon, lithium chloride, aqueous solution of sodium carbonate; method 33A: ethylene glycol dimethyl ether, dichloro[1,1'-bis(diphenylphosphino)ferrocene]palladium(II) dichloromethane adduct, abbreviated as [Pd(dppf)Cl$_2$.CH$_2$Cl$_2$], lithium chloride, potassium phosphate; method 33B: dioxane, tetrakis triphenylphosphine palladium (0), potassium bromide, potassium phosphate] afforded the derivatives 33.2, which were converted to compounds 33A-33K, 33M and 33N under acidic conditions. The derivatives 33.1 used in the Suzuki coupling step were either obtained from commercial sources (33.1 a-e,l,m) or prepared as follows. Coupling of 5-bromopyridine-3-carboxylic acid (33.3) or 6-bromopyridine-2-carboxylic acid (33.4) with diethylamine (1.12) using O-benzotriazol-1-yl-N,N,N',N'-tetramethyluronium tetrafluoroborate (TBTU) as coupling agent afforded the diethylaminocarbonyl derivative derivatives 33.1f and 33.1g, respectively. Treatment of 2,5-dibromopyridine (1.9) with n-butyllithium provided the corresponding lithiated derivative, which reacted with carbon dioxide to provide 5-bromopyridine-2-carboxylic acid 1.10. The carboxylic acid 1.10 was also obtained by acidic hydrolysis of commercially available 5-bromopyridine-2-carbonitrile (33.1e). Treatment of the carboxylic acid derivative 1.10 with oxalyl chloride furnished the acyl chloride 1.11, which reacted with dimethylamine (1.12), ethylamine (3.4c) or methylamine (3.4b) to provide the corresponding aminocarbonyl derivatives 33.1h, 33.1i and 33.1j, respectively. Treatment of commercially available 5-bromo-2-iodopyrimidine (33.5) with n-butyllithium provided the corresponding lithiated derivative, which reacted with carbon dioxide to provide 5-bromopyrimidine-2-carboxylic acid (33.6). Treatment of the carboxylic acid derivative 33.6 with oxalyl chloride furnished the acyl chloride 33.7, which reacted with diethylamine 1.12 to provide 5-bromo-2-(N,N-diethylaminoarbonyl)-pyrimidine 33.1k.

Hydrolysis of the nitrile derivative 33.2a under acidic conditions provided the carboxylic acid derivative compound 33E and compound 33L. Compound 33E and compound 33L were readily separated by column chromatography.

The synthesis of compounds 34A-34P is outlined in Scheme 34. Suzuki type coupling of the boronate derivative 32.1 with various aryl bromide derivatives 34.1 in ethylene glycol dimethyl ether in the presence of tetrakis triphenylphosphine palladium (0), lithium chloride, and an aqueous solution of sodium carbonate afforded compounds 34.2 which were converted to the final products compounds 34A-34P under acidic conditions. The derivatives 34.1 used in the Suzuki coupling step were prepared as follow. Coupling of 6-bromopyridine-3-carboxylic acid (34.3), 5-bromothiophene-2-carboxylic acid (34.4), 4-bromothiophene-2-carboxylic acid (34.7) or 5-bromofuran-2-carboxylic acid (34.6) with diethylamine (1.12) or diisopropylamine (3.4o) using O-benzotriazol-1-yl-N,N,N',N'-tetramethyluronium tetrafluoroborate (TBTU) as coupling agent afforded the diethylaminocarbonyl derivatives 34.1 a-d, f-i. Coupling of 5-bromothiophene-2-sulfonyl chloride (34.5) with diethylamine (1.12) in acetonitrile in the presence of triethylamine provided the sulfonamide 34.1e. Coupling of the commercially available carboxylic acid derivatives 34.8a-34.8f and 34.9 with diethylamine (1.12) using O-benzotriazol-1-yl-N,N,N',N'-tetramethyluronium tetrafluoroborate (TBTU) as coupling agent afforded the corresponding diethylaminocarbonyl derivatives 34.1j-34.1o and 34.1p.

The synthesis of compounds 35A and 35B is outlined in Scheme 35. Iodination of 3-hydroxybenzoic acid (35.1) afforded 3-hydroxy-4-iodobenzoic acid (35.2), which was converted to the methyl ester 35.3 under standard esterification conditions. Alkylation of the phenolic derivative 35.3 with methyl iodide (2.8c) in acetone in the presence of potassium carbonate afforded the methyl ether 35.4, which was converted to the carboxylic acid 35.5 in the presence of lithium hydroxide. Coupling of the carboxylic acid derivatives 35.5 with diethylamine (1.12) using O-benzotriazol-1-yl-N,N,N',N'-tetramethyluronium tetrafluoroborate (TBTU) as coupling agent afforded the corresponding diethylaminocarbonyl derivative 35.6. Demethylation of 35.6 using boron tribromide afforded the phenolic derivative 35.7 which was converted to the methyloxymethyl (MOM) ether derivative 35.8 using chloro(methoxy)methane 11.3. Suzuki type coupling of the boronate derivative 32.1 with 35.6 in ethylene glycol dimethyl ether in the presence of tetrakis triphenylphosphine palladium (0), lithium chloride, and an aqueous solution of sodium carbonate afforded compound 35.9 which was converted to the final product compound 35A under acidic conditions. Suzuki type coupling of the boronate derivative 32.1 with 35.8 in ethylene glycol dimethyl ether in the presence of palladium, 10 wt. % (dry basis) on activated carbon, lithium chloride, and an aqueous solution of sodium carbonate afforded compound 35.10 which was converted to the final product compound 35B under acidic conditions.

The synthesis of compounds 36A and 36B is outlined in Scheme 36. Coupling of 4-bromo-2-hydroxybenzoic acid (36.3) [obtained from 4-amino-2-hydroxybenzoic acid (36.1) under Sandmeyer conditions] with diethylamine (1.12) using O-(7-azabenzotriazol-1-yl)-N,N,N',N'-tetramethyluronium hexafluorophosphate (HATU) as coupling agent afforded the corresponding diethylaminocarbonyl derivative 36.4. Suzuki type coupling of the boronate derivative 32.1 with 36.4 in ethylene glycol dimethyl ether in the presence of tetrakis triphenylphosphine palladium (0), lithium chloride, and an aqueous solution of sodium carbonate afforded compound 36.5 which was converted to the final product (compound 36A) under acidic conditions. Compound 36B was obtained in 7 steps from 2-(3-methoxyphenyl)ethanamine (36.6). Coupling of 36.6 with ethyl chloroformate (36.7) afforded the ethyl carbamate derivative 36.8 which was cyclized to 3,4-dihydro-6-methoxyisoquinolin-1-(2H)-one (36.9) in the presence of polyphosphoric acid. Alkylation of 36.9 with ethyl iodide (36.10) in tetrahydrofuran in the presence of sodium hydride, afforded the methyl ether 36.11, which was converted to the phenolic derivative 36.12 by treatment with boron tribromide. Condensation of 36.12 with trifluoromethanesulfonic anhydride (36.13) in dichloromethane in the presence of pyridine afforded the triflate derivative 36.14. Suzuki type coupling of the boronate derivative 32.1 with 36.14 in N,N-dimethylformamide in the presence of dichloro[1,1'-bis(diphenylphosphino)ferrocene]palladium(II) dichloromethane adduct, abbreviated as [Pd(dppf)Cl$_2$.CH$_2$Cl$_2$], and potassium acetate afforded compound 36.15 which was converted to the final product (compound 36B) under acidic conditions.

The synthesis of compounds 37A-37B is outlined in Scheme 37. The 2'-hydroxyacetophenone 1.1a was condensed with 1-benzyl-3-methylpiperidin-4-one (37.1) (racemic mixture) in refluxing methanol in the presence of pyrrolidine to provide the racemic ketones 37.2 and 37.3. The diastereoisomers 37.2 and 37.3 were separated by column chromatography. Palladium catalyzed hydrogenation of 37.2 afforded the piperidine derivative 37.4, which was converted to 37.5 by treatment with tert-butyloxycarbonyl anhydride (4.7). Conversion of the ketone 37.5 to the enol triflate derivative 37.6 was achieved using N-phenylbis(trifluoromethanesulphonimide) 1.4 as triflating reagent. Suzuki type coupling of the enol triflate derivative 37.6 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the Boc derivative 37.7, which was converted to the final product compound 37A (racemic mixture) under acidic conditions. Similarly, palladium catalyzed hydrogenation of 37.3 afforded the piperidine derivative 37.8, which was converted to 37.9 by treatment with tert-butyloxycarbonyl anhydride (4.7). Conversion of the ketone 37.9 to the enol triflate derivative 37.10 was achieved using N-phenylbis(trifluoromethanesulphonimide) 1.4 as triflating reagent. Suzuki type coupling of the enol triflate derivative 37.10 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded the Boc derivative 37.11, which was converted to the final product compound 37B (racemic mixture) under acidic conditions.

The synthesis of compounds 38A-38D is outlined in Scheme 38. Condensation of benzyl 4-oxopiperidine-1-carboxylate (19.1) with 2,2-dimethyl-1,3-dioxane-4,6-dione (Meldrum's acid; 38.1) in the presence of pyridine and piperidine gave the derivative 38.2. Compound 38.2 was subjected to conjugate addition by reaction with organocuprate reagents derived from 4-fluorobenzyl magnesium chloride (38.3) and copper (I) iodide to yield, upon work-up, the sodium salt 38.4. Hydrolysis and decarboxylation of the conjugate addition product 38.4 proceeded by heating a solution of 38.4 in N,N-dimethylformamide in the presence of water. Treatment of the corresponding carboxylic acid derivative 38.5 with oxalyl chloride followed by reaction of the resulting acyl chloride with aluminum chloride yielded the corresponding spiro piperidine derivative which was further protected as its tert-butyloxycarbonyl (Boc) derivative 38.6 by treatment with tert-butyloxycarbonyl anhydride (4.7). Conversion of the ketone 38.6 to the enol triflate derivative 38.7 was achieved using N-phenylbis(trifluoromethanesulphonimide) 1.4 as triflating reagent. Suzuki type coupling of the enol triflate derivative 38.7 with 2-(N,N-diethylaminocarbonyl)-5-(4,4,5,5-tetramethyl-1,3,2-dioxoborolan-2-yl)pyridine 1.7 in dioxane in the presence of dichloro[1,1'-bis(diphenylphosphino)ferrocene]palladium(II) dichloromethane adduct {[Pd(dppf)Cl$_2$.CH$_2$Cl$_2$]}, and an aqueous solution of potassium carbonate afforded the derivative 38.8 which was converted to the compound 38A under acidic conditions. The compound 38B (racemic mixture) was obtained by hydrogenation of the unsaturated derivative 38A in methanol in the presence of palladium, 10 wt. % (dry basis) on activated carbon. Conversion of the enol triflate 38.7 to the corresponding boron derivative 38.9 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene]palladium(II) dichloromethane adduct {[Pd(dppf)Cl$_2$.CH$_2$Cl$_2$]}. Suzuki type coupling of the boron derivative 38.9 with the aryl iodide derivative 35.8 in dioxane in the presence of dichloro[1,1'-bis(diphenylphosphino)ferrocene]palladium(II) dichloromethane adduct {[Pd(dppf)Cl$_2$.CH$_2$Cl$_2$]}, and an aqueous solution of potassium carbonate afforded the derivative 38.10 which was converted to the compound 38C under acidic conditions. Hydrogenation of the unsaturated derivatives 38.10 in methanol in the presence of palladium, 10 wt. % (dry basis) on activated carbon provided the compound 38.11, which was converted to the compound 38D under acidic conditions.

The synthesis of compounds 39A-39G is outlined in Scheme 39. Compound 38.2 was subjected to conjugate addition by reaction with organocuprate reagents derived from benzyl magnesium chloride (28.3a) and copper (I) iodide to yield, upon work-up, the sodium salt 39.1. Hydrolysis and decarboxylation of the conjugate addition product 39.1 proceeded by heating a solution of 39.1 in N,N-dimethylformamide in the presence of water. Treatment of the corresponding carboxylic acid derivative 39.2 with oxalyl chloride followed by reaction of the resulting acyl chloride with aluminum chloride yielded the corresponding spiro piperidine derivative which was further protected as its CBz derivative 28.6a ($R^v$=H) by treatment with benzylchloroformate. Conversion of the ketone 28.6a to the enol triflate derivative 28.7a was achieved using N-phenylbis(trifluoromethanesulphonimide) 1.4 as triflating reagent. Suzuki type coupling of the enol triflate derivatives 28.7a 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded the derivative 28.12 which was converted to the compound 39A by hydrogenation in methanol in the presence of palladium, 10 wt. % (dry basis) on activated carbon. Treatment of compound 39A with tert-butyloxycarbonyl anhydride (4.7) provided the Boc derivative 39.3. Chiral separation of the enantiomers derived from 39.3 provided compounds 39.4 and 39.5. The enantiomers 39.4 and 39.5 were converted to compounds 39B and 39C, respectively under acidic conditions. Suzuki type coupling of the enol triflate derivatives 28.7a with N,N-diethyl-3-(methoxymethoxy)-4-(4,4,5,5-tetramethyl-1,3,2-dioxaborolan-2-yl)benzamide 39.6 in ethylene glycol dimethyl ether in the presence of tetrakis triphenylphosphine palladium (0), lithium chloride, and an aqueous solution of sodium carbonate afforded the derivative 39.7 which was converted to the compound 39D by treatment with iodotrimethylsilane followed by acidic cleavage of the MOM protecting group. Hydrogenation of 39.7 in methanol, in the presence of palladium, 10 wt. % (dry basis) on activated carbon, followed by acidic cleavage of the MOM protecting group, afforded compound 39E. Treatment of compound 39E with tert-butyloxycarbonyl anhydride (4.7) provided the Boc derivative 39.8. Chiral separation of the enantiomers derived from 39.8 provided compounds 39.9 and 39.10. The enantiomers 39.9 and 39.10 were converted to compounds 39F and 39G, respectively under acidic conditions.

The synthesis of compounds 40A-40C is outlined in Scheme 40. Compound 38.2 was subjected to conjugate addition by reaction with organocuprate reagents derived from 4-methoxybenzyl magnesium chloride (28.3b) and copper (I) iodide to yield, upon work-up, the sodium salt 40.1. Hydrolysis and decarboxylation of the conjugate addition product 40.1 proceeded by heating a solution of 40.1 in N,N-dimethylformamide in the presence of water. Treatment of the corresponding carboxylic acid derivative 28.11 with oxalyl chloride followed by reaction of the resulting acyl chloride with aluminum chloride yielded the corresponding spiro piperidine derivative which was further protected as its CBz derivative 28.6b ($R^v$=OCH$_3$) by treatment with benzylchloroformate. Conversion of the ketone 28.6b to the enol triflate derivative 28.7b was achieved using N-phenylbis(trifluoromethanesulphonimide) 1.4 as triflating reagent. Suzuki type coupling of the enol triflate derivatives 28.7b with 2-(N, N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded the derivative 40.2 which was converted to the compound 40A by treatment with iodotrimethylsilane. Hydrogenation of 40.2 in methanol in the presence of palladium, 10 wt. % (dry basis) on activated carbon afforded compound 40B (racemic mixture). Suzuki type coupling of the enol triflate derivatives 28.7b with N,N-diethyl-3-(methoxymethoxy)-4-(4,4,5,5-tetramethyl-1,3,2-dioxaborolan-2-yl)benzamide 39.6 in ethylene glycol dimethyl ether in the presence of tetrakis triphenylphosphine palladium (0), lithium chloride, and an aqueous solution of sodium carbonate afforded the derivative 40.3 which was converted to the compound 40C by treatment with iodotrimethylsilane.

The synthesis of compounds 41A-41E is outlined in Scheme 41. Coupling of the carboxylic acid 13.3 with N-ethyl-2-methoxyethanamine (41.1) using O-benzotriazol-1-yl-N,N,N',N'-tetramethyluronium tetrafluoroborate (TBTU) as coupling agent afforded the tertiary aminocarbonyl derivative 41.2, which was converted to compound 41A under acidic conditions. Coupling of the carboxylic acid 13.3 with N-ethyl-N,N-dimethylethane-1,2-diamine (41.3) using TBTU as coupling agent afforded the tertiary aminocarbonyl derivative 41.4, which was converted to compound 41B under acidic conditions. Coupling of the carboxylic acid 13.3 with N-(3-(ethylamino)propyl)-2,2,2-trifluoroacetamide (41.7) (obtained by treatment of N-ethylpropane-1,3-diamine 41.5 with ethyl 2,2,2-trifluoroacetate 41.6) using TBTU as coupling agent afforded the tertiary aminocarbonyl derivative 41.8, which was converted to 41.9 under basic conditions. Treatment of 41.9 with 2-nitrobenzene-1-sulfonyl chloride (41.10) afforded the sulfonamide derivative 41.11, which was converted to 41.12 by treatment with methyl iodide. Thiophenol-mediated deprotection of 41.12 afforded the derivative 41.13, which was converted to the final compound 41C under acidic conditions. Coupling of the carboxylic acid 13.3 with N,N-dimethylpropane-1,3-diamine (41.14) using TBTU as coupling agent afforded the tertiary aminocarbonyl derivative 41.15, which was converted to compound 41D under acidic conditions. Coupling of the carboxylic acid 13.3 with N-(2-(ethylamino)ethyl)-2,2,2-trifluoroacetamide (41.17) (obtained by treatment of N-ethylethane-1,2-diamine 41.16 with ethyl 2,2,2-trifluoroacetate 41.6) using TBTU as coupling agent afforded the tertiary aminocarbonyl derivative 41.18, which was converted to 41.19 under basic conditions. Treatment of compound 41.19 with tert-butyloxycarbonyl anhydride (4.7) provided the bis-Boc derivative 41.20. Treatment of 41.20 with methyl iodide in the presence of sodium hydride afforded the derivative 41.21, which was converted to the compound 41E under acidic conditions.

The synthesis of compounds 42A-42I is outlined in Scheme 42. Suzuki type coupling of the enol triflate derivatives 21.6 with 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded compound 42.1 (racemic mixture) which was converted to compound 42C under acidic conditions. Chiral separation of the enantiomers derived from 42.1 provided compounds 42.2 and 42.3. The enantiomers 42.2 and 42.3 were converted to compounds 42A and 42B, respectively under acidic conditions. Conversion of the enol triflate 21.6 to the corresponding boron derivative 42.4 was achieved using 4,4,5,5-tetramethyl-2-(4, 4,5,5-tetramethyl-1,3,2-dioxaborolan-2-yl)-1,3,2-dioxaborolane 1.14 and dichloro[1,1'-bis(diphenylphosphino)ferrocene]palladium(II) dichloromethane adduct {[Pd(dppf) Cl$_2$.CH$_2$Cl$_2$]}. Suzuki type coupling of the boron derivative 42.4 with the aryl bromide 34.1a in ethylene glycol dimethyl ether in the presence of tetrakis triphenylphosphine palladium (0), lithium chloride, and an aqueous solution of sodium carbonate afforded compound 42.5 (racemic mixture), which was converted to compound 42F under acidic conditions. Chiral separation of the enantiomers derived from 42.5 provided compounds 42.6 and 42.7. The enantiomers 42.6 and 42.7 were converted to compounds 42D and 42E, respectively under acidic conditions. Suzuki type coupling of the boron derivative 42.4 with the aryl iodide 35.8 in ethylene glycol dimethyl ether in the presence of tetrakis triphenylphosphine palladium (0), lithium chloride, and an aqueous solution of sodium carbonate afforded compound 42.8 (racemic mixture), which was converted to compound 42I under acidic conditions. Chiral separation of the enantiomers derived from 42.8 provided compounds 42.9 and 42.10. The enantiomers 42.9 and 42.10 were converted to compounds 42G and 42H, respectively under acidic conditions.

The synthesis of compounds 43A-43F is outlined in Scheme 43. The 2'-6'-dihydroxyacetophenone derivative 11.1 was condensed with tert-butyl 4-oxoazepane-1-carboxylate 21.4 in refluxing methanol in the presence of pyrrolidine to provide the derivative 43.1 which was converted to the methoxymethyl (MOM) ether derivative 43.2 using chloro(methoxy)methane (11.3). Conversion of the ketone 43.2 to the enol triflate derivative 43.3 was achieved using N-phenylbis(trifluoromethanesulphonimide) 1.4 as triflating reagent. Suzuki type coupling of the enol triflate derivative 43.3 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded compound 43.4 (racemic mixture). Removal of the MOM and the Boc protecting groups of 43.4 in methanol at room temperature in the presence of hydrochloric acid (anhydrous solution in dichloromethane) afforded compound 43C (racemic mixture). Chiral separation of the enantiomers derived from 43.4 provided compounds 43.5 and 43.6. The enantiomers 43.5 and 43.6 were converted to compounds 43A and 43B, respectively under acidic conditions. Suzuki type coupling of the enol triflate derivative 43.3 with 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded compound 43.7 (racemic mixture). Removal of the MOM and the Boc protecting groups of 43.7 in methanol at room temperature in the presence of hydrochloric acid (anhydrous solution in dichloromethane) afforded compound 43F (racemic mixture). Chiral separation of the enantiomers derived from 43.7 provided compounds 43.8 and 43.9. The enantiomers 43.8 and 43.9 were converted to compounds 43D and 43E, respectively under acidic conditions.

The synthesis of compounds 44A-44F is outlined in Scheme 44. The 5'-fluoro-2'-hydroxy-acetophenone derivative 1.1d was condensed with tert-butyl 4-oxoazepane-1-carboxylate 21.4 in refluxing methanol in the presence of pyrrolidine to provide the derivative 44.1. Conversion of the ketone 44.1 to the enol triflate derivative 44.2 was achieved using N-phenylbis(trifluoromethanesulphonimide) 1.4 as triflating reagent. Suzuki type coupling of the enol triflate derivative 44.2 with 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded compound 44.3 (racemic mixture) which was converted to compound 44C under acidic conditions. Chiral separation of the enantiomers derived from 44.3 provided compounds 44.4 and 44.5. The enantiomers 44.4 and 44.5 were converted to compounds 44A and 44B, respectively under acidic conditions. Conversion of the enol triflate 44.2 to the corresponding boron derivative 44.6 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene] palladium(II) dichloromethane adduct{[Pd(dppf)Cl₂.CH₂Cl₂]}. Suzuki type coupling of the boron derivative 44.6 with the aryl bromide 34.1a in ethylene glycol dimethyl ether in the presence of tetrakis triphenylphosphine palladium (0), lithium chloride, and an aqueous solution of sodium carbonate afforded compound 44.7 (racemic mixture), which was converted to compound 44F under acidic conditions. Chiral separation of the enantiomers derived from 44.7 provided compounds 44.8 and 44.9. The enantiomers 44.8 and 44.9 were converted to compounds 44D and 44E, respectively under acidic conditions.

The synthesis of compounds 45A-45F is outlined in Scheme 45. Suzuki type coupling of the boron derivative 44.6 with the aryl iodide 35.8 in ethylene glycol dimethyl ether in the presence of tetrakis triphenylphosphine palladium (0), lithium chloride, and an aqueous solution of sodium carbonate afforded compound 45.1 (racemic mixture), which was converted to compound 45C under acidic conditions. Chiral separation of the enantiomers derived from 45.1 provided compounds 45.2 and 45.3. The enantiomers 45.2 and 45.3 were converted to compounds 45A and 45B, respectively under acidic conditions. The 2'-5'-dihydroxyacetophenone derivative 2.1 was condensed with tert-butyl 4-oxoazepane-1-carboxylate 21.4 in refluxing methanol in the presence of pyrrolidine to provide the derivative 45.4 which was converted to the silyl ether derivative 45.5 using tert-butyldimethylsilyl chloride 2.3. Conversion of the ketone 45.5 to the enol triflate derivative 45.6 was achieved using N-phenylbis(trifluoromethanesulphonimide) 1.4 as triflating reagent. Suzuki type coupling of the enol triflate derivative 45.6 with 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded compound 45.7 (racemic mixture), which was converted to compound 45F under acidic conditions. Chiral separation of the enantiomers derived from 45.7 provided compounds 45.8 and 45.9. The enantiomers 45.8 and 45.9 were converted to compounds 45D and 45E, respectively under acidic conditions.

The synthesis of compounds 46A-46C is outlined in Scheme 46. Suzuki type coupling of the enol triflate derivative 45.6 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded compound 46.1 (racemic mixture), which was converted to compound 46C under acidic conditions. Treatment of 46.1 with chloro(methoxy)methane (11.3) provided the methoxymethyl (MOM) ether derivative 46.2 (racemic mixture). Chiral separation of the enantiomers derived from 46.2 provided compounds 46.3 and 46.4. The enantiomers 46.3 and 46.4 were converted to compounds 46A and 46B, respectively under acidic conditions.

The synthesis of compounds 47A-47F is outlined in Scheme 47. Suzuki type coupling of the enol triflate derivative 23.3a with 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded compound 47.1 (racemic mixture) which was converted to compound 47A under acidic conditions. Conversion of the enol triflate 23.3a to the corresponding boron derivative 47.2 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene]palladium (II) dichloromethane adduct {[Pd(dppf)Cl$_2$.CH$_2$Cl$_2$]}. Suzuki type coupling of the boron derivative 47.2 with the aryl iodide 35.8 in ethylene glycol dimethyl ether in the presence of tetrakis triphenylphosphine palladium (0), lithium chloride, and an aqueous solution of sodium carbonate afforded compound 47.3 (racemic mixture), which was converted to compound 47B under acidic conditions. The 2'-6'-dihydroxyacetophenone derivative 11.1 was condensed with tert-butyl 3-oxopyrrolidine-1-carboxylate 23.1a in refluxing methanol in the presence of pyrrolidine to provide the derivative 47.4 which was converted to the methoxymethyl (MOM) ether derivative 47.5 using chloro(methoxy)methane (11.3). Conversion of the ketone 47.5 to the enol triflate derivative 47.6 was achieved using N-phenylbis(trifluoromethanesulphonimide) 1.4 as triflating reagent. Suzuki type coupling of the enol triflate derivative 47.6 with compound 1.6 in ethylene glycol dimethyl ether in the presence of tetrakis triphenylphosphine palladium (0), lithium chloride, and an aqueous solution of sodium carbonate afforded compound 47.7 (racemic mixture). Removal of the MOM and the Boc protecting groups of 47.7 in methanol at room temperature in the presence of hydrochloric acid afforded compound 47C (racemic mixture). Suzuki type coupling of the enol triflate derivative 47.6 with 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded compound 47.8 (racemic mixture). Removal of the MOM and the Boc protecting groups of 47.8 in methanol at room temperature in the presence of hydrochloric acid afforded compound 47D (racemic mixture). The 2'-5'-dihydroxyacetophenone derivative 2.1 was condensed with tert-butyl 3-oxopyrrolidine-1-carboxylate 23.1a in refluxing methanol in the presence of pyrrolidine to provide the derivative 47.9 which was converted to the silyl ether derivative 47.10 using tert-butyldimethylsilyl chloride 2.3. Conversion of the ketone 47.10 to the enol triflate derivative 47.11 was achieved using N-phenylbis(trifluoromethanesulphonimide) 1.4 as triflating reagent. Suzuki type coupling of the enol triflate derivative 47.11 with compound 1.6 in ethylene glycol dimethyl ether in the presence of tetrakis triphenylphosphine palladium (0), lithium chloride, and an aqueous solution of sodium carbonate afforded compound 47.12 (racemic mixture), which was converted to compound 47E under acidic conditions. Suzuki type coupling of the enol triflate derivative 47.11 with 2-(N,N-diethylaminocarbonyl)-5-(4,4,5,5-tetramethyl-1,3,2-dioxoborolan-2-yl)pyridine 1.7 in ethylene glycol dimethyl ether in the presence of tetrakis triphenylphosphine palladium (0), lithium chloride, and an aqueous solution of sodium carbonate afforded compound 47.13 (racemic mixture), which was converted to compound 47F under acidic conditions.

The synthesis of compounds 48A-48F is outlined in Scheme 48. Suzuki type coupling of the enol triflate derivative 1.5f with 4-cyanophenylboronic acid (14.1) in dioxane in the presence of dichloro[1,1'-bis(diphenylphosphino)ferrocene]palladium(II) dichloromethane adduct, and an aqueous solution of potassium carbonate afforded the cyanide 48.1 which was converted to the tetrazole 48.2 using sodium azide (14.3) and zinc bromide in a solution isopropanol/water. Alkylation of 48.2 with methyl iodide (2.8c) in N,N-dimethylformamide in the presence of triethylamine afforded the two regioisomers 48.3 (major isomer) and 48.4 (minor isomer) separated by silica gel column chromatography. The Boc protecting group of 48.2, 48.3, and 48.4 was removed using hydrochloric acid to generate the compounds 48A-48C. Conversion of the enol triflate 1.5f to the corresponding boron derivative 48.5 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene]palladium(II) dichloromethane adduct{[Pd(dppf)Cl$_2$.CH$_2$Cl$_2$]}. Suzuki type coupling of the boron derivative 48.5 with the aryl bromide 34.1a in dioxane in the presence of tetrakis triphenylphosphine palladium (0), potassium bromide and potassium phosphate afforded compound 48.8 (racemic mixture), which was converted to compound 48F under acidic conditions. Suzuki type coupling of the boron derivative 48.5 with the bromothiophene derivatives 34.1c and 34.1d in dioxane in the presence of and dichloro[1,1'-bis(diphenylphosphino)ferrocene]palladium(II) dichloromethane adduct, and an aqueous solution o potassium carbonate afforded compound 48.6 and 48.7 respectively. Compounds 48.6 and 48.7 were converted to compound 48D and 48E, respectively, under acidic conditions.

The synthesis of compounds 49A-49D is outlined in Scheme 49. The 6'-fluoro-2'-hydroxy-acetophenone derivative 49.1 was condensed with 1-Boc-4-piperidone 1.2 in methanol at 0° C. in the presence of pyrrolidine to provide the derivative 49.2. Conversion of the ketone 49.2 to the enol triflate derivative 49.3 was achieved using N-phenylbis(trifluoromethanesulphonimide) 1.4 as triflating reagent. Suzuki type coupling of the enol triflate derivative 49.3 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded compound 49.4 which was converted to compound 49A under acidic conditions. Treatment of 49.2 with pyrrolidine afforded compound 49.5. Conversion of the ketone 49.5 to the enol triflate derivative 49.6 was achieved using N-phenylbis(trifluoromethanesulphonimide) 1.4 as triflating reagent. Suzuki type coupling of the enol triflate derivative 49.6 with 4-(N,N-diethylaminocarbonyl)phenyl boronic acid 1.6 in ethylene glycol dimethyl ether in the presence of tetrakis triphenylphosphine palladium (0), lithium chloride, and an aqueous solution of sodium carbonate afforded compound 49.7 which was converted to compound 49B under acidic conditions. Conversion of the enol triflate 1.5d to the corresponding boron derivative 49.8 was achieved using 4,4,5,5-tetramethyl-2-(4,4,5,5-tetramethyl-1,3,2-dioxaborolan-2-yl)-1,3,2-dioxaborolane 1.14 and dichloro[1,1'-bis(diphenylphosphino)ferrocene]palladium(II) dichloromethane adduct{[Pd(dppf)Cl$_2$.CH$_2$Cl$_2$]}. Suzuki type coupling of the boron derivative 49.8 with the aryl iodide 35.8 in dioxane in the presence of dichloro[1,1'-bis(diphenylphosphino)ferrocene]palladium (II) dichloromethane adduct and an aqueous solution of potassium carbonate afforded compound 49.9, which was converted to compound 49C under acidic conditions. Hydrogenation of the unsaturated derivative 49C in methanol in the presence of palladium, 10 wt. % (dry basis) on activated carbon provided the compound 49D (racemic mixture).

The synthesis of compounds 50A-50D is outlined in Scheme 50. Suzuki type coupling of the enol triflate derivative 2.5 with phenyl boronic acid 31.1 g in ethylene glycol dimethyl ether, in the presence of palladium, 10 wt. % (dry basis) on activated carbon, lithium chloride, and an aqueous solution of sodium carbonate afforded compound 50.1. Conversion of the phenol 50.1 to the triflate derivative 50.2 was achieved using the triflating reagent N-phenylbis(trifluoromethanesulphonimide) 1.4. Palladium catalyzed carbonylation of 50.2, conducted in a mixture of dimethylsulfoxide/methanol using palladium (II) acetate, 1,1'-bis(diphenylphosphino)ferrocene (dppf) and carbon monoxide, provided the methyl ester 50.3 which was hydrolyzed under basic conditions to give the carboxylic acid derivatives 50.4. Coupling of the carboxylic acid 50.4 with diethylamine (1.12) using TBTU as coupling agent afforded the tertiary amide 50.5. Treatment of the Boc derivatives 50.3, 50.4, 50.5 and 50.1 with hydrochloric acid provided the final compounds 50A-50D, respectively.

The synthesis of compounds 51A-51C is outlined in Scheme 51. The 2'-hydroxyacetophenone 1.1a was condensed with tert-butyl 2-methyl-4-oxopiperidine-1-carboxylate (51.1) (racemic mixture) in refluxing methanol in the presence of pyrrolidine to provide the racemic ketone 51.2. Conversion of the ketone 51.2 to the enol triflate derivative 51.3 was achieved using N-phenylbis(trifluoromethanesulphonimide) 1.4 as triflating reagent. Suzuki type coupling of the enol triflate derivative 51.3 with 4-(N,N-diethylaminocarbonyl)phenyl boronic acid 1.6 in ethylene glycol dimethyl ether in the presence of tetrakis triphenylphosphine palladium (0), potassium bromide, and potassium phosphate afforded the Boc derivative 51.4 (product eluted as a single peak), which was converted to compound 51C under acidic conditions. Chiral separation of the intermediate 51.4 provided resolved products 51.5 and 51.6. The resolved products 51.5 and 51.6 were converted to compounds 51A and 51B, respectively under acidic conditions.

The synthesis of compounds 52A-52F is outlined in Scheme 52. Treatment of compound 21C with trifluoroacetic anhydride (4.1) in tetrahydrofuran in the presence of triethylamine provided the trifluoroacetamide derivative 52.1 which was converted to the sulfonyl chloride 52.2 using sulfur trioxide N,N-dimethylformamide complex (4.3) as sulfating agent. Condensation of hydrazine hydrate (5.1) with the sulfonyl chloride derivative 52.2 provided the sulfonyl hydrazide 52.3, which was converted to the sulfone 52.4 by treatment with methyl iodide (2.8c) in the presence of sodium acetate. Deprotection of the trifluoroacetamide protecting group of 52.4 under basic conditions (potassium carbonate, methanol, water) provided the methyl sulfonyl analog (compound 52A) [Note: compound 52A (derived from compound 21C) and 22E (derived from compound 21B) are enantiomeric with respect to one another]. Palladium catalyzed hydrogenation of compound 22E affords compounds 52B and 52C, respectively. Palladium catalyzed hydrogenation of compounds 35B, 1Q, and 1F affords compounds 52D, 52E, and 52F, respectively.

The synthesis of compounds 53A-53F is outlined in Scheme 53. Treatment of compounds 48.2 and 48.3 with hydrobromic acid provided the phenolic derivatives 53A and 53B, respectively. Suzuki type coupling of the enol triflate derivative 11.5 with 4-(carboxy)phenylboronic acid (53.1) in dioxane in the presence of tetrakis triphenylphosphine palladium (0), and an aqueous solution of potassium carbonate afforded the carboxylic acid derivative 53.2 which was converted to 53D under acidic conditions. The carboxylic acid derivative 53D was converted to its methyl ester analog 53C under classical esterification conditions, i.e. in the presence of concentrated hydrochloric acid and methanol. Coupling of the carboxylic acid 53.2 with ammonium chloride (3.4a) in acetonitrile, in the presence of N,N-diisopropylethylamine (Hunig's base), using O-benzotriazol-1-yl-N,N,N',N'-tetramethyluronium tetrafluoroborate (TBTU) as coupling agent affords the primary aminocarbonyl derivative 53.3. Coupling of the carboxylic acid 53.2 with ethylamine (3.4c) in acetonitrile, in the presence of N,N-diisopropylethylamine (Hunig's base), using O-benzotriazol-1-yl-N,N,N',N'-tetramethyluronium tetrafluoroborate (TBTU) as coupling agent afforded the secondary aminocarbonyl derivative 53.4. Treatment of the derivative 53.4 with hydrochloric acid provided the final compounds 53F. Treatment of the derivative 53.3 with hydrochloric acid provides the final compound 53E.

The synthesis of compounds 54A and 54B is outlined in Scheme 54. Condensation of benzyl 4-oxoazepane-1-carboxylate (54.1) (obtained by treatment of azepan-4-one 21.3 with benzylchloroformate) with 2,2-dimethyl-1,3-dioxane-4,6-dione (Meldrum's acid; 38.1) in the presence of pyridine and piperidine gave the derivative 54.2. The compound 54.2 was subjected to conjugate addition by reaction with organo cuprate reagents derived from benzyl magnesium chloride (28.3a) and copper (I) iodide to yield, upon work-up, the sodium salt 54.3. Hydrolysis and decarboxylation of the conjugate addition product 54.3 proceeded by heating a solution of 54.3 in N,N-dimethylformamide in the presence of water. Treatment of the corresponding carboxylic acid derivative 54.4 with oxalyl chloride followed by reaction of the resulting acyl chloride with aluminum chloride yielded the corresponding spiro piperidine derivative which was further protected as its tert-butyloxycarbonyl (Boc) derivative 54.5 by treatment with tert-butyloxycarbonyl anhydride (4.7). Conversion of the ketone 54.5 to the enol triflate derivative 54.6 was achieved using N-phenylbis(trifluoromethanesulphonimide) 1.4 as triflating reagent. Suzuki type coupling of the enol triflate derivatives 54.6 with 4-(N,N-diethylaminocarbonyl)phenyl boronic acid 1.6 in dioxane in the presence of tetrakis triphenylphosphine palladium (0) and an aqueous solution of potassium carbonate afforded compound 54.7, which was converted to compound 54A under acidic conditions. Suzuki type coupling of the enol triflate derivative 54.6 with 2-(N,N-diethylaminocarbonyl)-5-(4,4,5,5-tetramethyl-1,3,2-dioxoborolan-2-yl)pyridine 1.7 in dioxane in the presence of dichloro[1,1'-bis(diphenylphosphino)ferrocene]palladium(II) dichloromethane adduct and an aqueous solution of potassium carbonate afforded compound 54.8, which was converted to compound 54B under acidic conditions.

The synthesis of compounds 55A-C is outlined in Scheme 55. The compound 38.2 was subjected to conjugate addition by reaction with organo cuprate reagents derived from 3,5-dimethoxybenzyl magnesium bromide (55.1) and copper (I) iodide to yield, upon work-up, the sodium salt 55.2. Hydrolysis and decarboxylation of the conjugate addition product 55.2 proceeded by heating a solution of 55.2 in N,N-dimethylformamide in the presence of water. Treatment of the corresponding carboxylic acid derivative 55.3 with oxalyl chloride followed by reaction of the resulting acyl chloride with aluminum chloride yielded the corresponding spiro piperidine derivative, which was further protected as its CBz derivative 55.4 by treatment with benzylchloroformate. Conversion of the ketone 55.4 to the enol triflate derivative 55.5 was achieved using N-phenylbis(trifluoromethanesulphonimide) 1.4 as triflating reagent. Suzuki type coupling of the enol triflate derivatives 55.5 with 4-(N,N-diethylaminocarbonyl) phenyl boronic acid 1.6 in ethylene glycol dimethyl ether in the presence of tetrakis triphenylphosphine palladium (0), lithium chloride and an aqueous solution of sodium carbonate afforded compound 55.6 which was converted to either the compound 55C by treatment with iodotrimethylsilane or the compound 55A by treatment with boron tribromide. Treatment of 55A with tert-butyloxycarbonyl anhydride (4.7) provided the corresponding Boc derivative 55.7. Condensation of 55.7 with N-phenylbis(trifluoromethanesulphonimide) 1.4 provided the corresponding monotriflate derivative 55.8 which was converted to compound 55.9 by treatment with triethylsilane in the presence of 1,3-bis(diphenylphosphino) propane (dppp) and palladium (II) acetate. Acidic deprotection of the Boc-protecting group of 55.9 provided the compound 55B.

The synthesis of compounds 56A-56D is outlined in Scheme 56. Boron tribromide-mediated demethylation of 28.8b provided the phenolic derivative 56A, which was converted to 56B under hydrogenation conditions. Similarly, boron tribromide-mediated demethylation of 40.3 provided the phenolic derivative 56C, which was converted to 56D under hydrogenation conditions.

The synthesis of compounds 57A-57D is outlined in Scheme 57. Treatment of compound 31J with trifluoroacetic anhydride (4.1) in tetrahydrofuran in the presence of triethylamine provided the trifluoroacetamide derivative 57.1 which was converted to the sulfonyl chloride 57.2 using sulfur trioxide N,N-dimethylformamide complex (4.3) as sulfonating agent. Condensation of 57.2 with methylamine (3.4b) and dimethylamine (3.4j) affords the corresponding sulfonamide derivatives 57.3 which are converted to compounds 57A, 57B under basic conditions. Condensation of 57.2 with ammonium hydroxide yields the compound 57C. Condensation of hydrazine hydrate (5.1) with the sulfonyl chloride derivative 57.2 provided the sulfonyl hydrazide 57.4, which was converted to the sulfone 57.5 by treatment with methyl iodide (2.8c) in the presence of sodium acetate. Deprotection of the trifluoroacetamide protecting group of 57.5 under basic conditions (potassium carbonate, methanol, water) provided the compound 57D.

The synthesis of compounds 58A-58D is outlined in Scheme 58. Suzuki type coupling of the enol triflate derivative 2.5 with either 3-(1,3,2-dioxaborinan-2-yl)pyridine (3.6a) or benzo[b]thiophen-2-ylboronic acid (31.1n) in dioxane in the presence of dichloro[1,1'-bis(diphenylphosphino) ferrocene]palladium(II) dichloromethane adduct (abbreviated as [Pd(dppf)Cl$_2$.CH$_2$Cl$_2$]) and an aqueous solution of potassium carbonate afforded compounds 58.1. The derivatives 58.1a and 58.1b were then converted to the final products 58A and 58B, resepectively, under acidic conditions. Suzuki type coupling of the enol triflate derivative 2.5 with phenyl boronic acid (31.1g) in ethylene glycol dimethyl ether in the presence of tetrakis triphenylphosphine palladium (0) and an aqueous solution of potassium carbonate afforded compound 58.2. Removal of the silyl protecting group of 58.2 using a solution of tetrabutylammonium fluoride (TBAF) in tetrahydrofuran gave the phenolic derivatives 58.3. Preparation of each of the ether derivatives 58.5 from the phenol 58.3 was achieved by alkylation reaction using the appropriate alkyl iodide or alky chloride (2.8c, 58.4) reagent. Treatment of the Boc derivatives 58.5 with hydrochloric acid provided the final compounds 58C-D.

The synthesis of compounds 59A-59L is outlined in Scheme 59. The alkyl bromide derivatives used as starting materials for the synthesis of compounds 59A-59L were either commercially available (59.2a, 59.2b) or prepared from the corresponding alcohols (preparation of 59.2c and 59.2d). Treatment of the amines 59.2 with ethyl 2,2,2-trifluoroacetate (59.3) in methanol in the presence of triethylamine provided the trifluoroacetamide derivatives 59.4. Alkylation of 5-(4-bromophenyl)-2H-tetrazole (59.6) (obtained by treatment of 4-bromobenzonitrile (59.5) with sodium azide and ammonium chloride in N,N-dimethylformamide) with the alkyl bromide derivatives 59.4, provided the derivatives 59.7. Suzuki type coupling of the boronate derivative 32.1 with the aryl bromide derivatives 59.7 in dioxane in the presence of tetrakis triphenylphosphine palladium (0) and an aqueous solution of potassium carbonate afforded the compounds 59.8 which were converted to the derivatives 59.9 under basic conditions. The Boc protecting group of 59.9 was removed using hydrochloric acid to generate the compounds 59A-59D. Treatment of the amines 59.9 with acetic anhydride in dichloromethane in the presence of triethylamine provided the acetamides 59.10, which were converted to the final products 59E-59H under acidic conditions. Treatment of the amines 59.9 with methane sulfonyl chloride in dichloromethane in the presence of triethylamine provided the sulfonamides 59.11, which were converted to the final products 59I-59L under acidic conditions.

The synthesis of compounds 60A-60C is outlined in Scheme 60. Treatment of the amine 60.1 with ethyl 2,2,2-trifluoroacetate (59.3) in methanol in the presence of triethylamine provided the trifluoroacetamide derivative 60.2. Treatment of the alcohol 60.2 with methane sulfonyl chloride in dichloromethane in the presence of triethylamine provided the mesylate derivative 60.3. Alkylation of 5-(4-bromophenyl)-2H-tetrazole (59.6) with the mesylate derivative 60.3, provided the derivative 60.4. Suzuki type coupling of the boronate derivative 32.1 with the aryl bromide derivative 60.4 in dioxane in the presence of tetrakis triphenylphosphine palladium (0) and an aqueous solution of potassium carbonate afforded the compound 60.5 which was converted to the derivative 60.6 under basic conditions. The Boc protecting group of 60.6 was removed using hydrochloric acid to generate the compound 60A. Treatment of the amine 60.6 with acetic anhydride in dichloromethane in the presence of triethylamine provided the acetamide 60.7, which was converted to the final products 60B under acidic conditions. Treatment of the amine 60.6 with methane sulfonyl chloride in dichloromethane in the presence of triethylamine provided the sulfonamide 60.8, which was converted to the final products 60C under acidic conditions.

The synthesis of compounds 61A-61B is outlined in Scheme 61. Chiral separation of the enantiomers derived from 61.1 (obtained by hydrogenation of 49.9) provided compounds 61.2a and 61.2b, which were converted to the final products 61A and 61B, respectively, under acidic conditions. Condensation of compound 21C with 6-bromo-2-naphthoic acid (61.3) (used as chiral resolving agent) in acetonitrile in the presence of TBTU and diisopropylethylamine (Hunig's base) provided the amide derivative 61.4. The absolute configuration of 61.4 was determined by X-ray crystallography, therefore establishing the absolute configuration of compound 21C, and therefore by inference, its enantiomer, compound 21B (see also Scheme 21).

In some instances, the compounds of the invention have the potential for chirality but were prepared in racemic form. As one skilled in the art would readily recognize, the racemic mixtures of intermediates or final products initially prepared as their racemates may be partially or completely resolved into any, some, or all of the enantiomers contained in the racemate as described herein, for example in the separation of intermediates leading to 39F and 39G. As such, racemic mixtures, mixtures enriched in or more stereoisomers, and pure enantiomers are considered to be within the ambit of the present invention.

Scheme 1:
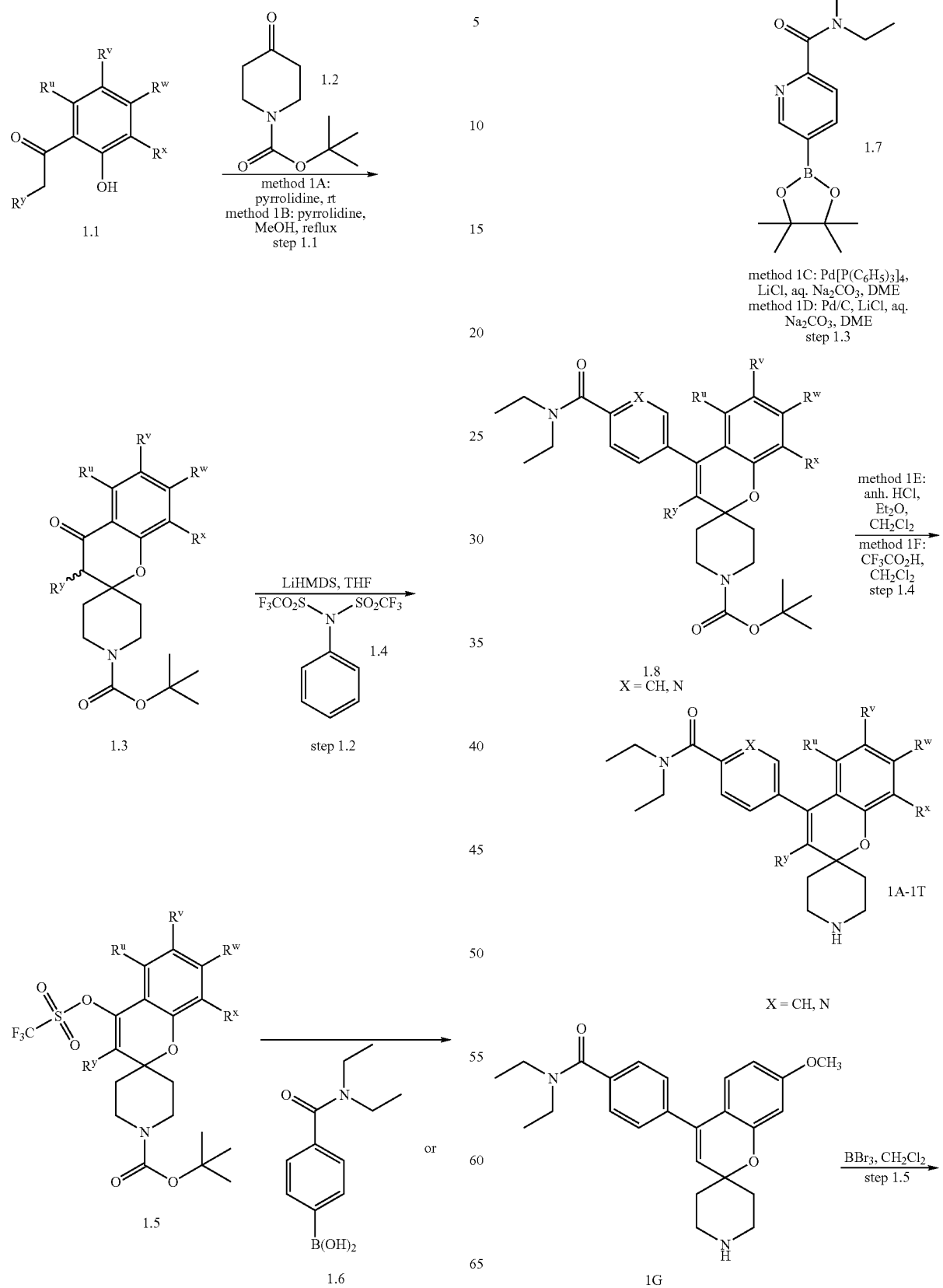

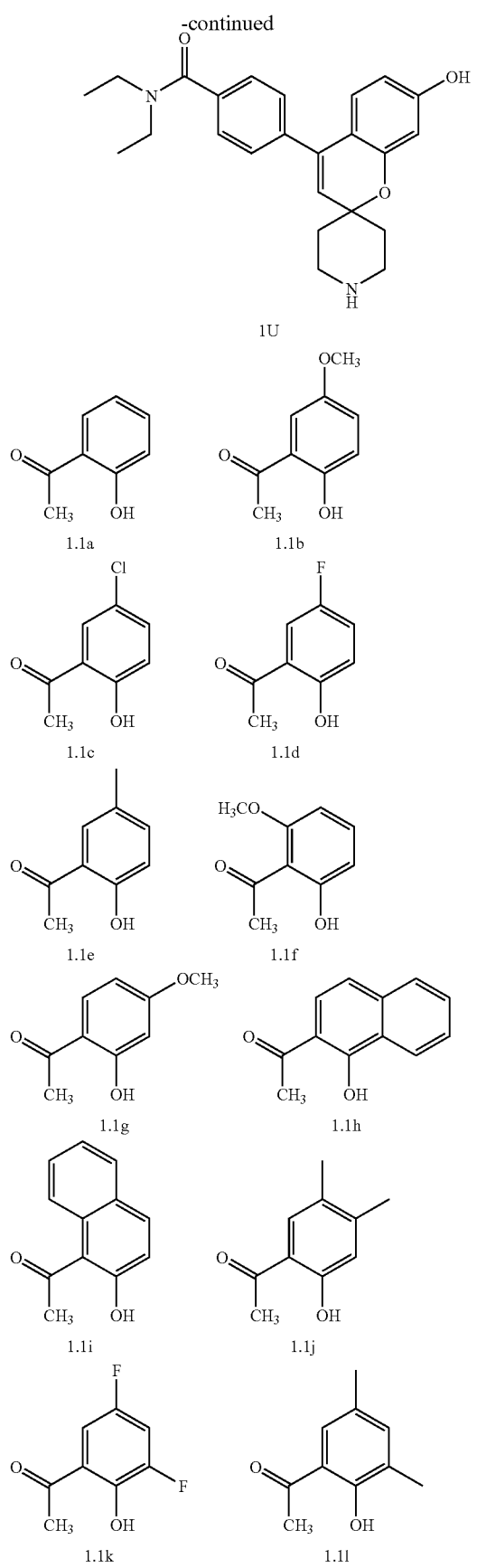
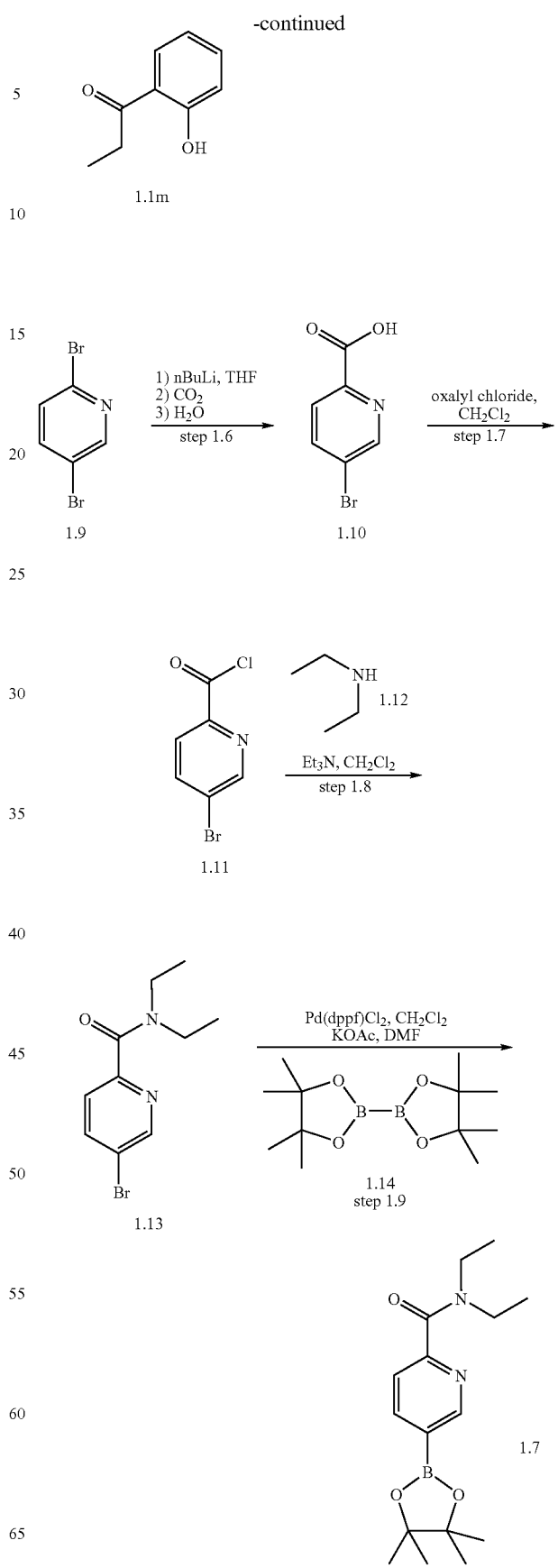

Scheme 2:
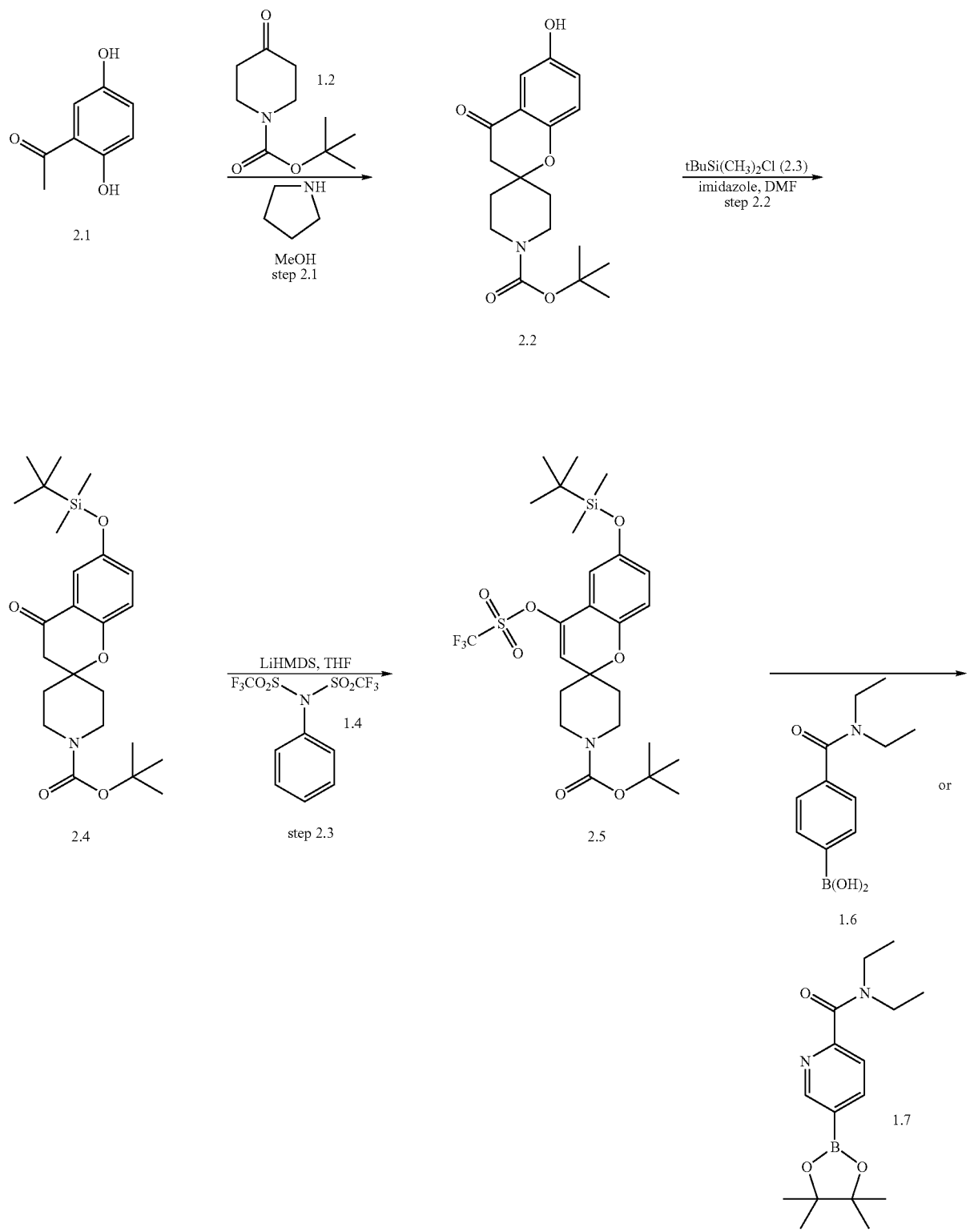

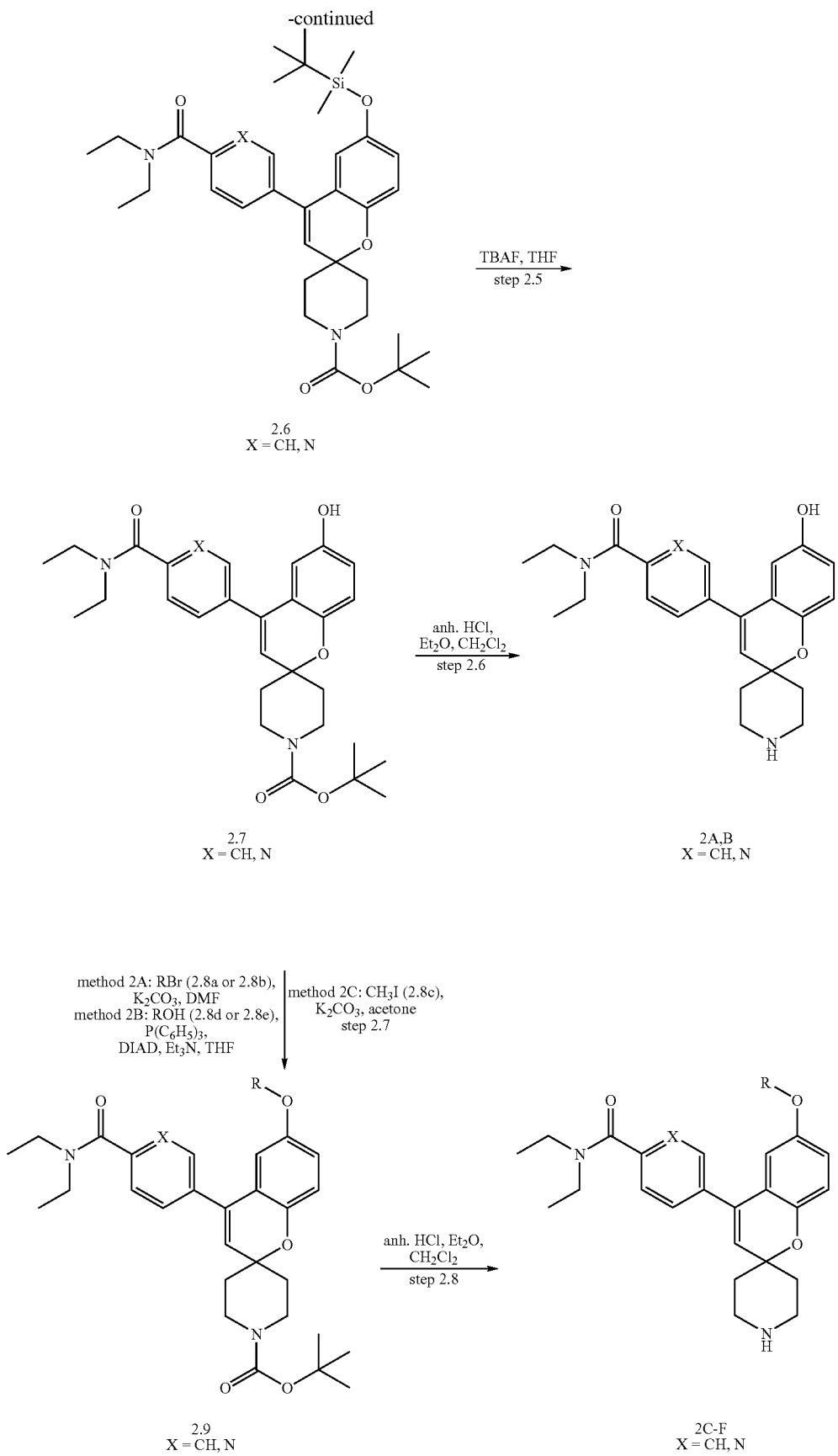

-continued
RX or ROH used in step 2.7:
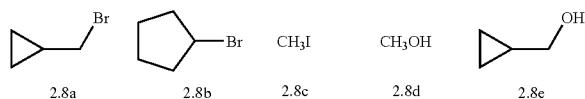
Scheme 3:
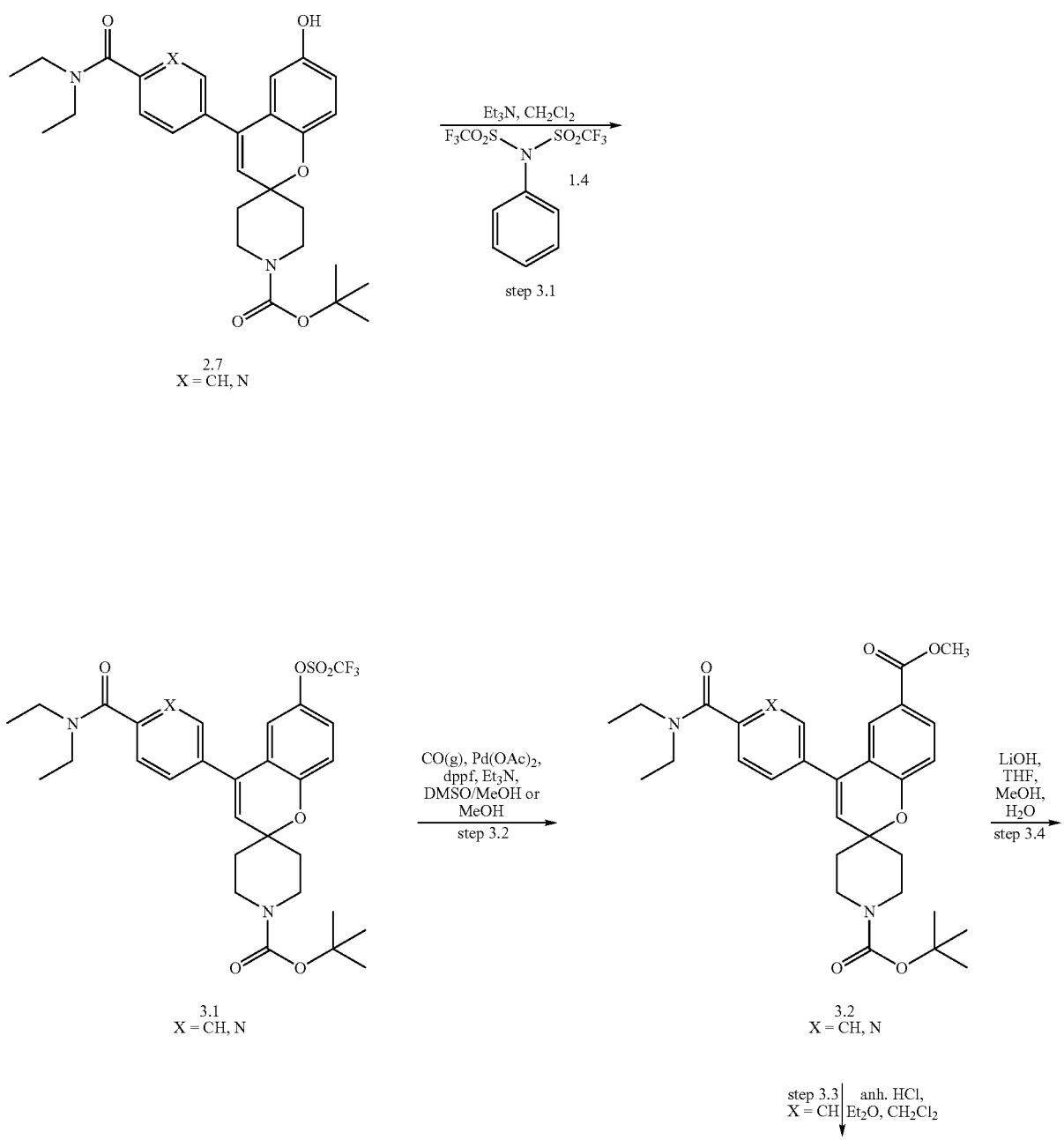

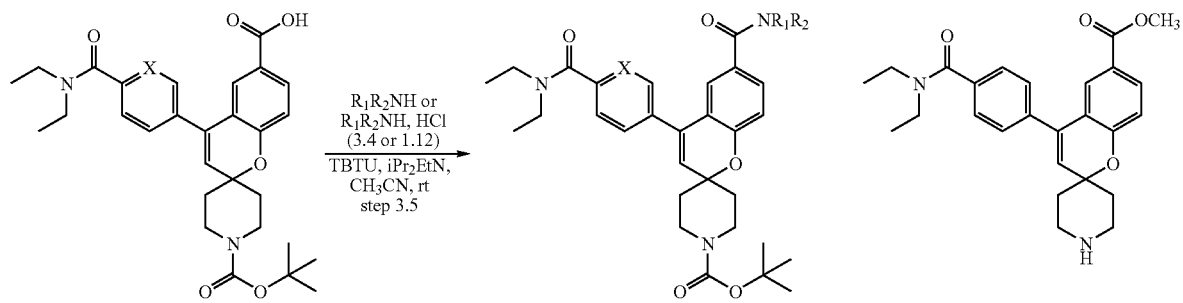
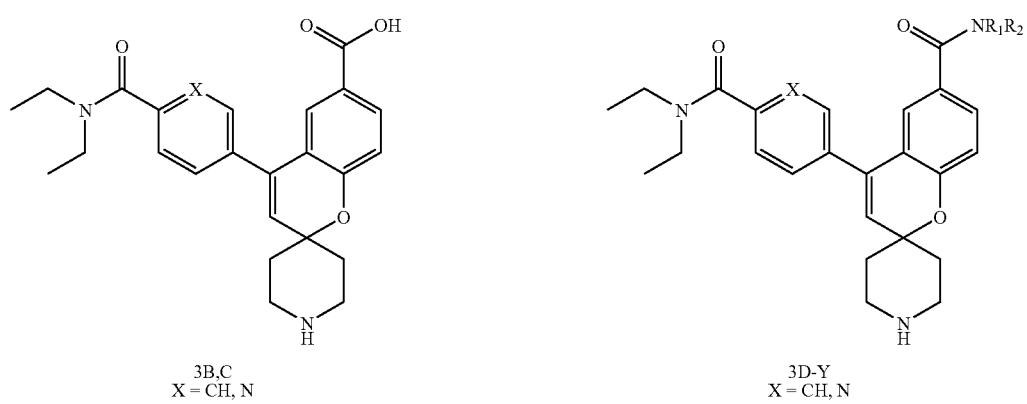
list of amines used in step 3.5:
NH₄Cl    CH₃NH₂    C₂H₅NH₂
3.4a    3.4b    3.4c    3.4d    3.4e    3.4f    3.4g -continued
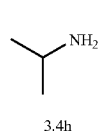 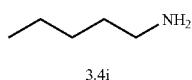 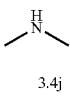 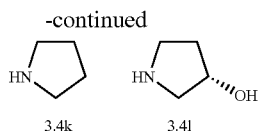
3.4h     3.4i     3.4j     3.4k     3.4l     3.4m
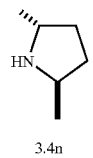 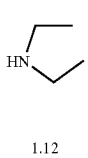 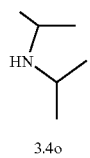 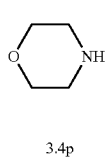 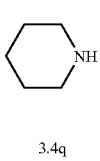
3.4n     1.12     3.4o     3.4p     3.4q
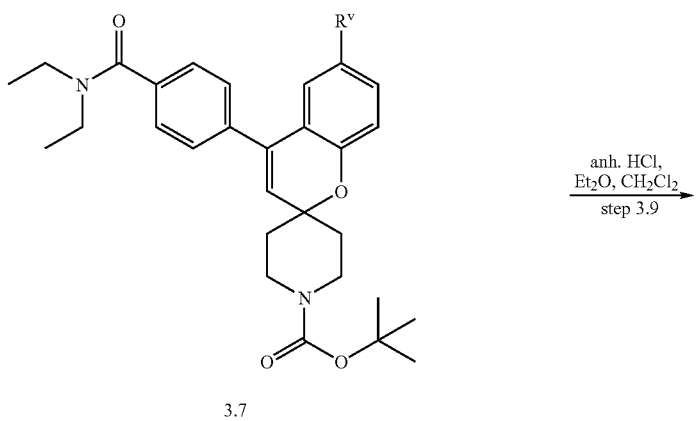
3.1a (X = CH)
→ $R^VBR_1R_2$ (3.6), Pd[P(C$_6$H$_5$)$_3$]$_4$ or/and Pd(dppf)Cl$_2$CH$_2$Cl$_2$, LiCl, aq. Na$_2$CO$_3$, DME, step 3.8 → 3.7
→ anh. HCl, Et$_2$O, CH$_2$Cl$_2$, step 3.9 → 3Z-AC
list of organoboron derivatives used in step 3.8:
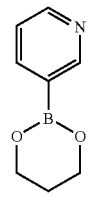 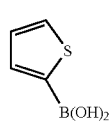 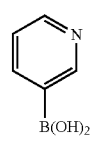 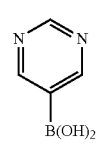
3.6a     3.6b     3.6c     3.6d Scheme 4:
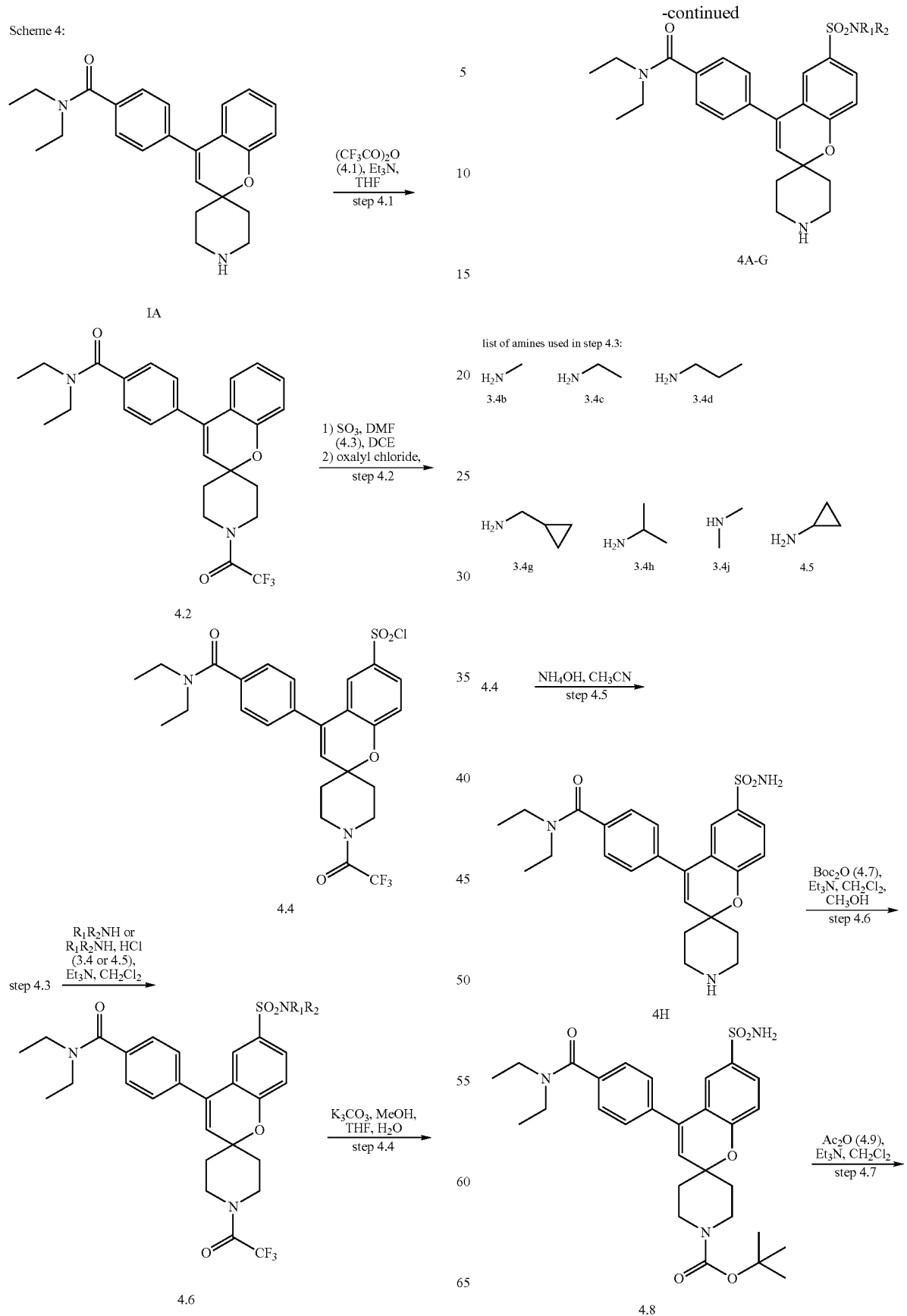

133
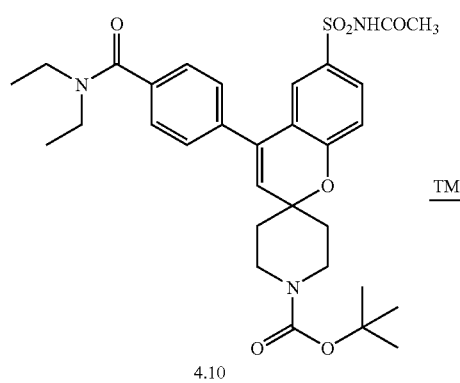
4.10
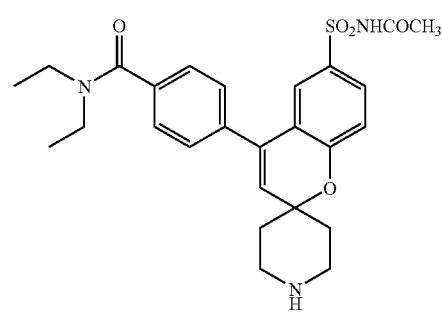
4I
Scheme 5:
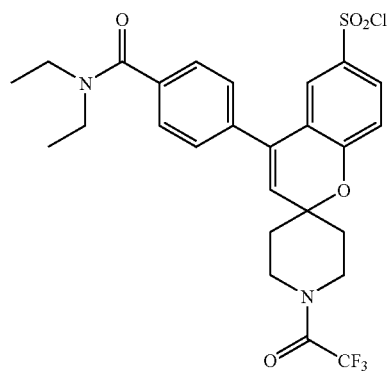
4.4
134
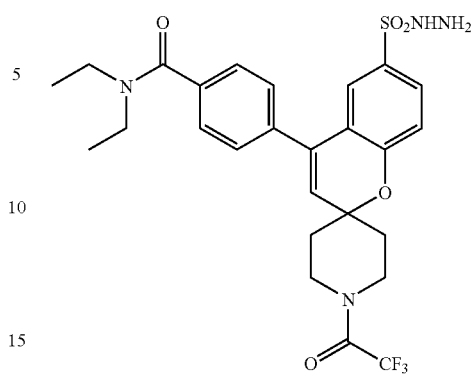
5.2
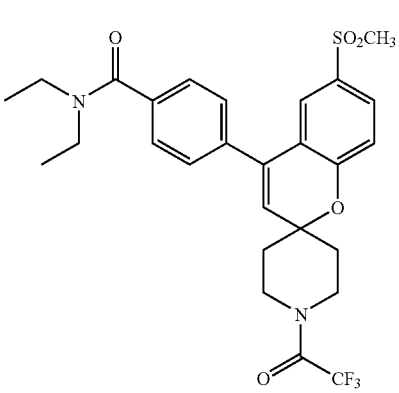
5.3
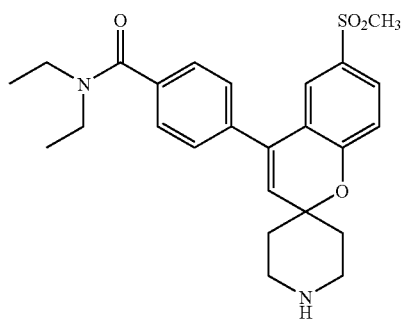
5A Scheme 6:
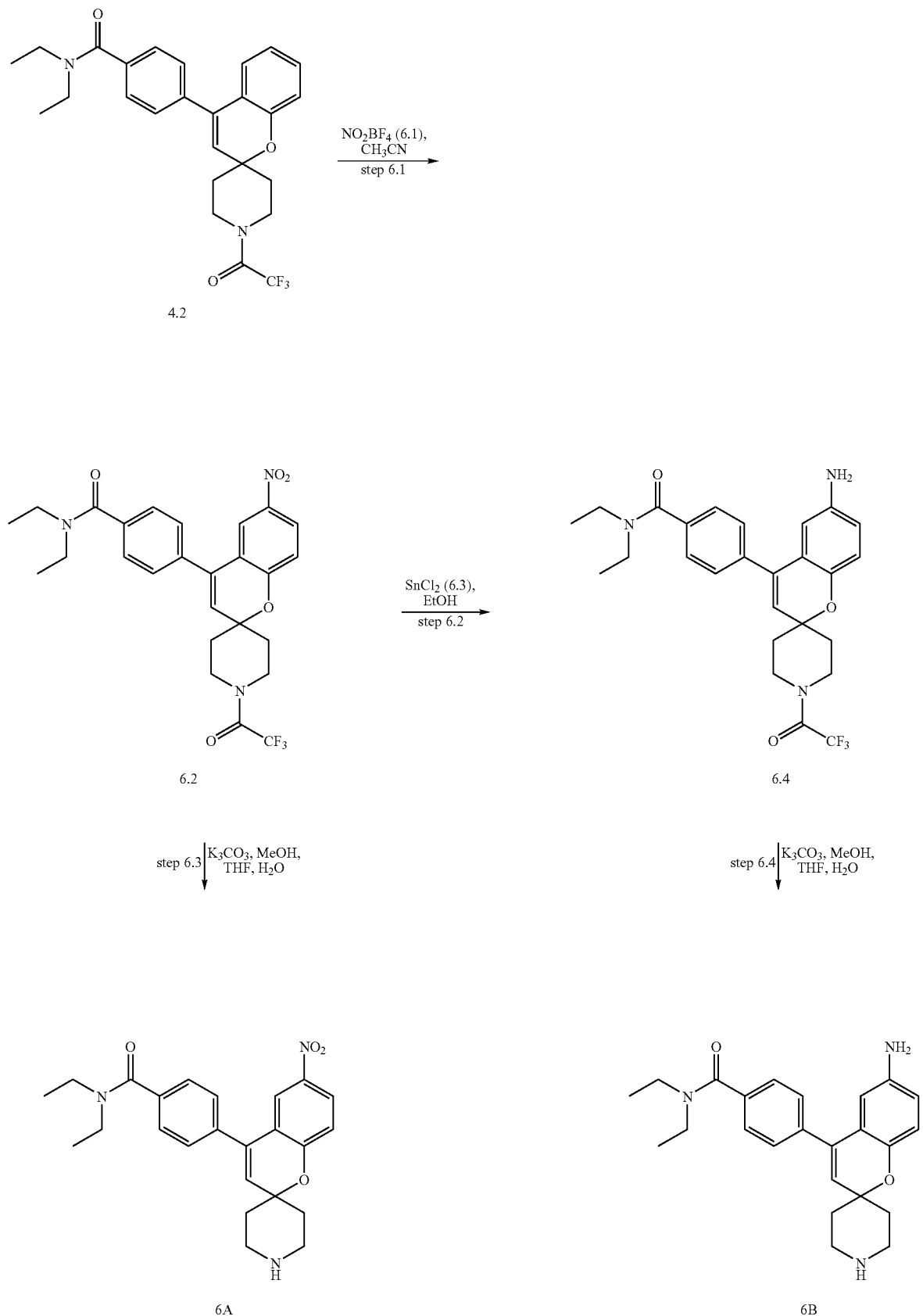

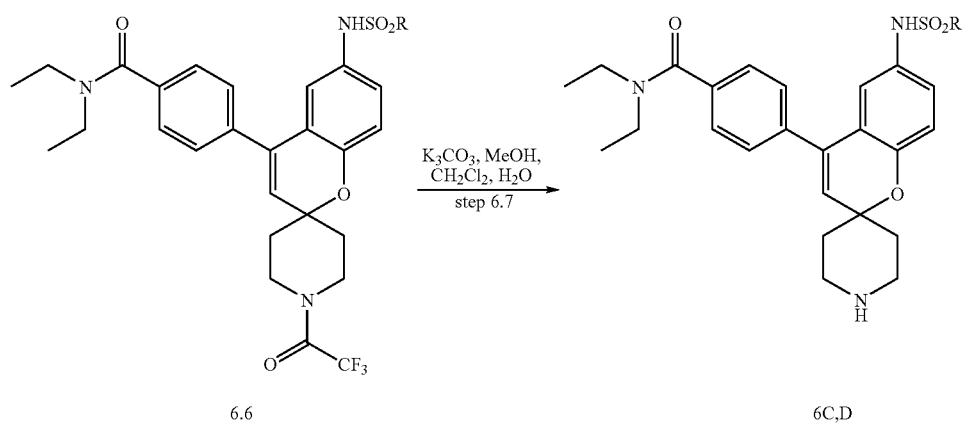
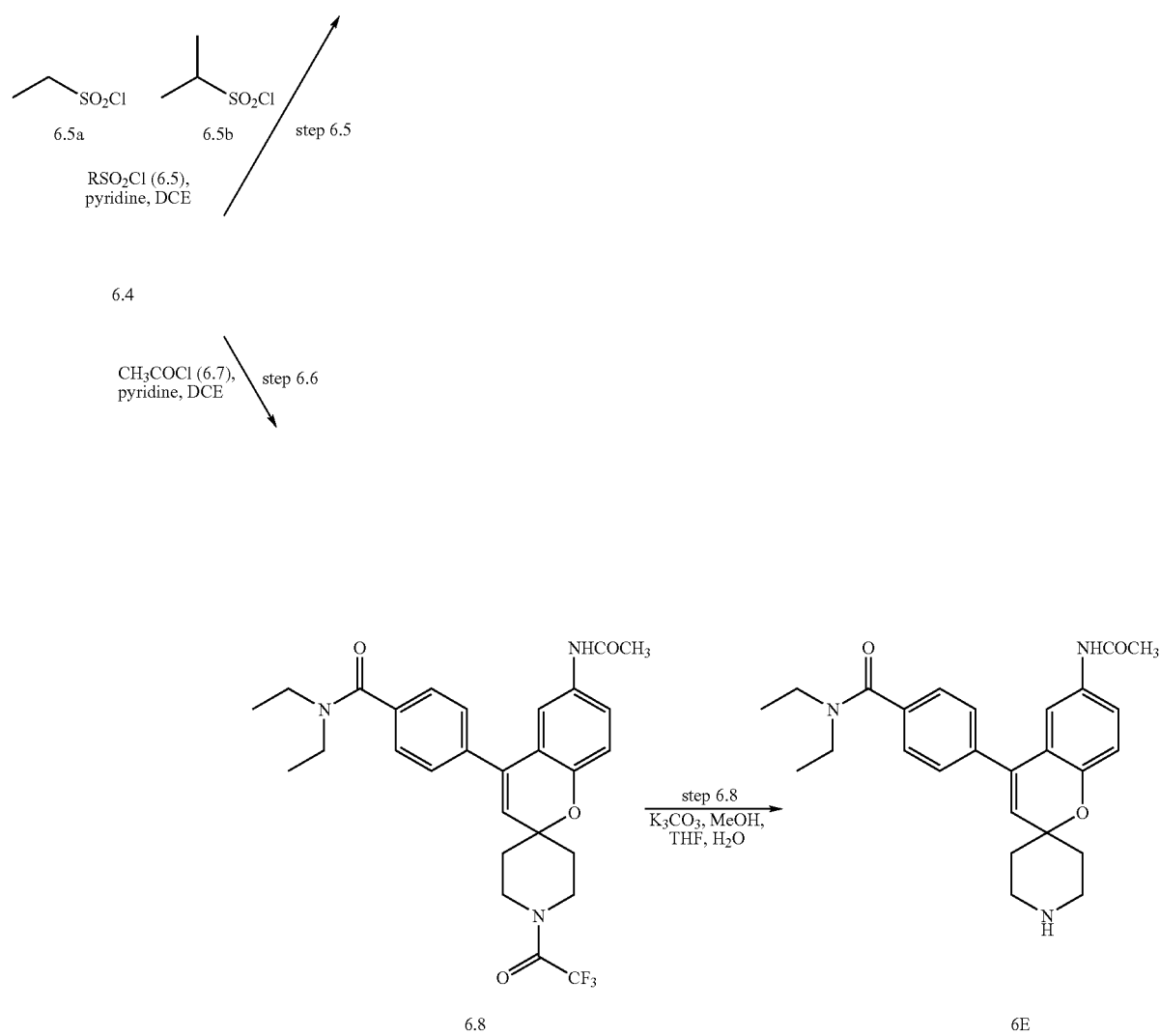

Scheme 7:
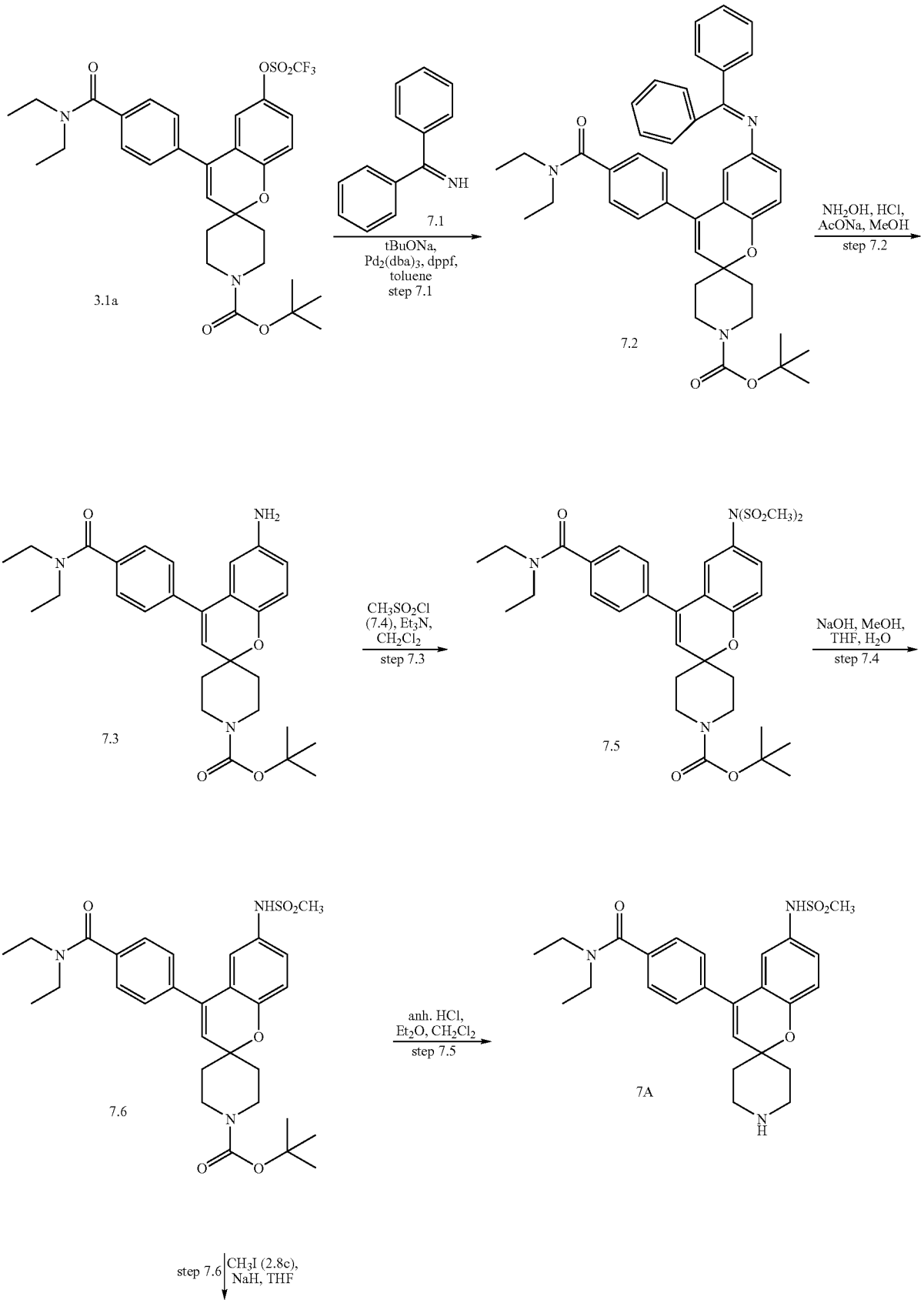

141 142
-continued
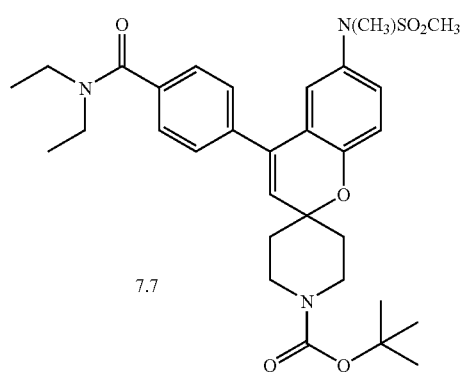
7.7
anh. HCl,
Et₂O, CH₂Cl₂
step 7.7
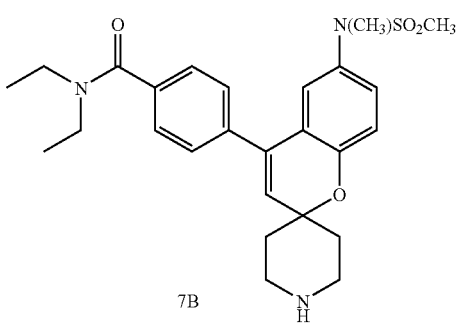
7B
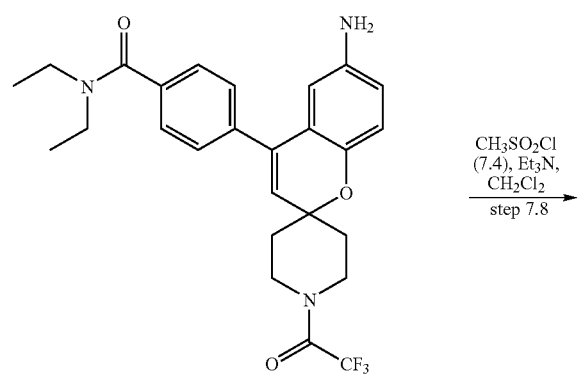
6.4
CH₃SO₂Cl
(7.4), Et₃N,
CH₂Cl₂
step 7.8
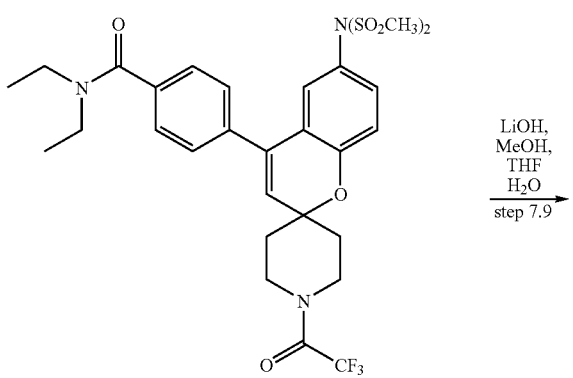
7.8
LiOH,
MeOH,
THF
H₂O
step 7.9
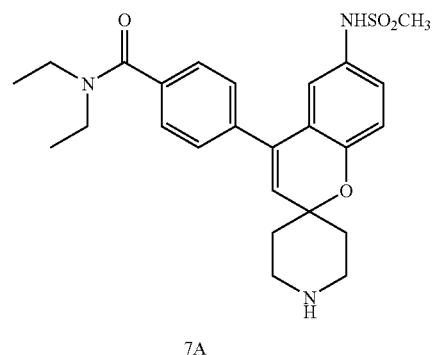
7A
+
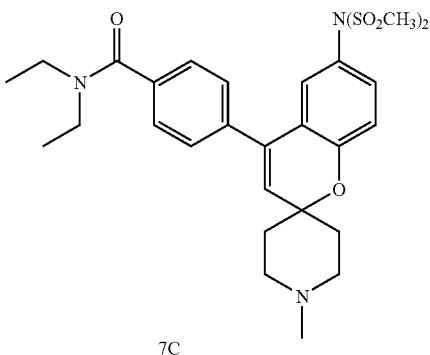
7C
step 7.10 | Boc₂O (4.7),
pyridine,
ClCH₂CH₂Cl
7.6

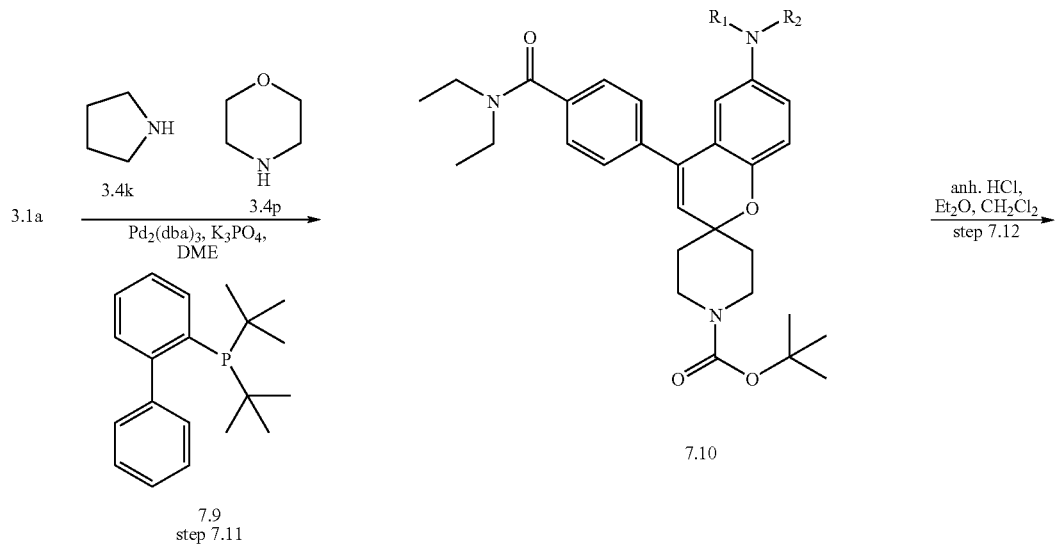
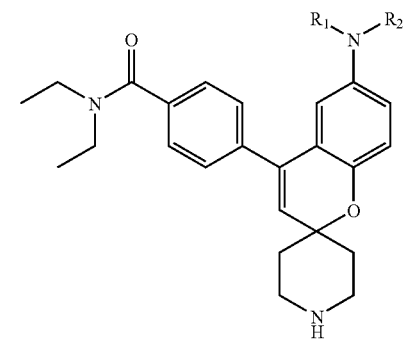
7D,E
Scheme 8:
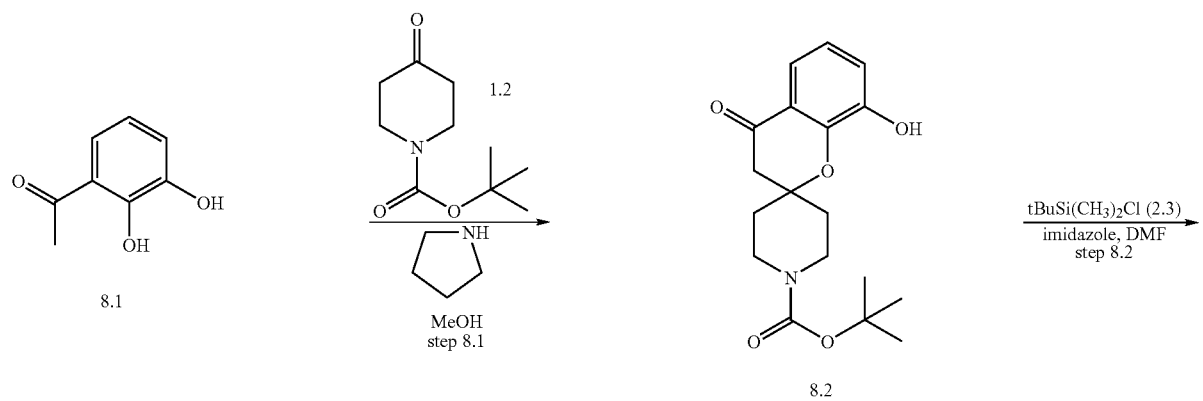

-continued
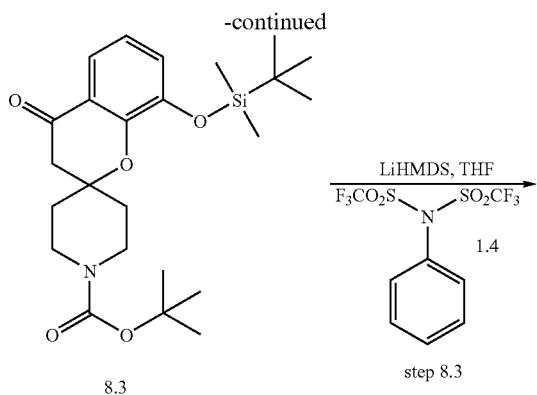
8.3
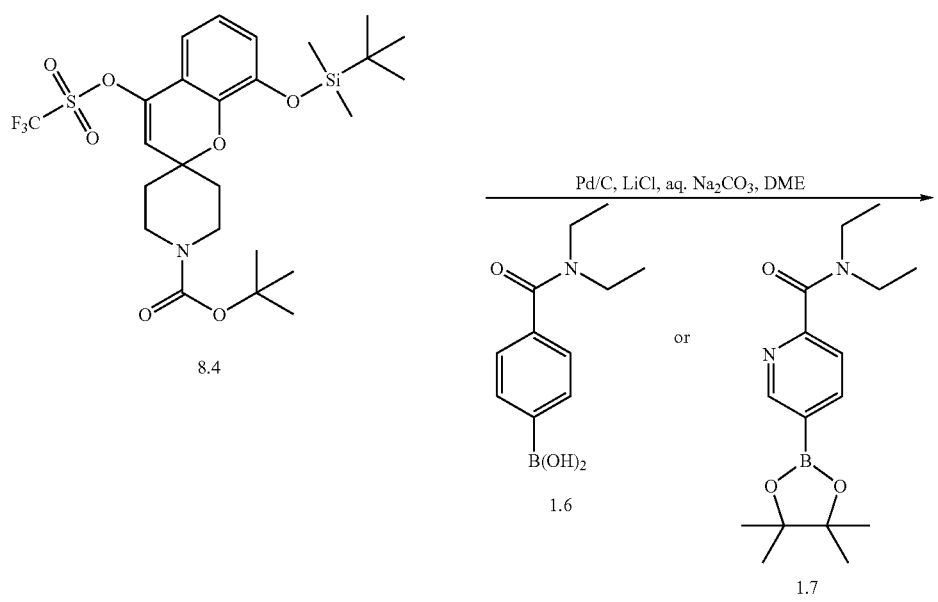
8.4
step 8.4
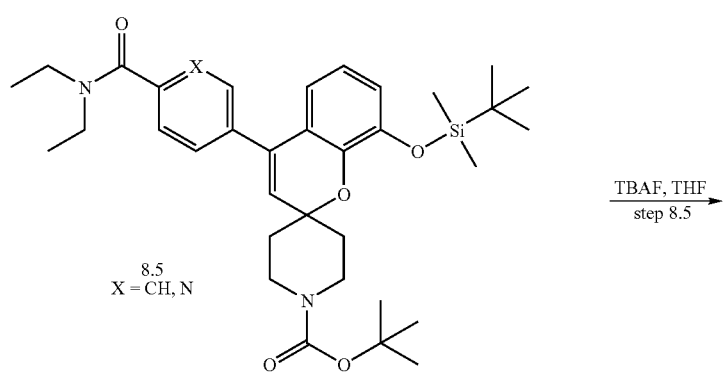
8.5
X = CH, N
TBAF, THF
step 8.5

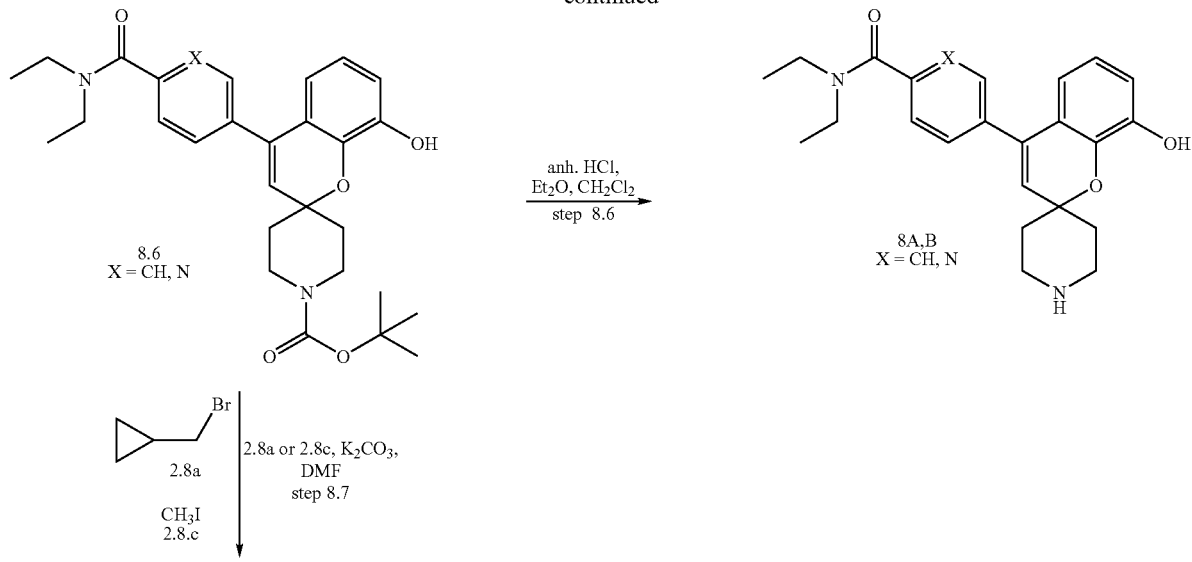
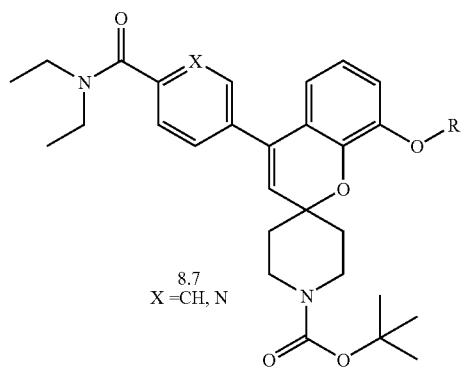
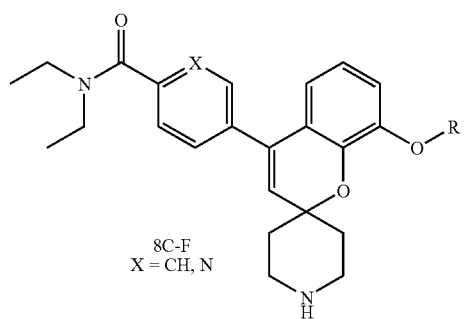

Scheme 9:
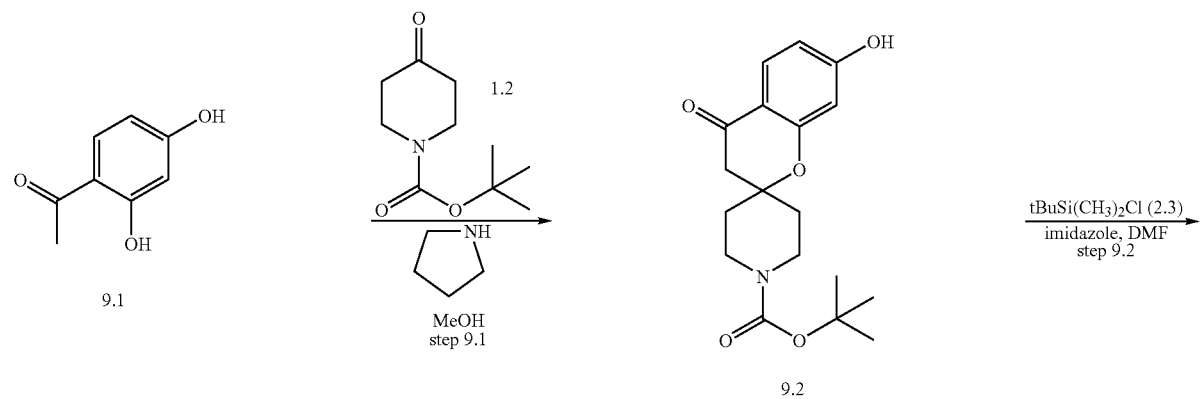
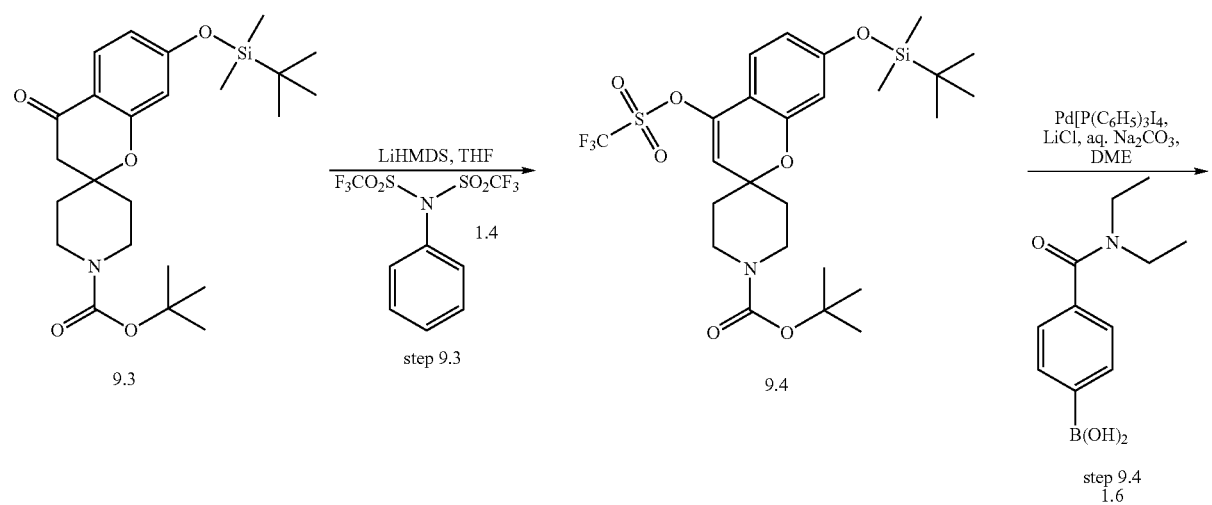

151 152
-continued
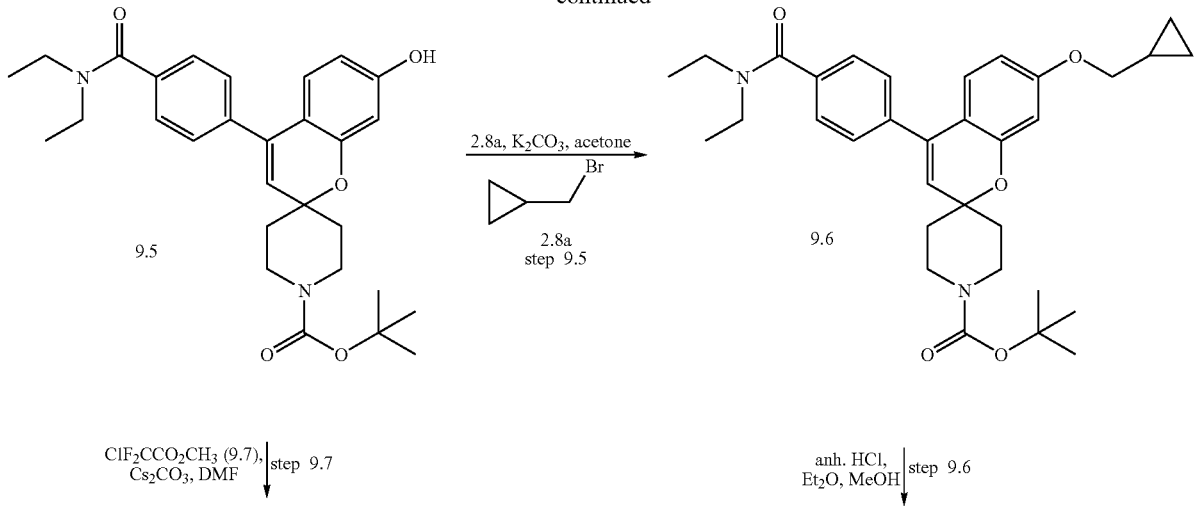
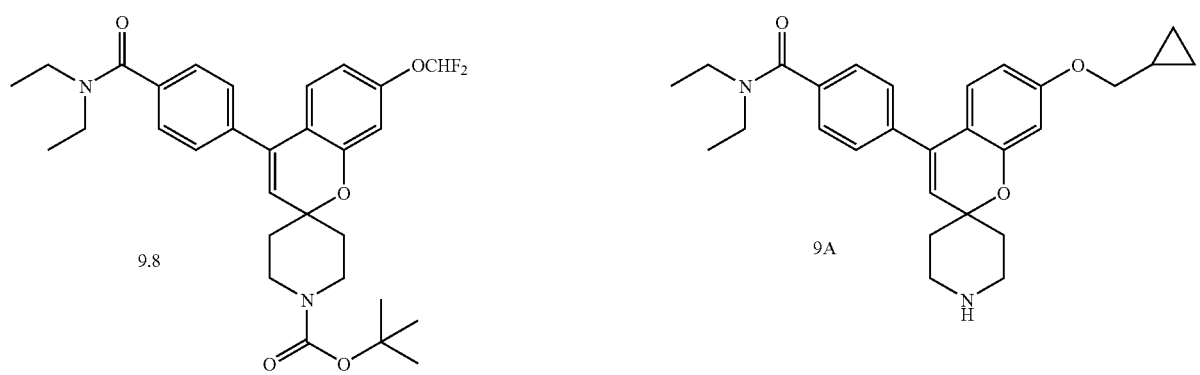
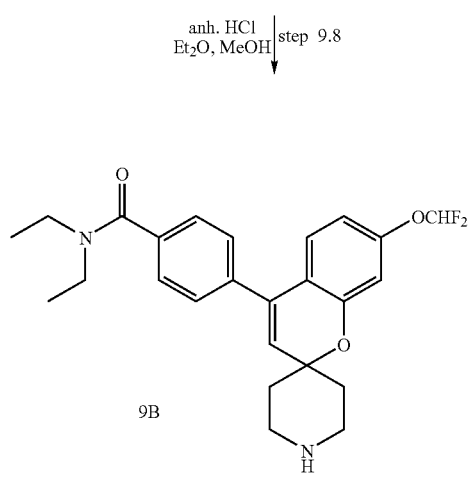

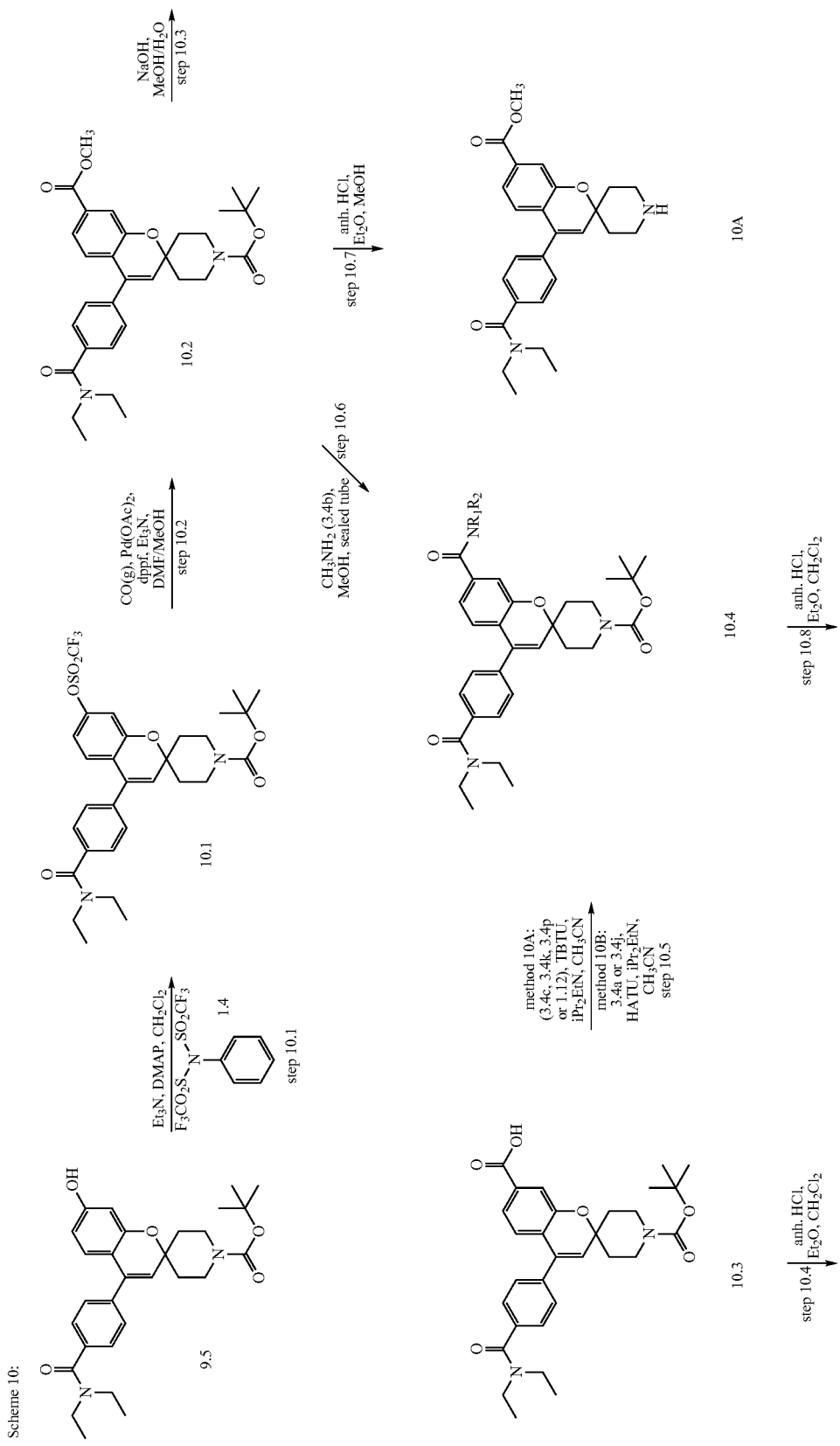

-continued
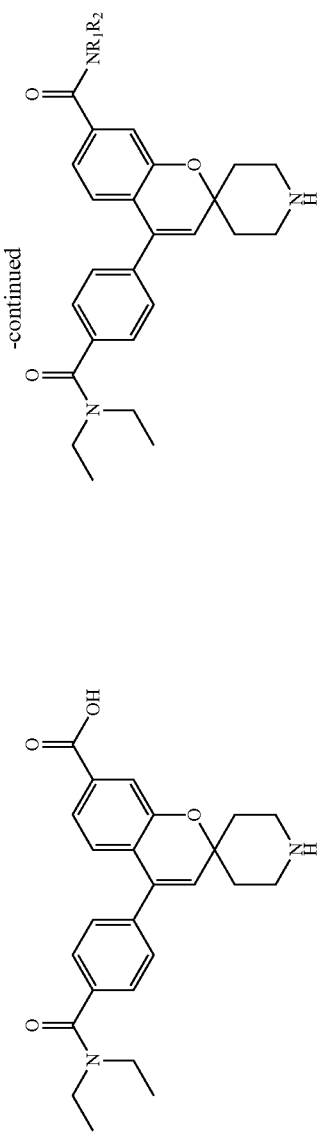
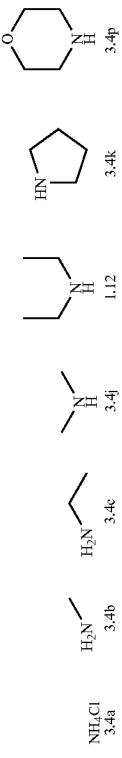
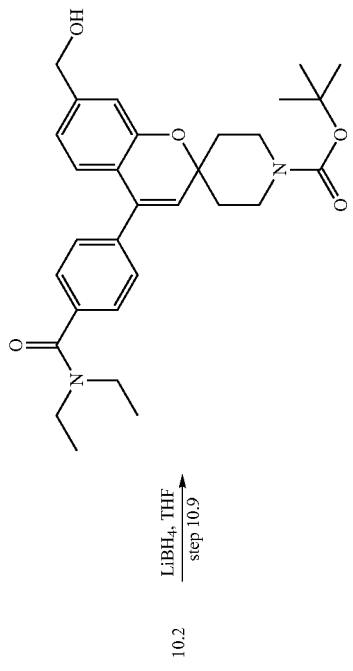
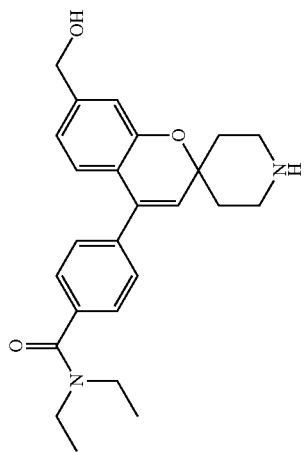

Scheme 11:
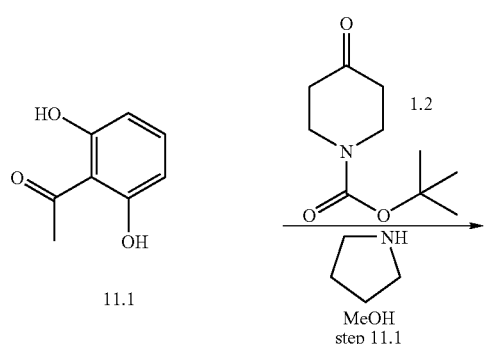
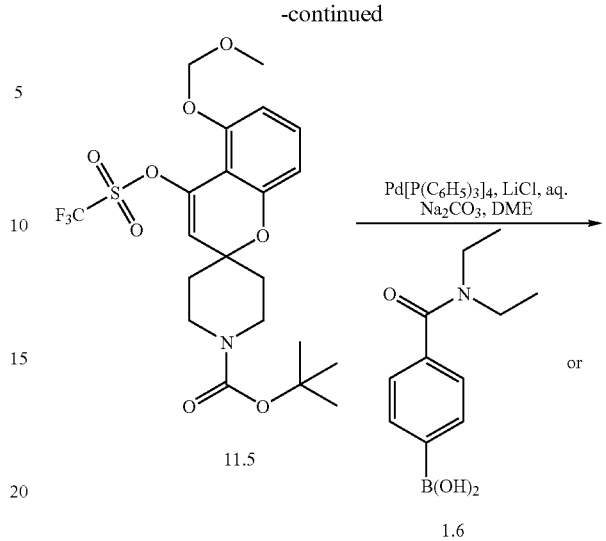
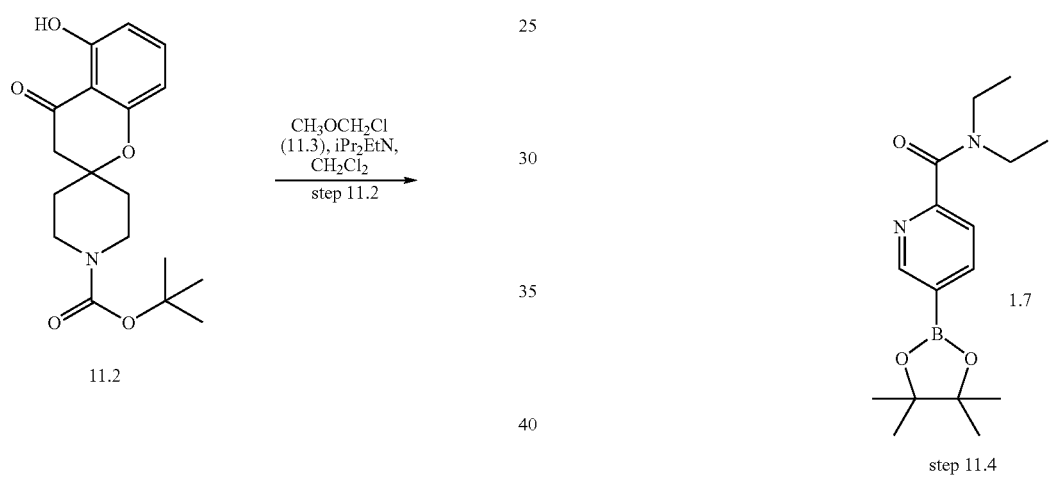
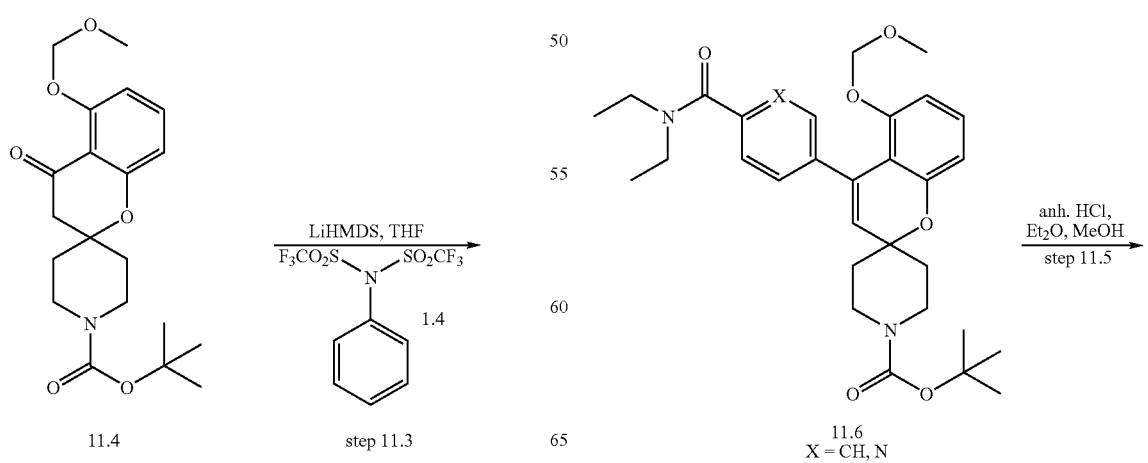

-continued
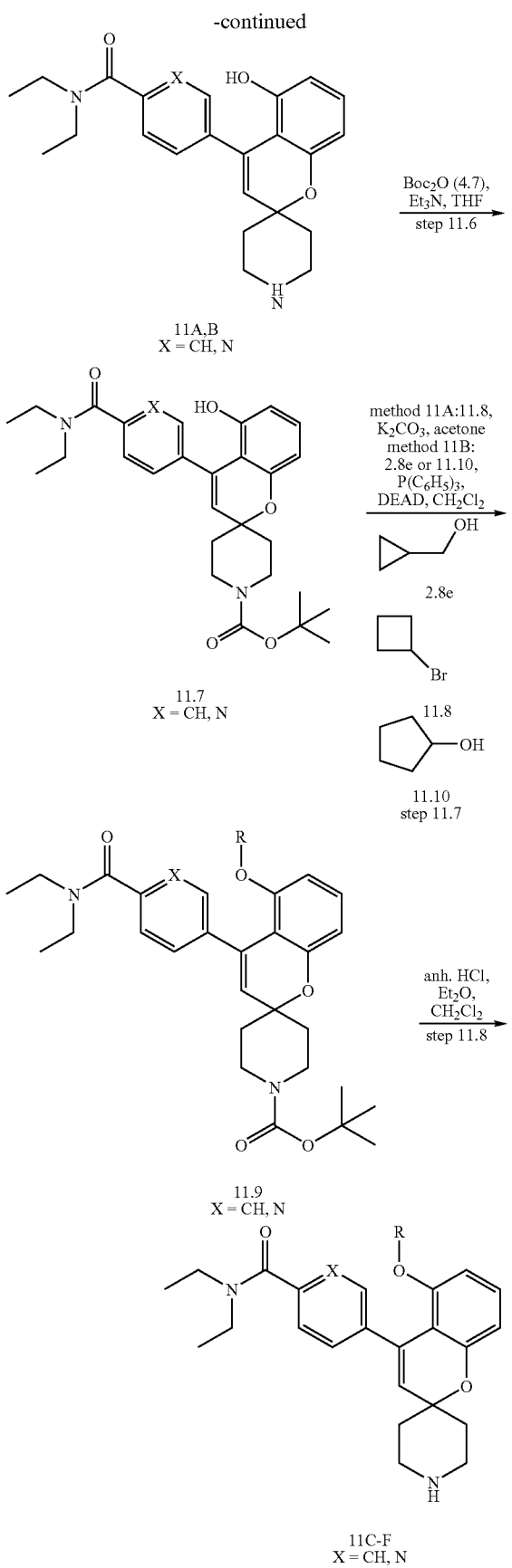
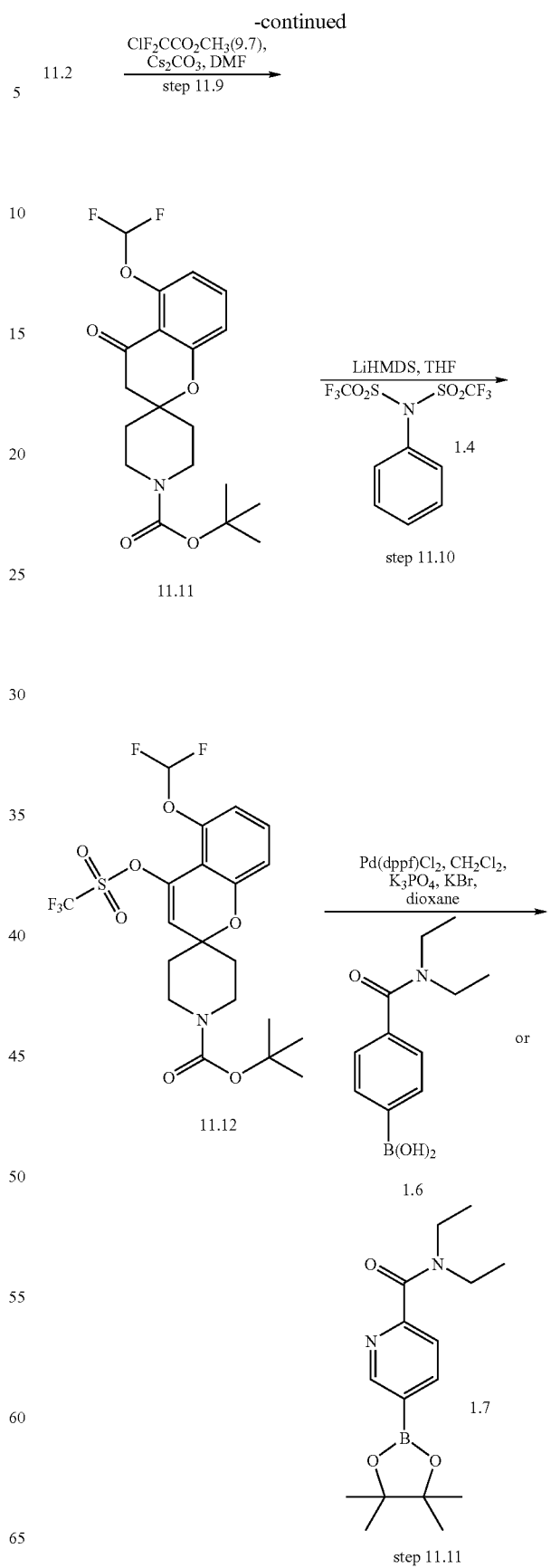

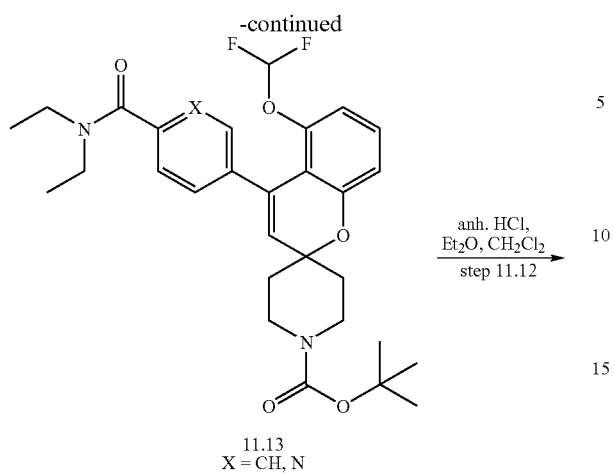
11.13
X = CH, N
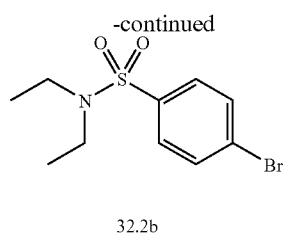
32.2b
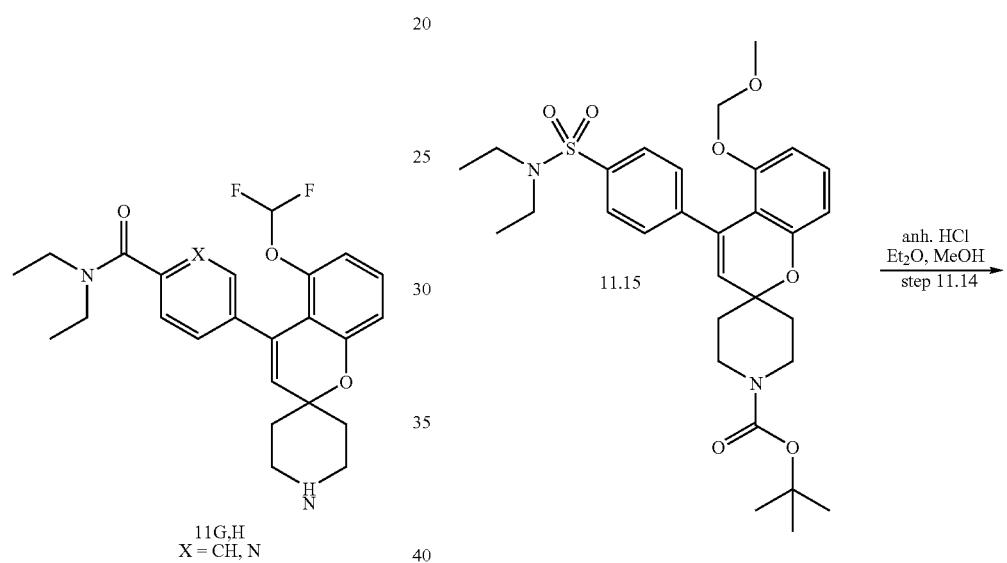
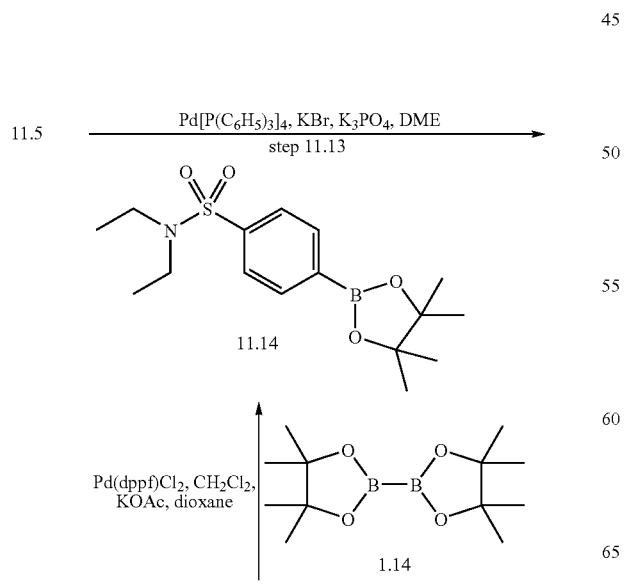

Scheme 12:
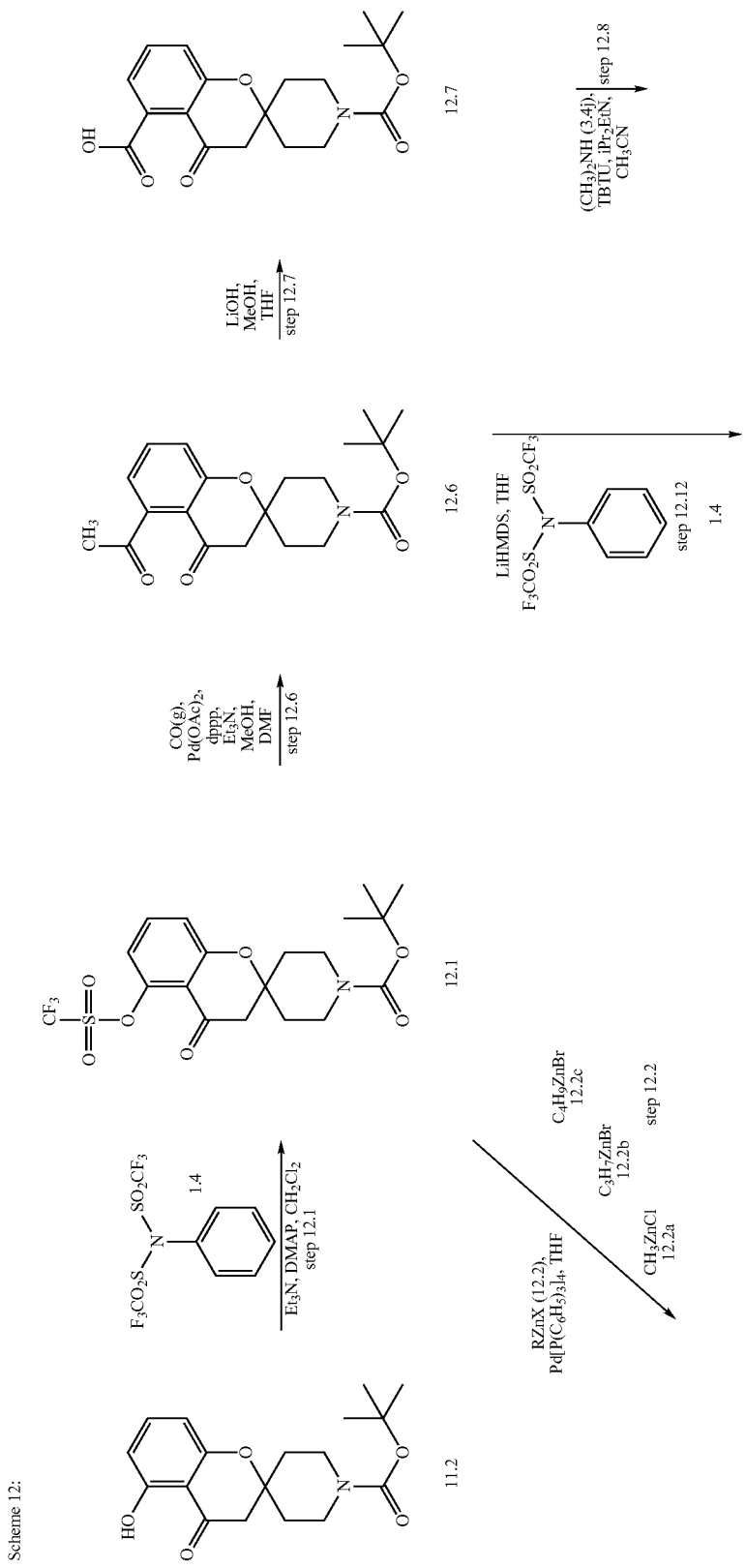

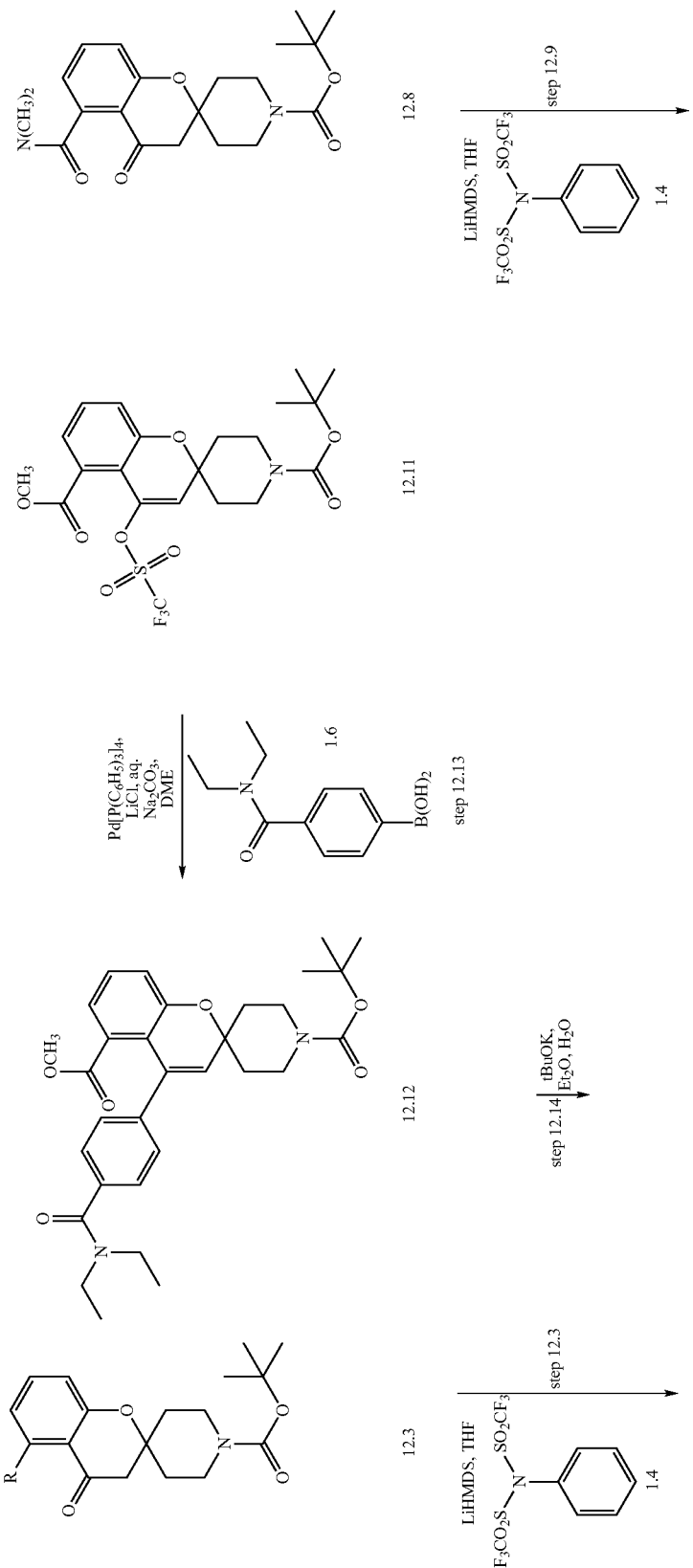

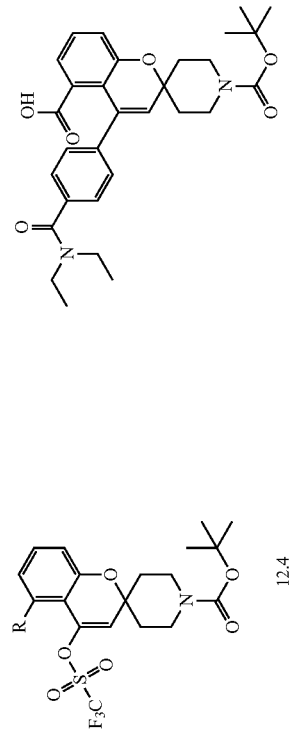

-continued
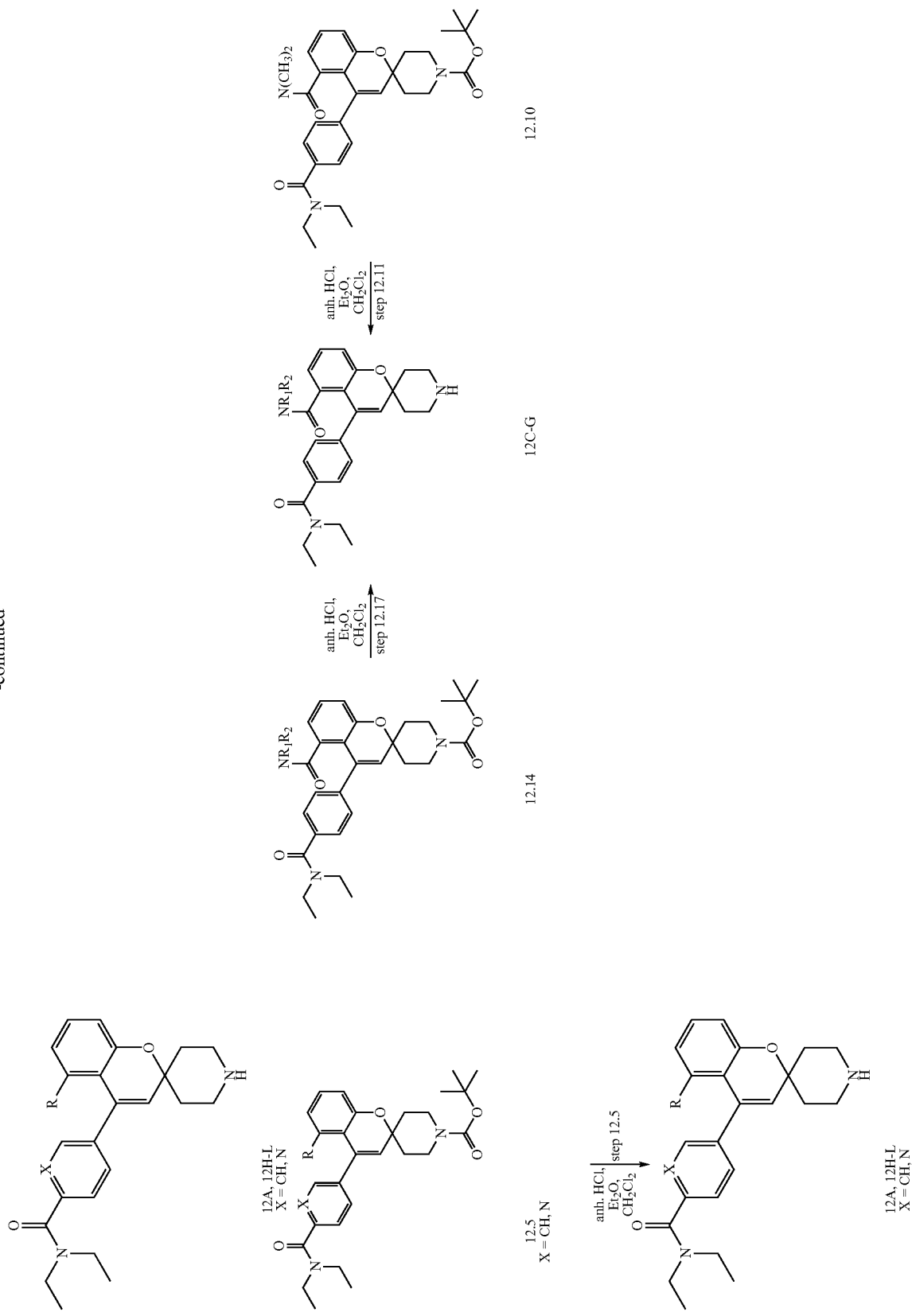

Scheme 13:
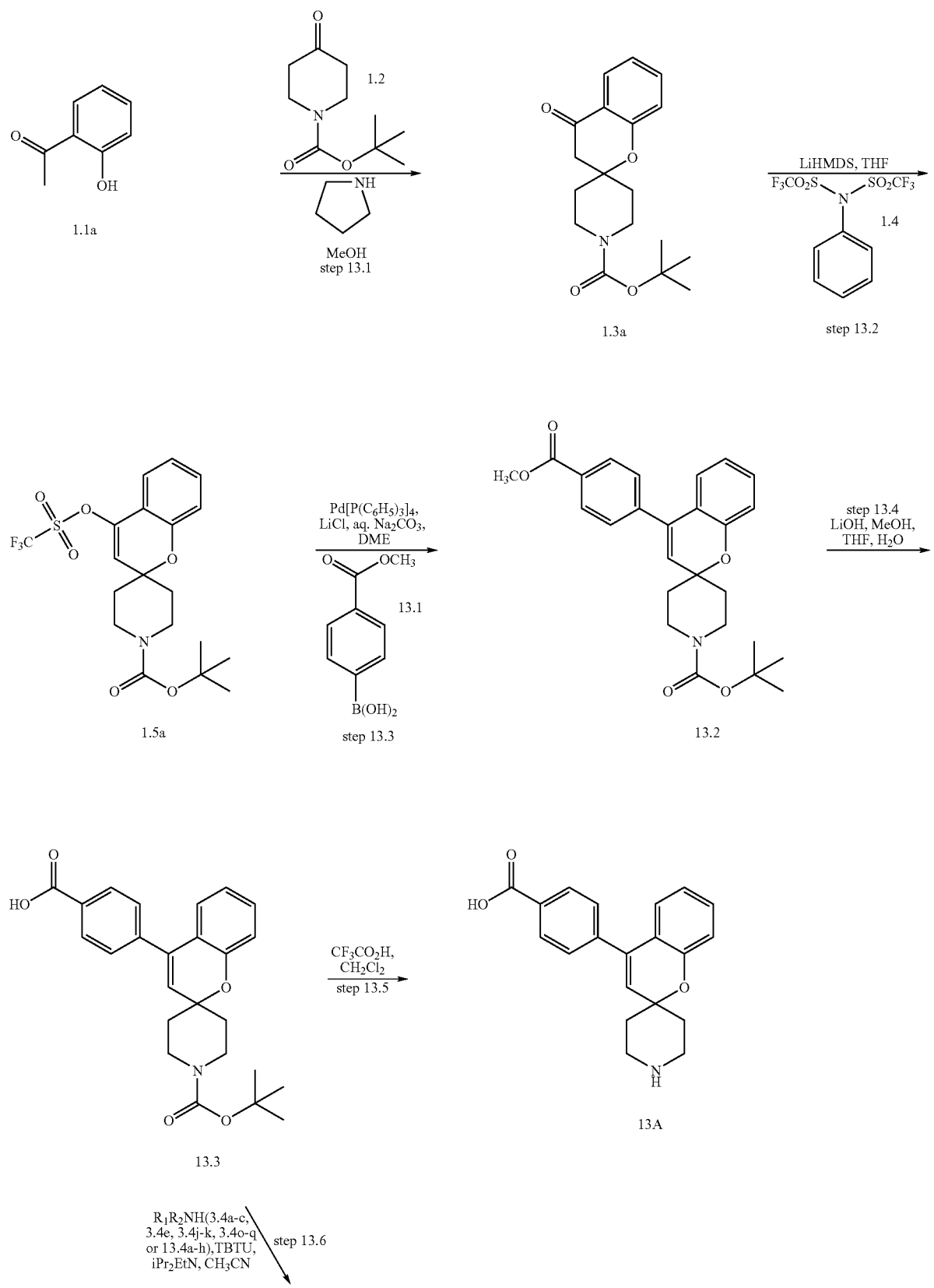

-continued
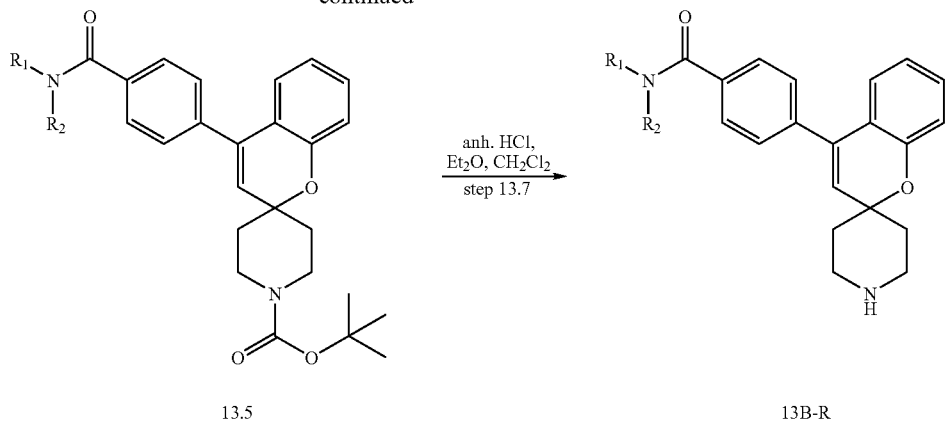
list of amines used in step 13.6:
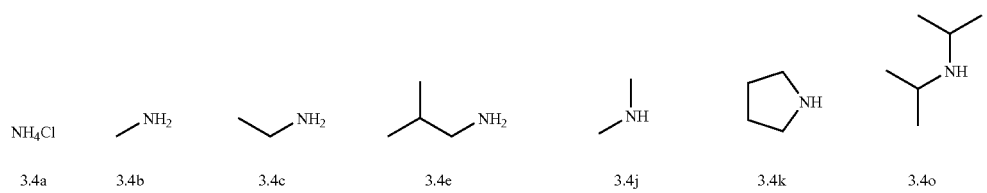
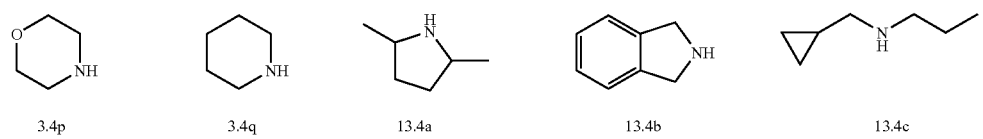
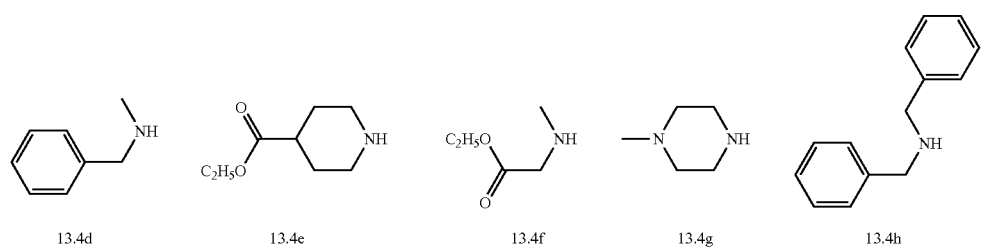
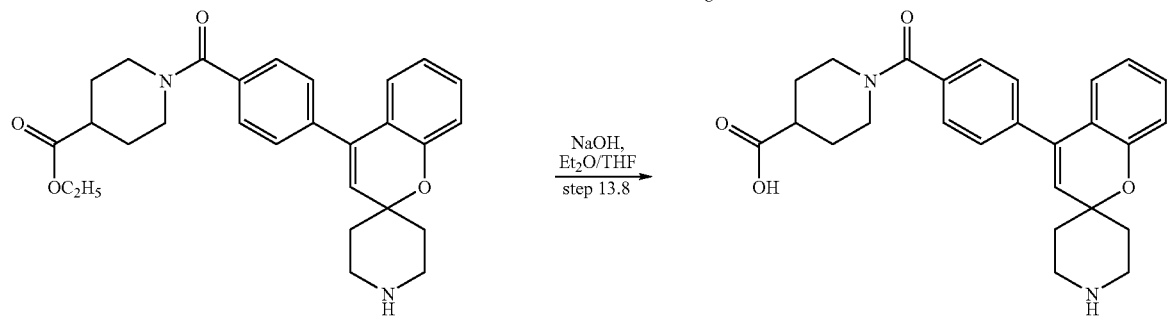

Scheme 14:
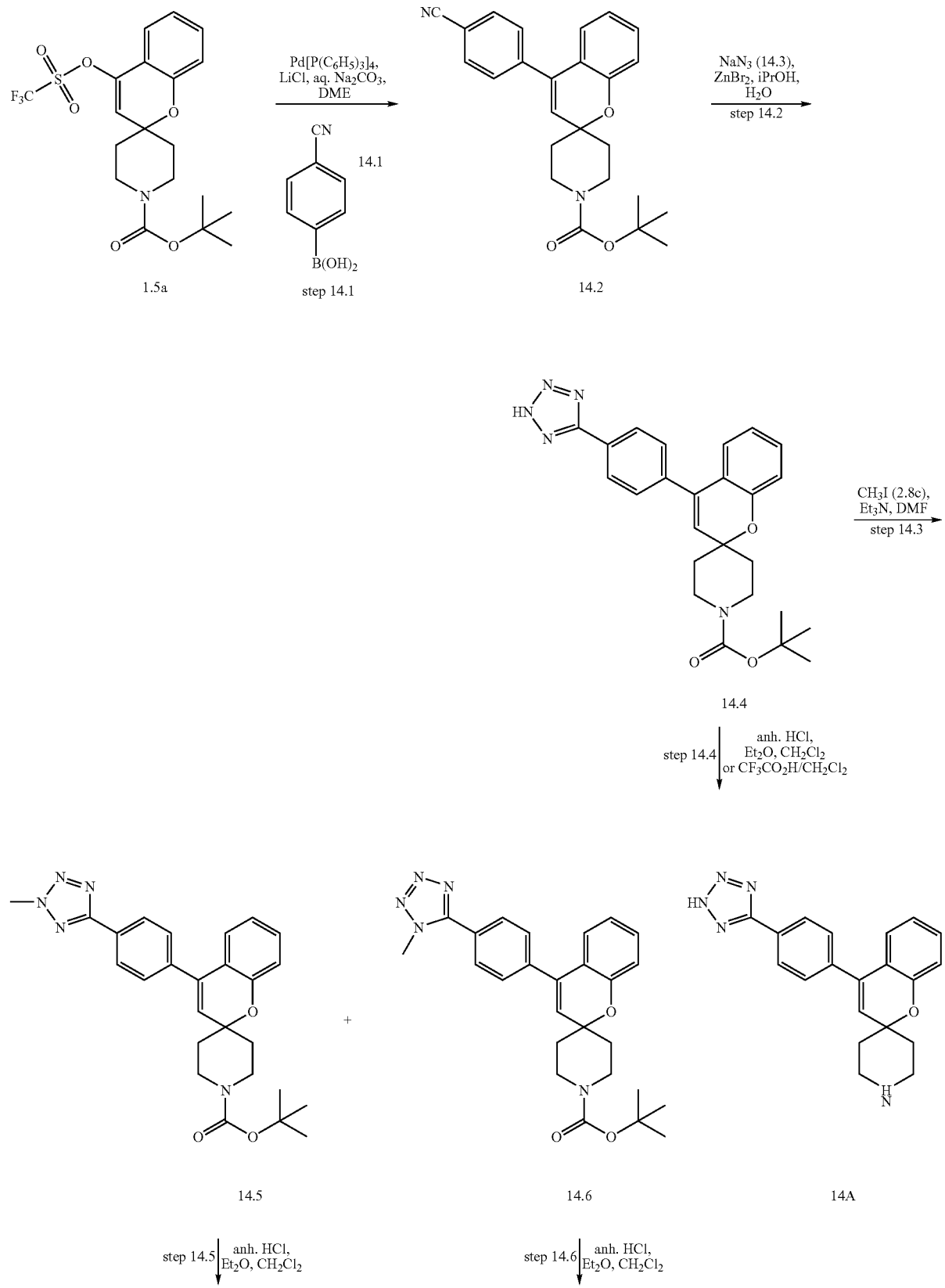

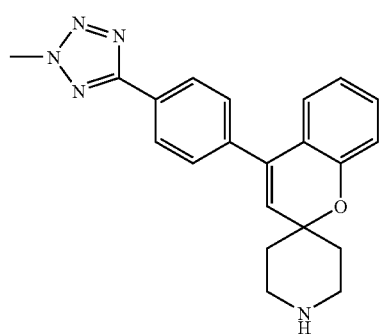
14B
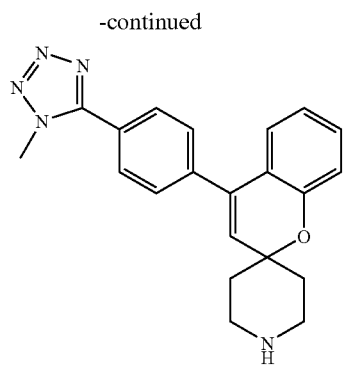
14C
Scheme 15:
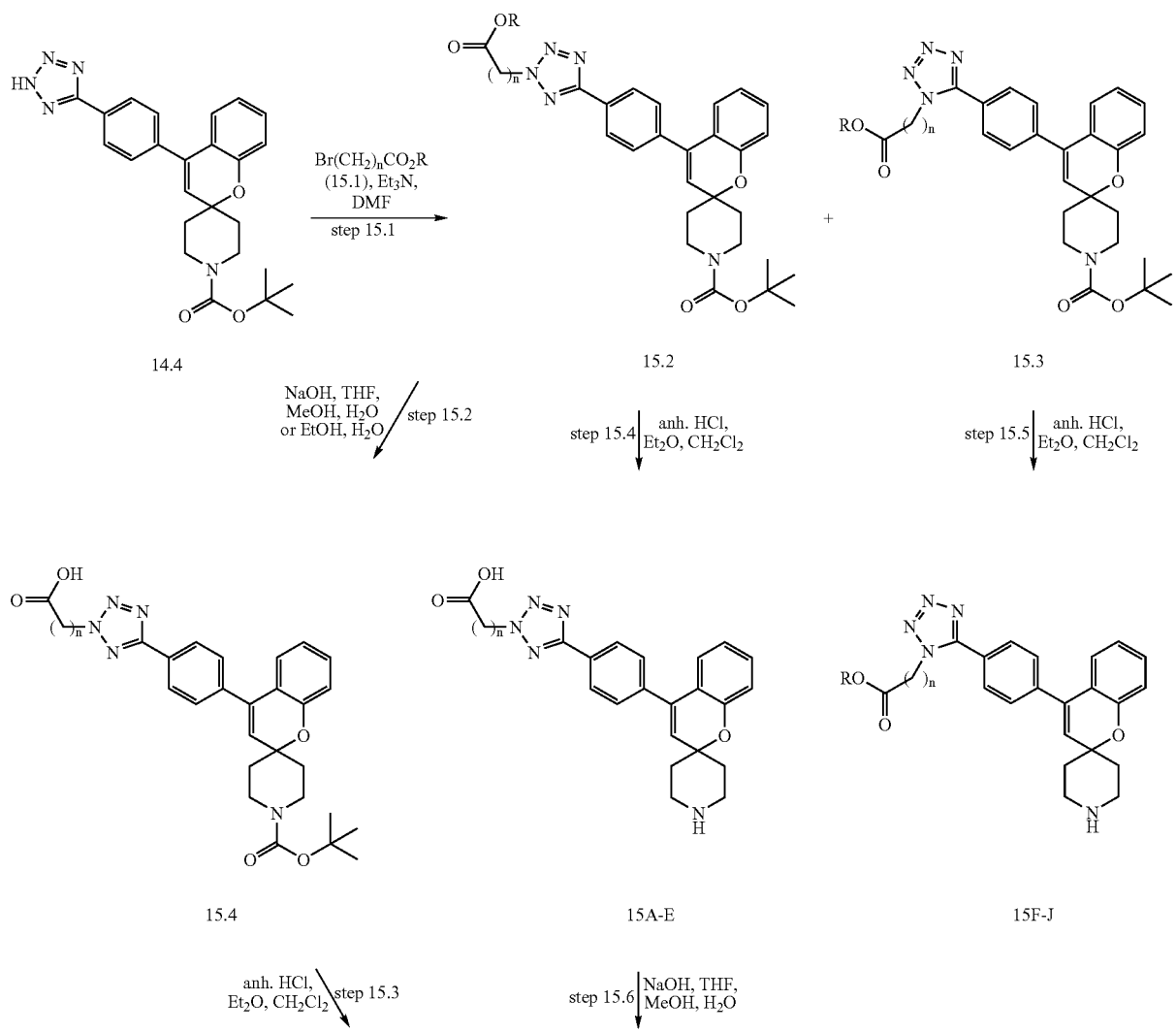

-continued
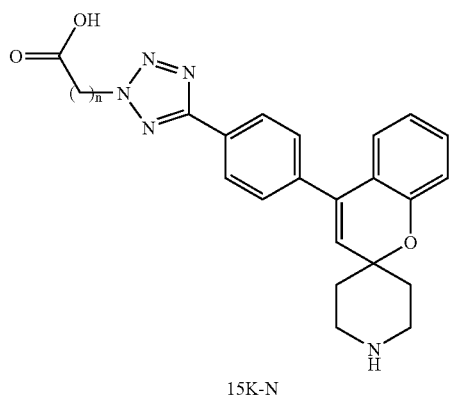
15K-N
Br(CH$_2$)$_2$nCO$_2$R used in step 15.1:
| BrCH$_2$CO$_2$Me | Br(CH$_2$)$_2$CO$_2$Me | Br(CH$_2$)$_3$CO$_2$Et | Br(CH$_2$)$_4$CO$_2$Et | Br(CH$_2$)$_5$CO$_2$Et |
|---|---|---|---|---|
| 15.1a | 15.1b | 15.1c | 15.1d | 15.1e |
Scheme 16:
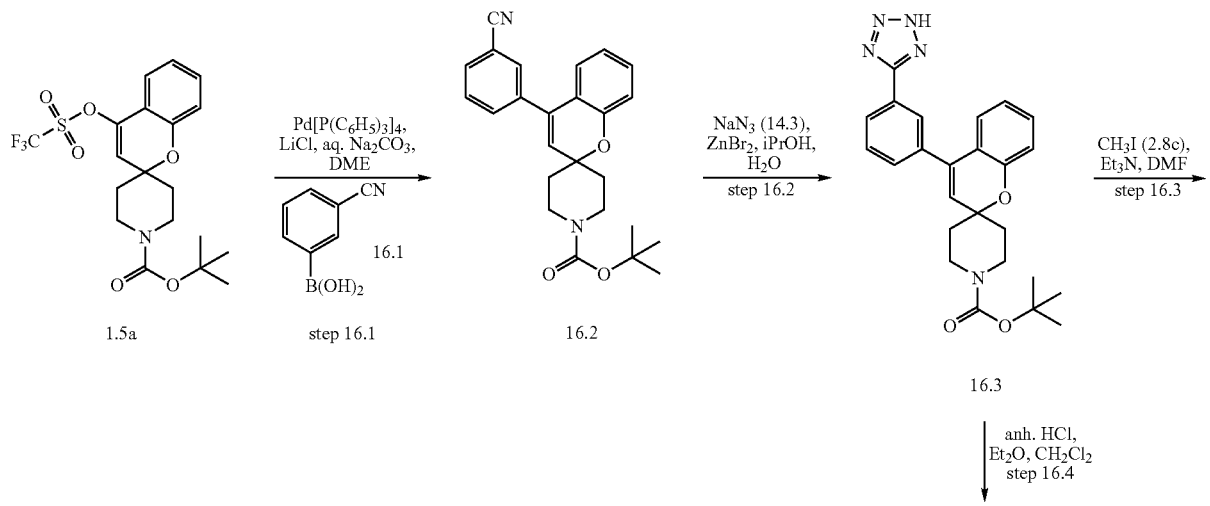

-continued
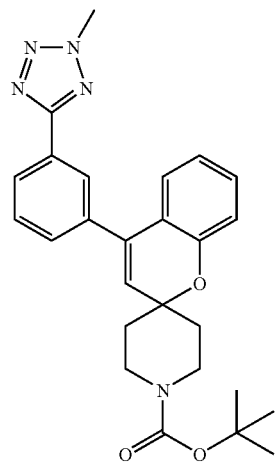 + 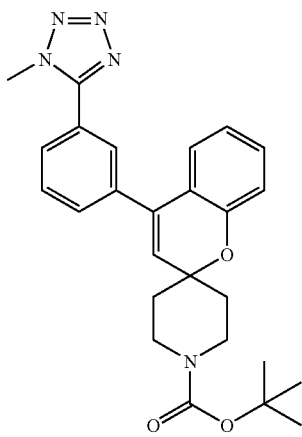
16.4          16.5
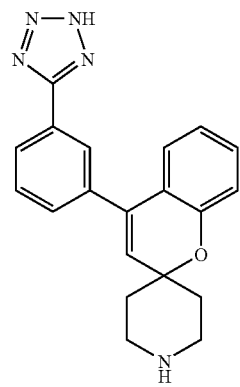
16A
step 16.5 | anh. HCl, Et₂O, CH₂Cl₂ ↓     step 16.6 | anh. HCl, Et₂O, CH₂Cl₂ ↓
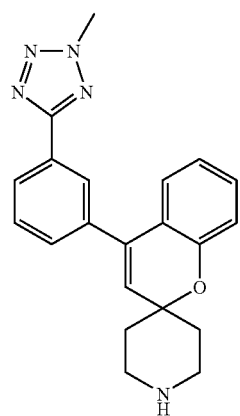      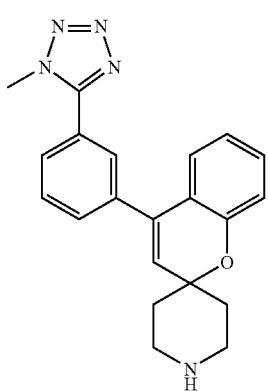
16B         16C Scheme 17:
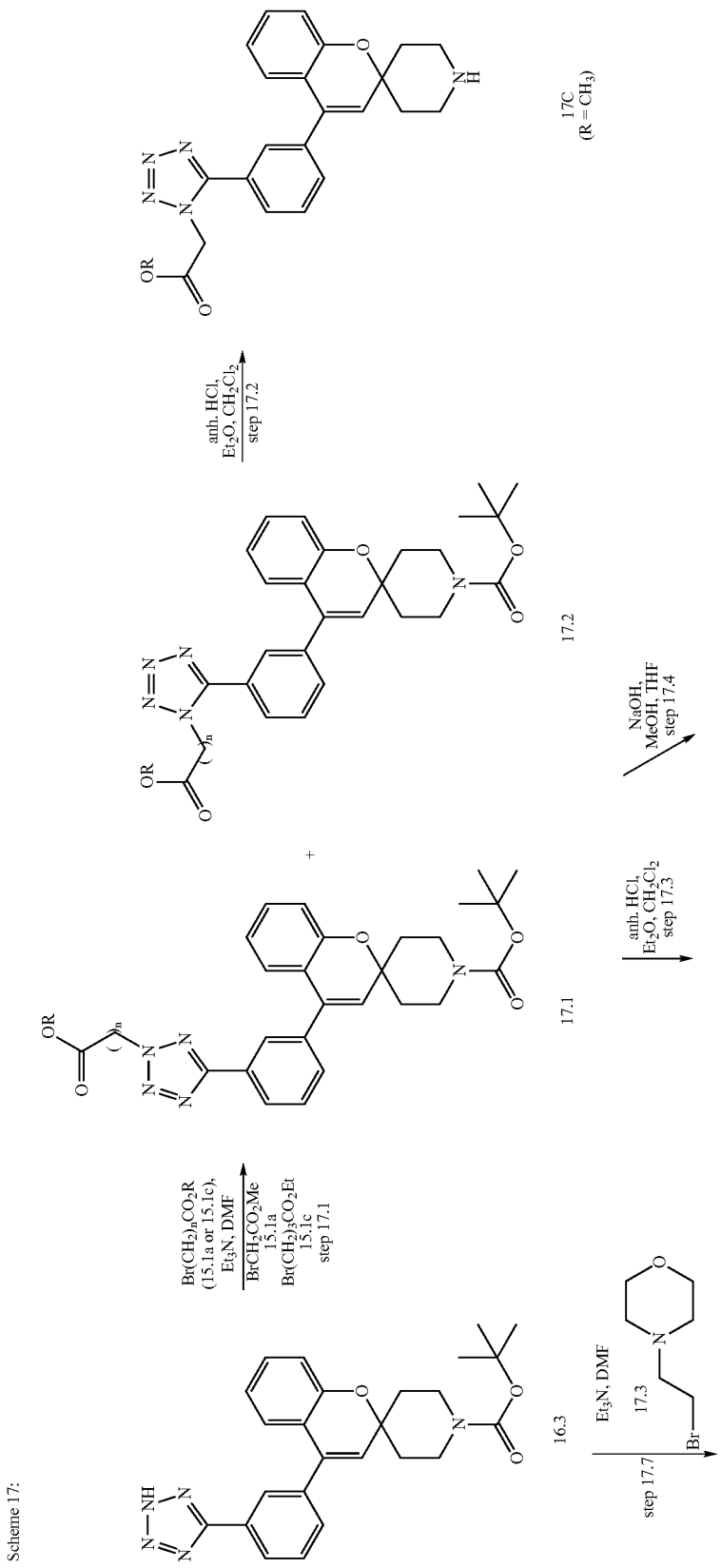

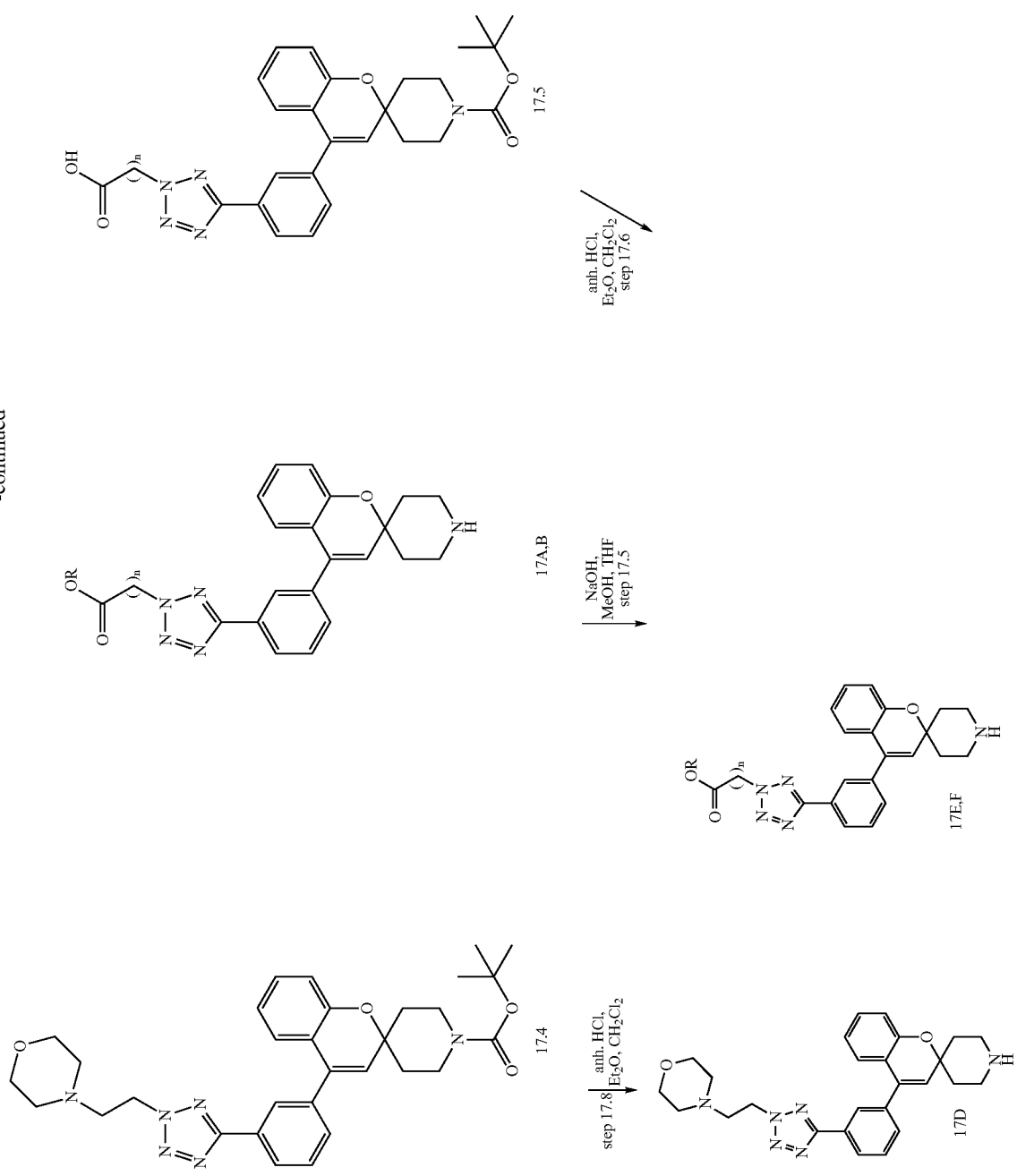

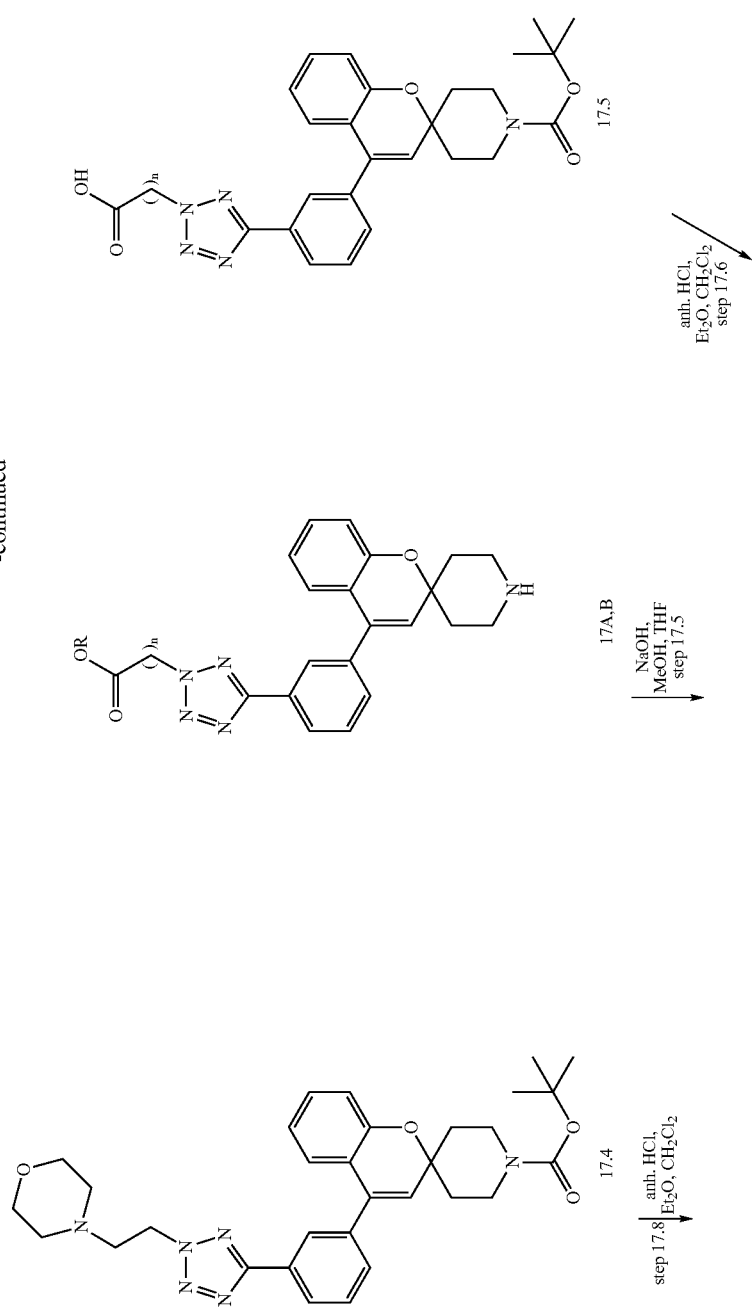

-continued
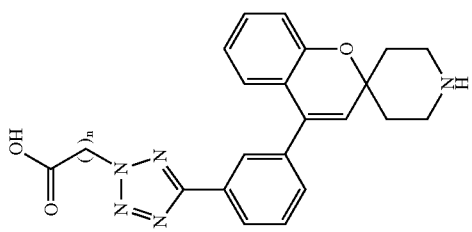
17E,F
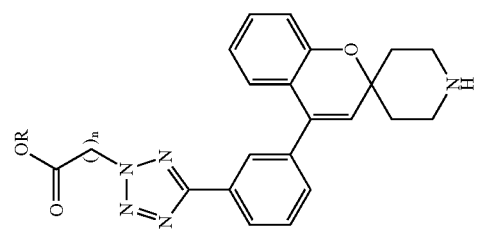
17E,F
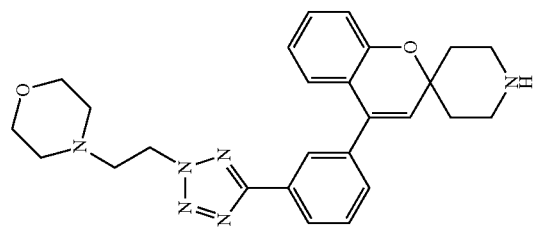
17D
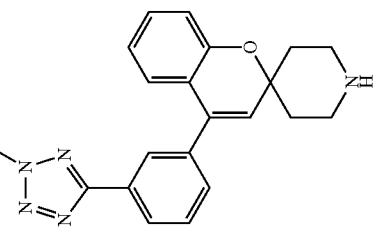
17D

Scheme 18:
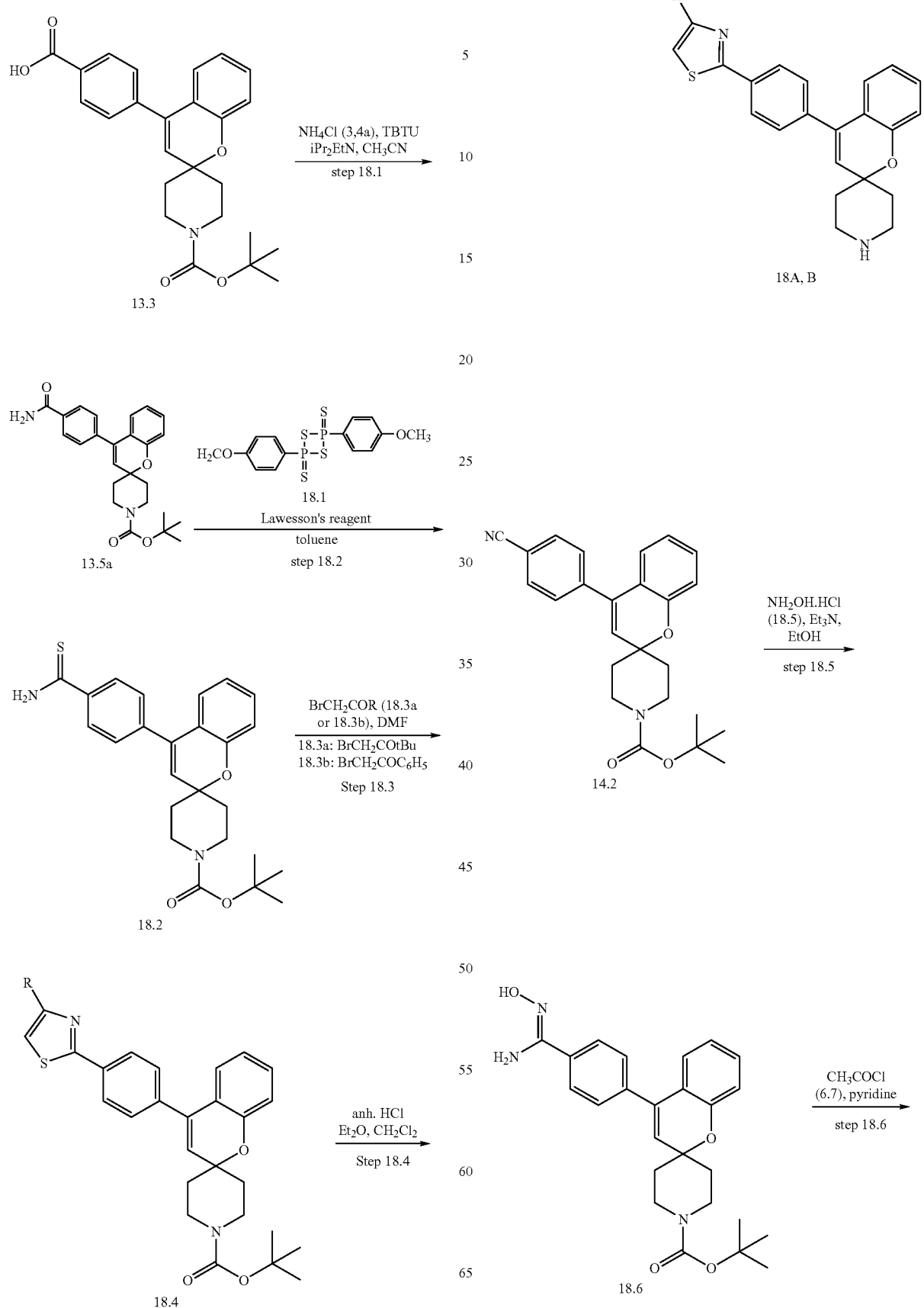

193
-continued
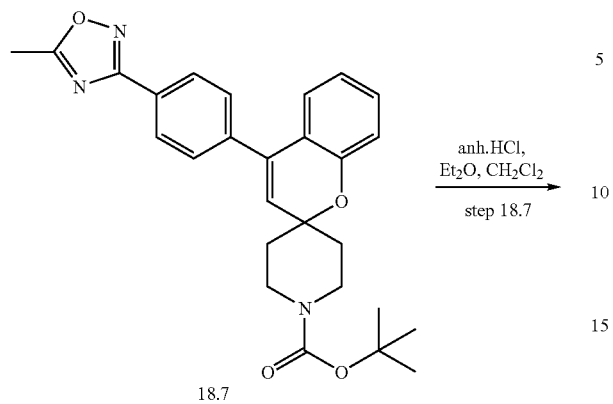
18.7
anh.HCl,
Et₂O, CH₂Cl₂
→
step 18.7
194
-continued
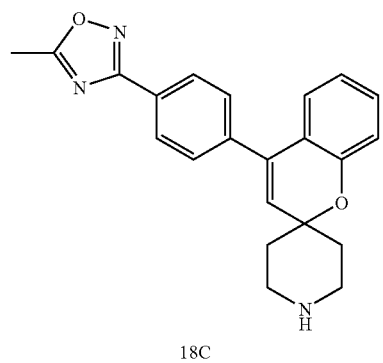
18C
Scheme 19:
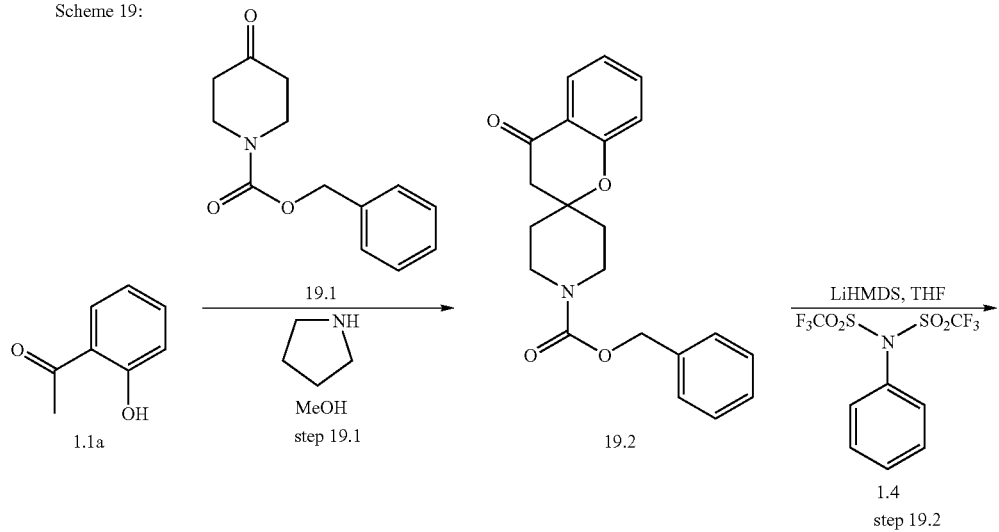
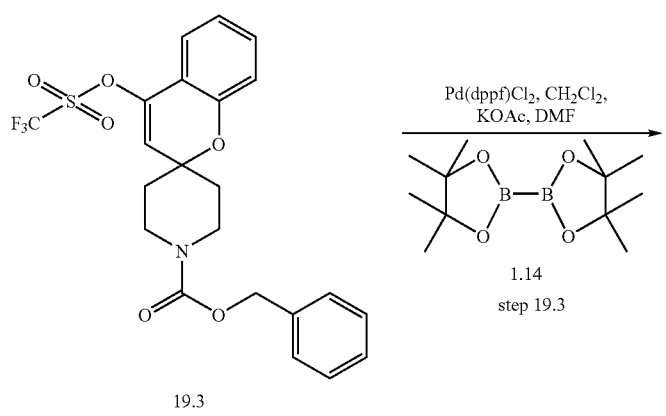
19.3

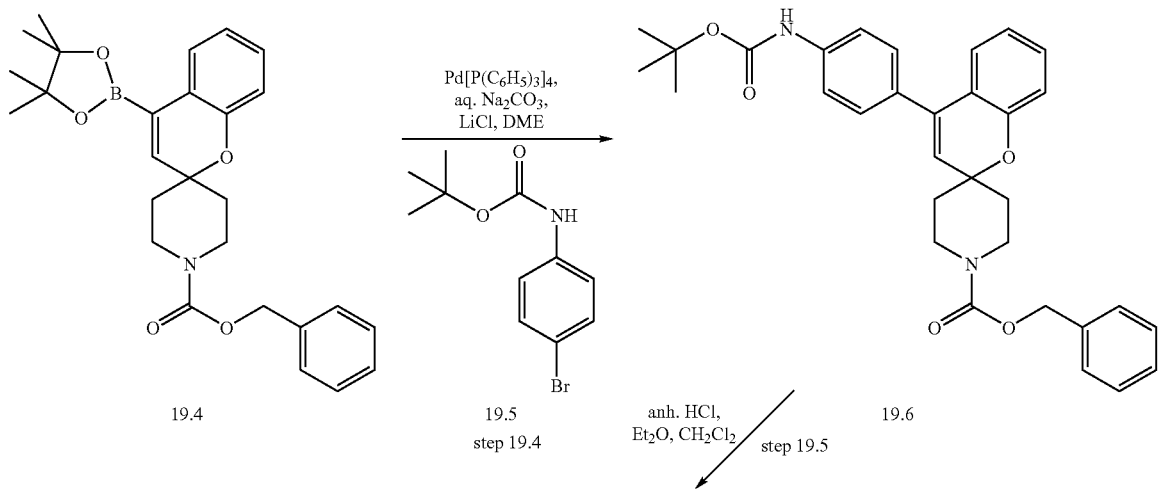
-continued
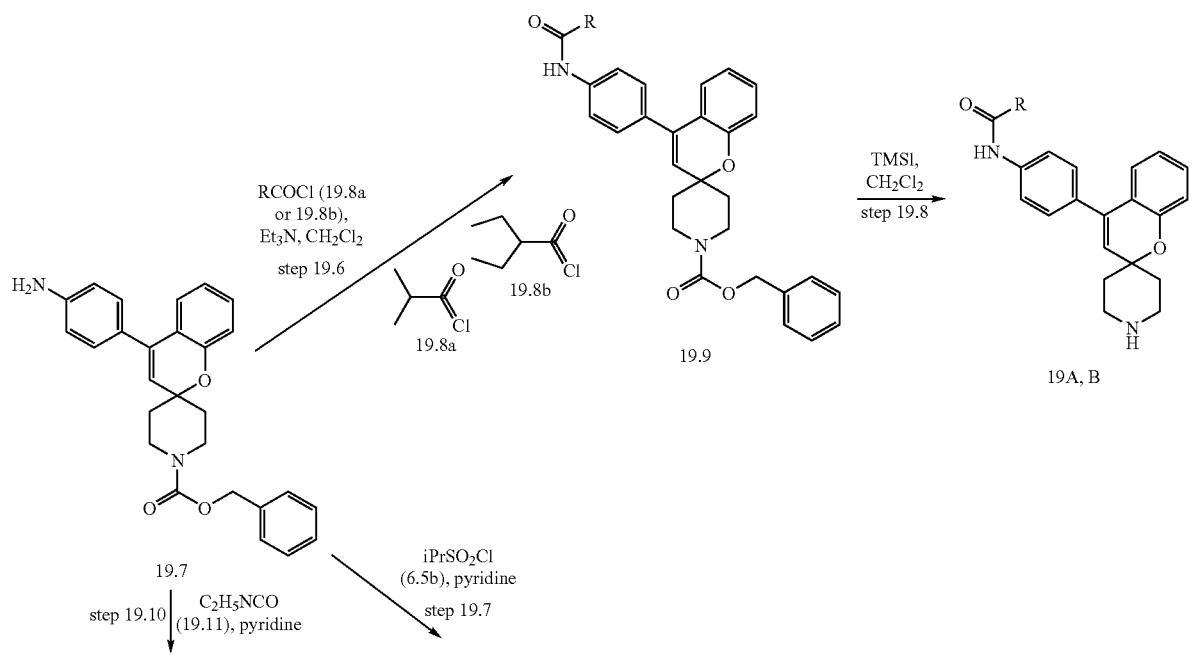

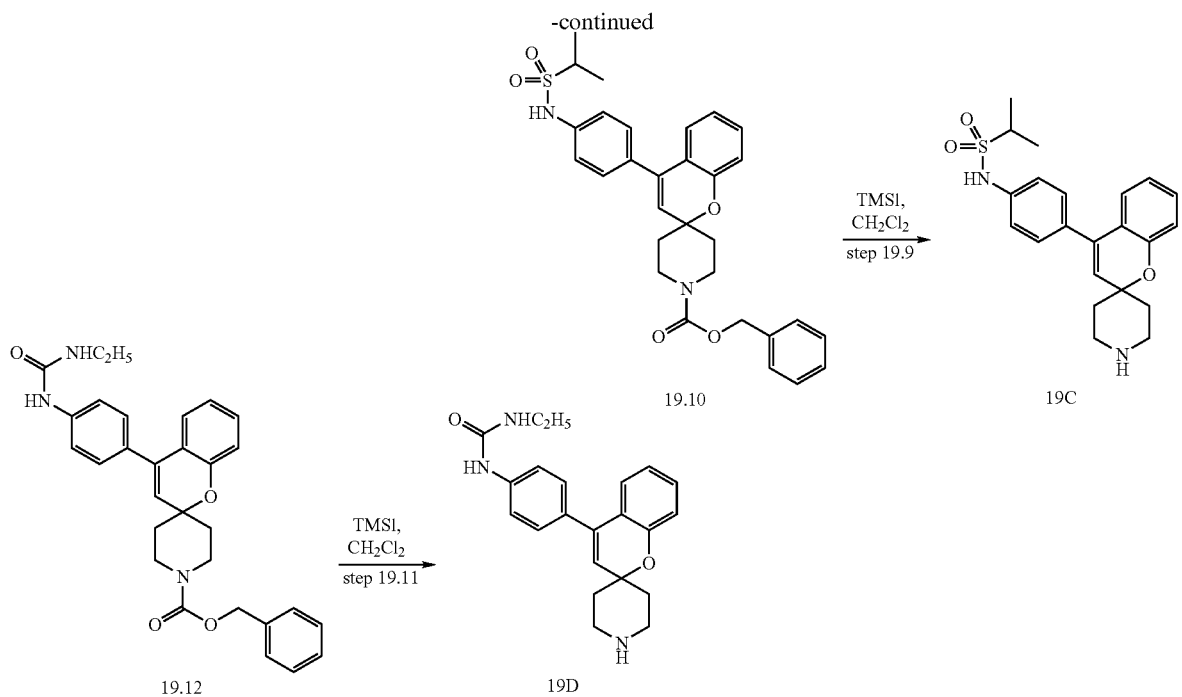
Scheme 20:
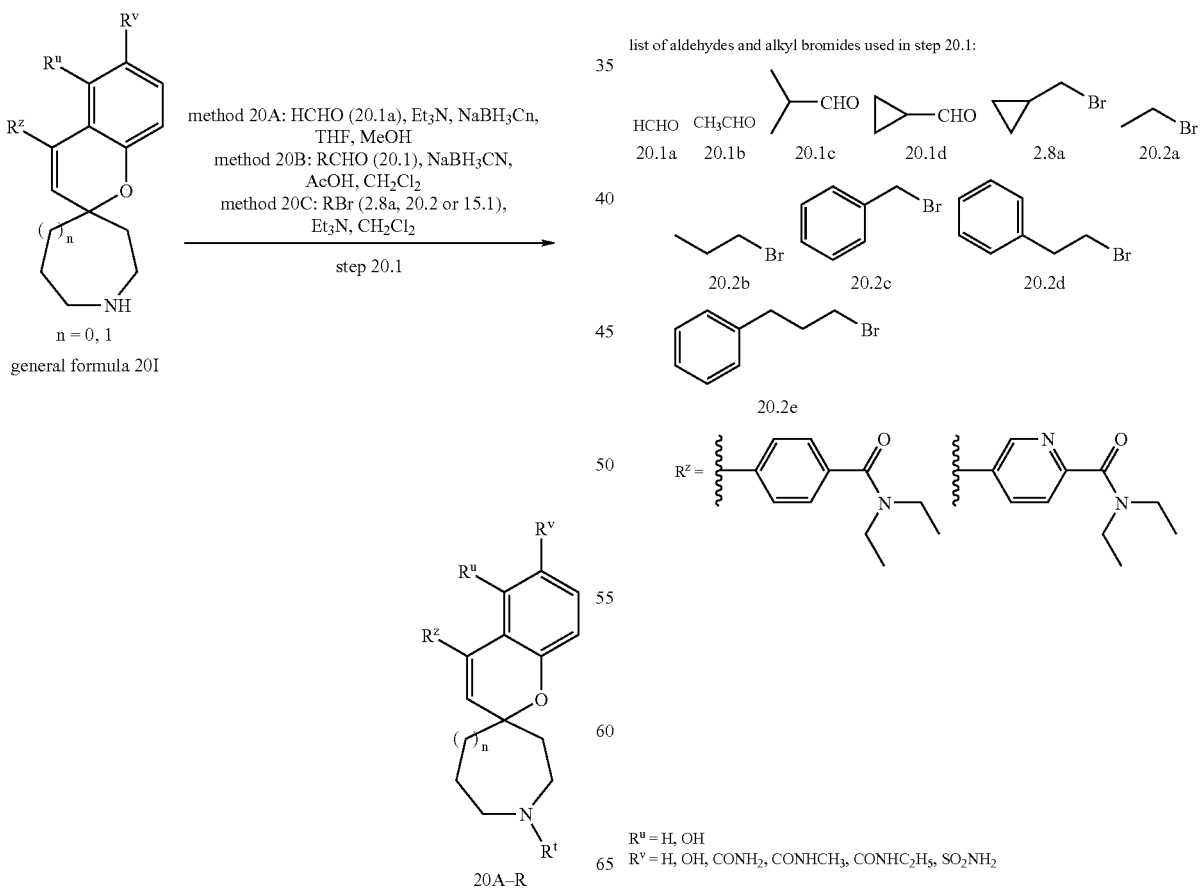

Scheme 21:
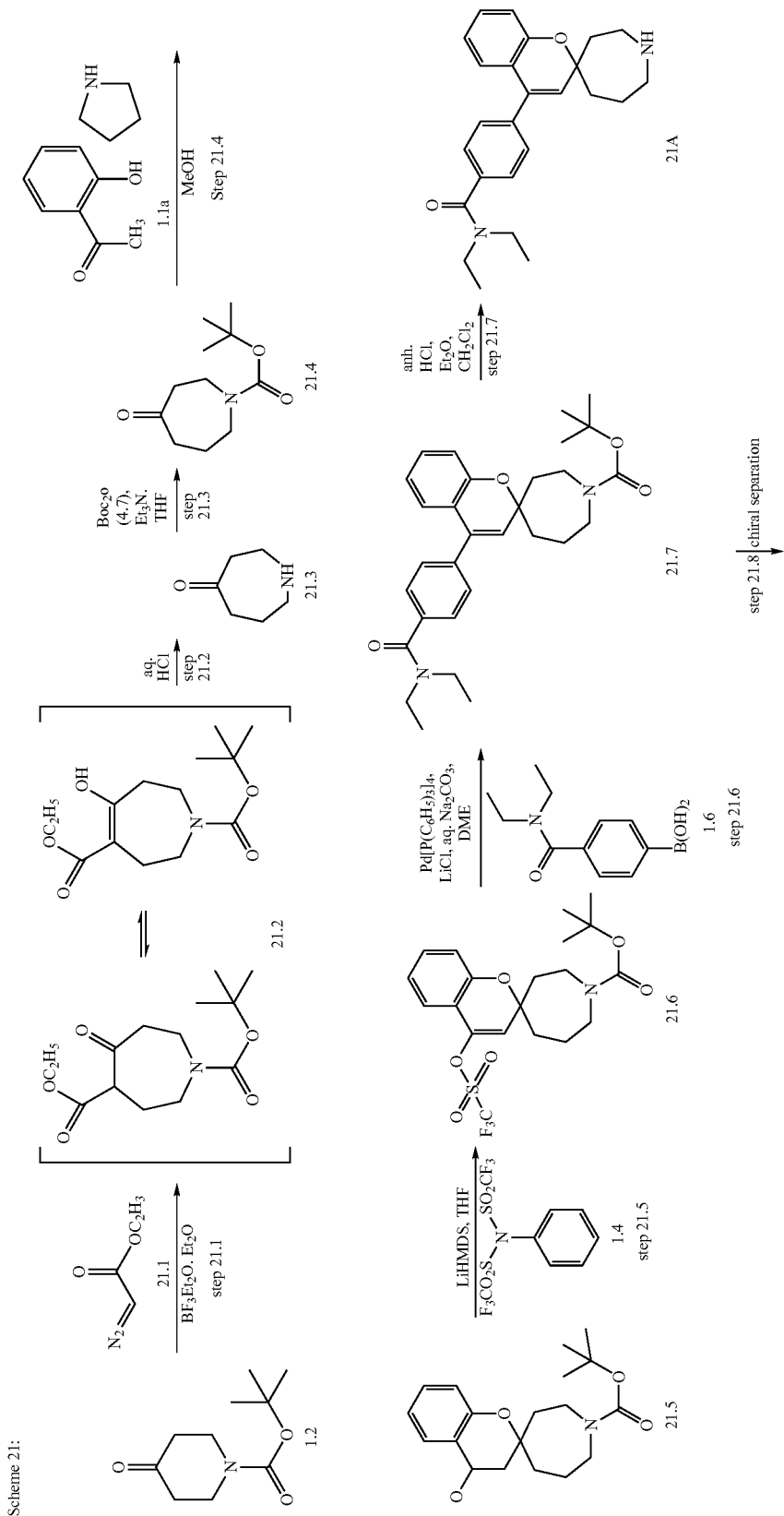

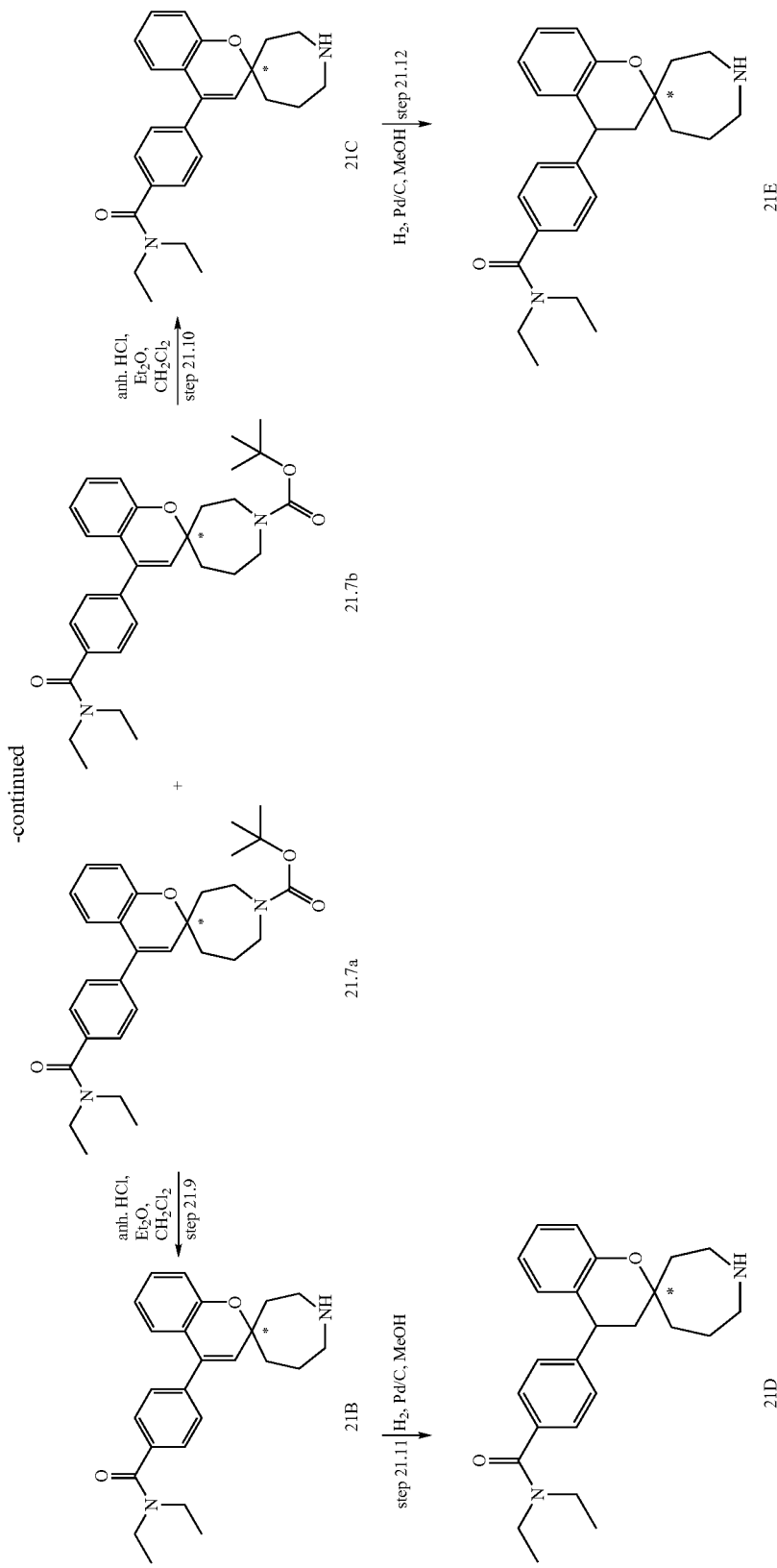

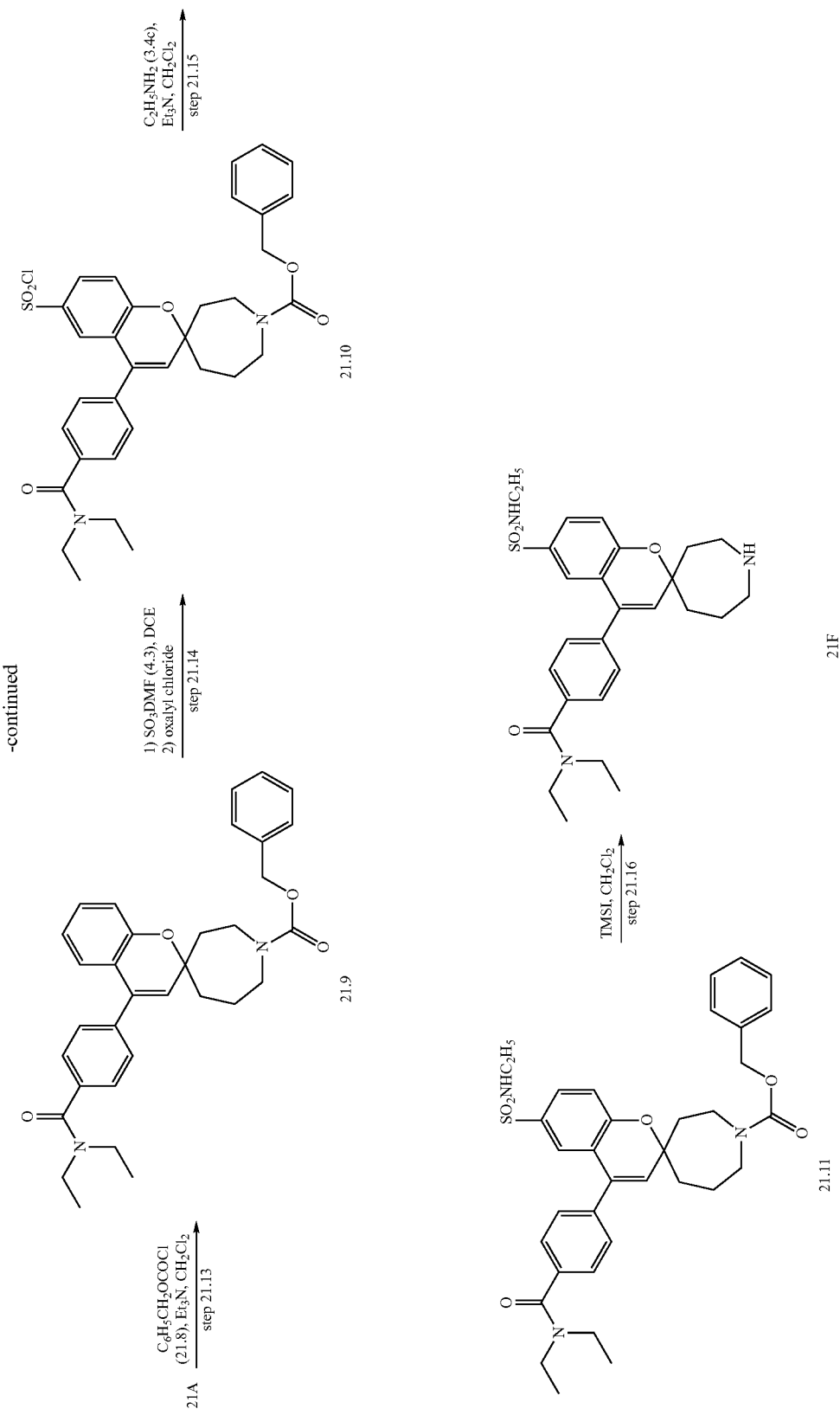

Scheme 22:
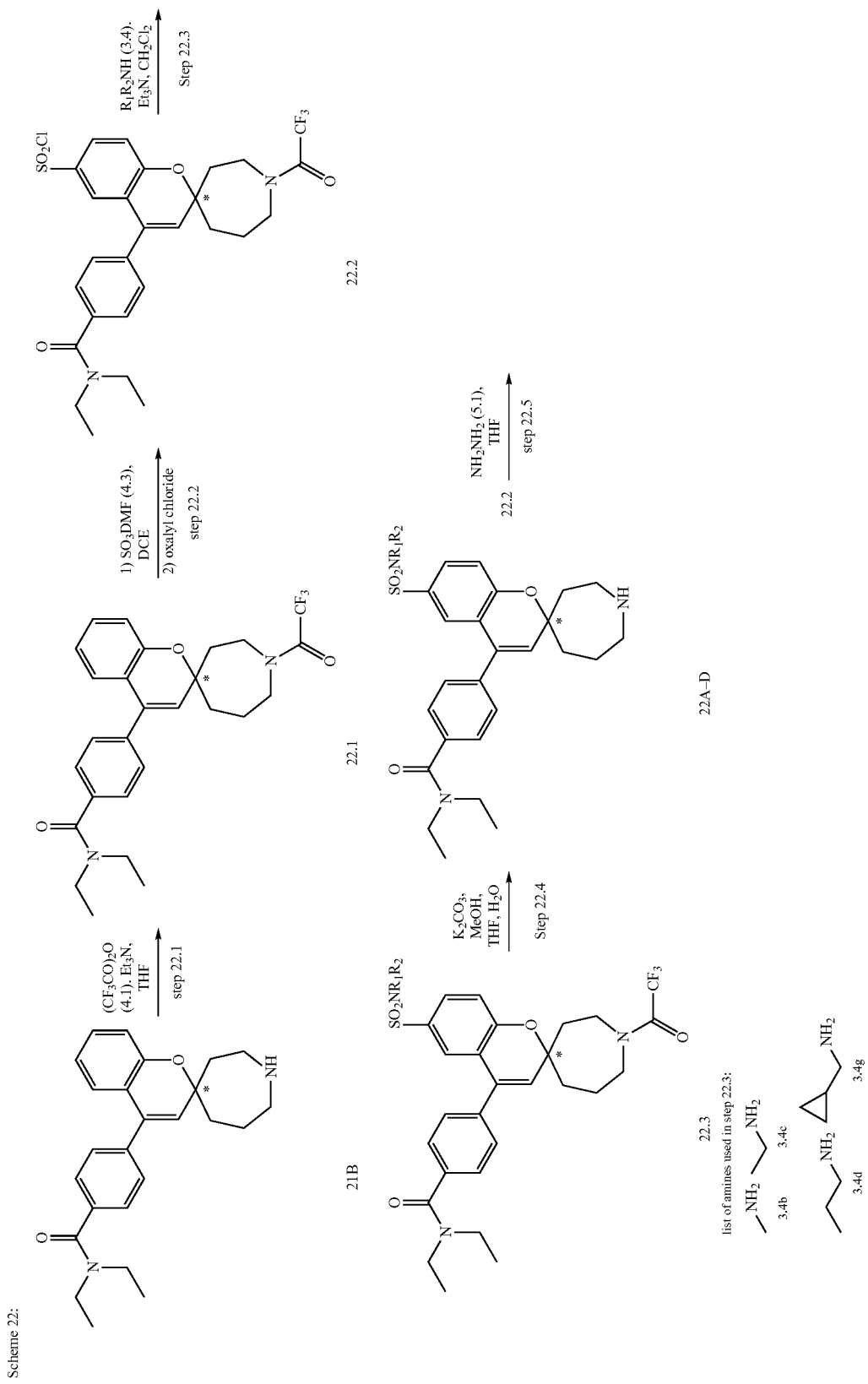

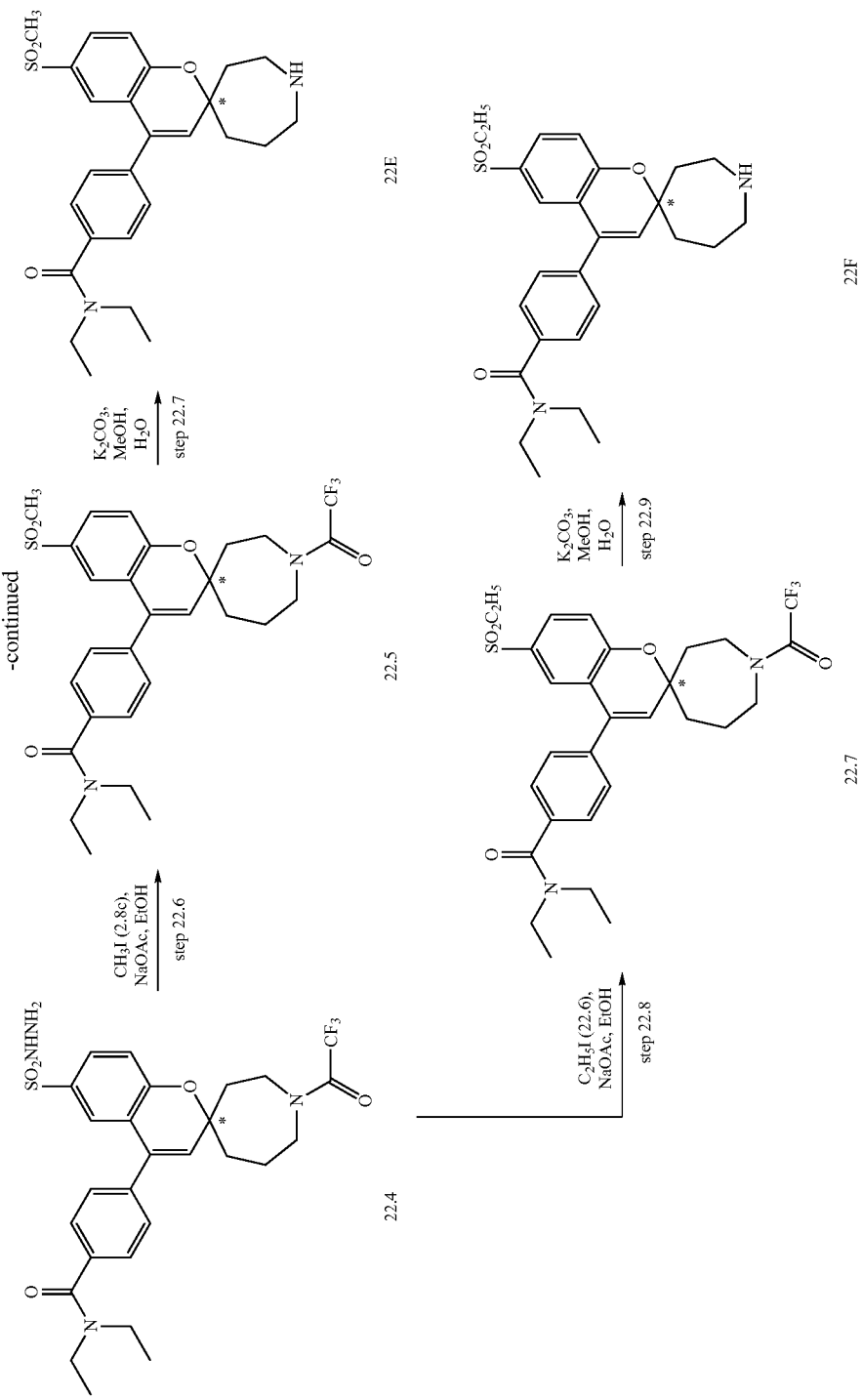

Scheme 23:
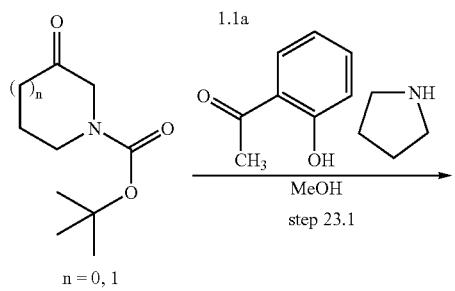
23.1a: n = 0
23.1b: n = 1
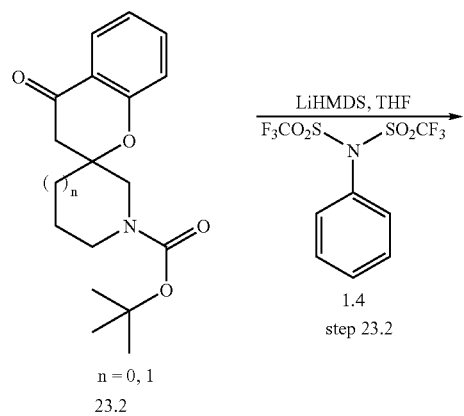
n = 0, 1
23.2
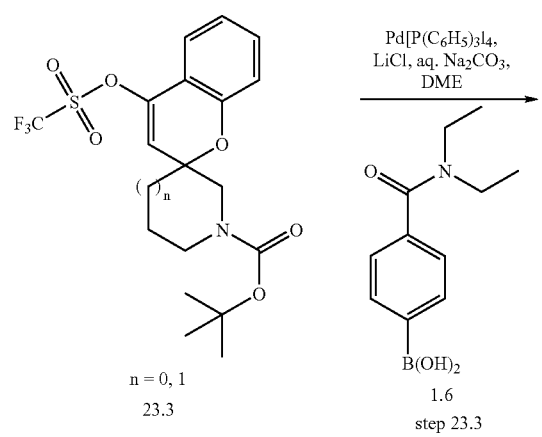
n = 0, 1
23.3
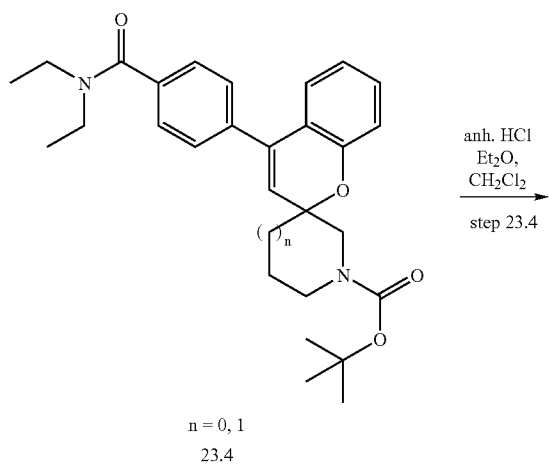
n = 0, 1
23.4
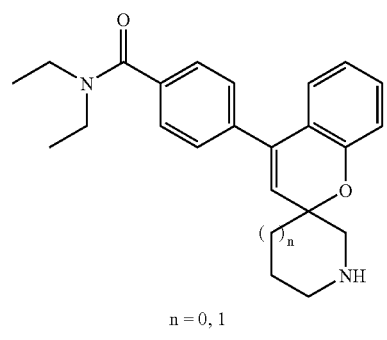
n = 0, 1
23A, B
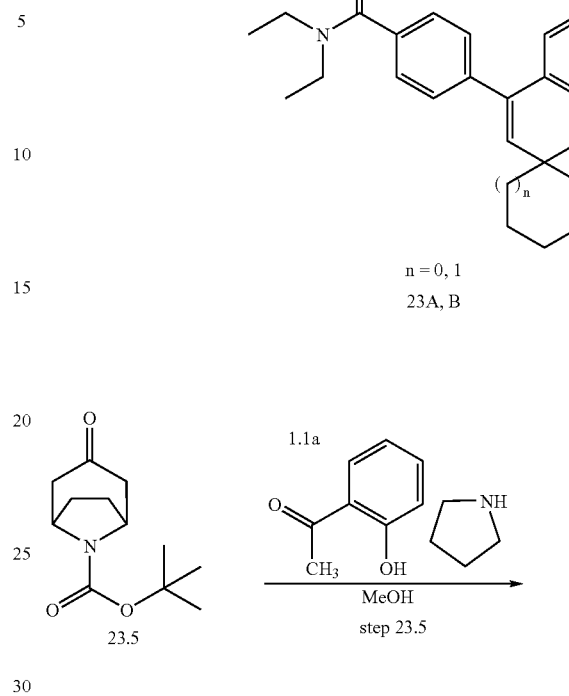
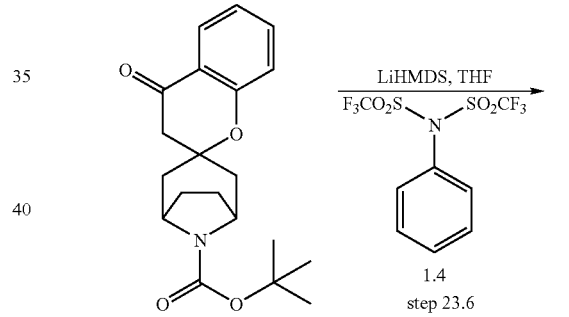
23.6
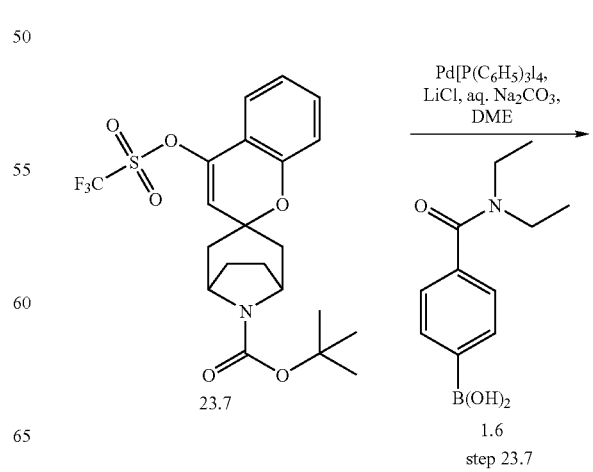
23.7

-continued
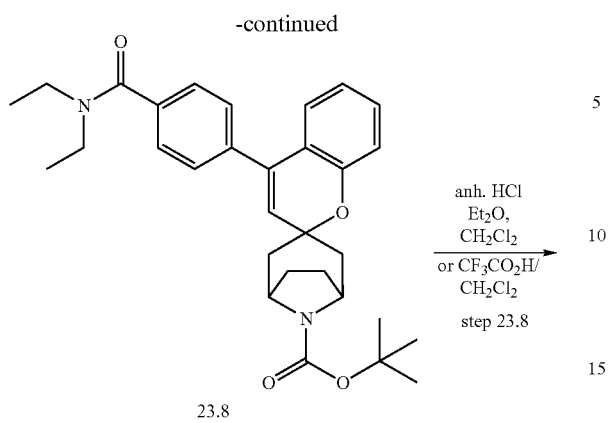
23.8
anh. HCl
Et₂O,
CH₂Cl₂
or CF₃CO₂H/
CH₂Cl₂
step 23.8
-continued
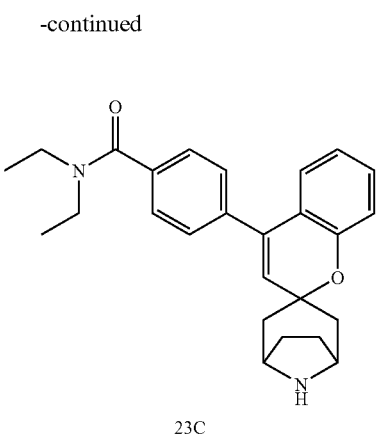
23C
Scheme 24:
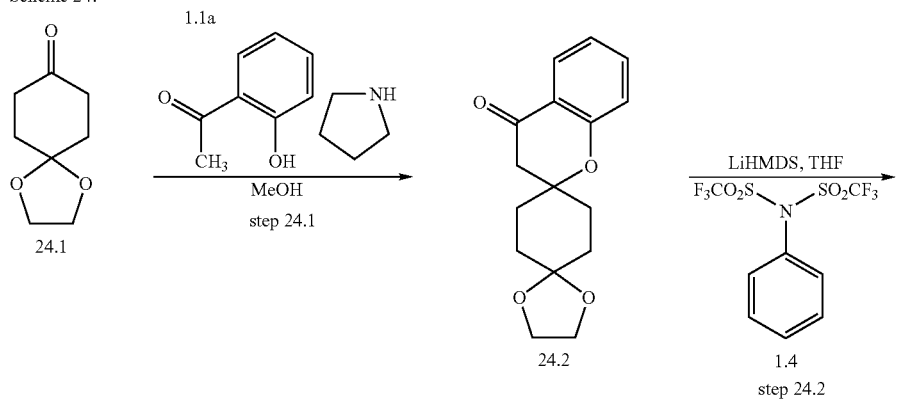
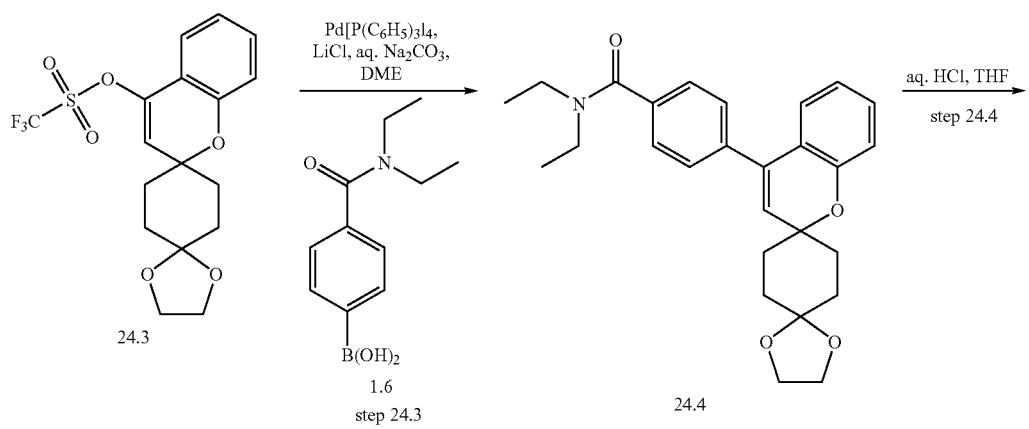

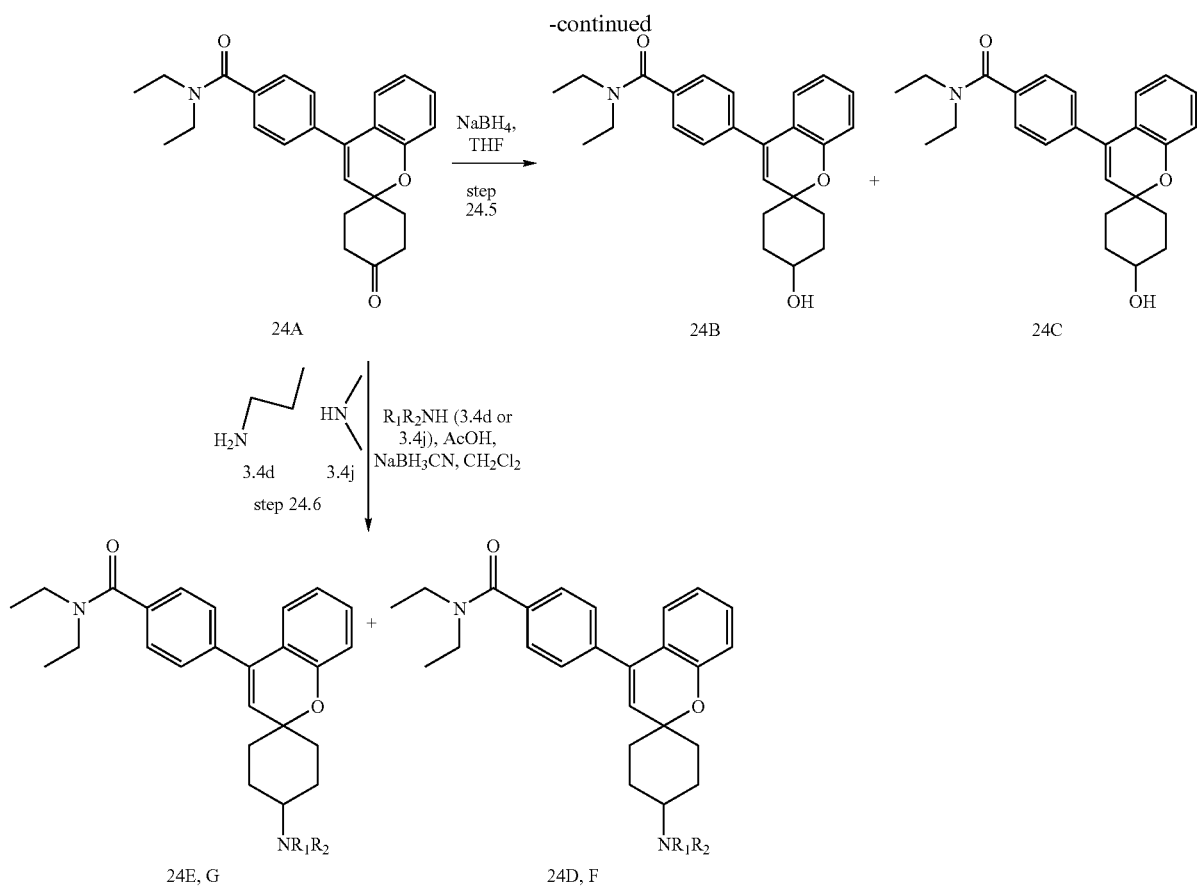
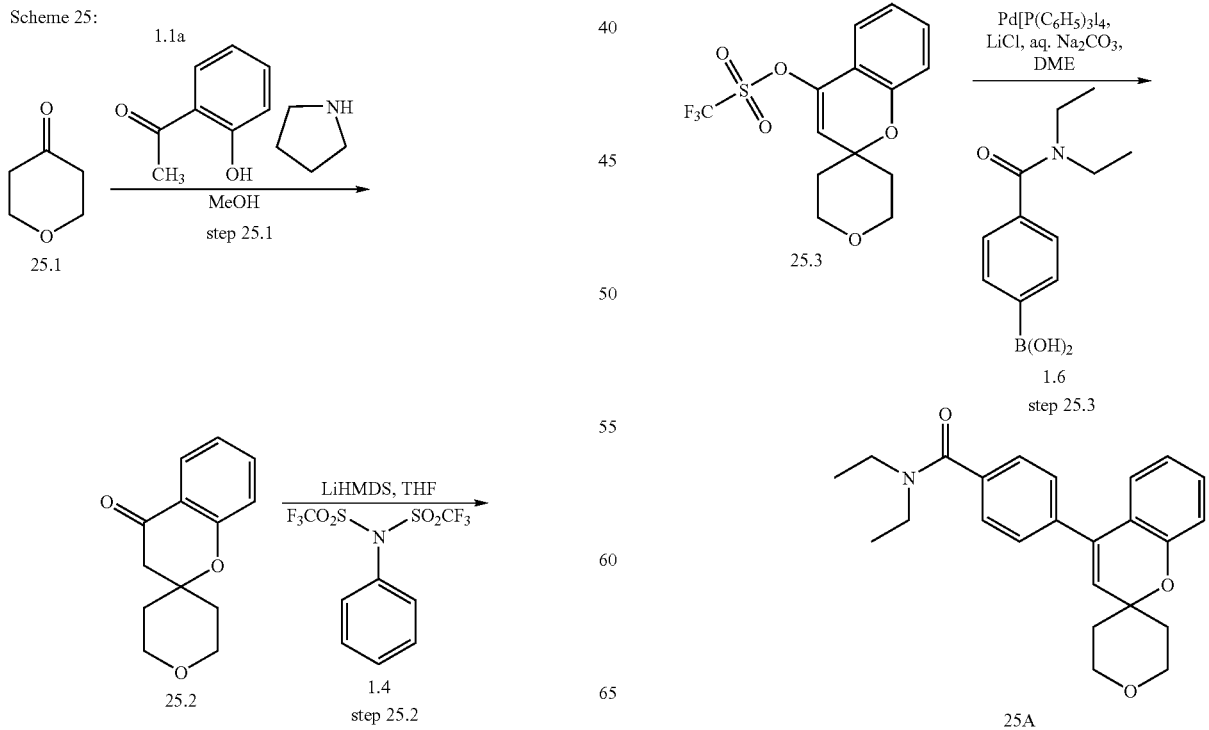
Scheme 25:

Scheme 26:
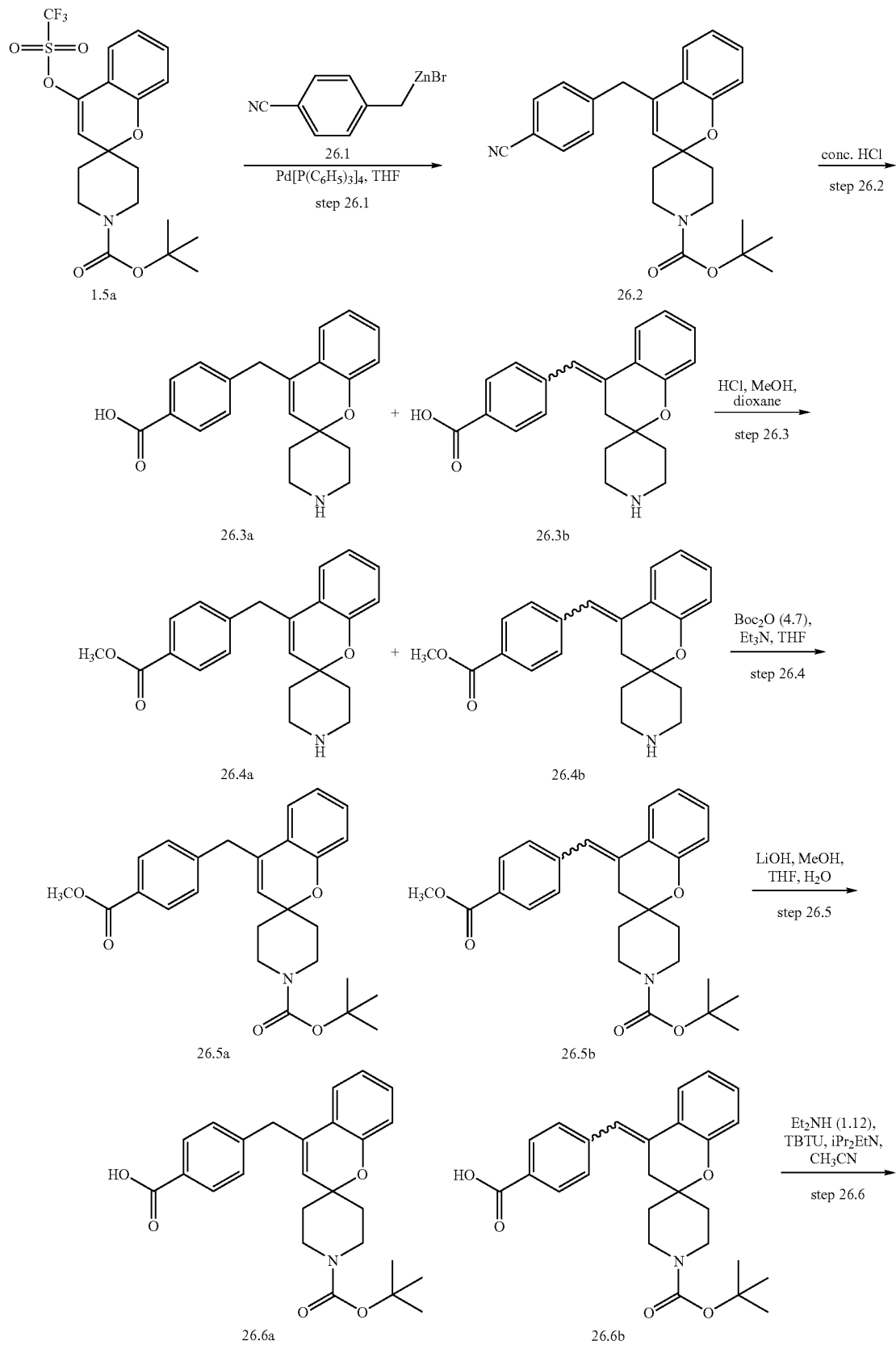

-continued
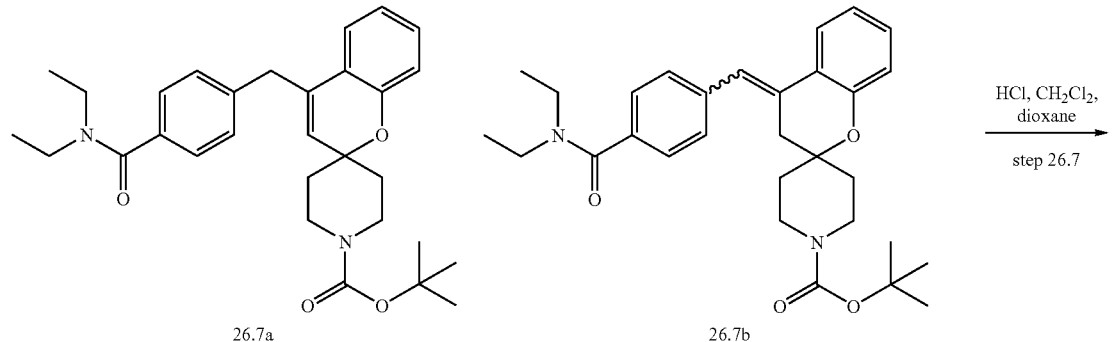
26.7a 26.7b
HCl, CH₂Cl₂, dioxane
→
step 26.7
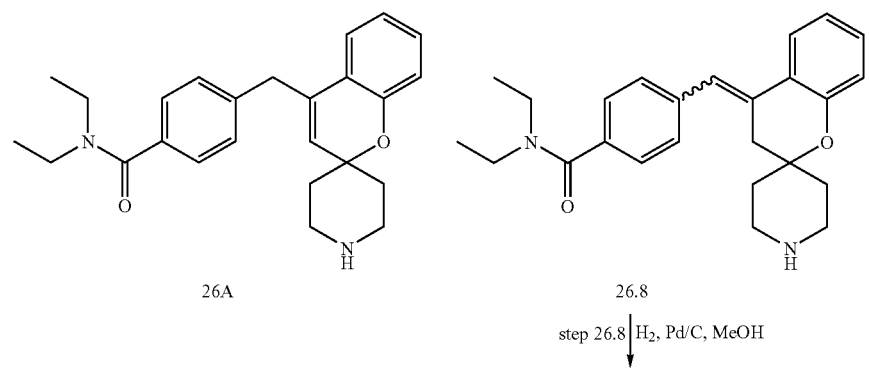
26A 26.8
step 26.8 | H₂, Pd/C, MeOH
↓
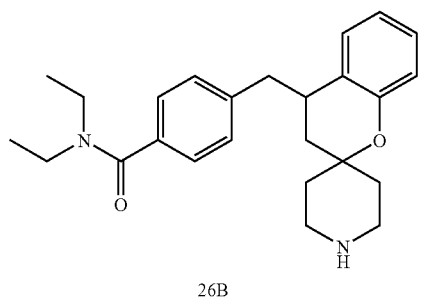
26B Scheme 27:
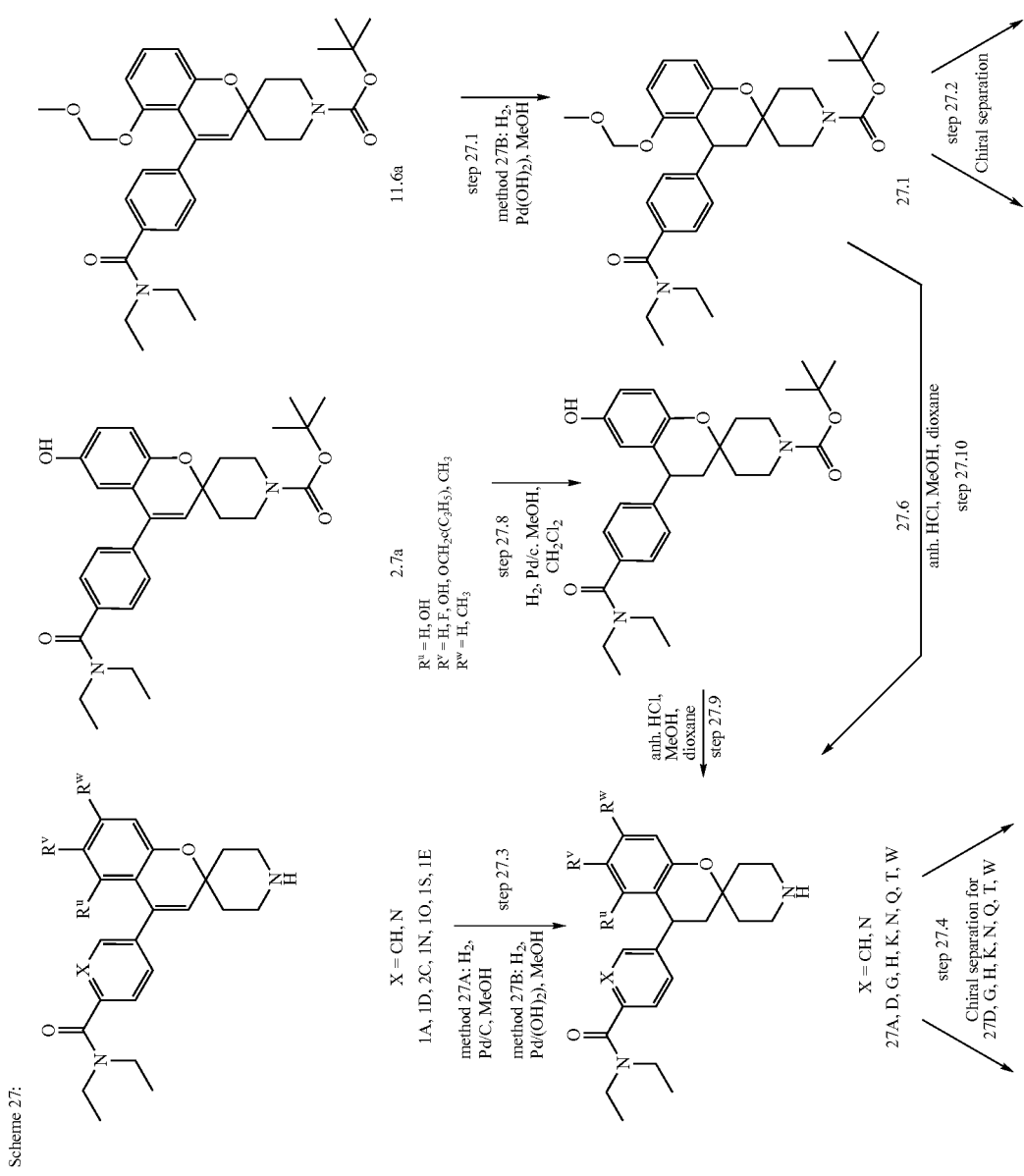

-continued
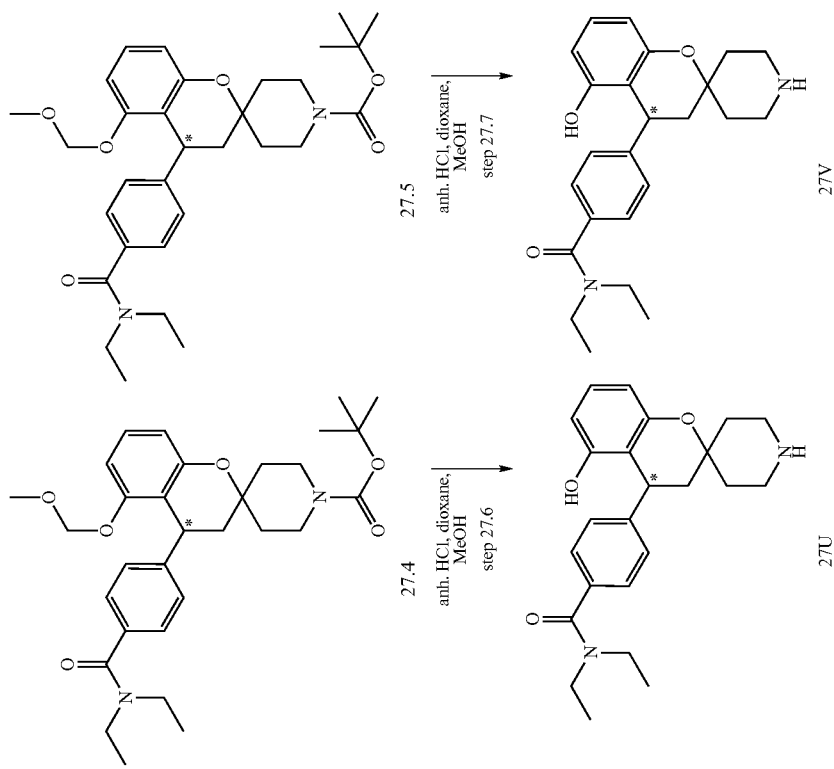
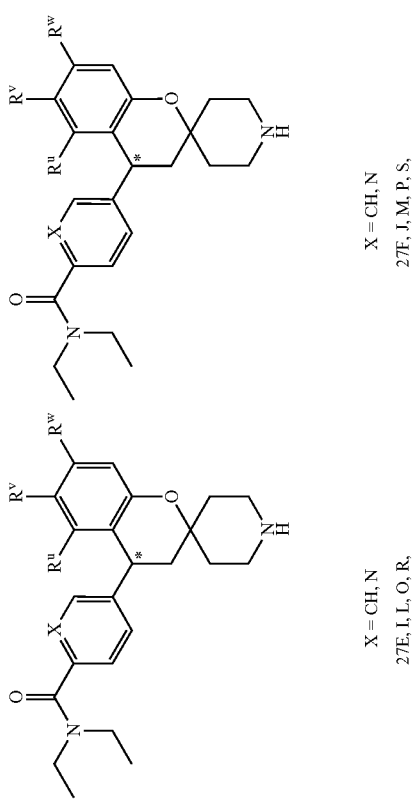
X = CH, N
27F, J, M, P, S,
X = CH, N
27E, I, L, O, R,

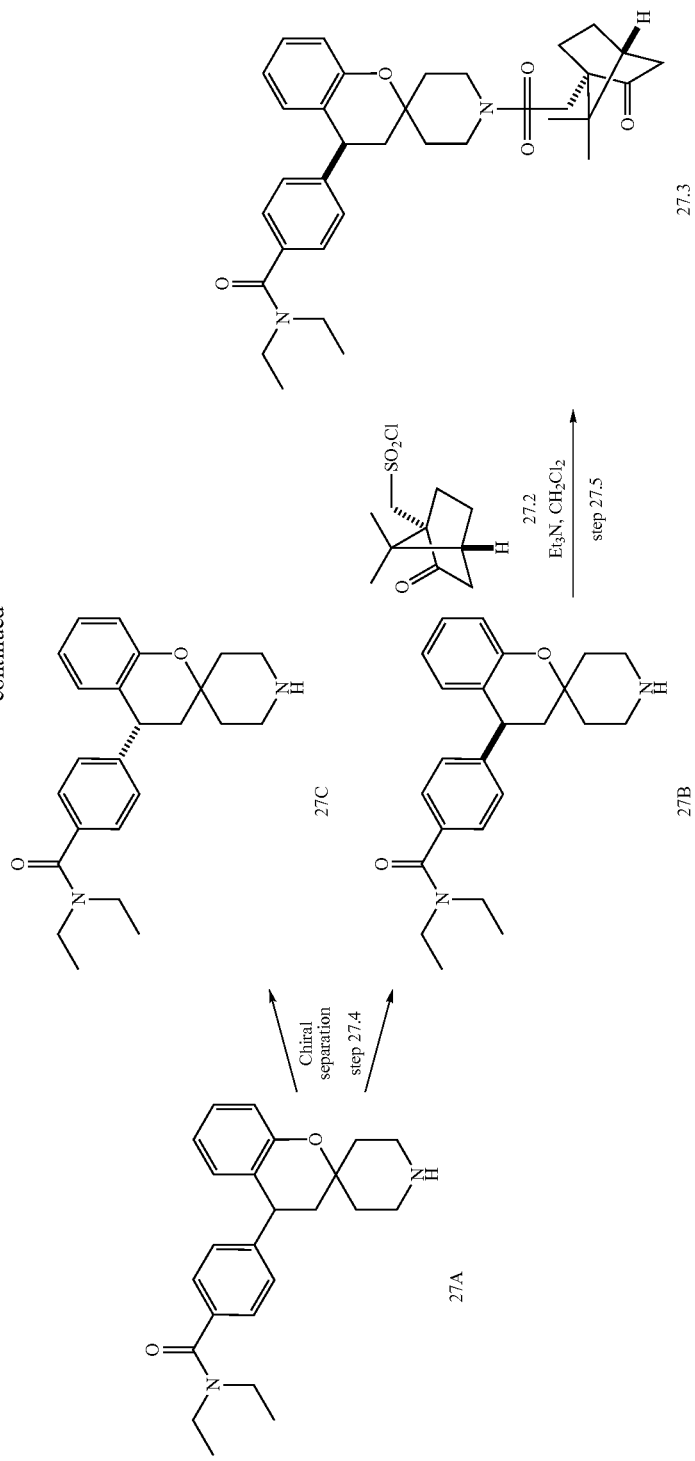

Scheme 28:
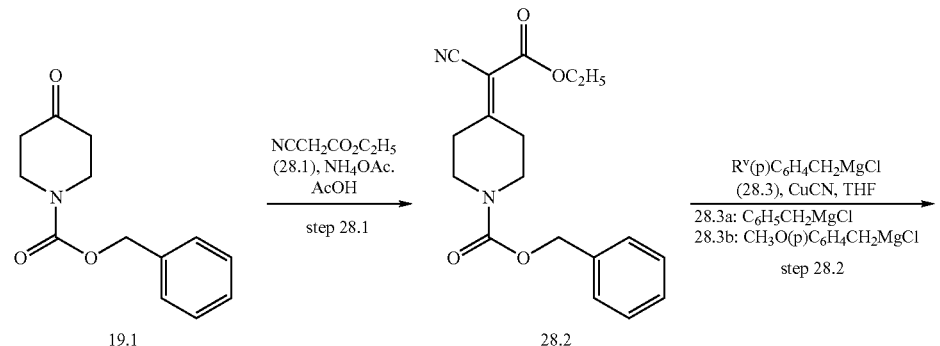
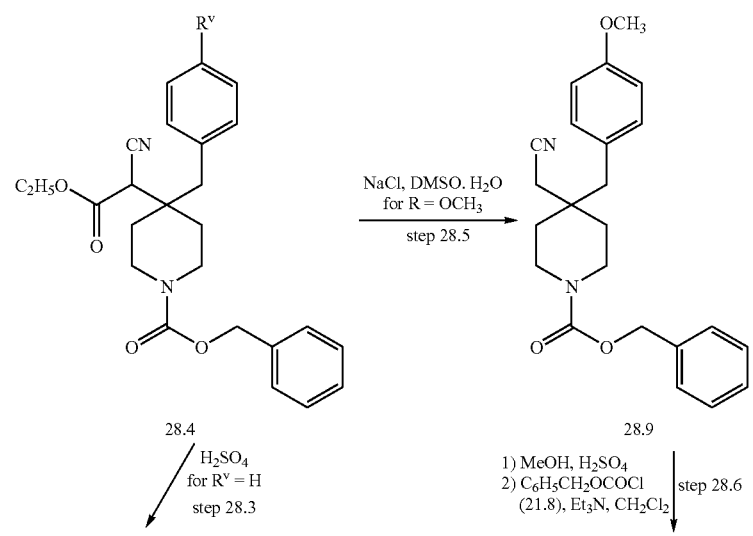
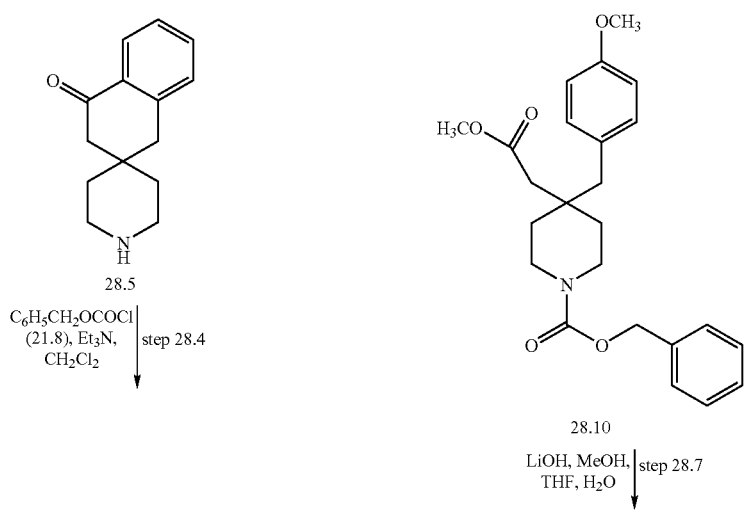

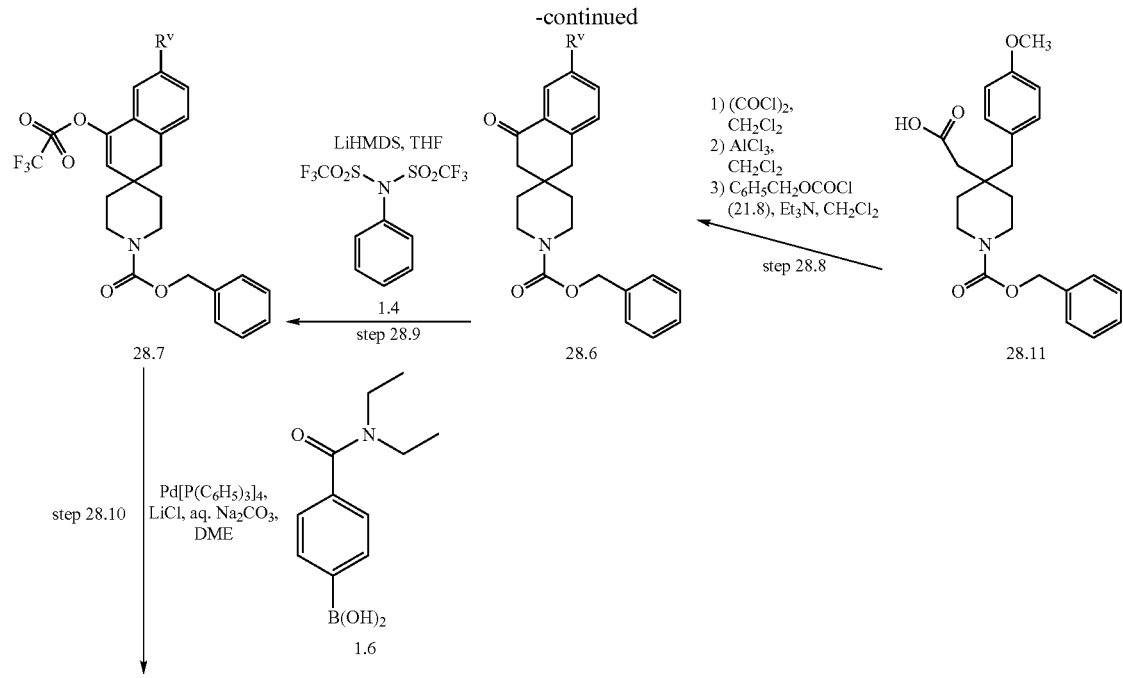
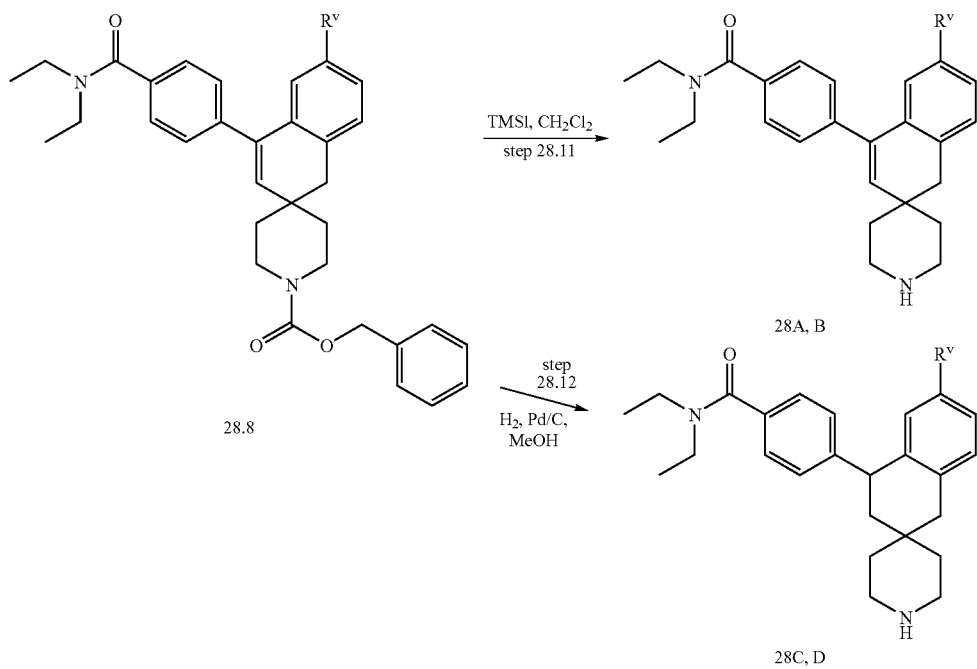

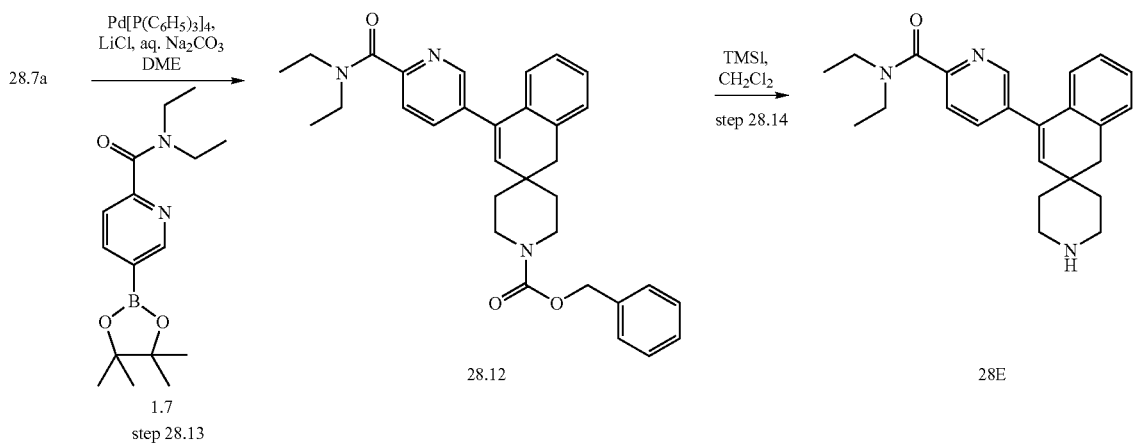
Scheme 29:
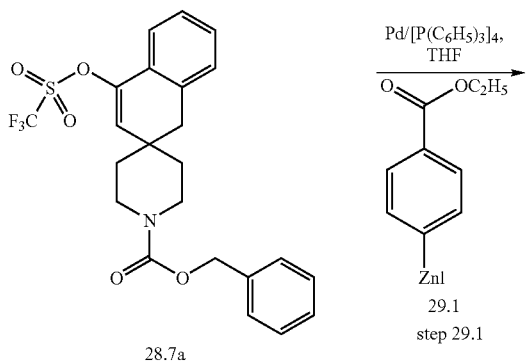
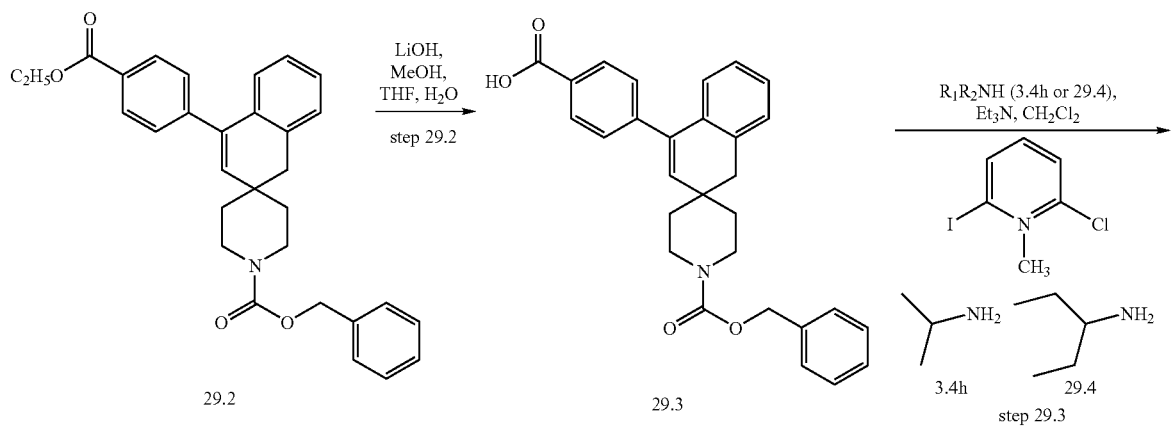

-continued
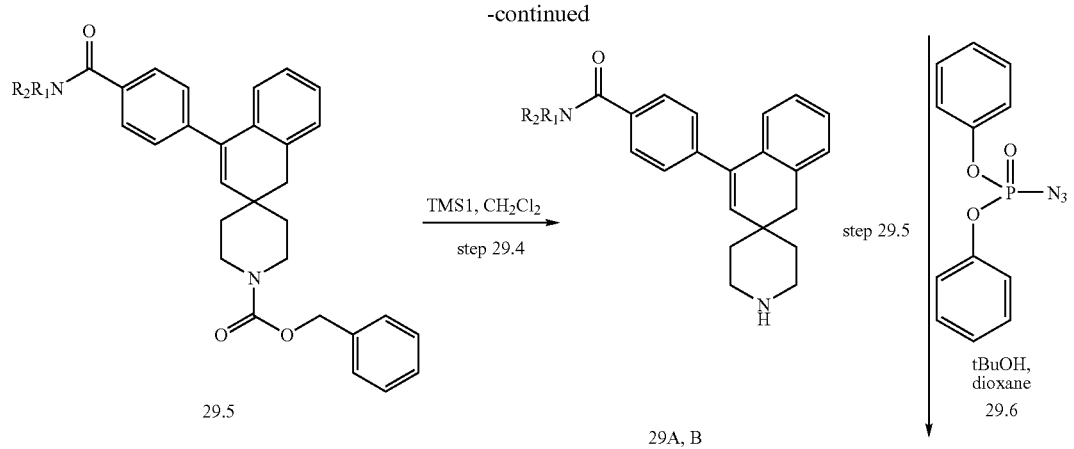
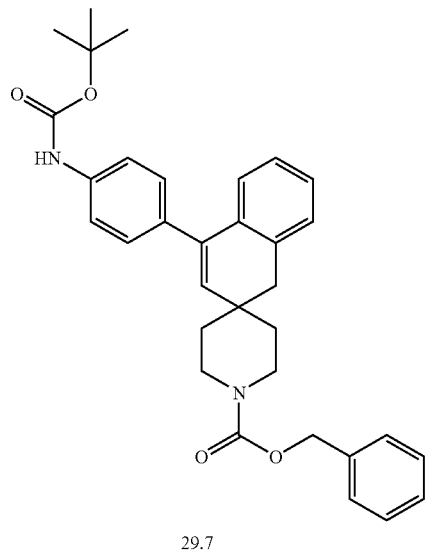
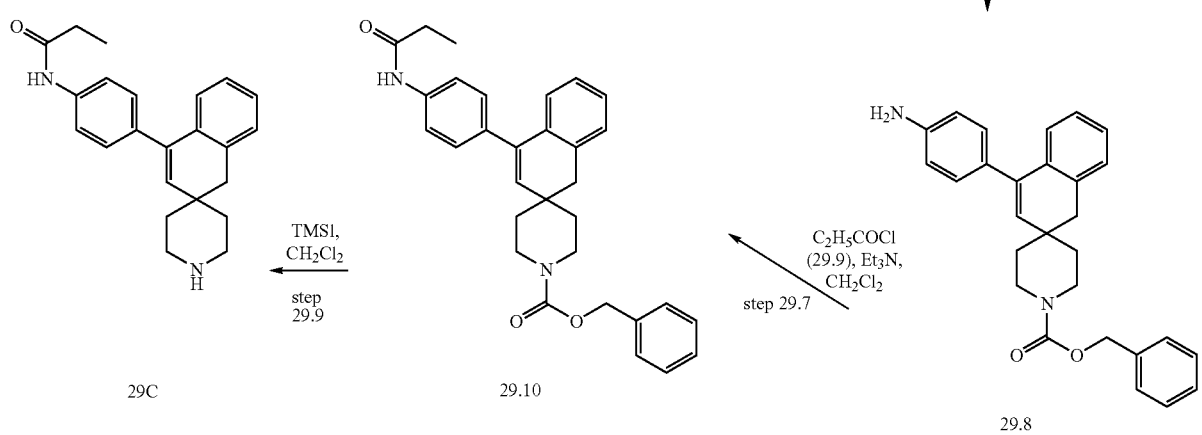

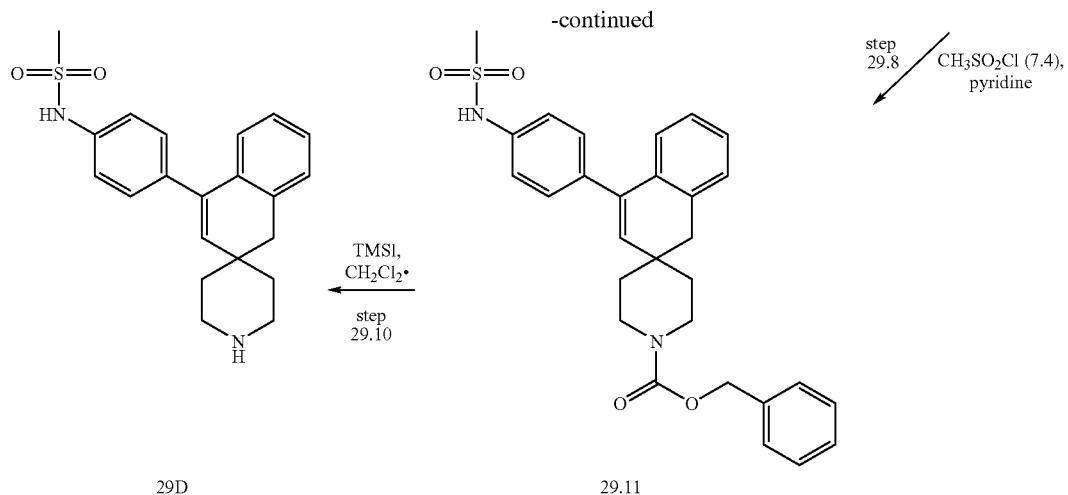
Scheme 30:
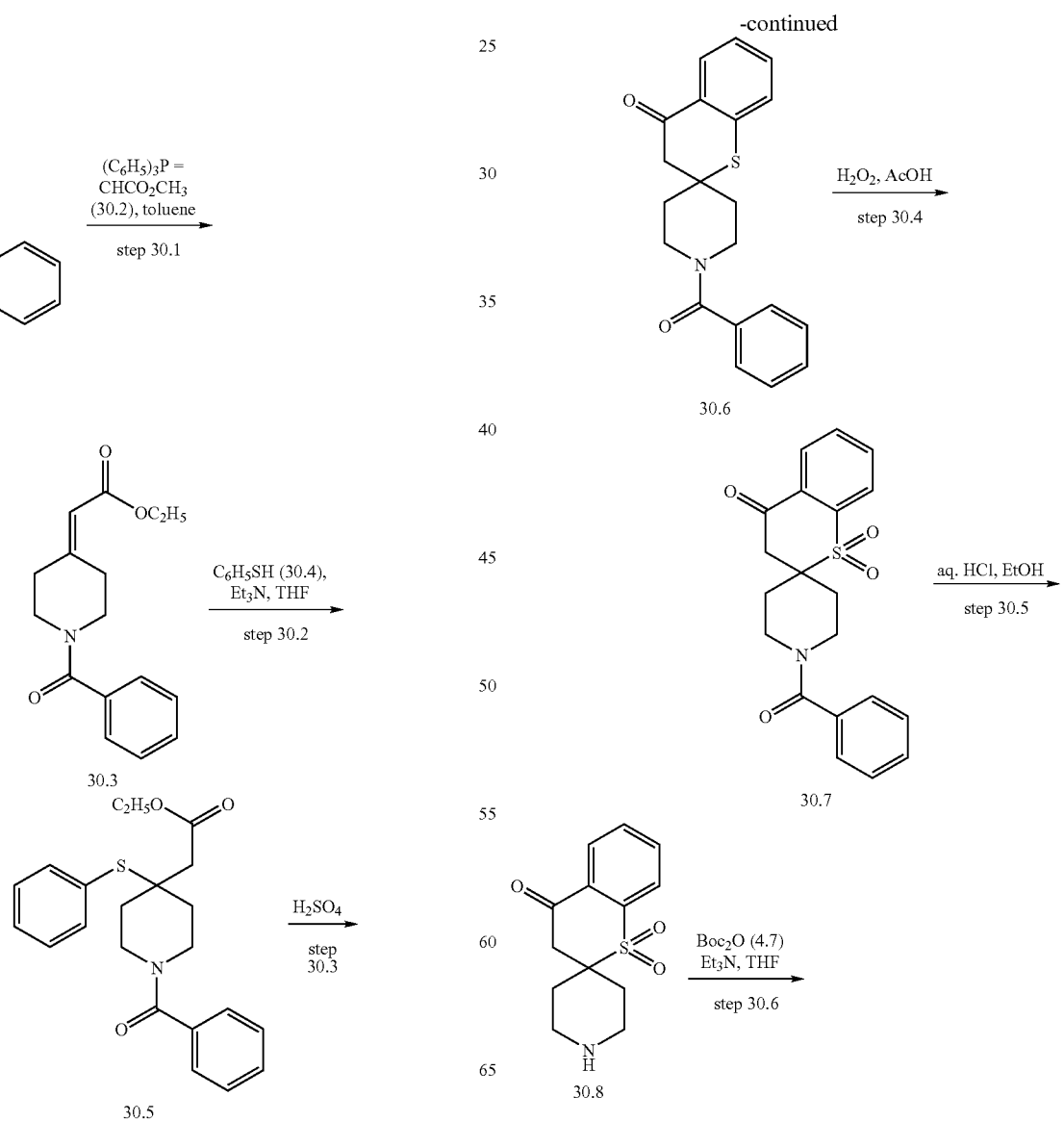

Scheme 31:
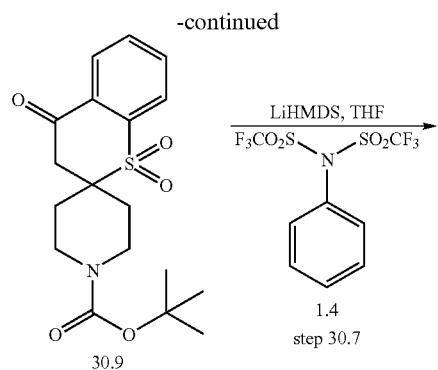
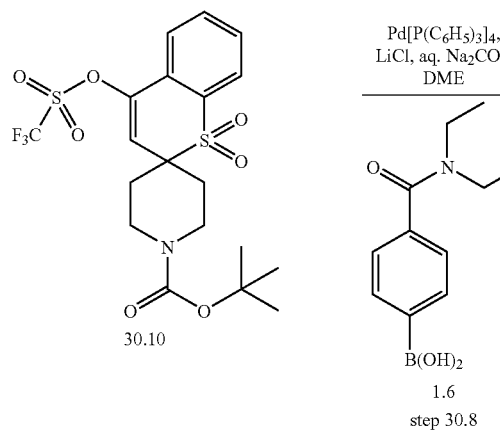
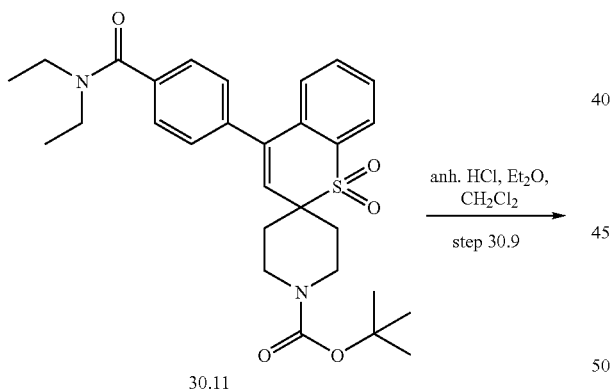
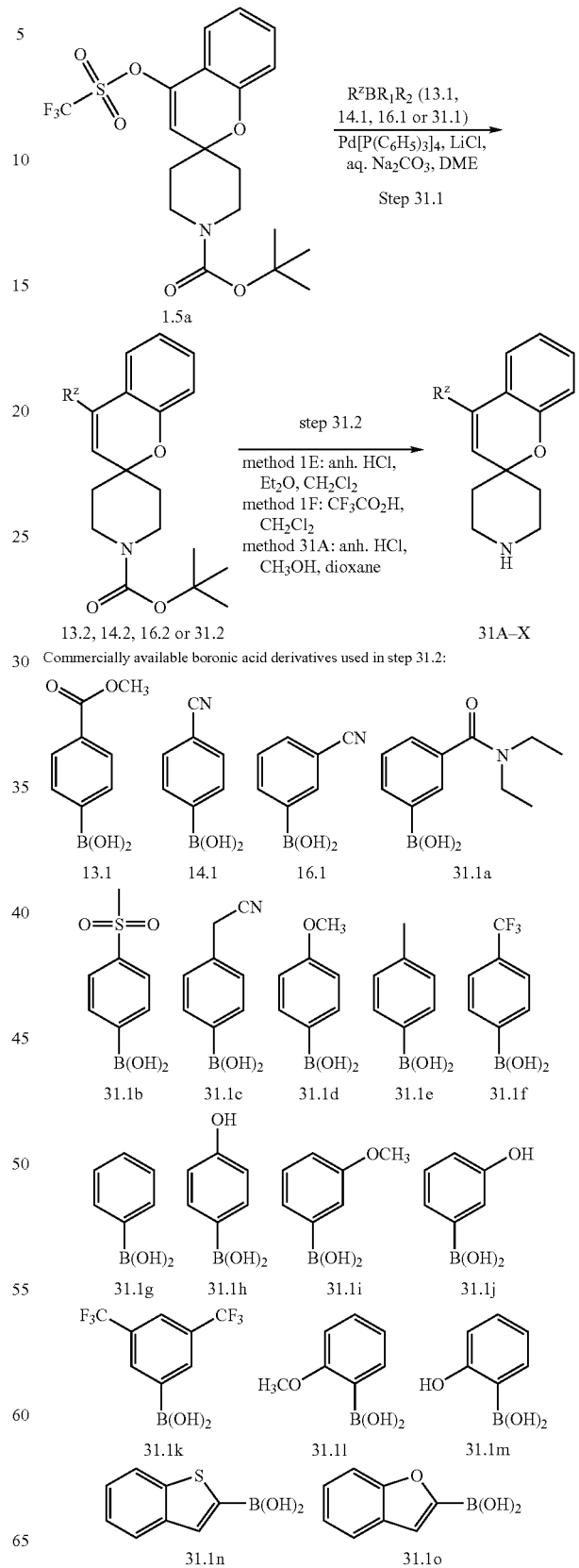

-continued
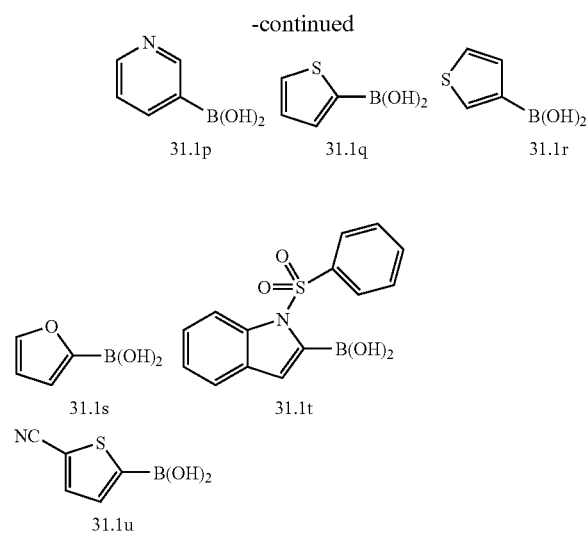
31.1p  31.1q  31.1r
31.1s  31.1t
31.1u
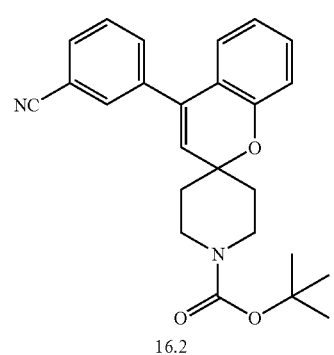
16.2
LiAlH₄, THF
step 31.3
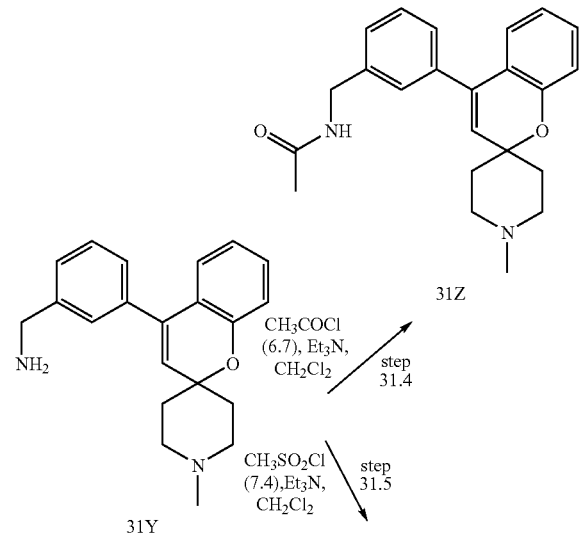
31Z
CH₃COCl
(6.7), Et₃N,
CH₂Cl₂
step 31.4
31Y
CH₃SO₂Cl
(7.4), Et₃N,
CH₂Cl₂
step 31.5
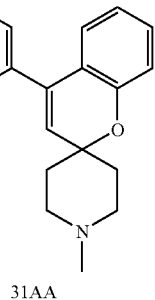
31AA
Scheme 32:
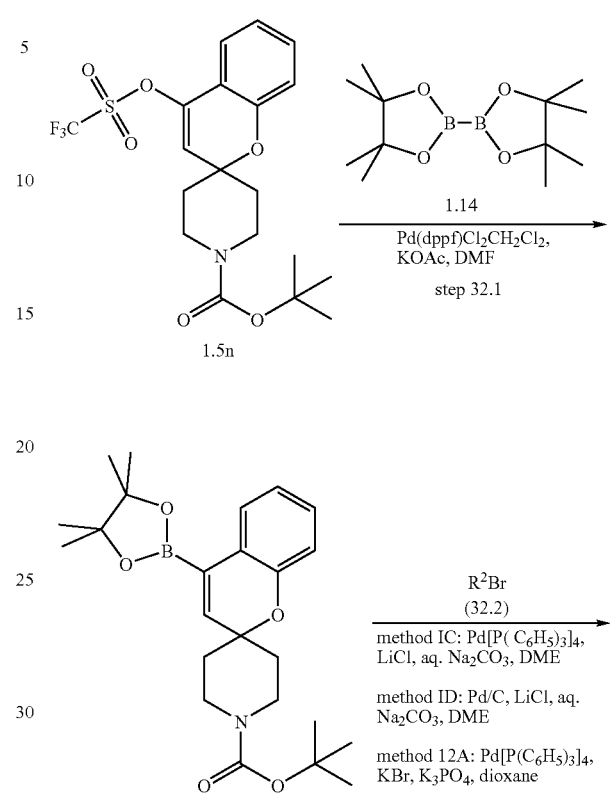
1.5n
1.14
Pd(dppf)Cl₂CH₂Cl₂,
KOAc, DMF
step 32.1
R²Br
(32.2)
method IC: Pd[P(C₆H₅)₃]₄,
LiCl, aq. Na₂CO₃, DME
method ID: Pd/C, LiCl, aq.
Na₂CO₃, DME
method 12A: Pd[P(C₆H₅)₃]₄,
KBr, K₃PO₄, dioxane
32.1  step 32.2
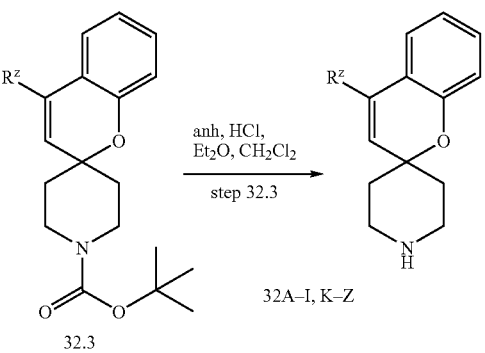
32.3
anh, HCl,
Et₂O, CH₂Cl₂
step 32.3
32A–I, K–Z
Description and preparation of arylbromides (32.2) used in step 32.2:
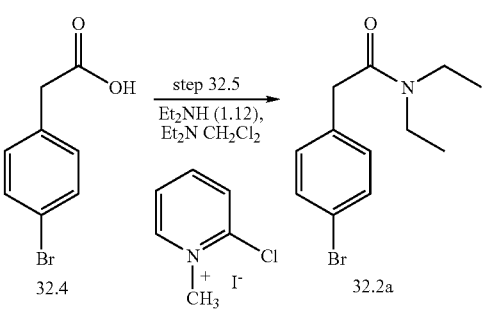
32.4
step 32.5
Et₂NH (1.12),
Et₃N CH₂Cl₂
32.2a

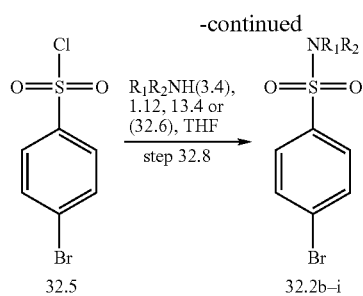
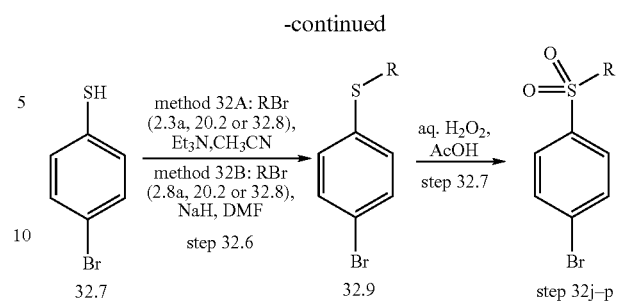
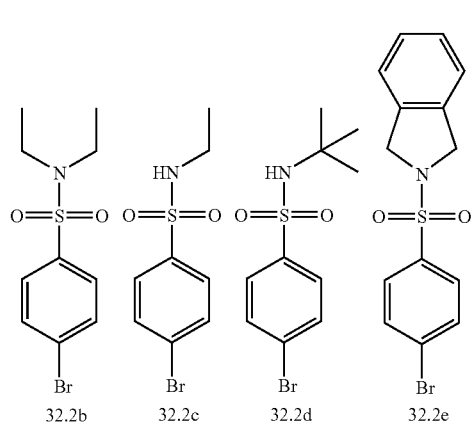
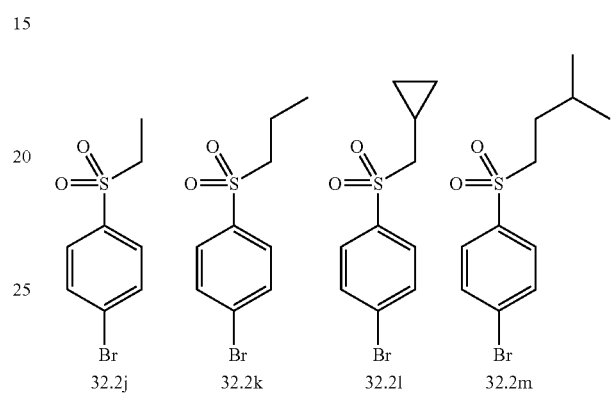
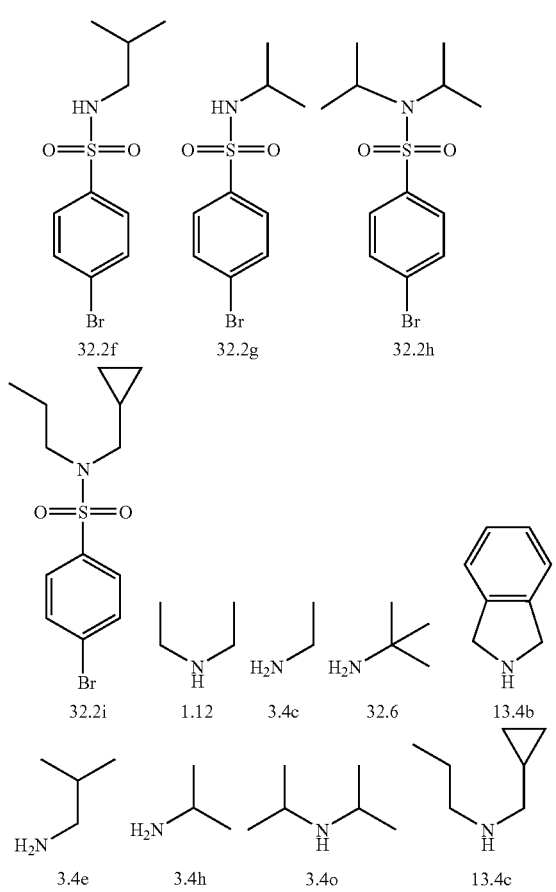
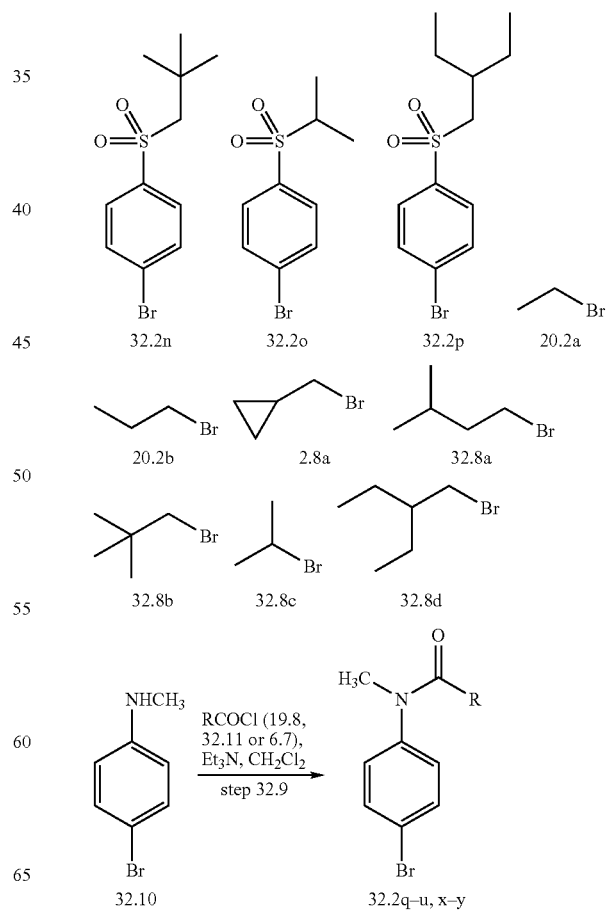

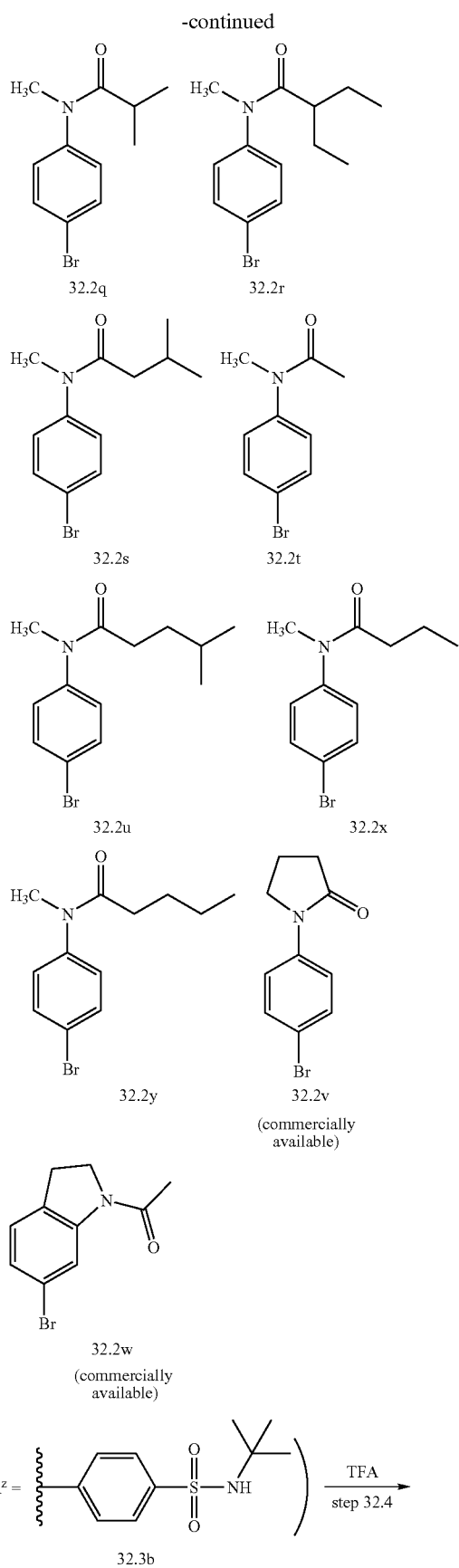
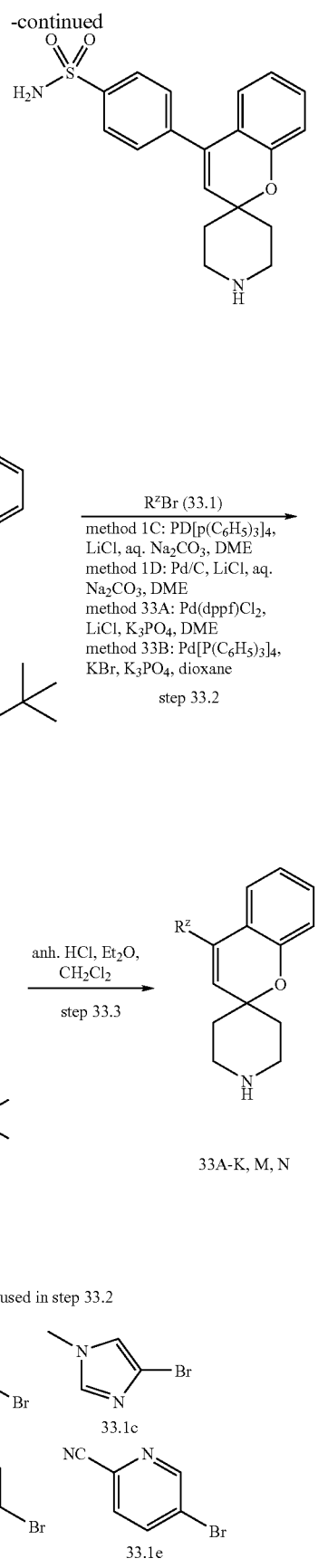
Scheme 33:
Commercially available R$^z$Br used in step 33.2

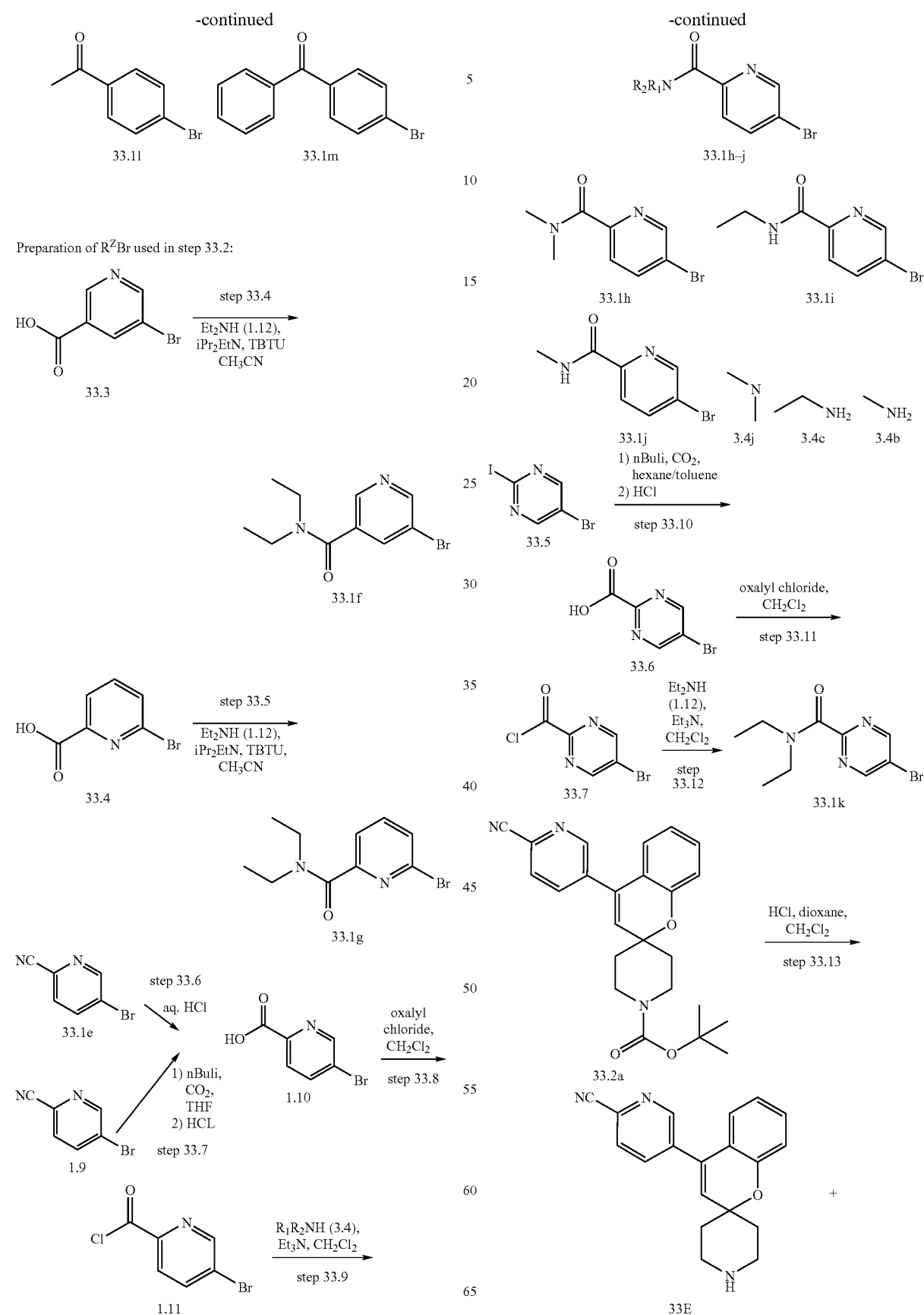

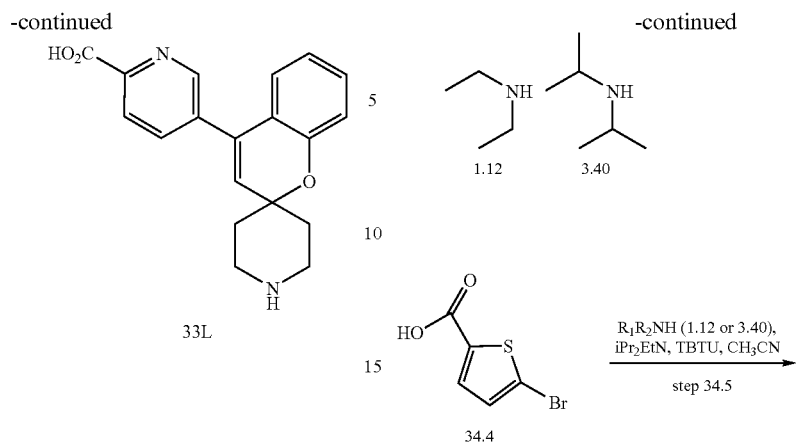
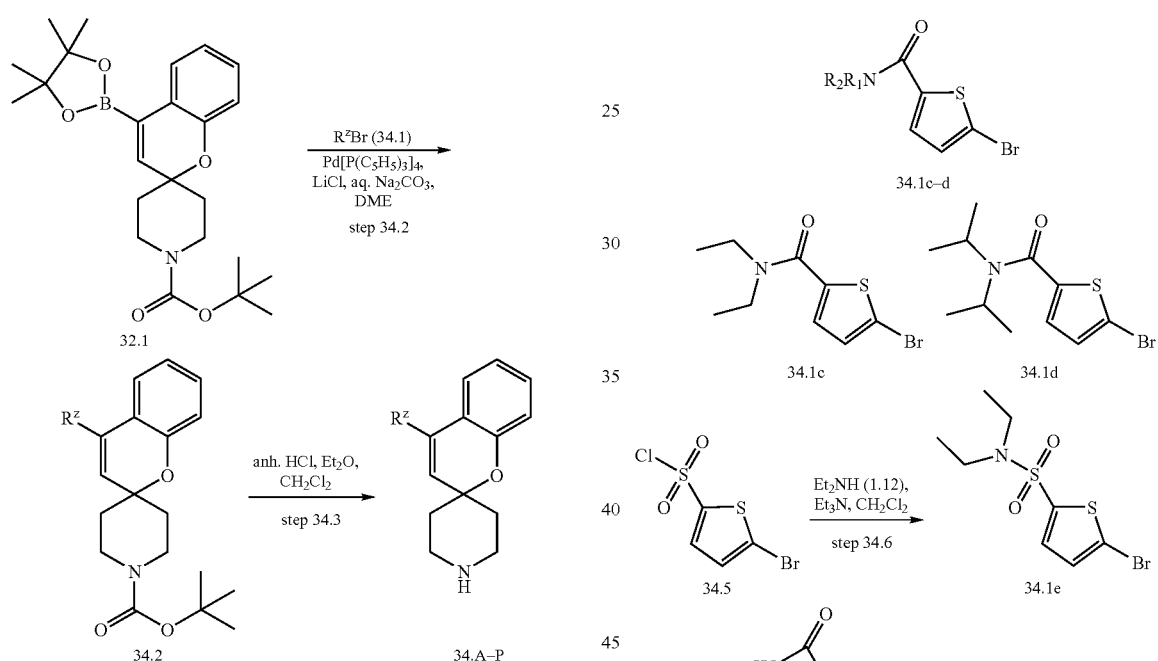
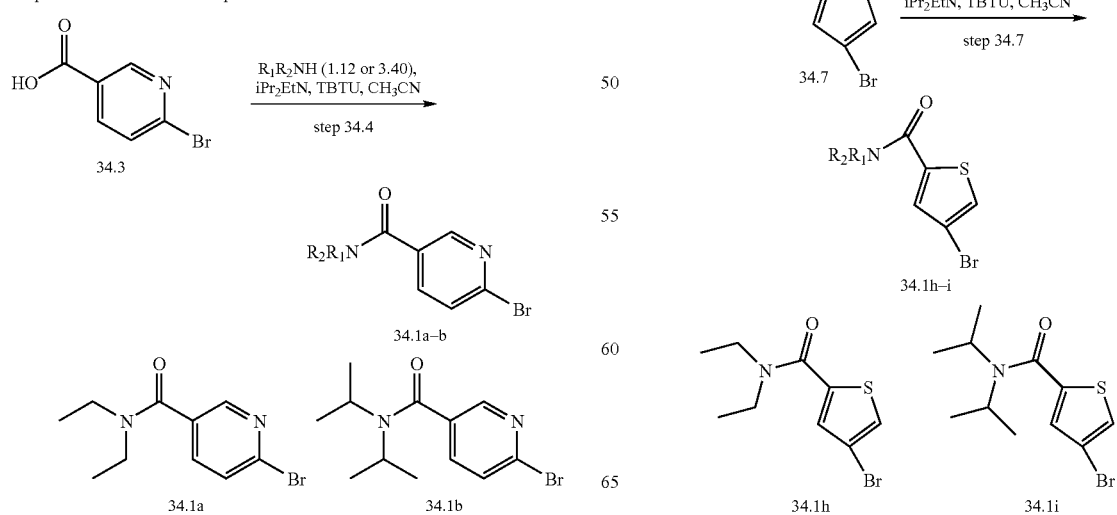

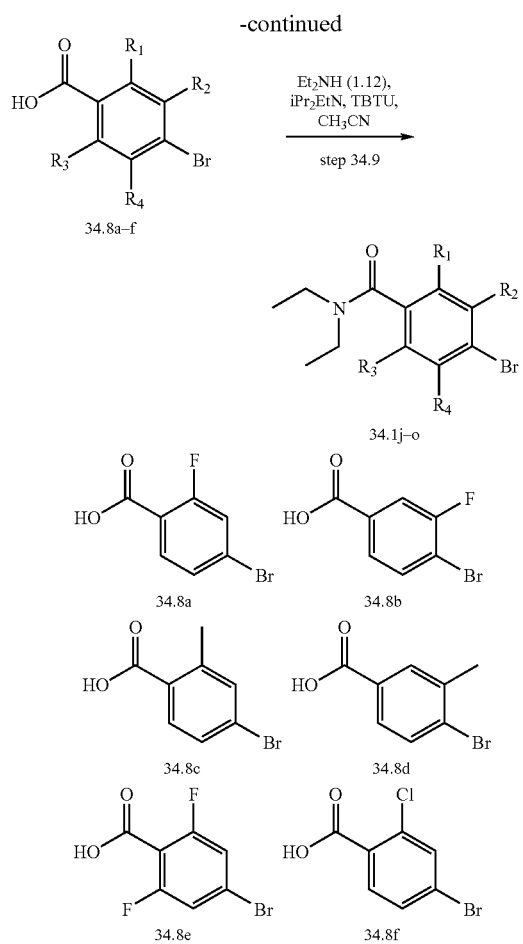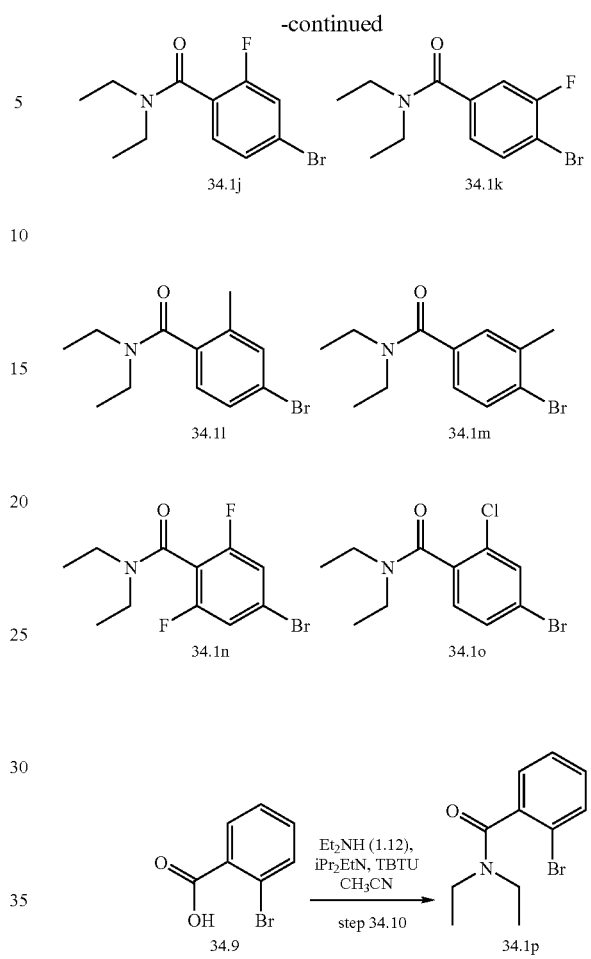
Scheme 35:
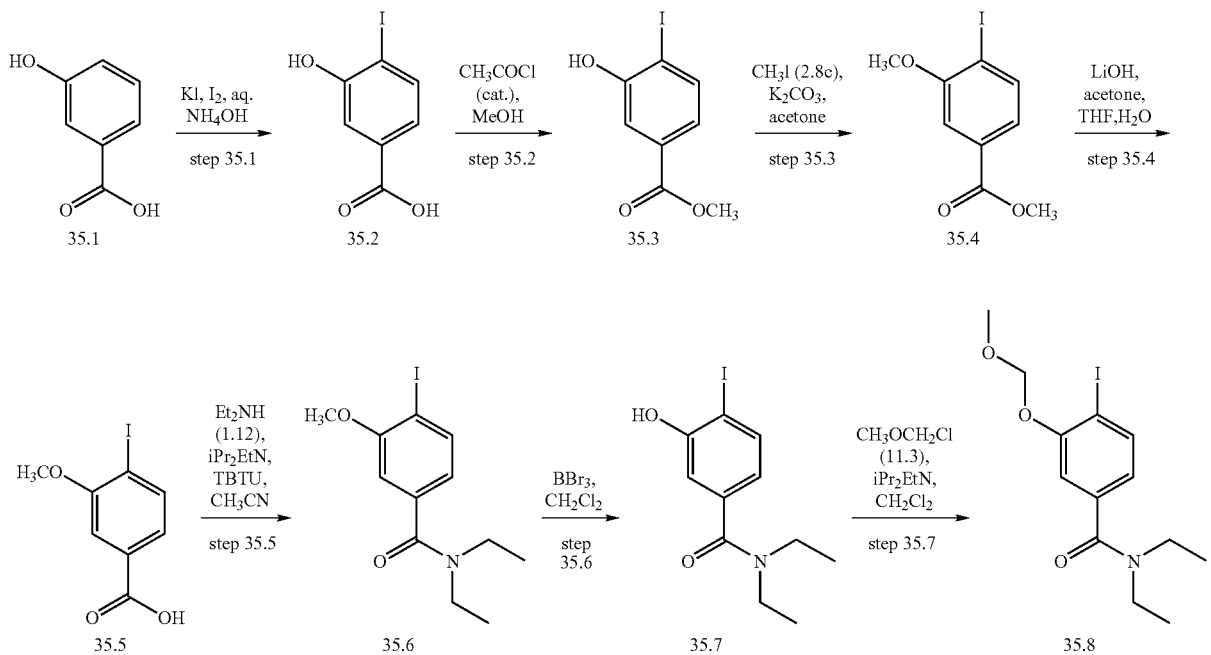

-continued
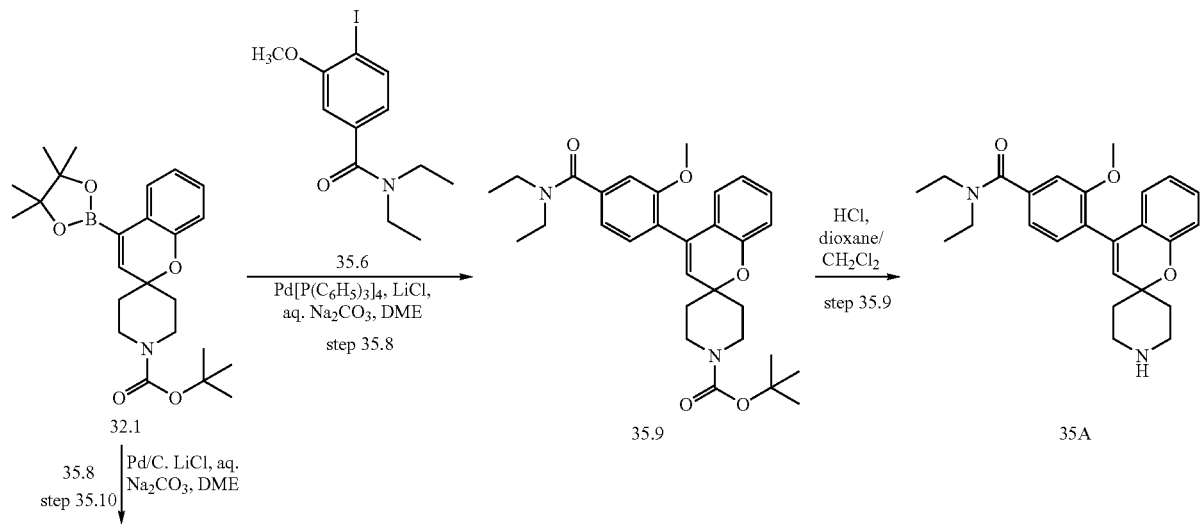
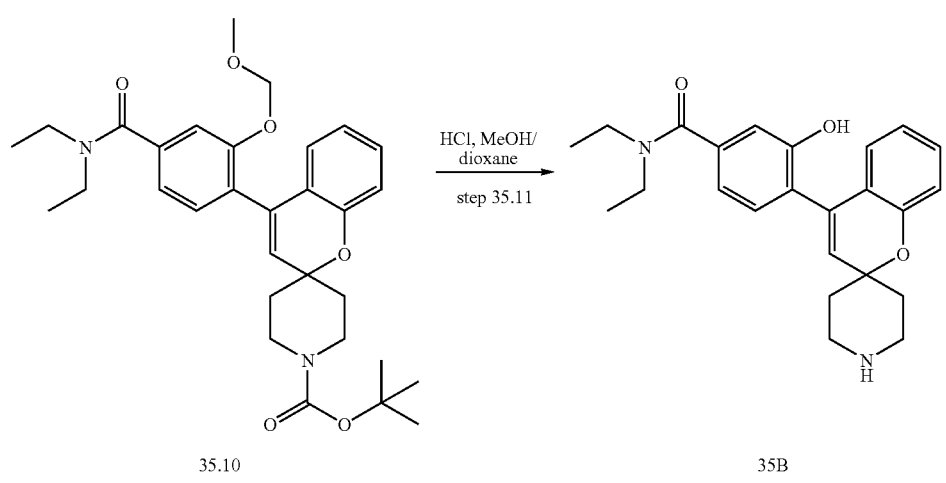

Scheme 36:
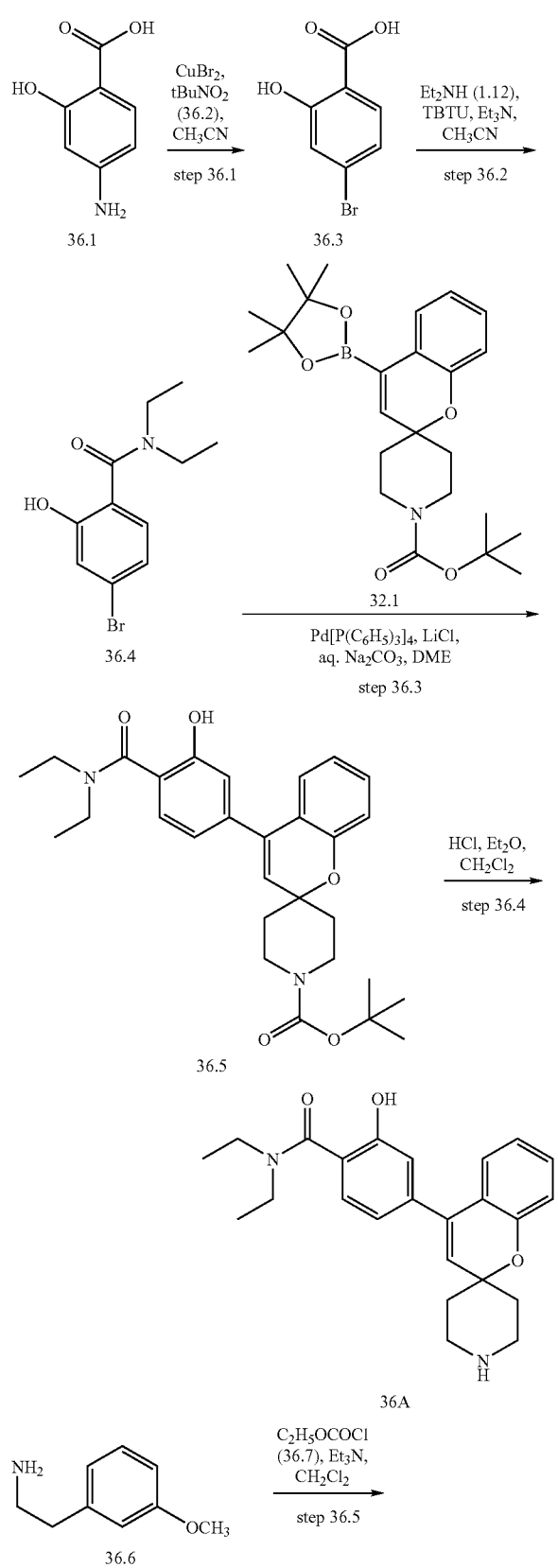
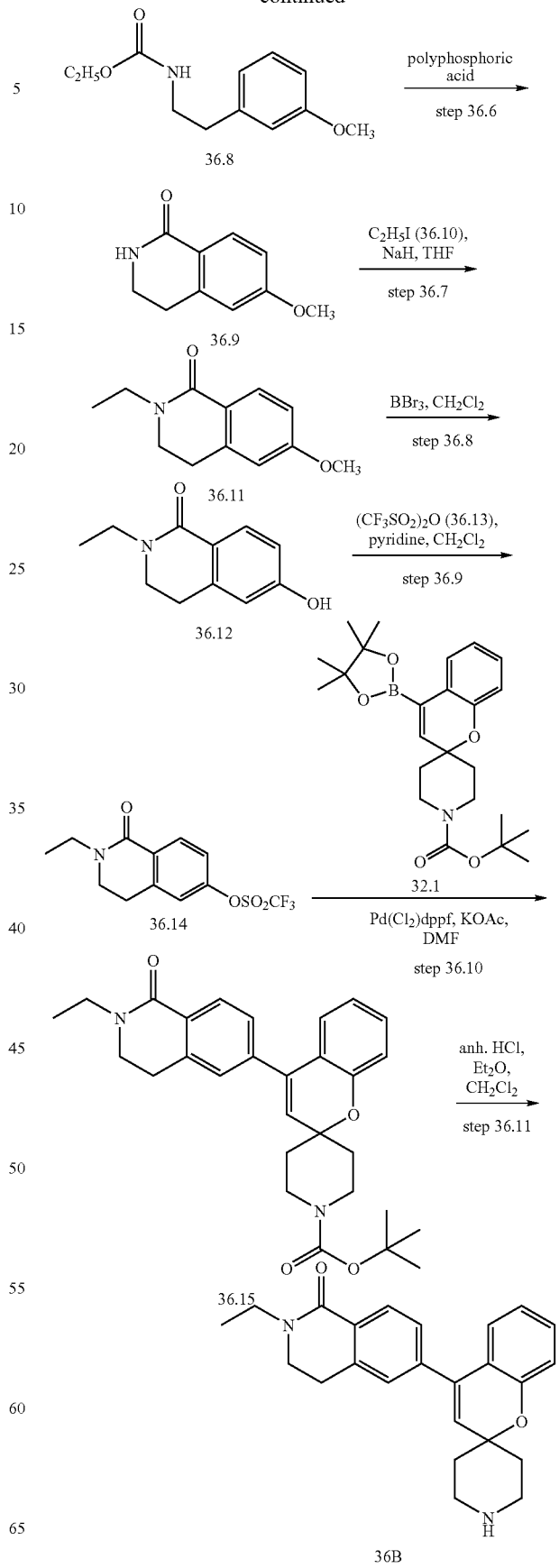

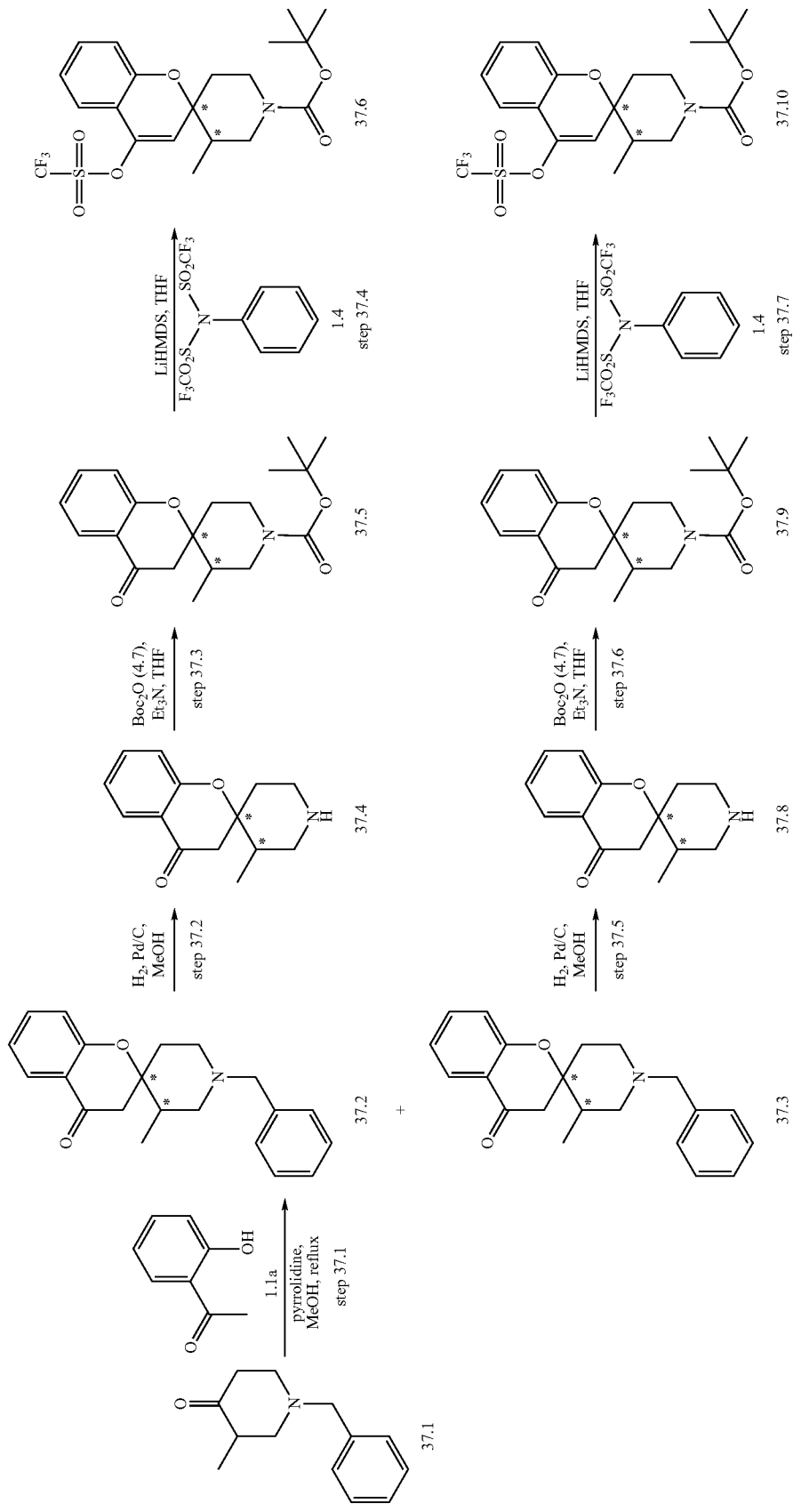
Scheme 37:

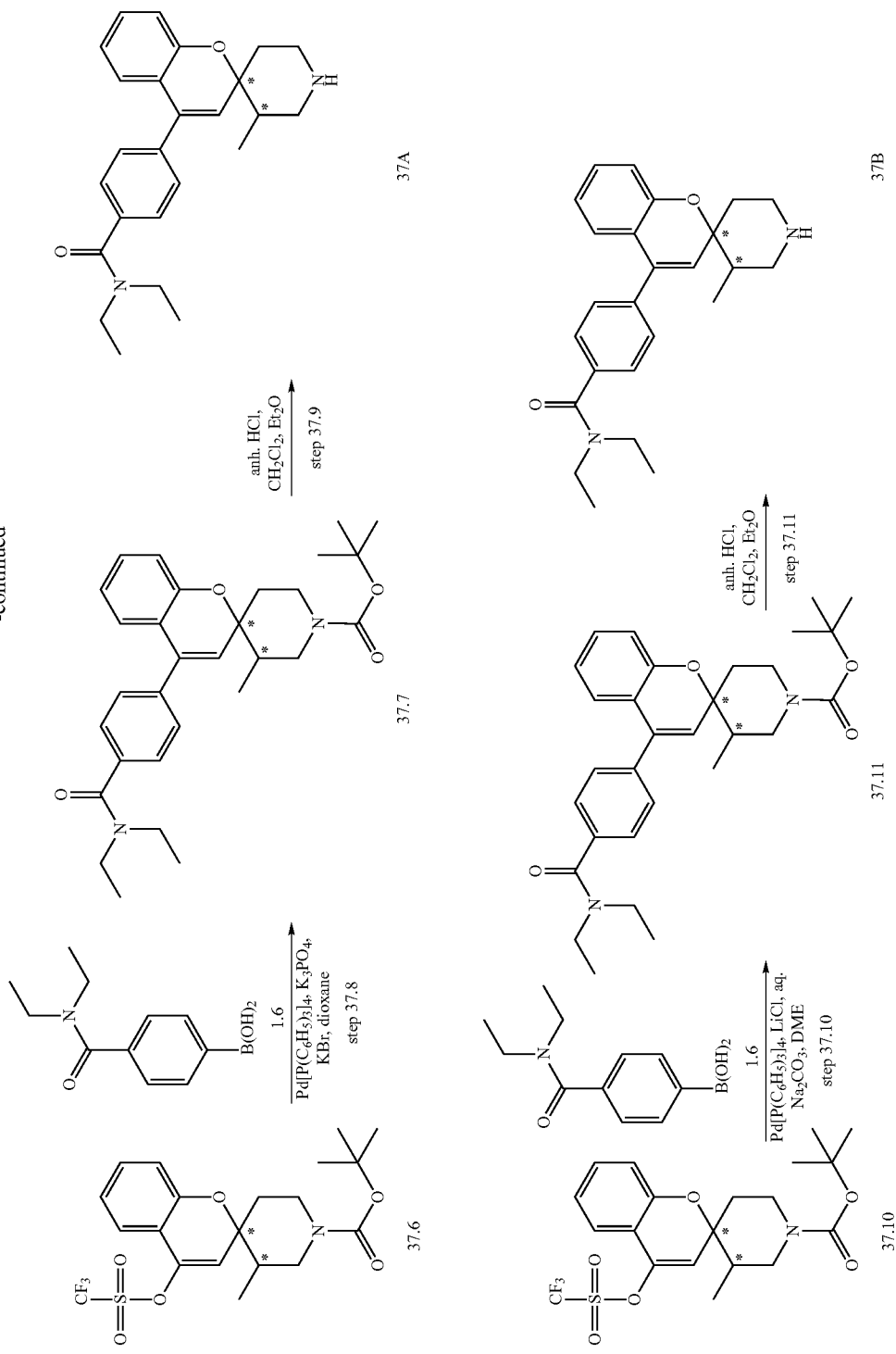

37A and 37B are diastereomeric with respect to one another, but each is a racemic mixture of its two possible enantiomers. Their absolute stereochemistry has not been conclusively established.

Scheme 38:
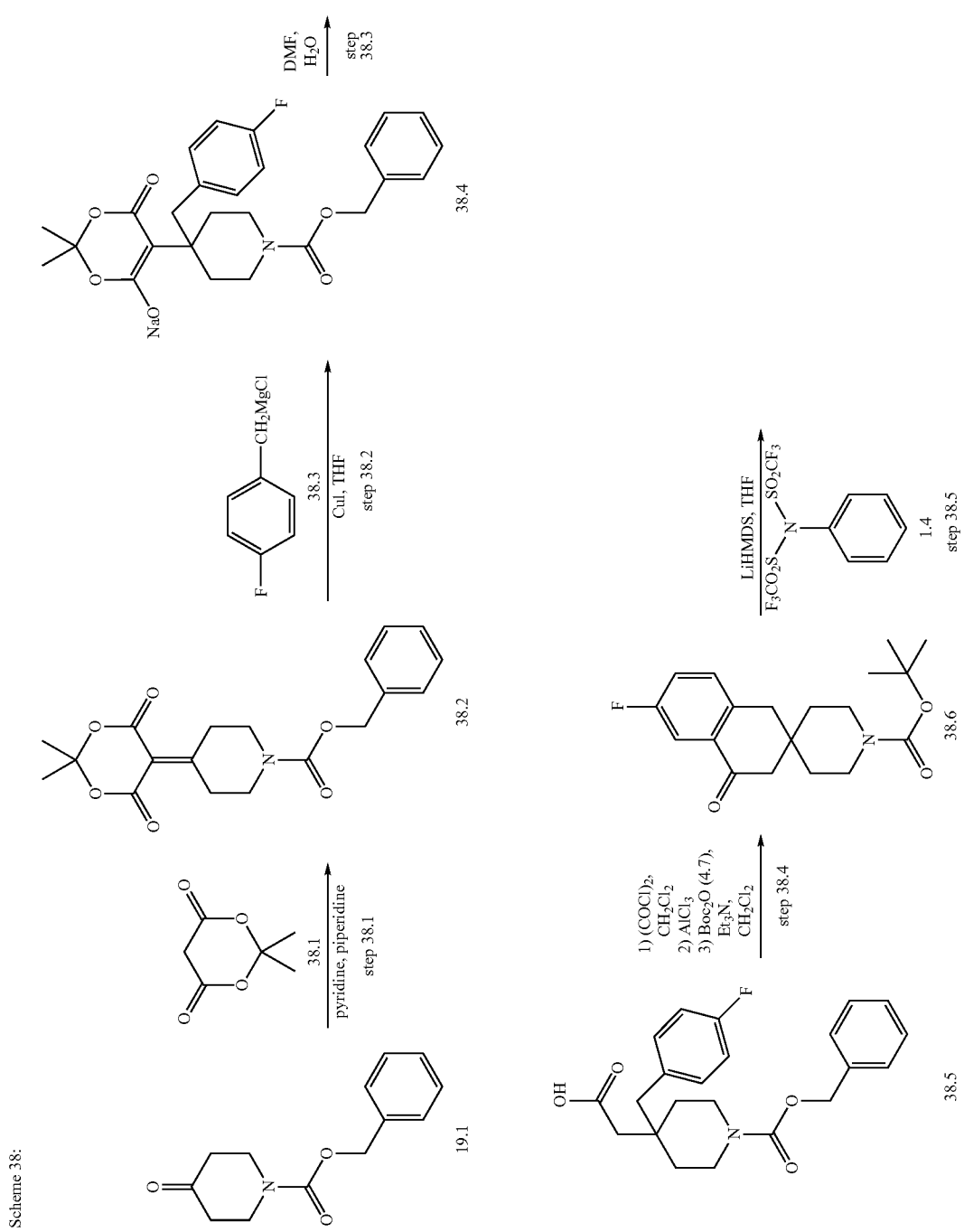

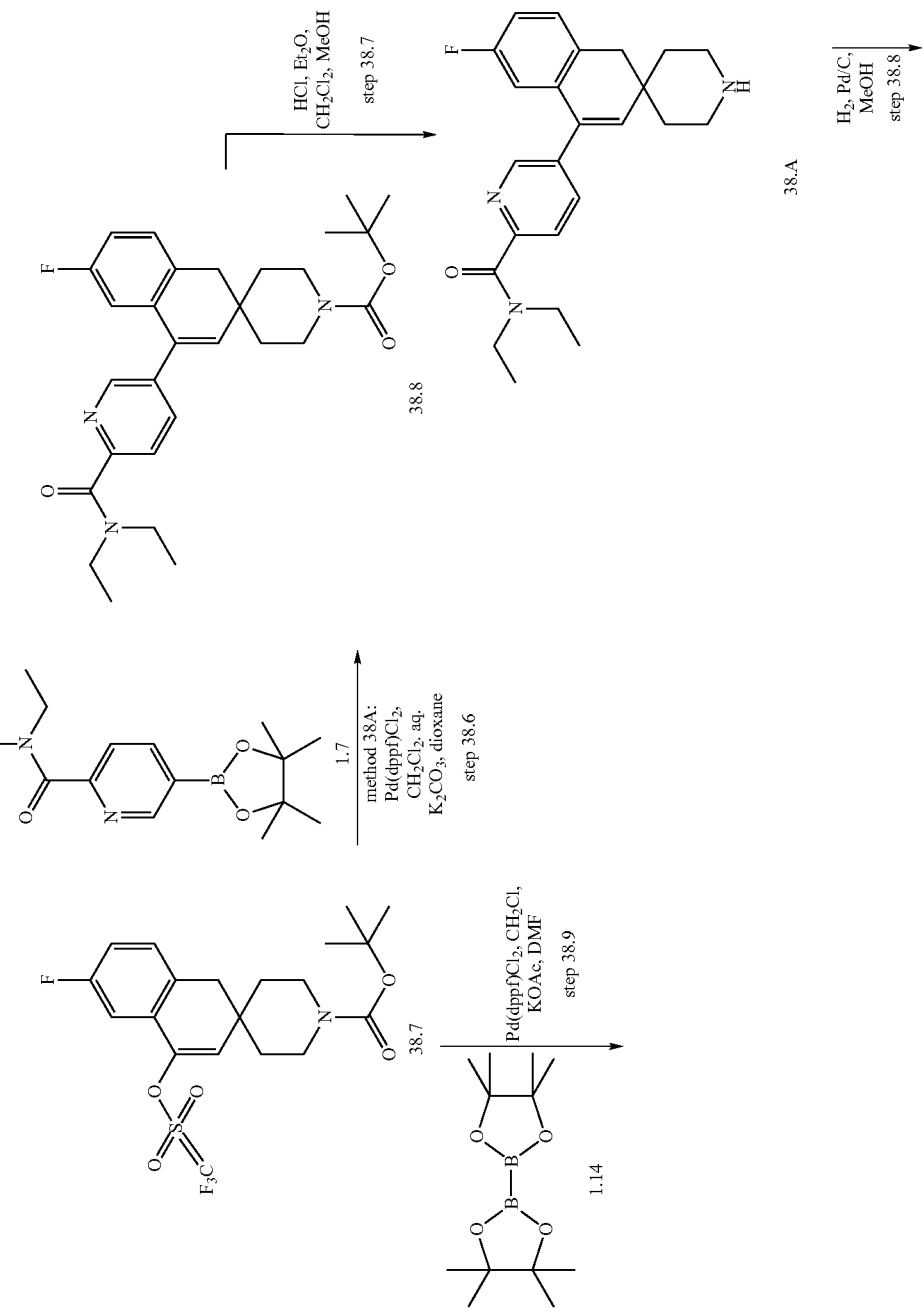

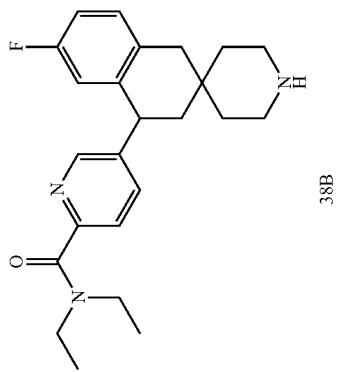
38B
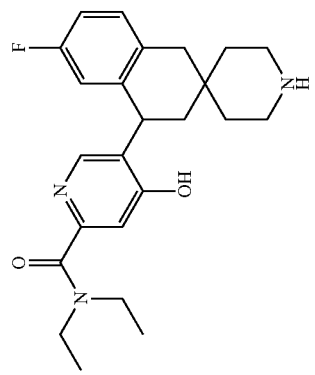
38C
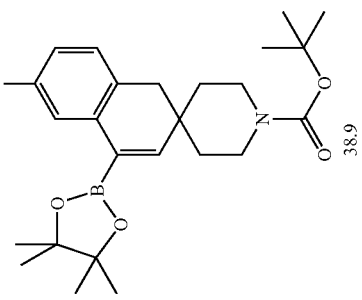
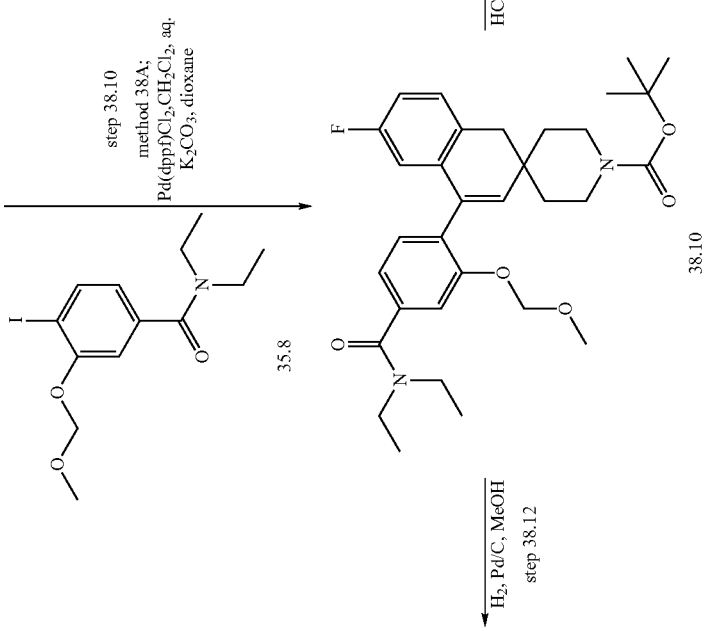
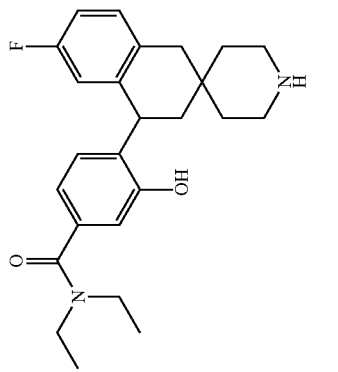
38D
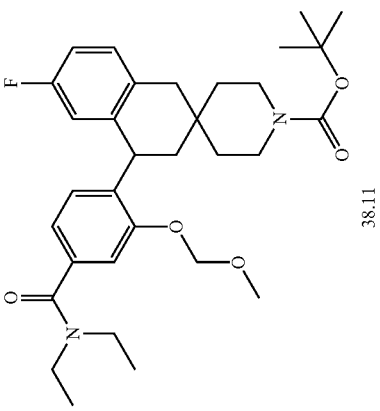

Scheme 39:
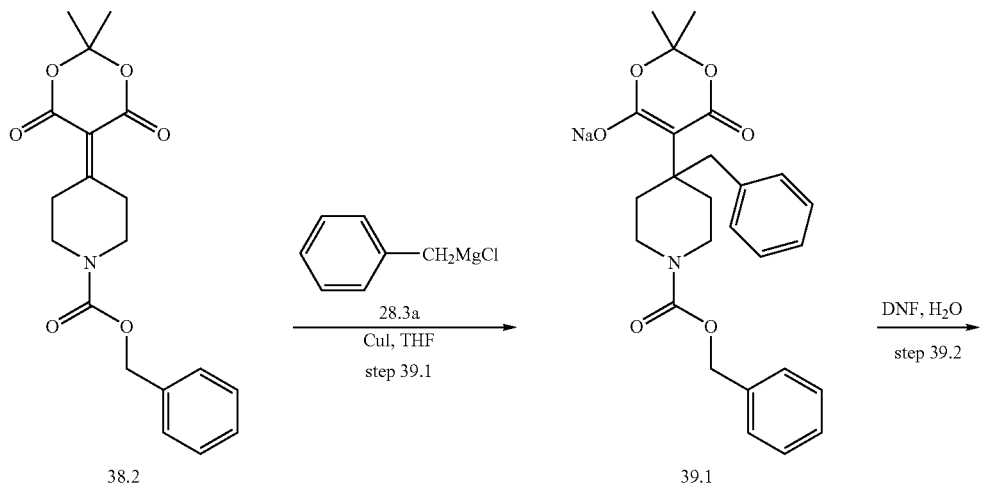
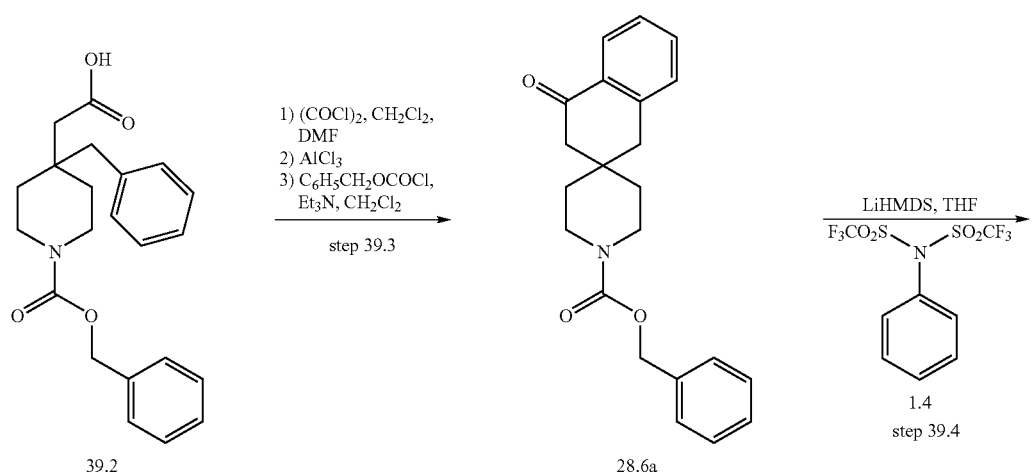
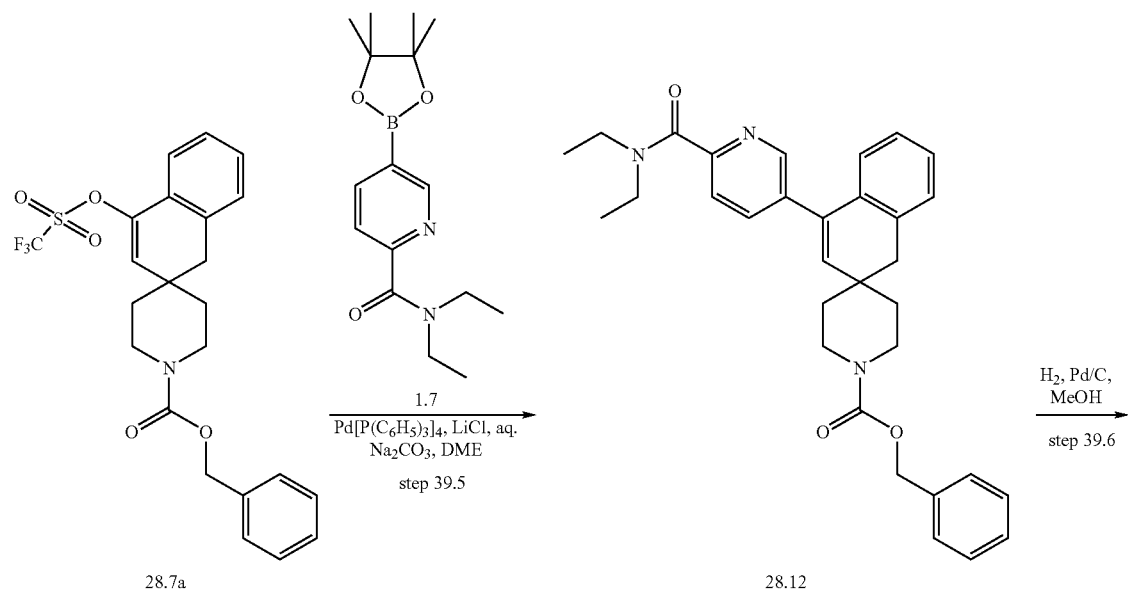

-continued

-continued
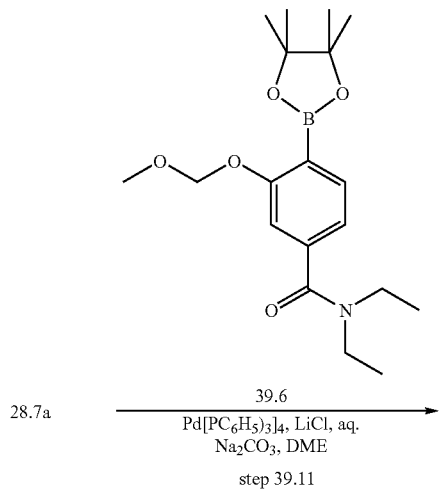
28.7a  →  39.6
Pd[PC$_6$H$_5$)$_3$]$_4$, LiCl, aq. Na$_2$CO$_3$, DME
step 39.11
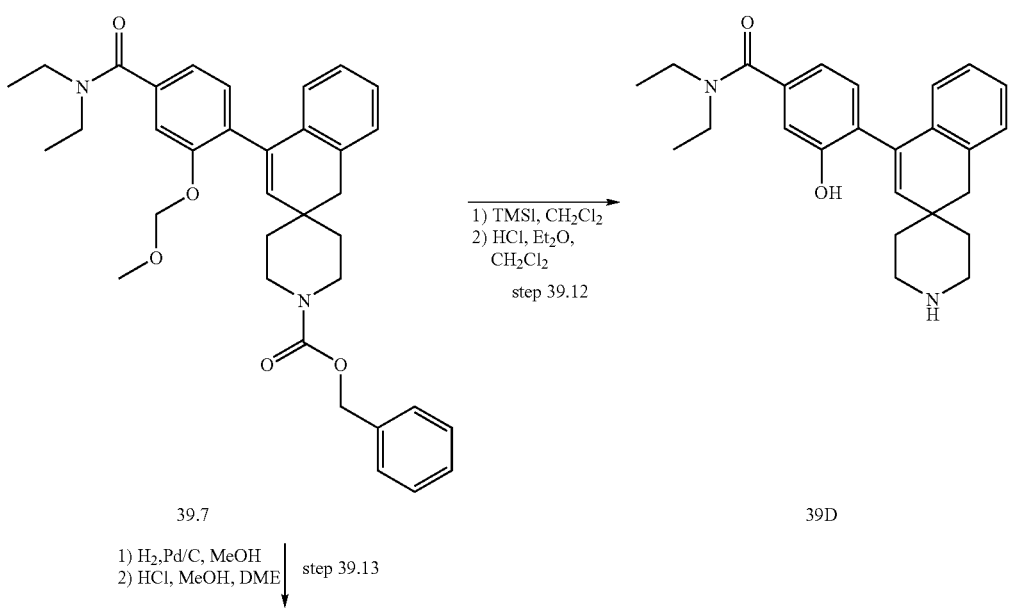
39.7
1) TMSI, CH$_2$Cl$_2$
2) HCl, Et$_2$O, CH$_2$Cl$_2$
step 39.12
39D
1) H$_2$, Pd/C, MeOH
2) HCl, MeOH, DME
step 39.13
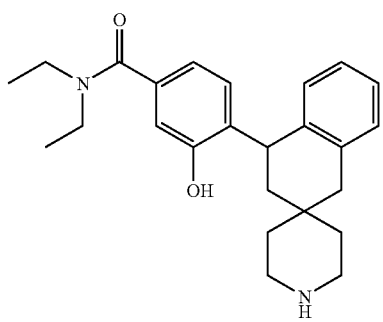
39E
Boc$_2$O (4.7), Et$_3$N, CH$_2$Cl$_2$
step 39.14
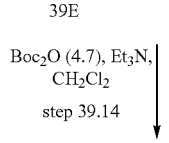

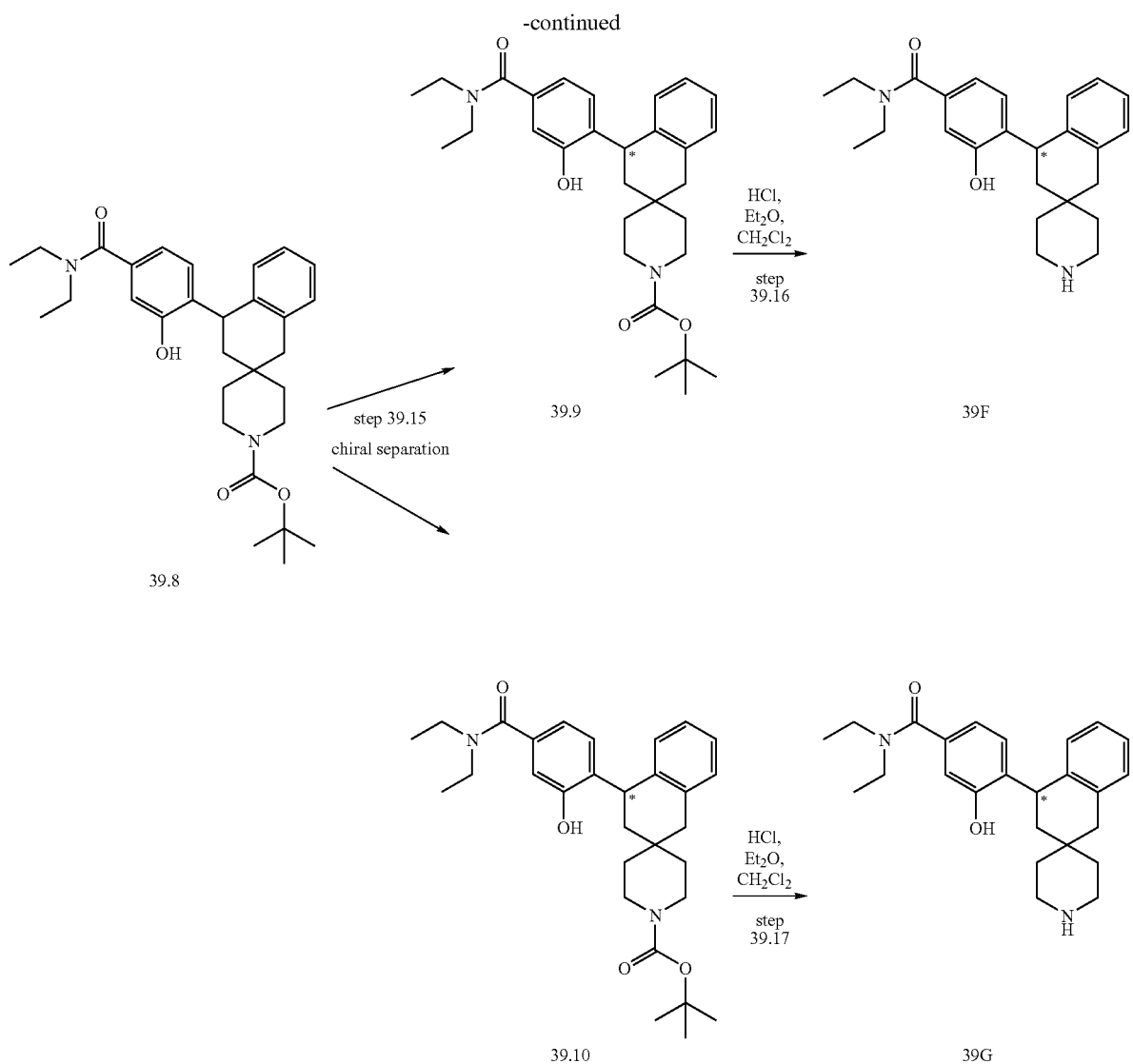
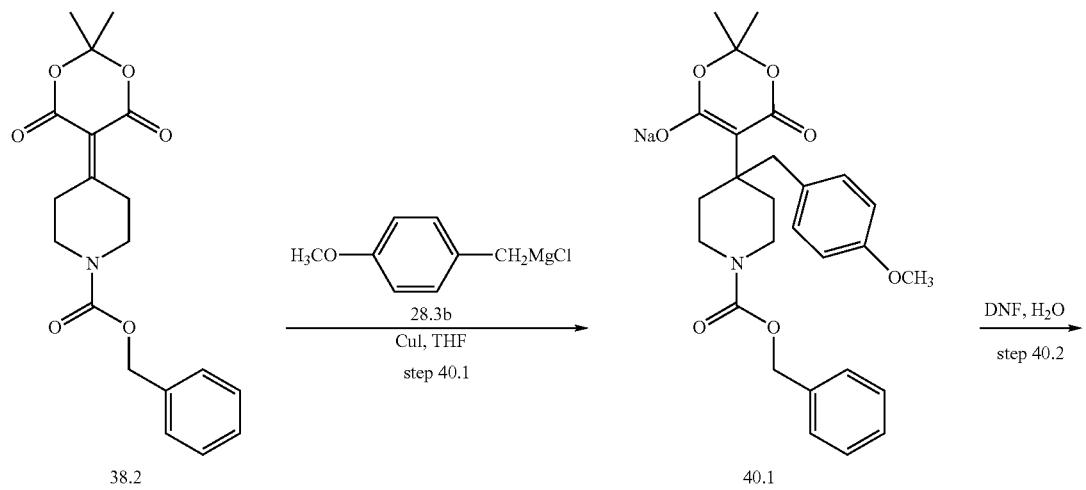
Scheme 40:

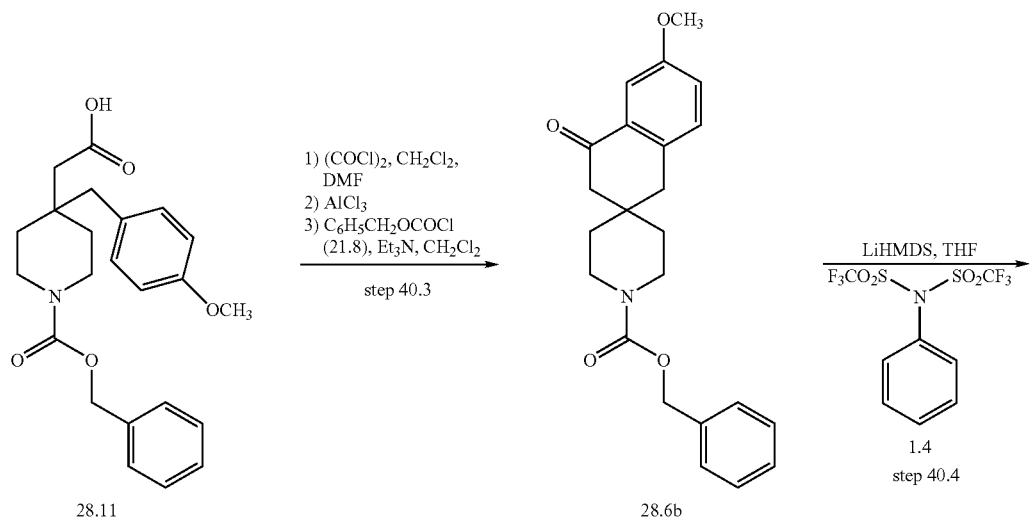
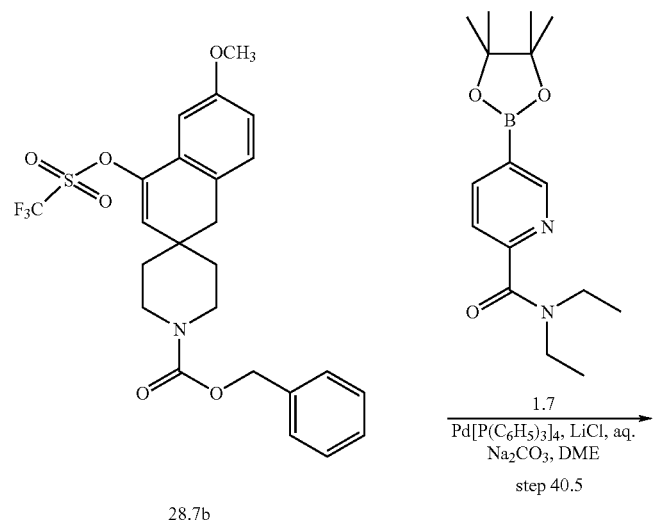
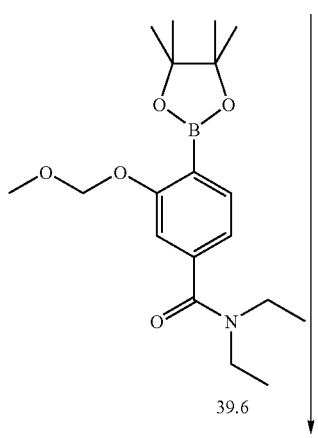

275
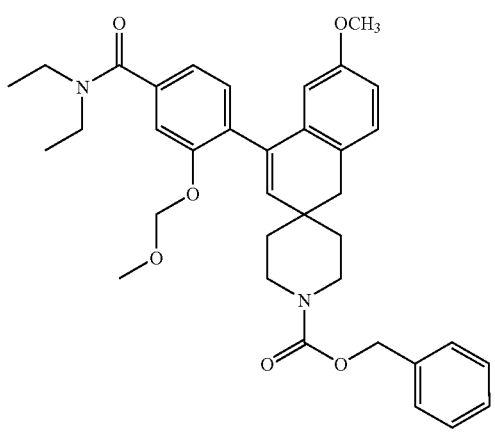
40.3
-continued
276
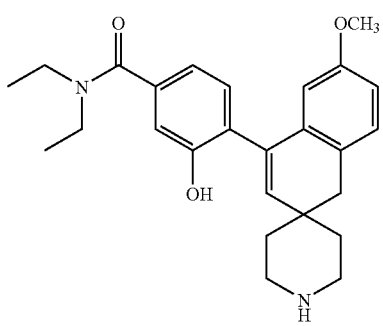
40C
1) TMSI, CH$_2$Cl$_2$
2) HCl, Et$_2$O, CH$_2$Cl$_2$, MeOH
step 40.9
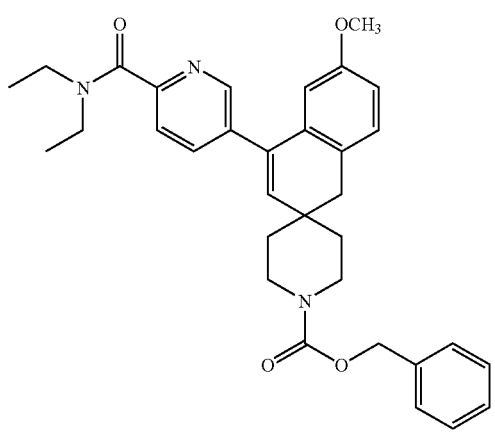
40.2
1) TMSI, CH$_2$Cl$_2$
2) HCl, Et$_2$O, CH$_2$Cl$_2$,
step 40.6
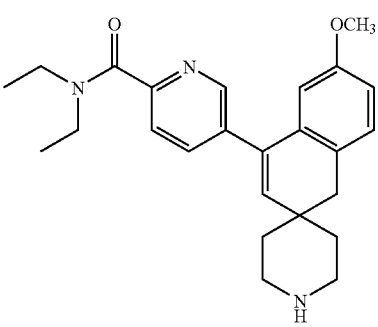
40A
H$_2$, Pd/C, MeOH
step 40.7
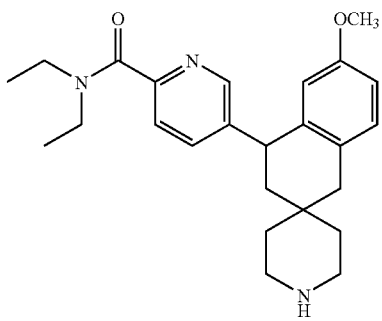
40B

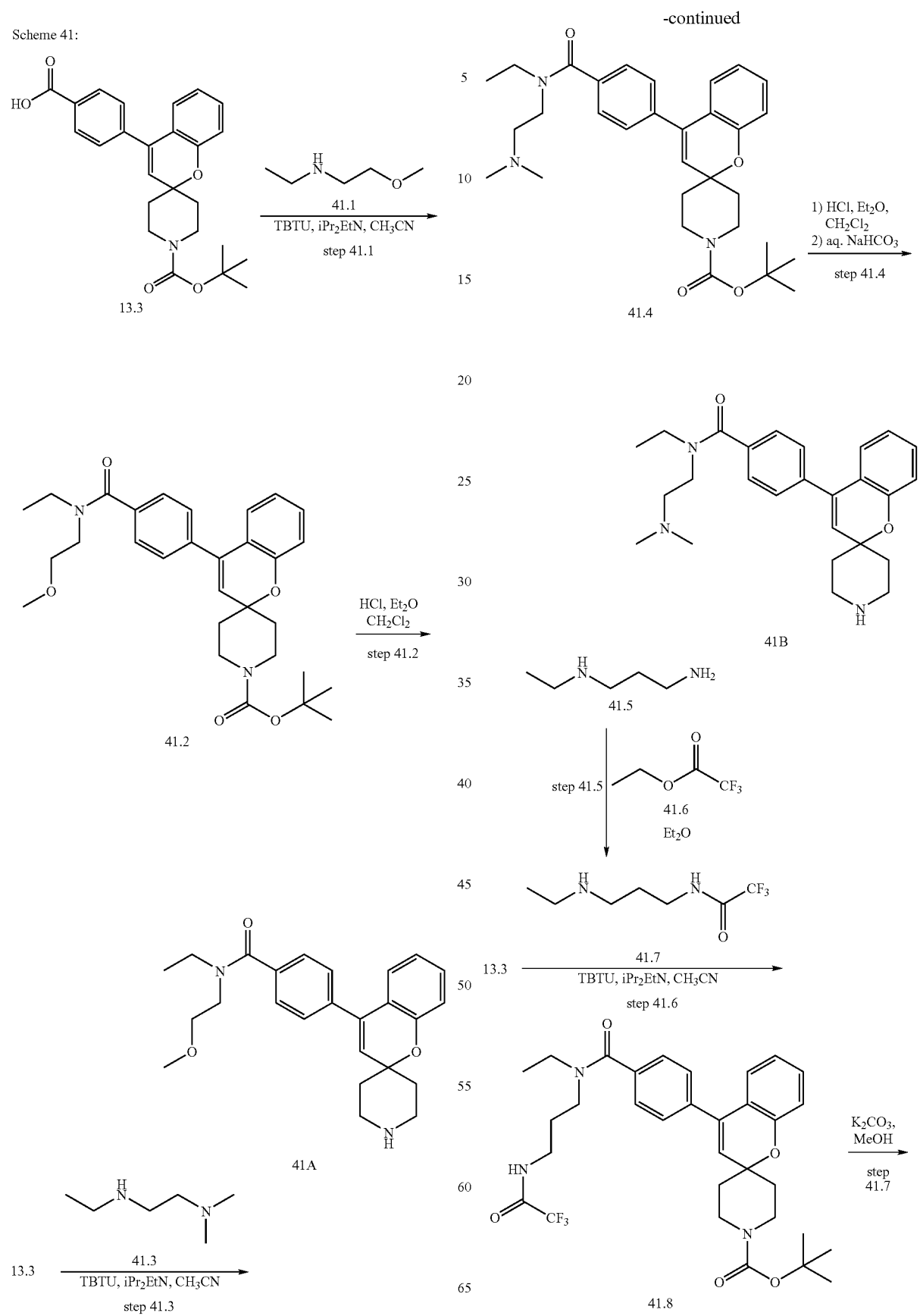

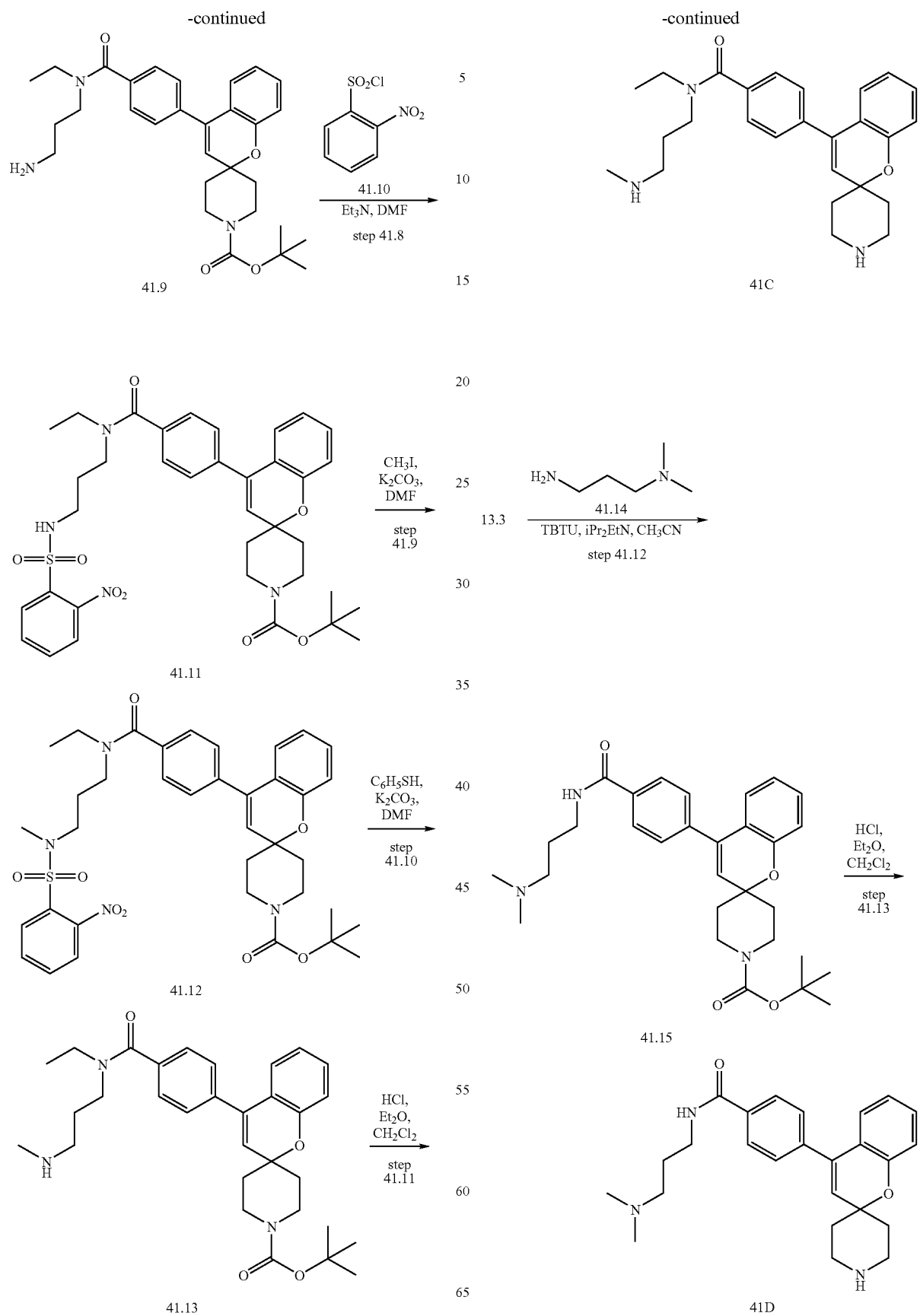

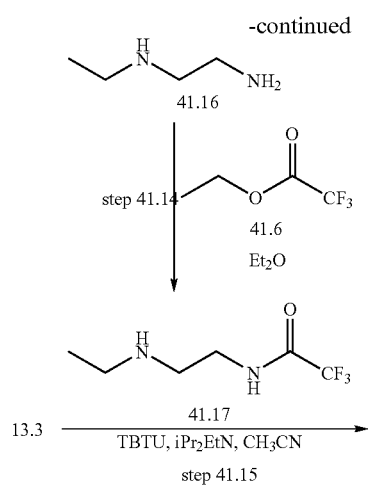
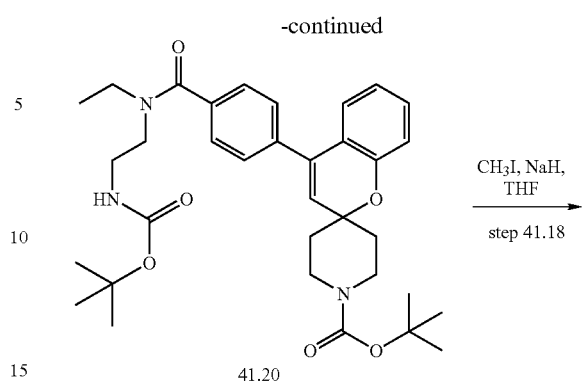
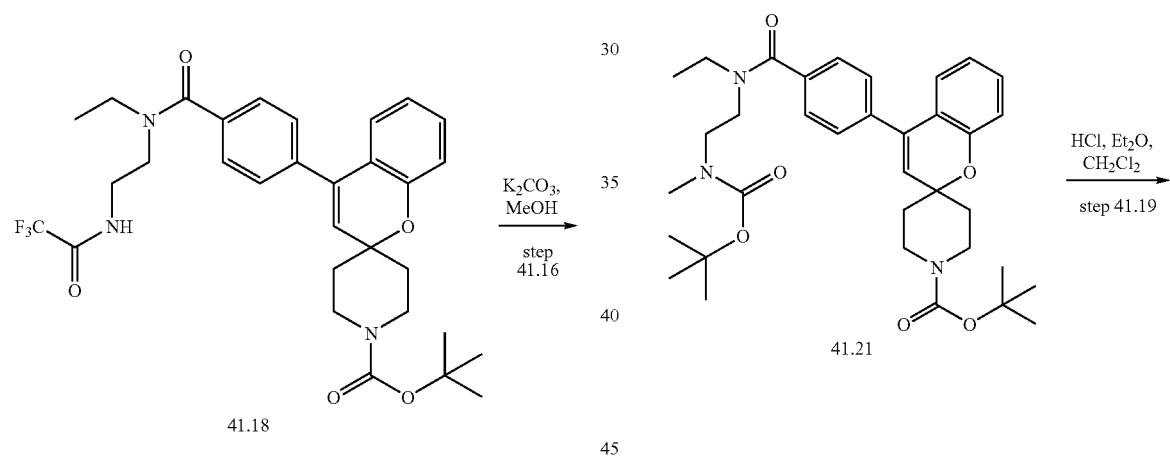
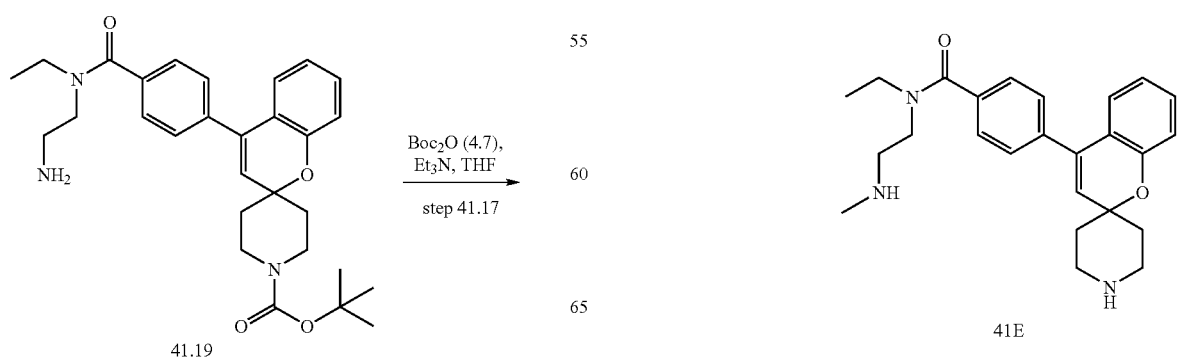

Scheme 42:
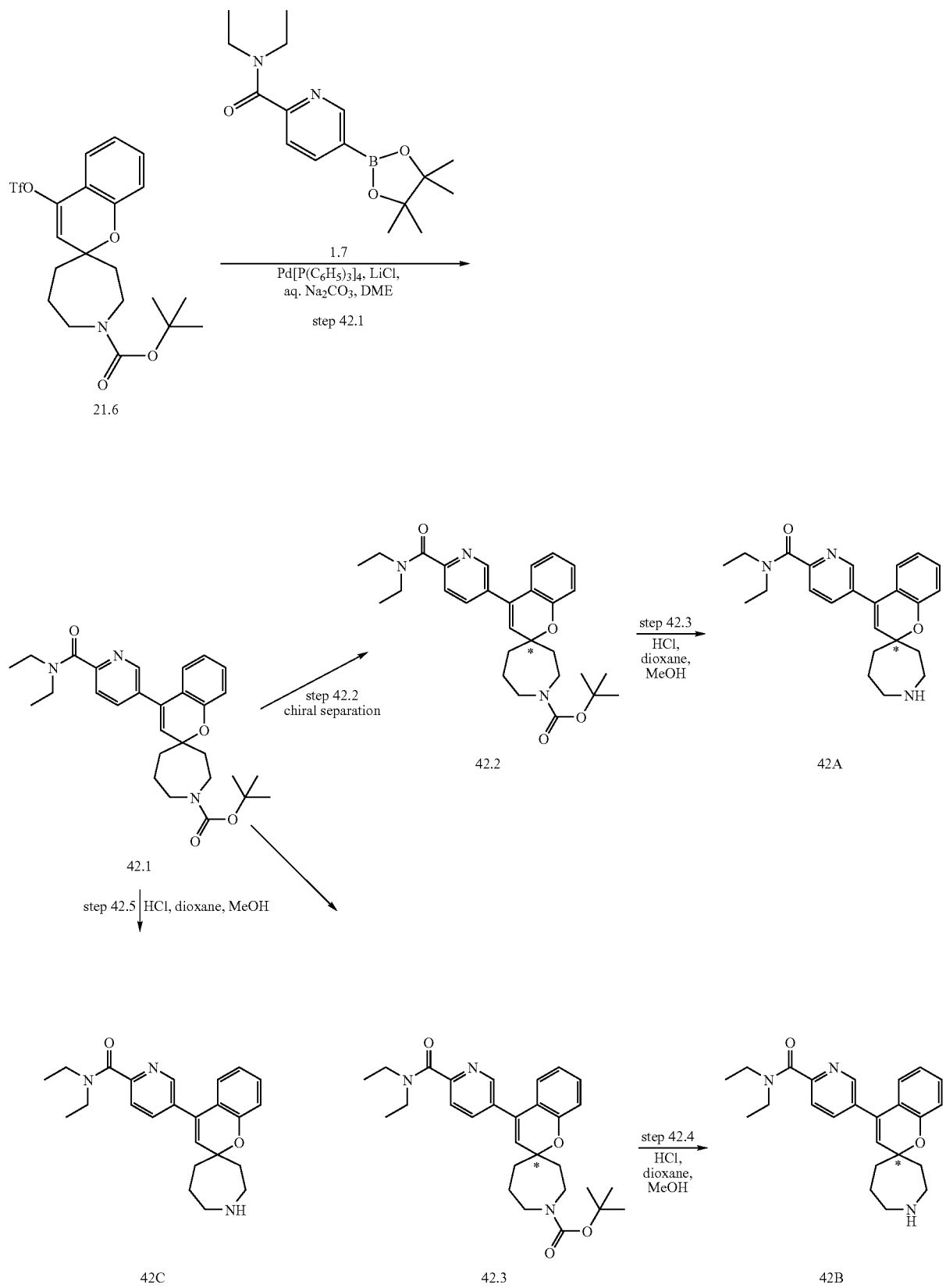

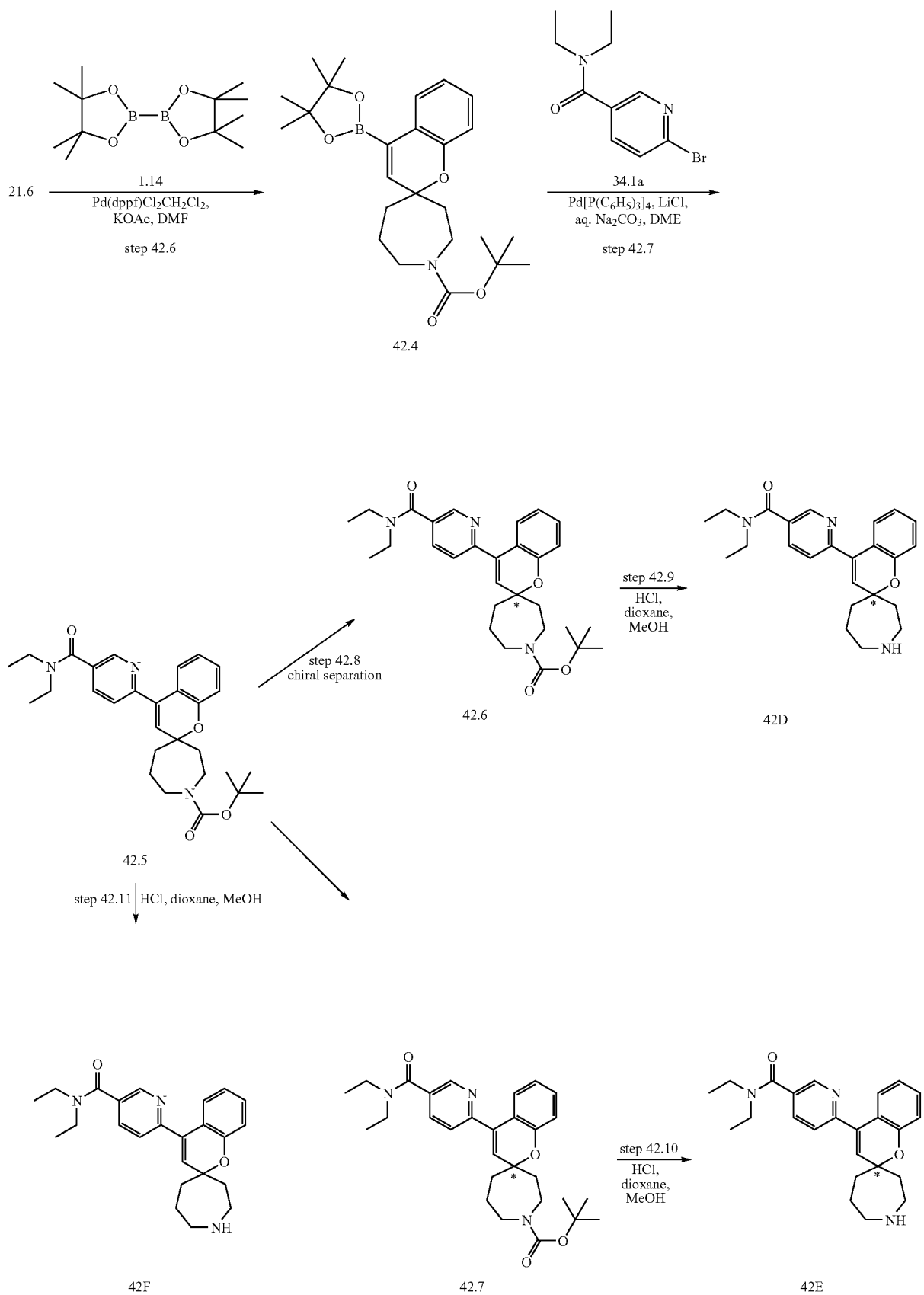

-continued
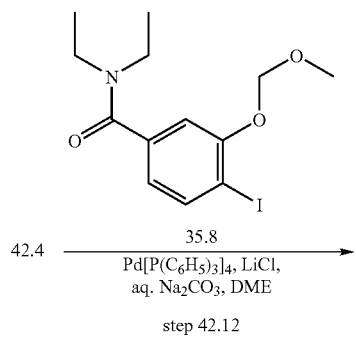
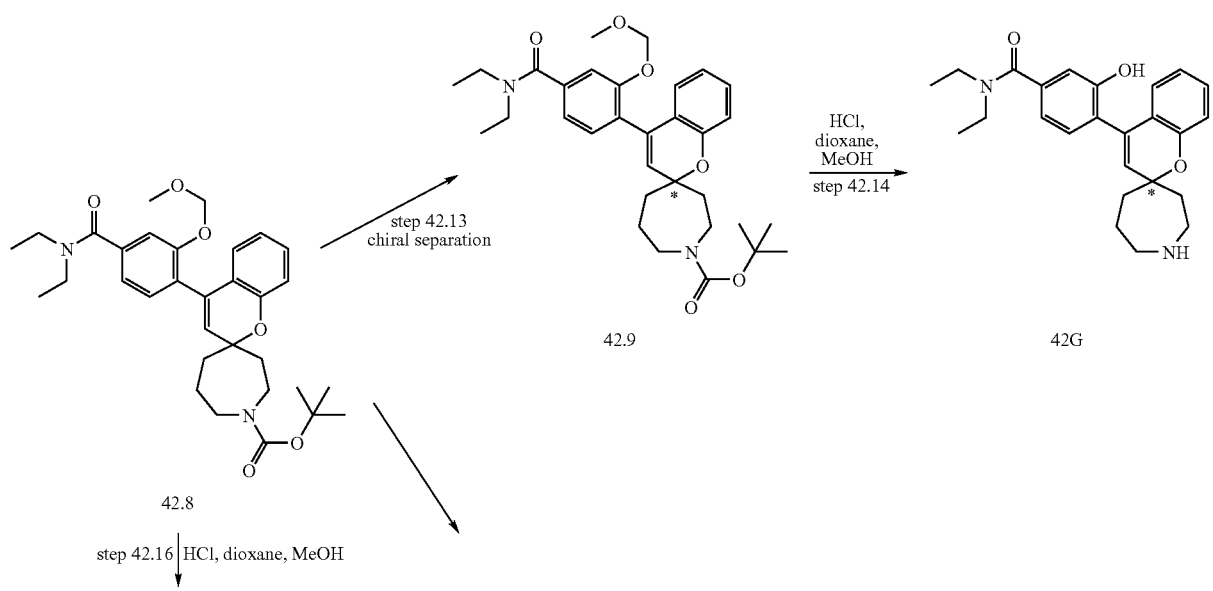
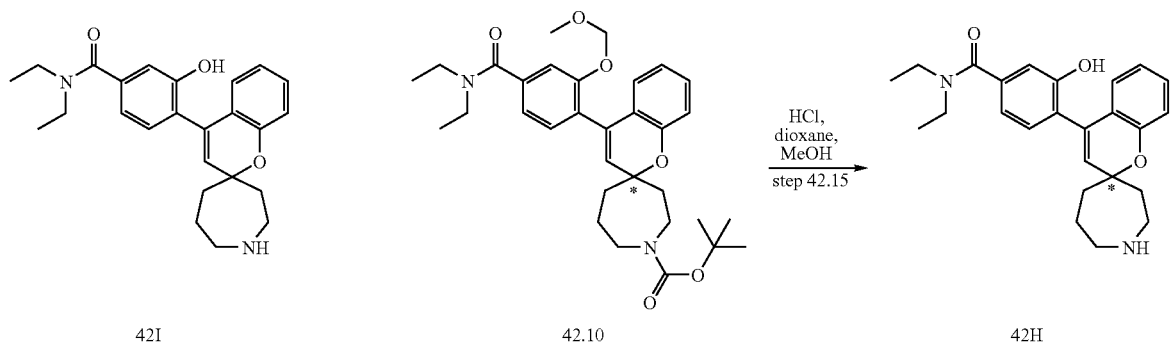

Scheme 43:
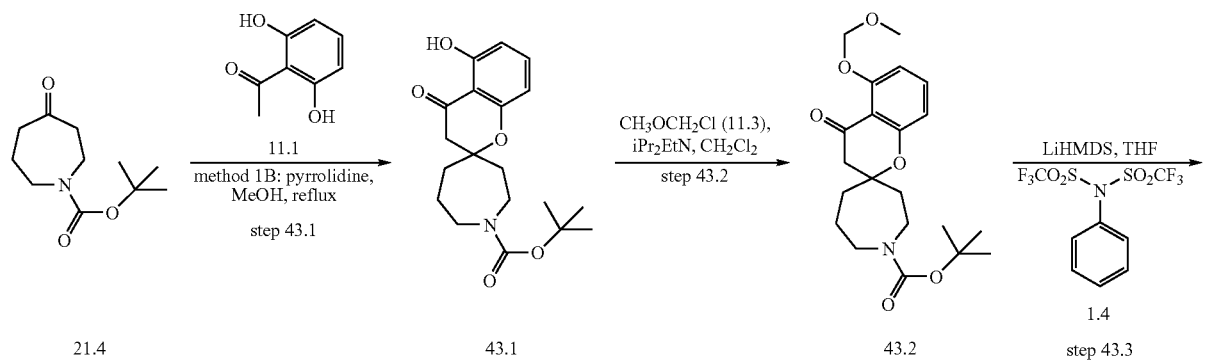
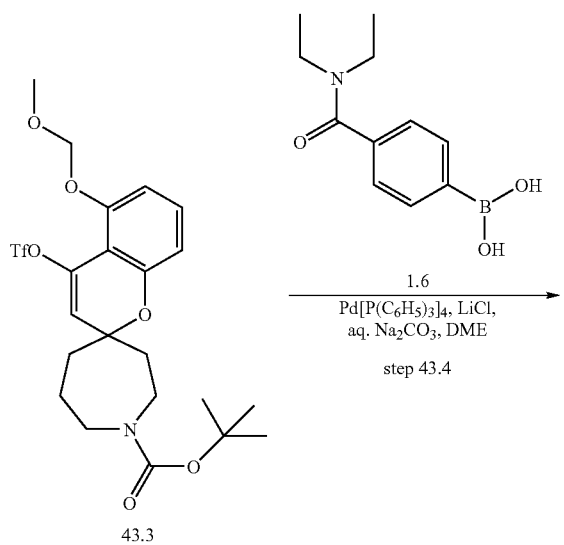
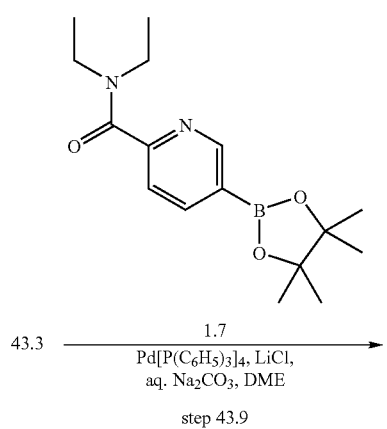

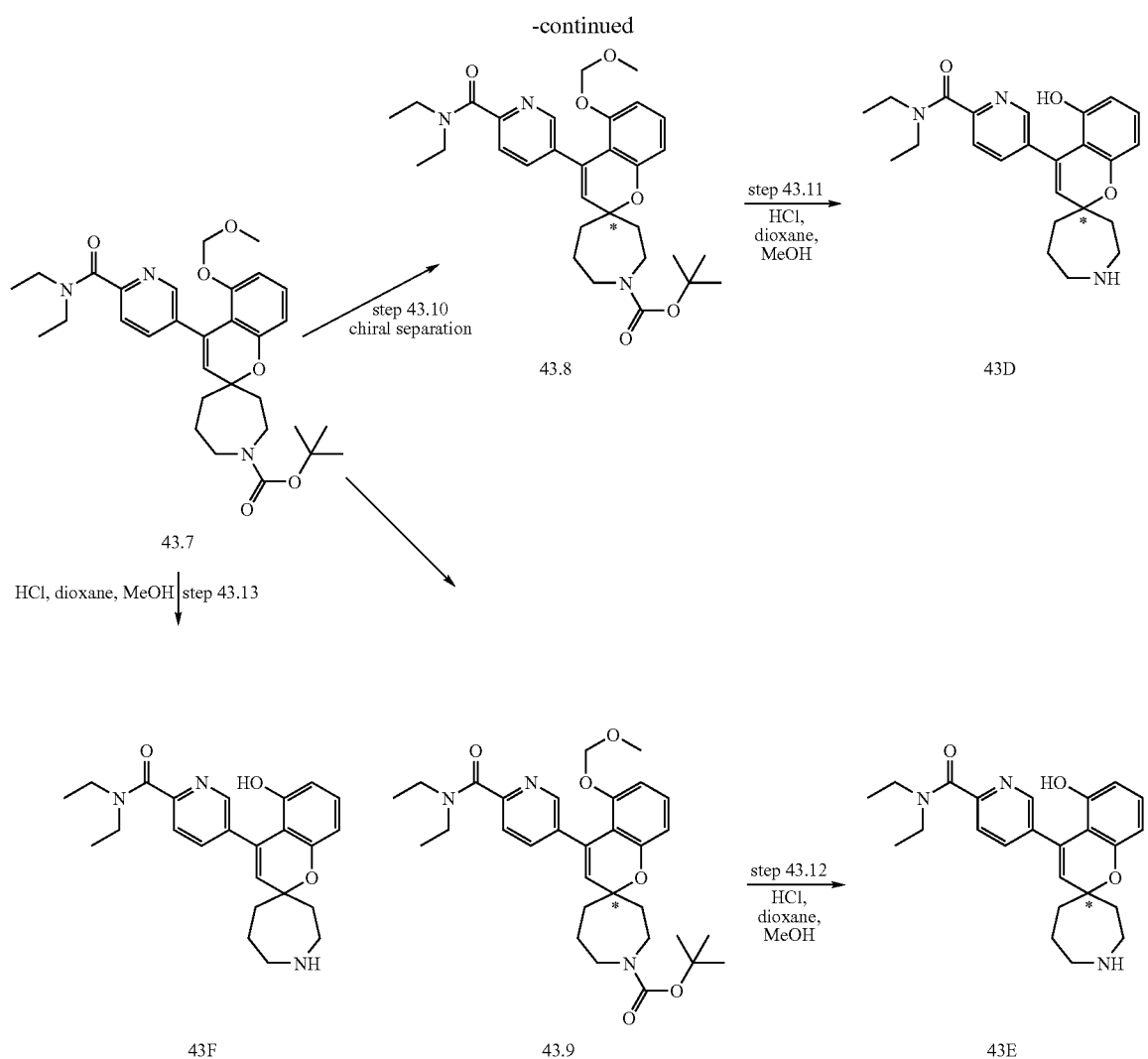
Scheme 44:
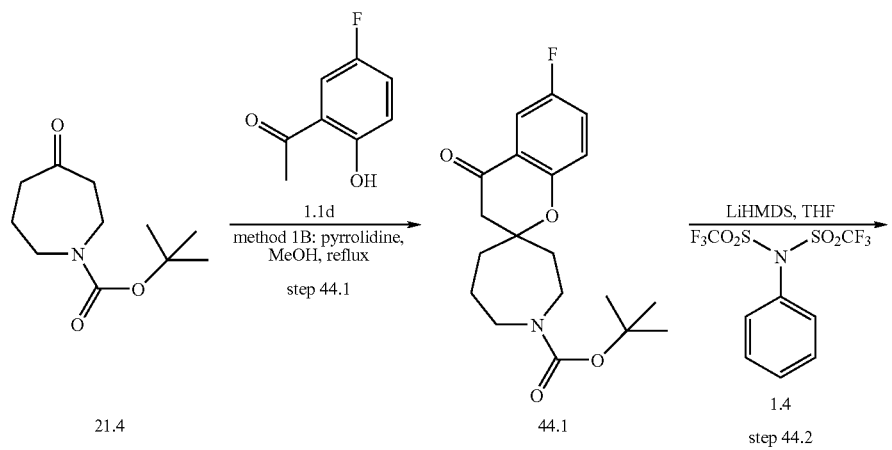

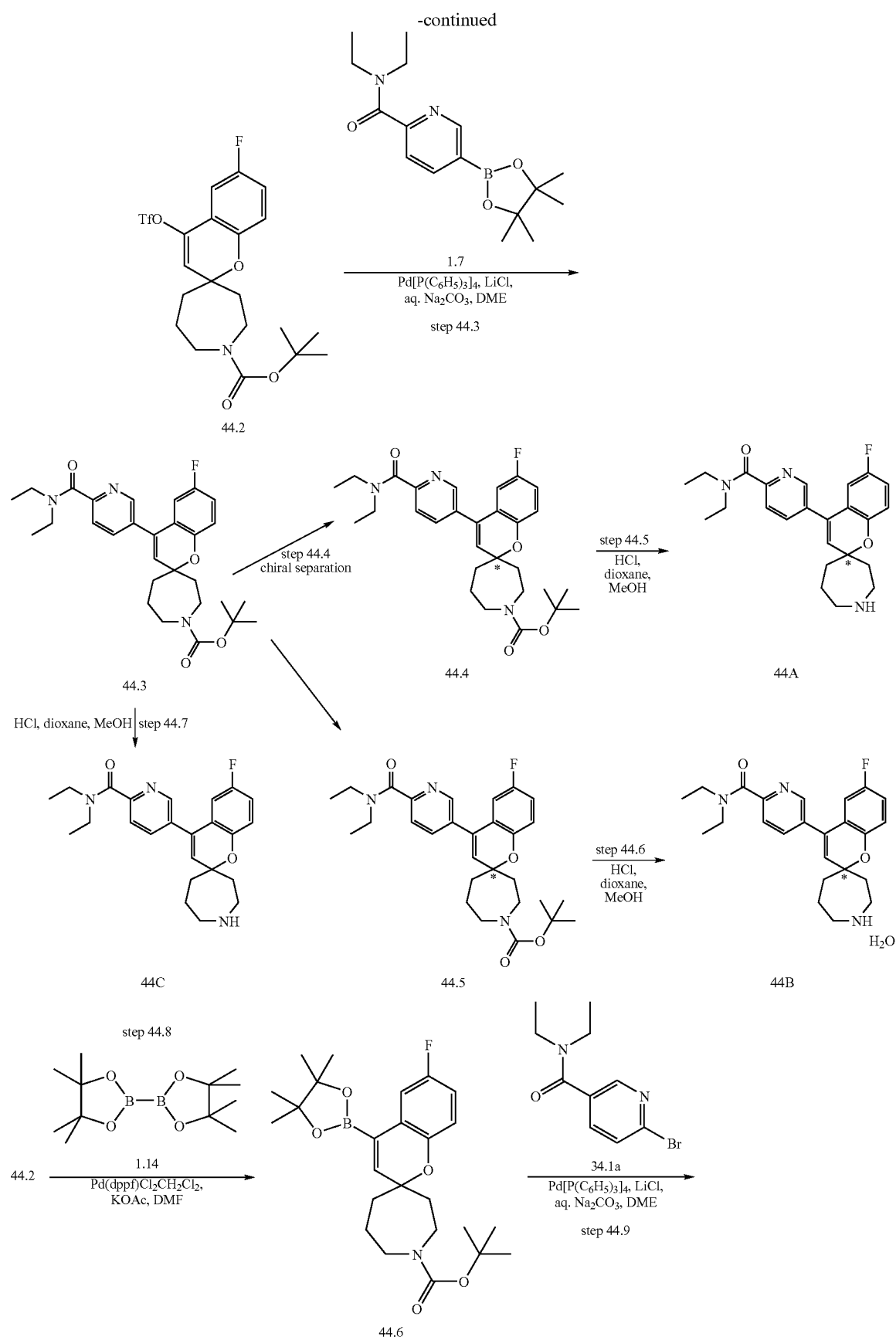

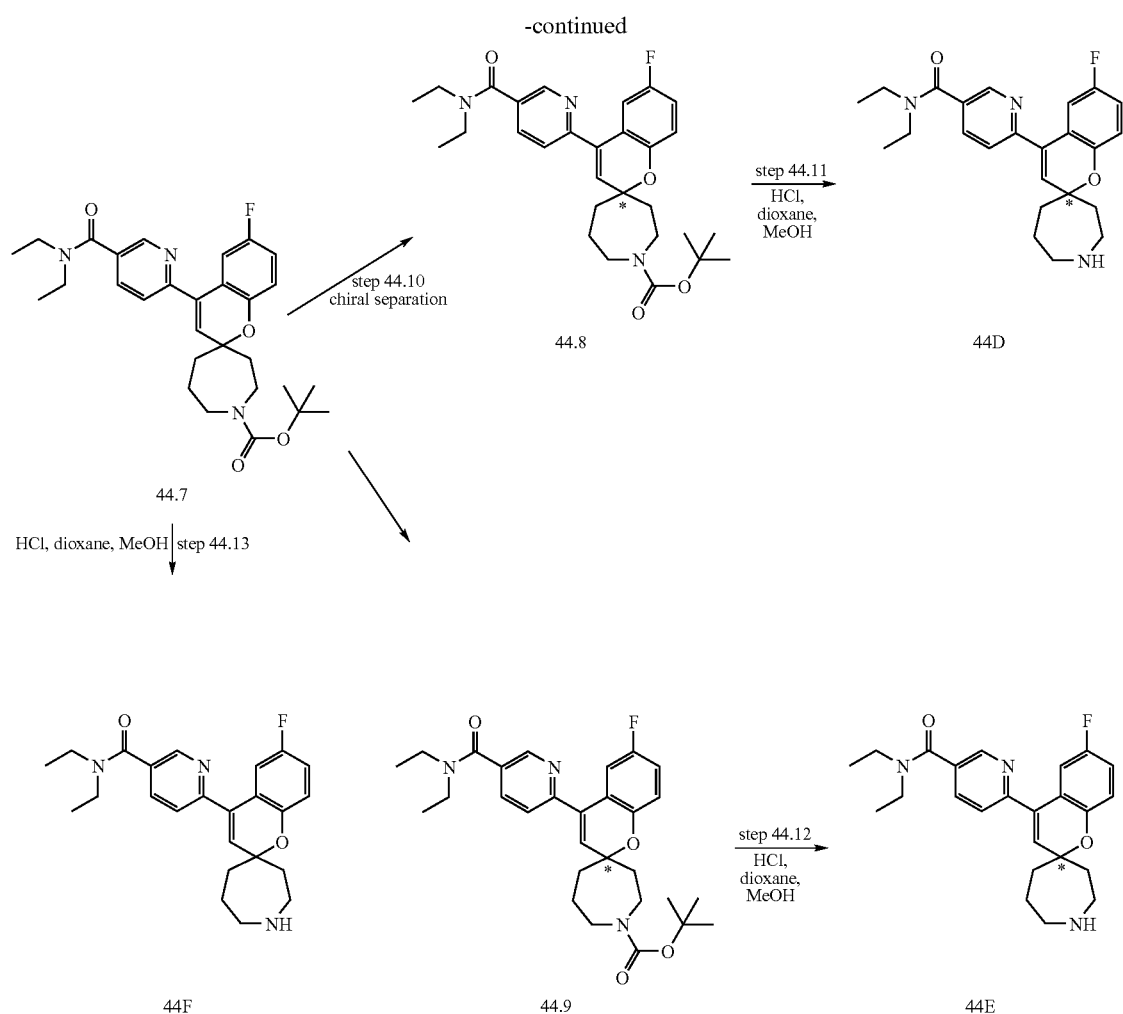
Scheme 45:
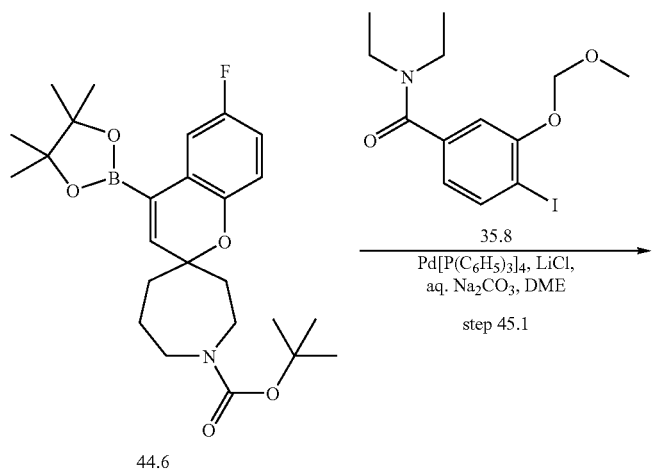

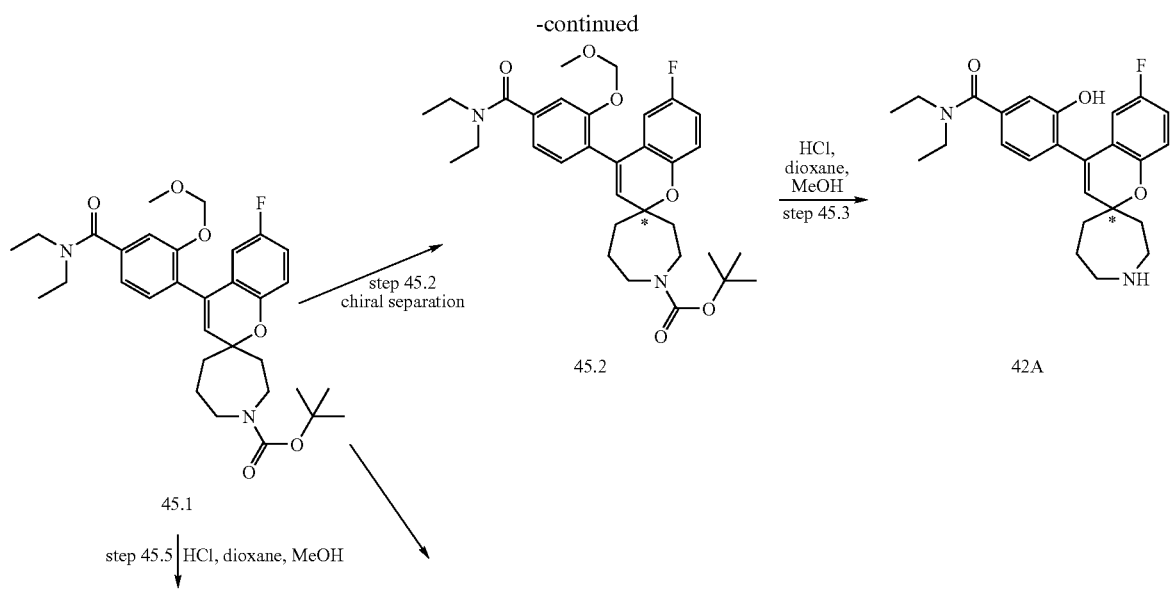
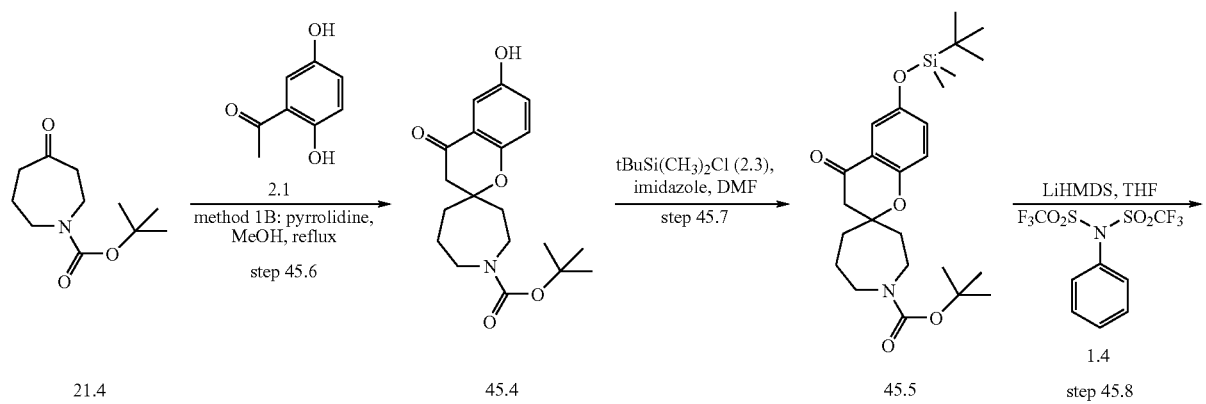
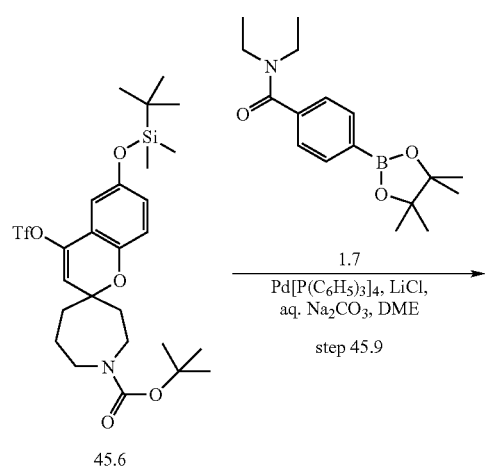

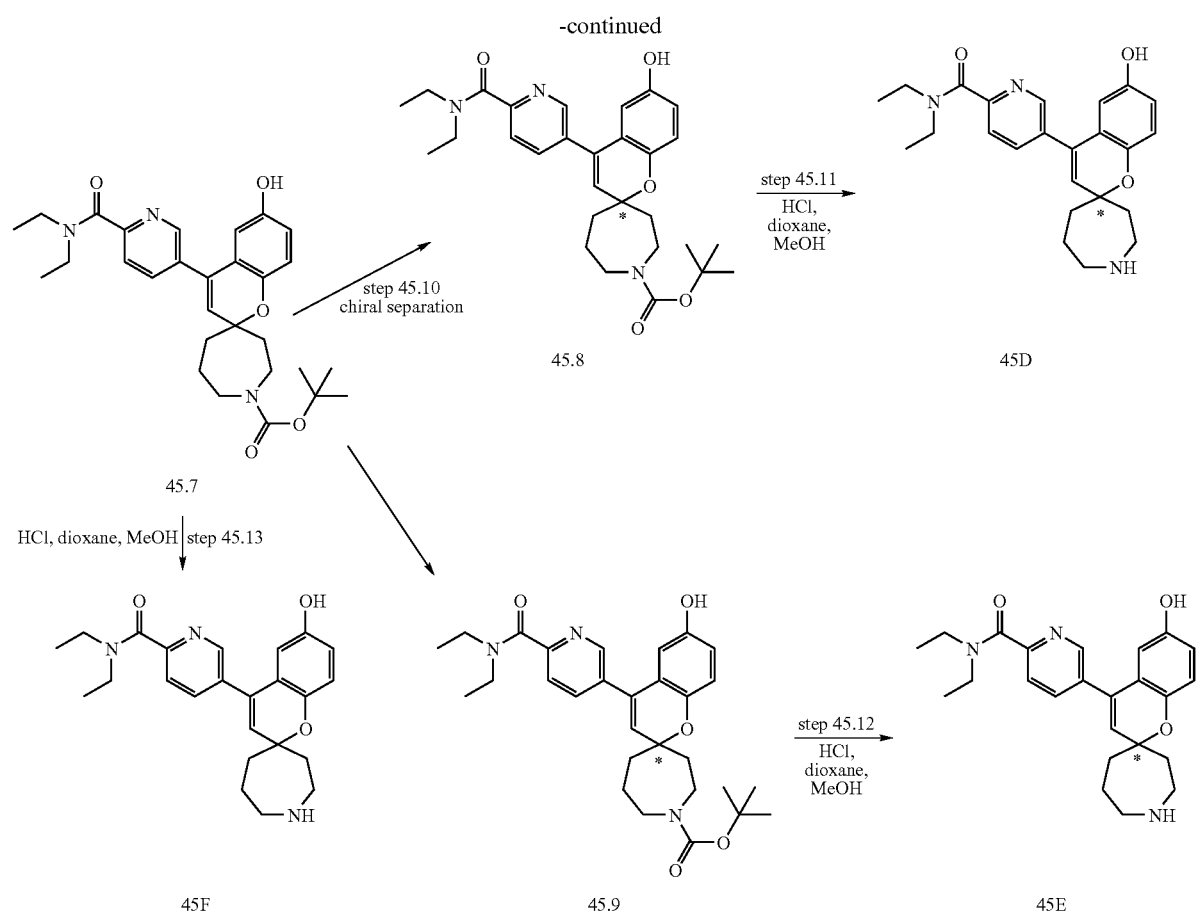
Scheme 46:
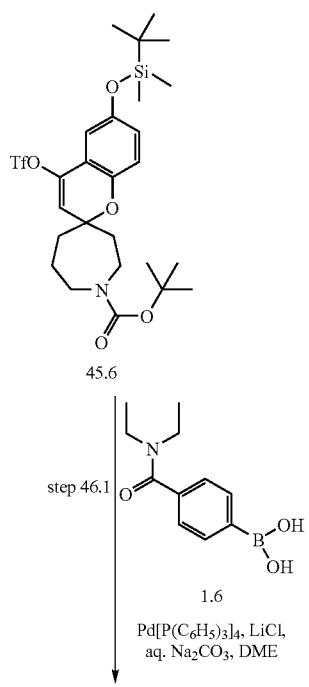

-continued
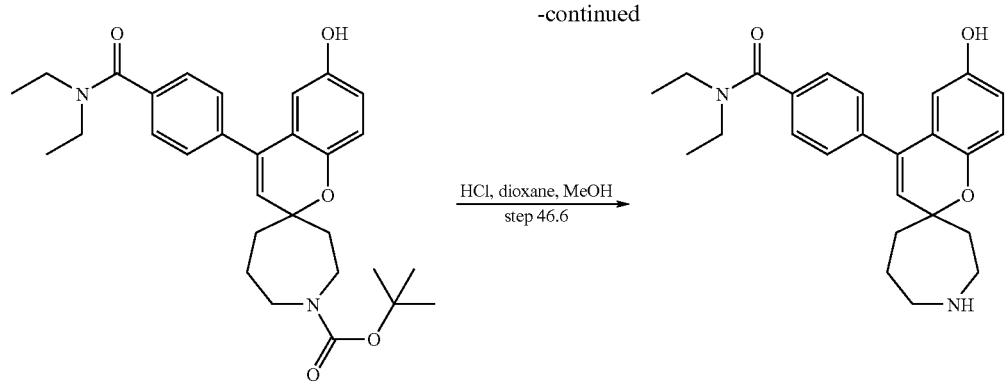
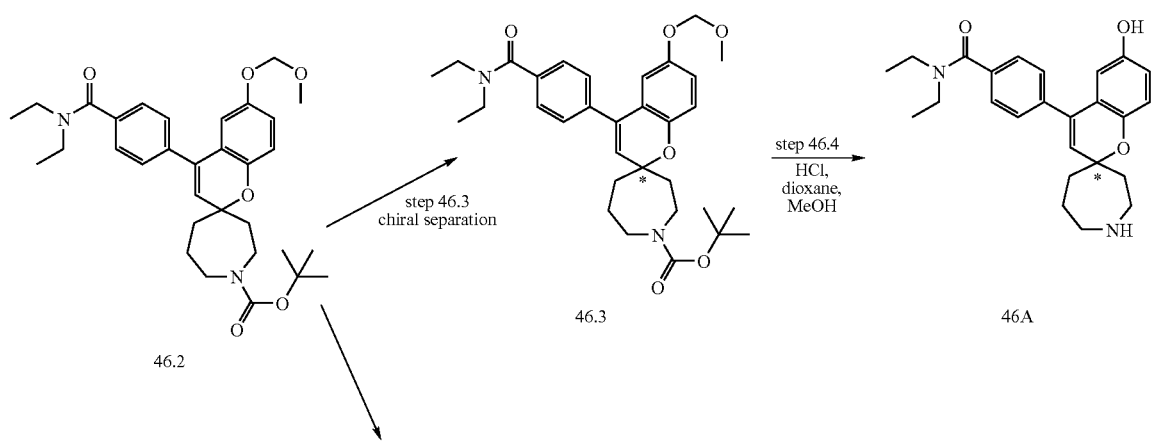
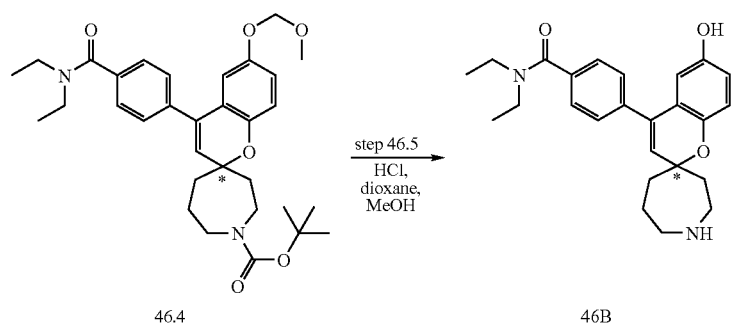

Scheme 47:
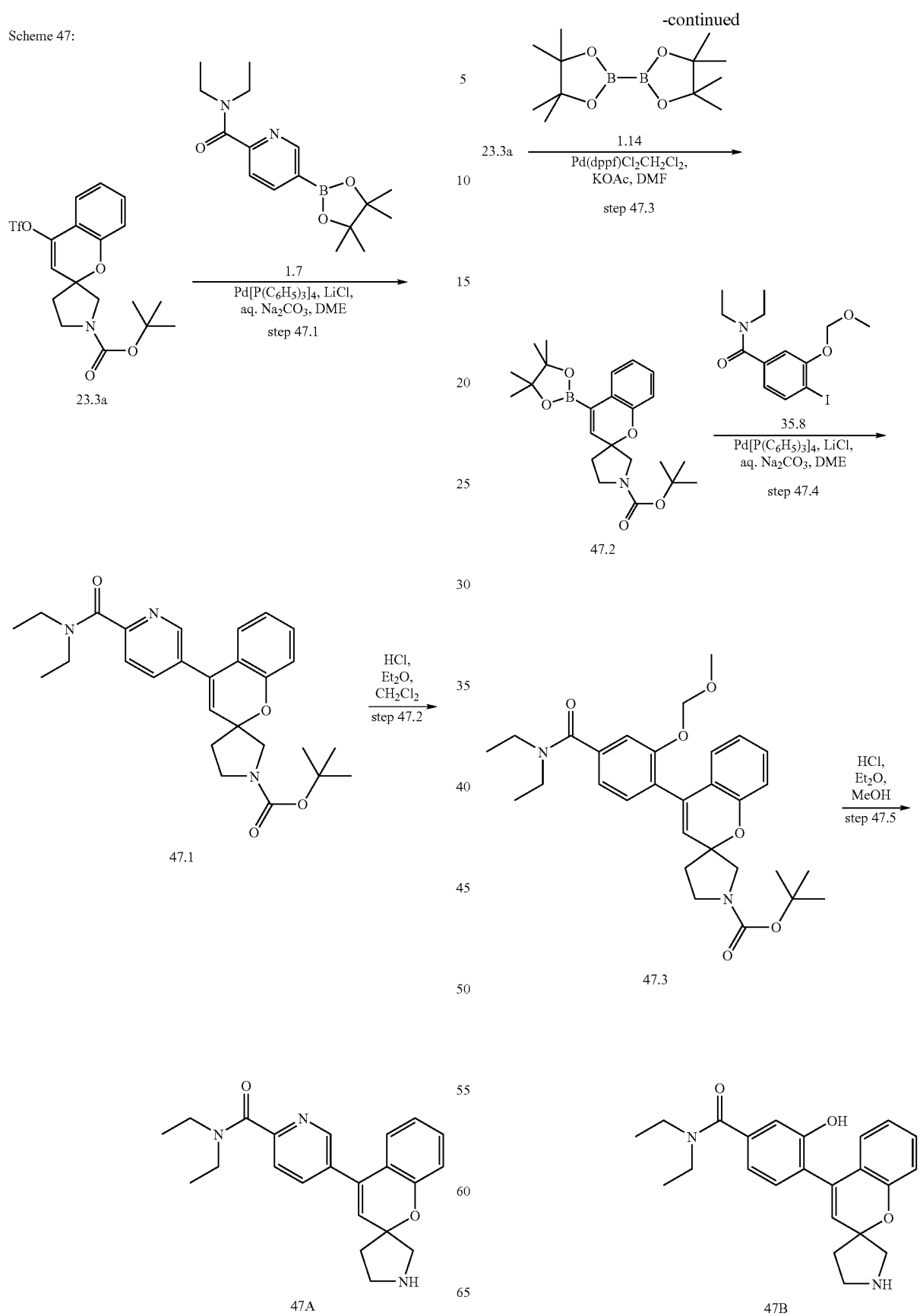

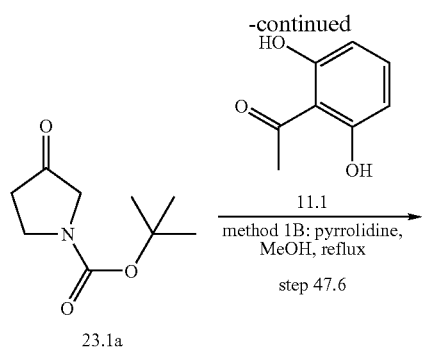
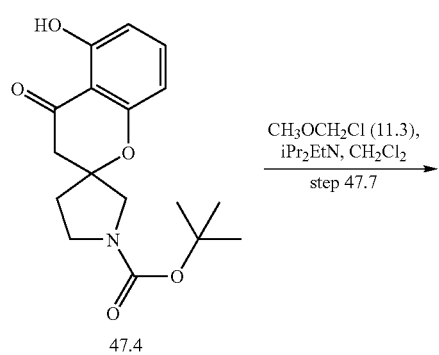
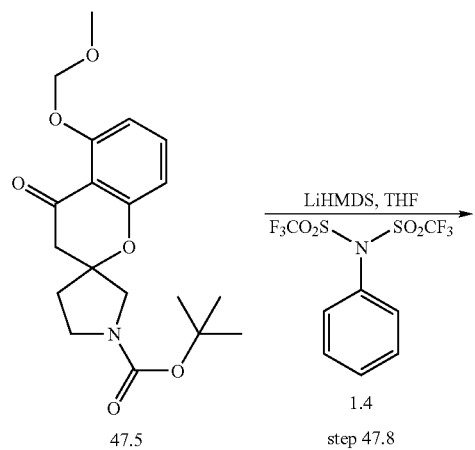
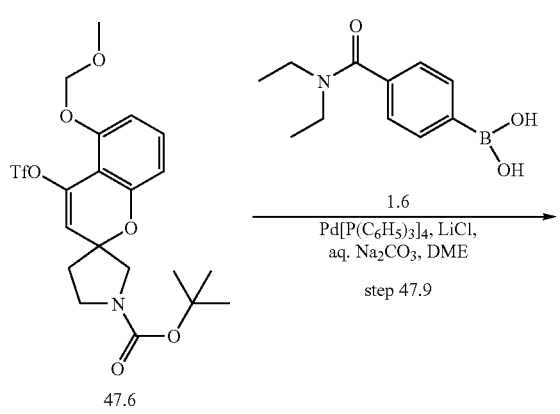
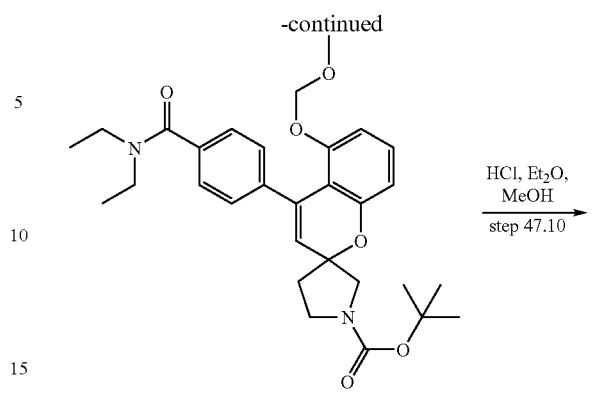
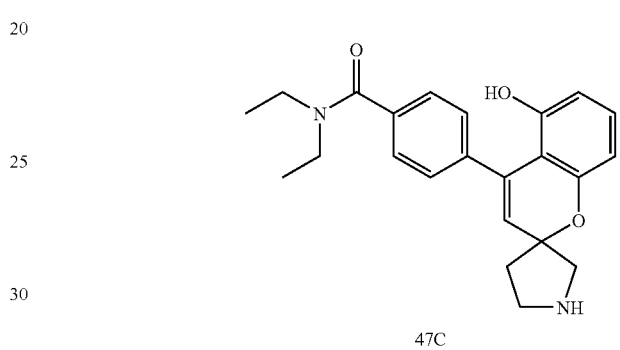
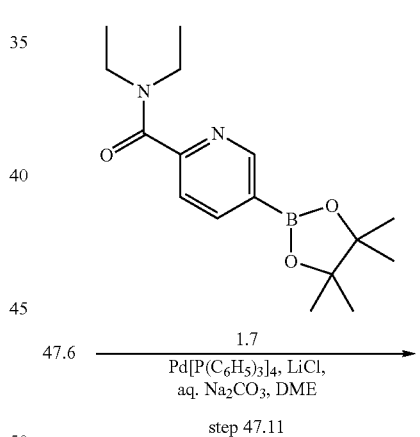
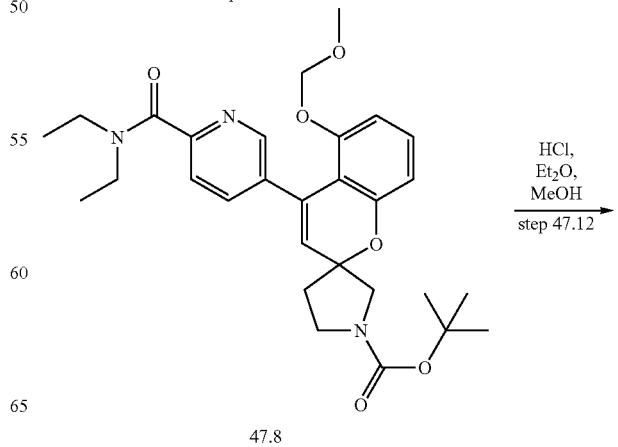

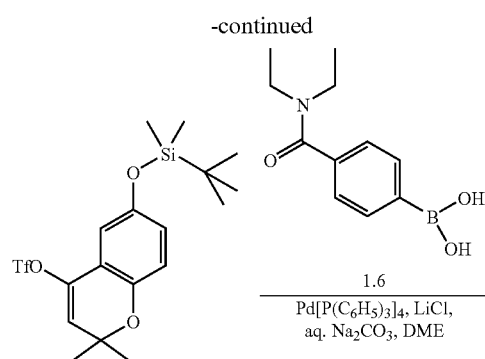
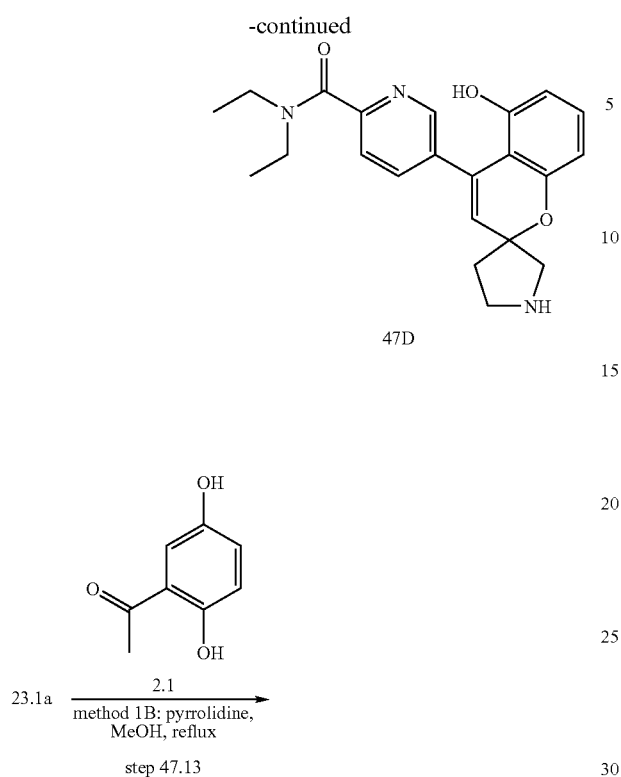
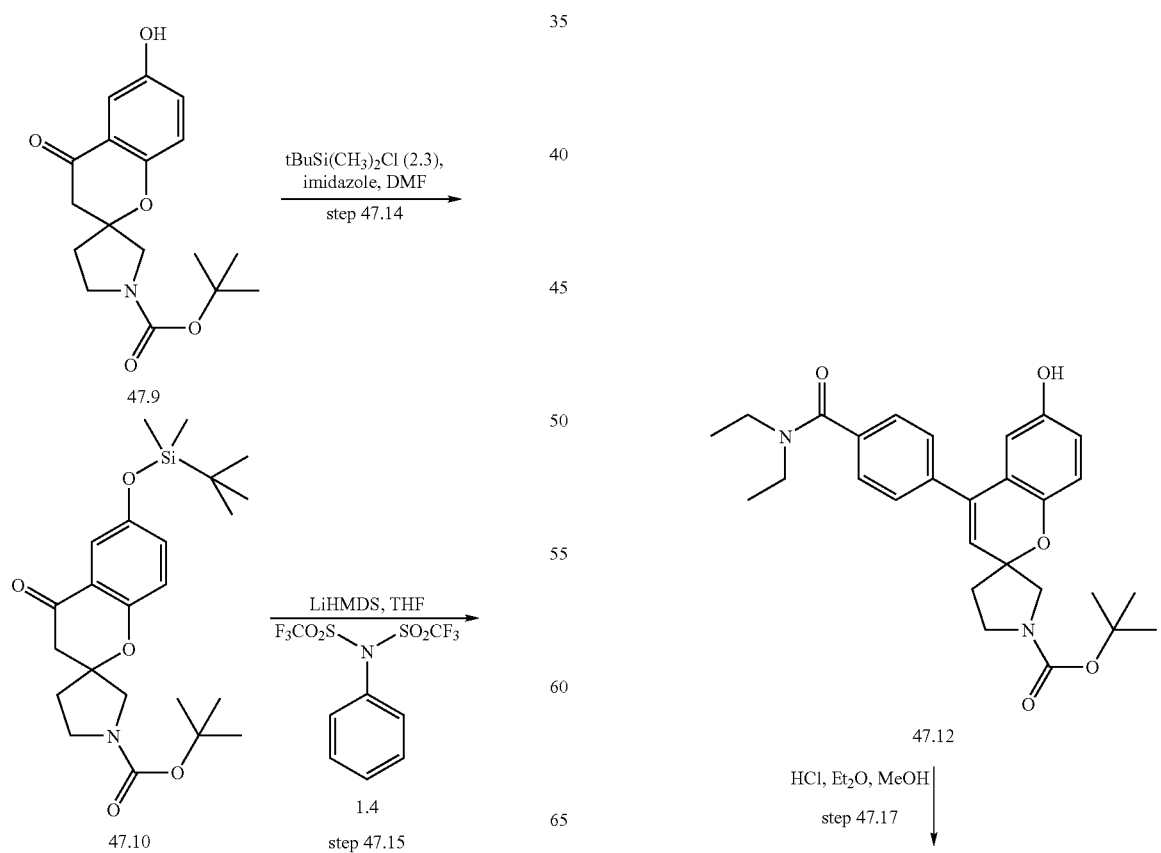

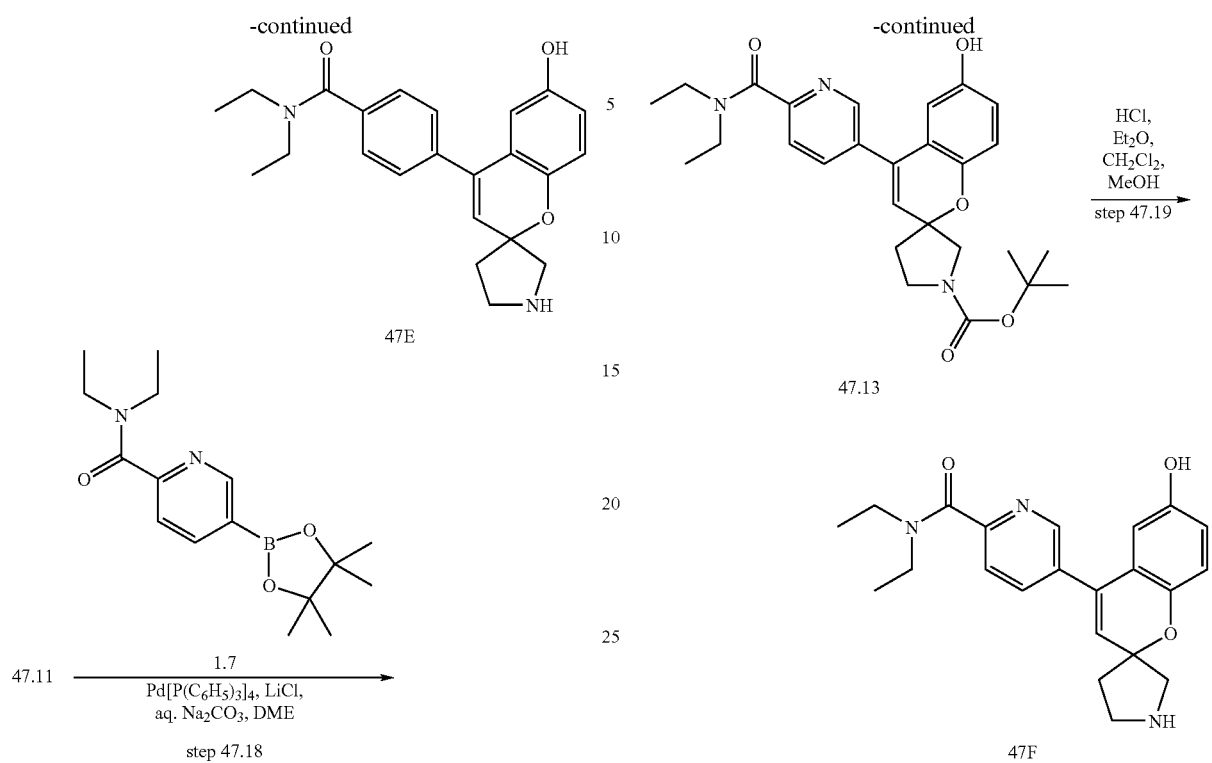
Scheme 48:
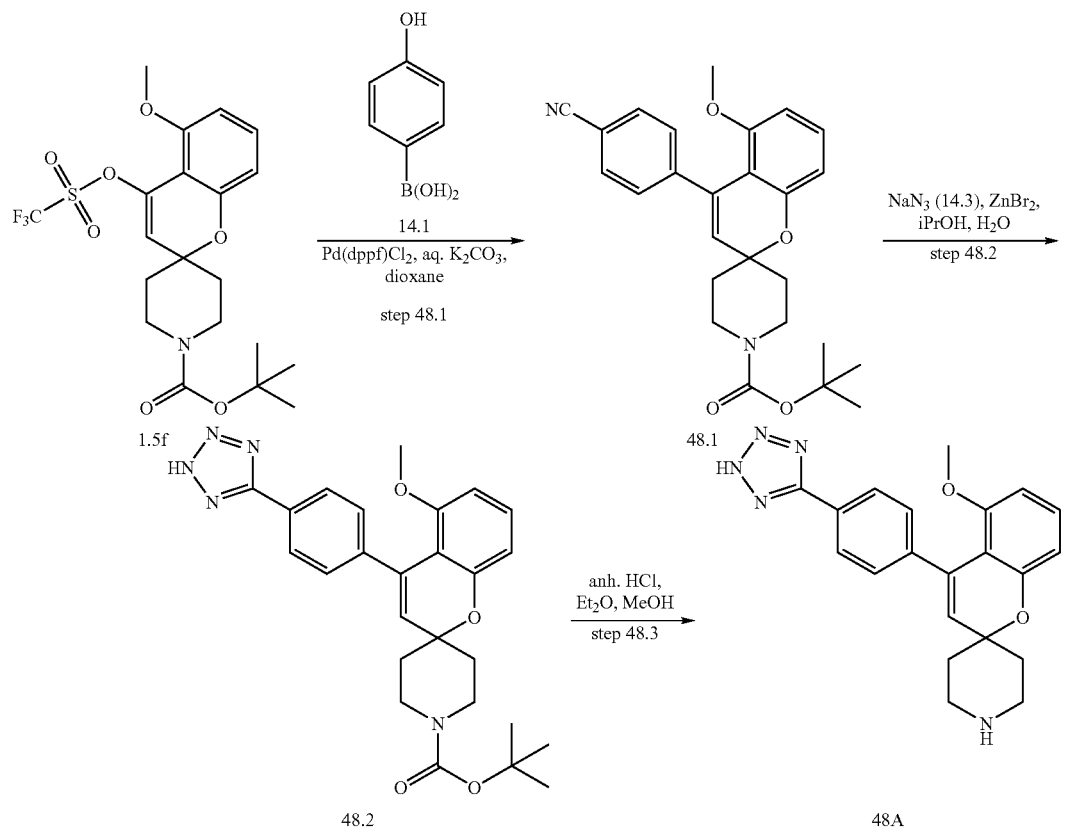

-continued
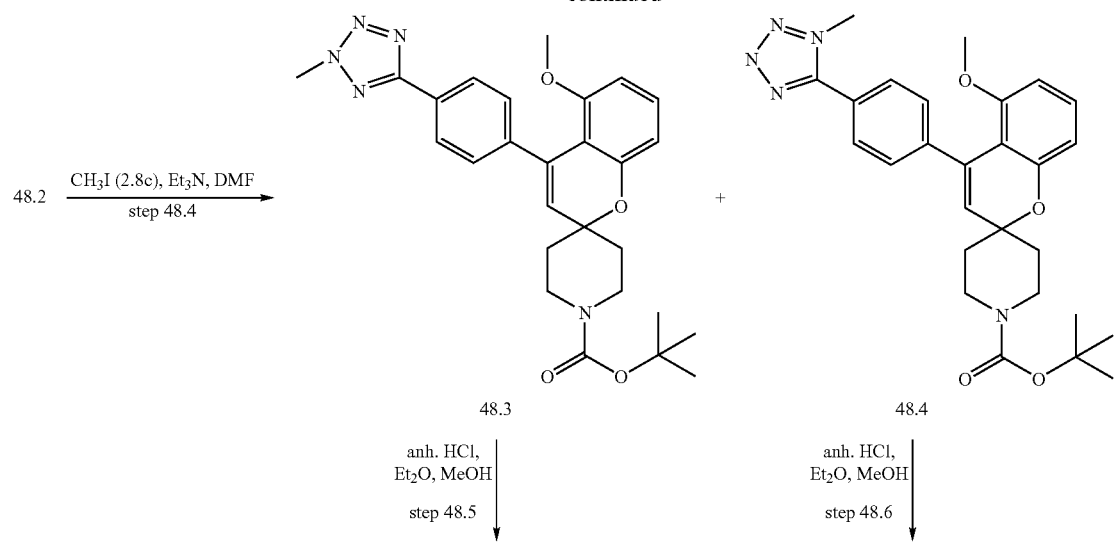
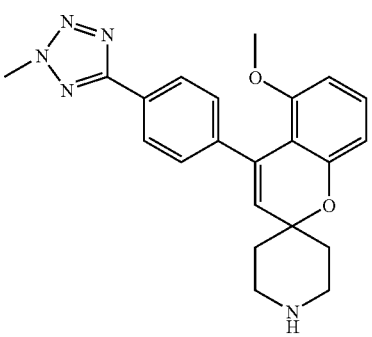
48B
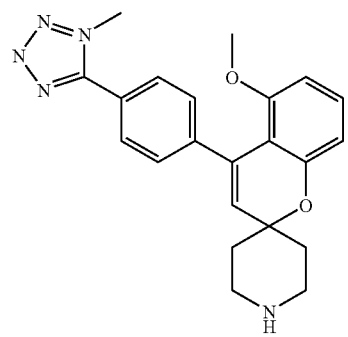
48C
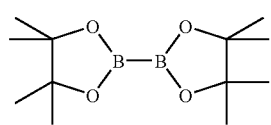
1.14

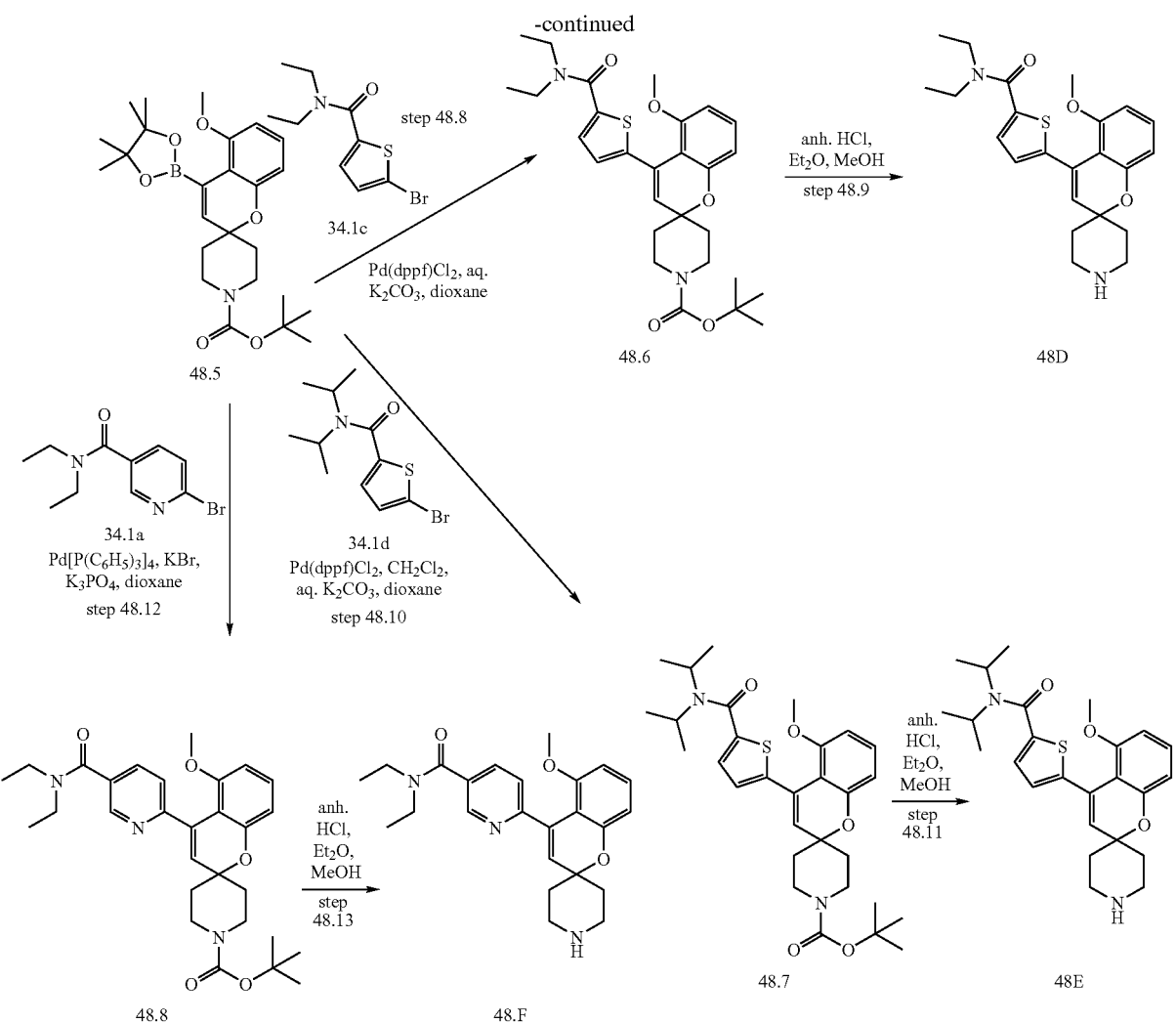
Scheme 49:
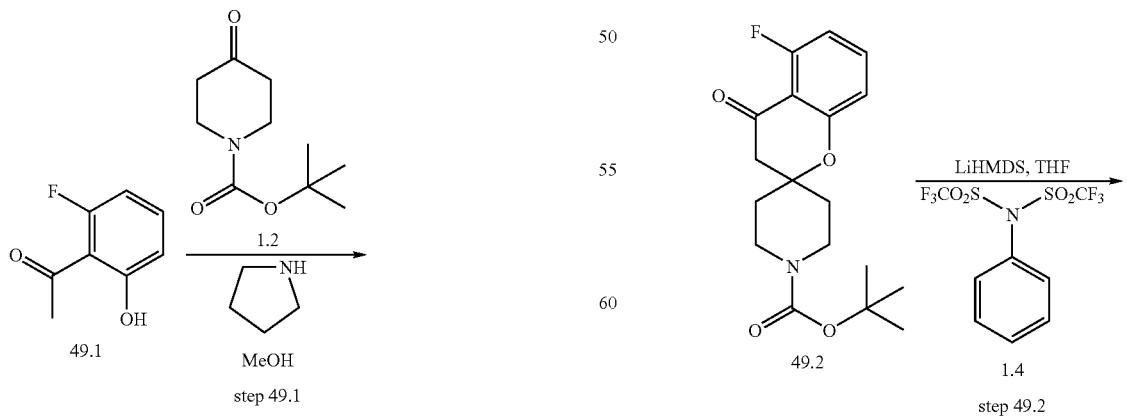

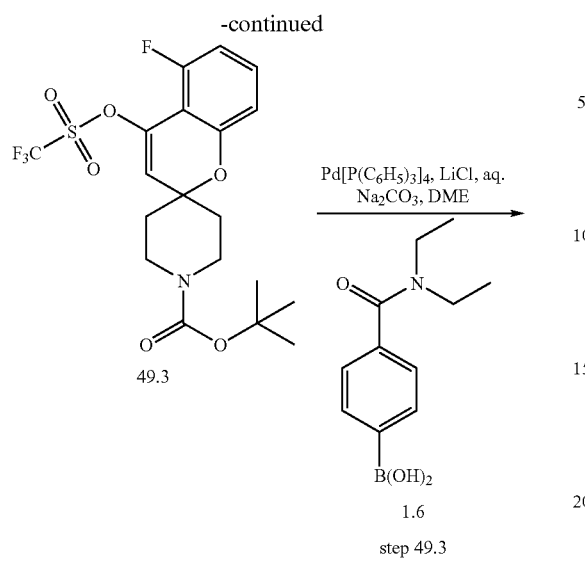
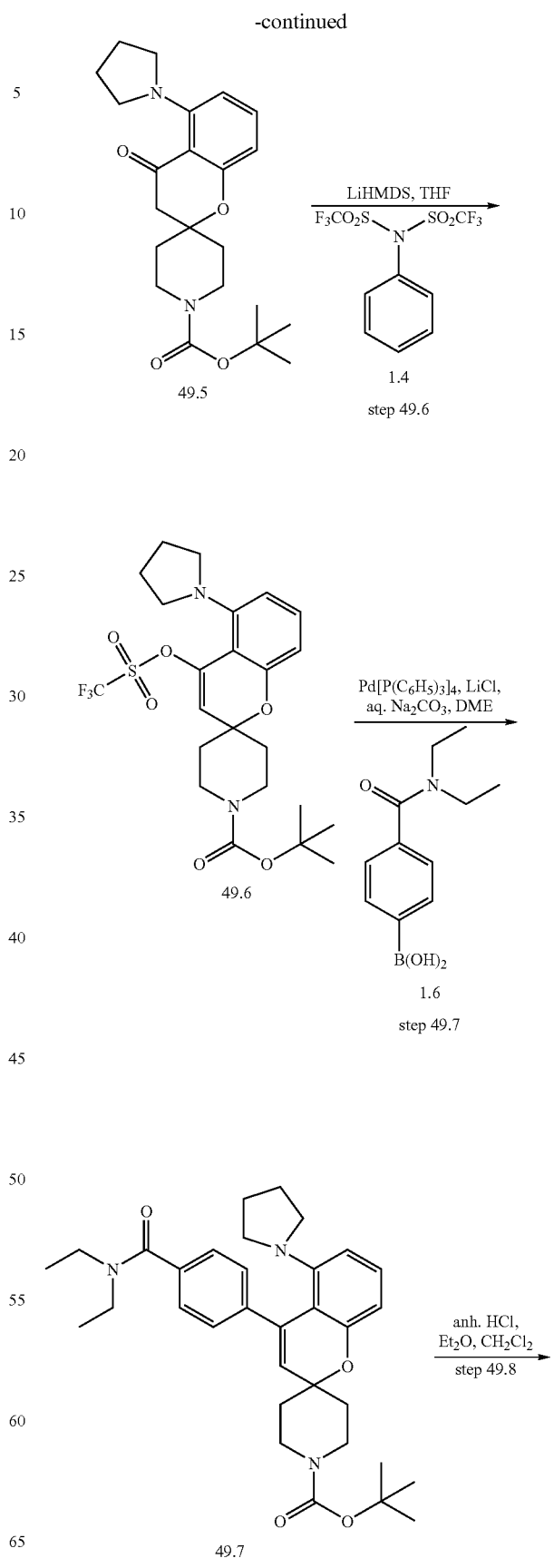

-continued
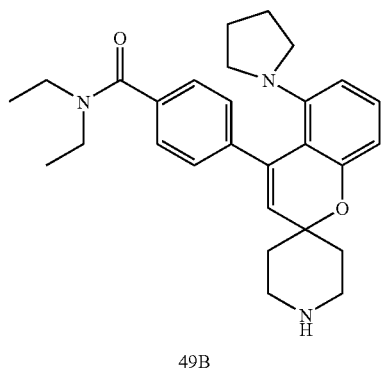
49B
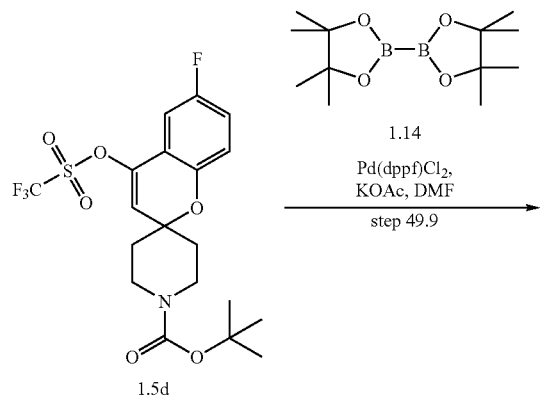
step 49.9
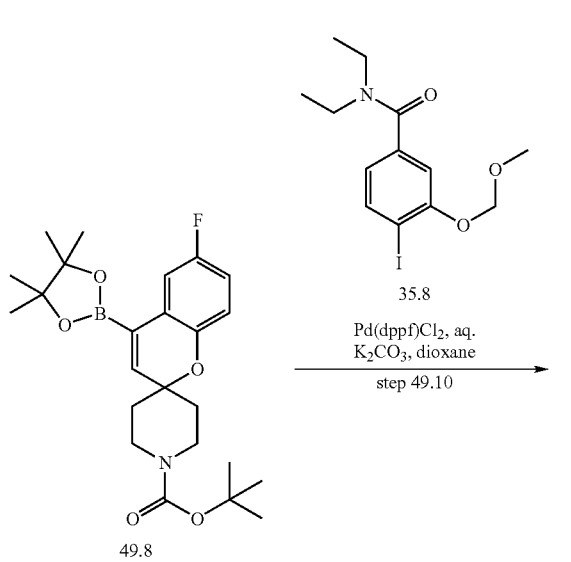
step 49.10
-continued
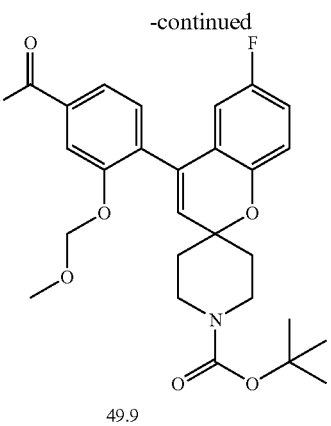
49.9
anh. HCl, Et₂O, CH₂Cl₂
step 49.11
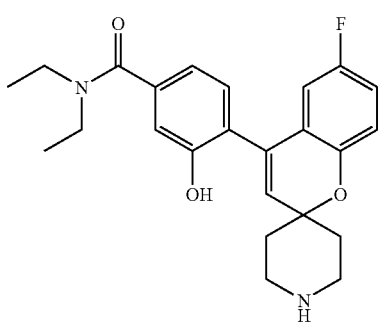
49C
H₂, Pd/C, MeOH
step 49.12
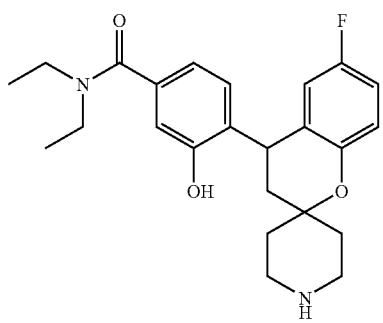
49D Scheme 50:
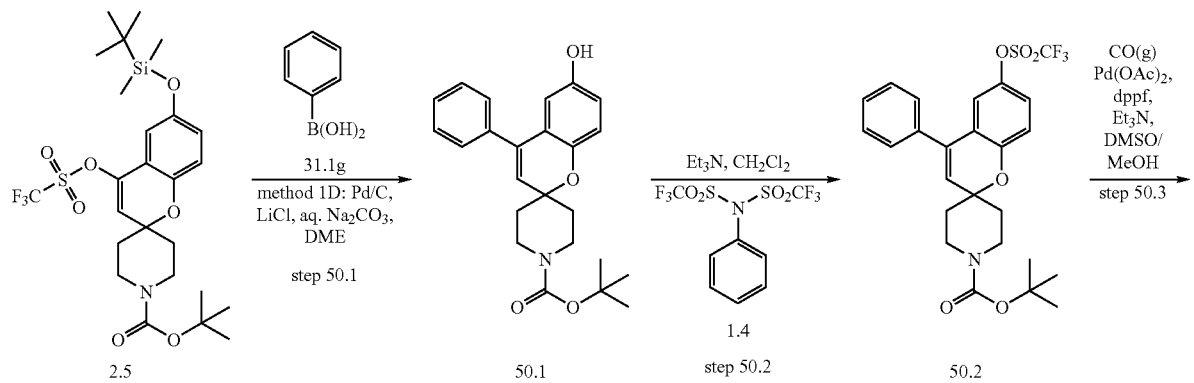
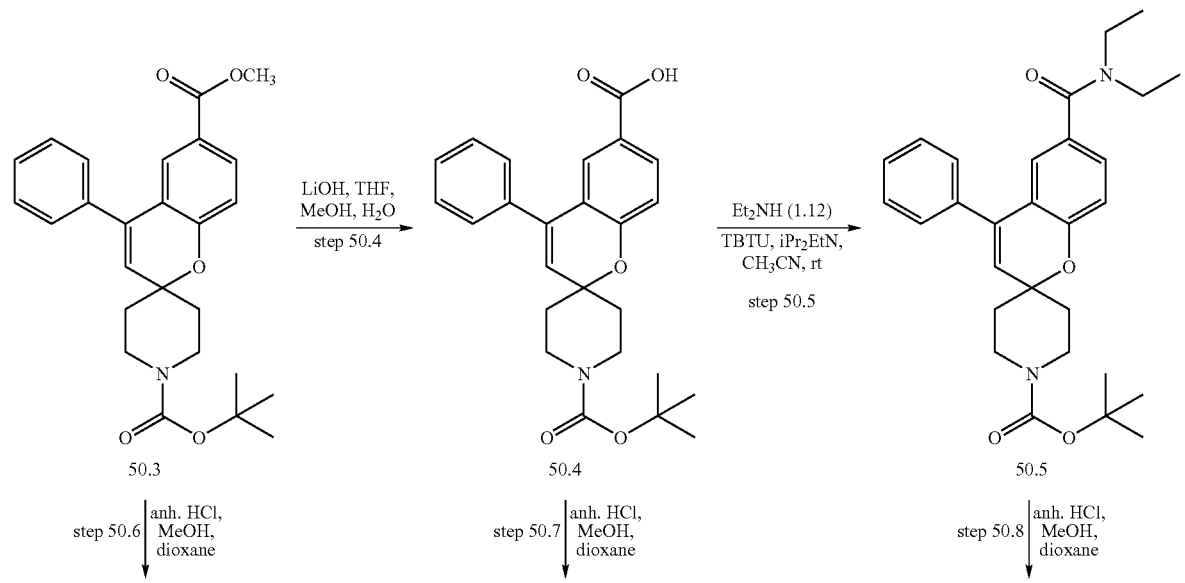
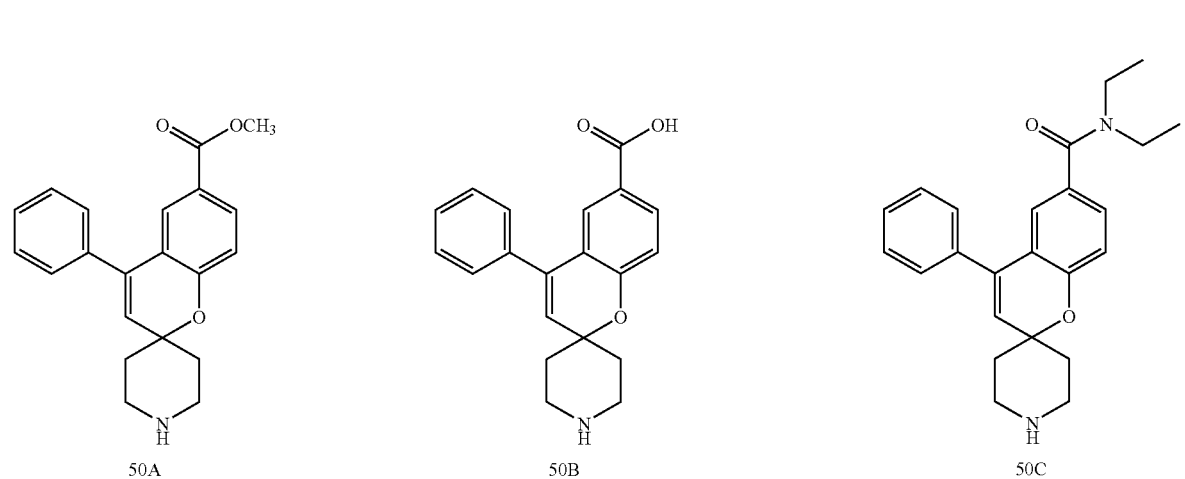

-continued
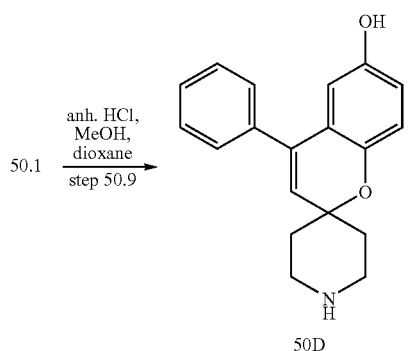
Scheme 51:
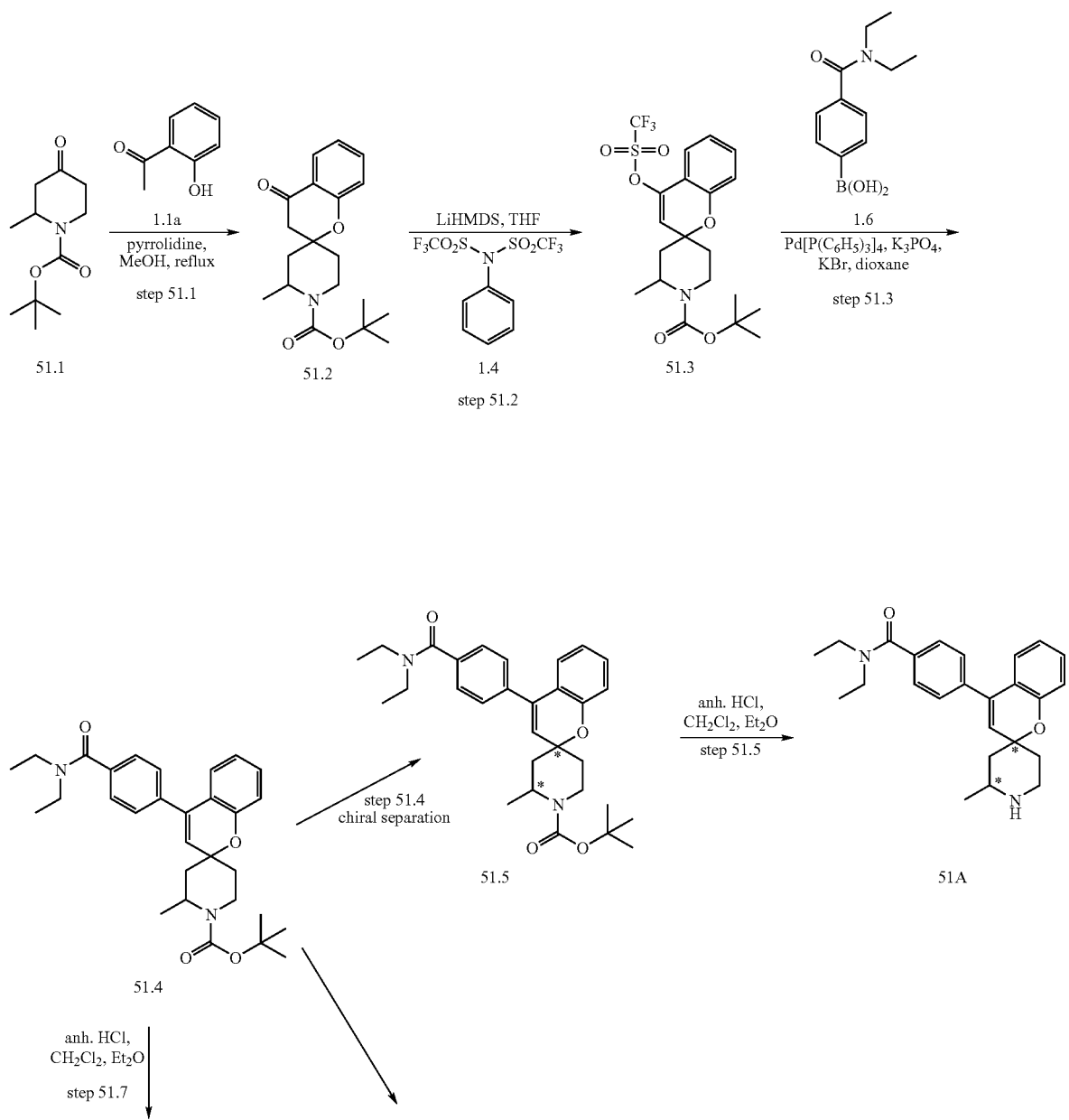

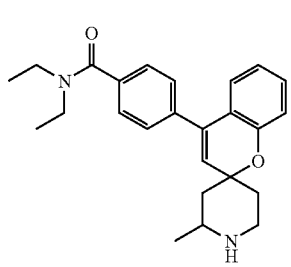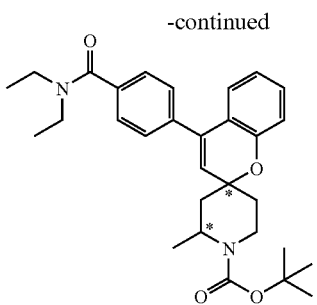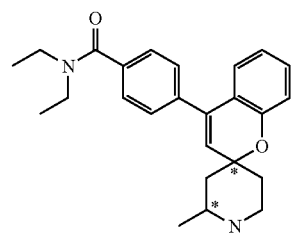
51A and 51B are chirally resolved products derived from 51C. Their absolute stereochemistries have not been conclusively established.
Scheme 52
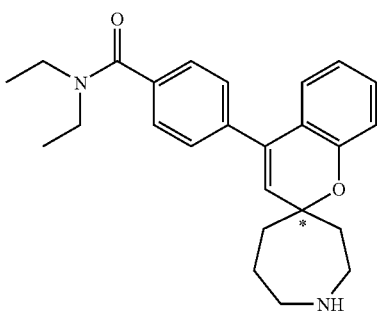
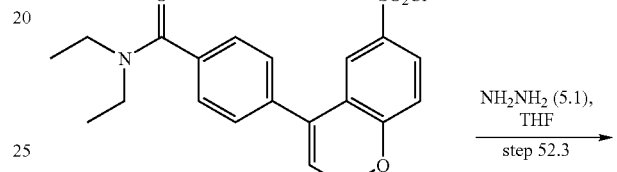
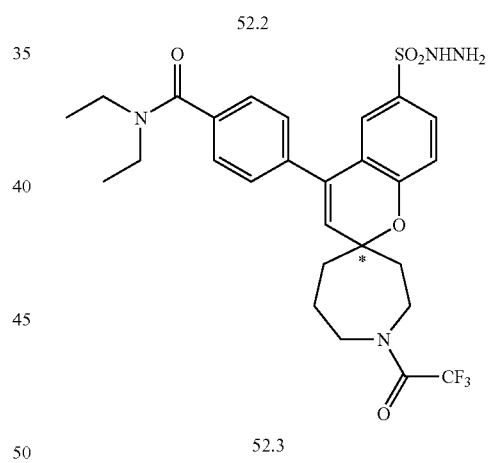
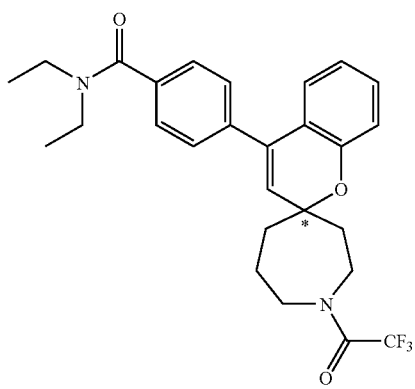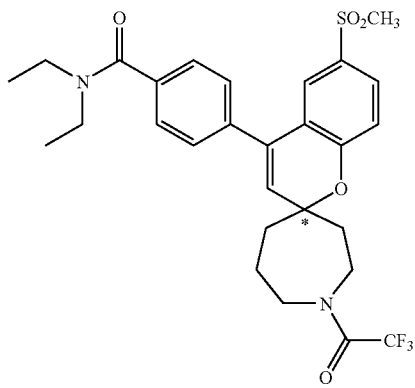

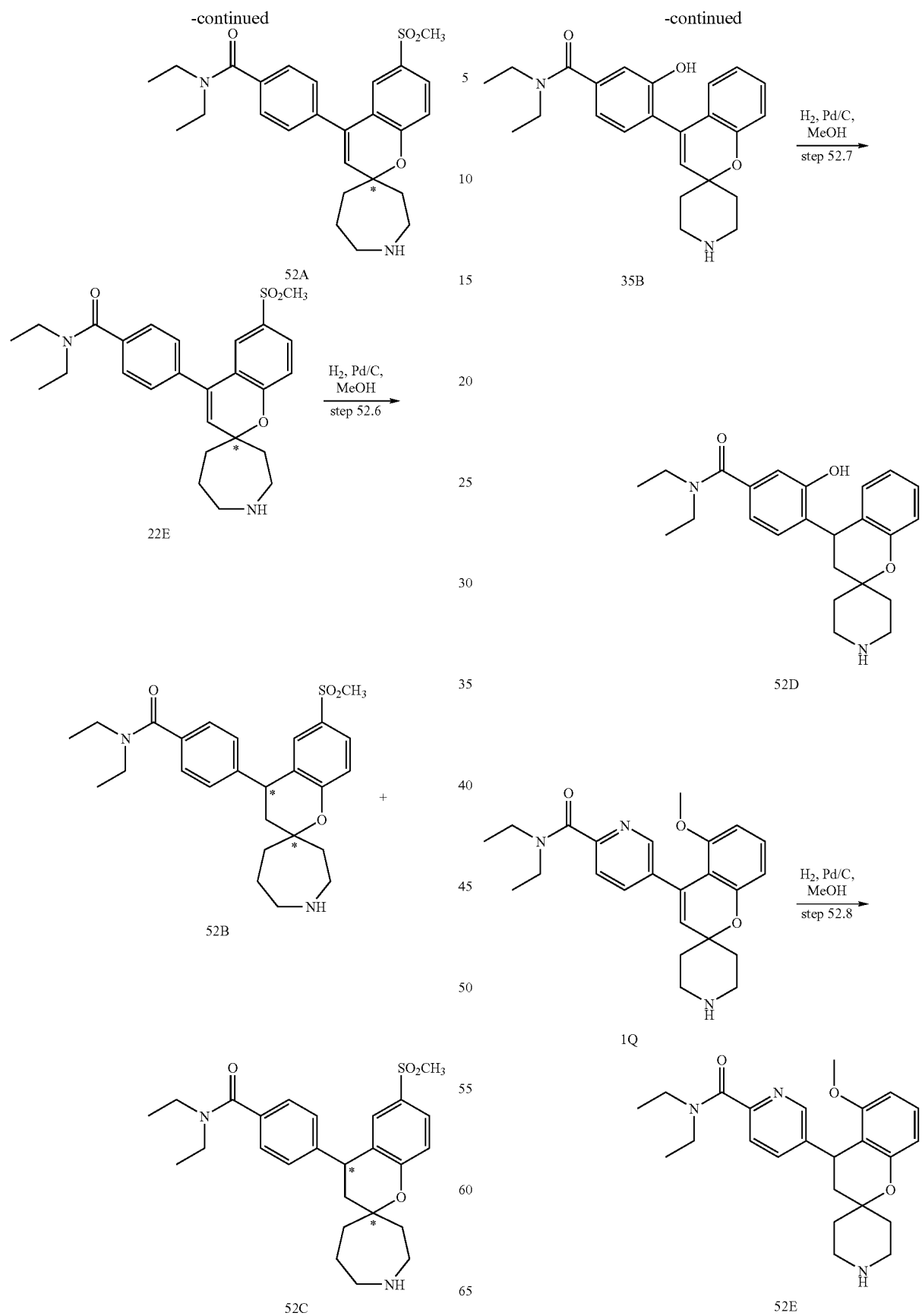

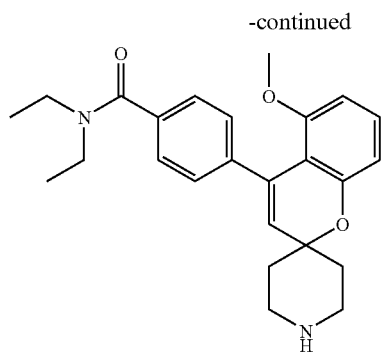
1F
H₂, Pd/C, MeOH
step 52.9
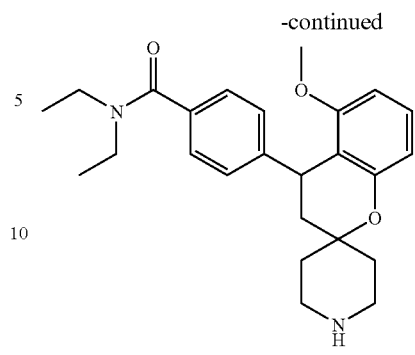
52F
52B and 52C are diastereomeric with respect to one another. 52B and 52C are chirally pure. Their absolute stereochemistry has not been conclusively established.
Scheme 53
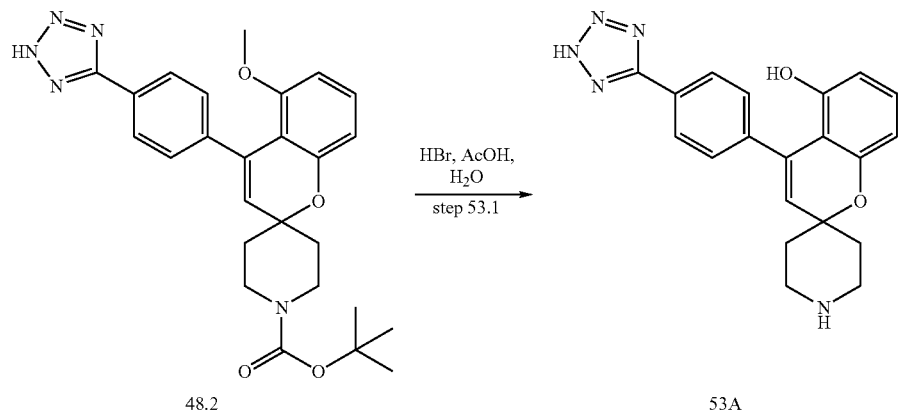
48.2     HBr, AcOH, H₂O, step 53.1     53A
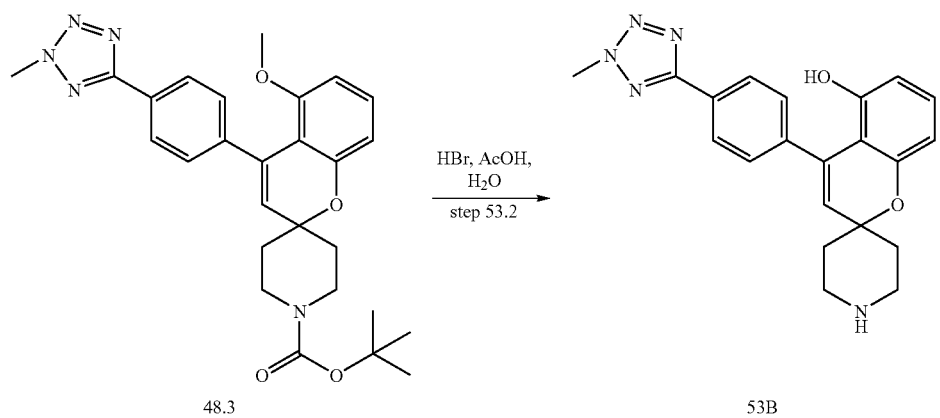
48.3     HBr, AcOH, H₂O, step 53.2     53B

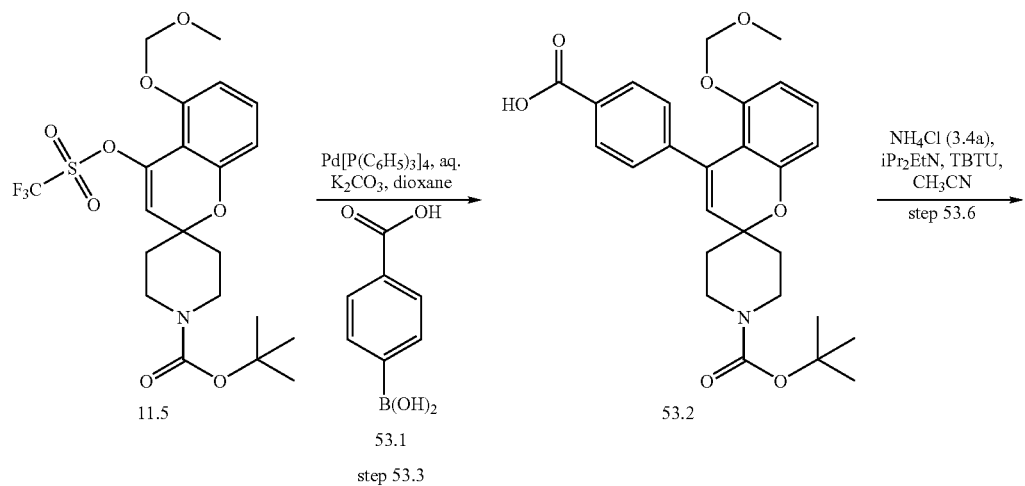
-continued
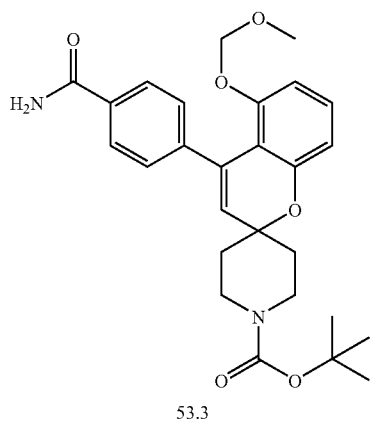
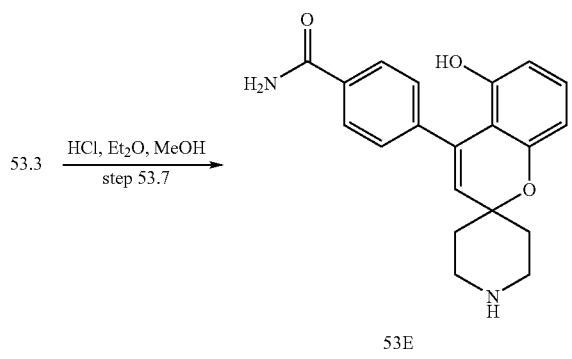

-continued
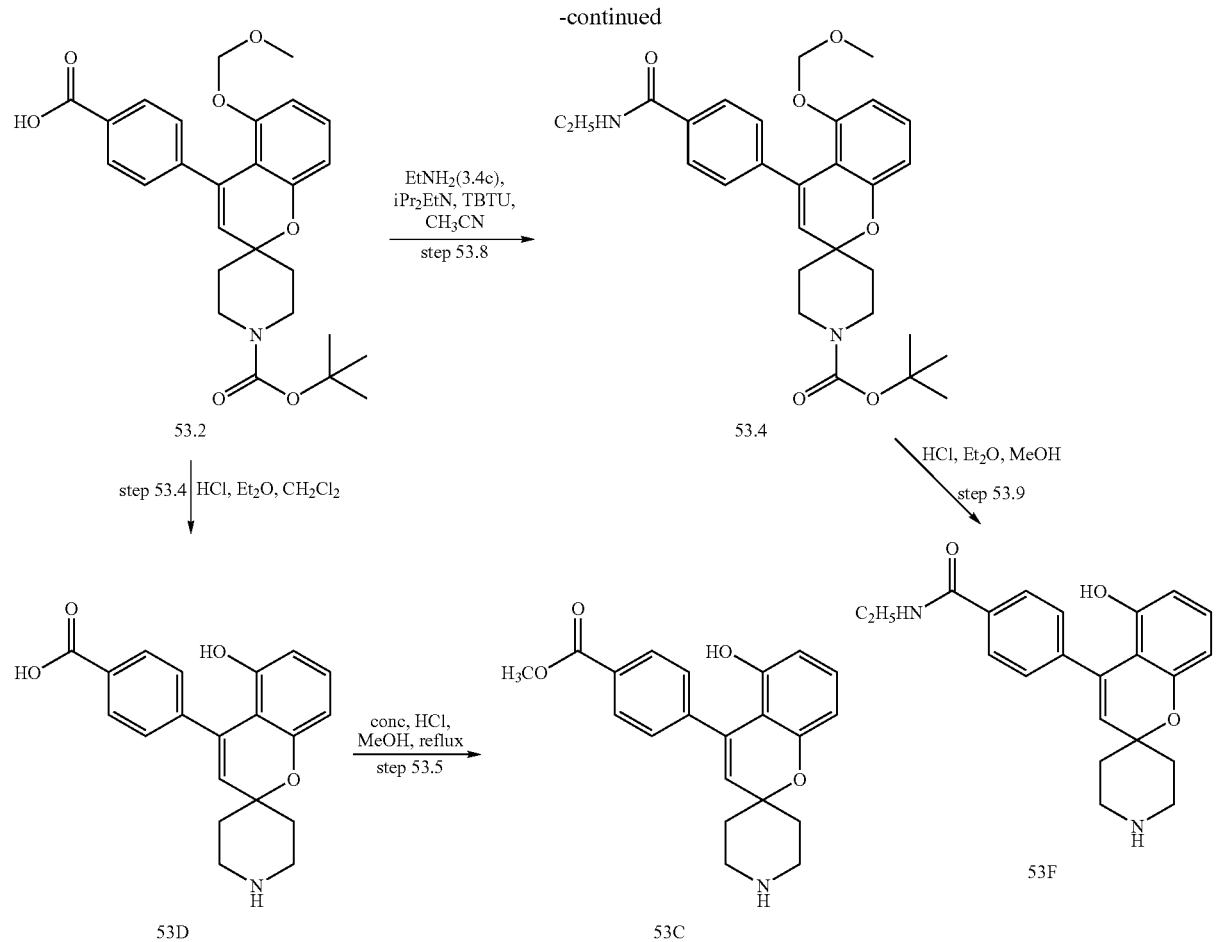
Scheme 54
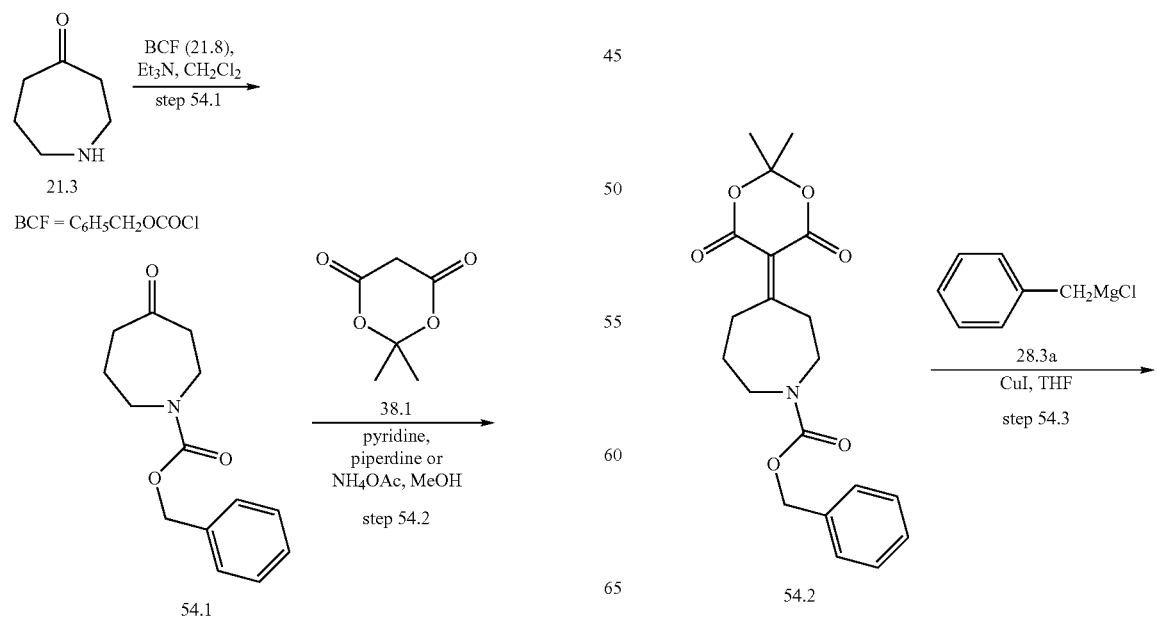
BCF = C₆H₅CH₂OCOCl

-continued
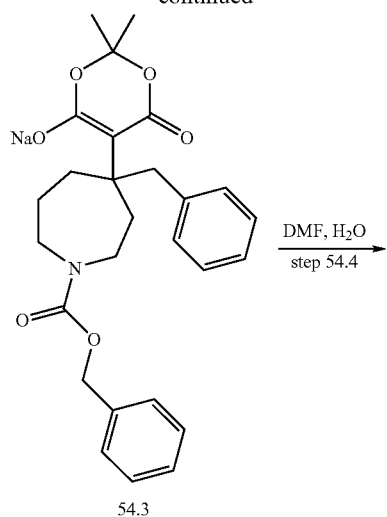
54.3
DMF, H₂O
step 54.4
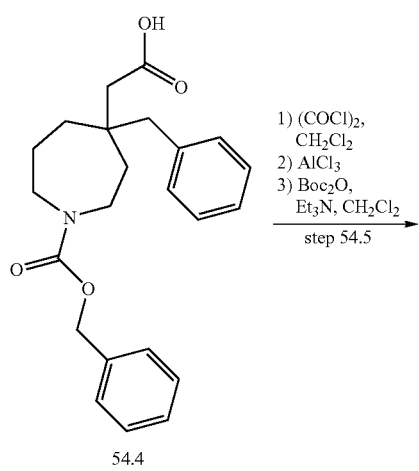
54.4
1) (COCl)₂, CH₂Cl₂
2) AlCl₃
3) Boc₂O, Et₃N, CH₂Cl₂
step 54.5
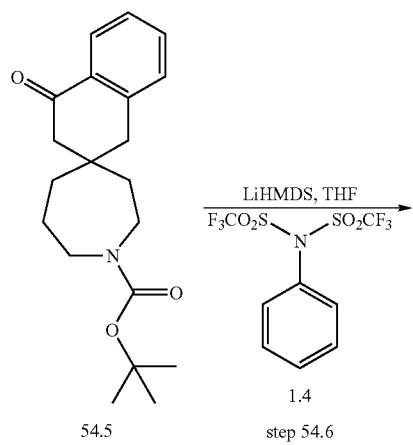
54.5
LiHMDS, THF
F₃CO₂S-N(Ph)-SO₂CF₃
1.4
step 54.6
-continued
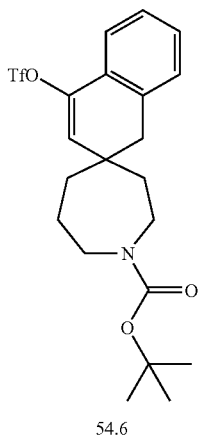
54.6
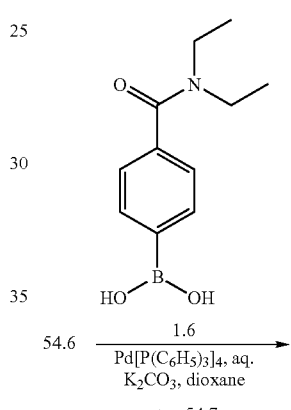
54.6
1.6
Pd[P(C₆H₅)₃]₄, aq. K₂CO₃, dioxane
step 54.7
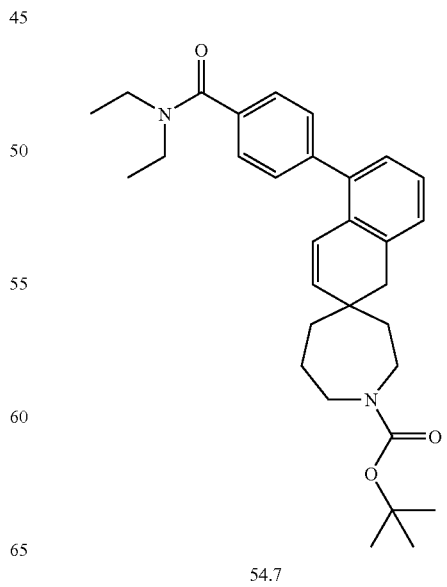
54.7
HCl, Et₂O, CH₂Cl₂, MeOH
step 54.8

-continued
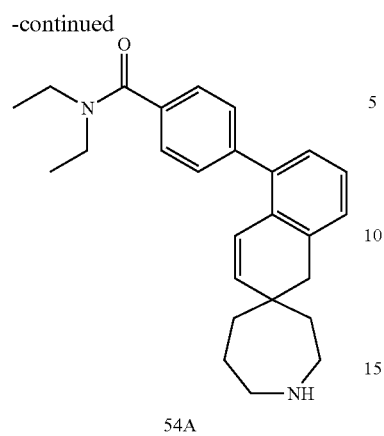
54A
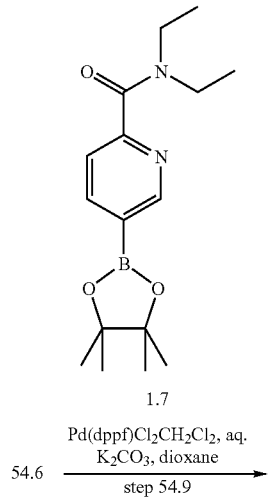
54.6
Pd(dppf)Cl₂CH₂Cl₂, aq.
K₂CO₃, dioxane
step 54.9
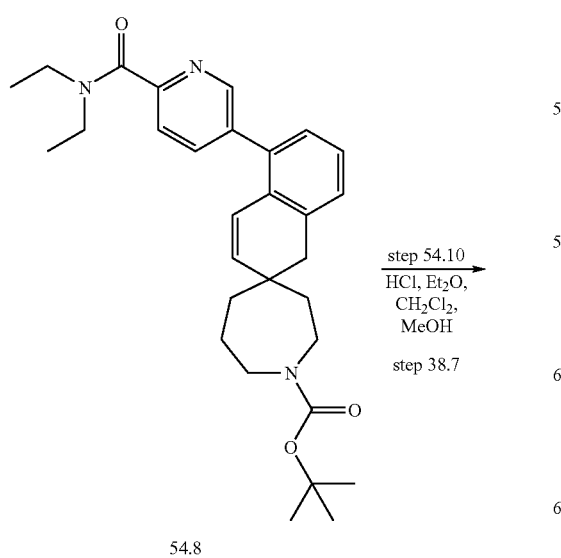
54.8
step 54.10
HCl, Et₂O,
CH₂Cl₂,
MeOH
step 38.7
-continued
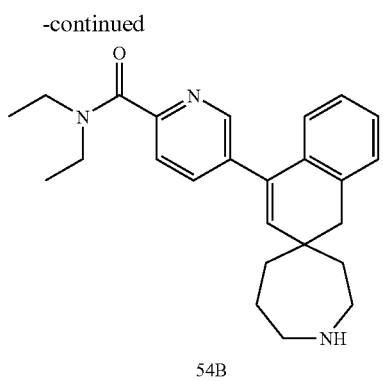
54B
Scheme 55
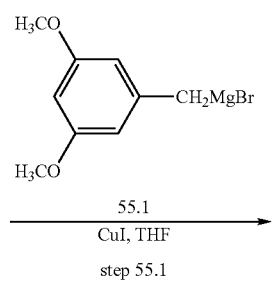
38.2
55.1
CuI, THF
step 55.1
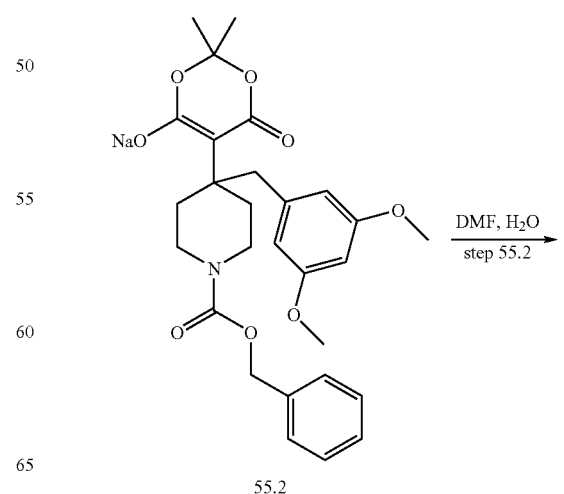
55.2
DMF, H₂O
step 55.2

337
-continued
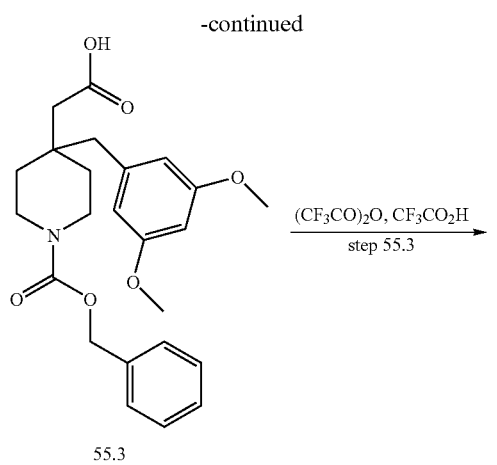
55.3
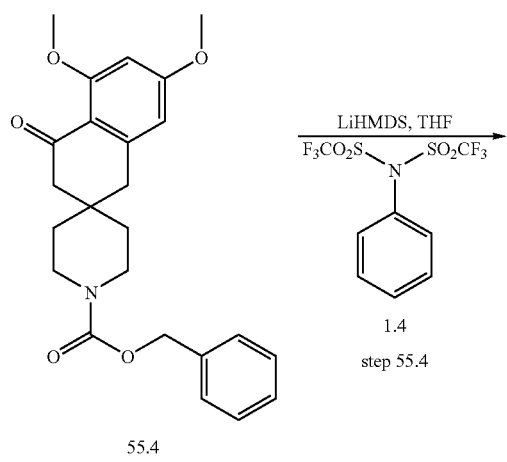
55.4
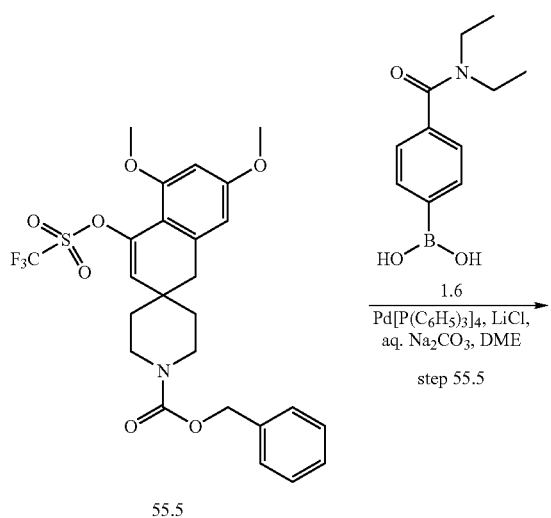
55.5
338
-continued
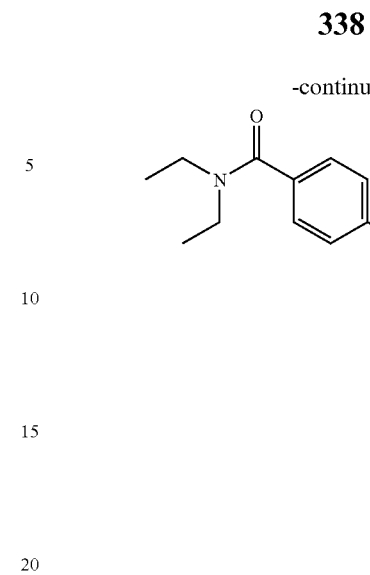
55.6
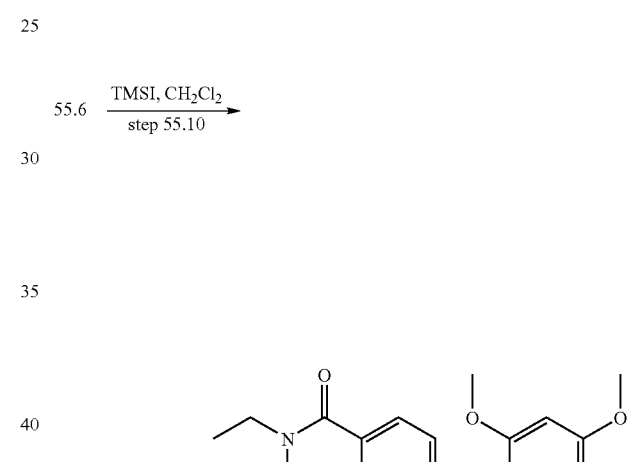
55C
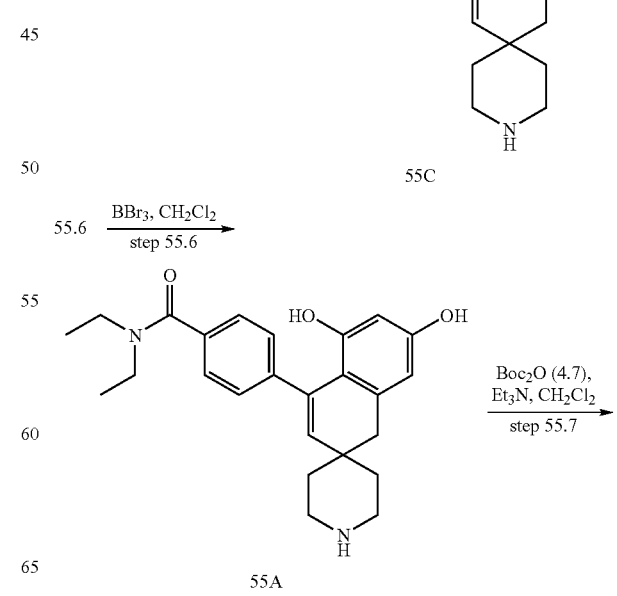
55A

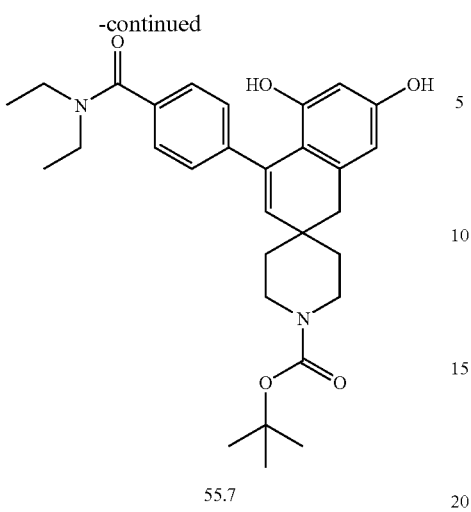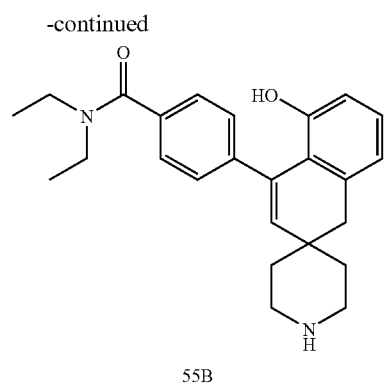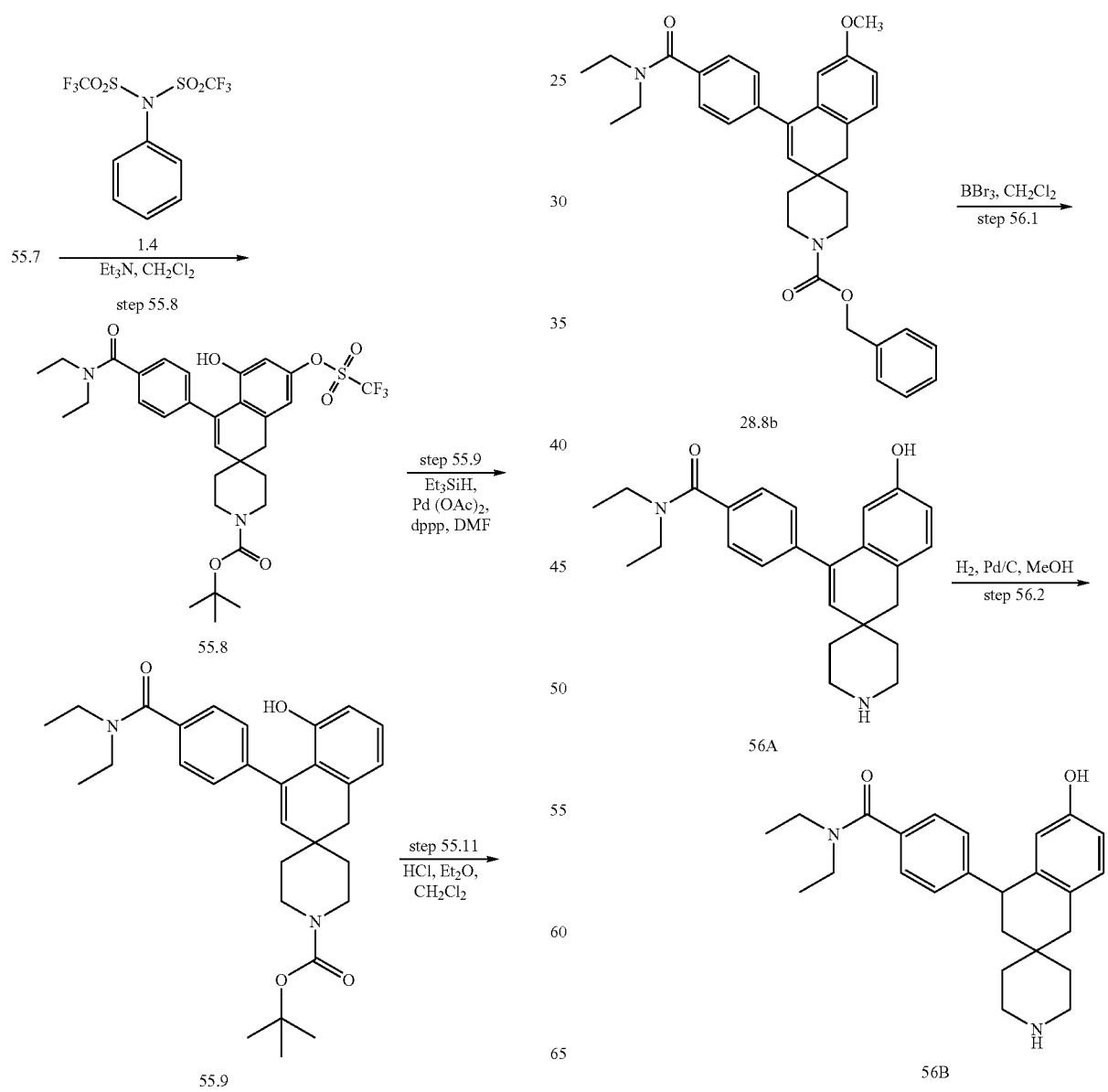

-continued
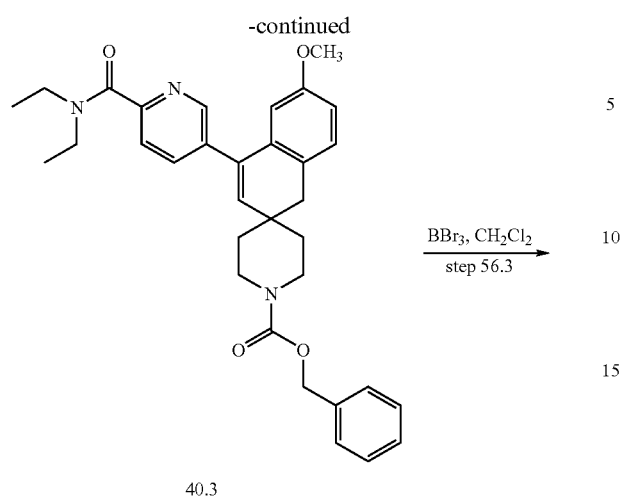
40.3
BBr₃, CH₂Cl₂
step 56.3
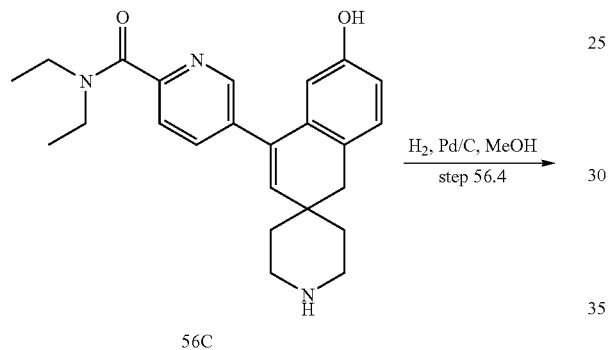
56C
H₂, Pd/C, MeOH
step 56.4
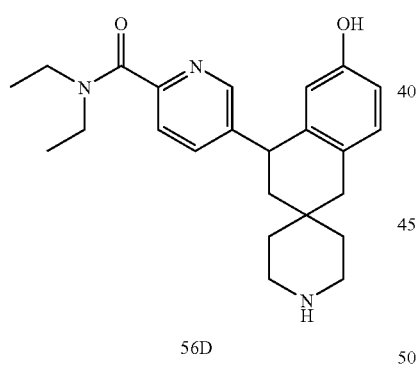
56D
Scheme 57
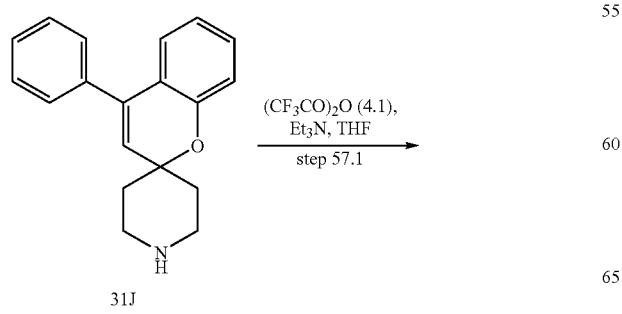
31J
(CF₃CO)₂O (4.1),
Et₃N, THF
step 57.1
-continued
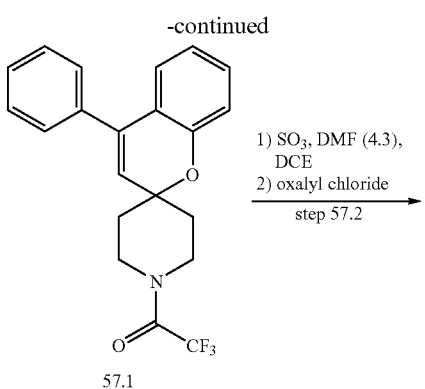
57.1
1) SO₃, DMF (4.3), DCE
2) oxalyl chloride
step 57.2
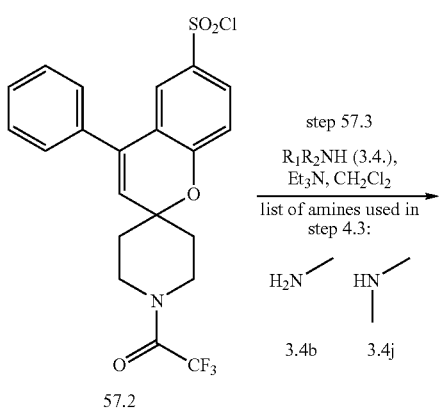
57.2
step 57.3
R₁R₂NH (3.4.),
Et₃N, CH₂Cl₂
list of amines used in step 4.3:
H₂N—   HN(—)—
3.4b    3.4j
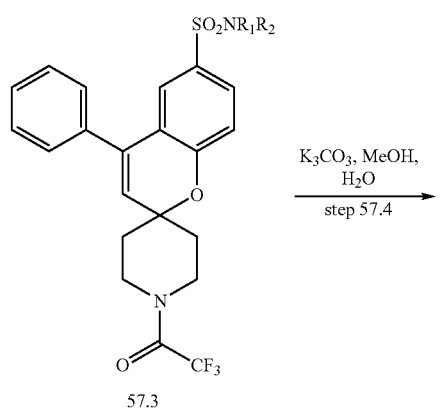
57.3
K₃CO₃, MeOH, H₂O
step 57.4
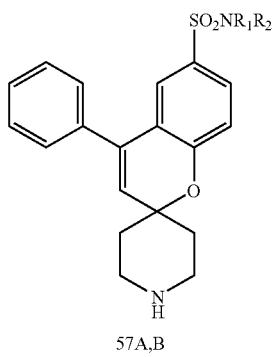
57A,B

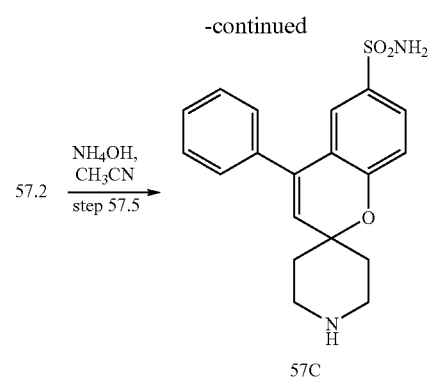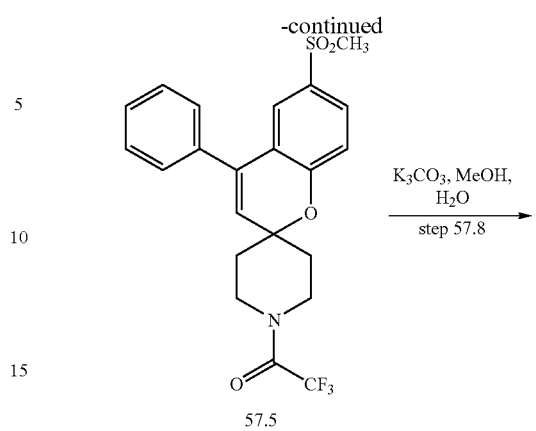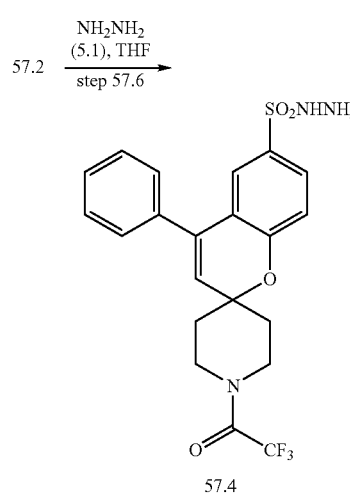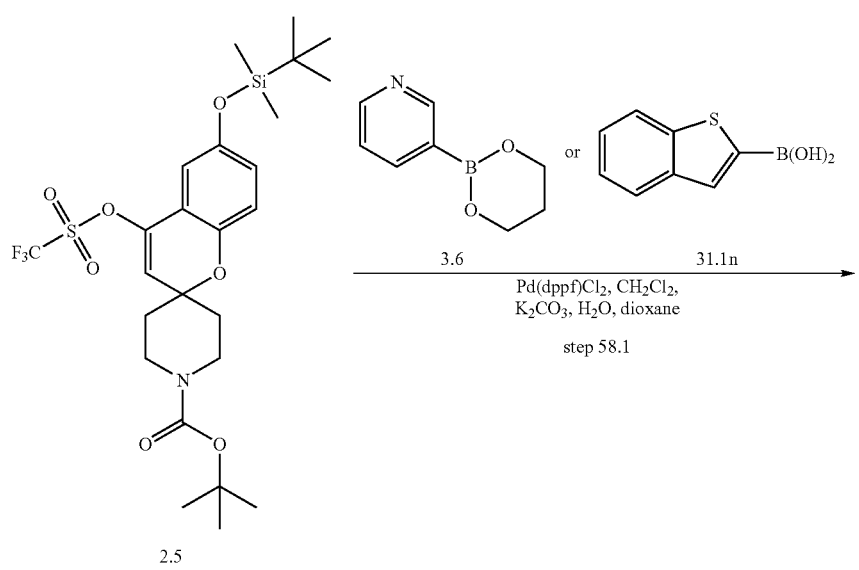

-continued
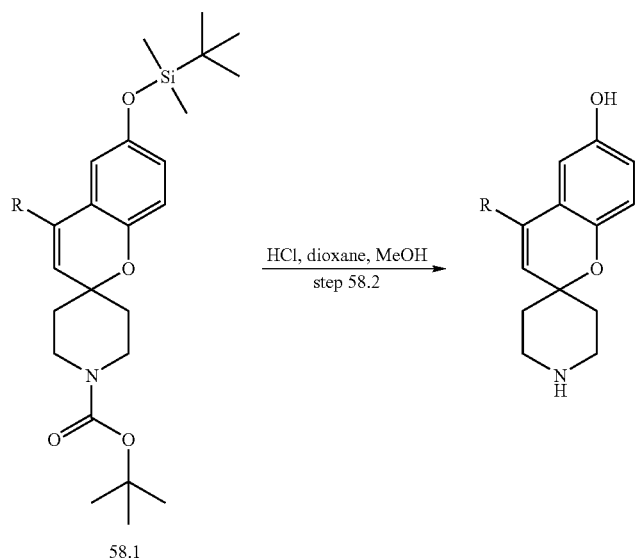
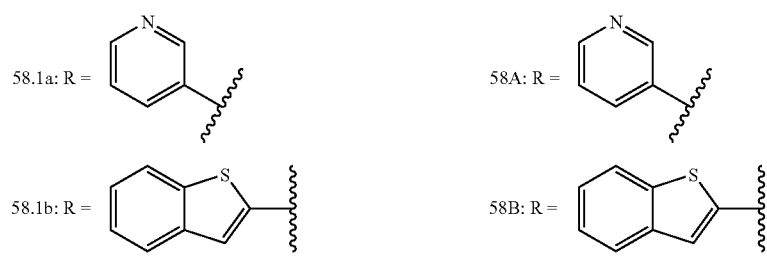
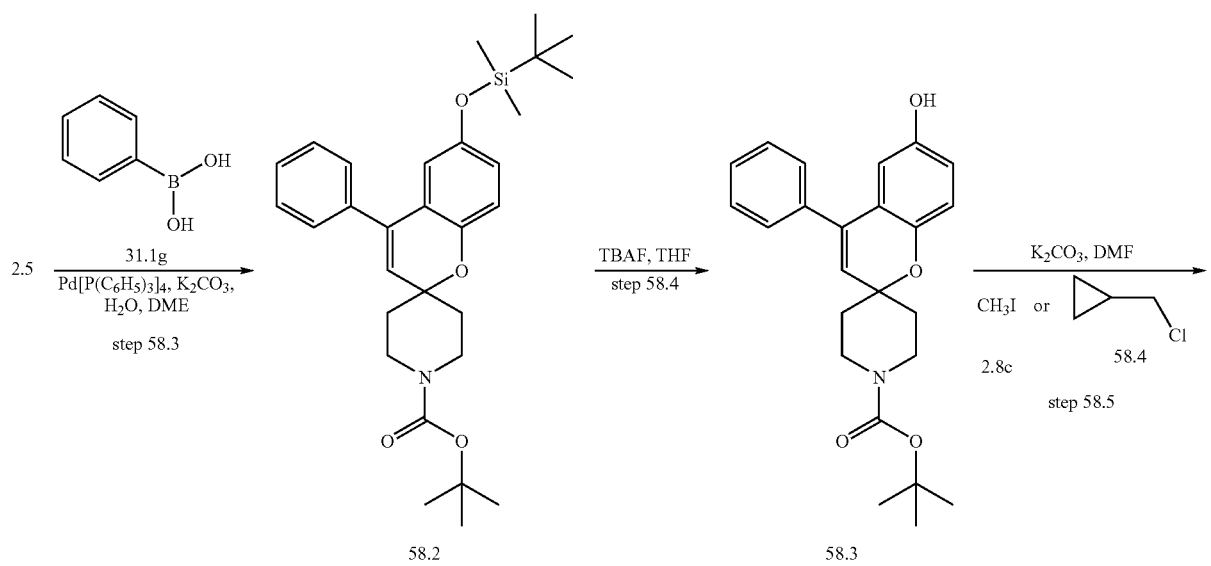

-continued
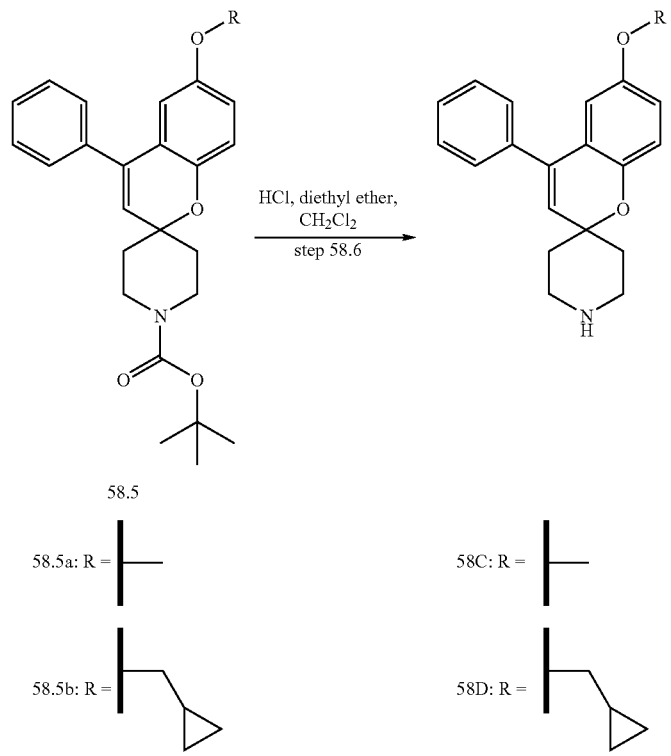
Scheme 59
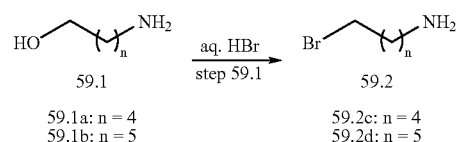
59.1
59.1a: n = 4
59.1b: n = 5
59.2
59.2c: n = 4
59.2d: n = 5
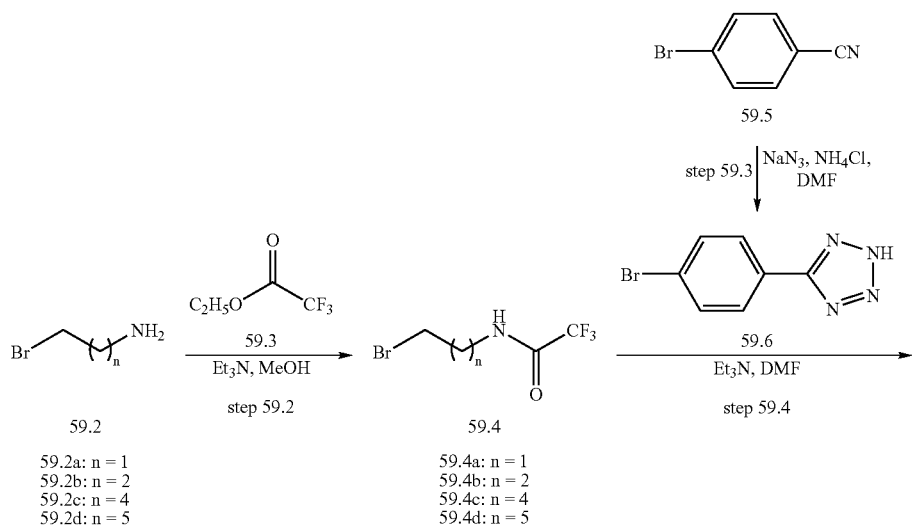

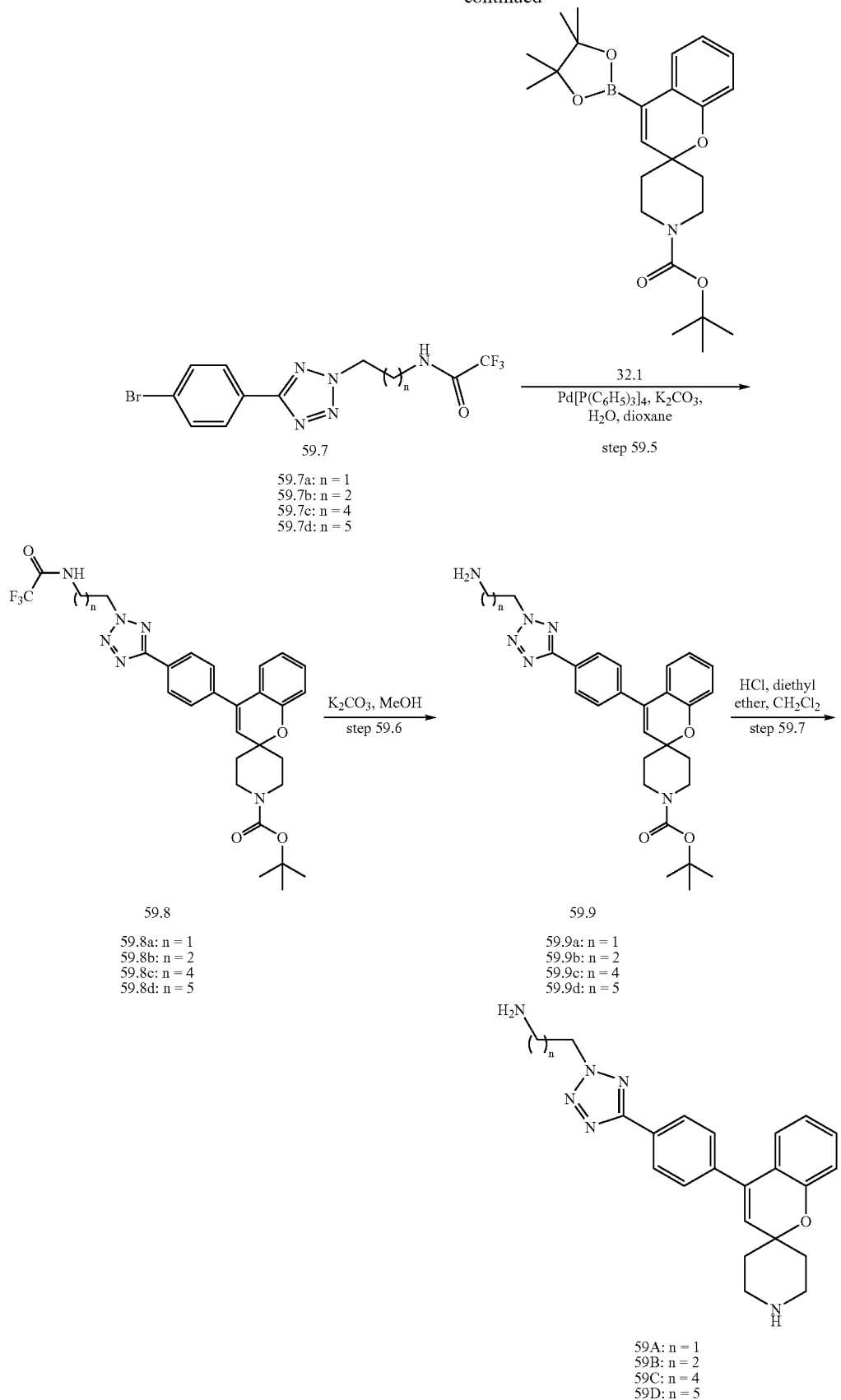

-continued
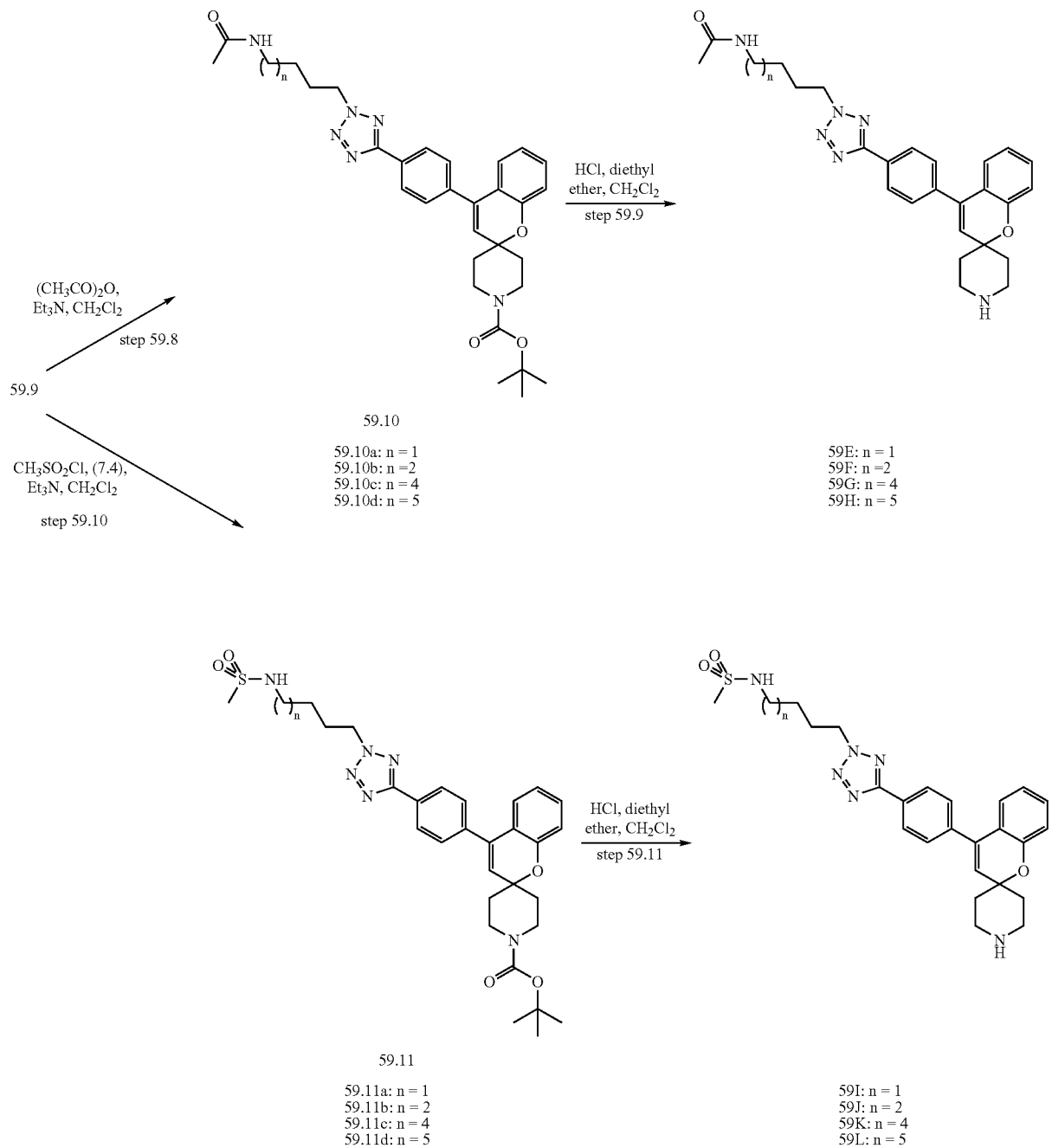
Scheme 60
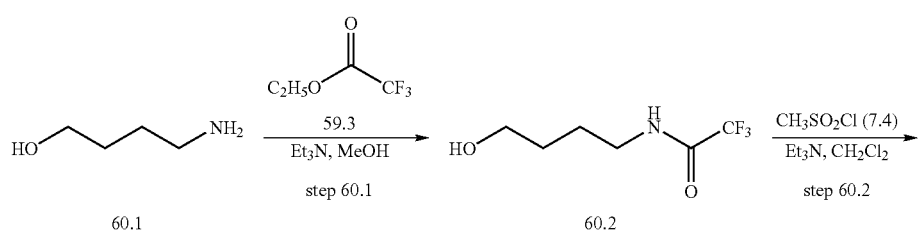

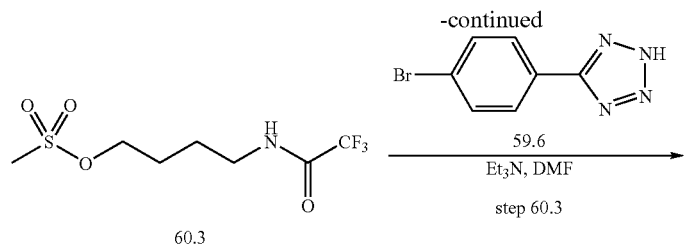
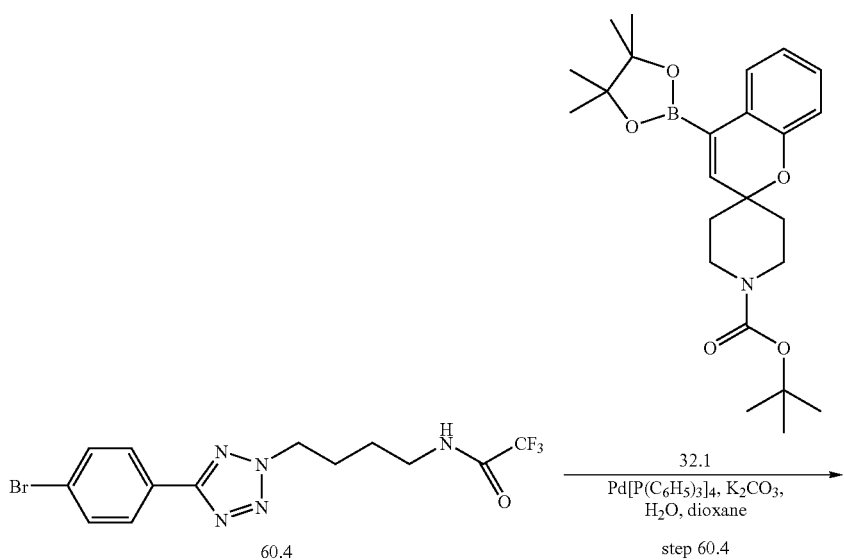
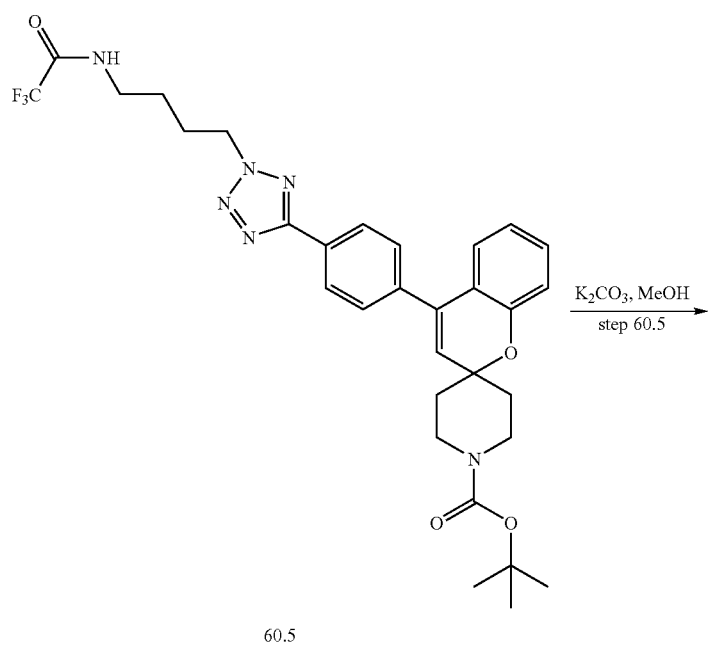

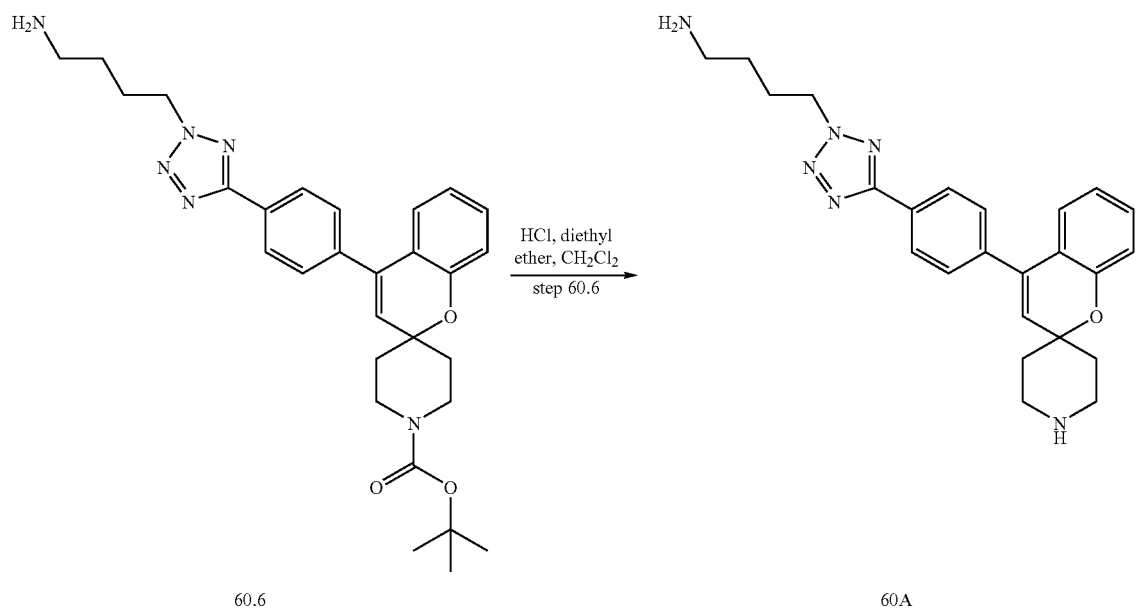
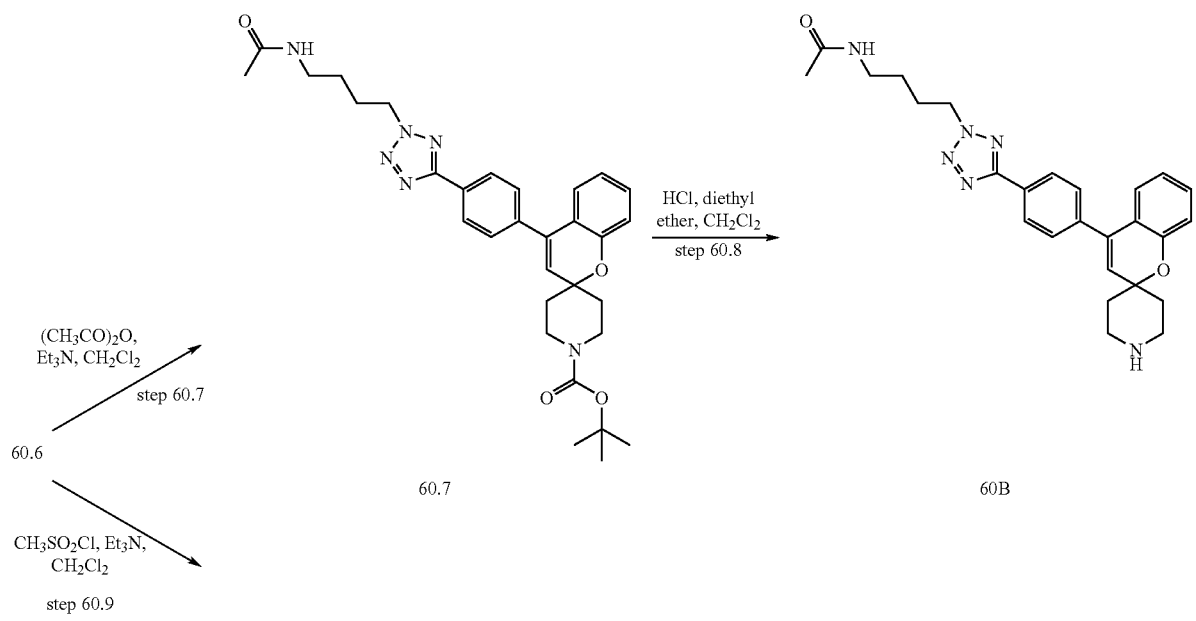

-continued
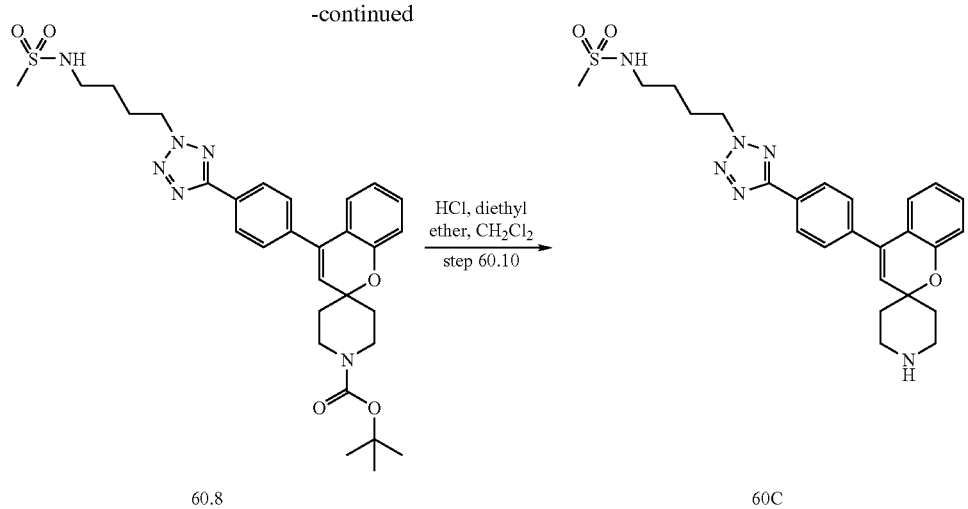
Scheme 61
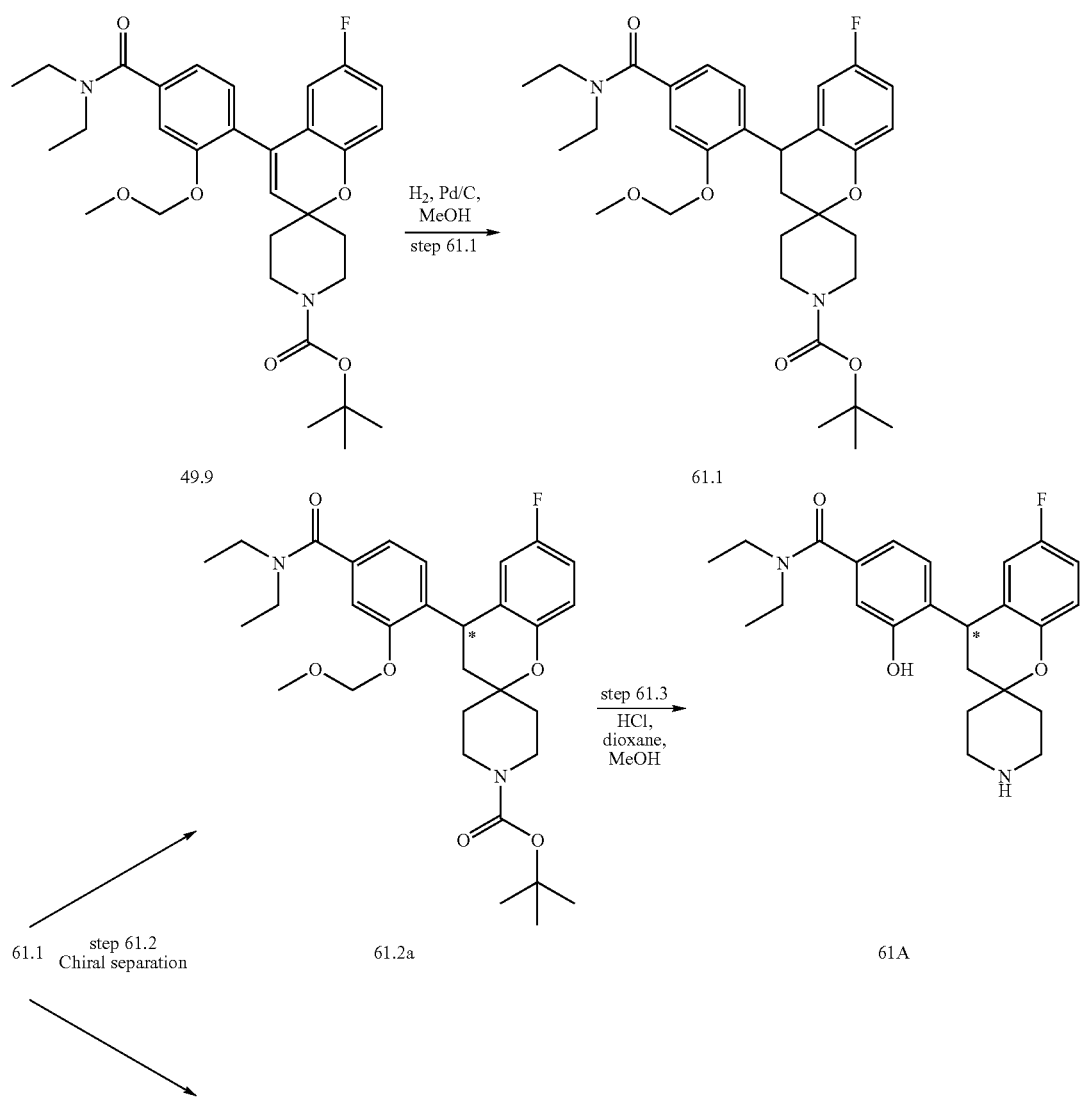

-continued
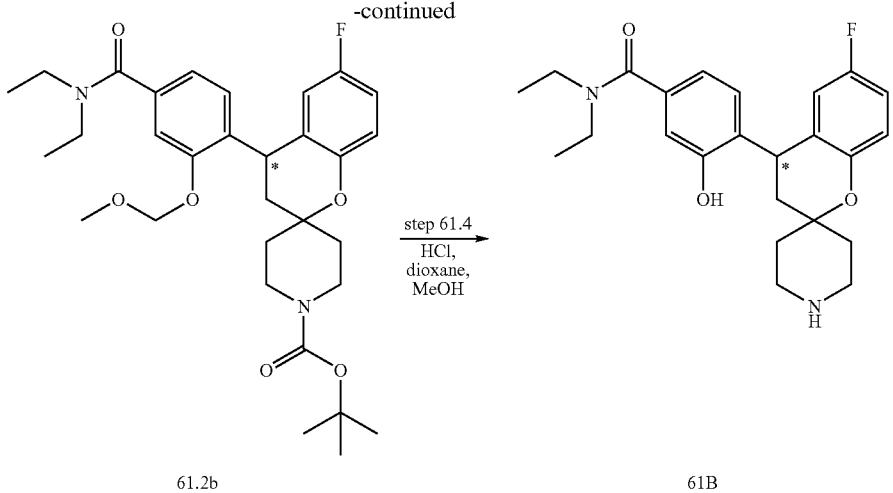
61.2b → step 61.4, HCl, dioxane, MeOH → 61B
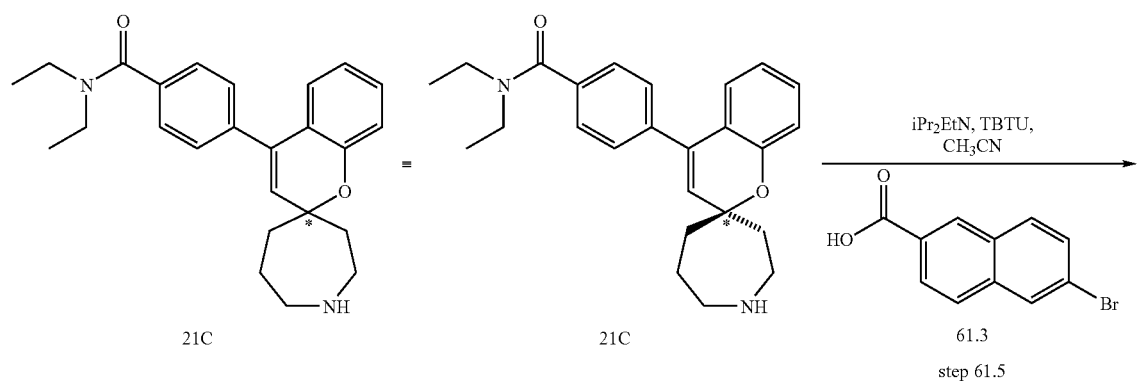
21C = 21C
iPr₂EtN, TBTU, CH₃CN
61.3
step 61.5
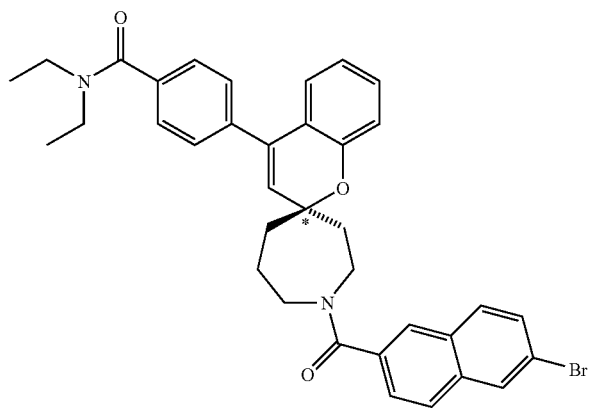
61.4

C. TABLE 1

| Example | Structure | [M + H]+ |
|---|---|---|
| 1A | 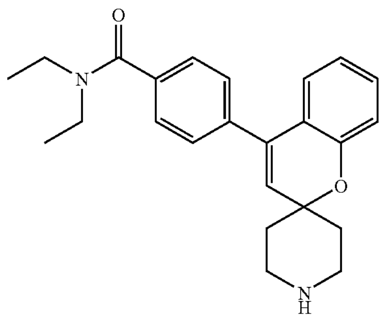 | 377.4 |
| 1B | 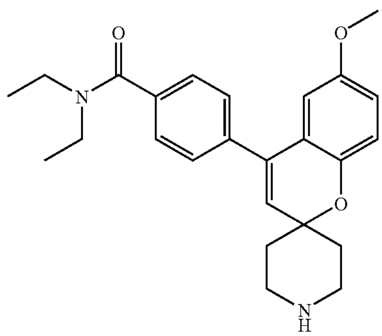 | 407.1 |
| 1C | 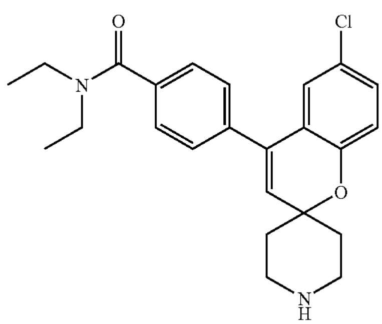 | 411.2 |
| 1D | 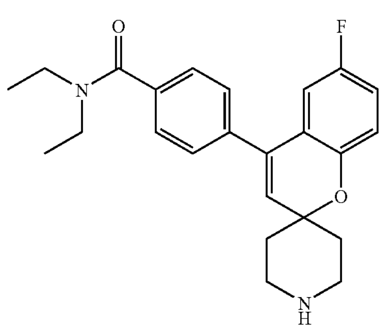 | 395.2 |

C. TABLE 1-continued

| Example | Structure | [M + H]+ |
|---|---|---|
| 1E | 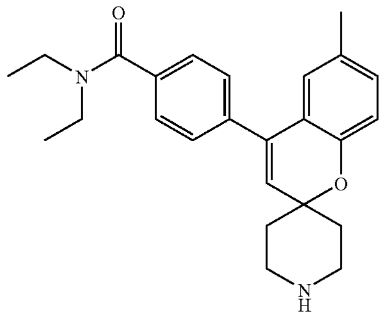 | 391.3 |
| 1F | 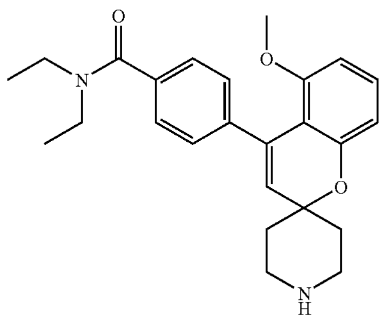 | 407.2 |
| 1G | 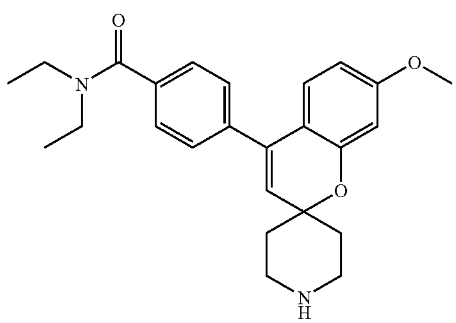 | 407.1 |
| 1H | 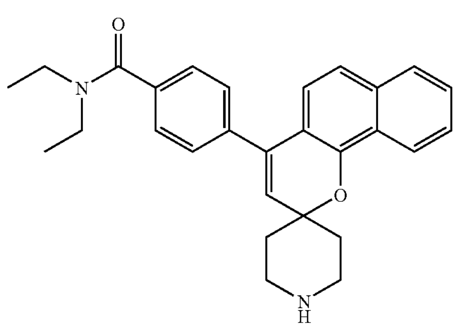 | 427.4 |

C. TABLE 1-continued

| Example | Structure | [M + H]+ |
|---------|-----------|----------|
| 1I | 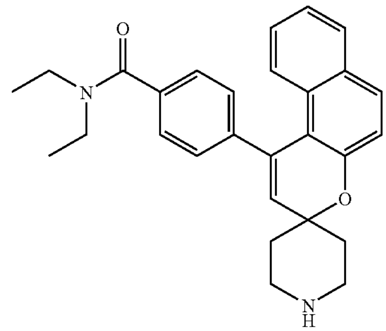 | 427.4 |
| 1J | 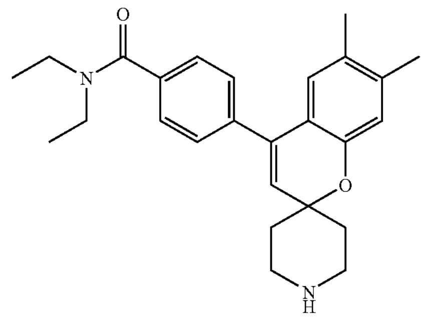 | 405.4 |
| 1K | 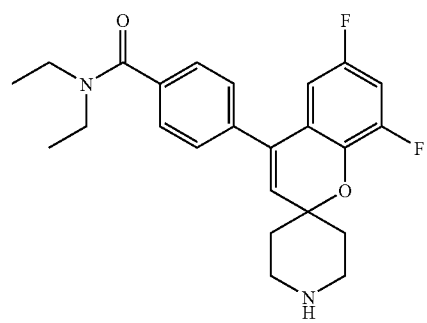 | 413.2 |
| 1L | 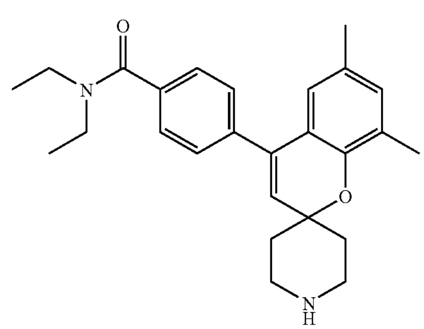 | 405.4 |

C. TABLE 1-continued
| Example | Structure | [M + H]⁺ |
|---|---|---|
| 1M | 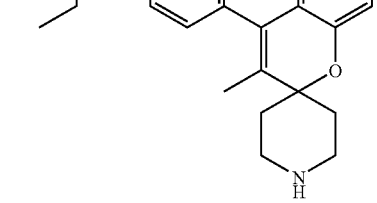 | 391.0 |
| 1N | 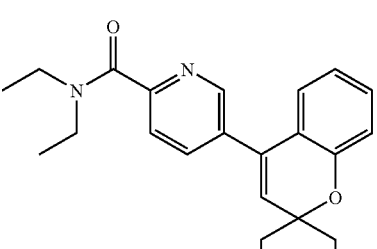 | 378.4 |
| 1O | 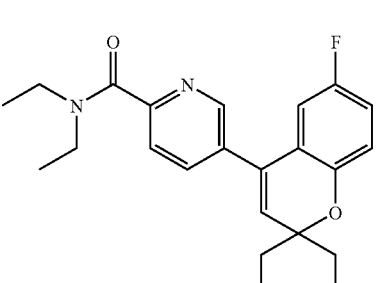 | 396.3 |
| 1P | 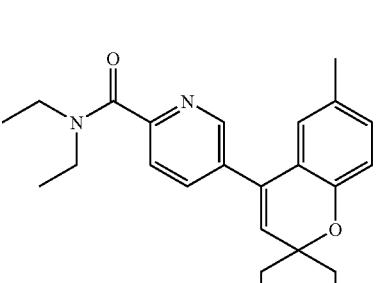 | 392.3 |

C. TABLE 1-continued

| Example | Structure | [M + H]+ |
|---|---|---|
| 1Q | 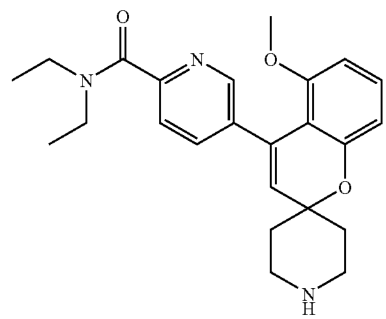 | 408.3 |
| 1R | 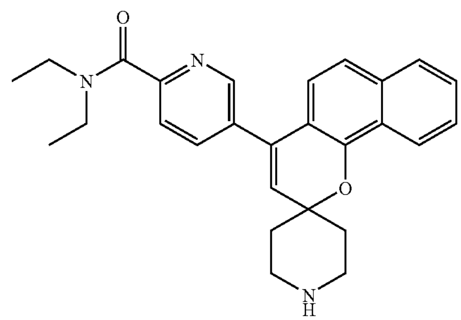 | 428.3 |
| 1S | 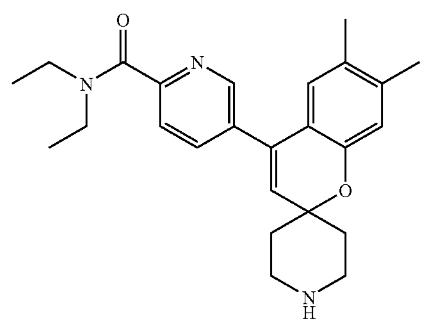 | 406.3 |
| 1T | 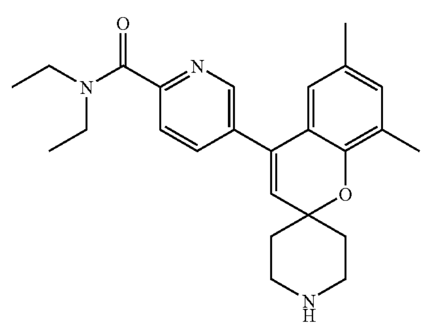 | 406.4 |

C. TABLE 1-continued

| Example | Structure | [M + H]⁺ |
|---|---|---|
| 1U | 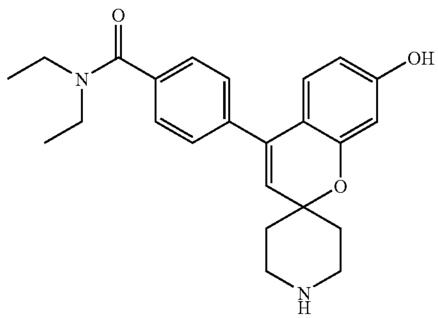 | 393.2 |
| 2A | 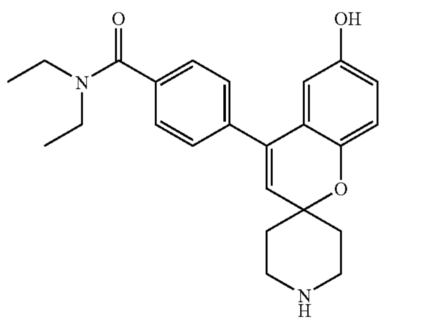 | 393.3 |
| 2B | 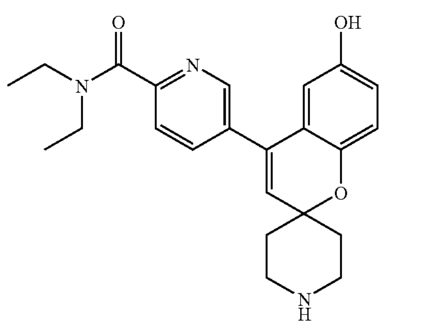 | 394 |
| 2C | 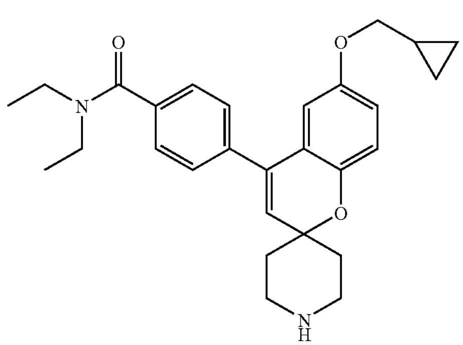 | 447.1 |

C. TABLE 1-continued

| Example | Structure | [M + H]+ |
|---|---|---|
| 2D | 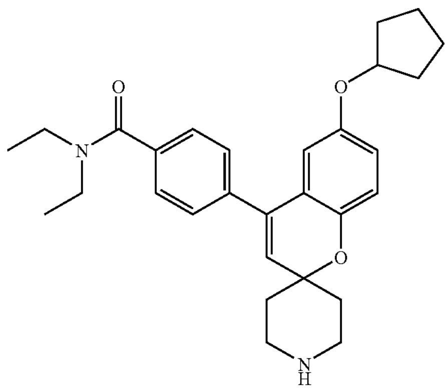 | 461.1 |
| 2E | 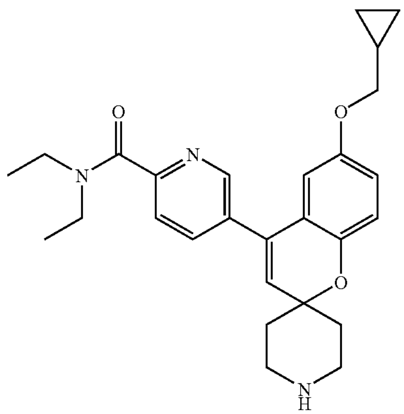 | 448.3 |
| 2F | 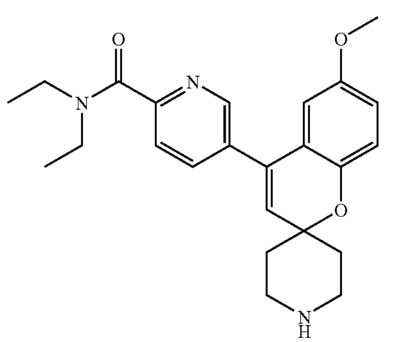 | 408.3 |
| 3A | 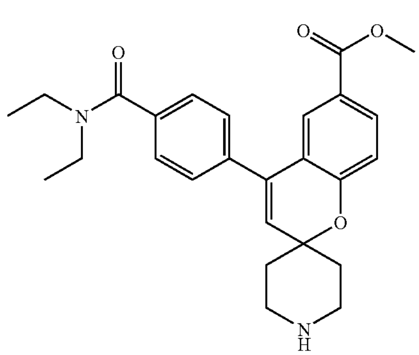 | 435.0 |

C. TABLE 1-continued
| Example | Structure | [M + H]+ |
|---|---|---|
| 3B | 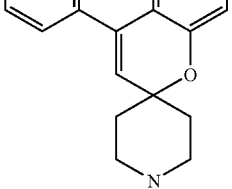 | 421.0 |
| 3C | 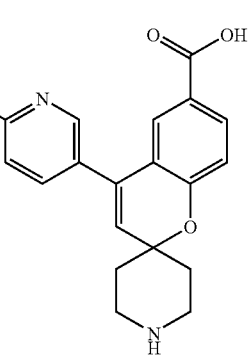 | 422.2 |
| 3D | 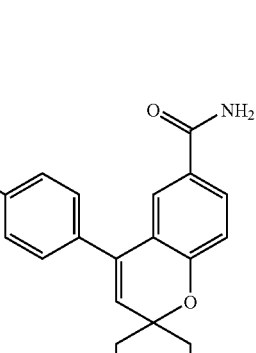 | 420.0 |
| 3E | 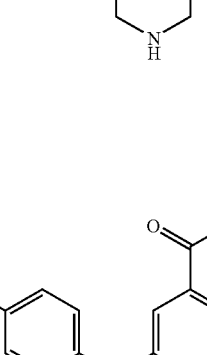 | 434.3 |

C. TABLE 1-continued

| Example | Structure | [M + H]+ |
|---|---|---|
| 3F | 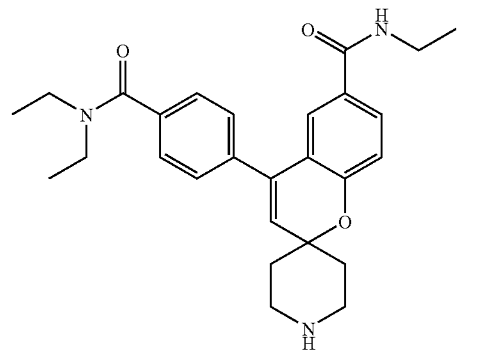 | 448.4 |
| 3G | 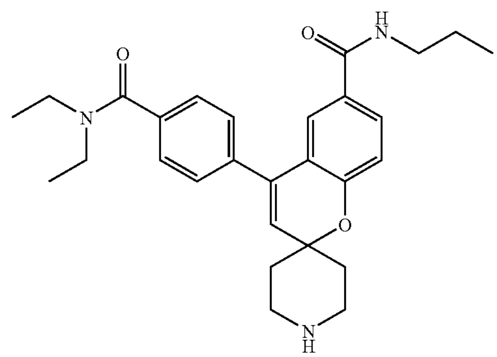 | 462.4 |
| 3H | 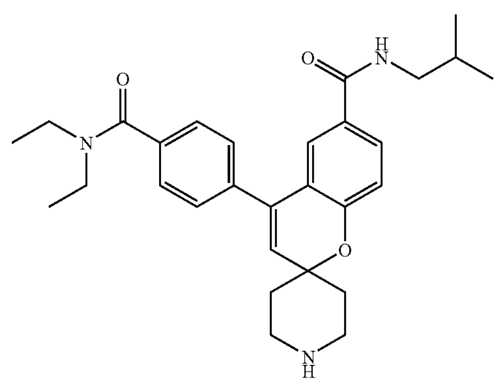 | 476.5 |
| 3I | 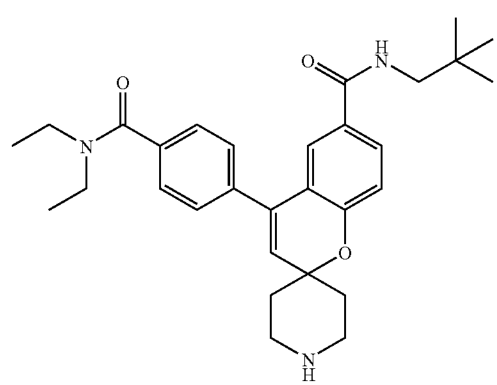 | 490.6 |

C. TABLE 1-continued
| Example | Structure | [M + H]+ |
|---|---|---|
| 3J | 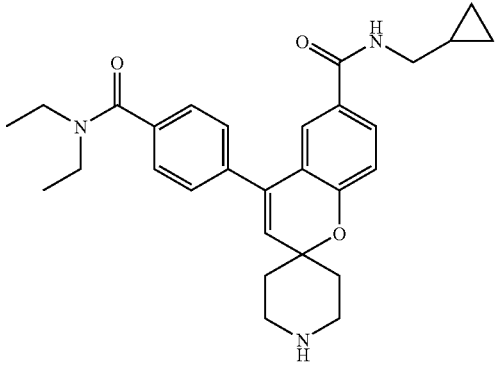 | 474.4 |
| 3K | 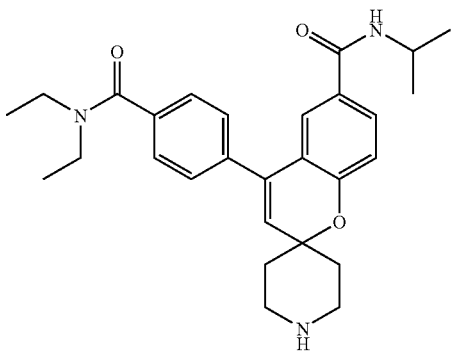 | 462.5 |
| 3L | 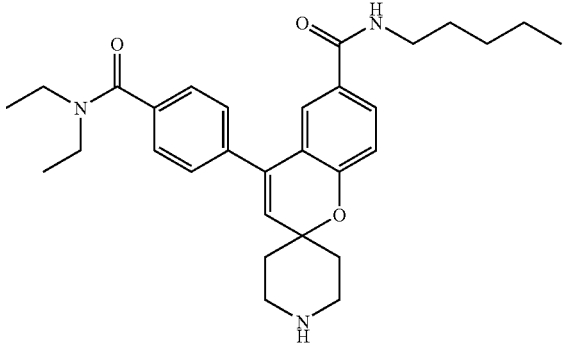 | 490.5 |
| 3M | 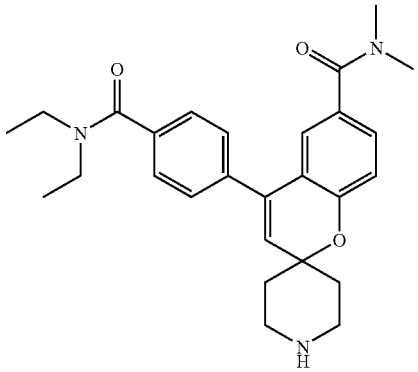 | 448.4 |

C. TABLE 1-continued

| Example | Structure | [M + H]+ |
| --- | --- | --- |
| 3N | 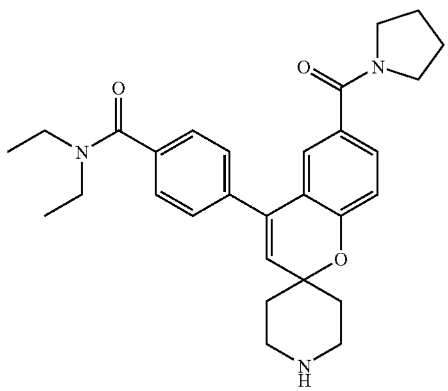 | 474.5 |
| 3O | 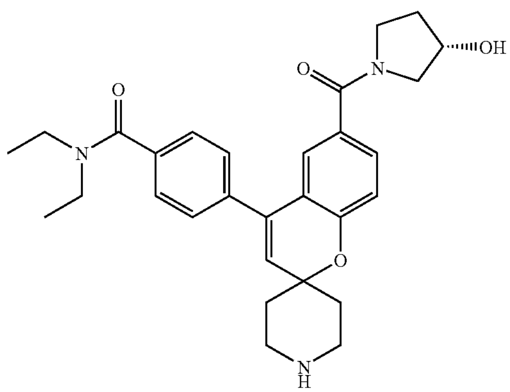 | 490.3 |
| 3P | 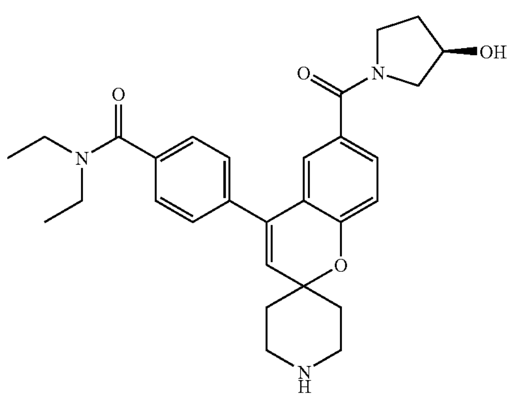 | 490.5 |
| 3Q | 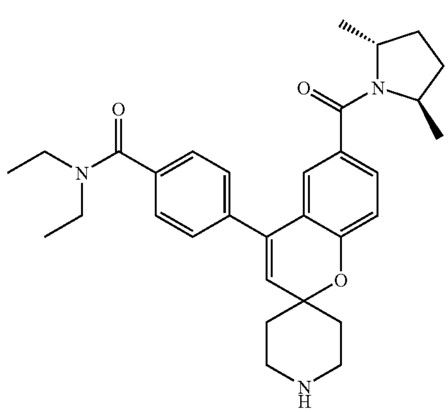 | 502.5 |

C. TABLE 1-continued

| Example | Structure | [M + H]+ |
|---|---|---|
| 3R | 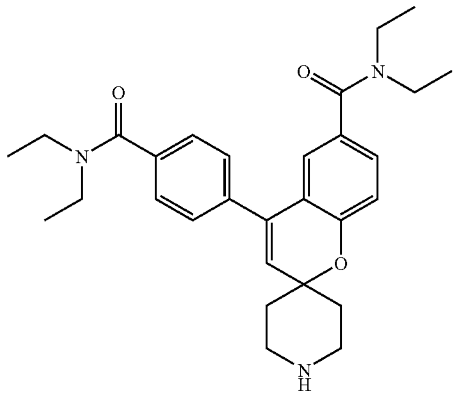 | 476.5 |
| 3S | 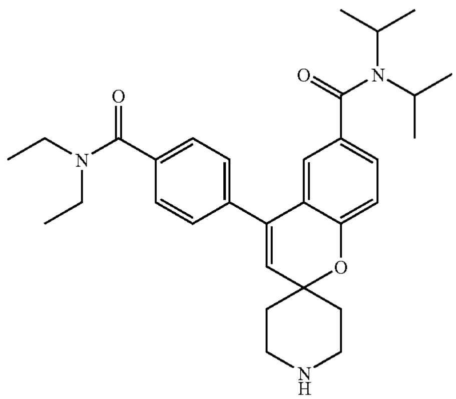 | 504.4 |
| 3T | 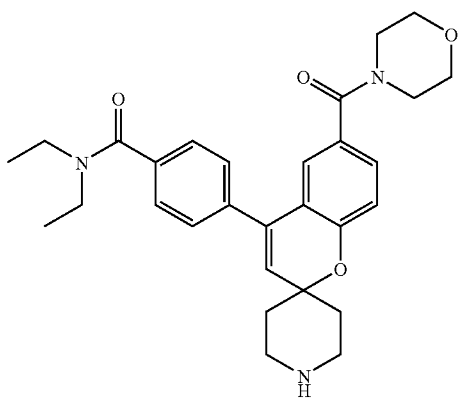 | 490.1 |
| 3U | 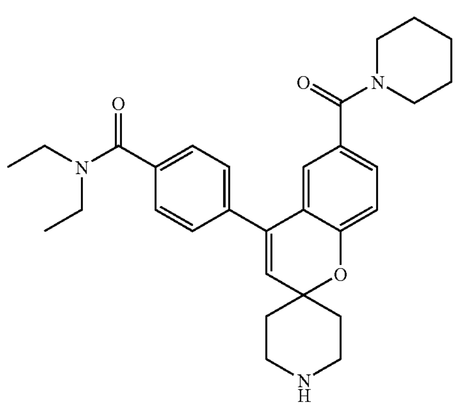 | 488.4 |

C. TABLE 1-continued
| Example | Structure | [M + H]+ |
|---|---|---|
| 3V | 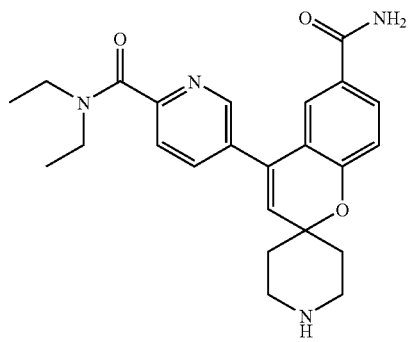 | 421.3 |
| 3W | 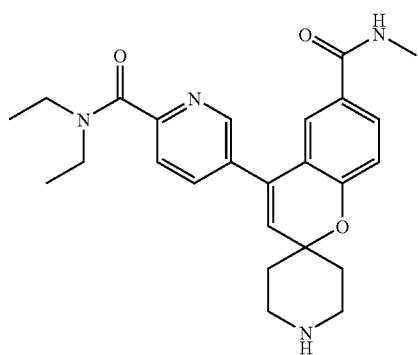 | 435.3 |
| 3X | 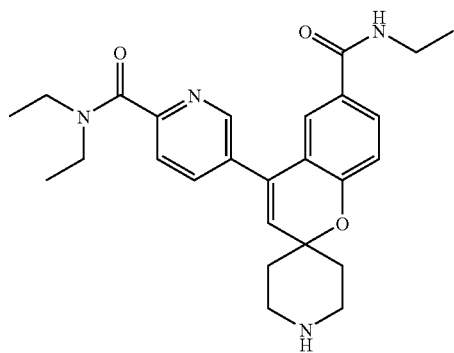 | 449.3 |
| 3Y | 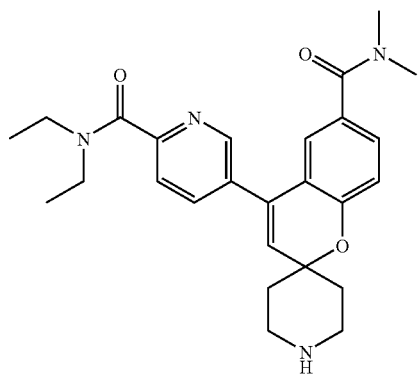 | 449.3 |

C. TABLE 1-continued

| Example | Structure | [M + H]+ |
|---------|-----------|----------|
| 3Z | 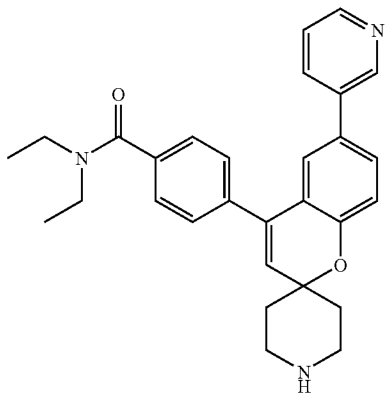 | 454.0 |
| 3AA | 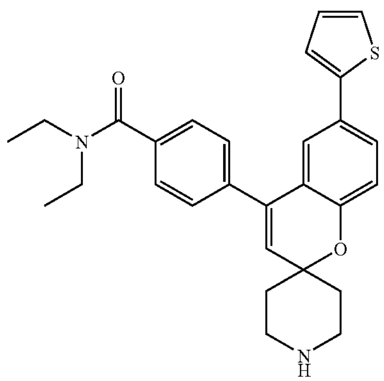 | 459.3 |
| 3AB | 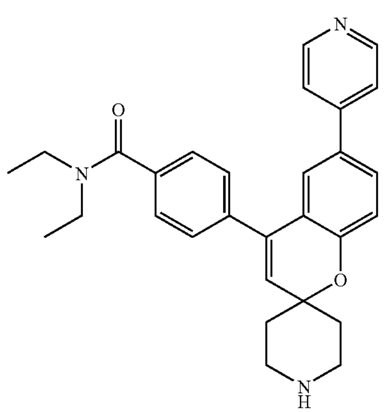 | 454.4 |
| 3AC | 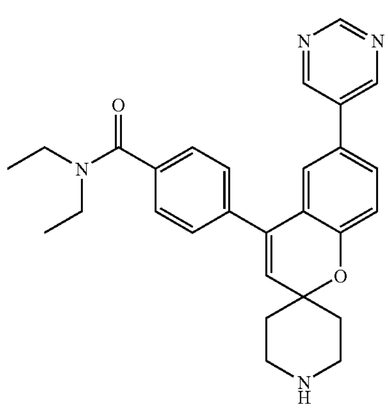 | 455.4 |

C. TABLE 1-continued

| Example | Structure | [M + H]+ |
|---|---|---|
| 4A | 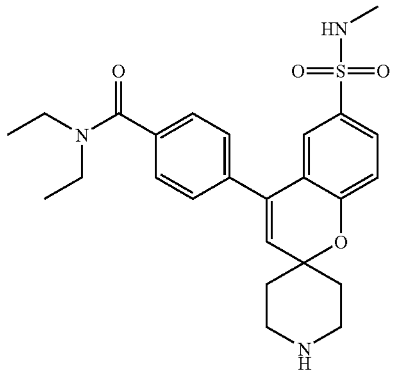 | 470.2 |
| 4B | 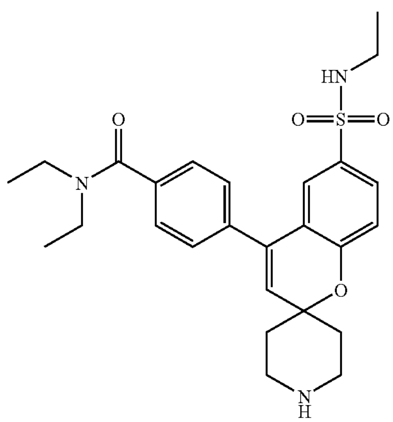 | 484.3 |
| 4C | 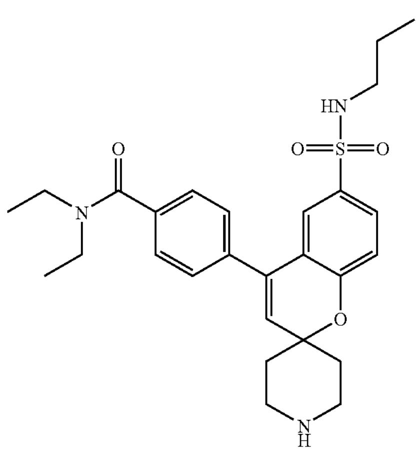 | 498.3 |

C. TABLE 1-continued
| Example | Structure | [M + H]+ |
|---|---|---|
| 4D | 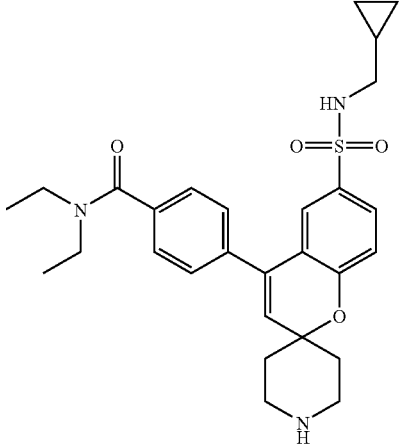 | 510.3 |
| 4E | 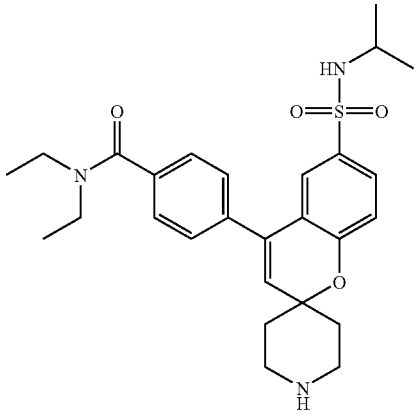 | 498.3 |
| 4F | 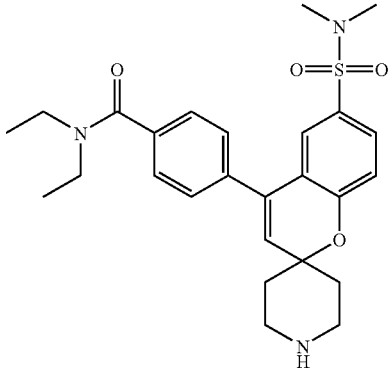 | 484.1 |

C. TABLE 1-continued

| Example | Structure | [M + H]+ |
|---------|-----------|----------|
| 4G | 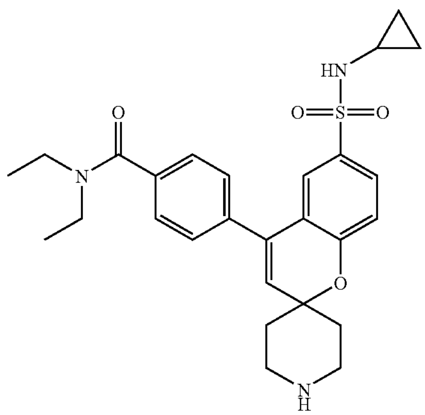 | 496.2 |
| 4H | 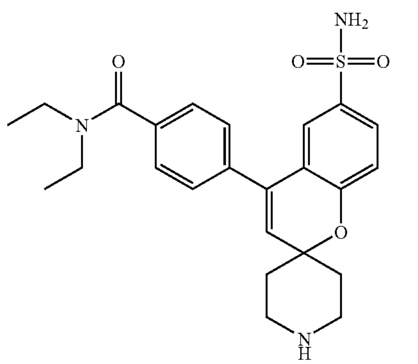 | 456.0 |
| 4I | 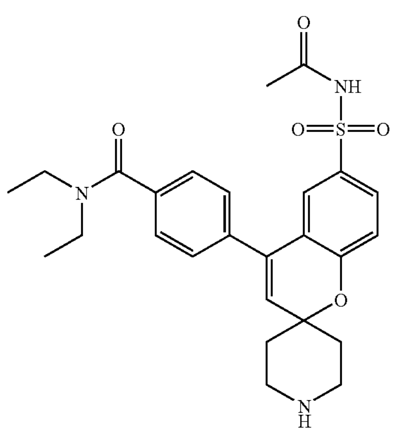 | 498.3 |
| 5A | 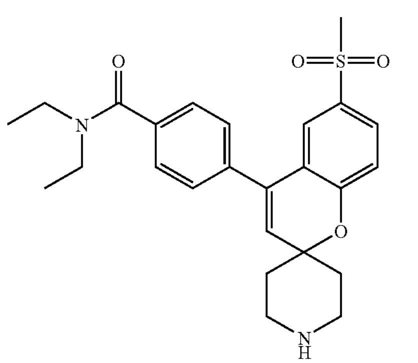 | 455.2 |

C. TABLE 1-continued
| Example | Structure | [M + H]+ |
|---|---|---|
| 6A | 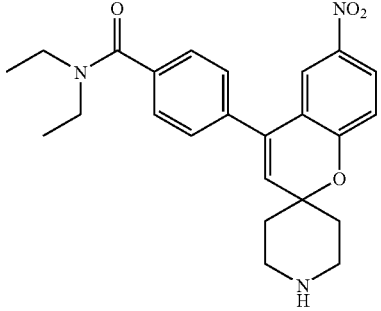 | 422.3 |
| 6B | 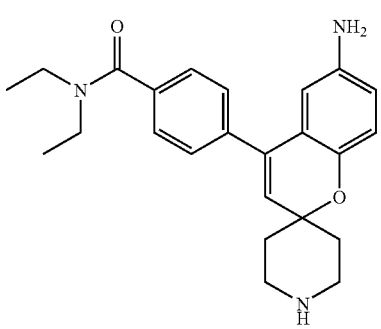 | 392.2 |
| 6C | 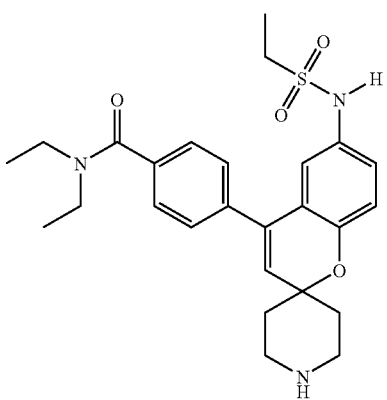 | 484.2 |
| 6D | 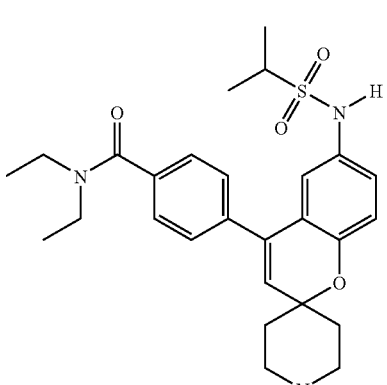 | 498.2 |

C. TABLE 1-continued

| Example | Structure | [M + H]+ |
|---|---|---|
| 6E | 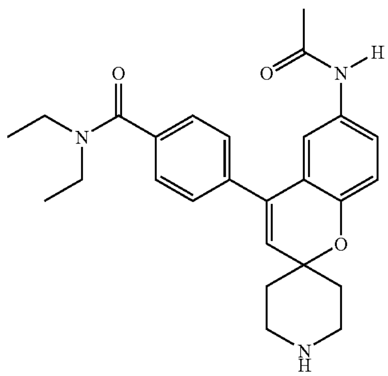 | 434.2 |
| 7A | 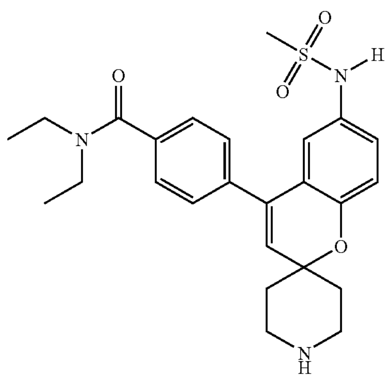 | 470.4 |
| 7B | 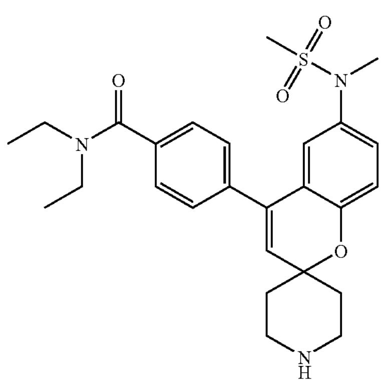 | 484.2 |
| 7C | 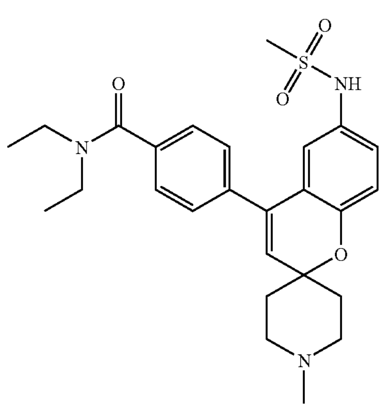 | 484.2 |

C. TABLE 1-continued

| Example | Structure | [M + H]+ |
|---|---|---|
| 8A | 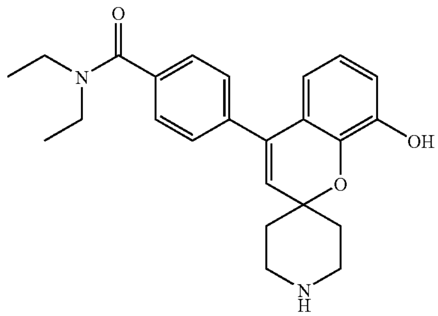 | 393.4 |
| 8B | 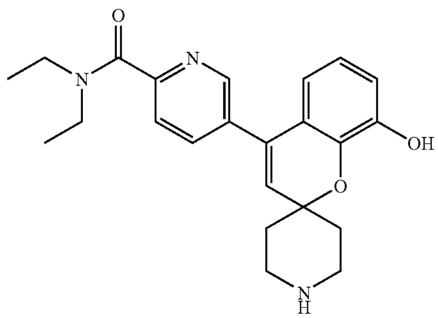 | 394.2 |
| 8C | 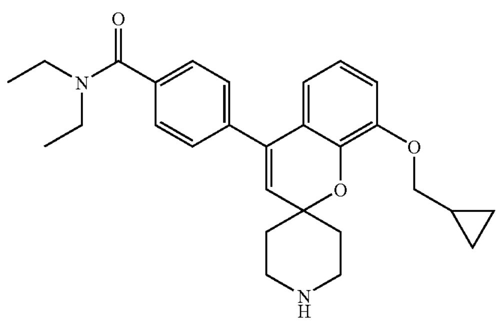 | 447.3 |
| 8D | 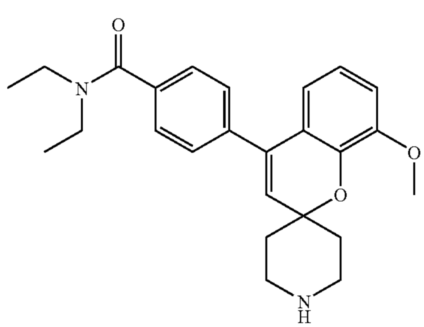 | 407.3 |

C. TABLE 1-continued

| Example | Structure | [M + H]⁺ |
|---|---|---|
| 8E | 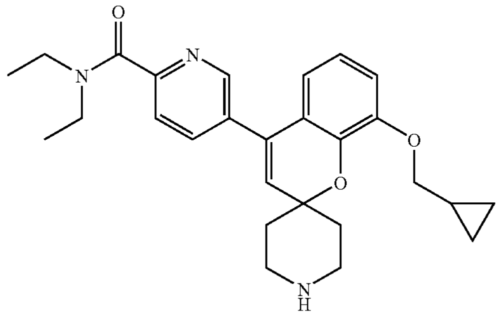 | 448.3 |
| 8F | 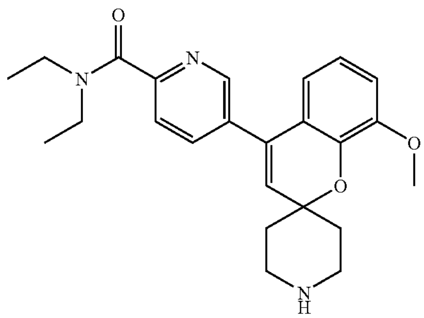 | 408.4 |
| 9A | 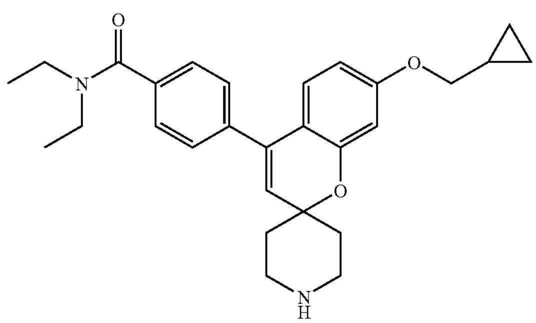 | 447.3 |
| 9B | 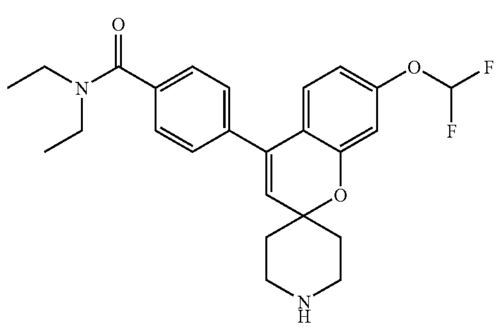 | 443.4 |

C. TABLE 1-continued
| Example | Structure | [M + H]+ |
|---|---|---|
| 10A | 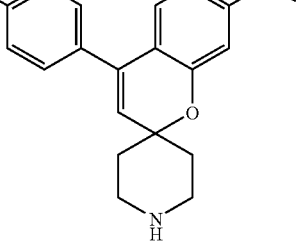 | 435.3 |
| 10B | 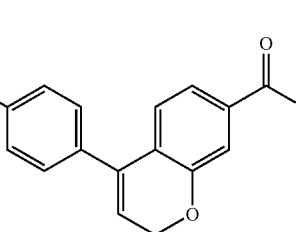 | 421.3 |
| 10C | 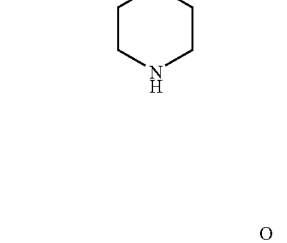 | 420.3 |
| 10D | 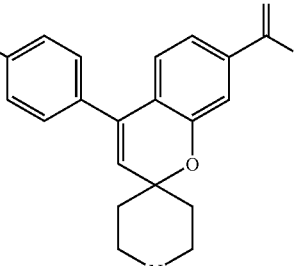 | 434.3 |

C. TABLE 1-continued

| Example | Structure | [M + H]+ |
|---------|-----------|----------|
| 10E | 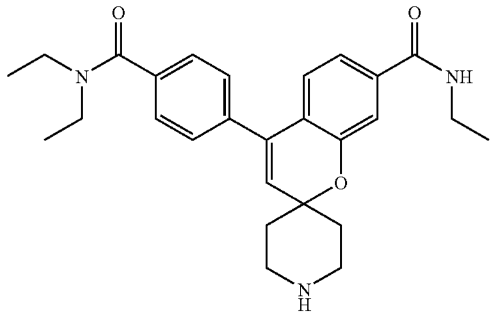 | 448.3 |
| 10F | 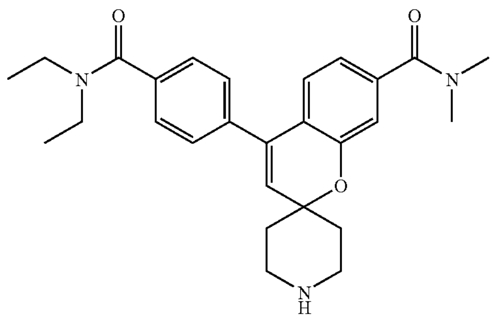 | 448.3 |
| 10G | 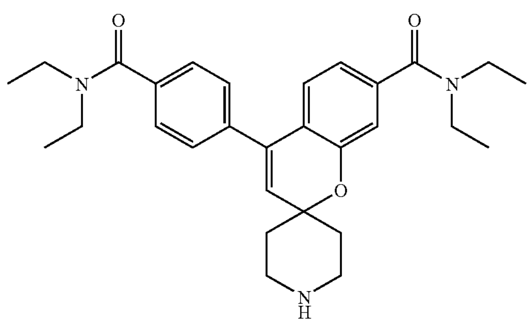 | 476.2 |
| 10H | 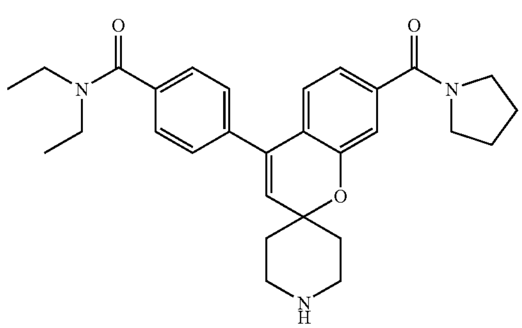 | 474.3 |

C. TABLE 1-continued

| Example | Structure | [M + H]⁺ |
|---|---|---|
| 10I | 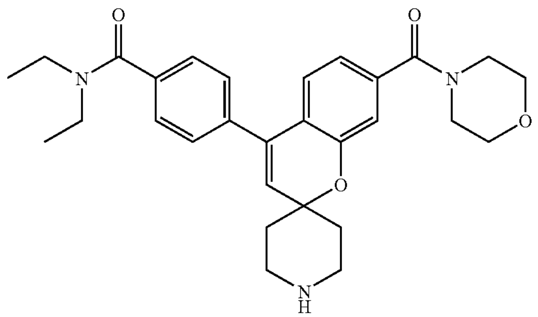 | 490.2 |
| 10J | 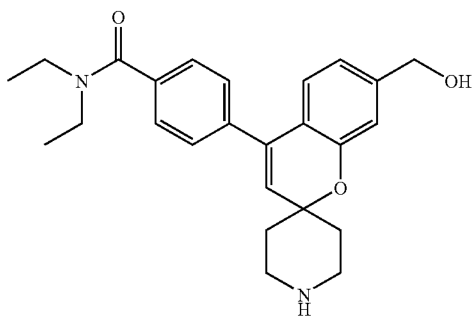 | 407.4 |
| 11A | 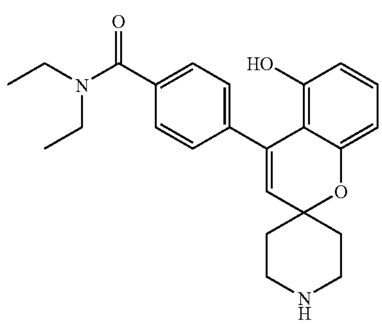 | 393.0 |
| 11B | 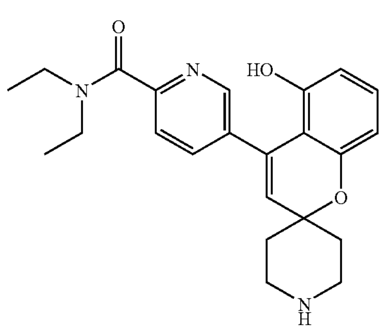 | 394.3 |

C. TABLE 1-continued

| Example | Structure | [M + H]+ |
|---|---|---|
| 11C | 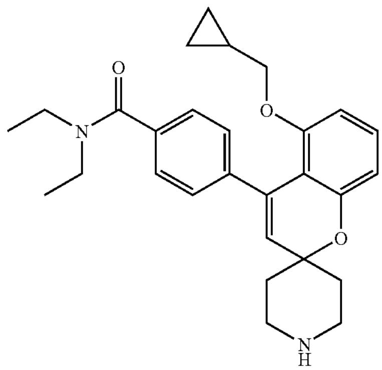 | 447.4 |
| 11D | 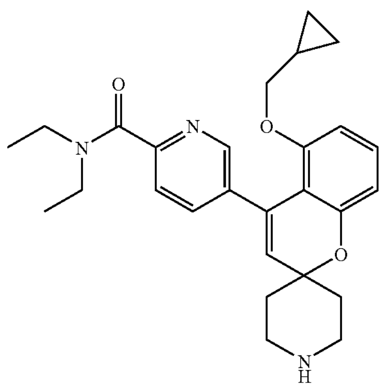 | 448.4 |
| 11E | 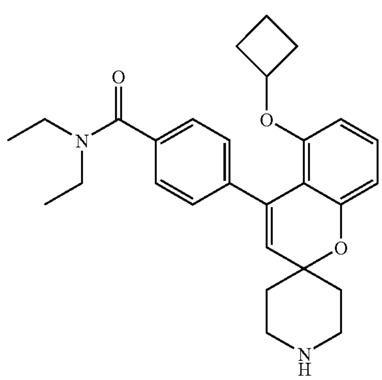 | 447.3 |
| 11F | 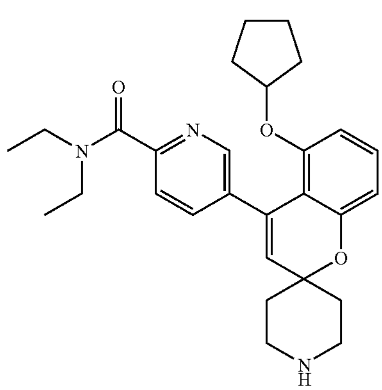 | 462.4 |

C. TABLE 1-continued

| Example | Structure | [M + H]+ |
|---|---|---|
| 12A | 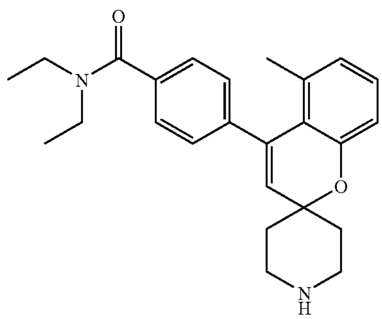 | 391.4 |
| 12B | 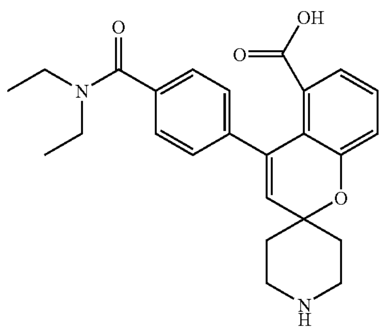 | 421.3 |
| 12C | 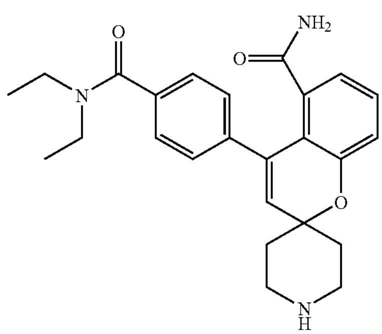 | 420.3 |
| 12D | 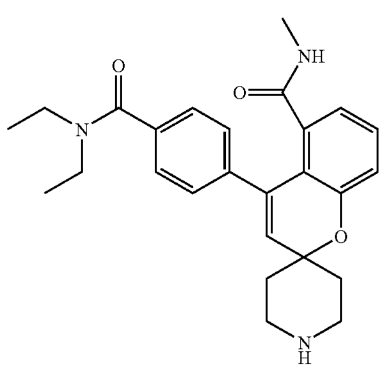 | 434.3 |

C. TABLE 1-continued
| Example | Structure | [M + H]+ |
|---------|-----------|----------|
| 12E | 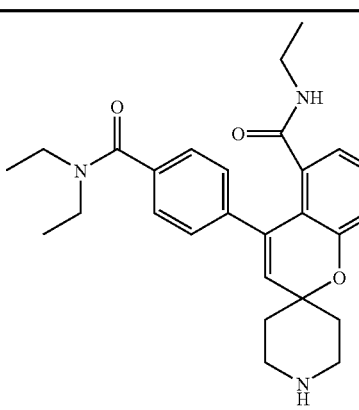 | 448.4 |
| 12F | 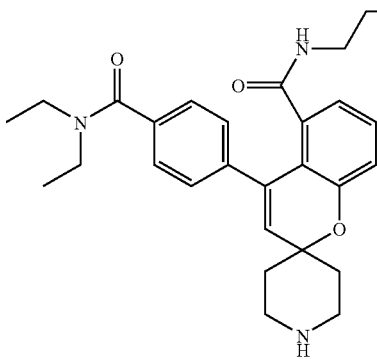 | 462.4 |
| 12G | 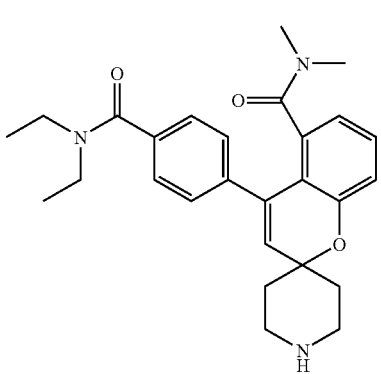 | 448.4 |
| 12H | 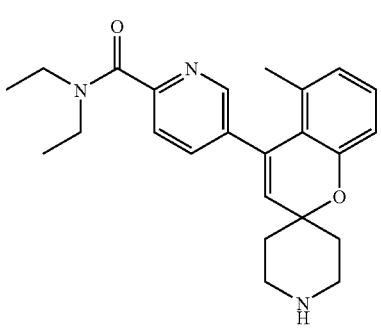 | 392.4 |

C. TABLE 1-continued

| Example | Structure | [M + H]⁺ |
|---------|-----------|----------|
| 12I | 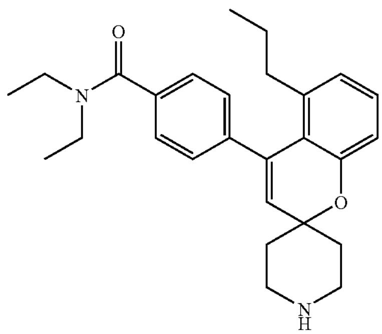 | 419.4 |
| 12J | 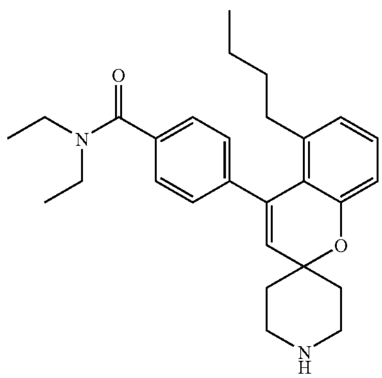 | 433.4 |
| 12K | 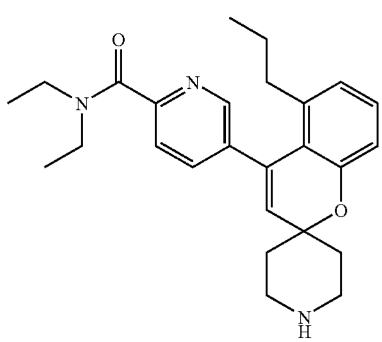 | 420.4 |
| 12L | 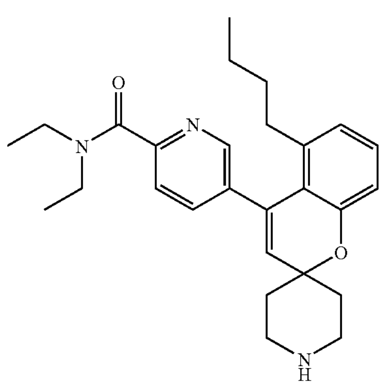 | 434.3 |

C. TABLE 1-continued

| Example | Structure | [M + H]+ |
|---------|-----------|----------|
| 13A | 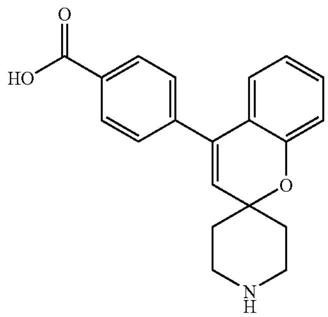 | 322.1 |
| 13B | 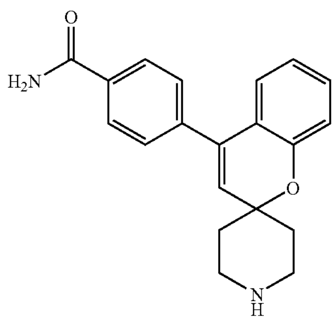 | 321.1 |
| 13C | 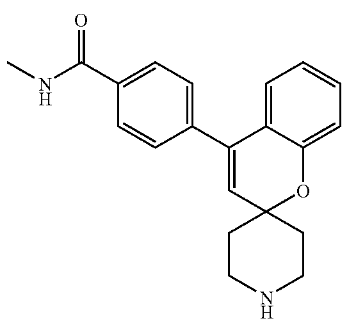 | 335.2 |
| 13D | 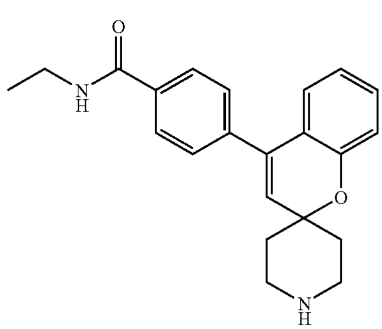 | 349.2 |

C. TABLE 1-continued

| Example | Structure | [M + H]+ |
|---|---|---|
| 13E | 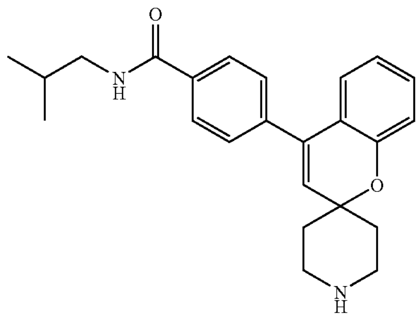 | 377.2 |
| 13F | 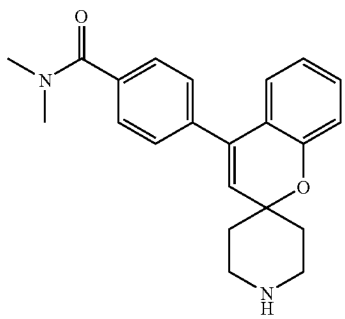 | 349.1 |
| 13G | 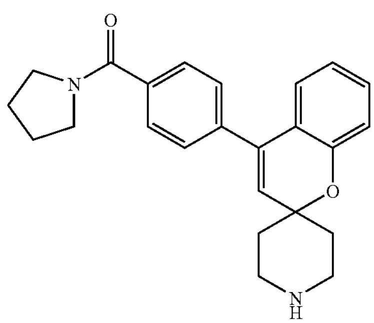 | 375.1 |
| 13H | 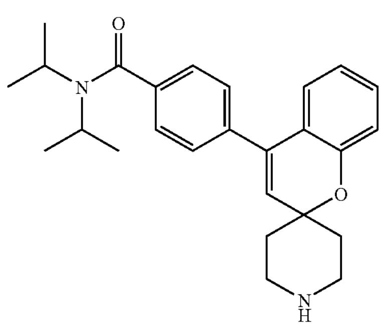 | 405.3 |

C. TABLE 1-continued

| Example | Structure | [M + H]+ |
|---------|-----------|----------|
| 13I | 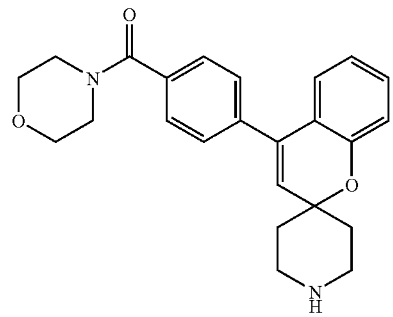 | 391.1 |
| 13J | 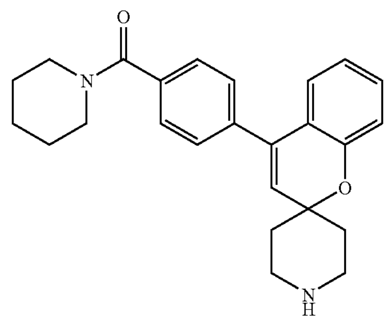 | 389.1 |
| 13K | 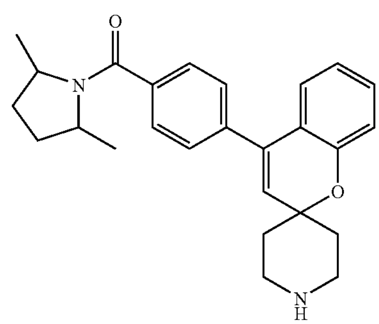 | 403.3 |
| 13L | 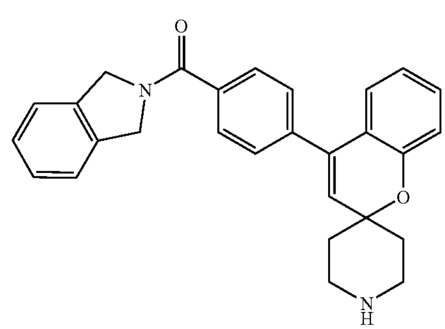 | 423.1 |

C. TABLE 1-continued
| Example | Structure | [M + H]⁺ |
|---|---|---|
| 13M | 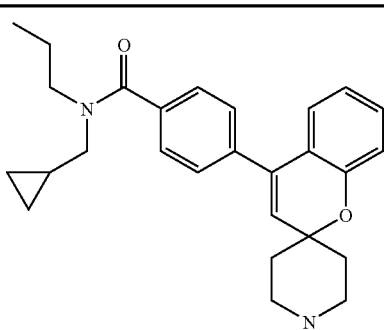 | 417.2 |
| 13N | 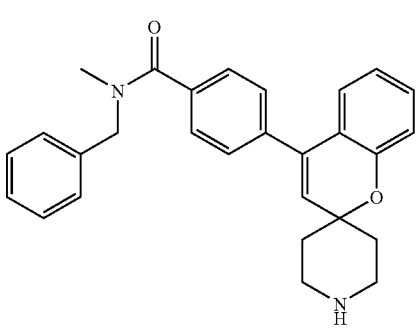 | 425.2 |
| 13O | 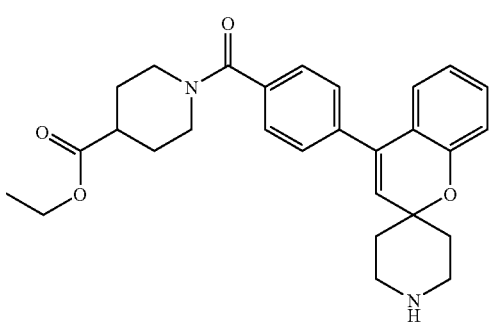 | 461.2 |
| 13P | 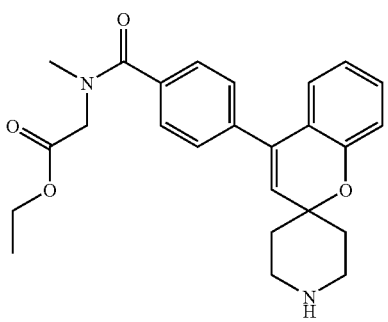 | 421.2 |

C. TABLE 1-continued

| Example | Structure | [M + H]+ |
|---|---|---|
| 13Q | 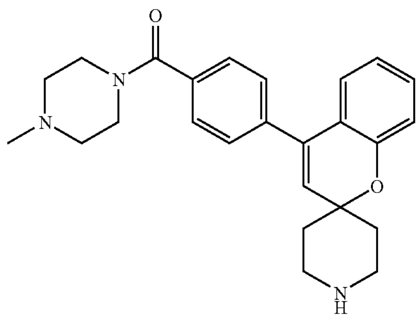 | 404.3 |
| 13R | 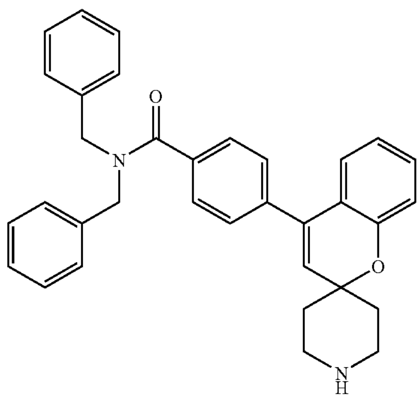 | 501.2 |
| 13S | 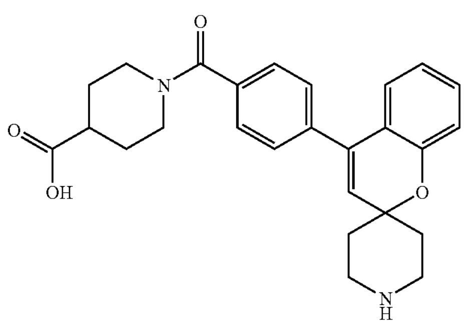 | 433.1 |
| 14A | 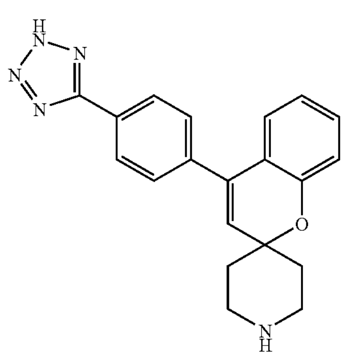 | 346.1 |

C. TABLE 1-continued
| Example | Structure | [M + H]+ |
|---|---|---|
| 14B | 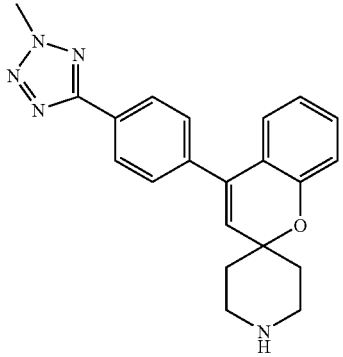 | 360.1 |
| 14C | 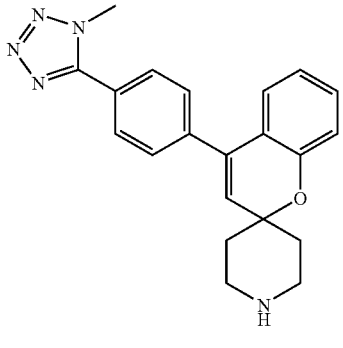 | 360.2 |
| 15A | 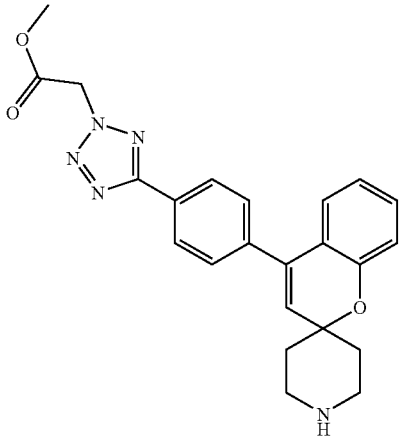 | 418.1 |
| 15B | 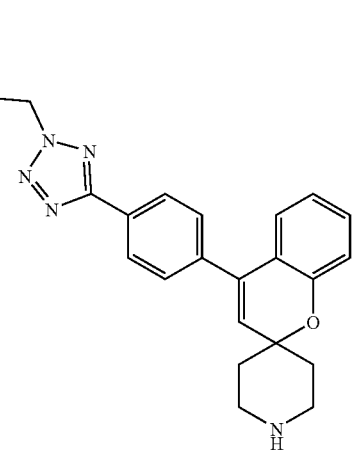 | 432.2 |

C. TABLE 1-continued
| Example | Structure | [M + H]+ |
|---|---|---|
| 15C | 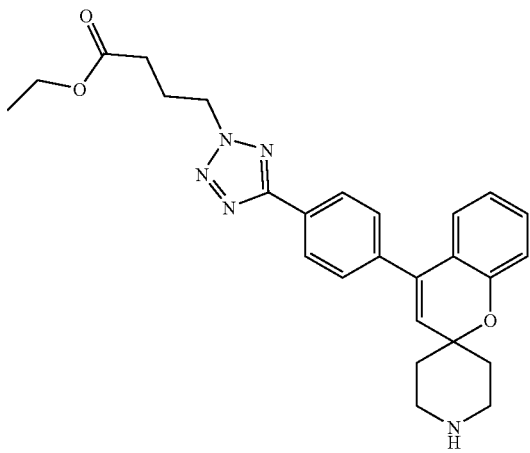 | 460.2 |
| 15D | 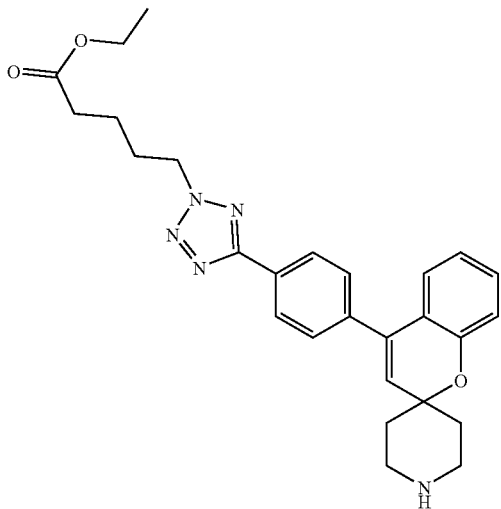 | 474.2 |
| 15E | 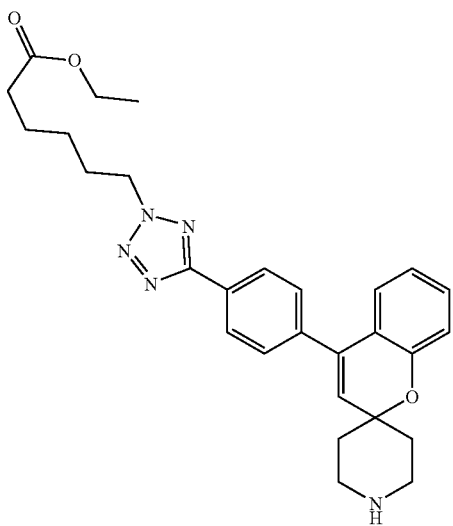 | 488.2 |

C. TABLE 1-continued
| Example | Structure | [M + H]+ |
|---|---|---|
| 15F | 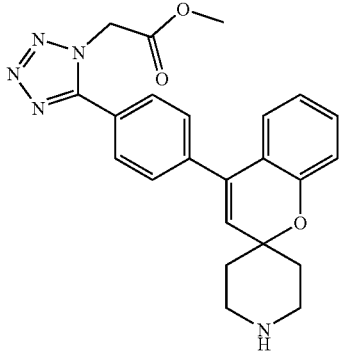 | 418.2 |
| 15G | 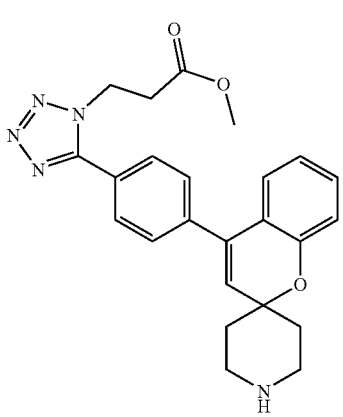 | 432.1 |
| 15H | 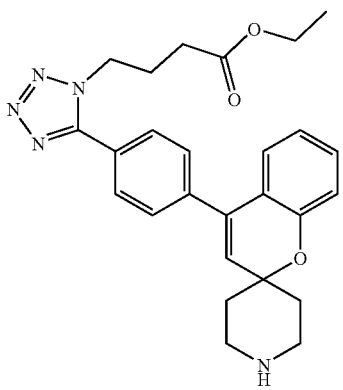 | 460.2 |
| 15I | 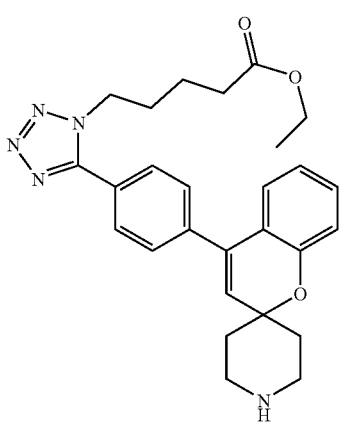 | 474.3 |

C. TABLE 1-continued
| Example | Structure | [M + H]+ |
|---|---|---|
| 15J | 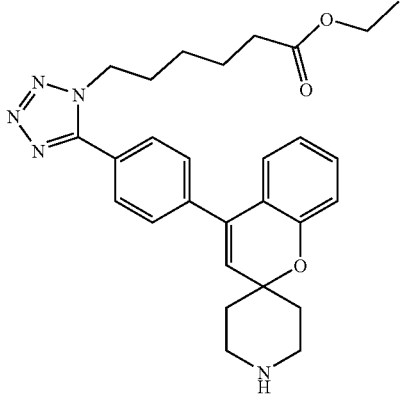 | 488.3 |
| 15K | 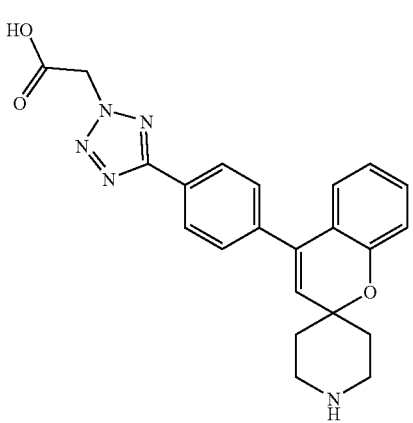 | 404.1 |
| 15L | 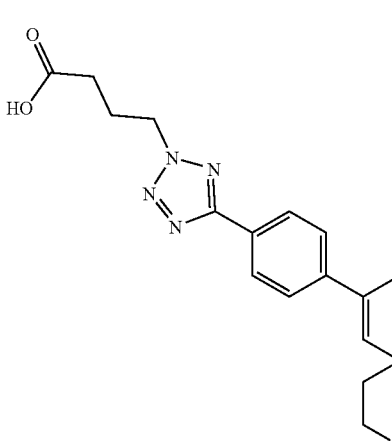 | 432.1 |

C. TABLE 1-continued
| Example | Structure | [M + H]+ |
|---|---|---|
| 15M | 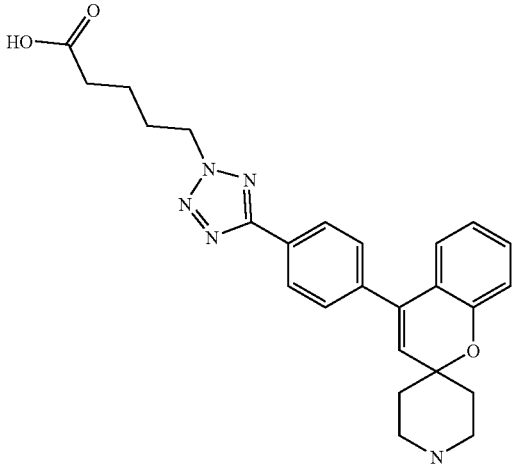 | 446.2 |
| 15N | 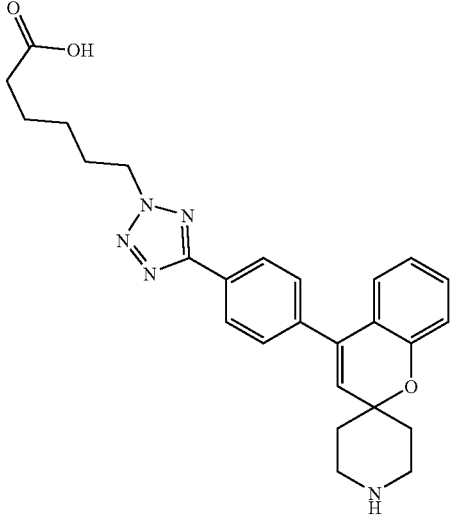 | 460.2 |
| 16A | 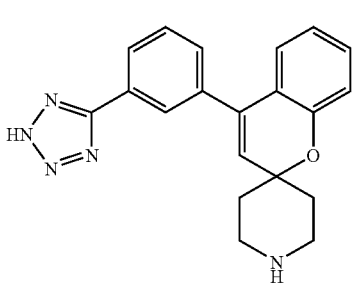 | 346.1 |
| 16B | 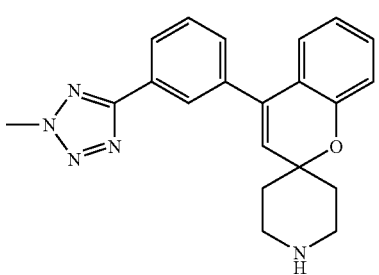 | 360.1 |

C. TABLE 1-continued

| Example | Structure | [M + H]⁺ |
|---|---|---|
| 16C | 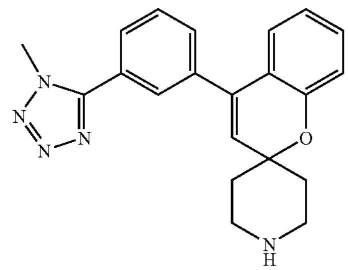 | 360.1 |
| 17A | 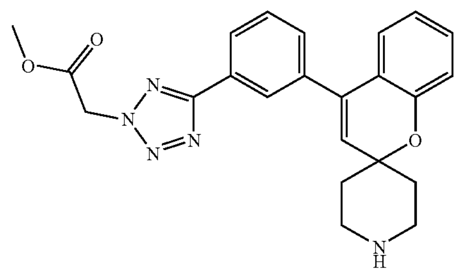 | 418.1 |
| 17B | 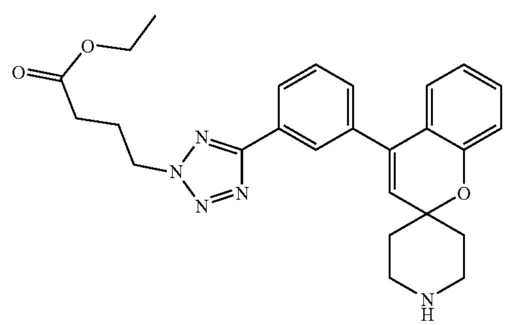 | 460.2 |
| 17C | 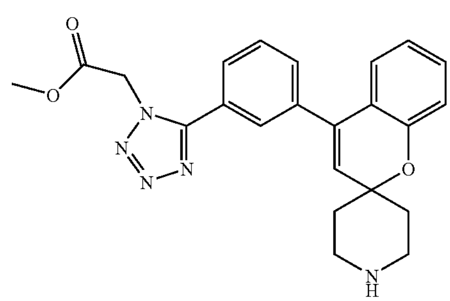 | 418.1 |
| 17D | 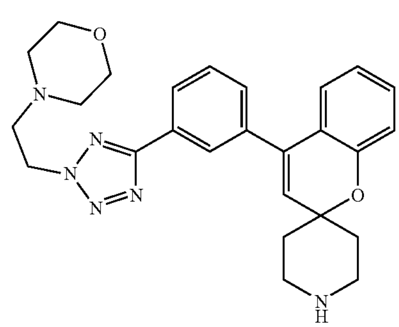 | 459.2 |

C. TABLE 1-continued
| Example | Structure | [M + H]+ |
|---------|-----------|----------|
| 17E | 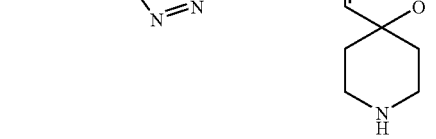 | 404.1 |
| 17F | 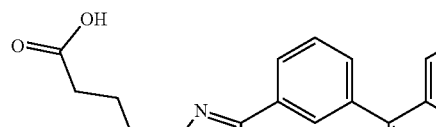 | 432.1 |
| 18A | 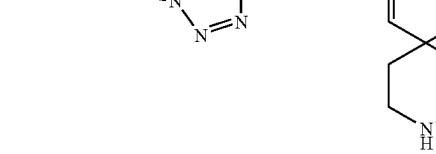 | 417.3 |
| 18B | 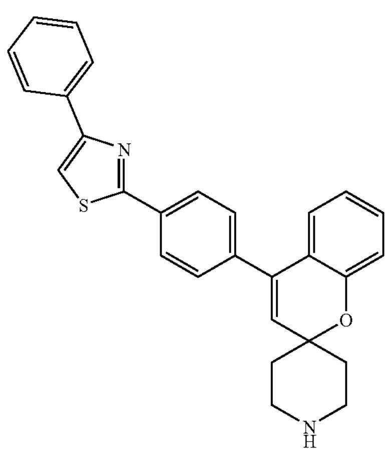 | 437.1 |

C. TABLE 1-continued
| Example | Structure | [M + H]⁺ |
|---|---|---|
| 18C | 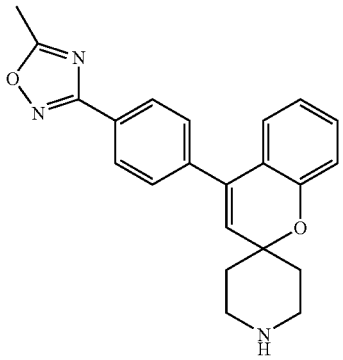 | 360.3 |
| 19A | 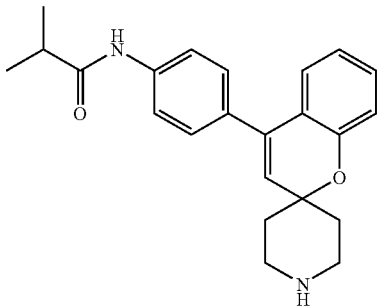 | 363.4 |
| 19B | 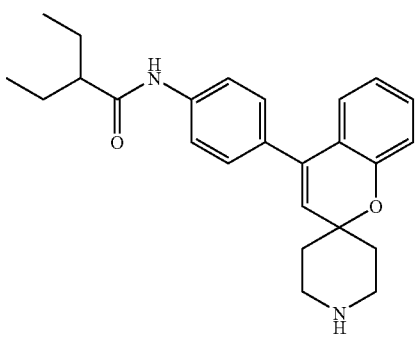 | 391.4 |
| 19C | 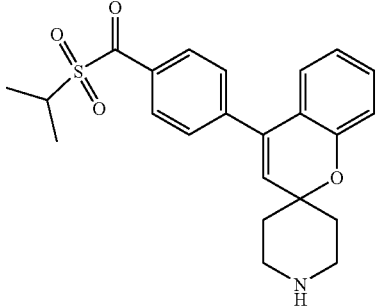 | 399.3 |

C. TABLE 1-continued

| Example | Structure | [M + H]⁺ |
|---|---|---|
| 19D | 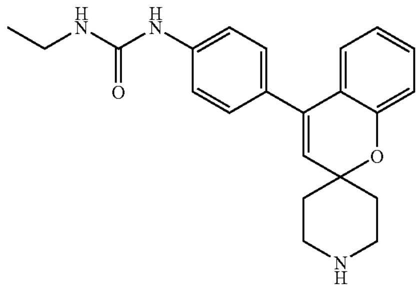 | 364.4 |
| 20A | 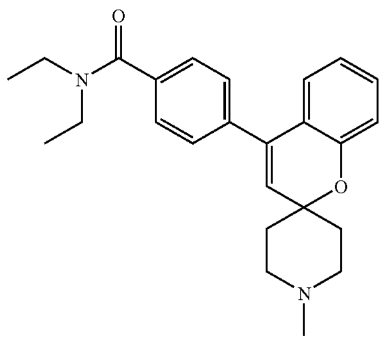 | 391.2 |
| 20B | 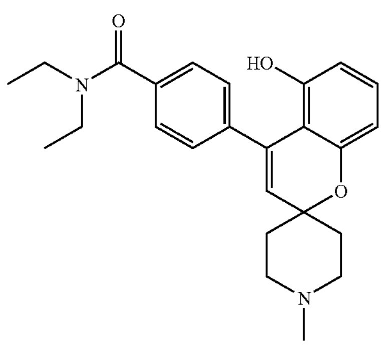 | 407.3 |
| 20C | 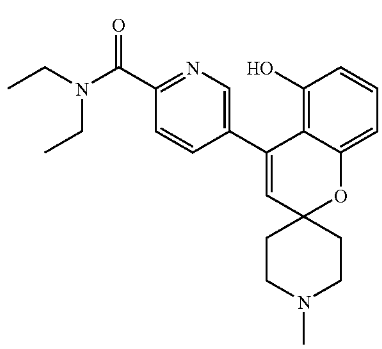 | 408.3 |

C. TABLE 1-continued

| Example | Structure | [M + H]+ |
|---------|-----------|----------|
| 20D | 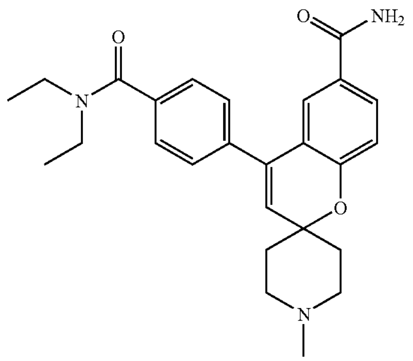 | 434.4 |
| 20E | 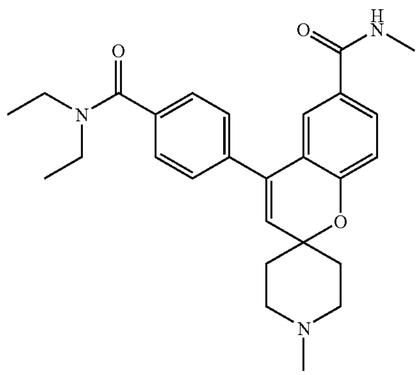 | 448.5 |
| 20F | 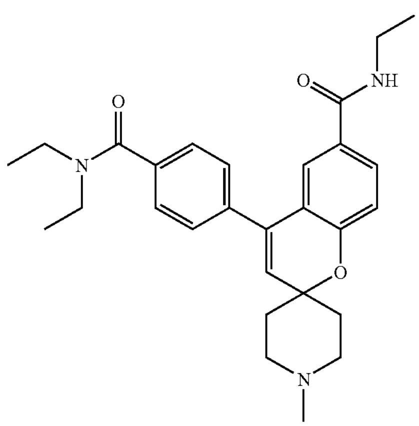 | 462.5 |
| 20G | 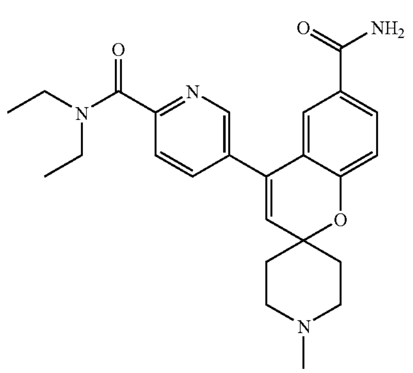 | 435.4 |

C. TABLE 1-continued
| Example | Structure | [M + H]+ |
|---|---|---|
| 20H | 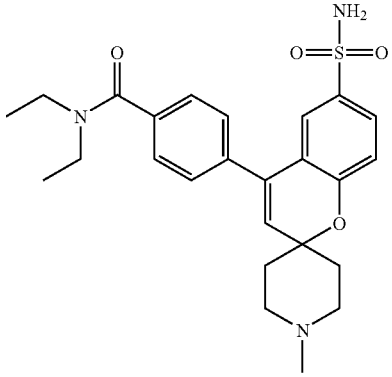 | 470.3 |
| 20I | 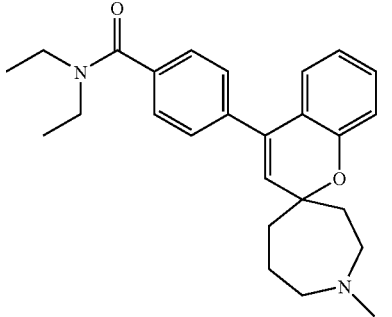 | 405.4 |
| 20J | 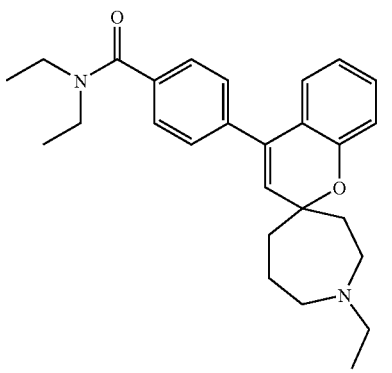 | 419.4 |
| 20K | 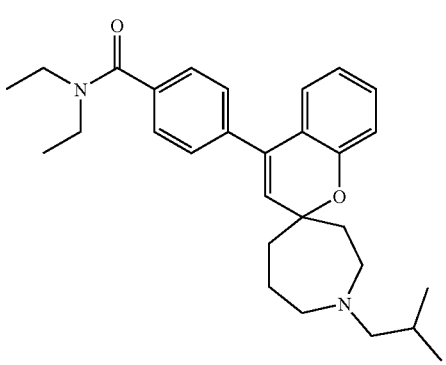 | 447.5 |

C. TABLE 1-continued

| Example | Structure | [M + H]+ |
|---|---|---|
| 20L | 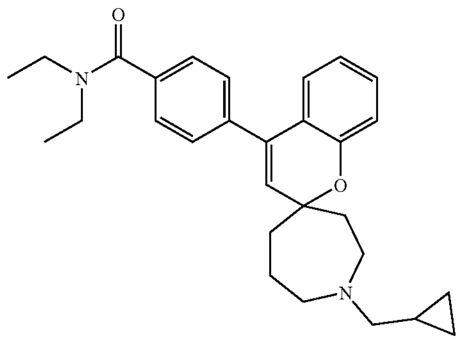 | 445.4 |
| 20M | 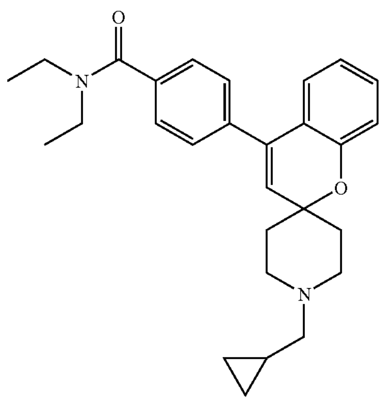 | 431.0 |
| 20N | 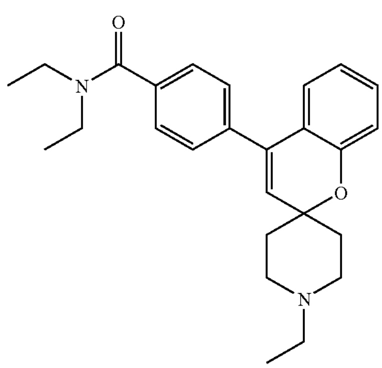 | 405.0 |
| 20O | 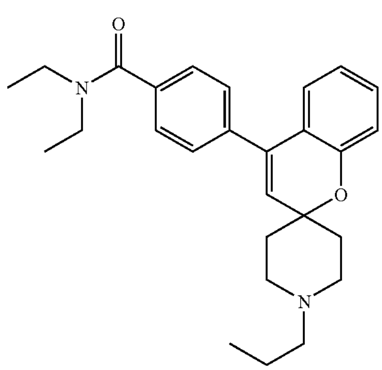 | 419.1 |

C. TABLE 1-continued

| Example | Structure | [M + H]+ |
|---|---|---|
| 20P | 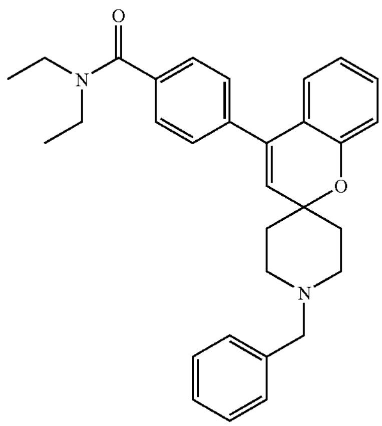 | 467.3 |
| 20Q | 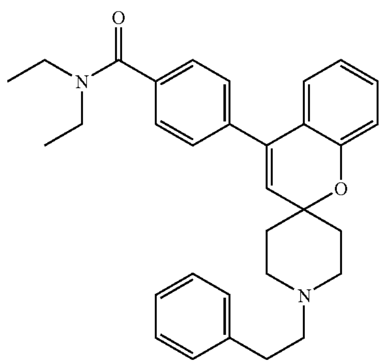 | 481.3 |
| 20R | 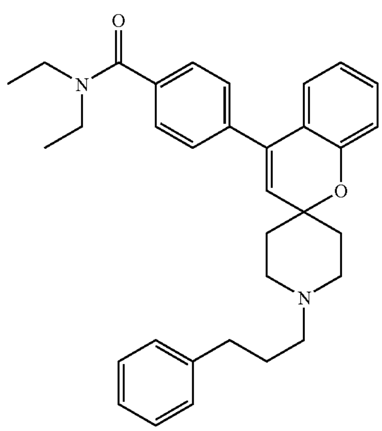 | 495.3 |
| 21A | 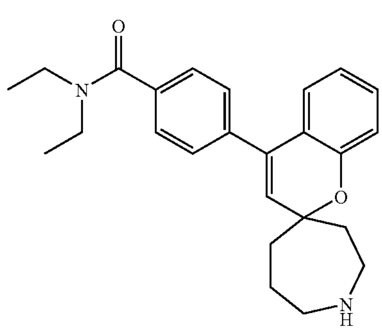 | 391.2 |

C. TABLE 1-continued

| Example | Structure | [M + H]+ |
|---------|-----------|----------|
| 21B | 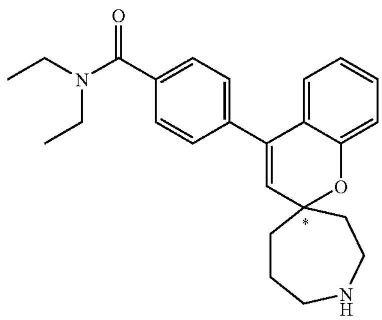 | 391.3 |
| 21C | 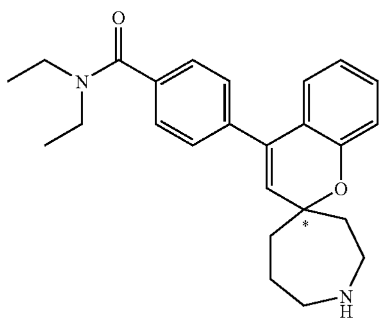 | 391.3 |
| 21D | 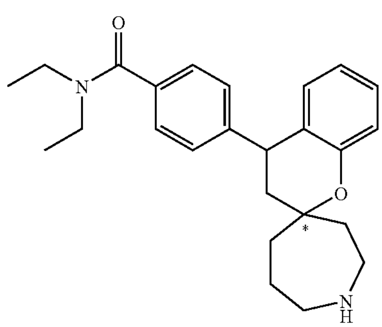 | 393.3 |
| 21E | 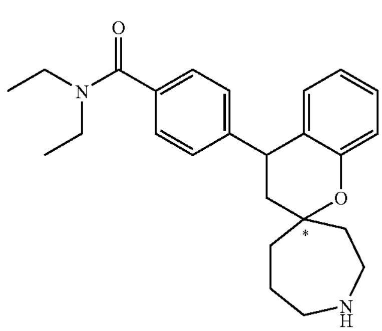 | 393.3 |

C. TABLE 1-continued
| Example | Structure | [M + H]+ |
|---|---|---|
| 21F | 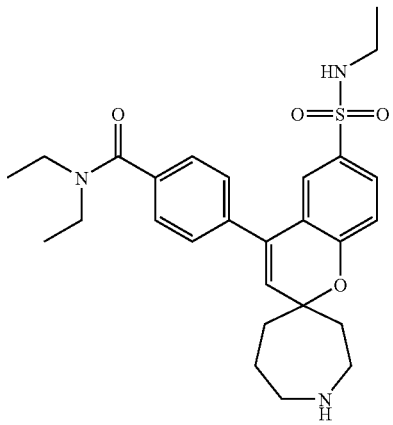 | 498.5 |
| 22A | 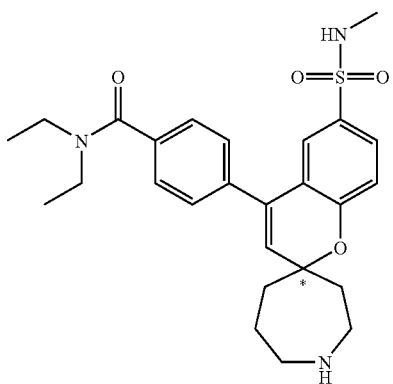 | 484.2 |
| 22B | 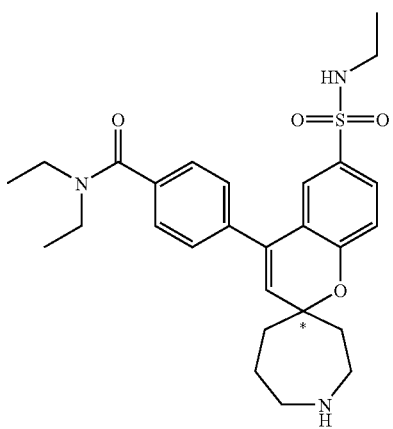 | 498.3 |

C. TABLE 1-continued

| Example | Structure | [M + H]+ |
|---|---|---|
| 22C | 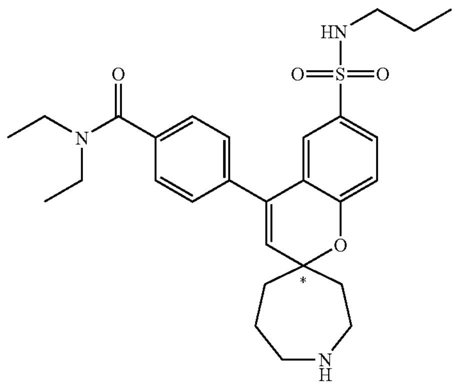 | 512.4 |
| 22D | 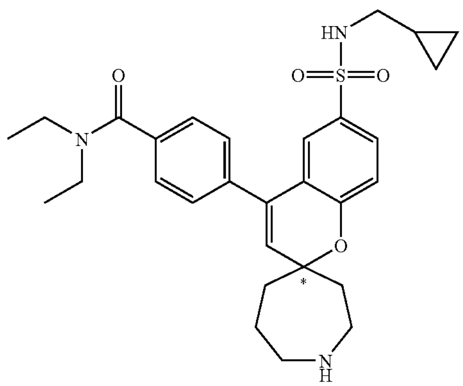 | 524.3 |
| 22E | 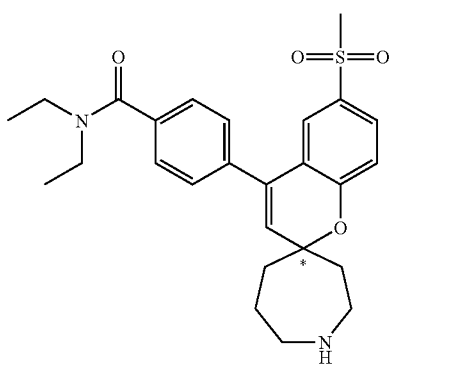 | 469.2 |
| 23A | 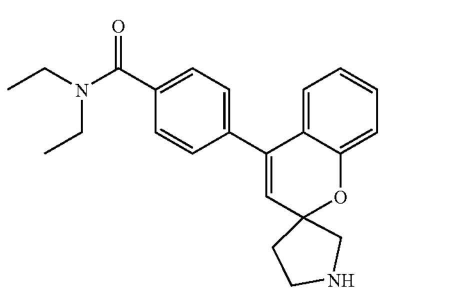 | 363.2 |

C. TABLE 1-continued

| Example | Structure | [M + H]+ |
|---|---|---|
| 23B | 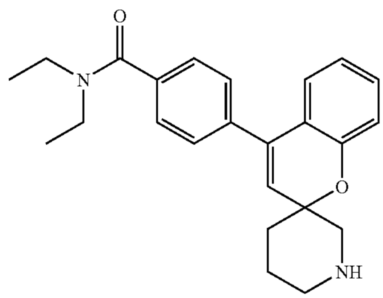 | 377.0 |
| 23C | 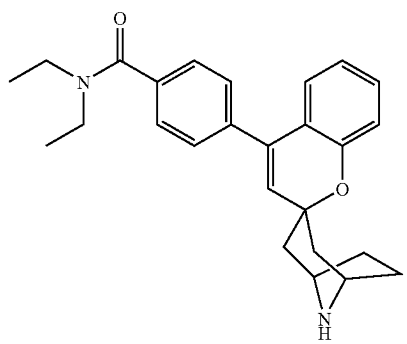 | 403.2 |
| 24A | 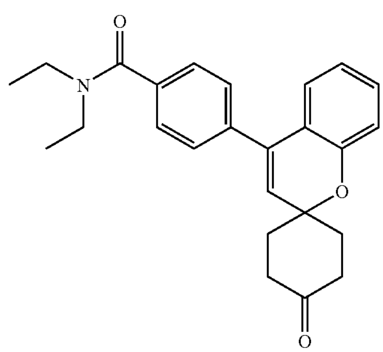 | 390.2 |
| 24B | 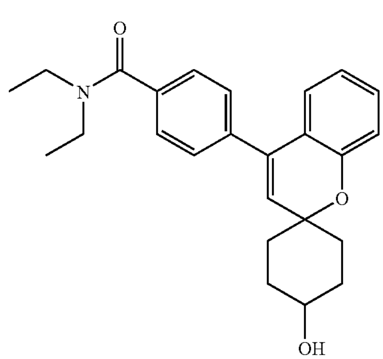 | 392.2 |

C. TABLE 1-continued

| Example | Structure | [M + H]⁺ |
|---|---|---|
| 24C | 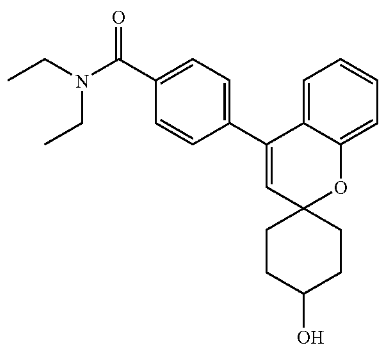 | 392.2 |
| 24D | 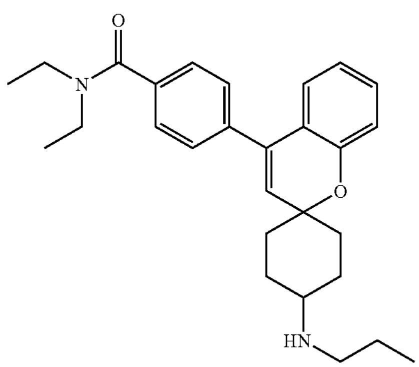 | 433.2 |
| 24E | 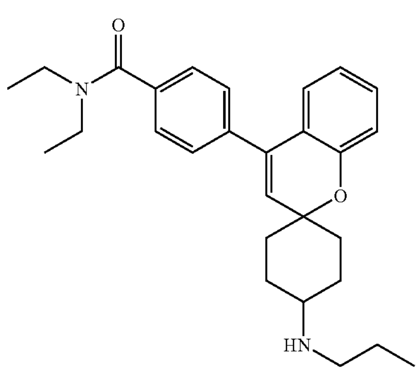 | 433.2 |
| 24F | 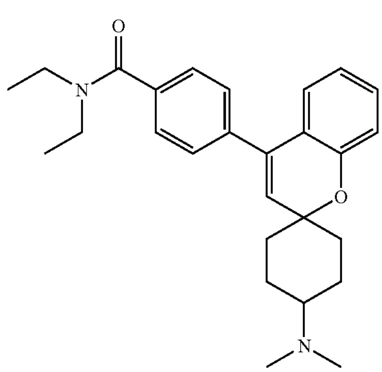 | 419.2 |

C. TABLE 1-continued

| Example | Structure | [M + H]+ |
|---------|-----------|----------|
| 24G | 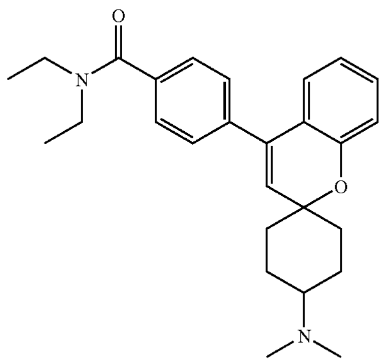 | 419.2 |
| 25A | 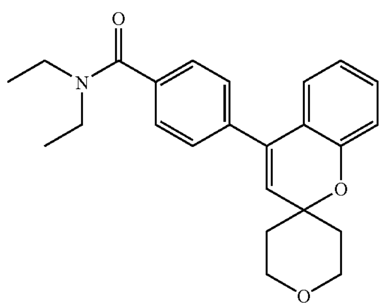 | 378.2 |
| 26A | 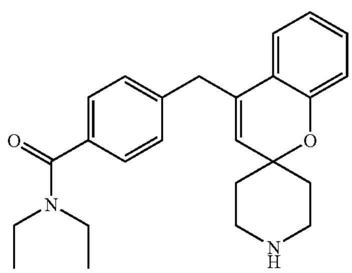 | 391.0 |
| 26B | 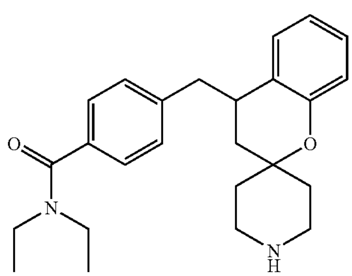 | 393.0 |
| 27A | 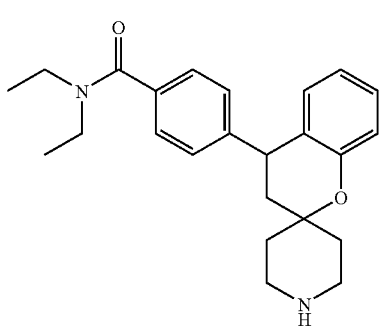 | 379.1 |

C. TABLE 1-continued

| Example | Structure | [M + H]+ |
|---------|-----------|----------|
| 27B | 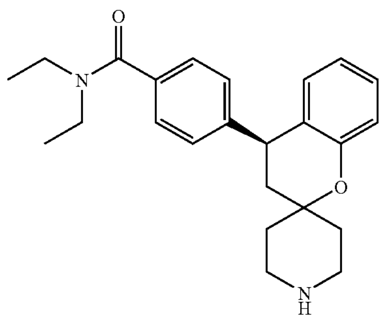 | 379.4 |
| 27C | 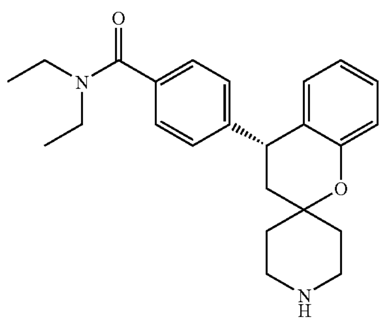 | 379.4 |
| 27D | 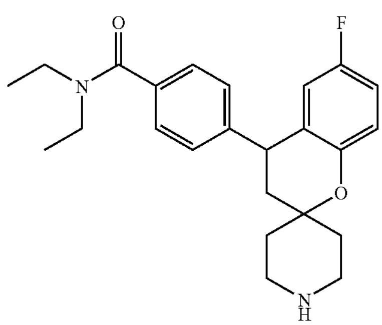 | 397.3 |
| 27E | 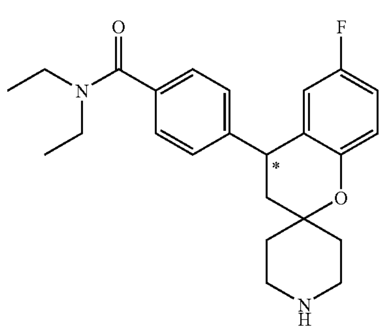 | 397.4 |

C. TABLE 1-continued

| Example | Structure | [M + H]+ |
|---|---|---|
| 27F | 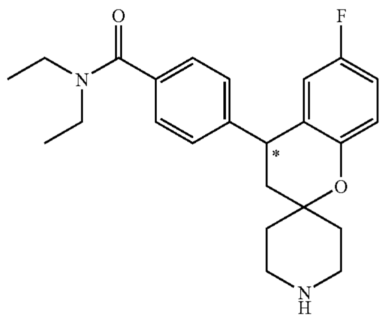 | 397.3 |
| 27G | 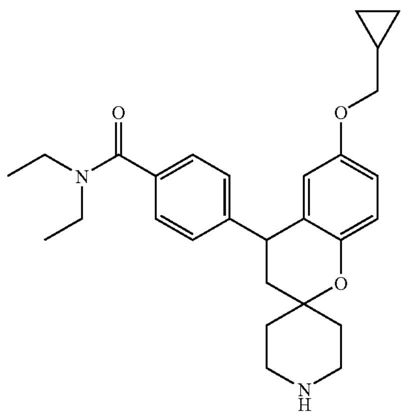 | 449.3 |
| 27H | 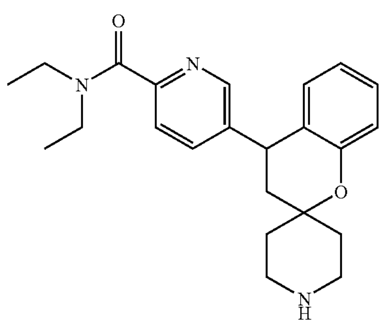 | 380.2 |
| 27I | 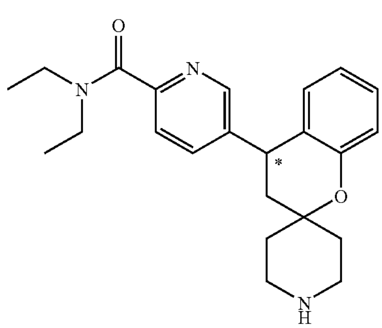 | 380.2 |

C. TABLE 1-continued

| Example | Structure | [M + H]+ |
|---|---|---|
| 27J | 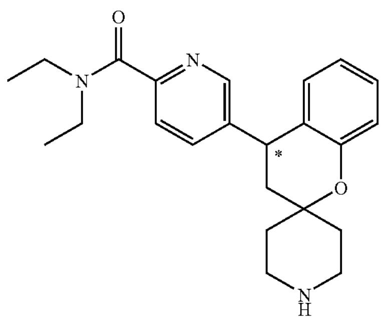 | 380.2 |
| 27K | 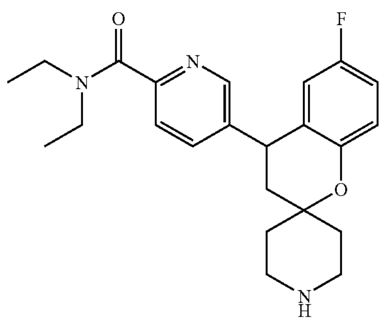 | 398.3 |
| 27L | 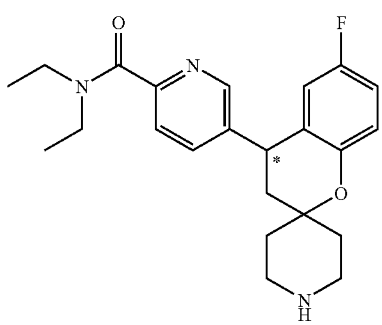 | 398.3 |
| 27M | 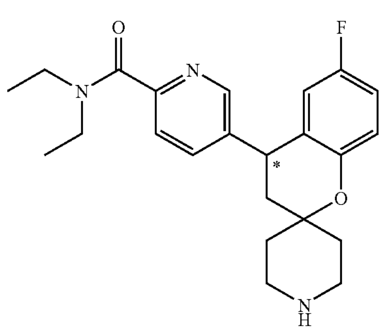 | 398.3 |

C. TABLE 1-continued

| Example | Structure | [M + H]⁺ |
|---------|-----------|----------|
| 27N | 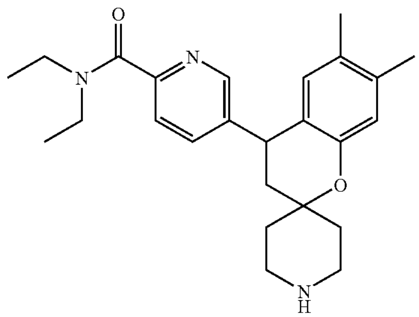 | 408.3 |
| 27O | 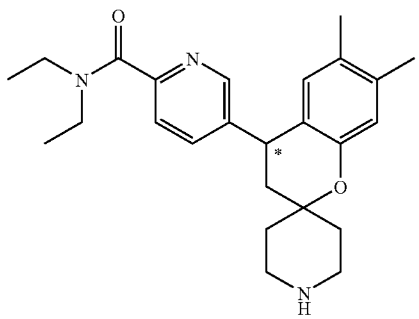 | 408.3 |
| 27P | 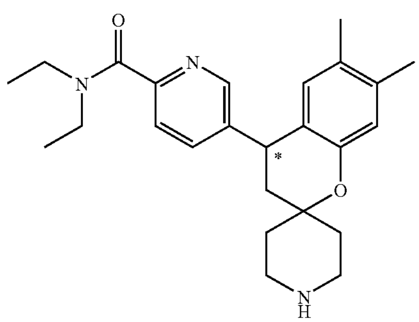 | 408.3 |
| 27Q | 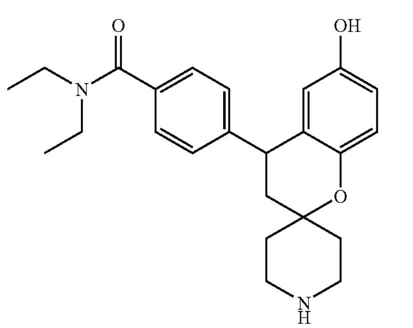 | 395.4 |

C. TABLE 1-continued

| Example | Structure | [M + H]+ |
| --- | --- | --- |
| 27R | 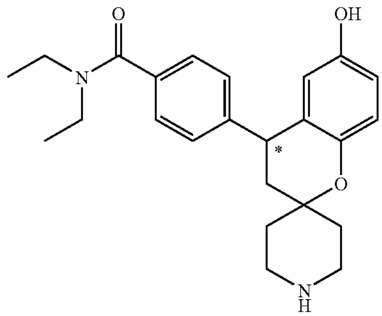 | 395.1 |
| 27S | 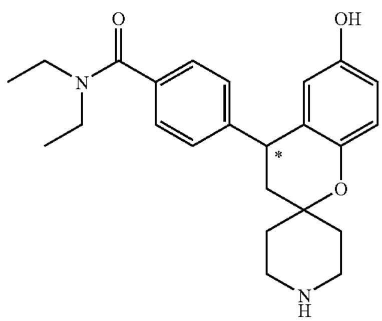 | 395.1 |
| 27T | 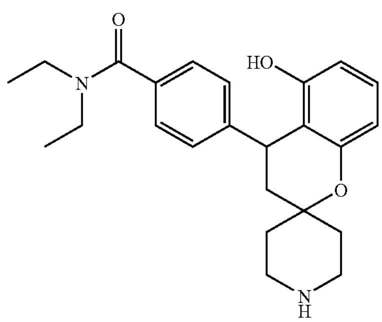 | 395.3 |
| 27U | 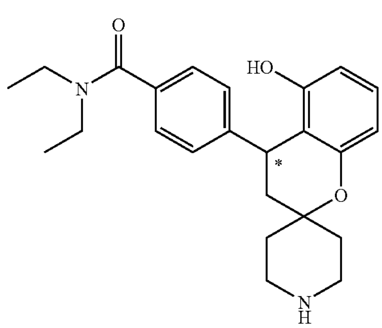 | 395.1 |

C. TABLE 1-continued

| Example | Structure | [M + H]+ |
|---------|-----------|----------|
| 27V | 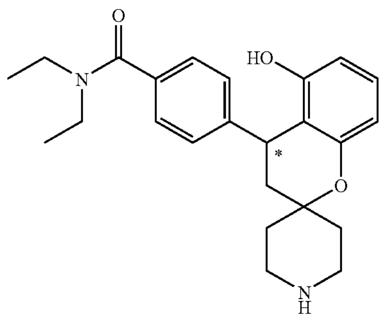 | 395.1 |
| 27W | 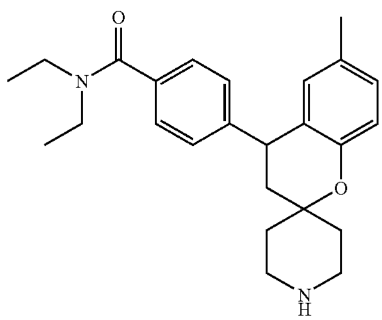 | 393.4 |
| 28A | 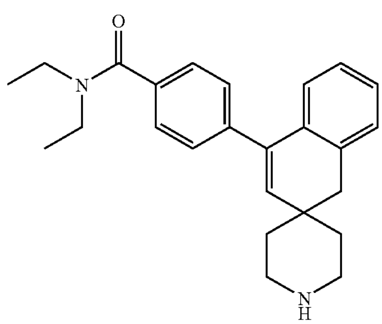 | 375.1 |
| 28B | 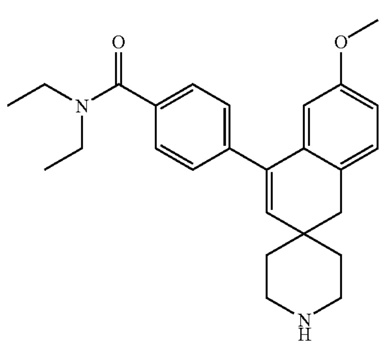 | 405.1 |

C. TABLE 1-continued

| Example | Structure | [M + H]+ |
|---|---|---|
| 28C | 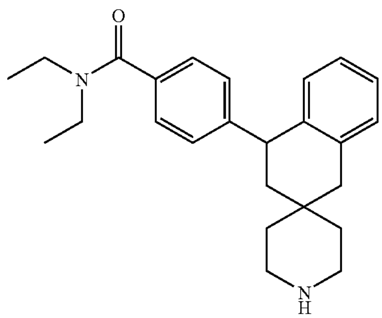 | 377.1 |
| 28D | 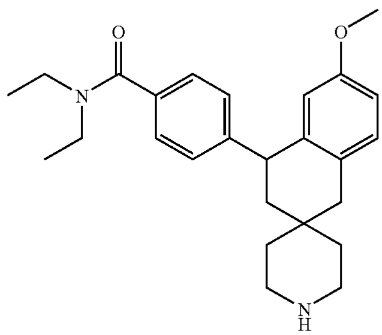 | 407.3 |
| 28E | 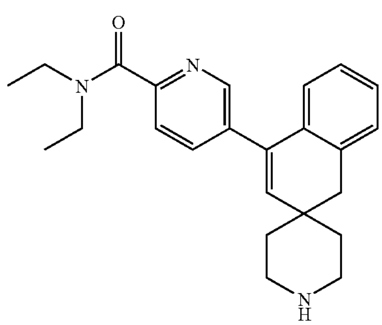 | 376.4 |
| 29A | 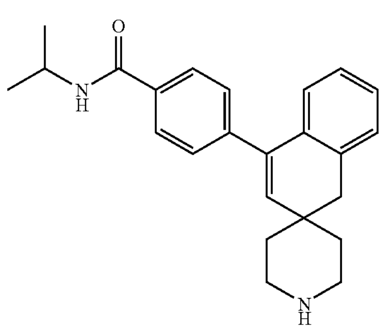 | 361.0 |

C. TABLE 1-continued

| Example | Structure | [M + H]+ |
|---|---|---|
| 29B | 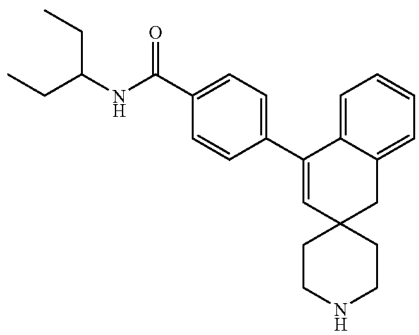 | 389.1 |
| 29C | 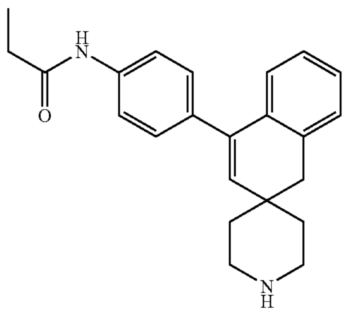 | 347.0 |
| 29D | 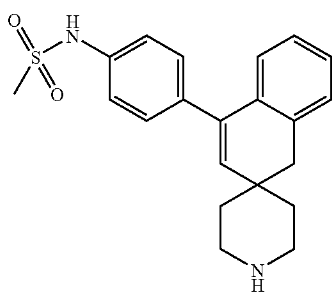 | 368.9 |
| 30A | 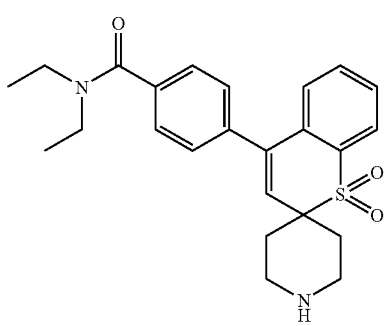 | 425.3 |
| 31A | 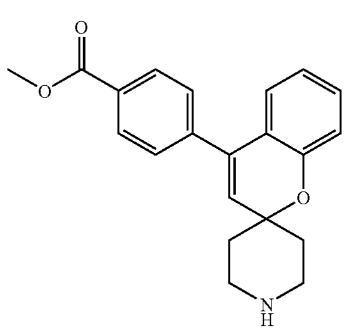 | 336.0 |

C. TABLE 1-continued

| Example | Structure | [M + H]+ |
|---------|-----------|----------|
| 31B | 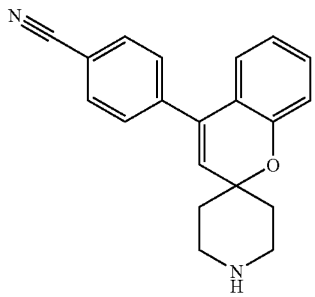 | 303.1 |
| 31C | 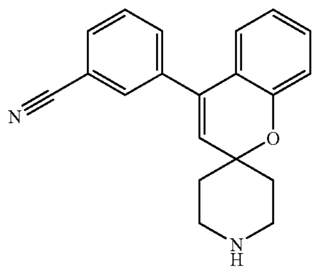 | 303.1 |
| 31D | 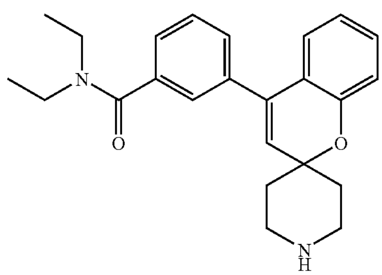 | 377.4 |
| 31E | 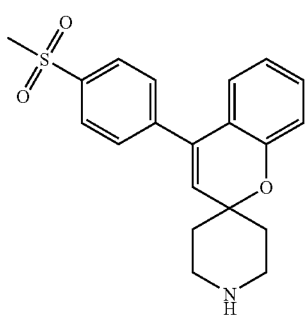 | 356.1 |
| 31F | 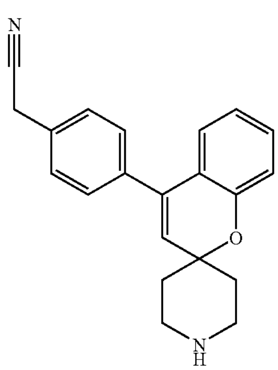 | 317.0 |

C. TABLE 1-continued

| Example | Structure | [M + H]⁺ |
|---|---|---|
| 31G | 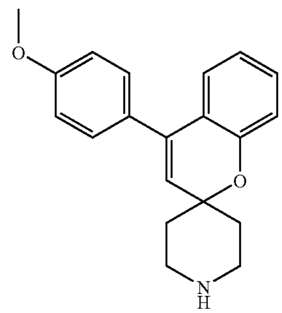 | 308.0 |
| 31H | 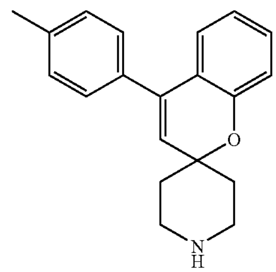 | 292.1 |
| 31I | 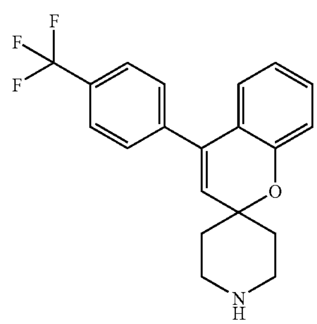 | 346.1 |
| 31J | 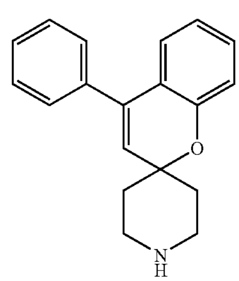 | 278.1 |
| 31K | 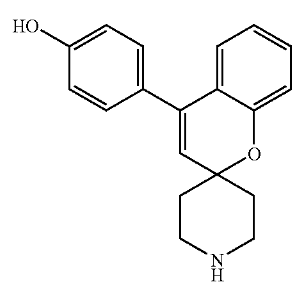 | 294.0 |

C. TABLE 1-continued

| Example | Structure | [M + H]+ |
|---|---|---|
| 31L | 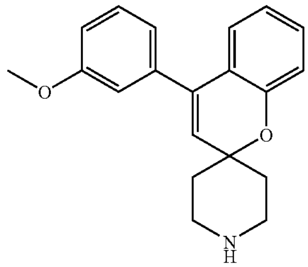 | 308.0 |
| 31M | 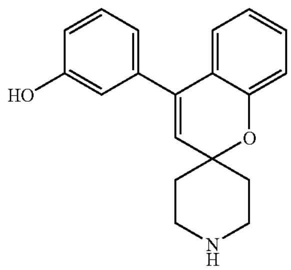 | 294.0 |
| 31N | 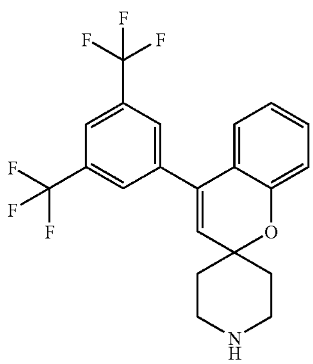 | 414.1 |
| 31O | 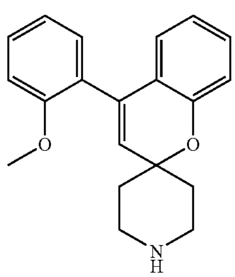 | 308.0 |
| 31P | 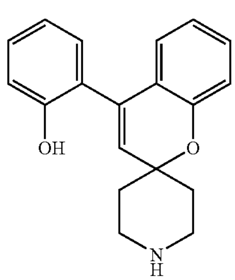 | 294.0 |

C. TABLE 1-continued

| Example | Structure | [M + H]+ |
|---|---|---|
| 31Q | 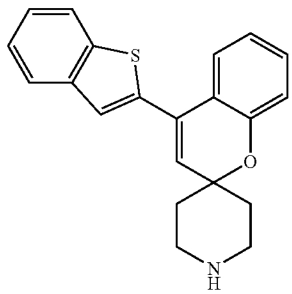 | 333.9 |
| 31R | 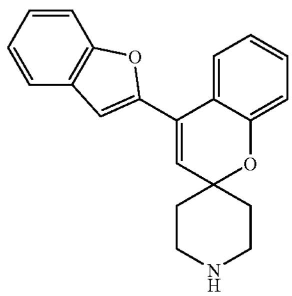 | 318.1 |
| 31S | 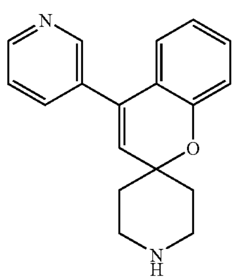 | 279.1 |
| 31T | 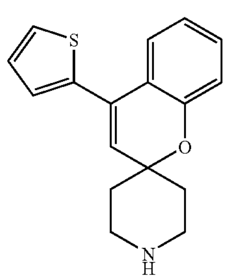 | 283.9 |
| 31U | 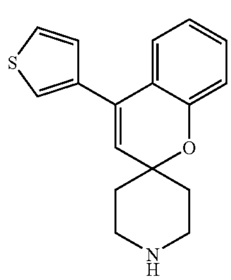 | 284.1 |

C. TABLE 1-continued

| Example | Structure | [M + H]⁺ |
|---|---|---|
| 31V | 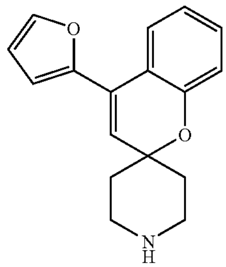 | 268.1 |
| 31W | 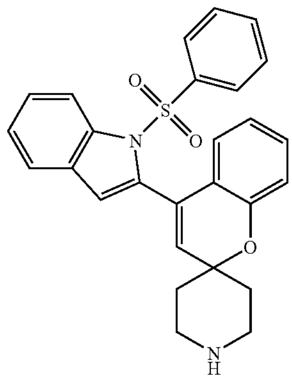 | 457.1 |
| 31X | 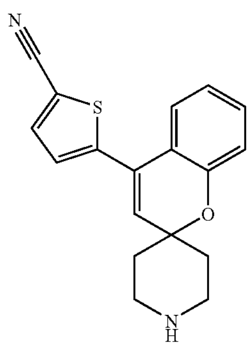 | 308.8 |
| 31Y | 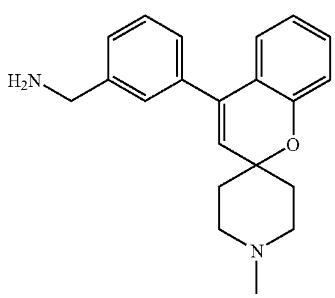 | 321.1 |
| 31Z | 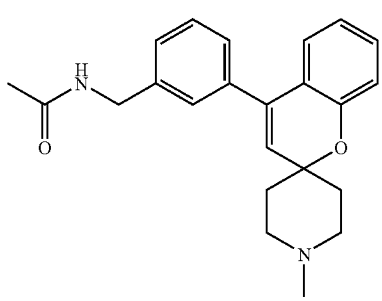 | 363.1 |

C. TABLE 1-continued
| Example | Structure | [M + H]+ |
|---------|-----------|----------|
| 31AA | 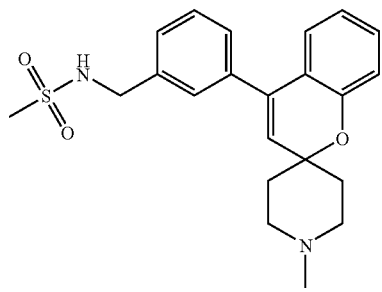 | 399.1 |
| 32A | 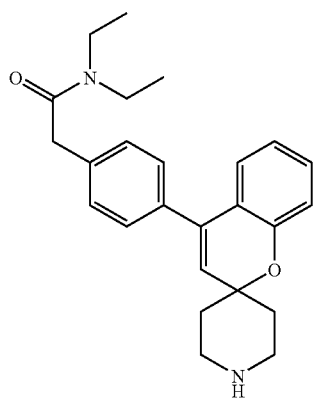 | 391.3 |
| 32B | 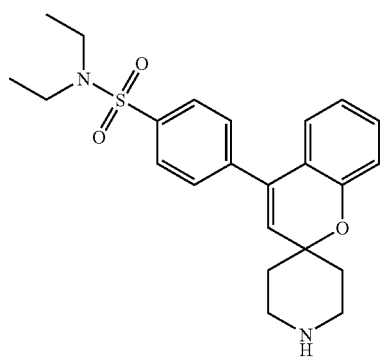 | 454.0 |
| 32C | 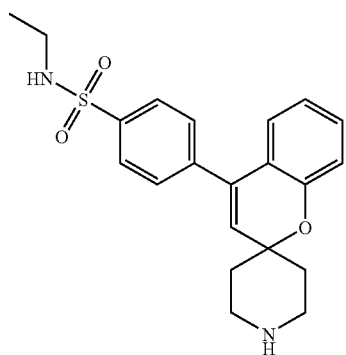 | 385.3 |

C. TABLE 1-continued

| Example | Structure | [M + H]+ |
|---|---|---|
| 32D | 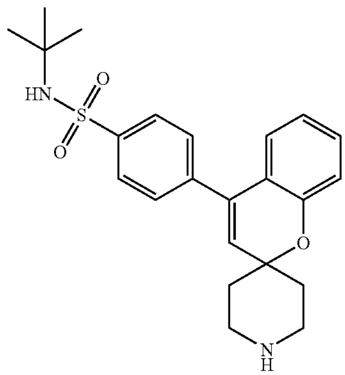 | 413.3 |
| 32E | 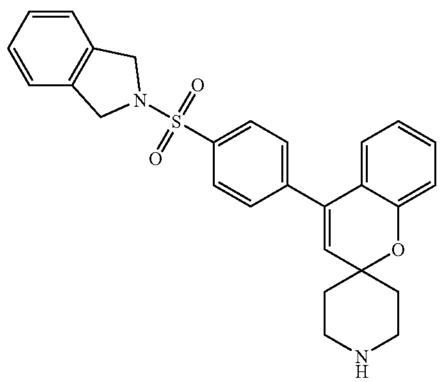 | 459.3 |
| 32F | 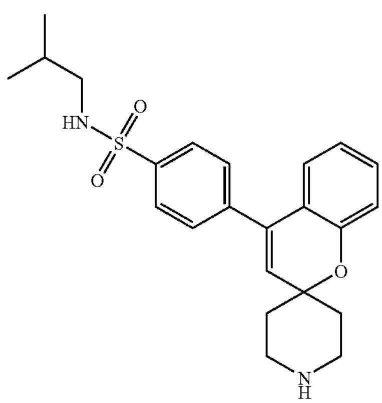 | 413.3 |
| 32G | 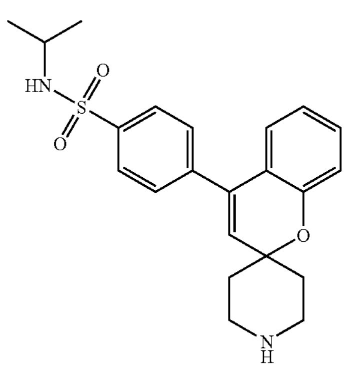 | 399.4 |

C. TABLE 1-continued

| Example | Structure | [M + H]+ |
|---|---|---|
| 32H | 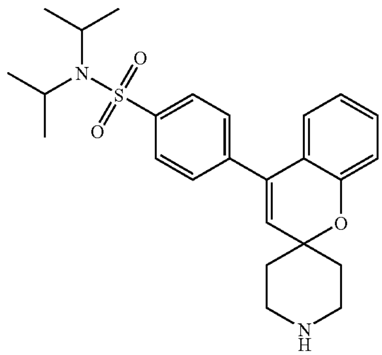 | 441.4 |
| 32I | 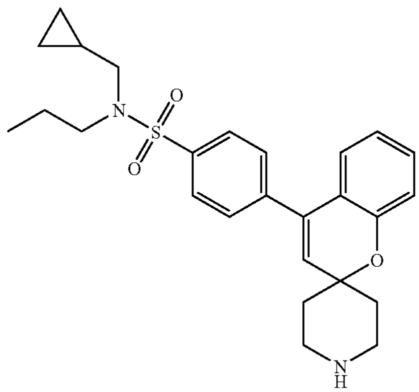 | 453.3 |
| 32J | 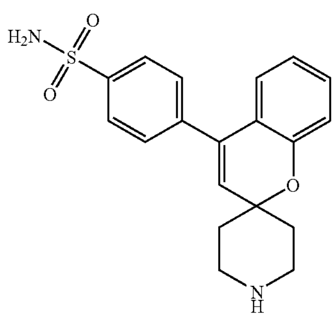 | 357.4 |
| 32K | 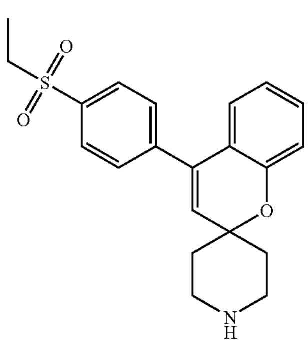 | 370.2 |

C. TABLE 1-continued

| Example | Structure | [M + H]⁺ |
|---------|-----------|----------|
| 32L | 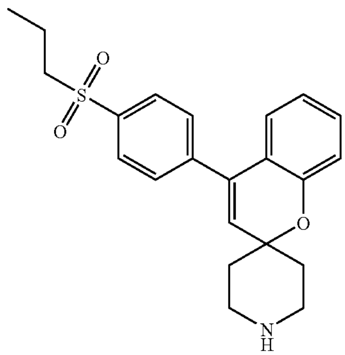 | 384.2 |
| 32M | 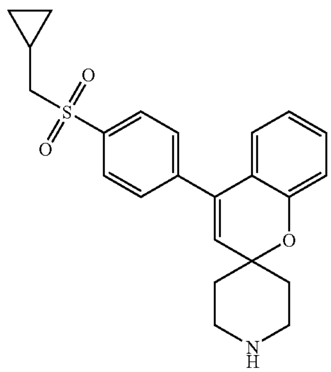 | 396.2 |
| 32N | 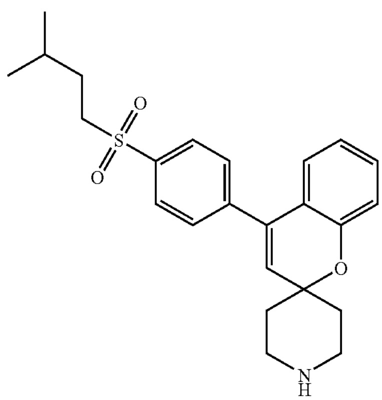 | 412.2 |
| 32O | 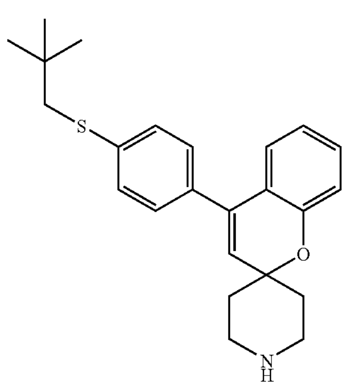 | 412.2 |

C. TABLE 1-continued

| Example | Structure | [M + H]⁺ |
|---|---|---|
| 32P | 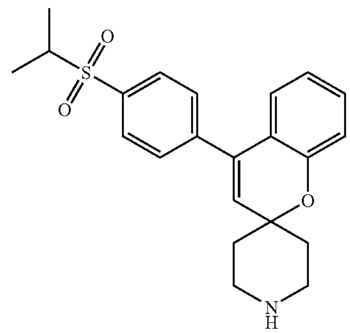 | 384.2 |
| 32Q | 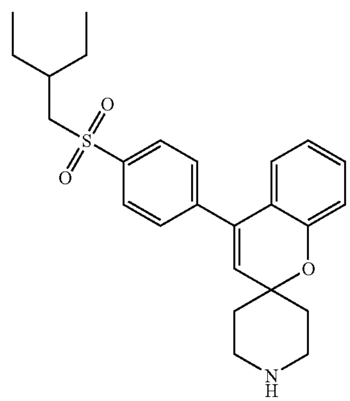 | 426.2 |
| 32R | 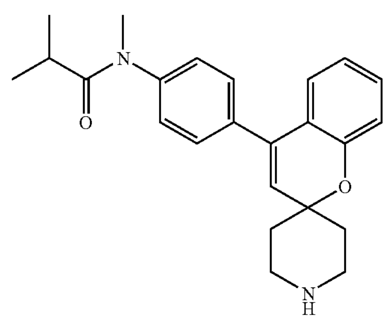 | 377.3 |
| 32S | 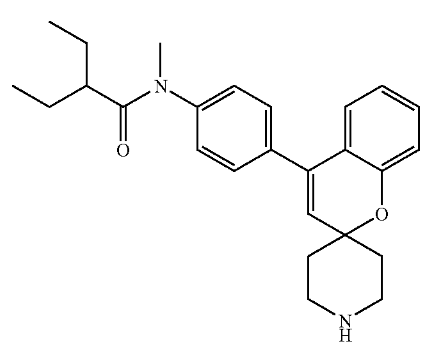 | 405.4 |

C. TABLE 1-continued

| Example | Structure | [M + H]+ |
|---|---|---|
| 32T | 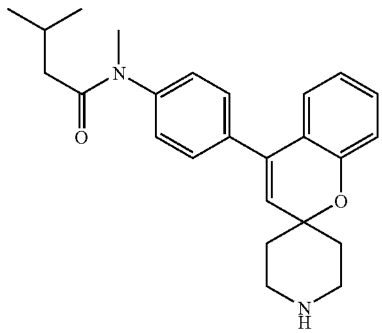 | 391.3 |
| 32U | 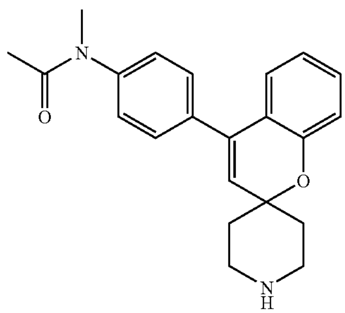 | 349.2 |
| 32V | 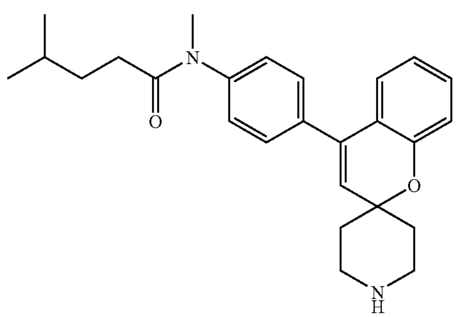 | 405.3 |
| 32W | 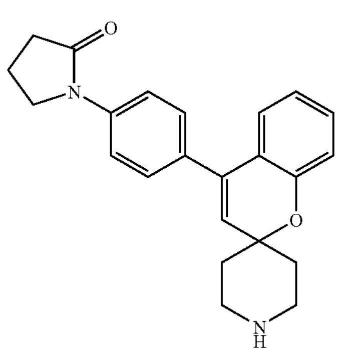 | 361.2 |

C. TABLE 1-continued

| Example | Structure | [M + H]⁺ |
|---|---|---|
| 32X | 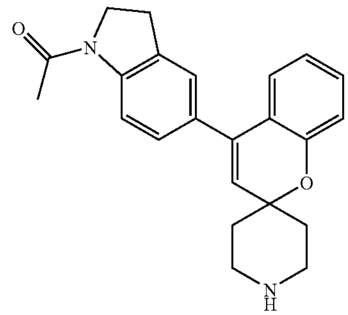 | 361.3 |
| 32Y | 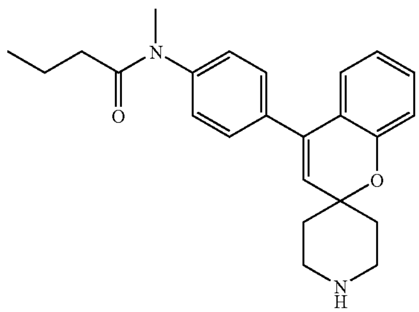 | 377.4 |
| 32Z | 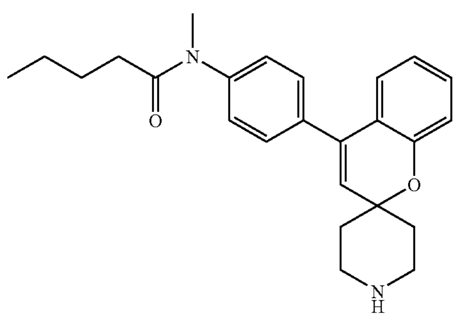 | 391.4 |
| 33A | 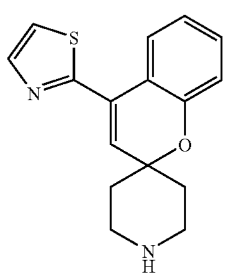 | 284.9 |
| 33B | 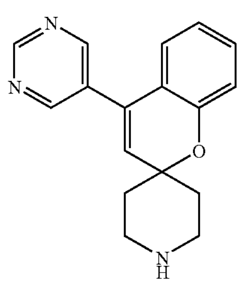 | 279.9 |

C. TABLE 1-continued

| Example | Structure | [M + H]+ |
|---|---|---|
| 33C | 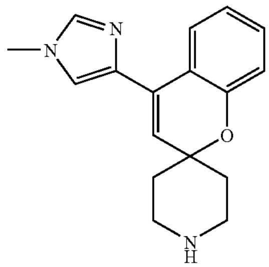 | 282.0 |
| 33D | 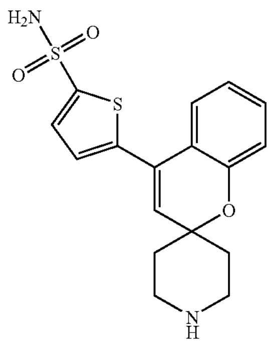 | 362.9 |
| 33E | 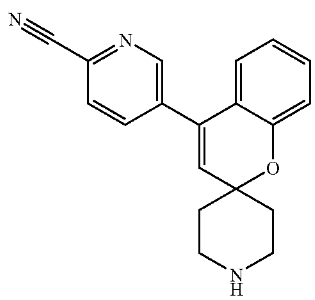 | 303.9 |
| 33F | 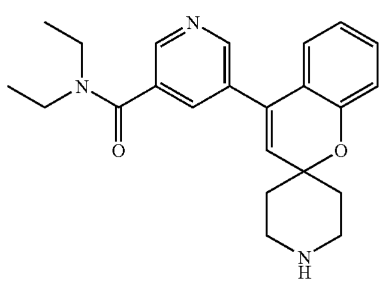 | 378.3 |
| 33G | 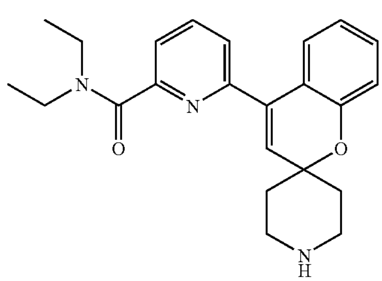 | 378.2 |

C. TABLE 1-continued

| Example | Structure | [M + H]+ |
|---------|-----------|----------|
| 33H | 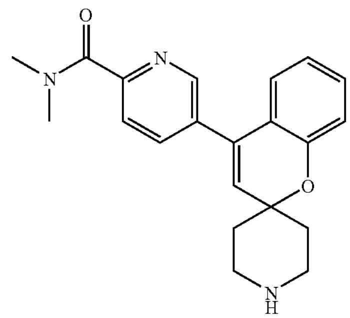 | 350.2 |
| 33I | 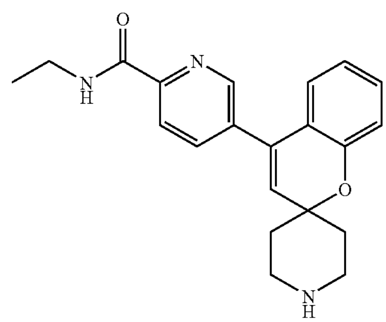 | 350.2 |
| 33J | 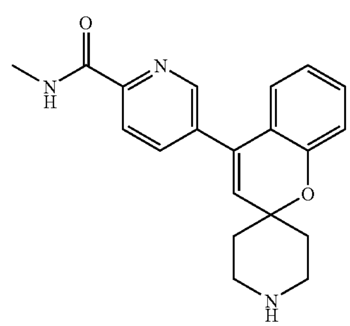 | 336.2 |
| 33K | 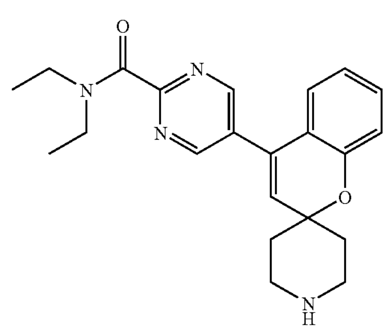 | 379.3 |

C. TABLE 1-continued

| Example | Structure | [M + H]⁺ |
|---|---|---|
| 33L | 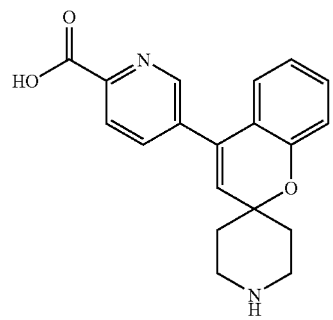 | 321.9 |
| 34A | 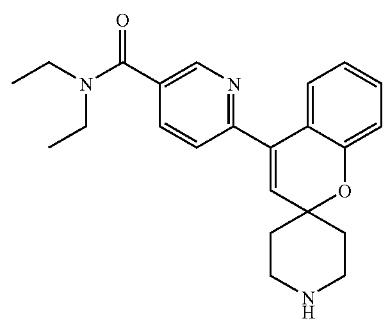 | 378.4 |
| 34B | 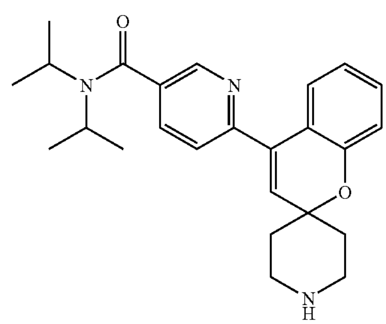 | 406.4 |
| 34C | 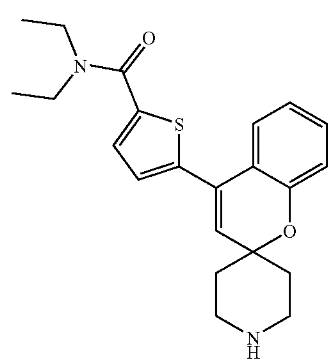 | 383.3 |

C. TABLE 1-continued
| Example | Structure | [M + H]+ |
|---|---|---|
| 34D | 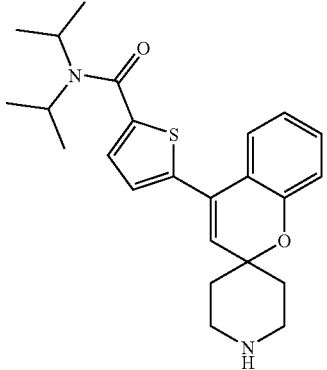 | 411.4 |
| 34E | 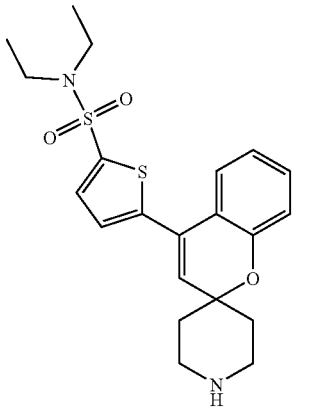 | 419.2 |
| 34F | 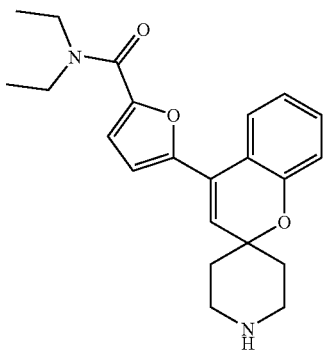 | 367.3 |
| 34G | 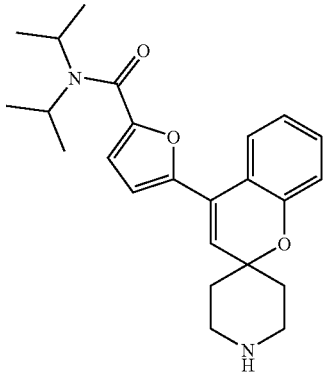 | 395.5 |

C. TABLE 1-continued
| Example | Structure | [M + H]+ |
|---|---|---|
| 34H | 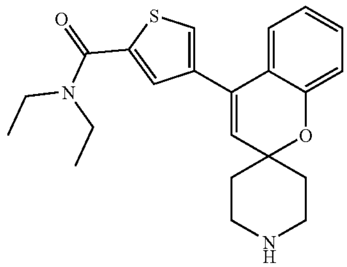 | 383.4 |
| 34I | 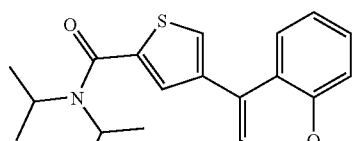 | 411.4 |
| 34J | 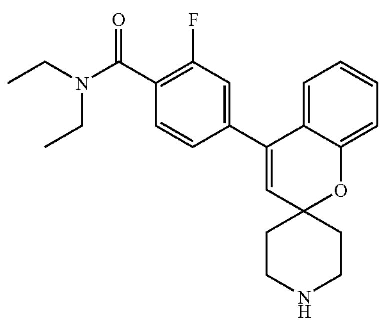 | 395.0 |
| 34K | 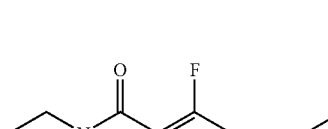 | 395.0 |
| 34L | 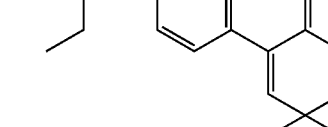 | 391.0 |

C. TABLE 1-continued

| Example | Structure | [M + H]+ |
|---|---|---|
| 34M | 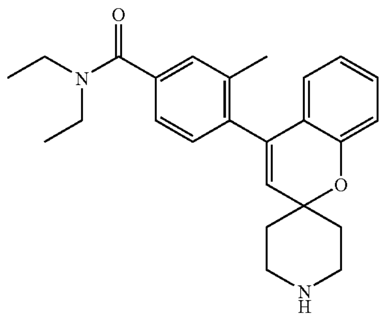 | 391.0 |
| 34N | 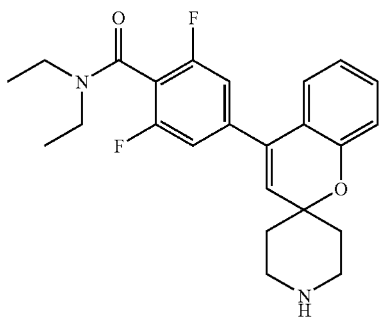 | 413.0 |
| 34O | 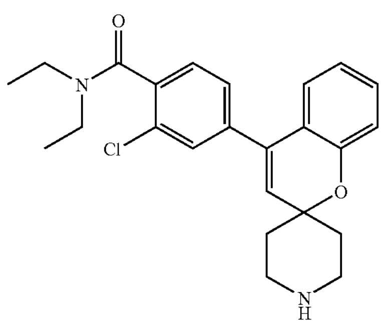 | 411.0 |
| 34P | 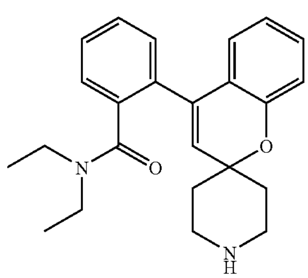 | 377.4 |
| 35A | 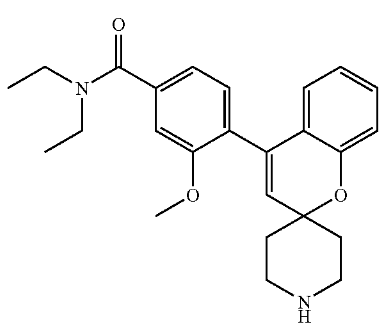 | 407.0 |

C. TABLE 1-continued

| Example | Structure | [M + H]+ |
|---|---|---|
| 35B | 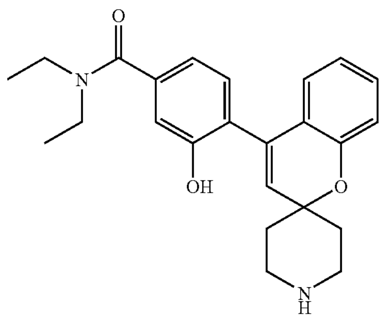 | 393.3 |
| 36A | 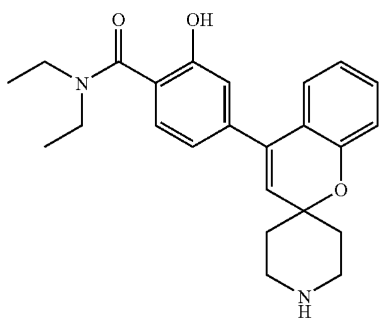 | 393.4 |
| 36B | 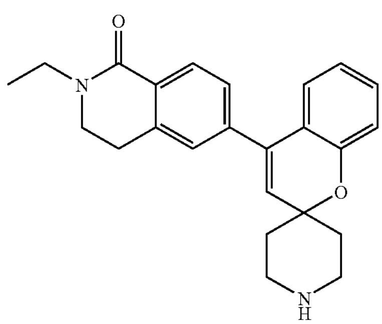 | 375.3 |
| 37A | 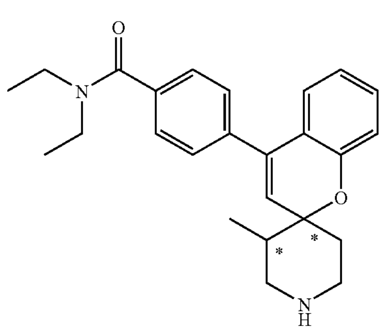 | 391.3 |

C. TABLE 1-continued

| Example | Structure | [M + H]+ |
|---------|-----------|----------|
| 37B | (structure) | 391.3 |

21B and 21C are enantiomeric with respect to one another, but their absolute stereochemistry has not been conclusively established.

21D and 21E are diastereomeric with respect to one another, but their absolute stereochemistry has not been conclusively established.

24B and 24C are geometric isomers with respect to one another (wherein the hydroxyl is either equatorial or axial), but the conformation of each has not been conclusively established.

24D and 24E are geometric isomers with respect to one another (wherein the hydroxyl is either equatorial or axial), but the conformation of each has not been conclusively established.

24F and 24G are geometric isomers with respect to one another (wherein the hydroxyl is either equatorial or axial), but the conformation of each has not been conclusively established.

27B and 27C are enantiomeric with respect to one another, and their absolute stereochemistry has been conclusively established using X-ray crystallography.

27E and 27F are enantiomeric with respect to one another, but their absolute stereochemistry has not been conclusively established.

27I and 27J are enantiomeric with respect to one another, but their absolute stereochemistry has not been conclusively established.

27L and 27M are enantiomeric with respect to one another, but their absolute stereochemistry has not been conclusively established.

27O and 27P are enantiomeric with respect to one another, but their absolute stereochemistry has not been conclusively established.

27R and 27S are enantiomeric with respect to one another, but their absolute stereochemistry has not been conclusively established.

27U and 27V are enantiomeric with respect to one another, but their absolute stereochemistry has not been conclusively established.

37A and 37B are diastereomeric with respect to one another, but each is a racemic mixture of its two possible enantiomers. Their absolute stereochemistry has not been conclusively established.

TABLE 2

| Example | Structure | [M + H]+ |
|---------|-----------|----------|
| 7D | (structure) | 446.4 |
| 7E | (structure) | 462.4 |

TABLE 2-continued
| Example | Structure | [M + H]+ |
|---|---|---|
| 11G | 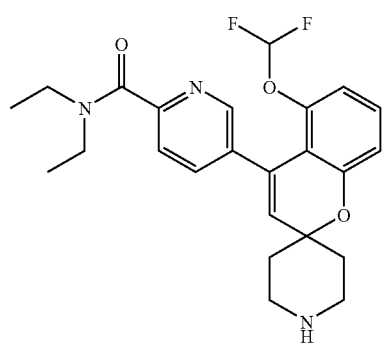 | 443.3 |
| 11H | 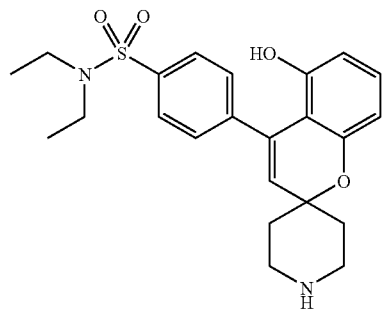 | 444.3 |
| 11I | 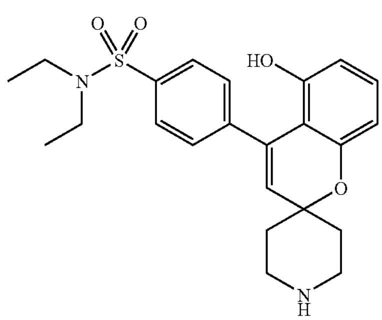 | 429.3 |
| 22F | 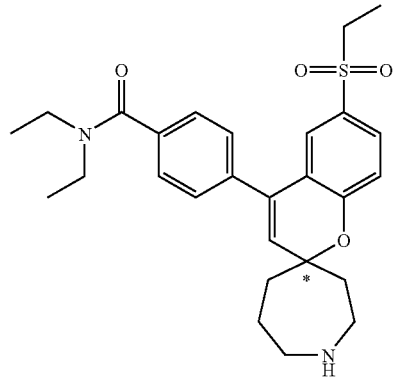 | 483.2 |
TABLE 2-continued
| Example | Structure | [M + H]+ |
|---|---|---|
| 33M | 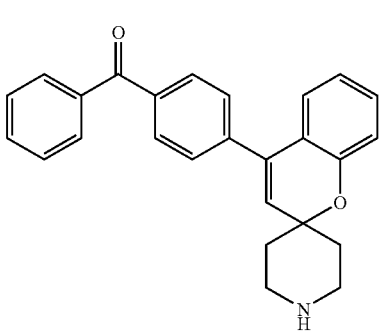 | 320.1 |
| 33N | 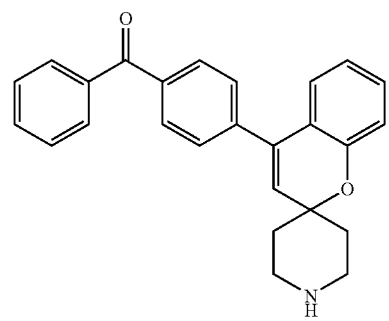 | 382.4 |
| 38A | 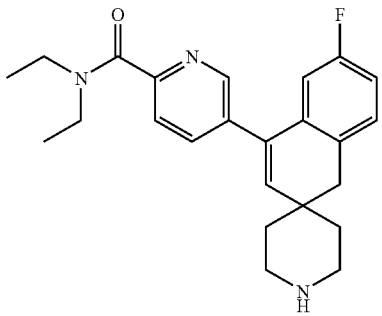 | 394.3 |
| 38B | 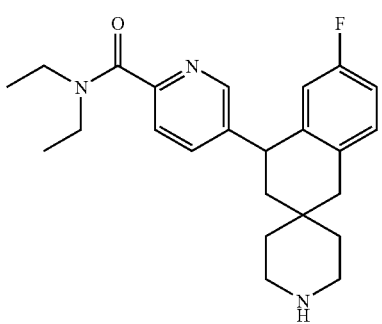 | 396.4 |

TABLE 2-continued
| Example | Structure | [M + H]+ |
|---|---|---|
| 38C | 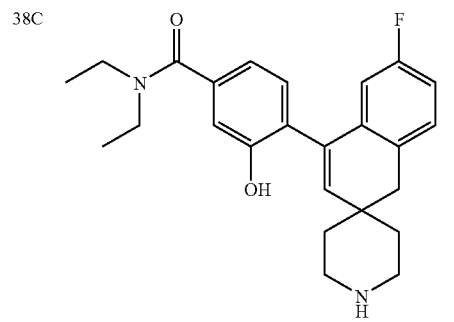 | 409.7 |
| 38D | 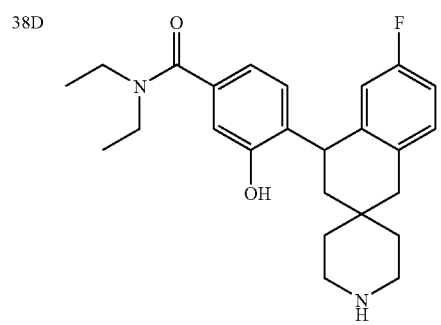 | 411.7 |
| 39A | 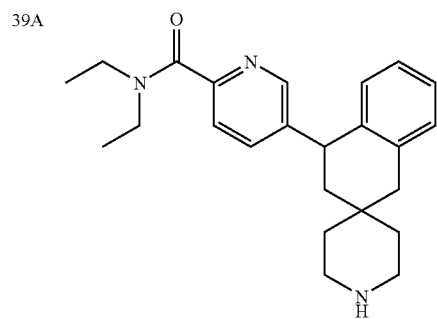 | 378.3 |
| 39B | 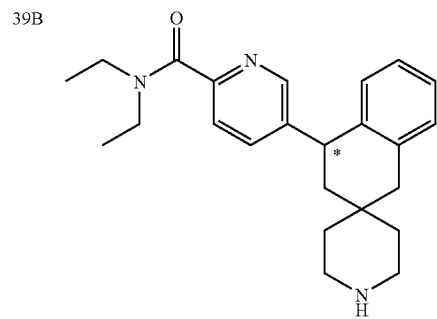 | 378.8 |
| 39C | 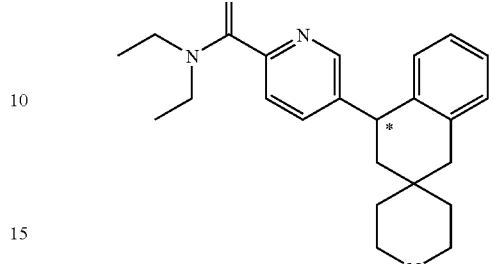 | 378.8 |
| 39D | 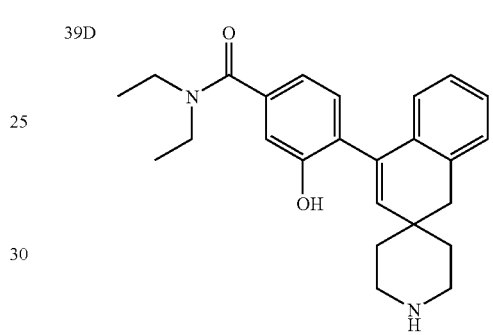 | 391.4 |
| 39E | 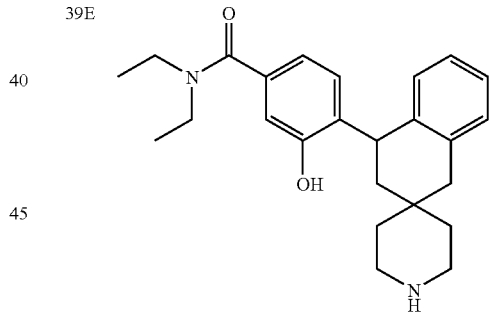 | 393.4 |
| 39F | 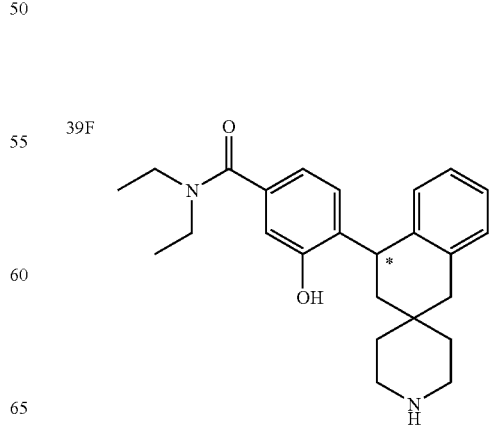 | 393.8 |

TABLE 2-continued
| Example | Structure | [M + H]+ |
|---|---|---|
| 39G | 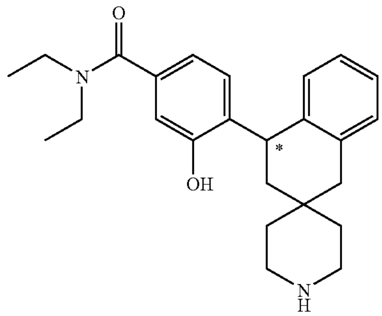 | 393.8 |
| 40A | 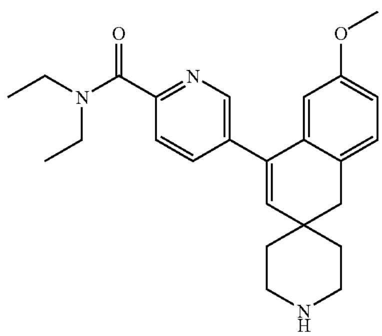 | 406.3 |
| 40B | 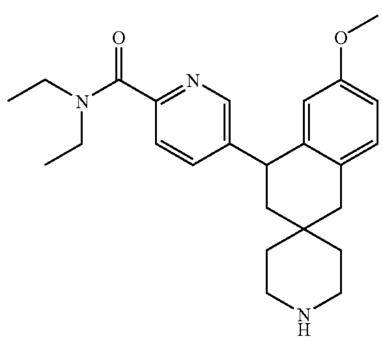 | 408.5 |
| 40C | 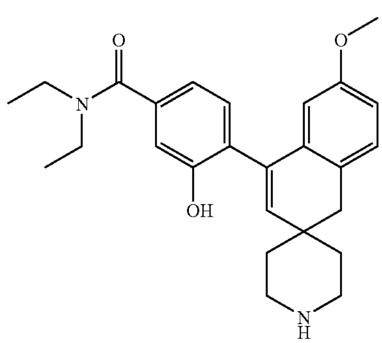 | 421.3 |
| 41A | | 407.4 |
| 41B | | 420.3 |
| 41C | | 420.3 |
| 41D | | 406.4 |
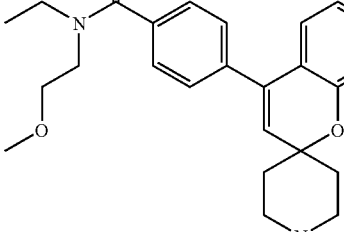
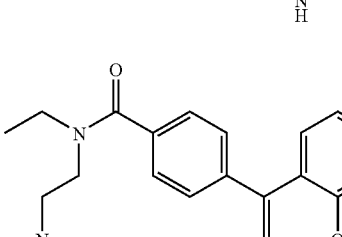
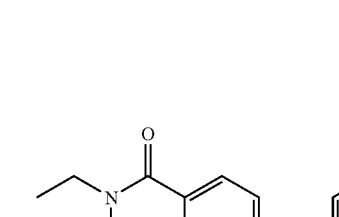

TABLE 2-continued
| Example | Structure | [M + H]+ |
|---|---|---|
| 41E | 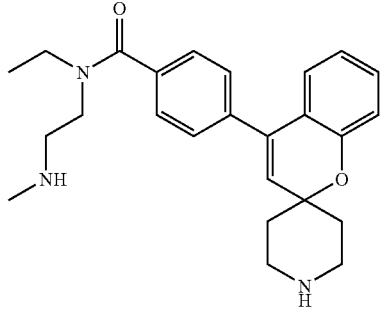 | 406.8 |
| 42A | 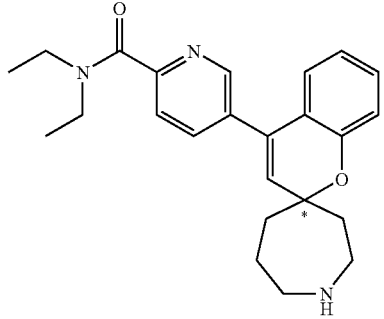 | 392.3 |
| 42B | 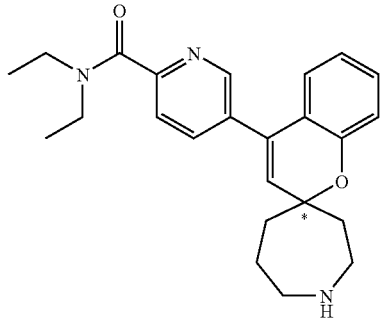 | 392.3 |
| 42C | 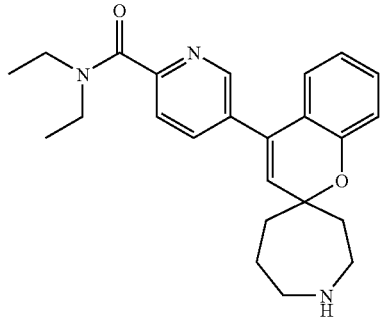 | 392.4 |
| 42D | 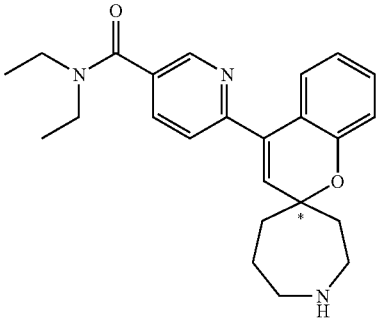 | 392.8 |
| 42E | 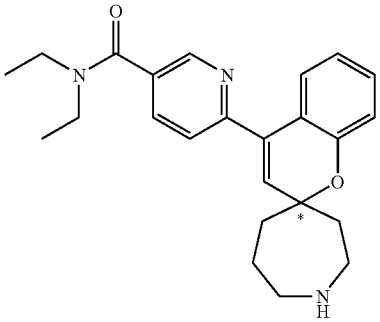 | 392.8 |
| 42F | 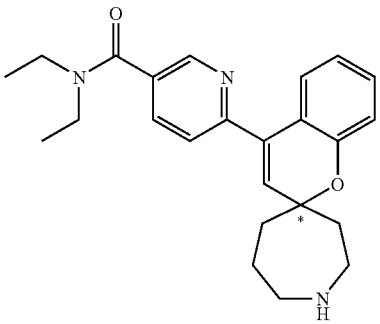 | 392.4 |
| 42G | 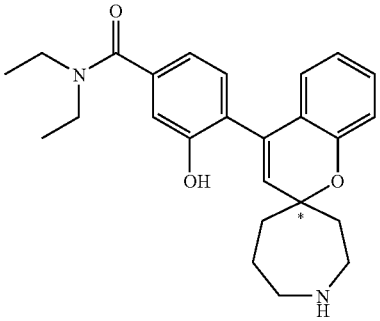 | 407.7 |

TABLE 2-continued
| Example | Structure | [M + H]+ |
|---|---|---|
| 42H | 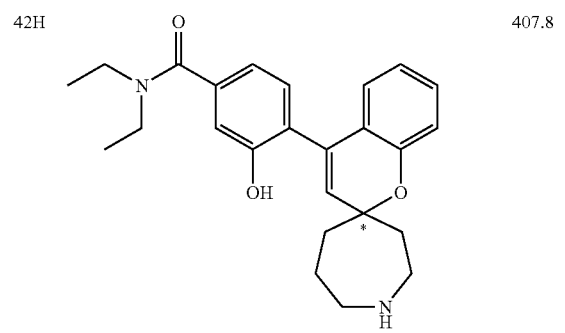 | 407.8 |
| 42I | 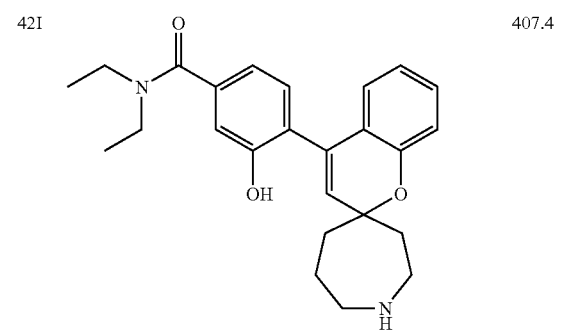 | 407.4 |
| 43A | 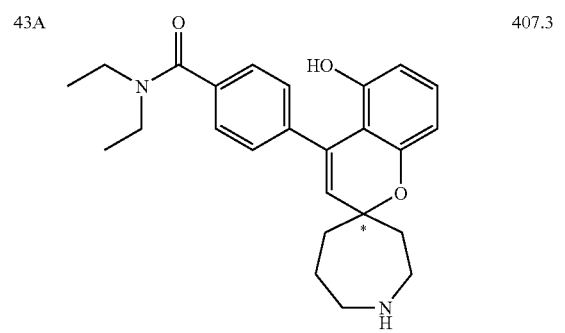 | 407.3 |
| 43B | 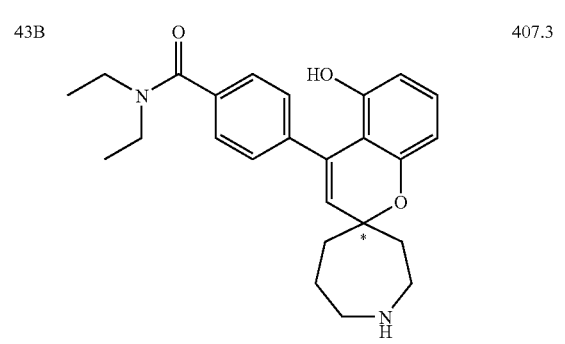 | 407.3 |
| 43C | 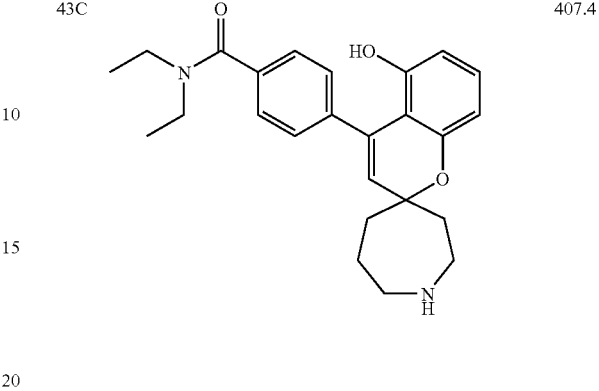 | 407.4 |
| 43D | 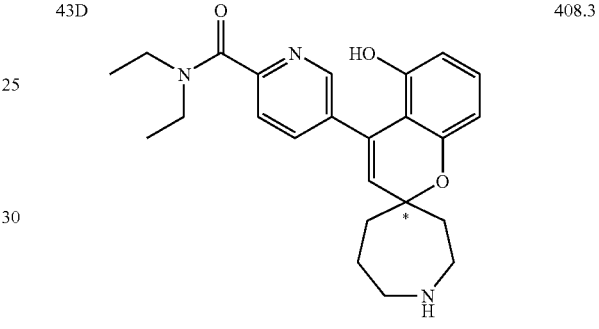 | 408.3 |
| 43E | 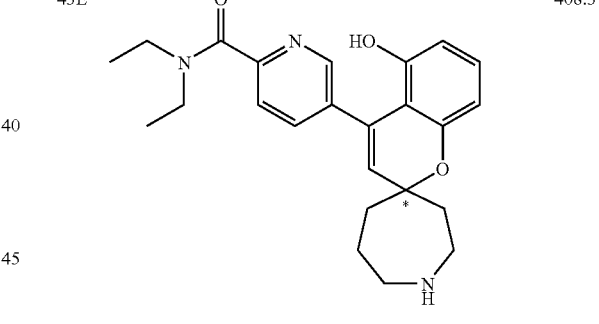 | 408.3 |
| 43F | 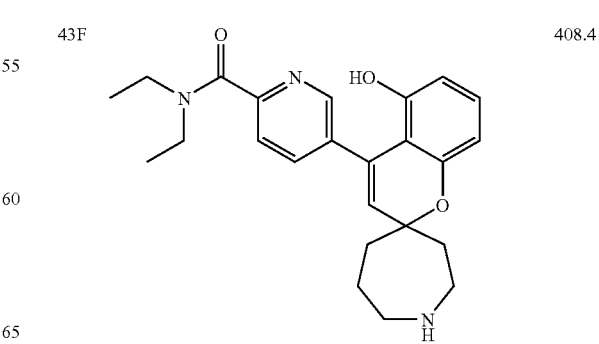 | 408.4 |

TABLE 2-continued
| Example | Structure | [M + H]+ |
|---|---|---|
| 44A | 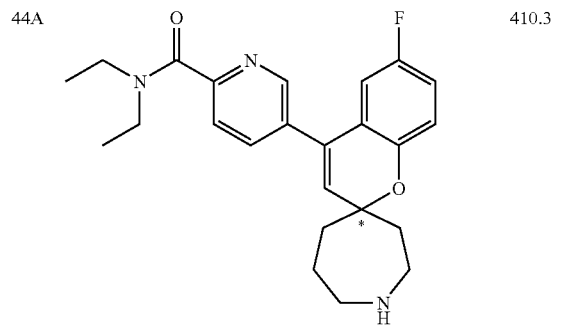 | 410.3 |
| 44B | 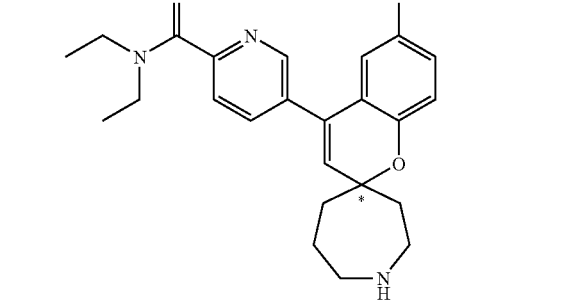 | 410.8 |
| 44C | 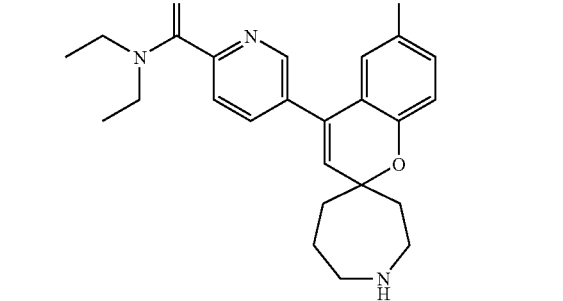 | 410.4 |
| 44D | 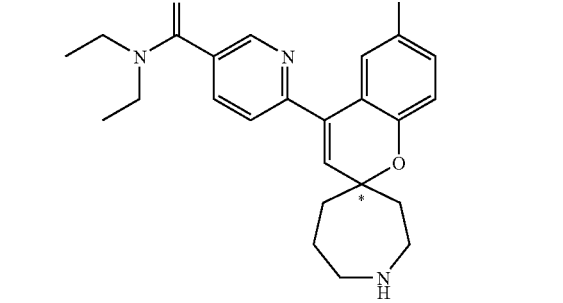 | 410.8 |
| 44E | 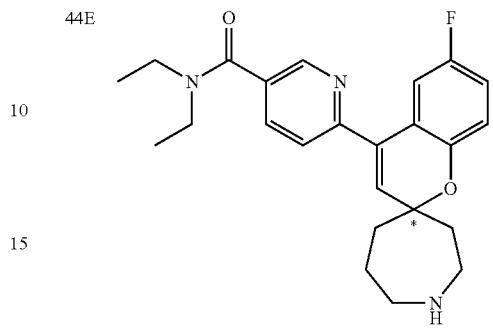 | 410.8 |
| 44F | 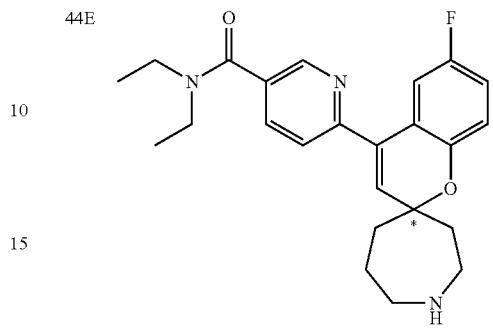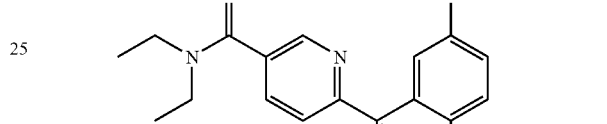 | 410.4 |
| 45A | 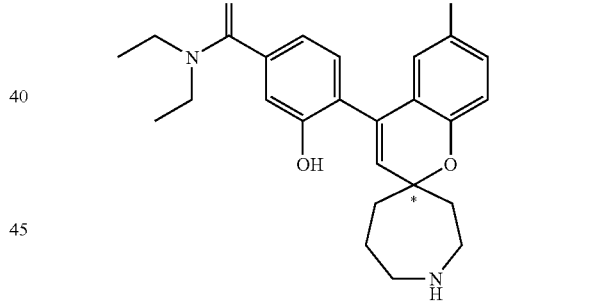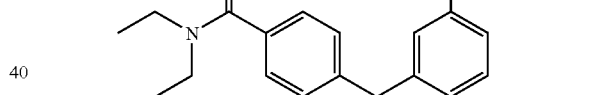 | 425.8 |
| 45B | 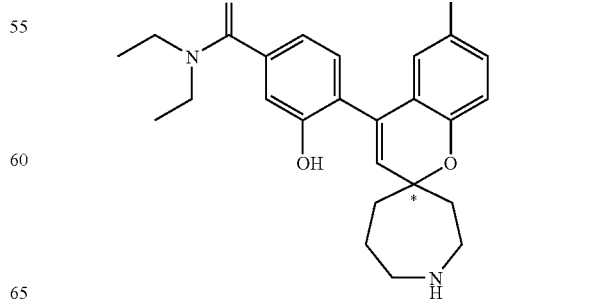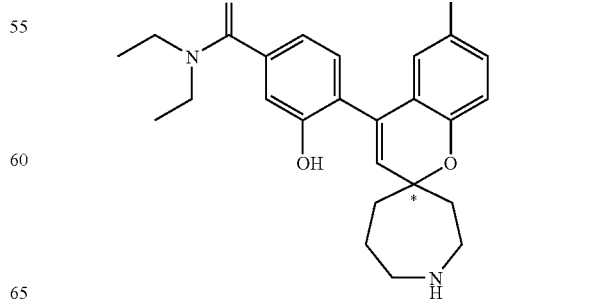 | 425.8 |

TABLE 2-continued
| Example | Structure | [M + H]+ |
|---|---|---|
| 45C | 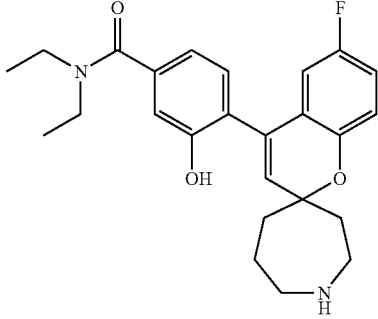 | 425.4 |
| 45D | 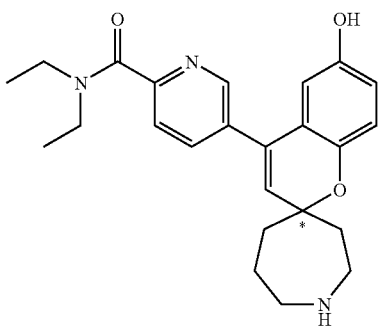 | 408.3 |
| 45E | 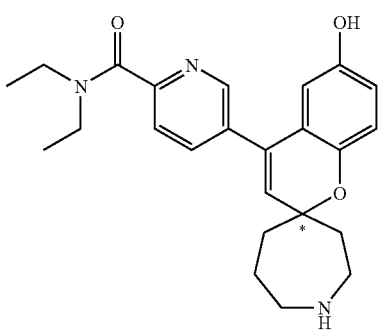 | 408.8 |
| 45F | 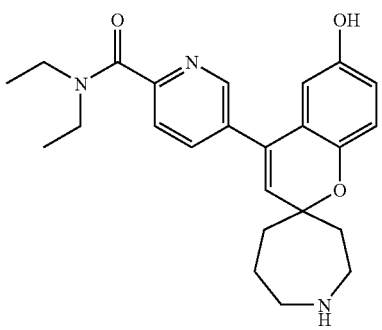 | 408.4 |
TABLE 2-continued
| Example | Structure | [M + H]+ |
|---|---|---|
| 46A | 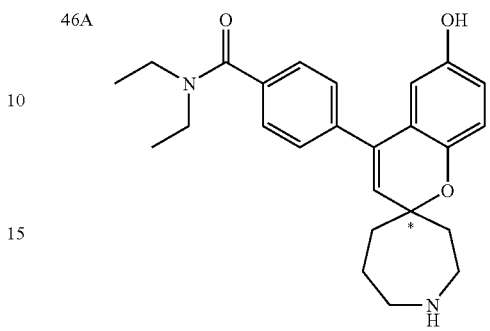 | 407.4 |
| 46B | 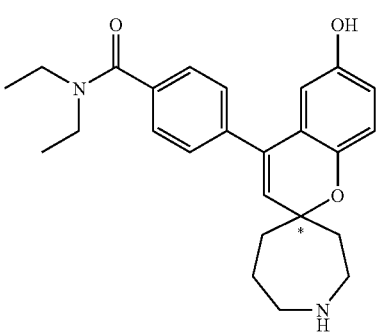 | 407.4 |
| 46C | 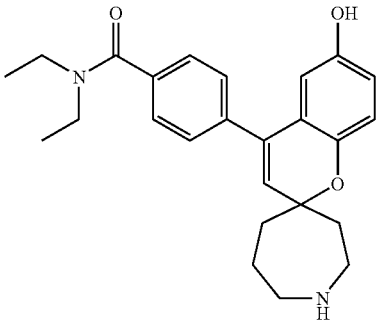 | 407.4 |
| 47A | 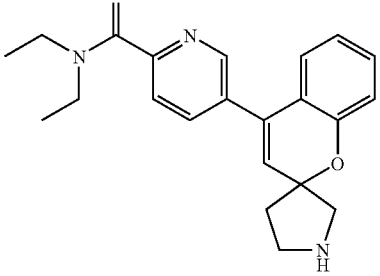 | 364.7 |

TABLE 2-continued

| Example | Structure | [M + H]+ |
|---|---|---|
| 47B | 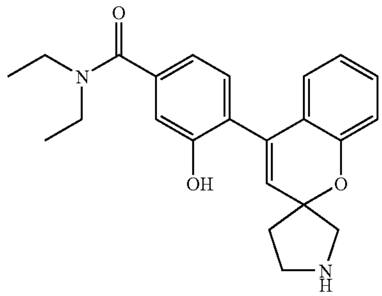 | 379.8 |
| 47C | 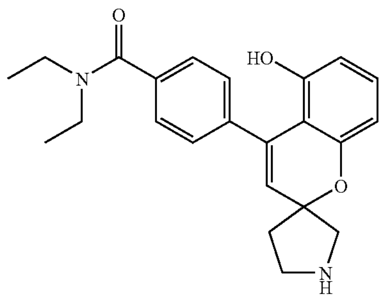 | 379.3 |
| 47D | 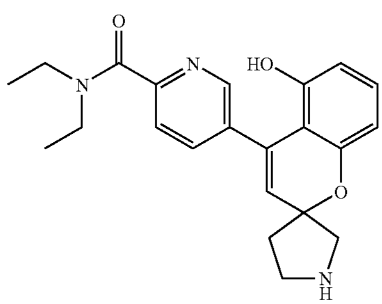 | 380.4 |
| 47E | 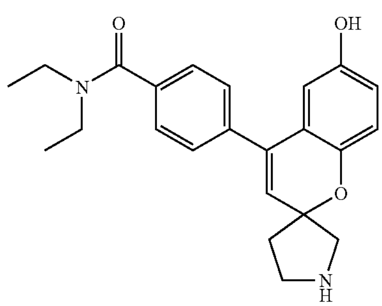 | 379.8 |
| 47F | 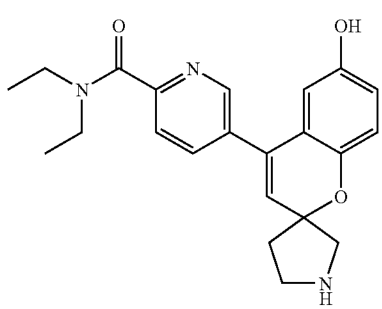 | 380.7 |

TABLE 2-continued

| Example | Structure | [M + H]+ |
|---|---|---|
| 48A | 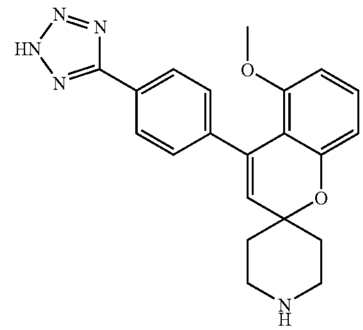 | 376.3 |
| 48B | 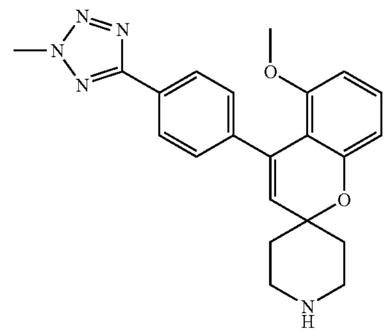 | 390.5 |
| 48C | 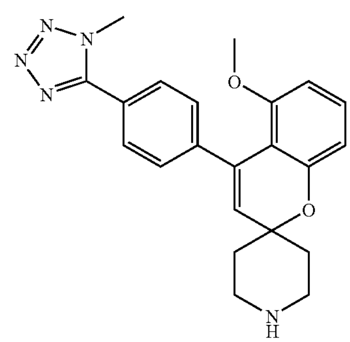 | 390.4 |
| 48D | 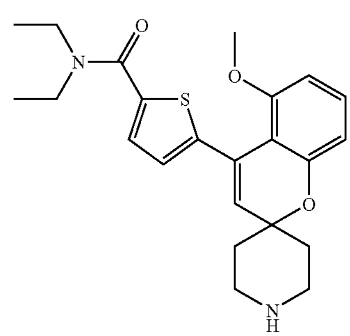 | 413.7 |

TABLE 2-continued
| Example | Structure | [M + H]+ |
|---|---|---|
| 48E | 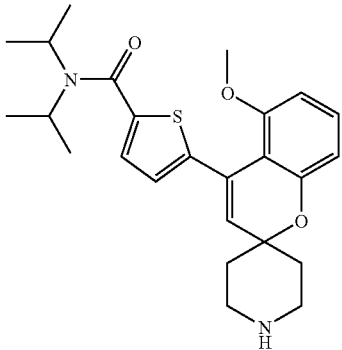 | 441.4 |
| 48F | 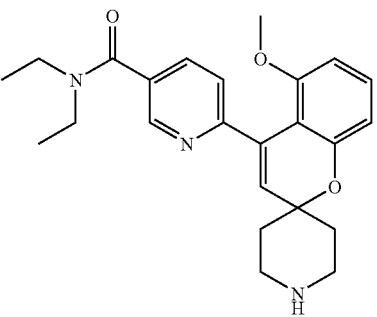 | 408.4 |
| 49A | 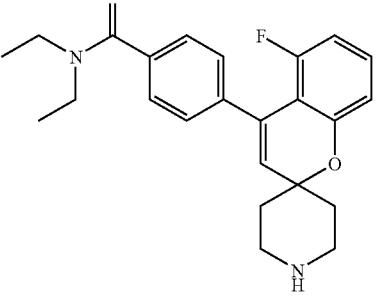 | 395.3 |
| 49B | 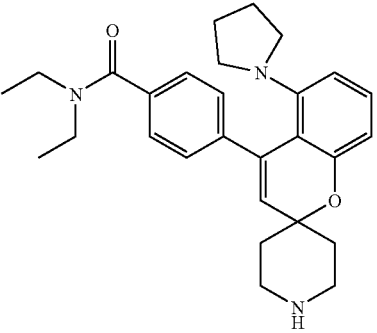 | 446.8 |
TABLE 2-continued
| Example | Structure | [M + H]+ |
|---|---|---|
| 49C | 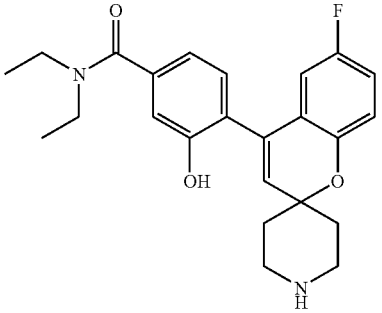 | 411.7 |
| 49D | 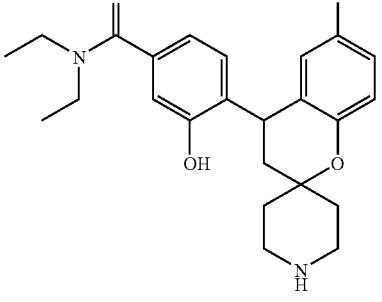 | 413.7 |
| 50A | 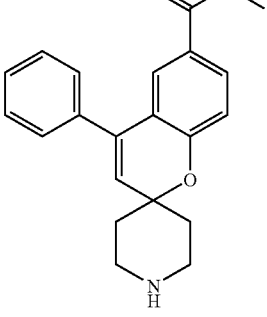 | 336.4 |
| 50B | 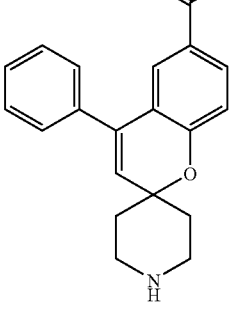 | 322.1 |

TABLE 2-continued

| Example | Structure | [M + H]+ |
|---|---|---|
| 50C | 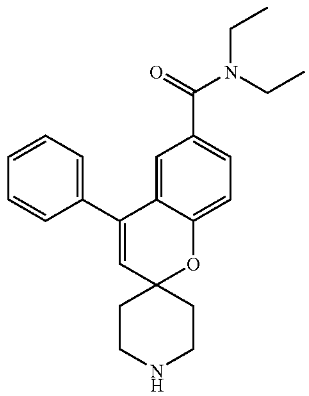 | 377.7 |
| 50D | 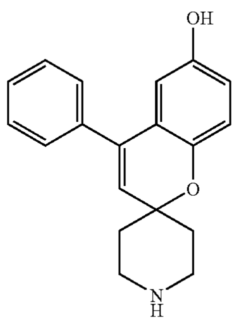 | 294.1 |
| 51A | 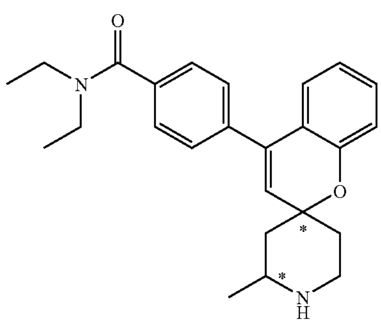 | 391.4 |
| 51B | 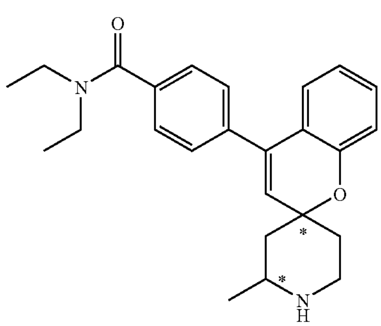 | 391.4 |
| 51C | 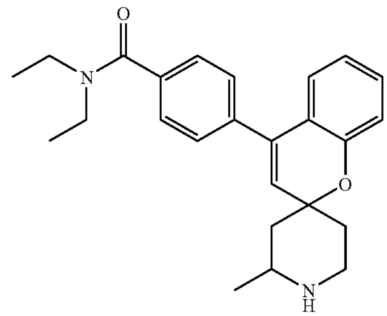 | 391.4 |

TABLE 3

| Example | Structure | [M + H]+ |
|---|---|---|
| 52A | 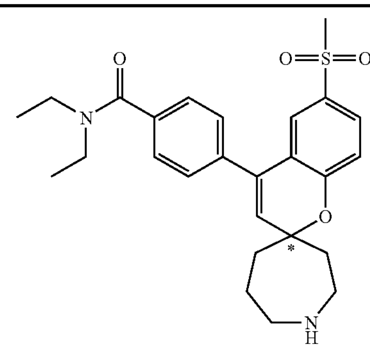 | 469.4 |
| 52B | 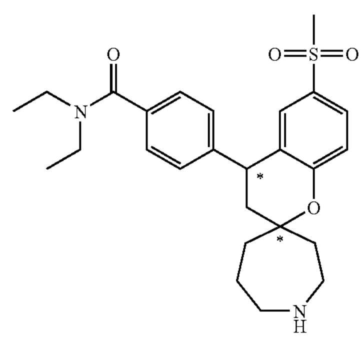 | |
| 52C | 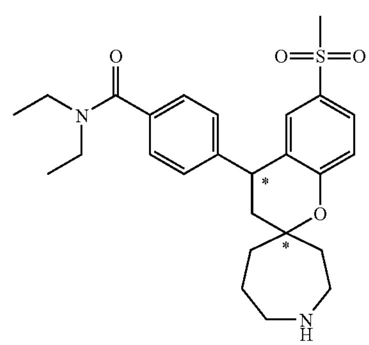 | |

TABLE 3-continued
| Example | Structure | [M + H]+ |
|---------|-----------|----------|
| 52D | 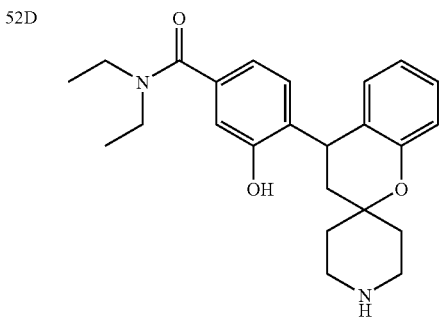 | |
| 52E | 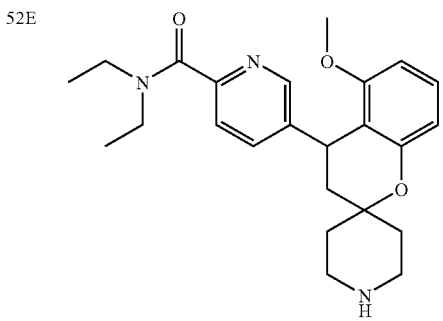 | |
| 52F | 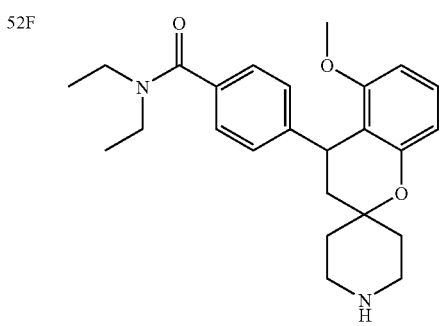 | |
| 53A | 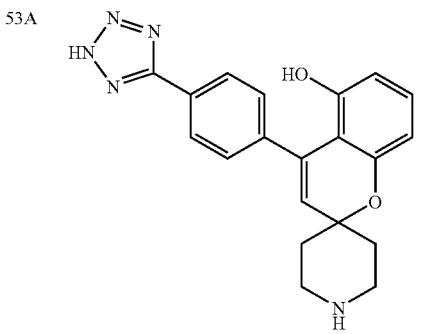 | 360.8 (note: [M − H]−) |
TABLE 3-continued
| Example | Structure | [M + H]+ |
|---------|-----------|----------|
| 53B | 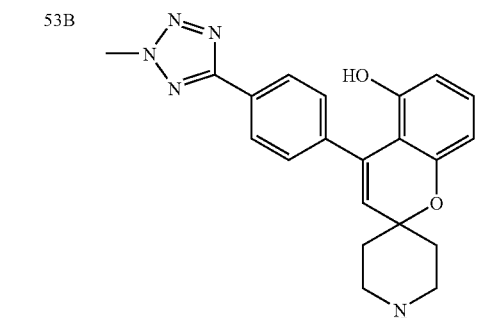 | 376.8 |
| 53C | 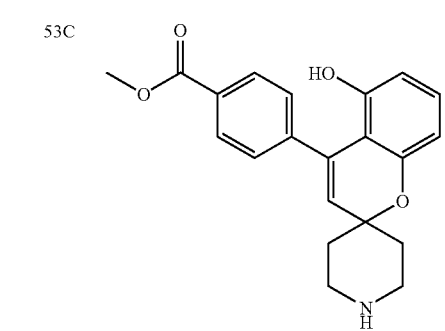 | 352.7 |
| 53D | 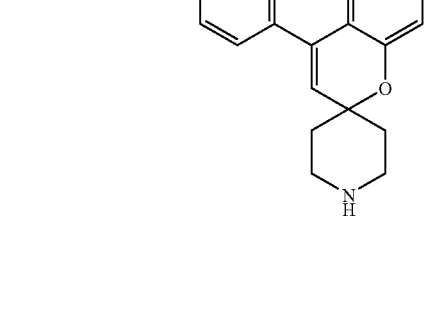 | 338.7 |
| 53E | 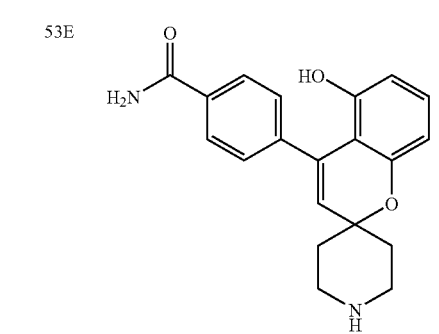 | |

TABLE 3-continued

| Example | Structure | [M + H]⁺ |
|---|---|---|
| 53F | 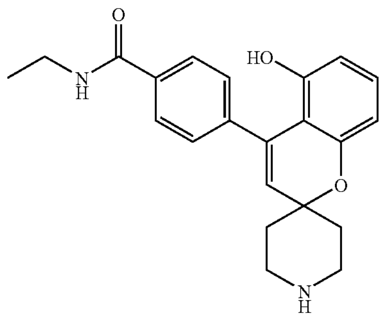 | 365.8 |
| 54A | 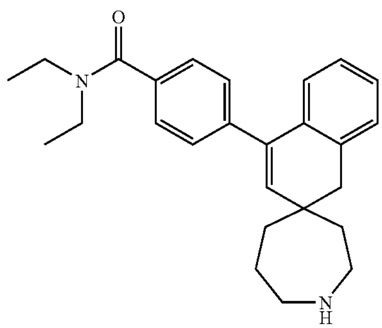 | 389.9 |
| 54B | 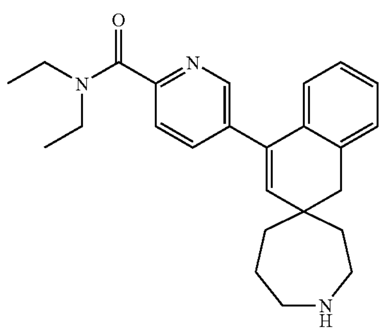 | 390.8 |
| 55A | 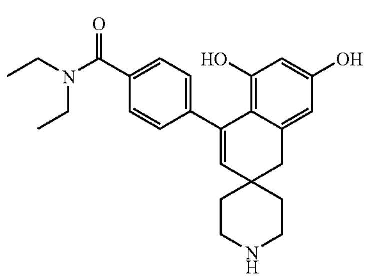 | 407.5 |
| 55B | 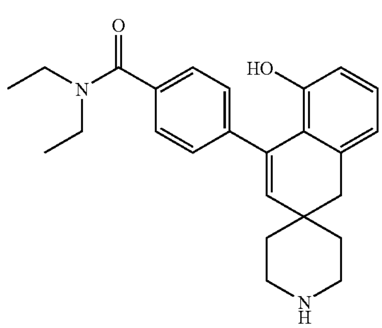 | 391.5 |
| 55C | | 435.7 |
| 56A | | 391.4 |
| 56B | | 393.5 |
| 56C | | 392.4 |
| 56D | | 394.5 |

TABLE 3-continued
| Example | Structure | [M + H]+ |
|---|---|---|
| 57A | 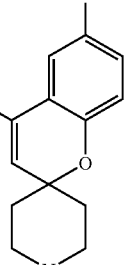 | |
| 57B | 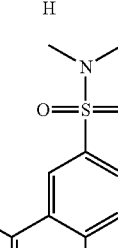 | |
| 57C | 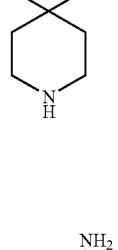 | |
| 57D | 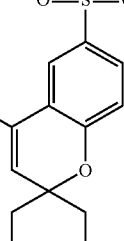 | 356.3 |
TABLE 3-continued
| Example | Structure | [M + H]+ |
|---|---|---|
| 58A | 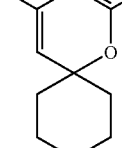 | 295.3 |
| 58B | 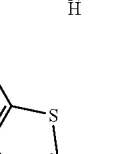 | 350.3 |
| 58C | 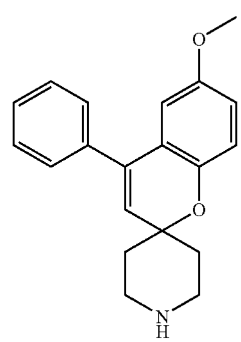 | 308.2 |
| 58D | 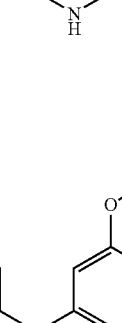 | 348.2 |

TABLE 3-continued
| Example | Structure | [M + H]+ |
|---|---|---|
| 59A | 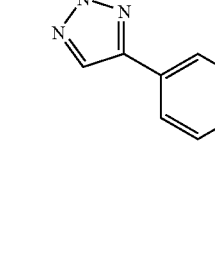 | 389.4 |
| 59B | 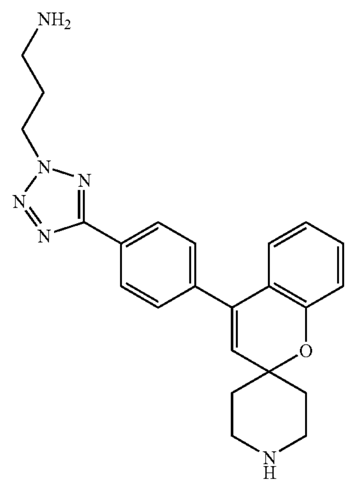 | 403.4 |
| 59C | 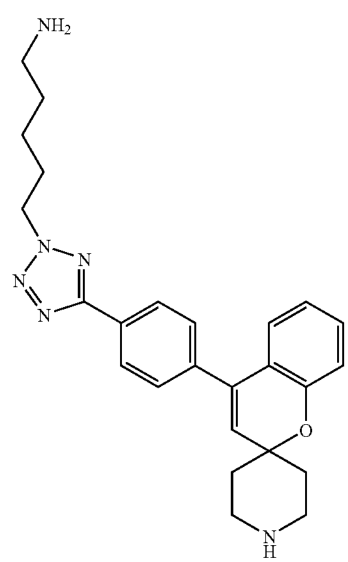 | 431.5 |
| 59D | 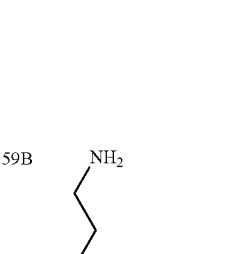 | 445.5 |
| 59E | 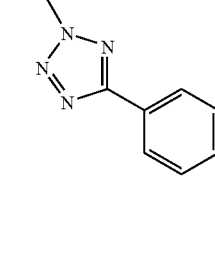 | 431.5 |

TABLE 3-continued
| Example | Structure | [M + H]+ |
|---|---|---|
| 59F | 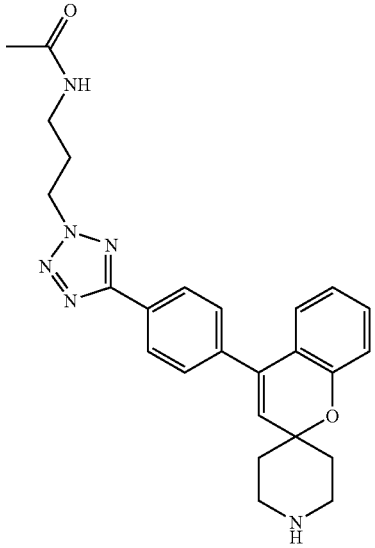 | 445.5 |
| 59G | 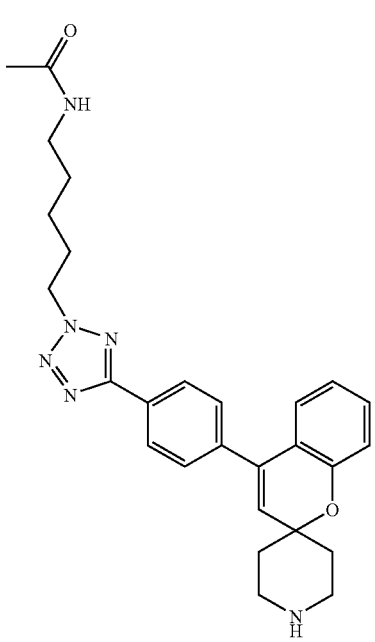 | 473.5 |
TABLE 3-continued
| Example | Structure | [M + H]+ |
|---|---|---|
| 59H | 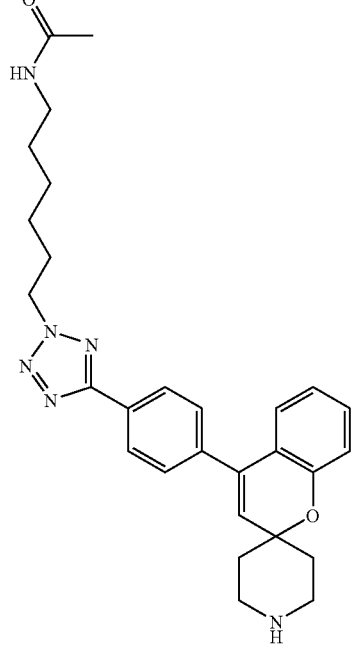 | 487.5 |
| 59I | 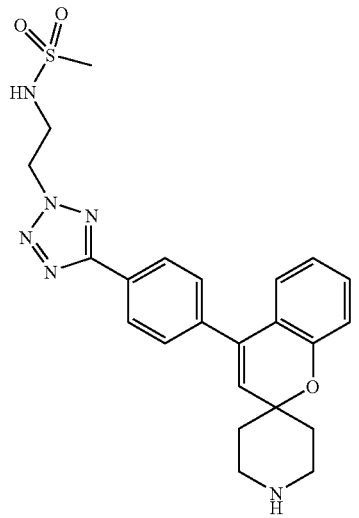 | 467.3 |

TABLE 3-continued

| Example | Structure | [M + H]+ |
|---|---|---|
| 59J | 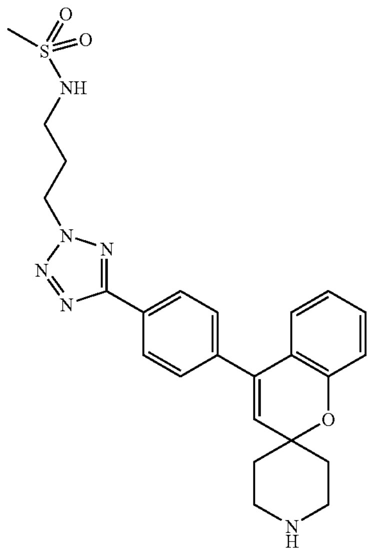 | 481.5 |
| 59K | 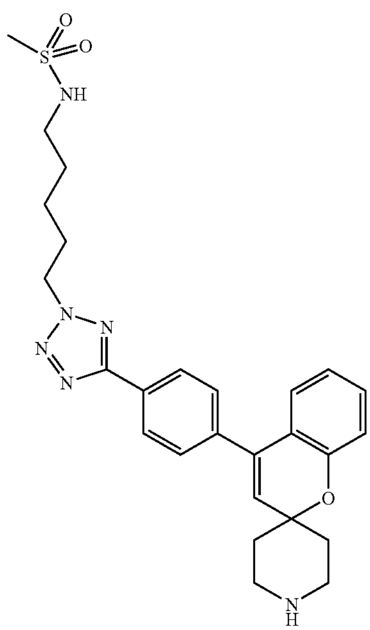 | 509.5 |
| 59L | | 523.6 |
| 60A | | 417.5 |

TABLE 3-continued

| Example | Structure | [M + H]⁺ |
|---|---|---|
| 60B | 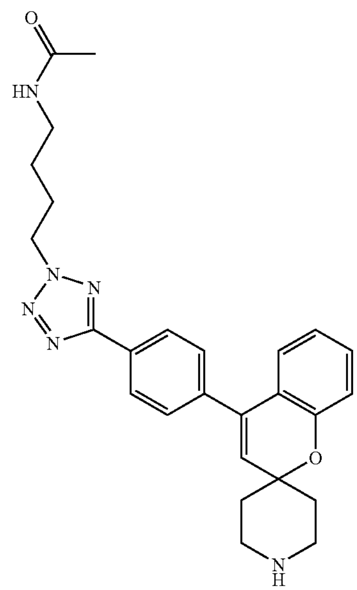 | 459.5 |
| 60C | 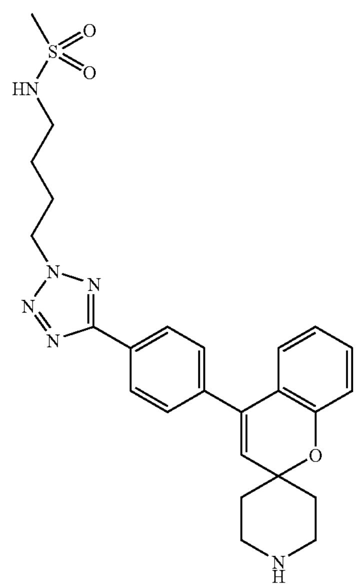 | 495.5 |
| 61A | 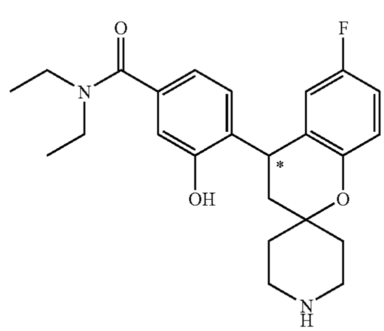 | 413.9 |
| 61B | 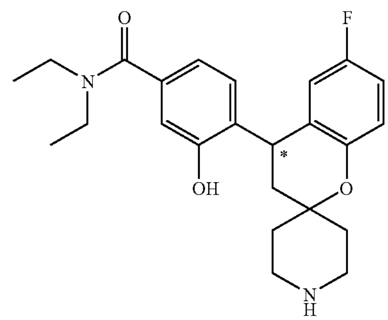 | 413.8 |

39B and 39C are enantiomeric with respect to one another, but their absolute stereochemistry has not been conclusively established.

39F and 39G are enantiomeric with respect to one another, but their absolute stereochemistry has not been conclusively established.

42A and 42B are enantiomeric with respect to one another, but their absolute stereochemistry has not been conclusively established.

42D and 42E are enantiomeric with respect to one another, but their absolute stereochemistry has not been conclusively established.

42G and 42H are enantiomeric with respect to one another, but their absolute stereochemistry has not been conclusively established.

43A and 43B are enantiomeric with respect to one another, but their absolute stereochemistry has not been conclusively established.

43D and 43E are enantiomeric with respect to one another, but their absolute stereochemistry has not been conclusively established.

44A and 44B are enantiomeric with respect to one another, but their absolute stereochemistry has not been conclusively established.

44D and 44E are enantiomeric with respect to one another, but their absolute stereochemistry has not been conclusively established.

45A and 45B are enantiomeric with respect to one another, but their absolute stereochemistry has not been conclusively established.

45D and 45E are enantiomeric with respect to one another, but their absolute stereochemistry has not been conclusively established.

46A and 46B are enantiomeric with respect to one another, but their absolute stereochemistry has not been conclusively established.

51A and 51B are resolvable by chiral column chromatography as individual peaks with respect to one another, but their absolute stereochemistry has not been conclusively established.

61A and 61B are enantiomeric with respect to one another, but their absolute stereochemistry has not been conclusively established.

EXPERIMENTAL SECTION

Introduction

Materials: All chemicals were reagent grade and used without further purification.

Analytical: Thin-layer chromatography (TLC) was performed on silica gel 60 flexible backed plates (250 microns) from Alltech and visualized by UV 254 irradiation and iodine. Flash chromatography was conducted using the ISCO CombiFlash with RediSep silica gel cartridges (4 g, 12 g, 40 g, 120 g). Flash chromatography was also conducted with silica gel (200-400 mesh, 60 Å, Aldrich). Chromatographic elution solvent systems are reported as volume:volume ratios. All $^1$H NMR spectra were recorded at ambient temperature on a Bruker-400 MHz spectrometer. They are reported in ppm on the δ scale, from TMS. LC-MS data were obtained using a Thermo-Finnigan Surveyor HPLC and a Thermo-Finnigan AQA MS using either positive or negative electrospray ionization. Program (positive) Solvent A: 10 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes. Program (negative) Solvent A: 1 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes.

The compounds set forth in Tables 1 and 2 are actual examples. The compounds set forth in Table 3 include actual and prophetic examples for which schemes and general procedure descriptions are set forth herein.

EXAMPLE 1A

Preparation of 1.3a:

Method 1A: Pyrrolidine (6.12 mL, 73.38 mmol, 2.0 eq) was added at room temperature to 1.2 (7.31 g, 36.69 mmol, 1.0 eq) and 1.1a (5.00 g, 36.69 mmol, 1.0 eq). The solution was stirred overnight at room temperature and then concentrated under reduced pressure. Diethyl ether (500 mL) was added. The organic mixture was washed with a 1N aqueous solution of hydrochloric acid, a 1N aqueous solution of sodium hydroxide, brine and dried over sodium sulfate. Hexane (300 mL) was added to the mixture. The resulting precipitate was collected by filtration, washed with hexane and used for the next step without further purification.

Yield: 68%

Method 1B: Pyrrolidine (42 mL, 73.38, 2.0 eq) was added drop wise at room temperature to a solution of 1.2 (49.8 g, 0.249 mol, 1.0 eq) and 1.1a (34 g, 0.184 mol, 1.0 eq) in anhydrous methanol (400 mL). The solution was refluxed overnight and then concentrated under reduced pressure. Diethyl ether (500 mL) was added. The organic mixture was washed with a 1N aqueous solution of hydrochloric acid, a 1N aqueous solution of sodium hydroxide, brine and dried over sodium sulfate. Hexane (300 mL) was added to the mixture. The resulting precipitate was collected by filtration, washed with hexane, and used for the next step without further purification.

Yield: 72%

$^1$H NMR (400 MHz, CDCl$_3$) δ 7.86 (d, 1H), 7.50 (t, 1H), 7.00 (m, 2H), 3.87 (m, 2H), 3.22 (m, 2H), 2.72 (s, 2H), 2.05 (d, 2H), 1.61 (m, 2H), 1.46 (s, 9H)

Mass Spectral Analysis m/z=318.0 (M+H)$^+$

Preparation of 1.5a:

To a solution of 1.3a (25 g, 0.078 mol, 1.0 eq) in tetrahydrofuran (250 mL) at −78° C. under nitrogen was added drop wise a 1.0M solution of lithium bis(trimethylsilyl)amide in tetrahydrofuran (94.5 mL, 0.095 mol, 1.2 eq). The mixture was stirred for 1 h at −78° C. A solution of 1.4 (33.8 g, 0.095 mol, 1.2 eq) in tetrahydrofuran (150 mL) was added drop wise. The mixture was warmed slowly to room temperature and stirring was continued for a further 12 h. The mixture was then poured into ice water and the two phases were separated. The organic phase was washed with a 1N aqueous solution of hydrochloric acid, a 1N aqueous solution of sodium hydroxide, brine and dried over sodium sulfate. The crude product was purified by column chromatography (eluent: hexane/ethyl acetate mixtures of increasing polarity).

Yield: 70%

$^1$H NMR (400 MHz, DMSO d$_6$) □ 7.45-7.20 (m, 2H), 7.00 (m, 2H), 6.15 (s, 1H), 3.70 (m, 2H), 3.20 (m, 2H), 1.90 (m, 2H), 1.75 (m, 2H), 1.40 (s, 9H)

Mass Spectral Analysis m/z=450.1 (M+H)$^+$

Preparation of 1.8a:

Method 1C: To a solution of 1.5a (15 g, 33.37 mmol, 1.0 eq) in dimethoxyethane (100 mL) was added sequentially a 2N aqueous solution of sodium carbonate (50.06 mL, 100.12 mmol, 3.0 eq), lithium chloride (4.24 g, 100.12 mmol, 3.0 eq), 1.6 (8.12 g, 36.71 mmol, 1.1 eq) and tetrakis(triphenylphosphine)palladium(0) (0.77 g, 0.67 mmol, 0.02 eq). The mixture was refluxed for 10 h under nitrogen. The mixture was then cooled to room temperature and water (250 mL) was added. The mixture was extracted with ethyl acetate. The organic layer was further washed with brine and dried over sodium sulfate. The crude product was purified by column chromatography (eluent: hexane/ethyl acetate mixtures of increasing polarity).

Yield: 73%

Method 1D: To a solution of 1.5a (10 g, 22.25 mmol, 1.0 eq) in dimethoxyethane (67 mL) was added sequentially a 2N aqueous solution of sodium carbonate (33.37 mL, 66.75 mmol, 3.0 eq), lithium chloride (2.83 g, 66.75 mmol, 3.0 eq), 1.6 (4.40 g, 24.47 mmol, 1.1 eq) and palladium, 10 weight % (dry basis) on activated carbon, wet, Degussa type E101 NE/W (0.24 g, 0.11 mmol, 0.005 eq). The mixture was refluxed for 2 h under nitrogen. The mixture was then cooled to room temperature and diluted with dichloromethane (350 mL). The mixture was filtered through a celite plug and dried over sodium sulfate, filtered and concentrated under reduced pressure. The crude product was triturated with diethyl ether. The precipitate was collected by filtration.

Yield: 60%

$^1$H NMR (400 MHz, CDCl$_3$) δ 7.35 (m, 4H), 7.15 (t, 1H), 7.00-6.80 (m, 3H), 5.55 (s, 1H), 3.85 (m, 2H), 3.55 (m, 2H), 3.30 (m, 4H), 2.00 (m, 2H), 1.65 (m, 2H), 1.40 (s, 9H); 1.20 (m, 6H)

Mass Spectral Analysis m/z=477.2 (M+H)$^+$

Preparation of 1A:

Method 1E: A 2.0M solution of hydrochloric acid in diethyl ether (34.6 mL, 69.24 mmol, 5.5 eq) was added drop wise to a cooled (0° C.) solution of 1.8a (6.00 g, 12.59 mmol, 1.0 eq) in anhydrous dichloromethane (70 mL). The mixture was warmed to room temperature and stirring was continued for an additional 10 h. Diethyl ether (100 mL) was added to the solution and the resulting precipitate was collected by filtration and washed with diethyl ether.

Yield: 99%

Method 1F: Trifluoroacetic acid (10.33 mL, 134.09 mmol, 5.5 eq) was added drop wise to a cold (0° C.) solution of 1.8a (11.62 g, 24.38 mmol, 1.0 eq) in anhydrous dichloromethane (50 mL). The mixture was warmed to room temperature and stirring was continued for an additional 10 h. The mixture was then concentrated under reduced pressure. A saturated solution of sodium bicarbonate (100 mL) was added to the mixture, which was extracted with dichloromethane. The organic phase was separated, washed with brine, dried over sodium sulfate and concentrated under reduced pressure. To a cold (0° C.) solution of the resulting oil in anhydrous dichloromethane was added drop wise a 2.0M solution of anhydrous hydrochloric acid in diethyl ether (36.5 mL, 0.073 mol, 3.0 eq). The mixture was then stirred for 1 h at room temperature and concentrated under reduced pressure. Diethyl ether was added. The resulting precipitate was collected by vacuum filtration and washed with diethyl ether.

Yield: 99%

$^1$H NMR (400 MHz, DMSO d$_6$) δ 9.06 (m, 2H), 7.43 (s, 4H), 7.27 (t, 1H), 7.00 (m, 3H), 5.95 (s, 1H), 3.45 (m, 2H), 3.23 (m, 6H), 2.00 (m, 4H), 1.12 (m, 6H)

Mass Spectral Analysis m/z=377.4 (M+H)$^+$

Elemental analysis:

$C_{24}H_{28}N_2O_2$, 1HCl

Theory: % C, 69.80; % H, 7.08; % N, 6.78.

Found: % C, 69.73; % H, 7.04; % N, 6.81.

EXAMPLE 1B 1B was obtained according to a procedure similar to the one described for 1A, with the following exceptions:

Step 1.1: 1.1a was replaced by 1.1b and Method 1B was used.

Step 1.3: Method 1C was used.

Step 1.4: Method 1E was used.

$^1$H NMR (400 MHz, DMSO d$_6$) δ 8.97 (m, 2H), 7.42 (m, 4H), 6.98 (m, 1H), 6.86 (m, 1H), 6.49 (m, 1H), 5.99 (s, 1H), 3.62 (m, 3H), 3.50 (m, 2H), 3.21 (m, 6H), 2.06 (m, 4H), 1.11 (m, 6H) Mass Spectral Analysis m/z=407.1 (M+H)$^+$ Elemental analysis:

$C_{25}H_{30}N_2O_3$, 1HCl, 1.25H$_2$O

Theory: % C, 64.51; % H, 7.25; % N, 6.02.

Found: % C, 64.53; % H, 7.11; % N, 5.89.

EXAMPLE 1C 1C was obtained according to a procedure similar to the one described for 1A, with the following exceptions:

Step 1.1: 1.1a was replaced by 1.1c and Method 1A was used.

Step 1.3: Method 1C was used.

Step 1.4: Method 1E was used.

$^1$H NMR (400 MHz, DMSO d$_6$) δ 9.05 (m, 1.5H), 7.45 (s, 4H), 7.30 (d, 1H), 7.10 (d, 1H), 6.90 (s, 1H), 6.00 (s, 1H), 3.1-3.55 (m, 8H), 2.05 (m, 4H), 1.10 (m, 6H)

Mass Spectral Analysis m/z=411.2 (M+H)$^+$

EXAMPLE 1D 1D was obtained according to a procedure similar to the one described for 1A, with the following exceptions:

Step 1.1: 1.1a was replaced by 1.1d and Method 1B was used.

Step 1.3: Method 1D was used.

Step 1.4: Method 1E was used.

$^1$H NMR (400 MHz, DMSO d$_6$) δ 8.95 (m, 1H), 7.40 (s, 4H), 7.10 (m, 2H), 6.70 (m, 1H), 6.05 (s, 1H), 3.10-3.50 (m, 8H), 2.00 (m, 4H), 1.10 (m, 6H)

Mass Spectral Analysis m/z=395.2 (M+H)$^+$

EXAMPLE 1E 1E was obtained according to a procedure similar to the one described for 1A, with the following exceptions:

Step 1.1: 1.1a was replaced by 1.1e and Method 1A was used.

Step 1.3: Method 1D was used.

Step 1.4: Method 1E was used.

$^1$H NMR (400 MHz, DMSO d$_6$) δ 8.92 (brm, 1H), 7.42 (s, 4H), 7.07 (dd, 1H), 6.94 (d, 1H), 6.79 (d, 1H), 5.92 (s, 1H), 3.45 (brs, 2H), 3.22 (brm, 6H), 2.18 (s, 3H), 2.08 (m, 2H), 1.97 (m, 2H), 1.12 (brd, 6H)

Mass Spectral Analysis m/z=391.3 (M+H)$^+$

Elemental analysis:

$C_{25}H_{30}N_2O_2$, 1HCl, 1.5H$_2$O

Theory: % C, 66.13; % H, 7.55; % N, 6.17.

Found: % C, 65.73; % H, 7.38; % N, 6.05.

EXAMPLE 1F 1F was obtained according to a procedure similar to the one described for 1A, with the following exceptions:

Step 1.1: 1.1a was replaced by 1.1f and Method 1B was used.

Step 1.3: Method 1C was used.

Step 1.4: Method 1F was used.

$^1$H NMR (400 MHz, DMSO d$_6$) δ 8.90 (m, 2H), 7.25 (m, 5H), 6.71 (m, 1H), 6.64 (m, 1H), 5.81 (s, 1H), 3.45 (m, 2H), 3.39 (m, 3H), 3.20 (m, 6H), 2.00 (m, 4H), 1.09 (m, 6H)

Mass Spectral Analysis m/z=407.2 (M+H)$^+$

Elemental analysis:

$C_{25}H_{30}N_2O_3$, 1HCl, 2H$_2$O

Theory: % C, 62.69; % H, 7.36; % N, 5.85.

Found: % C, 62.78; % H, 6.90; % N, 5.61.

EXAMPLE 1G 1G was obtained according to a procedure similar to the one described for 1A, with the following exceptions:

Step 1.1: 1.1a was replaced by 1.1g and Method 1B was used.

Step 1.3: Method 1C was used.

Step 1.4: Method 1E was used.

$^1$H NMR (400 MHz, DMSO d$_6$) δ 8.95 (m, 1H), 8.85 (m, 1H), 7.38 (m, 4H), 6.89 (m, 1H), 6.68 (m, 1H), 6.54 (m, 1H), 5.78 (s, 1H), 3.76 (m, 3H), 3.45 (m, 2H), 3.21 (m, 6H), 2.09 (m, 2H), 1.98 (m, 2H), 1.11 (m, 6H)

Mass Spectral Analysis m/z=407.1 (M+H)$^+$

Elemental analysis:

$C_{25}H_{30}N_2O_3$, 1HCl, 0.5H$_2$O

Theory: % C, 66.43; % H, 7.14; % N, 6.20.

Found: % C, 66.25; % H, 7.19; % N, 6.11.

EXAMPLE 1H 1H was obtained according to a procedure similar to the one described for 1A, with the following exceptions:

Step 1.1: 1.1a was replaced by 1.1 h and Method 1B was used.

Step 1.3: Method 1D was used.

Step 1.4: Method 1E was used.

$^1$H NMR (400 MHz, DMSO d$_6$) δ 8.80 (brm, 1H), 8.33 (d, 1H), 7.90 (m, 1H), 7.58 (m, 2H), 7.51 (d, 1H), 7.46 (d, 4H), 7.16 (d, 1H), 5.97 (s, 1H), 3.46 (brs, 2H), 3.30 (brm, 6H), 2.25 (d, 2H), 2.05 (m, 2H), 1.13 (brd, 6H)

Mass Spectral Analysis m/z=427.4 (M+H)$^+$

Elemental analysis:

$C_{28}H_{30}N_2O_2$, 1HCl, 1.5H$_2$O

Theory: % C, 68.63; % H, 6.99; % N, 5.72.
Found: % C, 68.96; % H, 6.82; % N, 5.75.

EXAMPLE 1I 1I was obtained according to a procedure similar to the one described for 1A, with the following exceptions:
Step 1.1: 1.1a was replaced by 1.1i and Method 1B was used.
Step 1.3: Method 1D was used.
Step 1.4: Method 1E was used.
$^1$H NMR (400 MHz, DMSO d$_6$) δ 8.90 (brm, 1H), 7.94 (d, 1H), 7.87 (d, 1H), 7.37 (m, 3H), 7.28 (t, 1H), 7.24 (d, 2H), 7.10 (t, 1H), 6.96 (d, 1H), 6.04 (s, 1H), 3.44 (brs, 2H), 3.23 (brs, 6H), 2.09 (brm, 4H), 1.12 (brd, 6H)
Mass Spectral Analysis m/z=427.4 (M+H)$^+$
Elemental analysis:
$C_{28}H_{30}N_2O_2$, 1HCl, 0.67H$_2$O
Theory: % C, 70.80; % H, 6.86; % N, 5.90.
Found: % C, 70.57; % H, 6.72; % N, 5.83.

EXAMPLE 1J 1J was obtained according to a procedure similar to the one described for 1A, with the following exceptions:
Step 1.1: 1.1a was replaced by 1.1j and Method 1A was used.
Step 1.3: Method 1D was used.
Step 1.4: Method 1E was used.
$^1$H NMR (400 MHz, DMSO d$_6$) δ 9.09 (brm, 1H), 7.41 (s, 4H), 6.87 (s, 1H), 6.75 (s, 1H), 5.84 (s, 1H), 3.45 (brs, 2H), 3.20 (brm, 6H), 2.19 (s, 3H), 2.08 (s, 3H), 2.05 (m, 2H), 1.97 (m, 2H), 1.12 (brd, 6H)
Mass Spectral Analysis m/z=405.4 (M+H)$^+$
Elemental analysis:
$C_{26}H_{32}N_2O_2$, 1HCl, 0.5H$_2$O
Theory: % C, 69.39; % H, 7.62; % N, 6.22.
Found: % C, 69.22; % H, 7.49; % N, 6.24.

EXAMPLE 1K 1K was obtained according to a procedure similar to the one described for 1A, with the following exceptions:
Step 1.1: 1.1a was replaced by 1.1k and Method 1B was used.
Step 1.3: Method 1C was used.
Step 1.4: Method 1F was used.
$^1$H NMR (400 MHz, DMSO d$_6$) δ 9.25 (m, 1H), 7.40 (m, 4H), 7.35 (m, 1H), 6.61 (s, 1H), 3.25 (m, 8H), 2.06 (m, 4H), 1.02 (m, 6H)
Mass Spectral Analysis m/z=413.2 (M+H)$^+$

EXAMPLE 1L 1L was obtained according to a procedure similar to the one described for 1A, with the following exceptions:
Step 1.1: 1.1a was replaced by 1.1l and Method 1B was used.
Step 1.3: Method 1D was used.
Step 1.4: Method 1E was used.
$^1$H NMR (400 MHz, DMSO d$_6$) δ 8.84 (brs, 1H), 7.41 (d, 4H), 6.96 (s, 1H), 6.61 (s, 1H), 5.86 (s, 1H), 3.45 (brs, 2H), 3.20 (brm, 6H), 2.23 (s, 3H), 2.13 (s, 3H), 2.08 (m, 2H), 1.96 (m, 2H), 1.12 (brd, 6H)
Mass Spectral Analysis m/z=405.4 (M+H)$^+$
Elemental analysis:
$C_{26}H_{32}N_2O_2$, 1HCl, 0.5H$_2$O
Theory: % C, 69.39; % H, 7.62; % N, 6.22.
Found: % C, 69.69; % H, 7.56; % N, 6.28.

EXAMPLE 1M 1M was obtained according to a procedure similar to the one described for 1A, with the following exceptions:
Step 1.1: 1.1a was replaced by 1.1m and Method 1B was used.
Step 1.3: Method 1C was used.
Step 1.4: Method 1E was used.
$^1$H NMR (400 MHz, DMSO d$_6$) δ 9.05 (m, 2H), 7.46 (m, 2H), 7.20 (m, 3H), 7.01 (m, 1H), 6.82 (m, 1H), 6.48 (m, 1H), 3.45 (m, 2H), 3.28 (m, 6H), 2.24 (m, 2H), 2.06 (m, 2H), 1.60 (m, 3H), 1.12 (m, 6H)
Mass Spectral Analysis m/z=391.0 (M+H)$^+$
Elemental analysis:
$C_{25}H_{30}N_2O_2$, 1HCl, 0.25H$_2$O
Theory: % C, 69.59; % H, 7.36; % N, 6.49.
Found: % C, 69.25; % H, 7.29; % N, 6.58.

EXAMPLE 1N

Preparation of 1.10:
To an oven-dried 2-necked 500 mL flask charged with anhydrous toluene (90 mL) at −78° C. was added n-butyl lithium (2.5 M solution in hexane, 40 mL, 0.1 mol, 1.0 eq). A solution of 2,5-dibromo-pyridine (1.9) (23.69 g, 0.1 mol, 1.0 eq) in anhydrous toluene (50 mL) was added dropwise. The reaction mixture was stirred at −78° C. for 2 h and then poured onto freshly crushed dry-ice (~500 g). The dry-ice mixture was then left at room temperature for 10 h. The volatiles were removed under reduced pressure and the residue was dissolved in water. The insoluble solids were filtered and the filtrate was acidified to pH 2, at which point a light brown solid precipitated out. The solids were collected by filtration and recrystallized from acetic acid (500 mL). This provided 1.10 isolated as its acetic acid salt.
Yield: 74%
$^1$H NMR (400 MHz, DMSO d$_6$) δ 8.84 (d, 1H), 8.25 (dd, 1H), 7.98 (d, 1H)
Mass Spectral Analysis m/z=202.06 (M+H)$^+$
Preparation of 1.11:
To a suspension of 5-bromo-pyridine-2-carboxylic acid (1.10) (808 mg, 3.01 mmol, 1.0 eq) in dry dichloromethane (5 mL) was added oxalyl chloride (0.34 mL, 3.96 mmol, 1.3 eq) followed by 2 drops of N,N-dimethylformamide. The reaction mixture was heated under reflux for 1 h. After cooling to room temperature, the mixture was concentrated under reduced pressure to provide the crude product 1.11, which was used for the next step without purification.
Preparation of 1.13:
To a suspension of 1.11 (crude, as of 3.01 mmol, 1.0 eq) in dry tetrahydrofuran (5 mL) was added N,N-diethylamine (1.12) (1.56 mL, 15.08 mmol, 5.0 eq) drop wise. The reaction mixture was stirred at room temperature for 2 h. Ethyl acetate (20 mL) was added and the mixture was washed with water (20 mL), saturated aqueous sodium bicarbonate (30 mL), 1M aqueous hydrochloric acid (20 mL) and brine. The organics were dried over sodium sulfate, filtered and concentrated under reduced pressure to give a red/brown crystalline solid.
Yield: 88% over two steps
$^1$H NMR (400 MHz, CDCl$_3$) δ 8.64 (d, 1H), 7.91 (dd, 1H), 7.53 (d, 1H), 3.56 (q, 2H), 3.39 (q, 2H), 1.27 (t, 3H), 1.17 (t, 3H)

Mass Spectral Analysis m/z=257.15 (M+H)+

Preparation of 1.7:

To a solution of bis(pinacolato)diboron (1.14) (2.18 g, 8.6 mmol, 1.2 eq) in N,N-dimethylformamide (10 mL) at 0° C. was added potassium acetate (2.3 g, 23.4 mmol, 3.0 eq), 1,1'-bis(diphenylphosphino)ferrocene palladium(II) chloride complex with dichloromethane (171 mg, 0.23 mmol, 0.03 eq). The reaction mixture was heated at 80° C. at which point a solution of 1.13 (2.0 g, 7.8 mmol, 1.0 eq) in N,N-dimethylformamide (10 mL) was added dropwise. The reaction mixture was stirred at 80° C. for another 10 h. Ethyl acetate (75 mL) and water (50 mL) were added and the two phases were separated. The organic phase was washed with brine (50 mL), dried over sodium sulfate, filtered, and concentrated under reduced pressure to give a dark brown oil, which solidified to needles. The crude product was triturated with hexane. The resulting solid was collected by filtration.

Yield: 52%

$^1$H NMR (400 MHz, CDCl$_3$) δ 8.92 (d, 1H), 8.14 (dd, 1H), 7.53 (d, 1H), 3.55 (q, 2H), 3.32 (q, 2H), 1.36 (s, 12H), 1.27 (t, 3H), 1.12 (t, 3H)

Preparation of 1.8b:

To a solution of 1.5a (1.48 g, 3.29 mmol, 1.0 eq) in dimethoxyethane (DME) (20 mL) under nitrogen was added sequentially a 2M aqueous solution of sodium carbonate (4.94 mL, 9.87 mmol, 3.0 eq), lithium chloride (0.42 g, 9.87 mmol, 3.0 eq), palladium (70 mg, 10 wt. % (dry basis) on activated carbon, 0.033 mmol, 0.01 eq), and 1.7 (1.0 g, 3.29 mmol, 1.0 eq). The mixture was heated under reflux for 10 h. Dichloromethane (200 mL) was added to dilute the reaction mixture and palladium(0) on carbon was filtered off on a celite pad. The filtrate was washed with brine, dried over sodium sulfate, filtered, and concentrated under reduced pressure. The crude product was purified by column chromatography (eluent: hexane/ethyl acetate mixtures of increasing polarity).

Yield: 76%

$^1$H NMR (400 MHz, CDCl$_3$) δ 8.56 (dd, 1H), 7.75 (dd, 1H), 7.64 (dd, 1H), 7.22 (m, 1H), 6.99-6.85 (m, 3H), 5.62 (s, 1H), 3.88 (m, 2H), 3.59 (q, 2H), 3.45 (q, 2H), 3.34 (m, 2H), 2.06 (m, 2H), 1.69 (m, 2H), 1.48 (s, 9H), 1.29 (t, 3H), 1.20 (t, 3H)

Mass Spectral Analysis m/z=478.0 (M+H)+

Preparation of 1N:

To a cold (0° C.) solution of 1.8b (2 g, 4.18 mmol, 1.0 eq) in anhydrous dichloromethane (20 mL) was slowly added a 4.0 M solution of hydrogen chloride in dioxane (5.2 mL, 20.8 mmol, 5.0 eq). The reaction mixture was stirred at room temperature for 10 h and then concentrated under reduced pressure. The resulting foamy solids were soaked in diethyl ether to give the fine powders, which were collected by filtration and washed sequentially with ethyl acetate and diethyl ether.

Yield: 95%

$^1$H NMR (400 MHz, DMSO d$_6$) δ 8.99 (m, 2H), 8.60 (d, 1H), 7.90 (dd, 1H), 7.61 (d, 1H), 7.29 (m, 1H), 7.06 (d, 1H), 6.98 (m, 2H), 6.09 (s, 1H), 3.47 (q, 2H), 3.35-3.13 (m, 6H), 2.06 (m, 4H), 1.17 (t, 3H), 1.11 (t, 3H)

Mass Spectral Analysis m/z=378.4 (M+H)+

Elemental analysis:

$C_{23}H_{27}N_3O_2$, 2HCl, 0.5H$_2$O

Theory: % C, 60.13; % H, 6.58; % N, 9.15.

Found: % C, 60.34; % H, 6.60; % N, 9.10.

EXAMPLE 1O 1O was obtained according to a procedure similar to the one described for 1N, with the following exception:

Step 1.1: 1.1a was replaced by 1.1d.

$^1$H NMR (400 MHz, DMSO d$_6$) δ 8.96 (m, 1H), 8.62 (d, 1H), 7.92 (dd, 1H), 7.61 (d, 1H), 7.12 (m, 2H), 6.78 (dd, 1H), 6.20 (s, 1H), 3.47 (q, 2H), 3.30 (q, 2H), 3.24 (m, 4H), 2.05 (m, 4H), 1.17 (t, 3H), 1.11 (t, 3H)

Mass Spectral Analysis m/z=396.3 (M+H)+

Elemental analysis:

$C_{23}H_{26}FN_3O_2$, 1.05HCl, 1H$_2$O

Theory: % C, 61.15; % H, 6.48; % N, 9.30; % Cl, 8.24.

Found: % C, 61.11; % H, 6.44; % N, 9.18; % Cl, 8.28.

EXAMPLE 1P 1P was obtained according to a procedure similar to the one described for 1N, with the following exception:

Step 1.1: 1.1a was replaced by 1.1e.

$^1$H NMR (400 MHz, DMSO d$_6$) δ 8.93 (brm, 1H), 8.60 (d, 1H), 7.89 (dd, 1H), 7.61 (d, 1H), 7.09 (dd, 1H), 6.96 (d, 1H), 6.77 (s, 1H), 6.07 (s, 1H), 3.47 (q, 2H), 3.30 (q, 2H), 2.21 (brm, 4H), 2.18 (s, 3H), 2.04 (brm, 4H), 1.17 (t, 3H), 1.11 (t, 3H)

Mass Spectral Analysis m/z=392.3 (M+H)+

Elemental analysis:

$C_{24}H_{29}N_3O_2$, 2HCl

Theory: % C, 62.07; % H, 6.73; % N, 9.05; % Cl, 15.27.

Found: % C, 61.81; % H, 6.69; % N, 8.95; % Cl, 15.42.

EXAMPLE 1Q 1Q was obtained according to a procedure similar to the one described for 1N, with the following exceptions:

Step 1.1: 1.1a was replaced by 1.1f and Method 1A was used.

$^1$H NMR (400 MHz, DMSO d$_6$) δ 9.20 (m, 2H), 8.38 (m, 1H), 7.69 (m, 1H), 7.48 (m, 1H), 7.28 (m, 1H), 6.75 (m, 1H), 6.69 (m, 1H), 5.99 (s, 1H), 3.40 (m, 5H), 3.26 (m, 6H), 2.08 (m, 4H), 1.20 (m, 3H), 1.10 (m, 3H)

Mass Spectral Analysis m/z=408.3 (M+H)+

Elemental analysis:

$C_{24}H_{29}N_3O_3$, 1HCl, 0.25H$_2$O

Theory: % C, 64.28; % H, 6.85; % N, 9.37; % Cl, 7.91.

Found: % C, 64.07; % H, 6.84; % N, 9.23; % Cl, 8.18.

EXAMPLE 1R 1R was obtained according to a procedure similar to the one described for 1N, with the following exception:

Step 1.1: 1.1a was replaced by 1.1h.

$^1$H NMR (400 MHz, DMSO d$_6$) δ 9.06 (brs, 0.5H), 8.90 (brs, 0.5H), 8.65 (d, 1H), 8.33 (d, 1H), 7.95 (dd, 1H), 7.91 (m, 1H), 7.64 (d, 1H), 7.59 (m, 2H), 7.53 (d, 1H), 7.14 (d, 1H), 6.11 (s, 1H), 3.48 (q, 2H), 3.32 (brm, 6H), 2.26 (d, 2H), 2.10 (m, 2H), 1.18 (t, 3H), 1.12 (t, 3H)

Mass Spectral Analysis m/z=428.3 (M+H)+

Elemental analysis:

$C_{27}H_{29}N_3O_2$, 1.8HCl, 1H$_2$O

Theory: % C, 63.44; % H, 6.47; % N, 8.22; % Cl, 12.48.

Found: % C, 63.36; % H, 6.22; % N, 8.14; % Cl, 12.87.

EXAMPLE 1S 1S was obtained according to a procedure similar to the one described for 1N, with the following exception:
Step 1.1: 1.1a was replaced by 1.1j.
$^1$H NMR (400 MHz, DMSO d$_6$) δ 8.89 (brm, 2H), 8.59 (d, 1H), 7.88 (dd, 1H), 7.61 (d, 1H), 6.89 (s, 1H), 6.73 (s, 1H), 5.99 (s, 1H), 3.47 (q, 2H), 3.30 (q, 2H), 3.20 (brm, 4H), 2.20 (s, 3H), 2.09 (s, 3H), 2.06 (m, 2H), 1.97 (m, 2H), 1.17 (t, 3H), 1.11 (t, 3H)
Mass Spectral Analysis m/z=406.3 (M+H)$^+$
Elemental analysis:
$C_{25}H_{31}N_3O_2$, 2HCl, 2H$_2$O
Theory: % C, 58.36; % H, 7.25; % N, 8.17; % Cl, 13.78.
Found: % C, 58.45; % H, 7.16; % N, 8.16; % Cl, 13.68.

EXAMPLE 1T 1T was obtained according to a procedure similar to the one described for 1N, with the following exception:
Step 1.1: 1.1a was replaced by 1.1l.
$^1$H NMR (400 MHz, DMSO d$_6$) δ 9.02 (brm, 1H), 8.56 (d, 1H), 7.87 (dd, 1H), 7.61 (d, 1H), 6.98 (s, 1H), 6.59 (s, 1H), 6.01 (s, 1H), 3.47 (q, 2H), 3.30 (q, 2H), 3.25 (m, 2H), 3.14 (brs, 2H), 2.24 (s, 3H), 2.15 (s, 3H), 2.09 (m, 2H), 2.02 (m, 2H), 1.17 (t, 3H), 1.11 (t, 3H)
Mass Spectral Analysis m/z=406.4 (M+H)$^+$
Elemental analysis:
$C_{25}H_{31}N_3O_2$, 1.9HCl, 0.5H$_2$O
Theory: % C, 62.06; % H, 7.06; % N, 8.69; % Cl, 13.92.
Found: % C, 61.90; % H, 7.03; % N, 8.45; % Cl, 13.85.

EXAMPLE 1U

Preparation of 1U:
A solution of 1G (1.00 g, 2.46 mmol, 1.0 eq) in dichloromethane (12 mL) was added drop wise to a cold (−78° C.) solution of boron tribromide, 1.0M, in anhydrous dichloromethane (13.53 mL, 13.53 mmol, 5.5 eq). The mixture was warmed to room temperature and stirring was continued for an additional 1 h. Water (1.2 mL) was added drop wise to the cooled (0° C.) reaction mixture and then a saturated solution of sodium bicarbonate (3.7 mL) was added. The resulting mixture was stirred for 1 h at room temperature. A saturated solution of sodium bicarbonate was added to the mixture until the solution was basic when tested with pH paper. The phases were separated and the aqueous phase was extracted with dichloromethane. The organic phases were combined and washed with brine. A gummy residue stuck to the walls of the separatory funnel. It was dissolved in methanol and combined with the dichloromethane extracts. The combined organic layers were dried over sodium sulfate, filtered and concentrated under reduced pressure. The crude product was purified by column chromatography (eluent: dichloromethane/methanol mixtures of increasing polarity).
Yield: 79%
$^1$H NMR (400 MHz, DMSO d$_6$) δ 9.66 (m, 1H), 7.37 (m, 4H), 6.77 (m, 1H), 6.32 (m, 2H), 5.62 (s, 1H), 3.32 (m, 5H), 2.89 (m, 2H), 2.76 (m, 2H), 1.78 (m, 2H), 1.67 (m, 2H), 1.11 (m, 6H)
Mass Spectral Analysis m/z=393.2 (M+H)$^+$
Elemental analysis:
$C_{24}H_{28}N_2O_3$, 0.5H$_2$O
Theory: % C, 71.80; % H, 7.28; % N, 6.98.
Found: % C, 71.79; % H, 7.13; % N, 6.94.

EXAMPLE 2A

Preparation of 2.2:
Pyrrolidine (104 mL, 1.256 mol, 2.0 eq) was added at room temperature to 1.2 (125.2 g, 0.628 mol, 1.0 eq) and 2.1 (95.6 g, 0.628 mol, 1.0 eq). The solution was stirred at 70° C. for 30 min and then cooled to room temperature and stirred for 48 h. The mixture was then concentrated under reduced pressure and ethyl acetate (800 mL) was added. The organic mixture was washed with a 1N aqueous solution of hydrochloric acid, water, brine and dried over sodium sulfate. Diethyl ether (500 mL) was added to the organics and the mixture was stirred overnight at room temperature. The resulting precipitate was collected by filtration, washed with hexane and used for the next step without further purification.
Yield: 75%
$^1$H NMR (400 MHz, CDCl$_3$) δ 7.31 (d, 1H), 7.08 (m, 1H), 6.87 (d, 1H), 6.06 (s, 1H), 3.86 (br s, 2H), 3.19 (br s, 2H), 2.69 (s, 2H), 2.02 (m, 2H), 1.58 (m, 2H), 1.47 (s, 9H)
Mass Spectral Analysis m/z=332.4 (M−H)$^-$
Preparation of 2.4:
To a solution of 2.3 (2.17 g, 14.4 mmol, 1.2 eq) and imidazole (2.04 g, 30.03 mmol, 2.5 eq) in dimethylformamide (20 mL) at room temperature under nitrogen was added drop wise a solution of 2.2 (4 g, 12.01 mmol, 1.0 eq) in dimethylformamide (15 mL). The mixture was stirred overnight at room temperature and then diluted with ethyl acetate. The organics were washed with water, dried over sodium sulfate, filtered and concentrated under reduced pressure. The crude product was triturated with methanol and then isolated using vacuum filtration and used without further purification.
Yield: 76%
$^1$H NMR (400 MHz, DMSO d$_6$) δ 7.10 (m, 2H), 6.99 (d, 1H), 3.70 (m, 2H), 3.11 (brs, 2H), 2.81 (s, 2H), 1.84 (m, 2H), 1.60 (m, 2H), 1.40 (s, 9H), 0.94 (s, 9H), 0.17 (s, 6H)
Preparation of 2.5:
To a solution of 2.4 (4 g, 8.94 mmol, 1.0 eq) in tetrahydrofuran (20 mL) at −78° C. under nitrogen was added drop wise a 1.0M solution of lithium bis(trimethylsilyl)amide in tetrahydrofuran (6.2 mL, 10.72 mmol, 1.2 eq). The mixture was stirred for 1 h at −78° C. A solution of 1.4 (3.83 g, 10.72 mmol, 1.2 eq) in tetrahydrofuran (20 mL) was added drop wise. The mixture was stirred and allowed to warm slowly to room temperature. The reaction was concentrated under reduced pressure. The crude product was purified by column chromatography (eluent: hexane/ethyl acetate mixtures of increasing polarity).
Yield: 90.5%
$^1$H NMR (400 MHz, CDCl$_3$) δ 6.76 (m, 3H), 5.56 (s, 1H), 3.85 (br s, 2H), 3.26 (m, 2H), 2.05 (m, 2H), 1.65 (m, 2H), 1.47 (s, 9H), 0.97 (s, 9H), 0.18 (s, 6H)
Preparation of 2.6a:
To a solution of 2.5 (4.47 g, 7.71 mmol, 1.0 eq) in dimethoxyethane (35 mL) was added sequentially a 2N aqueous solution of sodium carbonate (11.6 mL, 23.13 mmol, 3.0 eq), lithium chloride (0.98 g, 23.13 mmol, 3.0 eq), 1.6 (1.87 g, 8.48 mmol, 1.1 eq) and tetrakis(triphenylphosphine)palladium(0) (0.18 g, 0.15 mmol, 0.02 eq). The mixture was refluxed for 4 h under nitrogen. The mixture was then cooled to room temperature and water was added. The mixture was extracted with ethyl acetate. The organic layer was further washed with a 2N aqueous solution of sodium hydroxide, brine and dried over sodium sulfate. The crude product was triturated with hexanes and used without further purification.

Yield: 84%

$^1$H NMR (400 MHz, DMSO d$_6$) δ 7.39 (m, 4H), 6.87 (d, 1H), 6.69 (m, 1H), 6.37 (d, 1H), 5.89 (s, 1H), 3.71 (m, 2H), 3.45 (brs, 2H), 3.23 (m, 4H), 1.85 (m, 2H), 1.70 (m, 2H), 1.41 (s, 9H); 1.10 (m, 6H), 0.87 (s, 9H), 0.08 (s, 6H)

Mass Spectral Analysis m/z=607.0 (M+H)$^+$

Preparation of 2.7a:

To a solution of 2.6a (0.50 g, 0.82 mmol, 1.0 eq) in tetrahydrofuran (10 mL) was added a 1N solution of tetrabutylammonium fluoride (2.5 mL, 2.47 mmol, 3.0 eq) in tetrahydrofuran at 0° C. The mixture was stirred for 1 h at room temperature under nitrogen. The mixture was diluted with ethyl acetate. The organic layer was washed with a saturated solution of aqueous sodium bicarbonate, brine, a 1N solution of hydrochloric acid and brine. The solution was then dried over sodium sulfate, filtered and concentrated under reduced pressure. The crude product was triturated with a diethyl ether/hexanes mixture (3:7) and used without further purification.

Yield: 74%

$^1$H NMR (400 MHz, CDCl$_3$) δ 7.34 (s, 4H), 6.80 (d, 1H), 6.67 (m, 1H), 6.49 (d, 1H), 5.87 (s, 1H), 5.57 (s, 1H), 3.84 (brs, 2H), 3.56 (brs, 2H), 3.30 (brs, 4H), 2.00 (m, 2H), 1.64 (m, 2H), 1.47 (s, 9H), 1.20 (m, 6H)

Mass Spectral Analysis m/z=493.0 (M+H)$^+$

Preparation of 2A:

A 2.0M solution of hydrochloric acid in diethyl ether (1.7 mL, 3.35 mmol, 5.5 eq) was added drop wise to a cooled (0° C.) solution of 2.7a (0.30 g, 0.61 mmol, 1.0 eq) in anhydrous dichloromethane (5 mL). The mixture was warmed to room temperature and stirring was continued for an additional 10 h. Diethyl ether (100 mL) was added to the solution. The resulting precipitate was collected by filtration and washed with diethyl ether. The crude product was purified by column chromatography (eluent: dichloromethane/methanol mixtures of increasing polarity).

Yield: 50%

$^1$H NMR (400 MHz, DMSO d$_6$) δ 9.03 (m, 2H), 7.42 (s, 4H), 6.85 (d, 1H), 6.64 (m, 1H), 6.42 (d, 1H), 5.91 (s, 1H), 3.49 (m, 4H), 3.21 (m, 5H), 2.08 (m, 2H), 1.96 (m, 2H), 1.13 (m, 6H)

Mass Spectral Analysis m/z=393.3 (M+H)$^+$

Elemental analysis:

$C_{24}H_{28}N_2O_2$, 1HCl, 1H$_2$O

Theory: % C, 64.49; % H, 6.99; % N, 6.27.

Found: % C, 64.59; % H, 6.67; % N, 6.26.

EXAMPLE 2B 2B was obtained according to a procedure similar to the one described for 2A, with the following exception:

Step 2.4: 1.6 was replaced by 1.7.

$^1$H NMR (400 MHz, DMSO d$_6$) δ 8.94 (brm, 2H), 8.59 (s, 1H), 7.90 (dd, 1H), 7.62 (d, 1H), 6.88 (d, 1H), 6.67 (dd, 1H), 6.38 (d, 1H), 6.06 (s, 1H), 3.47 (q, 2H), 3.22 (m, 6H), 2.07 (m, 2H), 1.97 (m, 2H), 1.17 (t, 3H), 1.11 (t, 3H)

Mass Spectral Analysis m/z=394 (M+H)$^+$

Elemental analysis:

$C_{23}H_{27}N_3O_3$, 2HCl, 1.25H$_2$O

Theory: % C, 56.50; % H, 6.49; % N, 8.59; % Cl, 14.50.

Found: % C, 56.55; % H, 6.46; % N, 8.39; % Cl, 14.49.

EXAMPLE 2C

Preparation of 2.9a

A mixture of 2.7a (0.210 g, 0.00042 mol, 1.0 eq), cyclopropylmethyl bromide (2.8a) (0.12 mL, 0.0012 mol, 2.95 eq) and potassium carbonate (0.350 g, 0.0025 mole, 6.0 eq) in N,N-dimethylformamide (5 mL) was stirred for 48 h at 80° C. The mixture was cooled to room temperature, poured into water (50 mL) and extracted with ethyl acetate. The organic phase was washed with brine, dried over sodium sulfate, filtered and concentrated under reduced pressure. The crude product was purified by column chromatography (eluent: hexane/ethyl acetate mixtures of increasing polarity).

Yield: 96%

Mass Spectral Analysis m/z=547.12 (M+H)$^+$

Preparation of 2C

To a cold (0° C.) solution of 2.9a (0.200 g, 0.00036 mol, 1.0 eq) in anhydrous dichloromethane (10 mL) was added drop wise a 2.0 M solution of anhydrous hydrochloric acid in diethyl ether (1.8 mL, 0.0036 mole, 10.0 eq). The mixture was warmed slowly to room temperature and stirring was continued for 12 h at room temperature. The mixture was concentrated under reduced pressure. Diethyl ether was then added to the mixture, which was stirred for 1 h at room temperature. The precipitate was collected by filtration, washed with diethyl ether and dried under vacuum.

Yield: 63%

$^1$H NMR (400 MHz, DMSO d$_6$) δ 8.85 (m, 1H), 7.40 (s, 4H), 6.97 (d, 1H), 6.80 (m, 1H), 6.45 (d, 1H), 5.95 (s, 1H), 3.65 (d, 2H), 3.10-3.50 (m, 8H), 2.00 (m, 4H), 1.10 (m, 7H), 0.50 (m, 2H), 0.20 (m, 2H)

Mass Spectral Analysis m/z=447.1 (M+H)$^+$

EXAMPLE 2D 2D was obtained according to a procedure similar to the one described for 2C, with the following exception:

Step 2.7: 2.8a was replaced by 2.8b (method 2A).

$^1$H NMR (400 MHz, DMSO d$_6$) δ 9.00 (s, 1H), 7.45 (s, 4H), 7.00 (m, 1H), 6.80 (m, 1H), 6.45 (m, 1H), 6.00 (s, 1H), 4.55 (m, 1H), 3.10-3.55 (m, 8H), 2.00 (m, 4H), 1.80 (m, 2H), 1.60 (m, 4H), 1.50 (m, 2H), 1.10 (m, 6H)

Mass Spectral Analysis m/z=461.1 (M+H)$^+$

EXAMPLE 2E

Preparation of 2.7b:

Intermediate 2.7b was obtained according to a procedure similar to the one described for 2.7a (see 2A), except 1.6 was replaced by 1.7 in Step 2.4.

Preparation of 2.9b:

To a solution of 2.7b (1.0 g, 2.03 mmol, 1.0 eq), 2.8e (0.29 g, 4.06 mmol, 2.0 eq), triphenylphosphine (1.06 g, 4.06 mmol, 2.0 eq) and triethylamine (0.82 g, 8.12 mmol, 4.0 eq) in tetrahydrofuran (50 mL) at 0° C. was added diisopropyl azodicarboxylate (DIAD) (0.82 g, 4.06 mmol, 2.0 eq). The mixture was warmed to room temperature and stirred for 48 h at room temperature. Methylene chloride was added and the crude mixture was washed with water, concentrated under reduced pressure and purified by column chromatography (eluent: hexane/ethyl acetate mixtures of increasing polarity).

Yield: 45%

$^1$H NMR (400 MHz, CDCl$_3$) δ 8.56 (s, 1H), 7.76 (dd, 1H), 7.64 (d, 1H), 6.89 (d, 1H), 6.78 (m, 1H), 6.50 (d, 1H), 5.65 (s, 1H), 3.86 (brm, 2H), 3.62 (m, 4H), 3.45 (q, 2H), 3.32 (brm, 2H), 2.05 (brm, 2H), 1.67 (brm, 2H), 1.48 (s, 9H), 1.30 (m, 4H), 1.21 (t, 3H), 0.60 (m, 2H), 0.30 (m, 2H)

Mass Spectral Analysis m/z=548.4 (M+H)$^+$

Preparation of 2E:

To a solution of 2.9b (0.50 g, 0.913 mmol, 1.0 eq) in methylene chloride (3 mL) was slowly added an excess of a 1.0M solution of anhydrous hydrochloric acid in diethyl ether. The mixture was stirred for 16 h at room temperature and then concentrated under reduced pressure. This mixture (0.41 g) was purified by HPLC using a 20×150 mm XTerra Reversed Phase-HPLC column (eluent: 95:5 A:B to 1:99 A:B where A is 0.1% ammonia in Milli-Q water and B is acetonitrile). After HPLC purification, the pure product (0.10 g, 0.22 mmol, 1.0 eq) was obtained as the free amine, which was dissolved in methanol (10 mL) at 0° C. under nitrogen and treated with a 1.0M solution of anhydrous hydrochloric acid in diethyl ether (0.47 mL, 0.47 mmol, 2.1 eq). The mixture was stirred at 0° C. for 30 min. The mixture was concentrated under reduced pressure and dried under vacuum.

Yield: 26%

$^1$H NMR (400 MHz, CDCl$_3$) δ 9.75 (brs, 1H), 9.33 (brs, 1H), 9.18 (s, 1H), 8.45 (brd, 1H), 7.96 (brd, 1H), 6.94 (d, 1H), 6.80 (m, 1H), 6.42 (brm, 2H), 3.66 (brm, 4H), 3.46 (brm, 6H), 2.30 (brm, 4H), 1.35 (t, 3H), 1.22 (brm, 4H), 0.62 (m, 2H), 0.31 (m, 2H)

Mass Spectral Analysis m/z=448.3 (M+H)$^+$

Elemental analysis:

$C_{27}H_{33}N_3O_3$, 1.75HCl, 1.5H$_2$O

Theory: % C, 60.23; % H, 7.07; % N, 7.80; % Cl, 11.52.

Found: % C, 60.50; % H, 6.99; % N, 7.77; % Cl, 11.38.

EXAMPLE 2F 2F was obtained according to a procedure similar to the one described for 2E, with the following exception:
Step 2.7: 2.8e was replaced by 2.8d.

$^1$H NMR (400 MHz, DMSO d$_6$) δ 9.10 (brs, 2H), 8.62 (d, 1H), 7.93 (dd, 1H), 7.61 (d, 1H), 7.03 (d, 1H), 6.89 (dd, 1H), 6.47 (d, 1H), 6.13 (s, 1H), 3.64 (s, 3H), 3.47 (q, 2H), 3.24 (m, 6H), 2.05 (brm, 4H), 1.17 (t, 3H), 1.11 (t, 3H)

Mass Spectral Analysis m/z=408.3 (M+H)$^+$

Elemental analysis:

$C_{24}H_{29}N_3O_3$, 1.25 HCl, 1.25H$_2$O

Theory: % C, 60.61; % H, 6.94; % N, 8.84%; Cl, 9.32.

Found: % C, 60.69; % H, 6.87; % N, 8.66; % Cl, 9.35.

Note: 2F was also obtained according to a procedure similar to the one described for 2C with the following exceptions:
Step 2.7: 2.8a was replaced by 2.8c and method 2C was used (alkylation reaction conducted in acetone instead of N,N-dimethylformamide).

EXAMPLE 3A

Preparation of 3.1a:

To a cold (0° C.) solution of 2.7a (2.5 g, 0.0050 mol, 1.0 eq) in anhydrous dichloromethane (100 mL), was added N-triphenyltrifluoromethane sulfonimide (1.4) (2 g, 0.0055 mol, 1.1 eq) followed by addition of triethylamine (0.85 mL, 0.060 mol, 1.2 eq). The mixture was allowed to warm slowly to room temperature and stirring was continued for 12 h. The mixture was diluted with ethyl acetate and washed successively with water, aqueous 1N NaOH, water, and brine. The organic layer was dried over sodium sulfate, filtered and concentrated under vacuum. The crude product was purified by column chromatography (eluent: hexane/ethyl acetate mixtures of increasing polarity).

Yield: 78%

Mass Spectral Analysis m/z=666.06 (M+H+CH$_3$CN)$^+$

Preparation of 3.2a:

To a stirred solution of 3.1a (2.5 g, 0.040 mol, 1.0 eq) in a mixture of methanol (30 mL) and dimethylsulfoxide (40 mL) was added triethylamine (1.23 mL, 0.088 mol, 2.2 eq). Carbon monoxide gas was bubbled through the mixture for 5 min. To the mixture was added palladium (II) acetate (0.090 g, 0.00040 mol, 0.1 eq) followed by 1,1'-bis(diphenylphosphino)ferrocene (0.443 g, 0.00080 mol, 0.2 eq). Carbon monoxide gas was bubbled through the mixture for 15 min and the mixture was then stirred under an atmosphere of carbon monoxide and heated at 65° C. overnight. The mixture was cooled to room temperature and poured into water. The mixture was extracted with ethyl acetate. The combined organic extracts were washed with water, brine, dried over sodium sulfate and filtered. Evaporation of the solvent under reduced pressure afforded a dark oil. The crude product was purified by column chromatography (eluent: hexane/ethyl acetate mixtures of increasing polarity).

Yield: 75%

Mass Spectral Analysis m/z=576.08 (M+H+CH$_3$CN)$^+$

Preparation of 3A:

To a cold (0° C.) solution of 3.2a (0.140 g, 0.00026 mole, 1.0 eq) in anhydrous dichloromethane (10 mL) was added drop wise a 2.0 M solution of anhydrous hydrochloric acid in diethyl ether (2.6 mL, 0.0026 mole, 10.0 eq). The mixture was warmed slowly to room temperature and stirring was continued for 12 h at room temperature. An additional 1.0 mL of a 2.0 M solution of anhydrous hydrochloric acid in diethyl ether was added to the reaction mixture, which was allowed to stir for an additional 12 h at room temperature. The mixture was concentrated under reduced pressure. Diethyl ether was then added to the mixture, which was stirred for 2 h at room temperature. The resulting precipitate was collected by filtration, washed with diethyl ether and dried under vacuum.

Yield: 53%

$^1$H NMR (400 MHz, DMSO d$_6$) δ 9.08 (m, 2H), 7.90 (d, 1H), 7.60 (s, 1H), 7.40 (s, 4H), 7.15 (d, 1H), 6.00 (s, 1H), 3.70 (s, 3H), 3.10-3.50 (m, 8H), 2.1 (m, 4H), 1.10 (m, 6H) Mass Spectral Analysis m/z=435.0 (M+H)$^+$

EXAMPLE 3B

Preparation of 3.3a:

To a cold (0° C.) solution of 3.2a (1.41 g, 0.0026 mol, 1.0 eq) in tetrahydrofuran (20 mL), was added a solution of lithium hydroxide monohydrate (0.332 g, 0.0079 mole, 3.0 eq) in water (3 mL). Methanol (6 mL) was then added to the reaction mixture, which was stirred at room temperature for 12 h. A solution of lithium hydroxide monohydrate (0.165 g, 0.0058 mole, 1.5 eq) in water (3 mL) was added to the reaction mixture, which was stirred for an additional 12 h at room temperature. The mixture was concentrated under reduced pressure and the residue was dissolved in ethyl acetate. The organic solution was dried over sodium sulfate and filtered. Evaporation of the filtrate provided a solid, which was triturated in hexane. The precipitate was collected by filtration.

Yield: 85%

Mass Spectral Analysis m/z=562.08 (M+H+CH$_3$CN)$^+$

Preparation of 3B:

To a cold (0° C.) solution of 3.3a (0.200 g, 0.00038 mole, 1.0 eq) in anhydrous dichloromethane (10 mL) was added drop wise a 2.0 M solution of anhydrous hydrochloric acid in diethyl ether (1.9 mL, 0.0038 mole, 10 eq). The mixture was warmed slowly to room temperature and stirring was continued for 12 h at room temperature. The desired product precipitates from the reaction mixture. The precipitate was collected by filtration, washed with diethyl ether and dried under vacuum.

Yield: 60%

$^1$H NMR (400 MHz, DMSO d$_6$) δ 9.10 (m, 1.5H), 7.85 (d, 1H), 7.60 (s, 1H), 7.40 (s, 4H), 7.10 (d, 1H), 6.00 (s, 1H), 3.10-3.55 (m, 8H), 2.10 (m, 4H), 1.10 (m, 6H)

Mass Spectral Analysis m/z=421.0 (M+H)$^+$

EXAMPLE 3C 3C was obtained according to a procedure similar to the one described for 3B, with the following exception:
Step 3.1: 2.7a (X=H) was replaced by 2.7b (X=N).

$^1$H NMR (400 MHz, DMSO d$_6$) δ 9.02 (brm, 2H), 8.64 (d, 1H), 7.94 (dd, 1H), 7.87 (dd, 1H), 7.66 (d, 1H), 7.52 (d, 1H), 7.16 (d, 1H), 6.19 (s, 1H), 3.48 (q, 2H), 3.25 (brm, 6H), 2.10 (brm, 4H), 1.18 (t, 3H), 1.11 (t, 3H)

Mass Spectral Analysis m/z=422.2 (M+H)$^+$

EXAMPLE 3D 3D was obtained according to a procedure similar to the one described for 3E, with the following exception:
Step 3.5: 3.4b was replaced by 3.4a.

$^1$H NMR (400 MHz, DMSO d$_6$) δ 9.33 (m, 2H), 7.83 (m, 2H), 7.54 (m, 1H), 7.42 (m, 4H), 7.22 (m, 1H), 7.10 (m, 1H), 6.01 (s, 1H), 5.60 (m, 2H), 3.42 (m, 2H), 3.25 (m, 4H), 2.11 (m, 4H), 1.10 (m, 6H)

Mass Spectral Analysis m/z=420.0 (M+H)$^+$
Elemental analysis:
$C_{25}H_{29}N_3O_3$, 1HCl, 3H$_2$O
Theory: % C, 58.87; % H, 7.11; % N, 8.24.
Found: % C, 58.85; % H, 6.74; % N, 8.03.

EXAMPLE 3E

Preparation of 3.5a:
O-Benzotriazol-1-yl-N,N,N',N'-tetramethyluronium tetrafluoroborate (TBTU) (244.2 mg, 0.76 mmol, 1.1 eq) was added to a cooled (0° C.) solution of 3.3a (360.0 mg, 0.69 mmol, 1.0 eq), 3.4b (256.8 mg, 3.80 mmol, 5.5 eq), and N,N-diisopropylethylamine (1.06 mL, 6.08 mmol, 7.7 eq) in acetonitrile (8 mL). The solution was stirred overnight at room temperature and then concentrated under reduced pressure. Ethyl acetate (10 mL) and a saturated aqueous solution of sodium bicarbonate (10 mL) were added to the crude product and the mixture was stirred for 20 min. The phases were separated and the organic phase was washed with an aqueous saturated solution of sodium bicarbonate and brine, dried over sodium sulfate, filtered and concentrated under reduced pressure. The crude product was purified by column chromatography (eluent: hexane/ethyl acetate mixtures of increasing polarity).

Yield: 68%

$^1$H NMR (400 MHz, DMSO d$_6$) δ 8.28 (m, 1H), 7.70 (m, 1H), 7.50 (m, 1H), 7.42 (m, 4H), 7.04 (d, 1H), 5.94 (s, 1H), 3.72 (m, 2H), 3.45 (br s, 2H), 3.25 (m, 4H), 2.70 (d, 3H), 1.89 (m, 2H), 1.74 (m, 2H), 1.42 (s, 9H), 1.12 (m, 6H)

Mass Spectral Analysis m/z=534.3 (M+H)$^+$

Preparation of 3E:
A 2.0M solution of hydrochloric acid in diethyl ether (1.30 mL, 2.57 mmol, 5.5 eq) was added drop wise to a cooled (0° C.) solution of 3.5a (0.25 g, 0.47 mmol, 1.0 eq) in anhydrous dichloromethane (5 mL). The mixture was warmed to room temperature and stirring was continued for an additional 10 h. Diethyl ether (100 mL) was added to the solution. The resulting precipitate was collected by filtration and washed with diethyl ether.

Yield: 99%

$^1$H NMR (400 MHz, DMSO d$_6$) δ 9.14 (m, 2H), 8.34 (m, 1H), 7.77 (d, 1H), 7.54 (s, 1H), 7.44 (s, 4H), 7.12 (d, 1H), 6.01 (s, 1H), 3.63 (brs, 2H), 3.45 (brs, 2H), 3.24 (m, 4H), 2.69 (d, 3H), 2.09 (m, 4H), 1.11 (m, 6H)

Mass Spectral Analysis m/z=434.3 (M+H)$^+$
Elemental analysis:
$C_{26}H_{31}N_3O_3$, 1HCl, 1.25H$_2$O
Theory: % C, 63.40; % H, 7.06; % N, 8.53.
Found: % C, 63.13; % H, 6.94; % N, 8.39.

EXAMPLE 3F 3F was obtained according to a procedure similar to the one described for 3E, with the following exception:
Step 3.5: 3.4b was replaced by 3.4c.

$^1$H NMR (400 MHz, DMSO d$_6$) δ 9.20 (m, 2H), 8.37 (m, 1H), 7.79 (m, 1H), 7.55 (m, 1H), 7.44 (m, 4H), 7.10 (m, 1H), 6.01 (s, 1H), 3.61 (m, 2H), 3.45 (m, 2H), 3.22 (m, 6H), 2.10 (m, 4H), 1.10 (m, 9H)

Mass Spectral Analysis m/z=448.4 (M+H)$^+$
Elemental analysis:
$C_{27}H_{33}N_3O_3$, 1HCl, 1H$_2$O
Theory: % C, 64.59; % H, 7.23; % N, 8.37.
Found: % C, 64.70; % H, 7.16; % N, 8.30.

EXAMPLE 3G 3G was obtained according to a procedure similar to the one described for 3E, with the following exception:
Step 3.5: 3.4b was replaced by 3.4d.

$^1$H NMR (400 MHz, DMSO d$_6$) δ 9.16 (m, 2H), 8.36 (m, 1H), 7.78 (m, 1H), 7.55 (m, 1H), 7.44 (m, 4H), 7.10 (m, 1H), 6.00 (s, 1H), 3.44 (m, 2H), 3.20 (m, 8H), 2.10 (m, 4H), 1.45 (m, 2H), 1.12 (m, 6H), 0.80 (m, 3H)

Mass Spectral Analysis m/z=462.4 (M+H)$^+$
Elemental analysis:
$C_{28}H_{35}N_3O_3$, 1HCl, 1.5H$_2$O
Theory: % C, 64.05; % H, 7.49; % N, 8.00.
Found: % C, 63.76; % H, 7.41; % N, 7.76.

EXAMPLE 3H 3H was obtained according to a procedure similar to the one described for 3E, with the following exception:
Step 3.5: 3.4b was replaced by 3.4e.

$^1$H NMR (400 MHz, DMSO d$_6$) δ 9.23 (m, 2H), 8.36 (m, 1H), 7.79 (m, 1H), 7.55 (m, 1H), 7.45 (m, 4H), 7.12 (m, 1H), 6.01 (s, 1H), 3.45 (m, 2H), 3.24 (m, 6H), 3.01 (m, 2H), 2.06 (m, 4H), 1.76 (m, 1H), 1.11 (m, 6H), 0.81 (m, 6H)

Mass Spectral Analysis m/z=476.5 (M+H)$^+$
Elemental analysis:
$C_{29}H_{37}N_3O_3$, 1HCl, 1.5H$_2$O
Theory: % C, 64.61; % H, 7.67; % N, 7.79.
Found: % C, 64.94; % H, 7.39; % N, 7.77.

EXAMPLE 3I 3I was obtained according to a procedure similar to the one described for 3E, with the following exception:
Step 3.5: 3.4b was replaced by 3.4f.

$^1$H NMR (400 MHz, DMSO d$_6$) δ 9.14 (brs, 2H), 8.23 (m, 1H), 7.80 (m, 1H), 7.54 (m, 1H), 7.44 (m, 4H), 7.11 (m, 1H), 6.02 (s, 1H), 3.45 (m, 2H), 3.23 (m, 6H), 3.01 (m, 2H), 2.10 (m, 4H), 1.12 (m, 6H), 0.83 (m, 9H)

Mass Spectral Analysis m/z=490.6 (M+H)$^+$

Elemental analysis:

$C_{30}H_{39}N_3O_3$, 1HCl, 0.75$H_2O$

Theory: % C, 66.77; % H, 7.75; % N, 7.79.

Found: % C, 66.63; % H, 7.64; % N, 7.77.

EXAMPLE 3J 3J was obtained according to a procedure similar to the one described for 3E, with the following exception:

Step 3.5: 3.4b was replaced by 3.4g.

$^1$H NMR (400 MHz, DMSO d$_6$) δ 9.21 (m, 2H), 8.45 (m, 1H), 7.80 (m, 1H), 7.54 (m, 1H), 7.44 (m, 4H), 7.11 (m, 1H), 6.01 (s, 1H), 3.45 (m, 2H), 3.24 (m, 6H), 3.09 (m, 2H), 2.11 (m, 4H), 1.12 (m, 6H), 0.96 (m, 1H), 0.36 (m, 2H), 0.16 (m, 2H)

Mass Spectral Analysis m/z=474.4 (M+H)$^+$

Elemental analysis:

$C_{29}H_{35}N_3O_3$, 1HCl, 1.75$H_2O$

Theory: % C, 64.31; % H, 7.35; % N, 7.76.

Found: % C, 64.69; % H, 7.17; % N, 7.66.

EXAMPLE 3K 3K was obtained according to a procedure similar to the one described for 3E, with the following exception:

Step 3.5: 3.4b was replaced by 3.4h.

$^1$H NMR (400 MHz, DMSO d$_6$) δ 9.36 (m, 2H), 8.13 (m, 1H), 7.82 (m, 1H), 7.54 (m, 1H), 7.44 (m, 4H), 7.11 (m, 1H), 6.00 (s, 1H), 4.01 (m, 1H), 3.45 (m, 2H), 3.22 (m, 6H), 2.10 (m, 4H), 1.15 (m, 12H)

Mass Spectral Analysis m/z=462.5 (M+H)$^+$

Elemental analysis:

$C_{28}H_{35}N_3O_3$, 1HCl, 2.25$H_2O$

Theory: % C, 62.44; % H, 7.58; % N, 7.80.

Found: % C, 62.42; % H, 7.58; % N, 8.08.

EXAMPLE 3L 3L was obtained according to a procedure similar to the one described for 3E, with the following exception:

Step 3.5: 3.4b was replaced by 3.4i.

$^1$H NMR (400 MHz, DMSO d$_6$) δ 9.20 (m, 2H), 8.34 (m, 1H), 7.78 (m, 1H), 7.54 (m, 1H), 7.44 (m, 4H), 7.11 (m, 1H), 6.00 (s, 1H), 3.45 (m, 2H), 3.20 (m, 8H), 2.08 (m, 4H), 1.45 (m, 2H), 1.25 (m, 4H), 1.11 (m, 6H), 0.84 (m, 3H)

Mass Spectral Analysis m/z=490.5 (M+H)$^+$

Elemental analysis:

$C_{30}H_{39}N_3O_3$, 1HCl, 1.5$H_2O$

Theory: % C, 65.14; % H, 7.84; % N, 7.60.

Found: % C, 65.38; % H, 7.60; % N, 7.64.

EXAMPLE 3M 3M was obtained according to a procedure similar to the one described for 3E, with the following exception:

Step 3.5: 3.4b was replaced by 3.4j.

$^1$H NMR (400 MHz, DMSO d$_6$) δ 9.11 (m, 2H), 7.41 (m, 4H), 7.30 (m, 1H), 7.09 (m, 1H), 6.99 (m, 1H), 6.00 (s, 1H), 3.45 (m, 2H), 3.20 (m, 6H), 2.91 (m, 6H), 2.10 (m, 4H), 1.12 (m, 6H)

Mass Spectral Analysis m/z=448.4 (M+H)$^+$

Elemental analysis:

$C_{27}H_{33}N_3O_3$, 1HCl, 1.25$H_2O$

Theory: % C, 64.02; % H, 7.26; % N, 8.30.

Found: % C, 64.03; % H, 7.21; % N, 8.23.

EXAMPLE 3N 3N was obtained according to a procedure similar to the one described for 3E, with the following exception:

Step 3.5: 3.4b was replaced by 3.4k.

$^1$H NMR (400 MHz, DMSO d$_6$) δ 9.21 (m, 2H), 7.44 (m, 5H), 7.09 (m, 2H), 5.99 (s, 1H), 3.41 (m, 2H), 3.36 (m, 4H), 3.21 (m, 6H), 2.10 (m, 4H), 1.78 (m, 4H), 1.10 (m, 6H)

Mass Spectral Analysis m/z=474.5 (M+H)$^+$

Elemental analysis:

$C_{29}H_{35}N_3O_3$, 1HCl, 1.25$H_2O$

Theory: % C, 65.40; % H, 7.29; % N, 7.89.

Found: % C, 65.48; % H, 7.08; % N, 7.90.

EXAMPLE 3O 3O was obtained according to a procedure similar to the one described for 3E, with the following exception:

Step 3.5: 3.4b was replaced by 3.4l.

$^1$H NMR (400 MHz, DMSO d$_6$) δ 9.03 (brs, 2H), 7.44 (m, 5H), 7.13 (m, 2H), 6.01 (s, 1H), 4.96 (m, 1H), 4.24 (m, 1H), 3.44 (m, 6H), 3.22 (m, 6H), 2.09 (m, 4H), 1.86 (m, 1H), 1.75 (m, 1H), 1.12 (m, 6H)

Mass Spectral Analysis m/z=490.3 (M+H)$^+$

EXAMPLE 3P 3P was obtained according to a procedure similar to the one described for 3E, with the following exception:

Step 3.5: 3.4b was replaced by 3.4m.

$^1$H NMR (400 MHz, DMSO d$_6$) δ 9.25 (m, 2H), 7.44 (m, 5H), 7.10 (m, 2H), 6.00 (s, 1H), 4.93 (m, 1H), 4.24 (m, 1H), 3.45 (m, 6H), 3.21 (m, 6H), 2.11 (m, 4H), 1.88 (m, 1H), 1.76 (m, 1H), 1.11 (m, 6H)

Mass Spectral Analysis m/z=490.5 (M+H)$^+$

Elemental analysis:

$C_{29}H_{35}N_3O_4$, 1HCl, 1.5$H_2O$

Theory: % C, 62.98; % H, 7.11; % N, 7.60.

Found: % C, 62.79; % H, 6.98; % N, 7.58.

EXAMPLE 3Q 3Q was obtained according to a procedure similar to the one described for 3E, with the following exception:

Step 3.5: 3.4b was replaced by 3.4n.

$^1$H NMR (400 MHz, DMSO d$_6$) δ 9.25 (m, 2H), 7.40 (m, 5H), 7.09 (m, 1H), 6.99 (m, 1H), 6.01 (s, 1H), 4.10 (m, 2H), 3.45 (m, 2H), 3.25 (m, 6H), 2.11 (m, 6H), 2.51 (m, 2H), 1.19 (m, 9H), 0.80 (m, 3H)

Mass Spectral Analysis m/z=502.5 (M+H)$^+$

Elemental analysis:

$C_{31}H_{39}N_3O_3$, 1HCl, 2$H_2O$

Theory: % C, 64.85; % H, 7.72; % N, 7.32.

Found: % C, 64.54; % H, 7.37; % N, 7.35.

EXAMPLE 3R 3R was obtained according to a procedure similar to the one described for 3E, with the following exception:
Step 3.5: 3.4b was replaced by 1.12.
$^1$H NMR (400 MHz, DMSO $d_6$) δ 9.21 (m, 2H), 7.41 (m, 4H), 7.29 (m, 1H), 7.08 (m, 1H), 6.89 (m, 1H), 5.98 (s, 1H), 3.41 (m, 2H), 3.22 (m, 10H), 2.10 (m, 4H), 1.02 (m, 12H)
Mass Spectral Analysis m/z=476.5 (M+H)$^+$
Elemental analysis:
$C_{29}H_{37}N_3O_3$, 1HCl, 1.25H$_2$O
Theory: % C, 65.15; % H, 7.64; % N, 7.86.
Found: % C, 64.85; % H, 7.26; % N, 7.79.

EXAMPLE 3S 3S was obtained according to a procedure similar to the one described for 3E, with the following exception:
Step 3.5: 3.4b was replaced by 3.4o.
$^1$H NMR (400 MHz, DMSO $d_6$) δ 8.67 (m, 1H), 8.55 (m, 1H), 7.43 (m, 4H), 7.22 (m, 1H), 7.09 (m, 1H), 6.82 (m, 1H), 6.01 (s, 1H), 3.66 (m, 2H), 3.44 (m, 2H), 3.23 (m, 6H), 2.10 (m, 2H), 1.98 (m, 2H), 1.16 (m, 18H)
Mass Spectral Analysis m/z=504.4 (M+H)$^+$

EXAMPLE 3T 3T was obtained according to a procedure similar to the one described for 3E, with the following exception:
Step 3.5: 3.4b was replaced by 3.4p.
$^1$H NMR (400 MHz, DMSO $d_6$) δ 9.00 (m, 1.3H), 7.45 (s, 4H), 7.32 (d, 1H), 7.10 (d, 1H), 7.00 (s, 1H), 6.00 (s, 1H), 4.10 (m, 4H), 3.35-3.60 (m, 8H), 3.20 (m, 4H), 2.10 (m, 4H), 1.10 (m, 6H)
Mass Spectral Analysis m/z=490.1 (M+H)$^+$

EXAMPLE 3U 3U was obtained according to a procedure similar to the one described for 3E, with the following exception:
Step 3.5: 3.4b was replaced by 3.4q.
$^1$H NMR (400 MHz, DMSO $d_6$) δ 9.23 (brs, 2H), 7.44 (m, 4H), 7.30 (m, 1H), 7.12 (m, 1H), 6.96 (m, 1H), 6.01 (s, 1H), 3.40 (m, 6H), 3.22 (m, 6H), 2.11 (m, 4H), 1.56 (m, 2H), 1.43 (m, 4H), 1.12 (m, 6H)
Mass Spectral Analysis m/z=488.4 (M+H)$^+$
Elemental analysis:
$C_{30}H_{37}N_3O_3$, 1HCl, 1.75H$_2$O
Theory: % C, 64.85; % H, 7.53; % N, 7.56.
Found: % C, 64.99; % H, 7.37; % N, 7.46.

EXAMPLE 3V 3V was obtained according to a procedure similar to the one described for 3E, with the following exceptions:
Step 3.5: 3.3a (X═CH) was replaced by 3.3b (X═N).
Step 3.5: 3.4b was replaced by 3.4a.
$^1$H NMR (400 MHz, DMSO $d_6$) δ 9.20 (brm, 1H), 8.63 (d, 1H), 7.92 (m, 2H), 7.83 (dd, 1H), 7.64 (d, 1H), 7.53 (d, 1H), 7.25 (brs, 1H), 7.12 (d, 1H), 6.16 (s, 1H), 3.48 (q, 2H), 3.31 (q, 2H), 3.22 (brm, 4H), 2.10 (brm, 4H), 1.18 (t, 3H), 1.12 (t, 3H)
Mass Spectral Analysis m/z=421.3 (M+H)$^+$
Elemental analysis:
$C_{24}H_{28}N_4O_3$, 1.6HCl, 1.4H$_2$O
Theory: % C, 57.19; % H, 6.48; % N, 11.12; % Cl, 11.25.
Found: % C, 57.14; % H, 6.41; % N, 10.98; % Cl, 11.00.

EXAMPLE 3W 3W was obtained according to a procedure similar to the one described for 3E, with the following exception:
Step 3.5: 3.3a was replaced by 3.3b.
$^1$H NMR (400 MHz, DMSO $d_6$) δ 9.21 (brm, 2H), 8.63 (d, 1H), 8.36 (m, 1H), 7.93 (dd, 1H), 7.79 (dd, 1H), 7.64 (d, 1H), 7.49 (d, 1H), 7.13 (d, 1H), 6.16 (s, 1H), 3.48 (q, 2H), 3.25 (brm, 6H), 2.71 (d, 3H), 2.10 (m, 4H), 1.18 (t, 3H), 1.12 (t, 3H)
Mass Spectral Analysis m/z=435.3 (M+H)$^+$
Elemental analysis:
$C_{25}H_{30}N_4O_3$, 1.8HCl, 2H$_2$O
Theory: % C, 56.00; % H, 6.73; % N, 10.45; % Cl, 11.90.
Found: % C, 56.16; % H, 6.72; % N, 10.47; % Cl, 12.23.

EXAMPLE 3X 3X was obtained according to a procedure similar to the one described for 3E, with the following exceptions:
Step 3.5: 3.3a was replaced by 3.3b.
Step 3.5: 3.4b was replaced by 3.4c.
$^1$H NMR (400 MHz, DMSO $d_6$) δ 9.23 (brm, 2H), 8.63 (d, 1H), 8.40 (t, 1H), 7.93 (dd, 1H), 7.81 (dd, 1H), 7.64 (d, 1H), 7.49 (d, 1H), 7.13 (d, 1H), 6.16 (s, 1H), 3.48 (q, 2H), 3.25 (brm, 8H), 2.10 (brm, 4H), 1.18 (t, 3H), 1.12 (t, 3H), 1.05 (t, 3H)
Mass Spectral Analysis m/z=449.3 (M+H)$^+$
Elemental analysis:
$C_{26}H_{32}N_4O_3$, 2HCl, 1.5H$_2$O
Theory: % C, 56.93; % H, 6.80; % N, 10.21; % Cl, 12.93.
Found: % C, 56.64; % H, 6.86; % N, 10.13; % Cl, 12.59.

EXAMPLE 3Y 3Y was obtained according to a procedure similar to the one described for 3E, with the following exceptions:
Step 3.5: 3.3a was replaced by 3.3b.
Step 3.5: 3.4b was replaced by 3.4j.
$^1$H NMR (400 MHz, DMSO $d_6$) δ 9.06 (brs, 2H), 8.62 (d, 1H), 7.92 (dd, 1H), 7.63 (d, 1H), 7.36 (dd, 1H), 7.11 (d, 1H), 6.98 (d, 1H), 6.16 (s, 1H), 3.47 (q, 2H), 3.25 (brm, 6H), 2.91 (s, 6H), 2.10 (brm, 4H), 1.17 (t, 3H), 1.11 (t, 3H)
Mass Spectral Analysis m/z=449.3 (M+H)$^+$
Elemental analysis:
$C_{26}H_{32}N_4O_3$, 1.75HCl, 1.25H$_2$O
Theory: % C, 58.38; % H, 6.83; % N, 10.47; % Cl, 11.60.
Found: % C, 58.37; % H, 6.94; % N, 10.21; % Cl, 11.35.

EXAMPLE 3Z 3Z was obtained according to a procedure similar to the one described for 3AC, with the following exception:
Step 3.8: 3.6d was replaced by 3.6a; tetrakis(triphenylphosphine)palladium(0) was used.
$^1$H NMR (400 MHz, DMSO $d_6$) δ 9.21 (brm, 2H), 9.01 (s, 1H), 8.73 (d, 1H), 8.47 (d, 1H), 7.87 (m, 1H), 7.76 (dd, 1H), 7.53 (d, 2H), 7.44 (d, 2H), 7.38 (d, 1H), 7.28 (d, 1H), 6.07 (s, 1H), 3.44 (m, 2H), 3.23 (brm, 6H), 2.11 (brm, 4H), 1.12 (brd, 6H)
Mass Spectral Analysis m/z=454.0 (M+H)$^+$

EXAMPLE 3AA

3AA was obtained according to a procedure similar to the one described for 3AC, with the following exception:
Step 3.8: 3.6d was replaced by 3.6b; tetrakis(triphenylphosphine)palladium(0) was used.

$^1$H NMR (400 MHz, DMSO d$_6$) δ 8.84 (brm, 2H), 7.58 (dd, 1H), 7.46 (m, 5H), 7.27 (d, 1H), 7.18 (d, 1H), 7.12 (d, 1H), 7.06 (m, 1H), 6.04 (s, 1H), 3.46 (m, 2H), 3.23 (brm, 6H), 2.13 (m, 2H), 2.01 (m, 2H), 1.12 (brd, 6H)

Mass Spectral Analysis m/z=459.3 (M+H)$^+$
Elemental analysis:
$C_{28}H_{30}N_2O_2S$, 1HCl, 0.5H$_2$O
Theory: % C, 66.71; % H, 6.40; % N, 5.56; % Cl, 7.03.
Found: % C, 66.76; % H, 6.27; % N, 5.50; % Cl, 7.34.

EXAMPLE 3AB

3AB was obtained according to a procedure similar to the one described for 3AC, with the following exception:
Step 3.8: 3.6d was replaced by 3.6c; tetrakis(triphenylphosphine)palladium(0) was used.

$^1$H NMR (400 MHz, DMSO-d$_6$) δ 9.39 (b, 1H), 9.32 (b, 1H), 8.83 (d, 2H), 8.16 (d, 2H), 7.98 (d, 1H), 7.49 (m, 3H), 7.46 (d, 2H), 7.34 (d, 1H), 6.14 (s, 1H), 3.3-3.7 (m, 8H), 2.12 (m, 4H), 1.05-1.2 (b, 6H)

Mass Spectral Analysis m/z=454.4 (M+H)$^+$
Elemental analysis:
$C_{29}H_{33}Cl_2N_3O_2$, 2HCl, 2.75H$_2$O
Theory: % C, 60.47; % H, 6.74; % N, 7.29.
Found: % C, 60.35; % H, 6.46; % N, 7.32.

EXAMPLE 3AC

Preparation of 3.7a:
To a solution of 3.1a (1.50 g, 2.40 mmol, 1.0 eq) in dimethoxyethane (DME) (20 mL) was added sequentially a 2N aqueous solution of sodium carbonate (3.6 mL, 7.20 mmol, 3.0 eq), lithium chloride (0.305 g, 7.20 mmol, 3.0 eq), 3.6d (0.357 g, 2.88 mmol, 1.2 eq) and tetrakis(triphenylphosphine)palladium(0) (0.277 g, 0.24 mmol, 0.10 eq). The mixture was heated at 120° C. for 16 h. After this time, only starting material 3.1a was observed by LC/MS. Therefore, additional quantities of 3.6d (0.10 g, 0.81 mmol, 0.34 eq), tetrakis(triphenylphosphine)palladium(0) (0.10 g, 0.087 mmol, 0.036 eq) and [1,1'-bis(diphenylphosphino)ferrocene palladium (II) chloride, dichloromethane complex] (0.50 g, 0.68 mmol, 0.28 eq) were added to the reaction mixture, which was heated at 120° C. for 5 h. The crude mixture was cooled to room temperature, dissolved in ethyl acetate and the mixture was washed with water. The organic extract was dried over sodium sulfate, filtered and concentrated under reduced pressure. The crude product was purified column chromatography (eluent: hexane/ethyl acetate mixtures of increasing polarity), and the product was used without further purification.

Yield: 20%
Mass Spectral Analysis m/z=555.5 (M+H)$^+$

Preparation of 3AC:
To a solution of 3.7a (0.3 g, purity: 90%, 0.489 mmol, 1.0 eq) in methylene chloride (10 mL) was added an excess of a 1.0M solution of anhydrous hydrochloric acid in diethyl ether (10 mL). The mixture was stirred for 16 h at room temperature, concentrated under reduced pressure and purified by column chromatography (eluent: methylene chloride/methanol mixtures of increasing polarity).

Yield: 90%
$^1$H NMR (400 MHz, DMSO d$_6$) δ 9.26 (brs, 2H), 9.13 (s, 1H), 8.99 (s, 2H), 7.72 (d, 1H), 7.53 (d, 2H), 7.44 (d, 2H), 7.34 (s, 1H), 7.25 (d, 1H), 6.07 (s, 1H), 3.44 (brs, 2H), 3.23 (brm, 6H), 2.12 (brm, 4H), 1.12 (brd, 6H)

Mass Spectral Analysis m/z=455.4 (M+H)$^+$
Elemental analysis:
$C_{28}H_{30}N_4O_2$, 2HCl, 2.75H$_2$O
Theory: % C, 58.28; % H, 6.55; % N, 9.71.
Found: % C, 58.53; % H, 6.27; % N, 9.74.

EXAMPLE 4A

Preparation of 4.2:
To a suspension of 1A (21.9 g, 52.45 mmol, 1.0 eq) in tetrahydrofuran (200 mL) at 0° C. was added triethylamine (18.3 mL, 131 mmol, 2.5 eq), followed by trifluoroacetic anhydride (4.1) (8.75 ml, 63 mmol, 1.2 eq) dropwise. The reaction mixture was slowly warmed up to and stirred at room temperature for 10 h. Ethyl acetate (500 mL) was added and the organic layer was washed with a 1M aqueous solution of hydrochloric acid (5×100 mL) and brine, dried over sodium sulfate and filtered. The crude product was concentrated under reduced pressure and purified by column chromatography (eluent: hexane/ethyl acetate mixtures of increasing polarity).

Yield: 93%
$^1$H NMR (400 MHz, CDCl$_3$) δ 7.42 (m, 2H), 7.36 (m, 2H), 7.22 (m, 1H), 7.02 (m, 1H), 6.96 (m, 1H), 6.90 (m, 1H), 5.54 (s, 1H), 4.39 (m, 1H), 3.87 (m, 1H), 3.71 (m, 1H), 3.58 (m, 2H), 3.35 (m, 3H), 2.22 (m, 2H), 1.74 (m, 2H), 1.22 (m, 6H)

Mass Spectral Analysis m/z=473.3 (M+H)$^+$
Preparation of 4.4:
To a solution of 4.2 (4.0 g, 8.47 mmol, 1.0 eq) in dry dichloroethane (100 mL) was added sulfur trioxide N,N-dimethylformamide complex (4.3) (1.98 g, 12.9 mmol, 1.5 eq) portionwise. The reaction mixture was heated under reflux for 10 h and then cooled down to 0-10° C. at which point oxalyl chloride (1.2 mL, 13.55 mmol, 1.6 eq) was added drop wise. The reaction mixture was then stirred at 70° C. for another 3 h. The reaction was quenched with ice/water (100 mL). Dichloromethane (100 mL) was added and the two phases were separated. The aqueous phase was extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 79%
$^1$H NMR (400 MHz, CDCl$_3$) δ 7.90 (dd, 1H), 7.72 (d, 1H), 7.49 (m, 2H), 7.36 (m, 2H), 7.13 (d, 1H), 5.68 (s, 1H), 4.44 (m, 1H), 3.92 (m, 1H), 3.70 (m, 1H), 3.58 (m, 2H), 3.35 (m, 3H), 2.25 (m, 2H), 1.83 (m, 2H), 1.22 (m, 6H)

Mass Spectral Analysis m/z=571.2 (M+H)$^+$
Preparation of 4.6a:
To a solution of 4.4 (0.7 g, 1.22 mmol, 1.0 eq) in dry dichloromethane (30 mL) at 0° C. was added triethylamine (0.85 mL, 6.10 mmol, 5.0 eq) and methylamine (3.4b) hydrochloride salt (0.25 g, 3.66 mmol, 3.0 eq) in one portion. The reaction mixture was slowly warmed up to room temperature and stirred at room temperature for 10 h. Water (50 mL) and chloroform (50 mL) were added and the two phases were separated. The aqueous phase was extracted with chloroform (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 86%

$^1$H NMR (400 MHz, CDCl$_3$) δ 7.73 (dd, 1H), 7.53 (d, 1H), 7.45 (m, 2H), 7.35 (m, 2H), 7.07 (d, 1H), 5.63 (s, 1H), 4.42 (m, 1H), 4.29 (q, 1H), 3.90 (m, 1H), 3.69 (m, 1H), 3.58 (m, 2H), 3.35 (m, 3H), 2.63 (d, 3H), 2.22 (m, 2H), 1.79 (m, 2H), 1.22 (m, 6H)

Mass Spectral Analysis m/z=566.2 (M+H)$^+$

Preparation of 4A:

To a solution of 4.6a (0.63 g, 1.11 mmol, 1.0 eq) in a mixture of methanol (20 mL) and water (5 mL) at 0° C. was added potassium carbonate (0.92 g, 6.66 mmol, 6.0 eq) portionwise. The reaction mixture was warmed up to room temperature and stirred at room temperature for 10 h. Brine (50 mL) and chloroform (50 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil in anhydrous dichloromethane was added a 2.0M solution of hydrogen chloride in diethyl ether (1.11 mL, 2.22 mmol, 2 eq) drop wise. The mixture was then stirred for 1 h at room temperature, concentrated under reduced pressure, and dried under reduced pressure.

Yield: 85%

$^1$H NMR (400 MHz, DMSO d$_6$) δ 8.99 (m, 2H), 7.66 (dd, 1H), 7.49-7.37 (m, 6H), 7.25 (d, 1H), 6.10 (s, 1H), 3.45 (m, 2H), 3.22 (m, 6H), 2.36 (d, 3H), 2.01 (m, 4H), 1.12 (m, 6H)

Mass Spectral Analysis t/z=470.2 (M+H)$^+$

Elemental analysis:

$C_{25}H_{31}N_3O_4S$, 1HCl, 1.5H$_2$O

Theory: % C, 56.33; % H, 6.62; % N, 7.88.

Found: % C, 56.06; % H, 6.50; % N, 8.18.

EXAMPLE 4B 4B was obtained according to a procedure similar to the one described for 4A, with the following exception:

Step 4.3: 3.4b was replaced by 3.4c.

$^1$H NMR (400 MHz, DMSO d$_6$) δ 8.88 (brs, 1H), 7.67 (dd, 1H), 7.46 (m, 4H), 7.39 (d, 1H), 7.23 (d, 1H), 6.10 (s, 1H), 3.52-3.15 (m, 9H), 2.71 (m, 2H), 2.08 (m, 4H), 1.42 (m, 6H), 0.94 (t, 3H)

Mass Spectral Analysis m/z=484.3 (M+H)$^+$

Elemental analysis:

$C_{26}H_{33}N_3O_4S$, 1HCl, 1.25H$_2$O

Theory: % C, 57.55; % H, 6.78; % N, 7.74.

Found: % C, 57.61; % H, 6.75; % N, 7.60.

EXAMPLE 4C 4C was obtained according to a procedure similar to the one described for 4A, with the following exception:

Step 4.3: 3.4b was replaced by 3.4d.

$^1$H NMR (400 MHz, DMSO d$_6$) δ 8.85 (m, 2H), 7.67 (dd, 1H), 7.51 (t, 1H), 7.45 (m, 3H), 7.39 (d, 1H), 7.23 (d, 1H), 6.10 (s, 1H), 3.45 (m, 2H), 3.24 (m, 7H), 2.63 (m, 2H), 2.08 (m, 4H), 1.34 (m, 2H), 1.12 (m, 6H), 0.77 (t, 3H)

Mass Spectral Analysis m/z=498.3 (M+H)$^+$

Elemental analysis:

$C_{27}H_{35}N_3O_4S$, 1HCl, 1H$_2$O

Theory: % C, 58.74; % H, 6.94; % N, 7.61.

Found: % C, 58.82; % H, 6.78; % N, 7.56.

EXAMPLE 4D 4D was obtained according to a procedure similar to the one described for 4A, with the following exception:

Step 4.3: 3.4b was replaced by 3.4g.

$^1$H NMR (400 MHz, DMSO d$_6$) δ 8.90 (m, 2H), 7.68 (m, 2H), 7.45 (m, 3H), 7.40 (d, 1H), 7.22 (d, 1H), 6.09 (s, 1H), 3.45 (m, 2H), 3.24 (m, 7H), 2.59 (t, 2H), 2.07 (m, 4H), 1.12 (m, 6H), 0.75 (m, 1H), 0.32 (m, 2H), 0.04 (m, 2H)

Mass Spectral Analysis m/z=510.3 (M+H)$^+$

Elemental analysis:

$C_{28}H_{33}N_3O_4S$, 1HCl, 1H$_2$O

Theory: % C, 59.61; % H, 6.79; % N, 7.45.

Found: % C, 59.55; % H, 6.75; % N, 7.40.

EXAMPLE 4E 4E was obtained according to a procedure similar to the one described for 4A, with the following exception:

Step 4.3: 3.4b was replaced by 3.4h.

$^1$H NMR (400 MHz, DMSO d$_6$) δ 8.79 (m, 2H), 7.69 (dd, 1H), 7.54 (d, 1H), 7.44 (m, 4H), 7.22 (d, 1H), 6.10 (s, 1H), 3.51-3.09 (m, 10H), 2.07 (m, 4H), 1.12 (m, 6H), 0.92 (d, 6H)

Mass Spectral Analysis m/z=498.3 (M+H)$^+$

Elemental analysis:

$C_{27}H_{35}N_3O_4S$, 1HCl, 1.4H$_2$O

Theory: % C, 57.98; % H, 6.99; % N, 7.51. Found: % C, 57.99; % H, 7.04; % N, 7.38.

EXAMPLE 4F 4F was obtained according to a procedure similar to the one described for 4A, with the following exception:

Step 4.3: 3.4b was replaced by 3.4j.

$^1$H NMR (400 MHz, DMSO d$_6$) δ 9.11 (m, 2H), 7.64 (dd, 1H), 7.46 (m, 4H), 7.29 (d, 1H), 7.24 (d, 1H), 6.13 (s, 1H), 3.45 (m, 2H), 3.23 (m, 6H), 2.56 (s, 6H), 2.11 (m, 4H), 1.12 (m, 6H)

Mass Spectral Analysis m/z=484.1 (M+H)$^+$

Elemental analysis:

$C_{26}H_{33}N_3O_4S$, 1HCl, 2.75H$_2$O

Theory: % C, 54.82; % H, 6.99; % N, 7.38.

Found: % C, 54.66; % H, 6.89; % N, 7.30.

EXAMPLE 4G 4G was obtained according to a procedure similar to the one described for 4A, with the following exception:

Step 4.3: 3.4b was replaced by 4.5.

$^1$H NMR (400 MHz, DMSO d$_6$) δ 8.85 (m, 2H), 7.83 (d, 1H), 7.69 (dd, 1H), 7.45 (m, 3H), 7.41 (d, 1H), 7.25 (d, 1H), 6.11 (s, 1H), 3.45 (m, 2H), 3.25 (m, 7H), 2.09 (m 5H), 1.12 (m, 6H), 0.45 (m, 2H), 0.34 (m, 2H)

Mass Spectral Analysis m/z=496.2 (M+H)$^+$

Elemental analysis:

$C_{27}H_{33}N_3O_4S$, 1HCl, 0.75H$_2$O

Theory: % C, 59.44; % H, 6.56; % N, 7.70.
Found: % C, 59.37; % H, 6.46; % N, 7.60.

EXAMPLE 4H

Preparation of 4H:
To a solution of 4.4 (1.5 g, 2.82 mmol) in acetonitrile (20 mL) was added a concentrated aqueous solution of ammonium hydroxide (28-35%, 20 mL). The reaction mixture was heated under reflux for 10 h. Brine (100 mL) was added and the aqueous phase was adjusted to pH=10 with a 1M aqueous solution of sodium hydroxide. Chloroform (150 mL) was added and the two phases were separated. The aqueous phase was extracted with chloroform (3×50 mL). The combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil (0.32 g, 0.70 mmol, 1.0 eq) in dichloromethane/methanol was added drop wise a 2.0M solution of hydrogen chloride in diethyl ether (0.7 mL, 1.4 mmol, 2.0 eq). The mixture was then stirred for 1 h at room temperature, concentrated under reduced pressure, and dried under vacuum.
Yield: 80%
$^1$H NMR (400 MHz, DMSO $d_6$) δ 8.98 (m, 1.5H), 7.71 (dd, 1H), 7.45 (m, 5H), 7.27 (s, 2H), 7.22 (d, 1H), 6.09 (s, 1H), 3.46 (m, 2H), 3.23 (m, 6H), 2.07 (m, 4H), 1.12 (m, 6H)
Mass Spectral Analysis m/z=456.0 (M+H)$^+$
Elemental analysis:
$C_{24}H_{29}N_3O_4S$, 1HCl, 2H$_2$O
Theory: % C, 54.59; % H, 6.49; % N, 7.96.
Found: % C, 54.50; % H, 6.49; % N, 7.82.

EXAMPLE 4I

Preparation of 4.8:
To a suspension of 4H (1.12 g, 2.45 mmol, 1.0 eq) in a mixture of dichloromethane (50 mL) and methanol (5 mL) at 0° C. was added sequentially triethylamine (0.85 mL, 6.12 mmol, 2.5 eq), and di-tert-butyl dicarbonate 4.7 (0.80 g, 3.67 mmol, 1.5 eq) portion wise. The reaction mixture was slowly warmed to room temperature and stirred at room temperature for 10 h. The solvents were removed under reduced pressure. The crude product was purified by column chromatography (eluent: hexane/ethyl acetate mixtures of increasing polarity).
Yield: 92%
$^1$H NMR (400 MHz, CDCl$_3$) δ 7.75 (dd, 1H), 7.57 (d, 1H), 7.43 (m, 2H), 7.35 (m, 2H), 7.03 (d, 1H), 5.65 (s, 1H), 4.83 (s, 2H), 3.89 (m, 2H), 3.57 (m, 2H), 3.32 (m, 4H), 2.04 (m, 2H), 1.71 (m, 2H), 1.47 (s, 9H), 1.21 (m, 6H)
Mass Spectral Analysis m/z=556.3 (M+H)$^+$
Preparation of 4.10:
To a solution of 4.8 (1.25 g, 2.25 mmol, 1.0 eq) in dichloromethane (40 mL) was added triethylamine (0.94 mL, 6.75 mmol, 3.0 eq), and acetic anhydride (4.9) (0.64 mL, 6.75 mmol, 3.0 eq) drop wise. The mixture was stirred at room temperature for 10 h. Dichloromethane (100 mL) and water (100 mL) were added to the reaction mixture and the two phases were separated. The aqueous phase was extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).
Yield: 70%
Mass Spectral Analysis m/z=598.3 (M+H)$^+$
Preparation of 4I:
To a solution of 4.10 (0.16 g, 0.27 mmol, 1.0 eq) in dichloromethane (5 mL) was added iodotrimethylsilane (0.06 mL, 0.43 mmol, 1.6 eq) dropwise. The mixture was stirred at room temperature for 30 min. The mixture was diluted in chloroform (100 mL) and methanol (5 mL), washed with a 20% aqueous solution of sodium thiosulfate (2×30 mL) and a 1M aqueous solution of sodium carbonate (2×30 mL), dried over sodium sulfate, filtered, and concentrated under reduced pressure. The crude product was purified by column chromatography (eluent: dichloromethane/methanol mixtures of increasing polarity).
Yield: 60%
$^1$H NMR (400 MHz, DMSO $d_6$) δ 7.73 (dd, 1H), 7.51 (d, 1H), 7.45 (s, 4H), 7.17 (d, 1H), 6.01 (s, 1H), 3.45 (brs, 2H), 3.38-3.15 (m, 7H), 2.07 (m, 4H), 1.79 (s, 3H), 1.12 (m, 6H)
Mass Spectral Analysis m/z=498.3 (M+H)$^+$

EXAMPLE 5A

Preparation of 5.2:
To a solution of 4.4 (1.4 g, 2.45 mmol, 1.0 eq) in a mixture tetrahydrofuran (5 mL) and dichloromethane (1 mL) at 0° C. was added a 1.0 M solution of hydrazine (5.1) in tetrahydrofuran (24.5 mL, 24.5 mmol, 10.0 eq) in one portion. The reaction mixture was stirred at 0° C. for 30 min. Water (50 mL) and chloroform (100 mL) were added and the two phases were separated. The aqueous phase was extracted with chloroform (3×50 mL) and the combined organic layers were dried over sodium sulfate, filtered, and concentrated under reduced pressure. The crude product was purified by column chromatography (eluent: hexane/ethyl acetate mixtures of increasing polarity).
Yield: 70%
$^1$H NMR (400 MHz, CDCl$_3$) δ 7.78 (dd, 1H), 7.59 (d, 1H), 7.46 (d, 2H), 7.35 (d, 2H), 7.10 (d, 1H), 5.64 (s, 1H), 4.42 (m, 1H), 3.91 (m, 1H), 3.69 (m, 1H), 3.57 (m, 2H), 3.35 (m, 4H), 2.23 (m, 2H), 1.80 (m, 2H), 1.22 (m, 6H)
Mass Spectral Analysis m/z=567.4 (M+H)$^+$
Preparation of 5.3:
To a suspension of 5.2 (0.9 g, 1.59 mmol, 1.0 eq) in ethanol (10 mL) was added sodium acetate (0.87 g, 10.8 mmol, 6.65 eq) and iodomethane (2.8c) (0.54 mL, 8.85 mmol, 5.45 eq). The mixture was heated under reflux for 10 h. Water (100 mL) and dichloromethane (100 mL) were added and the two phases were separated. The aqueous phase was extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).
Yield: 74%
$^1$H NMR (400 MHz, CDCl$_3$) δ 7.81 (dd, 1H), 7.64 (d, 1H), 7.46 (d, 2H), 7.35 (d, 2H), 7.11 (d, 1H), 5.64 (s, 1H), 4.42 (m, 1H), 3.91 (m, 1H), 3.69 (m, 1H), 3.57 (m, 2H), 3.35 (m, 3H), 3.00 (s, 3H), 2.23 (m, 2H), 1.80 (m, 2H), 1.22 (m, 6H)
Mass Spectral Analysis m/z=551.2 (M+H)$^+$
Preparation of 5A:
To a solution of 5.3 (0.65 g, 1.18 mmol, 1.0 eq) in a mixture of methanol (20 mL) and water (5 mL) at 0° C. was added potassium carbonate (0.98 g, 7.08 mmol, 6.0 eq) portion wise. The mixture was warmed up to and stirred at room temperature for 10 h. Brine (50 mL) and chloroform (50 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil in anhydrous dichloromethane was added dropwise a 2.0M solution of hydrogen chloride in diethyl ether (1.18 mL, 2.36 mmol, 2.0 eq). The mixture was then stirred at room temperature for 1 h, concentrated under reduced pressure, and dried under vacuum.

Yield: 88%

$^1$H NMR (400 MHz, DMSO d$_6$) δ 9.07 (m, 2H), 7.83 (dd, 1H), 7.47 (m, 5H), 7.30 (d, 1H), 6.12 (s, 1H), 3.63-3.10 (m, 11H), 2.10 (m, 4H), 1.12 (m, 6H)

Mass Spectral Analysis m/z=455.2 (M+H)$^+$

Elemental analysis: C$_{25}$H$_{30}$N$_2$O$_4$S, 1HCl, 1.33H$_2$O

Theory: % C, 58.30; % H, 6.59; % N, 5.44. Found: % C, 58.35; % H, 6.56; % N, 5.37.

EXAMPLE 6A

Preparation of 6.2:

To a cold (0° C.) solution of 4.2 (0.23 g, 0.48 mmol, 1.0 eq) in dry acetonitrile (3 mL) under nitrogen was added nitronium tetrafluoroborate complex (6.1) (78.5 mg, 0.576 mmol, 1.2 eq) in one portion with rapid stirring. The reaction mixture was kept at 0° C. for 1 h and then quenched with ice/water (1:1) (15 mL). Dichloromethane (50 mL) was added and the two phases were separated. The aqueous phase was extracted with dichloromethane (3×30 mL) and the combined organic layers were dried over sodium sulfate, filtered, and concentrated under reduced pressure. The crude product was purified by column chromatography (eluent: hexane/ethyl acetate mixtures of increasing polarity).

Yield: 38%

$^1$H NMR (400 MHz, CDCl$_3$) δ 8.14 (dd, 1H), 7.97 (d, 1H), 7.48 (m, 2H), 7.36 (m, 2H), 7.06 (d, 1H), 5.66 (s, 1H), 4.43 (m, 1H), 3.92 (m, 1H), 3.70 (m, 1H), 3.58 (m, 2H), 3.36 (m, 3H), 2.23 (m, 2H), 1.82 (m, 2H), 1.23 (m, 6H)

Mass Spectral Analysis m/z=518.3 (M+H)$^+$

Preparation of 6A:

To a solution of 6.2 (0.2 g, 0.386 mmol, 1.0 eq) in a mixture of methanol (15 mL) and water (5 mL) at 0° C. was added potassium carbonate (0.32 g, 2.32 mmol, 6.0 eq) portionwise. The mixture was warmed up to room temperature and stirred at room temperature for 10 h. Brine (50 mL) and chloroform (50 mL) were added and the two phases were separated. The aqueous phase was extracted with chloroform (3×30 mL). The combined organic layers were dried over sodium sulfate, filtered, and concentrated under reduced pressure. The crude product was purified by preparative liquid chromatography (mobile phase: acetonitrile/water/trifluoroacetic acid). The desired fractions were combined and concentrated under reduced pressure. The product was dissolved in chloroform (100 mL), washed with a 1M aqueous solution of sodium carbonate (2×30 mL), dried over sodium sulfate, filtered, and concentrated under reduced pressure. To a cold (0° C.) solution of the resulting oil in anhydrous dichloromethane was added dropwise a 1.0M solution of hydrogen chloride in diethyl ether (0.8 mL, 0.8 mmol, 2.0 eq). The mixture was then stirred for 1 h at room temperature, concentrated under reduced pressure, and dried under vacuum.

Yield: 50%

$^1$H NMR (400 MHz, DMSO d$_6$) δ 9.01 (m, 2H), 8.19 (dd, 1H), 7.79 (d, 1H), 7.49 (m, 4H), 7.29 (d, 1H), 6.19 (s, 1H), 3.56-3.14 (m, 8H), 2.11 (m, 4H), 1.13 (m, 6H)

Mass Spectral Analysis m/z=422.3 (M+H)$^+$

EXAMPLE 6B

Preparation of 6.4:

To a cold (0° C.) solution of 6.2 (1.92 g, 3.71 mmol, 1.0 eq) in ethanol (50 mL) was added tin (II) chloride dihydrate (6.3) (2.51 g, 11.13 mmol, 3.0 eq) in one portion. The reaction mixture was heated under reflux for 10 h and then concentrated under reduced pressure to give the crude product, which was used for the next step without purification.

Mass Spectral Analysis m/z=488.2 (M+H)$^+$

Preparation of 6B:

To a suspension of 6.4 (1.3 g, crude, as of 0.91 mmol, 1.0 eq) in a mixture of methanol (30 mL) and water (10 mL) at 0° C. was added potassium carbonate (0.75 g, 5.46 mmol, 6.0 eq) portion wise. The reaction mixture was warmed up to room temperature and stirred at room temperature for 10 h. Brine (50 mL) and chloroform (50 mL) were added and the two phases were separated. The aqueous phase was extracted with chloroform (3×30 mL). The combined organic layers were dried over sodium sulfate, filtered, and concentrated under reduced pressure. The crude product was purified by preparative liquid chromatography (mobile phase: acetonitrile/water/trifluoroacetic acid). The desired fractions were combined, concentrated under reduced pressure, and dried under vacuum.

Yield: 27% over two steps $^1$H NMR (400 MHz, DMSO d$_6$) δ 9.98 (brs, 2.5H), 9.11 (m, 2H), 7.44 (m, 4H), 7.23 (dd, 1H), 7.15 (d, 1H), 7.00 (d, 1H), 6.06 (s, 1H), 3.78-3.10 (m, 8H), 2.06 (m, 4H), 1.12 (m, 6H)

Mass Spectral Analysis m/z=392.2 (M+H)$^+$

EXAMPLE 6C

Preparation of 6.6a:

To a suspension of 6.4 (1.5 g, crude, as of 1.05 mmol, 1.0 eq) in dichloroethane (50 mL) at 0° C. was added pyridine (0.42 g, 5.25 mmol, 5 eq) followed by drop wise addition of ethylsulfonyl chloride (6.5a) (0.30 mL, 3.15 mmol, 3.0 eq) dropwise. The mixture was stirred at 0° C. for another 2 h. A 1M aqueous solution of hydrochloric acid (100 mL) and chloroform (100 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: hexane/ethyl acetate mixtures of increasing polarity).

Yield: 90%

Mass Spectral Analysis m/z=580.3 (M+H)$^+$

Preparation of 6C:

To a solution of 6.6a (0.55 g, 0.9 mmol, 1.0 eq) in a mixture of methanol (20 mL) and water (5 mL) at 0° C. was added potassium carbonate (0.78 g, 5.4 mmol, 6.0 eq) portionwise. The mixture was warmed up to room temperature and stirred at room temperature for 10 h. Brine (100 mL) and chloroform (100 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: dichloromethane/methanol mixture of increasing polarity). The desired fractions were combined and concentrated under reduced pressure. To a cold (0° C.) solution of the resulting oil in anhydrous dichloromethane was added drop wise a 1.0M solution of hydrogen chloride in diethyl ether (1.8 mL, 1.8 mmol, 2.0 eq). The mixture was then stirred for 1 h at room temperature, concentrated under reduced pressure, and dried under vacuum.

Yield: 80%

$^1$H NMR (400 MHz, DMSO d$_6$) δ 9.49 (s, 1H), 8.91 (m, 2H), 7.43 (m, 4H), 7.11 (dd, 1H), 7.02 (d, 1H), 6.93 (d, 1H), 6.00 (s, 1H), 3.45 (brs, 2H), 3.21 (m, 6H), 2.97 (q, 2H), 2.03 (m, 4H), 1.20-1.00 (m, 9H)

Mass Spectral Analysis m/z=484.2 (M+H)$^+$

Elemental analysis:

$C_{26}H_{33}N_3O_4S$, 1HCl, 1.25H$_2$O

Theory: % C, 57.55; % H, 6.78; % N, 7.74. Found: % C, 57.52; % H, 6.67; % N, 7.73.

EXAMPLE 6D 6D was obtained according to a procedure similar to the one described for 6C, with the following exception:
Step 6.5: 6.5a was replaced by 6.5b.

$^1$H NMR (400 MHz, DMSO d$_6$) δ 9.48 (s, 1H), 8.66 (brm, 1H), 7.43 (s, 4H), 7.12 (dd, 1H), 7.01 (d, 1H), 6.95 (d, 1H), 6.00 (s, 1H), 3.46 (brs, 4H), 3.23 (brm, 4H), 3.12 (m, 1H), 2.06 (m, 2H), 1.95 (m, 2H), 1.20 (d, 6H), 1.12 (brd, 6H)

Mass Spectral Analysis m/z=498.2 (M+H)$^+$

EXAMPLE 6E

Preparation of 6.8:

To a suspension of 6.4 (1.0 g, crude, as of 0.58 mmol, 1.0 eq) in dichloroethane (30 mL) at 0° C. was added pyridine (0.23 mL, 2.9 mmol, 5.0 eq) followed by a drop wise addition of acetyl chloride (6.7) (0.16 mL, 2.32 mmol, 4.0 eq). The reaction mixture was slowly warmed up to room temperature and stirred at room temperature for 10 h. A 1M aqueous solution of hydrochloric acid (50 mL) and chloroform (50 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: hexane/ethyl acetate mixture of increasing polarity).

Yield: 88%

Mass Spectral Analysis m/z=530.2 (M+H)$^+$

Preparation of 6E:

To a solution of 6.8 (0.27 g, 0.5 mmol, 1.0 eq) in a mixture of methanol (20 mL) and water (5 mL) at 0° C. was added potassium carbonate (0.42 g, 3.0 mmol, 6.0 eq) portion wise. The reaction mixture was warmed up to room temperature and stirred at room temperature for 10 h. Brine (100 mL) and chloroform (100 mL) were added and the two phases were separated. The aqueous phase was extracted with chloroform (3×30 mL). The combined organic layers were dried over sodium sulfate, filtered, and concentrated under reduced pressure. The crude product was first purified by column chromatography (eluent: dichloromethane/methanol mixture of increasing polarity) and then repurified by preparative liquid chromatography (mobile phase: acetonitrile/water/trifluoroacetic acid). The desired fractions were combined and concentrated under reduced pressure. The product was dissolved in chloroform (100 mL) and washed with a 1M solution of sodium carbonate (2×30 mL), dried over sodium sulfate, filtered, and concentrated under reduced pressure. To a cold (0° C.) solution of the resulting oil in anhydrous dichloromethane was added dropwise 1.0M hydrogen chloride in diethyl ether (1.0 mL, 1.0 mmol, 2 eq). The mixture was then stirred for 1 h at room temperature, concentrated under reduced pressure, and dried under reduced pressure.

Yield: 73%

$^1$H NMR (400 MHz, DMSO d$_6$) δ 9.34 (s, 1H), 8.80 (brs, 2H), 7.68 (d, 1H), 7.42 (s, 4H), 6.90 (t, 1H), 6.77 (d, 1H), 5.95 (s, 1H), 3.45 (brs, 2H), 3.25 (m, 6H), 2.15 (s, 3H), 2.04 (m, 4H), 1.12 (m, 6H)

Mass Spectral Analysis m/z=434.2 (M+H)$^+$

Elemental analysis:

$C_{26}H_{31}N_3O_3$, 1HCl, 1.7H$_2$O

Theory: % C, 62.38; % H, 7.13; % N, 8.39.

Found: % C, 62.26; % H, 6.81; % N, 8.29.

EXAMPLE 7A

Preparation of 7.2:

To a solution of 3.1a (3 g, 4.80 mmol, 1.0 eq), sodium tert-butoxide (0.55 g, 5.67 mmol, 1.18 eq), tris(dibenzylideneacetone)dipalladium(0) (0.22 g, 0.24 mmol, 0.05 eq) and 1,1'-bis(diphenylphosphino)ferrocene (dppf) (0.39 g, 0.70 mmol, 0.145 eq) in anhydrous toluene (48 mL) was added 7.1 (0.95 mL, 5.67 mmol, 1.18 eq) at room temperature. The solution was stirred at 80° C. overnight and then cooled to room temperature. The mixture was diluted with ethyl acetate and vacuum filtered through a plug of celite. The filtrate was washed with brine, dried over sodium sulfate, filtered and concentrated under reduced pressure. The crude product was purified by column chromatography (eluent: hexane/ethyl acetate mixtures of increasing polarity).

Yield: 33%

Mass Spectral Analysis m/z=656.6 (M+H)$^+$

Preparation of 7.3:

To a solution of 7.2 (1.00 g, 1.52 mmol, 1.0 eq) in anhydrous methanol (5 mL) at room temperature under nitrogen was added hydroxylamine hydrochloride (0.21 g, 2.97 mmol, 1.95 eq) and sodium acetate (0.64 g, 7.78 mmol, 5.1 eq). The mixture was stirred overnight at room temperature. The mixture was then diluted with ethyl acetate, washed with a saturated aqueous solution of sodium bicarbonate and brine, dried over sodium sulfate and filtered. The organics were concentrated under reduced pressure and the crude product was purified by column chromatography (eluent: hexane/ethyl acetate mixtures of increasing polarity).

Yield: 99%

Mass Spectral Analysis m/z=492.5 (M+H)$^+$

Preparation of 7.5:

To a solution of 7.3 (0.75 g, 1.53 mmol, 1.0 eq) and triethylamine (1.06 mL, 7.63 mmol, 5.0 eq) in dichloromethane (10 mL) at 0° C. under nitrogen was added drop wise 7.4 (0.35 mL, 4.58 mmol, 3.0 eq). The mixture was stirred overnight at room temperature. An aqueous solution of sodium bicarbonate was added and the mixture was stirred for 20 min. The phases were separated and the organic phase was washed with an aqueous solution of sodium bicarbonate, brine, dried over sodium sulfate, filtered and concentrated under reduced pressure. The crude product was used for the next step without further purification.

Yield: 83%

Mass Spectral Analysis m/z=648.5 (M+H)$^+$

Preparation of 7.6:

To a solution of 7.5 (0.82 g, 1.27 mmol, 1.0 eq) in tetrahydrofuran (5 mL) and methanol (5 mL) was added a 1N aqueous solution of sodium hydroxide (5 mL, 5 mmol, 4.0 eq). The mixture was stirred at room temperature for 3 h under nitrogen. The mixture was then neutralized with a 1N aqueous solution of hydrochloric acid (50 mL). The mixture was extracted with ethyl acetate and the organic layer was further washed with brine, dried over sodium sulfate, filtered and concentrated under reduced pressure. The crude product was purified by column chromatography (eluent: hexane/ethyl acetate mixtures of increasing polarity).

Yield: 40%

$^1$H NMR (400 MHz, DMSO d$_6$) δ 9.35 (m, 1H), 7.41 (s, 4H), 7.09 (m, 1H), 6.97 (d, 1H), 6.91 (d, 1H), 5.92 (s, 1H), 3.72 (m, 2H), 3.44 (m, 2H), 3.23 (m, 4H), 2.87 (s, 3H), 1.86 (m, 2H), 1.71 (m, 2H), 1.42 (s, 9H), 1.11 (m, 6H)

Mass Spectral Analysis m/z=570.4 (M+H)$^+$

Preparation of 7A:

A 2.0M solution of hydrochloric acid in diethyl ether (1.4 mL, 2.78 mmol, 5.5 eq) was added drop wise to a cooled (0° C.) solution of 7.6 (0.29 g, 0.51 mmol, 1.0 eq) in anhydrous dichloromethane (5 mL). The mixture was warmed to room temperature and stirring was continued for an additional 10 h at room temperature. Diethyl ether (100 mL) was added to the solution and the resulting precipitate was collected by filtration and washed with diethyl ether. The crude product was purified by column chromatography (eluent: dichloromethane/methanol mixtures of increasing polarity).

Yield: 25%

$^1$H NMR (400 MHz, DMSO d$_6$) δ 9.42 (s, 1H), 8.85 (m, 2H), 7.43 (m, 4H), 7.12 (m, 1H), 7.05 (m, 1H), 6.93 (m, 1H), 6.00 (s, 1H), 3.45 (m, 2H), 3.37 (m, 2H), 3.24 (m, 4H), 2.88 (s, 3H), 2.07 (m, 2H), 1.98 (m, 2H), 1.11 (m, 6H)

Mass Spectral Analysis m/z=470.4 (M+H)$^+$

Elemental analysis:

$C_{25}H_{31}N_3O_4S$, 1HCl, 2H$_2$O

Theory: % C, 55.39; % H, 6.69; % N, 7.75.

Found: % C, 55.03; % H, 6.33; % N, 7.36.

EXAMPLE 7B

Preparation of 7.7:

To a solution of 7.6 (0.5 g, 0.88 mmol, 1.0 eq) in dry tetrahydrofuran (20 mL) at 0° C. was added sodium hydride (60% dispersion in mineral oil, 70 mg, 1.76 mmol, 2.0 eq) in one portion. The reaction mixture was kept at 0° C. for 1 h and methyliodide (2.8c) (0.08 mL, 1.1 mmol, 1.3 eq) was added drop wise. The mixture was kept at 0° C. for another 30 min, warmed up to room temperature, and then heated at 80° C. for 10 h. Water (50 mL) and chloroform (100 mL) were added and the two phases were separated. The aqueous phase was extracted with chloroform (3×50 mL). The combined organic layers were dried over sodium sulfate, filtered, and concentrated under reduced pressure. The crude product was purified by column chromatography (eluent: hexane/ethyl acetate mixtures of increasing polarity).

Yield: 83%

$^1$H NMR (400 MHz, CDCl$_3$) δ 7.43 (m, 2H), 7.36 (m, 2H), 7.19 (dd, 1H), 7.01 (d, 1H) 6.95 (d, 1H), 5.61 (s, 1H), 3.87 (brs, 2H), 3.57 (brs, 2H), 3.32 (m, 4H), 3.21 (s, 3H), 2.81 (s 3H), 2.05 (m, 2H), 1.68 (m, 2H), 1.48 (s, 9H), 1.20 (m, 6H)

Mass Spectral Analysis m/z=584.3 (M+H)$^+$

Preparation of 7B

To a cold (0° C.) solution of 7.7 (0.43 g, 0.73 mmol, 1.0 eq) in anhydrous dichloromethane (20 mL) was added drop wise a 1.0 M solution of hydrogen chloride in diethyl ether (4.38 mL, 4.38 mmol, 6.0 eq). The reaction mixture was stirred at room temperature for 10 h and then concentrated under reduced pressure. The crude product was purified by preparative liquid chromatography (mobile phase: acetonitrile/water/trifluoroacetic acid). The desired fractions were combined and concentrated under reduced pressure. The product was dissolved in chloroform (100 mL) and washed with a 1M solution of sodium carbonate (2×30 mL), dried over sodium sulfate, filtered, and concentrated under reduced pressure. To a cold (0° C.) solution of the resulting oil in anhydrous dichloromethane was added dropwise 1.0M hydrogen chloride in diethyl ether (1.46 mL, 1.46 mmol, 2.0 eq). The mixture was then stirred for 1 h at room temperature, concentrated under reduced pressure, and dried under vacuum.

Yield: 60%

$^1$H NMR (400 MHz, DMSO d$_6$) δ 8.79 (m, 2H), 7.44 (m, 4H), 7.34 (dd, 1H), 7.10 (d, 1H), 7.00 (d, 1H), 6.03 (s, 1H), 3.23 (m, 8H), 3.14 (s, 3H), 2.89 (s, 3H), 2.04 (m, 4H), 1.11 (m, 6H)

Mass Spectral Analysis m/z=484.2 (M+H)$^+$

Elemental analysis:

$C_{26}H_{33}N_3O_4S$, 1HCl, 1.3H$_2$O

Theory: % C, 57.46; % H, 6.79; % N, 7.73.

Found: % C, 57.46; % H, 6.86; % N, 7.80.

EXAMPLE 7C

Preparation of 7.8:

To a suspension of 6.4 (2 g, crude, as of 1.4 mmol, 1.0 eq) in dichloromethane (50 mL) at 0° C. was added triethylamine (0.98 mL, 7.0 mmol, 5 eq) followed by drop wise addition of methylsulfonyl chloride (7.4) (0.33 mL, 4.2 mmol, 3.0 eq). The reaction mixture was stirred at 0° C. for 1 h. A 1M aqueous solution of hydrochloric acid (100 mL) and chloroform (100 mL) were added and the two phases were separated. The aqueous phase was extracted with chloroform (3×50 mL). The combined organic layers were dried over sodium sulfate, filtered, and concentrated under reduced pressure to give the crude product, which was used for the next step without purification.

Mass Spectral Analysis m/z=644.2 (M+H)$^+$

Preparation of the Mixture of 7A & 7C:

To a suspension of 7.8 (1.57 g, crude, as of 1.4 mmol, 1.0 eq) in a mixture of methanol (20 mL), tetrahydrofuran (20 mL) and water (20 mL) was added lithium hydroxide hydrate (0.98 mL, 7.0 mmol, 5.0 eq). The reaction mixture was stirred at room temperature for 10 h and then concentrated under reduced pressure to give the crude product as a mixture of 7A and 7C, which was carried over for the next step without purification.

Mass Spectral Analysis m/z=470.2 (M+H)$^+$ (7A)

Mass Spectral Analysis m/z=484.2 (M+H)$^+$ (7C)

Preparation of 7C

To a suspension of the mixture of 7A and 7C (2.2 g, crude, as of 1.4 mmol, 1.0 eq) in dry dichloroethane (50 mL) at 0° C. was added pyridine (0.34 mL, 4.2 mmol, 3 eq) followed by di-tert-butyl dicarbonate (4.7) (0.46 g, 2.1 mmol, 1.5 eq) portion wise. The reaction mixture was slowly warmed up to room temperature and stirred at room temperature for 10 h. Water (50 mL) and chloroform (100 mL) were added. The two phases were separated and the aqueous phase was further extracted with chloroform (3×50 mL). The combined organic layers were dried over sodium sulfate, filtered, and concentrated under reduced pressure. The crude product was purified by column chromatography (eluent: hexane/ethyl acetate mixtures of increasing polarity to obtain 7.6 as pure compound; eluent: dichloromethane/methanol mixture of increasing polarity to obtain crude 7C).

Yield: 62% for 7.6 over three steps

The crude 7C (100 mg) was further purified by preparative liquid chromatography (mobile phase: acetonitrile/water/trifluoroacetic acid). The desired fractions were combined and concentrated under reduced pressure. The product was dissolved in chloroform (100 mL) and washed with a 1M aqueous solution of sodium carbonate (2×30 mL), dried over sodium sulfate, filtered, and concentrated under reduced pressure. To a cold (0° C.) solution of the resulting oil in anhydrous dichloromethane was added drop wise a 1.0M solution of hydrogen chloride in diethyl ether (0.41 mL, 0.41 mmol, 2.0 eq). The mixture was then stirred for 1 h at room temperature, concentrated under reduced pressure, and dried under vacuum.

$^1$H NMR (400 MHz, DMSO d$_6$) δ 10.47 (m, 1H), 9.435 & 9.422 (2s, 1H), 7.51-6.92 (m, 7H), 6.31 & 5.90 (2s, 1H,), 3.50-3.17 (m, 8H), 2.88 & 2.87 (2s, 3H,), 2.82 (d, 3H), 2.12 (m, 4H), 1.12 (m, 6H)

Mass Spectral Analysis m/z=484.2 (M+H)$^+$

Elemental analysis:

$C_{26}H_{33}N_3O_4S$, 1HCl, 0.9H$_2$O

Theory: % C, 58.23; % H, 6.73; % N, 7.84.

Found: % C, 58.02; % H, 6.68; % N, 8.20.

EXAMPLE 8A 8A was obtained according to a procedure similar to the one described for 2A, with the following exception:

Step 2.1: 2.1 was replaced by 8.1 (see also step 8.1).

$^1$H NMR (400 MHz, DMSO d$_6$) δ 9.16 (s, 1H), 8.92 (brs, 1H), 8.73 (brs, 1H), 7.40 (s, 4H), 6.78 (m, 2H), 6.43 (dd, 1H), 5.86 (s, 1H), 3.43 (brm, 4H), 3.20 (brm, 4H), 2.09 (m, 2H), 1.93 (m, 2H), 1.11 (brd, 6H)

Mass Spectral Analysis m/z=393.4 (M+H)$^+$

Elemental analysis:

$C_{24}H_{28}N_2O_3$, 1HCl, 0.33H$_2$O

Theory: % C, 66.27; % H, 6.87; % N, 6.44.

Found: % C, 66.24; % H, 6.77; % N, 6.44.

EXAMPLE 8B 8B was obtained according to a procedure similar to the one described for 2A, with the following exceptions:

Step 2.1: 2.1 was replaced by 8.1 (see also step 8.1).

Step 2.4: 1.6 was replaced by 1.7 (see also step 8.4).

$^1$H NMR (400 MHz, DMSO d$_6$) δ 9.12 (brm, 1H), 8.99 (brm, 1H), 8.57 (d, 1H), 7.88 (dd, 1H), 7.59 (d, 1H), 6.84 (m, 1H), 6.78 (t, 1H), 6.40 (dd, 1H), 6.00 (s, 1H), 3.47 (q, 2H), 3.40 (m, 2H), 3.29 (q, 2H), 3.19 (m, 2H), 2.10 (m, 2H), 1.97 (m, 2H), 1.17 (t, 3H), 1.10 (t, 3H)

Mass Spectral Analysis m/z=394.2 (M+H)$^+$

Elemental analysis:

$C_{24}H_{27}N_3O_3$, 2HCl, 0.67H$_2$O

Theory: % C, 57.74; % H, 6.39; % N, 8.78; % Cl, 14.82.

Found: % C, 57.70; % H, 6.28; % N, 8.73; % Cl, 14.47.

EXAMPLE 8C 8C was obtained according to a procedure similar to the one described for 2C, with the following exception:

Step 2.1: 2.1 was replaced by 8.1 (see also step 8.1).

$^1$H NMR (400 MHz, DMSO d$_6$) δ 8.88 (brm, 2H), 7.42 (s, 4H), 7.00 (d, 1H), 6.86 (t, 1H), 6.58 (d, 1H), 5.97 (s, 1H), 3.90 (d, 2H), 3.44 (m, 2H), 3.23 (brm, 6H), 2.09 (m, 2H), 1.98 (m, 2H), 1.26 (m, 1H), 1.12 (brd, 6H), 0.59 (m, 2H), 0.37 (m, 2H)

Mass Spectral Analysis m/z=447.3 (M+H)$^+$

Elemental analysis:

$C_{28}H_{34}N_2O_3$, 1HCl, 1.5H$_2$O

Theory: % C, 65.93; % H, 7.51; % N, 5.49.

Found: % C, 65.64; % H, 7.29; % N, 5.41.

EXAMPLE 8D 8D was obtained according to a procedure similar to the one described for 2C, with the following exceptions:

Step 2.1: 2.1 was replaced by 8.1 (see also step 8.1).

Step 2.7: 2.8a was replaced by 2.8c (method 2A was used) (see also step 8.7).

$^1$H NMR (400 MHz, DMSO d$_6$) δ 8.78 (brs, 2H), 7.41 (s, 4H), 7.04 (d, 1H), 6.90 (t, 1H), 6.58 (d, 1H), 5.97 (s, 1H), 3.83 (s, 3H), 3.44 (brs, 2H), 3.20 (brm, 6H), 2.08 (m, 2H), 1.97 (m, 2H), 1.12 (brd, 6H)

Mass Spectral Analysis m/z=407.3 (M+H)$^+$

Elemental analysis:

$C_{25}H_{30}N_2O_3$, 1HCl, 1H$_2$O

Theory: % C, 65.14; % H, 7.22; % N, 6.08.

Found: % C, 65.22; % H, 6.85; % N, 6.02.

EXAMPLE 8E 8E was obtained according to a procedure similar to the one described for 2C, with the following exceptions:

Step 2.1: 2.1 was replaced by 8.1 (see also step 8.1).

Step 2.4: 1.6 was replaced by 1.7 (see also step 8.4).

$^1$H NMR (400 MHz, DMSO d$_6$) δ 8.94 (brm, 2H), 8.59 (d, 1H), 7.88 (dd, 1H), 7.60 (d, 1H), 7.03 (d, 1H), 6.88 (t, 1H), 6.56 (d, 1H), 6.11 (s, 1H), 3.91 (d, 2H), 3.47 (q, 2H0, 3.29 (m, 4H), 3.17 (m, 2H), 2.10 (m, 2H), 2.01 (m, 2H), 1.26 (m, 1H), 1.17 (t, 3H), 1.11 (t, 3H), 0.59 (m, 2H), 0.37 (m, 2H)

Mass Spectral Analysis m/z=448.3 (M+H)$^+$

Elemental analysis:

$C_{27}H_{33}N_3O_3$, 1.2HCl, 0.8H$_2$O

Theory: % C, 64.12; % H, 7.14; % N, 8.31; % Cl, 8.41.

Found: % C, 64.09; % H, 7.20; % N, 8.18; % Cl, 8.15.

EXAMPLE 8F 8F was obtained according to a procedure similar to the one described for 2C, with the following exceptions:

Step 2.1: 2.1 was replaced by 8.1 (see also step 8.1).

Step 2.4: 1.6 was replaced by 1.7 (see also step 8.4).

Step 2.7: 2.8a was replaced by 2.8c (see also step 8.7).

$^1$H NMR (400 MHz, DMSO d$_6$) δ 8.96 (brm, 2H), 8.59 (d, 1H), 7.88 (dd, 1H), 7.60 (d, 1H), 7.06 (d, 1H), 6.92 (t, 1H), 6.56 (d, 1H), 6.12 (s, 1H), 3.84 (S, 3H), 3.47 (q, 2H), 3.28 (m, 4H), 3.14 (m, 2H), 2.09 (m, 2H), 2.02 (m, 2H), 1.17 (t, 3H), 1.11 (t, 3H)

Mass Spectral Analysis m/z=408.4 (M+H)$^+$

Elemental analysis:

$C_{24}H_{29}N_3O_3$, 2HCl, 1.5H$_2$O

Theory: % C, 56.81; % H, 6.75; % N, 8.28; % Cl, 13.97.

Found: % C, 56.80; % H, 6.48; % N, 8.24; % Cl, 13.89.

EXAMPLE 9A 9A was obtained according to a procedure similar to the one described for 2C, with the following exception:

Step 2.1: 2.1 was replaced by 9.1 (see also step 9.1).

$^1$H NMR (400 MHz, DMSO d$_6$) δ 9.68 (brd, 2H), 7.41 (d, 2H), 7.35 (d, 2H), 6.92 (d, 1H), 6.43 (s, 1H), 6.37 (d, 1H), 5.44 (s, 1H), 3.80 (d, 2H), 3.56 (brs, 2H), 3.40 (brs, 4H), 3.30 (brs, 2H), 2.30 (m, 2H), 2.19 (m, 2H), 1.27 (m, 4H), 1.17 (brs, 3H), 0.66 (m, 2H), 0.36 (m, 2H)

Mass Spectral Analysis m/z=447.3 (M+H)+
Elemental analysis:
C28H34N2O3, 1.0HCl, 1.3H2O
Theory: % C, 66.40; % H, 7.48; % N, 5.53.
Found: % C, 66.28; % H, 7.48; % N, 5.48.

EXAMPLE 9B

Preparation of 9.5:

9.5 was obtained according to a procedure similar to the one described for 2.7a except 2.1 was replaced by 9.1 in step 2.1 (see also step 9.1).

Preparation of 9.8:

To a solution of 9.5 (1.00 g, 2.02 mmol, 1.0 eq) in dimethylformamide (10 mL) was added sequentially cesium carbonate (3.30 g, 10.1 mmol, 5.0 eq) and methyl chlorodifluoroacetate (9.7) (1.47 g, 10.1 mmol, 5.0 eq.). The reaction mixture was heated at 90° C. for 48 h, poured into water (100 mL) and extracted with ethyl acetate. The organic extracts were washed with a 1N aqueous solution of sodium hydroxide and brine, dried over sodium sulfate, filtered, and concentrated under reduced pressure. The crude product was purified by column chromatography (eluent: hexane:ethyl acetate mixtures of increasing polarity).

Yield: 79%

$^1$H NMR (400 MHz, CDCl$_3$) δ 7.41 (d, 2H), 7.36 (d, 2H), 6.98 (d, 1H), 6.73 (d, 1H), 6.61 (dd, 1H), 6.52 (ts, 1H, J=73.8 Hz), 5.54 (s, 1H), 3.86 (brs, 2H), 3.57 (brm, 2H), 3.32 (brm, 4H), 2.03 (d, 2H), 1.68 (m, 2H), 1.47 (s, 9H) 1.20 (brd, 6H)

Mass Spectral Analysis m/z=543.4 (M+H)+

Preparation of 9B:

To a solution of 9.8 (860 mg, 1.58 mmol, 1.0 eq) in anhydrous methanol (15 mL) was added drop wise a 4.0M solution of hydrochloric acid in dioxane (4.0 mL, 15.8 mmol, 10.0 eq). The mixture was stirred at ambient temperature for 16 h and the solvent was evaporated under vacuum. The crude oil was purified by reverse phase HPLC chromatography (eluent: acetonitrile/water (0.1% trifluoroacetic acid) mixtures of decreasing polarity). The solvent was evaporated under vacuum and a 1N solution of HCl in diethyl ether (25 mL) was added. The resulting solid was filtered and washed with diethyl ether.

Yield: 23%

$^1$H NMR (400 MHz, CDCl$_3$) δ 7.42 (d, 2H), 7.35 (d, 2H), 7.02 (d, 1H), 6.75 (m, 1H), 6.66 (dd, 1H), 6.54 (ts, 1H, J=73.4 Hz), 5.59 (s, 1H), 3.57 (brs, 2H), 3.41 (brd, 4H), 3.31 (brs, 2H), 2.26 (m, 4H), 1.21 (brd, 6H)

Mass Spectral Analysis m/z=443.4 (M+H)+

Elemental analysis:
C28H34N2O3, 1.0 HCl, 1.2H2O
Theory: % C, 59.99; % H, 6.32; % N, 5.60.
Found: % C, 60.01; % H, 6.25; % N, 5.54.

EXAMPLE 10A 10A was obtained from 9.5 according to a procedure similar to the one described for 3A, with the following exception:
Step 3.1: 2.7a was replaced by 9.5 (see also step 10.1).

$^1$H NMR (400 MHz, DMSO d$_6$) δ 9.80 (brs, 1H), 7.60 (s, 1H), 7.58 (d, 1H), 7.42 (d, 2H), 7.36 (d, 2H), 7.09 (d, 1H), 5.75 (s, 1H), 3.91 (s, 3H), 3.61 (brs, 2H), 3.40 (m, 4H), 3.30 (brs, 2H), 2.27 (m, 4H), 1.20 (brd, 6H)

Mass Spectral Analysis m/z=435.3 (M+H)+
Elemental analysis:
C26H30N2O4, 1HCl, 1.1H2O
Theory: % C, 63.63; % H, 6.82; % N, 5.71.
Found: % C, 63.64; % H, 6.75; % N, 5.72.

EXAMPLE 10B 10B was obtained according to a procedure similar to the one described for 3B, with the following exception:
Step 3.1: 2.7a was replaced by 9.5 (see also step 10.1).

$^1$H NMR (400 MHz, DMSO-d$_6$) δ 13.10 (brs, 1H), 9.10 (brm, 2H), 7.57 (d, 1H), 7.52 (dd, 1H), 7.44 (s, 4H), 7.12 (d, 1H), 6.09 (s, 1H), 3.45 (brs, 2H), 3.35 (brm, 2H), 3.23 (brm, 4H), 2.08 (m, 4H), 1.10 (brd, 6H)

Mass Spectral Analysis m/z=421.3 (M+H)+

EXAMPLE 10C 10C was obtained according to a procedure similar to the one described for 3E, with the following exceptions:
Step 3.5: 3.3a was replaced by 10.3 and 3.4b was replaced by 3.4a (see also step 10.5).

$^1$H NMR (400 MHz, CDCl$_3$) δ 9.50 (brd, 2H), 7.64 (brm, 2H), 7.32 (brm, 5H), 7.00 (brs, 2H), 5.68 (s, 1H), 3.50 (brm, 4H), 3.27 (brm, 4H), 2.62 (brs, 2H), 2.19 (brs, 2H), 1.17 (brd, 6H)

Mass Spectral Analysis m/z=420.3 (M+H)+

EXAMPLE 10D

Preparation of 10.2:

Compound 10.2 was obtained according to a procedure similar to the one described for 3.2a except 2.7a was replaced by 9.5 in step 3.1 (see also step 10.1).

Preparation of 10.4:

To a solution of a 2N solution of methylamine (3.4b) in methanol (10.0 mL, 20.0 mmol, 11.0 eq) was added portion-wise at room temperature 10.2 (1.00 g, 1.86 mmol) in a sealed tube. The mixture was heated at 60° C. for 20 h to form a homogeneous solution. The mixture was poured into water (25 mL), extracted with methylene chloride, washed with brine, dried over sodium sulfate, filtered and evaporated solvent to an off-white solid. The crude product was purified by column chromatography (eluent: hexane/ethyl acetate mixtures of increasing polarity).

Yield: 80%

$^1$H NMR (400 MHz, CDCl$_3$) δ 7.53 (s, 1H), 7.47 (s, 1H), 7.45 (d, 2H), 7.23 (d, 1H), 7.04 (d, 1H), 6.20 (brs, 1H), 5.64 (s, 1H), 3.88 (brs, 2H), 3.57 (brm, 2H), 3.33 (brm, 4H), 3.00 (d, 3H), 2.03 (d, 2H), 1.68 (brm, 2H), 1.45 (s, 9H) 1.21 (brd, 6H)

Mass Spectral Analysis m/z=534.4 (M+H)+

Preparation of 10D:

To a solution of 10.4a (790 mg, 1.48 mmol, 1.0 eq) in anhydrous methanol (20 mL) was added drop wise a 4M solution of hydrochloric acid in dioxane (3.7 mL, 14.8 mmol, 10.0 eq). The mixture was stirred at ambient temperature for 16 h and the solvent evaporated under vacuum to a white solid. The white solid was triturated in diethyl ether (50 mL). The resulting solid was collected by filtration and washed with diethyl ether.

Yield: 85%

$^1$H NMR (400 MHz, CDCl$_3$) δ 7.43 (m, 3H), 7.34 (m, 3H), 7.05 (d, 1H), 6.90 (brd, 1H), 5.69, (s, 1H), 3.57 (brm, 2H), 3.35 (brm, 6H), 3.00 (d, 3H), 2.20 (brs, 4H), 1.19 (brd, 6H)

Mass Spectral Analysis m/z=434.3 (M+H)+
Elemental analysis:
C$_{26}$H$_{31}$N$_3$O$_3$, 1.0 HCl, 1.5H$_2$O
Theory: % C, 62.83; % H, 7.10; % N, 8.45.
Found: % C, 62.74; % H, 6.95; % N, 8.29.

EXAMPLE 10E 10E was obtained according to a procedure similar to the one described for 3E, with the following exceptions:
Step 3.5: 3.3a was replaced by 10.3 and 3.4b was replaced by 3.4c (see also step 10.5) (method 10A was used).
$^1$H NMR (400 MHz, CDCl$_3$) δ 9.68 (brs, 2H), 7.43 (m, 3H), 7.34 (m, 3H), 7.06 (d, 1H), 6.61 (brs, 1H), 5.68 (s, 1H), 3.57 (brs, 2H), 3.50 (brm, 2H), 3.40 (brs, 2H), 3.32 (brs, 2H), 2.25 (brs, 4H), 1.28 (brm, 6H), 1.15 (brs, 3H)
Mass Spectral Analysis m/z=448.3 (M+H)+

EXAMPLE 10F 10F was obtained according to a procedure similar to the one described for 3E, with the following exceptions:
Step 3.5: 3.3a was replaced by 10.3 and 3.4b was replaced by 3.4j (see also step 10.5) and TBTU was replaced by HATU (method 10B was used).
$^1$H NMR (400 MHz, DMSO d$_6$) δ 9.77 (brm, 2H), 7.42 (d, 2H), 7.36 (d, 2H), 7.08 (d, 1H), 7.03 (s, 1H), 6.97 (d, 1H), 5.66 (s, 1H), 3.59 (brs, 2H), 3.40 (brs, 4H), 3.32 (brs, 2H), 3.12 (s, 3H), 3.04 (s, 3H), 2.28 (m, 4H), 1.20 (brd, 6H)
Mass Spectral Analysis m/z=448.3 (M+H)+
Elemental analysis:
C$_{27}$H$_{33}$N$_3$O$_3$, 1HCl, 1.7H$_2$O
Theory: % C, 63.01; % H, 7.32; % N, 8.16.
Found: % C, 63.06; % H, 7.18; % N, 8.09.

EXAMPLE 10G 10G was obtained according to a procedure similar to the one described for 3E, with the following exceptions:
Step 3.5: 3.3a was replaced by 10.3 and 3.4b was replaced by 1.12 (see also step 10.5) (method 10A was used).
$^1$H NMR (400 MHz, DMSO d$_6$) δ 9.73 (brs, 2H), 7.43 (d, 2H), 7.36 (d, 2H), 7.07 (d, 1H), 6.98 (s, 1H), 6.92 (d, 1H), 5.67 (s, 1H), 3.56 (brs, 4H), 3.40 (brs, 4H), 3.31 (brs, 4H), 2.26 (brs, 4H), 1.22 (brd, 12H)
Mass Spectral Analysis m/z=476.2 (M+H)+
Elemental analysis:
C$_{29}$H$_{37}$N$_3$O$_3$, 1HCl, 1.7H$_2$O
Theory: % C, 64.18; % H, 7.69; % N, 7.74.
Found: % C, 64.08; % H, 7.45; % N, 7.60.

EXAMPLE 10H 10H was obtained according to a procedure similar to the one described for 3E, with the following exception:
Step 3.5: 3.3a was replaced by 10.3 and 3.4b was replaced by 3.4k (see also step 10.5) (method 10A was used).
$^1$H NMR (400 MHz, DMSO d$_6$) δ 9.77 (brs, 2H), 7.43 (d, 2H), 7.37 (d, 2H), 7.12 (s, 1H), 7.09 (s, 2H), 5.68 (s, 1H), 3.64 (m, 2H), 3.60 (brm, 2H), 3.47 (m, 2H), 3.40 (brm, 4H), 3.30 (brs, 2H), 2.30 (brs, 4H), 2.00 (m, 2H), 1.93 (m, 2H), 1.24 (brd, 6H)
Mass Spectral Analysis m/z=474.3 (M+H)+
Elemental analysis:
C$_{29}$H$_{35}$N$_3$O$_3$, 1HCl, 0.7H$_2$O
Theory: % C, 66.64; % H, 7.21; % N, 8.04.
Found: % C, 66.56; % H, 7.07; % N, 7.91.

EXAMPLE 10I 10I was obtained according to a procedure similar to the one described for 3E, with the following exception:
Step 3.5: 3.3a was replaced by 10.3 and 3.4b was replaced by 3.4c (see also step 10.5) (method 10A was used).
$^1$H NMR (400 MHz, CDCl$_3$) δ 9.70 (brs, 2H), 7.44 (d, 2H), 7.35 (d, 2H), 7.09 (d, 1H), 7.02 (s, 1H), 6.96 (dd, 1H), 5.68 (s, 1H), 3.73 (brm, 6H), 3.58 (brs, 4H), 3.41 (brm, 4H), 3.31 (brs, 2H), 2.28 (m, 4H), 1.21 (m, 6H)
Mass Spectral Analysis m/z=490.2 (M+H)+

EXAMPLE 10J

Preparation of 10.5:
To a slurry of LiBH$_4$ (82.0 mg, 3.75 mmol, 2.0 eq.) in tetrahydrofuran (20 mL) cooled to 0° C. under a nitrogen atmosphere was added drop wise a solution of 10.2 (1.00 g, 1.87 mmol, 1.0 eq) in tetrahydrofuran (10 mL). The reaction mixture was warmed to room temperature and stirred for 16 h at room temperature. The reaction mixture was quenched with water (0.54 mL, 8 eq.), extracted with ethyl acetate, washed with brine, dried over sodium sulfate and filtered. The solvent was removed under vacuum and the crude product was purified by column chromatography (eluent: hexane/ethyl acetate mixtures of increasing polarity).
Yield: 49%
$^1$H NMR (400 MHz, CDCl$_3$) δ 7.40 (d, 2H), 7.36 (d, 2H), 6.98 (m, 2H), 6.85 (d, 1H), 5.56 (s, 1H), 4.65 (s, 2H), 3.87 (brs, 2H), 3.57 (brs, 2H), 3.32 (brm, 4H), 2.05 (d, 2H), 1.91 (brt, 1H), 1.66 (m, 2H), 1.48 (s, 9H) 1.21 (brd, 6H)
Mass Spectral Analysis m/z=507.3 (M+H)+
Preparation of 10J:
To a solution of 10.5 (460 mg, 0.91 mmol, 1.0 eq) in anhydrous methanol (30 mL) was added drop wise a 4M solution of hydrochloric acid in dioxane (2.3 mL, 9.1 mmol, 10.0 eq). The mixture was stirred at room temperature for 16 h and the solvent was evaporated under vacuum. The residue was triturated in ethyl ether (50 mL); the solid was collected by filtration and washed with diethyl ether. The crude product was purified by column chromatography (eluent: methylene chloride/methanol mixtures of increasing polarity).
Yield: 46%
$^1$H NMR (400 MHz, CDCl$_3$) δ 9.62 (brs, 2H), 7.38 (brd, 4H), 7.00 (m, 2H), 6.90 (brd, 1H), 5.60, (brs, 1H), 4.66 (brs, 2H), 3.58 (brm, 2H), 3.40 (brm, 4H), 3.31 (brm, 2H), 2.50 (brs, 1H), 2.25 (brs, 4H), 1.21 (brd, 6H)
Mass Spectral Analysis m/z=407.4 (M+H)+
Elemental analysis:
C$_{26}$H$_{31}$N$_3$O$_3$, 1HCl, 0.7H$_2$O
Theory: % C, 65.91; % H, 7.17; % N, 6.15.
Found: % C, 65.93; % H, 6.99; % N, 6.08.

EXAMPLE 11A

Preparation of 11.2:
2',6'-hydroxyacetophenone (11.1) (200.0 g g, 1.31 mol, 1.0 eq) was added portion wise at room temperature to pyrrolidine (220 mL, 2.0 eq) followed by portion wise addition of 1-Boc-4-piperidone (1.2) (262.0 g, 1.31 mo, 1.0 eq). Anhydrous methanol (100 mL) was then added and the red slurry heated to reflux to dissolve all solids. On dissolution the reaction was cooled to room temperature overnight with stirring to form a solid mass. This solid mass was dissolved in ethyl acetate, washed with a 1N aqueous solution of hydrochloric acid, a 1N aqueous solution of sodium hydroxide and brine, dried over sodium sulfate and filtered. The solvent was evaporated under vacuum. A mixture of hexane and diethyl ether (80:20) (400 mL) was added to the mixture and the resulting precipitate was collected by filtration, washed with hexane and used for the next step without further purification.

Yield: 74%.

$^1$H NMR (400 MHz, CDCl$_3$) δ 11.61 (s, 1H), 7.37 (t, 1H), 6.49 (d, 1H), 6.44 (d, 1H), 3.89 (brs, 2H), 3.20 (brm, 2H), 2.73 (s, 2H), 2.02 (d, 2H), 1.64 (m, 2H), 1.46 (s, 9H)

Mass Spectral Analysis m/z=334.0 (M+H)$^+$

Preparation of 11.4:

To a solution of 11.2 (140.0 g, 0.420 mol, 1.0 eq) in dichloromethane (700 mL) at ambient temperature under nitrogen was added drop wise diisopropylethylamine (294.0 mL, 1.68 mol, 4.0 eq). To this solution was added drop wise chloro(methoxy)methane (11.3) (100.0 g, 1.26 mol, 3.0 eq). The mixture was heated to reflux for 16 h, cooled to room temperature and the solvent was removed under vacuum to afford a brown oil. This oil was dissolved in ethyl acetate (700 mL) and washed with a 1N aqueous solution of hydrochloric acid, an aqueous saturated solution of sodium bicarbonate and brine. The organic extracts were dried over sodium sulfate, filtered and the solvent was removed under vacuum to afford a brown oil. Diethyl ether (400 mL) was added and the resulting white precipitate was filtered and used for the next step without further purification.

Yield: 83%

$^1$H NMR (400 MHz, CDCl$_3$) δ 7.36 (t, 1H), 6.74 (d, 1H), 6.65 (d, 1H), 5.27 (s, 2H), 3.86 (brs, 2H), 3.52 (s, 3H), 3.22 (m, 2H), 2.69 (s, 2H), 2.02 (d, 2H), 1.60 (m, 2H), 1.46 (s, 9H)

Mass Spectral Analysis m/z=378.2 (M+H)$^+$

Preparation of 11.5:

To a solution of 11.4 (131.2 g, 0.348 mol) in tetrahydrofuran (600 mL) at −78° C. under nitrogen atmosphere was added drop wise a 1.0M solution of LiHMDS in tetrahydrofuran (420.0 mL, 1.2 eq). The mixture was stirred for 1 h at −78° C. A solution of 1.4 (149.4 g, 0.418 mol, 1.2 eq) in tetrahydrofuran (200 mL) was added drop wise. The mixture was warmed slowly to room temperature and stirring was continued for a further 12 h at room temperature. The mixture was then poured into ice water and the two phases were separated. The organic phase was washed with a 1N aqueous solution of hydrochloric acid, a 1N aqueous solution of sodium hydroxide and brine, dried over sodium sulfate and filtered. The solvent was removed under vacuum and the tan oily residue was used for the next step without further purification.

Yield: 100%

$^1$H NMR (400 MHz, CDCl$_3$) δ 6.98 (t, 1H), 6.62 (d, 1H), 6.39 (d, 1H), 5.24 (s, 1H), 5.03 (s, 2H), 3.62 (brs, 2H), 3.30 (s, 3H), 3.07 (m, 2H), 1.84 (d, 2H), 1.46 (m, 2H), 1.26 (s, 9H)

Mass Spectral Analysis m/z=510.0 (M+H)$^+$

Preparation of 11.6a:

To a solution of 11.5 (100 g, 196 mmol, 1.0 eq) in dimethoxyethane (DME) (600 mL) was added sequentially a 2N aqueous solution of sodium carbonate (294 mL, 588 mmol, 3.0 eq), lithium chloride (25.0 g, 588 mmol, 3.0 eq), 4-(N,N-diethylaminocarbonyl)phenylboronic acid (1.6) (36.9 g, 166 mmol, 1.1 eq) and tetrakis(triphenylphosphine)palladium(0) (4.54 g, 3.92 mmol, 0.02 eq). The mixture was refluxed for 10 h under nitrogen. The mixture was then cooled to room temperature, filtered through a celite pad and the filtercake was washed with DME (100 mL) and water (750 mL). The aqueous mixture was extracted with ethyl acetate. The organic layer was further washed with brine and dried over sodium sulfate. The crude product was purified by chromatography (eluent: hexane/ethyl acetate mixtures of increasing polarity).

Yield: 62%

$^1$H NMR (400 MHz, CDCl$_3$) δ 7.21 (d, 2H), 7.17 (d, 2H), 7.05 (t, 1H), 6.60 (m, 2H), 5.45 (s, 1H), 4.58 (s, 2H), 3.71 (brs, 2H), 3.45 (brm, 2H), 3.22 (brm, 4H), 3.06 (s, 3H), 1.90 (d, 2H), 1.56 (m, 2H), 1.38 (s, 9H), 1.09 (brd, 6H)

Mass Spectral Analysis m/z=537.4 (M+H)$^+$

Preparation of 11A:

To a solution of 11.6a (25.0 g, 46.6 mmol, 1.0 eq) in anhydrous methanol (250 mL) was added drop wise a 4M solution of hydrochloric acid in dioxane (58.2 mL, 233 mmol, 5.0 eq). The mixture was stirred at room temperature for 16 h and the solvent was evaporated under vacuum to afford a brown oil. Methanol (20 mL) followed by diethyl ether (300 mL) was added to the brown oil and the resulting precipitate was collected by filtration and washed with diethyl ether. The solid was used for the next step without further purification.

Yield: 100%

$^1$H NMR (400 MHz, DMSO d$_6$) δ 9.55 (s, 1H), 9.07 (brs, 2H), 7.27 (m, 4H), 7.06 (t, 1H), 6.52 (d, 1H), 6.47 (d, 1H), 5.76 (s, 1H), 3.42 (brm, 2H), 3.35 (s, 4H), 3.19, (brm, 6H), 2.03 (m, 4H), 1.11 (brm, 6H)

Mass Spectral Analysis m/z=393.0 (M+H)$^+$

Elemental analysis:

C$_{24}$H$_{28}$N$_2$O$_3$, 1HCl, 0.67H$_2$O

Theory: % C, 65.37; % H, 6.93; % N, 6.35.

Found: % C, 65.41; % H, 6.98; % N, 6.31.

EXAMPLE 11B 11B was obtained according to a procedure similar to the one described for 11A, with the following exception:

Step 11.4: 1.6 was replaced by 1.7.

$^1$H NMR (400 MHz, DMSO d$_6$) δ 9.67 (brs, 1H), 9.23 (brd, 2H), 8.50 (s, 1H), 7.79 (d, 1H), 7.52 (d, 1H), 7.09 (t, 1H), 6.57 (d, 1H), 6.50 (d, 1H), 5.93 (s, 1H), 3.43 (q, 2H), 3.26 (q, 2H), 3.21 (m, 2H), 3.14 (m, 2H), 2.05 (m, 4H), 1.18 (t, 3H), 1.11 (t, 3H)

Mass Spectral Analysis m/z=394.3 (M+H)$^+$

Elemental analysis:

C$_{23}$H$_{27}$N$_3$O$_3$, 2HCl, 1.5H$_2$O

Theory: % C, 55.99; % H, 6.54; % N, 8.52.

Found: % C, 56.11; % H, 6.54; % N, 8.53.

EXAMPLE 11C

Preparation of 11.7a:

To a slurry of 11A (10.0 g, 23.3 mmol, 1.0 eq) in tetrahydrofuran (200 mL) under a nitrogen atmosphere was added triethylamine (9.75 mL, 69.9 mmol, 3.0 eq). The reaction mixture was cooled to 0° C. A solution of di-tert-butyl dicarbonate (4.7) (4.58 g, 21.0 mmol, 0.9 eq) in tetrahydrofuran (50 mL) was added drop wise to the reaction mixture which was stirred for 3 h at room temperature. The solvent was evaporated under vacuum and the residue was dissolved in ethyl acetate (500 mL), washed with water and brine, and dried over sodium sulfate and filtered. The solvent was evaporated under vacuum. The residue was sonicated and triturated in a mixture ethyl acetate/methanol 95:5 (75 mL). The solid was collected by filtration and washed with ethyl acetate.

Yield: 100%

$^1$H NMR (400 MHz, DMSO d$_6$) δ 9.49 (s, 1H), 7.31 (s, 4H), 7.08 (t, 1H), 6.54 (d, 1H), 6.47 (d, 1H), 5.77 (s, 1H), 3.70 (m, 2H), 3.48 (brm, 2H), 3.30 (brm, 4H), 1.87 (d, 2H), 1.74 (m, 2H), 1.47 (s, 9H) 1.16 (brs, 6H)

Mass Spectral Analysis m/z=493.4 (M+H)$^+$

Preparation of 11.9a:

To a solution of 11.7a (1.00 g, 2.02 mmol, 1.0 eq) in dichloromethane (4 mL) under a nitrogen atmosphere was added sequentially cyclopropylmethanol (2.8e) (189 mg, 2.63 mmol, 1.3 eq) and triphenylphosphine (690 mg, 2.63 mmol, 1.3 eq). The reaction mixture was stirred for 5 min at room temperature and a solution of diethylazodicarboxylate (460 mg, 2.63 mmol, 1.3 eq) was added drop wise. The reaction was stirred an additional 30 min at room temperature and the solvent was evaporated under vacuum. The crude product was purified by chromatography (eluent: hexane/ethyl acetate mixtures of increasing polarity).

Yield: 42%

$^1$H NMR (400 MHz, CDCl$_3$) δ 7.31 (d, 2H), 7.27 (d, 2H), 7.13 (t, 1H), 6.64 (d, 1H), 6.42 (d, 1H), 5.50 (s, 1H), 3.78 (brd, 2H), 3.54 (brm, 2H), 3.49 (d, 2H), 3.35 (brt, 4H), 2.02 (d, 2H), 1.69 (m, 2H), 1.47 (s, 9H) 1.26 (brd, 6H), 0.53 (m, 1H), 0.29 (m, 2H), −0.07 (m, 2H)

Mass Spectral Analysis m/z=547.5 (M+H)$^+$

Preparation of 11C:

To a solution of 11.9a (460 mg, 0.84 mmol, 1.0 eq) in anhydrous methanol (15 mL) was added dropwise a 4M solution of hydrochloric acid in dioxane (2.0 mL, 8.4 mmol, 10.0 eq). The mixture was stirred at room temperature for 16 h and the solvent was evaporated under vacuum. The residue was triturated in diethyl ether (50 mL). The resulting solid was collected by filtration and washed with diethyl ether.

Yield: 97%

$^1$H NMR (400 MHz, CDCl$_3$) δ 9.67 (brs, 2H), 7.32 (d, 2H), 7.26 (d, 2H), 7.16 (t, 1H), 6.64 (d, 1H), 6.46 (d, 1H), 5.50 (s, 1H), 3.54 (brm, 2H), 3.49 (d, 2H), 3.36 (brm, 6H), 2.28 (d, 2H), 2.18 (m, 2H), 1.19 (brd, 6H), 0.53 (m, 1H), 0.30 (m, 2H), −0.07 (m, 2H)

Mass Spectral Analysis m/z=447.4 (M+H)$^+$

Elemental analysis:

C$_{28}$H$_{34}$N$_2$O$_3$, 1.0 HCl, 0.7H$_2$O

Theory: % C, 67.73; % H, 7.41; % N, 5.64.

Found: % C, 67.73; % H, 7.24; % N, 5.59.

EXAMPLE 11D 11D was obtained according to a procedure similar to the one described for 11C, with the following exceptions:

Step 11.4: 1.6 was replaced by 1.7.

$^1$H NMR (400 MHz, CDCl$_3$) δ 9.67 (brs, 1H), 8.44 (m, 1H), 7.61 (dd, 1H), 7.55 (d, 1H), 7.19 (t, 1H), 6.64 (d, 1H), 6.43 (d, 1H), 5.55 (s, 1H), 3.56 (q, 2H), 3.50 (d, 2H), 3.46 (q, 2H), 3.38 (m, 4H), 2.29 (m, 2H), 2.21 (m, 2H), 1.28 (t, 3H), 1.17 (t, 3H), 0.54 (m, 1H), 0.33 (m, 2H), −0.05 (m, 2H)

Mass Spectral Analysis m/z=448.4 (M+H)$^+$

EXAMPLE 11E

Preparation of 11.9b:

To a solution of 11.7a (1.00 g, 2.02 mmol, 1.0 eq) in acetone (20 mL) was added sequentially potassium carbonate (1.70 g, 12.1 mmol, 6.0 eq) and bromocyclobutane (11.8) (1.66 g, 12.1 mmol mmol, 6.0 eq). The reaction mixture was refluxed for 90 h, poured into water (100 mL) and extracted with ethyl acetate. The organic extracts were washed with a 1N aqueous solution of sodium hydroxide and brine, dried over sodium sulfate and filtered. The solvent was evaporated and the crude product was first purified by column chromatography (eluent: hexane/ethyl acetate mixtures of increasing polarity) and then repurified by reverse phase HPLC chromatography (eluent: acetonitrile/water (0.1% trifluoroacetic acid) mixtures of decreasing polarity).

Yield: 18%

$^1$H NMR (400 MHz, CDCl$_3$) δ 7.31 (d, 2H), 7.27 (d, 2H), 7.11 (t, 1H), 6.64 (d, 1H), 6.26 (d, 1H), 4.36 (m, 1H), 5.50 (s, 1H), 3.79 (brd, 2H), 3.54 (brm, 2H), 3.48 (d, 2H), 3.34 (brm, 4H), 2.12 (m, 2H), 2.02 (d, 2H), 1.67 (m, 2H), 1.55 (m, 2H), 1.47 (s, 9H) 1.19 (brd, 6H)

Mass Spectral Analysis m/z=547.5 (M+H)$^+$

Preparation of 11E:

To a solution of 11.9b (200 mg, 0.37 mmol, 1.0 eq) in anhydrous methanol (25 mL) was added drop wise a 2M solution of hydrochloric acid in diethyl ether (0.73 mL, 1.44 mmol, 4.0 eq). The mixture was stirred at room temperature for 16 h and the solvent was evaporated under vacuum. The residue was triturated in diethyl ether (50 mL). The solid was collected by filtration and washed with diethyl ether.

Yield: 96%

$^1$H NMR (400 MHz, DMSO d$_6$) δ 9.14 (brs, 2H), 7.29 (d, 2H), 7.24 (d, 2H), 7.19 (t, 1H), 6.68 (d, 1H), 6.42 (d, 1H), 5.79 (s, 1H), 4.43 (m, 1H), 3.40 (brm, 4H), 3.35 (brs, 4H), 3.17 (brm, 4H), 2.10 (m, 2H), 2.03 (m, 2H), 1.45 (m, 2H), 1.11 (m, 6H)

Mass Spectral Analysis m/z=447.3 (M+H)$^+$

EXAMPLE 11F 11F was obtained according to a procedure similar to the one described for 11C, with the following exceptions:

Step 11.4: 1.6 was replaced by 1.7.

Step 11.7: 2.8e was replaced by 11.10.

$^1$H NMR (400 MHz, CDCl$_3$) δ 9.71 (brd, 2H), 8.40 (s, 1H), 7.56 (m, 2H), 7.18 (t, 1H), 6.62 (d, 1H), 6.48 (d, 1H), 5.50 (s, 1H), 4.50 (m, 1H), 3.58 (m, 2H), 3.48 (m, 2H), 3.38 (brs, 4H), 2.30 (d, 2H), 2.22 (brs, 2H), 1.64 (m, 2H), 1.36 (m, 2H), 1.30 (m, 5H), 1.19 (m, 5H)

Mass Spectral Analysis m/z=462.4 (M+H)$^+$

EXAMPLE 12A

Preparation of 12.1:

To a solution of compound 11.2 (3.33 g, 10 mmol) in anhydrous methylene chloride (100 mL) was added sequentially triethylamine (3.48 mL, 25 mmol, 2.5 eq), 4-dimethylaminopyridine (122 mg, 1 mmol, 0.1 eq) and N-phenyltrifluoromethanesulfonimide (1.4) (4.48 g, 12.5 mmol, 1.25 eq). The reaction mixture was stirred at room temperature for 24 h, washed with a saturated aqueous solution of sodium bicarbonate, dried over sodium sulfate and filtered. The solvent was evaporated under vacuum and the residue was purified by column chromatography (eluent: hexane/ethyl acetate, 3:1).

Yield: 92.5%

$^1$H NMR (400 MHz, DMSO d$_6$) δ 7.52 (t, 1H), 7.09 (d, 1H), 6.88 (d, 1H), 3.90 (m, 2H), 3.21 (m, 2H), 2.80 (s, 2H), 2.03 (m, 2H), 1.63 (m, 2H), 1.48 (s, 9H)

Preparation of 12.3:

To a solution of 12.1 (5.4 g, 11.6 mmol) in tetrahydrofuran (100 mL) at room temperature was added tetrakis(triphenylphosphine)palladium(0) (670 mg, 0.58 mmol, 0.05 eq) followed by drop wise addition of a 2.0 M solution of methylzinc chloride (12.2a) in tetrahydrofuran (10 mL, 20 mmol, 1.72 eq). The mixture was stirred at room temperature for 2 days. The reaction mixture was then quenched with a saturated aqueous solution of ammonium chloride and extracted with ethyl acetate. The organic layer was washed with brine and dried over sodium sulfate. The solvent was evaporated under vacuum and the crude product was purified by column chromatography (eluent: hexane/ethyl acetate, 4:1).

Yield: 80.6%

$^1$H NMR (400 MHz, CDCl$_3$) δ 7.30 (t, 1H), 6.86 (d, 1H), 6.80 (d, 1H), 3.88 (m, 2H), 2.70 (s, 2H), 2.60 (s, 3H), 2.00 (m, 2H), 1.60 (m, 2H), 1.45 (s, 9H)

Preparation of 12.4:

To a solution of 12.3 (2.8 g, 8.46 mmol) in anhydrous tetrahydrofuran (80 mL) at −78° C. under nitrogen was added drop wise a 1.0 M solution of LiHMDS in tetrahydrofuran (11 mL, 11 mmol, 1.1 eq). The reaction mixture was stirred for 45 min at −78° C. A solution of N-phenyltrifluoromethanesulfonimide (1.4) (3.95 g, 11 mmol, 1.1 eq) in tetrahydrofuran (15 mL) was added drop wise to the reaction mixture. The mixture was warmed slowly to room temperature and stirring was continued for a further 3 h at room temperature. The mixture was then poured into ice water and extracted with a mixture of hexane and diethyl ether (1:1). The organic layer was washed with water and brine, and dried over sodium sulfate and filtered. The organics were concentrated under vacuum and the crude product was purified by column chromatography (eluent: hexane/ethyl acetate, 6:1).

Yield: 61.3%

$^1$H NMR (400 MHz, CDCl$_3$) δ 7.11 (t, 1H), 6.80 (m, 2H), 3.82 (m, 2H), 3.29 (m, 2H), 2.50 (s, 3H), 2.03 (m, 2H), 1.68 (m, 2H), 1.48 (s, 9H)

Preparation of 12.5:

To a solution of 12.4 (848 mg, 1.83 mmol) in dimethoxyethane (DME) (16 mL) was added sequentially a 2 N aqueous solution of sodium carbonate (3.1 mL, 6.2 mmol, 3.4 eq), lithium chloride (259 mg, 6.1 mmol, 3.3 eq), 4-(N,N-diethylaminocarbonyl)phenylboronic acid (1.6) (486 mg, 2.2 mmol, 1.2 eq) and tetrakis(triphenylphosphine)palladium(0) (64 mg, 0.055 mmol, 0.03 eq). The mixture was refluxed overnight under nitrogen. The mixture was then cooled to room temperature and water (20 mL) was added. The mixture was extracted with ethyl acetate. The organic layer was further washed with brine, dried over sodium sulfate, filtered and concentrated under vacuum. The crude product was purified by column chromatography (eluent: hexane/ethyl acetate, 1:1).

Yield: 96.9%

$^1$H NMR (400 MHz, CDCl$_3$) δ 7.36 (d, 2H), 7.26 (d, 2H), 7.10 (t, 1H), 6.86 (d, 1H), 6.70 (d, 1H), 5.60 (s, 1H), 3.80 (m, 2H), 3.55 (m, 2H), 3.30 (m, 4H), 2.00 (m, 2H), 1.74 (s, 3H), 1.65 (m, 2H), 1.49 (s, 9H), 1.20 (m, 6H)

Preparation of 12A:

To a solution of 12.5 (860 mg, 1.76 mmol) in methylene chloride (10 mL) was added a 2.0 M solution of anhydrous hydrochloric acid in diethyl ether (30 mL). The mixture was stirred at room temperature for 24 h and diethyl ether was added. The resulting precipitate was collected by filtration and washed with diethyl ether.

Yield: 97.8%

$^1$H NMR (400 MHz, DMSO d$_6$) δ 8.99 (m, 2H), 7.38 (d, 2H), 7.29 (d, 2H), 7.18 (t, 1H), 6.93 (d, 1H), 6.80 (d, 1H), 5.95 (s, 1H), 3.45 (m, 2H), 3.20 (m, 6H), 2.00 (m, 4H), 1.70 (s, 3H), 1.10 (m, 6H)

Mass Spectral Analysis m/z=391.4 (M+H)$^+$

Elemental analysis:

C$_{24}$H$_{28}$N$_2$O$_2$, 1HCl, 1/2H$_2$O

Theory: % C, 68.87; % H, 7.40; % N, 6.43.

Found: % C, 68.99; % H, 7.33; % N, 6.39.

EXAMPLE 12B

Preparation of 12.6:

To a solution of 12.1 (14.4 g, 31 mmol) in N,N-dimethylformamide was added sequentially methanol (50 mL), triethylamine (7 mL, 50 mmol, 1.6 eq), 1,3-bis(diphenylphosphino)propane (dppp) (1.04 g, 2.5 mmol, 0.08 eq) and palladium (II) acetate (565 mg, 2.5 mmol, 0.08 eq). The carbon monoxide was then bubbled through the reaction solution while the mixture was heated to 65-70° C. for 3.5 h. The reaction mixture was cooled to room temperature, diluted with diethyl ether and washed with water and brine. The organic layer was dried over sodium sulfate, filtered and concentrated under vacuum. The crude product was purified by column chromatography (eluent: hexane/ethyl acetate, 4:1).

Yield: 87.9%

$^1$H NMR (400 MHz, CDCl$_3$) δ 7.50 (t, 1H), 7.10 (d, 1H), 6.99 (d, 1H), 3.94 (s, 3H), 3.90 (m, 2H), 3.21 (m, 2H), 2.73 (s, 2H), 2.05 (m, 2H), 1.63 (m, 2H), 1.48 (s, 9H)

Preparation of 12.11:

To a solution of 12.6 (13.2 g, 35.2 mmol) in anhydrous tetrahydrofuran (300 mL) at −78° C. was added drop wise a 1.0 M solution of LiHMDS in tetrahydrofuran (42 mL, 42 mmol, 1.2 eq) under nitrogen. The reaction mixture was stirred for 45 min at −78° C. A solution of N-phenyltrifluoromethanesulfonimide (1.4) (15.1 g, 42 mmol, 1.2 eq) in tetrahydrofuran (60 mL) was added drop wise to the reaction mixture. The mixture was warmed slowly to room temperature and stirred for 3 h. The mixture was then poured into ice water and extracted with a mixture of hexane and diethyl ether (1:1). The organic layer was washed with water and brine, dried over sodium sulfate and filtered. The organics were concentrated under vacuum and the crude product was purified by column chromatography (eluent: hexane/ethyl acetate, 4:1).

Yield: 90.2%

$^1$H NMR (400 MHz, CDCl$_3$) δ 7.32 (d, 1H), 7.26 (t, 1H), 7.10 (d, 1H), 5.70 (s, 1H), 3.90 (s, 3H), 3.83 (m, 2H), 3.30 (m, 2H), 2.10 (m, 2H), 1.77 (m, 2H), 1.48 (s, 9H)

Preparation of 12.12:

To a solution of 12.11 (16 g, 31.6 mmol) in dimethoxyethane (DME) (260 mL) was added sequentially a 2 N aqueous solution of sodium carbonate (53 mL, 106 mmol, 3.4 eq), lithium chloride (4.5 mg, 106 mmol, 3.4 eq.), 4-(N,N-diethylaminocarbonyl)phenylboronic acid (1.6) (8.4 g, 38 mmol, 1.2 eq) and tetrakis(triphenylphosphine)palladium(0) (1.1 g, 0.95 mmol, 0.03 eq). The mixture was refluxed overnight under nitrogen and then cooled to room temperature. Water (300 mL) was added to the mixture and the crude product was extracted with ethyl acetate. The organic layer was further washed with brine, dried over sodium sulfate and filtered. The organics were concentrated under vacuum and the crude product was purified by column chromatography (eluent: hexane/ethyl acetate, 1:1).

Yield: 98.5%

$^1$H NMR (400 MHz, CDCl$_3$) δ 7.33 (d, 2H), 7.25 (m, 4H), 7.15 (d, 1H), 5.72 (s, 1H), 3.85 (m, 2H), 3.53 (m, 2H), 3.32 (m, 4H), 3.10 (s, 3H), 2.06 (m, 2H), 1.76 (m, 2H), 1.50 (s, 9H), 1.20 (m, 6H)

Preparation of 12.13:

To a suspension of potassium tert-butoxide (9 g, 80 mmol, 8.0 eq) in diethyl ether (200 mL) was added drop wise water (0.72 mL, 40 mmol, 4.0 eq) at 0° C. The slurry was stirred for 30 min. To this mixture was added 12.12 (5.34 g, 10 mmol). The ice-bath was removed and the reaction mixture was stirred at room temperature overnight and quenched by addition of ice water. The aqueous layer was separated, acidified to pH 2-3 with a 1N aqueous solution of hydrochloric acid and extracted with methylene chloride. The organic layers were combined, dried over sodium sulfate and concentrated under vacuum. The crude product was used for the next step without further purification.

Yield: 86.9%

$^1$H NMR (400 MHz, DMSO d$_6$) δ 12.55 (brs, 1H), 7.23 (m, 7H), 5.98 (s, 1H), 3.68 (m, 2H), 3.42-3.20 (m, 6H), 1.80 (m, 4H), 1.42 (s, 9H), 1.10 (m, 6H)

Preparation of 12B:

To a solution of 12.13 (300 mg, 0.58 mmol) in methylene chloride (4 mL) was added a 2.0 M solution of anhydrous hydrochloric acid in diethyl ether (15 mL). The mixture was stirred at room temperature for 24 h and diluted with diethyl ether. The resulting precipitate was collected by filtration and washed with diethyl ether.

Yield: 95%

$^1$H NMR (400 MHz, DMSO d$_6$) δ 12.61 (brs, 1H), 8.69 (m, 6H), 7.38-7.25 (m, 7H), 6.06 (s, 1H), 3.41 (m, 2H), 3.25 (m, 6H), 2.06 (m, 4H), 1.11 (m, 6H)

Mass Spectral Analysis m/z=421.3 (M+H)$^+$

EXAMPLE 12C

Preparation of 12.14a

To a solution of 12.13 (780 mg, 1.5 mmol) in acetonitrile (50 mL) was added sequentially diisopropylethylamine (1.75 mL, 10 mmol, 6.7 eq), a 0.5 M solution of ammonia (12.15) in dioxane (30 mL, 15 mmol, 10 eq) and TBTU (580 mg, 1.8 mmol, 1.2 eq). The reaction mixture was stirred at room temperature for 3 days and then concentrated under vacuum. The residue was dissolved in ethyl acetate and washed with a saturated aqueous solution of sodium bicarbonate. The organic layer was dried over sodium sulfate, filtered and concentrated under vacuum. The crude product was purified by column chromatography (eluent: hexane/acetone, 1:1).

Yield: 60.4%

$^1$H NMR (400 MHz, DMSO d$_6$) δ 7.51 (s, 1H), 7.29 (t, 1H), 7.22 (s, 4H), 7.10 (d, 1H), 7.05 (d, 1H), 6.97 (s, 1H), 5.90 (s, 1H), 3.63 (m, 2H), 3.41 (m, 2H), 3.32 (m, 2H), 3.20 (m, 2H), 1.80 (m, 4H), 1.42 (s, 9H), 1.10 (m, 6H)

Preparation of 12C:

To a solution of 12.14a (420 mg, 0.81 mmol) in methylene chloride (6 mL) was added a 2.0 M solution of anhydrous hydrochloric acid in diethyl ether (20 mL). The mixture was stirred at room temperature for 2 days and diluted with diethyl ether. The resulting precipitate was collected by filtration and washed with diethyl ether.

Yield: 87.5%

$^1$H NMR (400 MHz, DMSO d$_6$) δ 9.21 (m, 2H), 7.54 (s, 1H), 7.32-7.10 (m, 7H), 6.88 (s, 1H), 5.98 (s, 1H), 3.42 (m, 2H), 3.20 (m, 6H), 2.10 (m, 4H), 1.10 (m, 6H)

Mass Spectral Analysis m/z=420.3 (M+H)$^+$

EXAMPLE 12D 12D was obtained according to a procedure similar to the one described for 12C, with the following exception:
Step 12.16: 12.15 was replaced by 3.4b.

$^1$H NMR (400 MHz, DMSO d$_6$) δ 9.19 (m, 2H), 7.83 (m, 1H), 7.30-7.20 (m, 6H), 7.00 (d, 1H), 5.96 (s, 1H), 3.41 (m, 2H), 3.20 (m, 6H), 2.11 (m, 4H), 2.06 (d, 3H), 1.10 (m, 6H)

Mass Spectral Analysis m/z=434.3 (M+H)$^+$

EXAMPLE 12E 12E was obtained according to a procedure similar to the one described for 12C, with the following exception:
Step 12.16: 12.15 was replaced by 3.4c.

$^1$H NMR (400 MHz, DMSO d$_6$) δ 9.18 (m, 2H), 7.90 (t, 1H), 7.30-7.20 (m, 6H), 7.00 (d, 1H), 5.96 (s, 1H), 3.40 (m, 2H), 3.20 (m, 6H), 2.50 (m, 2H), 2.10 (m, 4H), 1.10 (m, 6H), 0.78 (t, 3H)

Mass Spectral Analysis m/z=448.4 (M+H)$^+$

Elemental analysis:

$C_{27}H_{33}N_3O_3$, 5/4 $H_2O$

Theory: % C, 68.99; % H, 7.61; % N, 8.94.

Found: % C, 69.27; % H, 7.43; % N, 8.93.

EXAMPLE 12F

12 F was obtained according to a procedure similar to the one described for 12C, with the following exception:
Step 12.16: 12.15 was replaced by 3.4d.

$^1$H NMR (400 MHz, DMSO d$_6$) δ 8.98 (m, 2H), 7.91 (t, 1H), 7.31 (m, 1H), 7.20 (m, 5H), 7.00 (m, 1H), 5.96 (s, 1H), 3.45 (m, 4H), 3.20 (m, 6H), 2.40 (m, 2H), 2.08 (m, 4H), 1.10 (m, 6H), 0.70 (t, 3H)

Mass Spectral Analysis m/z=462.4 (M+H)$^+$

Elemental analysis:

$C_{28}H_{35}N_3O_3$, 1HCl, 7/3$H_2O$

Theory: % C, 62.27; % H, 7.59; % N, 7.78.

Found: % C, 62.37; % H, 7.23; % N, 7.74.

EXAMPLE 12G

Preparation of 12.7:

To a solution of 12.6 (2.25 g, 6 mmol) in a mixed solvent of methanol (40 mL), tetrahydrofuran (40 mL) and water (40 mL) was added lithium hydroxide (1.52 g, 36.2 mmol, 6.0 eq) in one portion. The reaction mixture was stirred at room temperature overnight. The mixture was concentrated under vacuum and extracted with diethyl ether. The aqueous phase was acidified to pH 2-3 using a 1 N aqueous solution of hydrochloric acid. The acidified solution was extracted with methylene chloride. The organics were combined, dried over sodium sulfate, filtered and concentrated under vacuum. The crude product was used in the next step without further purification.

Yield: 100%

$^1$H NMR (400 MHz, DMSO d$_6$) δ 12.93 (brs, 1H), 7.59 (t, 1H), 7.15 (d, 1H), 6.97 (d, 1H), 3.71 (m, 2H), 3.12 (m, 2H), 1.90 (m, 2H), 1.65 (m, 2H), 1.40 (s, 9H)

Preparation of 12.8:

To a solution of 12.7 (1.63 g, 4.5 mmol) in acetonitrile (100 mL) was added sequentially diisopropylethylamine (5.23, 30 mmol, 6.7 eq), dimethylamine (3.4j) hydrochloride (1.14 g, 14 mmol, 3.0 eq) and TBTU (1.74 g, 5.4 mmol, 1.2 eq). The reaction mixture was stirred at room temperature for 3 days and then concentrated under vacuum. The residue was dissolved in ethyl acetate and washed with a saturated aqueous solution of sodium bicarbonate. The organic layer was dried over sodium sulfate, filtered and concentrated under vacuum. The crude product was purified by column chromatography (eluent: hexane/acetone, 2:1).

Yield: 60%

$^1$H NMR (400 MHz, DMSO d$_6$) δ 7.50 (t, 1H), 7.00 (d, 1H), 6.85 (d, 1H), 3.89 (m, 2H), 3.22 (m, 2H), 3.14 (s, 3H), 2.74 (s, 3H), 2.03 (m, 2H), 1.62 (m, 2H), 1.48 (s, 6H)

Preparation of 12.9:

To a solution of 12.8 (950 mg, 2.45 mmol) in anhydrous tetrahydrofuran (20 mL) at −78° C. under nitrogen was added drop wise a 1.0 M solution of LiHMDS in tetrahydrofuran (3.2 mL, 3.2 mmol, 1.3 eq). The reaction mixture was stirred for 45 min at −78° C. A solution of N-phenyltrifluoromethanesulfonimide (1.4) (1.15 g, 3.2 mmol, 1.3 eq) in tetrahydrofuran (8 mL) was added drop wise to the reaction mixture. The mixture was warmed slowly to room temperature and stirring was continued for an additional 2.5 h at room temperature. The mixture was then poured into ice water and extracted with a mixture of hexane and diethyl ether (1:1). The organic layer was washed with water and brine, and dried over sodium sulfate and filtered. The organic extracts were concentrated under vacuum and the crude product was purified by column chromatography (eluent: methylene chloride/ethyl acetate, 3:1).

Yield: 78.6%

$^1$H NMR (400 MHz, CDCl$_3$) δ 7.28 (t, 1H), 6.96 (d, 1H), 6.83 (d, 1H), 5.65 (s, 1H), 3.80 (m, 2H), 3.38 (m, 1H), 3.20 (m, 1H), 3.10 (s, 3H), 2.92 (s, 3H), 2.09 (m, 2H), 1.70 (m, 2H), 1.48 (s, 9H)

Preparation of 12.10:

To a solution of 12.9 (950 mg, 1.83 mmol) in dimethoxyethane (DME) (16 mL) was added sequentially a 2N aqueous solution of sodium carbonate (3.1 mL, 6.2 mmol, 3.4 eq), lithium chloride (259 mg, 6.1 mmol, 3.3 eq.), 4-(N,N-diethylaminocarbonyl)phenylboronic acid (1.6) (486 mg, 2.2 mmol, 1.2 eq) and tetrakis(triphenylphosphine)palladium(0) (64 mg, 0.055 mmol, 0.03 eq). The mixture was refluxed overnight under nitrogen and then cooled to room temperature. To this mixture was added water (20 mL) and the crude product was extracted with ethyl acetate. The organic layer was washed with brine, dried over sodium sulfate and filtered. The organics were concentrated under vacuum and the crude product was purified by column chromatography (eluent: hexane/acetone, 2:1).

Yield: 88%

$^1$H NMR (400 MHz, CDCl$_3$) δ 7.35 (d, 2H), 7.25 (m, 3H), 7.05 (d, 1H), 6.91 (d, 1H), 5.62 (s, 1H), 3.86 (m, 2H), 3.55 (m, 2H), 3.30 (m, 4H), 2.69 (s, 3H), 2.30 (s, 3H), 2.10 (m, 1H), 1.98 (m, 1H), 1.70 (m, 2H), 1.49 (s, 6H), 1.20 (m, 6H)

Preparation of 12G:

To a solution of 12.10 (840 mg, 1.54 mmol) in methylene chloride (10 mL) was added a 2.0 M solution of anhydrous hydrochloric acid in diethyl ether (30 mL). The mixture was stirred at room temperature for 2 days and diluted with diethyl ether. The resulting precipitate was collected by filtration and washed with diethyl ether.

Yield: 100%

$^1$H NMR (400 MHz, DMSO d$_6$) δ 9.28 (m, 2H), 7.35-7.19 (m, 6H), 6.90 (d, 1H), 5.96 (s, 1H), 3.43 (m, 2H), 3.22 (m, 6H), 2.66 (s, 3H), 2.18 (s, 3H), 2.18 (s, 3H), 2.09 (m, 4H), 1.11 (m, 6H)

Mass Spectral Analysis m/z=448.4 (M+H)$^+$

EXAMPLE 12H 12H was obtained according to a procedure similar to the one described for 12A, with the following exception:
Step 12.4: 1.6 was replaced by 1.7.

$^1$H NMR (400 MHz, DMSO d$_6$) δ 9.20 (m, 2H), 8.48 (s, 1H), 7.73 (d, 1H), 7.58 (d, 1H), 7.20 (t, 1H), 6.98 (d, 1H), 6.82 (d, 1H), 6.10 (s, 1H), 3.42-3.12 (m, 8H), 2.02 (m, 4H), 1.70 (s, 3H), 1.18 (t, 3H), 1.10 (t, 3H)

Mass Spectral Analysis m/z=392.4 (M+H)$^+$
Elemental analysis:
C$_{24}$H$_{29}$N$_3$O$_3$, 7/5HCl, 7/5H$_2$O
Theory: % C, 61.60; % H, 7.15; % N, 8.98; % Cl, 10.61.
Found: % C, 61.70; % H, 6.78; % N, 8.86; % Cl, 10.73.

EXAMPLE 12I 12I was obtained according to a procedure similar to the one described for 12A, with the following exception:
Step 12.2: 12.2a was replaced by 12.2b.

$^1$H NMR (400 MHz, DMSO d$_6$) δ 8.89 (brs, 2H), 7.12 (d, 2H), 7.04 (d, 2H), 6.95 (t, 1H), 6.71 (d, 1H), 6.58 (d, 1H), 5.66 (s, 1H), 3.20 (brs, 2H), 2.92 (brm, 6H), 1.75 (brm, 6H), 0.86 (brm, 8H), 0.22 (t, 3H)

Mass Spectral Analysis m/z=419.4 (M+H)$^+$
Elemental analysis:
C$_{27}$H$_{34}$N$_2$O$_2$, 1HCl, 1H$_2$O
Theory: % C, 68.55; % H, 7.88; % N, 5.92.
Found: % C, 68.42; % H, 7.73; % N, 5.92.

EXAMPLE 12J 12J was obtained according to a procedure similar to the one described for 12A, with the following exception:
Step 12.2: 12.2a was replaced by 12.2c.

$^1$H NMR (400 MHz, DMSO d$_6$) δ 9.12 (brs, 1.5H), 7.54 (d, 2H), 7.47 (d, 2H), 7.38 (t, 1H), 7.13 (d, 1H), 7.02 (d, 1H), 6.09 (s, 1H), 3.62 (brs, 2H), 3.36 (brm, 5H), 2.18 (brm, 6H), 1.30 (brm, 8H), 1.00 (m, 2H), 0.81 (t, 3H)

Mass Spectral Analysis m/z=433.4 (M+H)$^+$
Elemental analysis:
C$_{28}$H$_{36}$N$_2$O$_2$, 1HCl, 2H$_2$O
Theory: % C, 66.58; % H, 8.18; % N, 5.55.
Found: % C, 66.82; % H, 7.88; % N, 5.59.

EXAMPLE 12K 12K was obtained according to a procedure similar to the one described for 12A, with the following exceptions:
Step 12.2: 12.2a was replaced by 12.2b.
Step 12.4: 1.6 was replaced by 1.7 and Method 12A was used.

$^1$H NMR (400 MHz, DMSO d$_6$) δ 9.73 (brs, 1H), 9.61 (brs, 1H), 8.47 (s, 1H), 7.65 (m, 2H), 7.20 (m, 1H), 6.90 (d, 1H), 6.82 (d, 1H), 5.66 (s, 1H), 3.59 (q, 2H), 3.41 (brm, 6H), 2.24 (brs, 4H), 2.01 (brm, 2H), 1.25 (brm, 8H), 0.54 (t, 3H)

Mass Spectral Analysis m/z=420.4 (M+H)$^+$

EXAMPLE 12L 12L was obtained according to a procedure similar to the one described for 12A, with the following exceptions:
Step 12.2: 12.2a was replaced by 12.2c.
Step 12.4: 1.6 was replaced by 1.7 and Method 12A was used.

$^1$H NMR (400 MHz, DMSO d$_6$) δ 8.86 (brd, 1.5H), 8.43 (d, 1H), 7.66 (dd, 1H), 7.48 (d, 1H), 7.16 (t, 1H), 6.91 (d, 1H), 6.79 (d, 1H), 5.98 (s, 1H), 3.40 (q, 2H), 3.12 (brm, 5H), 1.94 (brm, 6H), 1.10 (m, 5H), 1.01 (t, 3H), 0.76 (m, 2H), 0.56 (t, 3H)

Mass Spectral Analysis m/z=434.3 (M+H)$^+$

EXAMPLE 13A

Preparation of 13.2:

To a solution of 1.5a (7.80 g, 17.35 mmol, 1.0 eq) in dimethoxyethane (75 mL) was added sequentially a 2N aqueous solution of sodium carbonate (26.03 mL, 52.06 mmol, 3.0 eq), lithium chloride (2.21 g, 52.06 mmol, 3.0 eq), 13.1 (3.44 g, 19.09 mmol, 1.1 eq) and tetrakis(triphenylphosphine)palladium(0) (0.40 g, 0.35 mmol, 0.02 eq). The mixture was refluxed overnight under nitrogen. The mixture was then cooled to room temperature and water (250 mL) was added. The mixture was extracted with ethyl acetate. The organic layer was further washed with brine and dried over sodium sulfate. The crude product was purified by column chromatography (eluent: hexane/ethyl acetate mixtures of increasing polarity).

Yield: 64%

$^1$H NMR (400 MHz, DMSO $d_6$) δ 8.02 (d, 2H), 7.49 (d, 2H), 7.23 (m, 1H), 6.99 (d, 1H), 6.92 (m, 2H), 5.92 (s, 1H), 3.88 (s, 3H), 3.70 (m, 2H), 3.27 (m, 2H), 1.89 (m, 2H), 1.71 (m, 2H), 1.42 (s, 9H)

Mass Spectral Analysis m/z=436.0 (M+H)$^+$

Preparation of 13.3:

A solution of 13.2 (4.71 g, 10.81 mmol, 1.0 eq) in tetrahydrofuran (30 mL) at 0° C. under nitrogen was added drop wise to a solution of lithium hydroxide monohydrate (0.54 g, 12.98 mmol, 1.2 eq) in water (30 mL). The mixture was stirred overnight at room temperature. The mixture was then concentrated under reduced pressure and redissolved in water. The mixture was then acidified to pH 2 using concentrated hydrochloric acid. The resulting precipitate was collected by filtration and the crude product was used for the next step without further purification.

Yield: 98%

$^1$H NMR (400 MHz, DMSO $d_6$) δ 13.03 (br s, 1H), 8.01 (d, 2H), 7.47 (d, 2H), 7.23 (m, 1H), 6.98 (d, 1H), 6.92 (m, 2H), 5.91 (s, 1H), 3.70 (m, 2H), 3.28 (m, 2H), 1.86 (m, 2H), 1.72 (m, 2H), 1.42 (s, 9H)

Mass Spectral Analysis m/z=420.1 (M–H)$^-$

Preparation of 13A:

Trifluoroacetic acid (0.15 mL, 1.96 mmol, 5.5 eq) was added drop wise to a cold (0° C.) solution of 13.3 (0.15 g, 0.36 mmol, 1.0 eq) in anhydrous dichloromethane (5 mL). The mixture was warmed to room temperature and stirred overnight at room temperature. The mixture was then concentrated under reduced pressure. The crude product was triturated with diethyl ether. The resulting precipitate was collected by filtration.

Yield: 87%

$^1$H NMR (400 MHz, DMSO $d_6$) δ 13.05 (brs, 1H), 8.67 (m, 2H), 8.02 (d, 2H), 7.49 (d, 2H), 7.27 (m, 1H), 7.05 (d, 1H), 6.96 (m, 2H), 5.98 (s, 1H), 3.26 (m, 4H), 2.08 (m, 2H), 1.97 (m, 2H)

Mass Spectral Analysis m/z=322.1 (M+H)$^+$

Elemental analysis:

$C_{20}H_{19}NO_3$, $CF_3CO_2H$, $0.2H_2O$

Theory: % C, 60.19; % H, 4.68; % N, 3.19.

Found: % C, 60.18; % H, 4.61; % N, 3.24.

EXAMPLE 13B

Preparation of 13.5a:

O-Benzotriazol-1-yl-N,N,N',N'-tetramethyluronium tetrafluoroborate (150.8 mg, 0.47 mmol, 1.1 eq) was added to a cooled (0° C.) solution of 13.3 (180.0 mg, 0.43 mmol, 1.0 eq), 3.4a (50.3 mg, 0.94 mmol, 2.2 eq), and N,N-diisopropylethylamine (0.25 mL, 0.94 mmol, 2.2 eq) in acetonitrile (5 mL). The solution was stirred overnight at room temperature and then concentrated under reduced pressure. Ethyl acetate (10 mL) and a saturated aqueous solution of sodium bicarbonate (10 mL) were added to the crude product and the mixture was stirred for 20 min at room temperature. The phases were separated and the organic phase was washed with a saturated aqueous solution of sodium bicarbonate, brine, dried over sodium sulfate and filtered. The organics were concentrated under reduced pressure and the crude product was purified by column chromatography (eluent: hexane/ethyl acetate mixtures of increasing polarity).

Yield: 10%

Mass Spectral Analysis m/z=421.2 (M+H)$^+$

Preparation of 13B:

A 2.0M solution of hydrochloric acid in diethyl ether (0.12 mL, 0.24 mmol, 5.5 eq) was added drop wise to a cooled (0° C.) solution of 13.5a (18 mg, 0.04 mmol, 1.0 eq) in anhydrous methanol (5 mL). The mixture was stirred overnight at room temperature and then concentrated under reduced pressure. The crude product was triturated with ethyl acetate. The resulting precipitate was collected by filtration.

Yield: 70%

$^1$H NMR (400 MHz, DMSO $d_6$) δ 8.99 (m, 2H), 8.06 (m, 1H), 7.95 (m, 2H), 7.46 (m, 3H), 7.27 (m, 1H), 7.06 (m, 1H), 6.96 (m, 2H), 5.95 (s, 1H), 3.24 (m, 4H), 2.08 (m, 4H)

Mass Spectral Analysis m/z=321.1 (M+H)$^+$

EXAMPLE 13C 13C was obtained according to a procedure similar to the one described for 13B, with the following exception:

Step 13.6: 3.4a was replaced by 3.4b.

$^1$H NMR (400 MHz, DMSO $d_6$) δ 9.05 (m, 2H), 8.55 (m, 1H), 7.92 (m, 2H), 7.41 (m, 2H), 7.26 (m, 1H), 7.06 (m, 1H), 6.95 (m, 2H), 5.95 (s, 1H), 3.20 (m, 4H), 2.81 (m, 3H), 2.08 (m, 4H)

Mass Spectral Analysis m/z 335.2 (M+H)$^+$

EXAMPLE 13D 13D was obtained according to a procedure similar to the one described for 13B, with the following exception:

Step 13.6: 3.4a was replaced by 3.4c.

$^1$H NMR (400 MHz, DMSO $d_6$) δ 8.50 (m, 1H), 7.90 (d, 2H), 7.40 (d, 2H), 7.20 (m, 1H), 6.90 (m, 3H), 5.85 (s, 1H), 3.30 (m, 2H), 2.90 (m, 2H), 2.70 (m, 2H), 1.85-1.70 (m, 4H), 1.10 (t, 3H)

Mass Spectral Analysis m/z=349.2 (M+H)$^+$

Elemental analysis:

$C_{22}H_{24}N_2O_2$, 0.25 $(CH_3)_2CO$, $0.25H_2O$

Theory: % C, 70.89; % H, 7.32; % N, 7.27.

Found: % C, 71.13; % H, 7.04; % N, 7.07.

EXAMPLE 13E 13E was obtained according to a procedure similar to the one described for 13B, with the following exception:

Step 13.6: 3.4a was replaced by 3.4e.

$^1$H NMR (400 MHz, CDCl$_3$) δ 9.75 (brs, 1H), 9.31 (brs, 1H), 7.81 (d, 2H), 7.39 (d, 2H), 7.21 (m, 1H), 6.98 (m, 2H), 6.90 (m, 1H), 6.25 (m, 1H), 5.56 (s, 1H), 3.46 (m, 2H), 3.33 (m, 4H), 2.30 (m, 2H), 2.12 (m, 2H), 1.94 (m, 1H), 1.04 (d, 6H)

Mass Spectral Analysis m/z=377.2 (M+H)$^+$

EXAMPLE 13F 13F was obtained according to a procedure similar to the one described for 13B, with the following exception:
Step 13.6: 3.4a was replaced by 3.4j.
$^1$H NMR (400 MHz, DMSO $d_6$) δ 9.08 (m, 2H), 7.42 (m, 4H), 7.24 (m, 1H), 7.00 (m, 3H), 5.91 (s, 1H), 3.25 (m, 4H), 2.96 (m, 6H), 2.07 (m, 4H)
Mass Spectral Analysis m/z=349.1 $(M+H)^+$

EXAMPLE 13G 13G was obtained according to a procedure similar to the one described for 13B, with the following exception:
Step 13.6: 3.4a was replaced by 3.4k.
$^1$H NMR (400 MHz, DMSO $d_6$) δ 8.91 (m, 2H), 7.58 (d, 2H), 7.41 (d, 2H), 7.25 (m, 1H), 7.00 (m, 3H), 5.92 (s, 1H), 3.49 (m, 2H), 3.41 (m, 2H), 3.24 (m, 4H), 2.09 (m, 2H), 2.00 (m, 2H), 1.84 (m, 4H)
Mass Spectral Analysis m/z=375.1 $(M+H)^+$

EXAMPLE 13H 13H was obtained according to a procedure similar to the one described for 13B, with the following exception:
Step 13.6: 3.4a was replaced by 3.4o.
$^1$H NMR (400 MHz, DMSO $d_6$) δ 8.98 (m, 2H), 7.39 (dd, 4H), 7.24 (m, 1H), 6.95 (m, 3H), 5.91 (s, 1H), 3.66 (brs, 2H), 3.22 (m, 4H), 2.10 (m, 4H), 1.30 (m, 12H)
Mass Spectral Analysis m/z=405.3 $(M+H)^+$
Elemental analysis:
$C_{26}H_{32}N_2O_2$, 1HCl, 0.5$H_2O$
Theory: % C, 69.39; % H, 7.62; % N, 6.22.
Found: % C, 69.31; % H, 7.64; % N, 6.19.

EXAMPLE 13I 13I was obtained according to a procedure similar to the one described for 13B, with the following exception:
Step 13.6: 3.4a was replaced by 3.4p.
$^1$H NMR (400 MHz, DMSO $d_6$) δ 8.91 (m, 2H), 7.46 (m, 4H), 7.26 (m, 1H), 7.01 (m, 3H), 5.94 (s, 1H), 3.61 (m, 6H), 3.35 (m, 2H), 3.21 (m, 4H), 2.09 (m, 2H), 1.98 (m, 2H)
Mass Spectral Analysis m/z=391.1 $(M+H)^+$

EXAMPLE 13J 13J was obtained according to a procedure similar to the one described for 13B, with the following exception:
Step 13.6: 3.4a was replaced by 3.4q.
$^1$H NMR (400 MHz, DMSO $d_6$) δ 8.90 (m, 2H), 7.44 (m, 4H), 7.26 (m, 1H), 7.00 (m, 3H), 5.91 (s, 1H), 3.59 (m, 2H), 3.21 (m, 6H), 2.09 (m, 2H), 1.99 (m, 2H), 1.55 (m, 6H)
Mass Spectral Analysis m/z=389.1 $(M+H)^+$

EXAMPLE 13K 13K was obtained according to a procedure similar to the one described for 13B, with the following exception:
Step 13.6: 3.4a was replaced by 13.4a.
$^1$H NMR (400 MHz, DMSO $d_6$) δ 8.75 (m, 2H), 7.49 (m, 2H), 7.41 (m, 2H), 7.26 (m, 1H), 7.05 (m, 1H), 6.97 (m, 2H), 5.95 (s, 1H), 4.00 (brm, 4H), 3.23 (m, 4H), 2.10 (m, 2H), 1.97 (m, 2H), 1.64 (m, 2H), 1.15 (brm, 6H)
Mass Spectral Analysis m/z=403.3 $(M+H)^+$
Elemental analysis:
$C_{26}H_{30}N_2O_2$, 1HCl, 0.3$H_2O$
Theory: % C, 70.27; % H, 7.17; % N, 6.30.
Found: % C, 70.02; % H, 7.04; % N, 6.27.

EXAMPLE 13L 13L was obtained according to a procedure similar to the one described for 13B, with the following exception:
Step 13.6: 3.4a was replaced by 13.4b.
$^1$H NMR (400 MHz, DMSO $d_6$) δ 8.90 (m, 2H), 7.70 (d, 2H), 7.50 (d, 2H), 7.40 (m, 1H), 7.30 (m, 4H), 7.00 (m, 3H), 5.95 (s, 1H), 4.90 (s, 2H), 4.80 (s, 2H), 3.30 (brm, 4H), 2.05 (m, 4H)
Mass Spectral Analysis m/z=423.1 $(M+H)^+$
Elemental analysis:
$C_{28}H_{26}N_2O_2$, 1HCl, 1$H_2O$
Theory: % C, 70.50; % H, 6.13; % N, 5.87.
Found: % C, 70.58; % H, 5.95; % N, 5.89.

EXAMPLE 13M 13M was obtained according to a procedure similar to the one described for 13B, with the following exception:
Step 13.6: 3.4a was replaced by 13.4c.
$^1$H NMR (400 MHz, DMSO $d_6$) δ 9.00 (m, 1H), 7.40 (m, 4H), 7.25 (m, 1H), 7.00 (m, 3H), 5.90 (s, 1H), 3.55-3.05 (m, 8H), 2.05 (m, 4H), 1.60 (m, 2H), 1.10 (m, 1H), 0.90 (m, 2H), 0.65 (m, 1H), 0.40 (m, 2H), 0.15 (m, 1H), 0.10 (m, 1H)
Mass Spectral Analysis m/z=417.2 $(M+H)^+$
Elemental analysis:
$C_{27}H_{32}N_2O_2$, 1HCl, 0.4$H_2O$
Theory: % C, 70.46; % H, 7.40; % N, 6.09.
Found: % C, 70.54; % H, 7.30; % N, 6.15.

EXAMPLE 13N 13N was obtained according to a procedure similar to the one described for 13B, with the following exception:
Step 13.6: 3.4a was replaced by 13.4d.
$^1$H NMR (400 MHz, DMSO $d_6$) δ 8.88 (m, 2H), 7.40 (brm, 10H), 7.00 (m, 3H), 5.94 (s, 1H), 4.70 (m, 1H), 4.52 (m, 1H), 3.21 (m, 4H), 2.88 (m, 3H), 2.02 (m, 4H)
Mass Spectral Analysis m/z=425.2 $(M+H)^+$
Elemental analysis:
$C_{28}H_{28}N_2O_2$, 1HCl, 0.6$H_2O$
Theory: % C, 71.28; % H, 6.45; % N, 5.94.
Found: % C, 71.13; % H, 6.51; % N, 5.97.

EXAMPLE 13O 13O was obtained according to a procedure similar to the one described for 13B, with the following exception:
Step 13.6: 3.4a was replaced by 13.4e.
$^1$H NMR (400 MHz, DMSO $d_6$) δ 8.65 (m, 2H), 7.45 (m, 4H), 7.26 (m, 1H), 7.00 (m, 3H), 5.95 (s, 1H), 4.36 (m, 2H), 4.11 (m, 2H), 3.88 (m, 2H), 3.60 (m, 2H), 3.00 (m, 2H), 2.65 (m, 1H), 2.09 (m, 2H), 1.99 (m, 4H), 1.52 (m, 2H), 1.19 (m, 3H)
Mass Spectral Analysis m/z=461.2 $(M+H)^+$

EXAMPLE 13P 13P was obtained according to a procedure similar to the one described for 13B, with the following exception:
Step 13.6: 3.4a was replaced by 13.4f.
$^1$H NMR (400 MHz, DMSO $d_6$) δ 8.60 (m, 2H), 7.47 (m, 4H), 7.25 (m, 1H), 7.00 (m, 3H), 5.95 (s, 1H), 4.18 (m, 2H), 3.80 (brs, 4H), 3.24 (m, 2H), 3.00 (s, 3H), 2.10 (m, 2H), 1.94 (m, 2H), 1.20 (m, 3H)
Mass Spectral Analysis m/z=421.2 (M+H)$^+$

EXAMPLE 13Q 13Q was obtained according to a procedure similar to the one described for 13B, with the following exception:
Step 13.6: 3.4a was replaced by 13.4g.
$^1$H NMR (400 MHz, DMSO $d_6$) δ 10.32 (brs, 1H), 8.80 (m, 2H), 7.54 (m, 2H), 7.46 (m, 2H), 7.27 (m, 1H), 7.00 (m, 3H), 5.92 (s, 1H), 4.54 (brs, 2H), 3.84 (brs, 2H), 3.45 (m, 2H), 3.24 (m, 4H), 3.12 (m, 2H), 2.83 (s, 3H), 2.10 (m, 2H), 1.97 (m, 2H)
Mass Spectral Analysis m/z=404.3 (M+H)$^+$

EXAMPLE 13R 13R was obtained according to a procedure similar to the one described for 13B, with the following exception:
Step 13.6: 3.4a was replaced by 13.4h.
$^1$H NMR (400 MHz, DMSO $d_6$) δ 9.55 (m, 1H), 8.95 (m, 1H), 7.55 (m, 5H), 7.30 (brm, 10H), 7.04 (m, 1H), 6.95 (m, 2H), 5.93 (s, 1H), 4.62 (s, 2H), 4.46 (s, 2H), 3.20 (m, 4H), 2.02 (m, 4H)
Mass Spectral Analysis m/z=501.2 (M+H)$^+$

EXAMPLE 13S

Preparation of 13S:
A 2N aqueous solution of sodium hydroxide (1.0 mL, 2 mmol, 9.2 eq) was added to a solution of 13O (0.10 g, 0.22 mmol, 1.0 eq) in tetrahydrofuran (5 mL) and anhydrous absolute ethanol (1 mL). The mixture was stirred for 10 h at room temperature and acidified to pH 6 using a 2N aqueous solution of hydrochloric acid. The mixture was concentrated under reduced pressure. The crude product was dissolved in dichloromethane. The mixture was filtered and the filtrate was concentrated under reduced pressure.
Yield: 60%
$^1$H NMR (400 MHz, DMSO $d_6$) δ 7.43 (m, 4H), 7.25 (m, 1H), 7.01 (m, 2H), 6.94 (m, 1H), 5.93 (s, 1H), 4.33 (br s, 2H), 3.65-2.90 (m, 9H), 1.91 (m, 6H), 1.52 (m, 2H)
Mass Spectral Analysis m/z=433.1 (M+H)$^+$

EXAMPLE 14A

Preparation of 14.2:
To a solution of 1.5a (5.00 g, 11.12 mmol, 1.0 eq) in dimethoxyethane (17 mL) was added sequentially a 2N aqueous solution of sodium carbonate (16.69 mL, 33.37 mmol, 3.0 eq), lithium chloride (1.41 g, 33.37 mmol, 3.0 eq), 14.1 (1.80 g, 12.24 mmol, 1.1 eq) and tetrakis(triphenylphosphine)palladium(0) (0.26 g, 0.22 mmol, 0.02 eq). The mixture was refluxed for 10 h under nitrogen. The mixture was then cooled to room temperature and a 1N aqueous solution of sodium hydroxide was added. The mixture was extracted with dichloromethane. The organic layer was further washed with brine, dried over sodium sulfate, filtered and concentrated under reduced pressure. The crude product was triturated with diethyl ether. The resulting solid was collected bu filtration.
Yield: 78%
$^1$H NMR (400 MHz, DMSO $d_6$) δ 7.90 (d, 2H), 7.50 (d, 2H), 7.20 (m, 1H), 7.00 (m, 1H), 6.90 (m, 2H), 5.95 (s, 1H), 3.70 (m, 2H), 3.25 (m, 2H), 1.85 (m, 2H), 1.70 (m, 2H), 1.40 (s, 9H)
Mass Spectral Analysis m/z=403.1 (M+H)$^+$
Preparation of 14.4:
A mixture of 14.2 (3.49 g, 8.67 mmol, 1.0 eq), 14.3 (1.13 g, 17.34 mmol, 2.0 eq) and zinc bromide (0.98 g, 4.34 mmol, 0.5 eq) in isopropanol (70 mL) and water (50 mL) was refluxed for 3 days. The reaction mixture was then cooled to 0° C. and acidified to pH 1 using a 3N aqueous solution of hydrochloric acid. The mixture was extracted with ethyl acetate. The organic phase was washed with brine, dried over sodium sulfate, filtered and concentrated under reduced pressure. Diethyl ether (30 mL) was added. The resulting precipitate was collected by filtration and washed with diethyl ether. The crude compound was used for the next step without further purification.
Yield: 89%
$^1$H NMR (400 MHz, DMSO $d_6$) δ 8.10 (d, 2H), 7.55 (d, 2H), 7.20 (m, 1H), 7.00 (m, 2H), 6.90 (m, 1H), 5.90 (s, 1H), 3.70 (m, 2H), 3.30 (m, 2H), 1.90 (m, 2H), 1.70 (m, 2H), 1.40 (s, 9H)
Mass Spectral Analysis m/z=446.0 (M+H)$^+$
Preparation of 14A:
A 2.0M solution of hydrochloric acid in diethyl ether (21.3 mL, 42.58 mmol, 5.5 eq) was added drop wise to a cooled (0° C.) solution of 14.4 (3.71 g, 7.74 mmol, 1.0 eq) in anhydrous dichloromethane (25 mL). The mixture was warmed to room temperature and stirring was continued for an additional 10 h at room temperature. Diethyl ether (100 mL) was added to the solution. The resulting precipitate was collected by filtration and washed with diethyl ether. The crude product was purified by column chromatography (eluent: dichloromethane/methanol mixtures of increasing polarity).
Yield: 20%
$^1$H NMR (400 MHz, DMSO $d_6$) δ 9.08 (brs, 2H), 8.16 (d, 2H), 7.61 (d, 2H), 7.28 (m, 1H), 7.02 (m, 3H), 6.02 (s, 1H), 3.59 (brs, 1H), 3.24 (m, 4H), 2.06 (m, 4H)
Mass Spectral Analysis m/z=346.1 (M+H)$^+$
Elemental analysis:
$C_{20}H_{19}N_5O$, 1HCl, 0.5$H_2O$
Theory: % C, 61.46; % H, 5.42; % N, 17.92.
Found: % C, 61.52; % H, 5.23; % N, 17.63.

EXAMPLE 14B

Preparation of 14.5 and 14.6
Methyl iodide (2.8c) (0.35 mL, 0.0056 mol, 5.0 eq) was added drop wise to a solution of 14.4 (0.500 g, 0.0011 mol, 1.0 eq) and triethylamine (0.80 mL, 0.0056 mol, 5.0 eq) in anhydrous dimethylformamide (5 mL) and the mixture was stirred at room temperature for 3 days. The mixture was poured into water (50 mL) and extracted with ethyl acetate. The organic phase was washed with brine, dried over sodium sulfate, filtered and concentrated under reduced pressure. The crude product was purified by flash column chromatography (eluent: hexane/ethyl acetate mixtures of increasing polarity).
Yield 14.5 (major regioisomer): 65%
Mass Spectral Analysis m/z=460.1 (M+H)$^+$ Yield 14.6 (minor regioisomer): 17%

Mass Spectral Analysis m/z=460.2 (M+H)$^+$

Preparation of 14B

A 2.0M anhydrous solution of hydrochloric acid in diethyl ether (10 mL) was added drop wise to a cold (0° C.) solution of 14.5 (0.330 g, 0.00071 mol, 1.0 eq) in anhydrous dichloromethane (10 mL). The mixture was warmed to room temperature and stirring was continued for an additional 16 h at room temperature. The mixture was concentrated under reduced pressure and diethyl ether was added to the residue. The resulting precipitate was collected by filtration and washed with diethyl ether.

Yield: 90%

$^1$H NMR (400 MHz, DMSO d$_6$) δ 8.80 (m, 1H), 8.10 (d, 2H), 7.55 (d, 2H), 7.25 (t, 1H), 6.90-7.10 (m, 3H), 6.00 (s, 1H), 4.45 (s, 3H), 3.15-3.40 (m, 4H), 1.95-2.15 (m, 4H)

Mass Spectral Analysis m/z=360.1 (M+H)$^+$

EXAMPLE 14C

Preparation of 14C

A 2.0M anhydrous solution of hydrochloric acid in diethyl ether (5 mL) was added drop wise to a cold (0° C.) solution of 14.6 (0.090 g, 0.00019 mol, 1.0 eq) in anhydrous dichloromethane (10 mL). The mixture was warmed to room temperature and stirring was continued for an additional 10 h at room temperature. The mixture was concentrated under reduced pressure and diethyl ether was added to the residue. The resulting precipitate was collected by filtration and washed with diethyl ether.

Yield: 88%

$^1$H NMR (400 MHz, DMSO d$_6$) δ 8.80 (m, 1.5H), 7.90 (d, 2H), 7.60 (d, 2H), 7.25 (t, 1H), 6.90-7.10 (m, 3H), 6.00 (s, 1H), 4.20 (s, 3H), 3.20 (m, 4H), 1.95-2.15 (m, 4H)

Mass Spectral Analysis m/z=360.2 (M+H)$^+$

EXAMPLE 15A 15A was obtained according to a procedure similar to the one described for 15C, with the following exception:

Step 15.1: 15.1c was replaced by 15.1a.

$^1$H NMR (400 MHz, DMSO d$_6$) δ 8.87 (brm, 1H), 8.16 (d, 2H), 7.59 (d, 2H), 7.29 (m, 1H), 7.06 (m, 2H), 6.97 (m, 1H), 6.02 (s, 1H), 5.96 (s, 2H), 3.77 (s, 3H), 3.23 (brm, 4H), 2.11 (brm, 2H), 2.00 (brm, 2H)

Mass Spectral Analysis m/z=418.1 (M+H)$^+$

EXAMPLE 15B 15B was obtained according to a procedure similar to the one described for 15C, with the following exception:

Step 15.1: 15.1c was replaced by 15.1b.

$^1$H NMR (400 MHz, DMSO d$_6$) δ 8.75 (m, 1H), 8.15 (d, 2H), 7.57 (d, 2H), 7.25 (t, 1H), 7.00 (m, 3H), 6.00 (s, 1H), 5.00 (t, 2H), 3.60 (s, 3H), 3.10-3.40 (m, 6H), 1.95-2.18 (m, 4H)

Mass Spectral Analysis m/z=432.2 (M+H)$^+$

EXAMPLE 15C

Preparation of 15.2a and 15.3a:

Ethyl bromobutyrate (15.1c) (0.40 mL, 0.0028 mol, 2.5 eq) was added drop wise to a solution of 14.4 (0.500 g, 0.0011 mol, 1.0 eq) and triethylamine (0.40 mL, 0.0028 mol, 2.5 eq) in anhydrous N,N-dimethylformamide and the mixture was stirred at room temperature for 3 days. The mixture was poured into water (50 mL) and extracted with ethyl acetate. The organic phase was washed with brine, dried over sodium sulfate, filtered and concentrated under reduced pressure. The crude product was purified by flash column chromatography (eluent: hexane/ethyl acetate mixtures of increasing polarity).

Yield 15.2a (major regioisomer): 82%.

(15.2a) $^1$H NMR (400 MHz, DMSO d$_6$) δ 8.10 (d, 2H), 7.50 (d, 2H), 7.20 (m, 1H), 7.00 (m, 2H), 6.90 (m, 1H), 5.90 (s, 1H), 4.70 (t, 2H), 4.00 (q, 2H), 3.70 (m, 2H), 3.30 (m, 2H), 2.40 (m, 2H), 2.10 (m, 2H), 1.90 (m, 2H), 1.70 (m, 2H), 1.40 (s, 9H), 1.15 (t, 3H)

Mass Spectral Analysis m/z=560.2 (M+H)$^+$

Yield 15.3a (minor regioisomer): 6%.

(15.3a) $^1$H NMR (400 MHz, DMSO d$_6$) δ 7.90 (d, 2H), 7.60 (d, 2H), 7.20 (m, 1H), 7.00 (m, 2H), 6.90 (m, 1H), 5.95 (s, 1H), 4.55 (t, 2H), 4.00 (q, 2H), 3.70 (m, 2H), 3.30 (m, 2H), 2.40 (m, 2H), 2.10 (m, 2H), 1.90 (m, 2H), 1.70 (m, 2H), 1.40 (s, 9H), 1.10 (t, 3H)

Mass Spectral Analysis m/z=560.2 (M+H)$^+$

Preparation of 15C:

A 2.0M anhydrous solution of hydrochloric acid in diethyl ether (10 mL) was added drop wise to a cold (0° C.) solution of 15.2a (0.520 g, 0.00092 mol, 1.0 eq) in anhydrous dichloromethane (10 mL). The mixture was warmed to room temperature and stirring was continued for an additional 10 h at room temperature. An additional amount of a 2.0M anhydrous solution of hydrochloric acid in diethyl ether (10 mL) was added to the mixture, which was stirred for an additional 6 h at room temperature. The mixture was concentrated under reduced pressure and diethyl ether was added. The resulting precipitate was collected by filtration and washed with diethyl ether.

Yield: 70%

$^1$H NMR (400 MHz, DMSO d$_6$) δ 8.80 (m, 1H), 8.15 (d, 2H), 7.60 (d, 2H), 7.25 (m, 1H), 7.00 (m, 3H), 6.00 (s, 1H), 4.80 (t, 2H), 4.00 (q, 2H), 3.35 (m, 2H), 3.20 (m, 2H), 2.40 (m, 2H), 2.20 (m, 2H), 2.10 (m, 2H), 1.95 (m, 2H), 1.15 (t, 3H)

Mass Spectral Analysis m/z=460.2 (M+H)$^+$

EXAMPLE 15D 15D was obtained according to a procedure similar to the one described for 15C, with the following exception:

Step 15.1: 15.1c was replaced by 15.1d.

$^1$H NMR (400 MHz, DMSO d$_6$) δ 8.90 (brm, 1.5H), 8.14 (d, 2H), 7.57 (d, 2H), 7.28 (t, 1H), 7.04 (m, 2H), 6.96 (m, 1H), 6.00 (s, 1H), 4.78 (t, 2H), 4.04 (q, 2H), 3.22 (brm, 4H), 2.37 (t, 2H), 2.11 (brm, 2H), 2.01 (brm, 4H), 1.57 (m, 2H), 1.16 (t, 3H)

Mass Spectral Analysis m/z=474.2 (M+H)$^+$

EXAMPLE 15E 15E was obtained according to a procedure similar to the one described for 15C, with the following exception:

Step 15.1: 15.1c was replaced by 15.1e.

$^1$H NMR (400 MHz, DMSO d$_6$) δ 8.88 (brm, 1.5H), 8.14 (d, 2H), 7.57 (d, 2H), 7.28 (t, 1H), 7.05 (m, 2H), 6.96 (m, 1H), 6.00 (s, 1H), 4.76 (t, 2H), 4.02 (q, 2H), 3.22 (brm, 4H), 2.29 (t, 2H), 2.10 (brm, 2H), 2.00 (brm, 4H), 1.57 (m, 2H), 1.30 (m, 2H), 1.14 (t, 3H)

Mass Spectral Analysis m/z=488.2 (M+H)$^+$

EXAMPLE 15F 15F was obtained according to a procedure similar to the one described for 15H, with the following exception:
Step 15.1: 15.1c was replaced by 15.1a.
$^1$H NMR (400 MHz, DMSO d$_6$) δ 8.86 (brm, 1H), 7.84 (d, 2H), 7.62 (d, 2H), 7.29 (m, 1H), 7.07 (d, 1H), 6.99 (m, 2H), 6.03 (s, 1H), 5.71 (s, 2H), 3.70 (s, 3H), 3.23 (m, 4H), 2.11 (brm, 2H), 2.00 (brm, 2H)
Mass Spectral Analysis m/z=418.2 (M+H)$^+$

EXAMPLE 15G 15G was obtained according to a procedure similar to the one described for 15H, with the following exception:
Step 15.1: 15.1c was replaced by 15.1b.
$^1$H NMR (400 MHz, DMSO d$_6$) δ 8.78 (brm, 1H), 7.91 (d, 2H), 7.64 (d, 2H), 7.29 (m, 1H), 7.05 (m, 2H), 6.98 (m, 1H), 6.04 (s, 1H), 4.71 (t, 2H), 3.56 (s, 3H), 3.23 (m, 4H), 3.11 (t, 2H), 2.12 (brm, 2H), 2.00 (brm, 2H)
Mass Spectral Analysis m/z=432.1 (M+H)$^+$

EXAMPLE 15H

Preparation of 15H
A 2.0M anhydrous solution of hydrochloric acid in diethyl ether (10 mL) was added drop wise to a cold (0° C.) solution of 15.3a (0.030 g, 0.000053 mol, 1.0 eq) in anhydrous dichloromethane (10 mL). The mixture was warmed to room temperature and stirring was continued for an additional 10 h at room temperature. An additional amount of a 2.0M anhydrous solution of hydrochloric acid in diethyl ether (10 mL) was added to the mixture, which was stirred for an additional 6 h at room temperature. The mixture was concentrated under reduced pressure and diethyl ether was added. The resulting precipitate was collected by filtration and washed with diethyl ether.
Yield: 57%
$^1$H NMR (400 MHz, DMSO d$_6$) δ 9.00 (m, 1.5H), 7.90 (d, 2H), 7.62 (d, 2H), 7.30 (m, 1H), 7.05 (m, 2H), 6.95 (m, 1H), 6.00 (s, 1H), 4.60 (t, 2H), 4.00 (q, 2H), 3.25 (m, 4H), 2.40 (m, 2H), 2.10 (m, 6H), 1.15 (t, 3H)
Mass Spectral Analysis m/z=460.2 (M+H)$^+$

EXAMPLE 15I 15I was obtained according to a procedure similar to the one described for 15H, with the following exception:
Step 15.1: 15.1c was replaced by 15.1d.
$^1$H NMR (400 MHz, DMSO d$_6$) δ 8.96 (brm, 1.5H), 7.89 (d, 2H), 7.63 (d, 2H), 7.29 (t, 1H), 7.06 (m, 2H), 6.97 (m, 1H), 6.03 (s, 1H), 4.55 (t, 2H), 4.01 (q, 2H), 3.22 (brm, 4H), 2.29 (t, 2H), 2.12 (brm, 2H), 2.02 (brm, 2H), 1.85 (m, 2H), 1.49 (m, 2H), 1.13 (t, 3H)
Mass Spectral Analysis m/z=474.3 (M+H)$^+$

EXAMPLE 15J 15J was obtained according to a procedure similar to the one described for 15H, with the following exception:
Step 15.1: 15.1c was replaced by 15.1e.
$^1$H NMR (400 MHz, DMSO d$_6$) δ 8.93 (brm, 1H), 7.87 (d, 2H), 7.62 (d, 2H), 7.29 (t, 1H), 7.05 (m, 2H), 6.97 (m, 1H), 6.03 (s, 1H), 4.52 (t, 2H), 4.01 (q, 2H), 3.23 (brm, 4H), 2.22 (t, 2H), 2.11 (brm, 2H), 2.02 (brm, 2H), 1.83 (m, 2H), 1.47 (m, 2H), 1.23 (m, 2H), 1.14 (t, 3H)
Mass Spectral Analysis m/z=488.3 (M+H)$^+$

EXAMPLE 15K 15K was obtained according to a procedure similar to the one described for 15L, with the following exception:
Step 15.6: 15C was replaced by 15A.
$^1$H NMR (400 MHz, DMSO d$_6$) δ 8.18 (d, 2H), 7.60 (d, 2H), 7.29 (t, 1H), 7.06 (t, 2H), 6.97 (m, 1H), 6.02 (s, 1H), 5.80 (s, 2H), 3.27 (brm, 4H), 2.13 (brm, 2H), 2.00 (brm, 2H)
Mass Spectral Analysis m/z=404.1 (M+H)$^+$

EXAMPLE 15L

Preparation of 15L
A 2N aqueous solution of sodium hydroxide (1.8 mL, 0.0036 mol, 5.5 eq) was added to a solution of 15C (0.300 g, 0.00060 mol, 1.0 eq) in tetrahydrofuran (10 mL) and absolute ethanol (1 mL). The mixture was stirred for 10 h at room temperature and acidified to pH 6 using a 2N aqueous solution of hydrochloric acid. The mixture was concentrated under reduced pressure and diethyl ether was added. The mixture was then stirred for 1 h at room temperature. The resulting precipitate was collected by filtration and washed several times with water and diethyl ether.
Yield: 98%
$^1$H NMR (400 MHz, DMSO d$_6$+CF$_3$CO$_2$D) δ 8.80 (m, 1H), 8.20 (m, 2H), 7.70 (m, 2H), 7.30 (m, 1H), 7.00 (m, 3H), 6.00 (s, 1H), 4.80 (m, 2H), 3.30 (m, 4H), 2.60-1.95 (m, 8H)
Mass Spectral Analysis m/z=432.1 (M+H)$^+$

EXAMPLE 15M 15M was obtained according to a procedure similar to the one described for 15L, with the following exception:
Step 15.6: 15C was replaced by 15D.
$^1$H NMR (400 MHz, DMSO d$_6$) δ 8.76 (brm 1H), 8.16 (d, 2H), 7.58 (d, 2H), 7.29 (t, 1H), 7.06 (t, 2H), 6.97 (m, 1H), 6.00 (s, 1H), 4.78 (t, 2H), 3.24 (m, 4H), 2.31 (t, 2H), 2.13 (brm, 2H), 2.01 (brm, 4H), 1.56 (m, 2H)
Mass Spectral Analysis m/z=446.2 (M+H)$^+$

EXAMPLE 15N 15N was obtained according to a procedure similar to the one described for 15L, with the following exception:
Step 15.6: 15C was replaced by 15E.
$^1$H NMR (400 MHz, DMSO d$_6$) δ 8.62 (brm, 1.5H), 8.15 (d, 2H), 7.57 (d, 2H), 7.28 (m, 1H), 7.05 (m, 2H), 6.97 (m, 1H), 6.00 (s, 1H), 4.76 (t, 2H), 3.25 (brm, 4H), 2.21 (t, 2H), 2.11 (brm, 2H), 1.98 (brm, 4H), 1.55 (m, 2H), 1.31 (m, 2H)
Mass Spectral Analysis m/z=460.2 (M+H)$^+$

EXAMPLE 16A 16A was obtained according to a procedure similar to the one described for 14A, with the following exception:
Step 14.1: 14.1 was replaced by 16.1 (see also step 16.1).
$^1$H NMR (400 MHz, DMSO d$_6$) δ 9.00 (brs, 2H), 8.12 (t, 2H), 7.70 (t, 1H), 7.60 (t, 1H), 7.25 (t, 1H), 7.00 (m, 3H), 6.00 (s, 1H), 3.30 (m, 4H), 2.05 (m, 4H)
Mass Spectral Analysis m/z=346.1 (M+H)$^+$

EXAMPLE 16B 16B was obtained according to a procedure similar to the one described for 14B, with the following exception:
Step 14.1: 14.1 was replaced by 16.1 (see also step 16.1).

$^1$H NMR (400 MHz, DMSO d$_6$) δ 8.66 (brm, 2H), 8.11 (m, 1H), 8.01 (m, 1H), 7.66 (t, 1H), 7.54 (m, 1H), 7.28 (m, 1H), 7.06 (d, 1H), 6.97 (m, 2H), 6.00 (s, 1H), 4.43 (s, 3H), 3.23 (brm, 4H), 2.12 (brm, 2H), 2.00 (brm, 2H)

Mass Spectral Analysis m/z=360.1 (M+H)$^+$

EXAMPLE 16C 16C was obtained according to a procedure similar to the one described for 14C, with the following exception:
Step 14.1: 14.1 was replaced by 16.1 (see also step 16.1).

$^1$H NMR (400 MHz, DMSO d$_6$) δ 8.73 (brm, 2H), 7.91 (m, 1H), 7.83 (t, 1H), 7.72 (t, 1H), 7.03 (m, 1H), 7.28 (m, 1H), 7.05 (m, 2H), 6.96 (m, 1H), 6.02 (s, 1H), 4.20 (s, 3H), 3.23 (brm, 4H), 2.11 (brm, 2H), 1.99 (brm, 2H)

Mass Spectral Analysis m/z=360.1 (M+H)$^+$

EXAMPLE 17A 17A was obtained according to a procedure similar to the one described for 15A, with the following exception:
Step 15.1: 14.4 was replaced by 16.3 (see also step 17.1).

$^1$H NMR (400 MHz, DMSO d$_6$) δ 8.93 (brs, 1.5H), 8.13 (m, 1H), 8.03 (t, 1H), 7.68 (t, 1H), 7.56 (m, 1H), 7.28 (m, 1H), 7.07 (m, 1H), 6.97 (m, 2H), 6.01 (s, 1H), 5.94 (s, 2H), 3.75 (s, 3H), 3.22 (brm, 4H), 2.12 (brm, 2H), 2.02 (brm, 2H)

Mass Spectral Analysis m/z=418.1 (M+H)$^+$

EXAMPLE 17B 17B was obtained according to a procedure similar to the one described for 15C, with the following exception:
Step 15.1: 14.4 was replaced by 16.3 (see also step 17.1).

$^1$H NMR (400 MHz, DMSO d$_6$) δ 9.07 (brs, 2H), 8.11 (m, 1H), 8.01 (t, 1H), 7.66 (t, 1H), 7.54 (m, 1H), 7.28 (m, 1H), 7.07 (dd, 1H), 6.96 (m, 2H), 5.99 (s, 1H), 4.79 (t, 2H), 4.03 (q, 2H), 3.22 (brm, 4H), 2.42 (t, 2H), 2.21 (m, 2H), 2.09 (brm, 4H), 1.16 (t, 3H)

Mass Spectral Analysis m/z=460.2 (M+H)$^+$

EXAMPLE 17C 17C was obtained according to a procedure similar to the one described for 15F, with the following exceptions:
Step 15.1: 14.4 was replaced by 16.3 (see also step 17.1).

$^1$H NMR (400 MHz, DMSO d$_6$) δ 8.95 (brs, 2H), 7.80 (m, 1H), 7.69 (m, 3H), 7.28 (m, 1H), 7.06 (d, 1H), 6.97 (m, 2H), 5.99 (s, 1H), 5.70 (s, 2H), 3.64 (s, 3H), 3.23 (brm, 4H), 2.10 (brm, 2H), 2.01 (brm, 2H)

Mass Spectral Analysis m/z=418.1 (M+H)$^+$

EXAMPLE 17D 17D was obtained according to a procedure similar to the one described for 15C, with the following exceptions:
Step 15.1: 14.4 was replaced by 16.3 (see also step 17.1).

$^1$H NMR (400 MHz, DMSO d$_6$) δ 8.37 (dt, 1H), 8.30 (t, 1H), 7.81 (t, 1H), 7.71 (dt, 1H), 7.44 (m, 1H), 7.22 (m, 2H), 7.10 (m, 1H), 5.98 (s, 1H), 5.47 (t, 2H), 4.22 (brs, 2H), 4.15 (t, 2H), 4.02-3.46 (brm, 10H), 2.48 (brm, 2H), 2.22 (brm, 2H)

Mass Spectral Analysis m/z=459.2 (M+H)$^+$

EXAMPLE 17E 17E was obtained according to a procedure similar to the one described for 15K, with the following exceptions:
Step 15.1: 14.4 was replaced by 16.3 (see also step 17.1).

$^1$H NMR (400 MHz, DMSO d$_6$) δ 8.87 (brm, 2H), 8.13 (dt, 1H), 8.03 (t, 1H), 7.68 (t, 1H), 7.56 (m, 1H), 7.28 (m, 1H), 7.07 (d, 1H), 6.98 (m, 2H), 6.01 (s, 1H), 5.77 (s, 2H), 3.24 (brm, 4H), 2.12 (brm, 2H), 2.02 (brm, 2H)

Mass Spectral Analysis m/z=404.1 (M+H)$^+$

EXAMPLE 17F 17F was obtained according to a procedure similar to the one described for 15L, with the following exception:
Step 15.1: 14.4 was replaced by 16.3 (see also step 17.1).

$^1$H NMR (400 MHz, DMSO d$_6$) δ 8.11 (dt, 1H), 8.01 (m, 1H), 7.66 (t, 1H), 7.54 (dt, 1H), 7.28 (m, 1H), 7.07 (d, 1H), 6.97 (m, 2H), 5.99 (s, 1H), 4.78 (t, 2H), 3.21 (brm, 4H), 2.34 (t, 2H), 2.18 (m, 2H), 2.10 (brm, 4H)

Mass Spectral Analysis m/z=432.1 (M+H)$^+$

EXAMPLE 18A

Preparation of 18.2:

A mixture of 13.5a (0.300 g, 0.00071 mole, 1.0 eq), and the Lawesson's reagent (18.1) (0.288 g, 0.00071 mole, 1 eq) in toluene (10 mL) was refluxed for 6 h. The mixture was cooled to room temperature, poured onto a saturated aqueous solution of sodium bicarbonate (50 mL) and extracted with ethyl acetate. The organic phase was washed with brine, dried over sodium sulfate, filtered and concentrated under reduced pressure. Diethyl ether was added to the mixture, which was stirred at room temperature for 1 h. The resulting precipitate was collected by filtration, washed with diethyl ether and used for the next step without further purification.

Yield: 64%

Mass Spectral Analysis m/z=434.93 (M−H)$^−$

Preparation of 18.4a:

A mixture of 18.2 (1 g, 0.0022 mole, 1.0 eq) and 1-bromopinacolone (18.3a) (0.30 mL, 0.0022 mole, 1.0 eq) in N,N-dimethylformamide (5 mL) was stirred at room temperature for 48 h. The mixture was poured into a saturated aqueous solution of sodium bicarbonate and extracted with ethyl acetate. The organic phase was washed with brine, dried over sodium sulfate, filtered and concentrated under reduced pressure. The crude product was purified by flash column chromatography (eluent: hexane/ethyl acetate mixtures of increasing polarity).

Yield: 55%

$^1$H NMR (400 MHz, DMSO d$_6$) δ 8.00 (d, 2H), 7.45 (d, 2H), 7.35 (s, 1H), 7.20 (t, 1H), 7.00 (d, 2H), 6.90 (t, 1H), 5.90 (s, 1H), 3.70 (m, 2H), 3.30 (m, 2H), 1.90 (m, 2H), 1.70 (m, 2H), 1.30 (s, 9H), 1.35 (s, 9H)

Mass Spectral Analysis m/z=517.2 (M+H)$^+$

Preparation of 18A:

To a cold (0° C.) solution of 18.4a (0.600 g, 0.0011 mole, 1.0 eq) in anhydrous dichloromethane (20 mL) was added drop wise a 2.0M solution of anhydrous hydrochloric acid in diethyl ether (5.8 mL, 0.0011 mole, 10.0 eq). The mixture was warmed slowly to room temperature and stirring was continued for 12 h. The mixture was concentrated under reduced pressure. Diethyl ether was then added to the mixture, which was stirred for 1 h at room temperature. The precipitate was collected by filtration, washed with diethyl ether and dried under vacuum.

Yield: 80%

$^1$H NMR (400 MHz, DMSO d$_6$) δ 9.00 (s, 2H), 8.00 (d, 2H), 7.50 (d, 2H), 7.40 (s, 1H), 7.25 (t, 1H), 7.00 (m, 3H), 6.00 (s, 1H), 3.20 (m, 4H), 2.00 (m, 4H), 1.30 (s, 9H)

Mass Spectral Analysis m/z=417.3 (M+H)$^+$

EXAMPLE 18B 18B was obtained according to a procedure similar to the one described for 18A, with the following exception:
Step 18.3: 18.3a was replaced by 18.3b.

$^1$H NMR (400 MHz, DMSO d$_6$) δ 8.93 (brs, 2H), 8.24 (s, 1H), 8.10 (m, 4H), 7.52 (m, 4H), 7.40 (m, 1H), 7.29 (m, 1H), 7.06 (t, 2H), 6.97 (m, 1H), 6.00 (s, 1H), 3.22 (brm, 4H), 2.07 (brm, 4H)

Mass Spectral Analysis m/z=437.1 (M+H)$^+$

EXAMPLE 18C

Preparation of 18.6:

A mixture of 14.2 (1 g, 0.00248 mole, 1.0 eq), hydroxylamine hydrochloride (18.5) (0.260 g, 0.0037 mole, 1.5 eq.) and triethylamine (0.70 mL, 0.0049 mole, 2.0 eq) in absolute ethanol (15 mL) was refluxed for 6 h. The mixture was cooled to room temperature and poured onto water. The resulting precipitate was collected by filtration, washed with water, dried under high vacuum and used for the next step without further purification.

Yield: 75%

Mass Spectral Analysis m/z=436.2 (M+H)$^+$

Preparation of 18.7

Acetyl chloride (6.7) (0.07 mL, 0.00097 mol, 2.0 eq) was added drop wise to a refluxing solution of 18.6 (0.212 g, 0.00048 mole, 1.0 eq) in pyridine (2 mL). The mixture was heated to reflux for 3 h. The mixture was cooled to room temperature, poured onto a saturated aqueous solution of sodium bicarbonate and extracted with ethyl acetate. The organic phase was washed with a 1N aqueous solution of hydrochloric acid and brine, dried over sodium sulfate and filtered. The organics were concentrated under reduced pressure and the crude product was purified by flash column chromatography (eluent: hexane/ethyl acetate mixtures of increasing polarity).

Yield: 35%

$^1$H NMR (400 MHz, CDCl$_3$) δ 8.10 (d, 2H), 7.45 (d, 2H), 7.20 (m, 1H), 7.00 (m, 1H), 6.95 (m, 1H), 6.85 (m, 1H), 5.60 (s, 1H), 3.90 (m, 2H), 3.35 (m, 2H), 2.65 (s, 3H), 2.05 (d, 2H), 1.70 (m, 2H), 1.55 (s, 4H), 1.40 (s, 5H)

Mass Spectral Analysis m/z=460.1 (M+H)$^+$

Preparation of 18C

To a cold (0° C.) solution of 18.7 (0.300 g, 0.00065 mole, 1.0 eq) in anhydrous dichloromethane (20 mL) was added drop wise a 2.0M solution of anhydrous hydrochloric acid in diethyl ether (3.2 mL, 0.0065 mole, 10.0 eq). The mixture was warmed slowly to room temperature and stirring was continued for 12 h. The mixture was concentrated under reduced pressure. Diethyl ether was then added to the mixture, which was stirred for 1 h at room temperature. The precipitate was collected by filtration, washed with diethyl ether and dried under vacuum.

Yield: 60%

$^1$H NMR (400 MHz, DMSO d$_6$) δ 9.00 (m, 2H), 8.10 (m, 2H), 7.60 (m, 2H), 7.30 (m, 1H), 7.05 (m, 3H), 6.00 (s, 1H), 3.30 (m, 4H), 2.45-2.80 (m, 3H), 2.10 (m, 4H)

Mass Spectral Analysis m/z=360.3 (M+H)$^+$

EXAMPLE 19A

Preparation of 19.2:

To a solution of 19.1 (29.75 g, 127.5 mmol, 1.2 eq) in dry methanol (200 mL) was added pyrrolidine (17.6 mL, 212.6 mmol, 2.0 eq) followed by 2'-hydroxyacetophenone (1.1a) (12.8 mL, 106.3 mmol, 1.0 eq). The mixture was heated under reflux for 10 h. The volatiles were removed under reduced pressure and the residue was dissolved in ethyl acetate (500 mL), washed with a 1M aqueous solution of hydrochloric acid (3×200 mL), a 1M aqueous solution of sodium hydroxide (3×200 mL) and brine. The organics were dried over sodium sulfate, filtered and concentrated under reduced pressure to give the crude product, which was used in the next step without further purification.

$^1$H NMR (400 MHz, CDCl$_3$) δ 7.86 (dd, 1H), 7.50 (m, 1H), 7.42-7.29 (m, 5H), 7.00 (m, 2H), 5.14 (s, 2H), 3.97 (brs, 2H), 3.29 (brs, 2H), 2.71 (s, 2H), 2.04 (m, 2H), 1.61 (m, 2H)

Mass Spectral Analysis m/z=352.1 (M+H)$^+$

Preparation of 19.3:

Under nitrogen, to an oven-dried two-necked 1 L flask charged with a solution of 19.2 (45.4 g, as of 106.3 mmol, 1.0 eq) in dry tetrahydrofuran (350 mL) at −78° C. was added a solution of 1.0M solution of lithium bis(trimethylsilyl)amide in tetrahydrofuran (127.6 mL, 127.6 mmol, 1.2 eq) over a 45 min time period. The reaction mixture was kept at −78° C. for 1 h and a solution of N-phenylbis(trifluoromethanesulfonamide) (1.4) (45.57 g, 127.6 mmol, 1.2 eq) in tetrahydrofuran (150 mL) was added over a 45 min time period. The reaction mixture was kept at −78° C. for 1 h, then slowly warmed up to room temperature and stirred for an additional 10 h at room temperature. Ice water (300 mL) was added to quench the reaction and the product was extracted with diethyl ether (500 mL). The organic phase was then washed with a 1M aqueous solution of hydrochloric acid (3×150 mL), a 1M aqueous solution of sodium hydroxide (3×150 mL), and brine, dried over sodium sulfate and filtered. The organics were concentrated under reduced pressure to give the crude product, which was used for the next step without further purification.

Mass Spectral Analysis m/z=484.0 (M+H)$^+$

Preparation of 19.4:

To a solution of 1.14 (53.58 g, 212.6 mmol, 2.0 eq) in N,N-dimethylformamide (200 mL) at 0° C. was added potassium acetate (31.3 g, 318.9 mmol, 3.0 eq), 1,1'-bis(diphenylphosphino)ferrocene palladium(II) chloride complex with dichloromethane (2.33 g, 3.19 mmol, 0.03 eq). The reaction mixture was heated to 80° C. at which point a solution of 19.3 (60 g, crude, as of 106.3 mmol, 1.0 eq) in N,N-dimethylformamide (100 mL) was added to the reaction mixture over a 30 min time period. The reaction mixture was then stirred at 80° C. for 10 h. Diethyl ether (500 mL) and water (300 mL) were added and the two phases were separated. The organic phase was washed with a 1M aqueous solution of hydrochloric acid (2×150 mL) and brine, dried over sodium sulfate and filtered.

The organics were concentrated under reduced pressure and the crude product was purified by column chromatography (eluent: hexane/ethyl acetate mixtures of increasing polarity).

Yield: 75% over three steps $^1$H NMR (400 MHz, CDCl$_3$) δ 7.71 (dd, 1H), 7.43-7.28 (m, 5H), 7.11 (m, 1H), 6.90 (m, 1H), 6.82 (dd, 1H), 6.27 (s, 1H), 5.14 (s, 2H), 3.94 (brs, 2H), 3.34 (brs, 2H), 1.96 (m, 2H), 1.61 (m, 2H), 1.33 (s, 12H)

Mass Spectral Analysis m/z=462.2 (M+H)$^+$

Preparation of 19.6:

To a solution of tert-butyl 4-bromophenylcarbamate (19.5) (20.7 g, 76 mmol, 1.04 eq) in dimethoxyethane (200 mL) was added sequentially a 2M aqueous solution of sodium carbonate (109.5 mL, 210 mmol, 3.0 eq), lithium chloride (9.28 g, 210 mmol, 3.0 eq), tetrakis(triphenylphosphine)palladium(0) (1.69 g, 1.46 mmol, 0.02 eq), and 19.4 (33.7 g, 73 mmol, 1.0 eq) under nitrogen. The reaction mixture was heated under reflux for 10 h. Water (500 mL) and diethyl ether (300 mL) were added and the two phases were separated. The organic phase was washed with brine, dried over sodium sulfate, filtered, and concentrated under reduced pressure. The resulting foamy solids were soaked with hexane and the fine powders were collected by filtration.

Yield: 91%

$^1$H NMR (400 MHz, CDCl$_3$) δ 7.43-7.30 (m, 7H), 7.28-7.23 (m, 2H), 7.17 (m, 1H), 7.02 (m, 1H), 6.92 (m, 1H), 6.85 (m, 1H), 6.53 (s, 1H), 5.50 (s, 1H), 5.15 (s, 2H), 3.96 (brs, 2H), 3.40 (brs, 2H), 2.06 (m, 2H), 1.67 (m, 2H), 1 53 (s, 9H)

Mass Spectral Analysis m/z=527.4 (M+H)$^+$

Preparation of 19.7:

To a cold (0° C.) solution of 19.6 (35.5 g, 67 mmol, 1.0 eq) in anhydrous dichloromethane (150 mL) was slowly added a 2.0M solution of hydrogen chloride in diethyl ether (167.5 mL, 335 mmol, 5.0 eq). The reaction mixture was stirred at room temperature for 10 h and then concentrated under reduced pressure. The resulting foamy solids were soaked in diethyl ether and the fine powders were collected by filtration. This crude product was used for the next steps without further purification.

Mass Spectral Analysis m/z=427.3 (M+H)$^+$

Preparation of 19.9a:

To a suspension of 19.7 (1.28 g, crude, as of 3 mmol, 1.0 eq) in dry dichloromethane (80 mL) at 0° C. was slowly added triethylamine (2.1 mL, 15 mmol, 5.0 eq) followed by drop wise addition of isobutyryl chloride (19.8a) (0.48 mL, 4.5 mmol, 1.5 eq). The mixture was slowly warmed to room temperature and stirred for 10 h at room temperature. Dichloromethane (100 mL) was added and the mixture was washed with a 1N aqueous solution of hydrochloric acid (3×50 mL), a saturated aqueous solution of sodium bicarbonate (2×50 mL) and brine, dried over sodium sulfate and filtered. The crude product was concentrated under reduced pressure and purified by column chromatography (eluent: hexane/ethyl acetate mixtures of increasing polarity).

Yield: 81% over two steps $^1$H NMR (400 MHz, CDCl$_3$) δ 7.57 (d, 2H), 7.40-7.27 (m, 8H), 7.17 (m, 1H), 7.01 (d, 1H), 6.93 (d, 1H), 6.85 (m, 1H), 5.50 (s, 1H), 5.15 (s, 2H), 3.96 (brs, 2H), 3.41 (brs, 2H), 2.53 (m, 1H), 2.06 (m, 2H), 1.67 (m, 2H), 1.28 (d, 6H)

Mass Spectral Analysis m/z=467.3 (M+H)$^+$

Preparation of 19A

To a stirred solution of 19.9a (1.2 g, 2.44 mmol, 1.0 eq) in dry dichloromethane (20 mL) was added iodotrimethylsilane (0.66 mL, 4.89 mmol, 2.0 eq) drop wise. After stirring at room temperature for 1 h, the mixture was concentrated to dryness under reduced pressure. A 1N aqueous solution of hydrochloric acid (300 mL) and diethyl ether (200 mL) were added to the residue. The resulting solid was collected by filtration, washed with diethyl ether, and dried under vacuum.

Yield: 92%

$^1$H NMR (400 MHz, DMSO d$_6$) δ 10.02 (s, 1H), 8.98 (brs, 2H), 7.70 (d, 2H), 7.36-7.22 (m, 3H), 7.02 (m, 2H), 6.94 (m, 1H), 5.82 (s, 1H), 3.21 (m, 4H), 2.63 (m, 1H), 2.03 (m, 4H), 1.11 (d, 6H)

Mass Spectral Analysis m/z=363.4 (M+H)$^+$

EXAMPLE 19B 19B was obtained according to a procedure similar to the one described for 19A, with the following exception:
Step 19.6: 19.8a was replaced by 19.8b.

$^1$H NMR (400 MHz, DMSO d$_6$) δ 10.04 (s, 1H), 8.90 (m, 2H), 7.71 (m, 2H), 7.29 (m, 2H), 7.25 (m, 1H), 7.03 (m, 2H), 6.94 (m, 1H), 5.82 (s, 1H), 3.44-3.11 (m, 4H), 2.25 (m, 1H), 2.02 (m, 4H), 1.51 (m, 4H), 0.86 (t, 6H)

Mass Spectral Analysis m/z=391.4 (M+H)$^+$

EXAMPLE 19C

Preparation of 19.10:

To a solution of 19.7 (4.63 g, crude, as of 10 mmol, 1.0 eq) in dry pyridine (10 mL) at 0° C. was slowly added isopropylsulfonyl chloride (6.5b) (1.68 mL, 15 mmol, 1.5 eq). The reaction mixture was stirred at room temperature for 10 h. Pyridine was removed under reduced pressure and the residue was dissolved in ethyl acetate (200 mL). The solution was washed with a 1M aqueous solution of hydrochloric acid (5×50 mL) and brine, dried over sodium sulfate and filtered. The filtrate was concentrated under reduced pressure and the crude product was purified by column chromatography (eluent: hexane/ethyl acetate mixtures of increasing polarity).

Yield: 55% over two steps $^1$H NMR (400 MHz, CDCl$_3$) δ 7.43-7.16 (m, 10H), 6.99 (dd, 1H), 6.94 (dd, 1H), 6.86 (m, 1H), 6.60 (s, 1H), 5.51 (s, 1H), 5.15 (s, 2H), 3.96 (brs, 2H), 3.49-3.30 (m, 3H), 2.06 (m, 2H), 1.67 (m, 2H), 1.43 (d, 6H)

Mass Spectral Analysis m/z=533.3 (M+H)$^+$

Preparation of 19C:

To a stirred solution of 19.9a (1.37 g, 2.57 mmol, 1.0 eq) in dry dichloromethane (20 mL) was added iodotrimethylsilane (0.70 mL, 5.14 mmol, 2.0 eq) dropwise. The mixture was stirred at room temperature for 1 h and then concentrated under reduced pressure. To the residue was added a 1M aqueous solution of hydrochloric acid (300 mL) and diethyl ether (200 mL). The resulting solid was collected by filtration and washed with diethyl ether. The crude compound was further purified by preparative liquid chromatography (mobile phase: acetonitrile/water/trifluoroacetic acid). The desired fractions were combined, concentrated under reduced pressure, and dried under vacuum.

Yield: 66%

$^1$H NMR (400 MHz, DMSO d$_6$) δ 9.93 (brs, 1H), 8.67 (brs, 2H), 7.36-7.22 (m, 5H), 7.05-6.91 (m, 3H), 5.83 (s, 1H), 3.32-3.14 (m, 5H), 2.06 (m, 2H), 1.93 (m, 2H), 1.26 (d, 6H)

Mass Spectral Analysis m/z=399.3 (M+H)$^+$

EXAMPLE 19D

Preparation of 19.12:

To a solution of 19.7 (1.28 g, crude, as of 2.67 mmol, 1.0 eq) in dry pyridine (15 mL) at 0° C. was slowly added ethyl isocyanate (19.11) (0.33 mL, 4.15 mmol, 1.5 eq). The reaction mixture was stirred at room temperature for 10 h. Pyridine was removed under reduced pressure and the residue was partitioned between water (100 mL) and dichlorometnane (200 mL). The organic layer was washed with brine, dried over sodium sulfate, filtered, and concentrated under reduced pressure. The crude product was purified by column chromatography (eluent: hexane/ethyl acetate mixtures of increasing polarity).

Yield: 78% over two steps $^1$H NMR (400 MHz, CDCl$_3$) δ 7.44-7.12 (m, 10H), 7.05-6.79 (m, 4H), 5.45 (s, 1H), 5.16 (m, 3H), 3.95 (brs, 2H), 3.50-3.26 (m, 4H), 2.04 (m, 2H), 1.65 (m, 2H), 1.16 (t, 3H)

Mass Spectral Analysis m/z=498.4 (M+H)$^+$

Preparation of 19D:

To a stirred solution of 19.12 (1.03 g, 2.09 mmol, 1.0 eq) in dry dichloromethane (20 mL) was added iodotrimethylsilane (0.57 mL, 4.18 mmol, 2.0 eq) drop wise. The reaction mixture was stirred at room temperature for 1 h and then concentrated under reduced pressure. The residue was suspended in methanol (50 mL) and stirred for another 1 h at room temperature. The resulting solid was collected by filtration and washed with methanol. The solid was further washed with a 1M aqueous solution of sodium hydroxide (3×10 mL) and water (2×10 mL), and then dried under vacuum.

Yield: 60%

$^1$H NMR (400 MHz, DMSO d$_6$) δ 8.54 (s, 1H), 7.44 (d, 2H), 7.18 (m, 3H), 6.98 (m, 1H), 6.91 (m, 1H), 6.86 (m, 1H), 6.13 (t, 1H), 5.72 (s, 1H), 3.11 (m, 2H), 2.89 (m, 2H), 2.74 (m, 2H), 1.77 (m, 2H), 1.67 (m, 2H), 1.06 (t, 3H)

Mass Spectral Analysis m/z=364.4 (M+H)$^+$

EXAMPLE 20A

Preparation of 20A:

Triethylamine (0.37 mL, 2.66 mmol, 2.2 eq) was added to a solution of 1A (0.50 g, 1.21 mmol, 1.0 eq) in anhydrous tetrahydrofuran (4 mL). Anhydrous methanol (4 mL) was then added followed by 20.1a (0.20 mL, 2.42 mmol, 2.0 eq). Sodium cyanoborohydride (0.09 g, 1.45 mmol, 1.2 eq) was added to the reaction mixture which was stirred for 30 min at room temperature under nitrogen. The mixture was concentrated under reduced pressure. Dichloromethane (30 mL) and water (10 mL) were added and the suspension was stirred at room temperature for 10 min. The phases were separated. The organic phase was further washed with water and brine, dried over sodium sulfate, filtered and concentrated under reduced pressure. To a cold (0° C.) solution of the resulting oil in anhydrous dichloromethane was added drop wise a 2.0M solution of anhydrous hydrochloric acid in diethyl ether (5 mL). The mixture was then stirred for 1 h at room temperature and concentrated under reduced pressure. Diethyl ether was added. The resulting precipitate was collected by filtration and washed with diethyl ether.

Yield: 65%

$^1$H NMR (400 MHz, DMSO d$_6$) δ 10.63 (brs, 0.25H), 10.50 (brs, 0.75H), 7.42 (m, 4H), 7.28 (m, 1H), 7.08 (d, 1H), 6.98 (m, 2H), 6.27 (s, 0.25H), 5.85 (s, 0.75H), 3.37 (brm, 8H), 2.82 (s, 3H), 2.11 (m, 4H), 1.12 (m, 6H)

Mass Spectral Analysis m/z=391.2 (M+H)$^+$

Elemental analysis:

C$_{25}$H$_{30}$N$_2$O$_2$, 1HCl, 0.9H$_2$O

Theory: % C, 67.75; % H, 7.46; % N, 6.32.

Found: % C, 67.89; % H, 7.32; % N, 6.26.

EXAMPLE 20B 20B was obtained according to a procedure similar to the one described for 20A, with the following exception:
Step 20.1: 1A was replaced by 11A.

$^1$H NMR (400 MHz, DMSO d$_6$) δ 10.42 (brs, 1H), 9.47 (s, 1H), 7.30 (m, 4H), 7.08 (t, 1H), 6.60 (d, 1H), 6.46 (d, 1H), 5.68 (s, 1H), 3.40 (m, 4H), 3.30 (s, 3H), 3.20 (m, 2H), 2.81 (s, 2H), 2.15 (m, 2H), 2.05 (m, 2H), 1.10 (m, 6H)

Mass Spectral Analysis m/z=407.3 (M+H)$^+$

Elemental analysis:

C$_{25}$H$_{30}$N$_2$O$_3$, 1HCl, 0.5H$_2$O

Theory: % C, 66.43; % H, 7.14; % N, 6.20.

Found: % C, 66.53; % H, 7.06; % N, 6.24.

EXAMPLE 20C 20C was obtained according to a procedure similar to the one described for 20A, with the following exception:
Step 20.1: 1A was replaced by 11B.

$^1$H NMR (400 MHz, DMSO d$_6$) δ 10.79 (brs, 1H), 9.74 (d, 1H), 8.41 (s, 1H), 7.69 (dd, 1H), 7.45 (d, 1H), 7.09 (t, 1H), 6.62 (d, 1H), 6.49 (d, 2H), 5.81 (s, 1H), 3.42 (m, 4H), 3.30 (m, 4H), 2.79 (d, 3H), 2.12 (m, 4H), 1.16 (m, 3H), 1.08 (m, 3H)

Mass Spectral Analysis m/z=408.3 (M+H)$^+$

EXAMPLE 20D 20D was obtained according to a procedure similar to the one described for 20A, with the following exception:
Step 20.1: 1A was replaced by 3D.

$^1$H NMR (400 MHz, DMSO d$_6$) δ 11.00 (m, 0.25H), 10.85 (m, 0.75H), 7.80 (m, 2H), 7.54 (m, 1H), 7.40 (m, 4H), 7.22 (m, 1H), 7.10 (m, 0.75H), 7.02 (m, 0.25H), 6.32 (s, 0.25H), 5.91 (s, 0.75H), 3.33 (m, 10H), 2.80 (m, 2H), 2.20 (m, 3H), 1.11 (m, 6H)

Mass Spectral Analysis m/z=434.4 (M+H)$^+$

Elemental analysis:

C$_{26}$H$_{31}$N$_3$O$_3$, 1HCl, 1H$_2$O

Theory: % C, 63.99; % H, 7.02; % N, 8.61.

Found: % C, 64.11; % H, 6.70; % N, 8.49.

EXAMPLE 20E 20E was obtained according to a procedure similar to the one described for 20A, with the following exception:
Step 20.1: 1A was replaced by 3E.

$^1$H NMR (400 MHz, DMSO d$_6$) δ 10.84 (m, 1H), 8.31 (m, 1H), 7.78 (m, 1H), 7.52 (m, 1H), 7.42 (m, 3H), 7.10 (m, 1H), 5.90 (s, 1H), 3.46 (m, 2H), 3.31 (m, 10H), 2.82 (m, 2H), 2.72 (m, 2H), 2.12 (m, 3H), 1.16 (m, 6H)

Mass Spectral Analysis m/z=448.5 (M+H)$^+$

Elemental analysis:

C$_{27}$H$_{33}$N$_3$O$_3$, 1HCl, 1H$_2$O

Theory: % C, 64.59; % H, 7.23; % N, 8.37.

Found: % C, 64.77; % H, 7.27; % N, 8.40.

EXAMPLE 20F 20F was obtained according to a procedure similar to the one described for 20A, with the following exception:
Step 20.1: 1A was replaced by 3F.

$^1$H NMR (400 MHz, DMSO d$_6$) δ 10.80 (brs, 1H), 8.35 (m, 1H), 7.78 (m, 1H), 7.50 (m, 1H), 7.40 (m, 3H), 7.09 (m, 1H), 5.93 (s, 1H), 3.41 (m, 2H), 3.20 (m, 10H), 2.72 (m, 2H), 2.10 (m, 3H), 1.10 (m, 9H)

Mass Spectral Analysis m/z=462.5 (M+H)+
Elemental analysis:
C28H35N3O3, 1HCl, 1H2O
Theory: % C, 65.17; % H, 7.42; % N, 8.14.
Found: % C, 65.28; % H, 7.37; % N, 8.21.

EXAMPLE 20G 20G was obtained according to a procedure similar to the one described for 20A, with the following exception:
Step 20.1: 1A was replaced by 3V.
$^1$H NMR (400 MHz, CDCl$_3$) δ 8.57 (s, 1H), 7.70 (m, 2H), 7.66 (d, 1H), 7.38 (s, 1H), 7.02 (d, 1H), 5.70 (s, 1H), 3.61 (m, 2H), 3.46 (m, 2H), 2.62 (m, 2H), 2.52 (m 2H), 2.12 (m, 2H), 2.78 (m, 2H), 1.30 (t, 3H), 1.23 (t, 3H)
Mass Spectral Analysis m/z=435.4 (M+H)+

EXAMPLE 20H 20H was obtained according to a procedure similar to the one described for 20L, with the following exception:
Step 20.1: 21A was replaced by 4H and 20.1d was replaced by 20.1a.
$^1$H NMR (400 MHz, DMSO d$_6$) δ 10.44-10.12 (m, 1H), 7.74 (dd, 0.7H), 7.67 (dd, 0.7H), 7.45 (m, 5H), 7.27 (m, 3H), 6.38 (s, 0.3H), 6.00 (s, 0.7H), 3.53-3.16 (m, 8H), 2.84 (m, 3H), 2.35-2.03 (m, 4H), 1.12 (brd, 6H)
Mass Spectral Analysis m/z=470.3 (M+H)+
Elemental analysis:
C25H31N3O4S, 1HCl, 1H2O
Theory: % C, 57.30; % H, 6.54; % N, 8.02.
Found: % C, 57.46; % H, 6.44; % N, 7.96.

EXAMPLE 20I 20I was obtained according to a procedure similar to the one described for 20L, with the following exception:
Step 20.1: 20.1d was replaced by 20.1a.
$^1$H NMR (400 MHz, DMSO d$_6$) δ 10.62 (brs, 1H), 7.41 (m, 4H), 7.24 (m, 1H), 6.97 (m, 2H), 6.93 (m, 1H), 5.92 & 5.86 (2s, 1H, rotamer), 3.55-2.92 (m, 8H), 2.80 & 2.77 (d, 3H), 2.56-1.76 (m, 6H), 1.12 (m, 6H)
Mass Spectral Analysis m/z=405.4 (M+H)+

EXAMPLE 20J 20J was obtained according to a procedure similar to the one described for 20L, with the following exception:
Step 20.1: 20.1d was replaced by 20.1b.
$^1$H NMR (400 MHz, DMSO d$_6$) δ 10.72 (m, 1H), 7.41 (m, 4H), 7.24 (m, 1H), 6.95 (m, 3H), 5.91 & 5.84 (2s, 1H, rotamer), 3.56-2.94 (m, 10H), 2.57-1.77 (m, 6H), 1.27 (m, 3H), 1.12 (m, 6H)
Mass Spectral Analysis m/z=419.4 (M+H)+

EXAMPLE 20K 20K was obtained according to a procedure similar to the one described for 20L, with the following exception:
Step 20.1: 20.1d was replaced by 20.1c.
$^1$H NMR (400 MHz, DMSO d$_6$) δ 9.99 (m, 1H), 7.41 (m, 4H), 7.25 (m, 1H), 6.95 (m, 3H), 5.88 & 5.86 (2s, 1H rotamer), 3.70-2.93 (m, 10H), 2.57-1.76 (m, 7H), 1.12 (m, 6H), 0.99 (m, 6H)
Mass Spectral Analysis m/z=447.5 (M+H)+

EXAMPLE 20L

Preparation of 20L:
To a stirred solution of cyclopropanecarbaldehyde (20.1d) (0.22 mL, 3.0 mmol, 2.0 eq) in dry dichloromethane (25 mL) was added sequentially 21A (0.64 g, 1.5 mmol, 1.0 eq), acetic acid (0.10 mL, 1.8 mmol, 1.2 eq), and sodium cyanoborohydride (0.14 g, 2.25 mmol, 1.5 eq). The reaction mixture was stirred at room temperature for 10 h. Water (40 mL) was added and the aqueous layer was basified to pH=10 with a 1M aqueous solution of sodium hydroxide. The two phases were separated and the aqueous phase was saturated with sodium chloride and extracted with dichloromethane (3×50 mL). The combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil in dichloromethane was added dropwise a 2.0M solution of hydrogen chloride in diethyl ether (1.0 mL, 2.0 mmol, 2.0 eq). The mixture was then stirred for 1 h at room temperature, concentrated under reduced pressure, and dried under vacuum.
Yield: 65%
$^1$H NMR (400 MHz, DMSO d$_6$) δ 10.66 (brs, 1H), 7.41 (m, 4H), 7.25 (m, 1H), 7.03-6.89 (m, 3H), 5.91 & 5.86 (2s, 1H, rotamer), 3.80-2.95 (m, 10H), 2.44-1.78 (m, 6H), 1.12 (m, 7H), 0.64 (m, 2H), 0.42 (m, 2H)
Mass Spectral Analysis m/z=445.4 (M+H)+

EXAMPLE 20M

Preparation of 20M:
Triethylamine (0.98 mL, 7.00 mmol, 3.3 eq) was added to a solution of 1A (0.80 g, 2.12 mmol, 1.0 eq) in anhydrous dichloromethane (5 mL). Compound 2.8a (0.68 mL, 7.00 mmol, 3.3 eq) was then added to the reaction mixture, which was stirred overnight at room temperature under nitrogen. The mixture was concentrated under reduced pressure. The crude product was purified by column chromatography (eluent: dichloromethane/methanol mixtures of increasing polarity). To a solution of the purified product in dichloromethane (5 mL) was added at 0° C. a 2.0 M solution of hydrochloric acid in diethyl ether (3.2 mL, 1.16 mmol, 5.5 eq). Diethyl ether was added to the mixture. The resulting precipitate was collected by filtration and washed with diethyl ether.
Yield: 46%
$^1$H NMR (400 MHz, DMSO d$_6$) δ 10.83 (m, 0.25H), 10.71 (m, 0.75H), 7.45 (m, 4H), 7.28 (m, 1H), 7.08 (m, 1H), 7.00 (m, 2H), 6.24 (s, 0.25H), 5.85 (s, 0.75H), 3.47 (m, 5H), 3.25 (m, 4H), 3.06 (m, 2H), 2.18 (m, 4H), 1.12 (m, 6H), 0.65 (m, 2H), 0.43 (m, 2H)
Mass Spectral Analysis m/z=431.0 (M+H)+

EXAMPLE 20N 20N was obtained according to a procedure similar to the one described for 20M, with the following exception:
Step 20.1: 2.8a was replaced by 20.2a.
$^1$H NMR (400 MHz, DMSO d$_6$) δ 10.10 (m, 1H), 7.43 (m, 4H), 7.28 (m, 1H), 7.09 (m, 1H), 6.98 (m, 2H), 6.28 (s, 0.25H), 5.85 (s, 0.75H), 3.35 (brm, 10H), 2.15 (m, 4H), 1.28 (m, 3H), 1.11 (m, 6H)

Mass Spectral Analysis m/z=405.0 (M+H)$^+$

EXAMPLE 20O 20O was obtained according to a procedure similar to the one described for 20M, with the following exception:
Step 20.1: 2.8a was replaced by 20.2b.

$^1$H NMR (400 MHz, DMSO d$_6$) δ 10.18 (m, 1H), 7.45 (m, 4H), 7.29 (m, 1H), 7.09 (m, 1H), 6.98 (m, 2H), 6.25 (m, 0.25H), 5.84 (m, 0.75H), 3.41 (m, 4H), 3.21 (m, 4H), 3.09 (m, 2H), 2.16 (m, 4H), 1.75 (m, 2H), 1.11 (m, 6H), 0.91 (m, 3H)

Mass Spectral Analysis m/z=419.1 (M+H)$^+$

EXAMPLE 20P 20P was obtained according to a procedure similar to the one described for 20M, with the following exception:
Step 20.1: 2.8a was replaced by 20.2c.

$^1$H NMR (400 MHz, CDCl$_3$) δ 7.35 (m, 9H), 7.17 (m, 1H), 6.98 (dd, 1H), 6.94 (dd, 1H), 6.84 (m, 1H), 5.61 (s, 1H), 3.58 (brs, 4H), 3.32 (brs, 2H), 2.60 (brm, 4H), 2.08 (brm, 2H), 1.81 (brm, 2H), 1.20 (brd, 6H)

Mass Spectral Analysis m/z=467.3 (M+H)$^+$

EXAMPLE 20Q 20Q was obtained according to a procedure similar to the one described for 20M, with the following exception:
Step 20.1: 2.8a was replaced by 20.2d.

$^1$H NMR (400 MHz, DMSO d$_6$) δ 10.95 (brs, 0.5H) 7.44 (m, 4H), 7.33 (m, 6H), 7.04 (d, 1H), 6.99 (m, 2H), 6.24 (s, 0.3H), 5.87 (s, 0.7H), 3.40 (brm, 10H), 3.12 (m, 2H), 2.18 (brm, 4H), 1.13 (brd, 6H)

Mass Spectral Analysis m/z=481.3 (M+H)$^+$

EXAMPLE 20R 20R was obtained according to a procedure similar to the one described for 20M, with the following exception:
Step 20.1: 2.8a was replaced by 20.2e.

$^1$H NMR (400 MHz, DMSO d$_6$) δ 10.70 (brm, 0.50H), 7.43 (m, 4H), 7.28 (m, 6H), 7.08 (d, 1H), 6.97 (m, 2H), 6.36 (s, 0.3H), 5.83 (s, 0.7H), 3.44 (m, 4H), 3.18 (brm, 6H), 2.67 (t, 2H), 2.12 (brm, 6H), 1.12 (brd, 6H)

Mass Spectral Analysis m/z=495.3 (M+H)$^+$

EXAMPLE 21A

Preparation of 21.2:

To a stirred solution of N-boc 4-piperidone (1.2) (2.0 g, 10 mmol, 1.0 eq) in dry diethyl ether (15 mL) at −25° C. was simultaneously but independently added ethyl diazoacetate (21.1) (1.35 mL, 13 mmol, 1.3 eq) and boron trifluoride diethyl ether complex (1.33 mL, 10.5 mmol, 1.05 eq) under nitrogen atmosphere over a 20 min time period. The reaction mixture was stirred for another 1 h at −25° C. A 1M aqueous solution of potassium carbonate was added drop wise to the stirred reaction mixture until gaseous evolution ceased. The two phases were separated and the organic phase was dried over sodium sulfate, filtered, and concentrated under reduced pressure. The crude product was used for the next step without further purification.

Preparation of 21.3:

A mixture of the crude 21.2 (3 g, as of 10 mmol) in a 4M aqueous hydrochloric acid solution (50 mL) was heated under reflux for 6 h. Water was removed under reduced pressure and the resulting solid was washed with diethyl ether and dried under vacuum.

Yield: 90% over two steps $^1$H NMR (400 MHz, DMSO d$_6$) δ 9.41 (brs, 2H), 3.30 (m, 2H), 3.21 (m, 2H), 2.77 (m, 2H), 2.62 (m, 2H), 1.94 (m, 2H)

Preparation of 21.4:

To a suspension of 21.3 (4.98 g, 33.3 mmol, 1.0 eq) in dry dichloromethane (100 mL) at 0° C. was slowly added triethylamine (11 mL, 79.92 mmol, 2.4 eq) followed by a solution of di-tert-butyl-dicarbonate (4.7) (8.72 g, 39.96 mmol, 1.2 eq) in dichloromethane (30 mL) over a 20 min time period. The reaction mixture was stirred at room temperature for 10 h and washed with a 1M aqueous solution of hydrochloric acid (3×100 mL), brine, dried over sodium sulfate and filtered. The filtrate was concentrated under reduced pressure and the crude product was used for next step without further purification.

$^1$H NMR (400 MHz, CDCl$_3$) δ 3.58 (m, 4H), 2.65 (m, 4H), 1.78 (m, 2H), 1.45 (s, 9H)

Preparation of 21.5:

To a solution of 21.4 (2.56 g, 12 mmol, 1.0 eq) in dry methanol (30 mL) was added pyrrolidine (2 mL, 24 mmol, 2.0 eq) followed by 2'-hydroxyacetophenone (1.1a) (1.44 mL, 12 mmol, 1.0 eq). The mixture was heated under reflux for 10 h. The volatiles were removed under reduced pressure and the residue was dissolved in ethyl acetate (200 mL) and washed with a 1M aqueous solution of hydrochloric acid (3×50 mL), a 1M aqueous solution of sodium hydroxide (3×50 mL) and brine, dried over sodium sulfate and filtered. The filtrate was concentrated under reduced pressure and the crude product was purified by column chromatography (eluent: hexane/ethyl acetate mixtures of increasing polarity).

Yield: 72% over two steps $^1$H NMR (400 MHz, CDCl$_3$) δ 7.85 (dd, 1H), 7.49 (m, 1H), 6.99 (m, 2H), 3.78-3.49 (m, 2H), 3.32 (m, 2H), 2.83-2.63 (m, 2H), 2.19 (m, 2H), 2.00-1.55 (m, 4H), 1.47 (s, 9H)

Mass Spectral Analysis m/z=331.9 (M+H)$^+$

Preparation of 21.6:

To an oven-dried two-neck 250 mL flask charged with a solution of 21.5 (2.86 g, 8.6 mmol, 1.0 eq) in dry tetrahydrofuran (40 mL) at −78° C. under nitrogen was added a 1.0M solution of lithium bis(trimethylsilyl)amide in tetrahydrofuran (10.3 mL, 10.3 mmol, 1.2 eq) over a 10 min time period. The mixture was kept at −78° C. for 1 h and a solution of N-phenylbis(trifluoromethanesulfonamide) (1.4) (3.68 g, 10.3 mmol, 1.2 eq) in tetrahydrofuran (20 mL) was added to the mixture over a 10 min time period. The mixture was kept at −78° C. for another 1 h, then slowly warmed to room temperature and stirred for an additional 10 h at room temperature. Ice water (50 mL) was added to quench the reaction and the product was extracted with diethyl ether (200 mL). The organic phase was then washed with a 1N aqueous solution of hydrochloric acid (3×50 mL), a 1N aqueous solution of sodium hydroxide (3×50 mL) and brine, dried over sodium sulfate and filtered. The filtrate was concentrated under reduced pressure and the crude product was purified by column chromatography (eluent: hexane/ethyl acetate mixtures of increasing polarity).

Yield: 85%

$^1$H NMR (400 MHz, CDCl$_3$) δ 7.30-7.23 (m, 2H), 6.97 (m, 1H), 6.89 (m, 1H), 5.60 (s, 1H), 3.80-3.53 (m, 2H), 3.36-3.24 (m, 2H), 2.30-2.06 (m, 3H), 1.90-1.64 (m, 3H), 1.47 (s, 9H)

Preparation of 21.7:

To a solution of 21.6 (3.38 g, 7.3 mmol, 1.0 eq) in dimethoxyethane (50 mL) was added sequentially a 2M aqueous solution of sodium carbonate (11 mL, 22 mmol, 3.0 eq), lithium chloride (0.93 g, 22 mmol, 3.0 eq), tetrakis(triphenylphosphine)palladium(0) (0.17 g, 0.15 mmol, 0.02 eq), and 4-N,N-diethylphenylboronic acid (1.6) (1.77 g, 8.02 mmol, 1.1 eq) under a nitrogen athmosphere. The reaction mixture was heated under reflux for 10 h and then cooled to room temperature. Water (200 mL) and diethyl ether (300 mL) were added and the two phases were separated. The organic phase was washed with brine, dried over sodium sulfate, filtered, and concentrated under reduced pressure. The crude product was purified by column chromatography (eluent: hexane/ethyl acetate mixtures of increasing polarity).

Yield: 81%

$^1$H NMR (400 MHz, CDCl$_3$) δ 7.39 (m, 4H), 7.18 (m, 1H), 6.99 (d, 1H), 6.92 (d, 1H), 6.85 (m, 1H), 5.60 (s, 1H), 3.86-3.50 (m, 4H), 3.42-3.24 (m, 4H), 2.27-1.68 (m, 6H), 1 48 (s, 9H), 1.21 (m, 6H)

Mass Spectral Analysis m/z=491.0 (M+H)$^+$

Preparation of 21A:

To a cold (0° C.) solution of 21.7 (1.15 g, 2.34 mmol, 1.0 eq) in anhydrous dichloromethane (20 mL) was added dropwise a 4.0M solution of hydrogen chloride in dioxane (3.51 mL, 14.04 mmol, 6.0 eq). The mixture was stirred at room temperature for 10 h and concentrated under reduced pressure. The resulting foamy solids were soaked in diethyl ether. The resulting fine powder was collected by filtration and washed with diethyl ether.

Yield: 98%

$^1$H NMR (400 MHz, CDCl$_3$) δ 9.76 (m, 2H), 7.41 (m, 2H), 7.36 (m, 2H), 7.20 (m, 1H), 7.00 (dd, 1H), 6.97 (dd, 1H), 6.88 (m, 1H), 5.63 (s, 1H), 3.68-3.23 (m, 8H), 2.50-2.23 (m, 4H), 2.02-1.82 (m, 2H), 1.35-1.07 (m, 6H)

Mass Spectral Analysis m/z=391.2 (M+H)$^+$

Elemental analysis:

$C_{25}H_{30}N_2O_2$, 1HCl

Theory: % C, 70.32; % H, 7.32; % N, 6.56.

Found: % C, 70.14; % H, 7.23; % N, 6.55.

EXAMPLE 21B

Preparation of 21.7a & 21.7b:

The racemic compound 21.7 (15 g) was resolved by chiral HPLC to provide 21.7a (6.7 g) and 21.7b (6.0 g) as pure enantiomers.

Chiral Separation Conditions:
Column: Chiralcel OJ, 4.6×250 mm
Flow: 1.0 mL/min
Temperature: room temperature
Detection: 335 nm
Mobile Phase: Methanol 21.7a: $^1$H NMR (400 MHz, CDCl$_3$) δ 7.38 (m, 4H), 7.18 (m, 1H), 6.99 (dd, 1H), 6.92 (dd, 1H), 6.85 (m, 1H), 5.60 (s, 1H), 3.84-3.49 (m, 4H), 3.31 (m, 4H), 2.25-1.65 (m, 6H), 1.48 (s, 9H), 1.21 (m, 6H)

Mass Spectral Analysis m/z=491.3 (M+H)$^+$ $[\alpha]_D^{25}$=−1.04 (c. 1.14 mg/mL, MeOH)

Chiral purity: ee=99%; $t_R$=4.6 min 21.7b: $^1$H NMR (400 MHz, CDCl$_3$) δ 7.39 (m, 4H), 7.18 (m, 1H), 6.99 (dd, 1H), 6.92 (dd, 1H), 6.85 (m, 1H), 5.60 (s, 1H), 3.85-3.48 (m, 4H), 3.31 (m, 4H), 2.25-1.66 (m, 6H), 1.48 (s, 9H), 1.21 (m, 6H)

Mass Spectral Analysis m/z=491.3 (M+H)$^+$ $[\alpha]_D^{25}$=+1.07 (c. 1.16 mg/mL, MeOH)

Chiral purity: ee=99%; $t_R$=5.2 min

Preparation of 21B:

To a cold (0° C.) solution of 21.7a (1.3 g, 2.65 mmol, 1.0 eq) in anhydrous dichloromethane (20 mL) was added drop wise a 4.0M solution of hydrogen chloride in dioxane (3.31 mL, 13.25 mmol, 5.0 eq). The reaction mixture was stirred at room temperature for 10 h and then concentrated under reduced pressure. The foamy solids were soaked in diethyl ether and the resulting fine powder was collected by filtration and washed with diethyl ether.

Yield: 87%

$^1$H NMR (400 MHz, DMSO d$_6$) δ 8.97 (brs, 2H), 7.41 (m, 4H), 7.24 (m, 1H), 7.00-6.89 (m, 3H), 5.89 (s, 1H), 3.54-3.01 (m, 8H), 2.30-2.10 (m, 3H), 2.03-1.88 (m, 2H), 1.78 (m, 1H), 1.23-0.99 (m, 6H)

Mass Spectral Analysis m/z=391.3 (M+H)$^+$

Elemental analysis:

$C_{25}H_{30}N_2O_2$, 1HCl, 1/6H$_2$O

Theory: % C, 69.83; % H, 7.35; % N, 6.51.

Found: % C, 69.84; % H, 7.27; % N, 6.46.

$[\alpha]_D^{25}$=+1.80 (c. 10.0 mg/mL, MeOH)

EXAMPLE 21C

Preparation of 21C:

To a cold (0° C.) solution of 21.7b (1.3 g, 2.65 mmol, 1.0 eq) in anhydrous dichloromethane (20 mL) was added drop wise a 4.0 M solution of hydrogen chloride in dioxane (3.31 mL, 13.25 mmol, 5.0 eq). The reaction mixture was stirred at room temperature for 10 h and then concentrated under reduced pressure. The foamy solids were soaked in diethyl ether and the resulting fine powder was collected by filtration and washed with diethyl ether.

Yield: 89%

$^1$H NMR (400 MHz, DMSO d$_6$) δ 9.00 (brs, 2H), 7.41 (m, 4H), 7.24 (m, 1H), 7.02-6.89 (m, 3H), 5.89 (s, 1H), 3.52-3.02 (m, 8H), 2.35-2.10 (m, 3H), 2.04-1.88 (m, 2H), 1.78 (m, 1H), 1.23-0.99 (m, 6H)

Mass Spectral Analysis m/z=391.3 (M+H)$^+$

Elemental analysis:

$C_{25}H_{30}N_2O_2$, 1HCl, 1/6H$_2$O

Theory: % C, 69.83; % H, 7.35; % N, 6.51.

Found: % C, 69.84; % H, 7.32; % N, 6.47.

$[\alpha]_D^{25}$=−1.81 (c. 10.25 mg/mL, MeOH)

EXAMPLE 21D

Preparation of 21D:

To a stirred solution of 21B (0.47 g, 1.1 mmol, 1.0 eq) in methanol (20 mL) was added palladium [90 mg, 10 wt. % (dry basis) on activated carbon, 20% wt. eq]. The reaction mixture was stirred under hydrogen atmosphere using a hydrogen balloon at room temperature for 10 h. The palladium on activated carbon was filtered off on a celite pad and the filtrate was concentrated under reduced pressure. The crude product was purified by column chromatography (eluent: dichloromethane/methanol/ammonium hydroxide mixtures of increasing polarity). The desired fractions were combined and concentrated under reduced pressure. To a cold (0° C.) solution of the resulting oil in dichloromethane was added dropwise a 2.0M solution of hydrogen chloride in diethyl ether (1.1 mL, 2.2 mmol, 2.0 eq). The mixture was then stirred for 1 h at room temperature, concentrated under reduced pressure, and dried under vacuum.

Yield: 89%

$^1$H NMR (400 MHz, DMSO d$_6$) δ 8.88 (brs, 2H), 7.30 (m, 4H), 7.12 (m, 1H), 6.86 (m, 1H), 6.78 (m, 1H), 6.62 (m, 1H), 4.20 (m, 1H), 3.50-2.96 (m, 8H), 2.29-1.66 (m, 8H), 1.10 (brm, 6H)

Mass Spectral Analysis m/z=393.3 (M+H)$^+$

EXAMPLE 21E

Preparation of 21E:

To a stirred solution of 21C (0.49 g, 1.14 mmol, 1.0 eq) in methanol (20 mL) was added palladium [98 mg, 10 wt. % (dry-basis) on activated carbon, 20% wt. eq]. The reaction mixture was stirred under hydrogen using a hydrogen balloon at room temperature for 10 h. The palladium on activated carbon was filtered off on a celite pad and the filtrate was concentrated under reduced pressure. The crude product was purified by column chromatography (eluent: dichloromethane/methanol/ammonium hydroxide mixtures of increasing polarity). The desired fractions were combined and concentrated under reduced pressure. To a cold (0° C.) solution of the resulting oil in dichloromethane was added dropwise a 2.0M solution of hydrogen chloride in diethyl ether (1.14 mL, 2.28 mmol, 2.0 eq). The mixture was then stirred for 1 h at room temperature, concentrated under reduced pressure, and dried under vacuum.

Yield: 93%

$^1$H NMR (400 MHz, DMSO d$_6$) δ 8.80 (brs, 2H), 7.29 (m, 4H), 7.12 (m, 1H), 6.85 (m, 1H), 6.77 (m, 1H), 6.62 (m, 1H), 4.20 (m, 1H), 3.52-2.96 (m, 8H), 2.22-1.66 (m, 8H), 1.10 (brm, 6H)

Mass Spectral Analysis m/z=393.3 (M+H)$^+$

EXAMPLE 21F

Preparation of 21.9:

To a stirred solution of 21A (1.93 g, 4.52 mmol, 1.0 eq) in dry dichloromethane (30 mL) at 0° C. was added triethylamine (1.51 mL, 10.85 mmol, 2.4 eq) followed by drop wise addition of benzyl chloroformate (21.8) (0.76 mL, 5.42 mmol, 1.2 eq). The reaction-mixture was slowly warmed to room temperature and stirred for 10 h at room temperature. The volatiles were removed under reduced pressure and the residue was partitioned between diethyl ether (200 mL) and water (100 mL). The organic layer was washed with a 1N aqueous solution of hydrochloric acid (3×50 mL) and brine, dried over sodium sulfate and filtered. The filtrate was concentrated under reduced pressure to give the crude product, which was used for the next step without further purification.

Mass Spectral Analysis m/z=525.0 (M+H)$^+$

Preparation of 21.10:

To a solution of 21.9 (0.9 g, crude, as of 1.71 mmol, 1.0 eq) in dry dichloroethane (10 mL) was added sulfur trioxide N,N-dimethylformamide complex (4.3) (315 mg, 2.06 mmol, 1.2 eq) portion wise. The reaction mixture was heated at 75° C. for 10 h and then cooled down to 0-10° C. at which point oxalyl chloride (0.2 mL, 2.22 mmol, 1.3 eq) was added drop wise. The mixture was then stirred at 65° C. for another 3 h and then quenched with ice water (50 mL) at room temperature. Dichloromethane (100 mL) was added and the two phases were separated. The aqueous phase was extracted with dichloromethane (3×50 mL) and the combined organic layers were dried over sodium sulfate, filtered, and concentrated under reduced pressure to give the crude product, which was used for next step without further purification.

Mass Spectral Analysis m/z=622.9 (M+H)$^+$

Preparation of 21.11:

To a solution of 21.10 (0.9 g, crude, as of 1.4 mmol, 1.0 eq) in dry dichloromethane (50 mL) at 0° C. was slowly added triethylamine (0.4 mL, 2.8 mmol, 2.0 eq) and a 2.0M solution of ethylamine (3.4c) in tetrahydrofuran (7 mL, 14 mmol, 10.0 eq) drop wise. The mixture was slowly warmed to room temperature and stirred for 10 h at room temperature. Water (50 mL) and chloroform (50 mL) were added and the two phases were separated. The aqueous phase was extracted with chloroform (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 34% over three steps $^1$H NMR (400 MHz, CDCl$_3$) δ 7.68 (m, 1H), 7.50 (m, 1H), 7.43 (m, 2H), 7.40-7.30 (m, 7H), 6.98 (d, 1H), 5.66 & 5.44 (2s, 1H), 5.18 & 5.16 (2s, 2H), 4.21 (t, 1H), 3.89-3.23 (m, 8H), 2.97 (m, 2H), 2.32-1.66 (m, 6H), 1.35-1.05 (m, 9H)

Mass Spectral Analysis m/z=631.95 (M+H)$^+$

Preparation of 21F:

To a solution of 21.11 (0.35 g, 0.55 mmol, 1.0 eq) in dichloromethane (10 mL) was added iodotrimethylsilane (0.15 mL, 1.1 mmol, 2.0 eq) drop wise. The mixture was stirred at room temperature for 2 h. The mixture was diluted with chloroform 9100 mL) and methanol (5 mL). The solution was washed with a 20% aqueous solution of sodium thiosulfate (2×30 mL), with a 1M aqueous solution of sodium carbonate (2×30 mL), dried over sodium sulfate and filtered. The filtrate was concentrated under reduced pressure and the crude product was purified by preparative liquid chromatography (mobile phase: acetonitrile/water/trifluoroacetic acid). The desired fractions were combined and concentrated under reduced pressure. The product was dissolved in dichloromethane (50 mL); the organic phase was washed with a 1N aqueous solution of sodium hydroxide (2×20 mL), dried over sodium sulfate, filtered, and concentrated under reduced pressure. To a cold (0° C.) solution of the resulting oil in anhydrous dichloromethane was added dropwise a 1.0M solution of hydrogen chloride in diethyl ether (1.1 mL, 1.1 mmol, 2.0 eq). The mixture was then stirred for 1 h at room temperature, concentrated under reduced pressure, and dried under vacuum.

Yield: 56%

$^1$H NMR (400 MHz, DMSO d$_6$) δ 9.03 (brs, 2H), 7.65 (dd, 1H), 7.54-7.36 (m, 6H), 7.16 (d, 1H), 6.04 (s, 1H), 3.54-3.02 (m, 8H), 2.71 (m, 2H), 2.37-2.13 (m, 3H), 2.06-1.72 (m, 3H), 1.22-1.03 (m, 6H), 0.94 (t, 3H)

Mass Spectral Analysis m/z=498.5 (M+H)$^+$

Elemental analysis:

$C_{27}H_{35}N_3O_4S$, 1HCl, 0.33H$_2$O

Theory: % C, 60.04; % H, 6.84; % N, 7.78.

Found: % C, 59.93; % H, 6.81; % N, 7.80.

EXAMPLE 22A

Preparation of 22.1:

To a suspension of 21B (4.06 g, 9.5 mmol, 1.0 eq) in tetrahydrofuran (50 mL) at 0° C. was added triethylamine (3.3 mL, 23.75 mmol, 2.5 eq) followed by drop wise addition of trifluoroacetic anhydride (4.1) (1.6 ml, 11.4 mmol, 1.2 eq). The reaction mixture was slowly warmed to room temperature and stirred for 10 h at room temperature. Ethyl acetate (200 mL) was added to the reaction mixture and the organic layer was washed with a 1M aqueous solution of hydrochloric acid (3×50 mL) and brine, dried over sodium sulfate and filtered. The filtrate was concentrated under reduced pressure to give the crude product, which was used for the next step without further purification.

Mass Spectral Analysis m/z=487.2 (M+H)$^+$

Preparation of 22.2:

To a solution of 22.1 (5.0 g, as of 9.5 mmol, 1.0 eq) in dry dichloroethane (100 mL) was added sulfur trioxide N,N- dimethylformamide complex (4.3) (2.18 g, 14.25 mmol, 1.5 eq) portion wise. The mixture was heated under reflux for 10 h and then cooled to 0-10° C. at which point oxalyl chloride (1.33 mL, 15.2 mmol, 1.6 eq) was added drop wise. The mixture was then stirred at 70° C. for another 3 h and quenched with ice water (1:1) (150 mL) at room temperature. Dichloromethane (100 mL) was added to the reaction mixture and the two phases were separated. The aqueous phase was further extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 84% over two steps $^1$H NMR (400 MHz, CDCl$_3$) δ 7.88 (m, 1H), 7.70 (m, 1H), 7.48 (m, 2H), 7.35 (m, 2H), 7.08 (d, 1H), 5.716 & 5.706 (2s, 1H), 4.03-3.26 (m, 8H), 2.49-2.21 (m, 3H), 2.03-1.72 (m, 3H), 1.33-1.11 (m, 6H)

Mass Spectral Analysis m/z=585.2 (M+H)$^+$

Preparation of 22.3a:

To a solution of 22.2 (0.6 g, 1.02 mmol, 1.0 eq) in dry dichloromethane (30 mL) at 0° C. was added triethylamine (0.71 mL, 5.10 mmol, 5.0 eq) and methylamine (3.4b) hydrochloride salt (0.21 g, 3.06 mmol, 3.0 eq) in one portion. The reaction mixture was slowly warmed to room temperature and stirred for 10 h at room temperature. Water (50 mL) and dichloromethane (50 mL) were added to the mixture and the two phases were separated. The aqueous phase was further extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 89%

$^1$H NMR (400 MHz, CDCl$_3$) δ 7.71 (dd, 1H), 7.51 (t, 1H), 7.45 (m, 2H), 7.34 (m, 2H), 7.02 (d, 1H), 5.665 & 5.657 (2s, 1H), 4.29 (m, 1H), 4.02-3.25 (m, 8H), 2.63 (d, 3H), 2.47-2.19 (m, 3H), 1.99-1.68 (m, 3H), 1.22 (m, 6H)

Mass Spectral Analysis m/z=580.3 (M+H)$^+$

Preparation of 22A:

To a solution of 22.3a (0.53 g, 0.91 mmol, 1.0 eq) in a mixture of methanol (20 mL) and water (5 mL) at 0° C. was added potassium carbonate (0.75 g, 5.46 mmol, 6.0 eq) portion wise. The reaction mixture was warmed to room temperature and stirred for 10 h at room temperature. Brine (50 mL) and chloroform (50 mL) were added to the reaction mixture and the two phases were separated. The aqueous phase was extracted with chloroform (3×50 mL) and the combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil in anhydrous dichloromethane was added drop wise a 2.0M solution of hydrogen chloride in diethyl ether (0.91 mL, 1.82 mmol, 2.0 eq). The mixture was stirred for 1 h at room temperature, concentrated under reduced pressure, and dried under vacuum.

Yield: 82%

$^1$H NMR (400 MHz, DMSO d$_6$) δ 9.04 (brs, 2H), 7.64 (dd, 1H), 7.49-7.34 (m, 6H), 7.17 (d, 1H), 6.04 (s, 1H), 3.45 (m, 2H), 3.31-3.15 (m, 5H), 3.09 (m, 1H), 2.35 (d, 3H), 2.28 (m, 2H), 2.18 (m, 1H), 1.99 (m, 2H), 1.80 (m, 1H), 1.12 (m, 6H)

Mass Spectral Analysis m/z=484.2 (M+H)$^+$

Elemental analysis:

$C_{26}H_{33}N_3O_4S$, 1HCl, 1.2H$_2$O

Theory: % C, 57.65; % H, 6.77; % N, 7.76.

Found: % C, 57.69; % H, 6.62; % N, 7.71.

$[α]_D^{25}$=−4.18 (c. 9.4 mg/mL, MeOH)

EXAMPLE 22B 22B was obtained according to a procedure similar to the one described for 22A, with the following exception:

Step 22.3: 3.4b was replaced by 3.4c.

$^1$H NMR (400 MHz, DMSO d$_6$) δ 8.98 (brs, 1H), 7.65 (dd, 1H), 7.44 (m, 5H), 7.37 (d, 1H), 7.16 (d, 1H), 6.04 (s, 1H), 3.45 (m, 2H), 3.32-3.05 (m, 6H), 2.71 (m, 2H), 2.35-1.75 (m, 6H), 1.12 (m, 6H), 0.94 (t, 3H)

Mass Spectral Analysis m/z=498.3 (M+H)$^+$

Elemental analysis:

$C_{27}H_{35}N_3O_4S$, 1HCl, 1.1H$_2$O

Theory: % C, 58.54; % H, 6.95; % N, 7.59.

Found: % C, 58.55; % H, 6.82; % N, 7.55.

$[α]_D^{25}$=−5.10 (c=9.25 mg/ml, MeOH)

EXAMPLE 22C 22C was obtained according to a procedure similar to the one described for 22A, with the following exception:

Step 22.3: 3.4b was replaced by 3.4d.

$^1$H NMR (400 MHz, DMSO d$_6$) δ 9.05 (brs, 2H), 7.65 (dd, 1H), 7.56 (t, 1H), 7.43 (m, 4H), 7.37 (d, 1H), 7.16 (d, 1H), 6.04 (s, 1H), 3.53-3.04 (m, 8H), 2.63 (m, 2H), 2.35-1.75 (m, 6H), 1.33 (m, 2H), 1.12 (m, 6H), 0.77 (t, 3H)

Mass Spectral Analysis m/z=512.4 (M+H)$^+$

Elemental analysis:

$C_{28}H_{37}N_3O_4S$, 1HCl, 0.5H$_2$O

Theory: % C, 60.36; % H, 7.06; % N, 7.54.

Found: % C, 60.28; % H, 7.10; % N, 7.53.

$[α]_D^{25}$=−5.95 (c=9.55 mg/ml, MeOH)

EXAMPLE 22D 22D was obtained according to a procedure similar to the one described for 22A, with the following exception:

Step 22.3: 3.4b was replaced by 3.4g.

$^1$H NMR (400 MHz, DMSO d$_6$) δ 9.0 (brs, 2H), 7.66 (m, 2H), 7.42 (m, 5H), 7.16 (d, 1H), 6.04 (s, 1H), 3.45 (m, 2H), 3.22 (m, 6H), 2.59 (m, 2H), 2.35-1.75 (m, 6H), 1.12 (m, 6H), 0.75 (m, 1H), 0.32 (m, 2H), 0.03 (m, 2H)

Mass Spectral Analysis m/z=524.3 (M+H)$^+$

Elemental analysis:

$C_{29}H_{37}N_3O_4S$, 1HCl, 0.66H$_2$O

Theory: % C, 60.88; % H, 6.93; % N, 7.34.

Found: % C, 60.92; % H, 6.96; % N, 7.37.

$[α]_D^{25}$=−5.89 (c=9.35 mg/ml, MeOH)

EXAMPLE 22E

Preparation of 22.4:

To a solution of 22.2 (0.86 g, 1.47 mmol, 1.0 eq) in tetrahydrofuran (5 mL) at 0° C. was added a 1.0M solution of hydrazine in tetrahydrofuran (5.1) (15 mL, 15 mmol, 15.0 eq) in one portion. The reaction mixture was stirred at 0° C. for 30 min. Water (50 mL) and dichloromethane (100 mL) were added and the two phases were separated. The aqueous phase was extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 72%

Mass Spectral Analysis m/z=581.2 (M+H)$^+$

Preparation of 22.5:

To a suspension of 22.4 (0.62 g, 1.06 mmol, 1.0 eq) in ethanol (10 mL) was added sodium acetate (0.58 g, 7.1 mmol, 6.7 eq) and iodomethane (2.8c) (0.37 mL, 5.8 mmol, 5.5 eq). The reaction mixture was heated under reflux for 10 h. Water (100 mL) and dichloromethane (100 mL) were added and the two phases were separated. The aqueous phase was extracted with dichloromethane (3×50 mL) and the combined organic layers were dried over sodium sulfate, filtered, and concentrated under reduced pressure. The crude product was purified by column chromatography (eluent: hexane/ethyl acetate mixtures of increasing polarity).

Yield: 78%

$^1$H NMR (400 MHz, CDCl$_3$) δ 7.78 (m, 1H), 7.61 (t, 1H), 7.45 (m, 2H), 7.35 (m, 2H), 7.06 (d, 1H), 5.685 & 5.675 (2s, 1H), 4.01-3.42 (m, 6H), 3.33 (brs, 2H), 3.00 (s, 3H), 2.46-2.22 (m, 3H), 2.00-1.69 (m, 3H), 1.22 (m, 6H)

Mass Spectral Analysis m/z=565.3 (M+H)$^+$

Preparation of 22E:

To a solution of 22.5 (0.45 g, 0.8 mmol, 1.0 eq) in a mixture of methanol (20 mL) and water (5 mL) at 0° C. was added potassium carbonate (0.86 g, 4.8 mmol, 6.0 eq) portion wise. The reaction mixture was warmed to room temperature and stirred for 10 h at room temperature. Brine (50 mL) and chloroform (50 mL) were added and the two phases were separated. The aqueous phase was extracted with chloroform (3×50 mL) and the combined organic layers were dried over sodium sulfate, filtered, and concentrated under reduced pressure. The crude product was purified by column chromatography (eluent: dichloromethane/methanol mixtures of increasing polarity). The desired fractions were combined and concentrated under reduced pressure. To a cold (0° C.) solution of the resulting oil in anhydrous dichloromethane was added dropwise a 2.0M solution of hydrogen chloride in diethyl ether (0.8 mL, 1.6 mmol, 2.0 eq). The mixture was then stirred for 1 h at room temperature, concentrated under reduced pressure, and dried under vacuum.

Yield: 86%

$^1$H NMR (400 MHz, DMSO d$_6$) δ 9.01 (brs, 2H), 7.80 (dd, 1H), 7.46 (m, 5H), 7.22 (d, 1H), 6.06 (s, 1H), 3.45 (m, 2H), 3.32-3.03 (m, 9H), 2.29 (m, 2H), 2.18 (m, 1H), 1.99 (m, 2H), 1.81 (m, 1H), 1.12 (m, 6H)

Mass Spectral Analysis m/z=469.2 (M+H)$^+$

Elemental analysis:

C$_{26}$H$_{32}$N$_2$O$_4$S, 1HCl

Theory: % C, 61.83; % H, 6.59; % N, 5.55.

Found: % C, 61.82; % H, 6.60; % N, 5.51.

$[\alpha]_D^{25}$=−4.50 (c. 10.3 mg/mL, MeOH)

EXAMPLE 23A 23A was obtained according to a procedure similar to the one described for 1A, with the following exceptions:

Step 1.1: Method 1B was used and 1.2 was replaced by 23.1a (see also step 23.1).

Step 1.3: Method 1C was used (see also step 23.3).

Step 1.4: Method 1E was used (see also step 23.4).

$^1$H NMR (400 MHz, CDCl$_3$) δ 10.20 (m, 2H), 7.40 (m, 4H), 7.22 (m, 1H), 7.04 (m, 2H), 6.91 (m, 1H), 5.66 (s, 1H), 3.85-3.50 (m, 5H), 3.31 (m, 3H), 2.60 (m, 2H), 2.13 (m, 1H), 1.27 (m, 3H), 1.16 (m, 3H)

Mass Spectral Analysis m/z=363.2 (M+H)$^+$

EXAMPLE 23B 23B was obtained according to a procedure similar to the one described for 1A, with the following exceptions:

Step 1.1: Method 1B was used and 1.2 was replaced by 23.1b (see also step 23.1).

Step 1.3: Method 1C was used (see also step 23.3).

Step 1.4: Method 1E was used (see also step 23.4).

$^1$H NMR (400 MHz, CDCl$_3$) δ 10.33 (m, 1H), 9.21 (m, 1H), 7.39 (m, 5H), 7.21 (m, 1H), 6.98 (m, 1H), 6.87 (m, 1H), 5.50 (s, 1H), 3.55 (m, 4H), 3.34 (m, 2H), 2.93 (m, 2H), 2.44 (m, 1H), 2.33 (m, 1H), 1.83 (m, 1H), 1.70 (m, 1H), 1.26 (m, 3H), 1.16 (m, 3H)

Mass Spectral Analysis m/z=377.0 (M+H)$^+$

EXAMPLE 23C 23C was obtained according to a procedure similar to the one described for 1A, with the following exceptions:

Step 1.1: Method 1B was used and 1.2 was replaced by 23.5 (see also step 23.5).

Step 1.3: Method 1C was used (see also step 23.7).

Step 1.4: Method 1E was used (see also step 23.8).

$^1$H NMR (400 MHz, DMSO d$_6$) δ 9.28 (brm, 2H), 7.43 (d, 2H), 7.35 (d, 2H), 7.27 (m, 1H), 7.01 (d, 1H), 6.97 (m, 2H), 5.57 (s, 1H), 4.01 (brs, 2H), 3.44 (brs, 2H), 3.22 (brs, 2H), 2.36 (m, 2H), 2.27 (m, 4H), 2.04 (m, 2H), 1.12 (brd, 6H)

Mass Spectral Analysis m/z=403.2 (M+H)$^+$

EXAMPLE 24A

Preparation of 24.2:

To a solution of 24.1 (9.37 g, 60 mmol, 1.0 eq) in dry methanol (100 mL) was added pyrrolidine (10 mL, 120 mmol, 2.0 eq) followed by 2'-hydroxyacetophenone (1.1a) (7.22 mL, 60 mmol, 1.0 eq). The reaction mixture was heated under reflux for 10 h. The volatiles were removed under reduced pressure and the residue was dissolved in ethyl acetate (200 mL). The mixture was washed with a 1M aqueous solution of hydrochloric acid (3×50 mL), with a 1M aqueous solution of sodium hydroxide (3×50 mL) and brine. The organic extracts were dried over sodium sulfate, filtered, and concentrated under reduced pressure. The crude product was purified by column chromatography (eluent: hexane/ethyl acetate mixtures of increasing polarity).

Yield: 100%

$^1$H NMR (400 MHz, CDCl$_3$) δ 7.86 (dd, 1H), 7.48 (m, 1H), 6.98 (m, 2H), 3.96 (m, 4H), 2.71 (s, 2H), 2.12 (m, 2H), 1.99 (m, 2H), 1.74 (m, 2H), 1.61 (m, 2H)

Preparation of 24.3:

To an oven-dried two-neck 500 mL flask charged with a solution of 24.2 (16.46 g, 60 mmol, 1.0 eq) in dry tetrahydrofuran (100 mL) at −78° C. under nitrogen was added a 1.0M solution of lithium bis(trimethylsilyl)amide in tetrahydrofuran (72 mL, 72 mmol, 1.2 eq) over a 30 min time period. The mixture was kept at −78° C. for 1 h and a solution of N-phenylbis(trifluoromethanesulfonamide) (1.4) (25.72 g, 72 mmol, 1.2 eq) in tetrahydrofuran (100 mL) was added to the mixture over a 30 min time period. The reaction mixture was kept at −78° C. for 1 h, and was slowly warmed to room temperature and stirred for 10 h at room temperature. Ice water (100 mL) was added to quench the reaction and the product was extracted with diethyl ether (200 mL). The organic phase was then washed with a 1M aqueous solution of hydrochloric acid (3×100 mL), with a 1M aqueous solution of sodium hydroxide (3×100 mL) and brine, dried over sodium sulfate and filtered. The filtrate was concentrated under reduced pressure and the crude product was purified by column chromatography (eluent: hexane/ethyl acetate mixtures of increasing polarity).

Yield: 90%

$^1$H NMR (400 MHz, CDCl$_3$) δ 7.34-7.19 (m, 2H), 6.97 (m, 1H), 6.89 (m, 1H), 5.60 (s, 1H), 4.03-3.91 (m, 4H), 2.20 (m, 2H), 2.09-1.97 (m, 2H), 1.81 (m, 2H), 1.62 (m, 2H)

Preparation of 24.4:

To a solution of 24.3 (22 g, 54.14 mmol, 1.0 eq) in dimethoxyethane (200 mL) under nitrogen was added sequentially a 2M aqueous solution of sodium carbonate (81.2 mL, 162.42 mmol, 3.0 eq), lithium chloride (6.88 g, 162.42 mmol, 3.0 eq), tetrakis(triphenylphosphine)palladium(0) (1.25 g, 1.08 mmol, 0.02 eq), and 4-N,N-diethylphenylboronic acid (1.6) (13.16 g, 59.55 mmol, 1.1 eq). The reaction mixture was heated under reflux for 10 h. Water (200 mL) and diethyl ether (300 mL) were added and the two phases were separated. The aqueous phase was further extracted with diethyl ether (2×100 mL) and the combined organic extracts were washed with brine, dried over sodium sulfate, filtered, and concentrated under reduced pressure. The crude product was purified by column chromatography (eluent: hexane/ethyl acetate mixtures of increasing polarity).

Yield: 95%

$^1$H NMR (400 MHz, CDCl$_3$) δ 7.38 (m, 4H), 7.18 (m, 1H), 6.99 (m, 1H), 6.93 (m, 1H), 6.85 (m, 1H), 5.62 (s, 1H), 3.99 (m, 4H), 3.57 (brs, 2H), 3.32 (brs, 2H), 2.24-2.02 (m, 4H), 1.80 (m, 2H), 1.65 (m, 2H), 1.21 (m, 6H)

Preparation of 24A:

To a cold (0° C.) solution of 24.4 (22.32 g, 51.48 mmol, 1.0 eq) in tetrahydrofuran (200 mL) was added a 1.0M aqueous solution of hydrochloric acid (155 mL, 155 mmol, 3.0 eq). The mixture was stirred at room temperature for 10 h and then concentrated under reduced pressure. The resulting solid was collected by filtration, washed with hexane/ethyl acetate mixture (20:1), and dried under vacuum.

Yield: 85%

$^1$H NMR (400 MHz, CDCl$_3$) δ 7.40 (m, 4H), 7.23 (m, 1H), 7.04 (d, 1H0, 7.00 (d, 1H), 6.91 (m, 1H), 5.62 (s, 1H), 3.57 (brs, 2H), 3.32 (brs, 2H), 2.87 (m, 2H), 2.50 (m, 2H), 2.33 (m, 2H), 1.94 (m, 2H), 1.21 (m, 6H)

Mass Spectral Analysis m/z=390.2 (M+H)$^+$

EXAMPLE 24B/EXAMPLE 24C

Preparation of 24B/24C:

To a solution of 24A (0.51 g, 1.3 mmol, 1.0 eq) in dry tetrafydrofuran (30 mL) at 0° C. was added sodium borohydride (50 mg, 1.3 mmol, 1.0 eq) in one portion under a nitrogen athmosphere. The reaction mixture was stirred at room temperature for 1 h. Water (50 mL) and diethyl ether (100 mL) were added and the two phases were separated. The aqueous phase was further extracted with diethyl ether (2×50 mL) and the combined organic layers were washed with brine, dried over sodium sulfate, filtered, and concentrated to give the mixture of two isomers. The crude product was purified by preparative liquid chromatography affording 24B and 24C.

(24B) $^1$H NMR (400 MHz, CDCl$_3$) δ 7.39 (m, 4H), 7.18 (m, 1H), 6.97 (m, 2H), 6.85 (m, 1H), 5.55 (s, 1H), 3.73 (m, 1H), 3.58 (brs, 2H), 3.33 (brs, 2H), 2.51 (brs, 1H), 2.21 (m, 2H), 1.52 (m, 2H), 1.22 (brd, 6H)

Mass Spectral Analysis m/z=392.2 (M+H)$^+$ (24C) $^1$H NMR (400 MHz, CDCl$_3$) δ 7.39 (m, 4H), 7.18 (m, 1H), 7.01-6.81 (m, 3H), 5.73,& 5.55 (2s, 1H), 4.07 & 3.74 (2m, 1H), 3.59 (brs, 2H), 3.34 (brs, 2H), 3.16 (brs, 4H), 2.31-1.89 (m, 2H), 1.68-1.46 (m, 2H), 1.22 (m, 6H)

Mass Spectral Analysis m/z=392.2 (M+H)$^+$

EXAMPLE 24D/EXAMPLE 24E

Preparation of 24D/24E:

To a stirred solution of 24A (0.63 mL, 1.62 mmol, 2.0 eq) in dry dichloromethane (20 mL) was added sequentially n-propylamine (3.4d) (0.16 g, 1.94 mmol, 1.2 eq), acetic acid (0.11 mL, 1.94 mmol, 1.2 eq), and sodium cyanoborohydride (0.153 g, 2.43 mmol, 1.5 eq). The reaction mixture was stirred at room temperature for 10 h. Water (40 mL) was added and the aqueous layer was basified to pH=10 with a 1M aqueous solution of sodium hydroxide. The two phases were separated and the aqueous phase was saturated with sodium chloride and extracted with dichloromethane (3×50 mL). The combined organic extracts were dried over sodium sulfate, filtered, and concentrated under reduced pressure to give the crude mixture, which was purified by column chromatography (eluent: dichloromethane/methanol mixtures of increasing polarity).

(24D) $^1$H NMR (400 MHz, CDCl$_3$) δ 7.38 (m, 4H), 7.17 (m, 1H), 6.99 (dd, 1H), 6.90 (dd, 1H), 6.84 (m, 1H), 5.91 (s, 1H), 3.57 (brs, 2H), 3.31 (brs, 2H), 2.75 (brs, 1H), 2.65 (t, 2H), 2.11 (m, 2H), 1.98 (m, 2H), 1.82-1.46 (m, 7H), 1.21 (m, 6H), 0.95 (t, 3H)

Mass Spectral Analysis m/z=433.2 (M+H)$^+$ (24E) $^1$H NMR (400 MHz, CDCl$_3$) δ 7.38 (m, 4H), 7.16 (m, 1H), 6.98 (dd, 1H), 6.93 (dd, 1H), 6.83 (m, 1H), 5.54 (s, 1H), 3.57 (brs, 2H), 3.31 (brs, 2H), 2.64 (t, 2H), 2.53 (m, 1H), 2.20 (m, 2H), 1.83-1.42 (m, 7H), 1.21 (m, 6H), 0.94 (t, 3H)

Mass Spectral Analysis m/z=433.2 (M+H)$^+$

EXAMPLE 24F 24F was obtained according to a procedure similar to the one described for 24D, with the following exception:

Step 24.6: 3.4d was replaced by 3.4j.

$^1$H NMR (400 MHz, CDCl$_3$) δ 7.38 (m, 4H), 7.17 (m, 1H), 6.96 (m, 2H), 6.84 (m, 1H), 5.54 (s, 1H), 3.57 (m, 2H), 3.32 (m, 2H), 2.35 (s, 6H), 2.25 (m, 3H), 1.79 (m, 4H), 1.46 (m, 2H), 1.26 (m, 3H), 1.16 (m, 3H)

Mass Spectral Analysis m/z=419.2 (M+H)$^+$

EXAMPLE 24G 24G was obtained according to a procedure similar to the one described for 24E, with the following exception:

Step 24.6: 3.4d was replaced by 3.4j.

$^1$H NMR (400 MHz, CDCl$_3$) δ 7.40 (m, 4H), 7.18 (m, 1H), 7.00 (m, 1H), 6.91 (m, 1H), 6.85 (m, 1H), 5.89 (s, 1H), 3.57 (m, 2H), 3.32 (m, 2H), 2.51 (m, 7H), 2.20 (m, 2H), 2.06 (m, 2H), 1.76 (m, 4H), 1.26 (m, 3H), 1.16 (m, 3H)

Mass Spectral Analysis m/z=419.2 (M+H)$^+$

EXAMPLE 25A 25A was obtained according to a procedure similar to the one described for compound 1.8a with the following exception:

Step 1.1: 1.2 was replaced by 25.1 (see also step 25.1).

$^1$H NMR (400 MHz, DMSO d$_6$) δ 7.42 (d, 2H), 7.38 (d, 2H), 7.19 (m, 1H), 6.97 (m, 2H), 6.86 (m, 1H), 5.62 (s, 1H), 3.96 (m, 2H), 3.79 (m, 2H), 3.57 (brs, 2H), 3.32 (brs, 2H), 2.03 (d, 2H), 1.84 (m, 2H), 1.21 (brd, 6H)

Mass Spectral Analysis m/z=378.2 (M+H)$^+$

EXAMPLE 26A

Preparation of 26.2:

To a solution of 1.5a (2.08 g, 4.63 mmol, 1 eq) in dry tetrahydrofuran (40 mL) was added tetrakis(triphenylphosphine)palladium(0) (0.535 g, 0.463 mmol, 0.1 eq), followed by 4-cyanobenzylzinc bromide (26.1) (0.5M solution in tetrahydrofuran, 23.16 mL, 11.58 mmol, 2.5 eq) drop wise under a nitrogen athmosphere. The reaction mixture was stirred at room temperature for 10 h. A saturated aqueous solution of ammonium chloride (40 mL) was added to quench the reaction and diethyl ether (50 mL) was added to partition the two phases. The aqueous phase was extracted with diethyl ether (3×50 mL) and the combined organic layers were washed with brine, dried over sodium sulfate, filtered, and concentrated under reduced pressure. The crude product was purified by column chromatography (eluent: hexane/ethyl acetate mixture of increasing polarity).

Yield: 62%

$^1$H NMR (400 MHz, CDCl$_3$) δ 7.59 (d, 2H), 7.34 (d, 2H), 7.14 (m, 1H), 7.00 (dd, 1H), 6.88 (dd, 1H), 6.82 (m, 1H), 5.28 (s, 1H), 3.95-3.75 (m, 4H), 3.28 (m, 2H), 1.99 (m, 2H), 1.59 (m, 2H), 1.46 (s, 9H)

Mass Spectral Analysis m/z=417 (M+H)$^+$

Preparation of 26.3a & 26.3b:

A mixture of 26.2 (1.2 g, 2.88 mmol) in concentrated hydrochloric acid (30 mL) was heated under reflux for 10 h and then concentrated under reduced pressure to give the crude mixture of 26.3a and 26.3b. A 80 mg quantity of the mixture was purified by preparative liquid chromatography. The remaining mixture (26.3a/26.3b) was used for the next step without further purification.

26.3a: $^1$H NMR (400 MHz, DMSO-d$_6$) δ 12.87 (s,b, 1H), 8.58 (m, 2H), 7.86 (m, 2H), 7.41 (m, 2H), 7.21-7.12 (m, 2H), 6.92 (dd, 1H), 6.86 (m, 1H), 5.70 (s, 1H), 3.85 (s, 2H), 3.19 (m, 4H), 2.06 (m, 2H), 1.86 (m, 2H)

Mass Spectral Analysis m/z=336.2 (M+H)$^+$ 26.3b: $^1$H NMR (400 MHz, DMSO-d$_6$) δ 13.00 (s,b, 1H), 8.68 (m, 1H), 8.29 (m, 1H), 7.97 (m, 2H), 7.84 (dd, 1H), 7.50 (m, 2H), 7.41 (s, 1H), 7.27 (m, 1H), 7.03-6.94 (m, 2H), 3.19-3.00 (m, 4H), 2.82 (s, 2H), 1.91 (m, 2H), 1.63 (m, 2H)

Mass Spectral Analysis m/z=336.2 (M+H)$^+$

Preparation of 26.4a & 26.4b:

To a solution of the mixture of 26.3a and 26.3b (1 g, 2.69 mmol) in methanol (50 mL) was slowly added a 4.0M solution of hydrogen chloride in dioxane (20 mL). The reaction mixture was stirred at room temperature for 10 h and concentrated under reduced pressure. The residue was dissolved in ethyl acetate (100 mL), washed with a 1M aqueous solution of sodium carbonate (4×50 mL), brine, dried over sodium sulfate, filtered, and concentrated under reduced pressure to give the crude mixture of 26.4a and 26.4b. A small amount (150 mg) of the crude mixture was purified by column chromatography (eluent: hexane/ethyl acetate mixture of increasing polarity) and repurified preparative liquid chromatography. The remaining mixture (26.4a/26.4b) was used for the next step without further purification.

Yield: 90%

26.4a: $^1$H NMR (400 MHz, CDCl$_3$) δ 9.05 (s,b, 1H), 8.72 (s,b, 1H), 7.98 (d, 2H), 7.29 (d, 2H), 7.17 (m, 1H), 7.11 (m, 1H), 6.93-6.85 (m, 2H), 5.29 (s, 1H), 3.91 (s, 3H), 3.80 (s, 2H), 3.37 (m, 4H), 2.24 (m, 2H), 1.95 (m, 2H)

Mass Spectral Analysis m/z=350.2 (M+H)$^+$ 26.4b: $^1$H NMR (400 MHz, CDCl$_3$) δ 9.42 (s,b, 1H), 8.95 (s,b, 1H), 8.05 (d, 2H), 7.66 (d, 1H), 7.40-7.22 (m, 4H), 7.00 (m, 1H), 6.92 (d, 1H), 3.94 (s, 3H), 3.25 (m, 4H), 2.78 (s, 2H), 2.04 (m, 2H), 1.75 (m, 2H)

Mass Spectral Analysis m/z=350.2 (M+H)$^+$

Preparation of 26.5a & 26.5b:

To a solution of the mixture of 26.4a and 26.4b (0.5 g, 1.5 mmol, 1 eq) in dry dichloromethane (30 mL) at 0° C. was slowly added triethylamine (0.42 mL, 3 mmol, 2 eq) and a solution of di-tert-butyl-dicarbonate 4.7 (0.38 g, 1.74 mmol, 1.2 eq) in dichloromethane (10 mL) drop wise. The reaction mixture was slowly warmed up to room temperature and stirred at room temperature for 10 h. Dichloromethane (50 mL) was added and the mixture was washed with a 1N aqueous solution of hydrochloric acid (3×50 mL), brine, dried over sodium sulfate, filtered, and concentrated under reduced pressure to give the crude mixture of 26.5a and 26.5b, which was used for the next step without purification.

Preparation of 26.6a & 26.6b:

To a solution of the mixture of 26.5a and 26.5b (0.57 g, 1.26 mmol, 1 eq) in a mixture methanol (15 mL), tetrahydrofuran (15 mL) and water (15 mL) was added lithium hydroxide monohydrate (0.21 g, 5 mmol, 4 eq) in one portion. The reaction mixture was stirred at room temperature for 10 h. The volatiles were removed under reduced pressure and the remaining aqueous solution was acidified to pH=3 with a 1N aqueous solution of hydrochloric acid while stirring. The mixture was stirred for 1 h at room temperature and left at room temperature for 10 h. The resulting solid was collected by filtration, washed with water, and dried under vacuum to give the mixture of 26.6a and 26.6b, which was used for the next step without further purification.

Preparation of 26.7a & 26.7b:

To a stirred solution of the mixture of 26.6a and 26.6b (0.49 g, 1.12 mmol, 1 eq) in acetonitrile (20 mL) was slowly added diisopropylethylamine (0.46 mL, 2.69 mmol, 2.4 eq), diethylamine 1.12 (0.24 g, 3.36 mmol, 3 eq) at room temperature. The mixture was stirred for 10 min at room temperature. The mixture was cooled to 0° C. and O-benzotriazol-1-yl-N,N,N',N'-tetramethyluronium tetrafluoroborate (TBTU) (0.43 g, 1.34 mmol, 1.2 eq) was added portion wise. The reaction mixture was slowly warmed up to room temperature and stirred at room temperature for an additional 10 h. The volatiles were removed under reduced pressure and the residue was partitioned between ethyl acetate (100 mL) and a 1M aqueous solution of sodium bicarbonate (100 mL). The organic phase was washed with a 1M aqueous solution of sodium bicarbonate (2×50 mL), a 1M aqueous solution of hydrochloric acid (3×50 mL), brine, dried over sodium sulfate, filtered, and concentrated under reduced pressure to give the crude mixture of 26.7a and 26.7b. The crude mixture was purified by column chromatography (eluent: hexane/ethyl acetate mixture of increasing polarity). A small amount (85 mg) of the purified mixture was separated by preparative liquid chromatography. The remaining mixture (26.7a/26.7b) was used for the next step without further purification.

Yield: 81% over three steps 26.7a: $^1$H NMR (400 MHz, CDCl$_3$) δ 7.33-7.24 (m, 4H), 7.15-7.07 (m, 2H), 6.89-6.80 (m, 2H), 5.25 (s, 1H), 3.84 (m, 2H), 3.74 (s, 2H), 3.55 (m, 2H), 3.28 (m, 4H), 1.98 (m, 2H), 1.57 (m, 2H), 1.46 (s, 9H), 1.18 (m, 6H)

Mass Spectral Analysis m/z=491.1 (M+H)$^+$ 26.7b: $^1$H NMR (400 MHz, CDCl$_3$) δ 7.63 (dd, 1H), 7.39 (m, 2H), 7.31 (m, 2H), 7.22 (m, 1H), 7.17 (s, 1H), 6.95 (m, 1H), 6.90 (dd, 1H), 3.81 (m, 2H), 3.58 (m, 2H), 3.34 (m, 2H), 3.17 (m, 2H), 2.71 (s, 2H), 1.82 (m, 2H), 1.43 (s, 9H), 1.38 (m, 2H), 1.22 (m, 6H)

Mass Spectral Analysis m/z=491.1 (M+H)$^+$

Preparation of 26A

To a cold (0° C.) stirred solution of the mixture of 26.7a and 26.7b (0.36 g, 0.73 mmol, 1 eq) in dry dichloromethane (20 mL) was added dropwise a 4.0 M solution of hydrogen chloride in dioxane (1.8 mL, 7.2 mmol, 10 eq). The mixture was stirred at room temperature for 10 h and concentrated under reduced pressure to give the crude mixture of 26A and 26.8. The crude mixture was purified by preparative liquid chromatography.

Yield: 85%

26A: $^1$H NMR (400 MHz, CDCl$_3$) δ 9.35 (s,b, 1H), 9.00 (s,b, 1H), 7.30 (m, 4H), 7.14 (m, 2H), 6.87 (m, 2H), 5.28 (s, 1H), 3.76 (s, 2H), 3.55 (m, 2H), 3.24 (m, 6H), 2.11 (m, 2H), 1.93 (m, 2H), 1.20 (m, 6H)

Mass Spectral Analysis m/z=391.0 (M+H)$^+$ 26.8: $^1$H NMR (400 MHz, CDCl$_3$) δ 9.12 (s,b, 1H), 8.71 (s,b, 1H), 7.65 (d, 1H), 7.39 (d, 2H), 7.31 (d, 2H), 7.28-7.19 (m, 2H), 7.00 (m, 1H), 6.92 (d, 1H), 3.59 (m, 2H), 3.29 (m, 6H), 2.78 (s, 2H), 2.05 (m, 2H), 1.78 (m, 2H), 1.23 (m, 6H)

Mass Spectral Analysis m/z=391.0 (M+H)$^+$

EXAMPLE 26B

Preparation of 26B:

To a stirred solution of 26.8 (0.12 g, 0.26 mmol, 1 eq) in methanol (10 mL) was added palladium [24 mg, 10 wt. % (dry basis) on activated carbon, 20% wt. eq]. The reaction mixture was stirred under hydrogen atmosphere using a hydrogen balloon at room temperature for 10 h. The palladium on activated carbon was filtered off on a celite pad and the filtrate was concentrated under reduced pressure. The crude product was purified by column chromatography (eluent: dichloromethane/methanol/ammonium hydroxide mixture of increasing polarity). The desired fractions were combined and concentrated under reduced pressure. To a cold (0° C.) solution of the resulting oil in dichloromethane was added dropwise a 2.0M solution of hydrogen chloride in diethyl ether (0.26 mL, 0.52 mmol, 2 eq). The mixture was then stirred for 1 h at room temperature, concentrated under reduced pressure, and dried under vacuum.

Yield: 88%

$^1$H NMR (400 MHz, CDCl$_3$) δ 9.41 (s,b, 1H), 8.95 (s,b, 1H), 7.40 (m, 1H), 7.33 (m, 2H), 7.25-7.14 (m, 3H), 6.97 (m, 1H), 6.86 (m, 1H), 3.62-3.04 (m, 10H), 2.63 (m, 1H), 2.03-1.49 (m, 6H), 1.20 (m, 6H)

Mass Spectral Analysis m/z=393.0 (M+H)$^+$

EXAMPLE 27A

Preparation of 27A:

A solution of 1A (0.66 g, 1.75 mmol, 1.0 eq) in anhydrous methanol (13 mL) was hydrogenated at atmospheric pressure in the presence of palladium hydroxide [Pd(OH)$_2$: Pearlman's catalyst] (0.120 g, 0.09 mmol, 0.05 eq) for 10 h. The mixture was then filtered through celite. The filtrate was concentrated and was hydrogenated at atmospheric pressure in the presence of palladium hydroxide (0.120 g) for an additional 10 h. The mixture was filtered through celite and the filtrate was concentrated to dryness under reduced pressure. To a cold (0° C.) solution of the resulting oil in anhydrous dichloromethane was added drop wise a 2.0M solution of anhydrous hydrochloric acid in diethyl ether (5 mL). The mixture was then stirred for 1 h at room temperature and concentrated under reduced pressure. Diethyl ether was added. The resulting precipitate was collected by filtration and washed with diethyl ether and ethyl acetate.

Yield: 63%

$^1$H NMR (400 MHz, DMSO d$_6$) δ 9.15 (m, 2H), 7.30 (m, 4H), 7.10 (m, 1H), 6.90 (m, 1H), 6.75 (m, 1H), 6.60 (m, 1H), 4.20 (m, 1H), 3.40 (m, 3H), 3.20 (m, 4H), 3.00 (m, 1H), 2.15 (m, 1H), 1.95 (m, 5H), 1.05 (m, 6H)

Mass Spectral Analysis m/z=379.1 (M+H)$^+$

Elemental analysis:

C$_{24}$H$_{30}$N$_2$O$_2$, 1HCl, 0.75H$_2$O

Theory: % C, 67.28; % H, 7.65; % N, 6.54.

Found: % C, 67.32; % H, 7.63; % N, 6.37.

EXAMPLE 27B

Preparation of 27B:

27A (racemic mixture) (10 g, 24.10 mmol, 1.0 eq) was resolved using Chiral HPLC method:

Column: Chiralpak AD-H, 4.6×250 mm, 5μ, Chiral Technologies PN# 19325

Column temperature: room temperature

Detection: UV photo diode array, 200 to 300 nm, extract at 275 nm

Injection volume: 40 μL of 2 mg/mL sample in EtOH:MeOH (80:20)

Flow: 1 mL/minute

Mobile Phase: 85% Solution A, 15% Solution B

Solution A: 0.1% Di-isopropylethylamine in Hexane (HPLC Grade)

Solution B: 80% Ethanol, 20% Methanol (both HPLC Grade)

Note: Methanol is miscible in Hexane only if first dissolved in Ethanol. Solution B should be pre-mixed Run time: 25 min.

HPLC: Waters Alliance 2695 (system dwell volume is ~350 μL)

Detector: Waters 996 (resolution: 4.8 nm, scan rate: 1 Hz)

Yield: 40%

$^1$H NMR (400 MHz, DMSO d$_6$) δ 9.10 (m, 2H), 7.28 (m, 4H), 7.14 (m, 1H), 6.90 (d, 1H), 6.80 (m, 1H), 6.63 (d, 1H), 4.25 (m, 1H), 3.42 (m, 3H), 3.24 (m, 4H), 2.97 (m, 1H), 2.20 (m, 1H), 1.97 (m, 5H), 1.10 (m, 6H)

Mass Spectral Analysis m/z=379.4 (M+H)$^+$

Chiral HPLC Method: t$_R$=8.64 min. (ee=97%)

Elemental analysis:

C$_{24}$H$_{30}$N$_2$O$_2$, 1HCl, 0.25H$_2$O

Theory: % C, 68.72; % H, 7.57; % N, 6.68.

Found: % C, 68.87; % H, 7.52; % N, 6.68.

[α]$_D^{25}$=+58.40 (c. 0.01, MeOH)

Determination of Absolute Configuration of Example 27B

Preparation of 27.3:

Compound 27.2 (0.45 g, 1.78 mmol, 1.1 eq) was added at 0° C. to a solution of 27B (0.67 g, 1.61 mmol, 1 eq) and triethylamine (0.74 mL, 5.33 mmol, 3.3 eq) in dichloromethane (6 mL). The reaction was warmed to room temperature and stirred overnight at room temperature. The mixture was washed with a saturated aqueous solution of sodium hydrogenocarbonate and brine, dried over sodium sulfate, filtered and concentrated under reduced pressure. The crude product was purified by column chromatography (eluent: hexane/ethyl acetate mixtures of increasing polarity).

Yield: 64%

$^1$H NMR (400 MHz, DMSO d$_6$) δ 7.30 (m, 4H), 7.11 (t, 1H), 6.90 (d, 1H), 6.77 (t, 1H), 6.61 (d, 1H), 4.23 (m, 1H), 3.39 (br m, 9H), 2.93 (d, 1H), 2.37 (m, 2H), 2.24 (m, 1H), 2.06

(m, 2H), 1.93 (m, 6H), 1.53 (m, 1H), 1.41 (m, 1H), 1.10 (m, 6H), 1.03 (s, 3H), 0.83 (s, 3H)

Mass Spectral Analysis m/z=593.4 (M+H)$^+$
Elemental analysis:
$C_{33}H_{44}N_2O_5S$, 0.25$H_2O$
Theory: % C, 68.37; % H, 7.51; % N, 4.69.
Theory: % C, 68.38; % H, 7.50; % N, 4.55.

X-Ray Crystallography Data:
Single crystals were grown as needles by dissolving 27.3 (10 mg, 0.017 mmol, 1 eq) in isopropanol (1 mL) and letting sit still at room temperature for 72 h.
Crystal data and structure refinement for 27.3:
Identification code: ptut001
Empirical formula: $C_{34}H_{44}N_2O_5S$
Formula weight: 592.77
Temperature: 120(2) K
Wavelength: 0.71073 A
Crystal system, space group: Monoclinic, P2(1)
Unit cell dimensions:
a=15.135(2) A, alpha=90 deg
b=6.1924(10) A, beta=91.802(2) deg
c=16.602(3) A, gamma=90 deg
Volume: 1555.2(4) A$^3$
Z, Calculated density: 2, 1.266 Mg/m$^3$
Absorption coefficient: 0.148 mm$^{-1}$
F(000): 636
Crystal size: 0.30×0.08×0.04 mm
Theta range for data collection: 1.79 to 27.79 deg
Limiting indices: −18<=h<=19, −7<=k<=7, −20<=l<=21
Reflections collected/unique: 12166/6251 [R(int)=0.0168]
Completeness to theta=27.79: 91.9%
Absorption correction: Semi-empirical from equivalents
Max. and min. transmission: 0.9941 and 0.9569
Refinement method: Full-matrix least-squares on F$^2$
Data/restraints/parameters: 6251/1/383
Goodness-of-fit on F$^2$: 1.040
Final R indices [I>2sigma(I)]: R1=0.0392, wR2=0.1030
R indices (all data): R1=0.0401, wR2=0.1041
Absolute structure parameter: −0.03(6)
Largest diff. peak and hole: 0.365 and −0.200 e.A$^{-3}$

EXAMPLE 27C

Preparation of 27C:
27A (racemic mixture) (10 g, 24.10 mmol, 1 eq) was resolved using Chiral HPLC method:
Column: Chiralpak AD-H, 4.6×250 mm, 5μ, Chiral Technologies PN# 19325
Column temperature: room temperature
Detection: UV photo diode array, 200 to 300 nm, extract at 275 nm
Injection volume: 40 μL of 2 mg/mL sample in EtOH:MeOH (80:20)
Flow: 1 mL/minute
Mobile phase: 85% Solution A, 15% Solution B
Solution A: 0.1% Di-isopropylethylamine in Hexane (HPLC Grade)
Solution B: 80% Ethanol, 20% Methanol (both HPLC Grade)
Run time: 25 min
HPLC: Waters Alliance 2695 (system dwell volume is ~350 μL.)
Detector: Waters 996 (Resolution: 4.8 nm, Scan Rate: 1 Hz)
Yield: 40%
$^1$H NMR (400 MHz, DMSO d$_6$) δ 9.12 (m, 2H), 7.28 (m, 4H), 7.14 (m, 1H), 6.90 (d, 1H), 6.79 (m, 1H), 6.63 (d, 1H), 4.25 (m, 1H), 3.44 (m, 3H), 3.24 (m, 4H), 2.96 (m, 1H), 2.18 (m, 1H), 1.97 (m, 5H), 1.10 (m, 6H)

Mass Spectral Analysis m/z=379.4 (M+H)$^+$
Chiral HPLC Method: t$_R$=11.914 min. (ee=100%)
Elemental analysis:
$C_{24}H_{30}N_2O_2$, 1HCl, 0.25$H_2O$
Theory: % C, 68.72; % H, 7.57; % N, 6.68.
Found: % C, 68.79; % H, 7.55; % N, 6.68.
$[α]_D^{25}$=−63.59 (c. 0.01, MeOH)

EXAMPLE 27D 27D was obtained according to a procedure similar to the one described for 27A, with the following exception:
Step 27.3: Method 27A was used and 1A was replaced by 1D.
$^1$H NMR (400 MHz, DMSO d$_6$) δ 9.05 (m, 2H), 7.31 (q, 4H), 6.98 (m, 2H), 6.36 (dd, 1H), 6.47 (dd, 1H), 3.51-3.33 (m, 2H), 3.29-3.11 (m, 5H), 2.96 (m, 1H), 2.19 (m, 1H), 2.05-1.82 (m, 5H), 1.20-1.00 (m, 6H)

Mass Spectral Analysis m/z=397.3 (M+H)$^+$

EXAMPLE 27E 27E was obtained from 27D by chiral HPLC chromatography
$^1$H NMR (400 MHz, DMSO d$_6$) δ 8.82 (m, 2H), 7.31 (m, 4H), 6.97 (m, 2H), 6.37 (m, 1H), 4.27 (m, 1H), 3.42 (m, 2H), 3.23 (m, 5H), 2.97 (m, 1H), 2.20 (m, 1H), 1.94 (m, 5H), 1.11 (m, 6H)

Mass Spectral Analysis m/z=397.4 (M+H)$^+$
Elemental analysis:
$C_{24}H_{29}FN_2O_2$, 1HCl, 0.33$H_2O$
Theory: % C, 65.71; % H, 7.09; % N, 6.36.
Found: % C, 65.68; % H, 7.07; % N, 6.41.
$[α]_D^{25}$=+65.32 (c=9.85 mg/mL, MeOH)

EXAMPLE 27F 27F was obtained from 27D by chiral HPLC chromatography
$^1$H NMR (400 MHz, DMSO d$_6$) δ 8.92 (m, 2H), 7.32 (m, 4H), 6.98 (m, 2H), 6.37 (m, 1H), 4.27 (m, 1H), 3.42 (m, 2H), 3.24 (m, 5H), 2.97 (m, 1H), 2.20 (m, 1H), 1.95 (m, 5H), 1.11 (m, 6H)

Mass Spectral Analysis m/z=397.3 (M+H)$^+$
Elemental analysis:
$C_{24}H_{29}FN_2O_2$, 1HCl, 0.2$H_2O$
Theory: % C, 66.03; % H, 7.02; % N, 6.42.
Found: % C, 66.07; % H, 6.99; % N, 6.34.
$[α]_D^{25}$=−65.36 (c=9.75 mg/mL, MeOH)

EXAMPLE 27G 27G was obtained according to a procedure similar to the one described for 27A, with the following exception:
Step 27.3: Method 27A was used and 1A was replaced by 2C.
$^1$H NMR (400 MHz, DMSO d$_6$) δ 9.12 (brs, 1H), 8.97 (brs, 1H), 7.32 (d, 2H), 7.27 (d, 2H), 6.84 (d, 1H), 6.73 (dd, 1H), 6.12 (d, 1H), 4.21 (m, 1H), 3.55 (m, 3H), 3.42 (brs, 1H), 3.20 (brm, 5H), 2.94 (m, 1H), 2.16 (m, 1H), 1.92 (m, 5H), 1.09 (m, 7H), 0.46 (m, 2H), 0.18 (m, 2H)

Mass Spectral Analysis m/z=449.3 (M+H)$^+$
Elemental analysis:
$C_{28}H_{36}N_2O_3$, 1HCl, 1H$_2$O
Theory: % C, 66.85; % H, 7.81; % N, 5.57; % Cl, 7.05.
Found: % C, 67.02; % H, 7.51; % N, 5.54; % Cl, 7.25.

EXAMPLE 27H 27H was obtained according to a procedure similar to the one described for 27A, with the following exception:
Step 27.3: Method 27A was used and 1A was replaced by 1N.
$^1$H NMR (400 MHz, DMSO d$_6$) δ 9.07 (m, 1.5H), 8.53 (d, 1H), 7.70 (dd, 1H), 7.52 (d, 1H), 7.16 (m, 1H), 6.93 (dd, 1H), 6.82 (m, 1H), 6.63 (d, 1H), 4.36 (dd, 1H), 3.45 (q, 2H), 3.33-3.15 (m, 5H), 2.98 (m, 1H), 2.22 (m, 1H), 2.07-1.85 (m, 5H), 1.15 (t, 3H), 1.09 (t, 3H)
Mass Spectral Analysis m/z=380.2 (M+H)$^+$

EXAMPLE 27I 27I was obtained from 27H by chiral HPLC chromatography
$^1$H NMR (400 MHz, DMSO d$_6$) δ 8.89 (m, 2H), 8.52 (d, 1H), 7.68 (dd, 1H), 7.51 (d, 1H), 7.16 (m, 1H), 6.94 (m, 1H), 6.82 (m, 1H), 6.62 (m, 1H), 4.35 (m, 1H), 3.44 (q, 2H), 3.26 (m, 5H), 2.98 (m, 1H), 2.23 (m, 1H), 1.95 (m, 5H), 1.15 (t, 3H), 1.09 (t, 3H)
Mass Spectral Analysis m/z=380.2 (M+H)$^+$
Elemental analysis:
$C_{23}H_{29}N_3O_2$, 1.3HCl, 1.4H$_2$O
Theory: % C, 61.10; % H, 7.38; % N, 9.29; % Cl, 10.19.
Found: % C, 61.01; % H, 7.35; % N, 9.21; % Cl, 10.41.
$[\alpha]_D^{25}$=+44.59 (c=9.65 mg/mL, MeOH)

EXAMPLE 27J 27J was obtained from 27H by chiral HPLC chromatography
$^1$H NMR (400 MHz, DMSO d$_6$) δ 9.08 (m, 2H), 8.53 (d, 1H), 7.70 (dd, 1H), 7.52 (d, 1H), 7.16 (m, 1H), 6.93 (m, 1H), 6.82 (m, 1H), 6.63 (m, 1H), 4.36 (m, 1H), 3.45 (q, 2H), 3.25 (m, 5H), 2.97 (m, 1H), 2.22 (m, 1H), 1.97 (m, 5H), 1.15 (t, 3H), 1.09 (t, 3H)
Mass Spectral Analysis m/z=380.2 (M+H)$^+$
Elemental analysis:
$C_{23}H_{29}N_3O_2$, 2HCl, 1.75H$_2$O
Theory: % C, 57.08; % H, 7.19; % N, 8.68; % Cl, 14.65.
Found: % C, 56.92; % H, 7.15; % N, 8.58; % CT 15.02.
$[\alpha]_D^{25}$=−35.54 (c=10.3 mg/ml, MeOH)

EXAMPLE 27K 27K was obtained according to a procedure similar to the one described for 27A, with the following exception:
Step 27.3: Method 27A was used and 1A was replaced by 1O.
$^1$H NMR (400 MHz, DMSO d$_6$) δ 9.17-8.85 (m, 2H), 8.53 (d, 1H), 7.70 (dd, 1H), 7.52 (d, 1H), 7.06-6.94 (m, 2H), 6.41 (dd, 1H), 4.37 (dd, 1H), 3.49-3.35 (m, 2H), 3.32-3.14 (m, 5H), 2.97 (m, 1H), 2.23 (m, 1H), 2.05-1.82 (m, 5H), 1.15 (t, 3H), 1.09 (t, 3H)
Mass Spectral Analysis m/z=398.3 (M+H)$^+$

EXAMPLE 27L 27L was obtained from 27K by chiral HPLC chromatography
$^1$H NMR (400 MHz, DMSO d$_6$) δ 9.15 (m, 2H), 8.54 (d, 1H), 7.72 (dd, 1H), 7.54 (d, 1H), 7.00 (m, 2H), 6.42 (dd, 1H), 4.38 (m, 1H), 3.45 (q, 2H), 3.25 (m, 5H), 2.96 (m, 1H), 2.22 (m, 1H), 1.96 (m, 5H), 1.15 (t, 2H), 1.09 (t, 3H)
Mass Spectral Analysis m/z=398.3 (M+H)$^+$
Elemental analysis:
$C_{23}H_{28}FN_3O_2$, 2HCl, 1.75H$_2$O
Theory: % C, 55.04; % H, 6.73; % Cl, 14.13; % N, 8.37.
Found: % C, 54.85; % H, 6.53; % Cl, 14.28; % N, 8.45.
$[\alpha]_D^{25}$=+41.88 (c=10.2 mg/mL, MeOH)

EXAMPLE 27M 27M was obtained from 27K by chiral HPLC chromatography
$^1$H NMR (400 MHz, DMSO d$_6$) δ 9.14 (m, 2H), 8.54 (d, 1H), 7.79 (dd, 1H), 7.54 (d, 1H), 7.00 (m, 2H), 6.42 (dd, 1H), 4.38 (m, 1H), 3.45 (q, 2H), 3.25 (m, 5H), 2.96 (m, 1H), 2.23 (m, 1H), 1.96 (m, 5H), 1.15 (t, 3H), 1.09 (t, 3H)
Mass Spectral Analysis m/z=398.3 (M+H)$^+$
Elemental analysis:
$C_{23}H_{28}FN_3O_2$, 2HCl, 1.75H$_2$O
Theory: % C, 55.04; % H, 6.73; % N, 8.37; % Cl, 14.13.
Found: % C, 54.85; % H, 6.66; % N, 8.37; % Cl, 14.31.
$[\alpha]_D^{25}$=−40.91 (c=10.25 mg/mL, MeOH)

EXAMPLE 27N 27N was obtained according to a procedure similar to the one described for 27A, with the following exception:
Step 27.3: 1A was replaced by 1S.
Mass Spectral Analysis m/z=408.3 (M+H)$^+$

EXAMPLE 27O 27O was obtained from 27N by chiral HPLC chromatography
$^1$H NMR (400 MHz, DMSO d$_6$) δ 8.93 (brs, 1H), 8.75 (brs, 1H), 8.50 (d, 1H), 7.65 (dd, 1H), 7.50 (d, 1H), 6.74 (s, 1H), 6.37 (s, 1H), 4.26 (m, 1H), 3.45 (q, 2H), 3.24 (m, 5H), 2.94 (m, 1H), 2.18 (m, 1H), 2.14 (s, 3H), 1.99 (s, 3H), 1.90 (m, 5H), 1.15 (t, 3H), 1.08 (t, 3H)
Mass Spectral Analysis m/z=408.3 (M+H)$^+$
Elemental analysis:
$C_{25}H_{33}N_3O_2$, 1.25HCl, 1.63H$_2$O
Theory: % C, 62.25; % H, 7.84; % N, 8.70; % Cl, 9.19.
Found: % C, 62.52; % H, 7.64; % N, 8.30; % Cl, 8.80.

EXAMPLE 27P 27P was obtained from 27N by chiral HPLC chromatography
$^1$H NMR (400 MHz, DMSO d$_6$) δ 9.00 (brs, 1H), 8.82 (brs, 1H), 8.50 (d, 1H), 7.65 (dd, 1H), 7.50 (d, 1H), 6.74 (s, 1H), 6.37 (s, 1H), 4.26 (m, 1H), 3.45 (q, 2H), 3.24 (m, 5H), 2.94 (m, 1H), 2.18 (m, 1H), 2.13 (s, 3H), 1.99 (s, 3H), 1.88 (m, 5H), 1.15 (t, 3H), 1.09 (t, 3H)
Mass Spectral Analysis m/z=408.3 (M+H)$^+$
Elemental analysis:
$C_{25}H_{33}N_3O_2$, 1.2HCl, 1.6H$_2$O Theory: % C, 62.54; % H, 7.85; % N, 8.75; % Cl, 8.86.
Found: % C, 62.61; % H, 7.73; % N, 8.44; % Cl, 8.52.

EXAMPLE 27Q

Preparation of 27.6:

A solution of 2.7a (15.00 g, 30.45 mmol, 1 eq) in anhydrous dichloromethane (50 mL) and anhydrous methanol (100 mL) was hydrogenated at 1 atm, in the presence of palladium, 10 weight % (dry basis) on activated carbon, wet, Degussa type E101 NE/W (3.24 g, 1.52 mmol, 0.05 eq) for 10 h. The mixture was then filtered through celite and the filtrate was concentrated to dryness under reduced pressure. The product was used without further purification.

Yield: 99%
Mass Spectral Analysis m/z=495.4 (M+H)$^+$

Preparation of 27Q:

A 4.0M solution of hydrochloric acid in dioxane (41.9 mL, 167.46 mmol, 5.5 eq) was added drop wise to a cooled (0° C.) solution of 27.6 (15.06 g, 30.45 mmol, 1 eq) in anhydrous methanol (50 mL). The mixture was warmed to room temperature and stirring was continued for an additional 10 h at room temperature. The mixture was concentrated under reduced pressure. Diethyl ether (100 mL) was added to the solution. The resulting precipitate was collected by filtration and washed with diethyl ether.

Yield: 85%
$^1$H NMR (400 MHz, DMSO d$_6$) δ 9.03 (m, 1H), 8.90 (m, 1H), 8.80 (s, 1H), 7.28 (m, 4H), 6.71 (d, 1H), 6.53 (m, 1H), 6.05 (d, 1H), 4.16 (m, 1H), 3.43 (m, 3H), 3.21 (m, 5H), 2.92 (m, 1H), 2.11 (m, 1H), 1.98 (m, 1H), 1.90 (m, 4H), 1.11 (m, 6H)
Mass Spectral Analysis m/z=395.4 (M+H)$^+$
Elemental analysis:
$C_{24}H_{30}N_2O_2$, 1HCl, 0.75H$_2$O
Theory: % C, 64.85; % H, 7.37; % N, 6.30.
Found: % C, 65.12; % H, 7.43; % N, 6.18.

EXAMPLE 27R

Preparation of 27R:
27R was obtained from 27Q by chiral HPLC chromatography
27Q (racemic mixture) (10 g, 23.20 mmol, 1 eq) was resolved using Chiral HPLC method:
Column: Chiralpak AD-H, 4.4×250 mm
Column temperature: 25° C.
Detection: UV at 230 nm
Flow: 2.0 mL/minute
Mobile phase: 80% carbon dioxide, 20% ethanol, 0.1% ethane sulfonic acid
Run time: 24 min.

The relevant fractions were combined and concentrated under reduced pressure. An aqueous 1N solution of sodium hydroxide was added to the resulting oil until the solution was basic using pH paper. The aqueous mixture was extracted with dichloromethane. The organic extracts were combined, dried over sodium sulfate, filtered and concentrated under reduced pressure. To a cold (0° C.) solution of the resulting oil in anhydrous methanol was added drop wise a 4M solution of anhydrous hydrochloric acid in dioxane (5.5 eq). The mixture was then stirred for 1 hour at room temperature and concentrated under reduced pressure. The crude product was purified by column chromatography (eluent: dichloromethane/methanol mixtures of increasing polarity).

Yield: 30%
$^1$H NMR (400 MHz, DMSO d$_6$) δ 9.19 (m, 1H), 9.05 (m, 1H), 7.31 (m, 4H), 6.73 (d, 1H), 6.54 (m, 1H), 6.05 (d, 1H), 4.16 (m, 1H), 3.42 (br s, 2H), 3.17 (br m, 6H), 2.91 (m, 1H), 2.11 (m, 1H), 1.98 (m, 1H), 1.90 (m, 4H), 1.10 (m, 6H)
Mass Spectral Analysis m/z=395.1 (M+H)$^+$
Chiral HPLC purity: t$_R$=9.932 min. (ee=>99%)
[α]$_D^{24.2}$=+21.49 (c. 0.01, MeOH)

EXAMPLE 27S

Preparation of 27S:
27S was obtained from 27Q by chiral HPLC chromatography
27Q (racemic mixture) (10 g, 23.20 mmol, 1 eq) was resolved using Chiral HPLC method:
Column: Chiralpak AD-H, 4.4×250 mm
Column Temperature: 25° C.
Detection: UV at 230 nm
Flow: 2.0 mL/minute
Mobile Phase: 80% carbon dioxide, 20% ethanol, 0.1% ethane sulfonic acid
Run Time: 24 min.

The relevant fractions were combined and concentrated under reduced pressure. An aqueous 1N solution of sodium hydroxide was added to the resulting oil until the solution was basic using pH paper. The aqueous mixture was extracted with dichloromethane. The organic extracts were combined, dried over sodium sulfate, filtered and concentrated under reduced pressure. To a cold (0° C.) solution of the resulting oil in anhydrous methanol was added drop wise a 4M solution of anhydrous hydrochloric acid in dioxane (5.5 eq). The mixture was then stirred for 1 h at room temperature and concentrated under reduced pressure. The crude product was purified by column chromatography (eluent: dichloromethane/methanol mixtures of increasing polarity).

Yield: 18%
$^1$H NMR (400 MHz, DMSO d$_6$) δ 9.03 (m, 1H), 8.87 (m, 1H), 8.80 (s, 1H), 7.31 (m, 4H), 6.71 (d, 1H), 6.55 (d, 1H), 6.05 (m, 1H), 4.18 (m, 1H), 3.36 (m, 2H), 3.18 (m, 5H), 2.93 (m, 1H), 2.11 (m, 1H), 1.98 (m, 1H), 1.87 (m, 4H), 1.10 (m, 6H)
Mass Spectral Analysis m/z=395.1 (M+H)$^+$
Chiral HPLC prity: t$_R$=13.371 min. (ee=98.1%)
[α]$_D^{24.2}$=−25.96 (c. 0.01, MeOH)

EXAMPLE 27T

Preparation of 27.1:
A solution of 11.6a (15.00 g, 27.95 mmol, 1 eq) in anhydrous methanol (100 mL) was hydrogenated at 70 psi in the presence of palladium hydroxide [Pd(OH)$_2$: Pearlman's catalyst] (1.96 g, 1.40 mmol, 0.05 eq) for 10 h. The mixture was filtered through celite. The filtrate was concentrated under reduced pressure and was hydrogenated at 70 psi in the presence of palladium hydroxide (1.96 g) for an additional 10 h. The mixture was filtered through celite and the filtrate was concentrated to dryness under reduced pressure. The crude product was used without further purification.

Yield: 84%
$^1$H NMR (400 MHz, DMSO d$_6$) δ 7.23 (d, 2H), 7.11 (m, 3H), 6.60 (d, 1H), 6.52 (d, 1H), 4.85 (d, 1H), 4.74 (d, 1H), 4.16 (m, 1H), 3.61 (m, 2H), 3.30 (br m, 6H), 2.83 (s, 3H), 2.24 (m, 1H), 1.75 (m, 2H), 1.64 (m, 1H), 1.52 (m, 2H), 1.39 (s, 9H), 1.06 (m, 6H)
Mass Spectral Analysis m/z=539.5 (M+H)$^+$ Preparation of 27T:
To a cold (0° C.) solution of 27.1 (2.00 g, 3.71 mmol, 1.0 eq) in anhydrous methanol (40 mL) was added drop wise a 4M solution of anhydrous hydrochloric acid in dioxane (9.3 mL, 37.20 mmol, 10.0 eq). The mixture was then stirred for 10 h at room temperature and concentrated under reduced pressure. Diethyl ether was added. The resulting precipitate was collected by filtration and washed with diethyl ether.

Yield: 99%

$^1$H NMR (400 MHz, DMSO d$_6$) δ 9.30 (br s, 1H), 9.03 (br s, 1H), 8.96 (br s, 1H), 7.21 (d, 2H), 7.14 (d, 2H), 6.99 (t, 1H), 6.43 (d, 1H), 6.35 (d, 1H), 4.15 (m, 1H), 3.87 (br s, 3H), 3.39 (m, 2H), 3.15 (m, 5H), 2.90 (m, 1H), 2.25 (m, 1H), 1.83 (br m, 5H), 1.09 (m, 6H)

Mass Spectral Analysis m/z=395.3 (M+H)$^+$

EXAMPLE 27U

Preparation of 27.4:

Compound 27.1 (racemic mixture) (10 g, 18.56 mmol, 1 eq) was resolved using Chiral HPLC method:

Column: Chiralpak AD-H, 4.4×250 mm
Column temperature: 25° C.
Detection: UV at 280 nm
Flow: 2.0 mL/minute
Mobile phase: 75% carbon dioxide, 25% isopropanol
Run time: 10 minutes.

The relevant fractions were combined and concentrated under reduced pressure. The crude product was used without further purification.

Yield: 79%

$^1$H NMR (400 MHz, DMSO d$_6$) δ 7.21 (d, 2H), 7.11 (m, 3H), 6.60 (d, 1H), 6.55 (d, 1H), 4.83 (d, 1H), 4.74 (d, 1H), 4.16 (m, 1H), 3.62 (m, 2H), 3.15 (br m, 6H), 2.83 (s, 3H), 2.24 (m, 1H), 1.75 (m, 2H), 1.61 (m, 1H), 1.50 (m, 2H), 1.39 (s, 9H), 1.06 (m, 6H)

Mass Spectral Analysis m/z=539.1 (M+H)$^+$

Chiral HPLC purity: t$_R$=4.728 min. (ee=>99%)

$[α]_D^{24.1}$=−32.97 (c. 0.01, MeOH)

Preparation of 27U:

To a cold (0° C.) solution of 27.4 (1.00 g, 1.86 mmol, 1 eq) in anhydrous methanol was added drop wise a 4M solution of anhydrous hydrochloric acid in dioxane (2.5 mL, 10.21 mmol, 5.5 eq). The mixture was stirred for 10 hours at room temperature and concentrated under reduced pressure. The crude product was purified by column chromatography (eluent: dichloromethane/methanol mixtures of increasing polarity).

Yield: 88%

$^1$H NMR (400 MHz, DMSO d$_6$) δ 9.30 (s, 1H), 9.00 (m, 2H), 7.21 (d, 2H), 7.14 (d, 2H), 6.99 (t, 1H), 6.41 (d, 1H), 6.35 (d, 1H), 4.15 (m, 1H), 3.42 (br s, 5H), 3.12 (m, 2H), 2.90 (m, 1H), 2.24 (m, 1H), 1.83 (m, 4H), 1.72 (m, 1H), 1.09 (m, 6H)

Mass Spectral Analysis m/z=395.1 (M+H)$^+$ $[α]_D^{24.2}$=+3.24 (c. 0.01, MeOH)

EXAMPLE 27V

Preparation of 27.5:

27.1 (racemic mixture) (10 g, 18.56 mmol, 1 eq) was resolved using Chiral HPLC method:

Column: Chiralpak AD-H, 4.4×250 mm
Column temperature: 25° C.
Detection: UV at 280 nm
Flow: 2.0 mL/minute
Mobile phase: 75% carbon dioxide, 25% isopropanol
Run time: 10 minutes.

The relevant fractions were combined and concentrated under reduced pressure. The crude product was used without further purification.

Yield: 83%

$^1$H NMR (400 MHz, DMSO d$_6$) δ 7.23 (d, 2H), 7.11 (m, 3H), 6.58 (d, 1H), 6.54 (d, 1H), 4.85 (d, 1H), 4.73 (d, 1H), 4.16 (m, 1H), 3.63 (m, 2H), 3.16 (br m, 6H), 2.83 (s, 3H), 2.24 (m, 1H), 1.75 (m, 2H), 1.61 (m, 1H), 1.52 (m, 2H), 1.39 (s, 9H), 1.05 (m, 6H)

Mass Spectral Analysis m/z=539.1 (M+H)$^+$

Chiral HPLC Method: t$_R$=5.943 min. (ee=98.7%)

$[α]_D^{24.0}$=+29.88 (c. 0.01, MeOH)

Preparation of 27V:

To a cold (0° C.) solution of 27.5 (1.00 g, 1.86 mmol, 1 eq) in anhydrous methanol was added drop wise a 4M solution of anhydrous hydrochloric acid in dioxane (2.5 mL, 10.21 mmol, 5.5 eq). The mixture was then stirred for 10 h at room temperature and concentrated under reduced pressure. The crude product was purified by column chromatography (eluent: dichloromethane/methanol mixtures of increasing polarity).

Yield: 92%

$^1$H NMR (400 MHz, DMSO d$_6$) δ 9.32 (s, 1H), 9.09 (br s, 2H), 7.21 (d, 2H), 7.12 (d, 2H), 6.99 (t, 1H), 6.41 (d, 1H), 6.38 (d, 1H), 4.16 (m, 1H), 3.36 (m, 5H), 3.13 (br m, 2H), 2.90 (m, 1H), 2.24 (m, 1H), 1.81 (br m, 5H), 1.09 (m, 6H)

Mass Spectral Analysis m/z=395.1 (M+H)$^+$ $[α]_D^{24.3}$=−6.35 (c. 0.01, MeOH)

EXAMPLE 27W 27W was obtained according to a procedure similar to the one described for 27A, with the following exception:

Step 27.3: 1A was replaced by 1E.

$^1$H NMR (400 MHz, CDCl$_3$) δ 7.34 (d, 2H), 7.18 (d, 2H), 6.96 (d, 1H), 6.78 (d, 1H), 6.54 (s, 1H), 4.06 (m, 1H), 3.72 (q, 1H), 3.55 (brm, 3H), 3.28 (brm, 3H), 3.17 (m, 1H), 3.03 (m, 1H), 2.14 (m, 5H), 1.97 (m, 2H), 1.49 (t, 1H), 1.20 (brd, 6H)

Mass Spectral Analysis m/z=393.4 (M+H)$^+$

EXAMPLE 28A

Preparation of 28.2:

To a solution of benzyl 4-oxopiperidine-1-carboxylate (19.1) (37.26 g, 160 mmol) in toluene (450 mL) were added ethyl cyanoacetate (28.1) (18.8 g, 166 mmol, 1.04 eq), acetic acid (2 mL) and ammonium acetate (1.24 g, 16 mmol, 0.1 eq). The reaction mixture was refluxed for 2 h with azeotropic removal of water formed during the reaction using a Dean-Stark trap. Additional ethyl cyanoacetate (10 g, 88.4 mmol, 0.55 eq), acetic acid (2 mL) and ammonium acetate (1.24 g, 6 mmol, 0.0375 eq) was added to the reaction mixture, which was then refluxed for 1.5 h. Additional ethyl cyanoacetate (10 g, 88.4 mmol, 0.55 eq), acetic acid (2 mL) and ammonium acetate (1.24 g, 6 mmol, 0.0375 eq) were added, and refluxed for an additional 1 h. The reaction mixture was cooled to room temperature and washed with a saturated aqueous solution of sodium bicarbonate, and dried over sodium sulfate. The mixture was filtered and the filtrate was concentrated under vacuum. To the residue was added hexane (300 mL) and ethyl acetate (20 mL). The mixture was kept at room temperature overnight. The solid was collected by filtration, washed with hexane and dried under vacuum.

Yield: 87.7%

$^1$H NMR (400 MHz, CDCl$_3$) δ 7.35 (m, 5H), 5.19 (s, 2H), 4.30 (q, 2H), 3.70 (m, 2H), 3.63 (m, 2H), 3.18 (m, 2H), 2.80 (m, 2H), 1.39 (t, 3H)

Preparation of 28.4a:

To a suspension of copper (I) cyanide (17.3 g, 193.2 mmol, 2.0 eq) in anhydrous tetrahydrofuran (400 mL) was added drop wise a 2.0 M solution of benzylmagnesium chloride (28.3a) (192 mL, 384 mmol, 4.0 eq) in tetrahydrofuran under a nitrogen atmosphere at 0° C. After the reaction mixture was stirred at room temperature for 2 h, a solution of compound 28.2 (31.5 g, 96 mmol) in tetrahydrofuran (100 mL) was added dropwise at −30° C. After the addition, the reaction mixture was stirred at room temperature overnight, and then quenched with a saturated aqueous solution of ammonium chloride, and filtered. The filtrate was extracted by diethyl ether and the combined organic extracts were dried over sodium sulfate. The organics were concentrated under reduced pressure and the residue was purified by column chromatography (eluent: hexane/methylene chloride/ethyl acetate, 4:1:1).

Yield: 100%

$^1$H NMR (400 MHz, CDCl$_3$) δ 7.35-7.20 (m, 10H), 5.11 (s, 2H), 4.25 (q, 2H), 3.72-3.50 (m, 5H), 3.06 (d, 1H), 2.91 (d, 1H), 1.90-1.65 (m, 4H), 1.32 (t, 3H)

Preparation of 28.6a:

Concentrated sulfuric acid (210 mL) was added slowly to 28.4a (38 g, 90.5 mmol) at 0° C. The mixture was warmed to room temperature, stirred for 30 min at room temperature, and then heated at 90° C. overnight. The reaction mixture was cooled in an ice bath and carefully basified to pH=9-10 with a 6 N aqueous solution of sodium hydroxide. The mixture was extracted with methylene chloride, and the organic extracts were combined, dried over sodium sulfate and concentrated under vacuum. The residue was dissolved in methylene chloride (500 mL). To this solution was added triethylamine (30 mL, 215.6 mmol, 2.4 eq) followed by drop wise addition of benzyl chloroformate (21.8) (16 mL, 106.5 mmol, 1.2 eq) at 0° C. The reaction mixture was stirred at 0° C. for 1 h and then washed with a saturated aqueous solution of sodium bicarbonate. The organic layer was dried over sodium sulfate and concentrated under vacuum. The residue was purified by column chromatography (eluent: hexane/methylene chloride/ethyl acetate, 4:1:1).

Yield: 41.2%

$^1$H NMR (400 MHz, CDCl$_3$) δ 8.00 (d, 1H), 7.50 (t, 1H), 7.33-7.23 (m, 7H), 5.11 (s, 2H), 2.98 (s, 2H), 2.62 (s, 2H), 1.50 (m, 4H)

Preparation of 28.7a:

A 1.0 M solution of lithium bis(trimethylsilyl)amide in tetrahydrofuran (3.6 mL, 3.6 mmol, 1.2 eq) was added at −78° C. to a solution of 28.6a (1.047 g, 3.0 mmol) in tetrahydrofuran (30 mL). After 45 min, a solution of 1.4 (1.3 g, 3.6 mmol, 1.2 eq) in tetrahydrofuran (8 mL) was added drop wise to the reaction mixture. The reaction mixture was then warmed to room temperature and stirred for 2.5 h, quenched by addition of water (40 mL), and extracted with a mixture of hexane and diethyl ether (1:1). The organic extracts were combined and washed with water, brine and dried over sodium sulfate. Evaporation of the solvent gave the crude product, which was used for the next step without further purification.

Yield: 100%

$^1$H NMR (400 MHz, CDCl$_3$) δ 7.35-7.18 (m, 9H), 5.98 (s, 1H), 5.11 (s, 2H), 3.70 (m, 2H), 3.40 (m, 2H), 2.83 (s, 2H), 1.66-1.56 (m, 4H)

Preparation of 28.8a:

To the solution of crude 28.7a (3 mmol) in dimethoxyethane (25 mL) was added sequentially a 2 N aqueous solution of sodium carbonate (5 mL, 10 mmol, 3.3 eq), lithium chloride (424 mg, 10 mmol, 3.3 eq), 4-(N,N-diethylaminocarbonyl)phenylboronic acid (796 mg, 3.6 mmol, 1.2 eq) and tetrakis(triphenylphosphine)palladium(0) (104 mg, 0.09 mmol, 0.03 eq). The reaction mixture was refluxed overnight, cooled to room temperature, diluted with water (30 mL) and extracted with diethyl ether. The combined organic extracts were dried over sodium sulfate and concentrated under vacuum. The residue was purified by column chromatography (eluent: hexane/methylene chloride/ethyl acetate, 2:1:1).

Yield: 91.9%

$^1$H NMR (400 MHz, CDCl$_3$) δ 7.36-7.12 (m, 12H), 7.00 (d, 1H), 6.00 (s, 1H), 5.13 (s, 2H), 3.70 (m, 2H), 3.58 (m, 2H), 3.45 (m, 2H), 3.30 (m, 2H), 2.82 (s, 2H), 1.65-1.52 (m, 4H), 1.21 (m, 6H)

Preparation of 28A:

Iodotrimethylsilane (0.29 mL, 2 mmol, 2 eq) was added to a solution of 28.8a (508 mg, 1 mmol) in anhydrous methylene chloride (10 mL) under a nitrogen athmosphere. The reaction mixture was stirred at room temperature for 2 h and quenched with a 1N aqueous solution of hydrochloric acid (30 mL) and extracted with diethyl ether. The aqueous phase was basified to pH=9-10 with a 3N aqueous solution of sodium hydroxide, and extracted with methylene chloride. The organic extracts were combined, dried over sodium sulfate and concentrated under vacuum. The residue was dissolved in methylene chloride (3 mL) and diluted with diethyl ether (15 mL). To this solution was added a 2.0 M solution of anhydrous hydrochloric acid in diethyl ether (1.5 mL, 3 mmol, 3.0 eq) and the reaction was stirred at room temperature for 30 min. The solid was collected by filtration, washed with diethyl ether and dried under vacuum.

Yield: 92.7%

$^1$H NMR (400 MHz, CDCl$_3$) δ 8.90 (m, 2H), 7.40-7.20 (m, 7H), 6.97 (d, 1H), 6.20 (s, 1H), 3.42 (m, 2H), 3.20 (m, 6H), 2.82 (s, 2H), 1.70 (m, 4H), 1.10 (m, 6H)

Mass Spectral Analysis m/z=375.1 (M+H)$^+$

EXAMPLE 28B

Preparation of 28.4b:

Compound 28.4b was prepared as described for 28.4a except 28.3a was replaced by 23.8b.

Preparation of 28.9:

To a solution of compound 28.4b (29 g, 64.4 mmol) in dimethylsulfoxide (200 mL) was added sodium chloride (1.5 g, 25.6 mmol, 0.4 eq) and water (3.0 mL, 167 mmol, 2.6 eq). The reaction mixture was heated at 160° C. for 2 h and then cooled to room temperature. Water (600 mL) was added to the mixture and the crude product was extracted with diethyl ether. The organic extracts were combined, washed with water and brine, dried over sodium sulfate, and concentrated under vacuum. The residue was purified by column chromatography (eluent: hexane/methylene chloride/ethyl acetate, 4:1:1).

Yield: 94.8%

$^1$H NMR (400 MHz, CDCl$_3$) δ 7.35 (m, 5H), 7.08 (d, 2H), 6.83 (d, 2H), 5.12 (s, 2H), 3.80 (s, 3H), 3.68 (m, 2H), 3.40 (m, 2H), 2.74 (s, 2H), 2.21 (s, 2H), 1.60-1.52 (m, 4H)

Preparation of 28.10:

To a solution of compound 28.9 (7.56 g, 20 mmol) in methanol (200 mL) was added concentrated sulfuric acid (40 mL). The mixture was heated at reflux for 2 days. The reaction mixture was cooled to 0° C., basified to pH=9 by slow addition of a 6 N aqueous solution of sodium hydroxide, and then concentrated under vacuum to remove the methanol. The mixture was extracted with methylene chloride. The organic extracts were combined, dried over sodium sulfate, filtered and concentrated under vacuum. The residue was dissolved in methylene chloride (80 mL) and cooled to 0° C. To this solution was added triethylamine (9.6 mL, 69 mmol, 3.5 eq) and followed by drop wise addition of benzyl chloroformate (21.8) (6.4 mL, 95%, 42.7 mmol, 2.1 eq). The reaction mixture was stirred at 0° C. for 1 h, washed with a saturated aqueous solution of sodium bicarbonate, dried over sodium sulfate, filtered and concentrated under vacuum. The residue was purified by column chromatography (eluent: hexane/methylene chloride/ethyl acetate, 4:1:1).

Yield: 94.8%

$^1$H NMR (400 MHz, CDCl$_3$) δ 7.38 (m, 5H), 7.10 (d, 2H), 6.80 (d, 2H), 5.12 (s, 2H), 3.80 (s, 3H), 3.75 (m, 2H), 3.70 (s, 3H), 3.32 (m, 2H), 2.73 (s, 2H), 2.30 (s, 2H), 1.50 (m, 4H)

Preparation of 28.11:

Compound 28.10 (2.06 g, 5 mmol) was dissolved in mixture of methanol (40 mL), tetrahydrofuran (40 mL) and water (40 mL). To this solution was added lithium hydroxide (1.52 g, 36 mmol, 7.2 eq) in one portion. The reaction mixture was stirred at room temperature overnight, concentrated under vacuum, acidified with a 3 N aqueous solution of hydrochloric acid and extracted with methylene chloride. The combined organic extracts were dried over sodium sulfate, filtered and concentrated under vacuum. The crude product was used fro the next step without further purification.

Yield: 100%

$^1$H NMR (400 MHz, DMSO d$_6$) δ 12.22 (brs, 1H), 7.33 (m, 5H), 7.10 (d, 2H), 6.86 (d, 2H), 5.06 (s, 2H), 3.73 (s, 3H), 3.60 (m, 2H), 3.32 (m, 2H), 2.69 (s, 2H), 2.17 (s, 2H), 1.45-1.35 (m, 4H)

Preparation of 28.6b:

To a solution of 28.11 (1.98 g, 5 mmol) in anhydrous methylene chloride (10 mL) was added a 2.0 M solution of oxalyl chloride in methylene chloride (20 mL, 40 mmol, 8.0 eq) followed by 2 drops of anhydrous N,N-dimethylformamide. The reaction mixture was stirred at room temperature for 4 h and then concentrated under vacuum. The resulting acyl chloride was dissolved in anhydrous methylene chloride (100 mL) and aluminum chloride (1.35 g, 10 mmol, 2.0 eq) was added in one portion. The reaction mixture was stirred at room temperature overnight and then quenched with water (60 mL) followed by addition of concentrated ammonium hydroxide to basify the aqueous layer. The organic layer was separated and the aqueous layer was further extracted with methylene chloride. The combined organic extracts were dried over sodium sulfate, filtered and concentrated under vacuum. The residue was then dissolved in methylene chloride (60 mL) and cooled to 0° C. To this solution was added triethylamine (3.0 mL, 21.6 mmol, 4.3 eq) followed by benzyl chloroformate (21.8) (2.0 mL, 13.3 mmol, 2.7 eq). The reaction mixture was stirred at 0° C. for 1 h and then washed with a saturated aqueous solution of sodium bicarbonate, dried over sodium sulfate, filtered and concentrated under vacuum. The residue was purified by column chromatography (eluent: hexane/methylene chloride/ethyl acetate, 4:1:1).

Yield: 89.7%

$^1$H NMR (400 MHz, CDCl$_3$) δ 7.48 (d, 1H), 7.35 (m, 5H), 7.16 (d, 1H), 7.10 (dd, 1H), 5.11 (s, 2H), 3.81 (s, 3H), 3.50 (m, 4H), 2.90 (s, 2H), 2.60 (s, 2H), 1.50 (m, 4H)

Preparation of 28B:

28B was obtained from 28.6b according to a procedure similar to the one described for 28A.

$^1$H NMR (DMSO d$_6$) δ 8.90 (m, 2H), 7.48 (d, 2H), 7.40 (d, 2H), 7.26 (d, 1H), 6.85 (dd, 1H), 6.45 (d, 1H), 6.20 (s, 1H), 3.64 (s, 3H), 3.42 (m, 4H), 3.18 (m, 4H), 2.78 (s, 2H), 1.70 (m, 4H), 1.11 (m, 6H)

Mass Spectral Analysis m/z=405.1 (M+H)$^+$

EXAMPLE 28C

Preparation of 28C:

Compound 28.8a (800 mg, 1.58 mmol) was dissolved in a mixture of methylene chloride (5 mL) and methanol (50 mL), and the reaction mixture was hydrogenated in the presence of 10% Pd/C (240 mg) using a hydrogen balloon. After 2 days at room temperature, the reaction mixture was filtered through celite and the filtrate was concentrated under vacuum. The residue was dissolved in methylene chloride (10 ml) and added 2.0 M solution of anhydrous hydrochloric acid in diethyl ether (2 mL, 4 mmol, 2.5 eq). The mixture was stirred for 1 h at room temperature and then concentrated under vacuum.

Yield: 100%

$^1$H NMR (400 MHz, DMSO d$_6$) δ 9.12 (brs, 2H), 7.28-7.03 (m, 7H), 6.66 (d, 1H), 4.10 (m, 1H), 3.40 (m, 2H), 3.20-3.08 (m, 6H), 2.85 (d, 1H), 2.78 (d, 1H), 2.10 (m, 1H), 1.60 (m, 5H), 1.10 (m, 6H).

Mass Spectral Analysis m/z=377.1 (M+H)$^+$

EXAMPLE 28D 28D was obtained according to a procedure similar to the one described for 28C, with the following exception:
Step 28.12: 28.8a was replaced by 28.8b.

$^1$H NMR (400 MHz, DMSO d$_6$) δ 8.77 (m, 2H), 7.28 (m, 4H), 7.89 (d, 1H), 6.75 (dd, 1H), 6.16 (d, 1H), 4.09 (m, 1H), 3.55 (s, 3H), 3.49-3.00 (m, 8H), 2.73 (m, 2H), 2.10 (m, 1H), 1.59 (m, 5H), 1.10 (m, 6H)

Mass Spectral Analysis m/z=407.3 (M+H)$^+$

EXAMPLE 28E 28E was obtained according to a procedure similar to the one described for 28A, with the following exception:
Step 28.10: 1.6 was replaced by 1.7 (see also step 28.13).

$^1$H NMR (400 MHz, DMSO d$_6$) δ 8.91 (m, 2H), 8.61 (s, 1H), 7.89 (d, 1H), 760 (d, 1H), 7.31-7.20 (m, 3H), 6.90 (d, 1H), 6.33 (s, 1H), 3.45-3.15 (m, 8H), 2.83 (s, 2H), 1.70 (m, 4H), 1.12 (m, 6H)

Mass Spectral Analysis m/z=376.4 (M+H)$^+$

Elemental analysis:

$C_{24}H_{29}N_3O$, ⅔HCl, 1H$_2$O

Theory: % C, 65.20; % H, 7.37; % N, 9.50; % C, 10.69.
Found: % C, 64.94; % H, 7.06; % N, 9.36; % Cl, 10.56.

EXAMPLE 29A

Preparation of 29.2:

To a solution of crude compound 28.7a (12 mmol) in anhydrous tetrahydrofuran (200 mL) at room temperature was added a 0.5 M solution of 4-(ethoxycarbonyl)phenylzinc iodide (29.1) in tetrahydrofuran (60 mL, 30 mmol, 2.5 eq) followed by tetrakis(triphenylphosphine)palladium(0) (833 mg, 0.72 mmol, 0.06 eq). The reaction mixture was heated at 40° C. for 2 days and then cooled to room temperature. The reaction was quenched by addition of a saturated aqueous solution of ammonium chloride and extracted with ethyl acetate. The organic extracts were combined, dried over sodium sulfate and filtered. The organic extracts were concentrated under reduced pressure and the residue was purified by column chromatography (eluent: hexane/ethyl acetate, 5:1).

Yield: 86.6%

$^1$H NMR (400 MHz, CDCl$_3$) δ 8.05 (d, 2H), 7.40-7.10 (m, 10H), 6.96 (d, 1H), 6.00 (s, 1H), 5.13 (s, 2H), 4.40 (q, 2H), 3.70 (m, 2H), 3.48 (m, 2H), 2.82 (s, 2H), 1.66-1.53 (m, 6H), 1.40 (t, 3H)

Preparation of 29.3:

Lithium hydroxide (3.36 g, 80 mmol, 8.0 eq) was added to a solution of 29.2 (4.81 g, 10 mmol) in a mixture of methanol (100 mL), tetrahydrofuran (100 mL) and water (100 mL). The reaction mixture was stirred at room temperature overnight, concentrated under vacuum and acidified to pH=1-2 with a 3N aqueous solution of hydrochloric acid. The acidified solution was extracted with methylene chloride and the organic extracts were combined, dried over sodium sulfate, filtered and concentrated under vacuum. The crude product was used for the next step without further purification.

Yield: 100%

$^1$H NMR (400 MHz, DMSO d$_6$) δ 13.00 (brs, 1H), 7.99 (d, 2H), 7.48 (d, 2H), 7.38-7.15 (m, 8H), 6.91 (d, 1H), 6.18 (s, 1H), 5.10 (s, 2H), 3.60-3.46 (m, 4H), 2.82 (s, 2H), 1.53 (m, 2H), 1.42 (m, 2H)

Preparation of 29.5a:

To a solution of 29.3 (680 mg, 1.5 mmol, 1.0 eq)) in methylene chloride (40 mL) was added isopropylamine (3.4h) (0.26 mL, 3 mmol, 2.0 eq) followed by triethylamine (0.84 ml, 6 mmol, 4.0 eq) and the Mukaiyama acylating reagent (2-chloro-1-methylpyridinium iodide) (461 mg, 1.8 mmol, 1.2 eq). The reaction mixture was stirred at room temperature overnight, washed with a saturated aqueous solution of sodium bicarbonate, dried over sodium sulfate, and filtered. The organic extracts were concentrated under reduced pressure and the residue was purified by column chromatography (eluent: hexane/methylene chloride/ethyl acetate, 2:1:1).

Yield: 95.8%

$^1$H NMR (400 MHz, CDCl$_3$) δ 7.78 (d, 2H), 7.40-7.10 (m, 10H), 6.94(d, 1H), 6.00 (s, 1H), 5.95 (d, 1H), 5.12 (s, 2H), 4.31 (m, 1H), 3.70 (m, 2H), 3.46 (m, 2H), 2.81 (s, 2H), 1.62-1.52 (m, 6H), 1.30 (d, 6H)

Preparation of 29A:

Iodotrimethylsilane (0.37 mL, 2.6 mmol, 2.0 eq) was added to a solution 29.5 (620 mg, 1.26 mmol) in anhydrous methylene chloride (20 mL) under a nitrogen athmosphere. The reaction mixture was stirred at room temperature for 2 h, quenched with a 1N aqueous solution of hydrochloric acid (40 mL), and the mixture was extracted with diethyl ether. The aqueous phase was basified to pH=9-10 with a 3N aqueous solution of sodium hydroxide and extracted with methylene chloride. The organic extracts were combined, dried over sodium sulfate, filtered and concentrated under vacuum. The residue was dissolved in methylene chloride (4 mL) and diluted with diethyl ether (20 mL). To this solution was added a 2.0 M solution of anhydrous hydrochloric acid in diethyl ether (2.0 mL, 4 mmol, 3.2 eq) and the mixture was stirred at room temperature for 30 min. The resulting precipitate was collected by filtration, washed with diethyl ether and dried under vacuum.

Yield: 100%

$^1$H NMR (400 MHz, DMSO d$_6$) δ 8.90 (brd, 2H), 8.29 (d, 1H), 7.90 (d, 2H), 7.43 (d, 2H), 7.31-7.16 (m, 3H), 6.90 (d, 1H), 6.18 (s, 1H), 4.11 (m, 1H), 3.16 (m, 4H), 2.86 (s, 2H), 1.70 (m, 4H), 1.20 (d, 6H)

Mass Spectral Analysis m/z=361.0 (M+H)$^+$

EXAMPLE 29B 29B was obtained according to a procedure similar to the one described for 29A, with the following exception:
Step 29.3: 3.4h was replaced by 29.4.

$^1$H NMR (400 MHz, DMSO d$_6$) δ 8.89 (m, 2H), 8.10 (d, 1H), 7.92 (d, 2H), 7.45 (d, 2H), 7.31 (d, 1H), 7.25 (t, 1H), 7.20 (t, 1H), 6.90 (d, 1H), 6.18 (s, 1H), 3.80 (m, 1H), 3.20 (m, 4H), 2.88 (s, 2H), 1.60 (m, 8H), 0.90 (t, 6H)

Mass Spectral Analysis m/z=389.1 (M+H)$^+$

EXAMPLE 29C

Preparation of 29.7:

To a solution of the carboxylic acid 29.3 (1.82 g, 4 mmol) in a mixture of dioxane (18 mL) and tert-butyl alcohol (18 mL) was added triethylamine (0.78 mL, 5.6 mmol, 1.4 eq) and diphenylphosphoryl azide (29.6) (1.12 mL, 5.2 mmol, 1.3 eq). The reaction mixture was refluxed overnight and concentrated under vacuum. The residue was purified by column chromatography (eluent: hexane/methylene chloride/ethyl acetate, 5:1:1) to afford the desired crude carbamate 29.7, which was used for the next step without further purification.

Yield: 33.4%

Preparation of 29.8:

To a solution of the crude carbamate 29.7 (700 mg) in methylene chloride (15 mL) was added a 2.0 M solution of anhydrous hydrochloric acid in diethyl ether (15 mL, 30 mmol). The reaction mixture was stirred at room temperature overnight and then diethyl ether was added to the reaction mixture, which was stirred for an additional 2 h at room temperature. The resulting precipitate was collected by filtration and used for the next step without further purification.

Yield: 57%

$^1$H NMR (400 MHz, DMSO d$_6$) δ 10.15 (brs, 3H), 7.40-7.15 (12H), 6.89 (d, 1H), 6.10 (s, 1H), 5.10 (s, 2H), 3.59 (m, 2H), 3.46 (m, 2H), 2.81 (s, 2H), 1.54 (m, 2H), 1.41 (m, 2H)

Preparation of 29.10:

Triethylamine (0.42 mL, 3 mmol) was added to a suspension of 29.8 (300 mg, 0.65 mmol) in methylene chloride (20 mL) at 0° C. followed by drop wise addition of propionyl chloride (29.9) (0.12 mL, 1.3 mmol, 2.0 eq). The reaction mixture was stirred at room temperature for 6 h and washed with a saturated aqueous solution of sodium bicarbonate. The organic layer was dried over sodium sulfate, filtered and concentrated under vacuum. The residue was purified by column chromatography (eluent: hexane/methylene chloride/ethyl acetate, 2:1:1).

Yield: 89.5%

$^1$H NMR (400 MHz, CDCl$_3$) δ 7.54 (d, 2H), 7.38-7.10 (m, 11H), 7.00 (d, 1H), 5.95 (s 1H), 5.12 (s, 2H), 3.70 (m, 2H), 3.44 (m, 2H), 2.80 (s, 2H), 2.42 (q, 2H), 1.60 (m, 2H), 1.50 (m, 2H), 1.28 (t, 3H)

Preparation of 29C:

Iodotrimethylsilane (0.21 mL, 1.47 mmol, 2.0 eq) was added to a solution of compound 29.10 (220 mg, 0.46 mmol) in anhydrous methylene chloride (8 mL) under a nitrogen athmosphere. The reaction mixture was stirred at room temperature for 2 h and quenched with a 1 N aqueous solution of hydrochloric acid (15 mL). The crude product was extracted with diethyl ether. The aqueous layer was basified to pH=9-10 with a 3M aqueous solution of sodium hydroxide and the mixture was extracted with methylene chloride. The organic extracts were combined, dried over sodium sulfate and concentrated under vacuum. The residue was dissolved in methylene chloride (3 mL) and diluted with diethyl ether (10 mL). To this solution was added a 2.0 M solution of anhydrous hydrochloric acid in diethyl ether (0.7 mL, 1.4 mmol, 3.0 eq) and the mixture was stirred at room temperature for 30 min. The solid was collected by filtration, washed with diethyl ether and dried under vacuum.

Yield: 83.9%

$^1$H NMR (400 MHz, DMSO d$_6$) δ 10.05 (s, 1H), 8.94 (brd, 2H), 7.66 (d, 2H), 7.30-7.20 (m, 5H), 6.96 (d, 1H), 6.08 (s, 1H), 3.15 (m, 4H), 2.82 (s, 2H), 2.34 (q, 2H), 1.68 (m, 4H), 1.10 (t, 3H)

Mass Spectral Analysis m/z=347.0 (M+H)$^+$

EXAMPLE 29D

Preparation of 29.11:

Methanesulfonyl chloride (7.4) (0.051 mL, 0.66 mmol, 2.0 eq) was added to a solution of 29.8 (150 mg, 0.326 mmol) in pyridine (6 mL) at 0° C. The reaction mixture was stirred at room temperature overnight, diluted with methylene chloride (40 mL) and washed with a 1N aqueous solution of hydrochloric acid and brine. The organic layer was dried over sodium sulfate and concentrated under vacuum. The residue was purified by column chromatography (eluent: hexane/ethyl acetate, 1:1).

Yield: 97.7%

$^1$H NMR (400 MHz, CDCl$_3$) δ 7.38-7.13 (m, 12H), 6.99 (d, 1H), 6.50 (s, 1H), 5.96 (s, 1H), 5.12 (s, 2H), 3.70 (m, 2H), 3.46 (m, 2H), 3.08 (s, 3H), 2.81 (s, 2H), 1.62-1.52 (m, 4H)

Preparation of 29D:

Iodotrimethylsilane (0.14 mL, 0.98 mmol, 3.5 eq) was added to a solution of 29.11 (140 mg, 0.28 mmol) in anhydrous methylene chloride (6 mL) under a nitrogen athmosphere. The reaction mixture was stirred at room temperature for 2 h and quenched with a 1N aqueous solution of hydrochloric acid (10 mL). The crude product was extracted with diethyl ether. The aqueous layer was basified to pH=9-10 with a 3N aqueous solution of sodium hydroxide and extracted with methylene chloride. The organic extracts were combined, dried over sodium sulfate, filtered and concentrated under vacuum. The residue was dissolved in methylene chloride (3 mL) and diluted with diethyl ether (10 mL). To this solution was added a 2.0 M solution of anhydrous hydrochloric acid in diethyl ether (0.42 mL, 0.84 mmol, 3.0 eq) and the mixture was stirred at room temperature for 30 min. The solid was collected by filtration, washed with diethyl ether and dried under vacuum.

Yield: 90.5%

$^1$H NMR (400 MHz, DMSO-d$_6$) δ 9.88 (s, 1H), 8.91 (brd, 2H), 7.35-7.18 (m, 7H), 6.96 (d, 1H), 6.09 (s, 1H), 3.12 (m, 4H), 3.02 (s, 3H), 2.82 (s, 2H), 1.68 (m, 4H)

Mass Spectral Analysis m/z=368.9 (M+H)$^+$

EXAMPLE 30A

Preparation of 30.3:

A mixture of 30.1 (10.2 g, 0.050 mol, 1.0 eq) and 30.2 (25 g, 0.075 mol, 1.5 eq) in toluene (100 mL) under nitrogen was refluxed for 2 h. The mixture was concentrated under reduced pressure and the crude product was purified by column chromatography (eluent: hexane/ethyl acetate, 1:1).

Yield: 92%

$^1$H NMR (400 MHz, CDCl$_3$) δ 7.42 (s, 5H), 5.78 (brs, 1H), 3.83 (brs, 2H), 3.70 (s, 3H), 3.49 (brs, 2H), 3.02 (brm, 2H), 2.37 (brm, 2H)

Mass Spectral Analysis m/z=259.9 (M+H)$^+$

Preparation of 30.5:

A solution of 30.3 (5.0 g, 19.3 mmol, 1.0 eq), 30.4 (16.39 g, 149 mmol, 7.7 eq), and triethylamine (3.90 g, 38.6 mmol, 2.0 eq) in tetrahydrofuran (100 mL) was refluxed for 12 h. The mixture was concentrated under reduced pressure and the crude product was purified by column chromatography (eluent: hexane/ethyl acetate, 60:40).

Yield: 98%

$^1$H NMR (400 MHz, CDCl$_3$) δ 7.56 (m, 2H), 7.37 (m, 8H), 4.40 (brs, 1H), 3.72 (s, 3H), 3.58 (brm, 3H), 2.56 (s, 2H), 1.76 (brm, 4H)

Mass Spectral Analysis m/z=369.9 (M+H)$^+$

Preparation of 30.6:

A solution of 30.5 (10.0 g, 27.07 mmol, 1.0 eq) and concentrated sulfuric acid (50 mL) was stirred at room temperature for 18 h. The mixture was poured onto ice water (1:1) (200 mL) and the crude product was extracted with ethyl acetate. The combined organic extracts were dried over magnesium sulfate, concentrated under reduced pressure and the crude product was purified by column chromatography (eluent: hexane/ethyl acetate, 70:30).

Yield: 22%

$^1$H NMR (400 MHz, CDCl$_3$) δ 8.08 (dd, 1H), 7.40 (m, 7H), 7.20 (m, 1H), 4.47 (brs, 1H), 3.44 (brm, 3H), 2.97 (brd, 2H), 1.92 (brm, 4H)

Mass Spectral Analysis m/z=337.9 (M+H)$^+$

Preparation of 30.7:

To a solution of 30.6 (1.2 g, 3.56 mmol, 1.0 eq) in acetic acid (5 mL) was added at room temperature a 30% aqueous solution of hydrogen peroxide (2 mL). The solution was heated at 90° C. for 2 h and then cooled to room temperature. The mixture was concentrated to ⅓ of its volume under reduced pressure. Water was added and the crude product was extracted with methylene chloride. The combined organic extracts were then washed with a saturated sodium thiosulfate solution, brine, dried over magnesium sulfate and filtered. The filtrate was concentrated under reduced pressure. The crude product was purified by column chromatography (eluent: hexane/ethyl acetate, 1:1).

Yield: 84%

$^1$H NMR (400 MHz, CDCl$_3$) δ 8.10 (m, 2H), 7.87 (m, 1H), 7.77 (m, 1H), 7.41 (m, 5H), 4.34 (brs, 1H), 3.90 (brm, 1H), 3.50 (brm, 4H), 2.36 (brs, 2H), 1.80 (brm, 2H)

Mass Spectral Analysis m/z=369.8 (M+H)$^+$

Preparation of 30.8:

A mixture of 30.7 (1.1 g, 2.98 mmol, 1.0 eq) and a 6N aqueous solution of hydrochloric acid (5 mL) in ethanol (20 mL) was heated at 90° C. for 12 h. The mixture was concentrated under reduced pressure and used for the next step without further purification.

Yield: 100%

Mass Spectral Analysis m/z=265.8 (M+H)$^+$

Preparation of 30.9:

To a solution of 30.8 (0.9 g, 2.98 mmol, 1.0 eq) in tetrahydrofuran (10 mL) at 0° C. was added triethylamine (1.2 g, 11.92 mmol, 4.0 eq) and 4.7 (0.78 g, 3.58 mmol, 1.2 eq). The mixture was stirred at 0° C. for 1 h and at room temperature for 1 h. Water (20 mL) was added and the crude mixture was extracted with ethyl acetate. The combined organics were washed with water, brine, dried over magnesium sulfate and filtered. The filtrate was concentrated under reduced pressure. The crude product was purified by column chromatography (eluent: eluent: hexane/ethyl acetate, 1:1).

Yield: 79%

$^1$H NMR (400 MHz, CDCl$_3$) δ 8.09 (m, 2H), 7.86 (m, 1H), 7.76 (m, 1H), 3.97 (brs, 2H), 3.39 (s, 2H), 3.20 (brm, 2H), 2.29 (m, 2H), 1.76 (brm, 2H), 1.46 (s, 9H)

Preparation of 30.10:

To a solution of 30.9 (0.84 g, 2.30 mmol, 1.0 eq) in tetrahydrofuran (10 mL) at −78° C. under a nitrogen athmosphere was added drop wise a 1.0M solution of LiHMDS in tetrahydrofuran (2.76 mL, 2.76 mmol, 1.2 eq). The mixture was stirred for 45 min at −78° C. A solution of 1.4 (0.986 g, 2.76 mmol, 1.2 eq) in tetrahydrofuran (3 mL) was added drop wise to the reaction mixture. The mixture was stirred for 3 h at 0° C. and at room temperature for 16 h. The mixture was poured into ice water (20 mL) and the crude product was extracted with ethyl acetate. The combined organic extracts were washed with water, brine, dried over magnesium sulfate and filtered. The crude product was purified by column chromatography (eluent: 85/15 hexane/ethyl acetate mixture).

Yield: 52%

$^1$H NMR (400 MHz, CDCl$_3$) δ 8.09 (dd, 1H), 7.76 (m, 1H), 7.69 (m, 1H), 7.61 (d, 1H), 6.36 (s, 1H), 4.17 (brs, 2H), 3.06 (brs, 2H), 2.24 (m, 2H), 1.82 (m, 2H), 1.47 (s, 9H)

Preparation of 30.11:

To a solution of 30.10 (0.15 g, 0.30 mmol, 1.0 eq) in dimethoxyethane (DME) (30 mL) was added sequentially a 2N aqueous solution of sodium carbonate (0.45 mL, 0.90 mmol, 3.0 eq), lithium chloride (0.038 g, 0.90 mmol, 3.0 eq), 1.6 (0.106 g, 0.33 mmol, 1.1 eq) and tetrakis(triphenylphosphine)palladium(0) (0.007 g, 0.006 mmol, 0.02 eq). The mixture was refluxed for 16 h under a nitrogen athmosphere. The mixture was then cooled to room temperature and ice water (20 mL) was added. The mixture was extracted with ethyl acetate. The combined organic extracts were further washed with water, brine, dried over magnesium sulfate and filtered. The filtrate was concentrated under reduced pressure. The crude product was purified by column chromatography (eluent: hexane/ethyl acetate, 70:30).

Yield: 86%

$^1$H NMR (400 MHz, CDCl$_3$) δ 8.09 (m, 1H), 7.56 (m, 2H), 7.44 (d, 2H), 7.38 (d, 2H), 7.15 (m, 1H), 6.22 (s, 1H), 4.16 (brs, 2H), 3.58 (brs, 2H), 3.30 (brs, 2H), 3.14 (brs, 2H), 2.23 (m, 2H), 1.88 (m, 2H), 1.47 (s, 9H), 1.23 (brd, 6H)

Mass Spectral Analysis m/z=525.9 (M+H)$^+$

Preparation of 30A:

To a solution of 30.11 (0.440 g, 0.84 mmol, 1.0 eq) in anhydrous methylene chloride (20 mL) was added a 2.0M solution of anhydrous hydrochloric acid in diethyl ether (8.0 mL, 16 mmol, 19 eq). The mixture was stirred for 48 h at room temperature. The mixture was concentrated under reduced pressure and treated with diethyl ether. The resulting precipitate was collected by filtration.

Yield: 100%

$^1$H NMR (400 MHz, DMSO d$_6$) δ 9.37 (brm, 1H), 8.80 (brm, 1H), 8.05 (d, 1H), 7.73 (m, 2H), 7.53 (d, 2H), 7.44 (d, 2H), 7.21 (d, 1H), 6.58 (s, 1H), 3.36 (brm, 8H), 2.26 (brm, 2H), 1.95 (brd, 2H), 1.13 (brd, 6H)

Mass Spectral Analysis m/z=425.3 (M+H)$^+$

EXAMPLE 31A

Preparation of 13.2a:

To a solution of 1.5a (7.80 g, 17.35 mmol, 1.0 eq) in dimethoxyethane (75 mL) was added sequentially a 2N aqueous solution of sodium carbonate (26.03 mL, 52.06 mmol, 3.0 eq), lithium chloride (2.21 g, 52.06 mmol, 3.0 eq), 13.1 (3.44 g, 19.09 mmol, 1.1 eq) and tetrakis(triphenylphosphine)palladium(0) (0.40 g, 0.35 mmol, 0.02 eq). The mixture was refluxed overnight under nitrogen. The mixture was then cooled to room temperature and water (250 mL) was added. The mixture was extracted with ethyl acetate. The organic layer was further washed with brine and dried over sodium sulfate. The mixture was filtered and the filtrate was concentrated under reduced pressure. The crude product was purified by column chromatography (eluent: hexane/ethyl acetate mixtures of increasing polarity).

Yield: 64%

$^1$H NMR (400 MHz, DMSO d$_6$) δ 8.02 (d, 2H), 7.49 (d, 2H), 7.23 (m, 1H), 6.99 (d, 1H), 6.92 (m, 2H), 5.92 (s, 1H), 3.88 (s, 3H), 3.70 (m, 2H), 3.27 (m, 2H), 1.89 (m, 2H), 1.71 (m, 2H), 1.42 (s, 9H)

Mass Spectral Analysis m/z=436.0 (M+H)$^+$

Preparation of 31A:

31A was obtained according to a procedure similar to the one described for 1A, with the following exceptions:

Step 1.4: method 1E was used; 1.8a was replaced by 13.2a (see also step 31.2).

$^1$H NMR (DMSO d$_6$) δ 8.81 (m, 2H), 8.00 (m, 2H), 7.45 (m, 2H), 7.24 (m, 1H), 7.03 (m, 1H), 6.91 (m, 2H), 5.99 (s, 1H), 3.90(s, 3H), 3.22 (m, 4H), 2.06 (m, 2H), 1.98 (m, 2H),

Mass Spectral Analysis m/z=336.0 (M+H)$^+$

Elemental analysis:

$C_{21}H_{21}NO_3$, 1HCl, 0.2H$_2$O

Theory: % C, 67.18; % H, 6.01; % N, 3.73.

Found: % C, 67.32; % H, 5.98; % N, 3.77.

EXAMPLE 31B 31B was obtained according to a procedure similar to the one described for 31A, with the following exceptions:

Step 31.1: 13.1 was replaced by 14.1.

Step 31.2: Method 1F was used.

$^1$H NMR (400 MHz, DMSO d$_6$) δ 8.92 (m, 2H), 7.94 (d, 2H), 7.59 (d, 2H), 7.29 (m, 1H), 7.06 (m, 1H), 6.94 (m, 2H), 6.02 (s, 1H), 3.22 (m, 4H), 2.05 (m, 4H)

Mass Spectral Analysis m/z=303.1 (M+H)$^+$

Elemental analysis:

$C_{20}H_{18}N_2O$, 1HCl, 0.8H$_2$O

Theory: % C, 68.00; % H, 5.88; % N, 7.93.

Found: % C, 67.89; % H, 5.59; % N, 7.79.

EXAMPLE 31C 31C was obtained according to a procedure similar to the one described for 31A, with the following exceptions:

Step 31.1: 13.1 was replaced by 16.1.

Step 31.2: Method 1F was used.

$^1$H NMR (400 MHz, DMSO d$_6$) δ 9.10 (brs, 1H), 7.90 (s, 2H), 7.65 (m, 2H), 7.25 (t, 1H), 7.10 (d, 1H), 6.00 (s, 1H), 3.20 (m, 4H), 2.00 (m, 4H)

Mass Spectral Analysis m/z=303.1 (M+H)$^+$

EXAMPLE 31D 31D was obtained according to a procedure similar to the one described for 31A, with the following exceptions:
Step 31.1: 13.1 was replaced by 31.1a.
Step 31.2: Method 1E was used.
$^1$H NMR (400 MHz, DMSO d$_6$) δ 9.18 (m, 2H), 7.51 (m, 1H), 7.41 (m, 2H), 7.26 (m, 2H), 7.05 (m, 1H), 6.94 (m, 2H), 5.92 (s, 1H), 3.46 (m, 2H), 3.20 (m, 6H), 2.06 (m, 4H), 1.11 (m, 6H)
Mass Spectral Analysis m/z=377.4 (M+H)$^+$

EXAMPLE 31E 31E was obtained according to a procedure similar to the one described for 31A, with the following exceptions:
Step 31.1: 13.1 was replaced by 31.1b.
Step 31.2: Method 1F was used.
$^1$H NMR (DMSO d$_6$) δ 8.95 (m, 2H), 8.00 (d, 2H), 7.65 (d, 2H), 7.25 (m, 1H), 7.05 (m, 2H), 6.95 (m, 1H), 6.00 (s, 1H), 3.30 (s, 3H), 3.20 (m, 4H), 2.10 (m, 4H); Mass Spectral Analysis m/z=356.1 (M+H)$^+$ t$_R$=1.54 minutes.
Mass Spectral Analysis m/z=356.1 (M+H)$^+$

EXAMPLE 31F 31F was obtained according to a procedure similar to the one described for 31A, with the following exceptions:
Step 31.1: 13.1 was replaced by 31.1c.
Step 31.2: Method 1F was used.
$^1$H NMR (400 MHz, DMSO d$_6$) δ 8.60 (m, 2H), 7.41 (m, 4H), 7.26 (m, 1H), 7.03 (m, 1H), 6.95 (m, 2H), 5.89 (s, 1H), 4.11 (s, 2H), 3.23 (m, 4H), 2.09 (m, 2H), 1.94 (m, 2H)
Mass Spectral Analysis m/z=317.0 (M+H)$^+$

EXAMPLE 31G 31G was obtained according to a procedure similar to the one described for 31A, with the following exceptions:
Step 31.1: 13.1 was replaced by 31.1d.
Step 31.2: Method 31A was used.
$^1$H NMR (400 MHz, DMSO d$_6$) δ 9.16 (brs, 2H), 7.30 (d, 2H), 7.24 (m, 1H), 7.02 (m, 4H), 6.93 (m, 1H), 5.80 (s, 1H), 3.80 (s, 3H), 3.20 (brm, 4H), 2.03 (brm, 4H)
Mass Spectral Analysis m/z=308.0 (M+H)$^+$

EXAMPLE 31H 31H was obtained according to a procedure similar to the one described for 31A, with the following exceptions:
Step 31.1: 13.1 was replaced by 31.1e.
Step 31.2: Method 1F was used.
$^1$H NMR (400 MHz, DMSO d$_6$) δ 9.07 (m, 2H), 7.26 (m, 5H), 6.98 (m, 3H), 5.82 (s, 1H), 3.21 (m, 4H), 2.35 (s, 3H), 2.03 (m, 4H)
Mass Spectral Analysis m/z=292.1 (M+H)$^+$

EXAMPLE 31I 31I was obtained according to a procedure similar to the one described for 31A, with the following exceptions:
Step 31.1: 13.1 was replaced by 31.1f.
Step 31.2: Method 1F was used.
$^1$H NMR (400 MHz, CDCl$_3$) δ 9.76 (m, 1H), 9.29 (m, 1H), 7.69 (m, 1H), 7.46 (m, 1H), 7.27 (brm, 4H), 6.96 (m, 2H), 5.64 (m, 1H), 3.44 (m, 2H), 3.30 (m, 2H), 2.29 (m, 2H), 2.11 (m, 2H)
Mass Spectral Analysis m/z=346.1 (M+H)$^+$

EXAMPLE 31J 31J was obtained according to a procedure similar to the one described for 31A, with the following exceptions:
Step 31.1: 13.1 was replaced by 31.1g.
Step 31.2: Method 31A was used.
$^1$H NMR (400 MHz, DMSO d$_6$) δ 8.92 (brs, 1.5H), 7.44 (m, 3H), 7.36 (m, 2H), 7.25 (m, 1H), 7.04 (d, 1H), 6.95 (m, 2H), 5.87 (s, 1H), 3.22 (brm, 4H), 2.09 (brm, 2H), 1.97 (brm, 2H)
Mass Spectral Analysis m/z=278.1 (M+H)$^+$

EXAMPLE 31K 31K was obtained according to a procedure similar to the one described for 31A, with the following exceptions:
Step 31.1: 13.1 was replaced by 31.1h.
Step 31.2: Method 31A was used.
$^1$H NMR (400 MHz, DMSO d$_6$) δ 9.66 (brs, 1H), 8.96 (brs, 2H), 7.50 (brm, 1H), 7.18 (brm, 3H), 6.97 (brm, 3H), 6.82 (brm, 1H), 5.67 (s, 1H), 3.18 (brm, 4H) 2.02 (brm, 4H) Mass Spectral Analysis m/z=294.0 (M+H)$^+$

EXAMPLE 31L 31L was obtained according to a procedure similar to the one described for 31A, with the following exceptions:
Step 31.1: 13.1 was replaced by 31.1i.
Step 31.2: Method 31A was used.
$^1$H NMR (400 MHz, DMSO d$_6$) δ 8.93 (brs, 2H), 7.37 (t, 1H), 7.25 (t, 1H), 6.97 (brm, 6H), 5.89 (s, 1H), 3.79 (s, 3H), 3.21 (brm, 4H), 2.03 (brm, 4H)
Mass Spectral Analysis m/z=308.0 (M+H)$^+$

EXAMPLE 31M 31M was obtained according to a procedure similar to the one described for 31A, with the following exceptions:
Step 31.1: 13.1 was replaced by 31.1j.
Step 31.2: Method 31A was used.
$^1$H NMR (400 MHz, DMSO d$_6$) δ 9.60 (s, 1H), 9.05 (brs, 2H), 7.24 (m, 2H), 7.02 (m, 2H), 6.94 (m, 1H), 6.82 (d, 1H), 6.76 (m, 2H), 5.82 (s, 1H), 3.20 (brm, 4H), 2.03 (brm, 4H)
Mass Spectral Analysis m/z=294.0 (M+H)$^+$

EXAMPLE 31N 31N was obtained according to a procedure similar to the one described for 31A, with the following exceptions:
Step 31.1: 13.1 was replaced by 31.1k.
Step 31.2: Method 1F was used.
$^1$H NMR (400 MHz, DMSO d$_6$) δ 9.10 (brm, 1.5H), 8.20 (s, 1H), 8.05 (s, 2H), 7.29 (m, 1H), 7.08 (d, 1H), 6.97 (t, 1H), 6.90 (dd, 1H), 6.16 (s, 1H), 3.23 (brm, 4H), 2.08 (brm, 4H)
Mass Spectral Analysis m/z=414.1 (M+H)$^+$

EXAMPLE 31O 31O was obtained according to a procedure similar to the one described for 31A, with the following exceptions:
Step 31.1: 13.1 was replaced by 31.1l.
Step 31.2: Method 31A was used.
$^1$H NMR (400 MHz, DMSO d$_6$) δ 8.88 (brs, 2H), 7.42 (m, 1H), 7.07 (brm, 5H), 6.83 (t, 1H), 6.60 (d, 1H), 5.73 (s, 1H), 3.65 (s, 3H), 3.18 (brm, 4H), 2.08 (brm, 2H), 1.96 (brm, 2H)
Mass Spectral Analysis m/z=308.0 (M+H)$^+$

EXAMPLE 31P 31P was obtained according to a procedure similar to the one described for 31A, with the following exceptions:
Step 31.1: 13.1 was replaced by 31.1m.
Step 31.2: Method 31A was used.
$^1$H NMR (400 MHz, DMSO d$_6$) δ 9.46 (s, 1H), 9.02 (brs, 2H), 7.22 (t, 1H), 7.16 (t, 1H), 7.10 (d, 1H), 6.93 (m, 2H), 6.84 (m, 2H), 6.70 (d, 1H), 5.71 (s, 1H), 3.20 (brm, 4H), 2.11 (brm, 2H), 1.97 (brm, 2H)
Mass Spectral Analysis m/z=294.0 (M+H)$^+$

EXAMPLE 31Q 31Q was obtained according to a procedure similar to the one described for 31A, with the following exceptions:
Step 31.1: 13.1 was replaced by 31.1n.
Step 31.2: Method 1E was used.
$^1$H NMR (400 MHz, CDCl$_3$) δ 9.75 (m, 2H), 7.85 (m, 1H), 7.78 (m, 1H), 7.49 (m, 1H), 7.37 (m, 3H), 7.28 (m, 1H), 6.99 (m, 2H), 5.88 (s, 1H), 3.42 (m, 4H), 2.27 (m, 4H)
Mass Spectral Analysis m/z=333.9 (M+H)$^+$

EXAMPLE 31R 31R was obtained according to a procedure similar to the one described for 31A, with the following exceptions:
Step 31.1: 13.1 was replaced by 31.1o.
Step 31.2: Method 1F was used.
$^1$H NMR (400 MHz, DMSO d$_6$) δ 9.04 (m, 2H), 7.66 (m, 3H), 7.34 (m, 4H), 7.10 (m, 2H), 6.48 (m, 1H), 3.23 (m, 4H), 2.09 (m, 4H)
Mass Spectral Analysis m/z=318.1 (M+H)$^+$

EXAMPLE 31S 31S was obtained according to a procedure similar to the one described for 31A, with the following exceptions:
Step 31.1: 13.1 was replaced by 31.1p.
Step 31.2: Method 31A was used.
$^1$H NMR (400 MHz, CDCl$_3$) δ 9.81 (brs, 1H), 9.40 (brs, 1H), 8.76 (brs, 2H), 7.98 (d, 1H), 7.67 (brs, 1H), 7.29 (m, 1H), 7.01 (d, 1H), 6.95 (t, 1H), 6.91 (d, 1H), 5.70 (s, 1H), 3.43 (m, 2H), 3.34 (m, 2H), 2.29 (m, 2H), 2.15 (m, 2H)
Mass Spectral Analysis m/z=279.1 (M+H)$^+$

EXAMPLE 31T 31T was obtained according to a procedure similar to the one described for 31A, with the following exceptions:
Step 31.1: 13.1 was replaced by 31.1q.
Step 31.2: Method 1E was used.
$^1$HNMR (400 MHz, CDCl$_3$) δ 9.71 (m, 2H), 7.44-7.21 (m, 3H), 7.11 (m, 2H), 6.96 (m 2H), 5.75 (s, 1H), 3.39 (m, 4H), 2.24 (m, 4H)
Mass Spectral Analysis m/z=283.9 (M+H)$^+$

EXAMPLE 31U 31U was obtained according to a procedure similar to the one described for 31A, with the following exceptions:
Step 31.1: 13.1 was replaced by 31.1r.
Step 31.2: Method 1F was used.
$^1$H NMR (400 MHz, DMSO d$_6$) δ 9.04 (brm, 1.5H), 7.66 (m, 1H), 7.62 (m, 1H), 7.26 (m, 1H), 7.20 (m, 2H), 7.03 (d, 1H), 6.97 (t, 1H), 5.96 (s, 1H), 3.20 (brm, 4H), 2.07 (brm, 2H), 1.98 (brm, 2H)
Mass Spectral Analysis m/z=284.1 (M+H)$^+$

EXAMPLE 31V 31V was obtained according to a procedure similar to the one described for 31A, with the following exceptions:
Step 31.1: 13.1 was replaced by 31.1s.
Step 31.2: Method 1F was used.
$^1$H NMR (400 MHz, CDCl$_3$) δ 9.71 (brs, 1H), 9.29 (brs, 1H), 7.52 (m, 3H), 6.99 (m, 2H), 6.59 (m, 1H), 6.49 (m, 1H), 5.95 (s, 1H), 3.42 (m, 2H), 3.32 (m, 2H), 2.25 (m, 2H), 2.10 (m, 2H)
Mass Spectral Analysis m/z=268.1 (M+H)$^+$

EXAMPLE 31W 31W was obtained according to a procedure similar to the one described for 31A, with the following exceptions:
Step 31.1: 13.1 was replaced by 31.1t.
Step 31.2: Method 1F was used.
$^1$H NMR (400 MHz, DMSO d$_6$) δ 9.34 (brm, 1.5H), 8.12 (d, 1H), 7.60 (m, 6H), 7.42 (t, 1H), 7.32 (t, 1H), 7.22 (t, 1H), 7.02 (d, 1H), 6.89 (m, 2H), 6.81 (d, 1H), 5.98 (s, 1H), 3.41 (brs, 2H), 2.20 (brm, 6H)
Mass Spectral Analysis m/z=457.1 (M+H)$^+$

EXAMPLE 31X 31X was obtained according to a procedure similar to the one described for 31A, with the following exceptions:
Step 31.1: 13.1 was replaced by 31.1u.
Step 31.2: Method 1E was used.
$^1$H NMR (400 MHz, DMSO d$_6$) δ 8.93 (m, 2H), 8.03 (d, 1H), 7.42 (d, 1H), 7.32 (m, 2H), 7.05 (m, 2H), 6.25 (s, 1H), 3.22 (m, 4H), 2.03 (m, 4H)
Mass Spectral Analysis m/z=308.8 (M+H)$^+$

EXAMPLE 31Y

Preparation of 31Y:
A solution of 16.2 (0.200 g, 0.0046 mol, 1.0 eq) in tetrahydrofuran (50 mL) was added drop wise to a cold (0° C.) suspension of lithium aluminum hydride (1.05 g, 0.027 mol, 6.0 eq) in tetrahydrofuran (50 mL). The mixture was allowed to warm to room temperature and was refluxed for 12 h under a nitrogen athmosphere. The reaction was cooled to room temperature and quenched by careful addition of water (3 mL). The mixture was stirred for 1 h at room temperature and filtered through celite. The celite was further rinsed with hot ethyl acetate. Evaporation of the filtrate afforded an oil which was dissolved in diethyl ether (20 mL). A 2.0M solution of hydrochloric acid in anhydrous diethyl ether (6.9 mL, 0.0138 mol, 3.0 eq) was added to the mixture. The resulting precipitate was collected by filtration and washed with diethyl ether.

Yield: 70%

$^1$H NMR (400 MHz, DMSO $d_6$) δ 8.60 (m, 1H), 8.40 (m, 2H), 7.50 (m, 3H), 7.35 (m, 1H), 7.25 (m, 1H), 6.90-7.10 (m, 3H), 5.80 (s, 1H), 4.10 (m, 2H), 3.30 (m, 7H), 2.10 (m, 4H)

Mass Spectral Analysis m/z=321.1 $(M+H)^+$

EXAMPLE 31Z

Preparation of 31Z:

Acetyl chloride (0.14 mL, 0.0019 mol, 1.5 eq) was added drop wise to a cold solution of 31Y (dihydrochloric acid salt) (0.500 g, 0.0012 mol, 1.0 eq) and triethylamine (0.90 mL, 0.006 mol, 5.0 eq) in dichloromethane (10 mL). The mixture was allowed to warm to room temperature and stirring was continued for 12 h at room temperature. The mixture was poured into water and ethyl acetate (30 mL) was added. The organic layer was separated, washed with brine, dried over sodium sulfate, filtered and evaporated. The crude product was purified by column chromatography (eluent: dichloromethane/methanol, mixtures of increasing polarity). The purified compound was dissolved in diethyl ether (20 mL). A 2.0M solution of anhydrous hydrochloric acid in diethyl ether (1.8 mL, 0.0036 mol, 3.0 eq) was added to the mixture. The resulting precipitate was collected by filtration and washed with diethyl ether.

Yield: 31% Mass Spectral Analysis m/z=363.1 $(M+H)^+$ $^1$H NMR (400 MHz, DMSO $d_6$) δ 10.70 (m, 1H), 8.35 (m, 1H), 7.35 (m, 1H), 7.20-7.30 (m, 3H), 7.05 (m, 1H), 6.90 (m, 3H), 5.75 (s, 1H), 4.20 (s, 2H), 3.30 (m, 4H), 2.80 (s, 3H), 2.15 (m, 4H), 1.85 (s, 3H)

EXAMPLE 31AA

Preparation of 31AA

Methane sulfonyl chloride (0.15 mL, 0.0019 mol, 1.5 eq) was added drop wise to a cold solution of 31Y (dihydrochloric acid salt) (0.500 g, 0.0012 mol, 1.0 eq) and triethylamine (0.90 mL, 0.006 mol, 5.0 eq) in dichloromethane (10 mL). The mixture was allowed to warm to room temperature and stirring was continued for 12 h at room temperature. The mixture was poured into water and ethyl acetate (30 mL) was added. The organic layer was separated, washed with brine, dried over sodium sulfate, filtered and evaporated. The crude product was purified by column chromatography (eluent: dichloromethane/methanol mixtures of increasing polarity). The purified compound was dissolved in diethyl ether (20 mL). A 2.0M solution of anhydrous hydrochloric acid in diethyl ether (1.8 mL, 0.0036 mol, 3.0 eq) was added to the mixture. The resulting precipitate was collected by filtration and washed with diethyl ether.

Yield: 30%

$^1$H NMR (400 MHz, DMSO $d_6$) δ 10.90 (m, 1H), 7.40 (m, 2H), 7.35 (m, 1H), 7.30 (m, 2H), 7.10 (m, 1H), 7.00 (m, 2H), 5.75 (s, 1H), 4.20 (d, 2H), 3.30 (m, 4H), 2.90 (s, 3H), 2.80 (s, 3H), 2.10 (m, 4H)

Mass Spectral Analysis m/z=399.1 $(M+H)^+$

EXAMPLE 32A

Preparation of 32.1:

To a solution of Bis(pinacolato)diboron 1.14 (14.7 g, 57.8 mmol, 2.0 eq) in N,N-dimethylformamide (200 mL) at room temperature under a nitrogen atmosphere was added 1,1'-bis (diphenylphosphino)ferrocene palladium(II) chloride complex with dichloromethane (710 mg, 0.867 mmol, 0.03 eq) followed by addition of potassium acetate (8.58 g, 86.7 mmol, 3.0 eq.) The mixture was heated to 80° C. followed by drop wise addition of a solution of the enol triflate 1.5a (13.0 g, 28.9 mmol, 1.0 eq) in N,N-dimethylformamide (100 mL). After the addition was complete, the reaction mixture was heated at 80° C. for an additional 16 h. The solvent was evaporated under vacuum and the residue was added to a 1N aqueous solution of hydrochloric acid. The aqueous residue was extracted with ethyl acetate. The organic extracts were washed with brine, dried over sodium sulfate, filtered and concentrated under reduced pressure to afford a brown semi-solid. The crude product was purified by column chromatography (eluent: hexane/ethyl acetate mixtures of increasing polarity).

Yield: 96.0%

$^1$H NMR (400 MHz, $CDCl_3$) δ 7.71 (d, 1H), 7.11 (t, 1H), 6.90 (t, 1H), 6.83 (d, 1H), 6.28 (s, 1H), 3.84 (brs, 2H), 3.27 (brm, 2H), 1.96 (d, 2H), 1.60 (m, 2H), 1.34 (s, 9H), 1.26 (s, 12H)

Mass Spectral Analysis m/z=428.0 $(M+H)^+$

Preparation of 32.2a:

To a solution of 4-bromophenylacetic acid (32.4) (3.21 g, 15 mmol) in methylene chloride (300 mL) was added diethylamine (1.12) (3.2 mL, 30 mmol, 2.0 eq) followed by triethylamine (8.4 ml, 60 mmol, 4.0 eq) and the Mukaiyama acylating reagent (2-chloro-1-methylpyridinium iodide) (4.61 mg, 18 mmol, 1.2 eq). The reaction mixture was stirred at room temperature overnight and the mixture was washed with a saturated aqueous solution of sodium bicarbonate, dried over sodium sulfate and filtered. The filtrate was concentrated under reduced pressure and the residue was purified by column chromatography (eluent: hexane/methylene chloride/ethyl acetate, 2:1:1).

Yield: 89.2%

$^1$H NMR (400 MHz, $CDCl_3$) δ 7.43 (d, 2H), 7.15 (d, 2H), 3.63 (s, 2H), 3.40 (q, 2H), 3.30 (q, 2H), 1.10 (t, 3H)

Preparation of 32.3a:

To a solution of 32.1 (2.14 g, 5 mmol) in dimethoxyethane (DME) (40 mL) was added sequentially a 2 N aqueous solution of sodium carbonate (8 mL, 16 mmol, 3.2 eq), lithium chloride (679 mg, 16 mmol, 3.2 eq.), 32.2a (1.62 mg, 6 mmol, 1.2 eq) and tetrakis(triphenylphosphine)palladium(0) (174 mg, 0.15 mmol, 0.03 eq). The mixture was refluxed overnight under a nitrogen athmosphere. The mixture was then cooled to room temperature and water (50 mL) was added. The mixture was extracted with ethyl acetate. The organic layer was further washed with brine, dried over sodium sulfate and concentrated under vacuum. The crude product was purified by column chromatography (eluent: hexane/ethyl acetate, 1:1).

Yield: 61%

$^1$H NMR (400 MHz, $CDCl_3$) δ 7.29 (s, 4H), 7.18 (t, 1H), 7.03 (d, 1H), 6.95 (d, 1H), 5.86 (t, 1H), 5.53 (s, 1H), 3.86 (m, 2H), 3.72 (s, 2H), 3.39 (m, 6H), 2.05 (m, 2H), 1.68 (m, 2H), 1.49 (s, 9H), 1.16 (m, 6H)

Preparation of 32A:

To a solution of 32.3a (1.4 g, 3.38 mmol) in methylene chloride (15 mL) was added a 2.0 M solution of anhydrous hydrochloric acid in diethyl ether (50 mL). The mixture was stirred at room temperature for 24 h and diluted by addition of diethyl ether was added. The resulting precipitate was collected by filtration and washed with diethyl ether.

Yield: 92%

$^1$H NMR (400 MHz, DMSO d$_6$) δ 9.20 (m, 2H), 7.20 (s, 4H), 7.24 (m, 1H), 7.00 (m, 3H), 5.83 (s, 1H), 3.40-3.20 (m, 8H), 2.03 (m, 4H), 1.08 (m, 6H)

Mass Spectral Analysis m/z=391.3 (M+H)$^+$

EXAMPLE 32B 32B was obtained according to a procedure similar to the one described for 32A, with the following exceptions:

Step 32.2: 32.2a was replaced by 32.2b and Method 1C was used.

Note: 32.2b was obtained according to a procedure similar to the one described for 32.2e (see 32E) except 13.4b was replaced by 1.12 in step 32.8.

$^1$H NMR (400 MHz, DMSO d$_6$) δ 9.02 (brs, 2H), 8.88 (s, 2H), 8.57 (s, 2H), 7.23 (s, 1H), 7.05 (s, 1H), 6.91 (s, 2H), 6.00 (s, 1H), 3.32 (s, 4H), 3.12 (brs, 4H), 2.08 (m, 4H), 1.02 (brd, 6H)

Mass Spectral Analysis m/z=454.0 (M+H)$^+$

Elemental analysis:

$C_{23}H_{28}N_2O_3S$, 1HCl, 1/3H$_2$O

Theory: % C, 60.71; % H, 6.57; % N, 6.16.
Found: % C, 60.64; % H, 6.36; % N, 6.16.

EXAMPLE 32C 32C was obtained according to a procedure similar to the one described for 32A, with the following exceptions:

Step 32.2: 32.2a was replaced by 32.2c and Method 1D was used.

Note: 32.2c was obtained according to a procedure similar to the one described for 32.2e (see 32E) except 13.4b was replaced by 3.4c in step 32.8.

$^1$H NMR (400 MHz, DMSO d$_6$) δ 9.00 (brs, 2H), 7.86 (d, 2H), 7.68 (t, 1H), 7.60 (d, 2H), 7.28 (m, 1H), 7.06 (d, 1H), 6.96 (d, 2H), 6.01 (s, 1H), 3.21 (brm, 4H), 2.81 (m, 2H), 2.10 (brm, 2H), 2.01 (brm, 2H), 1.00 (t, 3H)

Mass Spectral Analysis m/z=385.3 (M+H)$^+$

Elemental analysis:

$C_{21}H_{24}N_2O_3S$, 1HCl, 0.25H$_2$O

Theory: % C, 59.28; % H, 6.04; % N, 6.58.
Found: % C, 59.06; % H, 5.92; % N, 6.44.

EXAMPLE 32D 32D was obtained according to a procedure similar to the one described for 32A, with the following exceptions:

Step 32.2: 32.2a was replaced by 32.2d.

Note: 32.2d was obtained according to a procedure similar to the one described for 32.2e (see 32E) except 13.4b was replaced by 32.6 in step 32.8.

$^1$H NMR (400 MHz, DMSO d$_6$) δ 9.13 (brs, 2H), 7.90 (d, 2H), 7.64 (s, 1H), 7.56 (d, 2H), 7.27 (m, 1H), 7.06 (d, 1H), 6.95 (m, 2H), 6.01 (s, 1H), 3.22 (brm, 4H), 2.07 (brm, 4H), 1.12 (s, 9H)

Mass Spectral Analysis m/z=413.3 (M+H)$^+$

EXAMPLE 32E

Preparation of 32.2e:

13.4b (7.33 mL, 64.58 mmol, 3.3 eq) was added at room temperature to a solution of 32.5 (5 g, 19.57 mmol, 1 eq) in tetrahydrofuran (20 mL). The reaction was stirred at room temperature overnight. The mixture was concentrated under reduced pressure and dichloromethane was added. The mixture was washed with water, a saturated aqueous solution of sodium bicarbonate and brine, and then dried over sodium sulfate and filtered. The organic extracts were concentrated under reduced pressure and the crude product was used for the next step without further purification.

Yield: 40%

$^1$H NMR (400 MHz, DMSO d$_6$) δ 7.82 (s, 4H), 7.25 (s, 4H), 4.58 (s, 4H)

Mass Spectral Analysis m/z=337.9 (M+H)$^+$

Preparation of 32E:

32E was obtained according to a procedure similar to the one described for 32A, with the following exceptions:

Step 32.2: 32.2a was replaced by 32.2e.

$^1$H NMR (400 MHz, DMSO d$_6$) δ 9.06 (brs, 2H), 7.94 (d, 2H), 7.60 (d, 2H), 7.26 (m, 5H), 7.04 (d, 1H), 6.90 (m, 2H), 5.97 (s, 1H), 4.62 (s, 4H), 3.19 (brm, 4H), 2.03 (brm, 4H)

Mass Spectral Analysis m/z=459.3 (M+H)$^+$

EXAMPLE 32F 32F was obtained according to a procedure similar to the one described for 32A, with the following exceptions:

Step 32.2: 32.2a was replaced by 32.2f.

Note: 32.2f was obtained according to a procedure similar to the one described for 32.2e except 13.4b was replaced by 3.4e in step 32.8.

$^1$H NMR (400 MHz, DMSO d$_6$) δ 9.04 (brs, 2H), 7.86 (d, 2H), 7.72 (t, 1H), 7.59 (d, 2H), 7.28 (m, 1H), 7.06 (d, 1H), 6.95 (d, 2H), 6.01 (s, 1H), 3.22 brm, 4H), 2.57 (t, 2H), 2.10 (brm, 2H), 2.02 (brm, 2H), 1.65 (m, 1H), 0.83 (d, 6H)

Mass Spectral Analysis m/z=413.3 (M+H)$^+$

Elemental analysis:

$C_{23}H_{28}N_2O_3S$, 1HCl, 0.5H$_2$O

Theory: % C, 60.31; % H, 6.60; % N, 6.12.
Found: % C, 60.67; % H, 6.33; % N, 6.10.

EXAMPLE 32G 32G was obtained according to a procedure similar to the one described for 32A, with the following exceptions:

Step 32.2: 32.2a was replaced by 32.2g and Method 1D was used.

32.2g was obtained according to a procedure similar to the one described for 32.2e except 13.4b was replaced by 3.4h in step 32.8.

$^1$H NMR (400 MHz, DMSO d$_6$) δ 9.16 (brs, 2H), 7.87 (d, 2H), 7.70 (d, 1H), 7.59 (d, 2H), 7.28 (m, 1H), 7.06 (d, 1H), 6.95 (m, 2H), 6.01 (s, 1H), 3.24 (brm, 5H), 2.07 (brm, 4H), 0.98 (d, 6H)

Mass Spectral Analysis m/z=399.4 (M+H)$^+$

Elemental analysis:

$C_{22}H_{26}N_2O_3S$, 1HCl

Theory: % C, 60.75; % H, 6.26; % N, 6.44.
Found: % C, 60.58; % H, 6.29; % N, 6.36.

EXAMPLE 32H 32H was obtained according to a procedure similar to the one described for 32A, with the following exceptions:

Step 32.2: 32.2a was replaced by 32.2h.

32.2h was obtained according to a procedure similar to the one described for 32.2e except 13.4b was replaced by 3.4o in step 32.8.

¹H NMR (400 MHz, DMSO d₆) δ 9.09 (brs, 2H), 7.89 (d, 2H), 7.58 (d, 2H), 7.28 (m, 1H), 7.06 (d, 1H), 6.94 (m, 2H), 6.02 (s, 1H), 3.76 (m, 2H), 3.22 (brm, 4H), 2.05 (brm, 4H), 1.20 (d, 12H)

Mass Spectral Analysis m/z=441.4 (M+H)⁺

EXAMPLE 32I 32I was obtained according to a procedure similar to the one described for 32A, with the following exceptions:

Step 32.2: 32.2a was replaced by 32.2i.

32.2i was obtained according to a procedure similar to the one described for 32.2e except 13.4b was replaced by 13.4c in step 32.8.

¹H NMR (400 MHz, DMSO d₆) δ 9.03 (brs, 2H), 7.66 (d, 2H), 7.38 (d, 2H), 7.08 (m, 1H), 6.86 (d, 1H), 6.74 (m, 2H), 5.81 (s, 1H), 3.00 (brm, 6H), 2.82 (d, 2H), 1.87 (brm, 4H), 1.37 (m, 2H), 0.71 (m, 1H), 0.65 (t, 3H), 0.27 (m, 2H), 0.01 (m, 2H)

Mass Spectral Analysis m/z=453.3 (M+H)⁺

EXAMPLE 32J

Preparation of 32J:

Trifluoroacetic acid (5 mL, 64.90 mmol, 10.0 eq) was added drop wise to 32.3b (3.83 g, 7.47 mmol, 1.0 eq) at 0° C. The mixture was warmed to room temperature and stirring was continued for an additional 10 h at room temperature. The mixture was concentrated under reduced pressure. A saturated solution of sodium bicarbonate (50 mL) was added to the mixture, which was then extracted with dichloromethane. The organic phase was separated, washed with brine, dried over sodium sulfate, filtered and the filtrate was concentrated under reduced pressure. To a cold (0° C.) solution of the resulting oil in anhydrous dichloromethane (35 mL) was added drop wise a 2.0M solution of anhydrous hydrochloric acid in diethyl ether (17 mL, 35.70 mmol, 5.5 eq). The mixture was then stirred for 1 h at room temperature and concentrated under reduced pressure. Diethyl ether was added. The resulting precipitate was collected by filtration and washed with diethyl ether. The crude product was purified by column chromatography (eluent: dichloromethane/methanol mixtures of increasing polarity).

Yield: 10%

¹H NMR (400 MHz, DMSO d₆) δ 9.08 (m, 2H), 7.90 (m, 2H), 7.56 (m, 2H), 7.46 (m, 2H), 7.28 (m, 1H), 7.07 (m, 1H), 6.94 (m, 2H), 5.98 (s, 1H), 3.46 (m, 2H), 3.17 (m, 2H), 2.05 (m, 4H)

Mass Spectral Analysis m/z=357.4 (M+H)⁺

Elemental analysis:

$C_{19}H_{20}N_2O_3S$, 1HCl, 1H₂O

Theory: % C, 55.54; % H, 5.64; % N, 6.82.

Found: % C, 55.30; % H, 5.28; % N, 6.55.

EXAMPLE 32K

Preparation of 32.9a:

Triethylamine (0.96 mL, 6.88 mmol, 1.3 eq) was added to a solution of 20.2a (0.40 mL, 5.29 mmol, 1.0 eq) and 32.7 (1.0 g, 5.29 mmol, 1.0 eq) in acetonitrile (60 mL). The solution was refluxed for 1 h and then concentrated under reduced pressure. Methylene chloride was added and the organic mixture was washed with water. The organic mixture was dried over sodium sulfate, filtered, and concentrated under reduced pressure. The crude product was used for the next step without further purification.

Yield: 93%

¹HNMR (400 MHz, CDCl₃) δ 7.40 (d, 2H), 7.18 (d, 2H), 2.92 (q, 2H), 1.31 (t, 3H)

Preparation of 32.2j:

To a solution of 32.9a (1.07 g, 4.93 mmol, 1.0 eq) in acetic acid (7 mL) was added a 30% aqueous solution of hydrogen peroxide (3 mL). The mixture was heated at 90° C. for 2 h. The mixture was cooled to room temperature. Water was added and the mixture was extracted with methylene chloride. The organic mixture was then washed with a saturated aqueous sodium thiosulfate solution and brine. The organic mixture was dried over sodium sulfate and filtered. The filtrate was concentrated under reduced pressure. The crude product was used for the next step without further purification.

Yield: 92%

¹HNMR (400 MHz, CDCl₃) δ 7.78 (d, 2H), 7.72 (d, 2H), 3.11 (q, 2H), 1.28 (t, 3H)

Preparation of 32K:

32K was obtained according to a procedure similar to the one described for 32A, with the following exceptions:

Step 32.2: 32.2a was replaced by 32.2j and Method 1D was used.

¹H NMR (400 MHz, DMSO d₆) δ 8.86 (brs, 1H), 7.96 (d, 2H), 7.66 (d, 2H), 7.29 (m, 1H), 7.07 (d, 1H), 6.96 (d, 2H), 6.04 (s, 1H), 3.37 (m, 2H), 3.22 (m, 4H), 2.10 (m, 2H), 2.00 (m, 2H), 1.13 (t, 3H)

Mass Spectral Analysis m/z 370.2 (M+H)⁺

Elemental analysis:

$C_{21}H_{23}NO_3S$, 1HCl, 0.33H₂O

Theory: % C, 61.23; % H, 6.04; % N, 3.40; % S, 7.78.

Found: % C, 61.15; % H, 5.92; % N, 3.39; % S, 7.68.

EXAMPLE 32L 32L was obtained according to a procedure similar to the one described for 32A, with the following exceptions:

Step 32.2: 32.2a was replaced by 32.2k and Method 12A was used.

Note: 32.2k was obtained according to a procedure similar to the one described for 32.2j except 20.2a was replaced by 20.2b in step 32.6.

¹H NMR (400 MHz, DMSO d₆) δ 8.92 (brs, 1H), 7.96 (d, 2H), 7.66 (d, 2H), 7.29 (m, 1H), 7.07 (d, 1H), 6.96 (d, 2H), 6.04 (s, 1H), 3.31 (m, 2H), 3.22 (m, 4H), 2.10 (m, 2H), 2.00 (m, 2H), 1.58 (m, 2H), 0.94 (t, 3H)

Mass Spectral Analysis m/z=384.2 (M+H)⁺

Elemental analysis:

$C_{22}H_{25}NO_3S$, 1HCl, 0.5H₂O

Theory: % C, 61.60; % H, 6.34; % N, 3.27; % S, 7.47.

Found: % C, 61.88; % H, 6.28; % N, 3.36; % S, 7.36.

EXAMPLE 32M 32M was obtained according to a procedure similar to the one described for 32A, with the following exceptions:

Step 32.2: 32.2a was replaced by 32.2l and Method 12A was used.

Note: 32.2l was obtained according to a procedure similar to the one described for 32.2j except 20.2a was replaced by 2.8a in step 32.6.

¹H NMR (400 MHz, DMSO d₆) δ 8.93 (brs, 1H), 7.97 (d, 2H), 7.65 (d, 2H), 7.29 (m, 1H), 7.07 (d, 1H), 6.95 (m, 2H), 6.04 (s, 1H), 3.32 (m, 2H), 3.22 (m, 4H), 2.10 (m, 2H), 2.01 (m, 2H), 0.87 (m, 1H), 0.47 (m, 2H), 0.13 (m, 2H)

Mass Spectral Analysis m/z=396.2 (M+H)$^+$
Elemental analysis:
C$_{23}$H$_{25}$NO$_3$S, 1HCl
Theory: % C, 63.95; % H, 6.07; % N, 3.24; % S, 7.42.
Found: % C, 63.94; % H, 6.03; % N, 3.32; % S, 7.32.

EXAMPLE 32N 32N was obtained according to a procedure similar to the one described for 32A, with the following exceptions:
Step 32.2: 32.2a was replaced by 32.2m and Method 12A was used.
Note: 32.2m was obtained according to a procedure similar to the one described for 32.2j except 20.2a was replaced by 32.8a in step 32.6.
$^1$H NMR (400 MHz, DMSO d$_6$) δ 8.91 (brs, 1H), 7.98 (d, 2H), 7.66 (d, 2H), 7.29 (m, 1H), 7.07 (d, 1H), 6.96 (m, 2H), 6.04 (s, 1H), 3.32 (m, 2H), 3.22 (m, 4H), 2.10 (m, 2H), 2.02 (m, 2H), 1.62 (m, 1H), 1.46 (m, 2H), 0.84 (d, 6H)
Mass Spectral Analysis m/z=412.2 (M+H)$^+$
Elemental analysis:
C$_{24}$H$_{29}$NO$_3$S, 1HCl, 0.33H$_2$O
Theory: % C, 63.49; % H, 6.81; % N, 3.08.
Found: % C, 63.45; % H, 6.71; % N, 3.39.

EXAMPLE 32O 32O was obtained according to a procedure similar to the one described for 32A, with the following exceptions:
Step 32.2: 32.2a was replaced by 32.2n and Method 12A was used.
Note: 32.2n was obtained according to a procedure similar to the one described for 32.2p (see 32Q) except 32.8d was replaced by 32.8b in step 32.6.
$^1$H NMR (400 MHz, DMSO d$_6$) δ 8.93 (brm, 1H), 7.98 (d, 2H), 7.64 (d, 2H), 7.29 (m, 1H), 7.07 (d, 1H), 6.94 (m, 2H), 6.02 (s, 1H), 3.32 (m, 2H), 3.22 (m, 4H), 2.10 (m, 2H), 2.01 (m, 2H), 1.10 (s, 9H)
Mass Spectral Analysis m/z=412.2 (M+H)$^+$
Elemental analysis:
C$_{24}$H$_{29}$NO$_3$S, 1HCl, 0.33H$_2$O
Theory: % C, 63.49; % H, 6.81; % N, 3.08; % S, 7.06.
Found: % C, 63.49; % H, 6.70; % N, 3.25; % S, 6.78.

EXAMPLE 32P 32P was obtained according to a procedure similar to the one described for 32A, with the following exceptions:
Step 32.2: 32.2a was replaced by 32.2o and Method 12A was used.
Note: 32.2o was obtained according to a procedure similar to the one described for 32.2p (see 32Q) except 32.8d was replaced by 32.8c in step 32.6.
$^1$H NMR (400 MHz, DMSO d$_6$) δ 8.82 (brs, 2H), 7.93 (d, 2H), 7.66 (d, 2H), 7.29 (m, 1H), 7.07 (d, 1H), 6.96 (m, 2H), 6.05 (s, 1H), 3.47 (m, 1H), 3.23 (m, 4H), 2.10 (m, 2H), 2.00 (m, 2H), 1.19 (d, 6H)
Mass Spectral Analysis m/z=384.2 (M+H)$^+$
Elemental analysis:
C$_{22}$H$_{25}$NO$_3$S, 1HCl
Theory: % C, 62.92; % H, 6.24; % N, 3.34; % S, 7.63.
Found: % C, 63.18; % H, 6.26; % N, 3.46; % S, 7.54.

EXAMPLE 32Q

Preparation of 32.9b:
To a suspension of sodium hydride (0.33 g, 13.75 mmol, 1.3 eq) in N,N-dimethylformamide (10 mL) at 0° C. under nitrogen was added drop wise a solution of 32.7 (2.0 g, 10.58 mmol, 1.0 eq) in N,N-dimethylformamide (5 mL). The mixture was stirred for 10 min at 0° C. and 32.8d (1.48 mL, 10.58 mmol, 1.0 eq) was added drop wise. The mixture was allowed to warm to room temperature and stirring continued for a further 16 h at room temperature. The reaction was carefully quenched with water and the mixture was extracted with diethyl ether. The organic extracts were combined, dried over sodium sulfate, filtered and concentrated under reduced pressure. The crude product was used for the next step without further purification.
Yield: 87%
$^1$HNMR (400 MHz, CDCl$_3$) δ 7.38 (d, 2H), 7.18 (d, 2H), 2.87 (d, 2H), 1.45 (m, 5H), 0.88 (t, 6H)
Preparation of 32.2p:
To a solution of 32.9b (2.53 g, 9.26 mmol, 1.0 eq) in acetic acid (14 mL) was added a 30% aqueous solution of hydrogen peroxide (6 mL). The mixture was heated at 90° C. for 2 h. The mixture was cooled to room temperature. Water was added and the crude product was extracted with methylene chloride. The organic mixture was washed with a saturated aqueous sodium thiosulfate solution and brine. The mixture was dried over sodium sulfate and filtered. The filtrate was concentrated under reduced pressure. The crude product was used for the next step without further purification.
Yield: 80%
$^1$HNMR (400 MHz, CDCl$_3$) δ 7.78 (d, 2H), 7.71 (d, 2H), 3.00 (d, 2H), 1.88 (m, 1H), 1.46 (m, 4H), 0.82 (t, 6H)
Preparation of 32Q:
32Q was obtained according to a procedure similar to the one described for 32A, with the following exceptions:
Step 32.2: 32.2a was replaced by 32.2p and Method 12A was used.
(32Q) $^1$H NMR (400 MHz, DMSO d$_6$) δ 8.97 (brs, 2H), 7.99 (d, 2H), 7.65 (d, 2H), 7.29 (m, 1H), 7.07 (d, 1H), 6.94 (m, 2H), 6.03 (s, 1H), 3.23 (m, 6H), 2.10 (m, 2H), 2.02 (m, 2H), 1.73 (m, 1H), 1.40 (m, 4H), 0.77 (t, 6H)
Mass Spectral Analysis m/z=426.2 (M+H)$^+$
Elemental analysis:
C$_{25}$H$_{31}$NO$_3$S, 1HCl, 0.33H$_2$O
Theory: % C, 64.15; % H, 7.03; % N, 2.99; % S, 6.85.
Found: % C, 64.26; % H, 6.91; % N, 3.20; % S, 6.35.

EXAMPLE 32R

Preparation of 32.2q:
To a solution 4-bromo-N-methylaniline of (32.10) (0.74 g, 4 mmol, 1.0 eq) in dry dichloromethane (50 mL) at 0° C. was slowly added triethylamine (2.23 mL, 8 mmol, 2.0 eq). The mixture was stirred for 10 min at room temperature and 19.8a (0.63 mL, 6 mmol, 1.5 eq) was added drop wise to the reaction mixture. The reaction mixture was slowly warmed to room temperature and was stirred for 10 h at room temperature. Dichloromethane (100 mL) was added to the mixture which was washed with a 1M aqueous solution of hydrochloric acid (3×50 mL), a saturated aqueous sodium bicarbonate (2×50 mL) and brine. The organic extracts were dried over sodium sulfate, filtered, and concentrated under reduced pressure to give the crude product, which was used for next step without purification.
$^1$H NMR (400 MHz, CDCl$_3$) δ 7.56 (m, 2H), 7.08 (m, 2H), 3.23 (s, 3H), 2.49 (m, 1H), 1.02 (d, 6H)

Mass Spectral Analysis m/z=256.15 (M+H)+

Preparation of 32R:

32R was obtained according to a procedure similar to the one described for 32A, with the following exceptions:

Step 32.2: 32.2a was replaced by 32.2q and Method 1D was used.

$^1$H NMR (400 MHz, DMSO $d_6$) δ 8.91 (brs, 2H), 7.43 (m, 4H), 7.27 (m, 1H), 7.01 (m, 3H), 5.96 (s, 1H), 3.40-3.14 (m, 8H), 2.04 (m, 4H), 0.96 (m, 6H)

Mass Spectral Analysis m/z=377.3 (M+H)+

Elemental analysis:

$C_{24}H_{28}N_2O_3$, 1HCl, 2/3$H_2O$

Theory: % C, 67.83; % H, 7.19; % N, 6.59.

Found: % C, 67.78; % H, 7.19; % N, 6.50.

EXAMPLE 32S 32S was obtained according to a procedure similar to the one described for 32A, with the following exceptions:

Step 32.2: 32.2a was replaced by 32.2r and Method 1D was used.

Note: 32.2r was obtained according to a procedure similar to the one described for 32.2q except 19.8a was replaced by 19.8b in step 32.9.

$^1$H NMR (400 MHz, DMSO $d_6$) δ 8.98 (brs, 2H), 7.47 (m, 2H), 7.33 (m, 2H), 7.27 (m, 1H), 7.00 (m, 3H), 5.96 (s, 1H), 3.40-3.12 (m, 7H), 2.25-1.94 (m, 5H), 1.48 (m, 2H), 1.30 (m, 2H), 0.76 (m, 6H)

Mass Spectral Analysis m/z=405.4 (M+H)+

Elemental analysis:

$C_{26}H_{32}N_2O_2$, 1HCl, 1/5$H_2O$

Theory: % C, 70.24; % H, 7.57; % N, 6.30.

Found: % C, 70.20; % H, 7.50; % N, 6.19.

EXAMPLE 32T 32T was obtained according to a procedure similar to the one described for 32A, with the following exceptions:

Step 32.2: 32.2a was replaced by 32.2s and Method 1D was used.

Note: 32.2s was obtained according to a procedure similar to the one described for 32.2q except 19.8a was replaced by 32.11a in step 32.9.

$^1$H NMR (400 MHz, DMSO $d_6$) δ 8.95 (brs, 2H), 7.44 (m, 2H), 7.37 (m, 2H), 7.27 (m, 1H), 7.00 (m, 3H), 5.96 (s, 1H), 3.21 (m, 7H), 2.03 (m, 7H), 0.81 (m, 6H)

Mass Spectral Analysis m/z=391.3 (M+H)+

Elemental analysis:

$C_{25}H_{30}N_2O_2$, 1HCl, 0.1$H_2O$

Theory: % C, 70.03; % H, 7.33; % N, 6.53.

Found: % C, 69.97; % H, 7.33; % N, 6.57.

EXAMPLE 32U 32U was obtained according to a procedure similar to the one described for 32A, with the following exceptions:

Step 32.2: 32.2a was replaced by 32.2t and Method 1D was used.

Note: 32.2t was obtained according to a procedure similar to the one described for 32.2q except 19.8a was replaced by 6.7 in step 32.9.

$^1$H NMR (400 MHz, DMSO $d_6$) δ 8.95 (m, 2H), 7.42 (m, 4H), 7.26 (m, 1H), 7.00 (m, 3H), 5.93 (s, 1H), 3.20 (m, 7H), 2.04 (m, 4H), 1.83 (s, 3H)

Mass Spectral Analysis m/z=349.2 (M+H)+

Elemental analysis:

$C_{22}H_{24}N_2O_2$, 1HCl, 1.4$H_2O$

Theory: % C, 64.43; % H, 6.83; % N, 6.83.

Found: % C, 64.49; % H, 6.87; % N, 6.89.

EXAMPLE 32V 32V was obtained according to a procedure similar to the one described for 32A, with the following exceptions:

Step 32.2: 32.2a was replaced by 32.2u and Method 1D was used.

Note: 32.2u was obtained according to a procedure similar to the one described for 32.2q except 19.8a was replaced by 32.11b in step 32.9.

$^1$H NMR (400 MHz, DMSO $d_6$) δ 8.95 (m, 2H), 7.42 (m, 4H), 7.26 (m, 1H), 7.05 (m, 1H), 6.96 (m, 2H), 5.94 (s, 1H), 3.20 (m, 7H), 2.05 (m, 6H), 1.38 (m, 3H), 0.74 (m, 6H)

Mass Spectral Analysis m/z=405.3 (M+H)+

Elemental analysis:

$C_{26}H_{32}N_2O_2$, 1HCl, 1.5$H_2O$

Theory: % C, 66.72; % H, 7.75; % N, 5.99.

Found: % C, 66.57; % H, 7.67; % N, 5.93.

EXAMPLE 32W 32W was obtained according to a procedure similar to the one described for 32A, with the following exceptions:

Step 32.2: 32.2a was replaced by 32.2v and Method 1D was used.

Note: 32.2v is commercially available.

$^1$H NMR (400 MHz, DMSO $d_6$) δ 8.91 (brs, 2H), 7.74 (m, 2H), 7.37 (m, 2H), 7.25 (m, 1H), 7.02 (m, 2H), 6.94 (m, 1H), 5.86 (s, 1H), 3.87 (t, 2H), 3.20 (m, 4H), 2.52 (t, 2H), 2.08 (m, 4H), 1.99 (m, 2H)

Mass Spectral Analysis m/z=361.2 (M+H)+

Elemental analysis:

$C_{23}H_{24}N_2O_2$, 1HCl, 0.5$H_2O$

Theory: % C, 68.06; % H, 6.46; % N, 6.90. Found: % C, 68.10; % H, 6.42; % N, 6.96.

EXAMPLE 32X 32X was obtained according to a procedure similar to the one described for 32A, with the following exceptions:

Step 32.2: 32.2a was replaced by 32.2w and Method 1D was used.

Note: 32.2w is commercially available.

$^1$H NMR (400 MHz, DMSO $d_6$) δ 8.82 (brs, 2H), 8.07 (d, 1H), 7.24 (m, 2H), 7.14 (d, 1H), 7.02 (m, 2H), 6.94 (m, 1H), 5.82 (s, 1H), 4.13 (t, 2H), 3.19 (m, 6H), 2.18 (s, 3H), 2.06 (m, 2H), 1.96 (m, 2H)

Mass Spectral Analysis m/z=361.3 (M+H)+

Elemental analysis:

$C_{23}H_{24}N_2O_2$, 1HCl, 0.4$H_2O$

Theory: % C, 68.36; % H, 6.44; % N, 6.93.

Found: % C, 68.41; % H, 6.23; % N, 6.93.

EXAMPLE 32Y 32Y was obtained according to a procedure similar to the one described for 32A, with the following exceptions:

Step 32.2: 32.2a was replaced by 32.2X and Method 1D was used.

Note: 32.2x was obtained according to a procedure similar to the one described for 32.2q except 19.8a was replaced by 32.11c in step 32.9.

$^1$H NMR (400 MHz, DMSO $d_6$) δ 9.04 (brs, 2H), 7.41 (m, 4H), 7.26 (m, 1H), 7.00 (m, 3H), 5.94 (s, 1H), 3.20 (m, 7H), 2.05 (m, 6H), 1.49 (m, 2H), 3.79 (m, 3H)

Mass Spectral Analysis m/z=377.4 (M+H)+
Elemental analysis:
$C_{24}H_{28}N_2O_2$, 1HCl, 1.1$H_2O$
Theory: % C, 66.61; % H, 7.27; % N, 6.47.
Found: % C, 66.51; % H, 7.20; % N, 6.39.

EXAMPLE 32Z 32Z was obtained according to a procedure similar to the one described for 32A, with the following exceptions:
Step 32.2: 32.2a was replaced by 32.2y and Method 1D was used.
Note: 32.2y was obtained according to a procedure similar to the one described for 32.2q except 19.8a was replaced by 32.11d in step 32.9.
$^1$H NMR (400 MHz, DMSO $d_6$) δ 8.98 (brs, 2H), 7.41 (m, 4H), 7.26 (m, 1H), 7.00 (m, 3H), 5.94 (s, 1H), 3.20 (m, 7H), 2.05 (m, 6H), 1.46 (m, 2H), 1.18 (m, 2H), 3.79 (m, 3H)
Mass Spectral Analysis m/z=391.4 (M+H)+
Elemental analysis:
$C_{25}H_{30}N_2O_2$, 1HCl, 0.9$H_2O$
Theory: % C, 67.75; % H, 7.46; % N, 6.32.
Found: % C, 67.71; % H, 7.45; % N, 6.30.

EXAMPLE 33A 33A was obtained according to a procedure similar to the one described for 32A, with the following exception:
Step 32.2: 32.2a was replaced by 33.1a (see also step 33.2).
Note: 33.1a was commercially available.
$^1$H NMR (400 MHz, DMSO $d_6$) δ 7.98 (d, 1H), 7.89 (dd, 1H), 7.84 (d, 1H), 7.29 (m, 1H), 7.01 (m, 2H), 6.42 (s, 1H), 3.07 (m, 4H), 1.95 (m, 4H)
Mass Spectral Analysis m/z=284.9 (M+H)+

EXAMPLE 33B 33B was obtained according to a procedure similar to the one described for 32A, with the following exceptions:
Step 32.2: 32.2a was replaced by 33.1b and Method 33A was used (see also step 33.2).
Note: 33.1b was commercially available.
$^1$H NMR (400 MHz, DMSO $d_6$) δ 9.19 (m, 3H), 8.86 (m, 2H), 7.29 (m, 1H), 7.07 (m, 1H), 6.97 (m, 2H), 6.15 (s, 1H), 3.22 (m, 4H), 2.08 (m, 4H)
Mass Spectral Analysis m/z=279.9 (M+H)+

EXAMPLE 33C 33C was obtained according to a procedure similar to the one described for 32A, with the following exceptions:
Step 32.2: 32.2a was replaced by 33.1c and Method 33A was used (see also step 33.2).
Note: 33.1c is commercially available.
$^1$H NMR (400 MHz, DMSO $d_6$) δ 7.73 (m, 1H), 7.21 (m, 1H), 6.90 (m, 5H), 5.94 & 5.88 (2s, 1H rotamer), 3.6-2.7 (m, 7H), 1.91 (m, 4H)
Mass Spectral Analysis m/z=282.0 (M+H)+

EXAMPLE 33D 33D was obtained according to a procedure similar to the one described for 32A, with the following exceptions:
Step 32.2: 32.2a was replaced by 33.1d and Method 33A was used (see also step 33.2).
Note: 33.1d is commercially available.
$^1$H NMR (400 MHz, DMSO $d_6$) δ 8.87 (m, 2H), 7.80 (s, 2H), 7.56 (m, 1H), 7.32 (m, 2H), 7.26 (m, 1H), 7.15 (m, 2H), 6.18 (s, 1H), 3.30-3.07 (m, 4H), 2.03 (m, 4H)
Mass Spectral Analysis m/z=362.9 (M+H)+

EXAMPLE 33E 33E was obtained according to a procedure similar to the one described for 32A, with the following exceptions:
Step 32.2: 32.2a was replaced by 33.1e and Method 33A was used (see also step 33.2).
Note: 33.1e is commercially available.
$^1$H NMR (400 MHz, DMSO $d_6$) δ 8.99 (brs, 2H), 8.80 (s, 1H), 8.15 (m, 1H), 8.08 (m, 1H), 7.30 (m, 1H), 7.07 (m, 1H), 6.96 (m, 2H), 6.17 (s, 1H), 3.23 (m, 4H), 2.08 (m, 4H)
Mass Spectral Analysis m/z=303.9 (M+H)+

EXAMPLE 33F

Preparation of 33.1f:
To a stirred solution of 33.3 (3 g, 14.85 mmol, 1.0 eq) in acetonitrile (20 mL) was slowly added diisopropylethylamine (6.2 mL, 35.64 mmol, 2.4 eq) and diethylamine (1.12) (3.1 mL, 29.70 mmol, 2 eq) at room temperature. The mixture was stirred for 10 min at room temperature, cooled to 0° C. and O-benzotriazol-1-yl-N,N,N',N'-tetramethyluronium tetrafluoroborate (TBTU) (5.72 g, 17.82 mmol, 1.2 eq) was added portion wise. The reaction mixture was slowly warmed to room temperature and stirred for 10 h at room temperature. The volatiles were removed under reduced pressure and the residue was partitioned between ethyl acetate (200 mL) and a 1M aqueous solution of sodium bicarbonate (100 mL). The organic phase was washed with a 1M aqueous solution of sodium bicarbonate (2×50 mL), a 1M aqueous solution of hydrochloric acid (3×50 mL) and brine. The organic phase was dried over sodium sulfate, filtered, and concentrated under reduced pressure. The crude product was purified by column chromatography (eluent: hexane/ethyl acetate mixtures of increasing polarity).
Yield: 100%
$^1$H NMR (400 MHz, $CDCl_3$) δ 8.72 (d, 1H), 8.55 (d, 1H), 7.87 (m, 1H), 3.56 (q, 2H), 3.27 (q, 2H), 1.26 (t, 3H), 1.16 (t, 3H)
Mass Spectral Analysis m/z=256.81 (M+H)+
Preparation of 33F:
33F was obtained according to a procedure similar to the one described for 32A, with the following exceptions:
Step 32.2: 32.2a was replaced by 33.1f and Method 33A was used (see also step 33.2).
$^1$H NMR (400 MHz, DMSO $d_6$) δ 9.07 (brs, 2H), 8.65 (m, 2H), 7.80 (m, 1H), 7.29 (m, 1H), 7.07 (m, 1H), 6.96 (m, 2H), 6.09 (s, 1H), 3.52-3.10 (m, 8H), 2.05 (m, 4H), 1.12 (m, 6H)
Mass Spectral Analysis m/z=378.3 (M+H)+

EXAMPLE 33G

Preparation of 33.1g:
To a stirred solution of 33.4 (3 g, 14.85 mmol, 1.0 eq) in acetonitrile (20 mL) was slowly added diisopropylethylamine (6.2 mL, 35.64 mmol, 2.4 eq) and diethylamine (1.12)

(3.1 mL, 29.70 mmol, 2 eq) at room temperature. The mixture was stirred for 10 min, cooled to 0° C. and O-benzotriazol-1-yl-N,N,N',N'-tetramethyluronium tetrafluoroborate (TBTU) (5.72 g, 17.82 mmol, 1.2 eq) was added portion wise. The reaction mixture was slowly warmed to room temperature and stirred for 10 h at room temperature. The volatiles were removed under reduced pressure and the residue was partitioned between ethyl acetate (200 mL) and a 1M aqueous solution of sodium bicarbonate (100 mL). The organic phase was washed with a 1M aqueous solution of sodium bicarbonate (2×50 mL), a 1M aqueous solution of hydrochloric acid (3×50 mL) and brine. The organic phase was dried over sodium sulfate, filtered, and concentrated under reduced pressure. The crude product was purified by column chromatography (eluent: hexane/ethyl acetate mixtures of increasing polarity).

Yield: 100%

$^1$H NMR (400 MHz, CDCl$_3$) δ 7.64 (d, 1H), 7.59 (dd, 1H), 7.52 (dd, 1H), 3.54 (q, 2H) 3.38 (q, 2H), 1.25 (m, 6H)

Mass Spectral Analysis m/z=256.7 (M+H)$^+$

Preparation of 33G:

33G was obtained according to a procedure similar to the one described for 32A, with the following exceptions:

Step 32.2: 32.2a was replaced by 33.1g and Method 33A was used (see also step 33.2).

(33G) $^1$H NMR (400 MHz, DMSO d$_6$) δ 9.01 (m, 2H), 8.01 (m, 1H), 7.59 (m, 2H), 7.26 (m, 1H), 7.13 (m, 1H), 7.04 (m, 1H), 6.93 (m, 1H), 6.11 (s, 1H), 3.51-3.11 (m, 8H), 2.05 (m, 4H), 1.15 (t, 3H), 1.06 (t, 3H)

Mass Spectral Analysis m/z=378.2 (M+H)$^+$

EXAMPLE 33H 33H was obtained according to a procedure similar to the one described for 32A, with the following exceptions:

Step 32.2: 32.2a was replaced with 33.1h and Method 1D was used (see also step 33.2).

Note: 33.1h was obtained according to a procedure similar to the one described for 1.13 (see 1N) except 1.12 was replaced by 3.4j in step 1.8 (see also step 33.9).

$^1$H NMR (400 MHz, DMSO d$_6$) δ 8.99 (brs, 1H), 8.61 (d, 1H), 7.91 (dd, 1H), 7.64 (d, 1H), 7.29 (m, 1H), 7.06 (d, 1H), 6.97 (m, 2H), 6.09 (s, 1H), 3.23 (m, 4H), 3.04 (s, 3H), 2.99 (s, 3H), 2.11 (m, 2H), 2.02 (m, 2H)

Mass Spectral Analysis m/z=350.2 (M+H)$^+$

Elemental analysis:

$C_{21}H_{23}N_3O_2$, 1.35HCl, 0.8H$_2$O

Theory: % C, 61.06; % H, 6.33; % N, 10.17; % Cl, 11.59.

Found: % C, 60.72; % H, 6.23; % N, 10.05; % Cl, 11.26.

EXAMPLE 33I 33I was obtained according to a procedure similar to the one described for 32A, with the following exceptions:

Step 32.2: 32.2a was replaced with 33.1i and Method 1D was used (see also step 33.2).

Note: 33.1i was obtained according to a procedure similar to the one described for 1.13 (see 1N) except 1.12 was replaced by 3.4c in step 1.8 (see also step 33.9).

$^1$H NMR (400 MHz, DMSO d$_6$) δ 8.87 (m, 2H), 8.62 (d, 1H), 8.11 (d, 1H), 7.99 (dd, 1H), 7.30 (m, 1H), 7.08 (d, 1H), 6.96 (m, 2H), 6.10 (s, 1H), 3.35 (m, 2H), 3.24 (m, 4H), 2.11 (m, 2H), 2.02 (m, 2H), 1.14 (t, 3H)

Mass Spectral Analysis m/z=350.2 (M+H)$^+$

Elemental analysis:

$C_{21}H_{23}N_3O_2$, 1.4HCl, 1.8H$_2$O

Theory: % C, 58.26; % H, 6.52; % N, 9.71; % Cl, 11.47.

Found: % C, 58.26; % H, 6.23; % N, 9.59; % Cl, 11.83.

EXAMPLE 33J 33J was obtained according to a procedure similar to the one described for 32A, with the following exceptions:

Step 32.2: 32.2a was replaced with 33.1j and Method 1D was used (see also step 33.2).

Note: 33.1j was obtained according to a procedure similar to the one described for 1.13 (see 1N) except 1.12 was replaced by 3.4b in step 1.8 (see also step 33.9).

$^1$H NMR (400 MHz, DMSO d$_6$) δ 8.94 (brs, 1H), 8.83 (m, 1H), 8.62 (d, 1H), 8.11 (d, 1H), 7.98 (dd, 1H), 7.30 (m, 1H), 7.08 (d, 1H), 6.96 (m, 2H), 6.10 (s, 1H), 3.22 (m, 4H), 2.84 (d, 3H), 2.11 (m, 2H), 2.02 (m, 2H)

Mass Spectral Analysis m/z=336.2 (M+H)$^+$

Elemental analysis:

$C_{20}H_{21}N_3O_2$, 1.1HCl, 0.8H$_2$O

Theory: % C, 61.61; % H, 6.13; % N, 10.78; % Cl, 10.00.

Found: % C, 61.84; % H, 5.90; % N, 10.75; % Cl, 10.01.

EXAMPLE 33K

Preparation of 33.6:

To a mixture of a 2.5M solution of n-butyl lithium in hexanes (0.84 mL, 2.1 mmol, 1.05 eq) and toluene (4 mL) at −78° C. was added a solution of 33.5 (0.57 g, 2.0 mmol, 1.0 eq) in toluene (2 mL). The reaction was stirred for 1 h at −78° C. The reaction was quenched with freshly crushed dry ice. The mixture was warmed slowly to room temperature and was stirred for 2 h at room temperature. The mixture was concentrated under reduced pressure and the resulting solid was treated with acetic acid. The solid was collected by filtration, dried under vacuum and used for the next step without further purification.

Yield: 62%

$^1$H NMR (400 MHz, CD$_3$OD) δ 8.90 (s, 2H)

Preparation of 33.7:

To a solution of 33.6 (0.055 g, 0.27 mmol, 1.0 eq) in methylene chloride (5 mL) was added oxalyl chloride (0.050 mL, 0.58 mmol, 2.1 eq). The mixture was refluxed for 1 h and concentrated under reduced pressure. The crude acyl chloride was used for the next step without further purification.

Preparation of 33.1k:

To a solution of 33.7 (0.060 g, 0.27 mmol, 1.0 eq) in tetrahydrofuran (2.5 mL) was added 1.12 (0.11 mL, 1.06 mmol, 4.0 eq). The mixture was stirred for 16 h and then diluted with ethyl acetate. The organic mixture was washed with water, with a saturated aqueous solution of sodium bicarbonate, a 1N aqueous solution of hydrochloric acid and brine. The organic mixture was dried over sodium sulfate, filtered, concentrated under reduced pressure and the crude product was used for the next step without further purification. Note: the product was isolated with a 17% impurity corresponding to N,N-diethyl-2-iodopyrimidine-5-carboxamide.

Yield: 86%

$^1$H NMR (400 MHz, CDCl$_3$) δ 8.82 (s, 2H), 3.56 (q, 2H), 3.20 (q, 2H), 1.28 (t, 3H), 1.18 (t, 3H)

Preparation of 33K:

33K was obtained according to a procedure similar to the one described for 32A, with the following exceptions:

Step 32.2: 32.2a was replaced by 33.1k and Method 12A (see was used (see also step 33.2).

¹H NMR (400 MHz, DMSO d₆) δ 8.81 (m, 2H), 7.18 (m, 1H), 6.92 (m, 2H), 6.85 (m, 1H), 6.06 (s, 0.8H), 6.04 (s, 0.2H), 3.41 (q, 2H), 3.06 (q, 2H), 2.86 (m, 2H), 2.76 (m, 2H), 1.73 (brm, 4H), 1.10 (t, 3H), 1.00 (t, 3H)

Mass Spectral Analysis m/z=379.3 (M+H)⁺

EXAMPLE 33L

Preparation of 33L:

To a solution of 33.2a (0.27 g, 0.67 mmol, 1 eq) in dry dichloromethane (15 mL) was added dropwise a 4.0M solution of hydrogen chloride in dioxane (1.34 mL, 5.35 mmol, 8 eq). The reaction mixture was stirred at room temperature for 10 h and concentrated under reduced pressure. The crude mixture (containing a mixture of 33E and 33L) was purified by column chromatography (eluent: dichloromethane/methanol/ammonium hydroxide mixture of increasing polarity), affording the 33L in a pure form.

¹H NMR (400 MHz, DMSO d₆) δ 8.59 (d, 1H), 8.17 (s, 1H), 8.09 (d, 1H), 7.95 (dd, 1H), 7.71 (s, 1H), 7.23 (m, 1H), 6.97 (d, 1H), 6.91 (m, 2H), 6.02 (s, 1H), 2.91 (m, 2H), 2.77 (m, 2H), 1.82 (m, 2H), 1.73 (m, 2H)

Mass Spectral Analysis m/z=321.9

EXAMPLE 34A

Preparation of 34.1a:

To a stirred solution of 34.3 (2.5 g, 12.38 mmol, 1.0 eq) in acetonitrile (20 mL) was slowly added diisopropylethylamine (4.74 mL, 27.24 mmol, 2.2 eq) and diethylamine (1.12) (2.56 mL, 24.76 mmol, 2.0 eq) at room temperature. The mixture was stirred for 10 min at room temperature, cooled to 0° C. and O-benzotriazol-1-yl-N,N,N',N'-tetramethyluronium tetrafluoroborate (TBTU) (4.37 g, 13.62 mmol, 1.1 eq) was added portion wise to the reaction mixture. The reaction mixture was slowly warmed to room temperature and stirred for 10 h at room temperature. The volatiles were removed under reduced pressure and the residue was partitioned between ethyl acetate (200 mL) and 1M aqueous sodium bicarbonate (100 mL). The organic phase was washed with a 1M aqueous solution of sodium bicarbonate (2×50 mL), with a 1M aqueous solution of hydrochloric acid (3×50 mL) and brine. The organic phase was dried over sodium sulfate, filtered, and concentrated under reduced pressure. The crude product was purified by column chromatography (eluent: hexane/ethyl acetate mixtures of increasing polarity).

Yield: 78%

¹H NMR (400 MHz, CDCl₃) δ 8.41 (m, 1H), 7.59 (m, 1H), 7.55 (m, 1H), 3.55 (q, 2H), 3.27 (q, 2H), 1.25 (t, 3H), 1.15 (t, 3H)

Mass Spectral Analysis m/z=257.04 (M+H)⁺

Preparation of 34A:

34A was obtained according to a procedure similar to the one described for 32A, with the following exceptions:

Step 32.2: 32.2a was replaced by 34.1a (see also step 34.2).

¹H NMR (400 MHz, DMSO d₆) δ 8.94 (brm, 2H), 8.64 (s, 1H), 7.92 (dd, 1H), 7.65 (d, 1H), 7.29 (m, 2H), 7.05 (d, 1H), 6.96 (t, 1H), 6.22 (s, 1H), 3.48 (m, 2H), 3.24 (brm, 6H), 2.05 (brm, 4H), 1.14 (brd, 6H)

Mass Spectral Analysis m/z=378.4 (M+H)⁺

Elemental analysis:

C₂₃H₂₇N₃O₂, 1HCl, 1.3H₂O

Theory: % C, 63.16; % H, 7.05; % N, 9.61.

Found: % C, 63.05; % H, 6.75; % N, 9.50.

EXAMPLE 34B 34B was obtained according to a procedure similar to the one described for 32A, with the following exceptions:

Step 32.2: 32.2a was replaced by 34.1b (see also step 34.2).

Note: 34.1b was obtained according to a procedure similar to the one described for 34.1a except 1.12 was replaced by 3.4o in step 34.4.

¹H NMR (400 MHz, DMSO d₆) δ 9.04 (brs, 2H), 8.59 (d, 1H), 7.85 (dd, 1H), 7.64 (d, 1H), 7.28 (m, 2H), 7.05 (d, 1H), 6.96 (t, 1H), 6.21 (s, 1H), 3.67 (m, 2H), 3.22 (brm, 4H), 2.06 (brm, 4H), 1.45 (brs, 6H), 1.15 (brs, 6H)

Mass Spectral Analysis m/z=406.4 (M+H)⁺

Elemental analysis:

C₂₅H₃₁N₃O₂, 1.5HCl, 0.66H₂O

Theory: % C, 63.59; % H, 7.22; % N, 8.90; % Cl, 11.26.

Found: % C, 63.68; % H, 7.21; % N, 8.99; % Cl, 11.28.

EXAMPLE 34C

Preparation of 34.1c:

To a stirred solution of 34.4 (2.1 g, 10 mmol, 1.0 eq) in acetonitrile (20 mL) was slowly added diisopropylethylamine (4.2 mL, 24 mmol, 2.4 eq) and diethylamine (1.12) (2.1 mL, 20 mmol, 2 eq) at room temperature. The mixture was stirred for 10 min at room temperature, cooled to 0° C. and O-benzotriazol-1-yl-N,N,N',N'-tetramethyluronium tetrafluoroborate (TBTU) (3.85 g, 12 mmol, 1.2 eq) was added portion wise. The reaction mixture was slowly warmed to room temperature and stirred for 10 h at room temperature. The volatiles were removed under reduced pressure and the residue was partitioned between ethyl acetate (200 mL) and a 1M aqueous solution of sodium bicarbonate (100 mL). The organic phase was washed with a 1M aqueous solution of sodium bicarbonate (2×50 mL), with a 1N aqueous solution of hydrochloric acid (3×50 mL) and brine, dried over sodium sulfate and filtered. The filtrate was concentrated under reduced pressure. The crude product was used for next step without further purification.

Mass Spectral Analysis m/z=262.1 (M+H)⁺

Preparation of 34C:

34C was obtained according to a procedure similar to the one described for 32A, with the following exceptions:

Step 32.2: 32.2a was replaced by 34.1c (see also step 34.2).

¹H NMR (400 MHz, DMSO d₆) δ 9.07 (brs, 2H), 7.41 (d, 1H), 7.37 (d, 1H), 7.31 (t, 1H), 7.22 (d, 1H), 7.07 (d, 1H), 7.02 (t, 1H), 6.12 (s, 1H), 3.50 (brm, 4H), 3.21 (brm, 4H0, 2.03 (brm, 4H), 1.18 (brt, 6H)

Mass Spectral Analysis m/z=383.3 (M+H)⁺

Elemental analysis:

C₂₂H₂₆N₂O₂S, 1HCl

Theory: % C, 63.07; % H, 6.50; % N, 6.69.

Found: % C, 63.03; % H, 6.52; % N, 6.61.

EXAMPLE 34D 34D was obtained according to a procedure similar to the one described for 32A, with the following exceptions:

Step 32.2: 32.2a was replaced by 34.1d (see also step 34.2).

Note: 34.1d was obtained according to a procedure similar to the one described for 34.1c except 1.12 was replaced by 3.4o in step 34.5.

¹H NMR (400 MHz, DMSO d₆) δ 8.93 (brs, 2H), 7.38 (d, 1H), 7.31 (t, 1H), 7.26 (d, 1H), 7.19 (d, 1H), 7.07 (d, 1H), 7.02

(t, 1H), 6.10 (s, 1H), 3.97 (brs, 2H), 3.21 (brm, 4H), 2.07 (brm, 2H), 1.97 (brm, 2H), 1.31 (brd, 12H)

Mass Spectral Analysis m/z=411.4 (M+H)$^+$

Elemental analysis: $C_{24}H_{30}N_2O_2S$, 1HCl,

Theory: % C, 64.48; % H, 6.99; % N, 6.27.

Found: % C, 64.25; % H, 7.01; % N, 6.22.

EXAMPLE 34E

Preparation of 34.1e:

To a stirred solution of 34.5 (4.58 g, 17.5 mmol, 1.0 eq) in dichloromethane (100 mL) at 0° C. was slowly added triethylamine (7.32 mL, 52.5 mmol, 3 eq) followed by drop wise addition of diethylamine (1.12) (3.64 mL, 35.0 mmol, 2.0 eq). The reaction mixture was kept at 0° C. for 30 min. and then stirred at room temperature for 3 h. The mixture was washed with a 1N aqueous solution of hydrochloric acid (3×50 mL) and brine. The organic phase was dried over sodium sulfate, filtered and concentrated under reduced pressure to give the crude product, which was used for the next step without further purification.

Yield: 100%

$^1$H NMR (400 MHz, CDCl$_3$) δ 7.30 (d, 1H), 7.05 (d, 1H), 3.24 (q, 4H), 1.19 (t, 6H)

Mass Spectral Analysis m/z=297.92 (M+H)$^+$

Preparation of 34E:

34E was obtained according to a procedure similar to the one described for 32A, with the following exceptions:

Step 32.2: 32.2a was replaced by 34.1e (see also step 34.2).

(34E) $^1$H NMR (400 MHz, DMSO d$_6$) δ 8.98 (brs, 2H), 7.68 (d, 1H), 7.34 (brm, 3H), 7.06 (m, 2H), 6.23 (s, 1H), 3.22 (brm, 8H), 2.03 (brm, 4H), 1.12 (m, 6H)

Mass Spectral Analysis m/z=419.2 (M+H)$^+$

EXAMPLE 34F

Preparation of 34.1f:

To a stirred solution of 34.6 (2 g, 10.47 mmol, 1.0 eq) in acetonitrile (20 mL) was slowly added diisopropylethylamine (4 mL, 23.03 mmol, 2.2 eq) and diethylamine (1.12) (2.1 mL, 20.94 mmol, 2.0 eq) at room temperature. The mixture was stirred for 10 min at room temperature, cooled to 0° C. and O-benzotriazol-1-yl-N,N,N',N'-tetramethyluronium tetrafluoroborate (TBTU) (3.7 g, 11.52 mmol, 1.1 eq) was added portion wise. The reaction mixture was slowly warmed to room temperature and stirred for 10 h at room temperature. The volatiles were removed under reduced pressure and the residue was partitioned between ethyl acetate (200 mL) and a 1M aqueous solution of sodium bicarbonate (100 mL). The organic phase was washed with a 1M aqueous solution of sodium bicarbonate (2×50 mL), a 1M aqueous solution of hydrochloric acid (3×50 mL) and brine. The organic phase was dried over sodium sulfate, filtered, and concentrated under reduced pressure. The crude product was purified by column chromatography (eluent: hexane/ethyl acetate mixtures of increasing polarity).

Yield: 91%

$^1$H NMR (400 MHz, CDCl$_3$) δ 6.99 (d, 1H), 6.41 (d, 1H), 3.54 (brs, 4H), 1.26 (brs, 6H)

Mass Spectral Analysis m/z=246.0 (M+H)$^+$

Preparation of 34F:

34F was obtained according to a procedure similar to the one described for 32A, with the following exceptions:

Step 32.2: 32.2a was replaced by 34.1f (see also step 34.2).

$^1$H NMR (400 MHz, DMSO d$_6$) δ 9.05 (brs, 2H), 7.52 (d, 1H), 7.32 (t, 1H), 7.07 (brm, 3H), 6.91 (d, 1H), 6.26 (s, 1H), 3.50 (brs, 4H), 3.20 (brm, 4H), 2.05 (brm, 4H), 1.17 (brs, 6H)

Mass Spectral Analysis m/z=367.3 (M+H)$^+$

EXAMPLE 34G 34G was obtained according to a procedure similar to the one described for 32A, with the following exceptions:

Step 32.2: 32.2a was replaced by 34.1 g (see also step 34.2).

Note: 34.1 g was obtained according to a procedure similar to the one described for 34.1f except 1.12 was replaced by 3.4o in step 34.8.

$^1$H NMR (400 MHz, DMSO d$_6$) δ 8.89 (brs, 2H), 7.52 (d, 1H), 7.32 (t, 1H), 7.07 (m, 2H), 6.92 (d, 1H), 6.87 (d, 1H), 6.24 (s, 1H), 4.02 (brs, 2H), 3.20 (brm, 4H), 2.03 (brm, 4H), 1.31 (brs, 12H), Mass Spectral Analysis m/z=395.5 (M+H)$^+$

EXAMPLE 34H

Preparation of 34.1h:

To a stirred solution of 34.7 (2.1 g, 10 mmol, 1.0 eq) in acetonitrile (20 mL) was slowly added diisopropylethylamine (4.2 mL, 24 mmol, 2.4 eq) and diethylamine (1.12) (2.1 mL, 20 mmol, 2 eq) at room temperature. The mixture was stirred for 10 min at room temperature, cooled to 0° C. and O-benzotriazol-1-yl-N,N,N',N'-tetramethyluronium tetrafluoroborate (TBTU) (3.85 g, 12 mmol, 1.2 eq) was added portion wise. The reaction mixture was slowly warmed to room temperature and stirred for 10 h at room temperature. The volatiles were removed under reduced pressure and the residue was partitioned between ethyl acetate (200 mL) and a 1M aqueous solution of sodium bicarbonate (100 mL). The organic phase was washed with a 1M aqueous solution of sodium bicarbonate (2×50 mL), a 1M aqueous solution of hydrochloric acid (3×50 mL) and brine. The organic phase was dried over sodium sulfate, filtered, and concentrated under reduced pressure. The crude product was purified by column chromatography (eluent: hexane/ethyl acetate mixtures of increasing polarity).

Yield: 87%

Mass Spectral Analysis m/z=262.15 (M+H)$^+$

Preparation of 34H:

34H was obtained according to a procedure similar to the one described for 32A, with the following exceptions:

Step 32.2: 32.2a was replaced by 34.1 h (see also step 34.2).

$^1$H NMR (400 MHz, DMSO d$_6$) δ 9.01 (brs, 2H), 7.80 (s, 1H), 7.41 (s, 1H), 7.27 (t, 1H), 7.19 (d, 1H), 7.04 (d, 1H), 6.99 (t, 1H), 6.04 (s, 1H), 3.48 (brm, 4H), 3.21 (brm, 4H), 2.02 (brm, 4H), 1.16 (brt, 6H)

Mass Spectral Analysis m/z=383.4 (M+H)$^+$

EXAMPLE 34I 34I was obtained according to a procedure similar to the one described for 32A, with the following exceptions:

Step 32.2: 32.2a was replaced by 34.1i (see also step 34.2).

34.1i was obtained according to a procedure similar to the one described for 34.1 h except 1.12 was replaced by 3.4o in step 34.7.

¹H NMR (400 MHz, DMSO d₆) δ 8.99 (brs, 2H), 7.73 (d, 1H), 7.27 (m, 2H), 7.21 (dd, 1H), 7.04 (d, 1H), 6.99 (t, 1H), 6.04 (s, 1H), 3.90 (brs, 2H), 3.21 (bin, 4H), 2.07 (brm, 2H), 1.98 (brm, 2H), 1.30 (brd, 12H)

Mass Spectral Analysis m/z=411.4 (M+H)⁺

EXAMPLE 34J 34J was obtained according to a procedure similar to the one described for 32A, with the following exceptions:

Step 32.2: 32.2a was replaced by 34.1j (see also step 34.2).

Note: 34.1j was obtained according to a procedure similar to the one described for 34.1k (see 34K) except 34.8b was replaced by 34.8a in step 34.9.

¹H NMR (400 MHz, DMSO d₆) δ 8.85 (brs, 2H), 7.43 (t, 1H), 7.35 (d, 1H), 7.27 (m, 2H), 7.04 (m, 2H), 6.97 (m, 1H), 6.03 (s, 1H), 3.48 (q, 2H), 3.22 (brm, 6H), 2.04 (brm, 4H), 1.16 (t, 3H), 1.04 (t, 3H)

Mass Spectral Analysis m/z=395.0 (M+H)⁺

Elemental analysis:

$C_{24}H_{27}FN_2O_2$, 1HCl, 0.25$H_2O$

Theory: % C, 66.20; % H, 6.60; % N, 6.43.

Found: % C, 65.97; % H, 6.48; % N, 6.21.

EXAMPLE 34K

Preparation of 34.1k:

To a stirred solution of 34.8b (5.0 g, 22.83 mmol, 1.0 eq) in acetonitrile (50 mL) was added N,N-diisopropylethylamine (8.35 mL, 47.94 mmol, 2.1 eq), 1.12 (2.6 mL, 25.11 mmol, 1.1 eq) and O-benzotriazol-1-yl-N,N,N',N'-tetramethyluronium tetrafluoroborate (TBTU) (8.06 g, 25.11 mmol, 1.1 eq). The reaction mixture was stirred at room temperature for 16 h. The mixture was concentrated under reduced pressure and the residue was dissolved in ethyl acetate. The mixture was washed with a saturated aqueous solution of sodium bicarbonate, dried over sodium sulfate and filtered. The filtrate was concentrated under reduced pressure and the crude product was purified by column chromatography (eluent: hexane/ethyl acetate mixtures of increasing polarity).

Yield: 91%

¹H NMR (400 MHz, CDCl₃) δ 7.30 (m, 2H), 7.03 (m, 1H), 3.53 (q, 2H), 3.24 (q, 2H), 1.27 (t, 3H), 1.13 (t, 3H)

Preparation of 34K:

34K was obtained according to a procedure similar to the one described for 32A, with the following exceptions:

Step 32.2: 32.2a was replaced by 34.1k (see also step 34.2).

¹H NMR (400 MHz, DMSO d₆) δ 8.92 (brs, 2H), 7.29 (m, 3H), 7.13 (s, 1H), 7.05 (d, 1H), 6.98 (m, 2H), 6.01 (s, 1H), 3.43 (brm, 2H), 3.23 (brm, 6H), 2.04 (brm, 4H), 1.10 (brd, 6H)

Mass Spectral Analysis m/z=395.0 (M+H)⁺

Elemental analysis:

$C_{24}H_{27}FN_2O_2$, 1HCl, 0.25$H_2O$

Theory: % C, 66.20; % H, 6.60; % N, 6.43.

Found: % C, 66.17; % H, 6.57; % N, 6.32.

EXAMPLE 34L 34L was obtained according to a procedure similar to the one described for 32A, with the following exceptions:

Step 32.2: 32.2a was replaced by 34.1l (see also step 34.2).

Note: 34.1l was obtained according to a procedure similar to the one described for 34.1k except 34.8b was replaced by 34.8c in step 34.9.

¹H NMR (400 MHz, CDCl₃) δ 9.76 (brs, 1H), 9.63 (brs, 1H), 7.20 (m, 4H), 7.05 (dd, 1H), 6.93 (m, 2H), 5.60 (s, 1H), 3.76 (brs, 2H), 3.42 (brm, 4H), 3.18 (q, 2H), 2.32 (s, 3H), 2.21 (brm, 4H), 1.28 (t, 3H), 1.08 (t, 3H)

Mass Spectral Analysis m/z=391.0 (M+H)⁺

Elemental analysis:

$C_{25}H_{30}N_2O_2$, 1HCl

Theory: % C, 70.32; % H, 7.32; % N, 6.56. Found: % C, 69.92; % H, 7.27; % N, 6.49.

EXAMPLE 34M 34M was obtained according to a procedure similar to the one described for 32A, with the following exceptions:

Step 32.2: 32.2a was replaced by 34.1m (see also step 34.2).

Note: 34.1m was obtained according to a procedure similar to the one described for 34.1k except 34.8b was replaced by 34.8d in step 34.9.

¹H NMR (400 MHz, CDCl₃) δ 9.78 (brs, 1H), 9.62 (brs, 1H), 7.22 (m, 3H), 7.13 (d, 1H), 6.92 (d, 1H), 6.84 (t, 1H), 6.63 (dd, 1H), 5.48 (s, 1H), 3.42 (brm, 8H), 2.36 (brm, 2H), 2.21 (m, 2H), 2.13 (s, 3H), 1.21 (brd, 6H)

Mass Spectral Analysis m/z=391.0 (M+H)⁺

Elemental analysis:

$C_{25}H_{30}N_2O_2$, 1HCl

Theory: % C, 70.32; % H, 7.32; % N, 6.56.

Found: % C, 70.01; % H, 7.30; % N, 6.57.

EXAMPLE 34N 34N was obtained according to a procedure similar to the one described for 32A, with the following exceptions:

Step 32.2: 32.2a was replaced by 34.1n (see also step 34.2).

Note: 34.1n was obtained according to a procedure similar to the one described for 34.1k except 34.8b was replaced by 34.8e in step 34.9.

¹H NMR (400 MHz, CDCl₃) δ 9.78 (brs, 1H), 9.68 (brs, 1H), 7.28 (m, 1H), 7.03 (dd, 1H), 6.95 (m, 4H), 5.64 (s, 1H), 3.62 (q, 2H), 3.41 (brm, 4H), 3.28 (q, 2H), 2.26 (brm, 4H), 1.28 (t, 3H), 1.05 (t, 3H)

Mass Spectral Analysis m/z=413.0 (M+H)⁺

Elemental analysis:

$C_{24}H_{26}F_2N_2O_2$, 1HCl, 0.25$H_2O$

Theory: % C, 63.57; % H, 6.11; % N, 6.18.

Found: % C, 63.54; % H, 6.09; % N, 6.20.

EXAMPLE 34O 34O was obtained according to a procedure similar to the one described for 32A, with the following exceptions:

Step 32.2: 32.2a was replaced by 34.1o (see also step 34.2).

Note: 34.1o was obtained according to a procedure similar to the one described for 34.1k except 34.8b was replaced by 34.8f in step 34.9.

¹H NMR (400 MHz, CDCl₃) δ 9.78 (brs 1H), 9.66 (brs, 1 h), 7.38 (s, 1H), 7.33 (d 1H), 7.25 (m, 2H), 7.02 (d, 1H), 6.95 (m, 2H), 5.63 (s, 1H), 3.81 (brs, 1H), 3.42 (brm 5H), 3.21 (brm, 2H), 2.26 (brm, 4H), 1.28 (t, 3H), 1.12 (t, 3H)

Mass Spectral Analysis m/z=411.0 (M+H)$^+$
Elemental analysis:
C$_{24}$H$_{27}$ClN$_2$O$_2$, 1HCl
Theory: % C, 64.43; % H, 6.31; % N, 6.26.
Found: % C, 64.34; % H, 6.35; % N, 6.28.

EXAMPLE 34P 34P was obtained according to a procedure similar to the one described for 32A, with the following exceptions:
Step 32.2: 32.2a was replaced by 34.1p (see also step 34.2).
Note: 34.1p was obtained according to a procedure similar to the one described for 34.1k except 34.8b was replaced by 34.9 in step 34.9 (see also step 34.10).

$^1$H NMR (400 MHz, DMSO d$_6$) δ 9.10 (brs, 2H), 7.47 (m, 2H), 7.34 (m, 1H), 7.27 (m, 1H), 7.20 (m, 1H), 6.98 (m, 1H), 6.87 (m, 1H), 6.76 (m, 1H), 5.69 (s, 1H), 3.29 (m, 2H), 3.18 (m, 4H), 3.01 (m, 2H), 2.04 (m, 2H), 1.93 (m, 2H), 0.96 (m, 6H)

Mass Spectral Analysis m/z=377.4 (M+H)$^+$

EXAMPLE 35A

Preparation of 35.2:

To a solution of 35.1 (41.44 g, 0.3 mol, 1.0 eq) in ammonium hydroxide (105 mL, 30% solution in H$_2$O) was added drop wise a solution of 12 (61.23 g, 0.24 mol, 0.8 eq) and KI (47.71 g, 0.287 mol, 0.96 eq) in water (300 mL) over a 20 min period. The mixture was stirred at room temperature for 1 h, and the mixture was concentrated under reduced pressure to half of its volume. The pH was adjusted to 3-4 with a 6N aqueous solution of hydrochloric acid. The white solid was collected by filtration and washed by a small amount of water. The solid was re-crystallized from water/EtOH (2:1), and dried under high vacuum.

Yield: 22%

$^1$H NMR (400 MHz, DMSO-d$_6$) δ 12.96 (b, 1H), 10.70 (s, 1H), 7.80 (d, 1H), 7.42 (s, 1H), 7.12 (d, 1H)

Preparation of 35.3:

To an acidic methanolic solution, which was prepared by drop wise addition of acetyl chloride (0.5 mL) to anhydrous methanol (75 mL) was added 35.2 (20.0 g, 75.8 mmol). The mixture was heated to reflux for 18 h. The reaction mixture was allowed to cool to room temperature, and was concentrated under reduced pressure. The residue was diluted in ethyl acetate (100 mL), washed by water (100 mL), brine (100 mL), dried over Na$_2$SO$_4$. The solution was filtered and the filtrate was concentrated under reduced pressure. The crude product was dried under vacuum.

Yield: 92%

$^1$H NMR (400 MHz, DMSO-d$_6$) δ 10.79 (s, 1H), 7.85 (d, 1H), 7.46 (s, 1H), 7.15 (d, 1H), 3.84 (s, 3H)

Preparation of 35.4:

A mixture of 35.3 (2.0 g, 7.19 mmol, 1.0 eq), 2.8c (4.08 g, 28.8 mmol, 4.0 eq) and potassium carbonate (9.94 g, 71.9 mmol, 10.0 eq) in acetone (100 mL) was refluxed for 16 h. The reaction was cooled to room temperature and the solid was collected by filtration. The volume of the filtrate was reduced to 15 mL and this solution was taken on to the next step without further purification.

Preparation of 35.5:

To a solution of 35.4 (2.10 g, 7.19 mmol, 1.0 eq) in acetone (15 mL) was added lithium hydroxide (1.2 g, 28.8 mmol, 4.0 eq) and a 1:1 tetrahydrofuran/water solution (30 mL). The mixture was stirred at room temperature for 16 h. The mixture was reduced to half of its volume under reduced pressure and was acidified with a a 6N aqueous solution of hydrochloric acid (5 mL). The crude mixture was extracted with ethyl acetate. The organic layer was washed with brine, dried over magnesium sulfate, and filtered. The filtrate was concentrated under reduced pressure. The crude product was used for the next step without further purification.

$^1$H NMR (400 MHz, CDCl$_3$) δ 7.91 (d, 1H), 7.49 (d, 1H), 7.45 (dd, 1H), 3.96 (s, 3H)

Preparation of 35.6:

To a mixture of 35.5 (2.0 g, 7.19 mmol, 1.0 eq) and O-Benzotriazol-1-yl-N,N,N',N'-tetramethyluronium tetrafluoroborate (TBTU) (2.54 g, 7.91 mmol, 1.1 eq) in acetonitrile (75 mL) at 0° C. was added 1.12 (0.58 g, 7.91 mmol, 1.1 eq) and N,N-diisopropylethylamine (1.95 g, 15.1 mmol, 2.1 eq). The mixture was warmed to room temperature, stirred for 16 h at room temperature and concentrated under reduced pressure. The crude mixture was dissolved in ethyl acetate. The mixture was washed with a saturated aqueous solution of sodium bicarbonate, dried over magnesium sulfate and filtered. The filtrate was concentrated under reduced pressure. The crude product was purified by column chromatography (eluent: hexane/ethyl acetate mixture, 60:40).

Yield: 96%

$^1$H NMR (400 MHz, CDCl$_3$) δ 7.78 (d, 1H), 6.84 (d, 1H), 6.70 (dd, 1H), 3.90 (s, 3H), 3.54 (brs, 2H), 3.26 (brs, 2H), 1.19 (brd, 6H)

Mass Spectral Analysis m/z=334.1 (M+H)$^+$

Preparation of 35.9

To a solution of 35.6 (1.34 g, 4.02 mmol, 1.0 eq) in dimethoxyethane (DME) (20 mL) was added sequentially a 2N aqueous solution of sodium carbonate (6.03 mL, 12.06 mmol, 3.0 eq), lithium chloride (0.511 g, 12.06 mmol, 3.0 eq), 32.1 (2.06 g, 4.83 mmol, 1.2 eq) and tetrakis(triphenylphosphine)palladium(0) (0.232 g, 0.20 mmol, 0.05 eq). The Suzuki coupling reaction was conducted under microwave conditions (A. 25° C. to 170° C. for 10 min; B. 170° C. for 7 min). The crude mixture was dissolved in ethyl acetate, washed with water, dried over sodium sulfate and filtered. The filtrate was concentrated under reduced pressure. The crude product was purified by column chromatography (eluent: hexane/ethyl acetate mixtures of increasing polarity).

Yield: 74%

$^1$H NMR (400 MHz, CDCl$_3$) δ 7.18 (d, 1H), 7.13 (m, 1H), 6.98 (m, 2H), 6.90 (d, 1H), 6.79 (m, 1H), 6.70 (dd, 1H), 5.53 (s, 1H), 3.84 (brs, 2H), 3.72 (s, 3H), 3.56 (brs, 2H), 3.33 (brs, 4H), 2.07 (brm, 2H), 1.67 (brm, 2H), 1.47 (s, 9H), 1.22 (brd, 6H)

Mass Spectral Analysis mL/z=507.3 (M+H)$^+$

Preparation of 35A:

Compound 35.9 (1.50 g, 2.96 mmol, 1.0 eq) was dissolved in a 4.0M anhydrous solution of hydrochloric acid in dioxane (15 mL, 60 mmol, 20 eq) and the mixture was stirred at room temperature for 16 h. The mixture was concentrated under reduced pressure. The residue was dissolved in a minimum amount (until complete dissolution of the product) of methylene chloride, and ethyl acetate was added until the solution became cloudy. The mixture was stirred for 2 h at room temperature. The resulting precipitate was collected by filtration.

Yield: 77%

$^1$H NMR (400 MHz, CDCl$_3$) δ 9.75 (brs, 1H), 9.58 (brs, 1H), 7.16 (m, 2H), 6.98 (m, 2H), 6.90 (d, 1H), 6.83 (m, 1H), 6.72 (dd, 1H), 5.56 (s, 1H), 3.72 (s, 3H), 3.50 (brm, 8H), 2.35 (brm, 2H), 2.16 (brm, 2H), 1.23 (brd, 6H)

Mass Spectral Analysis m/z=407.0 (M+H)+
Elemental analysis:
$C_{25}H_{30}N_2O_3$, 1HCl, 0.5$H_2O$
Theory: % C, 66.43; % H, 7.14; % N, 6.20.
Found: % C, 66.28; % H, 7.10; % N, 5.94.

EXAMPLE 35B

Preparation of 35.7:

To a solution of 35.6 (1.10 g, 3.30 mmol, 1.0 eq) in methylene chloride (30 mL) at 0° C. was added a 1.0M solution of boron tribromide in methylene chloride (5.0 mL, 5.0 mmol, 1.5 eq). The reaction was warmed to room temperature and stirred for 16 h at room temperature. A saturated aqueous solution of sodium bicarbonate was added to the mixture and the crude product was extracted with methylene chloride. The combined organic extracts were dried over sodium sulfate, filtered and the filtrate was concentrated under reduced pressure. The crude product was used for the next step without further purification.

Yield: 87%

$^1$H NMR (400 MHz, CDCl$_3$) δ 8.28 (brs, 1H), 7.64 (d, 1H), 6.95 (d, 1H), 6.56 (dd, 1H), 3.54 (q, 2H), 3.25 (q, 2H), 1.24 (t, 3H), 1.10 (t, 3H)

Mass Spectral Analysis m/z=320.0 (M+H)+

Preparation of 35.8:

To a solution of 35.7 (0.90 g, 2.82 mmol, 1.0 eq) and N,N-diisopropylethylamine (2.91 g, 22.6 mmol, 8.0 eq) in methylene chloride (25 mL) at 0° C. under nitrogen was added drop wise 11.3 (0.86 mL, 11.3 mmol, 4.0 eq). The mixture was warmed to room temperature and stirred for 48 h at room temperature. The mixture was concentrated under reduced pressure, dissolved in ethyl acetate and the solution was washed with a saturated aqueous solution of sodium bicarbonate. The organic layer was dried over sodium sulfate, filtered and the filtrate was concentrated under reduced pressure. The crude product was used for the next step without further purification.

Mass Spectral Analysis m/z=364.1 (M+H)+

Preparation of 35.10:

To a solution of 35.8 (1.02 g, 2.82 mmol, 1.0 eq) in dimethoxyethane (DME) (20 mL) was added sequentially a 2N aqueous solution of sodium carbonate (4.23 mL, 8.46 mmol, 3.0 eq), lithium chloride (0.359 g, 8.46 mmol, 3.0 eq), 32.1 (1.44 g, 3.38 mmol, 1.2 eq) and palladium on carbon (10%, 50% water) (0.038 g, 0.007 mmol, 0.0025 eq). The reaction was conducted under microwave conditions (A. 25° C. to 170° C. for 10 min; B. 170° C. for 7 min). The mixture was dissolved in ethyl acetate, washed with water, dried over sodium sulfate. The mixture was filtered and the filtrate was concentrated under reduced pressure. The crude product was purified by column chromatography (eluent: hexane/ethyl acetate mixtures of increasing polarity).

Yield: 50%

$^1$H NMR (400 MHz, CDCl$_3$) δ 7.21 (m, 2H), 7.13 (m, 1H), 7.06 (dd, 1H), 6.90 (d, 1H) 6.76 (m, 2H), 5.53 (s, 1H), 5.04 (s, 2H), 3.87 (brs, 2H), 3.55 (brs, 2H), 3.34 (brs, 4H), 3.30 (s, 3H), 2.08 (brm, 2H), 1.67 (brm, 2H), 1.48 (s, 9H), 1.24 (brm, 6H)

Mass Spectral Analysis m/z=537.3 (M+H)+

Preparation of 35B:

To a solution of 35.10 (0.647 g, 1.21 mmole, 1 eq) in methanol (3 mL) was added an excess of a 4.0M solution of anhydrous hydrochloric acid in dioxane (20 mL). The mixture was stirred at room temperature for 16 h. The mixture was concentrated under reduced pressure and treated with a mixture of methylene chloride (15 mL) and ethyl acetate (25 mL). The resulting precipitate was collected by filtration and dried under vacuum.

Yield: 77%

$^1$H NMR (400 MHz, DMSO d$_6$) δ 9.75 (s, 1H), 8.84 (brm, 2H), 7.16 (m, 2H), 6.96 (d, 1H), 6.84 (m, 3H), 6.72 (d, 1H), 5.78 (s, 1H), 3.42 (brs, 2H), 3.22 (brs, 6H), 2.10 (brm, 2H), 1.96 (brm, 2H), 1.12 (brs, 6H)

Mass Spectral Analysis m/z=393.3 (M+H)+

EXAMPLE 36A

Preparation of 36.3:

To a mixture of copper (II) bromide (8.8 g, 39.4 mmol, 1.2 eq) in acetonitrile (50 mL) under a nitrogen athmosphere was added 36.2 (5.1 g, 49.5 mmol, 1.5 eq). The mixture was cooled to 0° C. and 36.1 (5.0 g, 32.6 mmol, 1.0 eq) was added in small portions. Additional amount of acetonitrile (25 mL) was added to the mixture, which was stirred at 0° C. for 2 h. The mixture was poured onto a 20% aqueous solution of hydrochloric acid (200 mL) and extracted with diethyl ether. The combined organic extracts were washed with a 20% aqueous solution of hydrochloric acid, dried over magnesium sulfate, filtered, and concentrated under reduced pressure. The residue was dissolved in diethyl ether. The mixtute was extracted with a 15% aqueous solution of sodium hydroxide. The aqueous portion was washed with diethyl ether, acidified to pH 1 with a 6N aqueous solution of hydrochloric acid and the mixture was extracted with diethyl ether. The combined organic extracts were washed with brine, dried over magnesium sulfate, filtered and concentrated under reduced pressure. The residue was treated with chloroform and the resulting precipitate was collected by filtration. The product was used for the next step without further purification.

Mass Spectral Analysis m/z=215.1 (M−H)−

Preparation of 36.4:

To a mixture of 1.12 (0.85 g, 11.58 mmol, 2.5 eq), O-Benzotriazol-1-yl-N,N,N',N'-tetramethyluronium tetrafluoroborate (TBTU) (1.93 g, 6.02 mmol, 1.3 eq) and N,N-diisopropylethylamine (1.25 g, 9.72 mmol, 2.1 eq) in acetonitrile (50 mL) at 0° C. was added drop wise a solution of 36.3 (1.0 g, 4.63 mmol, 1.0 eq) in acetonitrile (10 mL). The mixture was warmed to room temperature and stirred for 48 h at room temperature. An additional portion of TBTU (1.04 g, 3.24 mmol, 0.7 eq) was added to the mixture which was heated at 60° C. for 5 h. The mixture was concentrated under reduced pressure, and the residue was dissolved in ethyl acetate. The mixture was washed by water, brine, dried over magnesium sulfate and filtrate. The solution was concentrated under reduced pressure. The crude product was purified by column chromatography (eluent: hexane/ethyl acetate mixtures of increasing polarity)

Yield: 63%

$^1$H NMR (400 MHz, CDCl$_3$) δ 10.08 (s, 1H), 7.17 (d, 1H), 7.12 (d, 1H), 6.98 (dd, 1H), 3.50 (q, 4H), 1.27 (t, 6H)

Mass Spectral Analysis m/z=270.1 (M−H)−

Preparation of 36.5:

To a solution of 36.4 (0.30 g, 1.11 mmol, 1.0 eq) in dimethoxyethane (DME) (10 mL) was added sequentially a 2N aqueous solution of sodium carbonate (1.66 mL, 3.32 mmol, 3.0 eq), lithium chloride (0.141 g, 3.32 mmol, 3.0 eq), 32.1 (0.57 g, 1.33 mmol, 1.2 eq) and tetrakis(triphenylphosphine)palladium(0) (0.128 g, 0.11 mmol, 0.1 eq). The reaction was conducted under microwave conditions (A. 25° C. to 170° C. for 10 min; B. 170° C. for 10 min). The crude mixture was dissolved in ethyl acetate. The mixture was washed with a 0.5N aqueous solution of hydrochloric acid, brine, and dried over magnesium sulfate. The mixture was filtered and the filtrate was concentrated under reduced pressure. The crude product was purified by column chromatography (eluent: hexane/ethyl acetate mixtures of increasing polarity).

Yield: 37%

$^1$H NMR (400 MHz, CDCl$_3$) δ 9.94 (s, 1H), 7.29 (d, 1H), 7.18 (m, 1H), 7.06 (dd, 1H) 7.00 (d, 1H), 6.94 (d, 1H), 6.85 (m, 2H), 5.59 (s, 1H), 3.85 (brs, 2H), 3.55 (q, 4H), 3.34 (brs, 2H), 2.04 (brm, 2H), 1.66 (m, 2H), 1.48 (s, 9H), 1.30 (t, 6H)

Mass Spectral Analysis m/z=493.2 (M+H)$^+$

Preparation of 36A:

To a solution of 36.5 (0.20 g, 0.406 mmol, 1.0 eq) in methylene chloride (2 mL) was added a 1.0M solution of anhydrous hydrochloric acid in diethyl ether (10 mL, 10 mmol, 25 eq). The mixture was stirred at room temperature for 16 h. The mixture was concentrated under reduced pressure and treated with diethyl ether. The resulting precipitate was collected by filtration. By LC/MS some starting material remained; therefore, so the precipitate was treated with an excess of a 4.0M solution of anhydrous hydrochloric acid in dioxane. This mixture was stirred at room temperature for 16 h. The mixture was concentrated under reduced pressure and the crude product was purified by column chromatography (eluent: methylene chloride/methanol mixtures of increasing polarity).

Yield: 66%

$^1$H NMR (400 MHz, DMSO d$_6$) δ 9.91 (brs, 1H), 9.08 (brs, 2H), 7.26 (m, 1H), 7.13 (d, 1H), 7.04 (m, 2H), 6.95 (m, 1H), 6.84 (m, 2H), 5.87 (s, 1H), 3.66 (brs, 4H), 3.20 (brm, 4H), 2.05 (brm, 4H), 1.08 (brd, 6H)

Mass Spectral Analysis m/z=393.4 (M+H)$^+$

Elemental analysis:

C$_{24}$H$_{28}$N$_2$O$_3$, 1HCl, 1.5H$_2$O

Theory: % C, 63.22; % H, 7.07; % N, 6.14.

Found: % C, 63.45; % H, 6.88; % N, 6.09.

EXAMPLE 36B

Preparation of 36.8:

To a solution of 36.6 (13.0 mL, 89.41 mmol, 1.0 eq) and triethylamine (13.71 mL, 98.35 mmol, 1.1 eq) in methylene chloride (100 mL) at 0° C. under a nitrogen athmosphere was added drop wise ethyl chloroformate (9.40 mL, 98.35 mmol, 1.1 eq). The mixture was warmed to room temperature and stirred for 1 h at room temperature. Water and methylene chloride were added to the reaction mixture and the layers were separated. The organic layer was dried over sodium sulfate, filtered and concentrated under reduced pressure. The crude product was used for the next step without further purification.

Yield: 100%

$^1$H NMR (400 MHz, CDCl$_3$) δ 7.22 (t, 1H), 6.76 (m, 3H), 4.66 (brs, 1H), 4.11 (q, 2H), 3.80 (s, 3H), 3.43 (m, 2H), 2.78 (m, 2H), 1.23 (t, 3H)

Mass Spectral Analysis m/z=224.1 (M+H)$^+$

Preparation of 36.9:

A mixture of 36.8 (20 g, 89.58 mmol, 1.0 eq) and polyphosphoric acid (90 g) was heated at 120° C. under a nitrogen athmosphere for 1.5 h. The mixture was cooled to room temperature. Water (200 mL) was added to the mixture which was extracted with ethyl acetate. The organic extracts were combined, dried over sodium sulfate, filtered and concentrated under reduced pressure. The crude product was purified by column chromatography (eluent: ethyl acetate). Polyphosphoric acid was still present in the purified sample; therefore the residue was dissolved in ethyl acetate and the solution was washed with a saturated aqueous solution of sodium bicarbonate. The mixture was dried over sodium sulftate, filtered and concentrated under reduced pressure. Ethyl acetate (15 mL) was added to the mixture. The resulting precipitate was collected by filtration and was used for the next step without further purification.

Yield: 30%

$^1$H NMR (400 MHz, CDCl$_3$) δ 8.02 (d, 1H), 6.86 (dd, 1H), 6.71 (d, 1H), 6.22 (brs, 1H), 3.85 (s, 3H), 3.55 (m, 2H), 2.97 (t, 2H)

Mass Spectral Analysis m/z=178.1 (M+H)$^+$

Preparation of 36.11:

To a suspension of NaH (0.81 g, 33.86 mmol, 6.0 eq) in tetrahydrofuran (30 mL) under a nitrogen athmosphere was added drop wise a solution of 36.9 (1.0 g, 5.64 mmol, 1.0 eq) in tetrahydrofuran (15 mL). To this mixture was added drop wise 36.10 (2.28 mL, 28.22 mmol, 5.0 eq) and stirring was continued for 16 h at room temperature. A thick precipitate formed; therefore additional amount of tetrahydrofuran (15 mL) and 36.10 (1.0 mL, 12.39 mmol, 2.2 eq) were added and stirring was continued for an additional 24 h at room temperature. The reaction was quenched by addition of a 1N aqueous solution of hydrochloric acid followed by ethyl acetate and water. The layers were separated. The organic phase was dried over sodium sulfate, filtered and concentrated under reduced pressure. The crude product was purified by column chromatography (eluent: hexane/ethyl acetate mixtures of increasing polarity).

Yield: 83%.

$^1$H NMR (400 MHz, CDCl$_3$) δ 8.03 (d, 1H), 6.84 (dd, 1H), 6.65 (d, 1H), 3.84 (s, 3H), 3.61 (q, 2H), 3.53 (t, 2H), 2.95 (t, 2H), 1.21 (t, 3H)

Mass Spectral Analysis m/z=206.1 (M+H)$^+$

Preparation of 36.12:

To a solution of 36.11 (0.96 g, 4.68 mmol, 1.0 eq) in anhydrous methylene chloride (30 mL) at −78° C. under a nitrogen athmosphere was added drop wise a 1.0M solution of boron tribromide in methylene chloride (9.35 mL, 9.35 mmol, 2.0 eq). The reaction was warmed to room temperature and stirred for 16 h at room temperature. The mixture was cooled in an ice bath, quenched with methanol (10 mL) and concentrated under reduced pressure. The crude mixture was dissolved in ethyl acetate and the solution was washed with a 1N aqueous solution of hydrochloric acid and then brine. The organic phase was dried over sodium sulfate, filtered and concentrated under reduced pressure. The crude solid was triturated in a ethyl acetate/hexane (1:1). The precipitate was collected by filtration.

Yield: 74%.

$^1$H NMR (400 MHz, CDCl$_3$) δ 7.89 (d, 1H), 6.82 (dd, 1H), 6.68 (d, 1H), 3.63 (q, 2H), 3.54 (t, 2H), 2.91 (t, 2H), 1.22 (t, 3H)

Mass Spectral Analysis m/z=192.1 (M+H)$^+$

Preparation of 36.14:

To a solution of 36.12 (0.38 g, 1.99 mmol, 1.0 eq) and pyridine (0.32 mL, 3.98 mmol, 2.0 eq) in methylene chloride (10 mL) at 0° C. under a nitrogen athmosphere was added 36.13 (0.40 mL, 2.38 mmol, 1.2 eq). The reaction was warmed to room temperature and stirred for 2 h at room temperature. Methylene chloride was added to the mixture which was washed with a 1N aqueous solution of hydrochloric acid, and with a 1N aqueous solution of sodium hydroxide.

The organic phase was dried over sodium sulfate, filtered and concentrated under reduced pressure. The crude product was purified by column chromatography (eluent: hexane/ethyl acetate, 1:1).

Yield: 45%.

$^1$H NMR (400 MHz, CDCl$_3$) δ 8.18 (d, 1H), 7.23 (dd, 1H), 7.11 (d, 1H), 3.62 (m, 4H), 3.04 (t, 2H), 1.23 (t, 3H)

Mass Spectral Analysis m/z=324.1 (M+H)$^+$

Preparation of 36.15:

To a solution of 36.14 (0.100 g, 0.309 mmol, 1.0 eq) in N,N-dimethylformamide (5 mL) under a nitrogen athmosphere was added 32.1 (0.145 g, 0.340 mmol, 1.1 eq), potassium acetate (0.091 g, 0.928 mmol, 3.0 eq) and [1,1'-bis(diphenylphosphino)ferrocene]palladium(II), dichloromethane complex (0.005 g, 0.006 mmol, 0.02 eq). The reaction was stirred at 65° C. for 16 h. The mixture was cooled to room temperature. Water was added and the mixture was extracted with ethyl acetate. The organic phase was dried over sodium sulfate, filtered and concentrated under reduced pressure. The crude product was purified by column chromatography (eluent: hexane/ethyl acetate mixtures of increasing polarity).

Yield: 45%.

$^1$H NMR (400 MHz, CDCl$_3$) δ 8.11 (d, 1H), 7.31 (dd, 1H), 7.19 (m, 1H), 7.15 (s, 1H), 6.96 (m, 2H), 6.86 (m, 1H), 5.58 (s, 1H), 3.86 (brm, 2H), 3.65 (q, 2H), 3.59 (t, 2H), 3.34 (m, 2H), 3.01 (t, 2H), 2.05 (m, 2H), 1.67 (m, 2H), 1.48 (s, 9H), 1.26 (t, 3H)

Mass Spectral Analysis m/z=475.3 (M+H)$^+$

Preparation of 36B:

To a solution of 36.15 (0.150 g, 0.316 mmol, 1.0 eq) in anhydrous methylene chloride (5 mL) at 0° C. under a nitrogen athmosphere was added a 1.0M solution of anhydrous hydrochloric acid in diethyl ether (1.26 mL, 1.26 mmol, 4.0 eq). The reaction was warmed to room temperature and stirred for 4 days at room temperature. Diethyl ether was added (5 mL) and the resulting precipitate was collected by filtration.

Yield: 27%.

$^1$H NMR (400 MHz, DMSO d$_6$) δ 8.80 (brs, 2H), 7.92 (d, 1H), 7.29 (m, 3H), 7.05 (d, 1H), 6.97 (m, 2H), 5.94 (s, 1H), 3.54 (m, 4H), 3.23 (brm, 4H), 3.00 (t, 2H), 2.08 (brm, 2H), 1.97 (brm, 2H), 1.13 (t, 3H)

Mass Spectral Analysis m/z=375.3 (M+H)$^+$

Elemental analysis:

C$_{24}$H$_{26}$N$_2$O$_2$, 1HCl, 1H$_2$O

Theory: % C, 67.20; % H, 6.81; % N, 6.53.

Found: % C, 67.52; % H, 6.46; % N, 6.54.

EXAMPLE 37A

Preparation of 37.2 and 37.3:

To a solution of 37.1 (5.0 g, 24.60 mmol, 1.0 eq) and 1.1a (2.56 mL, 24.60 mmol, 1.0 eq) in methanol (100 mL) was added pyrrolidine (5.53 mL, 66.90 mmol, 2.72 eq). The mixture was refluxed for 16 h. The mixture was concentrated under reduced pressure, dissolved in ethyl acetate and the mixture was washed with a 1N aqueous solution of sodium hydroxide and brine. The organic phase was dried over sodium sulfate, filtered and concentrated under reduced pressure. The crude mixture was purified by column chromatography (eluent: hexane/ethyl acetate mixtures of increasing polarity) to give a mixture of 37.2/37.3 (1/1.7).

Yield: 80%

(37.2) $^1$H NMR (400 MHz, CDCl$_3$) δ 7.82 (dd, 1H), 7.47 (m, 1H), 7.28 (m, 5H), 6.96 (m, 2H), 3.50 (q, 2H), 2.76 (q, 2H), 2.64 (brm, 1H), 2.40 (brm, 1H), 2.18 (brm, 2H), 2.00 (brm, 1H), 1.82 (brm, 1H), 1.70 (brm, 1H), 1.07 (brd, 3H)

Mass Spectral Analysis m/z=322.3 (M+H)$^+$ (37.3) $^1$H NMR (400 MHz, CDCl$_3$) δ 7.84 (dd, 1H), 7.48 (m, 1H), 7.29 (m, 5H), 6.98 (m, 2H), 3.51 (m, 2H), 3.15 (d, 1H), 2.65 (m, 1H), 2.55 (m, 1H), 2.34 (m, 2H), 2.24 (m, 1H), 2.15 (m, 1H), 1.91 (m, 1H), 1.56 (m, 1H), 1.02 (d, 3H)

Mass Spectral Analysis m/z=322.3 (M+H)$^+$

Preparation of 37.4:

To a solution of 37.2 (2.30 g, 7.16 mmol, 1.0 eq) in methanol (25 mL) was added 10% Pd/C (0.50 g). The mixture was shaken for 6 h under 55 psi of hydrogen. The mixture was filtered through celite, and concentrated under reduced pressure. The crude product was used for the next step without further purification.

Yield: 99%

$^1$H NMR (400 MHz, CDCl$_3$) δ 7.83 (dd, 1H), 7.48 (m, 1H), 6.97 (m, 2H), 3.18 (dd, 1H), 3.02 (m, 1H), 2.77 (m, 2H), 2.55 (m, 1H), 2.06 (m, 1H), 1.80 (brm, 3H), 1.06 (d, 3H)

Mass Spectral Analysis m/z=232.3 (M+H)$^+$

Preparation of 37.5:

To a solution of 37.4 (1.65 g, 7.13 mmol, 1.0 eq) in tetrahydrofuran (50 mL) was added triethylamine (2.98 mL, 21.40 mmol, 3.0 eq) and 4.7 (1.87 g, 8.56 mmol, 1.2 eq). The mixture was stirred for 2 h at room temperature. Water (100 mL) was added and the crude mixture was extracted with ethyl acetate and washed with brine. The organic phase was dried over sodium sulfate, filtered and concentrated under reduced pressure. The crude product was purified by column chromatography (eluent: hexane/ethyl acetate, 70/30).

Yield: 100%

$^1$H NMR (400 MHz, CDCl$_3$) δ 7.85 (dd, 1H), 7.50 (m, 1H), 6.99 (m, 2H), 3.80 (brs, 1H), 3.56 (brm, 2H), 3.30 (brs, 1H), 2.73 (m, 2H), 2.12 (brs, 1H), 1.82 (brm, 2H), 1.46 (s, 9H), 1.03 (d, 3H)

Mass Spectral Analysis m/z=332.3 (M+H)$^+$

Preparation of 37.6:

To a solution of 37.5 (2.70 g, 8.15 mmol, 1.0 eq) in tetrahydrofuran (20 mL) at −78° C. under a nitrogen athmosphere was added drop wise a 1.0M solution of LiHMDS in tetrahydrofuran (9.78 mL, 9.78 mmol, 1.2 eq). The mixture was stirred for 45 min at −78° C. A solution of 1.4 (3.49 g, 9.78 mmol, 1.2 eq) in tetrahydrofuran (10 mL) was added drop wise to the mixture, which was warmed slowly to room temperature and stirred for 16 h at room temperature. The mixture was then poured into ice water. A, 1N aqueous solution of hydrochloric was added and the crude mixture was extracted with ethyl acetate. The organic extracts were washed with a 1N aqueous solution of sodium hydroxide, brine, dried over sodium sulfate, filtered and concentrated under reduced pressure. The crude product was purified by column chromatography (eluent: hexane/ethyl acetate mixtures of increasing polarity).

Yield: 62%

$^1$H NMR (400 MHz, DMSO d$_6$) δ 7.31 (m, 1H), 7.15 (m, 1H), 6.95 (m, 1H), 6.85 (m, 1H), 6.25 (s, 0.6H), 5.83 (s, 0.4H), 3.54 (brs, 2H), 3.19 (brm, 2H), 1.96 (brm, 2H), 1.55 (brm, 1H), 1.33 (s, 9H), 0.83 (d, 3H)

Mass Spectral Analysis m/z=464.2 (M+H)$^+$

Preparation of 37.7:

To a solution of 37.6 (1.17 g, 2.52 mmol, 1.0 eq) in dioxane (20 mL) was added sequentially 1.6 (0.61 g, 2.78 mmol, 1.1 eq), potassium phosphate (0.80 g, 3.79 mmol, 1.5 eq) and potassium bromide (0.33 g, 2.78 mmol, 1.1 eq). The mixture was placed under vacuum, flushed with nitrogen and then the process was repeated. Tetrakis(triphenylphosphine)palladium(0) (0.146 g, 0.13 mmol, 0.05 eq) was added and the mixture was heated at 100° C. for 16 h under a nitrogen athmosphere. The mixture was cooled to room temperature, dissolved in ethyl acetate and the mixture was washed with water. The organic phase was dried over sodium sulfate, filtered and concentrated under reduced pressure. The crude product was purified by column chromatography (eluent: hexane/ethyl acetate mixtures of increasing polarity).

Yield: 53%

$^1$H NMR (400 MHz, CDCl$_3$) δ 7.42 (d, 2H), 7.37 (d, 2H), 7.18 (m, 1H), 6.99 (d, 1H), 6.92 (d, 1H), 6.84 (m, 1H), 5.70 (s, 1H), 3.65 (brm, 5H), 3.32 (brs, 3H), 2.15 (brs, 1H), 2.04 (m, 1H), 1.77 (brs, 1H), 1.48 (s, 9H), 1.22 (brd, 6H), 1.02 (d, 3H)

Mass Spectral Analysis m/z=491.5 (M+H)$^+$

Preparation of 37 A:

To a solution of 37.7 (0.65 g, 1.33 mmol, 1.0 eq) in anhydrous methylene chloride (10 mL) at 0° C. under a nitrogen athmosphere was added a 1.0M solution of anhydrous hydrochloric acid in diethyl ether (5.31 mL, 5.31 mmol, 4.0 eq). The mixture was warmed to room temperature and stirred for 5 days at room temperature. The mixture was concentrated under reduced pressure and dissolved in methylene chloride (5 mL). Diethyl ether (10 mL) was added drop wise to the mixture which was stirred for 1 h at room temperature. The resulting precipitate was collected by filtration and dried under vacuum.

Yield: 82%

$^1$H NMR (400 MHz, DMSO d$_6$) δ 9.46 (brm, 1.5H), 7.71 (d, 2H), 7.67 (d, 2H), 7.48 (m, 1H), 7.21 (m, 2H), 7.15 (m, 1H), 6.44 (s, 1H), 3.70 (brs, 2H), 3.42 (brm, 6H), 2.52 (brm, 1H), 2.44 (brm, 1H), 2.13 (brm, 1H), 1.36 (brd, 6H), 1.22 (d, 3H)

Mass Spectral Analysis m/z=391.3 (M+H)$^+$

Elemental analysis:

C$_{25}$H$_{30}$N$_2$O$_2$, 1HCl, 0.25H$_2$O

Theory: % C, 69.59; % H, 7.36; % N, 6.49.

Found: % C, 69.29; % H, 7.28; % N, 6.40.

EXAMPLE 37B 37B was obtained according to a procedure similar to the one described for 37A, with the following exceptions:

Step 37.2: 37.2 was replaced by 37.3 (see also step 37.5).

$^1$H NMR (400 MHz, DMSO d$_6$) δ 9.40 (brm, 1.5H), 7.66 (s, 4H) 7.48 (m, 1H), 7.27 (d, 1H), 7.21 (m, 1H), 7.15 (m, 1H), 6.03 (s, 1H), 3.69 (brs, 2H), 3.43 (brm, 4H), 3.24 (brm, 2H), 2.47 (brm, 1H), 2.35 (brm, 1H), 2.08 (brm, 1H), 1.37 (brd, 6H), 1.20 (d, 3H)

Mass Spectral Analysis m/z=391.3 (M+H)$^+$

Elemental analysis:

C$_{25}$H$_{30}$N$_2$O$_2$, 1HCl, 0.25H$_2$O

Theory: % C, 69.59; % H, 7.36; % N, 6.49.

Found: % C, 69.69; % H, 7.18; % N, 6.49.

EXAMPLE 7D

Preparation of 7.10a:

3.4k (0.10 mL, 1.20 mmol, 1.2 eq) was added drop wise at room temperature to a 1 neck 100 mL round bottom flask which was flame dried under N$_2$ and contained a solution of 3.1a (625.0 mg, 1.00 mmol, 1 eq), tris(dibenzylideneacetone) dipalladium(0) (9.2 mg, 0.010 mmol, 0.01 eq), 7.9 (6.0 mg, 0.020 mmol, 0.02 eq) and potassium phosphate (297.3 mg, 1.40 mmol, 1.4 eq) in ethylene glycol dimethyl ether (5 mL). The solution was heated to 80° C. for 48 hours and then diluted with diethyl ether (90 mL) and filtered through a plug of celite. The crude product was purified by column chromatography (eluent: hexane/ethyl acetate mixtures of increasing polarity).

Yield: 37%

$^1$H NMR (400 MHz, CDCl$_3$) δ 7.41 (m, 4H), 7.16 (d, 1H), 6.85 (d, 1H), 6.44 (m, 1H), 5.86 (s, 1H), 3.71 (m, 2H), 3.44 (m, 2H), 3.21 (m, 4H), 3.05 (m, 4H), 1.87 (m, 4H), 1.66 (m, 2H), 1.41 (s, 9H), 1.37 (m, 2H), 1.11 (m, 6H)

Mass Spectral Analysis m/z=546.44 (M+H)$^+$

Preparation of 7D:

A 2M solution of hydrochloric acid in diethyl ether (1.8 mL, 3.53 mmol, 5.5 eq) was added drop wise to a cooled (0° C.) solution of 7.10a (0.35 g, 0.64 mmol, 1 eq) in anhydrous dichloromethane (4 mL). The mixture was warmed to room temperature and stirring was continued for an additional 64 hours at room temperature. The solution was concentrated in vacuo. The crude product was purified by column chromatography (eluent: dichloromethane/methanol mixtures of increasing polarity).

Yield: 20%

$^1$H NMR (400 MHz, DMSO d$_6$) δ 9.10 (m, 2H), 7.44 (M, 4H), 7.04 (m, 1H), 6.00 (s, 1H), 4.30 (br s, 5H), 3.44 (br s, 3H), 3.22 (m, 8H), 1.99 (m, 7H), 1.12 (m, 6H)

Mass Spectral Analysis m/z=446.40 (M+H)$^+$

EXAMPLE 7E

Preparation of 7.10b:

3.4p (167.4 mg, 1.92 mmol, 1.2 eq) was added drop wise at room temperature to a 1 neck 100 mL round bottom flask which was flame dried under N$_2$ and contained a solution of 3.1a (1.00 g, 1.60 mmol, 1 eq), tris(dibenzylideneacetone) dipalladium(0) (14.7 mg, 0.016 mmol, 0.01 eq), 7.9 (9.6 mg, 0.032 mmol, 0.02 eq) and potassium phosphate (475.7 mg, 2.24 mmol, 1.4 eq) in ethylene glycol dimethyl ether (10 mL). The solution was heated to 80° C. for 72 hours and then diluted with diethyl ether (90 mL) and filtered through a 1 inch plug of celite. The crude product was purified by column chromatography (eluent: hexane/ethyl acetate mixtures of increasing polarity).

Yield: 30%

Mass Spectral Analysis m/z=561.76 (M+H)$^+$

Preparation of 7E:

A 2M solution of hydrochloric acid in diethyl ether (1.3 mL, 2.55 mmol, 5.5 eq) was added drop wise to a cooled (0° C.) solution of 7.10b (0.26 g, 0.46 mmol, 1 eq) in anhydrous dichloromethane (4 mL). The mixture was warmed to room temperature and stirring was continued for an additional 20 hours at room temperature. The solution was concentrated in vacuo. The crude product was purified by column chromatography (eluent: dichloromethane/methanol mixtures of increasing polarity).

Yield: 10%

$^1$H NMR (400 MHz, DMSO d$_6$) δ 9.00 (m, 2H), 7.45 (m, 4H), 7.04 (m, 2H), 6.74 (m, 1H), 5.98 (s, 1H), 4.00 (br s, 5H), 3.74 (br s, 4H), 3.45 (br s, 2H), 3.22 (m, 4H), 3.03 (m, 2H), 2.02 (m, 4H), 1.15 (m, 6H)

Mass Spectral Analysis m/z=462.44 (M+H)$^+$

EXAMPLE 11G

Preparation of 11.11:

To a suspension of 11.2 (5.0 g, 15.00 mmol, 1.0 eq) and cesium carbonate (24.4 g, 75.00 mmol, 5.0 eq) in N,N-dimethylformamide (50 mL) under nitrogen was added 9.7 (7.91 mL, 75.00 mmol, 5.0 eq). Evolution of white smoke was observed. The reaction was heated at 90° C. for 16 h and then cooled to room temperature. Water was added and the product was extracted three times with diethyl ether. The combined organics were then washed three times with a 1N aqueous solution of sodium hydroxide to remove any unreacted starting material. The organic layer was concentrated and the crude product was purified by column chromatography (eluent: hexane/ethyl acetate mixtures of increasing polarity).

Yield: 26%

$^1$HNMR (400 MHz, CDCl$_3$) δ 7.44 (t, 1H), 6.91 (m, 1H), 6.80 (m, 1H), 6.57 (t, 1H, J=75, CF$_2$H), 3.87 (brs, 2H), 3.21 (brt, 2H), 2.72 (s, 2H), 2.00 (brd, 2H), 1.62 (m, 2H), 1.46 (s, 9H)

Mass Spectral Analysis m/z=384.4 (M+H)$^+$

Preparation of 11.12:

To a solution of 11.11 (1.47 g, 3.83 mmol, 1.0 eq) in tetrahydrofuran (30 mL) at −78° C. under nitrogen was added drop wise a 1.0M solution of LiHMDS in tetrahydrofuran (4.60 mL, 4.60 mmol, 1.2 eq). The mixture was stirred for 1 h at −78° C. A solution of 1.4 (1.64 g, 4.60 mmol, 1.2 eq) in tetrahydrofuran (15 mL) was added drop wise to the mixture, which was warmed slowly to room temperature. Stirring was continued for a further 5 h at room temperature. Ice was added to the reaction and the mixture was stirred for 15 min. Ethyl acetate and a 1N aqueous solution of sodium hydroxide were added and the layers were separated. The organics were washed again with a 1N aqueous solution of sodium hydroxide and concentrated. The crude product was purified by column chromatography (eluent: hexane/ethyl acetate mixtures of increasing polarity).

Yield: 56%

$^1$HNMR (400 MHz, CDCl$_3$) δ 7.24 (t, 1H), 6.82 (d, 2H), 6.57 (t, 1H, J=72, CF$_2$H), 5.59 (s, 1H), 3.84 (brs, 2H), 3.26 (brs, 2H), 2.06 (brd, 2H), 1.69 (m, 2H), 1.46 (s, 9H)

Preparation of 11.13a (X=CH):

To a solution of 11.12 (0.50 g, 0.97 mmol, 1.0 eq) in dioxane (15 mL) was added 1.6 (0.24 g, 1.07 mmol, 1.1 eq), potassium phosphate (0.31 g, 1.46 mmol, 1.5 eq), potassium bromide (0.13 g, 1.07 mmol, 1.1 eq) and [1,1'-bis(diphenylphosphino)ferrocene]dichloropalladium(II) (0.040 g, 0.049 mmol, 0.05 eq). The mixture was heated at 100° C. for 24 h and then cooled to room temperature. Ethyl acetate and water were added and the layers were separated. The organics were washed with brine, concentrated and purified by column chromatography (eluent: hexane/ethyl acetate mixtures of increasing polarity).

Yield: 67%

$^1$HNMR (400 MHz, CDCl$_3$) δ 7.33 (d, 2H), 7.23 (m, 3H), 6.90 (d, 1H), 6.67 (d, 1H), 6.00 (t, 1H, J=74, CF$_2$H), 5.61 (s, 1H), 3.82 (brs, 2H), 3.55 (brs, 2H) 3.28 (brs, 4H), 2.01 (brd, 2H), 1.69 (m, 2H), 1.47 (s, 9H), 1.26 (brs, 3H), 1.11 (brs, 3H)

Mass Spectral Analysis m/z=543.8 (M+H)$^+$

Preparation of 11G:

To a solution of 11.13a (X=CH) (0.35 g, 0.645 mmol, 1.0 eq) in anhydrous methylene chloride (7 mL) at 0° C. under nitrogen was added a 2.0M solution of anhydrous hydrochloric acid in diethyl ether (1.29 mL, 2.58 mmol, 4.0 eq). The reaction was warmed to room temperature and stirred for a further 16 h at room temperature. The reaction was concentrated and the resulting foam was sonicated in diethyl ether (10 mL) for 5 min., stirred for 1 h at room temperature, and the solids were collected by vacuum filtration.

Yield: 87%.

$^1$H NMR (400 MHz, DMSO d$_6$) δ 8.97 (brs, 2H), 7.35 (t, 1H), 7.28 (m, 4H), 7.02 (d, 1H), 6.81 (t, 1H, J=74, CF$_2$H), 6.77 (d, 1H), 5.97 (s, 1H), 3.40 (brm, 2H), 3.20 (brm, 6H), 2.04 (brm, 4H), 1.14 (brs, 3H), 1.04 (brs, 3H)

Mass Spectral Analysis m/z=443.3 (M+H)$^+$

Elemental analysis:

$C_{25}H_{28}F_2N_2O_3$, 1HCl

Theory: % C, 62.69; % H, 6.10; % N, 5.85.

Found: % C, 62.39; % H, 6.01; % N, 5.77.

EXAMPLE 11H

Preparation of 11.13b (X=N):

To a solution of 11.12 (0.50 g, 0.97 mmol, 1.0 eq) in dioxane (15 mL) was added 1.7 (0.32 g, 1.07 mmol, 1.1 eq), potassium phosphate (0.31 g, 1.46 mmol, 1.5 eq), potassium bromide (0.13 g, 1.07 mmol, 1.1 eq) and [1,1'-bis(diphenylphosphino)ferrocene]dichloropalladium(II) (0.040 g, 0.049 mmol, 0.05 eq). The mixture was heated at 100° C. for 24 h and then cooled to room temperature. Ethyl acetate and water were added and the layers were separated. The organics were washed with brine, concentrated and purified by column chromatography (eluent: hexane/ethyl acetate mixtures of increasing polarity).

Yield: 77%

$^1$HNMR (400 MHz, CDCl$_3$) δ 8.44 (s, 1H), 7.61 (dd, 1H), 7.54 (d, 1H), 7.22 (t, 1H), 6.91 (d, 1H), 6.67 (d, 1H), 6.06 (t, 1H, J=74, CF$_2$H), 5.64 (s, 1H), 3.85 (brs, 2H), 3.58 (q, 2H) 3.40 (q, 2H), 3.30 (brs, 2H), 2.03 (brd, 2H), 1.72 (m, 2H), 1.48 (s, 9H), 1.28 (t, 3H), 1.15 (t, 3H)

Mass Spectral Analysis m/z=544.8 (M+H)$^+$

Preparation of 11H:

To a solution of 11.13b (X=N) (0.40 g, 0.736 mmol, 1.0 eq) in anhydrous methylene chloride (7 mL) at 0° C. under nitrogen was added a 2.0M solution of anhydrous hydrochloric acid in diethyl ether (2.21 mL, 4.41 mmol, 6.0 eq). The reaction was warmed to room temperature and stirred for a further 16 h at room temperature. The reaction was concentrated and the resulting foam was sonicated in diethyl ether (10 mL) for 5 min., stirred for 1 h at room temperature, and the solids were collected by vacuum filtration.

Yield: 84%.

$^1$H NMR (400 MHz, DMSO d$_6$) δ 8.99 (brs, 2H), 8.45 (s, 1H), 7.75 (dd, 1H), 7.49 (d, 1H), 7.37 (t, 1H), 7.04 (d, 1H), 6.78 (d, 1H), 6.90 (t, 1H, J=74, CF$_2$H), 6.12 (s, 1H), 3.45 (m, 2H), 3.21 (brm, 6H), 2.06 (brm, 4H), 1.16 (t, 3H), 1.06 (t, 3H)

Mass Spectral Analysis m/z=444.3 (M+H)$^+$

Elemental analysis:

$C_{24}H_{27}F_2N_3O_3$, 1.25HCl, 1H$_2$O

Theory: % C, 56.85; % H, 6.01; % N, 8.29; % Cl, 8.74.

Found: % C, 56.93; % H, 6.01; % N, 8.23; % Cl, 8.84.

EXAMPLE 11I

Preparation of 11.14:

To a solution of 32.2b (2.05 g, 7.02 mmol, 1.0 eq) in dioxane (30 mL) under nitrogen was added 1.14 (2.14 g, 8.42 mmol, 1.2 eq), potassium acetate (2.07 g, 21.05 mmol, 3.0 eq) and [1,1'-bis(diphenylphosphino)ferrocene]dichloropalladium(II) (0.12 g, 0.14 mmol, 0.02 eq). The mixture was heated at 70° C. for 16 h and then cooled to room temperature. Ethyl acetate and water were added and the layers were separated. The aqueous phase was washed with ethyl acetate and the organics were combined and concentrated. The crude product was purified by column chromatography (eluent: ethyl acetate/hexane=3:7).

Yield: 87%

$^1$HNMR (400 MHz, CDCl$_3$) δ 7.92 (d, 2H), 7.79 (d, 2H), 3.24 (q, 4H), 1.36 (s, 12H), 1.11 (t, 6H)

Mass Spectral Analysis m/z=340.3 (M+H)+

Preparation of 11.15:

To a solution of 11.5 (0.70 g, 1.37 mmol, 1.0 eq) in dioxane (15 mL) was added 11.14 (0.513 g, 1.51 mmol, 1.1 eq), potassium phosphate (0.437 g, 2.06 mmol, 1.5 eq), potassium bromide (0.18 g, 1.51 mmol, 1.1 eq) and tetrakis(triphenylphosphine)palladium(0) (0.079 g, 0.069 mmol, 0.05 eq). The mixture was heated at 100° C. for 16 h and then cooled to room temperature. Ethyl acetate and water were added and the layers were separated. The aqueous layer was washed with ethyl acetate and the organics were combined, concentrated and purified by column chromatography (eluent: hexane/ethyl acetate mixtures of increasing polarity).

Yield: 47%

$^1$HNMR (400 MHz, CDCl$_3$) δ 7.74 (d, 2H), 7.36 (d, 2H), 7.16 (t, 1H), 6.70 (m, 2H), 5.56 (s, 1H), 4.65 (s, 2H), 3.81 (brs, 2H), 3.32 (brs, 2H), 3.25 (q, 4H), 3.13 (s, 3H), 2.02 (brd, 2H), 1.68 (m, 2H), 1.48 (s, 9H), 1.15 (t, 6H)

Mass Spectral Analysis m/z=573.4 (M+H)+

Preparation of 11I:

To a solution of 11.15 (0.365 g, 0.637 mmol, 1.0 eq) in methanol (20 mL) under nitrogen was added a 2.0M solution of anhydrous hydrochloric acid in diethyl ether (3.20 mL, 6.37 mmol, 10.0 eq). The reaction was stirred for 16 h at room temperature. The reaction was concentrated and the resulting solid was stirred in a methylene chloride (2 mL)/diethyl ether (15 mL) mixture for 30 min. at room temperature. The solids were then collected by vacuum filtration.

Yield: 79%

$^1$HNMR (400 MHz, DMSO d$_6$) δ 9.60 (s, 1H), 8.83 (brs, 2H), 7.71 (d, 2H), 7.43 (d, 2H), 7.08 (t, 1H), 6.55 (d, 1H), 6.45 (d, 1H), 5.84 (s, 1H), 3.17 (brm, 8H), 2.00 (brm, 4H), 1.05 (t, 6H)

Mass Spectral Analysis m/z=429.3 (M+H)+

Elemental analysis:

$C_{23}H_{28}N_2O_4S$, 1HCl, 0.5H$_2$O

Theory: % C, 58.28; % H, 6.38; % N, 5.91.

Found: % C, 58.29; % H, 6.20; % N, 5.78.

EXAMPLE 22F

Preparation of 22.7:

To a suspension of 22.4 (0.8 g, 80% pure by LC, as of 1.37 mmol, 1 eq.) in ethanol (15 mL) was added sodium acetate (0.77 g, 9.38 mmol, 6.8 eq.) and iodoethane 22.6 (0.62 mL, 7.68 mmol, 5.6 eq.). The reaction mixture was heated under reflux for 10 h. Water (50 mL) was added to the reaction mixture and the organics were extracted with dichloromethane (3×75 mL). The combined organic layers were dried over sodium sulfate, filtered, and concentrated under reduced pressure. The crude product was purified by column chromatography (eluent: hexane/ethyl acetate mixtures of increasing polarity).

Yield: 89%

$^1$H NMR (400 MHz, CDCl$_3$) δ 7.75 (m, 1H), 7.57 (m, 1H), 7.45 (m, 2H), 7.34 (m, 2H), 7.06 (d, 1H), 5.67 (d, 1H), 4.02-3.25 (m, 8H), 3.05 (q, 2H), 2.47-2.25 (m, 3H), 2.00-1.69 (m, 3H), 1.32-1.12 (m, 9H)

Mass Spectral Analysis m/z=579.26 (M+H)+

Preparation of 22F:

To a solution of 22.7 (0.57 g, 0.98 mmol, 1 eq.) in a mixture methanol (30 mL) and water (10 mL) at 0° C. was added potassium carbonate (0.81 g, 5.88 mmol, 6 eq.) in one portion. The reaction mixture was slowly warmed up to room temperature and stirring was continued for 10 h at room temperature. The methanol was removed under reduced pressure and the organics were extracted with dichloromethane (3×50 mL). The combined organic layers were dried over sodium sulfate, filtered, and concentrated under reduced pressure. The crude product was dissolved in anhydrous dichloromethane (10 mL). To this solution was added a 2M anhydrous solution of hydrogen chloride in diethyl ether (2 mL, 4 mmol, 4 eq.) dropwise at 0° C. The mixture was stirred for 1 h at room temperature and then concentrated under reduced pressure. The crude product was purified by column chromatography (eluent: dichloromethane/methanol mixture of increasing polarity).

Yield: 63%

$^1$H NMR (400 MHz, DMSO-d$_6$) δ 9.19 (m, 2H), 7.75 (dd, 1H), 7.45 (m, 4H), 7.39 (d, 1H), 7.23 (d, 1H), 6.07 (s, 1H), 3.53-3.40 (m, 2H), 3.31-3.04 (m, 8H), 2.31 (m, 2H), 2.18 (m, 1H), 2.01 (m, 2H), 1.82 (m, 1H), 1.22-1.02 (m, 9H)

Mass Spectral Analysis m/z=483.2 (M+H)+

Elemental analysis:

$C_{27}H_{34}N_2O_4S$, 1HCl, 1.5H$_2$O

Theory: % C, 59.38; % H, 7.01; % N, 5.13.

Found: % C, 59.26; % H, 6.64; % N, 5.15.

$[\alpha]_D^{25}$=−3.85 (c=10.25 mg/mL, MeOH)

EXAMPLE 33M

To a solution of 32.1 (1.0 g, 2.34 mmol, 1.0 eq) in dioxane (40 mL) under nitrogen was added 33.1l (0.51 g, 2.57 mmol, 1.1 eq), potassium phosphate (0.75 g, 3.51 mmol, 1.5 eq), potassium bromide (0.31 g, 2.57 mmol, 1.1 eq) and tetrakis(triphenylphosphine)palladium(0) (0.14 g, 0.12 mmol, 0.05 eq). The mixture was heated at 100° C. for 16 h. Additional quantity of tetrakis(triphenylphosphine) palladium(0) (0.10 g, 0.087 mmol, 0.04 eq) was added to the reaction mixture, which was heated at 100° C. for an additional 24 h and then cooled to room temperature. Ethyl acetate and water were added and the layers were separated. The organics were concentrated and purified by column chromatography (eluent: hexane/ethyl acetate mixtures of increasing polarity).

Yield: 65%

$^1$HNMR (400 MHz, CDCl$_3$) δ 7.99 (d, 2H), 7.44 (d, 2H), 7.20 (m, 1H), 6.96 (m, 2H), 6.86 (m, 1H), 5.60 (s, 1H), 3.88 (brs, 2H), 3.34 (brs, 2H), 2.64 (s, 3H), 2.06 (brd, 2H), 1.68 (m, 2H), 1.48 (s, 9H)

Mass Spectral Analysis m/z=420.2 (M+H)+

Preparation of 33M

To a solution of the Boc derivative, obtained previously, (0.63 g, 1.50 mmol, 1.0 eq) in methylene chloride (30 mL) at 0° C. under nitrogen was added a 2.0M solution of anhydrous hydrochloric acid in diethyl ether (3.00 mL, 6.00 mmol, 4.0 eq). The reaction mixture was stirred for 48 h at room temperature and the resulting precipitate was collected by vacuum filtration. A saturated aqueous solution of sodium bicarbonate was added to a suspension of the resulting solid in ethyl acetate. The organic layer was separated and concentrated under vacuum. The crude product was further purified by column chromatography [eluent: methanol/(methylene chloride/ammonium hydroxide=99:1) mixtures of increasing polarity].

Yield: 61%

$^1$HNMR (400 MHz, DMSO dr) δ 8.02 (d, 2H), 7.49 (d, 2H), 7.22 (m, 1H), 6.96 (d, 1H), 6.89 (m, 2H), 5.91 (s, 1H), 2.91 (m, 2H), 2.76 (m, 2H), 2.62 (s, 3H), 1.82 (m, 2H), 1.71 (m, 2H)

Mass Spectral Analysis m/z=320.1 (M+H)+
Elemental analysis:
$C_{21}H_{21}NO_2$, $0.6H_2O$
Theory: % C, 76.38; % H, 6.78; % N, 4.24.
Found: % C, 76.33; % H, 6.73; % N, 4.33.

EXAMPLE 33N

To a solution of 32.1 (1.0 g, 2.34 mmol, 1.0 eq) in dioxane (40 mL) under nitrogen was added 33.1m (0.67 g, 2.57 mmol, 1.1 eq), potassium phosphate (0.75 g, 3.51 mmol, 1.5 eq), potassium bromide (0.31 g, 2.57 mmol, 1.1 eq) and tetrakis (triphenylphosphine)palladium(0) (0.14 g, 0.12 mmol, 0.05 eq). The mixture was heated at 100° C. for 16 h. Additional quantity of tetrakis(triphenylphosphine) palladium(0) (0.10 g, 0.087 mmol, 0.04 eq) was added and the reaction was heated at 100° C. for an additional 24 h and then cooled to room temperature. Ethyl acetate and water were added and the layers were separated. The organics were concentrated and purified by column chromatography (eluent: hexane/ethyl acetate mixtures of increasing polarity).
Yield: 64%
$^1$HNMR (400 MHz, CDCl$_3$) δ 7.84 (m, 4H), 7.61 (m, 1H), 7.49 (m, 4H), 7.21 (m, 1H), 7.02 (dd, 1H), 6.96 (dd, 1H), 6.88 (m, 1H), 5.64 (s, 1H), 3.88 (brs, 2H), 3.35 (brs, 2H), 2.08 (brd, 2H), 1.70 (m, 2H), 1.49 (s, 9H)
Mass Spectral Analysis m/z=482.2 (M+H)+
Preparation of 33N
To a solution of the Boc derivative obtained previously (0.715 g, 1.48 mmol, 1.0 eq) in methylene chloride (30 mL) at 0° C. under nitrogen was added a 2.0M solution of anhydrous hydrochloric acid in diethyl ether (2.97 mL, 5.94 mmol, 4.0 eq). The reaction mixture was stirred for 48 h at room temperature and diluted with diethyl ether (5 mL). The precipitate was sonicated and collected by vacuum filtration.
Yield: 95%
$^1$HNMR (400 MHz, DMSO d$_6$) δ 8.75 (brs, 2H), 7.80 (m, 4H), 7.71 (m, 1H), 7.59 (m, 4H), 7.28 (m, 1H), 7.05 (m, 2H), 6.97 (m, 1H), 6.02 (s, 1H), 3.20 (brm, 4H), 2.06 (brm, 4H)
Mass Spectral Analysis m/z=382.4 (M+H)+
Elemental analysis:
$C_{26}H_{23}NO_2$, 1HCl, $0.5H_2O$
Theory: % C, 73.14; % H, 5.90; % N, 3.28.
Found: % C, 72.95; % H, 5.75; % N, 3.32.

EXAMPLES 38A, 38B, 38C, 38D

Preparation of 38.2:
To a mixture of 19.1 (29.8 g, 127.7 mmol, 1 eq.) and 38.1 (18.4 g, 127.7 mmol, 1 eq.) was added pyridine (12.5 mL) followed by 10 drops of piperidine. The mixture was stirred at 45° C. for 1 h and then stood at room temperature for 10 h. The resulting solids were washed with methanol and then dried in vacuo.
Yield: 82%
$^1$H NMR (400 MHz, CDCl$_3$) δ 7.41-7.30 (m, 5H), 5.17 (s, 2H), 3.70 (m, 4H), 3.18 (m, 4H), 1.75 (s, 6H)
Mass Spectral Analysis m/z=360.22 (M+H)+
Preparation of 38.4:
To a suspension of copper(I) iodide (0.636 g, 3.34 mmol, 0.04 eq.) in dry tetrahydrofuran (200 mL) at −10° C. was added 38.3 (500 mL, 0.25M in THF, 125 mmol, 1.5 eq.) over a 50 min time period. The mixture was kept at −10° C. for another 15 min and then solid 38.2 (30 g, 83.48 mmol, 1 eq.) was added in 10 portions waiting for the exotherm subside between additions. The reaction mixture was kept at −10° C. for another 2 h and then slowly added to a mixture of 13% ammonium hydroxide/saturated ammonium chloride/water (1/1/1, 200 mL) and ethyl acetate (300 mL). The mixture was stirred for 15 min and then the two layers were separated. The organic layer was washed with 13% ammonium hydroxide/saturated ammonium chloride/water (1/1/1, 2×200 mL), brine (3×200 mL), dried over sodium sulfate, filtered, and concentrated under reduced pressure. Diethyl ether (800 mL) was added to the crude mixture and the suspension was stirred at room temperature for 10 h. The resulting fine powders were collected by filtration, washed with diethyl ether (3×50 mL) and dried in vacuo.
Yield: 100%
$^1$H NMR (400 MHz, DMSO-d$_6$) δ 7.37-7.25 (m, 5H), 7.05-6.92 (m, 4H), 4.99 (s, 2H), 3.70 (m, 2H), 2.94 (m, 2H), 2.91-2.66 (m, 4H), 1.45 (s, 6H), 0.84 (m, 2H)
Mass Spectral Analysis m/z=468.25 (M−H)−
Preparation of 38.5:
A mixture of 38.4 (41 g, 83.48 mmol, 1 eq.) in N,N-dimethylformamide/water (1:1, 400 mL) was stirred at 120° C. for 10 h. The reaction mixture was cooled to room temperature and was acidified with 1N aqueous hydrochloric acid until pH 1-2. The mixture was stirred at room temperature for 15 min and the resulting solids were collected by filtration, washed with water (2×50 mL), and then dried in vacuum oven at 70° C.
Yield: 95%
$^1$H NMR (400 MHz, CDCl$_3$) δ 7.41-7.28 (m, 5H), 7.24 (m, 2H), 7.11 (m, 2H), 5.05 (s, 2H), 3.69-3.56 (m, 2H), 3.41-3.20 (m, 2H), 2.76 (s, 2H), 2.17 (s, 2H), 1.53-1.32 (m, 4H)
Mass Spectral Analysis m/z=384.35 (M−H)−
Preparation of 38.6:
To a stirred solution of 38.5 (20 g, 51.9 mmol, 1 eq.) in dry dichloromethane (300 mL) was added oxalyl chloride (27.2 mL, 311.4 mmol, 6 eq.) in one portion followed by 5 drops of N,N-dimethylformamide. The reaction mixture was stirred at room temperature for 1 h and then concentrated under reduced pressure. The crude mixture was further dried in vacuo for 4 h and then dissolved in dry dichloromethane (600 mL), to which was added anhydrous aluminum chloride (13.84 g, 103.8 mmol, 2 eq.) in one portion. The reaction mixture was stirred at room temperature for 10 h. The reaction was quenched with water at 0° C. and the mixture was basified with concentrated ammonium hydroxide until pH 8-9. The two phases were separated and the aqueous phase was extracted with dichloromethane (3×100 mL). The combined organics were dried over sodium sulfate, filtered, and concentrated under reduced pressure. The crude material was dissolved in dichloromethane (300 mL), to which were added triethylamine (21.7 mL, 155.7 mmol, 3 eq.) and 4.7 (13.6 g, 62.28 mmol, 1.2 eq.) portionwise at 0° C. The reaction mixture was slowly warmed up to and stirred at room temperature for 10 h. Dichloromethane was removed under reduced pressure. The crude product was dissolved in ethyl acetate (500 mL) and washed with 0.5 N aqueous hydrochloric acid (2×100 mL), water (2×200 mL), brine (200 mL), and dried over sodium sulfate, filtered, and concentrated under reduced pressure. The crude product was purified by column chromatography (eluent: hexane/ethyl acetate mixture of increasing polarity).
Yield: 62%
$^1$H NMR (400 MHz, CDCl$_3$) δ 7.67 (dd, 1H), 7.25-7.17 (M, 2H), 3.50-3.35 (m, 4H), 2.92 (s, 2H), 2.62 (s, 2H), 1.50 (m, 4H), 1.45 (s, 9H)
Mass Spectral Analysis m/z=334.23 (M+H)+
Preparation of 38.7:
To a stirred solution of 38.6 (19.3 g, 57.88 mmol, 1 eq.) in dry tetrahydrofuran (250 mL) at −78° C. under nitrogen was added as solution of lithium bis(trimethylsilyl)amide in tetrahydrofuran (1.0M, 69.46 mL, 69.46 mmol, 1.2 eq.) over a 20 min time period. The mixture was kept at −78° C. for 1 h and then N-phenylbis(trifluoromethanesulfonamide) 1.4 (24.81 g, 69.46 mmol, 1.2 eq.) in tetrahydrofuran (100 mL) was added to the mixture over a 20 min time period. The mixture was kept at −78° C. for another hour, then slowly warmed up to and stirred room temperature for 10 h. Tetrahydrofuran was removed under reduced pressure. The crude product was dissolved in diethyl ether (500 mL) and washed with water (2×150 mL), 0.5N aqueous hydrochloric acid (2×100 mL), 1N aqueous sodium hydroxide (3×100 mL), brine, dried over sodium sulfate, filtered, and concentrated under reduced pressure. The crude product was purified by column chromatography (eluent: hexane/ethyl acetate mixture of increasing polarity).

Yield: 91%

$^1$H NMR (400 MHz, CDCl$_3$) δ 7.15 (dd, 1H), 7.07 (dd, 1H), 6.98 (m, 1H), 6.05 (s, 1H), 3.65-3.53 (m, 2H), 3.36-3.27 (m, 2H), 2.79 (s, 2H), 1.69-1.60 (m, 2H), 1.56-1.48 (m, 2H), 1.46 (s, 9H)

Mass Spectral Analysis m/z=466.20 (M+H)$^+$

Preparation of 38.8:

To a solution of aqueous potassium carbonate (2M solution, 6.7 mL, 13.4 mmol, 3 eq.) was added dioxane (45 mL), 1.7 (1.63 g, 5.36 mmol, 1.2 eq.), and 38.7 (2.08 g, 4.46 mmol, 1 eq.) successively. The reaction flask was purged with nitrogen and 1,1'-bis(diphenylphosphino)ferrocene palladium(II) chloride complex with dichloromethane (163 mg, 0.22 mmol, 0.05 eq.) was added to the mixture. The mixture was stirred at room temperature for 30 min. Water (200 mL) and ethyl acetate (300 mL) were added and the two phases were separated. The aqueous phase was extracted with ethyl acetate (100 mL) and the combined organics were washed with brine (2×100 mL) and concentrated under reduced pressure. The crude product was purified by column chromatography (eluent: hexane/ethyl acetate mixtures of increasing polarity).

Yield: 94%

$^1$H NMR (400 MHz, CDCl$_3$) δ 8.54 (dd, 1H), 7.73 (m, 1H), 7.64 (dd, 1H), 7.17 (dd, 1H), 6.90 (m, 1H), 6.65 (dd, 1H), 6.10 (s, 1H), 3.60 (q, 4H), 3.51-3.35 (m, 4H), 2.80 (s, 2H), 1.68-1.49 (m, 4H), 1.47 (s, 9H), 1.33-1.18 (m, 6H)

Mass Spectral Analysis m/z=494.46 (M+H)$^+$

Preparation of 38A:

To a solution of 38.8 (4.5 g, 9 mmol, 1 eq.) in dichloromethane/methanol (5:1, 60 mL) was slowly added a 2M solution of hydrogen chloride in diethyl ether (2.0M, 22.5 mL, 45 mmol, 5 eq.). The mixture was stirred at room temperature for 10 h. The organic solvents were removed under reduced pressure and the crude product was purified by column chromatography (eluent: dichloromethane/methanol mixture of increasing polarity).

Yield: 81%

$^1$H NMR (400 MHz, DMSO-d$_6$) δ 9.15-8.92 (m, 2H), 8.64 (d, 1H), 7.91 (dd, 1H), 7.60 (dd, 1H), 7.38 (dd, 1H), 7.11 (m, 1H), 6.68 (dd, 1H), 6.44 (s, 1H), 3.47 (q, 2H), 3.32 (q, 2H), 3.27-3.08 (m, 4H), 2.83 (s, 2H), 1.79-1.62 (m, 4H), 1.17 (t, 3H), 1.12 (t, 3H)

Mass Spectral Analysis m/z=394.3 (M+H)$^+$

Elemental analysis:

$C_{24}H_{28}FN_{3}O$, 1.4HCl, 0.8H$_2$O

Theory: % C, 62.81; % H, 6.81; % Cl, 10.81; % N, 9.16. Found: % C, 62.61; % H, 6.67; % Cl, 10.96; % N, 9.04.

Preparation of 38B:

To a stirred solution of 38A (150 mg, 0.35 mmol, 1 eq.) in methanol (10 mL) was added palladium [30 mg, 10 wt. % (dry basis) on activated carbon, 20% wt. eq.]. The reaction mixture was stirred under a hydrogen atmosphere using a hydrogen balloon at room temperature for 10 h. The palladium on activated carbon was filtered off on a celite pad and the filtrate was concentrated under reduced pressure. The crude product was purified by column chromatography (eluent: dichloromethane/methanol mixture of increasing polarity).

Yield: 46%

$^1$H NMR (400 MHz, DMSO-d$_6$) δ 8.88-8.78 (m, 2H), 8.51 (d, 1H), 7.67 (dd, 1H), 7.51 (d, 1H), 7.73 (m, 1H), 7.01 (m, 1H), 6.40 (dd, 1H), 4.22 (m, 1H), 3.44 (q, 2H), 3.28 (q, 2H), 3.18-3.02 (m, 4H), 2.85 (d, 1H), 2.75 (d, 1H), 2.16 (m, 1H), 1.75-1.46 (m, 5H), 1.15 (t, 3H), 1.09 (t, 3H)

Mass Spectral Analysis m/z=396.4 (M+H)$^+$

Preparation of 38.9:

To a solution of 38.7 (11.88 g, 25.5 mmol, 1 eq.) in N,N-dimethylformamide (125 mL) at 0° C. was added potassium acetate (7.51 g, 76.5 mmol, 3 eq.), bis(pinacolato)diboron 1.14 (7.77 g, 30.6 mmol, 1.2 eq.), 1,1'-bis(diphenylphosphino)ferrocene palladium(II) chloride complex with dichloromethane (560 mg, 0.76 mmol, 0.03 eq.) successively. The reaction mixture was stirred at 100° C. for 10 h. The reaction mixture was cooled to room temperature, diethyl ether (300 mL) and water (300 mL) were added and the mixture was stirred for another 30 minute at room temperature. The two phases were separated and the organic phase was washed with water (2×150 mL), brine (200 mL), dried over sodium sulfate, filtered, and concentrated under reduced pressure. The crude product was purified by column chromatography (eluent: hexane/ethyl acetate mixtures of increasing polarity).

Yield: 60%

$^1$H NMR (400 MHz, CDCl$_3$) δ 7.54 (dd, 1H), 7.01 (dd, 1H), 6.84-6.77 (m, 2H), 3.51-3.37 (m, 4H), 2.65 (s, 2H), 1.61-1.38 (m, 13H), 1.34 (s, 12H)

Mass Spectral Analysis m/z=444.38 (M+H)$^+$

Preparation of 38.10:

To a solution of an aqueous solution of potassium carbonate (2M solution, 16.2 mL, 48.6 mmol, 3 eq.) was added dioxane (110 mL), 35.8 (3.926 g, 10.8 mmol, 1 eq.), and 38.9 (5.6 g, 12.6 mmol, 1.17 eq.) successively. The reaction flask was purged with nitrogen and 1,1'-bis(diphenylphosphino)ferrocene palladium(II) chloride complex with dichloromethane (403 mg, 0.95 mmol, 0.05 eq.) was added to the mixture. The mixture was stirred at room temperature for 1 h and then heated at 55° C. for 10 h. Water (200 mL) and ethyl acetate (300 mL) were added and the mixture was stirred for another 10 min at room temperature. The two phases were separated and the organic phase was washed with brine (200 mL), dried over sodium sulfate, filtered, and concentrated under reduced pressure. The crude product was purified by column chromatography (eluent: hexane/ethyl acetate mixtures of increasing polarity).

Yield: 81%

$^1$H NMR (400 MHz, CDCl$_3$) δ 7.22-7.16 (m, 2H), 7.13-7.07 (m, 2H), 6.82 (m, 1H), 6.48 (dd, 1H), 6.01 (s, 1H), 5.04 (s, 2H), 3.66-3.50 (m, 4H), 3.43-3.30 (m, 4H), 3.28 (s, 3H), 2.79 (s, 2H), 1.70-1.49 (m, 4H), 1.46 (s, 9H), 1.32-1.13 (m, 6H)

Mass Spectral Analysis m/z=553.51 (M+H)$^+$

Preparation of 38C:

To a stirred solution of 38.10 (1 g, 1.8 mmol, 1 eq.) in methanol (50 mL) was slowly added a 4M anhydrous solution of hydrogen chloride in dioxane (4.5 mL, 18 mmol, 10 eq.). The reaction mixture was stirred at room temperature for 10 h. The organic solvents were removed under reduced pressure and the crude material was purified by column chromatography (eluent: dichloromethane/methanol mixture of increasing polarity).

Yield: 80%

$^1$H NMR (400 MHz, DMSO-d$_6$) δ 9.68 (s, 1H), 8.85-8.66 (m, 2H), 7.29 (m, 1H), 7.19 (d, 1H), 7.01 (m, 1H), 6.87 (d, 1H), 6.83 (dd, 1H), 6.39 (dd, 1H), 6.12 (s, 1H), 3.51-3.07 (m, 8H), 2.82 (s, 2H), 1.79-1.57 (m, 4H), 1.20-1.04 (m, 6H)

Mass Spectral Analysis m/z=409.7 (M+H)$^+$

Elemental analysis:

C$_{25}$H$_{29}$FN$_2$O$_2$, 1HCl, 1.2H$_2$O

Theory: % C, 64.35; % H, 7.00; % N, 6.00.

Found: % C, 64.34; % H, 6.92; % N, 6.04.

Preparation of 38.11:

To a stirred solution of 38.10 (1.8 g, 3.25 mmol, 1 eq.) in methanol (32 mL) was added palladium [360 mg, 10 wt. % (dry basis) on activated carbon, 20% wt. eq.]. The reaction mixture was stirred under a hydrogen atmosphere using a hydrogen balloon at room temperature for 10 h. The palladium on activated carbon was filtered off on a celite pad and the filtrate was concentrated under reduced pressure and dried in vacuo.

Yield: 91%

$^1$H NMR (400 MHz, CDCl$_3$) δ 7.14 (d, 1H), 7.04 (m, 2H), 6.96 (dd, 1H), 6.80 (m, 1H), 6.51 (m, 1H), 5.13 (s, 2H), 4.46 (m, 1H), 3.60-3.25 (m, 11H), 2.78 (d, 1H), 2.65 (d, 1H), 2.04 (m, 1H), 1.68-1.38 (m, 14H), 1.30-1.10 (m, 6H)

Mass Spectral Analysis m/z=555.53 (M+H)$^+$

Preparation of 38D:

To a solution of 38.11 (0.30 g, 0.54 mmol, 1 eq.) in methanol (20 mL) was slowly added a 4M anhydrous solution of hydrogen chloride in dioxane (1.35 mL, 5.4 mmol, 10 eq.). The reaction mixture was stirred at room temperature for 10 h. The organic solvents were removed under reduced pressure and the crude material was purified by column chromatography (eluent: dichloromethane/methanol mixture of increasing polarity).

Yield: 79%

$^1$H NMR (400 MHz, DMSO-d$_6$) δ 9.84 (s, 1H), 8.92-8.73 (m, 2H), 7.17 (m, 1H), 7.03-6.91 (m, 2H), 6.86 (d, 1H), 6.73 (dd, 1H), 6.41 (dd, 1H), 4.37 (m, 1H), 3.58-2.97 (m, 8H), 2.86 (d, 1H), 2.68 (d, 1H), 1.99 (m, 1H), 1.80-1.49 (m, 5H), 1.17-1.02 (m, 6H)

Mass Spectral Analysis m/z=411.76 (M+H)$^+$

EXAMPLE 39A

Preparation of 39.1:

To a suspension of copper (I) iodide (550 mg, 2.88 mmol, 0.036 eq) in anhydrous tetrahydrofuran (600 mL) was added dropwise a 2.0 M solution of benzylmagnesium chloride (28.3a) (100 mL, 200 mmol, 2.5 eq) in tetrahydrofuran under a nitrogen atmosphere at −10° C. After the reaction mixture was stirred at −10° C. for 30 min, solid 38.2 (28.72 g, 80 mmol, 1.0 eq) was added in ten portions over a 1 h period. After the addition was complete, the reaction mixture was stirred between −10° C. and −0° C. for 3 h, and then quenched by a mixture of concentrated ammonium hydroxide/saturated aqueous ammonium chloride/water (1:2:3, 400 mL). The mixture was extracted with ethyl acetate, and the combined organic layers were washed with a mixture of concentrated ammonium hydroxide/saturated aqueous ammonium chloride/water (1:2:3) and brine, dried over sodium sulfate and concentrated in vacuo. To the residue was added diethyl ether and the mixture was stirred overnight at room temperature.

The solid was collected by filtration, washed with diethyl ether and dried in vacuo.

Yield: 100%

$^1$H NMR (400 MHz, DMSO d$_6$) δ 7.30-7.00 (m, 10H), 4.96 (s, 2H), 3.70 (m, 2H), 2.98 (m, 2H), 2.80 (s+m, 4H), 1.49 (s, 6H), 0.83 (m, 2H).

Mass Spectral Analysis m/z=450.36 (M−Na)$^+$

Preparation of 39.2:

Compound 39.1 (39 g, 82.5 mmol) was dissolved in a mixture of N,N dimethylformamide (200 mL) and water (200 mL) and heated at ~135° C. for 2 days, then cooled to room temperature. To the reaction mixture was added a 1 N aqueous sodium hydroxide (125 mL) and water (500 mL), the resulting mixture was washed with diethyl ether, acidified with a 6 N aqueous solution of hydrochloric acid and extracted with diethyl ether. The combined organic extracts were washed with water and brine, dried over sodium sulfate and concentrated in vacuo.

Yield: 92.9%.

$^1$H NMR (400 MHz, DMSO-d$_6$) δ 12.25 (brs, 1H), 7.36-7.20 (m, 10H), 5.08 (s, 2H), 3.60 (m, 2H), 3.33 (m, 2H), 2.79 (s, 2H), 2.19 (s, 2H), 1.50-1.40 (m, 4H).

Preparation of 28.6a:

To a solution of 39.2 (1.1 g, 3 mmol, 1 eq) in anhydrous methylene chloride (20 mL) was added oxalyl chloride (1.6 mL, 18.3 mmol, 6.1 eq) in one portion followed by 2 drops of anhydrous N,N dimethylformamide. The reaction mixture was stirred at room temperature for 4 h and then concentrated in vacuo. The resulting acyl chloride was dissolved in anhydrous methylene chloride (60 mL) and aluminum chloride (804 mg, 6 mmol, 2 eq) was added in one portion. The reaction mixture was stirred at room temperature overnight and then quenched by water (40 mL) followed by addition of concentrated ammonium hydroxide to basify the aqueous layer. The organic layer was separated and the aqueous layer was extracted with methylene chloride. The combined organic layers were dried over sodium sulfate and concentrated in vacuo. The residue was then dissolved in methylene chloride (30 mL) and cooled to 0° C. To this solution was added triethylamine (1.3 mL, 9.34 mmol, 3.1 eq) followed by benzyl chloroformate (0.9 mL, 6.0 mmol, 2 eq). The reaction mixture was stirred at 0° C. for 1 h and then washed with a saturated aqueous solution of sodium bicarbonate, dried over sodium sulfate and concentrated in vacuo. The residue was purified by column chromatography on silica gel (hexane-ethyl acetate-methylene chloride, 4:1:1), to yield the spiro ketone 28.6a Yield: 95.5%.

$^1$H NMR (400 MHz, CDCl$_3$) δ 8.0 (d, 1H), 7.50 (t, 1H), 7.33-7.23 (m, 7H), 5.11 (s, 2H), 2.98 (s, 2H), 2.62 (s, 2H), 1.50 (m, 4H).

Preparation of 28.7a:

A 1.0 M solution of lithium bis(trimethylsilyl)amide in tetrahydrofuran (3.6 mL, 3.6 mmol, 1.2 eq) was added at −78° C. to a solution of compound 28.6a (1.047 g, 3.0 mmol, 1 eq) in tetrahydrofuran (30 mL). After 45 minutes, a solution of N-phenyltrifluoromethanesulfonimide (1.4) (1.3 g, 3.6 mmol, 1.2 eq) in tetrahydrofuran (8 mL) was added dropwise to the reaction mixture. The reaction mixture was then warmed to room temperature and stirred for 2.5 h, quenched by addition of water (40 mL), and extracted with a mixture of hexane and diethyl ether (1:1). The organic extracts were combined and washed with water, brine and dried over sodium sulfate. Evaporation of the solvent provided 28.7a used for the next step without further purification.

Yield: 100%

¹H NMR (400 MHz, CDCl$_3$) δ 7.35-7.18 (m, 9H), 5.98 (s, 1H), 5.11 (s, 2H), 3.70 (m, 2H), 3.40 (m, 2H), 2.83 (s, 2H), 1.66-1.56 (m, 4H).

Preparation of 28.12:

To the solution of the enol triflate 28.7a (2.91 g, 6.04 mmol) in dimethoxyethane (60 mL) was added sequentially 2 N aqueous solution of sodium carbonate (10.4 mL, 20.8 mmol, 3.4 eq), lithium chloride (860 mg, 20.3 mmol, 3.4 eq), 5-(4, 4,5,5-tetramethyl-[1,3,2]dioxaborolan-2-yl)-pyridine-2-carboxylic acid diethylamide (1.7) (2.13 g, 7.0 mmol, 1.16 eq) and tetrakis(triphenylphosphine)palladium(0) (212 mg, 0.183 mmol, 0.03 eq). The reaction mixture was refluxed overnight, cooled to room temperature, diluted with water (60 mL) and extracted with diethyl ether. The combined organic extracts were dried over sodium sulfate, and concentrated in vacuo. The residue was purified by column chromatography (eluent: hexane/ethyl acetate, 1:1).

Yield: 99%

¹H NMR (400 MHz, CDCl$_3$) δ 8.53 (d, 1H), 7.76 (dd, 1H), 7.60 (d, 1H), 7.35-7.12 (m, 8H), 6.92 (d, 1H), 6.05 (s, 1H), 5.12 (s, 1H), 3.70 (m, 2H), 3.60 (m, 2H), 3.48 (m, 2H), 2.82 (s, 2H), 1.65-1.55 (m, 4H), 1.30 (t, 3H), 1.20 (t, 3H).

Preparation of 39A:

Compound 28.12 (1.0 g, 2.7 mmol) was dissolved in methylene chloride (10 mL) and methanol (80 mL), and the mixture was hydrogenated in the presence of 10% Pd/C (300 mg) using a hydrogen balloon. After 2 days at room temperature, the reaction mixture was filtered and the filtrate was concentrated in vacuo. The residue was purified by column chromatography (eluent: methylene chloride/methanol/conc. ammonia hydroxide, 10:1:1).

Yield: 80%

¹H NMR (400 MHz, CDCl$_3$) δ 8.42 (d, 1H), 7.52 (m, 2H), 7.12 (m, 2H), 7.05 (m, 1H), 6.70 (d, 1H), 4.10 (m, 1H), 3.56 (q, 2H), 3.42 (q, 2H), 3.10-2.50 (m, 6H), 2.10 (m, 1H), 1.60 (m, 5H), 1.28 (t, 3H), 1.20 (t, 3H).

Mass Spectral Analysis m/z=378.3 (M+H)$^+$

EXAMPLES 39B, 39C

Preparation of 39.3:

To the solution of compound 39A (650 mg, 1.72 mmol) in methylene chloride (10 mL) was added triethylamine (0.34 mL, 2.4 mmol, 1.4 eq) followed by di-t-butyl dicarbonate (4.7) (450 mg, 2.06 mmol, 1.2 eq.). The reaction mixture was stirred at room temperature for 4 h and then concentrated in vacuo. The residue was purified by column chromatography (eluent: hexane/ethyl acetate, 1:1).

Yield: 91.2%

¹H NMR (400 MHz, CDCl$_3$) δ 8.41 (d, 1H), 7.52 (m, 2H), 7.12 (m, 2H), 7.05 (m, 1H), 6.70 (d, 1H), 4.10 (m, 1H), 3.58-3.33 (m, 8H), 2.90 (d, 1H), 2.72 (d, 1H), 2.09 (m, 1H), 1.65-1.52 (m, 5H), 1.47 (s, 9H), 1.29 (t, 3H), 1.20 (t, 3H).

Preparation of 39.4 & 39.5:

Chiral separation of 39.3 (680 mg) gave the two enantiomers 39.4 and 39.5.

Column: Chiralpak ADH, 21×250 nm, 35° C.; SFC

Eluent: 35% MeOH/65% CO$_2$; 50 mL/min, 200 bar

UV wavelength: 260 nm

Polarimeter: 670 nm

Sample: 80 mg/mL in MeOH, 2 mL injected

Positive polarimeter peak elutes first at about 6.5 minutes and the negative polarimeter peak elutes second at about 9 minutes in 35% MeOH/CO$_2$ 39.4: (−) enantiomer; ee>96% (268 mg)

39.5: (+) enantiomer; ee>99% (295 mg)

Preparation of 39B:

To the solution of pure enantiomer 39.4 (268 mg, 0.56 mmol) in methylene chloride (5 mL) was added 2.0 M hydrochloric acid in diethyl ether (10 mL, 20 mmol, 35.7 eq.) The mixture was stirred at ambient temperature for 24 h and the solvent was evaporated in vacuo. The resulting solid was triturated in diethyl ether, filtered and washed with diethyl ether.

Yield: 86.2%.

¹H NMR (400 MHz, DMSO-d$_6$) δ 8.90 (brs, 2H), 8.50 (s, 1H), 7.65 (d, 1H), 7.50 (d, 1H), 7.14 (m, 2H), 7.05 (m, 1H), 6.62 (d, 1H), 4.20 (m, 1H), 3.42 (q, 2H), 3.28 (q, 2H), 3.09 (m, 4H), 2.85 (d, 1H), 2.78 (d, 1H), 2.15 (m, 1H), 1.70-1.50 (m, 5H), 1.12 (t, 3H), 1.08 (t, 3H).

Mass Spectral Analysis m/z=378.83 (M+H)$^+$

Elemental analysis:

C$_{24}$H$_{31}$N$_3$O, 8/7HCl, 6/7H$_2$O

Theory: % C, 66.32; % H, 7.85; % N, 9.67.

Found: % C, 66.33; % H, 7.72; % N, 9.53.

$[\alpha]^{25}_D$ −69.1° (c=0.5, MeOH)

Preparation of 39C:

To the solution of enantiomer 39.5 (295 mg, 0.62 mmol) in methylene chloride (5 mL) was added a 2.0 M solution of hydrochloric acid in diethyl ether (10 mL, 20 mmol, 32 eq.) The mixture was stirred at ambient temperature for 24 h and the solvent was evaporated in vacuo. The resulting solid was triturated in diethyl ether, filtered and washed with diethyl ether.

Yield: 88.2%

¹H NMR (400 MHz, DMSO-d$_6$) δ 8.90 (brs, 2H), 8.50 (s, 1H), 7.65 (d, 1H), 7.50 (d, 1H), 7.14 (m, 2H), 7.05 (m, 1H), 6.62 (d, 1H), 4.20 (m, 1H), 3.42 (q, 2H), 3.28 (q, 2H), 3.09 (m, 4H), 2.85 (d, 1H), 2.78 (d, 1H), 2.15 (m, 1H), 1.70-1.50 (m, 5H), 1.12 (t, 3H), 1.08 (t, 3H).

Mass Spectral Analysis m/z=378.83 (M+H)$^+$

Elemental analysis:

C$_{24}$H$_{31}$N$_3$O, 6/5 HCl, 6/5 H$_2$O

Theory: % C, 65.09; % H, 7.87; % N, 9.49.

Found: % C, 65.03; % H, 7.68; % N, 9.34.

$[\alpha]^{25}_D$ +70.2° (c=0.7, MeOH)

EXAMPLES 39D, 39E

Preparation of 39.7:

To the solution of the enol triflate 28.7a (2.91 g, 6.04 mmol) in dimethoxyethane (60 mL) was added sequentially a 2 N aqueous solution of sodium carbonate (10.4 mL, 20.8 mmol, 3.4 eq), lithium chloride (860 mg, 20.3 mmol, 3.4 eq), 39.6 (2.792 g, 7.69 mmol, 1.27 eq) and tetrakis(triphenylphosphine)palladium(0) (212 mg, 0.183 mmol, 0.03 eq). The reaction mixture was refluxed overnight, cooled to room temperature, diluted with water (60 mL) and extracted with diethyl ether. The combined organic extracts were dried over sodium sulfate, and concentrated in vacuo. The residue was purified by column chromatography (eluent: hexane/acetone, 2:1).

Yield: 98.4%

¹H NMR (400 MHz, CDCl$_3$) δ 7.38-7.05 (m, 11H), 6.72 (d, 1H), 5.95 (s, 1H), 5.12 (s, 2H), 5.00 (s, 2H), 3.69 (m, 2H), 3.53 (m, 2H), 3.45 (m, 2H), 3.32 (m, 2H), 3.25 (s, 3H), 2.80 (s, 2H), 1.66 (m, 2H), 1.55 (m, 2H), 1.26 (brs, 3H), 1.18 (brs, 3H).

Preparation of 39D:

Iodotrimethylsilane (1.02 mL, 7.5 mmol, 2.84 eq) was added to the solution of compound 39.7 (1.5 g, 2.64 mmol) in anhydrous methylene chloride (30 mL) under nitrogen. The reaction mixture was stirred at room temperature for 2 h, quenched with a 1N aqueous solution of hydrochloric acid (40 mL) and washed with diethyl ether. The aqueous phase was basified to pH=9-10 by addition of a 3N aqueous solution of sodium hydroxide, and extracted with methylene chloride. The organic extracts were combined, dried over sodium sulfate and concentrated in vacuo. The residue was dissolved in methylene chloride (10 mL) and methanol (20 mL). To this solution was added a 2.0 M anhydrous solution of hydrochloric acid in diethyl ether (30 mL, 60 mmol, 22.7 eq) and stirred at room temperature for 2 days. The reaction mixture was concentrated in vacuo and the residue was purified by column chromatography (eluent: methylene chloride/methanol, 5:1).

Yield: 100%

$^1$H NMR (400 MHz, DMSO-$d_6$) δ 9.60 (s, 1H), 8.82 (brs, 2H), 7.24-7.10 (m, 4H), 6.86 (s, 1H), 6.80 (d, 1H), 6.70 (d, 1H), 6.00 (s, 1H), 3.40 (m, 2H), 3.23 (m, 2H), 3.12 (m, 4H), 2.82 (s, 2H), 1.66 (m, 4H), 1.10 (m, 6H).

Mass Spectral Analysis m/z=391.4 (M+H)$^+$

Elemental analysis:

$C_{25}H_{30}N_2O_2$, 1 HCl, 4/5 $H_2O$

Theory: % C, 68.03; % H, 7.44; % N, 6.35.

Found: % C, 67.94; % H, 7.27; % N, 6.34.

Preparation of 39E:

Compound 39.7 (1.7 g, 2.99 mmol) was dissolved in a mixed solvent of methylene chloride (15 mL) and methanol (120 mL), and the mixture was hydrogenated in the presence of 10% Pd/C (510 mg) using a hydrogen balloon. After 2 days of stirring at room temperature, the reaction mixture was filtered and the filtrate was concentrated in vacuo. The residue was dissolved in methylene chloride (10 mL) and methanol (20 mL). To this solution was added a 2.0 M anhydrous solution of hydrochloric acid in diethyl ether (30 mL, 60 mmol, 22.7 eq) and the mixture was stirred at room temperature for 2 days. The reaction mixture was concentrated in vacuo and the residue was dissolved in methylene chloride. The organic solution was washed with a saturated aqueous solution of sodium bicarbonate, dried over sodium sulfate and concentrated in vacuo. The residue was purified by column chromatography (eluent: methylene chloride/methanol, 5:1).

Yield: 90.4%

$^1$H NMR (400 MHz, CDCl$_3$) δ 7.10 (m, 2H), 7.03 (m, 1H), 6.94 (d, 1H), 6.82 (d, 1H), 6.76 (d, 1H), 6.70 (d, 1H), 4.70 (m, 1H), 3.50 (m, 2H), 3.32 (m, 2H), 2.98 (m, 5H), 2.62 (d, 1H), 2.11 (m, 1H), 1.78 (m, 1H), 1.55 (m, 2H), 1.40 (m, 2H), 1.21 (brs, 3H), 1.12 (brs, 3H).

Mass Spectral Analysis m/z=393.4 (M+H)$^+$

EXAMPLES 39F, 39G

Preparation of 39.8:

To the solution of compound 39E (800 mg, 2.04 mmol) in methylene chloride (15 mL) was added triethylamine (0.42 mL, 3.0 mmol, 1.47 eq) followed by di-t-butyl dicarbonate (4.7) (446 mg, 2.04 mmol, 1.0 eq.). The reaction mixture was stirred at room temperature for 45 min and then concentrated in vacuo. The residue was purified by column chromatography (eluent: hexane/ethyl acetate, 1:2).

Yield: 81%

$^1$H NMR (400 MHz, CDCl$_3$) δ 7.98 (brs, 1H), 7.09 (m, 2H), 7.00 (m, 2H), 6.90 (d, 1H), 6.80 (d, 1H), 6.72 (d, 1H), 4.43 (m, 1H), 3.56 (m, 2H), 3.40 (m, 4H), 3.30 (m, 2H), 2.75 (d, 1H), 2.66 (d, 1H), 2.00 (m, 1H), 1.51-1.37 (m, 5H), 1.43 (s, 9H), 1.22 (m, 3H), 1.11 (m, 3H).

Preparation of 39.9 and 39.10:

Chiral separation of 39.8 (800 mg) gave the two enantiomers 39.9 and 39.10.

Column: Chiralpak ADH, 21×250 nm, 35° C.; SFC

Eluent: 35% MeOH/65% $CO_2$; 50 mL/min, 200 bar

UV wavelength: 260 nm

Polarimeter: 670 nm

Sample: 40 mg/mL in MeOH, 1.5 mL injected

Negative polarimeter peak elutes first at about 7.2 minutes and the positive polarimeter peak elutes second at about 10.8 minutes in 35% MeOH/$CO_2$ 39.9: (−) enantiomer; ee>99% (363 mg)

39.10: (+) enantiomer; ee>99% (304 mg)

Preparation of 39F:

To the solution of pure enantiomer 39.9 (305 mg, 0.62 mmol) in methylene chloride (5 mL) was added a 2.0 M anhydrous solution of hydrochloric acid in diethyl ether (10 mL, 20 mmol, 32.3 eq.) The mixture was stirred at ambient temperature for 24 h and the solvent was evaporated in vacuo. The resulting solid was triturated in diethyl ether, filtered and washed with diethyl ether.

Yield: 90.5%.

$^1$H NMR (400 MHz, DMSO-$d_6$) δ 9.80 (s, 1H), 8.80 (brs, 2H), 7.10-6.93 (m, 4H), 6.83 (s, 1H), 6.70 (m, 2H), 4.40 (m, 1H), 3.35-3.03 (m, 8H), 2.86 (d, 1H), 2.72 (d, 1H), 2.00 (m, 1H), 1.60 (m, 5H), 1.10 (m, 6H).

Mass Spectral Analysis m/z=393.8 (M+H)$^+$

Elemental analysis:

$C_{25}H_{32}N_2O_2$, 1 HCl, 3/5 $H_2O$

Theory: % C, 68.27; % H, 7.84; % N, 6.37.

Found: % C, 68.17; % H, 7.72; % N, 6.41.

$[α]^{25}_D$ −59.6° (c=0.55, MeOH)

Preparation of 39G:

To the solution of pure enantiomer 39.10 (280 mg, 0.57 mmol) in methylene chloride (5 mL) was added a 2.0 M anhydrous solution of hydrochloric acid in diethyl ether (10 mL, 20 mmol, 35 eq.) The mixture was stirred at ambient temperature for 24 h and the solvent was evaporated in vacuo. The resulting solid was triturated in diethyl ether, filtered and washed with diethyl ether.

Yield: 90.3%

$^1$H NMR (400 MHz, DMSO-$d_6$) δ 9.80 (s, 1H), 8.80 (brs, 2H), 7.10-6.93 (m, 4H), 6.83 (s, 1H), 6.70 (m, 2H), 4.40 (m, 1H), 3.35-3.03 (m, 8H), 2.86 (d, 1H), 2.72 (d, 1H), 2.00 (m, 1H), 1.60 (m, 5H), 1.10 (m, 6H).

Mass Spectral Analysis m/z=393.8 (M+H)$^+$

Elemental analysis:

$C_{24}H_{31}N_{30}$, 1 HCl, 3/5$H_2O$

Theory: % C, 68.27; % H, 7.84; % N, 6.37.

Found: % C, 68.02; % H, 7.63; % N, 6.33.

$[α]^{25}_D$ +52.6° (c=0.85, MeOH)

EXAMPLE 40A

Preparation of 40.1:

To a suspension of copper (I) iodide (553 mg, 2.90 mmol, 0.036 eq) in anhydrous tetrahydrofuran (50 mL) was added dropwise a 0.25 M solution of 4-methoxybenzylmagnesium chloride (28.3b) (640 mL, 160 mmol, 2.0 eq) in tetrahydrofuran under nitrogen atmosphere at −10° C. After the reaction mixture was stirred at −10° C. for 30 min, solid 38.2 (28.8 g, 80 mmol, 1.0 eq) was added to the mixture in ten portions over a 1 h period. After the addition, the reaction mixture was stirred between −10° C. and −0° C. for 3 h, and then quenched by a mixture of concentrated ammonium hydroxide/aqueous saturated ammonium chloride/water (1:2:3, 400 mL) The mixture was extracted with ethyl acetate, and the combined organic layers were washed with concentrated ammonium hydroxide/aqueous saturated ammonium chloride/water (1:2:3) and brine, dried over sodium sulfate and concentrated in vacuo. To the residue was added diethyl ether and the mixture was stirred overnight at room temperature. The solid was collected by filtration, washed with diethyl ether and dried in vacuo.

Yield: 100%

$^1$H NMR (400 MHz, DMSO d$_6$) δ 7.29 (m, 5H), 6.91 (δ, 2H), 6.73 (δ, 2H), 4.98 (s, 2H), 3.70 (s+m, 5H), 2.93 (m, 2H), 2.80 (m, 2H), 2.70 (s, 2H), 1.49 (s, 6H), 0.82 (m, 2H).

Mass Spectral Analysis m/z=480.40 (M−Na)$^+$

Preparation of 28.11:

Compound 40.1 (40.2 g, 79.92 mmol) was dissolved in a mixture of N,N dimethylformamide (200 mL) and water (200 mL) and the mixture was heated at −135° C. for 2 days, then cooled to room temperature. To the reaction mixture was added a 1N aqueous solution of sodium hydroxide (125 mL) and water (500 mL). The resulting mixture was washed with diethyl ether, acidified with a 6 N aqueous solution of hydrochloric acid and extracted with diethyl ether. The combined organic extracts were washed water and brine, dried over sodium sulfate and concentrated in vacuo.

Yield: 100%.

$^1$H NMR (400 MHz, DMSO d$_6$) δ 12.22 (brs, 1H), 7.33 (m, 5H), 7.10 (d, 2H), 6.86 (d, 2H), 5.06 (s, 2H), 3.73 (s, 3H), 3.60 (m, 2H), 3.32 (m, 2H), 2.69 (s, 2H), 2.17 (s, 2H), 1.45-1.35 (m, 4H).

Preparation of 28.6b:

To a solution of 28.11 (1.98 g, 5 mmol) in anhydrous methylene chloride (10 mL) was added a 2.0 M solution of oxalyl chloride in methylene chloride (20 mL, 40 mmol, 8 eq) followed by 2 drops of anhydrous N,N-dimethylformamide. The reaction mixture was stirred at room temperature for 4 h and then concentrated in vacuo. The resulting acyl chloride was dissolved in anhydrous methylene chloride (100 mL) and aluminum chloride (1.35 g, 10 mmol, 2 eq) was added in one portion. The reaction mixture was stirred at room temperature overnight and then quenched with water (60 mL) followed by addition of concentrated ammonium hydroxide to basify the aqueous layer. The organic layer was separated and the aqueous layer was extracted with methylene chloride. The combined organic layers were dried over sodium sulfate and concentrated in vacuo. The residue was then dissolved in methylene chloride (60 mL) and cooled to 0° C. To this solution was added triethylamine (3.0 mL, 21.6 mmol, 4.3 eq) followed by benzyl chloroformate (2.0 mL, 13.3 mmol, 2.7 eq). The reaction mixture was stirred at 0° C. for 1 h and then washed with saturated aqueous solution of sodium bicarbonate, dried over sodium sulfate, and concentrated in vacuo. The residue was purified by column chromatography (eluent: hexane/methylene chloride/ethyl acetate, 4:1:1).

Yield: 89.7%

$^1$H NMR (400 MHz, CDCl$_3$) δ 7.48 (d, 1H), 7.35 (m, 5H), 7.16 (d, 1H), 7.10 (dd, 1H), 5.11 (s, 2H), 3.81 (s, 3H), 3.50 (m, 4H), 2.90 (s, 2H), 2.60 (s, 2H), 1.50 (m, 4H).

Preparation of 28.7b:

A 1.0 M solution of lithium bis(trimethylsilyl)amide in tetrahydrofuran (100 mL, 100 mmol, 1.22 eq) was added at −78° C. to a solution of compound 28.6b (31 g, 81.8 mmol, 1 eq) in tetrahydrofuran (600 mL). After 45 minutes, a solution of N-phenyltrifluoromethanesulfonimide (1.4) (38 g, 106.4 mmol, 1.3 eq) in tetrahydrofuran (120 mL) was added dropwise. The reaction mixture was then warmed to room temperature, stirred for 4.5 h at room temperature, quenched by addition of water (500 mL), and extracted with a mixture of hexane and diethyl ether (1:1). The organic extracts were combined and washed with water and brine, dried over sodium sulfate and concentrated in vacuo. The residue was purified by column chromatography (eluent: hexane/ethyl acetate, 1:4).

Yield: 98%.

$^1$H NMR (400 MHz, CDCl$_3$) δ 7.33 (m, 5H), 7.09 (d, 1H), 6.90 (d, 1H), 6.80 (dd, 1H), 5.98 (s, 1H), 5.12 (s, 2H), 3.80 (s, 3H), 3.68 (m, 2H), 3.40 (m, 2H), 2.76 (s, 2H), 1.65 (m, 2H), 1.55 (m, 2H).

Preparation of 40.2:

To the solution of the enol triflate 28.7b (4.0 g, 7.83 mmol) in dimethoxyethane (80 mL) was added sequentially a 2 N aqueous solution of sodium carbonate (13.6 mL, 27.2 mmol, 3.47 eq), lithium chloride (1.12 g, 26.4 mmol, 3.37 eq), 1.7 (2.74 g, 9.0 mmol, 1.15 eq) and tetrakis(triphenylphosphine)palladium(0) (276 mg, 0.238 mmol, 0.03 eq). The reaction mixture was refluxed overnight, cooled to room temperature, diluted with water (120 mL) and extracted with diethyl ether. The combined organic extracts were dried over sodium sulfate, and concentrated in vacuo. The residue was purified by column chromatography (eluent: hexane/ethyl acetate, 2:3).

Yield: 100%

$^1$H NMR (400 MHz, CDCl$_3$) δ 8.57 (d, 1H), 7.73 (dd, 1H), 7.60 (d, 1H), 7.32 (m, 5H), 7.11 (d, 1H), 6.76 (dd, 1H), 6.50 (d, 1H), 6.05 (s, 1H), 5.12 (s, 1H), 3.70 (m, 2H), 3.68-3.43 (m, 8H), 2.78 (s, 2H), 1.66 (m, 2H), 1.55 (m, 2H), 1.30 (t, 3H), 1.22 (t, 3H).

Preparation of 40A:

Iodotrimethylsilane (0.86 mL, 6 mmol, 3 eq) was added to a solution of compound 40.2 (1.08 g, 2 mmol) in anhydrous methylene chloride (15 mL) under nitrogen. The reaction mixture was stirred at room temperature for 1.5 h and quenched with a 1N aqueous solution of hydrochloric acid (40 mL). The aqueous phase was washed with diethyl ether. The aqueous was basified to pH=9-10 by addition of a 3N aqueous solution of sodium hydroxide, and extracted with methylene chloride. The organic extracts were combined, dried over sodium sulfate and concentrated in vacuo. The residue was dissolved in methylene chloride (10 mL) and diluted with diethyl ether (40 mL). To this solution was added a 2.0 M anhydrous solution of hydrochloric acid in diethyl ether (20 mL, 40 mmol, 20 eq) and the mixture was stirred at room temperature overnight. The precipitated solid was collected by filtration and washed with ether, dried in vacuo.

Yield: 87%

$^1$H NMR (400 MHz, DMSO-d$_6$) δ 9.08 (brs, 1H), 8.96 (brs, 1H), 8.66 (d, 1H), 7.91 (dd, 1H), 7.60 (d, 1H), 7.27 (d, 1H), 6.84 (dd, 1H), 6.40 (d, 1H), 6.35 (s, 1H), 3.65 (s, 3H), 3.47 (q, 2H), 3.30-3.10 (m, 6H), 2.78 (s, 2H), 1.70 (m, 4H), 1.12 (m, 6H).

Mass Spectral Analysis m/z=406.3 (M+H)$^+$

Elemental analysis:

$C_{25}H_{31}N_3O_2$, 3/2HCl, 3/4 H$_2$O

Theory: % C, 63.38; % H, 7.23; % N, 8.87; % Cl, 11.23.

Found: % C, 63.25; % H, 7.24; % N, 8.70; % Cl, 11.24.

EXAMPLE 40B

Preparation of 40B:

Compound 40.2 (1.3 g, 2.41 mmol) was dissolved in methylene chloride (10 mL) and methanol (80 mL), and hydrogenated in the presence of 10% Pd/C (400 mg) using a hydrogen balloon. After 3 days at room temperature, the reaction mixture was filtered through celite and the filtrate was concentrated in vacuo. The residue was purified by column chromatography (eluent: methylene chloride/methanol/concentrated ammonium hydroxide, 10:1:1).

Yield: 92.7%

$^1$H NMR (400 MHz, CDCl$_3$) δ 8.46 (d, 1H), 7.53 (m, 2H), 7.12 (m, 2H), 7.05 (d, 1H), 6.72 (dd, 1H), 6.23 (d, 1H), 4.10 (m, 1H), 3.63 (s, 3H), 3.58 (q, 2H), 3.44 (q, 2H), 2.90 (m, 5H), 2.60 (d, 1H), 2.08 (m, 1H), 1.52 (m, 5H), 1.28 (t, 3H), 1.20 (t, 3H).

Mass Spectral Analysis m/z=408.5 (M+H)$^+$

EXAMPLE 40C

Preparation of 40.3:

To a solution of the enol triflate 28.7b (2.05 g, 4 mmol) in dimethoxyethane (40 mL) was added sequentially 2 N aqueous solution of sodium carbonate (7.0 mL, 14 mmol, 3.5 eq), lithium chloride (580 mg, 13.7 mmol, 3.43 eq), 39.6 (1.96 g, 5.4 mmol, 1.35 eq) and tetrakis(triphenylphosphine)palladium(0) (142 mg, 0.123 mmol, 0.03 eq). The reaction mixture was refluxed overnight, cooled to room temperature, diluted with water (50 mL) and extracted with diethyl ether. The combined organic extracts were dried over sodium sulfate, and concentrated in vacuo. The residue was purified by column chromatography (eluent: hexane/acetone, 2:1).

Yield: 96.6%

$^1$H NMR (400 MHz, CDCl$_3$) δ 7.35 (m, 5H), 7.20 (m, 2H), 7.08 (m, 2H), 6.69 (dd, 1H), 6.35 (d, 1H), 5.95 (s, 1H), 5.12 (s, 2H), 5.00 (s, 2H), 3.70 (m, 2H), 3.68 (s, 3H), 3.54 (m, 2H), 3.44 (m, 2H), 3.30 (m, 2H), 3.27 (s, 3H), 2.79 (s, 2H), 1.68 (m, 2H), 1.52 (m, 2H), 1.28 (brs, 3H), 1.20 (brs, 3H).

Preparation of 40C:

Iodotrimethylsilane (1.02 mL, 7.5 mmol, 2.84 eq) was added to a solution of compound 40.3 (1.5 g, 2.64 mmol) in anhydrous methylene chloride (30 mL) under nitrogen. The reaction mixture was stirred at room temperature for 2 h, quenched with 1N aqueous solution of hydrochloric acid (40 mL). The queous phase was washed with diethyl ether. The aqueous phase was basified o pH=9-10 by addition of a 3 N aqueous solution of sodium hydroxide, and extracted with methylene chloride. The organic extracts were combined, dried over sodium sulfate and concentrated in vacuo. The residue was dissolved in methylene chloride (10 mL) and methanol (20 mL). To this solution was added a 2.0 M solution of anhydrous hydrochloric acid in diethyl ether (30 mL, 60 mmol, 22.7 eq) and stirred at room temperature for 2 days. The reaction mixture was concentrated in vacuo and the residue was purified by column chromatography (eluent: methylene chloride/methanol, 5:1).

Yield: 94%

$^1$H NMR (400 MHz, DMSO-d$_6$) δ 9.63 (brs, 1H), 8.98 (brd, 2H), 7.14 (m, 2H), 6.89 (s, 1H), 6.80 (d, 1H), 6.73 (dd, 1H), 6.21 (d, 1H), 6.00 (s, 1H), 3.60 (s, 3H), 3.40 (m, 2H), 3.23 (m, 2H), 3.12 (m, 4H), 2.75 (s, 2H), 1.69 (m, 4H), 1.12 (m, 6H).

Mass Spectral Analysis m/z=421.3 (M+H)$^+$

Elemental analysis:

C$_{26}$H$_{32}$N$_2$O$_3$, 1 HCl, 1 H$_2$O

Theory: % C, 65.74; % H, 7.43; % N, 5.90.

Found: % C, 66.02; % H, 7.32; % N, 5.89.

EXAMPLE 41A

Preparation of 41.2:

To a solution of 13.3 (0.50 g, 1.19 mmol, 1.0 eq) in acetonitrile (15 mL) under nitrogen was added N,N-diisopropylethylamine (0.50 mL, 2.85 mmol, 2.4 eq) and 41.1 (0.30 mL, 2.37 mmol, 2.0 eq). The mixture was stirred for 10 min. at room temperature, cooled to 0° C. and O-benzotriazol-1-yl-N,N,N',N'-tetramethyluronium tetrafluoroborate (TBTU) (0.46 g, 1.42 mmol, 1.2 eq) was slowly added to the reaction mixture which was warmed to room temperature and stirring was continued for 16 h at room temperature. The reaction mixture was concentrated, dissolved in ethyl acetate and washed three times with a saturated aqueous solution of sodium bicarbonate, then brine. The organics were concentrated and purified by column chromatography (eluent: 50% hexane/ethyl acetate).

Yield: 75%

$^1$HNMR (400 MHz, CDCl$_3$) δ 7.43 (d, 2H), 7.37 (d, 2H), 7.19 (m, 1H), 7.00 (dd, 1H), 6.94 (dd, 1H), 6.86 (m, 1H), 5.57 (s, 1H), 3.86 (brs, 2H), 3.69 (brs, 3H), 3.46-3.30 (brm, 8H), 2.05 (brd, 2H), 1.67 (m, 2H), 1.48 (s, 9H), 1.14 (brs, 3H)

Mass Spectral Analysis m/z=507.5 (M+H)$^+$

Preparation of 41A

To a solution of 41.2 (0.45 g, 0.888 mmol, 1.0 eq) in methylene chloride (10 mL) at 0° C. under nitrogen was added a 2.0M solution of anhydrous hydrochloric acid in diethyl ether (1.78 mL, 3.55 mmol, 4.0 eq). The reaction was warmed to room temperature, stirred for 48 h and concentrated to a foam, which was sonicated in 25 mL of a 4:1 hexane/diethyl ether solution. The resulting solid was collected by vacuum filtration.

Yield: 71%

$^1$HNMR (400 MHz, DMSO d$_6$) δ 8.96 (brs, 2H), 7.35 (s, 4H), 7.18 (m, 1H), 6.97 (d, 1H), 6.88 (m, 2H), 5.86 (s, 1H), 3.52-3.10 (brm, 13H), 1.96 (brm, 4H), 1.02 (brd, 3H)

Mass Spectral Analysis m/z=407.4 (M+H)$^+$

Elemental analysis:

C$_{25}$H$_{30}$N$_2$O$_3$, 1HCl, 0.50H$_2$O

Theory: % C, 66.43; % H, 7.14; % N, 6.20.

Found: % C, 66.43; % H, 7.00; % N, 6.10.

EXAMPLE 41B

Preparation of 41.4:

To a solution of 13.3 (0.50 g, 1.19 mmol, 1.0 eq) in acetonitrile (15 mL) under nitrogen was added N,N-diisopropylethylamine (0.50 mL, 2.85 mmol, 2.4 eq) and 41.3 (0.37 mL, 2.37 mmol, 2.0 eq). The mixture was stirred for 10 min at room temperature, cooled to 0° C. and O-benzotriazol-1-yl-N,N,N',N'-tetramethyluronium tetrafluoroborate (TBTU) (0.46 g, 1.42 mmol, 1.2 eq) was slowly added to the reaction mixture, which was warmed to room temperature and stirred for 16 h at room temperature. The reaction was concentrated, dissolved in ethyl acetate and washed three times with a saturated aqueous solution of sodium bicarbonate, then brine. The organics were concentrated and purified by column chromatography (eluent: methanol/methylene chloride, 5:95).

Yield: 77%

$^1$HNMR (400 MHz, CDCl$_3$) δ 7.42 (d, 2H), 7.37 (d, 2H), 7.19 (m, 1H), 6.99 (brs, 1H), 6.94 (dd, 1H), 6.85 (m, 1H), 5.57 (s, 1H), 3.86 (brs, 2H), 3.61 (brs, 2H), 3.35 (brs, 4H), 2.62 (brs, 1H), 2.34 (brs, 4H), 2.06 (brm, 5H), 1.68 (m, 2H), 1.48 (s, 9H), 1.15 (brs, 3H)

Mass Spectral Analysis m/z=520.5 (M+H)$^+$

Preparation of 41B

To a solution of 41.4 (0.47 g, 0.904 mmol, 1.0 eq) in methylene chloride (10 mL) at 0° C. under nitrogen was added a 2.0M solution of anhydrous hydrochloric acid in diethyl ether (2.71 mL, 5.43 mmol, 6.0 eq). The reaction was warmed to room temperature, stirred for 48 h at room temperature and diluted with diethyl ether (10 mL). The precipitate was filtered and partitioned in a saturated aqueous solution of sodium bicarbonate and ethyl acetate. The organic layer was separated. The aqueous phase was further extracted with methylene chloride and all organics were combined and concentrated.

Yield: 72%

¹HNMR (400 MHz, CDCl₃) δ 7.39 (m, 4H), 7.19 (m, 1H), 6.97 (m, 2H), 6.85 (t, 1H), 5.63 (s, 1H), 3.62 (brs, 2H), 3.36 (brs, 2H), 3.19 (m, 2H), 2.98 (m, 2H), 2.60 (brs, 3H), 2.33 (brs, 3H), 2.09 (brm, 4H), 1.81 (brm, 2H), 1.22 (brd, 3H)

Mass Spectral Analysis m/z=420.3 (M+H)⁺

Elemental analysis:

$C_{26}H_{33}N_3O_2$, $0.67H_2O$

Theory: % C, 72.36; % H, 8.02; % N, 9.74.

Found: % C, 72.02; % H, 7.80; % N, 9.55.

EXAMPLE 41C

Preparation of 41.7:

To a solution of 41.6 (5.82 mL, 48.93 mmol, 1.0 eq) in diethyl ether (15 mL) at 0° C. under nitrogen was added drop wise a solution of 41.5 (5.0 g, 48.93 mmol, 1.0 eq) in diethyl ether (10 mL). The reaction was stirred at 0° C. for 30 min. and then at room temperature for 2 h. The reaction was concentrated. The crude product was used for the next step without further purification.

Yield: 99%

¹HNMR (400 MHz, CDCl₃) δ 9.91 (brs, 1H), 3.48 (t, 2H), 2.87 (t, 2H), 2.64 (q, 2H), 1.70 (m, 2H), 1.11 (t, 3H)

Preparation of 41.8:

To a solution of 13.3 (3.0 g, 7.12 mmol, 1.0 eq) in acetonitrile (60 mL) under nitrogen was added N,N-diisopropylethylamine (2.98 mL, 17.08 mmol, 2.4 eq) and 41.7 (2.82 g, 14.23 mmol, 2.0 eq). The mixture was stirred for 10 min at room temperature, cooled to 0° C. and O-benzotriazol-1-yl-N,N,N',N'-tetramethyluronium tetrafluoroborate (TBTU) (2.74 g, 8.54 mmol, 1.2 eq) was slowly added. The reaction mixture was warmed to room temperature and stirred for 16 h at room temperature. The reaction was concentrated, dissolved in ethyl acetate and the solution was washed with a saturated aqueous solution of sodium bicarbonate, then brine. The organics were concentrated to a solid, which was triturated in a ethyl acetate/hexane solution (1:9, 50 mL). The reuslting precipitate was collected by vacuum filtration.

Yield: 74%

¹HNMR (400 MHz, CDCl₃) δ 8.42 (brs, 1H), 7.41 (s, 4H), 7.20 (m, 1H), 6.96 (m, 2H), 6.86 (m, 1H), 5.57 (s, 1H), 3.87 (brs, 2H), 3.65 (brt, 2H), 3.46-3.30 (brm, 6H), 2.06 (brd, 2H), 1.87 (brm, 2H), 1.67 (m, 2H), 1.48 (s, 9H), 1.19 (t, 3H)

Mass Spectral Analysis m/z=602.4 (M+H)⁺

Preparation of 41.9:

To a suspension of 41.8 (1.0 g, 1.66 mmol, 1.0 eq) in methanol (30 mL) was added potassium carbonate (0.69 g, 4.99 mmol, 3.0 eq). The reaction was stirred for 48 h at room temperature and concentrated. Water was added and the product was extracted three times with ethyl acetate. The organics were combined and concentrated to a solid, which was triturated in hexane and collected by vacuum filtration.

Yield: 75%

¹HNMR (400 MHz, DMSO d₆) δ 7.47 (s, 4H), 7.29 (m, 1H), 7.05 (m, 2H), 6.97 (m, 1H), 5.95 (s, 1H), 3.79 (brd, 2H), 3.58-3.25 (brm, 8H), 1.94 (m, 2H), 1.78 (brm, 4H), 1.49 (s, 9H), 1.17 (brd, 3H)

Mass Spectral Analysis m/z=506.5 (M+H)⁺

Preparation of 41.11:

To a solution of 41.9 (0.466 g, 0.922 mmol, 1.0 eq) in N,N dimethylformamide (10 mL) was added triethylamine (0.19 mL, 1.38 mmol, 1.5 eq) and 41.10 (0.22 g, 0.968 mmol, 1.05 eq). The reaction was stirred for 3.5 h at room teperature. Ethyl acetate and a saturated aqueous solution of sodium bicarbonate were added to the mixture. The layers were separated and the aqueous phase was further extracted with ethyl acetate. The organics were combined, concentrated and used for the next step without further purification.

Yield: 100% (crude)

Mass Spectral Analysis m/z=691.8 (M+H)⁺

Preparation of 41.12:

To a solution of 41.11 (0.64 g, 0.926 mmol, 1.0 eq) in N,N dimethylformamide (10 mL) was added potassium carbonate (0.196 g, 1.42 mmol, 1.5 eq) and methyl iodide (0.12 mL, 1.85 mmol, 2.0 eq). The reaction was stirred at room temperature for 16 h. Ethyl acetate and water were added to the mixture. The layers were separated and the organics were concentrated. The crude product was used for the next step without further purification.

Yield: 96%

Mass Spectral Analysis m/z=705.7 (M+H)⁺

Preparation of 41.13:

To a solution of 41.12 (0.626 g, 0.888 mmol, 1.0 eq) in N,N dimethylformamide (10 mL) under nitrogen was added potassium carbonate (0.307 g, 2.22 mmol, 2.5 eq) and benzenethiol (0.14 mL, 1.33 mmol, 1.5 eq). The reaction was stirred for 2 h at room temperature. Ethyl acetate and a saturated aqueous solution of sodium bicarbonate were added to the mixture. The layers were separated. The organics were concentrated and the crude product was purified by column chromatography [eluent: methanol/(methylene chloride/ammonium hydroxide, 99:1) mixtures of increasing polarity].

Yield: 68%

¹HNMR (400 MHz, CDCl₃) δ 7.39 (m, 4H), 7.19 (m, 1H), 6.96 (m, 2H), 6.87 (m, 1H), 5.57 (s, 1H), 3.87 (brs, 2H), 3.60 (brs, 2H), 3.34 (brs, 4H), 2.70 (brs, 1H), 2.50 (brs, 2H), 2.35 (brs, 1H), 2.06 (brd, 2H), 1.91 (brs, 1H), 1.68 (m, 4H), 1.48 (s, 9H), 1.21 (brd, 3H)

Mass Spectral Analysis m/z=520.5 (M+H)⁺

Preparation of 41C

To a solution of 41.13 (0.31 g, 0.60 mmol, 1.0 eq) in methylene chloride (10 mL) at 0° C. under nitrogen was added a 2.0M solution of anhydrous hydrochloric acid in diethyl ether (1.80 mL, 3.58 mmol, 6.0 eq). The reaction mixture was warmed to room temperature, stirred for 48 h at room temperature and concentrated to a foam, which was triturated in diethyl ether (7 mL). The resulting solid was collected by vacuum filtration.

Yield: 82%

¹HNMR (400 MHz, DMSO d₆) δ 9.22 (brs, 2H), 8.93 (brs, 2H), 7.52 (m, 4H), 7.33 (m, 1H), 7.12 (d, 1H), 7.06 (m, 2H), 6.00 (s, 1H), 3.57 (brs, 2H), 3.26 (brm, 6H), 3.00 (brs, 2H), 2.62 (brs, 2H), 2.18-1.92 (brm, 7H), 1.15 (brm, 3H)

Mass Spectral Analysis m/z=420.3 (M+H)⁺

Elemental analysis:

$C_{26}H_{33}N_3O_2$, 2HCl, $0.50H_2O$

Theory: % C, 62.27; % H, 7.24; % N, 8.38; % Cl, 14.14.

Found: % C, 62.15; % H, 7.05; % N, 8.31; % Cl, 14.19.

EXAMPLE 41D

Preparation of 41.15:

To a solution of 13.3 (1.00 g, 2.37 mmol, 1.0 eq) in acetonitrile (15 mL) under nitrogen was added N,N-diisopropylethylamine (1.45 mL, 8.30 mmol, 3.5 eq) and 41.14 (0.60 mL, 4.74 mmol, 2.0 eq). The mixture was stirred for 10 min at room temperature, cooled to 0° C. and O-benzotriazol-1-yl-N,N,N',N'-tetramethyluronium tetrafluoroborate (TBTU) (0.91 g, 2.85 mmol, 1.2 eq) was slowly added to the reaction mixture, which was warmed to room temperature and stirred for 40 h at room temperature. Water was added and the product was extracted two times with ethyl acetate. The organics were concentrated and the crude product was purified by column chromatography (eluent: methanol/methylene chloride mixtures of increasing polarity).

Yield: 51%

$^1$HNMR (400 MHz, CDCl$_3$) δ 8.32 (brt, 1H), 7.85 (d, 2H), 7.41 (d, 2H), 7.19 (m, 1H), 6.96 (m, 2H), 6.85 (m, 1H), 5.58 (s, 1H), 3.86 (brs, 2H), 3.61 (q, 2H), 3.34 (brs, 2H), 2.77 (t, 2H), 2.53 (s, 6H), 2.04 (brd, 2H), 1.94 (m, 2H), 1.67 (m, 2H), 1.47 (s, 9H)

Mass Spectral Analysis m/z=506.5 (M+H)$^+$

Preparation of 41D

To a solution of 41.15 (0.090 g, 0.18 mmol, 1.0 eq) in methylene chloride (5 mL) at 0° C. under nitrogen was added a 2.0M solution of anhydrous hydrochloric acid in diethyl ether (0.53 mL, 1.07 mmol, 6.0 eq). The reaction was warmed to room temperature and stirred for 16 h at room temperature. Additional amount of an anhydrous solution of hydrochloric acid in diethyl ether (0.50 mL) was added to the reaction which was stirred for an additional 16 h at room temperature. The precipitate was collected by vacuum filtration.

Yield: 65%

$^1$HNMR (400 MHz, DMSO d$_6$) δ 9.98 (brs, 1H), 8.94 (brs, 2H), 8.77 (t, 1H), 7.96 (d, 2H), 7.47 (d, 2H), 7.27 (m, 1H), 7.06 (d, 1H), 6.95 (d, 2H), 5.94 (s, 1H), 3.36 (m, 2H), 3.22 (brm, 4H), 3.09 (m, 2H), 2.76 (s, 6H), 2.12-1.89 (brm, 6H)

Mass Spectral Analysis m/z=406.4 (M+H)$^+$

EXAMPLE 41E

Preparation of 41.17:

To a solution of 41.6 (6.75 mL g, 56.72 mmol, 1.0 eq) in diethyl ether (15 mL) at 0° C. under nitrogen was added drop wise 41.16 (5.97 mL, 56.72 mmol, 1.0 eq). The reaction was stirred at 0° C. for 30 min and then at room temperature for 2 h. The reaction mixture was concentrated to a solid, which was triturated in hexanes. The suspension was stirred overnight at room temperature and the precipitate was collected by vacuum filtration.

Yield: 90%

$^1$HNMR (400 MHz, CDCl$_3$) δ 7.15 (brs, 1H), 3.41 (t, 2H), 2.83 (t, 2H), 2.66 (q, 2H), 1.11 (t, 3H)

Preparation of 41.18:

To a solution of 13.3 (2.0 g, 4.74 mmol, 1.0 eq) in acetonitrile (50 mL) under nitrogen was added N,N-diisopropylethylamine (1.98 mL, 11.39 mmol, 2.4 eq) and 41.17 (1.75 g, 9.48 mmol, 2.0 eq). The mixture was stirred for 10 min at room temperature, cooled to 0° C. and O-benzotriazol-1-yl-N,N,N',N'-tetramethyluronium tetrafluoroborate (TBTU) (1.83 g, 5.69 mmol, 1.2 eq) was slowly added to the reaction mixture, which was warmed to room temperature and stirred for 16 h at room temperature. The reaction mixture was concentrated, dissolved in ethyl acetate and washed with a saturated aqueous solution of sodium bicarbonate, then brine. The organics were concentrated to a solid, which was triturated in a ethyl acetate/hexane solution (1:9; 50 mL). The precipitate was collected by vacuum filtration.

Yield: 72%

$^1$HNMR (400 MHz, CDCl$_3$) δ 8.23 (brs, 1H), 7.41 (s, 4H), 7.20 (m, 1H), 6.96 (m, 2H), 6.86 (m, 1H), 5.58 (s, 1H), 3.97 (brs, 2H), 3.79 (brs, 2H), 3.66 (brs, 2H), 3.38 (brm, 4H), 2.05 (m, 2H), 1.68 (m, 2H), 1.48 (s, 9H), 1.22 (t, 3H)

Mass Spectral Analysis m/z=588.5 (M+H)$^+$

Preparation of 41.19:

To a suspension of 41.18 (1.0 g, 1.70 mmol, 1.0 eq) in methanol (30 mL) was added potassium carbonate (0.71 g, 5.11 mmol, 3.0 eq). The reaction was stirred for 48 h at room temperature and concentrated. Water was added to the mixture and the product was extracted with ethyl acetate. The organics were combined and concentrated to a solid, which was triturated in hexane and collected by vacuum filtration.

Yield: 72%

$^1$HNMR (400 MHz, CDCl$_3$) δ 7.82 (d, 1H), 7.40 (m, 2H), 7.19 (m, 1H), 6.95 (m, 2H), 6.85 (m, 2H), 5.58 (s, 1H), 3.86 (brs, 2H), 3.56 (q, 2H), 3.34 (brs, 2H), 2.89 (t, 1H), 2.70 (q, 1H), 2.05 (m, 2H), 1.68 (m, 2H), 1.48 (s, 11H), 1.13 (t, 3H)

Mass Spectral Analysis m/z=492.5 (M+H)$^+$

Preparation of 41.20:

To a solution of 41.19 (0.90 g, 1.83 mmol, 1.0 eq) and triethylamine (0.77 mL, 5.49 mmol, 3.0 eq) in tetrahydrofuran (20 mL) at 0° C. under nitrogen was added 4.7 (0.44 g, 2.01 mmol, 1.1 eq). The ice bath was removed and the reaction was stirred at room temperature for 30 min. Water was added and the product was extracted with ethyl acetate. The organics were combined, concentrated and the crude product was purified by column chromatography (eluent: hexane/ethyl acetate mixtures of increasing polarity).

Yield: 67%

$^1$HNMR (400 MHz, CDCl$_3$) δ 7.86 (d, 2H), 7.67 (s, 1H), 7.38 (d, 2H), 7.19 (m, 1H), 6.94 (d, 2H), 6.85 (m, 1H), 5.58 (s, 1H), 3.86 (brs, 2H), 3.61 (m, 2H), 3.53 (s, 2H), 3.30 (brm, 4H), 2.05 (m, 2H), 1.68 (m, 2H), 1.48 (s, 9H), 1.46 (s, 9H), 1.14 (t, 3H)

Mass Spectral Analysis m/z=592.6 (M+H)$^+$

Preparation of 41.21:

To a solution of 41.20 (0.70 g, 1.18 mmol, 1.0 eq) in tetrahydrofuran (30 mL) under nitrogen was added sodium hydride (0.085 g, 3.55 mmol, 3.0 eq) and the mixture was stirred for 10 min at room temperature. Methyl iodide (0.22 mL, 3.55 mmol, 3.0 eq) was added to the reaction mixture, which was stirred for 16 h at room temperature. The reaction mixture was carefully quenched with water and the product was extracted with ethyl acetate. The organics were concentrated and the crude product was purified by column chromatography (eluent: hexane/ethyl acetate mixtures of increasing polarity).

Yield: 96%

$^1$HNMR (400 MHz, CDCl$_3$) δ 7.40 (brm, 4H), 7.19 (m, 1H), 6.96 (m, 2H), 6.85 (m, 1H), 5.54 (s, 1H), 3.86 (brs, 2H), 3.70 (brs, 2H), 3.48 (m, 1H), 3.32 (brs, 4H), 3.15 (brs, 2H), 3.07 (brs, 2H), 2.05 (m, 2H), 1.67 (m, 2H), 1.48 (s, 9H), 1.41 (s, 9H), 1.14 (brt, 3H)

Mass Spectral Analysis m/z=606.7 (M+H)$^+$

Preparation of 41E

To a solution of 41.21 (0.68 g, 1.12 mmol, 1.0 eq) in methylene chloride (10 mL) at 0° C. under nitrogen was added a 2.0M solution of anhydrous hydrochloric acid in diethyl ether (6.74 mL, 13.47 mmol, 12.0 eq). The reaction mixture was warmed to room temperature and stirred for 16 h at room temperature. The precipitate was collected by vacuum filtration.

Yield: 90%

$^1$HNMR (400 MHz, DMSO d$_6$) δ 9.16 (brs, 2H), 8.97 (brs, 2H), 7.62 (m, 2H), 7.44 (d, 2H), 7.27 (m, 1H), 7.06 (d, 1H), 6.97 (m, 2H), 5.94 (s, 1H), 3.77 (brs, 2H), 3.34 (s, 3H), 3.20 (brm, 4H), 3.00 (brs, 4H), 2.06 (brm, 4H), 1.24 (brt, 3H)

Mass Spectral Analysis m/z=406.8 (M+H)$^+$

Elemental analysis:

C$_{25}$H$_{31}$N$_3$O$_2$, 2HCl, 0.50H$_2$O

Theory: % C, 61.60; % H, 7.03; % N, 8.62; % Cl, 14.55.

Found: % C, 61.45; % H, 6.78; % N, 8.64; % Cl, 14.78.

EXAMPLE 42A

Preparation of 42.1:

To a solution of 21.6 (6.03 g, 13.0 mmol) and 1.7 (3.95 g, 13.0 mmol, 1 eq) in dimethoxyethane (DME) (125 mL) was added sequentially a 2N aqueous solution of sodium carbonate (19.5 mL, 39.0 mmol, 3 eq), lithium chloride (1.65 g, 39.0 mmol, 3 eq) and tetrakis(triphenylphosphine)palladium(0) (0.45 g, 0.39 mmol, 0.03 eq). The reaction mixture was evacuated for 2 min and then purged with argon and heated under reflux for 23 h. The mixture was then cooled to room temperature and diluted with ethyl acetate (100 mL) and filtered through a 1 inch plug of celite. The cake was further washed with ethyl acetate, the organic layer was washed with water followed by brine and dried over sodium sulfate. The crude product was purified by column chromatography (eluent: hexane/ethyl acetate mixtures of increasing polarity).

Yield: 65%

$^1$H NMR (400 MHz, CDCl$_3$) δ 8.50 (br.s, 1H), 7.71 (dd, 1H), 7.58 (dd, 1H), 7.15 (dt, 1H), 6.87-6.80 (m, 3H), 5.62 (br.s, 1H), 3.85-3.51 (m, 4H), 3.50-3.20 (m, 4H), 2.29-2.04 (m, 2H), 2.00-1.80 (m, 2H), 1.47 (s, 9H), 1.29-1.14 (m, 6H)

Mass Spectral Analysis m/z=492.39 (M+H)$^+$

Preparation of 42.2:

42.1 (1 g, 2.03 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 40%

Mass Spectral Analysis m/z=492.36 (M+H)$^+$

Chiral HPLC Method: t$_R$=6.611 min. (ee>99%)

Preparation of 42A:

Hydrochloric acid, 4M, in 1,4-dioxane (1.1 mL, 4.26 mmol, 5.5 eq) was added drop wise to a cooled (0° C.) solution of 42.2 (0.38 g, 0.77 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 90%

$^1$H NMR (400 MHz, DMSO d$_6$) δ 9.23 (br s, 2H), 8.56 (d, 1H), 7.89 (dd, 1H), 7.62 (d, 1H), 7.26 (m, 1H), 6.99 (d, 1H), 6.95 (m, 2H), 6.03 (s, 1H), 3.79 (br s, 2H), 3.46 (q, 2H), 3.29 (q, 2H), 3.21 (brs, 2H), 3.10 (br s, 1H), 2.26 (m, 2H), 2.17 (m, 1H), 1.95 (m, 2H), 1.79 (m, 1H), 1.17 (t, 3H), 1.11 (t, 3H)

Mass Spectral Analysis m/z=392.3 (M+H)$^+$

Elemental analysis:

C$_{24}$H$_{29}$N$_3$O$_2$, 1.25HCl, 0.75 H$_2$O

Theory: % C, 63.97; % H, 7.10; % N, 9.33; % Cl, 9.83.

Found: % C, 63.78; % H, 7.04; % N, 9.17; % Cl, 9.81.

[α]$_D^{25}$=−1.93 (c. 0.01, MeOH)

EXAMPLE 42B

Preparation of 42.3:

42.1 (1 g, 2.03 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 40%

Mass Spectral Analysis m/z=492.29 (M+H)$^+$

Chiral HPLC Method: t$_R$=8.399 min. (ee>99%)

Preparation of 42B:

A 4M anhydrous solution of hydrochloric acid in 1,4-dioxane (1.1 mL, 4.35 mmol, 5.5 eq) was added drop wise to a cooled (0° C.) solution of 42.3 (0.39 g, 0.79 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 90%

$^1$H NMR (400 MHz, DMSO d$_6$) δ 9.18 (br s, 2H), 8.56 (d, 1H), 7.87 (dd, 1H), 7.62 (d, 1H), 7.26 (m, 1H), 7.01 (d, 1H), 6.95 (m, 2H), 6.03 (s, 1H), 3.61 (br s, 2H), 3.46 (q, 2H), 3.29 (q, 2H), 3.22 (br s, 2H), 3.10 (br s, 1H), 2.56 (m, 2H), 2.17 (m, 1H), 1.95 (m, 2H), 1.79 (m, 1H), 1.17 (t, 3H), 1.11 (t, 3H)

Mass Spectral Analysis m/z=392.30 (M+H)$^+$

Elemental analysis:

C$_{24}$H$_{29}$N$_3$O$_2$, 1.25HCl, 0.75 H$_2$O

Theory: % C, 63.97; % H, 7.10; % N, 9.33; % Cl, 9.83.

Found: % C, 64.04; % H, 7.03; % N, 9.18; % Cl, 9.43.

[α]$_D^{25}$=+0.57 (c. 0.01, MeOH)

EXAMPLE 42C

Preparation of 42C:

A 4M anhydrous solution of hydrochloric acid in 1,4-dioxane (1.38 mL, 5.50 mmol, 5.5 eq) was added drop wise to a cooled (0° C.) solution of 42.1 (0.49 g, 1.00 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the suspension was stirred for 1 hour at room temperature. The resulting solids were isolated by vacuum filtration.

Yield: 90%

$^1$HNMR (400 MHz, DMSO d$_6$) δ 9.44 (brs, 2H), 8.58 (d, 1H), 7.90 (dd, 1H), 7.62 (d, 1H), 7.26 (m, 1H), 7.01 (d, 1H), 6.93 (m, 2H), 6.04 (s, 1H), 3.48 (q, 2H), 3.30 (q, 2H), 3.15 (brm, 4H), 2.28 (brm, 2H), 2.16 (m, 1H), 1.97 (m, 2H), 1.81 (brm, 1H), 1.18 (t, 3H), 1.11 (t, 3H)

Mass Spectral Analysis m/z=392.4 (M+H)$^+$

EXAMPLE 42D

Preparation of 42.4:

A solution of 1.14 (5.58 g, 22.0 mmol), potassium acetate (5.89 g, 60.0 mmol, 3 eq) and [1,1'bis(diphenylphosphino) ferrocene]palladium(II) chloride Pd(dppf)Cl$_2$ (0.44 g, 0.60 mmol, 0.03 eq) in anhydrous N,N-dimethylformamide (30 mL) was evacuated for 2 min and then purged with argon and heated to 85° C. A solution of 21.6 (9.27 g, 20.0 mmol) in anhydrous N,N-dimethylformamide (20 mL) was added to this reaction mixture and the resultant mixture was stirred at 85° C. under argon for 22 h. The mixture was then cooled to room temperature, N,N-dimethylformamide was removed under reduced pressure and o solution of the resultant residue in ethyl acetate (150 mL) was filtered through a plug of celite. The cake was further washed with ethyl acetate (50 mL), the organic layer was then washed with water (2×250 mL), brine and dried over sodium sulfate. The crude product was purified by column chromatography (eluent: hexane/ethyl acetate mixtures of increasing polarity).

Yield: 80%

$^1$H NMR (400 MHz, CDCl$_3$), δ 7.69 (dd, 1H), 7.10 (dt, 1H), 6.88 (dt, 1H), 6.80 (d, 1H) 6.31 (s, 1H), 3.77-3.52 (m, 2H), 3.36-3.23 (m, 2H), 2.17-2.05 (m, 3H), 2.00 (m, 2H), 1.81-1.53 (m, 3H), 1.46 (s, 9H); 1.32 (s, 12H)

Preparation of 42.5:

To a solution of 42.4 (7.94 g, 18.0 mmol, 1 eq) and 34.1a (4.62 g, 18.0 mmol) in dimethoxyethane (DME) (130 mL) was added sequentially a 2N aqueous solution of sodium carbonate (27 mL, 54.0 mmol, 3 eq), lithium chloride (2.29 g, 54.0 mmol, 3 eq), and tetrakis(triphenylphosphine)palladium (0) (0.62 g, 0.54 mmol, 0.03 eq). The mixture was evacuated and then purged with argon and heated under reflux for 17 h. The mixture was then cooled to room temperature and diluted with ethyl acetate (125 mL) and filtered through a 1 inch plug of celite. The cake was further washed with ethyl acetate, the organic layer was washed with water followed by brine and dried over sodium sulfate. The crude product was purified by column chromatography (eluent: hexane/ethyl acetate mixtures of increasing polarity).

Yield: 75%

$^1$H NMR (400 MHz, CDCl$_3$) δ 8.65 (m, 1H), 7.70 (d, 1H), 7.41 (dd, 1H), 7.20-7.10 (m 2H), 6.90-6.80 (m, 2H), 5.91 and 5.89 (s, 1H), 3.78-3.62 (m, 1H), 3.60-3.47 (m, 4H), 3.35-3.20 (m, 4H), 2.21-2.13 (m, 2H), 1.92-1.75 (m, 1H), 1.73-1.62 (m, 2H), 1.43 and 1.41 (s, 9H), 1.27-1.15 (m, 6H)

Mass Spectral Analysis m/z=492.37 (M+H)$^+$

Preparation of 42.6:

42.5 (1 g, 2.03 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 50%

Mass Spectral Analysis m/z=492.84 (M+H)$^+$

Chiral HPLC Method: t$_R$=9.178 min. (ee=97.62%)

Preparation of 42D:

A 4M anhydrous solution of hydrochloric acid in 1,4-dioxane (1.40 mL, 5.59 mmol, 5.5 eq) was added drop wise to a cooled (0° C.) solution of 42.6 (0.50 g, 1.02 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the suspension was stirred for 1 hour at room temperature. The resulting solids were isolated by vacuum filtration.

Yield: 99%

$^1$H NMR (400 MHz, DMSO d$_6$) δ 9.21 (br s, 2H), 8.65 (d, 1H), 7.91 (dd, 1H), 7.60 (d, 1H), 7.29 (d, 1H), 7.25 (t, 1H), 6.98 (d, 1H), 6.92 (t, 1H), 6.18 (s, 1H), 4.23 (br s, 2H), 3.47 (m, 2H), 3.24 (m, 4H), 3.10 (m, 1H), 2.26 (m, 2H), 2.15 (m, 1H), 1.99 (m, 2H), 1.78 (m, 1H), 1.18 (br s, 3H), 1.10 (br s, 3H)

Mass Spectral Analysis m/z=392.81 (M+H)$^+$

Elemental analysis:

C$_{24}$H$_{29}$N$_3$O$_2$, 1HCl, 1.25H$_2$O

Theory: % C, 63.99; % H, 7.27; % N, 9.33.

Found: % C, 63.90; % H, 6.98; % N, 9.14.

[α]$_D^{25}$=−1.48 (c. 0.01, MeOH)

EXAMPLE 42E

Preparation of 42.7:

42.5 (1 g, 2.03 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 50%

Mass Spectral Analysis m/z=492.84 (M+H)$^+$

Chiral HPLC Method: t$_R$=12.364 min. (ee=96.90%)

Preparation of 42E:

A 4M anhydrous solution of hydrochloric acid in 1,4-dioxane (1.40 mL, 5.59 mmol, 5.5 eq) was added drop wise to a cooled (0° C.) solution of 42.7 (0.50 g, 1.02 mmol, 1 eq) in anhydrous methanol (5 mL). The reaction mixture was warmed to room temperature and stirring was continued for an additional 16 hours at room temperature. The reaction mixture was concentrated under reduced pressure. Ethyl acetate was added to the resulting oil and stirred for 1 hour at room temperature. The resulting solids were isolated by vacuum filtration.

Yield: 99%

$^1$H NMR (400 MHz, DMSO d$_6$) δ 9.27 (br s, 2H), 8.65 (d, 1H), 7.93 (dd, 1H), 7.61 (d, 1H), 7.28 (d, 1H), 7.25 (t, 1H), 6.98 (d, 1H), 6.92 (t, 1H), 6.18 (s, 1H), 4.40 (br s, 2H), 3.47 (m, 2H), 3.24 (m, 4H), 3.10 (m, 1H), 2.27 (m, 2H), 2.15 (m, 1H), 1.99 (m, 2H), 1.79 (m, 1H), 1.17 (br s, 3H), 1.10 (br s, 3H)

Mass Spectral Analysis m/z=392.80 (M+H)$^+$

Elemental analysis:

C$_{24}$H$_{29}$N$_3$O$_2$, 1HCl, 1.25H$_2$O

Theory: % C, 63.99; % H, 7.27; % N, 9.33.

Found: % C, 64.02; % H, 7.08; % N, 9.11.

[α]$_D^{25}$=−2.83 (c. 0.01, MeOH)

EXAMPLE 42F

Preparation of 42F:

A 4M anhydrous solution of hydrochloric acid in 1,4-dioxane (1.38 mL, 5.50 mmol, 5.5 eq) was added drop wise to a cooled (0° C.) solution of 42.5 (0.49 g, 1.00 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$HNMR (400 MHz, DMSO d$_6$) δ 9.42 (brs, 2H), 8.69 (d, 1H), 7.99 (dd, 1H), 7.67 (d, 1H), 7.26 (m, 2H), 7.00 (d, 1H), 6.93 (t, 1H), 6.21 (s, 1H), 3.48 (brs, 2H), 3.18 (brm, 6H), 2.28 (brm, 2H), 2.16 (m, 1H), 1.98 (m, 2H), 1.78 (brm, 1H), 1.14 (brd, 6H)

Mass Spectral Analysis m/z=392.4 (M+H)$^+$

EXAMPLE 42G

Preparation of 42.8:

To a solution of 42.4 (4.41 g, 10.0 mmol) and 35.8 (3.45 g, 9.50 mmol, 0.95 eq) in dimethoxyethane (DME) (60 mL) was added sequentially a 2N aqueous solution of sodium carbonate (15 mL, 30.0 mmol, 3 eq), lithium chloride (1.27 g, 30.0 mmol, 3 eq), and tetrakis(triphenylphosphine)palladium(0) (0.58 g, 0.50 mmol, 0.03 eq). The mixture was evacuated and then purged with argon and heated under reflux for 20 h. The mixture was then cooled to room temperature and diluted with ethyl acetate (50 mL) and filtered through a 1 inch plug of celite. The cake was further washed with ethyl acetate; the organic layer was washed with brine, dried over sodium sulfate and concentrated. The crude product was triturated with a 10:1 hexane/ether mixture and the resultant colorless crystalline precipitate was collected by vacuum filtration. The filtrate was collected, concentrated and the crude product was purified by column chromatography (eluent: hexane/ethyl acetate mixtures of increasing polarity).

Yield: 42%

$^1$H NMR (300 MHz, CDCl$_3$) δ 7.22-7.16 (m, 2H), 7.13-7.07 (m, 1H), 7.03 (dd, 1H), 6.89-6.85 (m, 1H), 6.79-6.69 (m, 2H), 5.58 (s, 1H), 5.05 (s, 2H), 3.74-3.48 (m, 4H), 3.40-3.25 (m, 4H), 3.32 (s, 3H), 2.29-2.08 (m, 2H), 1.97-1.67 (m, 4H), 1.48 (s, 9H), 1.32-1.12 (m, 6H)

Mass Spectral Analysis m/z=551.45 (M+H)$^+$

Preparation of 42.9:

42.8 (1 g, 1.82 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Isopropanol

Flow: 1.0 mL min

Detector: UV 275 nm

Yield: 30%

Mass Spectral Analysis m/z=551.84 (M+H)$^+$

Chiral HPLC Method: t$_R$=9.796 min. (ee=97.60%)

Preparation of 42G:

A 4M anhydrous solution of hydrochloric acid in 1,4-dioxane (0.83 mL, 3.30 mmol, 5.5 eq) was added drop wise to a cooled (0° C.) solution of 42.9 (0.33 g, 0.60 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$H NMR (400 MHz, DMSO d$_6$) δ 9.78 (s, 1H), 9.12 (br s, 2H), 7.13 (m, 2H), 6.89 (m, 2H), 6.83 (m, 2H), 6.69 (m, 1H), 5.73 (s, 1H), 3.42 (br s, 2H), 3.25 (br s, 5H), 3.09 (br s, 1H), 2.20 (m, 3H), 1.95 (m, 2H), 1.77 (m, 1H), 1.12 (br s, 6H)

Mass Spectral Analysis m/z=407.7 (M+H)$^+$

Elemental analysis:

C$_{25}$H$_{30}$N$_2$O$_3$, 1HCl

Theory: % C, 67.78; % H, 7.05; % N, 6.32.

Found: % C, 67.50; % H, 6.93; % N, 6.18.

[α]$_D^{25}$=+1.11 (c. 0.01, MeOH)

EXAMPLE 42H

Preparation of 42.10:

42.8 (1 g, 1.82 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Isopropanol

Flow: 1.0 mL min

Detector: UV 275 nm

Yield: 30%

Mass Spectral Analysis m/z=551.97 (M+H)$^+$

Chiral HPLC Method: t$_R$=15.281 min. (ee=98.30%)

Preparation of 42H:

A 4M anhydrous solution of hydrochloric acid in 1,4-dioxane (0.83 mL, 3.30 mmol, 5.5 eq) was added drop wise to a cooled (0° C.) solution of 42.10 (0.33 g, 0.60 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$H NMR (400 MHz, DMSO d$_6$) δ 9.78 (s, 1H), 9.10 (br s, 2H), 7.13 (m, 2H), 6.89 (m, 2H), 6.83 (m, 2H), 6.69 (m, 1H), 5.73 (s, 1H), 3.42 (br s, 2H), 3.25 (br s, 5H), 3.09 (br s, 1H), 2.20 (m, 3H), 1.95 (m, 2H), 1.77 (m, 1H), 1.12 (br s, 6H)

Mass Spectral Analysis m/z=407.8 (M+H)$^+$

Elemental analysis:

C$_{25}$H$_{30}$N$_2$O$_3$, 1HCl, 0.25H$_2$O

Theory: % C, 67.10; % H, 7.10; % N, 6.26.

Found: % C, 67.13; % H, 7.04; % N, 6.19.

[α]$_D^{25}$=−5.36 (c. 0.01, MeOH)

EXAMPLE 42I

Preparation of 42I:

A 4M anhydrous solution of hydrochloric acid in 1,4-dioxane (1.38 mL, 5.50 mmol, 5.5 eq) was added drop wise to a cooled (0° C.) solution of 42.8 (0.55 g, 1.00 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$HNMR (400 MHz, DMSO d$_6$) δ 9.81 (brs, 1H), 9.22 (brs, 2H), 7.14 (m, 2H), 6.90 (m, 2H), 6.82 (m, 2H), 6.69 (dd, 1H), 5.72 (s, 1H), 3.77 (brs, 3H), 3.42 (brs, 2H), 3.16 (brm, 3H), 2.20 (m, 3H), 1.95 (m, 2H), 1.76 (brm, 1H), 1.12 (brs, 6H)

Mass Spectral Analysis m/z=407.4 (M+H)$^+$

EXAMPLE 43A

Preparation of 43.1:

To a round bottomed flask was added successively 11.1 (7.60 g, 50.0 mmol) followed by pyrrolidine (8.3 mL, 100.0 mmol, 2 eq), 21.4 (10.66 g, 50.0 mmol) and a minimum amount of methanol used to wash any remaining material. The resultant reaction was heated to 80° C. for 30 min to dissolve all solids. The mixture was then cooled to room temperature and diluted with ethyl acetate (50 mL). The mixture was washed with a 1N aqueous solution of hydrochloric acid, water, brine and dried over sodium sulfate. The crude material was triturated with hexanes and then left to stand at room temperature over 2 days. A pale yellow solid was formed which was filtered, washed with hexanes and collected.

Yield: 65%

$^1$H NMR (400 MHz, CDCl$_3$) δ 11.61 and 11.60 (s, 1H), 7.34 (t, 1H), 6.50-6.40 (m, 2H), 3.80-3.49 (m, 2H), 3.38-3.21 (m, 2H), 2.27-2.10 (m, 2H), 2.08-1.57 (m, 4H), 1.46 (s, 9H)

Preparation of 43.2:

To a solution of 43.1 (41.69 g, 0.12 mol) and N,N-diisopropylethylamine (62.7 mL, 0.36 mol, 3 eq) in dichloromethane (200 mL) was added dropwise, 11.3 (27.5 mL, 0.36 mol, 3 eq) under argon. The resultant reaction mixture was heated under reflux for 16 h then allowed to cool to room temperature. The mixture was concentrated to remove the majority of dichloromethane then diluted with ethyl acetate (200 mL) and washed with a 2N aqueous solution of hydrochloric acid until the aqueous layer was acidic. The organic layer was washed with brine and dried over sodium sulfate. The crude product was purified by column chromatography (eluent: hexane/ethyl acetate mixtures of increasing polarity).

Yield: 68%

$^1$H NMR (400 MHz, CDCl$_3$) δ 7.34 (t, 1H), 6.70 (d, 1H), 6.60 (d, 1H), 5.27 (s, 2H), 3.67-3.44 (m, 2H), 3.52 (s, 3H), 3.37-3.23 (m, 2H), 2.80-2.58 (m, 2H), 2.13-2.09 (m, 2H), 2.05-1.54 (m, 4H), 1.45 (s, 9H)

Preparation of 43.3:

To a solution of 43.2 (32.11 g, 82.0 mmol) in tetrahydrofuran (275 mL) at -78° C. under argon was added drop wise, a 1.0M solution of LiHMDS in tetrahydrofuran (95 mL). The mixture was stirred for 1 h at -78° C. A solution of 1.4 (33.94 g, 1.16 eq) in tetrahydrofuran (175 mL) was added drop wise to the reaction mixture. The mixture was warmed slowly to room temperature and stirring was continued for a further 12 h at room temperature. The mixture was then poured into ice water and the two phases were separated. The organic phase was washed with a 1N aqueous solution of hydrochloric acid, a 1N aqueous solution of sodium hydroxide, brine and dried over sodium sulfate. The crude product was used for the next step without further purification.

Yield: 87%.

$^1$H NMR (300 MHz, CDCl$_3$) δ 7.14 (t, 1H), 6.77 (d, 1H), 6.55 (d, 1H), 5.48 (s, 1H), 5.21 (s, 2H), 3.78-3.43 (m, 2H), 3.49 (s, 3H), 3.33-3.20 (m, 2H), 2.27-2.13 (m, 2H), 2.11-1.95 (m, 1H), 1.88-1.57 (m, 3H), 1.48 (s, 9H)

Preparation of 43.4:

To a solution of 43.3 (10.47 g, 20.0 mmol) in dimethoxyethane (DME) (175 mL) was added sequentially a 2N aqueous solution of sodium carbonate (30.0 mL, 60.0 mmol, 3 eq), lithium chloride (2.54 g, 60.0 mmol, 3 eq), 1.6 (4.20 g, 19.0 mmol, 0.95 eq) and tetrakis(triphenylphosphine)palladium (0) (0.69 g, 0.6 mmol, 0.03 eq). The reaction mixture was evacuated for 2 min and then purged with argon and heated under reflux for 18 h. The reaction mixture was then cooled to room temperature, diluted with ethyl acetate (120 mL) and filtered through a 1 inch plug of celite. The cake was further washed with ethyl acetate; the organic layer was washed with water followed by brine and dried over sodium sulfate. The crude product was purified by column chromatography (eluent: hexane/ethyl acetate mixtures of increasing polarity).

Yield: 60%

$^1$H NMR (300 MHz, CDCl$_3$) δ 7.35-7.24 (m, 4H), 7.13 (t, 1H), 6.65 (d, 2H), 5.55 (s, 1H), 4.67 (s, 2H), 3.81-3.45 (m, 4H), 3.37-3.20 (m, 4H), 3.18 (s, 3H), 2.22-2.10 (m, 2H), 1.97-1.64 (m, 4H), 1.49 and 1.48 (s, 9H), 1.30-1.04 (m, 6H)

Mass Spectral Analysis m/z=551.50 (M+H)$^+$

Preparation of 43.5:

43.4 (1 g, 1.81 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 40%

Mass Spectral Analysis m/z=551.49 (M+H)$^+$

Chiral HPLC Method: $t_R$=5.305 min. (ee>99%)

Preparation of 43A:

A 4M anhydrous solution of hydrochloric acid in 1,4-dioxane (1.0 mL, 4.09 mmol, 5.5 eq) was added drop wise to a cooled (0° C.) solution of 43.5 (0.41 g, 0.74 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the reaction mixture was stirred for 1 hour at room temperature. The resulting solids were isolated by vacuum filtration.

Yield: 99%

$^1$H NMR (400 MHz, DMSO d$_6$) δ 9.49 (s, 1H), 9.14 (br s, 2H), 7.25 (s, 4H), 7.04 (t, 1H), 6.49 (d, 1H), 6.42 (d, 1H), 5.70 (s, 1H), 3.39 (s, 2H), 3.21 (br s, 4H), 3.11 (br s, 2H), 2.18 (m, 2H), 2.10 (m, 1H), 1.92 (m, 2H), 1.75 (m, 1H), 1.10 (br s, 6H)

Mass Spectral Analysis m/z=407.3 (M+H)$^+$

Elemental analysis:

C$_{25}$H$_{30}$N$_2$O$_3$, 1HCl, 1.75 H$_2$O

Theory: % C, 63.28; % H, 7.33; % N, 5.90.

Found: % C, 63.36; % H, 7.07; % N, 5.71.

$[α]_D^{25}$=+0.53 (c. 0.01, MeOH)

EXAMPLE 43B

Preparation of 43.6:

43.4 (1 g, 1.81 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 40%

Mass Spectral Analysis m/z=551.43 (M+H)$^+$

Chiral HPLC Method: $t_R$=6.361 min. (ee=98.52%)

Preparation of 43B:

A 4M anhydrous solution of hydrochloric acid in 1,4-dioxane (1.1 mL, 4.59 mmol, 5.5 eq) was added drop wise to a cooled (0° C.) solution of 43.6 (0.46 g, 0.83 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$H NMR (400 MHz, DMSO d$_6$) δ 9.49 (s, 1H), 9.13 (br s, 2H), 7.25 (s, 4H), 7.04 (t, 1H), 6.49 (d, 1H), 6.42 (d, 1H), 5.70 (s, 1H), 3.39 (br s, 2H), 3.22 (br s, 4H), 3.11 (br s, 2H), 2.18 (m, 2H), 2.11 (m, 1H), 1.92 (m, 2H), 1.75 (m, 1H), 1.11 (br s, 6H)

Mass Spectral Analysis m/z=407.3 (M+H)$^+$

Elemental analysis:

$C_{25}H_{30}N_2O_3$, 1HCl, 1.75 H$_2$O

Theory: % C, 63.28; % H, 7.33; % N, 5.90.

Found: % C, 63.13; % H, 7.14; % N, 5.81.

$[α]_D^{25}$=−1.43 (c. 0.01, MeOH)

EXAMPLE 43C

Preparation of 43C:

A 4M anhydrous solution of hydrochloric acid in 1,4-dioxane (1.38 mL, 5.50 mmol, 5.5 eq) was added drop wise to a cooled (0° C.) solution of 43.4 (0.55 g, 1.00 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$HNMR (400 MHz, DMSO d$_6$) δ 9.49 (s, 1H), 9.13 (brs, 2H), 7.25 (s, 4H), 7.04 (t, 1H), 6.48 (d, 1H), 6.42 (d, 1H), 5.70 (s, 1H), 3.40 (brs, 2H), 3.16 (brm, 6H), 2.18 (brm, 2H), 2.10 (m, 1H), 1.90 (m, 2H), 1.75 (brm, 1H), 1.11 (brs, 6H)

Mass Spectral Analysis m/z=407.4 (M+H)$^+$

EXAMPLE 43D

Preparation of 43.7:

To a solution of 43.3 (6.81 g, 13.0 mmol) and 1.7 (3.95 g, 13.0 mmol, 1 eq) in dimethoxyethane (DME) (125 mL) was added sequentially a 2N aqueous solution of sodium carbonate (19.5 mL, 39.0 mmol, 3 eq), lithium chloride (1.65 g, 39.0 mmol, 3 eq) and tetrakis(triphenylphosphine)palladium(0) (0.45 g, 0.39 mmol, 0.03 eq). The reaction mixture was evacuated for 2 min and then purged with argon and heated under reflux for 20 h. The mixture was then cooled to room temperature, diluted with ethyl acetate (100 mL) and filtered through a 1 inch plug of celite. The cake was further washed with ethyl acetate, the organic layer was washed with water followed by brine and dried over sodium sulfate. The crude product was purified by column chromatography (eluent: hexane/ethyl acetate mixtures of increasing polarity).

Yield: 59%

$^1$H NMR (300 MHz, CDCl$_3$) δ 8.41 (br.s, 1H), 7.62 (dd, 1H), 7.57 (dd, 1H), 7.13 (t, 1H), 6.69 (d, 2H), 5.56 (br.s, 1H), 4.70 (s, 2H), 3.82-3.60 (m, 1H), 3.55 (q, 2H), 3.40 (q, 2H), 3.37-3.22 (m, 3H), 3.17 (s, 3H), 2.25-2.10 (m, 2H), 2.10-1.82 (m, 1H), 1.80-1.63 (m, 3H), 1.45 (s, 9H), 1.29 (t, 3H), 1.16 (t, 3H)

Mass Spectral Analysis m/z=552.50 (M+H)$^+$

Preparation of 43.8:

43.7 (1 g, 1.81 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 40%

Mass Spectral Analysis m/z=552.47 (M+H)$^+$

Chiral HPLC Method: $t_R$=6.387 min. (ee>99%)

Preparation of 43D:

A 4M anhydrous solution of hydrochloric acid in 1,4-dioxane (0.9 mL, 3.48 mmol, 5.5 eq) was added drop wise to a cooled (0° C.) solution of 43.8 (0.35 g, 0.63 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 80%

$^1$HNMR (400 MHz, DMSO d$_6$) δ 9.75 (brs, 1H), 9.37 (brs, 2H), 8.45 (d, 1H), 7.77 (dd, 1H), 7.53 (d, 1H), 7.06 (t, 1H), 6.49 (m, 2H), 5.87 (s, 1H), 3.46 (q, 2H), 3.29 (q, 2H), 3.15 (brm, 4H), 2.22 (brm, 2H), 2.11 (m, 1H), 1.94 (brm, 2H), 1.78 (brm, 1H), 1.17 (t, 3H), 1.09 (t, 3H)

Mass Spectral Analysis m/z=408.3 (M+H)$^+$

Elemental analysis:

$C_{24}H_{29}N_3O_3$, 2HCl, 1.75H$_2$O

Theory: % C, 56.31; % H, 6.79; % N, 8.21; % Cl, 13.85.

Found: % C, 56.36; % H, 6.73; % N, 7.94; % Cl, 13.59.

$[α]_D^{25}$=+1.76 (c. 0.01, MeOH)

EXAMPLE 43E

Preparation of 43.9:

43.7 (1 g, 1.81 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 40%

Mass Spectral Analysis m/z=552.42 (M+H)$^+$

Chiral HPLC Method: $t_R$=7.915 min. (ee=98.36%)

Preparation of 43E:

A 4M anhydrous solution of hydrochloric acid in 1,4-dioxane (0.9 mL, 3.69 mmol, 5.5 eq) was added drop wise to a cooled (0° C.) solution of 43.9 (0.37 g, 0.67 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 74%

$^1$HNMR (400 MHz, DMSO d$_6$) δ 9.72 (brs, 1H), 9.32 (brs, 2H), 8.44 (d, 1H), 7.75 (dd, 1H), 7.51 (d, 1H), 7.06 (t, 1H), 6.48 (m, 2H), 5.86 (s, 1H), 3.46 (q, 2H), 3.29 (q, 2H), 3.15 (brm, 4H), 2.22 (brm, 2H), 2.12 (m, 1H), 1.93 (brm, 2H), 1.78 (brm, 1H), 1.16 (t, 3H), 1.09 (t, 3H)

Mass Spectral Analysis m/z=408.3 (M+H)$^+$
Elemental analysis:
C$_{24}$H$_{29}$N$_3$O$_3$, 2HCl, 2H$_2$O
Theory: % C, 55.82; % H, 6.83; % N, 8.14; % Cl, 13.73.
Found: % C, 55.56; % H, 6.71; % N, 7.84; % Cl, 13.38.
$[\alpha]_D^{25}$=−1.42 (c. 0.01, MeOH)

EXAMPLE 43F

Preparation of 43F:
A 4M anhydrous solution of hydrochloric acid in 1,4-dioxane (1.38 mL, 5.50 mmol, 5.5 eq) was added drop wise to a cooled (0° C.) solution of 43.7 (0.55 g, 1.00 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.
Yield: 99%
$^1$HNMR (400 MHz, DMSO d$_6$) δ 9.71 (brs, 1H), 9.31 (brs, 2H), 8.44 (d, 1H), 7.74 (dd, 1H), 7.51 (d, 1H), 7.06 (t, 1H), 6.48 (m, 2H), 5.86 (s, 1H), 3.46 (q, 2H), 3.29 (q, 2H), 3.15 (brm, 4H), 2.22 (brm, 2H), 2.11 (m, 1H), 1.93 (m, 2H), 1.78 (brm, 1H), 1.16 (t, 3H), 1.09 (t, 3H)
Mass Spectral Analysis m/z=408.4 (M+H)$^+$

EXAMPLE 44A

Preparation of 44.1:
To a roud bottomed flas was added successively 1.1d (13.87 g, 0.09 mol, 0.90 eq) followed by pyrrolidine (20.7 mL, 0.25 mol, 2.5 eq), 21.4 (21.33 g, 0.10 mol) and a minimum amount of methanol used to wash any remaining material. The resultant reaction mixture was heated to 80° C. for 30 min to dissolve all solids. The mixture was then cooled to room temperature and diluted with ethyl acetate (100 mL). The mixture was washed with a 1N aqueous solution of hydrochloric acid, a 1N aqueous solution of sodium hydroxide, brine and dried over sodium sulfate. The crude product was purified by column chromatography (eluent: hexane/ethyl acetate mixtures of increasing polarity).
Yield: 64%
$^1$H NMR (400 MHz, CDCl$_3$) δ 7.47 (dd, 1H), 7.24-7.15 (m, 1H), 6.92 (dd, 1H), 3.77-3.48 (m, 2H), 3.37-3.23 (m, 2H), 2.82-2.62 (m, 2H), 2.22-2.11 (m, 2H), 2.02-1.57 (m, 4H), 1.47 (s, 9H)
Preparation of 44.2:
To a solution of 44.1 (14.91 g, 42.7 mmol) in tetrahydrofuran (175 mL) at −78° C. under argon was added drop wise, a 1.0M solution of LiHMDS in tetrahydrofuran (49 mL). The mixture was stirred for 1 h at −78° C. A solution of 1.4 (17.51 g, 49.0 mmol, 1.15 eq) in tetrahydrofuran (100 mL) was added drop wise to the reacgtion mixture. The mixture was warmed slowly to room temperature and stirring was continued for a further 15 h at room temperature. The mixture was then poured into ice water and the two phases were separated. The organic phase was washed with a 1N aqueous solution of hydrochloric acid, a 1N aqueous solution of sodium hydroxide, brine and dried over sodium sulfate. The crude product was used for the next step without further purification.
Yield: 100% (crude).
Preparation of 44.3:
To a solution of 44.2 (6.50 g, 13.5 mmol) and 1.7 (3.95 g, 13.0 mmol, 1 eq) in dimethoxyethane (DME) (125 mL) was added sequentially a 2N aqueous solution of sodium carbonate (20.5 mL, 41.0 mmol, 3 eq), lithium chloride (1.72 g, 40.6 mmol, 3 eq) and tetrakis(triphenylphosphine)palladium(0) (0.47 g, 0.41 mmol, 0.03 eq). The reaction mixture was evacuated for 2 min, purged with argon and heated under reflux for 17 h. The mixture was then cooled to room temperature, diluted with ethyl acetate (100 mL) and filtered through a 1 inch plug of celite. The cake was further washed with ethyl acetate, the organic layer was washed with water followed by brine and dried over sodium sulfate. The crude product was purified by column chromatography (eluent: hexane/ethyl acetate mixtures of increasing polarity).
Yield: 64%
$^1$H NMR (300 MHz, CDCl$_3$) δ 8.52 (br.s, 1H), 7.72 (dd, 1H), 7.63 (dd, 1H), 6.61 (d, 1H), 5.69 (br.s, 1H), 3.84-3.52 (m, 4H), 3.43 (q, 2H), 3.38-3.25 (m, 2H), 2.24-2.00 (m, 2H), 1.82-1.65 (m, 4H), 1.47 (s, 9H), 1.29 (t, 3H), 1.19 (t, 3H)
Mass Spectral Analysis m/z=510.44 (M+H)$^+$
Preparation of 44.4:
44.3 (1 g, 1.96 mmol, 1 eq) was resolved using Chiral HPLC method:
Column: Chiral Technologies Chiralcel OD-H, 4.6×250 mm
Mobile Phase: 90% Hexane/0.2% Diisopropylethylamine 10% Ethanol
Flow: 1.0 mL min
Detector: UV 275 nm
Yield: 40%
Mass Spectral Analysis m/z=510.37 (M+H)$^+$
Chiral HPLC Method: $t_R$=7.430 min. (ee>99%)
Preparation of 44A:
A 4M anhydrous solution of hydrochloric acid in 1,4-dioxane (1.1 mL, 4.32 mmol, 5.5 eq) was added drop wise to a cooled (0° C.) solution of 44.4 (0.40 g, 0.78 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.
Yield: 99%
$^1$HNMR (400 MHz, DMSO d$_6$) δ 9.32 (brs, 2H), 8.59 (d, 1H), 7.92 (dd, 1H), 7.62 (d, 1H), 7.11 (m, 1H), 7.05 (m, 1H), 6.74 (dd, 1H), 6.13 (s, 1H), 3.47 (q, 2H), 3.30 (q, 2H), 3.15 (brm, 4H), 2.27 (brm, 2H), 2.15 (m, 1H), 1.96 (brm, 2H), 1.80 (brm, 1H), 1.18 (t, 3H), 1.11 (t, 3H)
Mass Spectral Analysis m/z=410.80 (M+H)$^+$
Elemental analysis:
C$_{24}$H$_{28}$FN$_3$O$_2$, 1HCl, 1.5H$_2$O
Theory: % C, 60.95; % H, 6.82; % N, 8.88.
Found: % C, 60.93; % H, 6.68; % N, 8.73.
$[\alpha]_D^{25}$=−2.77 (c. 0.01, MeOH)

EXAMPLE 44B

Preparation of 44.5:
44.3 (1 g, 1.96 mmol, 1 eq) was resolved using Chiral HPLC method:
Column: Chiral Technologies Chiralcel OD-H, 4.6×250 mm
Mobile Phase: 90% Hexane/0.2% Diisopropylethylamine 10% Ethanol
Flow: 1.0 mL min
Detector: UV 275 nm
Yield: 40%

Mass Spectral Analysis m/z=510.97 (M+H)$^+$

Chiral HPLC Method: $t_R$=11.689 min. (ee=98.2%)

Preparation of 44B:

A 4M anhydrous solution of hydrochloric acid in 1,4-dioxane (1.1 mL, 4.32 mmol, 5.5 eq) was added drop wise to a cooled (0° C.) solution of 44.5 (0.40 g, 0.78 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 80%

$^1$HNMR (400 MHz, DMSO d$_6$) δ 9.30 (brs, 2H), 8.59 (d, 1H), 7.92 (dd, 1H), 7.62 (d, 1H), 7.12 (m, 1H), 7.05 (m, 1H), 6.74 (dd, 1H), 6.13 (s, 1H), 3.47 (q, 2H), 3.30 (q, 2H), 3.15 (brm, 4H), 2.27 (brm, 2H), 2.15 (m, 1H), 1.96 (brm, 2H), 1.80 (brm, 1H), 1.17 (t, 3H), 1.11 (t, 3H)

Mass Spectral Analysis m/z=410.7 (M+H)$^+$

Elemental analysis:

C$_{24}$H$_{28}$FN$_3$O$_2$, 2HCl, 1H$_2$O

Theory: % C, 57.60; % H, 6.45; % N, 8.40.

Found: % C, 57.68; % H, 6.32; % N, 8.17.

$[\alpha]_D^{25}$=−1.50 (c. 0.01, MeOH)

EXAMPLE 44C

Preparation of 44C:

A 4M anhydrous solution of hydrochloric acid in 1,4-dioxane (1.38 mL, 5.50 mmol, 5.5 eq) was added drop wise to a cooled (0° C.) solution of 44.3 (0.51 g, 1.00 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$HNMR (400 MHz, DMSO d$_6$) δ 9.36 (brs, 2H), 8.59 (d, 1H), 7.92 (dd, 1H), 7.62 (d, 1H), 7.12 (m, 1H), 7.05 (m, 1H), 6.74 (dd, 1H), 6.13 (s, 1H), 3.48 (q, 2H), 3.30 (q, 2H), 3.16 (brm, 4H), 2.27 (brm, 2H), 2.12 (m, 1H), 1.96 (m, 2H), 1.80 (brm, 1H), 1.18 (t, 3H), 1.12 (t, 3H)

Mass Spectral Analysis m/z=410.41 (M+H)$^+$

EXAMPLE 44D

Preparation of 44.6:

A solution of 1.14 (3.56 g, 14.0 mmol), potassium acetate (4.42 g, 45.0 mmol, 3 eq) and Pd(dppf)Cl$_2$ (0.33 g, 0.45 mmol, 0.03 eq) in anhydrous N,N dimethylformamide (25 mL) was evacuated for 2 min, purged with argon and heated to 85° C. A solution of 44.2 (7.22 g, 15.0 mmol) in anhydrous N,N dimethylformamide (15 mL) was added to this reaction mixture, which was stirred at 85° C. under argon for 18 h. The mixture was then cooled to room temperature. The N,N dimethylformamide was removed under reduced pressure. The resultant residue was dissolved in ethyl acetate (120 mL) and filtered through a plug of celite. The cake was further washed with ethyl acetate (35 mL), the organic layer was then washed with water, brine and dried over sodium sulfate. The crude product was used for the next step without further purification.

Yield: 64% (crude)

$^1$H NMR (400 MHz, CDCl$_3$), δ 7.13-7.05 (m, 1H), 6.90-6.76 (m, 2H), 6.25 (br.s, 1H), 3.78-3.49 (m, 2H), 3.35-3.2 (m, 2H), 2.08-2.03 (m, 3H), 1.83-1.51 (m, 3H), 1.45 (s, 9H); 1.32 (s, 12H)

Preparation of 44.7:

To a solution of 44.6 (4.37 g, 9.5 mmol, 1 eq) and 34.1a (2.44 g, 9.5 mmol) in dimethoxyethane (DME) (75 mL) was added sequentially a 2N aqueous solution of sodium carbonate (14.25 mL, 28.5 mmol, 3 eq), lithium chloride (1.21 g, 28.5 mmol, 3 eq), and tetrakis(triphenylphosphine)palladium (0) (0.35 g, 0.54 mmol, 0.03 eq). The mixture was evacuated, purged with argon and heated under reflux for 22 h. The mixture was then cooled to room temperature and diluted with ethyl acetate (80 mL) and filtered through a 1 inch plug of celite. The cake was further washed with ethyl acetate, the organic layer was washed with water followed by brine and dried over sodium sulfate. The crude product was purified by column chromatography (eluent: hexane/ethyl acetate mixtures of increasing polarity).

Yield: 70%

$^1$H NMR (400 MHz, CDCl$_3$) δ 8.69 (br.s, 1H), 7.78 (dd, 1H), 7.45 (dd, 1H), 6.96 (dd, 1H), 6.92-6.85 (m, 2H), 5.98 and 5.97 (s, 1H), 3.82-3.53 (m, 4H), 3.38-3.25 (m, 4H), 2.25-2.03 (m, 2H), 1.96-1.65 (m, 4H), 1.47 and 1.45 (s, 9H), 1.30-1.15 (m, 6H)

Mass Spectral Analysis m/z=510.35 (M+H)$^+$

Preparation of 44.8:

44.7 (1 g, 1.96 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 30%

Mass Spectral Analysis m/z=510.89 (M+H)$^+$

Chiral HPLC Method: $t_R$=8.818 min. (ee=98.98%)

Preparation of 44D:

A 4M anhydrous solution of hydrochloric acid in 1,4-dioxane (0.8 mL, 3.24 mmol, 5.5 eq) was added drop wise to a cooled (0° C.) solution of 44.8 (0.30 g, 0.59 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 95%

$^1$HNMR (400 MHz, DMSO d$_6$) δ 9.35 (brd, 2H), 8.67 (d, 1H), 7.95 (dd, 1H), 7.69 (d, 1H), 7.21 (dd, 1H), 7.10 (m, 1H), 7.03 (m, 1H), 6.31 (s, 1H), 3.49 (brm, 2H), 3.24 (brm, 5H), 3.09 (brs, 1H), 2.28 (brm, 2H), 2.15 (m, 1H), 1.98 (m, 2H), 1.79 (brm, 1H), 1.14 (brd, 6H)

Mass Spectral Analysis m/z=410.8 (M+H)$^+$

Elemental analysis:

C$_{24}$H$_{28}$FN$_3$O$_2$, 1HCl, 1.75H$_2$O

Theory: % C, 60.37; % H, 6.86; % N, 8.80.
Found: % C, 60.32; % H, 6.61; % N, 8.56.
$[\alpha]_D^{25}=-3.34$ (c. 0.01, MeOH)

EXAMPLE 44E

Preparation of 44.9:

44.7 (1 g, 1.96 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 36%

Mass Spectral Analysis m/z=510.87 $(M+H)^+$ $^1$HNMR (400 MHz, DMSO $d_6$) δ 8.64 (m, 1H), 7.90 (m, 1H), 7.65 (d, 1H), 7.19 (m, 1H), 7.06 (m, 1H), 6.96 (m, 1H), 6.28 (s, 0.5H), 6.25 (s, 0.5H), 3.48 (brm, 4H), 3.28 (brm, 4H), 2.12-1.87 (brm, 4H), 1.72 (brm, 2H), 1.43 (s, 4.5H), 1.41 (s, 4.5H), 1.14 (brd, 6H)

Chiral HPLC Method: $t_R$=11.120 min. (ee=98.17%)

Preparation of 44E:

A 4M anhydrous solution of hydrochloric acid in 1,4-dioxane (1.0 mL, 3.89 mmol, 5.5 eq) was added drop wise to a cooled (0° C.) solution of 44.9 (0.36 g, 0.71 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$HNMR (400 MHz, DMSO $d_6$) δ 9.46 (brd, 2H), 8.70 (d, 1H), 8.00 (dd, 1H), 7.72 (d, 1H), 7.21 (dd, 1H), 7.11 (m, 1H), 7.04 (m, 1H), 6.34 (s, 1H), 3.57 (s, 2H), 3.48 (m, 2H), 3.25 (m, 4H), 3.10 (m, 1H), 2.28 (m, 2H), 2.15 (m, 1H), 1.98 (m, 2H), 1.79 (m, 1H), 1.18 (m, 3H), 1.11 (m, 3H)

Mass Spectral Analysis m/z=410.8 $(M+H)^+$ $[\alpha]_D^{25}=+1.87$ (c. 0.01, MeOH)

EXAMPLE 44F

Preparation of 44F:

A 4M anhydrous solution of hydrochloric acid in 1,4-dioxane (1.38 mL, 5.50 mmol, 5.5 eq) was added drop wise to a cooled (0° C.) solution of 44.7 (0.51 g, 1.00 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$HNMR (400 MHz, DMSO $d_6$) δ 9.39 (brd, 2H), 8.68 (d, 1H), 7.96 (dd, 1H), 7.69 (d, 1H), 7.21 (dd, 1H), 7.10 (m, 1H), 7.03 (m, 1H), 6.32 (s, 1H), 3.48 (brs, 2H), 3.18 (brm, 6H), 2.28 (brm, 2H), 2.15 (m, 1H), 1.97 (m, 2H), 1.80 (brm, 1H), 1.14 (brd, 6H)

Mass Spectral Analysis m/z=410.4 $(M+H)^+$

EXAMPLE 45A

Preparation of 45.1:

To a solution of 44.6 (4.44 g, 9.70 mmol) and 35.8 (3.45 g, 9.50 mmol, 0.98 eq) in dimethoxyethane (DME) (60 mL) was added sequentially a 2N aqueous solution of sodium carbonate (15 mL, 30.0 mmol, 3 eq), lithium chloride (1.27 g, 30.0 mmol, 3 eq), and tetrakis(triphenylphosphine)palladium(0) (0.56 g, 0.48 mmol, 0.03 eq). The mixture was evacuated, purged with argon and heated under reflux for 20 h. The mixture was then cooled to room temperature, diluted with ethyl acetate (50 mL) and filtered through a 1 inch plug of celite. The cake was further washed with ethyl acetate; the organic layer was washed with brine and dried over sodium sulfate and concentrated. The crude product was triturated with a 10:1 hexane/ether mixture and the resultant colorless crystalline precipitate was filtered. The filtrate was collected, concentrated and the crude product was purified by column chromatography (eluent: hexane/ethyl acetate mixtures of increasing polarity).

Yield: 64%

$^1$HNMR (400 MHz, DMSO $d_6$) δ 7.26 (dd, 1H), 7.12 (s, 1H), 7.00 (m, 2H), 6.90 (m, 1H), 6.36 (dd, 1H), 5.85 (s, 0.5H), 5.83 (s, 0.5H), 5.14 (s, 1H), 5.13 (s, 1H), 3.44 (brm, 4H), 3.32-3.20 (brm, 7H), 2.10-1.82 (brm, 4H), 1.73 (brm, 2H), 1.42 (s, 4.5H), 1.40 (s, 4.5H), 1.13 (brd, 6H)

Mass Spectral Analysis m/z=569.43 $(M+H)^+$

Preparation of 45.2:

45.1 (1 g, 1.76 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Isopropanol

Flow: 1.0 mL min

Detector: UV 275 nm

Yield: 25%

Mass Spectral Analysis m/z=569.78 $(M+H)^+$

Chiral HPLC Method: $t_R$=11.024 min. (ee=97.96%)

Preparation of 45A:

A 4M anhydrous solution of hydrochloric acid in 1,4-dioxane (0.6 mL, 2.42 mmol, 5.5 eq) was added drop wise to a cooled (0° C.) solution of 45.2 (0.25 g, 0.44 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 80%

$^1$HNMR (400 MHz, DMSO $d_6$) δ 9.92 (s, 1H), 9.19 (brs, 2H), 7.15 (d, 1H), 7.00 (m, 1H), 6.93 (m, 2H), 6.84 (d, 1H), 6.42 (dd, 1H), 5.84 (s, 1H), 3.42 (brs, 2H), 3.23 (brm, 5H), 3.08 (brs, 1H), 2.20 (brm, 3H), 1.95 (m, 2H), 1.77 (brm, 1H), 1.12 (brs, 6H)

Mass Spectral Analysis m/z=425.80 $(M+H)^+$

Elemental analysis:

$C_{25}H_{29}FN_2O_3$, 1HCl, 0.5$H_2O$

Theory: % C, 63.89; % H, 6.65; % N, 5.96.
Found: % C, 63.70; % H, 6.51; % N, 5.67.
$[\alpha]_D^{25}=+1.87$ (c. 0.01, MeOH)

EXAMPLE 45B

Preparation of 45.3:

45.1 (1 g, 1.76 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Isopropanol

Flow: 1.0 mL min

Detecor: UV 275 nm

Yield: 25%

$^1$HNMR (400 MHz, DMSO $d_6$) δ 7.26 (d, 1H), 7.13 (s, 1H), 7.04 (d, 1H), 6.98 (m, 1H), 6.90 (m, 1H), 6.37 (dd, 1H), 5.85 (s, 0.5H), 5.83 (s, 0.5H), 5.14 (s, 1H), 5.13 (s, 1H), 4.12 (q, 2H), 3.46 (brm, 4H), 3.30-3.16 (brm, 5H), 2.14-1.84 (brm, 4H), 1.73 (brm, 2H), 1.41 (s, 4.5H), 1.40 (s, 4.5H), 1.13 (brd, 6H)

Mass Spectral Analysis m/z=569.98 (M+H)$^+$

Chiral HPLC Method: $t_R$=18.406 min. (ee=98.27%)

Preparation of 45B:

A 4M anhydrous solution of hydrochloric acid in 1,4-dioxane (0.6 mL, 2.51 mmol, 5.5 eq) was added drop wise to a cooled (0° C.) solution of 45.3 (0.26 g, 0.46 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$H NMR (400 MHz, DMSO $d_6$) δ 9.94 (br s, 1H), 9.23 (br s, 2H), 7.15 (d, 1H), 6.99 (m, 1H), 6.93 (m, 2H), 6.83 (d, 1H), 6.41 (dd, 1H), 5.83 (s, 1H), 3.42 (br s, 2H), 3.24 (m, 4H), 3.09 (m, 2H), 2.24 (m, 2H), 2.15 (m, 1H), 1.95 (m, 2H), 1.77 (m, 1H), 1.12 (br s, 6H)

Mass Spectral Analysis m/z=425.8 (M+H)$^+$ $[α]_D^{25}$=−3.05 (c. 0.01, MeOH)

EXAMPLE 45C

Preparation of 45C:

A 4M anhydrous solution of hydrochloric acid in 1,4-dioxane (1.38 mL, 5.50 mmol, 5.5 eq) was added drop wise to a cooled (0° C.) solution of 45.1 (0.57 g, 1.00 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$HNMR (400 MHz, DMSO $d_6$) δ 9.92 (brs, 1H), 9.20 (brs, 2H), 7.14 (d, 1H), 6.97 (m, 2H), 6.91 (s, 1H), 6.84 (d, 1H), 6.42 (dd, 1H), 5.84 (s, 1H), 3.64 (brs, 3H), 3.42 (brs, 2H), 3.18 (brm, 3H), 2.20 (m, 3H), 1.95 (m, 2H), 1.76 (brm, 1H), 1.12 (brs, 6H)

Mass Spectral Analysis m/z=425.4 (M+H)$^+$

EXAMPLE 45D

Preparation of 45.4:

To a round bottomed flask was added successively 2.1 (15.21 g, 0.1 mol) followed by pyrrolidine (20.7 mL, 0.25 mol, 2.5 eq), 21.4 (21.33 g, 0.10 mol) and a minimum amount of methanol used to wash any remaining material. The resultant reaction was heated to 80° C. for 30 min to dissolve all solids. The mixture was then cooled to room temperature and diluted with ethyl acetate (100 mL). The mixture was washed with a 1N aqueous solution of hydrochloric acid, water, brine and dried over sodium sulfate. The crude material was used for the next step without further purification.

Yield: 100% (crude)

Preparation of 45.5:

To a cooled (0° C.) and stirring solution of 45.4 (34.74 g, 0.10 mol) and imidazole (14.30 g, 0.21 mol, 2.1 eq) in anhydrous N,N-dimethylformamide (200 mL) was added drop wise, a solution of 2.3 (17.33 g, 0.12 mol, 1.2 eq) in N,N-dimethylformamide. The resultant mixture was allowed to warm to room temperature and stirring was continued for 16 h at room temperature. The N,N-dimethylformamide was removed and the residue diluted with ethyl acetate. The organic solution was washed with water, brine and dried over sodium sulfate. The crude product was purified by column chromatography (eluent: hexane/ethyl acetate mixtures of increasing polarity).

Yield: 51%

$^1$H NMR (400 MHz, CDCl$_3$) δ 7.22 (d, 1H), 6.95 (dd, 1H), 6.80 (d, 1H), 3.72-3.44 (m, 2H), 3.33-3.21 (m, 2H), 2.75-2.58 (m, 2H), 2.20-2.07 (m, 2H), 2.02-1.52 (m, 4H), 1.43 (s, 9H), 0.94 (s, 9H), 0.15 (s, 6H)

Preparation of 45.6:

To a solution of 45.5 (23.55 g, 51.0 mmol) in tetrahydrofuran (250 mL) at −78° C. under argon was added drop wise, a 1.0M solution of LiHMDS in tetrahydrofuran (59 mL). The mixture was stirred for 1 h at −78° C. A solution of 1.4 (21.08 g, 59.0 mmol, 1.16 eq) in tetrahydrofuran (175 mL) was added drop wise to the mixture, which was warmed slowly to room temperature. Stirring was continued for a further 15 h at room temperature. The mixture was then poured into ice water and the two phases were separated. The organic phase was washed with a 1N aqueous solution of hydrochloric acid, a 1N aqueous solution of sodium hydroxide, brine and dried over sodium sulfate. The crude product was used for the next step without further purification.

Yield: 100% (crude)

$^1$H NMR (400 MHz, CDCl$_3$) δ 7.13 (m, 1H), 6.75-6.68 (m, 2H), 5.58 (s, 1H), 3.78-3.50 (m, 2H), 3.37-3.20 (m, 2H), 2.27-2.04 (m, 3H), 1.97-1.62 (m, 3H), 1.47 (s, 9H), 0.98 (s, 9H), 0.19 (s, 6H)

Preparation of 45.7:

To a solution of 45.6 (9.50 g, 16.0 mmol) and 1.7 (4.87 g, 16.0 mmol, 1 eq) in dimethoxyethane (DME) (165 mL) was added sequentially a 2N aqueous solution of sodium carbonate (24 mL, 48.0 mmol, 3 eq), lithium chloride (2.03 g, 48.0 mmol, 3 eq) and tetrakis(triphenylphosphine)palladium(0) (0.56 g, 0.48 mmol, 0.03 eq). The reaction mixture was evacuated for 2 min, purged with argon and heated under reflux for 23 h. The mixture was then cooled to room temperature, diluted with ethyl acetate (150 mL) and filtered through a 1 inch plug of celite. The cake was further washed with ethyl acetate. The organic layer was washed with water followed by brine and dried over sodium sulfate. The crude product was purified by column chromatography (eluent: hexane/ethyl acetate mixtures of increasing polarity).

Yield: 47%

$^1$H NMR (300 MHz, CDCl$_3$) δ 8.46 (br.s, 1H), 7.77-7.72 (m, 1H), 7.51 (dd, 1H), 6.87-6.81 (m, 1H), 6.76 (dd, 1H), 6.35 (m, 1H), 5.62 and 5.61 (s, 1H), 3.76-3.55 (m, 2H), 3.51 (q, 2H), 3.35 (q, 2H), 3.31-3.19 (m, 2H), 2.19-2.02 (m, 2H), 1.86-1.55 (m, 4H), 1.44 and 1.43 (s, 9H), 1.26-1.17 (m, 3H), 1.14 (t, 3H)

Mass Spectral Analysis m/z=508.37 (M+H)+

Preparation of 45.8:

45.7 (1 g, 1.97 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 40%

$^1$H NMR (400 MHz, DMSO $d_6$) δ 8.98 (s, 1H), 8.54 (d, 1H), 7.86 (m, 1H), 7.60 (dd, 1H), 6.77 (dd, 1H), 6.62 (dd, 1H), 6.34 (d, 1H), 5.96 (s, 0.5H), 5.92 (s, 0.5H), 3.47 (brm, 4H), 3.30 (brm, 4H), 2.08-1.84 (brm, 4H), 1.70 (brm, 2H), 1.42 (s, 4.5H), 1.41 (s, 4.5H), 1.17 (t, 3H), 1.11 (t, 3H)

Mass Spectral Analysis m/z=508.39 (M+H)+

Chiral HPLC Method: $t_R$=8.583 min. (ee=97.58%)

Preparation of 45D:

A 4M anhydrous solution of hydrochloric acid in 1,4-dioxane (1.1 mL, 4.33 mmol, 5.5 eq) was added drop wise to a cooled (0° C.) solution of 45.8 (0.40 g, 0.79 mmol, 1 eq) in anhydrous methanol (4 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 95%

$^1$H NMR (400 MHz, DMSO $d_6$) δ 9.31 (brs, 2H), 8.56 (d, 1H), 7.89 (dd, 1H), 7.62 (d, 1H), 6.82 (d, 1H), 6.65 (dd, 1H), 6.36 (d, 1H), 6.00 (s, 1H), 3.48 (q, 2H), 3.30 (q, 2H), 3.15 (brm, 4H), 2.22 (brm, 2H), 2.14 (m, 1H), 1.94 (m, 2H), 1.78 (brm, 1H), 1.18 (t, 3H), 1.11 (t, 3H)

Mass Spectral Analysis m/z=408.3 (M+H)+

Elemental analysis:

$C_{24}H_{29}N_3O_3$, 1.9HCl, 1.6H$_2$O

Theory: % C, 57.01; % H, 6.80; % N, 8.31; % Cl, 13.32.

Found: % C, 57.24; % H, 6.82; % N, 8.24; % Cl, 13.40.

$[\alpha]_D^{25}$=+1.71 (c. 0.01, MeOH)

EXAMPLE 45E

Preparation of 45.9:

45.7 (1 g, 1.97 mmol, 1 eq) was resolved using Chiral HPLC method:

Column: Chiral Technologies Chiralcel OD-H, 4.6×250 mm

Mobile Phase: 90% Hexane/0.2% Diisopropylethylamine 10% Ethanol

Flow: 1.0 mL min

Detector: UV 275 nm

Yield: 35%

$^1$H NMR (400 MHz, DMSO $d_6$) δ 8.99 (s, 1H), 8.54 (d, 1H), 7.86 (m, 1H), 7.60 (dd, 1H), 6.77 (dd, 1H), 6.62 (dd, 1H), 6.34 (d, 1H), 5.96 (s, 0.5H), 5.92 (s, 0.5H), 3.47 (brm, 4H), 3.30 (brm, 4H), 2.08-1.84 (brm, 4H), 1.70 (brm, 2H), 1.42 (s, 4.5H), 1.41 (s, 4.5H), 1.17 (t, 3H), 1.11 (t, 3H)

Mass Spectral Analysis m/z=508.34 (M+H)+

Chiral HPLC Method: $t_R$=11.101 min. (ee>99%)

Preparation of 45E:

A 4M anhydrous solution of hydrochloric acid in 1,4-dioxane (1.0 mL, 3.79 mmol, 5.5 eq) was added drop wise to a cooled (0° C.) solution of 45.9 (0.35 g, 0.69 mmol, 1 eq) in anhydrous methanol (4 mL). The mixture was warmed to room temperature and stirring was continued for an additional 16 hours at room temperature. The reaction mixture concentrated under reduced pressure. Ethyl acetate was added to the resulting oil and the mixture was stirred for 1 hour at room temperature. The resulting solids were isolated by vacuum filtration.

Yield: 95%

$^1$H NMR (400 MHz, DMSO $d_6$) δ 9.31 (brs, 2H), 8.56 (d, 1H), 7.89 (dd, 1H), 7.62 (d, 1H), 6.83 (d, 1H), 6.66 (dd, 1H), 6.36 (d, 1H), 6.00 (s, 1H), 3.48 (q, 2H), 3.30 (q, 2H), 3.16 (brm, 4H), 2.22 (brm, 2H), 2.13 (m, 1H), 1.94 (m, 2H), 1.78 (brm, 1H), 1.18 (t, 3H), 1.11 (t, 3H)

Mass Spectral Analysis m/z=408.8 (M+H)+

Elemental analysis:

$C_{24}H_{29}N_3O_3$, 1HCl, 2.25H$_2$O

Theory: % C, 59.50; % H, 7.18; % N, 8.67.

Found: % C, 59.37; % H, 7.05; % N, 8.40.

$[\alpha]_D^{25}$=−2.98 (c. 0.01, MeOH)

EXAMPLE 45F

Preparation of 45F:

A 4M anhydrous solution of hydrochloric acid in 1,4-dioxane (1.38 mL, 5.50 mmol, 5.5 eq) was added drop wise to a cooled (0° C.) solution of 45.7 (0.51 g, 1.00 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$H NMR (400 MHz, DMSO $d_6$) δ 9.38 (brs, 2H), 8.56 (d, 1H), 7.90 (dd, 1H), 7.63 (d, 1H), 6.83 (d, 1H), 6.66 (dd, 1H), 6.37 (d, 1H), 6.00 (s, 1H), 3.48 (q, 2H), 3.30 (q, 2H), 3.15 (brm, 4H), 2.23 (brm, 2H), 2.13 (m, 1H), 1.94 (m, 2H), 1.78 (brm, 1H), 1.18 (t, 3H), 1.12 (t, 3H)

Mass Spectral Analysis m/z=408.4 (M+H)+

EXAMPLES 46A, 46B

Preparation of 46.1:

To a solution of 45.6 (8.91 g, 15.0 mmol) in dimethoxyethane (DME) (150 mL) was added sequentially a 2N aqueous solution of sodium carbonate (22.5 mL, 45.0 mmol, 3 eq), lithium chloride (1.91 g, 45.1 mmol, 3 eq), compound 45.6 (3.32 g, 15.0 mmol, 1 eq) and tetrakis(triphenylphosphine)palladium(0) (0.52 g, 0.45 mmol, 0.03 eq). The reaction mixture was evacuated for 2 min, purged with argon and heated under reflux for 42 h. The mixture was then cooled to room temperature, diluted with ethyl acetate (120 mL) and the mixture was filtered through a 1 inch plug of celite. The cake was further washed with ethyl acetate, the organic layer was washed with water followed by brine and dried over sodium sulfate. The crude product was purified by column chromatography (eluent: hexane/ethyl acetate mixtures of increasing polarity).

Yield: 69%

$^1$H NMR (300 MHz, CDCl$_3$) δ 7.37-7.29 (m, 4H), 6.75 (d, 1H), 6.64 (dd, 1H), 6.60-6.50 (m, 1H), 6.48 (d, 1H), 5.60 (s, 1H), 3.77-3.48 (m, 4H), 3.36-3.18 (m, 4H), 2.21-2.04 (m, 2H), 1.87-1.61 (m, 4H), 1.47 (s, 9H), 1.31-1.08 (m, 6H)

Preparation of 46.2:

To a solution of 46.1 (3.20 g, 6.32 mmol, 1.0 eq) in methylene chloride (100 mL) was added N,N-diisopropylethylamine (4.40 mL, 25.56 mmol, 4.0 eq) and then 11.3 (1.54 g, 18.95 mmol, 3.0 eq) was added drop wise to the reaction mixture. The reaction mixture was stirred for 48 h at room temperature and then poured onto water (150 mL). The layers were separated and the aqueous was washed two times with methylene chloride (50 mL). The combined organics were washed with a 0.1N aqueous solution of hydrochloric acid, a saturated aqueous solution of sodium bicarbonate and brine. The organics were dried over sodium sulfate and concentrated. The crude product was purified by column chromatography (eluent: methanol/methylene chloride mixtures of increasing polarity).

Yield: 50% Mass Spectral Analysis z/z=551.2 (M+H)$^+$ $^1$H NMR (400 MHz, CDCl$_3$) δ 7.39 (m, 4H), 6.87 (m, 2H), 6.68 (d, 1H), 5.63 (s, 1H), 5.03 (s, 2H), 3.84-3.55 (brm, 4H), 3.43 (s, 3H), 3.31(brm, 4H), 2.16 (brm, 3H), 1.94-1.68 (brm, 3H), 1.49 (s, 4.5H), 1.47 (s, 4.5H), 1.21 (brd, 6H)

Preparation of 46.3 and 46.4:

The racemic 46.2 was separated into pure enantiomers 46.3 and 46.4 by chiral chromatography.

Column: Chiral Technologies Chiralcel OD-H, 4.6×250 mm

Mobile Phase: 90% Hexane/0.2% Diisopropylethylamine 10% Isopropanol

Flow: 1.0 mL min

Detector: UV 275 nm 46.3: $^1$HNMR (400 MHz, CDCl$_3$) δ 7.39 (m, 4H), 6.87 (m, 2H), 6.68 (d, 1H), 5.63 (s, 1H), 5.03 (s, 2H), 3.84-3.52 (brm, 4H), 3.43 (s, 3H), 3.31(brm, 4H), 2.16 (brm, 3H), 1.93-1.68 (brm, 3H), 1.48 (s, 4.5H), 1.47 (s, 4.5H), 1.21 (brd, 6H)

46.4: $^1$HNMR (400 MHz, CDCl$_3$) δ 7.39 (m, 4H), 6.87 (m, 2H), 6.68 (d, 1H), 5.63 (s, 1H), 5.03 (s, 2H), 3.82-3.52 (brm, 4H), 3.43 (s, 3H), 3.31(brm, 4H), 2.17 (brm, 3H), 1.92-1.68 (brm, 3H), 1.48 (s, 4.5H), 1.47 (s, 4.5H), 1.21 (brd, 6H)

Preparation of 46A:

To a solution of 46.3 (0.83 g, 1.51 mmol, 1.0 eq) in methanol (40 mL) under nitrogen was added a 4.0M solution of anhydrous hydrochloric acid in dioxane (3.80 mL, 15.1 mmol, 10.0 eq). The reaction was stirred for 16 h at room temperature and concentrated. The crude product was purified by column chromatography (eluent: methanol/methylene chloride mixtures of increasing polarity). The resulting solid was triturated in diethyl ether and collected by vacuum filtration.

Yield: 93%

$^1$H NMR (400 MHz, DMSO d$_6$) δ 9.19 (brs, 2H), 9.03 (s, 1H), 7.40 (q, 4H), 6.80 (d, 1H), 6.63 (dd, 1H), 6.40 (d, 1H), 5.86 (s, 1H), 3.45 (brs, 2H), 3.28-3.02 (brm, 6H), 2.20 (brm, 2H), 2.12 (m, 1H), 1.92 (brm, 2H), 1.76 (brm, 1H), 1.12 (brd, 6H)

Mass Spectral Analysis m/z=407.4 (M+H)$^+$

Elemental analysis:

C$_{25}$H$_{30}$N$_2$O$_3$, 1HCl, 2H$_2$O

Theory: % C, 62.69; % H, 7.36; % N, 5.85.

Found: % C, 62.37; % H, 7.20; % N, 5.83.

[α]$_D$=+1.67 (c=10.5 mg/mL, MeOH, 22.6° C.)

Preparation of 46B:

To a solution of 46.4 (0.86 g, 1.56 mmol, 1.0 eq) in methanol (40 mL) under nitrogen was added a 4.0M solution of anhydrous hydrochloric acid in dioxane (3.90 mL, 15.6 mmol, 10.0 eq). The reaction was stirred for 16 h at room temperature and concentrated under reduced pressure. The crude product was purified by column chromatography (eluent: methanol/methylene chloride mixtures of increasing polarity). The resulting solid was triturated in diethyl ether and collected by vacuum filtration.

Yield: 85%

$^1$H NMR (400 MHz, DMSO d$_6$) δ 9.22 (brs, 2H), 9.03 (s, 1H), 7.40 (q, 4H), 6.80 (d, 1H), 6.63 (dd, 1H), 6.40 (d, 1H), 5.86 (s, 1H), 3.45 (brs, 2H), 3.30-3.02 (brm, 6H), 2.20 (brm, 2H), 2.12 (m, 1H), 1.92 (brm, 2H), 1.76 (brm, 1H), 1.12 (brd, 6H)

Mass Spectral Analysis m/z=407.4 (M+H)$^+$

Elemental analysis:

C$_{25}$H$_{30}$N$_2$O$_3$, 1HCl, 2.3H$_2$O

Theory: % C, 61.99; % H, 7.41; % N, 5.78.

Found: % C, 62.08; % H, 7.38; % N, 5.86.

[α]$_D$=−1.52 (c=10.0 mg/mL, MeOH, 22.6° C.)

EXAMPLE 46C

Preparation of Compound 46.1:

To a solution of 45.6 (8.91 g, 15.0 mmol) in dimethoxyethane (DME) (150 mL) was added sequentially a 2N aqueous solution of sodium carbonate (22.5 mL, 45.0 mmol, 3 eq), lithium chloride (1.91 g, 45.1 mmol, 3 eq) 1.6 (3.32 g, 15.0 mmol, 1 eq) and tetrakis(triphenylphosphine)palladium(0) (0.52 g, 0.45 mmol, 0.03 eq). The reaction mixture was evacuated for 2 min, purged with argon and heated under reflux for 42 h. The mixture was then cooled to room temperature, diluted with ethyl acetate (120 mL) and filtered through a 1 inch plug of celite. The cake was further washed with ethyl acetate, the organic layer was washed with water followed by brine and dried over sodium sulfate. The crude product was purified by column chromatography (eluent: hexane/ethyl acetate mixtures of increasing polarity).

Yield: 69%

$^1$H NMR (400 MHz, DMSO d$_6$) δ 8.94 (s, 1H), 7.39 (s, 4H), 6.75 (d, 1H), 6.60 (dd, 1H), 6.38 (d, 1H), 5.82 (s, 0.5H), 5.79 (s, 0.5H), 3.46 (brm, 4H), 3.24 (brm, 4H), 2.08-1.82 (brm, 4H), 1.68 (brm, 2H), 1.42 (s, 4.5H), 1.40 (s, 4.5H), 1.12 (brd, 6H)

Mass Spectral Analysis m/z=507.59 (M+H)$^+$

Preparation of 46C:

A 4M anhydrous solution of hydrochloric acid in 1,4-dioxane (1.38 mL, 5.50 mmol, 5.5 eq) was added drop wise to a cooled (0° C.) solution of 46.1 (0.51 g, 1.00 mmol, 1 eq) in anhydrous methanol (5 mL). The mixture was warmed to room temperature and stirring was continued for an additional 16 hours at room temperature. The reaction mixture was concentrated under reduced pressure. Ethyl acetate was added to the resulting oil and the mixture was stirred for 1 hour at room temperature. The resulting solids were isolated by vacuum filtration.

Yield: 99%

$^1$H NMR (400 MHz, DMSO d$_6$) δ 9.21 (brs, 2H), 9.03 (brs, 1H), 7.40 (q, 4H), 6.80 (d, 1H), 6.63 (dd, 1H), 6.40 (d, 1H), 5.86 (s, 1H), 3.43 (brs, 2H), 3.16 (brm, 6H), 2.21 (brm, 2H), 2.12 (m, 1H), 1.92 (m, 2H), 1.76 (brm, 1H), 1.13 (brd, 6H)

Mass Spectral Analysis m/z=407.4 (M+H)$^+$

EXAMPLE 47A

Preparation of 47.1:

To a solution of 23.3a (2.71 g, 6.20 mmol, 1.0 eq) and compound 1.7 (1.89 g, 6.20 mmol, 1.0 eq) in dimethoxyethane (DME) (65 mL) was added sequentially a 2N aqueous solution of sodium carbonate (9.30 mL, 18.60 mmol, 3.0 eq), lithium chloride (0.79 g, 18.60 mmol, 3.0 eq) and tetrakis(triphenylphosphine)palladium(0) (0.23 g, 0.20 mmol, 0.03 eq). The reaction mixture was evacuated for 2 min. and purged with argon and heated under reflux for 19 h. The mixture was then cooled to room temperature, diluted with ethyl acetate (100 mL) and filtered through a 1 inch plug of celite. The cake was washed with ethyl acetate. The organics were washed with water and brine, and dried over sodium sulfate. The crude product was purified by column chromatography (eluent: hexane/ethyl acetate mixtures of increasing polarity).

Yield: 61%

$^1$H NMR (400 MHz, CDCl$_3$) δ 8.56 (brs, 1H), 7.75 (dd, 1H), 7.64 (d, 1H), 7.25-7.17 (m, 1H), 6.96-6.85 (m, 3H), 5.70 (brs, 1H), 3.94-3.81 (m, 1H), 3.68-3.54 (m, 3H), 3.48-3.33 (m, 3H), 2.46-2.39 (m, 1H), 2.00-1.80 (m, 1H), 1.82-1.69 (m, 1H), 1.47 (s, 9H), 1.28 (t, 3H), 1.19 (t, 3H)

Preparation of 47A

To a solution of 47.1 (1.40 g, 3.02 mmol, 1.0 eq) in methylene chloride (40 mL) at 0° C. under nitrogen was added a 2.0M solution of anhydrous hydrochloric acid in diethyl ether (9.06 mL, 18.12 mmol, 6.0 eq). The reaction was warmed to room temperature and stirred for 48 h at room temperature. Diethyl ether (15 mL) was added and stirring was continued for 10 min at room temperature. The solids were collected by vacuum filtration.

Yield: 92%

$^1$H NMR (400 MHz, DMSO d$_6$) δ 9.92 (brs, 1H), 9.70 (brs, 1H), 8.61 (m, 1H), 7.92 (dd, 1H), 7.63 (dd, 1H), 7.30 (m, 1H), 6.99 (m, 3H), 6.13 (s, 1H), 3.57 (brm, 1H), 3.45 (brm, 4H), 3.31 (m, 3H), 2.42 (brm, 1H), 2.16 (m, 1H), 1.18 (t, 3H), 1.11 (t, 3H)

Mass Spectral Analysis m/z=364.7 (M+H)$^+$

EXAMPLE 47B

Preparation of 47.2:

A solution of bis(pinacolato)diboron (1.14) (4.06 g, 16.0 mmol, 1.14 eq), potassium acetate (4.12 g, 42.0 mmol, 3.0 eq) and [1,1'-bis(diphenylphosphino)ferrocene]dichloropalladium(II) (0.31 g, 0.42 mmol, 0.03 eq) in anhydrous N,N-dimethylformamide (35 mL) was evacuated for 2 min, purged with argon and heated to 85° C. A solution of 23.3a (6.10 g, 14.0 mmol, 1.0 eq) in anhydrous N,N-dimethylformamide (20 mL) was added to this reaction mixture, which was stirred at 85° C. under argon for 15 h. The mixture was then cooled to room temperature and concentrated. The residue was dissolved in ethyl acetate (120 mL) and filtered through a plug of celite. The cake was washed with ethyl acetate. The organics were washed with water and brine, and dried over sodium sulfate. The crude product was used for the next step without further purification.

Yield: 100% (crude)

Preparation of 47.3:

To a solution of 47.2 (7.94 g, 19.2 mmol, 1.0 eq) and compound 35.8 (4.72 g, 13.0 mmol, 0.68 eq) in dimethoxyethane (DME) (110 mL) was added sequentially a 2N aqueous solution of sodium carbonate (19.5 mL, 39.0 mmol, 3.0 eq), lithium chloride (1.65 g, 39.0 mmol, 3.0 eq), and tetrakis(triphenylphosphine)palladium(0) (0.45 g, 0.39 mmol, 0.03 eq). The mixture was evacuated, purged with argon and heated under reflux for 17 h. The mixture was then cooled to room temperature, diluted with ethyl acetate (60 mL) and filtered through a 1 inch plug of celite. The filtrate was concentrated under reduced pressure. The crude product was purified by column chromatography (eluent: hexane/ethyl acetate mixtures of increasing polarity).

Yield: 28%

$^1$H NMR (300 MHz, CDCl$_3$) δ 7.26-7.02 (m, 4H), 6.82-6.69 (m, 2H), 6.85 (d, H), 5.60 (s, 1H), 5.30 (s, 2H), 3.95-3.83 (m, 1H), 3.69-3.43 (m, 3H), 3.40-3.23 (m, 3H), 3.26 (s, 3H), 2.49-2.40 (m, 1H), 2.00-1.88 (m, 1H), 1.76-1.64 (brs, 1H), 1.47 (s, 9H), 1.31-1.10 (m, 6H)

Preparation of 47B

To a solution of 47.3 (2.16 g, 4.13 mmol, 1.0 eq) in methanol (35 mL) at 0° C. under nitrogen was added a 2.0M solution of anhydrous hydrochloric acid in diethyl ether (12.4 mL, 24.80 mmol, 6.0 eq). The reaction mixture was warmed to room temperature and stirred for 48 h at room temperature. The reaction was concentrated to a solid and triturated in a mixture of methylene chloride (5 mL) and diethyl ether (25 mL). The solids were collected by vacuum filtration.

Yield: 100% Mass Spectral Analysis m/z=379.8 (M+H)$^+$ $^1$H NMR (400 MHz, DMSO d$_6$) δ 9.85 (brs, 1H), 9.65 (brs, 1H), 9.53 (brs, 1H), 7.19 (m, 2H), 6.87 (m, 4H), 6.74 (d, 1H), 5.84 (s, 1H), 3.57 (brm, 1H), 3.43 (brm, 4H), 3.25 (brm, 3H), 2.42 (brm, 1H), 2.12 (brm, 1H), 1.12 (brs, 6H)

EXAMPLE 47C

Preparation of 47.4:

To a roud bottomed flask was added successively 2',6'-dihydroxyacetophenone (11.1) (9.12 g, 60.0 mmol, 1.0 eq) followed by pyrrolidine (12.4 mL, 150.0 mmol, 2.5 eq), N-Boc-pyrrolidin-3-one (23.1a) (11.11 g, 60.0 mmol, 1.0 eq) and a minimum amount of methanol used to wash any remaining material. The reaction mixture was heated to 80° C. for 30 min. to dissolve all solids. The mixture was then cooled to room temperature and diluted with ethyl acetate (80 mL). The mixture was washed with a 1N aqueous solution of hydrochloric acid, water and brine, and dried over sodium sulfate. The crude product was purified by column chromatography (eluent: hexane/ethyl acetate mixtures of increasing polarity).

Yield: 52%

$^1$H NMR (400 MHz, CDCl$_3$) δ 11.50 (s, 1H), 7.30 (dd, 1H), 6.52-6.32 (m, 2H), 3.82-3.40 (m, 3H), 3.38-3.20 (m, 1H), 3.00-2.60 (m, 2H), 2.34-2.20 (m, 1H), 1.98-1.74 (m, 1H), 1.43 (s, 9H)

Preparation of 47.5:

To a solution of 47.4 (5.15 g, 16.1 mmol, 1.0 eq) and N,N-diisopropylethylamine (8.5 mL, 48.8 mmol, 3.0 eq) in methylene chloride (30 mL) was added drop wise compound 11.3 (3.7 mL, 48.7 mmol, 3.0 eq) under argon. The reaction mixture was heated under reflux for 15 h and then allowed to cool to room temperature. The mixture was concentrated, diluted with ethyl acetate (50 mL) and washed with a 2N aqueous solution of hydrochloric acid until the aqueous layer was acidic. The organic layer was washed with brine and dried over sodium sulfate. The crude product was purified by column chromatography (eluent: hexane/ethyl acetate mixtures of increasing polarity).

Yield: 52%

Preparation of 47.6:

To a solution of 47.5 (3.07 g, 8.4 mmol, 1.0 eq) in tetrahydrofuran (25 mL) at −78° C. under argon was added drop wise a 1.0M solution of LiHMDS in tetrahydrofuran (10.1 mL, 10.1 mmol, 1.2 eq). The mixture was stirred for 1 h at −78° C. A solution of N-phenyltrifluoromethanesulfonimide (1.4) (3.32 g, 9.29 mmol, 1.11 eq) in tetrahydrofuran (20 mL) was added drop wise to the reaction mixture. The mixture was warmed slowly to room temperature and stirring was continued for a further 15 h at room temperature. The mixture was poured into ice water and the two phases were separated. The organic layer was washed with a 1N aqueous solution of hydrochloric acid, a 1N aqueous solution of sodium hydroxide and brine, and dried over sodium sulfate. The crude product was used for the next step without further purification.

Yield: 100% (crude)

Preparation of 47.7:

To a solution of 47.6 (2.34 g, 4.7 mmol, 1.0 eq) in dimethoxyethane (DME) (50 mL) was added sequentially a 2N aqueous solution of sodium carbonate (6.75 mL, 13.5 mmol, 3.0 eq), lithium chloride (0.57 g, 13.5 mmol, 3.0 eq), compound 1.6 (1.00 g, 4.5 mmol, 0.96 eq) and tetrakis(triphenylphosphine)palladium(0) (0.16 g, 0.14 mmol, 0.03 eq). The reaction mixture was evacuated for 2 min, purged with argon and heated under reflux for 20 h. The mixture was cooled to room temperature, diluted with ethyl acetate (40 mL) and filtered through a 1 inch plug of celite. The cake was rinsed with ethyl acetate. The filtrate was washed with water and brine, and dried over sodium sulfate. The crude product was purified by column chromatography (eluent: hexane/ethyl acetate mixtures of increasing polarity).

Yield: 51%

$^1$H NMR (300 MHz, CDCl$_3$) δ 7.36-7.29 (m, 4H), 7.18-7.09 (m, 1H), 6.72-6.62 (m, 2H), 5.65 (s, 1H), 4.68 (s, 2H), 3.92-3.74 (m, 2H), 3.68-3.19 (m, 6H), 3.16 (s, 3H), 2.43-2.31 (m, 1H), 2.00-1.85 (m, 1H), 1.49 (s. 4.5H), 1.47 (s, 4.5H), 1.30-1.04 (m, 6H)

Preparation of 47C

To a solution of 47.7 (1.29 g, 2.47 mmol, 1.0 eq) in methanol (20 mL) under nitrogen was added a 2.0M solution of anhydrous hydrochloric acid in diethyl ether (7.40 mL, 14.81 mmol, 6.0 eq). The reaction was stirred for 24 h at room temperature. The reaction was concentrated to an oil and stirred in a 1:1 mixture of methylene chloride and diethyl ether for 20 min. The solids that precipitated were collected by vacuum filtration.

Yield: 73%

$^1$H NMR (400 MHz, DMSO d$_6$) δ 9.62 (s, 1H), 9.55 (brs, 1H), 9.44 (brs, 1H), 7.27 (m, 4H), 7.08 (t, 1H), 6.49 (m, 2H), 5.86 (s, 1H), 3.56-3.16 (brm, 8H), 2.36 (m, 1H), 2.07 (m, 1H), 1.11 (brs, 6H)

Mass Spectral Analysis m/z=379.3 (M+H)$^+$

EXAMPLE 47D

Preparation of 47.8:

To a solution of 47.6 (2.34 g, 4.7 mmol, 1.0 eq) and compound 1.7 (1.37 g, 4.5 mmol, 0.96 eq) in dimethoxyethane (DME) (60 mL) was added sequentially a 2N aqueous solution of sodium carbonate (6.75 mL, 13.5 mmol, 3.0 eq), lithium chloride (0.57 g, 13.5 mmol, 3.0 eq) and tetrakis(triphenylphosphine)palladium(0) (0.16 g, 0.14 mmol, 0.03 eq). The reaction mixture was evacuated for 2 min, purged with argon and heated under reflux for 20 h. The mixture was then cooled to room temperature, diluted with ethyl acetate (100 mL) and filtered through a 1 inch plug of celite. The cake was rinsed with ethyl acetate. The filtrate was washed with water, brine, and dried over sodium sulfate. The crude product was purified by column chromatography (eluent: hexane/ethyl acetate mixtures of increasing polarity).

Yield: 54%

$^1$H NMR (400 MHz, CDCl$_3$) δ 8.42 (brs, 1H), 7.57 (dd, 1H), 7.38 (d, 1H), 7.17-7.07 (m, 1H), 6.73-6.60 (m, 2H), 5.65 (brs, 1H), 4.69 (s, 2H), 3.91-3.74 (m, 1H), 3.65-3.49 (m, 4H), 3.48-3.28 (m, 3H), 3.14 (s, 3H), 2.43-2.30 (m, 1H), 1.99-1.85 (m, 1H), 1.49 (s, 4.5H), 1.47 (s, 4.5H), 1.21 (t, 3H), 1.14 (t, 3H)

Preparation of 47D

To a solution of 47.8 (1.36 g, 2.60 mmol, 1.0 eq) in methanol (20 mL) under nitrogen was added a 2.0M solution of anhydrous hydrochloric acid in diethyl ether (7.79 mL, 15.58 mmol, 6.0 eq). The reaction was stirred for 24 h at room temperature. The reaction was concentrated to a foamy solid and dissolved in methylene chloride (5 mL). With stirring, diethyl ether (20 mL) was added and the mixture was stirred for 10 min at room temperature. The resulting solid was collected by vacuum filtration.

Yield: 87%

$^1$H NMR (400 MHz, DMSO d$_6$) δ 9.79 (brs, 1H), 9.57 (brs, 1H), 9.46 (brs, 1H), 8.46 (dd, 1H), 7.71 (dd, 1H), 7.49 (dd, 1H), 7.11 (t, 1H), 6.50 (m, 2H), 5.98 (s, 1H), 3.58-3.25 (brm, 8H), 2.38 (m, 1H), 2.10 (m, 1H), 1.16 (t, 3H), 1.08 (t, 3H)

Mass Spectral Analysis m/z=380.4 (M+H)$^+$

EXAMPLE 47E

Preparation of 47.9:

To a round bottomed flask was added successively 2',5'-dihydroxyacetophenone (2.1) (10.19 g, 67.0 mmol, 0.96 eq) followed by pyrrolidine (14.5 mL, 175 mmol, 2.5 eq), N-Boc-pyrrolidin-3-one (23.1a) (12.97 g, 70.0 mmol, 1.0 eq) and a minimum amount of methanol used to wash any remaining material. The resultant reaction was heated to 80° C. for 30 min. to dissolve all solids. The mixture was then cooled to room temperature and diluted with ethyl acetate (65 mL). The mixture was washed with a 1N aqueous solution of hydrochloric acid, water and brine, and dried over sodium sulfate. The crude material was used without further purification.

Yield: 100% (crude)

Preparation of 47.10:

To a cooled (0° C.) and stirring solution of 47.9 (19.55 g, 61.2 mmol, 1.0 eq) and imidazole (8.78 g, 129.0 mmol, 2.11 eq) in anhydrous N,N-dimethylformamide (110 mL) was added drop wise a solution of tert-butyldimethylsilyl chloride (2.3) (10.25 g, 68.0 mmol, 1.11 eq) under argon. The mixture was allowed to warm to room temperature and was stirred for 17 h at room temperature. The N,N-dimethylformamide was removed and the residue was diluted with ethyl acetate. The organic phase was washed with water and brine, and dried over sodium sulfate. The crude product was purified by column chromatography (eluent: hexane/ethyl acetate mixtures of increasing polarity).

Yield: 65%

$^1$H NMR (300 MHz, CDCl$_3$) δ 7.24 (d, 1H), 7.01-6.91 (m, 1H), 6.81 (d, 1H), 3.82-3.44 (m, 3H), 3.37-3.24 (m, 1H), 2.93-2.71 (m, 2H), 2.32-2.22 (m, 1H), 1.95-1.78 (m, 1H), 1.42 (s, 9H), 0.98 (s, 9H), 0.20 (s, 6H)

Preparation of 47.11:

To a solution of 47.10 (17.34 g, 40.0 mmol, 1.0 eq) in tetrahydrofuran (150 mL) at −78° C. under argon was added drop wise a 1.0M solution of LiHMDS in tetrahydrofuran (48 mL, 48 mmol, 1.2 eq). The mixture was stirred for 1 h at −78° C. A solution of N-phenyltrifluoromethanesulfonimide (1.4) (15.72 g, 44.00 mmol, 1.1 eq) in tetrahydrofuran (100 mL) was added dropwise to the mixture. The mixture was warmed slowly to room temperature and stirring was continued for a further 16 h at room temperature. The mixture was then poured into ice water and the layers were separated. The organics were washed with a 1N aqueous solution of hydrochloric acid, a 1N aqueous solution of sodium hydroxide, brine, and dried over sodium sulfate. The crude product was used for the next step without further purification.

Yield: 100% (crude)

Preparation of compound 47.12:

To a solution of 47.11 (9.56 g, 17.4 mmol, 1.0 eq) in dimethoxyethane (DME) (190 mL) was added sequentially a 2N aqueous solution of sodium carbonate (21.75 mL, 43.5 mmol, 3.0 eq), lithium chloride (1.84 g, 43.5 mmol, 3.0 eq), compound 1.6 (3.20 g, 14.5 mmol, 0.83 eq) and tetrakis (triphenylphosphine)palladium(0) (0.51 g, 0.44 mmol, 0.03 eq). The reaction mixture was evacuated for 2 min, purged with argon and heated under reflux for 42 h. The mixture was then cooled to room temperature, diluted with ethyl acetate (200 mL) and filtered through a 1 inch plug of celite. The cake was rinsed with ethyl acetate. The organic layer was washed with water, brine, and dried over sodium sulfate. The crude product was purified by column chromatography (eluent: hexane/ethyl acetate mixtures of increasing polarity).

Yield: 44%

$^1$H NMR (300 MHz, CDCl$_3$) δ 7.39-7.31 (m, 4H), 6.95-6.66 (m, 3H), 6.49 (m, 1H), 5.67 (s, 1H), 3.94-3.80 (m, 1H), 3.66-3.50 (m, 4H), 3.41-3.27 (m, 3H), 2.47-2.37 (m, 1H), 2.02-1.85 (m, 1H), 1.47 (s, 4.5H), 1.45 (s, 4.5H), (s, 9H), 1.36-1.10 (m, 6H)

Preparation of 47E

To a solution of 47.12 (3.66 g, 7.65 mmol, 1.0 eq) in methanol (40 mL) under nitrogen was added a 2.0M solution of anhydrous hydrochloric acid in diethyl ether (15.3 mL, 30.59 mmol, 4.0 eq). The reaction mixture was stirred for 24 h, concentrated to a foam and diethyl ether (20 mL) was added. The mixture was sonicated and methylene chloride (10 mL) was added with stirring. The mixture was stirred for 20 min. and the solids were collected by vacuum filtration.

Yield: 85%

$^1$H NMR (400 MHz, DMSO d$_6$) δ 9.66 (brs, 1H), 9.51 (brs, 1H), 9.14 (brs, 1H), 7.43 (m, 4H), 6.81 (d, 1H), 6.66 (dd, 1H), 6.43 (d, 1H), 5.98 (s, 1H), 3.56-3.20 (brm, 8H), 2.38 (m, 1H), 2.08 (m, 1H), 1.11 (brd, 6H)

Mass Spectral Analysis m/z=379.8 (M+H)$^+$

EXAMPLE 47F

Preparation of 47.13:

To a solution of 47.11 (9.56 g, 17.4 mmol, 1.2 eq) and compound 1.7 (4.41 g, 14.5 mmol, 1.0 eq) in dimethoxyethane (DME) (165 mL) was added sequentially a 2N aqueous solution of sodium carbonate (21.75 mL, 43.5 mmol, 3.0 eq), lithium chloride (1.84 g, 43.5 mmol, 3.0 eq) and tetrakis (triphenylphosphine)palladium(0) (0.51 g, 0.44 mmol, 0.03 eq). The reaction mixture was evacuated for 2 min, purged with argon and heated under reflux for 19 h. The mixture was then cooled to room temperature, diluted with ethyl acetate (150 mL) and filtered through a 1 inch plug of celite, which was further rinsed with ethyl acetate. The organic layer was washed with water, brine, and dried over sodium sulfate. The crude product was purified by column chromatography (eluent: hexane/ethyl acetate mixtures of increasing polarity).

Yield: 33%

$^1$H NMR (300 MHz, CDCl$_3$) δ 8.49 (brs, 1H), 7.77 (dd, 1H), 7.55-7.41 (m, 2H), 6.80-6.67 (m, 2H), 6.39 (brs, 1H), 5.70 (s, 1H), 3.90-3.78 (m, 1H), 3.64-3.50 (m, 4H), 3.43-3.27 (m, 3H), 2.44-2.34 (m, 1H), 1.95-1.83 (m, 1H), 1.48 (s, 4.5H), 1.46 (s, 4.5H), 1.25 (t, 3H), 1.17 (t, 3H)

Preparation of 47F

To a solution of 47.13 (2.65 g, 5.53 mmol, 1.0 eq) in methanol (30 mL) under nitrogen was added a 2.0M solution of anhydrous hydrochloric acid in diethyl ether (16.6 mL, 33.15 mmol, 6.0 eq). The reaction was stirred for 24 h at room temperature, concentrated to a foam and diethyl ether (20 mL) was added. The mixture was sonicated and methylene chloride (10 mL) was added with stirring. The mixture was stirred for 20 min. and the solids were collected by vacuum filtration.

Yield: 81%

$^1$H NMR (400 MHz, DMSO d$_6$) δ 9.88 (brs, 1H), 9.62 (brs, 1H), 8.59 (m, 1H), 7.92 (dd, 1H), 7.58 (m, 1H), 6.83 (d, 1H), 6.70 (dd, 1H), 6.40 (d, 1H), 6.11 (s, 1H), 3.56-3.26 (brm, 8H), 2.40 (m, 1H), 2.11 (m, 1H), 1.18 (t, 3H), 1.11 (t, 3H)

Mass Spectral Analysis m/z=380.7 (M+H)$^+$

EXAMPLE 48A

Preparation of 48.1:

To a solution of 1.5f (20.0 g, 41.71 mmol, 1.0 eq) in dioxane (300 mL) was added potassium carbonate (17.3 g, 125 mmol, 3.0 eq), water (50 mL), 14.1 (6.7 g, 45.88 mmol, 1.1 eq) and [1,1'-bis(diphenylphosphino)ferrocene]dichloropalladium(II) (1.70 g, 2.09 mmol, 0.05 eq). The mixture was stirred at room temperature for 1 h. Water (500 mL) was added and product was extracted with ethyl acetate. The organics were combined, concentrated and the crude product was purified by column chromatography (eluent: ethyl acetate/hexane=3:7). Pure Fractions were concentrated to an oil, which was dissolved in diethyl ether (30 mL). Hexane was added to the stirred solution and the precipitated solid was collected by vacuum filtration.

Yield: 76%

$^1$H NMR (400 MHz, CDCl$_3$) δ 7.59 (d, 2H), 7.31 (d, 2H), 7.19 (t, 1H), 6.67 (dd, 1H), 6.47 (d, 1H), 5.54 (s, 1H), 3.80 (brs, 2H), 3.42 (s, 3H), 3.32 (brs, 2H), 2.02 (brd, 2H), 1.68 (m, 2H), 1.47 (s, 9H)

Mass Spectral Analysis m/z=433.5 (M+H)$^+$

Preparation of 48.2:

To a suspension of 48.1 (5.0 g, 11.56 mmol, 1.0 eq) in isopropanol (100 mL) was added 14.3 (1.50 g, 23.12 mmol, 2.0 eq), zinc bromide (1.30 g, 5.78 mmol, 0.50 eq) and water (50 mL). The reaction mixture was heated to reflux (105° C.). Additional amount of water (10 mL) and isopropanol (30 mL) were added to the reaction mixture, which was heated for 5 days at 105° C. The reaction mixture was then cooled to room temperature and then cooled in an ice/brine bath. A 3N aqueous solution of hydrochloric acid (10 mL) was slowly added to the mixture until the pH ~1. The homogeneous mixture was stirred for 10 min at room temperature. Water (200 mL) and ethyl acetate were added to the mixture followed by diethyl ether (100 mL). The organics were concentrated to a solid. This solid was triturated in methanol (20 mL), and collected by vacuum filtration. The filtrate was concentrated and the crude product was purified by column chromatography (eluent: hexane/ethyl acetate mixtures of increasing polarity, then methanol/ethyl acetate mixtures of increasing polarity). The starting material (48.1, 1.28 g white solid) was isolated along with 983 mg of the desired product (48.2).

Yield: 58%

$^1$H NMR (400 MHz, CDCl$_3$) δ 8.01 (brd, 2H), 7.30 (m, 2H), 7.15 (t, 1H), 6.64 (d, 1H), 6.42 (d, 1H), 5.50 (s, 1H), 3.81 (brd, 2H), 3.33 (brs, 5H), 1.99 (m, 2H), 1.63 (m, 2H), 1.50 (s, 9H)

Mass Spectral Analysis m/z=474.9 (M−H)$^-$

Preparation of 48A:

To a solution of 48.2 (0.434 g, 0.913 mmol, 1.0 eq) in methylene chloride (15 mL) at 0° C. under nitrogen was added a 2.0M solution of anhydrous hydrochloric acid in diethyl ether (2.74 mL, 5.48 mmol, 6.0 eq). The reaction was warmed to room temperature, stirred for 3 days at room temperature and diluted with diethyl ether (10 mL). The solids were collected by vacuum filtration.

Yield: 87%

$^1$H NMR (400 MHz, DMSO d$_6$) δ 8.89 (brs, 2H), 8.02 (d, 2H), 7.42 (d, 2H), 7.28 (t, 1H), 6.75 (dd, 1H), 6.69 (d, 1H), 5.92 (s, 1H), 3.41 (s, 3H), 3.20 (brm, 4H), 2.02 (brm, 4H)

Mass Spectral Analysis m/z=376.3 (M+H)$^+$

Elemental analysis:

C$_{21}$H$_{21}$N$_5$O$_2$, 1HCl, 1H$_2$O:

Theory: % C, 58.67; % H, 5.63; % N, 16.29.

Found: % C, 58.79; % H, 5.30; % N, 16.12.

EXAMPLES 48B, 48C

Preparation of 48.3 and 48.4:

To a solution of 48.2 (2.20 g, 4.63 mmol, 1.0 eq) in N,N-dimethylformamide (20 mL) under nitrogen was added potassium carbonate (3.20 g, 23.13 mmol, 5.0 eq) and 2.8c (0.87 mL, 13.88 mmol, 3.0 eq). The mixture was stirred for 4 days at room temperature. Water was added and product was extracted with ethyl acetate. The combined organics were washed with brine, concentrated and the crude product was purified by column chromatography (eluent: hexane/ethyl acetate mixtures of increasing polarity). The major product was 48.3 (1.36 g) and the minor product was 48.4 (365 mg).

Yield: 76% (combined yield)

48.3: $^1$H NMR (400 MHz, DMSO d$_6$) δ 7.99 (d, 2H), 7.34 (d, 2H), 7.23 (t, 1H), 6.66 (m, 2H), 5.83 (s, 1H), 4.43 (s, 3H), 3.64 (m, 2H), 3.39 (s, 3H), 3.27 (brs, 2H), 1.84 (m, 2H), 1.71 (m, 2H), 1.41 (s, 9H)

Mass Spectral Analysis m/z=490.4 (M+H)$^+$ 48.4: $^1$H NMR (400 MHz, DMSO d$_6$) δ 7.81 (d, 2H), 7.40 (d, 2H), 7.24 (t, 1H), 6.67 (m, 2H), 5.85 (s, 1H), 4.19 (s, 3H), 3.66 (m, 2H), 3.41 (s, 3H), 3.28 (brs, 2H), 1.84 (m, 2H), 1.72 (m, 2H), 1.42 (s, 9H)

Mass Spectral Analysis m/z=490.6 (M+H)$^+$

Preparation of 48B:

To a solution of 48.3 (0.40 g, 0.817 mmol, 1.0 eq) in methylene chloride (10 mL) at 0° C. under nitrogen was added a 2.0M solution of anhydrous hydrochloric acid in diethyl ether (1.63 mL, 3.27 mmol, 4.0 eq). The reaction was warmed to room temperature, stirred for 16 h at room temperature and diluted with diethyl ether (10 mL). The solids were collected by vacuum filtration.

Yield: 84%

$^1$H NMR (400 MHz, DMSO d$_6$) δ 8.88 (brs, 2H), 8.01 (d, 2H), 7.38 (d, 2H), 7.27 (t, 1H), 6.74 (d, 1H), 6.67 (d, 1H), 5.90 (s, 1H), 4.44 (s, 3H), 3.40 (s, 3H), 3.19 (m, 4H), 2.01 (m, 4H)

Mass Spectral Analysis m/z=390.5 (M+H)$^+$

Elemental analysis:

C$_{22}$H$_{23}$N$_5$O$_2$, 1HCl

Theory: % C, 62.04; % H, 5.68; % N, 16.44.

Found: % C, 62.05; % H, 5.79; % N, 16.51.

Preparation of 48C:

To a solution of 48.4 (0.36 g, 0.735 mmol, 1.0 eq) in methylene chloride (10 mL) at 0° C. under nitrogen was added a 2.0M solution of anhydrous hydrochloric acid in diethyl ether (1.47 mL, 2.94 mmol, 4.0 eq). The reaction was stirred for 16 h at room temperature and diluted with diethyl ether (10 mL). The solids were collected by vacuum filtration.

Yield: 80%

$^1$H NMR (400 MHz, DMSO d$_6$) δ 8.96 (brs, 2H), 7.82 (d, 2H), 7.43 (d, 2H), 7.28 (t, 1H), 6.75 (d, 1H), 6.69 (d, 1H), 5.92 (s, 1H), 4.19 (s, 3H), 3.42 (s, 3H), 3.19 (m, 4H), 2.06 (m, 4H)

Mass Spectral Analysis m/z=390.4 (M+H)$^+$

EXAMPLE 48D

Preparation of 48.5:

To a mixture of 1.14 (2.91 g, 11.47 mmol, 1.1 eq), potassium carbonate (2.16 g, 15.64 mmol, 1.5 eq), dichlorobis (triphenylphosphine)palladium (II) (0.22 g, 0.313 mmol, 0.03 eq) and triphenylphosphine (0.17 g, 0.626 mmol, 0.06 eq) in dioxane (75 mL) was added 1.5f (5.0 g, 10.43 mmol, 1.0 eq). The reaction was heated at 50° C. for 16 h. Additional amount of dichlorobis(triphenylphosphine)palladium (II) (0.22 g) and triphenylphosphine (0.17 g) were added to the reaction mixture, which was heated for another 2 days at 50° C. The mixture was then cooled to room temperature. Water was added and the product was extracted with ethyl acetate. The organics were concentrated and purified by column chromatography (eluent: hexane/ethyl acetate mixtures of increasing polarity).

Yield: 64%

$^1$H NMR (400 MHz, CDCl$_3$) δ 7.06 (t, 1H), 6.51 (dd, 1H), 6.45 (d, 1H), 5.82 (s, 1H), 3.81 (brs, 5H), 3.25 (brs, 2H), 1.93 (brd, 2H), 1.57 (m, 2H), 1.46 (s, 9H), 1.34 (s, 12H)

Mass Spectral Analysis m/z=458.4 (M+H)$^+$

Preparation of 48.6:

To a solution of 48.5 (1.96 g, 4.29 mmol, 1.0 eq) in dioxane (40 mL) was added potassium carbonate (1.78 g, 12.86 mmol, 3.0 eq), water (6 mL), 34.1c (1.24 g, 4.71 mmol, 1.1 eq) and [1,1'-bis(diphenylphosphino)ferrocene]dichloropalladium (II) (0.17 g, 0.214 mmol, 0.05 eq). The reaction was stirred at room temperature for 16 h. Water was added and the product was extracted with ethyl acetate. The organics were concentrated and purified by column chromatography (eluent: hexane/ethyl acetate mixtures of increasing polarity).

Yield: 48%

$^1$H NMR (400 MHz, CDCl$_3$) δ 7.23 (d, 1H), 7.18 (t, 1H), 6.82 (d, 1H), 6.64 (dd, 1H) 6.50 (d, 1H), 5.70 (s, 1H), 3.78 (brs, 2H), 3.56 (m, 7H), 3.32 (brs, 2H), 2.00 (m, 2H), 1.67 (m, 2H), 1.47 (s, 9H), 1.26 (t, 6H)

Mass Spectral Analysis m/z=513.4 (M+H)$^+$

Preparation of 48D:

To a solution of 48.6 (1.06 g, 2.07 mmol, 1.0 eq) in methylene chloride (15 mL) at 0° C. under nitrogen was added a 2.0M solution of anhydrous hydrochloric acid in diethyl ether (4.14 mL, 8.27 mmol, 4.0 eq). The reaction mixture was warmed to room temperature and stirred for 16 h, diluted with diethyl ether (10 mL) and stirred for an additional 30 min at room temperature. The solids were collected by vacuum filtration.

Yield: 86%

$^1$H NMR (400 MHz, DMSO d$_6$) δ 9.02 (brs, 2H), 7.34 (m, 2H), 7.00 (d, 1H), 6.77 (m, 2H), 6.05 (s, 1H), 3.59 (s, 3H), 3.54 (brm, 4H), 3.23 (brm, 4H), 2.12-1.99 (brm 4H), 1.23 (brt, 6H)

Mass Spectral Analysis m/z=413.7 (M+H)$^+$

Elemental analysis:

C$_{23}$H$_{28}$N$_2$O$_3$S, 1HCl, 1H$_2$O:

Theory: % C, 59.36; % H, 6.50; % N, 5.86.

Found: % C, 59.15; % H, 6.69; % N, 6.00.

EXAMPLE 48E

Preparation of 48.7:

To a solution of 48.5 (2.0 g, 4.37 mmol, 1.0 eq) in dioxane (40 mL) was added potassium carbonate (1.81 g, 13.12 mmol, 3.0 eq), water (6 mL), 34.1d (1.40 g, 4.81 mmol, 1.1 eq) and [1,1'-bis(diphenylphosphino)ferrocene]dichloropalladium (II) (0.18 g, 0.22 mmol, 0.05 eq). The reaction mixture was stirred at room temperature for 24 h. Water was added and the product was extracted with ethyl acetate. The combined organics were concentrated and purified by column chromatography (eluent: hexane/ethyl acetate mixtures of increasing polarity).

Yield: 49%

$^1$H NMR (400 MHz, CDCl$_3$) δ 7.17 (t, 1H), 7.07 (d, 1H), 6.79 (d, 1H), 6.63 (d, 1H), 6.50 (d, 1H), 5.70 (s, 1H), 4.00 (brs, 2H), 3.77 (brs, 2H), 3.57 (s, 3H), 3.32 (brs, 2H), 1.99 (m, 2H), 1.67 (m, 2H), 1.46 (s, 9H), 1.37 (brd, 12H)

Mass Spectral Analysis m/z=541.8 (M+H)$^+$

Preparation of 48E:

To a solution of 48.7 (1.16 g, 2.15 mmol, 1.0 eq) in methylene chloride (30 mL) at 0° C. under nitrogen was added a 2.0M solution of anhydrous hydrochloric acid in diethyl ether (4.29 mL, 8.58 mmol, 4.0 eq). The reaction mixture was warmed to room temperature, stirred for 16 h and concentrated to a foam. Diethyl ether (15 mL) was added to the mixture, which was stirred for 1 h at room temperature. The solids were collected by vacuum filtration.

Yield: 77%

$^1$H NMR (400 MHz, DMSO d$_6$) δ 8.83 (brs, 2H), 7.14 (t, 1H), 6.96 (d, 1H), 6.78 (d, 1H), 6.57 (m, 2H), 5.83 (s, 1H), 3.82 (brs, 2H), 3.39 (s, 3H), 3.02 (brm, 4H), 1.94-1.80 (brm, 4H), 1.16 (brd, 6H)

Mass Spectral Analysis m/z=441.4 (M+H)$^+$

Elemental analysis:

C$_{25}$H$_{32}$N$_2$O$_3$S, 1HCl, 1H$_2$O:

Theory: % C, 60.65; % H, 7.13; % N, 5.66.

Found: % C, 61.02; % H, 6.90; % N, 5.57.

EXAMPLE 48F

Preparation of 48.8:

To a solution of 48.5 (1.50 g, 3.28 mmol, 1.0 eq) in dioxane (30 mL) was added potassium phosphate (1.04 g, 4.92 mmol, 1.5 eq), potassium bromide (0.43 g, 3.61 mmol, 1.1 eq), 34.1a (0.93 g, 3.61 mmol, 1.1 eq) and tetrakis(triphenylphosphine)palladium(0) (0.38 g, 0.328 mmol, 0.10 eq). The mixture was heated at 100° C. for 6 days and then cooled to room temperature. Ethyl acetate and water were added and the layers were separated. The organics were concentrated and purified by column chromatography (eluent: hexane/ethyl acetate mixtures of increasing polarity). The resulting solid was triturated in diethyl ether and filtered. The filtrate, which contained the product, was concentrated.

Yield: 40%

$^1$H NMR (400 MHz, CDCl$_3$) δ 8.60 (dd, 1H), 7.67 (m, 2H), 7.19 (m, 1H), 6.67 (dd, 1H), 6.48 (d, 1H), 5.87 (s, 1H), 3.82 (brs, 2H), 3.57 (brs, 2H), 3.44 (s, 3H), 3.32 (brs, 4H), 2.04 (brd, 2H), 1.72 (m, 2H), 1.47 (s, 9H), 1.22 (brd, 6H)

Mass Spectral Analysis m/z=508.5 (M+H)$^+$

Preparation of 48F:

To a solution of 48.8 (0.668 g, 1.32 mmol, 1.0 eq) in methylene chloride (15 mL) at 0° C. under nitrogen was added a 2.0M solution of anhydrous hydrochloric acid in diethyl ether (3.95 mL, 7.89 mmol, 6.0 eq). The reaction mixture was warmed to room temperature, stirred for 16 h at room temperature and concentrated to a foam. Diethyl ether (15 mL) was added to the mixture and the solids were collected by vacuum filtration.

Yield: 75%

$^1$H NMR (400 MHz, DMSO d$_6$) δ 9.11 (brd, 2H), 8.54 (s, 1H), 7.90 (d, 1H), 7.43 (d, 1H), 7.21 (t, 1H), 6.68 (dd, 1H), 6.61 (d, 1H), 6.07 (s, 1H), 3.41 (brm, 2H), 3.32 (s, 3H), 3.13 (brm, 6H), 1.98 (brm, 4H), 1.07 (brd, 6H)

Mass Spectral Analysis m/z=408.4 (M+H)$^+$

Elemental analysis:

C$_{24}$H$_{29}$N$_3$O$_3$, 2HCl, 1H$_2$O:

Theory: % C, 57.83; % H, 6.67; % N, 8.43; % Cl, 14.23.

Found: % C, 57.98; % H, 6.41; % N, 8.29; % Cl, 14.21.

EXAMPLE 49A

Preparation of 49.2:

Pyrrolidine (2.09 mL, 25.09 mmol, 1.0 eq) was added at 0° C. to 1.2 (5.00 g, 25.09 mmol, 1.0 eq) and 49.1 (3.87 g, 25.09 mmol, 1.0 eq) in methanol (50 mL). The solution was stirred overnight at room temperature and then concentrated under reduced pressure. Ethyl acetate (100 mL) was added to the mixture. The organic mixture was washed with a 1N aqueous solution of hydrochloric acid, a 1N aqueous solution of sodium hydroxide, brine and dried over sodium sulfate. The crude product was purified by column chromatography (eluent: hexane/ethyl acetate mixtures of increasing polarity).

Yield: 40%

$^1$H NMR (400 MHz, CDCl$_3$) δ 7.56 (m, 1H), 6.92 (d, 1H), 6.83 (m, 1H), 3.69 (m, 2H), 3.12 (m, 2H), 2.83 (s, 2H), 1.86 (d, 2H), 1.63 (m, 2H), 1.40 (s, 9H)

Mass Spectral Analysis m/z=336.14 (M+H)$^+$

Preparation of 49.3:

To a solution of 49.2 (3.00 g, 8.95 mmol, 1 eq) in tetrahydrofuran (10 mL) at −78° C. under nitrogen was added drop wise a 1M solution of lithium bis(trimethylsilyl)amide in tetrahydrofuran (10.73 mL, 10.73 mmol, 1.2 eq). The mixture was stirred for 1 hour at −78° C. A solution of 1.4 (3.83 g, 10.73 mmol, 1.2 eq) in tetrahydrofuran (2 mL) was added drop wise to the mixture. The mixture was warmed slowly to room temperature and stirring was continued for 1 hour at room temperature. The reaction was then concentrated under reduced pressure. The crude product was used without further purification.

Yield: 85%

$^1$H NMR (400 MHz, DMSO d$_6$) δ 7.38 (m, 1H), 6.92 (m, 1H), 6.74 (m, 1H), 6.23 (s, 1H), 3.71 (m, 2H), 3.17 (br s, 2H), 1.89 (m, 2H), 1.76 (m, 2H), 1.41 (s, 9H)

Mass Spectral Analysis m/z=468.48 (M+H)$^+$

Preparation of 49.4:

To a solution of 49.3 (1.00 g, 2.14 mmol, 1.0 eq) in dimethoxyethane (5 mL) was added sequentially a 2N aqueous solution of sodium carbonate (3.2 mL, 6.42 mmol, 3 eq), lithium chloride (0.27 g, 6.42 mmol, 3 eq), 1.6 (0.52 g, 2.35 mmol, 1.1 eq) and tetrakis(triphenylphosphine)palladium(0) (0.05 g, 0.04 mmol, 0.02 eq). The mixture was refluxed for 16 hours under nitrogen, then cooled to room temperature. Water (250 mL) was added to the mixture, which was extracted with ethyl acetate. The organic layer was further washed with brine and dried over sodium sulfate. The crude product was purified by column chromatography (eluent: hexane/ethyl acetate mixtures of increasing polarity).

Yield: 50%

Mass Spectral Analysis m/z=495.36 (M+H)$^+$

Preparation of 49A:

A 2M anhydrous solution of hydrochloric acid in diethyl ether (2.95 mL, 5.89 mmol, 5.5 eq) was added drop wise to a cooled (0° C.) solution of 49.4 (0.53 g, 1.07 mmol, 1 eq) in anhydrous dichloromethane (6 mL). The mixture was warmed to room temperature and stirring was continued for an additional 16 hours at room temperature. The reaction was concentrated under reduced pressure. The crude product was purified by column chromatography (eluent: dichloromethane/methanol mixtures of increasing polarity).

Yield: 97%

¹H NMR (400 MHz, DMSO d$_6$) δ 9.15 (m, 2H), 7.35 (m, 5H), 6.99 (d, 1H), 6.82 (m, 1H), 6.03 (s, 1H), 3.44 (br s, 2H), 3.19 (m, 6H), 2.07 (m, 4H), 1.10 (m, 6H)

Mass Spectral Analysis m/z=395.3 (M+H)$^+$

Elemental analysis:

C$_{24}$H$_{27}$FN$_2$O$_2$, 1HCl, 1H$_2$O:

Theory: % C, 64.21; % H, 6.74; % N, 6.24.

Found: % C, 64.27; % H, 6.30; % N, 6.28.

EXAMPLE 49B

Preparation of 49.5:

3.4k (270.8 mL, 3.24 mmol, 5.0 eq) was added at room temperature to a solution of 49.2 (100 mg, 0.65 mmol, 1.0 eq) in N,N-dimethylformamide (5 mL). The solution was stirred overnight at 80° C. and then concentrated under reduced pressure. The crude product was used for the next step without further purification.

Yield: 90%

¹H NMR (400 MHz, CDCl$_3$) δ 7.23 (t, 1H), 6.38 (d, 1H), 6.25 (d, 1H), 3.69 (m, 2H), 3.10 (m, 6H), 2.70 (s, 2H), 1.94 (m, 2H), 1.87 (m, 4H), 1.62 (m, 2H), 1.39 (s, 9H)

Mass Spectral Analysis m/z=387.25 (M+H)$^+$

Preparation of 49.6:

To a solution of 49.5 (7.50 g, 19.40 mmol, 1 eq) in tetrahydrofuran (20 mL) at −78° C. under nitrogen was added drop wise a 1M solution of lithium bis(trimethylsilyl)amide in tetrahydrofuran (23.29 mL, 23.29 mmol, 1.2 eq). The mixture was stirred for 1 hour at −78° C. A solution of 1.4 (8.32 g, 23.29 mmol, 1.2 eq) in tetrahydrofuran (5 mL) was added drop wise to the mixture, which was warmed slowly to room temperature. Stirring was continued for 16 hours at room temperature. The reaction was then concentrated under reduced pressure and dissolved in ethyl acetate. The organic solution was washed with a 1N aqueous solution of hydrochloric acid, a 1N aqueous solution of sodium hydroxide, brine and dried over sodium sulfate. The crude product was purified by column chromatography (eluent: hexane/ethyl acetate mixtures of increasing polarity).

Yield: 50%

¹H NMR (400 MHz, DMSO d$_6$) δ 7.15 (t, 1H), 6.56 (d, 1H), 6.50 (d, 1H), 5.91 (s, 1H), 3.61 (m, 2H), 3.21 (br s, 2H), 3.10 (m, 4H), 1.86 (m, 6H), 1.76 (m, 2H), 1.40 (s, 9H)

Mass Spectral Analysis m/z=519.30 (M+H)$^+$

Preparation of 49.7:

To a solution of 49.6 (1.00 g, 1.93 mmol, 1.0 eq) in dimethoxyethane (5 mL) was added sequentially a 2N aqueous solution of sodium carbonate (2.9 mL, 5.79 mmol, 3 eq), lithium chloride (0.25 g, 5.79 mmol, 3 eq), 1.6 (0.47 g, 2.12 mmol, 1.1 eq) and tetrakis(triphenylphosphine)palladium(0) (0.05 g, 0.04 mmol, 0.02 eq). The mixture was refluxed for 16 hours under nitrogen, then cooled to room temperature. Water (250 mL) was added to the mixture, which was extracted with ethyl acetate. The organic layer was further washed with brine and dried over sodium sulfate. The crude product was purified by column chromatography (eluent: hexane/ethyl acetate mixtures of increasing polarity).

Yield: 10%

Mass Spectral Analysis m/z=546.47 (M+H)$^+$

Preparation of 49B:

A 2M anhydrous solution of hydrochloric acid in diethyl ether (0.4 mL, 0.81 mmol, 5.5 eq) was added drop wise to a cooled (0° C.) solution of 49.7 (0.08 g, 0.15 mmol, 1 eq) in anhydrous dichloromethane (4 mL). The mixture was warmed to room temperature and stirring was continued for an additional 16 hours at room temperature. The reaction mixture was concentrated under reduced pressure. The crude product was purified by column chromatography (eluent: dichloromethane/methanol mixtures of increasing polarity).

Yield: 97%

¹H NMR (400 MHz, DMSO d$_6$) δ 9.01 (m, 2H), 7.26 (q, 4H), 7.15 (t, 1H), 6.55 (m, 2H), 5.89 (s, 1H), 3.54 (br s, 5H), 3.42 (br s, 2H), 3.18 (m, 6H), 2.76 (br s, 2H), 2.11 (m, 4H), 1.28 (br s, 2H), 1.08 (m, 6H)

Mass Spectral Analysis m/z=446.8 (M+H)$^+$

EXAMPLES 49C, 49D

Preparation of 49.8:

To a solution of 1.5d (14.02 g, 30 mmol, 1 eq.) in N,N-dimethylformamide (150 mL) at 0° C. was added successively potassium acetate (8.83 g, 90 mmol, 3 eq.), bis(pinacolato)diboron 1.14 (9.14 g, 36 mmol, 1.2 eq.) and 1,1′-bis(diphenylphosphino)ferrocene palladium(II) chloride complex with dichloromethane (658 mg, 0.9 mmol, 0.03 eq.). The reaction mixture was stirred at 100-110° C. for 10 h. The mixture was cooled to room temperature. Diethyl ether (300 mL) and water (300 mL) were added to the mixture, which was stirred for an additional 30 minutes at room temperature. The two phases were separated and the organic phase was washed with water (2×150 mL), brine (200 mL), dried over sodium sulfate, filtered, and concentrated under reduced pressure. The crude product was purified by column chromatography (eluent: hexane/ethyl acetate mixtures of increasing polarity).

Yield: 82%

¹H NMR (400 MHz, CDCl$_3$) δ 7.49 (dd, 1H), 6.78 (m, 2H), 6.34 (s, 1H), 3.95-3.72 (m, 2H), 3.37-3.15 (m, 2H), 1.97-1.87 (m, 2H), 1.66-1.53 (m, 2H), 1.46 (s, 9H), 1.34 (s, 12H)

Mass Spectral Analysis m/z=446.31 (M+H)$^+$

Preparation of 49.9:

To a solution of a 2M aqueous solution of potassium carbonate (3.08 mL, 6.15 mmol, 3 eq.) was added dioxane (20 mL), 35.8 (0.745 g, 2.05 mmol, 1 eq.), and 49.8 (1.37 g, 3.075 mmol, 1.5 eq.) successively. The reaction flask was purged with nitrogen and 1,1′-bis(diphenylphosphino)ferrocene palladium(II) chloride complex with dichloromethane (75 mg, 0.1 mmol, 0.05 eq) was added to the mixture. The mixture was stirred at room temperature for 1 h and then heated at 55° C. for 10 h. The mixture was then cooled to room temperature. Water (50 mL) and ethyl acetate (150 mL) were added and the two phases were separated. The organic phase was washed with brine (100 mL) and concentrated under reduced pressure. The crude product was purified by column chromatography (eluent: hexane/ethyl acetate mixtures of increasing polarity).

Yield: 94%

¹H NMR (400 MHz, CDCl$_3$) δ 7.23-7.17 (m, 2H), 7.06 (dd, 1H), 6.88-6.78 (m, 2H), 6.47 (dd, 1H), 5.59 (s, 1H), 5.07 (s, 2H), 3.97-3.77 (m, 2H), 3.63-3.47 (m, 2H), 3.42-3.22 (m, 7H), 2.11-2.01 (m, 2H), 1.73-1.61 (m, 2H), 1.48 (s, 9H)

Mass Spectral Analysis m/z=555.47 (M+H)$^+$

Preparation of 49C:

To a solution of 49.9 (1.2 g, 2.16 mmol, 1 eq.) in methanol (50 mL) was slowly added a 4M anhydrous solution of hydrogen chloride in dioxane (3.2 mL, 12.8 mmol, 6 eq.). The reaction mixture was stirred at room temperature for 10 h. Additional amount of 4M anhydrous solution of hydrogen chloride in dioxane (2.16 mL, 8.64 mmol, 4 eq.) was slowly added to the mixture, which was stirred at room temperature for an additional 10 h. The mixture was concentrated under reduced pressure. The resulting foamy solids were soaked in diethyl ether to give the fine powders, which were collected by filtration, washed with ethyl acetate and diethyl ether.

Yield: 90%

$^1$H NMR (400 MHz, DMSO-d$_6$) δ 9.87 (s, 1H), 9.00-8.75 (m, 2H), 7.18 (d, 1H), 7.07-6.97 (m, 2H), 6.91-6.82 (m, 2H), 6.44 (dd, 1H), 5.89 (s, 1H), 3.53-3.10 (m, 8H), 2.15-2.05 (m, 2H), 2.03-1.92 (m, 2H), 1.20-1.03 (m, 6H)

Mass Spectral Analysis m/z=411.7 (M+H)$^+$

Elemental analysis:

C$_{24}$H$_{27}$FN$_2$O$_3$, 1HCl, 0.5H$_2$O:

Theory: % C, 63.22; % H, 6.41; % N, 6.14.

Found: % C, 63.32; % H, 6.34; % N, 6.13.

Preparation of 49D:

To a stirred solution of 49C (0.20 g, 0.45 mmol, 1 eq.) in methanol (20 mL) was added palladium [40 mg, 10 wt. % (dry basis) on activated carbon, 20% wt. eq]. The reaction mixture was stirred under hydrogen atmosphere using a hydrogen balloon at room temperature for 10 h. The mixture was filtered through celite and the filtrate was concentrated under reduced pressure. The crude product was purified by column chromatography (eluent: dichloromethane/methanol mixture of increasing polarity).

Yield: 80%

$^1$H NMR (400 MHz, DMSO-d$_6$) δ 9.87 (s, 1H), 8.85-8.55 (m, 2H), 7.08-6.89 (m, 3H), 6.84 (s, 1H), 6.75 (dd, 1H), 6.41 (dd, 1H), 4.47 (m, 1H), 3.50-2.91 (m, 8H), 2.15-1.74 (m, 6H), 1.20-1.11 (m, 6H)

Mass Spectral Analysis m/z=413.7 (M+H)$^+$

EXAMPLE 50A

Preparation of 50.1:

To a solution of 2.5 (15.00 g, 25.88 mmol, 1.0 eq) in dimethoxyethane (78 mL) was added sequentially a 2N aqueous solution of sodium carbonate (38.8 mL, 77.63 mmol, 3 eq), lithium chloride (3.29 g, 77.63 mmol, 3 eq), 31.1 g (3.47 g, 28.46 mmol, 1.1 eq) and palladium, 10 weight % (dry basis) on activated carbon, wet, (Degussa type E101) (0.28 g, 0.13 mmol, 0.005 eq). The mixture was refluxed for 6 days under nitrogen. The mixture was then cooled to room temperature and diluted with dichloromethane (350 mL). The mixture was then filtered through a celite plug. The filtrate was dried over sodium sulfate, filtered and concentrated. The crude product was purified by column chromatography (eluent: ethyl acetate/hexanes mixtures of increasing polarity).

Yield: 49%

$^1$H NMR (400 MHz, DMSO d$_6$) δ 8.98 (br s, 1H), 7.42 (m, 3H), 7.33 (m, 2H), 6.79 (d, 1H), 6.58 (m, 1H), 6.38 (m, 1H), 5.76 (s, 1H), 3.68 (m, 2H), 3.23 (m, 2H), 1.82 (m, 2H), 1.65 (m, 2H), 1.41 (s, 9H)

Mass Spectral Analysis m/z=394.46 (M+H)$^+$

Preparation of 50.2:

To a solution of 50.1 (4.30 g, 10.9 mmol, 1.0 eq) in dichloromethane (20 mL) was added sequentially triethylamine (1.83 mL, 13.1 mmol, 1.2 eq) and 1.4 (4.29 g, 12.0 mmol, 1.1 eq). The mixture was stirred at room temperature overnight under nitrogen. The mixture was then concentrated under reduced pressure. Ethyl acetate (800 mL) was added. The organic mixture was washed with a 1N aqueous solution of sodium hydroxide, water, brine and dried over sodium sulfate. The crude product was used for the next step without further purification.

Yield: 87%

Mass Spectral Analysis m/z=525.93 (M+H)$^+$

Preparation of 50.3:

A solution of 50.2 (5.00 g, 9.51 mmol, 1.0 eq), triethylamine (2.9 mL, 20.93 mmol, 2.2 eq), palladium(II) acetate (0.21 g, 0.95 mmol, 0.1 eq) and 1,1'-bis(diphenylphosphino)ferrocene (1.05 g, 1.90 mmol, 0.2 eq) was stirred at 65° C. under a carbon monoxide atmosphere for 4 days. The mixture was then cooled to room temperature and diluted with ethyl acetate (350 mL). The mixture was then filtered through a celite plug. The filtrate was washed with brine, dried over sodium sulfate, filtered and concentrated under reduced pressure. The crude product was purified by column chromatography (eluent: ethyl acetate/hexanes mixtures of increasing polarity).

Yield: 49%

$^1$H NMR (400 MHz, DMSO d$_6$) δ 7.82 (m, 1H), 7.57 (m, 1H), 7.47 (m, 3H), 7.35 (m, 2H), 7.07 (d, 1H), 5.90 (s, 1H), 3.74 (s, 3H), 3.34 (m, 4H), 1.91 (m, 2H), 1.75 (m, 2H), 1.42 (s, 9H)

Mass Spectral Analysis m/z=436.07 (M+H)$^+$

Preparation of 50A:

A 4M anhydrous solution of hydrochloric acid in 1,4-dioxane (1.6 mL, 6.31 mmol, 5.5 eq) was added drop wise to a cooled (0° C.) solution of 50.3 (0.50 g, 1.15 mmol, 1 eq) in anhydrous methanol (5 mL). The mixture was warmed to room temperature and stirring was continued for an additional 16 hours at room temperature. The reaction mixture was concentrated under reduced pressure. The crude product was purified by column chromatography (eluent: dichloromethane/methanol mixtures of increasing polarity).

Yield: 10%

$^1$H NMR (400 MHz, DMSO d$_6$) δ 9.07 (m, 2H), 7.87 (m, 1H), 7.58 (d, 1H), 7.48 (m, 3H), 7.38 (m, 2H), 7.17 (d, 1H), 5.97 (s, 1H), 3.75 (s, 3H), 3.24 (m, 4H), 2.08 (m, 4H)

Mass Spectral Analysis m/z=336.4 (M+H)$^+$

EXAMPLE 50B

Preparation of 50.4:

To a solution of 50.3 (0.90 g, 2.07 mmol, 1.0 eq) in tetrahydrofuran (3 mL) and methanol (3 mL) was added a solution of lithium hydroxide monohydrate (0.48 g, 11.37 mmol, 5.5 eq) dissolved in water (3 mL). The reaction was stirred at room temperature overnight. The mixture was concentrated under reduced pressure. Water (100 mL) was added and any undissolved material was removed by filtration. A 6N aqueous solution of hydrochloric acid was added dropwise to the filtrate until the solution was acidic (pH=2). The precipitate was collected by vacuum filtration. The crude product was further purified by column chromatography (eluent: ethyl acetate/hexanes mixtures of increasing polarity).

Yield: 40%

Mass Spectral Analysis m/z=420.31 (M–H)$^-$

Preparation of 50B:

A 4M anhydrous solution of hydrochloric acid in 1,4-dioxane (1.11 mL, 4.44 mmol, 5.5 eq) was added drop wise to a cooled (0° C.) solution of 50.4 (0.34 g, 0.81 mmol, 1 eq) in anhydrous methanol (4 mL). The mixture was warmed to room temperature and stirring was continued for an additional 16 hours at room temperature. The reaction mixture was concentrated under reduced pressure. The crude product was purified by column chromatography (eluent: dichloromethane/methanol mixtures of increasing polarity).

Yield: 10%

$^1$H NMR (400 MHz, DMSO d$_6$) δ 12.76 (br s, 1H), 9.17 (br s, 2H), 7.83 (m, 1H), 7.58 (d, 1H), 7.48 (m, 3H), 7.37 (d, 2H), 7.13 (d, 1H), 5.95 (s, 1H), 3.23 (m, 4H), 2.08 (m, 4H)

Mass Spectral Analysis m/z=322.1 (M+H)$^+$

EXAMPLE 50C

Preparation of 50.5:

O-Benzotriazol-1-yl-N,N,N',N'-tetramethyluronium tetrafluoroborate (0.10 g, 0.31 mmol, 1.1 eq) was added to a cooled (0° C.) solution of 50.4 (0.12 g, 0.28 mmol, 1.0 eq), 1.12 (0.034 g, 0.31 mmol, 1.1 eq), and N,N-diisopropylethylamine (0.11 mL, 0.63 mmol, 2.2 eq) dissolved in acetonitrile (5 mL). The solution was stirred for 2 hours at room temperature and then concentrated under reduced pressure. Ethyl acetate (10 mL) and a saturated aqueous solution of sodium hydrogenocarbonate (10 mL) were added to the crude product and the resulting mixture was stirred for 20 minutes at room temperature. The phases were separated and the organic phase was washed with a saturated aqueous solution of sodium hydrogenocarbonate, brine dried over sodium sulfate, filtered and concentrated under reduced pressure. The crude product was purified by column chromatography (eluent: hexane/ethyl acetate mixtures of increasing polarity).

Yield: 55%

Mass Spectral Analysis m/z=477.43 (M+H)$^+$

Preparation of 50C:

A 4M anhydrous solution of hydrochloric acid in 1,4-dioxane (0.17 mL, 0.69 mmol, 5.5 eq) was added drop wise to a cooled (0° C.) solution of 50.5 (60 mg, 0.13 mmol, 1 eq) in anhydrous methanol (4 mL). The mixture was warmed to room temperature and stirring was continued for an additional 16 hours at room temperature. The reaction mixture was concentrated under reduced pressure. The crude product was purified by column chromatography (eluent: dichloromethane/methanol mixtures of increasing polarity).

Yield: 54%

$^1$H NMR (400 MHz, DMSO d$_6$) δ 9.12 (br s, 2H), 7.45 (m, 3H), 7.36 (m, 2H), 7.27 (m, 1H), 7.09 (d, 1H), 6.89 (d, 1H), 5.93 (s, 1H), 3.23 (br s, 8H), 2.07 (m, 4H), 1.02 (br s, 6H)

Mass Spectral Analysis m/z=377.7 (M+H)$^+$

EXAMPLE 50D

Preparation of 50D:

A 4M anhydrous solution of hydrochloric acid in 1,4-dioxane (1.7 mL, 6.99 mmol, 5.5 eq) was added drop wise to a cooled (0° C.) solution of 50.1 (0.50 g, 1.27 mmol, 1 eq) in anhydrous methanol (3 mL). The mixture was warmed to room temperature and stirring was continued for an additional 16 hours at room temperature. The reaction mixture was concentrated under reduced pressure. The crude product was purified by column chromatography (eluent: dichloromethane/methanol mixtures of increasing polarity).

Yield: 55%

$^1$H NMR (400 MHz, DMSO d$_6$) δ 9.04 (s, 3H), 7.46 (m, 3H), 7.35 (m, 2H), 6.84 (d, 1H), 6.64 (d, 1H), 6.42 (s, 1H), 5.83 (s, 1H), 3.16 (m, 4H), 2.07 (m, 2H), 1.96 (m, 2H)

Mass Spectral Analysis m/z=294.1 (M+H)$^+$

Elemental analysis:

C$_{19}$H$_{19}$NO$_2$, 1HCl, 1H$_2$O:

Theory: % C, 65.61; % H, 6.38; % N, 4.03.

Found: % C, 65.89; % H, 6.29; % N, 3.95.

EXAMPLES 51A, 51B, 51C

Preparation of 51.2:

To a solution of 51.1 (2.0 g, 9.38 mmol, 1.0 eq) in methanol (50 mL) was added 1.1a (1.13 mL, 9.38 mmol, 1.0 eq) and pyrrolidine (2.11 mL, 25.51 mmol, 2.72 eq). The reaction mixture was refluxed for 16 h and then concentrated. The crude product was dissolved in ethyl acetate. The organic solution was washed with water, with a 1N aqueous solution of sodium hydroxide and then brine. The organics were concentrated and the crude product was purified by column chromatography (eluent: hexane/ethyl acetate mixtures of increasing polarity).

Yield: 29%

$^1$H NMR (400 MHz, CDCl$_3$) δ 7.88 (dd, 1H), 7.50 (m, 1H), 7.02 (t, 1H), 6.96 (d, 1H), 4.38 (brs, 1H), 3.96 (brd, 1H), 3.30 (brt, 1H), 2.66 (q, 2H), 2.05 (m, 2H), 1.65 (m, 2H), 1.46 (s, 9H), 1.28 (d, 3H)

Mass Spectral Analysis m/z=332.3 (M+H)$^+$

Preparation of 51.3:

To a solution of 51.2 (0.89 g, 2.69 mmol, 1.0 eq) in tetrahydrofuran (30 mL) at −78° C. under nitrogen was added drop wise a 1.0M solution of LiHMDS in tetrahydrofuran (3.22 mL, 3.22 mmol, 1.2 eq). The mixture was stirred for 1 h at −78° C. A solution of 1.4 (1.15 g, 3.22 mmol, 1.2 eq) in tetrahydrofuran (10 mL) was added drop wise to the mixture. The mixture was warmed slowly to room temperature and stirring was continued for 5 h at room temperature. Ice was added to the reaction mixture, which was stirred for 5 min. Ethyl acetate and a 1N aqueous solution of sodium hydroxide were added to the mixture and the layers were separated. The organics were washed with a 1N aqueous solution of sodium hydroxide and then brine. The mixture was concentrated and the crude product was purified by column chromatography (eluent: hexane/ethyl acetate mixtures of increasing polarity).

Yield: 78%

$^1$H NMR (400 MHz, CDCl$_3$) δ 7.28 (m, 2H), 6.99 (t, 1H), 6.89 (d, 1H), 5.46 (s, 1H), 4.38 (brs, 1H), 3.97 (brd, 1H), 3.33 (brt, 1H), 2.18 (m, 1H), 2.06 (m, 1H), 1.72 (m, 1H), 1.62 (m, 1H), 1.47 (s, 9H), 1.34 (d, 3H)

Mass Spectral Analysis m/z=464.1 (M+H)$^+$

Preparation of 51.4:

To a solution of 51.3 (0.95 g, 2.05 mmol, 1.0 eq) in dioxane (25 mL) was added 1.6 (0.50 g, 2.25 mmol, 1.1 eq), potassium phosphate (0.65 g, 3.07 mmol, 1.5 eq), potassium bromide (0.27 g, 2.25 mmol, 1.1 eq) and tetrakis(triphenylphosphine) palladium(0) (0.12 g, 0.102 mmol, 0.05 eq). The mixture was heated at 100° C. for 16 h and then cooled to room temperature. Ethyl acetate and water were added to the mixture and the layers were separated. The organics were concentrated and the crude product was purified by column chromatography (eluent: hexane/ethyl acetate mixtures of increasing polarity). The resulting solid was triturated in diethyl ether (15 mL) and collected by vacuum filtration.

Yield: 75%

$^1$H NMR (400 MHz, CDCl$_3$) δ 7.40 (d, 2H), 7.36 (d, 2H), 7.19 (m, 1H), 7.00 (dd, 1H), 6.93 (d, 1H), 6.85 (t, 1H), 5.46 (s, 1H), 4.39 (brs, 1H), 3.96 (brd, 1H), 3.57 (brs, 2H), 3.33 (brm, 3H), 2.14 (m, 1H), 2.04 (m, 1H), 1.72 (m, 1H), 1.63 (m, 1H), 1.48 (s, 9H), 1.39 (d, 3H), 1.21 (brd, 6H)

Mass Spectral Analysis m/z=491.2 (M+H)$^+$

Preparation of 51.5 and 51.6:

Chiral separation of 51.4 (720 mg) gave the two enantiomers 51.5 and 51.6.

Column: Chiralpak ADH, 21×250 nm, 35° C.; SFC

Eluent: 20% EtOH/80% CO$_2$; 50 mL/min, 200 bar

UV wavelength: 260 nm

Polarimeter: 670 nm

Sample: 10 mg/mL in MeOH, 2.1 mL injected

Negative polarimeter peak elutes first at about 5 minutes and the positive polarimeter peak elutes second at about 6.5 minutes in 20% EtOH/CO$_2$ 51.5: (+) enantiomer; ee>99% (226 mg) 51.6: (−) enantiomer; ee>98% (238 mg)

Preparation of 51A:

To a solution of 51.5 (0.226 g, 0.461 mmol, 1.0 eq) in methylene chloride (7 mL) at 0° C. under nitrogen was added a 2.0M solution of anhydrous hydrochloric acid in diethyl ether (0.92 mL, 1.84 mmol, 4.0 eq). The reaction was warmed to room temperature and stirred for an additional 16 h at room temperature. The reaction was concentrated to a solid, which was triturated in diethyl ether (5 mL), and the solids were collected by vacuum filtration.

Yield: 79%

$^1$H NMR (400 MHz, DMSO d$_6$) δ 9.04 (brs, 1H), 8.62 (brs, 1H), 7.40 (d, 2H), 7.35 (d, 2H), 7.18 (m, 1H), 6.89 (m, 3H), 6.23 (s, 1H), 3.48 (brs, 2H), 3.37 (brs, 2H), 3.24 (brs, 1H), 3.14 (brs, 2H), 2.12 (brm, 2H), 1.86 (brm, 1H), 1.67 (brm, 1H), 1.19 (d, 3H), 1.04 (brd, 6H)

Mass Spectral Analysis m/z=391.4 (M+H)$^+$

Elemental analysis:

$C_{25}H_{30}N_2O_2$, 1HCl, 0.5H$_2$O:

Theory: % C, 68.87; % H, 7.40; % N, 6.43.

Found: % C, 69.01; % H, 7.36; % N, 6.39.

[α]$_D$=−4.62 (c=8.25 mg/mL, MeOH)

Preparation of 51B:

To a solution of 51.6 (0.238 g, 0.485 mmol, 1.0 eq) in methylene chloride (7 mL) at 0° C. under nitrogen was added a 2.0M solution of anhydrous hydrochloric acid in diethyl ether (0.97 mL, 1.94 mmol, 4.0 eq). The reaction was warmed to room temperature and stirred for an additional 16 h at room temperature. The reaction was concentrated to a solid, which was triturated in diethyl ether (5 mL), and the solids were collected by vacuum filtration.

Yield: 77%

$^1$H NMR (400 MHz, DMSO d$_6$) δ 9.12 (brs, 1H), 8.72 (brs, 1H), 7.40 (d, 2H), 7.34 (d, 2H), 7.17 (m, 1H), 6.89 (m, 3H), 6.23 (s, 1H), 3.47 (brs, 2H), 3.36 (brs, 2H), 3.23 (brs, 1H), 3.14 (brs, 2H), 2.10 (brm, 2H), 1.87 (brm, 1H), 1.68 (t, 1H), 1.19 (d, 3H), 1.04 (brd, 6H)

Mass Spectral Analysis m/z=391.4 (M+H)$^+$

Elemental analysis:

$C_{25}H_{30}N_2O_2$, 1HCl, 0.33H$_2$O:

Theory: % C, 69.35; % H, 7.37; % N, 6.47.

Found: % C, 69.44; % H, 7.37; % N, 6.46.

[α]$_D$=+5.89 (c=9.60 mg/mL, MeOH).

Preparation of 51C:

To a solution of 51.4 (0.75 g, 1.53 mmol, 1.0 eq) in methylene chloride (15 mL) at 0° C. under nitrogen was added a 2.0M solution of anhydrous hydrochloric acid in diethyl ether (3.06 mL, 6.11 mmol, 4.0 eq). The reaction was warmed to room temperature and stirred for an additional 16 h at room temperature. The reaction mixture was diluted with diethyl ether (20 mL) and the mixture was stirred for 15 min at room temperature. The solids were collected by vacuum filtration.

Yield: 95%

$^1$H NMR (400 MHz, DMSO d$_6$) δ 9.24 (brs, 1H), 8.87 (brs, 1H), 7.49 (d, 2H), 7.42 (d, 2H), 7.26 (m, 1H), 6.97 (m, 3H), 6.31 (s, 1H), 3.55 (brs, 1H), 3.45 (brs, 2H), 3.26 (brm, 4H), 2.19 (brm, 2H), 1.96 (brm, 1H), 1.77 (t, 1H), 1.28 (d, 3H), 1.12 (brd, 6H)

Mass Spectral Analysis m/z=391.4 (M+H)$^+$

EXAMPLE 52A

Preparation of 52.1:

4.1 (1.78 mL, 12.60 mmol, 1.2 eq) was added dropwise to a cooled (0° C.) solution of Example 21C (4.10 g, 10.50 mmol, 1.0 eq) and triethylamine (4.39 mL, 31.50 mmol, 3.0 eq) in tetrahydrofuran (25 mL). The reaction was stirred overnight at room temperature. Dichloromethane (10 mL) was added to help solubilize the reaction. An additional portion of 4.1 (1.00 mL, 7.11 mmol, 0.68 eq) was added dropwise and stirring was continued for 3 hours. The reaction was diluted with an aqueous solution of 1N hydrochloric acid (200 mL) and extracted with dichloromethane (2×100 mL). The organic extracts were combined, dried over sodium sulfate, filtered, and concentrated under reduced pressure. The crude product was purified by column chromatography (eluent: hexane/ethyl acetate mixtures of increasing polarity).

Yield: 85%

$^1$H NMR (400 MHz, DMSO-d$_6$) δ 7.39 (q, 4H), 7.23 (t, 1H), 6.93 (m, 3H), 5.87 (d, 1H), 3.51-3.78 (br m, 4H), 3.44 (br s, 2H), 3.23 (br s, 2H), 1.91-2.29 (br m, 4H), 1.80 (m, 2H), 1.12 (m, 6H)

Mass Spectral Analysis m/z=487.45 (M+H)$^+$

Preparation of 52.2:

To a solution of 52.1 (4.22 g, 8.67 mmol, 1.0 eq) in 1,2-dichloroethane (20 mL) was added 4.3 (1.99 g, 13.01 mmol, 1.5 eq) portionwise. The reaction mixture was refluxed at 65° C. overnight. The reaction mixture was cooled to room temperature and then to 0° C. in an ice/brine bath. A 2M solution of oxalyl chloride in methylene chloride (6.94 mL, 13.88 mmol, 1.6 eq) was added dropwise to the reaction mixture. The reaction mixture was warmed to room temperature, then heated to 65° C. for 3 hours. The reaction was quenched by cooling to 0° C. and adding water (50 mL). The layers were separated and the aqueous was extracted with dichloromethane (2×100 mL). The organic extracts were combined, washed with brine, dried over sodium sulfate, filtered, and concentrated under reduced pressure. The crude product was purified by column chromatography (eluent: hexane/ethyl acetate mixtures of increasing polarity).

Yield: 58%

$^1$H NMR (400 MHz, DMSO d$_6$) δ 7.44 (t, 3H), 7.36 (d, 2H), 7.25 (s, 1H), 6.87 (q, 1H), 5.88 (d, 1H), 3.51-3.78 (br m, 4H), 3.45 (br s, 2H), 3.25 (br s, 2H), 1.91-2.34 (br m, 4H), 1.79 (m, 2H), 1.12 (m, 6H)

Mass Spectral Analysis m/z=585.44 (M+H)$^+$

Preparation of 52.3:

To a solution of 52.2 (2.50 g, 4.27 mmol, 1.0 eq) and tetrahydrofuran (10 mL) at 0° C. under an atmosphere of nitrogen was added 5.1 (0.88 mL, 28.20 mmol, 6.6 eq) dropwise. The reaction mixture was stirred at 0° C. for 30 minutes. The reaction mixture was concentrated under reduced pressure. Dichloromethane (50 mL) and water (50 mL) were added and the reaction mixture was stirred for 10 minutes. The phases were separated and the aqueous phase was extracted with dichloromethane (2×50 mL). The organic extracts were combined, dried over sodium sulfate, filtered, and concentrated under reduced pressure. The crude product was used without further purification.

Yield: 90%

$^1$H NMR (400 MHz, DMSO-d$_6$) 8.23 (s, 1H), 7.65 (d, 1H), 7.44 (m, 5H), 7.11 (q, 1H), 6.01 (d, 1H), 4.06 (m, 2H), 3.52-3.80 (br m, 4H), 3.45 (br s, 2H), 3.23 (br s, 2H), 1.95-2.34 (br m, 4H), 1.85 (m, 2H), 1.13 (m, 6H)

Mass Spectral Analysis m/z=581.45 (M+H)$^+$

Preparation of 52.4:

To a solution of 52.3 (2.00 g, 3.44 mmol, 1.0 eq) in ethanol (10 mL) at room temperature under an atmosphere of nitrogen was added sodium acetate (1.89 g, 23.08 mmol, 6.7 eq) and 2.8c (1.18 mL, 18.94 mmol, 5.5 eq). The reaction mixture was refluxed at 90° C. overnight. The reaction mixture was concentrated under reduced pressure. The resulting oil was diluted with water (50 mL) then extracted with dichloromethane (3×50 mL). The organic extracts were combined, washed with brine, dried over sodium sulfate, filtered, and concentrated under reduced pressure. The crude product was purified by column chromatography (eluent: hexane/ethyl acetate mixtures of increasing polarity).

Yield: 82%

$^1$H NMR (400 MHz, DMSO-d$_6$) δ 7.80 (m, 1H), 7.45 (m, 5H), 7.15 (q, 1H), 6.04 (d, 1H), 3.53-3.81 (br m, 4H), 3.45 (br s, 2H), 3.23 (br s, 2H), 3.13 (s, 3H), 1.99-2.36 (br m, 4H), 1.84 (m, 2H), 1.12 (m, 6H)

Mass Spectral Analysis m/z=565.51 (M+H)$^+$

Preparation of 52A:

To a solution of 52.4 (1.50 g, 2.66 mmol, 1.0 eq) in methanol (9 mL) and water (1 mL) at room temperature and under an atmosphere of nitrogen was added potassium carbonate (2.42 g, 17.53 mmol, 6.6 eq). The reaction mixture was stirred at room temperature overnight. The reaction mixture was diluted with water and ethyl acetate. The phases were separated and the organic phase was washed with brine, dried over sodium sulfate, filtered, and concentrated under reduced pressure. The crude product was used without further purification.

Yield: 93%

$^1$H NMR (400 MHz, DMSO d$_6$) δ 7.75 (m, 1H), 7.44 (m, 5H), 7.16 (d, 1H), 6.06 (d, 1H), 3.17-3.55 (br m, 8H), 2.72-2.96 (br m, 4H), 1.98-2.16 (br m, 4H), 1.83 (br s, 1H), 1.62 (br s, 1H), 1.12 (m, 6H)

Mass Spectral Analysis m/z=469.43 (M+H)$^+$

EXAMPLE 53A

Preparation of 53A:

To a solution of 48.2 (0.335 g, 0.704 mmol, 1.00 eq) in acetic acid (4 mL) was added a 48% aqueous solution of HBr (4 mL). The reaction mixture was refluxed at 110° C. for 8 hours and then cooled to room temperature. The reaction mixture was concentrated and a saturated aqueous solution of sodium bicarbonate was added until the mixture was basic. The product was extracted with 5% methanol/methylene chloride and purified by HPLC using the following conditions to give 40 mg of a light orange solid.

HPLC conditions:

Column: Waters Xterra Prep RP18 OBD Column, 19×150 mm

Detection: UV 210 nm

Flow: 15 mL/min

Mobile Phase A: 0.1% TFA in HPLC Water

Mobile Phase B: Acetonitrile

Gradient: Linear, 15% B to 90% B in 15 min.

Yield: 12%

$^1$H NMR (400 MHz, DMSO) δ 9.58 (s, 1H), 8.62 (brs, 2H), 7.98 (d, 2H), 7.46 (d, 2H), 7.09 (t, 1H), 6.56 (dd, 1H), 6.46 (dd, 1H), 5.85 (s, 1H), 3.20 (brm, 4H), 2.08-1.92 (brm, 4H)

Mass Spectral Analysis m/z=360.8 (M−H)$^−$

EXAMPLE 53B

Preparation of 53B:

To a solution of 48.3 (0.500 g, 1.02 mmol, 1.00 eq) in acetic acid (5 mL) was added a 48% aqueous solution HBr (5 mL). The reaction mixture was refluxed at 110° C. for 8 hours and then cooled to room temperature and stirred for an additional 48 h at room temperature. A precipitate formed and the reaction was concentrated. The solid was collected by filtration. The crude product was purified by column chromatography (eluent: methanol/methylene chloride mixtures of increasing polarity, methanol contained 5% ammonium hydroxide). The resulting solid was triturated in a methylene chloride/diethyl ether mixture (5 mL/10 mL), filtered, and dried to give 168 mg of a white solid.

Yield: 44%

$^1$H NMR (400 MHz, DMSO) δ 9.39 (brs, 1H), 7.97 (d, 2H), 7.38 (d, 2H), 7.02 (t, 1H), 6.46 (d, 1H), 6.39 (d, 1H), 5.74 (s, 1H), 4.43 (s, 3H), 2.86 (brm, 2H), 2.70 (brm, 2H), 1.70 (brm, 4H)

Mass Spectral Analysis m/z=376.8 (M+H)$^+$

EXAMPLE 53C

Preparation of 53C:

To a solution of 53D (0.300 g, 0.802 mmol, 1.00 eq) in anhydrous methanol (15 mL) was added concentrated hydrochloric acid (0.50 mL) and the reaction mixture was refluxed for 16 hours and then concentrated. The crude product was dissolved in methanol (2 mL) and then diethyl ether (10 mL) was added with stirring. The resulting solid was filtered, rinsed with diethyl ether, and dried to give 272 mg of an off-white solid.

Yield: 87%

$^1$H NMR (400 MHz, DMSO) δ 9.56 (s, 1H), 8.86 (brs, 2H), 7.89 (d, 2H), 7.37 (d, 2H), 7.08 (t, 1H), 6.55 (dd, 1H), 6.46 (dd, 1H), 5.82 (s, 1H), 3.86 (s, 3H), 3.18 (brm, 4H), 2.08-1.92 (brm, 4H)

Mass Spectral Analysis m/z=352.7 (M+H)$^+$ $C_{21}H_{21}NO_4$, 0.5$H_2O$, 1HCl

Theory: % C, 63.56; % H, 5.84; % N, 3.53.

Found: % C, 63.39; % H, 5.72; % N, 3.53.

EXAMPLE 53D

Preparation of 53.2:

To a solution of 11.5 (0.500 g, 0.981 mmol, 1.00 eq) in dioxane (8 mL) was added potassium carbonate (0.407 g, 2.94 mmol, 3.00 eq), water (2 mL), 53.1 (0.180 g, 1.08 mmol, 1.10 eq) and tetrakis(triphenylphosphine)palladium(0) (0.060 g, 0.05 mmol, 0.05 eq). The reaction mixture was stirred for 30 minutes at room temperature and no product was detected by LC/MS. Water (5 mL) was added and the reaction was homogeneous. The reaction mixture was heated at 50° C. for 20 hours. Additional quantities of tetrakis(triphenylphosphine)palladium(0) (0.060 g, 0.05 mmol, 0.05 eq) were added and the reaction mixture was heated at 80° C. for 3 hours. The reaction mixture was complete by LC/MS. The reaction mixture was cooled, acidified with a 1N aqueous solution of hydrochloric acid and product was extracted two times with ethyl acetate. The crude product was concentrated and purified by column chromatography (eluent: hexane/ethyl acetate mixtures of increasing polarity, then methanol/ethyl acetate mixtures of increasing polarity). The product was dissolved in diethyl ether (3 mL) and hexane (10 mL) was added to precipitate the product, which was filtered and rinsed with hexane to give 400 mg of a pale orange solid.

Yield: 85%

$^1$H NMR (400 MHz, DMSO) δ 7.89 (d, 2H), 7.32 (d, 2H), 7.19 (t, 1H), 6.70 (m, 2H), 5.83 (s, 1H), 4.71 (s, 2H), 3.65 (brm, 2H), 3.32 (s, 2H), 3.01 (s, 3H), 1.84-1.70 (brm, 4H), 1.41 (s, 9H)

Mass Spectral Analysis m/z=480.6 (M−H)$^−$

Preparation of 53D:

A 2.0 M solution of hydrochloric acid in diethyl ether (1.66 mL, 3.32 mmol, 4.00 eq) was added dropwise to a solution of 53.2 (0.400 g, 0.83 mmol, 1.00 eq) in anhydrous methylene chloride (15 mL). The reaction mixture was stirred for 3 days.

The precipitate was filtered and purified by HPLC using the following conditions to give 75 mg of an off-white solid.

HPLC conditions:
Column: Waters Xterra Prep RP18 OBD Column, 19×150 mm
Detection: UV 210 nm
Flow: 15 mL/min
Mobile Phase A: 0.2% Ammonium Hydroxide in HPLC Water
Mobile Phase B: Acetonitrile
Gradient: Linear, 15% B to 90% B in 15 min.
Yield: 27%
$^1$H NMR (400 MHz, DMSO) δ 7.91 (d, 2H), 7.37 (d, 2H), 7.09 (t, 1H), 6.57 (dd, 1H), 6.48 (dd, 1H), 5.82 (s, 1H), 3.24 (brm, 4H), 2.08 (brm, 2H), 1.97 (brm, 2H)
Mass Spectral Analysis m/z=338.7 (M+H)$^+$
$C_{20}H_{19}NO_4$, 1H$_2$O
Theory: % C, 67.59; % H, 5.96; % N, 3.94.
Found: % C, 67.57; % H, 5.92; % N, 4.00.

EXAMPLE 53F

Preparation of 53.4:
To a solution of 53.2 (0.600 g, 1.25 mmol, 1.00 eq), N,N-diisopropylethylamine (0.65 mL, 3.75 mmol, 3.00 eq), and ethylamine hydrochloride (3.4c) (0.203 g, 2.50 mmol, 2.00 eq) in acetonitrile (15 mL) under nitrogen and cooled in an ice/water bath was added O-benzotriazol-1-yl-N,N,N',N'-tetramethyluronium tetrafluoroborate (TBTU) (0.480 g, 1.50 mmol, 1.20 eq). The ice bath was removed and the reaction was stirred at room temperature for 2 hours and then concentrated. The residue was dissolved in ethyl acetate and the resulting mixture was washed with water and brine. The organic extracts were concentrated and purified by column chromatography (eluent: methanol/methylene chloride mixtures of increasing polarity, methanol contained 5% ammonium hydroxide) to give 520 mg of a pale yellow foam.
Yield: 82%
$^1$H NMR (400 MHz, DMSO) δ 8.46 (t, 1H), 7.80 (d, 2H), 7.27 (d, 2H), 7.19 (t, 1H), 6.71 (m, 2H), 5.80 (s, 1H), 4.70 (s, 2H), 3.65 (brm, 2H), 3.29 (brm, 4H), 3.02 (s, 3H), 1.83 (brm, 2H), 1.71 (brm, 2H), 1.41 (s, 9H), 1.13 (t, 3H)
Mass Spectral Analysis m/z=509.5 (M+H)$^+$
Preparation of 53F:
A 2.0 M solution of hydrochloric acid in diethyl ether (4.05 mL, 8.10 mmol, 8.00 eq) was added drop wise to a solution of 53.4 (0.515 g, 1.01 mmol, 1.00 eq) in anhydrous methanol (10 mL) cooled in an ice/water bath. The mixture was warmed to room temperature and stirring was continued for an additional 3.5 hours. Diethyl ether (10 mL) was added to the solution and the resulting precipitate was collected by filtration, washed with diethyl ether, and dried to give 275 mg of a white solid.
Yield: 68%
$^1$H NMR (400 MHz, DMSO) δ 9.50 (s, 1H), 8.92 (brs, 2H), 8.47 (t, 1H), 7.78 (d, 2H), 7.29 (d, 2H), 7.07 (t, 1H), 6.54 (dd, 1H), 6.46 (dd, 1H), 5.76 (s, 1H), 3.30-3.11 (brm, 6H), 2.00 (brm, 4H), 1.13 (t, 3H)
Mass Spectral Analysis m/z=365.8 (M+H)$^+$
Elemental analysis:
$C_{22}H_{24}N_2O_3$, 1HCl
Theory: % C, 65.91; % H, 6.29; % N, 6.99.
Found: % C, 65.54; % H, 6.20; % N, 6.87.

EXAMPLE 54A

Preparation of 54.1:
To a suspension of the crude HCl salt of ketone 21.3 (mother liquor of the recrystallization) (61 g, 400 mmol) in methylene chloride (1200 mL) at 0° C. was added triethylamine (223 mL, 1.6 mol, 4 eq) followed by dropwise addition of benzyl chloroformate (112.6 mL, 800 mmol, 2 eq). The reaction mixture was slowly warmed up to room temperature and stirred overnight, washed with 1 N aqueous solution of hydrochloric acid, 1 N aqueous solution of sodium hydroxide and brine. The organic layer was separated, dried over sodium sulfate, and concentrated in vacuo. The crude product was purified by column chromatography (eluent: hexane/ethyl acetate mixtures of increasing polarity).
Yield: 19%
$^1$H NMR (400 MHz, CDCl$_3$) δ 7.32 (m, 5H), 5.12 (s, 2H), 3.68 (m, 4H), 2.78 (s, 2H), 2.65 (m, 4H), 1.80 (m, 2H).
Preparation of 54.2:
To a solution of Meldrum's acid (38.1) (11.07 g, 76.8 mmol) in methanol (190 mL) was added ammonium acetate (1.18 g, 15.36 mmol, 0.2 eq) followed by compound 54.1 in one portion. The reaction mixture was stirred at room temperature overnight, and concentrated in vacuo. The residue was purified by column chromatography (eluent: hexane/ethyl acetate mixtures of increasing polarity), to yield 26 g (90.6%) of the crude product contaminated with Meldrum's acid and 54.1, which was used without further purification for the next step.
Preparation of 54.3:
To a suspension of CuI (270 mg, 1.4 mmol, 0.03 eq) in anhydrous tetrahydrofuran (200 mL) was added dropwise a 2.0 M solution of benzylmagnesium chloride (28.3a) (35.25 mL, 70.5 mmol, 1.5 eq) in anhydrous tetrahydrofuran under nitrogen atmosphere at −10° C. After the reaction mixture was stirred at −10° C. for 15 min, a solution of crude 54.2 (17.7 g, 47 mmol, 1 eq) in anhydrous tetrahydrofuran (100 mL) was added during a 30 min period. After the addition, the reaction mixture was stirred between −10° C. and −5° C. for 3 hours, and then quenched by a mixture of conc. NH$_4$OH:sat. NH$_4$Cl:H$_2$O (200 mL, 1:2:3). The mixture was extracted with ethyl acetate, and the combined organic layers were washed with a mixture of conc. NH$_4$OH:sat. NH$_4$Cl:H$_2$O (1:2:3) and brine, dried over sodium sulfate, and concentrated in vacuo. Diethyl ether was added to the residue and the mixture was stirred at room temperature overnight. The resulting solid was collected by filtration, washed with diethyl ether, and dried in vacuo.
Yield: 60.6%
$^1$H NMR (400 MHz, DMSO-d$_6$) δ 7.31-7.08 (m, 10H), 5.02 (d, 1H), 4.90 (d, 1H), 3.50-2.85 (m, 7H), 2.70 (d, 1H), 1.53 (m, 2H), 1.43 (s, 6H), 1.0 (m, 1H), 0.75 (m, 1H).
Preparation of 54.4:
Compound 54.3 (14 g, 28.72 mmol) was dissolved in a mixture of N,N-dimethylformamide (70 mL) and water (70 mL) and the reaction mixture was heated at ~120° C. overnight, then cooled to room temperature. The reaction mixture was acidified by adding 1 N aqueous solution of hydrochloric acid to pH 2-3, and kept overnight at room temperature. The upper solvent was decanted, and the sticky residue at the bottom was dissolved in diethyl ether (400 mL). This solution was washed with water, brine, and dried over sodium sulfate. Evaporation of the solvent provided the crude product, which was purified by column chromatography (eluent: hexane/ethyl acetate mixtures of increasing polarity).

Yield: 86%

$^1$H NMR (400 MHz, CDCl$_3$) δ 9.7 (brs, 1H), 7.35-7.20 (m, 10H), 5.12 (s, 2H), 3.50 (m, 4H), 2.80 (m, 2H), 2.29 (s, 2H), 1.82-1.50 (m, 6H).

Preparation of 54.5:

To a solution of 54.4 (9.5 g, 24.9 mmol, 1 eq) in anhydrous methylene chloride (150 mL) was added oxalyl chloride (4.36 mL, 49.8 mmol, 2 eq) in one portion followed by 5 drops of anhydrous N,N-dimethylformamide. The reaction mixture was stirred at room temperature for 2 hours and then concentrated in vacuo. The resulting acyl chloride was dissolved in anhydrous methylene chloride (450 mL) and aluminum chloride (6.7 g, 49.8 mmol, 2 eq) was added in one portion. The reaction mixture was stirred at room temperature overnight and then quenched by water (400 mL) followed by addition of concentrated ammonium hydroxide to make the aqueous layer basic. The organic layer was separated and the aqueous layer was extracted with methylene chloride. The combined organic layers were dried over sodium sulfate, and concentrated in vacuo.

To the solution of the above crude product in methylene chloride (250 mL) was added triethylamine (6.94 mL, 49.8 mmol, 2 eq) followed by di-tert-butyl dicarbonate (4.7) (7.08 g, 32.37 mmol, 1.3 eq.). The reaction mixture was stirred at room temperature overnight, washed with 0.5 N aqueous solution of hydrochloric acid, brine, dried over sodium sulfate, and concentrated in vacuo. The residue was purified by column chromatography (eluent: hexane/ethyl acetate mixtures of increasing polarity).

Yield: 85%.

$^1$H NMR (400 MHz, CDCl$_3$) δ 8.0 (m, 1H), 7.50 (t, 1H), 7.30 (m, 1H), 7.22 (m, 6H), 3.50-3.23 (m, 4H), 2.92 (d, 1H), 2.83 (d, 1H), 2.60 (d, 1H), 2.52 (d, 1H), 1.60 (m, 6H), 1.47 (s, 9H).

Preparation of 54.6:

A 1.0 M solution of lithium bis(trimethylsilyl)amide in tetrahydrofuran (25.4 mL, 25.4 mmol, 1.2 eq) was added at −78° C. to a solution of compound 54.5 (7 g, 21 mmol, 1 eq) in tetrahydrofuran (200 mL). After 1 hour, a solution of N-phenyltrifluoromethanesulfonimide (1.4) (9.1 g, 25.4 mmol, 1.2 eq) in tetrahydrofuran (80 mL) was added dropwise. The reaction mixture was then slowly warmed up to room temperature, stirred overnight at room temperature and concentrated in vacuo. The residue was dissolved in diethyl ether, washed with 0.5 N aqueous solution of hydrochloric acid, 1 N aqueous solution of sodium hydroxide, brine, dried over sodium sulfate, and concentrated in vacuo.

Yield: 100%.

$^1$H NMR (400 MHz, CDCl$_3$) δ 7.33 (m, 1H), 7.27 (m, 2H), 7.16 (m, 1H), 5.90 (s, 1H), 3.40 (m, 4H), 2.80 (m, 2H), 1.70 (m, 6H), 1.49 (s, 9H).

Preparation of 54.7:

To a solution of 54.6 (1.48 g, 3.2 mmol, 1.0 eq) in dioxane (50 mL) was added sequentially a 2N aqueous solution of potassium carbonate (4.8 mL, 9.6 mmol, 3.0 eq), 1.6 (780 mg, 3.52 mmol, 1.1 eq) and tetrakis(triphenylphosphine)palladium(0) (111 mg, 0.096 mmol, 0.03 eq). The mixture was stirred at room temperature for 2 hours under nitrogen. Ethyl acetate (200 mL) and water (100 mL) were added. The organic layer was separated, washed with water, brine, dried over sodium sulfate, and concentrated in vacuo. The crude product was purified by column chromatography (eluent: hexane/ethyl acetate mixtures of increasing polarity).

Yield: 83%

$^1$H NMR (400 MHz, CDCl$_3$) δ 7.40 (m, 4H), 7.18 (m, 1H), 7.11 (m, 1H), 7.0 (d, 1H), 5.90 (d, 1H), 3.54-3.30 (m, 8H), 2.78 (m, 2H), 1.82-1.62 (m, 6H), 1.50 (s, 9H), 1.23 (m, 3H), 1.12 (m, 3H).

Preparation of 54A:

To the solution of 54.7 (1.3 g, 2.6 mmol) in methylene chloride (50 mL) was added a 2.0 M solution of hydrochloric acid in diethyl ether (7.8 mL, 15.6 mmol, 6 eq). The mixture was stirred at ambient temperature for 24 hours and the solvent was evaporated in vacuo. The crude product was purified by column chromatography (eluent: methylene chloride/methanol mixtures of increasing polarity).

Yield: 44.3%.

$^1$H NMR (400 MHz, DMSO-d$_6$) δ 8.80 (brs, 2H), 7.40 (s, 4H), 7.20 (m, 3H), 6.90 (d, 1H), 6.0 (s, 1H), 3.43 (m, 2H), 3.20 (m, 4H), 3.10 (m, 2H), 2.79 (s, 2H), 1.83-1.62 (m, 6H), 1.10 (m, 6H).

Mass Spectral Analysis m/z=389.98 (M+H)$^+$

EXAMPLE 54B

Preparation of 54.8:

To a solution of 54.6 (1.55 g, 3.3 mmol, 1.0 eq) in dioxane (50 mL) was added sequentially a 2N aqueous solution of potassium carbonate (5.0 mL, 10 mmol, 3.0 eq), 5-(4,4,5,5-tetramethyl-[1,3,2]dioxaborolan-2-yl)-pyridine-2-carboxylic acid diethylamide (1.7) (1.1 g, 3.63 mmol, 1.1 eq) and 1,1'-bis(diphenylphosphin0)ferrocene palladium (II) chloride complex with methylene chloride (72 mg, 0.099 mmol, 0.03 eq). The mixture was stirred at room temperature for 45 min under nitrogen. Ethyl acetate (200 mL) and water (100 mL) were added. The organic layer was separated, washed with water, brine, dried over sodium sulfate, and concentrated in vacuo. The crude product was purified by column chromatography (eluent: hexane/ethyl acetate mixtures of increasing polarity).

Yield: 81%

$^1$H NMR (400 MHz, CDCl$_3$) δ 8.56 (δ, 1H), 7.78 (m, 1H), 7.60 (t, 1H), 7.18 (m, 2H), 7.11 (m, 1H), 6.92 (d, 1H), 5.93 (d, 1H), 3.58-3.30 (m, 8H), 2.80 (m, 2H), 1.82-1.62 (m, 6H), 1.49 (s, 9H), 1.22 (m, 6H).

Preparation of 54B:

To the solution of 54.8 (1.31 g, 2.6 mmol) in methylene chloride (50 mL) was added a 2.0 M solution of hydrochloric acid in diethyl ether (9.1 mL, 18.2 mmol, 7 eq). The mixture was stirred at ambient temperature for 24 hours and the solvent was evaporated in vacuo. The crude product was purified by column chromatography (eluent: methylene chloride/methanol mixtures of increasing polarity).

Yield: 44.2%.

$^1$H NMR (400 MHz, DMSO-d$_6$) δ 8.90 (brs, 2H), 8.55 (s, 1H), 7.83 (d, 1H), 7.59 (d, 1H), 7.26 (m, 2H), 7.16 (t, 1H), 6.88 (d, 1H), 6.13 (s, 1H), 3.48 (q, 2H), 3.30 (q, 2H), 3.20-3.10 (m, 4H), 2.80 (s, 2H), 1.86-1.62 (m, 6H), 1.16 (t, 3H), 1.10 (t, 3H).

Mass Spectral Analysis m/z=390.88 (M+H)$^+$

EXAMPLE 55A

Preparation of 55.2:

To a suspension of CuI (343 mg, 1.8 mmol, 0.036 eq) in anhydrous tetrahydrofuran (500 mL) was added dropwise a 0.25 M solution of 3,5-dimethoxybenzylmagnesium chloride (55.1) (500 mL, 125 mmol, 2.5 eq) in tetrahydrofuran under a nitrogen atmosphere at −10° C. After the reaction mixture was stirred at −10° C. for 30 min, 4-(2,2-dimethyl-4,6-dioxo-

[1,3]dioxan-5-ylidene)-piperidine-1-carboxylic acid benzyl ester (38.2) (17.95 g, 50 mmol, 1.0 eq) was added in ten portions to the mixture in a 1 hour period. After the addition, the reaction mixture was stirred between −10° C. and 0° C. for 3 hours, and then quenched by a mixture of conc. NH$_4$OH:sat. NH$_4$Cl:H$_2$O (300 mL, 1:2:3). The mixture was extracted with ethyl acetate, and the combined organic layers were washed with a mixture of conc. NH$_4$OH: sat. NH$_4$Cl:H$_2$O (1:2:3), brine, dried over sodium sulfate, and concentrated in vacuo. To the residue was added diethyl ether and the mixture was stirred overnight. The solid was collected by filtration, washed with diethyl ether, and dried in vacuo.

Yield: 100%

$^1$H NMR (400 MHz, DMSO-d$_6$) δ 7.32 (m, 5H), 6.23 (s, 1H), 6.20 (s, 2H), 5.0 (s, 2H) 3.70 (s+m, 8H), 2.98 (m, 2H), 2.81 (m, 2H), 2.70 (s, 2H), 1.46 (s, 6H), 0.90 (m, 2H).

Preparation of 55.3:

Compound 55.2 (26 g, 48.8 mmol) was dissolved in a mixture of N,N-dimethylformamide (150 mL) and water (150 mL) and heated at ~120° C. for 3 days, then cooled to room temperature. To the reaction mixture was added 1 N aqueous solution of sodium hydroxide (125 mL) and water (500 mL). The resulting mixture was extracted with diethyl ether. The aqueous phase was then acidified with 6 N aqueous hydrochloric acid, and extracted with diethyl ether. The combined organic extracts were washed with water and brine, dried over sodium sulfate, and concentrated in vacuo.

Yield: 98.4%.

$^1$H NMR (400 MHz, CDCl$_3$) δ 11.0 (brs, 1H), 7.35 (m, 5H), 5.10 (s, 2H), 3.75 (s+m, 8H), 3.32 (m, 2H), 2.78 (s, 2H), 2.38 (s, 2H), 1.59 (m, 4H).

Preparation of 55.4:

To a solution of compound 55.3 (23.8 g, 55.73 mmol) in trifluoroacetic acid (250 mL) was added dropwise trifluoroacetic anhydride (93 mL, 669 mmol, 12 eq) under nitrogen atmosphere at room temperature. The reaction was stirred for 2 hours and concentrated in vacuo. The residue was dissolved in methylene chloride. The mixture was washed with a saturated aqueous solution of sodium bicarbonate. The organic layer was separated, dried over sodium sulfate, and concentrated in vacuo. The residue was purified by column chromatography on silica gel (ethyl acetate-methylene chloride, 1:1), to yield the spiro ketone 55.4.

Yield: 70.8%.

$^1$H NMR (400 MHz, CDCl$_3$) δ 7.33 (m, 5H), 6.33 (s, 1H), 6.30 (s, 1H), 5.10 (s, 2H), 3.90 (s, 3H), 3.86 (s, 3H), 3.59 (m, 2H), 3.41 (m, 2H), 2.85 (s, 2H), 2.56 (s, 2H), 1.50 (m, 4H).

Preparation of 55.5:

A 1.0 M solution of lithium bis(trimethylsilyl)amide in tetrahydrofuran (28 mL, 28 mmol, 1.24 eq) was added at −78° C. to a solution of compound 55.4 (9.26 g, 22.64 mmol, 1 eq) in tetrahydrofuran (200 mL). After 45 minutes, a solution of N-phenyltrifluoromethanesulfonimide (1.4) (9.8 g, 27.4 mmol, 1.2 eq) in tetrahydrofuran (80 mL) was added dropwise. The reaction mixture was then warmed up to room temperature and stirred for 2 hours at room temperature, quenched by addition of water (200 mL), and extracted with a mixture of hexane and diethyl ether (1:1). The organic extracts were combined and washed with water, brine and dried over sodium sulfate. Evaporation of the solvent gave the crude compound, which was purified by column chromatography on silica gel (hexane-ethyl acetate, 2:1), to yield the enol triflate derivative 55.5.

Yield: 83.3%

$^1$H NMR (400 MHz, CDCl$_3$) δ 7.33 (m, 5H), 6.33 (m, 2H), 5.70 (s, 1H), 5.11 (s, 2H), 3.86 (s, 3H), 3.81 (s, 3H), 3.73 (m, 2H), 3.29 (m, 2H), 2.69 (s, 2H), 1.61 (m, 2H), 1.45 (m, 2H).

Preparation of 55.6:

To a solution of the enol triflate derivative 55.5 (9.8 g, 18.12 mmol) in dimethoxyethane (150 mL) was added sequentially a 2 N aqueous solution of sodium carbonate (30 mL, 60 mmol, 3.3 eq), lithium chloride (2.6 g, 61.3 mmol, 3.4 eq), 4-(N,N-diethylaminocarbonyl)phenylboronic acid) 1.6 (4.81 g, 21.77 mmol, 1.2 eq) and tetrakis(triphenylphosphine)palladium(0) (630 mg, 0.55 mmol, 0.03 eq). The reaction mixture was refluxed overnight, cooled to room temperature, diluted with water (200 mL) and extracted with diethyl ether. The combined organic extracts were dried over sodium sulfate, and concentrated in vacuo. The residue was purified by column chromatography (eluent: hexane-ethyl acetate, 1:2).

Yield: 98.2%

$^1$H NMR (400 MHz, CDCl$_3$) δ 7.36-7.22 (m, 10H), 6.40 (s, 1H), 6.30 (s, 1H), 5.89 (s, 1H), 5.11 (s, 2H), 3.81 (s, 3H), 3.78 (m, 2H), 3.53 (m, 2H), 3.39 (s, 3H), 3.30 (m, 4H), 2.68 (s, 2H), 1.62 (m, 2H), 1.43 (m, 2H), 1.22 (m, 3H), 1.10 (m, 3H).

Preparation of 55A:

To a solution of 55.6 (3.41 g, 6 mmol) in methylene chloride (60 mL) was added dropwise a 1.0 M solution of boron tribromide in methylene chloride (60 mL, 60 mmol, 10 eq) under nitrogen atmosphere at −40° C. The reaction was slowly warmed to room temperature and stirred overnight at room temperature. A 1 N aqueous solution of hydrochloric acid was added to quench the reaction and the resulting mixture was extracted with diethyl ether. The aqueous layer was basified to pH 9 with a 3 N aqueous solution of sodium hydroxide, and extracted with methylene chloride. The organic extracts were combined, dried over sodium sulfate, and concentrated in vacuo to yield 1.46 g (60%) of the crude product, which was further purified by column chromatography (eluent: methylene chloride-methanol-ammonium hydroxide, 20:1:1).

$^1$H NMR (400 MHz, DMSO-d$_6$) δ 9.42 (s, 1H), 9.07 (s, 1H), 8.90 (br, 2H), 7.28 (d, 2H), 7.20 (d, 2H), 6.20 (s, 1H), 6.13 (s, 1H), 5.80 (s, 1H), 3.33-3.10 (m, 8H), 2.55 (s, 2H), 1.68 (m, 2H), 1.58 (m, 2H), 1.10 (m, 6H).

Mass Spectral Analysis m/z=407.51 (M+H)$^+$

EXAMPLE 55B

Preparation of 55.7:

To the solution of crude 55A (1.46 g, 3.6 mmol) in methylene chloride (50 mL) was added triethylamine (2 mL, 14.4 mmol, 4 eq) followed by di-t-butyl dicarbonate (4.7) (787 mg, 3.6 mmol, 1.0 eq.). The reaction mixture was stirred at room temperature for 1 hour, and then concentrated in vacuo. The residue was purified by column chromatography (eluent: hexane-acetone, 3:2).

Yield: 42.8% for two steps.

$^1$H NMR (400 MHz, CDCl$_3$) δ 8.30 (s, 1H), 7.39 (s, 4H), 6.35 (s, 1H), 5.80 (s, 1H), 5.66 (s, 1H), 5.02 (s, 1H), 3.60 (m, 4H), 3.30 (m, 4H), 2.60 (s, 2H), 2.00 (m, 1H), 1.60 (m, 2H), 1.43 (s+m, 11H), 1.28 (m, 3H), 1.12 (m, 3H).

Preparation of 55.8:

To a solution of 55.7 (506 mg, 1 mmol) in dichloromethane was added added triethylamine (0.35 mL, 2.5 mmol, 2.5 eq) followed by N-phenyltrifluoromethanesulfonimide (1.4) (368 mg, 1.03 mmol, 1.03 eq). The reaction mixture was stirred at room temperature overnight and additional quantities of N-phenyltrifluoromethanesulfonimide (1.4) (90 g, 0.25 mmol, 0.25 eq) were added to the reaction mixture. The reaction mixture was stirred for an additional 24 hours at room temperature, washed with a saturated aqueous solution of sodium bicarbonate. The organic layer was separated, dried over sodium sulfate, and concentrated in vacuo. The residue was purified by column chromatography on silica gel (hexane-acetone-triethylamine, 3:1:0.1), to yield 55.8.

Yield: 50.2%

$^1$H NMR (400 MHz, CDCl$_3$) δ 7.40 (d, 2H), 7.37 (d, 2H), 6.73 (s, 1H), 6.70 (s, 1H), 6.06 (s, 1H), 3.69 (m, 2H), 3.55 (m, 2H), 3.28 (m, 2H), 2.73 (s, 2H), 1.60 (m, 2H), 1.48 (s+m, 11H), 1.28 (m, 3H), 1.12 (m, 3H).

Preparation of 55.9:

To a mixture of 55.8 (383 mg, 0.6 mmol), palladium acetate (4.5 mg, 0.02 mmol), 1,3-bis(diphenylphosphine)propane (8 mg, 0.02 mmol) in anhydrous N,N-dimethylformamide (6 mL) was added under nitrogen atmosphere at 60° C. triethylsilane (0.40 mL, 2.5 mmol). The reaction mixture was stirred at 60° C. for 24 hours, cooled to room temperature, and diluted with diethyl ether. The mixture was washed successively with water, a saturated aqueous solution of sodium bicarbonate, brine and dried over sodium sulfate. Evaporation of the solvent provided the crude residue, which was purified by column chromatography on silica gel (ethyl acetate-methylene chloride 1:3), to yield 80 mg (30%) of the desired phenol 55.9, and 120 mg (33%) of the corresponding silyl ether.

Compound 55.9: $^1$H NMR (400 MHz, CDCl$_3$) δ 7.42 (s, 4H), 7.10 (t, 1H), 6.80 (d, 1H), 6.72 (d, 1H), 6.0 (s, 1H), 5.0 (s, 1H), 3.64 (m, 2H), 3.52 (m, 2H), 3.28 (m, 4H), 2.71 (s, 2H), 1.60 (m, 2H), 1.45 (s+m, 11H), 1.23 (m, 3H), 1.12 (m, 3H).

Preparation of 55B:

To the solution of 55.9 (78 mg, 0.16 mmol) in methylene chloride (4 mL) was added a 2.0 M hydrochloric acid in diethyl ether (10 mL, 20 mmol). The mixture was stirred at ambient temperature for 2 days. To the solution of the silyl ether of 55.9 (110 mg, 0.18 mmol) in methylene chloride (4 mL) was added 2.0 M hydrochloric acid in diethyl ether (10 mL, 20 mmol). The mixture was stirred at ambient temperature for 2 days. The two reaction mixtures were diluted with diethyl ether, combined and filtered. The solid was collected and dried in vacuo.

Yield: 75.3%.

$^1$H NMR (400 MHz, DMSO-d$_6$) δ 9.20 (s, 1H), 8.90 (brs, 1H), 8.72 (brs, 1H), 7.30 (d, 2H), 7.21 (d, 2H), 7.06 (t, 1H), 6.75 (d, 1H), 6.69 (d, 1H), 6.03 (s, 1H), 3.50-3.10 (m, 8H), 2.66 (s, 2H), 1.68 (m, 2H), 1.53 (m, 2H), 1.10 (m, 6H).

Mass Spectral Analysis m/z=391.53 (M+H)$^+$

EXAMPLE 55C

Iodotrimethylsilane (0.62 mL, 4.4 mmol, 2.9 eq) was added to the solution of compound 55.6 (852 mg, 1.5 mmol) in anhydrous methylene chloride (10 mL) under nitrogen. The reaction mixture was stirred at room temperature for 1 hour, quenched with 1 N aqueous solution of hydrochloric acid (20 mL), and extracted with diethyl ether. The aqueous phase was basified to pH 9-10 with a 3 N aqueous solution of sodium hydroxide, and extracted with methylene chloride. The organic extracts were combined, dried over sodium sulfate, and concentrated in vacuo. The residue was purified by column chromatography on silica gel (methylene chloride-methanol-ammonium hydroxide, 10:1:1).

Yield: 60%.

$^1$H NMR (400 MHz, CDCl$_3$) δ 7.30 (d, 2H), 7.25 (d, 2H), 7.21 (d, 2H), 6.43 (d, 1H), 6.30 (d, 1H), 5.93 (s, 1H), 3.80 (s, 3H), 3.53 (m, 2H), 3.38 (s, 3H), 2.90 (m, 4H), 2.68 (s, 2H), 1.60 (m, 2H), 1.41 (m, 2H), 1.22 (m, 3H), 1.12 (m, 3H).

Mass Spectral Analysis m/z=435.70 (M+H)$^+$
Elemental analysis:
$C_{27}H_{34}N_2O_3$, 1 H$_2$O:
Theory: % C, 71.65; % H, 8.02; % N, 6.19.
Found: % C, 71.32; % H, 7.80; % N, 6.11.

EXAMPLE 56A

To a solution of 28.8b (3.23 g, 6 mmol) in methylene chloride (50 mL) was added dropwise a 1.0 M solution of boron tribromide in methylene chloride (60 mL, 60 mmol, 10 eq) under nitrogen atmosphere at −50° C. The reaction was kept between −50° C. and −10° C. for 1 hour, and then slowly warmed up to room temperature and stirred overnight at room temperature. A 1 N aqueous solution of hydrochloric acid was added to quench the reaction mixture, which was extracted with diethyl ether. The aqueous layer was basified to pH 9 with a 3 N aqueous solution of sodium hydroxide, and extracted with methylene chloride (small amount of methanol was added to increase the solubility). The organic extracts were combined, dried over sodium sulfate, and concentrated in vacuo.

Yield: 98.3%.

$^1$H NMR (400 MHz, DMSO-d$_6$) δ 9.10 (brs, 1H), 9.07 (s, 1H), 7.38 (d, 2H), 7.32 (d, 2H), 7.03 (d, 1H), 6.58 (dd, 1H), 6.35 (d, 1H), 6.0 (s, 1H), 3.40-3.25 (m, 4H), 2.72 (m, 4H), 2.63 (s, 2H), 1.42 (m, 2H), 1.35 (m, 2H), 1.10 (m, 6H).

Mass Spectral Analysis t/z=391.45 (M+H)$^+$
Elemental analysis:
$C_{25}H_{30}N_2O_2$, 1/4 H$_2$O:
Theory: % C, 76.01; % H, 7.78; % N, 7.09.
Found: % C, 75.90; % H, 7.67; % N, 7.09.

EXAMPLE 56B

Compound 56A (190 mg, 1 mmol) was dissolved in methanol (30 mL), and hydrogenated in the presence of 10% Pd/C (120 mg) using a hydrogen balloon. After 3 days at room temperature, the reaction mixture was filtered and the filtrate was concentrated in vacuo. The residue was purified by column chromatography (eluent: methylene chloride-methanol-conc. ammonia hydroxide, 8:1:1).

Yield: 94.4%

$^1$H NMR (400 MHz, CDCl$_3$) δ 7.28 (d, 2H), 7.18 (d, 2H), 6.91 (d, 1H), 6.60 (dd, 1H), 6.19 (d, 1H), 4.4 (br, 1H), 3.97 (m, 1H), 3.50 (m, 2H), 3.25 (m, 2H), 2.80 (m, 2H), 2.75 (m, 2H), 2.54 (d, 1H), 2.0 (m, 1H), 1.55-1.43 (m, 4H), 1.21 (m, 3H), 1.11 (m, 3H).

Mass Spectral Analysis m/z=393.59 (M+H)$^+$

EXAMPLE 56C

To a solution of 40.3 (850 mg, 1.58 mmol) in methylene chloride (15 mL) was added dropwise a 1.0 M solution of boron tribromide in methylene chloride (11 mL, 11 mmol, 7 eq) under nitrogen atmosphere at −50° C. The reaction was kept between −50° C.--10° C. for 1 hour, and then slowly warmed up to room temperature and stirred overnight at room temperature. A 1 N aqueous solution of hydrochloric acid was added to quench the reaction mixture, which was extracted with diethyl ether. The aqueous layer was basified to pH 9 with a 3 N aqueous solution of sodium hydroxide, and extracted with methylene chloride (small amount of methanol was added to increase the solubility). The organic extracts were combined, dried over sodium sulfate, and concentrated in vacuo. The residue was purified by column chromatography on silica gel (methylene chloride-methanol-ammonium hydroxide, 6:1:1).

Yield: 73%.

$^1$H NMR (400 MHz, DMSO-d$_6$) δ 9.22 (brs, 1H), 8.51 (d, 1H), 7.83 (dd, 1H), 7.58 (d, 1H), 7.04 (d, 1H), 6.60 (dd, 1H), 6.30 (d, 1H), 6.12 (s, 1H), 3.48 (q, 2H), 3.30 (q, 2H), 2.77 (m, 4H), 2.69 (s, 2H), 1.50 (m, 2H), 1.32 (m, 2H), 1.18 (t, 3H), 1.11 (t, 3H).

Mass Spectral Analysis m/z=392.44 (M+H)$^+$

Elemental analysis:

C$_{25}$H$_{30}$N$_2$O$_2$, 1/4 H$_2$O:

Theory: % C, 71.44; % H, 7.58; % N, 10.41.

Found: % C, 71.44; % H, 7.40; % N, 10.38.

EXAMPLE 56D

Compound 56C (190 mg, 1 mmol) was dissolved in methanol (20 mL) and hydrogenated in the presence of 10% Pd/C (120 mg) using a hydrogen balloon. After 3 days at room temperature, the reaction mixture was filtered and the filtrate was concentrated in vacuo. The residue was purified by column chromatography (eluent: methylene chloride-methanol-conc. ammonia hydroxide, 8:1:1).

Yield: 53.9%

$^1$H NMR (400 MHz, CDCl$_3$) δ 8.40 (d, 1H), 7.52 (dd, 1H), 7.48 (d, 1H), 6.96 (d, 1H), 6.62 (dd, 1H), 6.12 (d, 1H), 4.50 (br, 1H), 4.01 (m, 1H), 3.53 (q, 2H), 3.40 (q, 2H), 2.88 (m, 2H), 2.80 (m, 2H), 2.60 (d, 1H), 2.0 (m, 1H), 1.50 (m, 4H), 1.25 (t, 3H), 1.18 (m, 3H).

Mass Spectral Analysis m/z=394.51 (M+H)$^+$

EXAMPLE 57D

Preparation of 57.1:

4.1 (0.27 mL, 1.91 mmol, 1.2 eq) was added dropwise to a cooled 0° C. solution of 31J (0.50 g, 1.59 mmol, 1.0 eq) and triethylamine (0.67 mL, 4.78 mmol, 3.0 eq) in tetrahydrofuran (5 mL). The reaction mixture was stirred overnight at room temperature. Dichloromethane (1 mL) was added to help solubilizing the reaction mixture. An additional portion of 4.1 (1.00 mL, 7.11 mmol, 4.5 eq) was added dropwise. Stirring was continued for 3 hours. The reaction mixture was diluted with a 1N aqueous solution of hydrochloric acid (100 mL) and extracted with dichloromethane (2×100 mL). The organic extracts were combined, dried over sodium sulfate, filtered, and concentrated under reduced pressure. The crude product was purified by column chromatography (eluent: hexane/ethyl acetate mixtures of increasing polarity).

Yield: 87%

$^1$H NMR (400 MHz, DMSO-d$_6$) δ 7.43 (m, 3H), 7.33 (m, 2H), 7.23 (t, 1H), 7.01 (d, 1H), 6.97 (m, 1H), 6.91 (m, 1H), 5.81 (s, 1H), 4.11 (m, 1H), 3.79 (m, 1H), 3.66 (m, 1H), 3.40 (m, 1H), 2.04 (m, 2H), 1.85 (m, 2H)

Preparation of 57.2:

To a solution of 57.1 (0.50 g, 1.34 mmol, 1.0 eq) in 1,2-dichloroethane (5 mL) was added 4.3 (0.31 g, 2.01 mmol, 1.5 eq) portionwise. The reaction mixture was refluxed at 65° C. overnight. The reaction mixture was cooled to room temperature and then to 0° C. in an ice/brine bath. A 2M solution of oxalyl chloride in methylene chloride (1.07 mL, 2.14 mmol, 1.6 eq) was added dropwise to the reaction mixture. The reaction mixture was warmed to room temperature, then heated to 65° C. for 3 hours. The reaction mixture was cooled to 0° C. and quenched by addition of water (50 mL). The layers were separated and the aqueous was extracted with dichloromethane (2×100 mL). The organic extracts were combined, washed with brine, dried over sodium sulfate, filtered, and concentrated under reduced pressure. The crude product was purified by column chromatography (eluent: hexane/ethyl acetate mixtures of increasing polarity).

Yield: 74%

$^1$H NMR (400 MHz, DMSO d$_6$) δ 7.46 (m, 4H), 7.31 (m, 2H), 7.24 (d, 1H), 6.95 (d, 1H), 5.81 (s, 1H), 4.10 (m, 1H), 3.75 (m, 1H), 3.66 (m, 1H), 3.40 (m, 1H), 2.04 (m, 2H), 1.85 (m, 2H)

Preparation of 57.4:

To a solution of 57.2 (0.40 g, 0.85 mmol, 1.0 eq) in tetrahydrofuran (5 mL) at 0° C. under an atmosphere of nitrogen was added 5.1 (0.18 mL, 5.60 mmol, 6.6 eq) dropwise. The reaction mixture was stirred at 0° C. for 30 minutes. The reaction mixture was concentrated under reduced pressure. Dichloromethane (50 mL) and water (50 mL) were added and the reaction mixture was stirred for 10 minutes. The phases were separated and the aqueous phase was extracted with dichloromethane (2×50 mL). The organic extracts were combined, dried over sodium sulfate, filtered, and concentrated under reduced pressure. The crude product was purified by column chromatography (eluent: hexane/ethyl acetate mixtures of increasing polarity).

Yield: 67% Mass Spectral Analysis m/z=466.43 (M−H)$^−$ $^1$H NMR (400 MHz, DMSO-d6) δ 8.22 (s, 1H), 7.65 (m, 1H), 7.47 (m, 4H), 7.39 (m, 2H), 7.20 (d, 1H), 5.94 (s, 1H), 4.13 (m, 1H), 3.80 (m, 1H), 3.68 (m, 1H), 3.41 (m, 1H), 3.34 (s, 2H), 2.07 (m, 2H), 1.91 (m, 2H)

Preparation of 57.5:

To a solution of 57.4 (0.25 g, 0.54 mmol, 1.0 eq) in ethanol (5 mL) at room temperature under an atmosphere of nitrogen was added sodium acetate (0.29 g, 3.58 mmol, 6.7 eq) and 2.8c (0.18 mL, 2.94 mmol, 5.5 eq). The reaction mixture was refluxed at 90° C. overnight. The reaction mixture was concentrated under reduced pressure. The resulting oil was diluted with water (50 mL) then extracted with dichloromethane (3×50 mL). The organic extracts were combined, washed with brine, dried over sodium sulfate, filtered, and concentrated under reduced pressure. The crude product was purified by column chromatography (eluent: hexane/ethyl acetate mixtures of increasing polarity).

Yield: 73%

$^1$H NMR (400 MHz, DMSO-d$_6$) δ 7.81 (m, 1H), 7.48 (m, 4H), 7.38 (m, 2H), 7.26 (d, 1H), 5.97 (s, 1H), 4.14 (m, 1H), 3.79 (m, 1H), 3.69 (m, 1H), 3.41 (m, 1H), 3.13 (s, 3H), 2.08 (m, 2H), 1.93 (m, 2H)

Mass Spectral Analysis m/z=451.33 (M+H)$^+$

Preparation of 57D:

To a solution of 57.5 (0.15 g, 0.33 mmol; 1.0 eq) in methanol (4 mL) and water (1 mL) at room temperature and under an atmosphere of nitrogen was added potassium carbonate (0.30 g, 2.19 mmol, 6.6 eq). The reaction mixture was stirred at room temperature overnight. The reaction mixture was diluted with water and ethyl acetate. The phases were separated and the organic phase was washed with brine, dried over sodium sulfate, filtered, and concentrated under reduced pressure.

Yield: 94%

$^1$H NMR (400 MHz, DMSO d$_6$) δ 7.76 (m, 1H), 7.47 (m, 4H), 7.37 (m, 2H), 7.20 (d, 1H), 5.96 (s, 1H), 3.12 (s, 3H), 3.03 (s, 1H), 2.93 (m, 2H), 2.83 (m, 2H), 1.85 (m, 2H), 1.78 (m, 2H)

Mass Spectral Analysis m/z=356.30 (M+H)$^+$

EXAMPLE 58A

Preparation of 58.1a:

To a solution of 2.5 (3.58 g, 6.18 mmol, 1.0 eq) in 1,4-dioxane (18 mL) at room temperature and under an atmosphere of nitrogen was added 2M solution of potassium carbonate in water (9.26 mL, 18.53 mmol, 3.0 eq), 3.6a (1.11 g, 6.79 mmol, 1.1 eq) and [1,1'-bis(diphenylphosphino)ferrocene]dichloropalladium(II) complex with dichloromethane (1:1) (0.25 g, 0.31 mmol, 0.05 eq). The reaction mixture was heated at 60° C. for 4 hours. The reaction mixture was cooled to room temperature then diluted with water (20 mL) and stirred for an additional 20 minutes at room temperature. The mixture was then extracted with diethyl ether (1×20 mL). The organic layer was dried over sodium sulfate, filtered, and concentrated under reduced pressure. The crude product was purified by column chromatography (eluent: hexane/ethyl acetate mixtures of increasing polarity).

Yield: 54%

$^1$H NMR (400 MHz, DMSO-$d_6$) δ 8.61 (d, 1H), 8.56 (s, 1H), 7.77 (m, 1H), 7.47 (m, 1H), 6.88 (d, 1H), 6.72 (m, 1H), 6.31 (d, 1H), 5.95 (s, 1H), 3.69 (m, 2H), 3.34 (m, 2H), 1.84 (m, 2H), 1.70 (m, 2H), 1.41 (s, 9H), 0.87 (s, 9H), 0.83 (s, 6H)

Mass Spectral Analysis m/z=509.56 (M+H)$^+$

Preparation of 58A:

To a solution of 58.1a (0.60 g, 1.18 mmol, 1.0 eq) in methanol (5 mL) at room temperature and under an atmosphere of nitrogen was added a 4M solution of hydrogen chloride in 1,4-dioxane (0.59 mL, 2.40 mmol, 2.0 eq). The reaction mixture was stirred for 2 days at room temperature. The reaction mixture was concentrated under reduced pressure to dryness. The resulting oil was purified by column chromatography (eluent: dichloromethane/methanol mixtures of increasing polarity, methanol contains 10% ammonium hydroxide).

Yield: 25%

$^1$H NMR (400 MHz, DMSO $d_6$) δ 9.38 (br s, 2H), 9.19 (br s, 1H), 8.74 (s, 2H), 8.04 (d, 1H), 7.70 (m, 1H), 6.90 (d, 1H), 6.68 (d, 1H), 6.37 (s, 1H), 6.06 (s, 1H), 4.05 (br s, 1H), 3.17 (m, 4H), 2.06 (m, 4H)

Mass Spectral Analysis m/z=295.32 (M+H)$^+$

EXAMPLE 58B

Example 58B was obtained according to a procedure similar to the one described for 58A, with the following exceptions:

Step 58.1: 3.6a was replaced by 31.1n.
Step 58.2: 58.1a was replaced by 58.1b.

$^1$H NMR (400 MHz, DMSO $d_6$) δ 9.20 (s, 1H), 9.14 (br s, 2H), 8.00 (m, 1H), 7.89 (m, 1H), 7.58 (s, 1H), 7.42 (m, 2H), 6.90 (m, 2H), 6.72 (m, 1H), 6.14 (s, 1H), 3.17 (m, 4H), 2.02 (m, 4H)

Mass Spectral Analysis m/z=350.33 (M+H)$^+$

EXAMPLE 58C

Preparation of 58.2:

To a solution of 2.5 (15.00 g, 25.87 mmol, 1.00 eq) in 1,4-dioxane (65 mL) at room temperature and under an atmosphere of nitrogen was added a solution of potassium carbonate (10.73 g, 77.63 mmol, 3.0 eq) in water (32 mL), phenylboronic acid (3.47 g, 28.46 mmol, 1.1 eq) and tetrakis(triphenylphosphine)palladium(0) (1.49 g, 1.29 mmol, 0.05 eq). The reaction mixture was stirred at 80° C. overnight. The reaction mixture was cooled to room temperature then diluted with water (20 mL) and stirred for an additional 20 minutes at room temperature. The mixture was then extracted with diethyl ether (1×20 mL). The organic layer was dried over sodium sulfate, filtered, and concentrated under reduced pressure. The crude product was purified by column chromatography (eluent: hexane/ethyl acetate mixtures of increasing polarity).

Yield: 39%

Mass Spectral Analysis m/z=508.53 (M+H)$^+$

Preparation of 58.3:

To a solution of 58.2 (5.11 g, 10.06 mmol, 1.0 eq) in tetrahydrofuran (10 mL) at 0° C., under an atmosphere of nitrogen, was added dropwise a 1M solution of tetra-n-butylammonium fluoride in tetrahydrofuran (30.19 mL, 30.19 mmol, 3.0 eq). The reaction mixture was allowed to warm to room temperature and stirred overnight at room temperature. The reaction mixture was diluted with saturated sodium bicarbonate (50 mL) then extracted with ethyl acetate (2×50 mL). The organic layer was washed with a 1N aqueous solution of hydrogen chloride (50 mL) then brine (50 mL), dried over sodium sulfate, filtered, and concentrated under reduced pressure. The product was triturated with diethyl ether then isolated by vacuum filtration and dried under vacuum overnight Yield: 89%

$^1$H NMR (400 MHz, DMSO $d_6$) δ 8.92 (s, 1H), 7.43 (m, 3H), 7.34 (m, 2H), 6.78 (d, 1H), 6.58 (m, 1H), 6.40 (d, 1H), 5.77 (s, 1H), 3.71 (m, 2H), 3.23 (m, 2H), 1.82 (m, 2H), 1.65 (m, 2H), 1.41 (s, 9H)

Mass Spectral Analysis m/z=394.44 (M+H)$^+$

Preparation of 58.5a:

To a solution of 58.3 (0.50 g, 1.27 mmol, 1.0 eq) and potassium carbonate (0.58 g, 4.19 mmol, 3.3 eq) in N,N-dimethylformamide (5 mL) at 0° C. and under an atmosphere of nitrogen was added dropwise 2.8c (0.26 mL, 4.19 mmol, 3.3 eq). The reaction mixture was stirred for 3 days at 100° C. The reaction mixture was cooled to room temperature and partitioned between water (50 mL) and diethyl ether (50 mL). The phases were separated and the organic layer was dried over sodium sulfate, filtered, and concentrated under reduced pressure. The crude product was purified by column chromatography (eluent: hexane/ethyl acetate mixtures of increasing polarity).

Yield: 58%

$^1$H NMR (400 MHz, DMSO-d6) δ 7.43 (m, 3H), 7.35 (m, 2H), 6.92 (d, 1H), 6.81 (m, 1H), 6.46 (d, 1H), 5.84 (s, 1H), 3.71 (m, 2H), 3.61 (s, 3H), 3.24 (m, 2H), 1.83 (m, 2H), 1.68 (m, 2H), 1.41 (s, 9H)

Mass Spectral Analysis m/z=408.86 (M+H)$^+$

Preparation of 58C:

To a solution of 58.5a (0.30 g, 0.74 mmol, 1.0 eq) in methylene chloride (4 mL) at room temperature and under an atmosphere of nitrogen was added a 2M solution of hydrogen chloride in diethyl ether (2.02 mL, 4.04 mmol, 5.5 eq). The reaction mixture was stirred overnight at room temperature. The reaction mixture was concentrated under reduced pressure, then triturated with ethyl acetate. The product was isolated by vacuum filtration and dried under vacuum overnight.

Yield: 69%

$^1$H NMR (400 MHz, DMSO $d_6$) δ 9.17 (br s, 2H), 7.44 (m, 3H), 7.37 (m, 2H), 7.00 (d, 1H), 6.84 (m, 1H), 6.47 (d, 1H), 5.90 (s, 1H), 3.62 (s, 3H), 3.20 (m, 4H), 2.03 (m, 4H)

Mass Spectral Analysis m/z=308.28 (M+H)$^+$

EXAMPLE 58D 58D was obtained according to a procedure similar to the one described for 58C, with the following exceptions:
Step 58.5: 2.8c was replaced by 58.4.
Step 58.6: 58.5a was replaced by 58.5b.

$^1$H NMR (400 MHz, DMSO d$_6$) δ 9.07 (br s, 2H), 7.45 (m, 3H), 7.37 (m, 2H), 6.97 (d, 1H), 6.82 (m, 1H), 6.45 (d, 1H), 5.89 (s, 1H), 3.64 (d, 2H), 3.20 (m, 4H), 2.01 (m, 4H), 1.10 (m, 1H), 0.50 (m, 2H), 0.22 (m, 2H)
Mass Spectral Analysis m/z=348.26 (M+H)$^+$

EXAMPLE 59A

Preparation of 59.4a:
To a solution of 59.2a (3.00 g, 14.6 mmol, 1.00 eq) in methanol (75 mL) was added triethylamine (2.24 mL, 16.1 mmol, 1.10 eq). The solution was cooled in an ice/water bath and 59.3 (1.92 mL, 16.1 mmol, 1.10 eq) was added slowly. The reaction mixture was stirred at 0° C. for 2.5 hours and then concentrated. The residue was dissolved in methylene chloride. The organic phase was washed with water, a saturated solution of sodium bicarbonate and brine. The organic extracts were concentrated under reduced pressure and dried to give 2.85 g of a white solid.
Yield: 89%
$^1$H NMR (400 MHz, DMSO) δ 9.67 (brs, 1H), 3.59 (m, 4H)
Preparation of 59.6:
To a solution of 59.5 (20.0 g, 0.110 mol, 1.00 eq) in N,N-dimethylformamide (100 mL) was added sodium azide (7.86 g, 0.121 mol, 1.10 eq) and ammonium chloride (6.46 g, 0.121 mol, 1.10 eq). The reaction mixture was heated at 125° C. for 20 hours, cooled to room temperature and then cooled in a brine/ice bath. A 1N solution of hydrochloric acid (50 mL) was slowly added to the reaction mixture. A thick precipitate formed and water (200 mL) was added to facilitate stirring. To reach pH 1, a 6N solution of hydrochloric acid (20 mL) was added carefully. The solids were filtered and dried to give 25 g of a off-white solid.
Yield: 100%
$^1$H NMR (400 MHz, DMSO) δ 8.00 (d, 2H), 7.84 (d, 2H)
Mass Spectral Analysis m/z=223.5 (M−H)$^-$
Preparation of 59.7a:
To a solution of 59.6 (2.33 g, 10.4 mmol, 1.00 eq) in N,N-dimethylformamide (50 mL) was added triethylamine (2.89 mL, 20.7 mmol, 2.00 eq). 59.4a (2.85 g, 13.0 mmol, 1.25 eq) was then added to the reaction mixture, which was stirred at room temperatue for 16 hours. The reaction was not complete as evidenced by LC/MS, so it was heated at 50° C. for 24 hours. The reaction mixture was diluted with cold water and the product was extracted two times with ethyl acetate. The crude product was concentrated and purified by column chromatography (eluent: hexane/ethyl acetate mixtures of increasing polarity) and the resulting solid was triturated in hexanes, filtered, and dried to give 1.67 g of a white solid.
Yield: 44%
$^1$H NMR (400 MHz, DMSO) δ 9.64 (t, 1H), 7.99 (d, 2H), 7.79 (d, 2H), 4.90 (m, 2H), 3.76 (m, 2H)
Mass Spectral Analysis m/z=362.2 (M−H)$^-$
Preparation of 59.8a:
To a solution of 59.7a (1.00 g, 2.75 mmol, 1.00 eq), 32.1 (2.35 g, 5.49 mmol, 2.00 eq), and potassium carbonate (1.14, 8.24 mmol, 3.00 eq) in dioxane (25 mL) and water (5 mL) was added tetrakis(triphenylphosphine)palladium(0) (0.200 g, 0.10 mmol, 0.05 eq). The reaction mixture was stirred at room temperature for 16 hours, heated at 45° C. for 1 hour, and then diluted with water. Methylene chloride was added and the layers were separated. The aqueous layer was washed again with methylene chloride and the organic extracts were combined and concentrated under reduced pressure. The crude product was purified by column chromatography (eluent: hexane/ethyl acetate mixtures of increasing polarity) to give 1.52 g of a light yellow foam.
Yield: 95%
$^1$H NMR (400 MHz, CDCl$_3$) δ 8.15 (d, 2H), 7.49 (d, 2H), 7.20 (m, 1H), 7.08 (brs, 1H), 7.02 (dd, 1H), 6.96 (dd, 1H), 6.87 (m, 1H), 5.62 (s, 1H), 4.90 (m, 2H), 4.07 (m, 2H), 3.87 (m, 2H), 3.34 (m, 2H), 2.06 (m, 2H), 1.68 (m, 2H), 1.48 (s, 9H)
Mass Spectral Analysis m/z=583.6 (M−H)$^-$
Preparation of 59.9a:
To a solution of 59.8a (1.50 g, 2.56 mmol, 1.00 eq) in methanol (40 mL) was added potassium carbonate (1.77 g, 12.8 mmol, 5.00 eq). The reaction mixture was heated at 50° C. for 24 hours and then at 60° C. for an additional 24 hours. The reaction mixture was concentrated under reduced pressure. The crude residue was purified by column chromatography (eluent: methanol/methylene chloride mixtures of increasing polarity, methanol containing 5% ammonium hydroxide) to give 1.11 g of a light orange foam.
Yield: 88%
$^1$H NMR (400 MHz, DMSO) δ 8.13 (d, 2H), 7.54 (d, 2H), 7.23 (m, 1H), 7.00 (m, 2H), 6.92 (m, 1H), 5.93 (s, 1H), 4.69 (t, 2H), 3.73 (m, 2H), 3.33 (s, 2H), 3.13 (t, 2H), 1.89 (m, 2H), 1.73 (m, 2H), 1.42 (s, 9H)
Mass Spectral Analysis m/z=489.5 (M+H)$^+$
Preparation of 59A:
To a solution of 59.9a (0.500 g, 1.02 mmol, 1.00 eq) in methylene chloride (15 mL) was added a 2.0 M solution of hydrochloric acid in diethyl ether (3.10 mL, 6.10 mmol, 6.00 eq). The reaction mixture was stirred at room temperature for 3 days. The resulting solid was filtered, rinsed with diethyl ether, and dried to give 458 mg of a pale orange solid.
Yield: 96%
$^1$H NMR (400 MHz, DMSO) δ 9.05 (brs, 2H), 8.27 (brs, 3H), 8.17 (d, 2H), 7.60 (d, 2H), 7.29 (m, 1H), 7.07 (dd, 1H), 7.04 (dd, 1H), 6.97 (m, 1H), 6.00 (s, 1H), 5.05 (t, 2H), 3.51 (t, 2H), 3.22 (brm, 4H), 2.05 (brm, 4H)
Mass Spectral Analysis m/z=389.4 (M+H)$^+$
Elemental analysis:
C$_{22}$H$_{24}$N$_6$O, 2HCl, 1.5H$_2$O:
Theory: % C, 54.10; % H, 5.98; % N, 17.21; % Cl, 14.52.
Found: % C, 54.43; % H, 5.94; % N, 16.90; % Cl, 14.80.

EXAMPLE 59B 59B was obtained according to a procedure similar to the one described for 59A, with the following exceptions:
Step 59.2: 59.2a was replaced by 59.2b.
Step 59.4: 59.4a was replaced by 59.4b.
Step 59.5: 59.7a was replaced by 59.7b.
Step 59.6: 59.8a was replaced by 59.8b.
Step 59.7: 59.9a was replaced by 59.9b.

$^1$H NMR (400 MHz, DMSO d$_6$) δ 9.21 (brs, 2H), 8.15 (m, 5H), 7.59 (d, 2H), 7.28 (m, 1H), 7.07 (m, 1H), 7.03 (dd, 1H), 6.96 (m, 1H), 5.99 (s, 1H), 4.91 (t, 2H), 3.22 (brm, 4H), 2.93 (brm, 2H), 2.32 (m, 2H), 2.06 (brm, 4H)
Mass Spectral Analysis m/z=403.4 (M+H)$^+$
Elemental analysis:
C$_{23}$H$_{26}$N$_6$O, 2HCl, 1H$_2$O:

Theory: % C, 55.99; % H, 6.13; % N, 17.03.
Found: % C, 56.01; % H, 6.23; % N, 16.93.

EXAMPLE 59C

Preparation of 59.2c:
A solution of 59.1a (4.79 g, 46.4 mmol, 1.00 eq) in 48% aqueous hydrobromic acid (10 mL) was refluxed at 105° C. for 4 hours. The reaction was concentrated and dried to give 10.1 g of a sticky, tan solid.
Yield: 88%
$^1$H NMR (400 MHz, DMSO) δ 7.76 (brs, 3H), 3.54 (t, 1H), 3.35 (m, 1H), 2.78 (brm, 2H), 1.82 (m, 1H), 1.60-1.30 (brm, 5H)
59C was obtained according to a procedure similar to the one described for 59A, with the following exceptions:
Step 59.2: 59.2a was replaced by 59.2c.
Step 59.4: 59.4a was replaced by 59.4c.
Step 59.5: 59.7a was replaced by 59.7c.
Step 59.6: 59.8a was replaced by 59.8c.
Step 59.7: 59.9a was replaced by 59.9c.
$^1$H NMR (400 MHz, DMSO d$_6$) δ 9.16 (brs, 2H), 8.14 (d, 2H), 7.90 (brs, 3H), 7.58 (d, 2H), 7.28 (m, 1H), 7.07 (m, 1H), 7.02 (m, 1H), 6.96 (m, 1H), 5.98 (s, 1H), 4.77 (t, 2H), 3.21 (brm, 4H), 2.77 (m, 2H), 2.06 (brm, 6H), 1.61 (m, 2H), 1.36 (m, 2H)
Mass Spectral Analysis m/z=431.5 (M+H)$^+$
Elemental analysis:
$C_{25}H_{30}N_6O$, 2HCl, 2/3H$_2$O:
Theory: % C, 58.25; % H, 6.52; % N, 16.30; % Cl, 13.76.
Found: % C, 58.01; % H, 6.45; % N, 16.24; % Cl, 14.10.

EXAMPLE 59D

Preparation of 59.2d:
A solution of 59.1b (5.00 g, 42.7 mmol, 1.00 eq) in 48% aqueous hydrobromic acid (10 mL) was refluxed at 105° C. for 4 hours. The reaction was concentrated and dried to give 9.27 g of an orange/brown oil.
Yield: 83%
$^1$H NMR (400 MHz, DMSO) δ 7.70 (brs, 3H), 3.38 (m, 3H), 2.77 (m, 2H), 1.53 (m, 2H), 1.35 (brm, 5H)
59D was obtained according to a procedure similar to the one described for 59A, with the following exceptions:
Step 59.2: 59.2a was replaced by 59.2d.
Step 59.4: 59.4a was replaced by 59.4d.
Step 59.5: 59.7a was replaced by 59.7d.
Step 59.6: 59.8a was replaced by 59.8d.
Step 59.7: 59.9a was replaced by 59.9d.
$^1$H NMR (400 MHz, DMSO d$_6$) δ 9.18 (brs, 2H), 8.14 (d, 2H), 7.91 (brs, 3H), 7.58 (d, 2H), 7.28 (m, 1H), 7.07 (dd, 1H), 7.03 (dd, 1H), 6.96 (m, 1H), 5.98 (s, 1H), 4.77 (t, 2H), 3.22 (brm, 4H), 2.75 (brs, 2H), 2.13-1.96 (brm, 6H), 1.55 (m, 2H), 1.34 (brm, 4H)
Mass Spectral Analysis m/z=445.5 (M+H)$^+$
Elemental analysis:
$C_{26}H_{32}N_6O$, 2HCl, 1.25H$_2$O:
Theory: % C, 57.83; % H, 6.81; % N, 15.56.
Found: % C, 57.99; % H, 6.83; % N, 15.63.

EXAMPLE 59E

Preparation of 59.10a:
To a solution of 59.9a (0.400 g, 0.82 mmol, 1.00 eq) and triethylamine (0.342 mL, 2.46 mmol, 3.00 eq) in methylene chloride (20 mL) in an ice/water bath was added acetic anhydride (0.085 mL, 0.900 mmol, 1.10 eq). The reaction mixture was warmed to room temperature, stirred for an additional 6 hours at room temperature and diluted with a 1N solution of hydrochloric acid. The layers were separated and the aqueous phase was extracted with methylene chloride. The organic extracts were combined and concentrated under reduced pressure. The crude residue was purified by column chromatography (eluent: ethyl acetate/hexane mixtures of increasing polarity) to give 400 mg of a white foam.
Yield: 91%
$^1$H NMR (400 MHz, DMSO) δ 8.14 (d, 2H), 8.07 (t, 1H), 7.55 (d, 2H), 7.24 (m, 1H), 7.00 (m, 2H), 6.92 (m, 1H), 5.93 (s, 1H), 4.78 (m, 2H), 3.73 (m, 2H), 3.63 (m, 2H), 3.31 (s, 2H), 1.89 (m, 2H), 1.77 (s, 3H), 1.72 (m, 2H), 1.42 (s, 9H)
Mass Spectral Analysis m/z=531.4 (M+H)$^+$
Preparation of 59E:
To a solution of 59.10a (0.390 g, 0.735 mmol, 1.00 eq) in methylene chloride (10 mL) was added a 2.0 M solution of hydrochloric acid in diethyl ether (1.50 mL, 2.90 mmol, 4.00 eq). The reaction mixture was stirred at room temperature for 3 days. The solids were filtered, rinsed with methylene chloride and diethyl ether, and dried to give 335 mg of a white solid.
Yield: 98%
$^1$H NMR (400 MHz, DMSO) δ 8.93 (brs, 2H), 8.15 (d, 2H), 8.09 (t, 1H), 7.58 (d, 2H), 7.28 (m, 1H), 7.05 (m, 2H), 6.96 (m, 1H), 6.00 (s, 1H), 4.78 (m, 2H), 3.63 (m, 2H), 3.22 (brm, 4H), 2.05 (brm, 4H), 1.77 (s, 3H)
Mass Spectral Analysis m/z=431.5 (M+H)$^+$
Elemental analysis:
$C_{24}H_{26}N_6O_2$, 1HCl, 0.5H$_2$O:
Theory: % C, 60.56; % H, 5.93; % N, 17.66.
Found: % C, 60.39; % H, 5.81; % N, 17.53.

EXAMPLE 59F 59F was obtained according to a procedure similar to the one described for 59E, with the following exceptions:
Step 59.8: 59.9a was replaced by 59.9b.
Step 59.9: 59.10a was replaced by 59.10b.
$^1$H NMR (400 MHz, DMSO) δ 8.98 (brs, 2H), 8.14 (d, 2H), 8.01 (brt, 1H), 7.57 (d, 2H), 7.28 (m, 1H), 7.05 (m, 2H), 6.96 (m, 1H), 6.00 (s, 1H), 4.77 (t, 2H), 3.22 (brm, 4H), 3.13 (m, 2H), 2.16-1.97 (brm, 6H), 1.80 (s, 3H)
Mass Spectral Analysis m/z=445.5 (M+H)$^+$
Elemental analysis:
$_{25}$H$_{28}$N$_6$O$_2$, 1HCl, 1.5H$_2$O:
Theory: % C, 59.11; % H, 6.35; % N, 16.54.
Found: % C, 59.46; % H, 6.27; % N, 16.60.

EXAMPLE 59G 59G was obtained according to a procedure similar to the one described for 59E, with the following exceptions:
Step 59.8: 59.9a was replaced by 59.9c.
Step 59.9: 59.10a was replaced by 59.10c.
$^1$H NMR (400 MHz, DMSO) δ 8.88 (brs, 2H), 8.14 (d, 2H), 7.82 (brt, 1H), 7.58 (d, 2H), 7.28 (m, 1H), 7.07 (dd, 1H), 7.03 (dd, 1H), 6.96 (m, 1H), 5.99 (s, 1H), 4.75 (t, 2H), 3.22 (brm, 4H), 3.00 (q, 2H), 2.10 (m, 2H), 1.99 (brm, 4H), 1.76 (s, 3H), 1.43 (m, 2H), 1.29 (m, 2H)
Mass Spectral Analysis m/z=473.5 (M+H)$^+$
Elemental analysis:
$C_{27}H_{32}N_6O_2$, 1HCl, 2/3H$_2$O:

Theory: % C, 62.24; % H, 6.64; % N, 16.13.
Found: % C, 61.92; % H, 6.65; % N, 15.91.

EXAMPLE 59H 59H was obtained according to a procedure similar to the one described for 59E, with the following exceptions:
Step 59.8: 59.9a was replaced by 59.9d.
Step 59.9: 59.10a was replaced by 59.10d.

$^1$H NMR (400 MHz, DMSO) δ 8.99 (brs, 2H), 8.14 (d, 2H), 7.80 (brt, 1H), 7.57 (d, 2H), 7.28 (m, 1H), 7.07 (dd, 1H), 7.03 (dd, 1H), 6.96 (m, 1H), 5.99 (s, 1H), 4.75 (t, 2H), 3.22 (brm, 4H), 2.99 (q, 2H), 2.12-1.94 (brm, 6H), 1.77 (s, 3H), 1.34 (brm, 6H)

Mass Spectral Analysis m/z=487.5 (M+H)$^+$
Elemental analysis:
$C_{28}H_{34}N_6O_2$, 1HCl, 1H$_2$O:
Theory: % C, 62.15; % H, 6.89; % N, 15.53.
Found: % C, 62.27; % H, 6.83; % N, 15.48.

EXAMPLE 59I

Preparation of 59.11a:

To a solution of 59.9a (0.250 g, 0.512 mmol, 1.00 eq) and triethylamine (0.214 mL, 1.54 mmol, 3.00 eq) in methylene chloride (20 mL) cooled in an ice/water bath was added methanesulfonyl chloride (7.4) (0.044 mL, 0.563 mmol, 1.10 eq). The reaction was stirred at 0° C. for 30 minutes and diluted with water. The layers were separated and the aqueous was extracted with methylene chloride. The organic extracts were combined and concentrated under reduced pressure. The crude residue was purified by column chromatography (eluent: ethyl acetate/hexane mixtures of increasing polarity) to give 164 mg of a white foam.

Yield: 57%

$^1$H NMR (400 MHz, DMSO) δ 8.14 (d, 2H), 7.56 (d, 2H), 7.38 (brs, 1H), 7.23 (m, 1H), 7.00 (m, 2H), 6.92 (m, 1H), 5.93 (s, 1H), 4.85 (t, 2H), 3.73 (m, 2H), 3.61 (m 2H), 3.32 (brs, 2H), 2.91 (s, 3H), 1.89 (m, 2H), 1.73 (m, 2H), 1.42 (s, 9H)

Mass Spectral Analysis m/z=565.6 (M−H)$^−$

Preparation of 59I:

To a solution of 59.11a (0.155 g, 0.274 mmol, 1.00 eq) in methylene chloride (10 mL) was added a 2.0 M solution of hydrochloric acid in diethyl ether (0.55 mL, 1.10 mmol, 4.00 eq). The reaction was stirred at room temperature for 16 hours. The solids were filtered, rinsed with methylene chloride and diethyl ether, and dried to give 83 mg of a white solid.

Yield: 58%

$^1$H NMR (400 MHz, DMSO) δ 9.04 (brs, 2H), 8.15 (d, 2H), 7.58 (d, 2H), 7.41 (t, 1H), 7.28 (m, 1H), 7.05 (m, 2H), 6.96 (m, 1H), 6.00 (s, 1H), 4.85 (t, 2H), 3.62 (m, 2H), 3.23 (brm, 4H), 2.92 (s, 3H), 2.07 (brm, 4H)

Mass Spectral Analysis m/z=467.3 (M+H)$^+$
Elemental analysis:
$C_{23}H_{26}N_6O_3S$, 1HCl, 0.5H$_2$O:
Theory: % C, 53.95; % H, 5.51; % N, 16.41.
Found: % C, 54.00; % H, 5.39; % N, 16.10.

EXAMPLE 59J 59J was obtained according to a procedure similar to the one described for 59I, with the following exceptions:
Step 59.10: 59.9a was replaced by 59.9b.
Step 59.11: 59.11a was replaced by 59.11b.

$^1$H NMR (400 MHz, DMSO) δ 8.90 (brs, 2H), 8.15 (d, 2H), 7.57 (d, 2H), 7.28 (m, 1H), 7.21 (t, 1H), 7.05 (m, 2H), 6.96 (m, 1H), 6.00 (s, 1H), 4.83 (t, 2H), 3.22 (brm, 4H), 3.06 (q, 2H), 2.92 (s, 3H), 2.20 (m, 2H), 2.11 (brm, 2H), 2.01 (brm, 2H)

Mass Spectral Analysis m/z=481.5 (M+H)$^+$
Elemental analysis:
$C_{24}H_{28}N_6O_3S$, 1HCl, 0.5H$_2$O:
Theory: % C, 54.80; % H, 5.75; % N, 15.98.
Found: % C, 54.96; % H, 5.64; % N, 15.67.

EXAMPLE 59K 59K was obtained according to a procedure similar to the one described for 59I, with the following exceptions:
Step 59.10: 59.9a was replaced by 59.9c.
Step 59.11: 59.11a was replaced by 59.11c.

$^1$H NMR (400 MHz, DMSO) δ 8.13 (d, 2H), 7.54 (d, 2H), 7.22 (m, 1H), 6.98 (m, 3H), 6.90 (m, 1H), 5.92 (s, 1H), 4.76 (t, 2H), 2.92 (brm, 4H), 2.86 (s, 3H), 2.78 (m, 2H), 1.99 (m, 2H), 1.82 (m, 2H), 1.73 (m, 2H), 1.51 (m, 2H), 1.33 (m, 2H)

Mass Spectral Analysis m/z=509.5 (M+H)$^+$
Elemental analysis:
$C_{26}H_{32}N_6O_3S$, 1.45H$_2$O:
Theory: % C, 58.40; % H, 6.58; % N, 15.71.
Found: % C, 58.79; % H, 6.58; % N, 15.31.

EXAMPLE 59L 59L was obtained according to a procedure similar to the one described for 59I, with the following exceptions:
Step 59.10: 59.9a was replaced by 59.9d.
Step 59.11: 59.11a was replaced by 59.11d.

$^1$H NMR (400 MHz, DMSO) δ 8.92 (brs, 2H), 8.14 (d, 2H), 7.57 (d, 2H), 7.28 (m, 1H), 7.07 (dd, 1H), 7.03 (dd, 1H), 6.96 (m, 2H), 5.99 (s, 1H), 4.76 (t, 2H), 3.22 (brm, 4H), 2.91 (q, 2H), 2.86 (s, 3H), 2.05 (brm, 6H), 1.39 (brm, 6H)

Mass Spectral Analysis m/z=523.6 (M+H)$^+$
Elemental analysis:
$C_{27}H_{34}N_6O_3S$, 1HCl, 0.5H$_2$O:
Theory: % C, 57.08; % H, 6.39; % N, 14.79.
Found: % C, 57.36; % H, 6.34; % N, 14.81.

EXAMPLE 60A

Preparation of 60.2:

To a solution of 60.1 (5.00 g, 56.1 mmol, 1.00 eq) and triethylamine (15.6 mL, 112 mmol, 2.00 eq) in methanol (100 mL) cooled in an ice/water bath was added 59.3 (7.34 mL, 61.7 mmol, 1.10 eq). The reaction mixture was stirred at 0° C. for 1.5 hours and then concentrated. The mixture was dissolved in methylene chloride and washed with a 0.5N solution of hydrochloric acid. The aqueous phase was extracted three times with 5% methanol/methylene chloride. The organic extracts were combined, concentrated, and dried to give 6.96 g of an orange oil.

Yield: 67%

$^1$H NMR (400 MHz, CDCl$_3$) δ 3.72 (t, 2H), 3.41 (q, 2H), 1.94 (s, 1H), 1.70 (m, 4H)

Preparation of 60.3:

To a solution of 60.2 (3.69 g, 19.9 mmol, 1.00 eq) and triethylamine (5.56 mL, 39.9 mmol, 2.00 eq) in methylene chloride (100 mL) cooled in an ice/water bath was added 7.4 (2.31 mL, 29.9 mmol, 1.50 eq). The reaction mixture was warmed to room temperature, stirred for an additional 1 hour at room temperature and then diluted with water. The layers were separated and the aqueous phase was extracted with methylene chloride. The organic extracts were combined and washed with a 0.5M solution of hydrochloric acid. The organic extracts were concentrated and dried to give 4.96 g of an orange oil.

Yield: 95%

$^1$H NMR (400 MHz, DMSO) δ 9.46 (brm, 1H), 4.21 (t, 2H), 3.22 (q, 2H), 3.16 (s, 3H), 1.62 (m, 4H)

Mass Spectral Analysis m/z=262.6 (M–H)$^-$ 60A was obtained according to a procedure similar to the one described for 59A, with the following exceptions:
Step 60.3: 59.4a from Step 59.4 was replaced by 60.3.
Step 60.4: 59.7a from Step 59.5 was replaced by 60.4.
Step 60.5: 59.8a from Step 59.6 was replaced by 60.5.
Step 60.6: 59.9a from Step 59.7 was replaced by 60.6.

$^1$H NMR (400 MHz, DMSO d$_6$) δ 9.22 (brs, 2H), 8.14 (d, 2H), 7.97 (brs, 3H), 7.57 (d, 2H), 7.28 (m, 1H), 7.08 (dd, 1H), 7.02 (dd, 1H), 6.96 (m, 1H), 5.99 (s, 1H), 4.82 (t, 2H), 3.21 (brm, 4H), 2.83 (t, 2H), 2.06 (brm, 6H), 1.61 (m, 2H)

Mass Spectral Analysis m/z=417.5 (M+H)$^+$

Elemental analysis:
$C_{24}H_{28}N_6O$, 2HCl, 3/2H$_2$O:
Theory: % C, 55.81; % H, 6.44; % N, 16.27; % Cl, 13.73.
Found: % C, 55.95; % H, 6.48; % N, 16.28; % Cl, 14.00.

EXAMPLE 60B 60B was obtained according to a procedure similar to the one described for 59E, with the following exceptions:
Step 60.7: 59.9a from Step 59.8 was replaced by 60.6.
Step 60.8: 59.10a from Step 59.9 was replaced by 60.7.

$^1$H NMR (400 MHz, DMSO d$_6$) δ 9.09 (brs, 2H), 8.14 (d, 2H), 7.90 (brt, 1H), 7.57 (d, 2H), 7.28 (m, 1H), 7.07 (dd, 1H), 7.03 (dd, 1H), 6.96 (m, 1H), 5.99 (s, 1H), 4.78 (t, 2H), 3.22 (brm, 4H), 3.07 (q, 2H), 2.04 (brm, 6H), 1.78 (s, 3H), 1.42 (m, 2H)

Mass Spectral Analysis m/z=459.5 (M+H)$^+$

Elemental analysis:
$C_{26}H_{30}N_6O$, 1HCl, 3/2H$_2$O:
Theory: % C, 59.82; % H, 6.56; % N, 16.10.
Found: % C, 59.77; % H, 6.31; % N, 16.05.

EXAMPLE 60C 60C was obtained according to a procedure similar to the one described for 59I, with the following exceptions:
Step 60.9: 59.9a from Step 59.10 was replaced by 60.6.
Step 60.10: 59.11a from Step 59.11 was replaced by 60.8.

$^1$H NMR (400 MHz, DMSO d$_6$) δ 8.13 (d, 2H), 7.54 (d, 2H), 7.23 (m, 1H), 7.01 (m, 3H), 6.91 (m, 1H), 5.93 (s, 1H), 4.78 (t, 2H), 2.97 (m, 4H), 2.88 (s, 3H), 2.84 (m, 2H), 2.03 (m, 2H), 1.86 (m, 2H), 1.76 (m, 2H), 1.50 (m, 2H)

Mass Spectral Analysis m/z=495.5 (M+H)$^+$

Elemental analysis:
$C_{25}H_{30}N_6O_3S$, 1H$_2$O:
Theory: % C, 58.58; % H, 6.29; % N, 16.39.
Found: % C, 58.78; % H, 5.94; % N, 16.40.

EXAMPLE 61A, 61B

Preparation of 61.1:
To a stirred solution of 49.9 (1.47 g, 2.65 mmol, 1 eq) in methanol (80 mL) was added 10% Pd/C (294 mg). The reaction mixture was stirred under a hydrogen atmosphere using a hydrogen balloon overnight. The reaction mixture was then filtered, the catalyst was washed with methanol, and the filtrate was concentrated in vacuo. The crude product was purified by column chromatography (eluent: hexane/ethyl acetate mixtures of increasing polarity).

Yield:~100%.

Preparation of 61.2a, 61.2b:
Compound 61.1 (1.47 g, 2.64 mmol) was subjected to chiral separation to yield two enantiomeric pure isomers 61.2a (600 mg, 40.8%) and 61.2b (550 mg, 37.4%).

HPLC conditions:
Column: Chiralcel AD 2×15 cm
Flow: 20 mL/min, 75% A, 25% B
Detection: UV 254 nm
Mobile phase A: hexane
Mobile phase B: 60 EtOH/40 MeOH 61.2a: $^1$H NMR (400 MHz, CDCl$_3$) δ 7.16 (s, 1H), 7.08 (m, 1H), 6.99 (d, 1H), 6.80 (m, 2H), 6.46 (dd, 1H), 5.12 (brs, 2H), 4.58 (m, 1H), 3.89 (m, 2H), 3.53 (m, 2H), 3.38-3.10 (m, 7H), 1.98 (m, 3H), 1.78 (m, 1H), 1.67-1.52 (m, 2H), 1.48 (s, 9H), 1.27 (m, 3H), 1.18 (m, 3H).

$[α]^{25}_D$ –62.10° (c=1.34, MeOH)

61.2b: $^1$H NMR (400 MHz, CDCl$_3$) δ 7.16 (s, 1H), 7.08 (m, 1H), 6.99 (d, 1H), 6.80 (m, 2H), 6.46 (dd, 1H), 5.12 (brs, 2H), 4.58 (m, 1H), 3.89 (m, 2H), 3.53 (m, 2H), 3.38-3.10 (m, 7H), 1.98 (m, 3H), 1.78 (m, 1H), 1.67-1.52 (m, 2H), 1.48 (s, 9H), 1.27 (m, 3H), 1.18 (m, 3H).

$[α]^{25}_D$ +62.82° (c=1.19, MeOH)

Preparation of 61A:
To a solution of pure enantiomer 61.2a (590 mg, 1.06 mmol) in methanol (30 mL) was added 4.0 M hydrochloric acid in dioxane (2.65 mL, 10.6 mmol, 10 eq). The mixture was stirred at ambient temperature for 24 hours, An additional amount of a 4.0 M hydrochloric acid in dioxane (1.0 mL, 4 mmol, 3.8 eq) was added to the reaction mixture, which was stirred for another 3 days at room temperature. The solvent was evaporated in vacuo. The residue was purified by column chromatography (eluent: methylene chloride-methanol, 10:1).

Yield: 77.5%

$^1$H NMR (400 MHz, DMSO-d$_6$) δ 9.90 (brs, 1H), 8.93 (brs, 1H), 8.78 (brs, 1H), 7.02-6.86 (m, 4H), 6.73 (d, 1H), 6.40 (dd, 1H), 4.49 (m, 1H), 3.39-3.18 (m, 7H), 2.98 (m, 1H), 2.05-1.82 (m, 6H), 1.10 (m, 6H).

$[α]^{25}_D$ –47.31° (c=0.96, MeOH)

Mass Spectral Analysis m/z=413.91 (M+H)$^+$

Elemental analysis:
$C_{24}H_{29}FN_2O_3$, 1HCl, 9/10H$_2$O:
Theory: % C, 61.97; % H, 6.89; % N, 6.02.
Found: % C, 61.89; % H, 6.72; % N, 5.95.

Preparation of 61B:
To a solution of pure enantiomer 61.2b (550 mg, 0.988 mmol) in methanol (30 mL) was added 4.0 M hydrochloric acid in dioxane (2.47 mL, 9.88 mmol, 10 eq). The mixture was stirred at ambient temperature for 24 hours. An additional amount of a 4.0 M hydrochloric acid in dioxane (1.0 mL, 4 mmol, 4 eq) was added to the reaction mixture, which was stirred for another 3 days at room temperature. The solvent was evaporated in vacuo. The residue was purified by column chromatography (eluent: methylene chloride-methanol, 10:1).

Yield: 86%

$^1$H NMR (400 MHz, DMSO-d$_6$) δ 9.94 (brs, 1H), 9.08 (brs, 1H), 8.90 (brs, 1H), 7.0-6.86 (m, 4H), 6.72 (d, 1H), 6.40 (dd, 1H), 4.49 (m, 1H), 3.39-3.16 (m, 7H), 2.98 (m, 1H), 2.03-1.82 (m, 6H), 1.10 (m, 6H).

$[\alpha]^{25}_D$ +46.78° (c=1.17, MeOH)

Mass Spectral Analysis m/z=413.88 (M+H)$^+$

Elemental analysis:

$C_{24}H_{29}FN_2O_3$, 1 HCl, 13/10$H_2O$:

Theory: % C, 61.02; % H, 6.96; % N, 5.93.

Found: % C, 61.00; % H, 6.78; % N, 5.88.

Preparation of 61.4:

O-benzotriazol-1-yl-N,N,N',N'-tetramethyluronium tetrafluoroborate (0.41 g, 1.28 mmol, 1.1 eq) was added at 0° C. to a solution of 21C (0.50 g, 1.28 mmol, 1.1 eq), 61.3 (0.29 g, 1.16 mmol, 1.0 eq) and diisopropylethylamine (0.46 mL, 2.56 mmol, 2.2 eq) in acetonitrile (4 mL). The reaction mixture was warmed to room temperature and stirred for an additional 2 days at room temperature. The reaction mixture was concentrated under reduced pressure, then re-dissolved in ethyl acetate. The solution was washed with a saturated aqueous solution of sodium hydrogen carbonate (50 mL) and brine (50 mL) then dried over sodium sulfate, filtered, and concentrated under reduced pressure. The crude product was purified by column chromatography (eluent: hexane/ethyl acetate mixtures of increasing polarity).

Yield: 95%

$^1$H NMR (400 MHz, DMSO d$_6$) δ 8.28 (s, 1H), 8.07 (d, 1H), 7.99 (m, 2H), 7.70 (m, 1H), 7.62 (m, 1H), 7.42 (m, 2H), 7.38 (d, 1H), 7.31 (d, 1H), 7.21 (m, 1H), 6.98 (m, 1H), 6.91 (m, 1H), 6.88 (m, 1H), 5.89 (d, 1H), 3.93 (m, 1H), 3.72 (m, 1H), 3.55 (m, 2H), 3.45 (m, 2H), 3.24 (m, 2H), 2.22 (m, 1H), 2.07 (m, 2H), 1.85 (m, 2H), 1.63 (m, 1H), 1.13 (m, 6H)

Mass Spectral Analysis m/z=642.13 (M+H)$^+$

X-Ray Crystallography:

Single crystals were grown as plates by dissolving 61.4 (50 mg, 0.008 mmol, 1 eq) in an aqueous methanolic solution (MeOH/water=80:20) and letting sit still at room temperature for 9 months.

Crystal data and structure refinement for 61.4:

Empirical formula: C36H35BrN2O3

Formula weight: 623.57

Temperature: 120(2) K

Wavelength: 0.71073 A

Crystal system, space group: Monoclinic, P2(1)

Unit cell dimensions:

a=7.435(3) A; alpha=90 deg.

b=14.851(6) A; beta=93.695(6) deg.

c=13.628(5) A; gamma=90 deg.

Volume: 1501.7(10) A$^3$

Z, Calculated density: 2, 1.379 Mg/m$^3$

Absorption coefficient: 1.408 mm$^{-1}$

F(000): 648

Crystal size: 0.22×0.10×0.04 mm

Theta range for data collection: 2.03 to 28.27 deg.

Limiting indices: −9<=h<=9, −19<=k<=18, −17<=l<=17

Reflections collected/unique: 16930/6798 [R(int)=0.0287]

Completeness to theta=28.27: 94.1%

Absorption correction: Semi-empirical from equivalents

Max. and min. transmission: 0.9458 and 0.7470

Refinement method: Full-matrix least-squares on F$^2$

Data/restraints/parameters: 6798/1/381

Goodness-of-fit on F$^2$ −1.034

Final R indices [I>2sigma(I)]: R1=0.0340, wR2=0.0846

R indices (all data): R1=0.0354, wR2=0.0857

Absolute structure parameter: −0.002(5)

Largest diff. peak and hole: 0.792 and −0.236 e.A$^{-3}$

Biological Methods

In Vitro Assays

The potencies of the compounds listed in Table 2 were determined by testing the ability of a range of concentrations of each compound to inhibit the binding of the non-selective opioid antagonist, [$^3$H]diprenorphine, to the cloned human μ, κ, and δ opioid receptors, expressed in separate cell lines. IC$_{50}$ values were obtained by nonlinear analysis of the data using GraphPad Prism version 3.00 for Windows (GraphPad Software, San Diego). K$_i$ values were obtained by Cheng-Prusoff corrections of IC$_{50}$ values.

Receptor Binding

The receptor binding method (DeHaven and DeHaven-Hudkins, 1998) was a modification of the method of Raynor et al. (1994). After dilution in buffer A and homogenization as before, membrane proteins (10-80 μg) in 250 μL were added to mixtures containing test compound and [$^3$H]diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 μM naloxone. K$_i$ values were determined by Cheng-Prusoff corrections of IC$_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors (K$_i$), radioligand bound (cpm) in the presence of various concentrations of test compounds was measured. The concentration to give half-maximal inhibition (EC$_{50}$) of radioligand binding was determined from a best nonlinear regression fit to the following equation, $$Y = \text{Bottom} + \frac{(\text{Top} - \text{Bottom})}{1 + 10^{X-\text{Log}EC50}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and LogEC$_{50}$ is the log of the concentration of test compound where the amount of radioligand bound is half-way between Top and Bottom. The nonlinear regression fit was performed using the program Prism® (GraphPad Software, San Diego, Calif.). The K$_i$ values were then determined from the EC$_{50}$ values by the following equation, $$K_i = \frac{EC_{50}}{1 + \frac{[ligand]}{K_d}}$$

where [ligand] is the concentration of radioligand and $K_d$ is the equilibrium dissociation constant for the radioligand.

Receptor-Mediated [$^{35}$S]GTPγS Binding

The potency and efficacy of compounds at each of the receptors are assessed by modifications of the methods of Selley et al., 1997 and Traynor and Nahorski, 1995 using receptor-mediated [$^{35}$S]GTPγS binding in the same membrane preparations used to measure receptor binding. Assays are carried out in 96-well FlashPlates® (Perkin Elmer Life Sciences, Inc, Boston, Mass.). Membranes prepared from CHO cells expressing the appropriate receptor (50-100 µg of protein) are added to assay mixtures containing agonist with or without antagonists, 100 pM [$^{35}$S]GTPγS (approx. 100,000 dpm), 3.0 µM GDP, 75 mM NaCl, 15 mM MgCl$_2$, 1.0 mM ethylene glycol-bis(β-aminoethyl ether)-N,N,N',N'-tetracetic acid, 1.1 mM dithiothreitol, 10 µg/mL leupeptin, 10 µg/mL pepstatin A, 200 µg/mL bacitracin, and 0.5 µg/mL aprotinin in 50 mM Tris-HCl buffer, pH 7.8. After incubation at room temperature for one hour, the plates are sealed, centrifuged at 800×g in a swinging bucket rotor for 5 min and bound radioactivity determined with a TopCount microplate scintillation counter (Packard Instrument Co., Meriden, Conn.).

$EC_{50}$ values for agonists are determined from nonlinear regression fits of 8- or 12-point titration curves to the 4-parameter equation for a sigmoidal dose-response with a slope factor of 1.0 using GraphPad Prism® version 3.00 for Windows (GraphPad Software, San Diego, Calif.).

To determine $IC_{50}$ values, the concentrations to give half-maximal inhibition of agonist-stimulated [$^{35}$S]GTPγS binding, the amount of [$^{35}$S]GTPγS bound in the presence of a fixed concentration of agonist and various concentrations of antagonist was measured. The fixed concentration of agonist was the $EC_{80}$, the concentration to give 80% of the relative maximum stimulation of [$^{35}$S]GTPγS binding. The agonists loperamide (100 nM), U50,488 (50 nM), and BW373U86 (2.0 nM) were used to stimulate [$^{35}$S]GTPγS binding via the µ, δ, and κ opioid receptors, respectively. The $IC_{50}$ value was determined from a best nonlinear regression fit of the data to the 4-parameter equation for a sigmoidal dose-response with a slope factor of 1.0 using GraphPad Prism® version 3.00 for Windows.

The potencies of the compounds were determined by testing the ability of a range of concentrations of each compound to inhibit the binding of the non-selective opioid antagonist, [$^3$H]diprenorphine, to the cloned human µ, κ, and δ opioid receptors, expressed in separate cell lines. All the compounds tested (compounds included in Table 2) bind with affinity to the human cloned δ opioid receptor less than 2 µM ($K_i$ values). These compounds display high selectivity δ/κ and δ/µ (at least 10-fold). The potencies of the agonists were assessed by their abilities to stimulate [$^{35}$S]GTPγS binding to membranes containing the cloned human δ opioid receptors. All the compounds listed in Table 2 were shown to be agonists at the δ opioid receptor.

As example, 33M (Table 2) binds to the delta, mu, and kappa opioid receptors with affinity (expressed as $K_i$ value) of 9.7 nM, >1000 nM and >1000 nM, respectively. Furthermore, 33M displayed in vitro agonist activity ($EC_{50}$=287 nM).

As further example, 43D (Table 2) binds to the delta, mu, and kappa opioid receptors with affinity (expressed as $K_i$ value) of 2.5 nM, >100 nM and >1000 nM, respectively. Furthermore, 43D displayed potent in vitro agonist activity ($EC_{50}$=63 nM).

Example 61A (Table 3) and 61B (enantiomeric analog of Example 61A) bind to the δ opioid receptor with affinity (expressed as $K_i$ value) of 0.59 nM, and 75 nM, respectively.

Furthermore, Example 61A displayed potent in vitro δ agonist activity ($EC_{50}$=16.8 nM), whereas Example 61B displayed weaker in vitro δ agonist activity ($EC_{50}$=1282 nM), when compared to Example 61A.

In Vivo Assay

Freunds Complete Adjuvant (FCA)-Induced Hyperalgesia

Rats were injected intraplantar with FCA and 24 h later treated with tested compounds administered orally. Paw Pressure Thresholds (PPT) was assessed 60 minutes after drug treatment. In this assay, 43D produced siginificant anti-hyperalgesic activity (193±47% antihyperalgesia) after oral administration (3 mg/kg dose).

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula XIV:

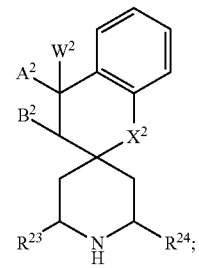

XIV wherein:
W$^2$ is aryl or heteroaryl, wherein the aryl or heteroaryl is substituted with 0-3 groups selected independently from hydroxy, aminocarbonyl (—C(=O)—NH$_2$), N-alkylaminocarbonyl (—C(=O)—NH(alkyl)), and N,N-dialkylaminocarbonyl (—C=O)—N(alkyl)(alkyl));

R$^{23}$ and R$^{24}$ are each independently H or alkyl, provided that at least one of R$^{23}$ and R$^{24}$ is alkyl;

A$^2$ and B$^2$ are each H, or together form a double bond; and

X$^2$ is —CH$_2$— or —O—;

or a stereoisomer, pharmaceutically acceptable salt, or N-oxide thereof.

2. A compound according to claim 1, wherein W$^2$ is:

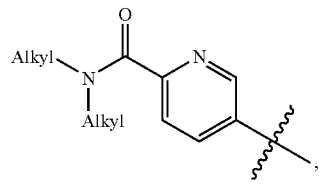

-continued

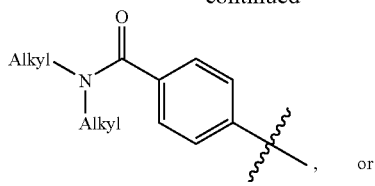

or

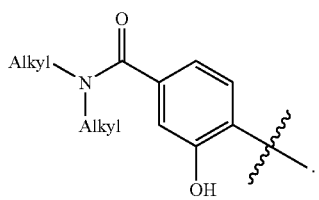

3. A compound according to claim 2, wherein $W^2$ is:

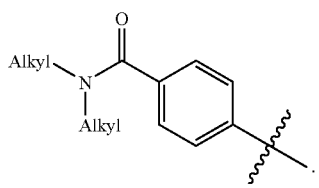

4. A compound according to claim 1, wherein $X^2$ is —O—.

5. A compound according to claim 1, wherein $A^2$ and $B^2$ together form a double bond.

6. A compound according to claim 1, of formula XV:

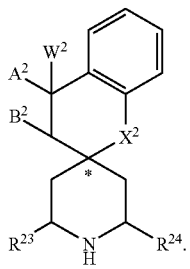
XV

7. A compound according to claim 1, of formula XVI:

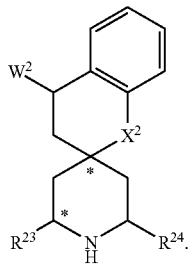
XVI

8. A compound according to claim 1, wherein the compound is:

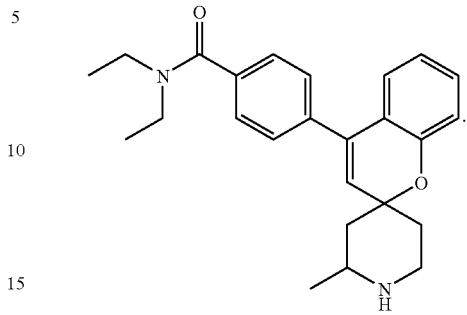

9. A compound according to claim 1, wherein the compound is:

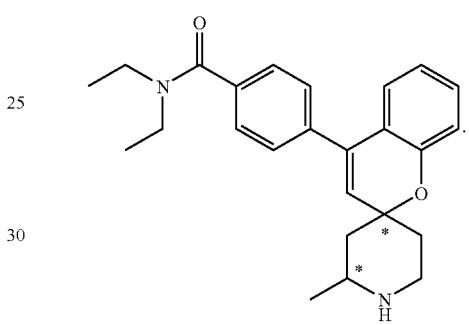

10. A compound of formula XXII:

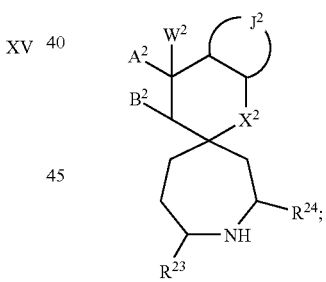
XVII wherein:
$W^2$ is aryl or heteroaryl, wherein the aryl or heteroaryl is substituted with 0-3 groups selected independently from heteroaryl, hydroxy, carboxy (—COOH), —C(=O)-alkyl, —C(=O)-aryl, —C(=O)—O-alkyl, —S(=O)$_2$—N(alkyl)(alkyl); aminocarbonyl (—C(=O)—NH$_2$), N-alkylaminocarbonyl (—C(=O)—NH(alkyl)), and N,N-dialkylaminocarbonyl (—C(=O)—N(alkyl) (alkyl));
$R^{23}$ and $R^{24}$ are each independently H or alkyl;
$A^2$ and $B^2$ are each H, or together form a double bond; and
$J^2$ when taken together with the carbon atoms to which it is attached forms a 6-membered aryl ring substituted with 0-3 groups selected independently from halo, heterocycloalkyl, hydroxy, alkoxy, —S(=O)$_2$-alkyl, —S(=O)$_2$—NH$_2$, —S(=O)$_2$—NH(alkyl), —S(=O)₂—N(alkyl)(alkyl), carboxy (—COOH), —C(=O)—O-alkyl, and N,N-dialkylaminocarbonyl (—C(=O)—N(alkyl)(alkyl));

or a stereoisomer, pharmaceutically acceptable salt, or N-oxide thereof;

provided that:

when W² is para-diethylaminocarbonylphenyl, para-prop-2-ylaminocarbonylphenyl, orpara-pent-3-ylaminocarbonylphenyl, R²³ and R²⁴ are each H, and A and B are each H or together form a double bond, then J² is other than unsubstituted phenyl or anisyl; and when W² is:

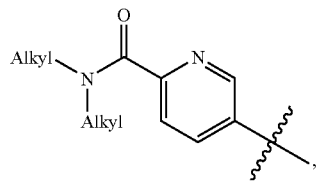

R²³ and R²⁴ are each H, and A and B together form a double bond; then J² is other than unsubstituted phenyl.

11. A compound according to claim 10, wherein W² is:

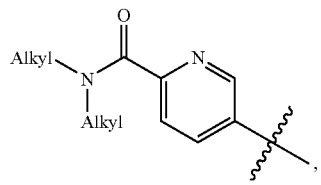

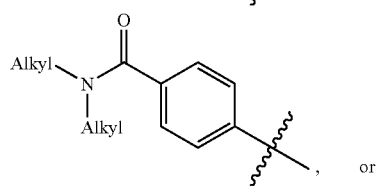

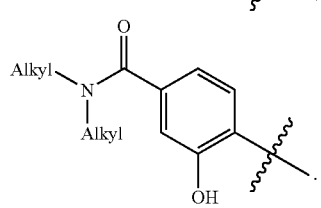

12. A compound according to claim 10, wherein R²³ and R²⁴ are each H.

13. A compound according to claim 10, of formula XXIII:

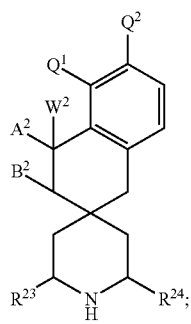

XXIII wherein:

Q¹ and Q² are each independently H, halo, heterocycloalkyl, hydroxy, alkoxy, —S(=O)₂-alky, —S(=O)₂—NH₂, —S(=O)₂—N(alkyl)(alkyl), carboxy (—COOH), —C(=O)—O-alkyl, or N,N-dialkylaminocarbonyl (—C(=O)—N(alkyl)(alkyl)).

14. A compound according to claim 13, wherein W² is:

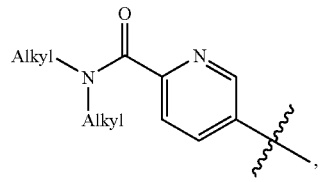

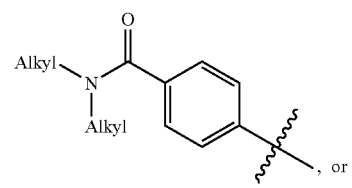

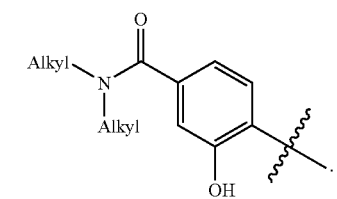

15. A compound according to claim 14, wherein R²³ and R²⁴ are each H.

16. A compound according to claim 10, of formula XXIV:

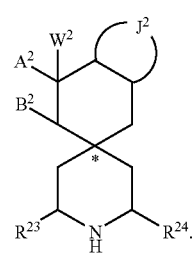

XXIV

17. A compound according to claim 10, wherein the compound is:

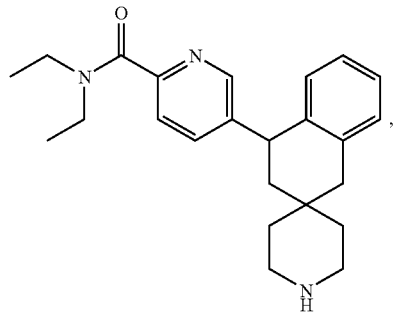

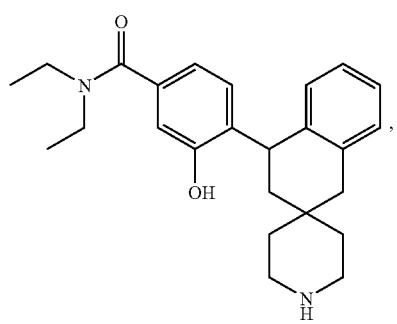, or

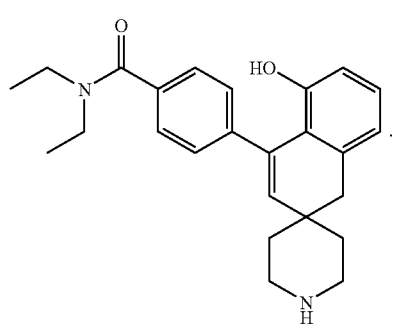

18. A compound according to claim 17, wherein the compound is:

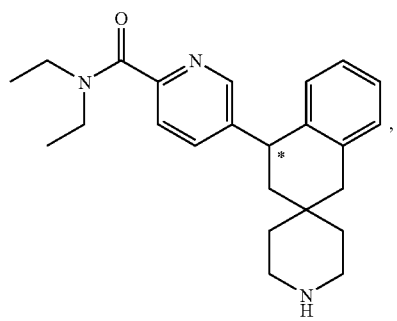

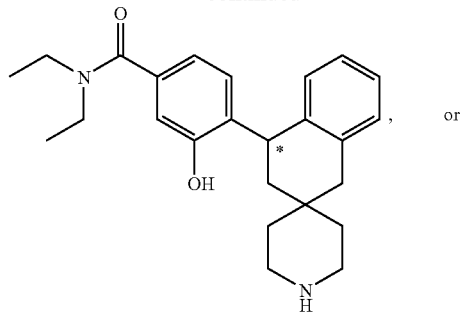, or

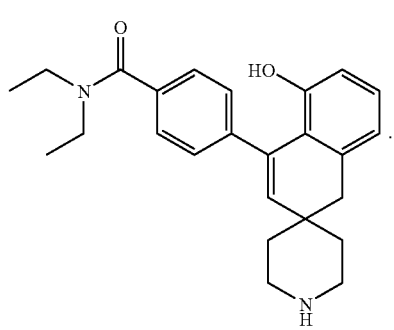

19. A compound of formula XXV:

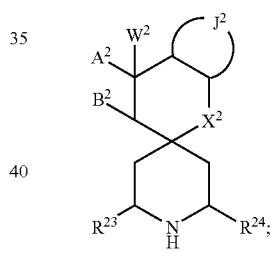

XXV wherein:
W² is aryl optionally substituted with —C(=O)-alkyl or —C(=O)-aryl;
R²³ and R²⁴ are each independently H or alkyl;
A² and B² are each H, or together form a double bond;
X² is —CH₂— or —O—; and
J² when taken together with the carbon atoms to which it is attached forms a 6-membered aryl ring substituted with 0-3 groups selected independently from hydroxy, alkoxy, —S(=O)₂-alkyl, —S(=O)₂—NH₂, —S(=O)₂—NH(alkyl), —S(=O)₂—N(alkyl)(alkyl), —C(=O)—N(alkyl)(alkyl), carboxy (—COOH), and —C(=O)—O-alkyl;
or a stereoisomer, pharmaceutically acceptable salt, or N-oxide thereof;
provided that the compound of formula XXV is other than 4-phenyl-spiro[2H,1-benzopyran-2,4'-piperidine].

20. A compound according to claim 19, wherein R²³ and R²⁴ are each H.

21. A compound according to claim 19 of formula XXVI:

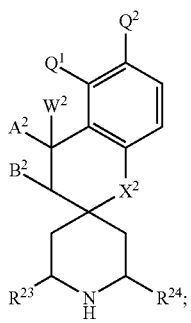

XXVI wherein:

Q$^1$ and Q$^2$ are each independently H, hydroxy, alkoxy, —S(=O)$_2$-alkyl, —S(=O)$_2$—NH$_2$, —S(=O)$_2$—NH(alkyl), —S(=O)$_2$—N(alkyl)(alkyl), —C(=O)—N(alkyl)(alkyl), carboxy (—COOH), or —C(=O)—O-alkyl.

22. A compound according to claim 19, wherein A$^2$ and B$^2$ taken together form a double bond.

23. A compound according to claim 22, wherein X$^2$ is —O—.

24. A compound of formula XXVII:

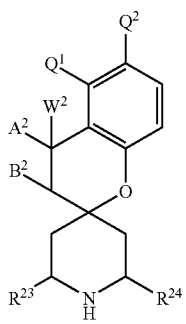

XXVII wherein:

W$^2$ is para-dialkylaminocarbonylphenyl, the phenyl group of which is further optionally substituted with 1-2 groups independently selected from tetrazolyl, N-alkyltetrazolyl, hydroxy, carboxy (—COOH), and aminocarbonyl (—C(=O)—NH$_2$);

R$^{23}$ and R$^{24}$ are each independently H or alkyl;

A$^2$ and B$^2$ are each H, or together form a double bond;

Q$^1$ and Q$^2$ are each independently H, hydroxy, alkoxy, haloalkoxy, halo, or heterocycloalkyl;

or a stereoisomer, pharmaceutically acceptable salt, or N-oxide thereof; provided that:

when one of Q$^1$ and Q$^2$ is hydroxy and the other is H, or both Q$^1$ and Q$^2$ are hydroxy, then the phenyl group of W$^2$ is further substituted with 1-2 groups selected from tetrazolyl, N-alkyltetrazolyl, hydroxy, carboxy (—COOH), and aminocarbonyl (—C(=O)—NH$_2$);

when Q$^1$, Q$^2$, R$^{23}$, and R$^{24}$ are each H and the phenyl group of W$^2$ is further substituted with one hydroxy, then A$^2$ and B$^2$ are each H;

when W$^2$ is para-dialkylaminocarbonylphenyl, then at least one of Q$^1$, Q$^2$, R$^{23}$, and R$^{24}$ is other than H;

when W$^2$ is para-dialkylaminocarbonylphenyl, R$^{23}$ and R$^{24}$ are each H, and Q$^2$ is halo, then Q$^1$ is other than H or hydroxy;

when W$^2$ is para-dialkylaminocarbonylphenyl, R$^{23}$ and R$^{24}$ are each H, Q$^1$ is methoxy, or cyclopropylmethoxy, and Q$^2$ is H, then A$^2$ and B$^2$ are each H; and when W$^2$ is para-dialkylaminocarbonylphenyl, R$^{23}$ and R$^{24}$ are each H, and Q$^1$ is H or OH, then Q$^2$ is other than methoxy, cyclopropylmethoxy.

25. A compound according to claim 24, wherein W$^2$ is:

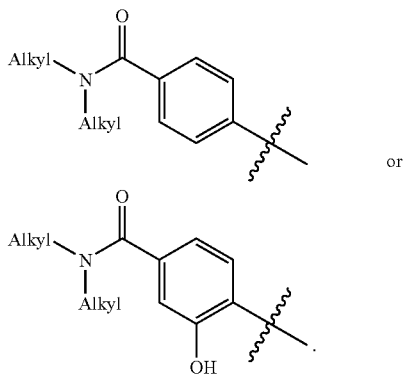

26. A compound according to claim 24, wherein R$^{23}$ and R$^{24}$ are each H.

27. A compound according to claim 25, wherein R$^{23}$ and R$^{24}$ are each H.

28. A compound according to claim 24, wherein the compound is:

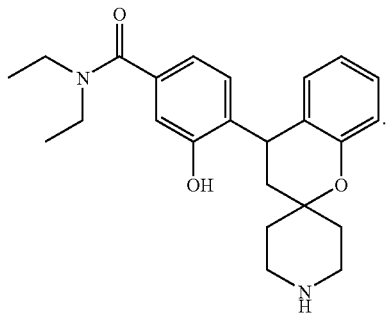

29. A compound of formula XXVIII:

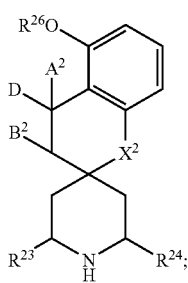

XXVIII wherein:
D is:

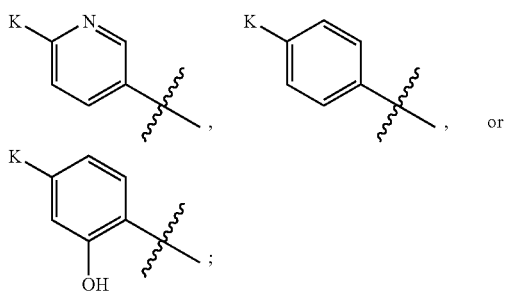

K is carboxy (—COOH), —C(=O)—O-alkyl, —S(=O)₂—N(alkyl)(alkyl), heteroaryl, alkylheteroaryl, aminocarbonyl (—C(=O)—NH₂), or N-alkylaminocarbonyl (—C(=O)—NH(alkyl));
R²³, R²⁴, and R²⁶ are each independently H or alkyl;
A² and B² are each H, or together form a double bond; and
X² is —CH₂— or —O—;
or a stereoisomer, pharmaceutically acceptable salt, or N-oxide thereof.

30. A compound according to claim 29, wherein R²³ and R²⁴ are each H.

31. A compound according to claim 29, wherein R²⁶ is H.

32. A compound according to claim 29, wherein the compound is:

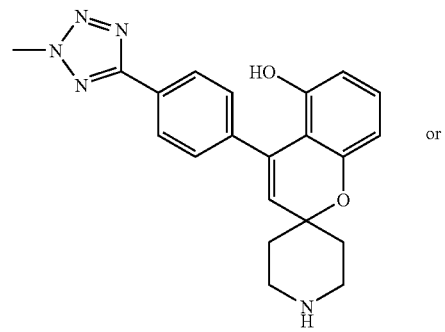

or

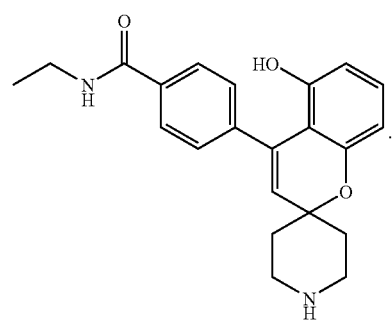

33. A compound of formula XXIX:

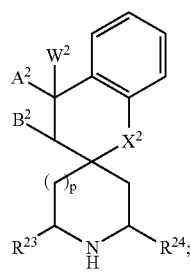

XXIX wherein:
W² is para-N(alkyl),N(alkyl-Z)aminocarbonylaryl or para-N(alkyl),N(alkyl-Z)aminocarbonylheteroaryl, wherein the aryl or heteroaryl ring of W² is substituted with 0-2 groups selected independently from hydroxy and alkoxy;
Z is alkoxy, alkylamino, or dialkylamino;
R²³ and R²⁴ are each independently H or alkyl;
A² and B² are each H, or together form a double bond; and
X² is —CH₂— or —O—;
or a stereoisomer, pharmaceutically acceptable salt, or N-oxide thereof.

34. A compound according to claim 33, wherein W² is:

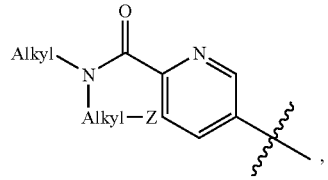

,

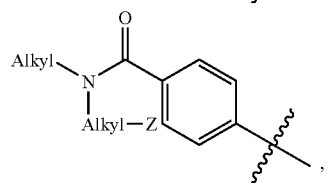

, or

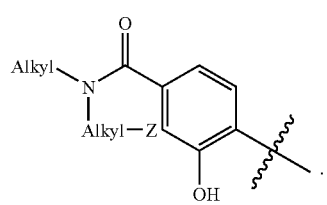

.

35. A compound according to claim 34, wherein W² is:

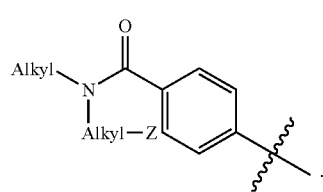

.

36. A compound according to claim 33, wherein $A^2$ and $B^2$ together form a double bond.

37. A compound according to claim 33, wherein $X^2$ is —O—.

38. A compound according to claim 33, wherein $R^{23}$ and $R^{24}$ are each H.

39. A compound according to claim 33, wherein the compound is:

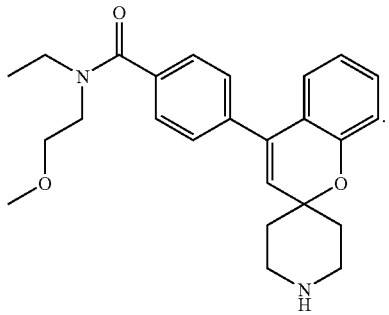

40. A compound of formula XXX:

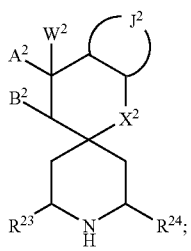

wherein:

$W^2$ is:

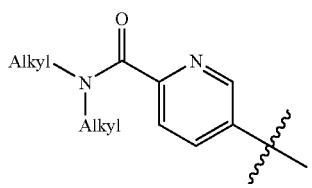

or

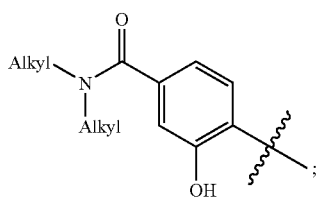

$R^{23}$ and $R^{24}$ are each independently H or alkyl;

$A^2$ and $B^2$ are each H, or together form a double bond;

$X^2$ is —CH$_2$— or —O—; and $J^2$ when taken together with the carbon atoms to which it is attached forms a 6-membered aryl ring substituted with 1-3 groups selected independently from halo and haloalkoxy;

or a stereoisomer, pharmaceutically acceptable salt, or N-oxide thereof;

provided that when $W^2$ is:

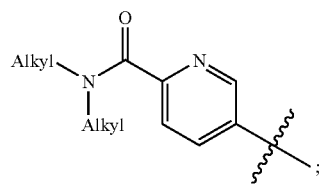

then the aryl ring of $J^2$ is substituted with at least one haloalkoxy.

41. A compound according to claim 40, wherein $R^{23}$ and $R^{24}$ are each H.

42. A compound according to claim 40, of formula XXXI:

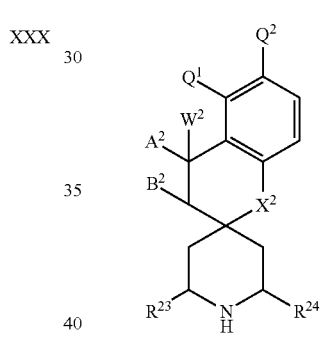

wherein:

$Q^1$ and $Q^2$ are each independently H, halo, or haloalkoxy, provided that at least one of $Q^1$ and $Q^2$ is other than H.

43. A compound according to claim 42, wherein $R^{23}$ and $R^{24}$ are each H.

44. A compound according to claim 40, wherein the compound is:

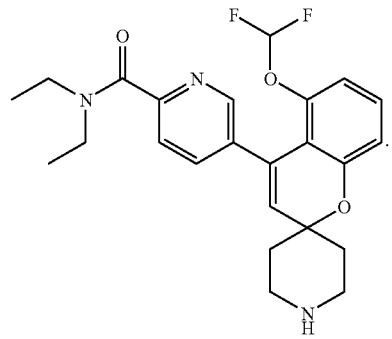

45. A compound of formula XXXII:

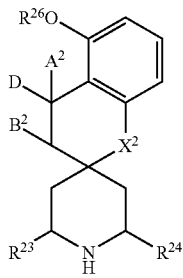

XXXII wherein:
D is N(alkyl),N(alkyl)aminocarbonylheteroaryl;
$R^{23}$, $R^{24}$, and $R^{26}$ are each independently H or alkyl;
$A^2$ and $B^2$ are each H, or together form a double bond; and
$X^2$ is —$CH_2$— or —O—;
or a stereoisomer, pharmaceutically acceptable salt, or N-oxide thereof;
provided that when D is:

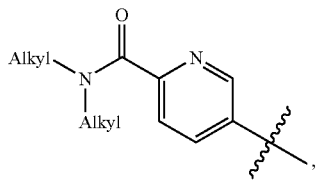

and $X^2$ is —O—, then $A^2$ and $B^2$ are each H.

46. A compound according to claim 45, wherein $A^2$ and $B^2$ are each H.

47. A compound according to claim 45, wherein $X^2$ is —O—.

48. A compound according to claim 45, wherein the heteroaryl ring of D is thienyl or pyridyl.

49. A compound according to claim 45, wherein the compound is:

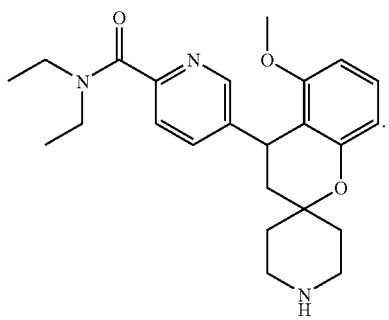

50. A pharmaceutical composition, comprising:
a pharmaceutically acceptable carrier; and a compound of formula XIV:

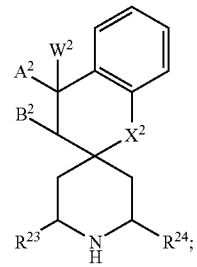

XIV wherein:
$W^2$ is aryl or heteroaryl, wherein the aryl or heteroaryl is substituted with 0-3 groups selected independently from hydroxy, aminocarbonyl (—C(=O)—$NH_2$), N-alkylaminocarbonyl (—C(=O)—NH(alkyl)), and N,N-dialkylaminocarbonyl (—C(=O)—N(alkyl)(alkyl));
$R^{23}$ and $R^{24}$ are each independently H or alkyl, provided that at least one of $R^{23}$ and $R^{24}$ is alkyl;
$A^2$ and $B^2$ are each H, or together form a double bond; and
$X^2$ is —$CH_2$— or —O—;
or a stereoisomer, pharmaceutically acceptable salt, or N-oxide thereof.

51. A pharmaceutical composition, comprising:
a pharmaceutically acceptable carrier; and a compound of formula XXII:

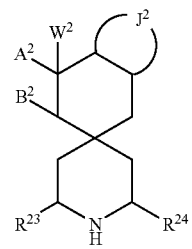

XXII wherein:
$W^2$ is aryl or heteroaryl, wherein the aryl or heteroaryl is substituted with 0-3 groups selected independently from heteroaryl, hydroxy, carboxy (—COOH), —C(=O)-alkyl, —C(=O)-aryl, —C(=O)—O-alkyl, —S(=O)$_2$—N(alkyl)(alkyl); aminocarbonyl (—C(=O)—$NH_2$), N-alkylaminocarbonyl (—C(=O)—NH(alkyl)), and N,N-dialkylaminocarbonyl (—C(=O)—N(alkyl)(alkyl));
$R^{23}$ and $R^{24}$ are each independently H or alkyl;
$A^2$ and $B^2$ are each H, or together form a double bond; and
$J^2$ when taken together with the carbon atoms to which it is attached forms a 6-membered aryl ring substituted with 0-3 groups selected independently from halo, heterocycloalkyl, hydroxy, alkoxy, —S(=O)$_2$-alkyl, —S(=O)$_2$—$NH_2$, —S(=O)$_2$—NH(alkyl), —S(=O)$_2$—N(alkyl)(alkyl), carboxy (—COOH), —C(=O)—O-alkyl, and N,N-dialkylaminocarbonyl (—C(=O)—N(alkyl)(alkyl));
or a stereoisomer, pharmaceutically acceptable salt, or N-oxide thereof;
provided that:
when W² is para-diethylaminocarbonylphenyl, para-prop-2-ylaminocarbonylphenyl, or para-pent-3-ylaminocarbonylphenyl, R²³ and R²⁴ are each H, and A and B are each H or together form a double bond, then J² is other than unsubstituted phenyl or anisyl; and
when W² is:

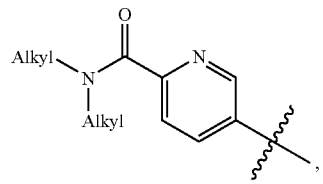

R²³ and R²⁴ are each H, and A and B together form a double bond; then J² is other than unsubstituted phenyl.

52. A pharmaceutical composition, comprising:
a pharmaceutically acceptable carrier; and a compound of formula XXV:

XXV

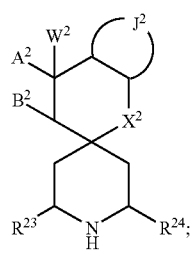

wherein:
W² is aryl optionally substituted with —C(=O)-alkyl or —C(=O)-aryl;
R²³ and R²⁴ are each independently H or alkyl;
A² and B² are each H, or together form a double bond;
X² is —CH₂— or —O—; and
J² when taken together with the carbon atoms to which it is attached forms a 6-membered aryl ring substituted with 0-3 groups selected independently from hydroxy, alkoxy, —S(=O)₂-alkyl, —S(=O)₂—NH₂, —S(=O)₂—NH(alkyl), —S(=O)₂—N(alkyl)(alkyl), —C(=O)—N(alkyl)(alkyl), carboxy (—COOH), and —C(=O)—O-alkyl;
or a stereoisomer, pharmaceutically acceptable salt, or N-oxide thereof;
provided that the compound of formula XXV is other than 4-phenyl-spiro[2H,1-benzopyran-2,4'-piperidine].

53. A pharmaceutical composition, comprising:
a pharmaceutically acceptable carrier; and a compound of formula XXVIIA:

XXVIIA

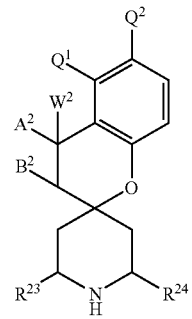

wherein:
W² is para-dialkylaminocarbonylphenyl, the phenyl group of which is further optionally substituted with 1-2 groups independently selected from tetrazolyl, N-alkyltetrazolyl, hydroxy, carboxy (—COOH), and aminocarbonyl (—C(=O)—NH₂);
R²³ and R²⁴ are each independently H or alkyl;
A² and B² are each H, or together form a double bond;
Q¹ and Q² are each independently H, hydroxy, alkoxy, haloalkoxy, halo, or heterocycloalkyl;
or a stereoisomer, pharmaceutically acceptable salt, or N-oxide thereof;
provided that:
when one of Q¹ and Q² is hydroxy and the other is H, then the phenyl group of W² is further substituted with 1-2 groups selected from tetrazolyl, N-alkyltetrazolyl, hydroxy, carboxy (—COOH), and aminocarbonyl (—C(=O)—NH₂);
when Q¹, Q², R²³, and R²⁴ are each H and the phenyl group of W² is further substituted with one hydroxy, then A² and B² are each H;
when W² is para-dialkylaminocarbonylphenyl, then at least one of Q¹, Q², R²³, and R²⁴ is other than H;
when W² is para-dialkylaminocarbonylphenyl, R²³ and R²⁴ are each H, and Q² is halo, then Q¹ is other than H;
when W² is para-dialkylaminocarbonylphenyl, R²³ and R²⁴ are each H, Q¹ is methoxy, cyclopropylmethoxy, and Q² is H, then A² and B² are each H; and
when W² is para-dialkylaminocarbonylphenyl, R²³ and R²⁴ are each H, and Q¹ is H, or OH, then Q² is other than methoxy, cyclopropylmethoxy.

54. A pharmaceutical composition, comprising:
a pharmaceutically acceptable carrier; and a compound of formula XXVIII:

XXVIII

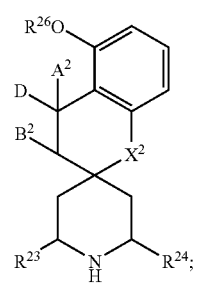

wherein:

D is:

K is carboxy (—COOH), —C(=O)—O-alkyl, —S(=O)$_2$—N(alkyl)(alkyl), heteroaryl, alkylheteroaryl, aminocarbonyl (—C(=O)—NH$_2$), or N-alkylaminocarbonyl (—C(=O)—NH(alkyl));

R$^{23}$, R$^{24}$, and R$^{26}$ are each independently H or alkyl;

A$^2$ and B$^2$ are each H, or together form a double bond; and

X$^2$ is —CH$_2$— or —O—;

or a stereoisomer, pharmaceutically acceptable salt, or N-oxide thereof.

55. A pharmaceutical composition, comprising:

a pharmaceutically acceptable carrier; and a compound of formula XXIX:

XXIX wherein:

W$^2$ is para-N(alkyl),N(alkyl-Z)aminocarbonylaryl or para-N(alkyl),N(alkyl-Z)aminocarbonylheteroaryl, wherein the aryl or heteroaryl ring of W$^2$ is substituted with 0-2 groups selected independently from hydroxy and alkoxy;

Z is alkoxy, alkylamino, or dialkylamino;

R$^{23}$ and R$^{24}$ are each independently H or alkyl;

A$^2$ and B$^2$ are each H, or together form a double bond; and

X$^2$ is —CH$_2$— or —O—;

or a stereoisomer, pharmaceutically acceptable salt, or N-oxide thereof.

56. A pharmaceutical composition, comprising:

a pharmaceutically acceptable carrier; and a compound of formula XXX:

XXX wherein:

W$^2$ is:

or

;

R$^{23}$ and R$^{24}$ are each independently H or alkyl;

A$^2$ and B$^2$ are each H, or together form a double bond;

X$^2$ is —CH$_2$— or —O—; and

J$^2$ when taken together with the carbon atoms to which it is attached forms a 6-membered aryl ring substituted with 1-3 groups selected independently from halo or haloalkoxy;

or a stereoisomer, pharmaceutically acceptable salt, or N-oxide thereof;

provided that when W$^2$ is:

;

then the aryl ring of J$^2$ is substituted with at least one haloalkoxy.

57. A pharmaceutical composition, comprising:
a pharmaceutically acceptable carrier; and a compound of formula XXXII:

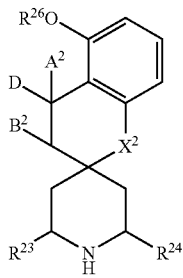

XXXII wherein:
D is N(alkyl),N(alkyl)aminocarbonylheteroaryl;
$R^{23}$, $R^{24}$, and $R^{26}$ are each independently H or alkyl;
$A^2$ and $B^2$ are each H, or together form a double bond; and
$X^2$ is —CH$_2$— or —O—;
or a stereoisomer, pharmaceutically acceptable salt, or N-oxide thereof;
provided that when D is:

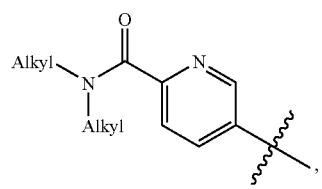

and $X^2$ is —O—, then $A^2$ and $B^2$ are each H.

58. A compound according to claim 10, wherein the compound is:

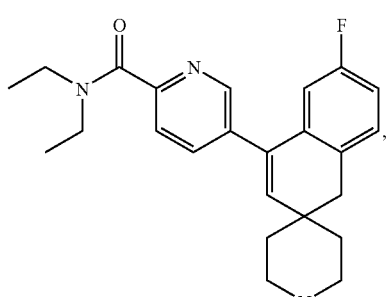

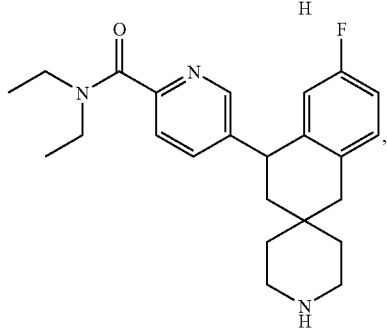

-continued

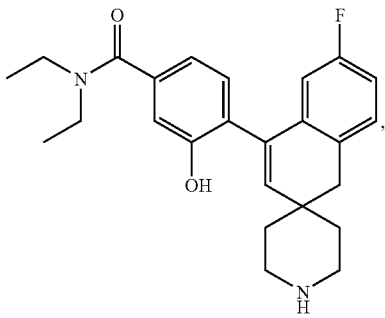

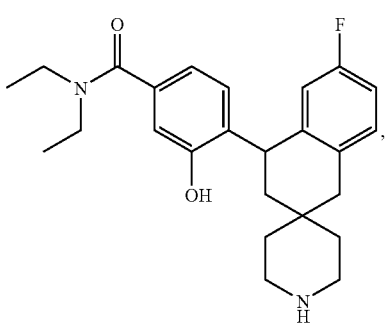

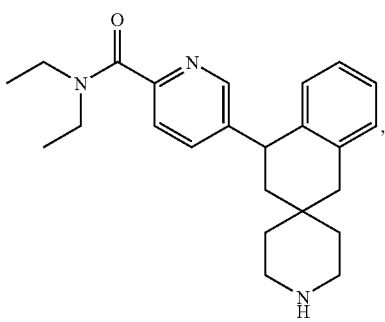

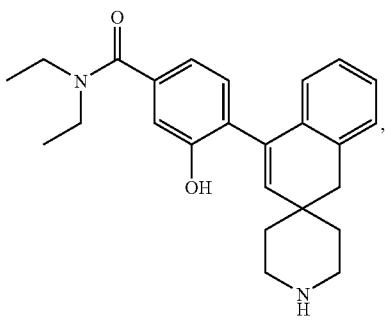

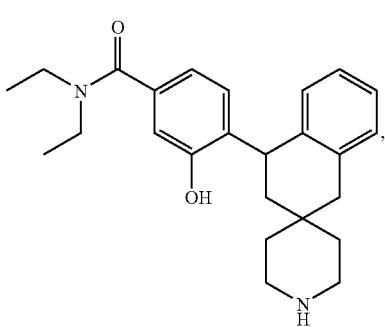

-continued
799
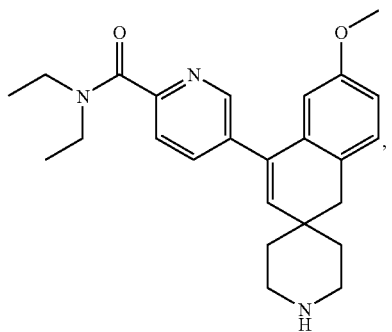
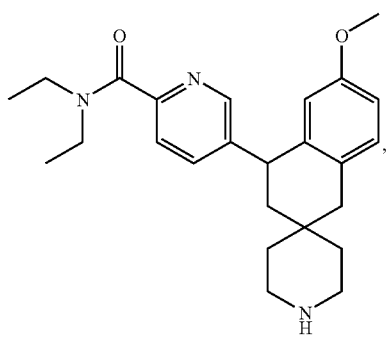
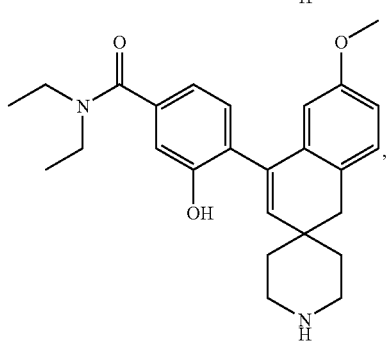
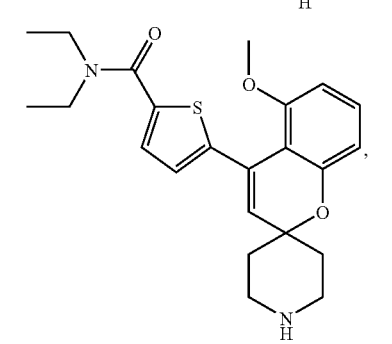
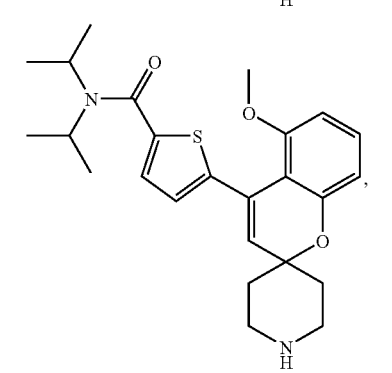
-continued
800
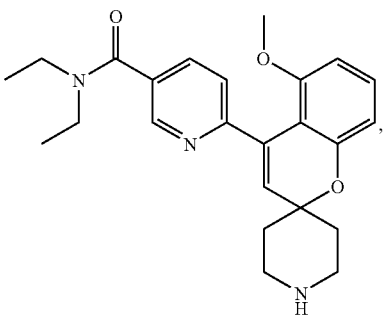
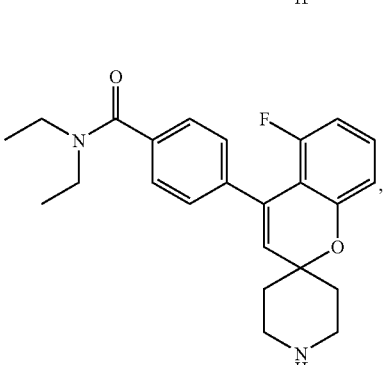
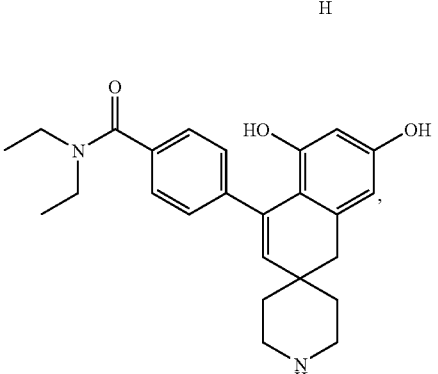
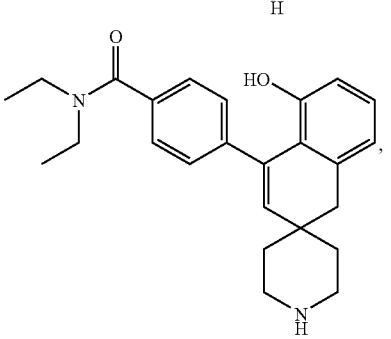
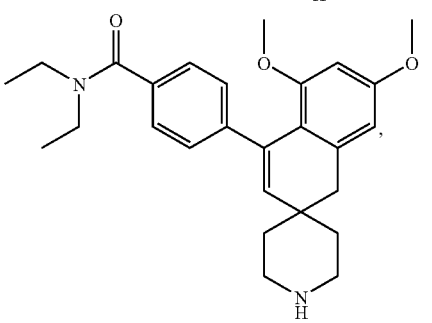

-continued
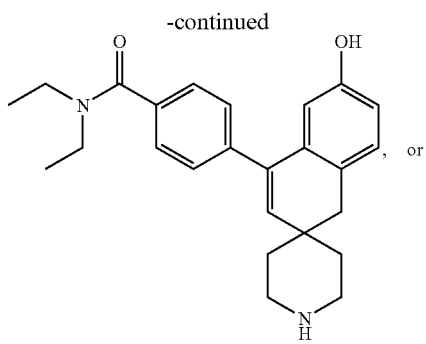 , or
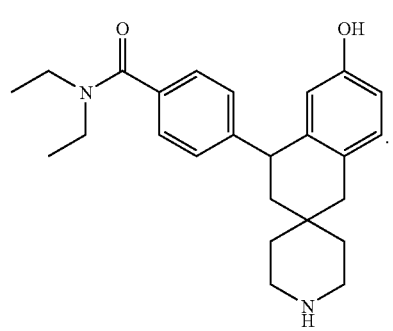
59. A compound according to claim 19, wherein the compound is:
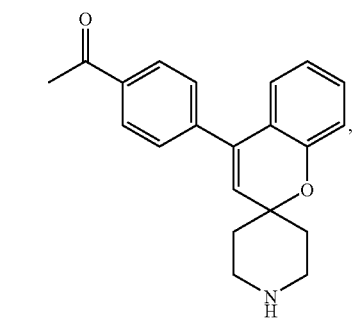
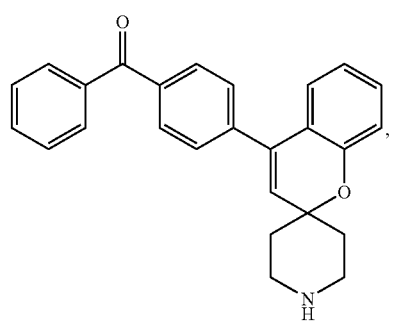
-continued
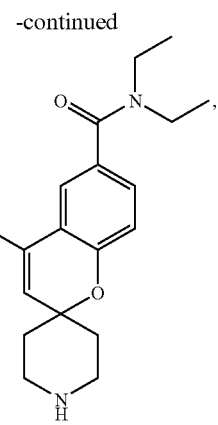 ,
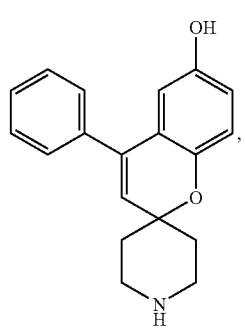 ,
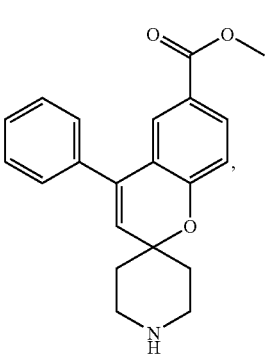 ,
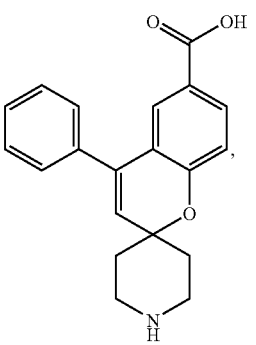 ,

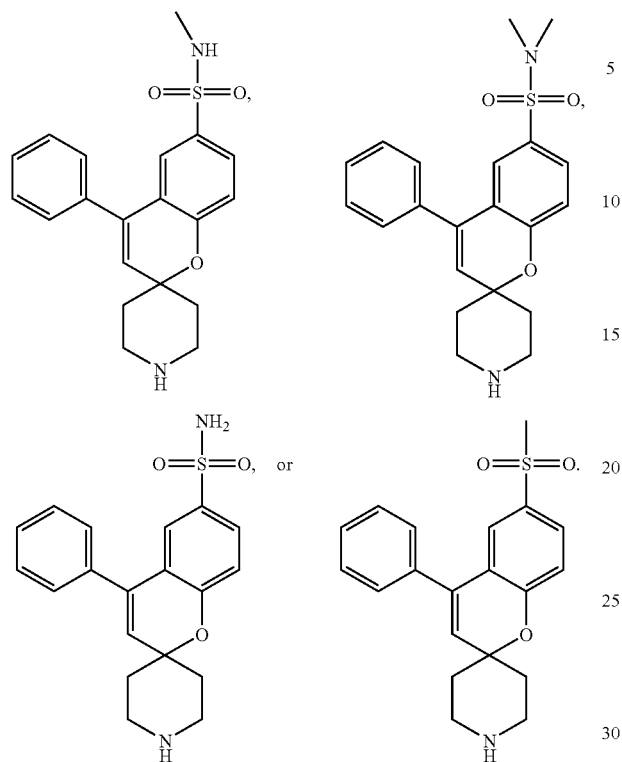
60. A compound according to claim 24, wherein the compound is:
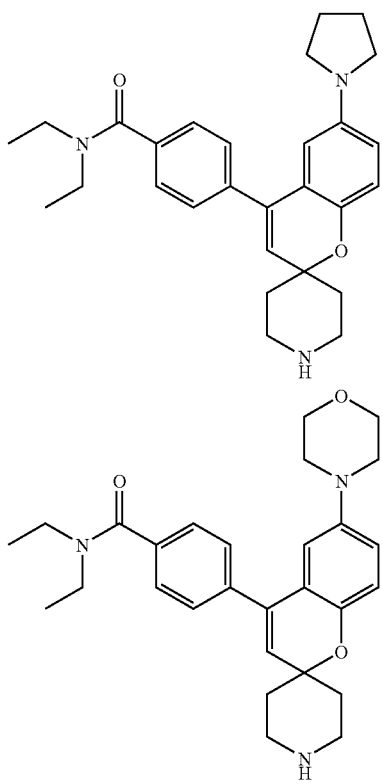
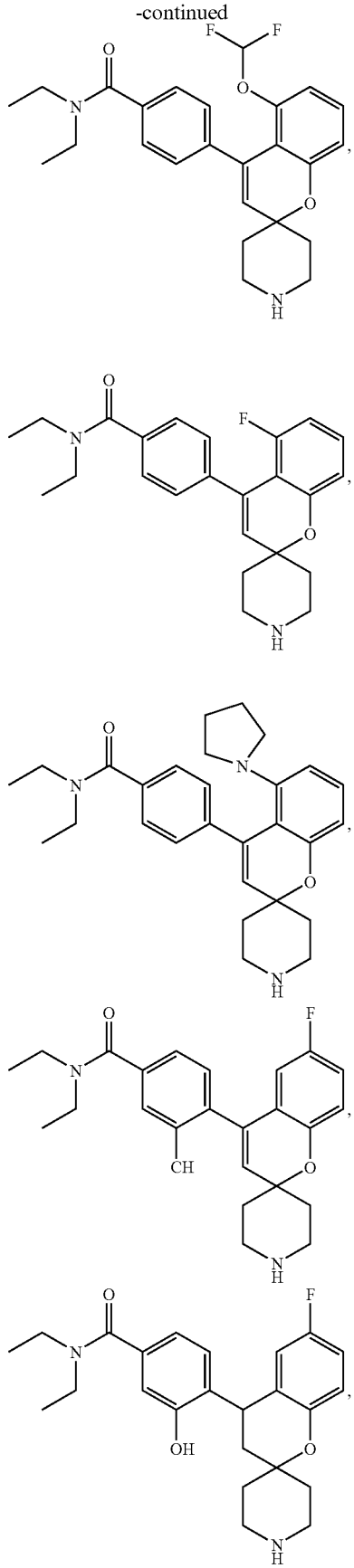

805
-continued
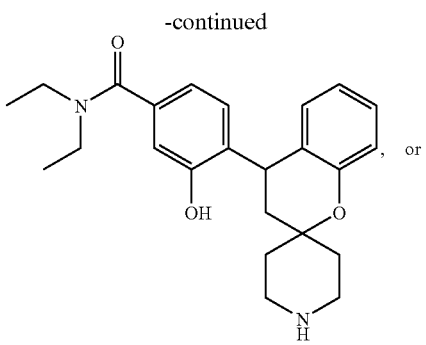
, or
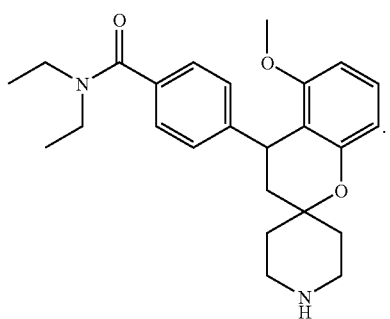
.
61. A compound according to claim 29, wherein the compound is:
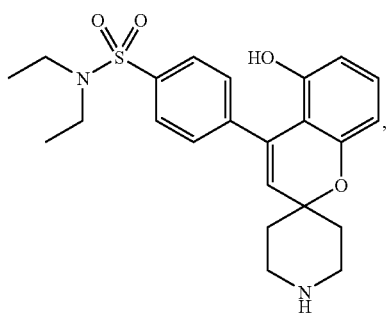
,
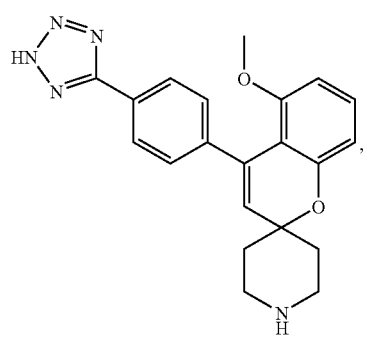
,
806
-continued
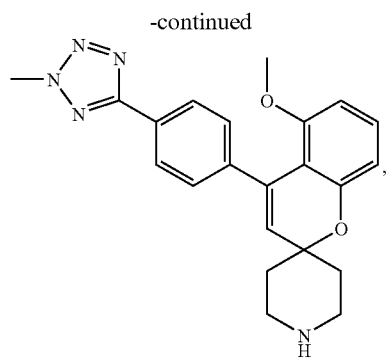
,
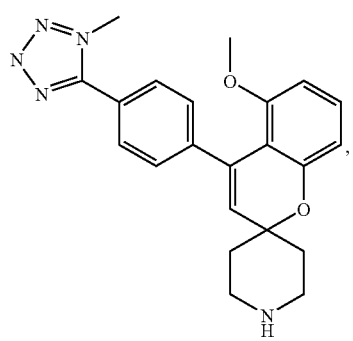
,
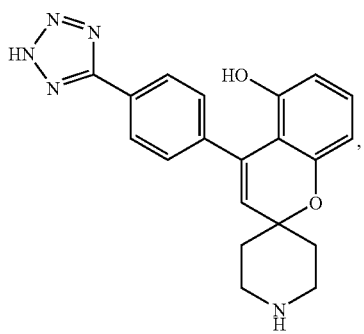
,
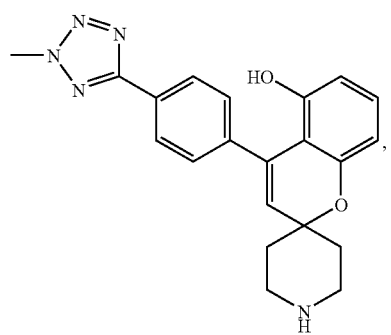
, 807
-continued
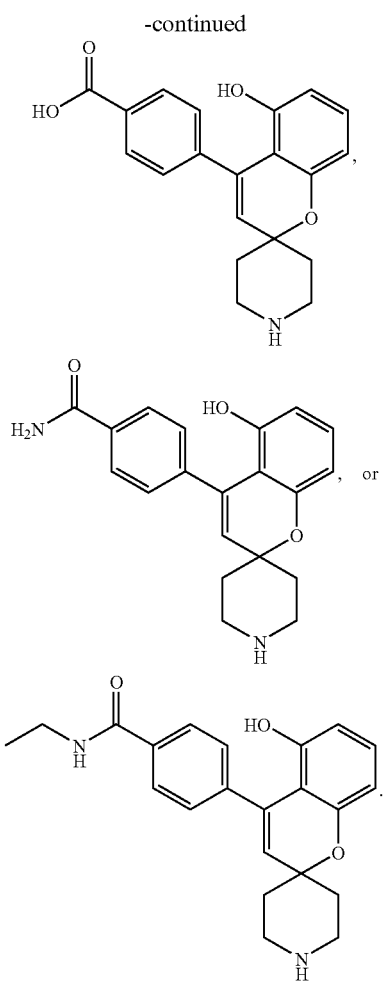
808
-continued
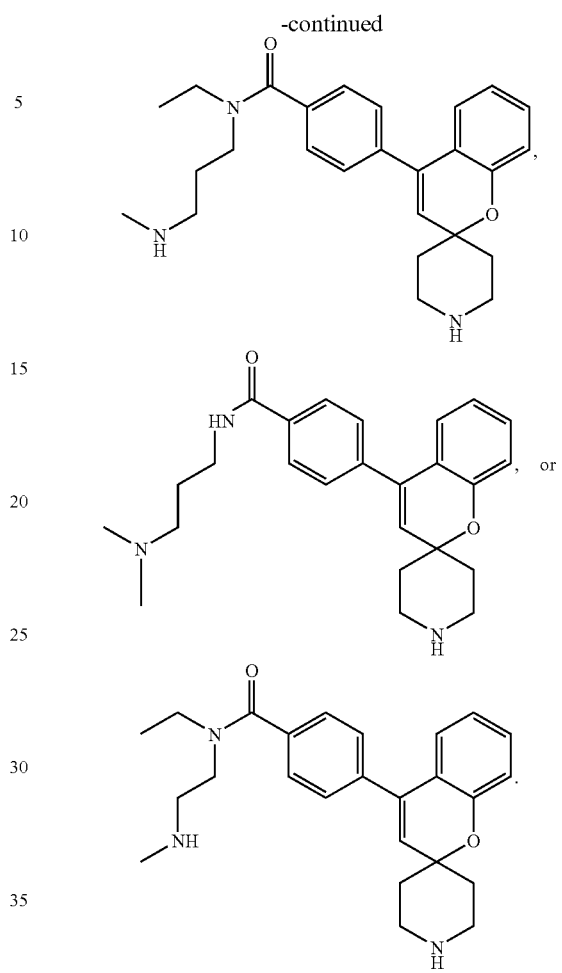
62. A compound according to claim 33, wherein the compound is:
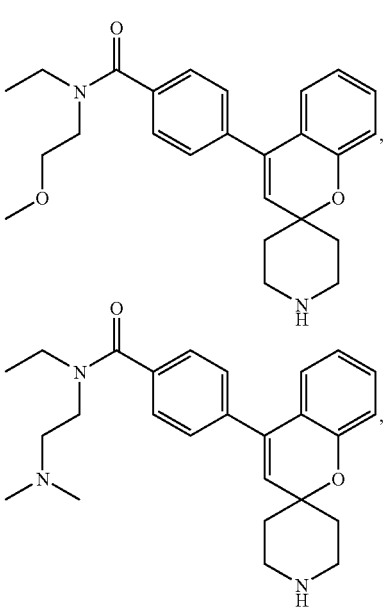
63. A compound according to claim 40, wherein the compound is:
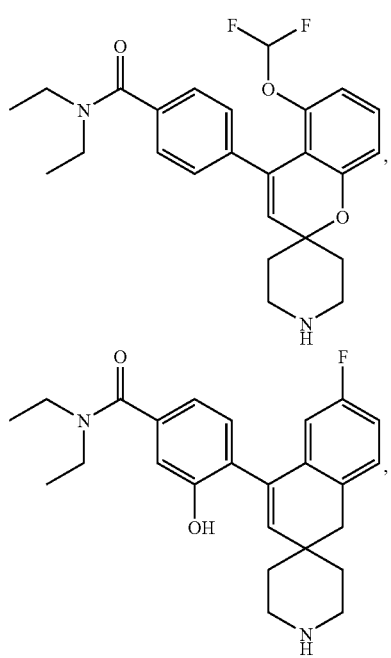

-continued

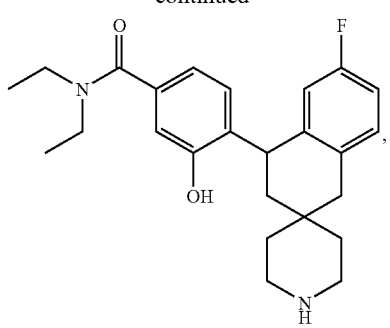

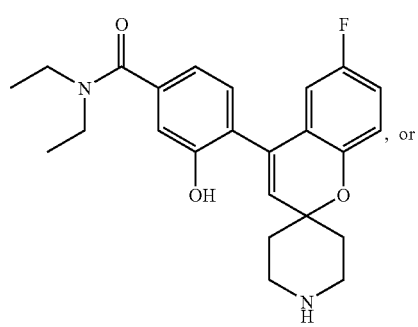, or

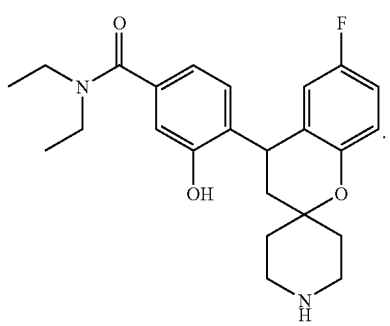.

64. A compound according to claim 45, wherein the compound is:

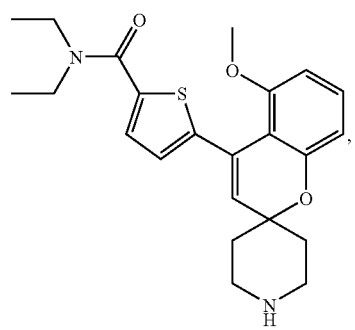,

-continued

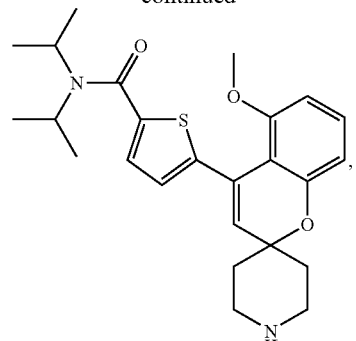,

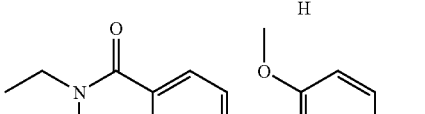, or

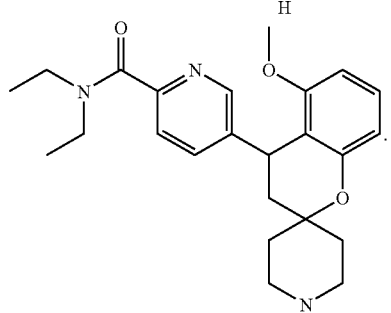.

65. A compound of formula XXXIII:

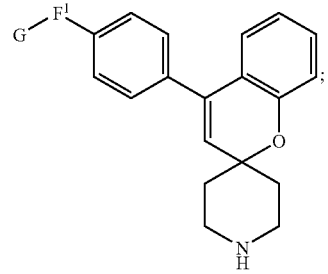

XXXIII wherein:
 F¹ is heteroaryl; and
 G is $C_{1-6}$alkylene substituted with $NH_2$, $NHC(=O)$alkyl, $NH(C(O)N(H)$alkyl, or $NHS(=O)_2$alkyl;
 or a stereoisomer, pharmaceutically acceptable salt, or N-oxide thereof.

66. A compound according to claim 65, wherein the heteroaryl is a 5- or 6-membered heteroaryl having 1 to 4 heteroatoms.

67. A compound according to claim 66, wherein the heteroaryl is a 5- or 6-membered heteroaryl having 2 to 4 heteroatoms.

68. A compound according to claim 67, wherein the heteroaryl is a 5-membered heteroaryl.

69. A compound according to claim 68, wherein the heteroaryl is a tetrazole.

70. A compound according to claim 69, wherein F¹-G is:

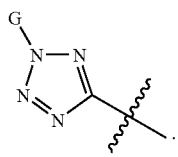

71. A compound according to claim 65, wherein G is $C_{4-6}$alkylene substituted with $NH_2$, NHC(=O)alkyl, or NHS(=O)$_2$alkyl.

72. A compound according to claim 71, wherein the alkyl is $C_{1-6}$alkyl.

73. A compound according to claim 72, wherein the alkyl is $C_1$alkyl.

74. A compound according to claim 71, wherein G is $C_{4-6}$alkylene substituted with $NH_2$.

75. A compound according to claim 70, wherein G is $C_{4-6}$alkylene substituted with $NH_2$, NHC(=O)alkyl, or NHS(=O)$_2$alkyl.

76. A compound according to claim 75, wherein G is $C_{4-6}$alkylene substituted with $NH_2$.

77. A compound according to claim 65, selected from the group consisting of:

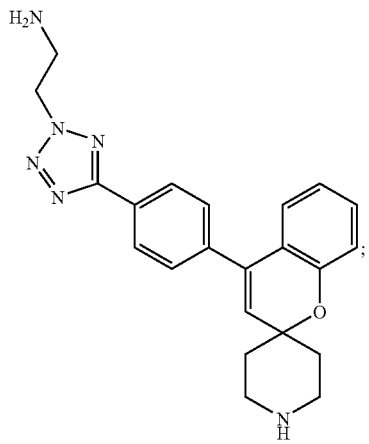

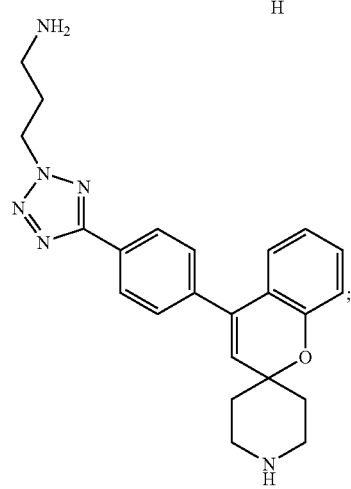

-continued

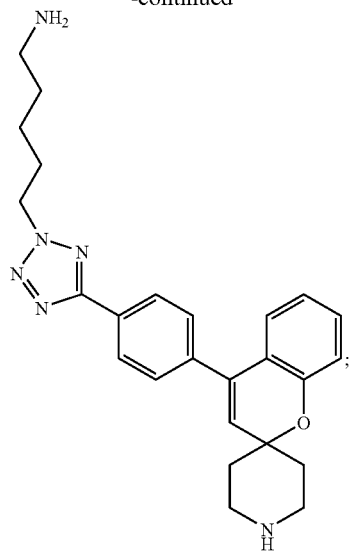

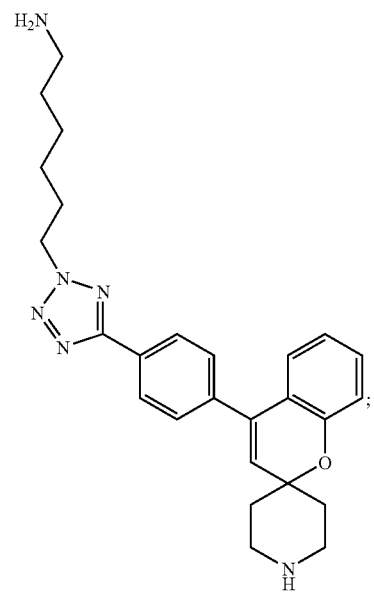

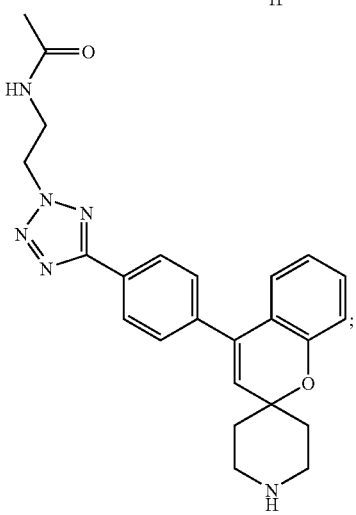

813
-continued
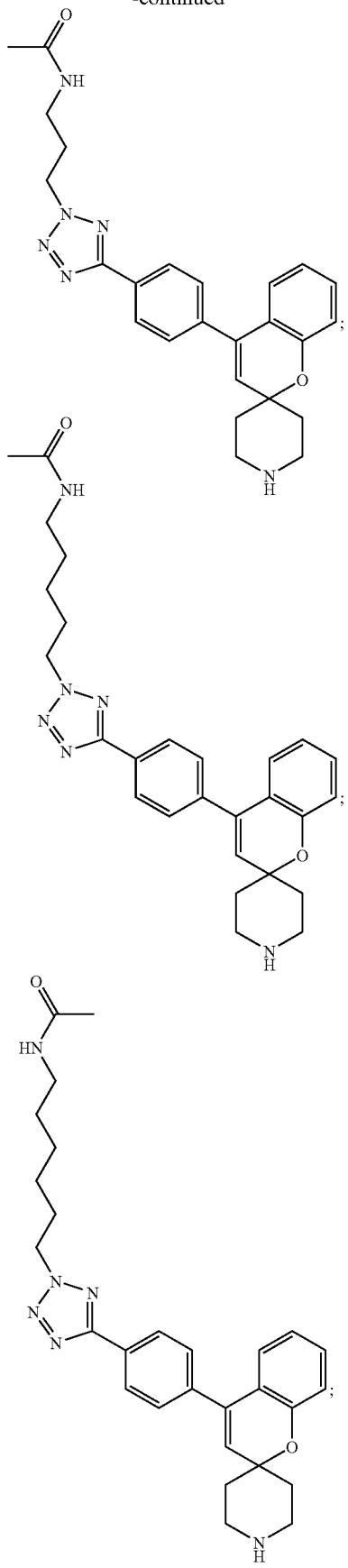
814
-continued
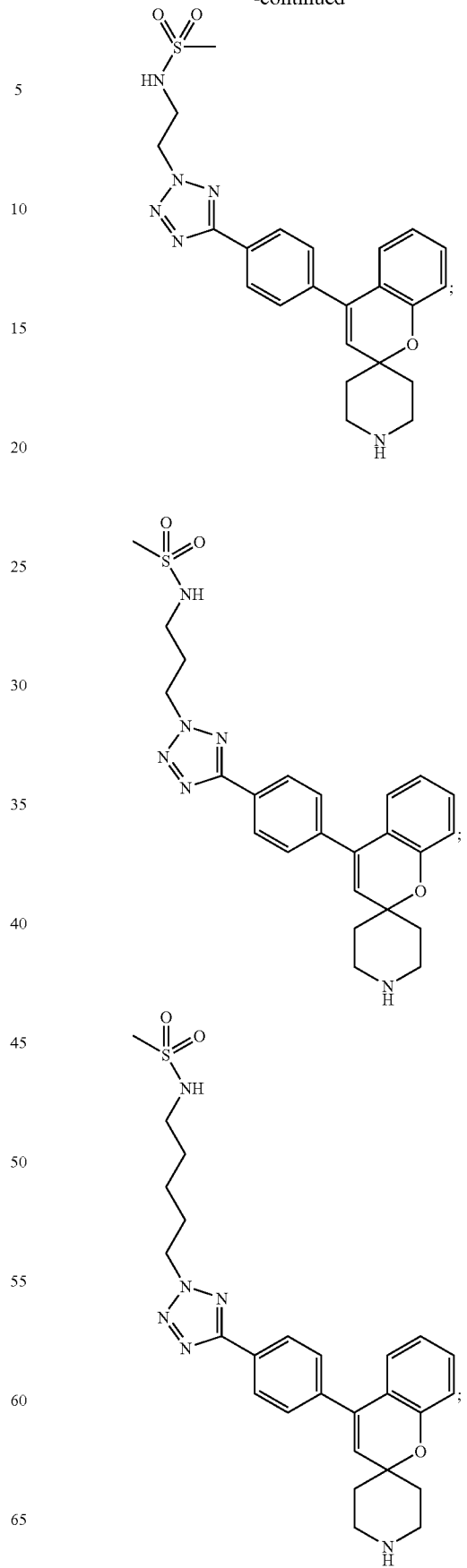

-continued
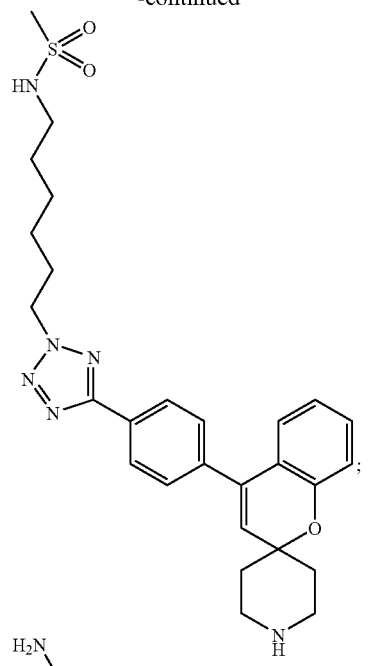
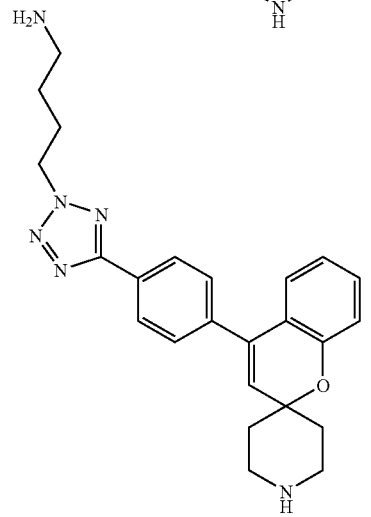
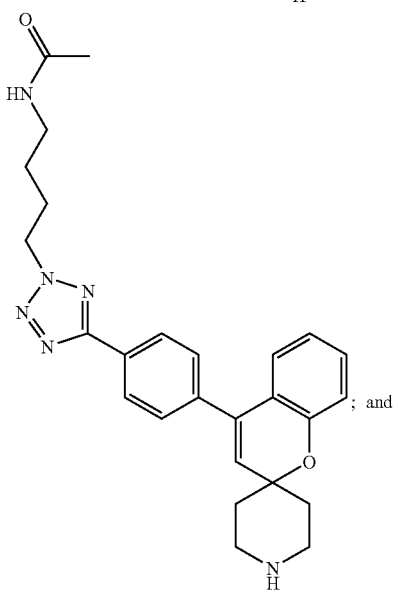
-continued
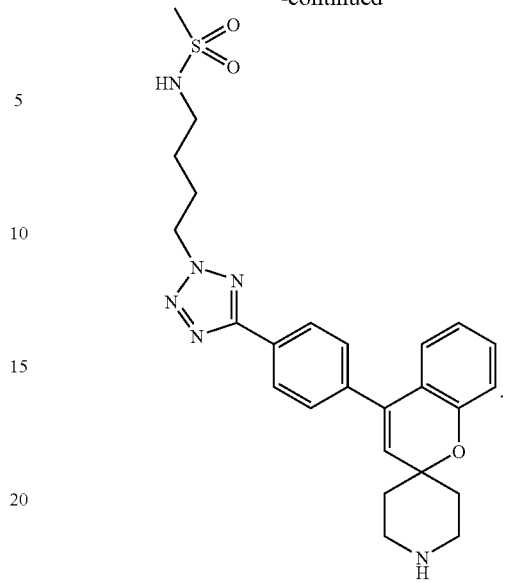
78. A compound according to claim 14, selected from the group consisting of:
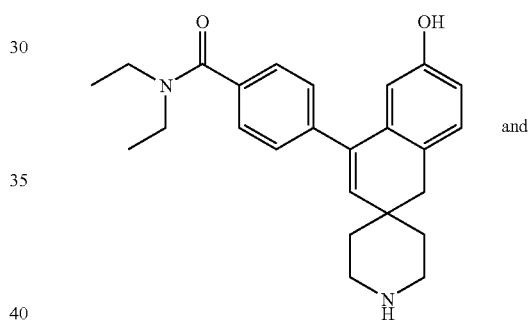
and
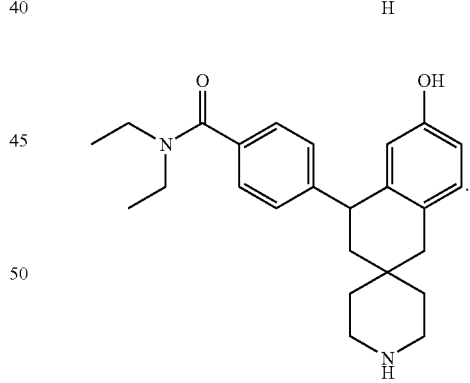
79. A compound according to claim 14, wherein $Q^2$ is hydroxy and $W^2$ is:
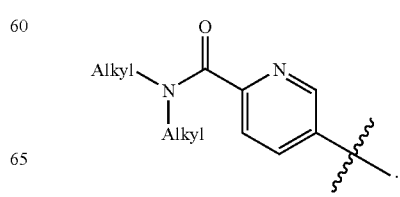

80. A compound according to claim 79, wherein $R^{23}$ and $R^{24}$ are H and $W^2$ is:

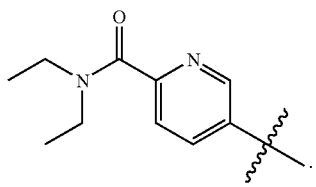

81. A compound according to claim 80, wherein $Q^1$ is H.

82. A compound of formula XXXIV:

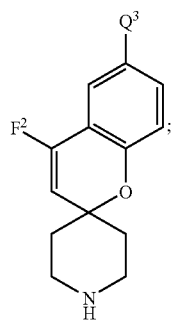

XXXIV wherein:

F$^2$ is aryl or heteroaryl; and
Q$^3$ is hydroxy or alkoxy;
or a stereoisomer, pharmaceutically acceptable salt, or N-oxide thereof.

83. A compound according to claim 82, wherein F$^2$ is phenyl.

84. A compound according to claim 82, wherein F$^2$ is pyridyl or benzothiophenyl.

85. A compound according to claim 82, wherein Q$^3$ is hydroxy, methoxy, or cyclopropylmethoxy.

86. A compound according to claim 83, wherein Q$^3$ is methoxy or cyclopropylmethoxy.

87. A compound according to claim 84, wherein Q$^3$ is hydroxy.

88. A compound according to claim 27, which is:

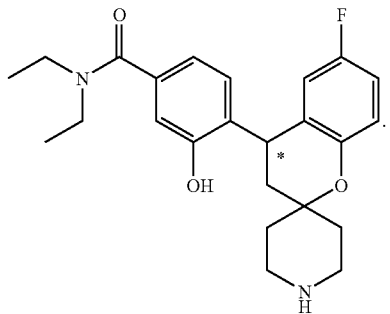

89. A compound according to claim 88, wherein the compound is substantially enantiomerically pure.

90. A compound selected from the group consisting of:

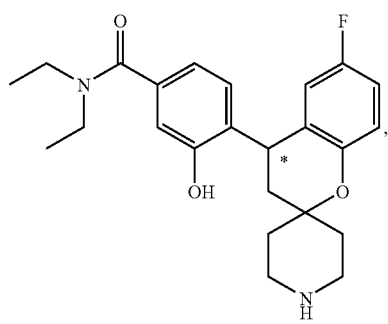

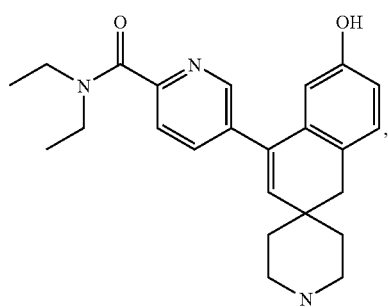

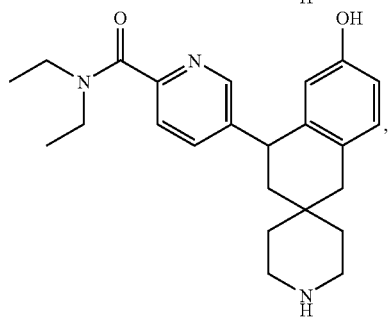

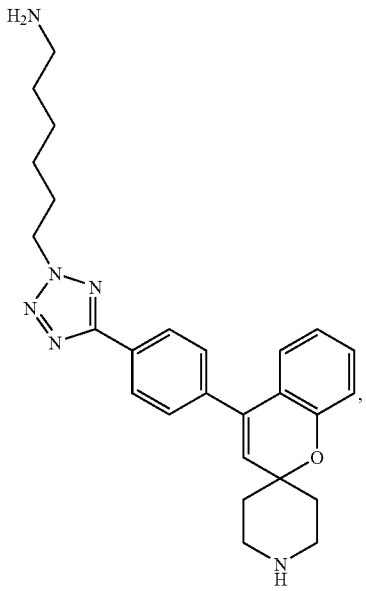

-continued
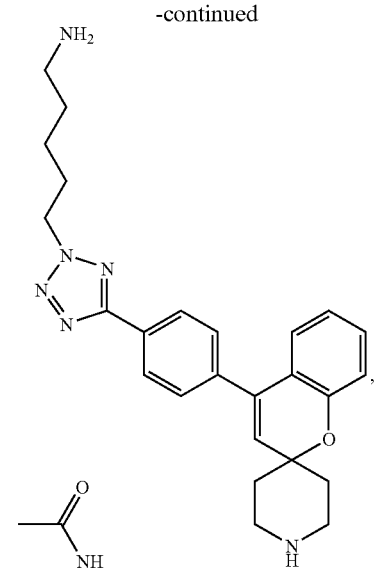
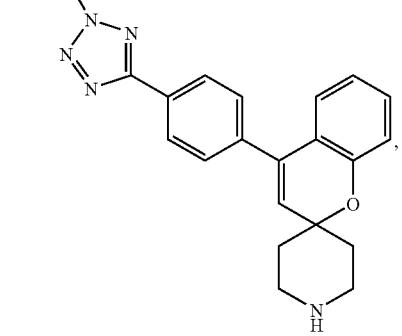
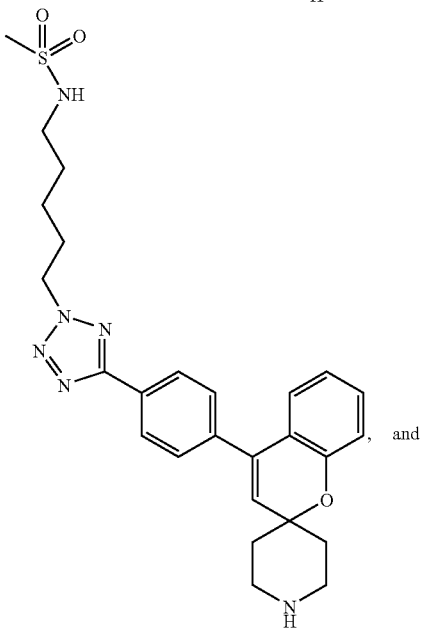
-continued
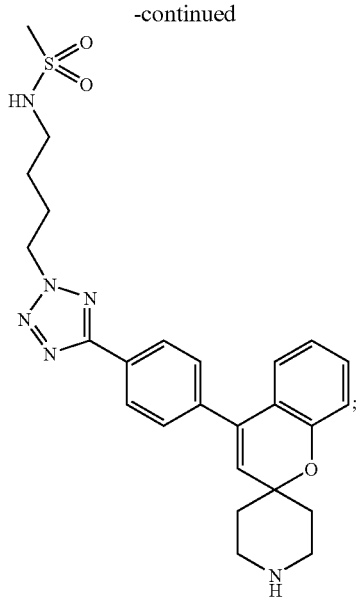
or a stereoisomer, pharmaceutically acceptable salt, or N-oxide thereof.
91. A compound according to claim 90, selected from the group consisting of:
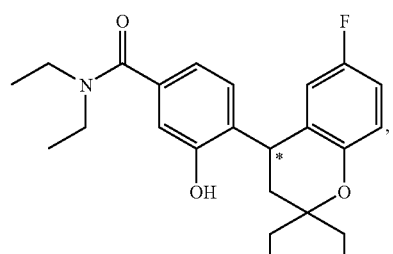
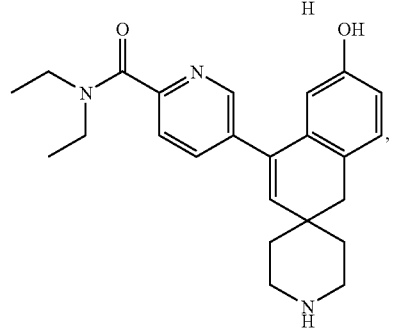
and
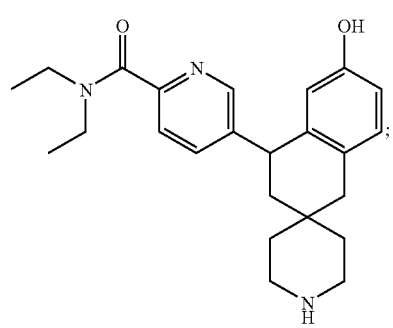

or a stereoisomer, pharmaceutically acceptable salt, or N-oxide thereof.

92. A pharmaceutical composition, comprising:
a pharmaceutically acceptable carrier; and a compound of claim 65.

93. A pharmaceutical composition, comprising:
a pharmaceutically acceptable carrier; and a compound of claim 82.

* * * * *

UNITED STATES PATENT AND TRADEMARK OFFICE
CERTIFICATE OF CORRECTION

PATENT NO.       : 7,598,261 B2
APPLICATION NO.  : 11/393133
DATED            : October 6, 2009
INVENTOR(S)      : Roland E. Dolle, Bertrand Le Bourdonnec and Guo-Hua Chu It is certified that error appears in the above-identified patent and that said Letters Patent is hereby corrected as shown below:

In column 780, lines 38-50, please replace Formula XXII

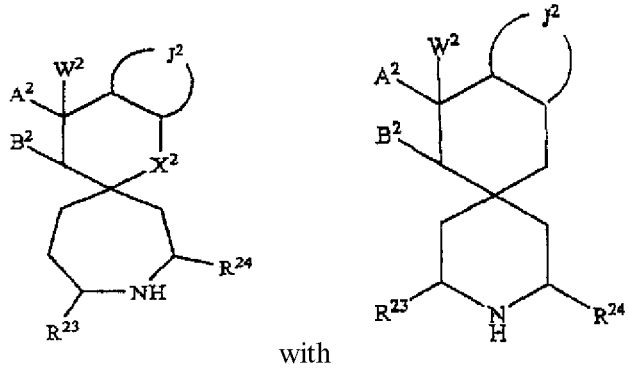

with

In column 781, line 8, after "prop-2-ylaminocarbonylphenyl" please change "orpara" to -- or para --

In column 782, line 4, after "-S(=O)$_2$" please change "-alky," to -- -alkyl, --

In column 788, lines 4-14, Formula XXIX, please replace

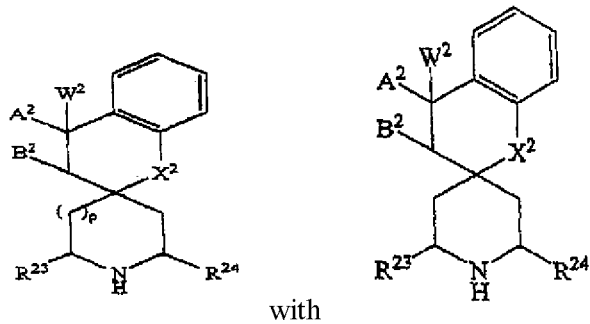

with

In column 794, line 47, after "methoxy", please insert -- or --

In column 817, line 36, after "F$^2$ is", please change "aryl or heteroaryl" to -- unsubstituted aryl or unsubstituted heteroaryl; --

Signed and Sealed this
Eighth Day of May, 2012

David J. Kappos
*Director of the United States Patent and Trademark Office*